US011078170B2

(12) United States Patent
Turner, Jr. et al.

(10) Patent No.: US 11,078,170 B2
(45) Date of Patent: Aug. 3, 2021

(54) CYCLIC SULFAMIDE COMPOUNDS AND METHODS OF USING SAME

(71) Applicant: Assembly Biosciences, Inc., San Francisco, CA (US)

(72) Inventors: William W. Turner, Jr., Bloomington, IN (US); Leping Li, Carmel, IN (US); Simon Nicolas Haydar, Carmel, IN (US); Mark G. Bures, Carmel, IN (US); Roopa Rai, Carmel, IN (US); Samson Francis, Indianapolis, IN (US); Lee D. Arnold, Bloomington, IN (US)

(73) Assignee: Assembly Biosciences, Inc., South San Francisco, CA (US)

( * ) Notice: Subject to any disclaimer, the term of this patent is extended or adjusted under 35 U.S.C. 154(b) by 0 days.

(21) Appl. No.: 16/490,223

(22) PCT Filed: Mar. 1, 2018

(86) PCT No.: PCT/US2018/020515
§ 371 (c)(1),
(2) Date: Aug. 30, 2019

(87) PCT Pub. No.: WO2018/160878
PCT Pub. Date: Sep. 7, 2018

(65) Prior Publication Data
US 2020/0157070 A1    May 21, 2020

Related U.S. Application Data

(60) Provisional application No. 62/549,728, filed on Aug. 24, 2017, provisional application No. 62/529,874, filed on Jul. 7, 2017, provisional application No. 62/465,986, filed on Mar. 2, 2017.

(51) Int. Cl.
| | | |
|---|---|---|
| *C07D 285/16* | (2006.01) |
| *A61P 31/20* | (2006.01) |
| *C07D 417/04* | (2006.01) |
| *C07D 417/10* | (2006.01) |
| *C07D 417/14* | (2006.01) |

(52) U.S. Cl.
CPC ............ *C07D 285/16* (2013.01); *A61P 31/20* (2018.01); *C07D 417/04* (2013.01); *C07D 417/10* (2013.01); *C07D 417/14* (2013.01)

(58) Field of Classification Search
CPC .. C07D 285/16; C07D 417/04; C07D 417/10; C07D 417/14; A61P 31/20
USPC .................................................... 514/222.5
See application file for complete search history.

(56) References Cited

U.S. PATENT DOCUMENTS

| | | | |
|---|---|---|---|
| 5,512,563 A | 4/1996 | Albright et al. |
| 8,618,090 B2 | 12/2013 | Desai et al. |
| 9,399,619 B2 | 7/2016 | Guo et al. |
| 9,873,684 B2 | 1/2018 | Kahraman et al. |
| 10,377,748 B2 | 8/2019 | Turner et al. |
| 10,392,379 B2 | 8/2019 | Turner et al. |
| 10,766,890 B2 | 9/2020 | Turner et al. |
| 2007/0105819 A1 | 5/2007 | Olsson et al. |
| 2007/0105835 A1 | 5/2007 | Kazantsev |
| 2015/0368261 A1 | 12/2015 | Demin et al. |
| 2017/0107185 A1 | 4/2017 | Grammneos et al. |
| 2017/0267685 A1 | 9/2017 | D'Agostino et al. |
| 2018/0265484 A1 | 9/2018 | Turner et al. |
| 2020/0002325 A1 | 1/2020 | Li et al. |
| 2020/0157070 A1 | 5/2020 | Turner, Jr. et al. |

FOREIGN PATENT DOCUMENTS

| | | | |
|---|---|---|---|
| CL | 2015002706 A1 | 4/2016 | |
| CL | 2015003456 A1 | 7/2016 | |
| CL | 20105002628 | 8/2016 | |
| CL | 2016003175 A1 | 8/2017 | |
| CN | 103889953 B | 6/2016 | |
| CN | 106413402 A | 2/2017 | |
| GB | 1480553 A | 7/1977 | |
| JP | 58225074 | 12/1983 | |
| WO | WO-92/19277 A1 | 11/1992 | |
| WO | WO-2005/072741 A1 | 8/2005 | |
| WO | WO-2007/105819 A1 | 9/2007 | |
| WO | WO-2008/045558 A3 | 8/2008 | |
| WO | WO-2008/036139 A3 | 12/2008 | |
| WO | WO-2008/118141 A3 | 12/2008 | |
| WO | WO-2009/064852 A1 | 5/2009 | |
| WO | WO-2010/011537 A1 | 1/2010 | |
| WO | WO-2012/045194 A1 | 4/2012 | |
| WO | WO-2013/006394 A1 | 1/2013 | |
| WO | WO-2015/017412 A1 | 2/2015 | |
| WO | WO-2015/138895 A1 | 9/2015 | |
| WO | WO-2015181676 A1 * | 12/2015 | .............. A61P 27/16 |
| WO | WO-2015/181676 A4 | 2/2016 | |
| WO | WO-2017/048950 A1 | 3/2017 | |
| WO | WO-2017/048954 A1 | 3/2017 | |
| WO | WO-2017048962 A1 | 3/2017 | |

(Continued)

OTHER PUBLICATIONS

Achenbach et al. MedChemComm (2013), 4(6), 920-924.*
International Search Report and Written Opinion dated Mar. 22, 2018, for International Application No. PCT/US2017/051605.
STN Registry Database Entry for 443670-41-5 entered STN Aug. 12, 2002.
STN Registry Database Entry for 688762-71-2 entered STN Jun. 3, 2004.
STN Registry Database Entry for 903147-56-8 entered STN Aug. 22, 2006.
STN Registry Database Entry for 931950-46-8 entered STN Apr. 22, 2007.
Supplemental European Search Report issued by the European Patent Office (Munich), dated Apr. 11, 2018, for related Application No. EP 15761201; 21 pages.

(Continued)

*Primary Examiner* — Kahsay Habte
(74) *Attorney, Agent, or Firm* — Barnes & Thornburg LLP

(57) ABSTRACT

The present disclosure provides, in part, cyclic sulfamide compounds, and pharmaceutical compositions thereof, useful as modulators of Hepatitis B (HBV) core protein, and methods of treating Hepatitis B (HBV) infection.

35 Claims, 1 Drawing Sheet

Specification includes a Sequence Listing.

(56) References Cited

FOREIGN PATENT DOCUMENTS

| WO | WO-2018/053157 A1 | 3/2018 |
|---|---|---|
| WO | WO-2018160878 A1 | 9/2018 |
| WO | WO-2018169907 A1 | 9/2018 |

OTHER PUBLICATIONS

Takeda, M., et al., "Synthesis of Dibenzo [b,e) [1,4] Diazepine Derivatives as Anti-depressants," Yakugaku Zahhi, vol. 89, No. 2, (1969), 6 pages.
National Center for Biotechnology Information, PubChem Compound Database; CID-4152425, XP-002779931, modified Apr. 7, 2017, created Sep. 13, 2005; 3 pages.
National Center for Biotechnology Information, PubChem Compound Database; CID-46260649, XP-002779932, modified Apr. 7, 2017, created Jul. 21, 2010; 3 pages.
National Center for Biotechnology Information, PubChem Compound Database; CID-4163919, XP-002779933, modified Apr. 7, 2018, created Sep. 13, 2005; 3 pages.
National Center for Biotechnology Information, PubChem Compound Database; CID-4167865, XP-002779934, modified Apr. 7, 2018, created Sep. 13, 2005; 3 pages.
National Center for Biotechnology Information, PubChem Compound Database; CID-4338109, XP-002779935, modified Apr. 7, 2018, created Sep. 14, 2005; 3 pages.
National Center for Biotechnology Information, PubChem Compound Database; CID-4163918, XP-002779936, modified Apr. 7, 2018, created Sep. 13, 2005; 3 pages.
National Center for Biotechnology Information, PubChem Compound Database; CID-3576843, XP-002779937, modified Apr. 7, 2018, created Sep. 9, 2005; 3 pages.
National Center for Biotechnology Information, PubChem Compound Database; CID-4577044, XP-002779938, modified Apr. 7, 2018, created Sep. 15, 2005; 3 pages.
National Center for Biotechnology Information, PubChem Compound Database; CID-4097179, XP-002779940, modified Apr. 7, 2018, created Sep. 13, 2005; 3 pages.
National Center for Biotechnology Information, PubChem Compound Database; CID-23797169, XP-002779941, modified Apr. 7, 2018, created Feb. 20, 2008; 3 pages.
National Center for Biotechnology Information, PubChem Compound Database; CID-53384785, XP-002779942, modified Apr. 7, 2018, created Oct. 13, 2011; 3 pages.
National Center for Biotechnology Information, PubChem Compound Database; CID-20885138, XP-002775927, modified Nov. 18, 2018, created Dec. 5, 2007; 3 pages.
National Center for Biotechnology Information, PubChem Compound Database; CID-20885146, XP-002775928, modified Nov. 18, 2017, created Dec. 5, 2007; 3 pages.
National Center for Biotechnology Information, PubChem Compound Database; CID-20885149, XP-002775929, modified Nov. 18, 2017, created Dec. 5, 2007; 3 pages.
National Center for Biotechnology Information, PubChem Compound Database; CID-20885150, XP-002775930, modified Nov. 18, 2017, created Dec. 5, 2007; 3 pages.
National Center for Biotechnology Information, PubChem Compound Database; CID-20885171, XP-002775931, modified Nov. 18, 2017, created Dec. 5, 2007; 3 pages.
Letter Exam Report from the Australian Patent Office, dated May 6, 2018, for Australian Application No. 2015229174; 6 pages.
Office Action issued by the Belize Intellectual Property Office, dated May 18, 2018, for Belize Patent Application No. 887.16; 2 pages.
English translation of the First Official Action issued by the Mexican Patent Office for Mexican Patent Application No. MX/a/2016/011800, dated Jul. 4, 2018; 3 pages.
Letter dated Jun. 27, 2018 regarding Examination Report issued by the National Office of Industrial Property for Dominican Republic Patent Application No. P2016-0233; 2 pages.

Supplemental Partial European Search Report issued by the European Patent Office (Munich), dated Nov. 23, 2017, for related Application No. EP 15761201; 14 pages.
Letter Exam Report issued by The Patent Office of the People's Republic of China (translated in English language), dated Jun. 29, 2018, for Chinese Application No. 201580024580.0; (3 pages).
Letter Exam Report issued by the Chilean Patent Office, dated Jun. 12, 2018, for Chilean Application No. 2269-2016; 15 pages.
National Center for Biotechnology Information, PubChem Compound Database; CID-23734106, XP-002779939, modified Apr. 7, 2018, created Feb. 20, 2008; 3 pages.
Hall, Pamela R., et al., "*Small molecule inhibitors of hantavirus infection*," Bioorganic & Medicinal Chemistry Letters, vol. 20, (2010), pp. 7085-7091.
Xiao, et al., "Discovery, Optimization, and Characterization of Novel D2 Dopamine Receptor Selective Antagonists," Journal of Medicinal Chemistry, Mar. 25, 2014, vol. 57, pp. 3450-3463.
International Preliminary Report on Patentability issued by The International Bureau of WIPO, dated Sep. 13, 2016, for International Application No. PCT/US2015/020444; 6 pages.
International Search Report and Written Opinion issued by the ISA/US, Commissioner for Patents, dated Jul. 6, 2015, for International Application No. PCT/US2015/020444; 10 pages.
National Center for Biotechnology Information. PubChem Compound Database; CID=20885151; available at https://pubchem.ncbi.nlm.nih.gov/compound/20885151 (accessed Sep. 13, 2016; deposit date Dec. 5, 2007); 10 pages.
National Center for Biotechnology Information. PubChem Compound Database; CID=4 II 9 I71, available at https://pubchem.ncbi.nlm.nih.gov/compound/4119171 (accessed Sep. 13, 2016; deposit date Sep. 3, 2005); 12 pages.
National Center for Biotechnology Information. PubChem Compound Database; CID=4167865, https://pubchem.ncbi.nlm.nih.gov/compound/4167865 (accessed Sep. 13, 2016; deposit date Sep. 13, 2005); 12 pages.
International Preliminary Report on Patentability dated Mar. 20, 2018, for International Application No. PCT/US2016/051934 (6 pages).
International Search Report and Written Opinion issued on Dec. 29, 2016 for International Application No. PCT/US16/51934.
International Preliminary Report on Patentability dated Dec. 29, 2016, for International Application No. PCT/US2016/051949.
International Search Report and Written Opinion dated Dec. 29, 2016 for International Application No. PCT/US16/51949.
International Preliminary Report on Patentability dated Oct. 28, 2016, for International Application No. PCT/US2016/051940.
International Search Report and Written Opinion dated Oct. 28, 2016 for International Application No. PCT/US16/51949.
National Center for Biotechnology Information, PubChem Compound Database; CID-201327, create date: Aug. 9, 2005; 3 pages.
Supplementary European Search Report issued for EP16847298, dated Jan. 28, 2019 (6 pages).
Notice of Reasons for Rejection issued for Japanese Patent Application No. 2016-557019, dated Oct. 30, 2018 (6 pages).
Official Office Action issued in Eurasian application No. 201890731, dated Oct. 31, 2018.
Office Action issued by the Belize Intellectual Property Office, dated Nov. 21, 2018, for Belize Patent Application No. 925.18 (3 pages).
Extended European Search Report issued in EP16847298.3, dated Jan. 2, 2019.
Extended European Search Report issued for European Patent Application No. 16847295.9, dated Apr. 15, 2019.
Xiao, et al.. "Discovery, Optimization, and Characterization of Novel D2 Dopamine Receptor Selective Antagonists", Journal of Medicinal Chemistry, vol. 57, p. 3450-63 (2014).
Office Action issued by the Chinese Intellectual Property Office, dated Mar. 17, 2020, for Chinese Patent Application No. 201680065139.1.
Ito, et. al. "A Medium-Term Rat Liver Bioassay for Rapid In Vivo Detection of Carcinogenic Potential of Checmicals," Cancer Sci, Jan. 2003, vol. 94, pp. 3-8.
STN Registry Database Entry for CAS RN688762_67_6—Jun. 3, 2004, Accessed Aug. 8, 2019.

(56) References Cited

OTHER PUBLICATIONS

Ito et al. in Cancer Science 94(1), 3-8 (2003).
STN Registry database entry for CAS RN 688762-67-6, Entered STN Jun. 3, 2004, Accessed Aug. 8, 2019.
European Search Report and Search Opinion Received for EP Application No. 16847295.9, dated Apr. 15, 2019, 6 pages.
European Search Report and Search Opinion Received for EP Application No. 16847298.3, dated Feb. 1, 2019, 7 pages.
European Search Report and Search Opinion Received for EP Application No. 16847305.6, dated Mar. 26, 2019, 8 pages.
Pubchem CD 201327; Aug. 9, 2005.
International Search Report and Written Opinion dated Sep. 20, 2018, for International Application No. PCT/US2018/002100.
Takehiko Nishio Et al: "Thionation of [omega]-Acylamino Ketones with Lawesson's Reagent: Convenient Synthesis of 1,3-Thiazoles and 4H-1,3-Thiazines", vol. 84, No. 8, Aug. 15, 2001 (Aug. 15, 2001), pp. 2347-2354.
International Search Report and Written Opinion dated Sep. 7, 2018, for International Application No. PCT/US2018/020515.

\* cited by examiner

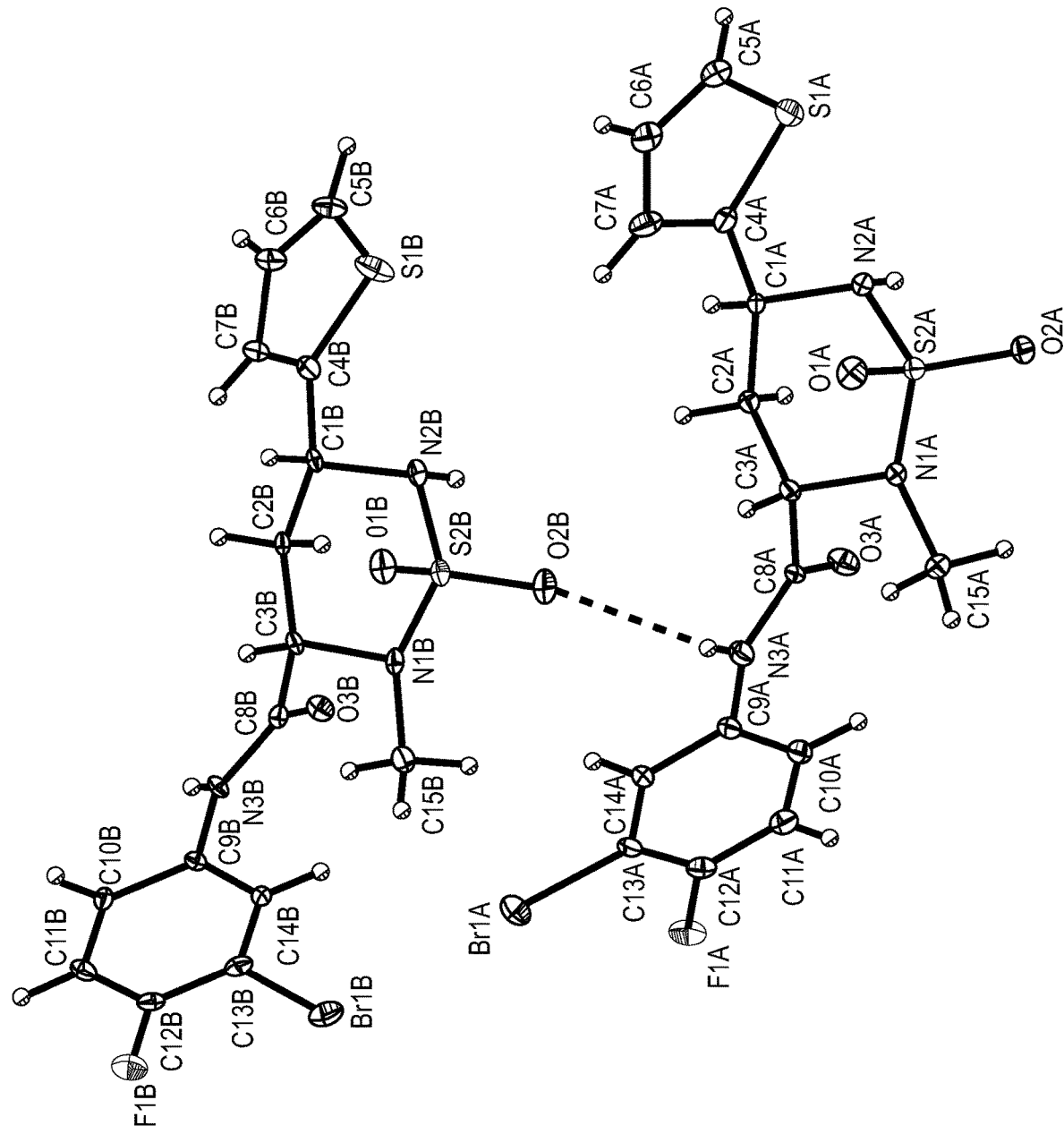

CYCLIC SULFAMIDE COMPOUNDS AND METHODS OF USING SAME

RELATED APPLICATIONS

This application is a national stage entry under 35 U.S.C. 371 of international patent application number PCT/US2018/020515 filed Mar. 1, 2018, which claims priority to and the benefit of U.S. provisional application No. 62/465,986, filed Mar. 2, 2017, U.S. provisional application No. 62/529,874 filed Jul. 7, 2017, and U.S. provisional application No. 62/549,728 filed Aug. 24, 2017, each of which is incorporated by reference in its entirety.

BACKGROUND

Hepatitis B (HBV) causes viral hepatitis that can further lead to chronic liver disease and increase the risk of liver cirrhosis and liver cancer (hepatocellular carcinoma). Worldwide, about 2 billion people have been infected with HBV, around 360 million people are chronically infected, and every year HBV infection causes more than one half million deaths. HBV can be spread by body fluids: from mother to child, by sex, and via blood products. Children born to HBV-positive mothers may also be infected, unless vaccinated at birth.

The hepatitis virus particle is composed of a lipid envelope studded with surface protein (HBsAg) that surrounds the viral core. The core is composed of a protein shell, or capsid, built of 120 core protein (Cp) dimers, which in turn contains the relaxed circular DNA (rcDNA) viral genome as well as viral and host proteins. In an infected cell, the genome is found as a covalently closed circular DNA (cccDNA) in the host cell nucleus. The cccDNA is the template for viral RNAs and thus viral proteins. In the cytoplasm, Cp assembles around a complex of full-length viral RNA (the so-called pregenomic RNA or pgRNA and viral polymerase (P). After assembly, P reverse transcribes the pgRNA to rcDNA within the confines of the capsid to generate the DNA-filled viral core.

At present, chronic HBV is primarily treated with nucleotide analogs (e.g., entecavir) that suppress the virus while the patient remains on treatment, but do not eliminate the infection, even after many years of treatment. Once a patient starts taking nucleotide analogs, most must continue taking them or risk the possibility of a life threatening immune response due to viral rebound. Further, nucleotide therapy may lead to the emergence of antiviral drug resistance.

The only FDA approved alternative to nucleotide analogs is treatment with interferon α or pegylated interferon α. Unfortunately, the adverse event incidence and profile of interferon α can result in poor tolerability, and many patients are unable to complete therapy. Moreover, only a small percentage of patients are considered appropriate for interferon therapy, as only a small subset of patients are likely to have a sustained clinical response to a course of interferon therapy. As a result, interferon-based therapies are used in only a small percentage of all diagnosed patients who elect treatment.

Thus, current HBV treatments can range from palliative to watchful waiting. Nucleotide analogs suppress virus production, treating the symptom, but leave the infection intact. Interferon α has severe side effects and less tolerability among patients and is successful as a finite treatment strategy in only a small minority of patients. There is a clear on-going need for more effective treatments for HBV infections.

SUMMARY

The present disclosure provides, in part, cyclic sulfamide compounds and pharmaceutical compositions thereof, useful for modulation of HBV core protein, and methods of treating HBV infections.

In one aspect, the disclosure provides compounds of Formula I:

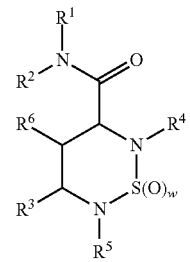

Formula I or a pharmaceutically acceptable salt thereof, where the variables are described in the detailed description.

In another aspect, the disclosure provides pharmaceutical compositions comprising a compound of Formula I, or a pharmaceutically acceptable salt thereof, and a pharmaceutically acceptable excipient.

In another aspect, the disclosure provides a method of treating HBV infection in a subject in need thereof comprising: administering to the subject an effective amount of compound of Formula I, or a pharmaceutically acceptable salt thereof.

In another aspect, the disclosure provides a method of treating HBV infection in a subject in need thereof comprising: administering to the subject a pharmaceutical composition comprising a compound of Formula I, or a pharmaceutically acceptable salt thereof, and a pharmaceutically acceptable excipient.

BRIEF DESCRIPTION OF DRAWINGS

FIG. 1 is the crystal structure of HBV-CSU-016-ISO-I as described herein.

DETAILED DESCRIPTION

The features and other details of the disclosure will now be more particularly described. Before further description of the present disclosure, certain terms employed in the specification, examples and appended claims are collected here. These definitions should be read in light of the remainder of the disclosure and as understood by a person of skill in the art. Unless defined otherwise, all technical and scientific terms used herein have the same meaning as commonly understood by a person of ordinary skill in the art.

Definitions

"Treating" includes any effect, e.g., lessening, reducing, modulating, or eliminating, that results in the improvement of the condition, disease, disorder and the like.

The term "alkenyl" as used herein refers to an unsaturated straight or branched hydrocarbon having at least one carbon-carbon double bond. Exemplary alkenyl groups include, but are not limited to, a straight or branched group of 2-6 or 3-4 carbon atoms, referred to herein as $C_{2-6}$alkenyl, and $C_{3-4}$alkenyl, respectively. Exemplary alkenyl groups include, but are not limited to, vinyl, allyl, butenyl, pentenyl, etc.

The term "alkoxy" as used herein refers to a straight or branched alkyl group attached to oxygen (alkyl-O—). Exemplary alkoxy groups include, but are not limited to, alkoxy groups of 1-6 or 2-6 carbon atoms, referred to herein as $C_{1-6}$alkoxy, and $C_{2-6}$alkoxy, respectively. Exemplary alkoxy groups include, but are not limited to methoxy, ethoxy, isopropoxy, etc.

The term "alkoxyalkyl" as used herein refers to an alkyl group substituted with an alkoxy group. Examples include but are not limited to $CH_3CH_2OCH_2$—, $CH_3OCH_2CH_2$— and $CH_3OCH_2$—.

The term "alkyl" as used herein refers to a saturated straight or branched hydrocarbon. Exemplary alkyl groups include, but are not limited to, straight or branched hydrocarbons of 1-6, 1-4, or 1-3 carbon atoms, referred to herein as $C_{1-6}$alkyl, $C_{1-4}$alkyl, and $C_{1-3}$alkyl, respectively. Exemplary alkyl groups include, but are not limited to, methyl, ethyl, propyl, isopropyl, 2-methyl-1-butyl, 3-methyl-2-butyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, hexyl, etc.

The term "alkynyl" as used herein refers to an unsaturated straight or branched hydrocarbon having at least one carbon-carbon triple bond. Exemplary alkynyl groups include, but are not limited to, straight or branched groups of 2-6, or 3-6 carbon atoms, referred to herein as $C_{2-6}$alkynyl, and $C_{3-6}$alkynyl, respectively. Exemplary alkynyl groups include, but are not limited to, ethynyl, propynyl, butynyl, pentynyl, hexynyl, methylpropynyl, etc.

The term "carbonyl" as used herein refers to the radical —C(O)—.

The term "cyano" as used herein refers to the radical —CN.

The terms "cycloalkyl" or a "carbocyclic group" as used herein refers to a saturated or partially unsaturated hydrocarbon group of, for example, 3-6, or 4-6 carbons, referred to herein as $C_{3-6}$cycloalkyl or $C_{4-6}$cycloalkyl, respectively. Exemplary cycloalkyl groups include, but are not limited to, cyclohexyl, cyclopentyl, cyclopentenyl, cyclobutyl or cyclopropyl.

The terms "halo" or "halogen" as used herein refer to F, Cl, Br, or I.

The term "haloalkyl" as used herein refers to an alkyl group substituted with one or more halogen atoms. Examples include but are not limited to —$CH_2F$, —$CHCl_2$, —$CF_3$, —$CH_2CF_3$, —$CF_2CH_3$, $CCl_2CF_3$ and —$CF_2CF_3$.

The term "haloalkoxy" as used herein refers to an alkoxy group substituted with one or more halogen atoms. Examples include but are not limited to $CF_3$—O—, $CF_3CH_2$—O—, and $CF_3CF_2$—O—.

The terms "heteroaryl" or "heteroaromatic group" as used herein refers to a monocyclic aromatic 5-6 membered ring system or bicyclic aromatic 8-12 membered ring system containing one or more heteroatoms, for example one to three heteroatoms, such as nitrogen, oxygen, and sulfur. Where possible, said heteroaryl ring may be linked to the adjacent radical though carbon or nitrogen. Examples of 5-6 membered monocyclic heteroaryls include but are not limited to: furanyl, thiophenyl (also referred to as thienyl), pyrrolyl, thiazolyl, oxazolyl, isothiazolyl, isoxazolyl, imidazolyl, pyrazolyl, 1H-1,2,3-triazolyl, 2H-1,2,3-triazolyl, 1,2,4-triazolyl, pyridinyl, pyridazinyl, pyrimidinyl, pyrazinyl, 1,3,5-triazinyl, 1,2,4-triazinyl, 1,2,3-triazinyl, 1,2,4-oxadiazolyl, 1,3,4-oxadiazolyl, 1,2,5-oxadiazolyl, 1,2,4-thiadiazolyl, 1,3,4-thiadiazolyl, and 1,2,5-thiadiazolyl. Examples of 8-12 membered bicyclic heteroaryls include but are not limited to: benzofuranyl, isobenzofuranyl, benzo[b]thiophenyl, benzo[c]thiophenyl, indolyl, isoindolyl, benzo[d]isoxazolyl, benzo[c]isoxazolyl, benzo[d]oxazolyl, benzo[d]isothiazolyl, benzo[c]isothiazolyl, benzo[d]thiazolyl, indazolyl, benzo[d]imidazolyl, benzo[d]imidazolyl, and benzo[d][1,2,3]triazolyl.

The terms "heterocyclyl" or "heterocyclic group" are art-recognized and refer to saturated or partially unsaturated 4-7 membered ring structures, whose ring structures include one to three heteroatoms, such as nitrogen, oxygen, and sulfur. Where possible, heterocyclyl rings may be linked to the adjacent radical through carbon or nitrogen. Examples of heterocyclyl groups include, but are not limited to, pyrrolidinyl, piperidinyl, morpholinyl, thiomorpholinyl, piperazinyl, oxetanyl, azetidinyl, tetrahydrofuranyl or dihydrofuranyl etc.

The terms "hydroxy" and "hydroxyl" as used herein refers to the radical —OH.

The term "hydroxyalkyl" as used herein refers to an alkyl group substituted with one or more hydroxy groups. Examples include but are not limited to $HOCH_2$—, $HOCH_2CH_2$— and $CH_3CH(OH)CH_2$—.

The term "hydroxyalkoxy" as used herein refers to an alkoxy group substituted with one or more hydroxy groups. Examples include but are not limited to $HOCH_2$—O—, $HOCH_2CH_2$—O— and $CH_3CH(OH)CH_2$—O—.

The term "$R^aR^bN$—$C_{1-6}$alkyl-," as used herein refers to an alkyl group substituted with a $R^aR^bN$— group, as defined herein. Examples include but are not limited to $NH_2CH_2$—, $NH(CH_3)CH_2$—, $N(CH_3)_2CH_2CH_2$— and $CH_3CH(NH_2)CH_2$—.

The term "$R^aR^bN$—$C_{1-6}$alkoxy," as used herein refers to an alkoxy group substituted with one or more $R^aR^bN$— groups, as defined herein. Examples include but are not limited to $NH_2CH_2$—, $NH(CH_3)CH_2$—O—, $N(CH_3)_2CH_2CH_2$—O— and $CH_3CH(NH_2)CH_2$—O—.

The term "oxo" as used herein refers to the radical =O.

"Pharmaceutically acceptable" include molecular entities and compositions that do not produce an adverse, allergic or other untoward reaction when administered to an animal, or a human, as appropriate. For human administration, preparations should meet sterility, pyrogenicity, and general safety and purity standards as required by FDA Office of Biologics standards.

The term "pharmaceutically acceptable carrier" or "pharmaceutically acceptable excipient" as used herein refers to any and all solvents, dispersion media, coatings, isotonic and absorption delaying agents, and the like, that are compatible with pharmaceutical administration. The use of such media and agents for pharmaceutically active substances is well known in the art. The compositions may also contain other active compounds providing supplemental, additional, or enhanced therapeutic functions.

The term "pharmaceutical composition" as used herein refers to a composition comprising at least one compound as disclosed herein formulated together with one or more pharmaceutically acceptable excipients.

"Individual," "patient," or "subject" are used interchangeably and include any animal, including mammals, preferably mice, rats, other rodents, rabbits, dogs, cats, swine, cattle, sheep, horses, or primates, and most preferably humans. The compounds or pharmaceutical compositions of the disclosure can be administered to a mammal, such as a human, but can also be administered to other mammals such as an animal in need of veterinary treatment, e.g., domestic animals (e.g., dogs, cats, and the like), farm animals (e.g., cows, sheep, pigs, horses, and the like) and laboratory animals (e.g., rats, mice, guinea pigs, and the like). The mammal treated in the methods of the disclosure is desirably a mammal in which treatment of HBV infection is desired. "Modulation" includes antagonism (e.g., inhibition), agonism, partial antagonism and/or partial agonism.

The term "therapeutically effective amount" or "effective amount" as used herein refers to the amount of the subject compound that will elicit the biological or medical response of a tissue, system or animal, (e.g. mammal or human) that is being sought by the researcher, veterinarian, medical doctor or other clinician. The compounds or pharmaceutical compositions of the disclosure are administered in therapeutically effective amounts to treat a disease. Alternatively, a therapeutically effective amount of a compound is the quantity required to achieve a desired therapeutic and/or prophylactic effect.

The term "pharmaceutically acceptable salt(s)" as used herein refers to salts of acidic or basic groups that may be present in compounds used in the compositions. Compounds included in the present compositions that are basic in nature are capable of forming a wide variety of salts with various inorganic and organic acids. The acids that may be used to prepare pharmaceutically acceptable acid addition salts of such basic compounds are those that form non-toxic acid addition salts, i.e., salts containing pharmacologically acceptable anions, including, but not limited to, malate, oxalate, chloride, bromide, iodide, nitrate, sulfate, bisulfate, phosphate, acid phosphate, isonicotinate, acetate, lactate, salicylate, citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)) salts. Compounds included in the present compositions that are acidic in nature are capable of forming base salts with various pharmacologically acceptable cations. Examples of such salts include alkali metal or alkaline earth metal salts, particularly calcium, magnesium, sodium, lithium, zinc, potassium, and iron salts. Compounds included in the present compositions that include a basic or acidic moiety may also form pharmaceutically acceptable salts with various amino acids. The compounds of the disclosure may contain both acidic and basic groups; for example, one amino and one carboxylic acid group. In such a case, the compound can exist as an acid addition salt, a zwitterion, or a base salt.

The compounds of the disclosure may contain one or more chiral centers and, therefore, exist as stereoisomers. The term "stereoisomers" when used herein consist of all enantiomers or diastereomers. These compounds may be designated by the symbols "(+)," "(−)," "R" or "S," depending on the configuration of substituents around the stereogenic carbon atom, but the skilled artisan will recognize that a structure may denote a chiral center implicitly. The present disclosure encompasses various stereoisomers of these compounds and mixtures thereof. Mixtures of enantiomers or diastereomers may be designated "(±)" in nomenclature, but the skilled artisan will recognize that a structure may denote a chiral center implicitly.

The compounds of the disclosure may contain one or more double bonds and, therefore, exist as geometric isomers resulting from the arrangement of substituents around a carbon-carbon double bond. The symbol $\rightleftharpoons$ denotes a bond that may be a single, double or triple bond as described herein. Substituents around a carbon-carbon double bond are designated as being in the "Z" or "E" configuration wherein the terms "Z" and "E" are used in accordance with IUPAC standards. Unless otherwise specified, structures depicting double bonds encompass both the "E" and "Z" isomers. Substituents around a carbon-carbon double bond alternatively can be referred to as "cis" or "trans," where "cis" represents substituents on the same side of the double bond and "trans" represents substituents on opposite sides of the double bond.

Compounds of the disclosure may contain a carbocyclic or heterocyclic ring and therefore, exist as geometric isomers resulting from the arrangement of substituents around the ring. The arrangement of substituents around a carbocyclic or heterocyclic ring are designated as being in the "Z" or "E" configuration wherein the terms "Z" and "E" are used in accordance with IUPAC standards. Unless otherwise specified, structures depicting carbocyclic or heterocyclic rings encompass both "Z" and "E" isomers. Substituents around a carbocyclic or heterocyclic rings may also be referred to as "cis" or "trans", where the term "cis" represents substituents on the same side of the plane of the ring and the term "trans" represents substituents on opposite sides of the plane of the ring. Mixtures of compounds wherein the substituents are disposed on both the same and opposite sides of plane of the ring are designated "cis/trans." Individual enantiomers and diastereomers of compounds of the present disclosure can be prepared synthetically from commercially available starting materials that contain asymmetric or stereogenic centers, or by preparation of racemic mixtures followed by resolution methods well known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary, (2) salt formation employing an optically active resolving agent, (3) direct separation of the mixture of optical enantiomers on chiral liquid chromatographic columns or (4) kinetic resolution using stereoselective chemical or enzymatic reagents. Racemic mixtures can also be resolved into their component enantiomers by well known methods, such as chiral-phase liquid chromatography or crystallizing the compound in a chiral solvent. Stereoselective syntheses, a chemical or enzymatic reaction in which a single reactant forms an unequal mixture of stereoisomers during the creation of a new stereocenter or during the transformation of a pre-existing one, are well known in the art. Stereoselective syntheses encompass both enantio- and diastereoselective transformations, and may involve the use of chiral auxiliaries. For examples, see Carreira and Kvaerno, *Classics in Stereoselective Synthesis*, Wiley-VCH: Weinheim, 2009.

The compounds disclosed herein can exist in solvated as well as unsolvated forms with pharmaceutically acceptable solvents such as water, ethanol, and the like, and it is intended that the disclosure embrace both solvated and unsolvated forms. In one embodiment, the compound is amorphous. In one embodiment, the compound is a single polymorph. In another embodiment, the compound is a mixture of polymorphs. In another embodiment, the compound is in a crystalline form.

The disclosure also embraces isotopically labeled compounds of the disclosure which are identical to those recited herein, except that one or more atoms are replaced by an atom having an atomic mass or mass number different from the atomic mass or mass number usually found in nature. Examples of isotopes that can be incorporated into compounds of the disclosure include isotopes of hydrogen, carbon, nitrogen, oxygen, phosphorus, sulfur, fluorine and chlorine, such as $^2$H, $^3$H, $^{13}$C, $^{14}$C, $^{15}$N, $^{18}$O, $^{17}$O, $^{31}$P, $^{32}$P, $^{35}$S, $^{18}$F, and $^{36}$Cl, respectively. For example, a compound of the disclosure may have one or more H atom replaced with deuterium.

Certain isotopically-labeled disclosed compounds (e.g., those labeled with $^3$H and $^{14}$C) are useful in compound and/or substrate tissue distribution assays. Tritiated (i.e., $^3$H) and carbon-14 (i.e., $^{14}$C) isotopes are particularly preferred for their ease of preparation and detectability. Further, substitution with heavier isotopes such as deuterium (i.e., $^2$H) may afford certain therapeutic advantages resulting from greater metabolic stability (e.g., increased in vivo half-life or reduced dosage requirements) and hence may be preferred in some circumstances. Isotopically labeled compounds of the disclosure can generally be prepared by following procedures analogous to those disclosed in the examples herein by substituting an isotopically labeled reagent for a non-isotopically labeled reagent.

The term "prodrug" refers to compounds that are transformed in vivo to yield a disclosed compound or a pharmaceutically acceptable salt, hydrate or solvate of the compound. The transformation may occur by various mechanisms (such as by esterase, amidase, phosphatase, oxidative and or reductive metabolism) in various locations (such as in the intestinal lumen or upon transit of the intestine, blood or liver). Prodrugs are well known in the art (for example, see Rautio, Kumpulainen, et al, Nature Reviews Drug Discovery 2008, 7, 255). For example, if a compound of the disclosure or a pharmaceutically acceptable salt, hydrate or solvate of the compound contains a carboxylic acid functional group, a prodrug can comprise an ester formed by the replacement of the hydrogen atom of the acid group with a group such as (C$_{1-8}$)alkyl, (C$_{2-12}$)alkylcarbonyloxymethyl, 1-(alkylcarbonyloxy)ethyl having from 4 to 9 carbon atoms, 1-methyl-1-(alkylcarbonyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—(C$_{1-2}$)alkylamino(C$_{2-3}$)alkyl (such as β-dimethylaminoethyl), carbamoyl-(C$_{1-2}$)alkyl, N,N-di(C$_{1-2}$)alkylcarbamoyl-(C$_{1-2}$)alkyl and piperidino-, pyrrolidino- or morpholino(C$_{2-3}$)alkyl.

I. Cyclic Sulfamide Compounds

In one aspect, the disclosure provides a compound of Formula I:

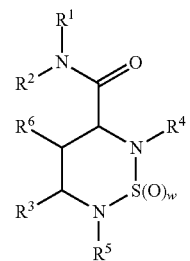

Formula I or a pharmaceutically acceptable salt thereof, wherein:

R$^1$ is selected from the group consisting of phenyl, naphthyl, and 5-6 membered monocyclic or 8-12 membered bicyclic heteroaryl having one, two, or three heteroatoms each selected from O, N, and S, wherein the phenyl, naphthyl, and heteroaryl may be optionally substituted with one, two, or three substituents independently selected from the group consisting of halogen, —OH, —CN, —S(O)$_q$—C$_{1-6}$alkyl, —NR$^a$R$^b$, —NR$^c$—S(O)$_t$—C$_{1-6}$alkyl, —S(O)$_t$—NR$^a$R$^b$, C$_{1-6}$alkyl, C$_{2-6}$alkenyl, C$_{2-6}$alkynyl, haloC$_{1-6}$alkyl, C$_{1-6}$alkoxy, haloC$_{1-6}$alkoxy, —C(O)NR$^a$R$^b$, —C(O)—C$_{1-6}$alkyl, —C(O)OH, and —C(O)O—C$_{1-6}$alkyl, wherein q is 0, 1, or 2, wherein t is 1 or 2;

R$^2$ is hydrogen or C$_{1-6}$alkyl;

R$^3$ is selected from the group consisting of 5-6 membered monocyclic or 8-12 membered bicyclic heteroaryl having one, two, or three heteroatoms selected from the group consisting of O, N, and S; phenyl; C$_{1-6}$alkyl; and C$_{3-6}$cycloalkyl, wherein the heteroaryl, phenyl, C$_{1-6}$alkyl, and C$_{3-6}$cycloalkyl may be optionally substituted with one or two substituents independently selected from the group consisting of: halogen, —OH, —CN, —S(O)$_q$—C$_{1-6}$alkyl, —NR$^a$R$^b$, —NR$^c$—S(O)$_t$—C$_{1-6}$alkyl, —S(O)$_t$—NR$^a$R$^b$, C$_{1-6}$alkyl, C$_{2-6}$alkenyl, C$_{2-6}$alkynyl, C$_{1-6}$haloalkyl, C$_{1-6}$alkoxy, haloC$_{1-6}$alkoxy, —C(O)NR$^a$R$^b$, —C(O)—C$_{1-6}$alkyl, —C(O)OH, —C(O)O—C$_{1-6}$alkyl, R$^a$R$^b$N—C$_{1-4}$alkoxy, benzyl, thienyl, thiazolyl, pyrazolyl, imidazolyl, triazolyl, phenyl, pyridyl, and pyrimidinyl, wherein the thienyl, thiazolyl, pyrazolyl, imidazolyl, triazolyl, phenyl, pyridyl and pyrimidinyl are optionally substituted with one, two or three substituents independently selected from the group consisting of: halo, C$_{1-4}$alkyl, haloC$_{1-4}$alkyl, hydroxyC$_{1-4}$alkyl, C$_{1-4}$alkoxy and C$_{1-4}$alkylsulfonylamino, wherein q is 0, 1, or 2, wherein t is 1 or 2;

R$^4$ is hydrogen or C$_{1-6}$alkyl optionally substituted with one, two, or three substituents independently selected from the group consisting of halogen, —OH, —CN, —S(O)$_q$—C$_{1-6}$alkyl, —NR$^a$R$^b$, —NR$^c$—S(O)$_t$—C$_{1-6}$alkyl, —S(O)$_t$—NR$^a$R$^b$, C$_{2-6}$alkenyl, C$_{2-6}$alkynyl, C$_{1-6}$ haloalkyl, C$_{1-6}$alkoxy, haloC$_{1-6}$alkoxy, —C(O)NR$^a$R$^b$, —C(O)—C$_{1-6}$alkyl, formyl, —C(O)OH, a-C(O)O—C$_{1-6}$alkyl, benzyloxy, C$_{1-4}$alkoxyphenyl, pyrrolidinyl, morpholinyl, tetrahydrofuranyl and triazolyl, wherein q is 0, 1, or 2, wherein t is 1 or 2;

R$^5$ is hydrogen or C$_{1-6}$alkyl optionally substituted with a substituent selected from the group consisting of halogen, —OH, C$_{1-6}$alkoxy, —NR$^a$R$^b$, and R$^a$R$^b$N—C$_{1-4}$alkyl;

R$^6$ is hydrogen or C$_{1-6}$alkyl;

R$^a$ and R$^b$ are independently hydrogen or C$_{1-6}$alkyl; or

R$^a$ and R$^b$ may be taken together with the nitrogen to which R$^a$ and R$^b$ are attached to form:

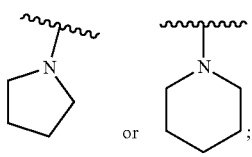 [SMILES: *N1CCCC1 ; *N1CCCCC1]

$R^c$ is hydrogen or $C_{1-6}$alkyl; and
w is 1 or 2.

In certain embodiments, $R^3$ is a 5-6 membered monocyclic heteroaryl having one, two, or three heteroatoms selected from the group consisting of O, N and S, optionally substituted with one, two, or three substituents independently selected from the group consisting of: halogen, —OH, —CN, —S(O)$_q$—C$_{1-6}$alkyl, —NR$^a$R$^b$, —NR$^c$—S(O)$_t$—C$_{1-6}$alkyl, —S(O)$_t$—NR$^a$R$^b$, C$_{1-6}$alkyl, C$_{2-6}$alkenyl, C$_{2-6}$alkynyl, haloC$_{1-6}$alkyl, C$_{1-6}$alkoxy, haloC$_{1-6}$alkoxy, —C(O)NR$^a$R$^b$, —C(O)—C$_{1-6}$alkyl, —C(O)OH, —C(O)O—C$_{1-6}$alkyl, R$^a$R$^b$N—C$_{1-4}$alkoxy, benzyl, thienyl, thiazolyl, pyrazolyl, imidazolyl, triazolyl, phenyl, pyridyl, and pyrimidinyl, wherein the thienyl, thiazolyl, pyrazolyl, imidazolyl, triazolyl, phenyl, pyridyl and pyrimidinyl are optionally substituted with one or two substituents independently selected from the group consisting of: halo, C$_{1-4}$alkyl, haloC$_{1-4}$alkyl, hydroxyC$_{1-4}$alkyl, C$_{1-4}$alkoxy and C$_{1-4}$alkylsulfonylamino.

In certain embodiments, $R^3$ is furanyl, thienyl, pyrazolyl, isoxazolyl, thiazolyl, isothiazolyl, or 1,3,4-thiadiazolyl, each of which is optionally substituted with one or two substituents independently selected from the group consisting of: halo, C$_{1-4}$alkyl, haloC$_{1-4}$alkyl, C$_{1-4}$alkoxy, R$^a$R$^b$N—C$_{1-4}$alkoxy, benzyl, thienyl, thiazolyl, pyrazolyl optionally substituted with C$_{1-4}$alkyl or hydroxyC$_{1-4}$alkyl, imidazolyl optionally substituted with C$_{1-4}$ alkyl, triazolyl optionally substituted with C$_{1-4}$alkyl, phenyl, pyridyl, and pyrimidinyl, wherein the phenyl, pyridyl and pyrimidinyl are optionally substituted with one or two substituents independently selected from the group consisting of: halo, C$_{1-4}$alkyl, haloC$_{1-4}$ alkyl, C$_{1-4}$alkoxy, and C$_{1-4}$alkylsulfonylamino.

In certain embodiments, $R^3$ is selected from the group consisting of:

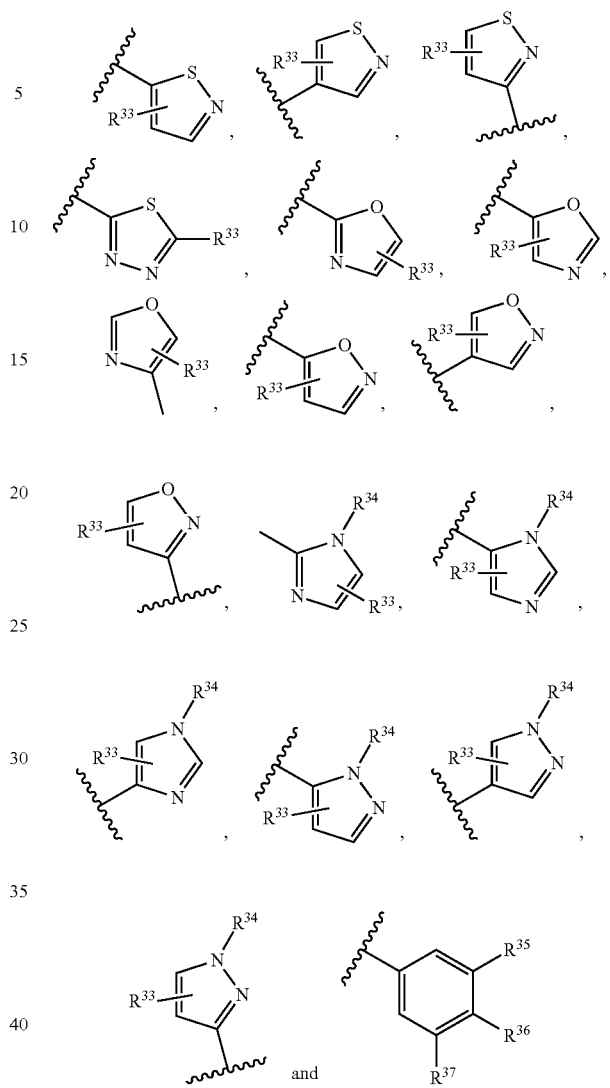

wherein:

$R^{33}$ is selected from the group consisting of: hydrogen, halo, C$_{1-4}$alkyl, haloC$_{1-4}$ alkyl, C$_{1-4}$alkoxy, R$^a$R$^b$N—C$_{1-4}$alkoxy, benzyl, thienyl, thiazolyl, pyrazolyl optionally substituted with C$_{1-4}$alkyl, imidazolyl optionally substituted with C$_{1-4}$alkyl, triazolyl optionally substituted with C$_{1-4}$alkyl, phenyl, pyridyl, and pyrimidinyl, wherein the phenyl, pyridyl and pyrimidinyl are optionally substituted with one or two substituents independently selected from the group consisting of halo, C$_{1-4}$alkyl, haloC$_{1-4}$alkyl, C$_{1-4}$alkoxy, and C$_{1-4}$ alkylsulfonylamino;

$R^{33a}$ is hydrogen, halo or C$_{1-4}$alkyl;

$R^{34}$ is selected from the group consisting of hydrogen and C$_{1-4}$alkyl; and $R^{35}$, $R^{36}$ and $R^{37}$ are independently selected from the group consisting of hydrogen, halo, hydroxy, cyano, carboxy, carbamoyl, haloC$_{1-4}$alkyl, C$_{1-4}$alkoxy, haloC$_{1-4}$alkoxy, carboxyC$_{1-4}$alkoxy, R$^a$R$^b$N—C$_{1-4}$alkoxy, C$_{1-4}$alkoxycarbonyl, thienyl, thiazolyl, pyrazolyl optionally substituted with C$_{1-4}$alkyl, and imidazolyl optionally substituted with C$_{1-4}$ alkyl.

In certain embodiments, $R^3$ is

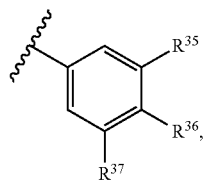

wherein $R^{35}$, $R^{36}$ and $R^{37}$ are independently selected from the group consisting of hydrogen, halo, hydroxy, cyano, carboxy, carbamoyl, haloC$_{1-4}$alkyl, C$_{1-4}$alkoxy, haloC$_{1-4}$alkoxy, carboxyC$_{1-4}$alkoxy, R$^a$R$^b$N—C$_{1-4}$alkoxy, C$_{1-4}$alkoxycarbonyl, thienyl, thiazolyl, pyrazolyl optionally substituted with C$_{1-4}$alkyl, and imidazolyl optionally substituted with C$_{1-4}$ alkyl.

In certain embodiments, $R^3$ is

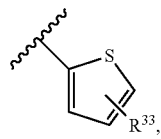

wherein $R^{33}$ is selected from the group consisting of: hydrogen, halo, C$_{1-4}$alkyl, haloC$_{1-4}$alkyl, C$_{1-4}$alkoxy, R$^a$R$^b$N—C$_{1-4}$alkoxy, benzyl, thienyl, thiazolyl, pyrazolyl optionally substituted with C$_{1-4}$alkyl or hydroxyC$_{1-4}$alkyl, imidazolyl optionally substituted with C$_{1-4}$alkyl, phenyl, pyridyl, and pyrimidinyl, wherein the phenyl, pyridyl and pyrimidinyl are optionally substituted with one or two substituents independently selected from the group consisting of halo, C$_{1-4}$alkyl, haloC$_{1-4}$alkyl, C$_{1-4}$alkoxy, and C$_{1-4}$alkylsulfonylamino.

In certain embodiments, $R^3$ is:

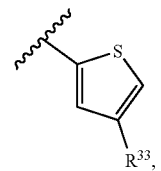

wherein $R^{33}$ is selected from the group consisting of: hydrogen, halo, C$_{1-4}$alkyl, haloC$_{1-4}$alkyl, C$_{1-4}$alkoxy, R$^a$R$^b$N—C$_{1-4}$alkoxy, benzyl, thienyl, thiazolyl, pyrazolyl optionally substituted with C$_{1-4}$alkyl or hydroxyC$_{1-4}$alkyl, imidazolyl optionally substituted with C$_{1-4}$alkyl, phenyl, pyridyl, and pyrimidinyl, wherein the phenyl, pyridyl and pyrimidinyl are optionally substituted with one or two substituents independently selected from the group consisting of halo, C$_{1-4}$alkyl, haloC$_{1-4}$alkyl, C$_{1-4}$alkoxy, and C$_{1-4}$alkylsulfonylamino.

In certain embodiments, $R^3$ is:

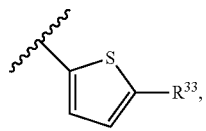

wherein $R^{33}$ is selected from the group consisting of: hydrogen, halo, C$_{1-4}$ alkyl, haloC$_{1-4}$alkyl, C$_{1-4}$alkoxy, R$^a$R$^b$N—C$_{1-4}$alkoxy, benzyl, thienyl, thiazolyl, pyrazolyl optionally substituted with C$_{1-4}$alkyl or hydroxyC$_{1-4}$alkyl, imidazolyl optionally substituted with C$_{1-4}$alkyl, phenyl, pyridyl, and pyrimidinyl, wherein the phenyl, pyridyl and pyrimidinyl are optionally substituted with one or two substituents independently selected from the group consisting of halo, C$_{1-4}$alkyl, haloC$_{1-4}$alkyl, C$_{1-4}$alkoxy, and C$_{1-4}$alkylsulfonylamino.

In certain embodiments, $R^3$ is:

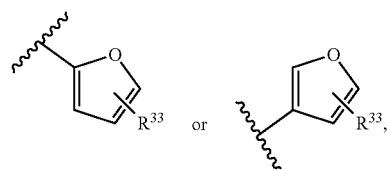

wherein: $R^{33}$ is selected from the group consisting of: hydrogen, halo, C$_{1-4}$alkyl, haloC$_{1-4}$alkyl, C$_{1-4}$alkoxy, R$^a$R$^b$N—C$_{1-4}$alkoxy, benzyl, thienyl, pyrazolyl optionally substituted with C$_{1-4}$alkyl, imidazolyl optionally substituted with C$_{1-4}$alkyl, phenyl, pyridyl, and pyrimidinyl, wherein the phenyl, pyridyl and pyrimidinyl are optionally substituted with one or two substituents independently selected from the group consisting of halo, C$_{1-4}$alkyl, haloC$_{1-4}$alkyl, C$_{1-4}$alkoxy, and C$_{1-4}$alkylsulfonylamino.

In certain embodiments, $R^3$ is:

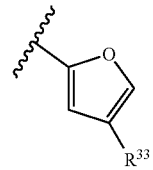

wherein: $R^{33}$ is selected from the group consisting of: hydrogen, halo, C$_{1-4}$alkyl, haloC$_{1-4}$alkyl, C$_{1-4}$alkoxy, R$^a$R$^b$N—C$_{1-4}$alkoxy, benzyl, thienyl, thiazolyl, pyrazolyl optionally substituted with C$_{1-4}$alkyl, imidazolyl optionally substituted with C$_{1-4}$alkyl, phenyl, pyridyl, and pyrimidinyl, wherein the phenyl, pyridyl and pyrimidinyl are optionally substituted with one or two substituents independently selected from the group consisting of halo, C$_{1-4}$alkyl, haloC$_{1-4}$alkyl, C$_{1-4}$alkoxy, and C$_{1-4}$alkylsulfonylamino.

In certain embodiments, $R^3$ is:

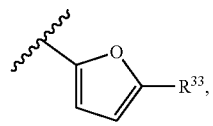

wherein: $R^{33}$ is selected from the group consisting of hydrogen, halo, C$_{1-4}$ alkyl, haloC$_{1-4}$alkyl, C$_{1-4}$alkoxy, R$^a$R$^b$N—C$_{1-4}$alkoxy, benzyl, thienyl, thiazolyl, pyrazolyl optionally substituted with C$_{1-4}$alkyl, imidazolyl optionally substituted with C$_{1-4}$alkyl, phenyl, pyridyl, and pyrimidinyl, wherein the phenyl, pyridyl and pyrimidinyl are optionally substituted with one or two substituents independently selected from the group consisting of halo, $C_{1-4}$alkyl, halo$C_{1-4}$alkyl, $C_{1-4}$alkoxy, and $C_{1-4}$alkylsulfonylamino.

In certain embodiments:
w is 2;
$R^1$ is phenyl optionally substituted with one to three substituents independently selected from the group consisting of halo, cyano, $C_{1-4}$alkyl and halo$C_{1-4}$alkyl;
$R^2$ is hydrogen;
$R^3$ is $C_{1-4}$alkyl, $C_{3-6}$cycloalkyl,
furanyl, thienyl, thiazolyl, pyrazolyl, imidazolyl, isoxazolyl, thiazolyl, isothiazolyl, or 1,3,4-thiadiazolyl, each of which is optionally substituted with one or two substituents independently selected from the group consisting of: halo, $C_{1-4}$alkyl, halo$C_{1-4}$ alkyl, $C_{1-4}$alkoxy, $R^aR^bN$—$C_{1-4}$alkoxy, thienyl, thiazolyl, pyrazolyl optionally substituted with one two or three substituents independently selected from $C_{1-4}$alkyl and hydroxy$C_{1-4}$alkyl, imidazolyl optionally substituted with $C_{1-4}$alkyl, triazolyl optionally substituted with $C_{1-4}$ alkyl, benzyl, phenyl, pyridyl, and pyrimidinyl, wherein the phenyl, pyridyl and pyrimidinyl are optionally substituted with one or two substituents independently selected from the group consisting of halo, $C_{1-4}$alkyl, halo$C_{1-4}$alkyl, $C_{1-4}$alkoxy, and $C_{1-4}$alkylsulfonylamino,
phenyl or pyridinyl, each of which is optionally substituted with one, two or three substituents independently selected from the group consisting of halo, hydroxy, cyano, carboxy, carbamoyl, halo$C_{1-4}$alkyl, $C_{1-4}$alkoxy, halo$C_{1-4}$alkoxy, carboxy$C_{1-4}$alkoxy, $R^aR^bN$—$C_{1-4}$alkoxy, 1-methylpyrazolyl, $C_{1-4}$alkoxycarbonyl, thienyl, thiazolyl, pyrazolyl optionally substituted with $C_{1-4}$alkyl, and imidazolyl optionally substituted with $C_{1-4}$alkyl;
$R^4$ is hydrogen, $C_{2-6}$alkenyl, $C_{2-6}$alkynyl, $C_{1-4}$alkyl optionally substituted with hydroxy, cyano, $C_{1-4}$alkoxy, halo$C_{1-4}$alkoxy, $C_{1-4}$alkylsulfonyl, $R^aR^bN$—, formyl carboxy, carbamoyl, benzyloxy, $C_{1-4}$alkoxyphenyl, pyrrolidinyl, morpholinyl, tetrahydrofuranyl or triazolyl;
$R^5$ is hydrogen, $C_{1-4}$alkyl, $C_{1-4}$alkoxy, or $R^aR^bN$—$C_{1-4}$alkyl;
$R^6$ is hydrogen; and
$R^a$ and $R^b$ are independently hydrogen or $C_{1-4}$alkyl.

In certain embodiments:
w is 2;
$R^1$ is phenyl optionally substituted with one to three substituents independently selected from the group consisting of halo, cyano, $C_{1-4}$alkyl and halo$C_{1-4}$alkyl;
$R^2$ is hydrogen;
$R^3$ is furanyl, thienyl, or thiazolyl, each of which is optionally substituted with one or two substituents independently selected from the group consisting of: halo, $C_{1-4}$alkyl, halo$C_{1-4}$alkyl, $C_{1-4}$alkoxy, $R^aR^bN$—$C_{1-4}$alkoxy, thienyl, thiazolyl, pyrazolyl optionally substituted with $C_{1-4}$alkyl or hydroxC$_{1-4}$alkyl, imidazolyl optionally substituted with $C_{1-4}$alkyl, benzyl, phenyl, pyridyl, and pyrimidinyl, wherein the phenyl, pyridyl and pyrimidinyl are optionally substituted with one or two substituents independently selected from the group consisting of halo, $C_{1-4}$alkyl, halo$C_{1-4}$alkyl, $C_{1-4}$alkoxy and $C_{1-4}$alkylsulfonylamino,
phenyl or pyridinyl, each or which is optionally substituted with one to three substituents independently selected from the group consisting of halo, hydroxy, cyano, carboxy, carbamoyl, halo$C_{1-4}$alkyl, $C_{1-4}$alkoxy, halo$C_{1-4}$alkoxy, carboxy$C_{1-4}$alkoxy, $R^aR^bN$—$C_{1-4}$alkoxy, $C_{1-4}$alkoxycarbonyl, thienyl, thiazolyl, pyrazolyl optionally substituted with $C_{1-4}$ alkyl, and imidazolyl optionally substituted with $C_{1-4}$alkyl;
$R^4$ is hydrogen, $C_{2-6}$alkenyl, $C_{2-6}$alkynyl, $C_{1-4}$alkyl optionally substituted with hydroxy, cyano, $C_{1-4}$alkoxy, halo$C_{1-4}$alkoxy, $C_{1-4}$alkylsulfonyl, $R^aR^bN$—, carboxy, carbamoyl, benzyloxy, formyl, $C_{1-4}$alkoxyphenyl, pyrrolidinyl, morpholinyl, tetrahydrofuranyl or triazolyl;
$R^5$ is hydrogen, $C_{1-4}$alkyl, $C_{1-4}$alkoxy, or $R^aR^bN$—$C_{1-4}$alkyl;
$R^6$ is hydrogen; and
$R^a$ and $R^b$ are independently hydrogen or $C_{1-4}$alkyl.

In certain embodiments:
w is 2;
$R^1$ is phenyl optionally substituted with one to three substituents independently selected from the group consisting of halo, cyano, $C_{1-4}$alkyl and halo$C_{1-4}$alkyl;
$R^2$ is hydrogen;
$R^3$ is $C_{1-4}$alkyl, $C_{3-6}$cycloalkyl,
furanyl, isoxazolyl, isothiazolyl, pyrazolyl, pyridinyl or 1,3,4-thiadiazolyl, each of which is optionally substituted with halo, $C_{1-4}$alkyl or phenyl,
thiazolyl optionally substituted with one or two substituents independently selected from the group consisting of: halo, $C_{1-4}$alkyl, halo$C_{1-4}$alkyl, thienyl, thiazolyl, pyrazolyl, 1-methylpyrazolyl, pyridinyl optionally substituted with halo, and phenyl optionally substituted with one or two substituents independently selected from the group consisting of halo and $C_{1-4}$alkoxy,
thienyl optionally substituted with one or two substituents independently selected from the group consisting of: halo, $C_{1-4}$alkyl, $R^aR^bN$—$C_{1-4}$alkoxy, thienyl, pyrimidinyl, pyrazolyl, 1-methylpyrazolyl, benzyl, pyridinyl optionally substituted with halo or halo$C_{1-4}$alkyl, and phenyl optionally substituted with one or two substituents independently selected from the group consisting of halo, cyano, $C_{1-4}$alkoxy, halo$C_{1-4}$alkyl and $C_{1-4}$ alkylsulfonylamino, or
phenyl optionally substituted with one to three substituents independently selected from the group consisting of: halo, hydroxy, cyano, carboxy, carbamoyl, halo$C_{1-4}$alkyl, $C_{1-4}$ alkoxy, halo$C_{1-4}$alkoxy, carboxy$C_{1-4}$alkoxy, $R^aR^bN$—$C_{1-4}$alkoxy, 1-methylpyrazolyl and $C_{1-4}$alkoxycarbonyl;
$R^4$ is hydrogen, $C_{2-6}$alkenyl, $C_{2-6}$alkynyl, $C_{1-4}$alkyl optionally substituted with hydroxy, cyano, $C_{1-4}$alkoxy, halo$C_{1-4}$alkoxy, $C_{1-4}$alkylsulfonyl, $R^aR^bN$—, carboxy, carbamoyl, benzyloxy, formyl, $C_{1-4}$alkoxyphenyl, pyrrolidinyl, morpholinyl, tetrahydrofuranyl or triazolyl;
$R^5$ is hydrogen, $C_{1-4}$alkyl, $C_{1-4}$alkoxy, or $R^aR^bN$—$C_{1-4}$alkyl;
$R^6$ is hydrogen; and
$R^a$ and $R^b$ are independently hydrogen or $C_{1-4}$alkyl.

In certain embodiments, $R^3$ is $C_{1-6}$alkyl or $C_{3-6}$cycloalkyl, wherein the $C_{1-6}$alkyl or $C_{3-6}$cycloalkyl is optionally substituted with one, two, or three substituents independently selected from the group consisting of: halogen, —OH, —CN, —S(O)$_q$—$C_{1-6}$alkyl, —NR$^a$R$^b$, —NR$^c$—S(O)$_t$—$C_{1-6}$alkyl, —S(O)$_t$—NR$^a$R$^b$, $C_{1-6}$alkyl, $C_{2-6}$alkenyl, $C_{2-6}$alkynyl, $C_{1-6}$haloalkyl, $C_{1-6}$alkoxy, $C_{1-6}$haloalkoxy, —C(O)NR$^a$R$^b$, —C(O)—$C_{1-6}$alkyl, —C(O)OH, —C(O)O—$C_{1-6}$alkyl, $R^aR^bN$—$C_{1-4}$ alkoxy, benzyl, thienyl, thiazolyl, pyrazolyl, imidazolyl, triazolyl, phenyl, pyridyl, and pyrimidinyl, wherein the thienyl, thiazolyl, pyrazolyl, imidazolyl, triazolyl, phenyl, pyridyl and pyrimidinyl are optionally substituted with one or two substituents independently selected from the group consisting of: halo, $C_{1-4}$alkyl, halo$C_{1-4}$alkyl, hydroxy$C_{1-4}$alkyl, $C_{1-4}$ alkoxy and $C_{1-4}$alkylsulfonylamino, wherein q is 0, 1, or 2, and wherein t is 1 or 2.

In certain embodiments, $R^3$ is $C_{1-6}$alkyl or $C_{3-6}$cycloalkyl.

In another aspect, the disclosure provides a compound of Formula I:

Formula I

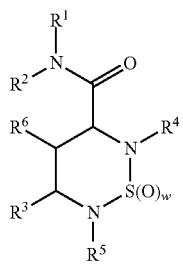

or a pharmaceutically acceptable salt thereof, wherein:

$R^1$ is selected from the group consisting of phenyl, naphthyl, and 5-6 membered monocyclic or 8-12 membered bicyclic heteroaryl having one, two, or three heteroatoms each selected from O, N, and S, wherein the phenyl, naphthyl, and heteroaryl may be optionally substituted with one, two, or three substituents independently selected from the group consisting of: halo, —OH, —CN, —NO$_2$, oxo, hydrazino, formyl, azido, silyl, siloxy, —S(O)$_q$—C$_{1-6}$ alkyl, —NR$^a$R$^b$, —NR$^c$—S(O)$_t$—C$_{1-6}$alkyl, —S(O)$_t$—NR$^a$R$^b$, C$_{1-6}$alkyl, C$_{2-6}$alkenyl, C$_{2-6}$alkynyl, C$_{3-6}$ cycloalkyl, haloC$_{1-6}$alkyl, hydroxyC$_{1-6}$alkyl, R$^a$R$^b$N—C$_{1-6}$alkyl-, C$_{1-6}$alkoxy, haloC$_{1-6}$alkoxy, hydroxyC$_{1-6}$alkoxy-, R$^a$R$^b$N—C$_{1-6}$alkoxy-, C$_{1-6}$alkoxyC$_{1-6}$alkyl, —C(O)NR$^a$R$^b$, —C(O)—C$_{1-6}$alkyl, —C(O)OH, and —C(O)O—C$_{1-6}$alkyl;

$R^2$ is hydrogen or C$_{1-6}$alkyl optionally substituted with a substituent selected from the group consisting of halogen, —OH, C$_{1-6}$alkoxy, —NR$^a$R$^b$, and R$^a$R$^b$N—C$_{1-6}$alkyl;

$R^3$ is selected from the group consisting of 5-6 membered monocyclic or 8-12 membered bicyclic heteroaryl having one, two, or three heteroatoms selected from the group consisting of O, N, and S; phenyl; C$_{1-6}$alkyl; and C$_{3-6}$cycloalkyl, wherein the heteroaryl, phenyl, C$_{1-6}$alkyl, and C$_{3-6}$cycloalkyl are optionally substituted with one, two or three substituents independently selected from the group consisting of: halo, —OH, —CN, —NO$_2$, oxo, hydrazino, formyl, azido, silyl, siloxy, —S(O)$_q$—C$_{1-6}$alkyl, —NR$^a$R$^b$, —NR$^c$—S(O)$_t$—C$_{1-6}$alkyl, —S(O)$_t$—NR$^a$R$^b$, C$_{1-6}$alkyl, C$_{2-6}$alkenyl, C$_{2-6}$alkynyl, C$_{3-6}$cycloalkyl, haloC$_{1-6}$alkyl, hydroxyC$_{1-6}$ alkyl, R$^a$R$^b$N—C$_{1-6}$alkyl-, C$_{1-6}$alkoxy, haloC$_{1-6}$alkoxy, hydroxyC$_{1-6}$alkoxy-, R$^a$R$^b$N—C$_{1-6}$alkoxy-, C$_{1-6}$alkoxyC$_{1-6}$alkyl, —C(O)NR$^a$R$^b$, —C(O)—C$_{1-6}$alkyl, —C(O)OH, and —C(O)O—C$_{1-6}$alkyl, phenyl, and a 5-6 membered monocyclic heteroaryl having one, two or three heteroatoms selected from the group consisting of O, N, and S, wherein the phenyl or 5-6 membered monocyclic heteroaryl is optionally substituted with one, two or three substituents independently selected from the group consisting of halo, —OH, —CN, —NO$_2$, oxo, hydrazino, formyl, azido, silyl, siloxy, —S(O)$_q$—C$_{1-6}$alkyl, —NR$^a$R$^b$, —NR$^c$—S(O)$_t$—C$_{1-6}$alkyl, —S(O)$_t$—NR$^a$R$^b$ C$_{1-6}$alkyl, C$_{2-6}$alkenyl, C$_{2-6}$alkynyl, C$_{3-6}$cycloalkyl, haloC$_{1-6}$alkyl, hydroxyC$_{1-6}$alkyl, R$^a$R$^b$N—C$_{1-6}$alkyl-, C$_{1-6}$alkoxy, haloC$_{1-6}$alkoxy, hydroxyC$_{1-6}$alkoxy-, R$^a$R$^b$N—C$_{1-6}$alkoxy-, C$_{1-6}$ alkoxyC$_{1-6}$alkyl, —C(O)NR$^a$R$^b$, —C(O)—C$_{1-6}$alkyl, —C(O)OH, and —C(O)O—C$_{1-6}$alkyl;

$R^4$ is hydrogen or C$_{1-6}$alkyl optionally substituted with one, two or three substituents independently selected from the group consisting of halogen, —OH, —CN, —S(O)$_q$—C$_{1-6}$alkyl, —NR$^a$R$^b$, —NR$^c$—S(O)$_t$—C$_{1-6}$alkyl, —S(O)$_t$—NR$^a$R$^b$, C$_{2-6}$alkenyl, C$_{2-6}$alkynyl, haloC$_{1-6}$alkyl, C$_{1-6}$alkoxy, haloC$_{1-6}$alkoxy, —C(O)NR$^a$R$^b$, —C(O)—C$_{1-6}$alkyl, formyl, —C(O)OH, a-C(O)O—C$_{1-6}$alkyl, benzyloxy, C$_{1-4}$alkoxyphenyl, pyrrolidinyl, morpholinyl, tetrahydrofuranyl and triazolyl;

$R^5$ is hydrogen or C$_{1-6}$alkyl optionally substituted with a substituent selected from the group consisting of halogen, —OH, C$_{1-6}$alkoxy, —NR$^a$R$^b$, and R$^a$R$^b$N—C$_{1-6}$alkyl;

$R^6$ is hydrogen, halo, —OH, —CN, —NO$_2$, oxo, hydrazino, formyl, azido, silyl, siloxy, —S(O)$_q$—C$_{1-6}$alkyl, —NR$^a$R$^b$, —NR$^c$—S(O)$_t$—C$_{1-6}$alkyl, —S(O)$_t$—NR$^a$R$^b$, C$_{1-6}$alkyl, C$_{2-6}$alkenyl, C$_{2-6}$alkynyl, C$_{3-6}$cycloalkyl, haloC$_{1-6}$alkyl, hydroxyC$_{1-6}$alkyl, R$^a$R$^b$N—C$_{1-6}$alkyl-, C$_{1-6}$alkoxy, haloC$_{1-6}$alkoxy, hydroxyC$_{1-6}$alkoxy-, R$^a$R$^b$N—C$_{1-6}$alkoxy-, C$_{1-6}$alkoxyC$_{1-6}$alkyl, —C(O)NR$^a$R$^b$, —C(O)—C$_{1-6}$alkyl, —C(O)OH, and —C(O)O—C$_{1-6}$alkyl;

$R^a$ and $R^b$ are independently hydrogen or C$_{1-6}$alkyl; or $R^a$ and $R^b$ may be taken together with the nitrogen to which $R^a$ and $R^b$ are attached to form:

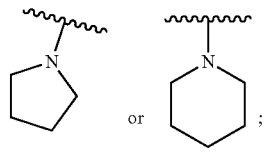 [SMILES: *N1CCCC1 ; *N1CCCCC1]

$R^c$ is hydrogen or C$_{1-6}$alkyl;

for each occurrence, q is 0, 1 or 2;

for each occurrence, t is 1 or 2; and w is 1 or 2;

with the provisos that:

when $R^3$ is thiophen-2-yl or furan-2-yl, the thiophen-2-yl or furan-2-yl is substituted with at least one substituent;

when $R^3$ is pyrazol-4-yl, the pyrazol-4-yl is substituted with at least one substituent other than C$_{1-6}$alkyl; and when $R^3$ is phenyl, the phenyl is substituted with at least one substituent other than halo and C$_{1-6}$alkoxy.

In certain embodiments, the 5-6 membered monocyclic heteroaryl having one, two, or three heteroatoms each selected from O, N, and S, is selected from the group consisting of: furanyl, thienyl, pyrrolyl, thiazolyl, oxazolyl, isothiazolyl, isoxazolyl, imidazolyl, pyrazolyl, 1H-1,2,3-triazolyl, 2H-1,2,3-triazolyl, 1,2,4-triazolyl, pyridinyl pyridazinyl, pyrimidinyl, pyrazinyl, 1,3,5-triazinyl, 1,2,4-triazinyl, 1,2,3-triazinyl, 1,2,4-oxadiazolyl, 1,3,4-oxadiazolyl, 1,2,5-oxadiazolyl, 1,2,4-thiadiazolyl, 1,3,4-thiadiazolyl and 1,2,5-thiadiazolyl.

In certain embodiments, the 8-12 membered bicyclic heteroaryl having one, two, or three heteroatoms each selected from O, N, and S, is selected from the group consisting of: benzofuranyl, isobenzofuranyl, benzo[b]thiophenyl, benzo[c]thiophenyl, indolyl, isoindolyl, benzo[d]isoxazolyl, benzo[c]isoxazolyl, benzo[d]oxazolyl, benzo[d]isothiazolyl, benzo[c]isothiazolyl, benzo[d]thiazolyl, indazolyl, benzo[d]imidazolyl, benzo[d]imidazolyl, and benzo[d][1,2,3]triazolyl.

In certain embodiments, the 5-6 membered monocyclic heteroaryl having one, two, or three heteroatoms each selected from O, N, and S, is selected from the group consisting of: furanyl, thienyl, pyrrolyl, thiazolyl, oxazolyl, isothiazolyl, isoxazolyl, imidazolyl, pyrazolyl, 1H-1,2,3-triazolyl, 2H-1,2,3-triazolyl, 1,2,4-triazolyl, pyridinyl, pyridazinyl, pyrimidinyl, pyrazinyl, 1,3,5-triazinyl, 1,2,4-triazinyl, 1,2,3-triazinyl, 1,2,4-oxadiazolyl, 1,3,4-oxadiazolyl, 1,2,5-oxadiazolyl, 1,2,4-thiadiazolyl, 1,3,4-thiadiazolyl and 1,2,5-thiadiazolyl; and the 8-12 membered bicyclic heteroaryl having one, two, or three heteroatoms each selected from O, N, and S, is selected from the group consisting of: benzofuranyl, isobenzofuranyl, benzo[b]thiophenyl, benzo[c]thiophenyl, indolyl, isoindolyl, benzo[d]isoxazolyl, benzo[c]isoxazolyl, benzo[d]oxazolyl, benzo[d]isothiazolyl, benzo[c]isothiazolyl, benzo[d]thiazolyl, indazolyl, benzo[d]imidazolyl, benzo[d]imidazolyl, and benzo[d][1,2,3]triazolyl.

In certain embodiments, the compound of Formula I is a compound of Formula II

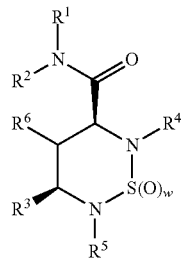

Formula II

In certain embodiments, the compound of Formula I is a compound of Formula III:

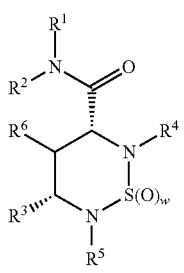

Formula III or a pharmaceutically acceptable salt thereof.

In certain embodiments, the compound of Formula I is a compound of Formula II

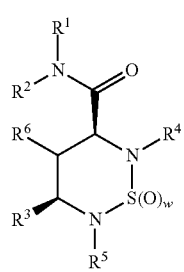

Formula II or a pharmaceutically acceptable salt thereof.

In certain embodiments, the compound of Formula I is a compound of Formula III:

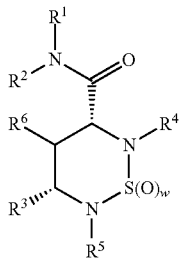

Formula III or a pharmaceutically acceptable salt thereof.

In certain embodiments, the compound of Formula I is a compound of Formula IV or V:
or a pharmaceutically acceptable salt thereof.

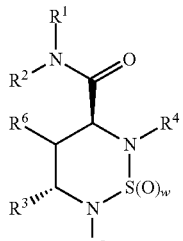

Formula IV

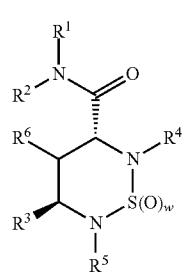

Formula V

In certain embodiments, the compound of Formula I is a compound of Formula IV:

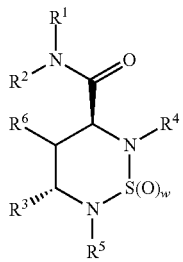

Formula IV or a pharmaceutically acceptable salt thereof.
In certain embodiments, the compound of Formula I is a compound of Formula V:
or a pharmaceutically acceptable salt thereof.

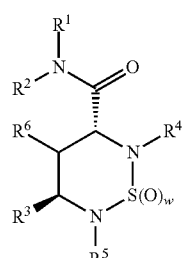

Formula V

In certain embodiments, w is 2.

In certain embodiments, $R^1$ is a 5-6 membered monocyclic heteroaryl having one, two, or three heteroatoms each selected from O, N, and S, optionally substituted with one, two, or three substituents independently selected from the group consisting of halo, —OH, —CN, —NO$_2$, oxo, hydrazino, formyl, azido, silyl, siloxy, —S(O)$_q$—C$_{1-6}$alkyl, —NR$^a$R$^b$, —NR$^c$—S(O)$_t$—C$_{1-6}$alkyl, —S(O)$_t$—NR$^a$R$^b$, C$_{1-6}$alkyl, C$_{2-6}$alkenyl, C$_{2-6}$alkynyl, C$_{3-6}$cycloalkyl, haloC$_{1-6}$alkyl, hydroxyC$_{1-6}$alkyl, R$^a$R$^b$N—C$_{1-6}$alkyl-, C$_{1-6}$alkoxy, haloC$_{1-6}$alkoxy, hydroxyC$_{1-6}$alkoxy-, R$^a$R$^b$N—C$_{1-6}$alkoxy-, C$_{1-6}$alkoxyC$_{1-6}$alkyl, —C(O)NR$^a$R$^b$, —C(O)—C$_{1-6}$alkyl, —C(O)OH, and —C(O)O—C$_{1-6}$alkyl.

In certain embodiments, R$^1$ is a 5-6 membered monocyclic heteroaryl having one, two, or three heteroatoms each selected from O, N, and S, optionally substituted with one, two, or three substituents independently selected from the group consisting of halo, —OH, —CN, —NO$_2$, oxo, hydrazino, formyl, azido, silyl, siloxy, —S(O)$_q$—C$_{1-6}$alkyl, —NR$^a$R$^b$, —NR$^c$—S(O)$_t$—C$_{1-6}$alkyl, —S(O)$_t$—NR$^a$R$^b$, C$_{1-6}$alkyl, C$_{2-6}$alkenyl, C$_{2-6}$alkynyl, C$_{3-6}$cycloalkyl, haloC$_{1-6}$alkyl, hydroxyC$_{1-6}$alkyl, R$^a$R$^b$N—C$_{1-6}$alkyl-, C$_{1-6}$alkoxy, haloC$_{1-6}$alkoxy, hydroxyC$_{1-6}$alkoxy-, R$^a$R$^b$N—C$_{1-6}$alkoxy-, C$_{1-6}$alkoxyC$_{1-6}$alkyl, —C(O)NR$^a$R$^b$, —C(O)—C$_{1-6}$alkyl, —C(O)OH, and —C(O)O—C$_{1-6}$ alkyl;

wherein the 5-6 membered monocyclic heteroaryl having one, two, or three heteroatoms each selected from O, N, and S, is selected from the group consisting of: furanyl, thienyl, pyrrolyl, thiazolyl, oxazolyl, isothiazolyl, isoxazolyl, imidazolyl, pyrazolyl, 1H-1,2,3-triazolyl, 2H-1,2,3-triazolyl, 1,2,5-triazolyl, pyridinyl, pyridazinyl, pyrimidinyl, pyrazinyl, 1,3,5-triazinyl, 1,2,4-triazinyl, 1,2,3-triazinyl, 1,2,4-oxadiazolyl, 1,3,4-oxadiazolyl, 1,2,5-oxadiazolyl, 1,2,4-thiadiazolyl, 1,3,4-thiadiazolyl and 1,2,5-thiadiazolyl.

In certain embodiments, R$^1$ is a 8-12 membered bicyclic heteroaryl having one, two, or three heteroatoms each selected from O, N, and S, optionally substituted with one, two, or three substituents independently selected from the group consisting of halo, —OH, —CN, —NO$_2$, oxo, hydrazino, formyl, azido, silyl, siloxy, —S(O)$_q$—C$_{1-6}$alkyl, —NR$^a$R$^b$, —NR$^c$—S(O)$_t$—C$_{1-6}$alkyl, —S(O)$_t$—NR$^a$R$^b$, C$_{1-6}$alkyl, C$_{2-6}$alkenyl, C$_{2-6}$alkynyl, C$_{3-6}$cycloalkyl, haloC$_{1-6}$alkyl, hydroxyC$_{1-6}$alkyl, R$^a$R$^b$N—C$_{1-6}$alkyl-, C$_{1-6}$alkoxy, haloC$_{1-6}$alkoxy, hydroxyC$_{1-6}$alkoxy-, R$^a$R$^b$N—C$_{1-6}$alkoxy-, C$_{1-6}$alkoxyC$_{1-6}$alkyl, —C(O)NR$^a$R$^b$, —C(O)—C$_{1-6}$alkyl, —C(O)OH, and —C(O)O—C$_{1-6}$ alkyl.

In certain embodiments, R$^1$ is a 8-12 membered bicyclic heteroaryl having one, two, or three heteroatoms each selected from O, N, and S, optionally substituted with one, two, or three substituents independently selected from the group consisting of halo, —OH, —CN, —NO$_2$, oxo, hydrazino, formyl, azido, silyl, siloxy, —S(O)$_q$—C$_{1-6}$alkyl, —NR$^a$R$^b$, —NR$^c$—S(O)$_t$—C$_{1-6}$alkyl, —S(O)$_t$—NR$^a$R$^b$, C$_{1-6}$alkyl, C$_{2-6}$alkenyl, C$_{2-6}$alkynyl, C$_{3-6}$cycloalkyl, haloC$_{1-6}$alkyl, hydroxyC$_{1-6}$alkyl, R$^a$R$^b$N—C$_{1-6}$alkyl-, C$_{1-6}$alkoxy, haloC$_{1-6}$alkoxy, hydroxyC$_{1-6}$alkoxy-, R$^a$R$^b$N—C$_{1-6}$alkoxy-, C$_{1-6}$alkoxyC$_{1-6}$alkyl, —C(O)NR$^a$R$^b$, —C(O)—C$_{1-6}$alkyl, —C(O)OH, and —C(O)O—C$_{1-6}$ alkyl;

wherein the 8-12 membered bicyclic heteroaryl having one, two, or three heteroatoms each selected from O, N, and S, is selected from the group consisting of: benzofuranyl, isobenzofuranyl, benzo[b]thiophenyl, benzo[c]thiophenyl, indolyl, isoindolyl, benzo[d]isoxazolyl, benzo[c]isoxazolyl, benzo[d]oxazolyl, benzo[d]isothiazolyl, benzo[c]isothiazolyl, benzo[d]thiazolyl, indazolyl, benzo[d]imidazolyl, benzo[d]imidazolyl, and benzo[d][1,2,3]triazolyl.

In certain embodiments, R$^1$ is phenyl optionally substituted with one, two, or three substituents independently selected from the group consisting of halo, —OH, —CN, —NO$_2$, oxo, hydrazino, formyl, azido, silyl, siloxy, —S(O)$_q$—C$_{1-6}$alkyl, —NR$^a$R$^b$, —NR$^c$—S(O)$_t$—C$_{1-6}$alkyl, —S(O)$_t$—NR$^a$R$^b$, C$_{1-6}$alkyl, C$_{2-6}$alkenyl, C$_{2-6}$alkynyl, C$_{3-6}$cycloalkyl, haloC$_{1-6}$alkyl, hydroxyC$_{1-6}$ alkyl, R$^a$R$^b$N— C$_{1-6}$alkyl-, C$_{1-6}$alkoxy, haloC$_{1-6}$alkoxy, hydroxy C$_{1-6}$alkoxy-, R$^a$R$^b$N—C$_{1-6}$alkoxy-, C$_{1-6}$alkoxyC$_{1-6}$alkyl, —C(O)NR$^a$R$^b$, —C(O)—C$_{1-6}$alkyl, —C(O)OH, and —C(O)O—C$_{1-6}$alkyl.

In certain embodiments, R$^1$ is

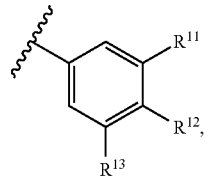

wherein R$^{11}$, R$^{12}$ and R$^{13}$ are independently selected from the group consisting of halo, cyano, C$_{1-6}$alkyl and C$_{1-6}$haloalkyl.

In certain embodiments, R$^1$ is

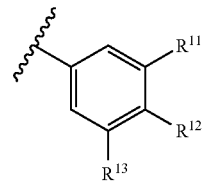

wherein R$^{11}$, R$^{12}$ and R$^{13}$ are independently selected from the group consisting of F, Cl, and Br.

In certain embodiments, R$^1$ is

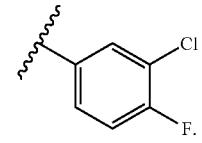

In certain embodiments, R$^1$ is pyridyl, optionally substituted with one, two, or three substituents independently selected from the group consisting of halo, cyano, C$_{1-6}$alkyl and C$_{1-6}$haloalkyl.

In certain embodiments, R$^2$ is hydrogen or C$_{1-6}$alkyl.
In certain embodiments, R$^2$ is hydrogen or methyl.
In certain embodiments, R$^2$ is hydrogen.

In certain embodiments, R$^3$ is a 5-6 membered monocyclic heteroaryl having one, two, or three heteroatoms selected from the group consisting of O, N, and S, optionally substituted with one, two or three substituents independently selected from the group consisting of: halo, —OH, —CN, —NO$_2$, oxo, hydrazino, formyl, azido, silyl, siloxy, —S(O)$_q$—C$_{1-6}$ alkyl, —NR$^a$R$^b$, —NR$^c$—S(O)$_t$—C$_{1-6}$alkyl, —S(O)$_t$—NR$^a$R$^b$, C$_{1-6}$alkyl, C$_{2-6}$alkenyl, C$_{2-6}$alkynyl, C$_{3-6}$cycloalkyl, haloC$_{1-6}$alkyl, hydroxyC$_{1-6}$alkyl, R$^a$R$^b$N— C$_{1-6}$alkyl-, C$_{1-6}$alkoxy, haloC$_{1-6}$alkoxy, hydroxyC$_{1-6}$alkoxy-, R$^a$R$^b$N—C$_{1-6}$alkoxy-, C$_{1-6}$alkoxyC$_{1-6}$alkyl, —C(O)NR$^a$R$^b$, —C(O)—C$_{1-6}$alkyl, —C(O)OH, and —C(O)O—C$_{1-6}$alkyl phenyl, and a 5-6 membered monocyclic heteroaryl having one, two, or three heteroatoms selected from the group consisting of O, N, and S, wherein the phenyl or 5-6 membered monocyclic heteroaryl is optionally substituted with one, two or three substituents independently selected from the group consisting of: halo, —OH, —CN, —NO$_2$, oxo, hydrazino, formyl, azido, silyl, siloxy, —S(O)$_q$—C$_{1-6}$alkyl, —NR$^a$R$^b$, —NR$^c$—S(O)$_t$—C$_{1-6}$alkyl, —S(O)$_t$—NR$^a$R$^b$, C$_{1-6}$alkyl, C$_{2-6}$alkenyl, C$_{2-6}$alkynyl, C$_{3-6}$cycloalkyl, haloC$_{1-6}$alkyl, hydroxyC$_{1-6}$alkyl, R$^a$R$^b$N—C$_{1-6}$alkyl-, C$_{1-6}$alkoxy, haloC$_{1-6}$alkoxy, hydroxyC$_{1-6}$alkoxy-, R$^a$R$^b$N—C$_{1-6}$alkoxy-, C$_{1-6}$alkoxyC$_{1-6}$alkyl, —C(O)NR$^a$R$^b$, —C(O)—C$_{1-6}$alkyl, —C(O)OH, and —C(O)O—C$_{1-6}$alkyl.

In certain embodiments, R$^3$ is a 5-6 membered monocyclic heteroaryl having one, two, or three heteroatoms selected from the group consisting of O, N, and S, optionally substituted with one, two or three substituents independently selected from the group consisting of: halo, —OH, —CN, —NO$_2$, oxo, hydrazino, formyl, azido, silyl, siloxy, —S(O)$_q$—C$_{1-6}$ alkyl, —NR$^a$R$^b$, —NR$^c$—S(O)$_t$—C$_{1-6}$alkyl, —S(O)$_t$—NR$^a$R$^b$, C$_{1-6}$alkyl, C$_{2-6}$alkenyl, C$_{2-6}$alkynyl, C$_{3-6}$cycloalkyl, haloC$_{1-6}$alkyl, hydroxyC$_{1-6}$alkyl, R$^a$R$^b$N—C$_{1-6}$alkyl-, C$_{1-6}$alkoxy, haloC$_{1-6}$alkoxy, hydroxyC$_{1-6}$alkoxy-, R$^a$R$^b$N—C$_{1-6}$alkoxy-, C$_{1-6}$alkoxyC$_{1-6}$alkyl, —C(O)NR$^a$R$^b$, —C(O)—C$_{1-6}$alkyl, —C(O)OH, and —C(O)O—C$_{1-6}$alkyl phenyl, and a 5-6 membered monocyclic heteroaryl having one, two, or three heteroatoms selected from the group consisting of O, N, and S, wherein the phenyl or 5-6 membered monocyclic heteroaryl is optionally substituted with one, two or three substituents independently selected from the group consisting of: halo, —OH, —CN, —NO$_2$, oxo, hydrazino, formyl, azido, silyl, siloxy, —S(O)$_q$—C$_{1-6}$alkyl, —NR$^a$R$^b$, —NR$^c$—S(O)$_t$—C$_{1-6}$alkyl, —S(O)$_t$—NR$^a$R$^b$, C$_{1-6}$alkyl, C$_{2-6}$alkenyl, C$_{2-6}$alkynyl, C$_{3-6}$cycloalkyl, haloC$_{1-6}$alkyl, hydroxyC$_{1-6}$alkyl, R$^a$R$^b$N—C$_{1-6}$alkyl-, C$_{1-6}$alkoxy, haloC$_{1-6}$alkoxy, hydroxyC$_{1-6}$alkoxy-, R$^a$R$^b$N—C$_{1-6}$alkoxy-, C$_{1-6}$alkoxy C$_{1-6}$alkyl, —C(O)NR$^a$R$^b$, —C(O)—C$_{1-6}$alkyl, —C(O)OH, and —C(O)O—C$_{1-6}$alkyl;

wherein the 5-6 membered monocyclic heteroaryl having one, two, or three heteroatoms each selected from O, N, and S, is selected from the group consisting of: furanyl, thienyl, pyrrolyl, thiazolyl, oxazolyl, isothiazolyl, isoxazolyl, imidazolyl, pyrazolyl, 1H-1,2,3-triazolyl, 2H-1,2,3-triazolyl, 1,2,4-triazolyl, pyridinyl, pyridazinyl, pyrimidinyl, pyrazinyl, 1,3,5-triazinyl, 1,2,4-triazinyl, 1,2,3-triazinyl, 1,2,4-oxadiazolyl, 1,3,4-oxadiazolyl, 1,2,5-oxadiazolyl, 1,2,4-thiadiazolyl, 1,3,4-thiadiazolyl and 1,2,5-thiadiazolyl.

In certain embodiments, R$^3$ is a 8-12 membered bicyclic heteroaryl having one, two, or three heteroatoms selected from the group consisting of O, N, and S, optionally substituted with one, two or three substituents independently selected from the group consisting of: halo, —OH, —CN, —NO$_2$, Oxo, hydrazino, formyl, azido, silyl, siloxy, —S(O)$_q$—C$_{1-6}$ alkyl, —NR$^a$R$^b$, —NR$^c$—S(O)$_t$—C$_{1-6}$alkyl, —S(O)$_t$—NR$^a$R$^b$, C$_{1-6}$alkyl, C$_{2-6}$alkenyl, C$_{2-6}$alkynyl, C$_{3-6}$cycloalkyl, haloC$_{1-6}$alkyl, hydroxyC$_{1-6}$alkyl, R$^a$R$^b$N—C$_{1-6}$alkyl-, C$_{1-6}$alkoxy, haloC$_{1-6}$alkoxy, hydroxy C$_{1-6}$alkoxy-, R$^a$R$^b$N—C$_{1-6}$alkoxy-, C$_{1-6}$alkoxyC$_{1-6}$alkyl, —C(O)NR$^a$R$^b$, —C(O)—C$_{1-6}$alkyl, —C(O)OH, and —C(O)O—C$_{1-6}$alkyl phenyl, and a 5-6 membered monocyclic heteroaryl having one, two, or three heteroatoms selected from the group consisting of O, N, and S, wherein the phenyl or 5-6 membered monocyclic heteroaryl is optionally substituted with one, two or three substituents independently selected from the group consisting of: halo, —OH, —CN, —NO$_2$, oxo, hydrazino, formyl, azido, silyl, siloxy, —S(O)$_q$—C$_{1-6}$alkyl, —NR$^a$R$^b$, —NR$^c$—S(O)$_t$—C$_{1-6}$alkyl, —S(O)$_t$—NR$^a$R$^b$, C$_{1-6}$alkyl, C$_{2-6}$alkenyl, C$_{2-6}$alkynyl, C$_{3-6}$cycloalkyl, haloC$_{1-6}$alkyl, hydroxyC$_{1-6}$alkyl, R$^a$R$^b$N—C$_{1-6}$alkyl-, C$_{1-6}$alkoxy, haloC$_{1-6}$alkoxy, hydroxyC$_{1-6}$alkoxy-, R$^a$R$^b$N—C$_{1-6}$alkoxy-, C$_{1-6}$alkoxyC$_{1-6}$alkyl, —C(O)NR$^a$R$^b$, —C(O)—C$_{1-6}$alkyl, —C(O)OH, and —C(O)O—C$_{1-6}$alkyl;

wherein the 5-6 membered monocyclic heteroaryl having one, two, or three heteroatoms each selected from O, N, and S, is selected from the group consisting of: furanyl, thienyl, pyrrolyl, thiazolyl, oxazolyl, isothiazolyl, isoxazolyl, imidazolyl, pyrazolyl, 1H-1,2,3-triazolyl, 2H-1,2,3-triazolyl, 1,2,4-triazolyl, pyridinyl, pyridazinyl, pyrimidinyl, pyrazinyl, 1,3,5-triazinyl, 1,2,4-triazinyl, 1,2,3-triazinyl, 1,2,4-oxadiazolyl, 1,3,4-oxadiazolyl, 1,2,5-oxadiazolyl, 1,2,4-thiadiazolyl, 1,3,4-thiadiazolyl and 1,2,5-thiadiazolyl; and the 8-12 membered bicyclic heteroaryl having one, two, or three heteroatoms each selected from O, N, and S, is selected from the group consisting of: benzofuranyl, isobenzofuranyl, benzo[b]thiophenyl, benzo[c]thiophenyl, indolyl, isoindolyl, benzo[d]isoxazolyl, benzo[c]isoxazolyl, benzo[d]oxazolyl, benzo[d]isothiazolyl, benzo[c]isothiazolyl, benzo[d]thiazolyl, indazolyl, benzo[d]imidazolyl, benzo[d]imidazolyl, and benzo[d][1,2,3]triazolyl.

In certain embodiments, R$^3$ is phenyl optionally substituted with one, two or three substituents independently selected from the group consisting of: halo, —OH, —CN, —NO$_2$, oxo, hydrazino, formyl, azido, silyl, siloxy, —S(O)$_q$—C$_{1-6}$alkyl, —NR$^a$R$^b$, —NR$^c$—S(O)$_t$—C$_{1-6}$alkyl, —S(O)$_t$—NR$^a$R$^b$, C$_{1-6}$alkyl, C$_{2-6}$alkenyl, C$_{2-6}$alkynyl, C$_{3-6}$cycloalkyl, haloC$_{1-6}$alkyl, hydroxyC$_{1-6}$ alkyl, R$^a$R$^b$N—C$_{1-6}$alkyl-, C$_{1-6}$alkoxy, haloC$_{1-6}$alkoxy, hydroxy C$_{1-6}$alkoxy-, R$^a$R$^b$N—C$_{1-6}$alkoxy-, C$_{1-6}$alkoxyC$_{1-6}$alkyl, —C(O)NR$^a$R$^b$, —C(O)—C$_{1-6}$alkyl, —C(O)OH, and —C(O)O—C$_{1-6}$alkyl, phenyl, and a 5-6 membered monocyclic heteroaryl having one, two, or three heteroatoms selected from the group consisting of O, N, and S, wherein the phenyl or 5-6 membered monocyclic heteroaryl is optionally substituted with one, two or three substituents independently selected from the group consisting of: halo, —OH, —CN, —NO$_2$, oxo, hydrazino, formyl, azido, silyl, siloxy, —S(O)$_q$—C$_{1-6}$alkyl, —NR$^a$R$^b$, —NR$^c$—S(O)$_t$—C$_{1-6}$alkyl, —S(O)$_t$—NR$^a$R$^b$ C$_{1-6}$alkyl, C$_{2-6}$alkenyl, C$_{2-6}$alkynyl, C$_{3-6}$cycloalkyl, haloC$_{1-6}$alkyl, hydroxyC$_{1-6}$alkyl, R$^a$R$^b$N—C$_{1-6}$alkyl-, C$_{1-6}$alkoxy, haloC$_{1-6}$alkoxy, hydroxyC$_{1-6}$alkoxy-, R$^a$R$^b$N—C$_{1-6}$alkoxy-, C$_{1-6}$ alkoxy C$_{1-6}$alkyl, —C(O)NR$^a$R$^b$, —C(O)—C$_{1-6}$alkyl, —C(O)OH, and —C(O)O—C$_{1-6}$alkyl.

In certain embodiments, R$^3$ is phenyl optionally substituted with one, two or three substituents independently selected from the group consisting of: halo, —OH, —CN, —NO$_2$, oxo, hydrazino, formyl, azido, silyl, siloxy, —S(O)$_q$—C$_{1-6}$alkyl, —NR$^a$R$^b$, —NR$^c$—S(O)$_t$—C$_{1-6}$alkyl, —S(O)$_t$—NR$^a$R$^b$, C$_{1-6}$alkyl, C$_{2-6}$alkenyl, C$_{2-6}$alkynyl, C$_{3-6}$cycloalkyl, haloC$_{1-6}$alkyl, hydroxyC$_{1-6}$ alkyl, R$^a$R$^b$N—C$_{1-6}$alkyl-, C$_{1-6}$alkoxy, haloC$_{1-6}$alkoxy, hydroxy C$_{1-6}$alkoxy-, R$^a$R$^b$N—C$_{1-6}$alkoxy-, C$_{1-6}$alkoxyC$_{1-6}$alkyl, —C(O)NR$^a$R$^b$, —C(O)—C$_{1-6}$alkyl, —C(O)OH, and —C(O)O—C$_{1-6}$alkyl, phenyl, and a 5-6 membered monocyclic heteroaryl having one, two, or three heteroatoms selected from the group consisting of O, N, and S, wherein the phenyl or 5-6 membered monocyclic heteroaryl is optionally substituted with one, two or three substituents independently selected from the group consisting of: halo, —OH, —CN, —NO$_2$, oxo, hydrazino, formyl, azido, silyl, siloxy, —S(O)$_q$—C$_{1-6}$alkyl, —NR$^a$R$^b$, —NR$^c$—S(O)$_t$—C$_{1-6}$alkyl, —S(O)$_t$—NR$^a$R$^b$, C$_{1-6}$alkyl, C$_{2-6}$alkenyl, C$_{2-6}$alkynyl, C$_{3-6}$cycloalkyl, haloC$_{1-6}$alkyl, hydroxyC$_{1-6}$alkyl, R$^a$R$^b$N—C$_{1-6}$alkyl-, C$_{1-6}$alkoxy, haloC$_{1-6}$alkoxy, hydroxyC$_{1-6}$alkoxy-, R$^a$R$^b$N—C$_{1-6}$alkoxy-, C$_{1-6}$ alkoxy C$_{1-6}$alkyl, —C(O)NR$^a$R$^b$, —C(O)—C$_{1-6}$alkyl, —C(O)OH, and —C(O)O—C$_{1-6}$alkyl;

wherein the 5-6 membered monocyclic heteroaryl having one, two, or three heteroatoms each selected from O, N, and S, is selected from the group consisting of: furanyl, thienyl, pyrrolyl, thiazolyl, oxazolyl, isothiazolyl, isoxazolyl, imidazolyl, pyrazolyl, 1H-1,2,3-triazolyl, 2H-1,2,3-triazolyl, 1,2,4-triazolyl, pyridinyl, pyridazinyl, pyrimidinyl, pyrazinyl, 1,3,5-triazinyl, 1,2,4-triazinyl, 1,2,3-triazinyl, 1,2,4-oxadiazolyl, 1,3,4-oxadiazolyl, 1,2,5-oxadiazolyl, 1,2,4-thiadiazolyl, 1,3,4-thiadiazolyl and 1,2,5-thiadiazolyl.

In certain embodiments, R$^3$ C$_{3-6}$cyclolkyl optionally substituted with one, two or three substituents independently selected from the group consisting of halo, —OH, —CN, —NO$_2$, oxo, hydrazino, formyl, azido, silyl, siloxy, —S(O)$_q$—C$_{1-6}$alkyl, —NR$^a$R$^b$, —NR$^c$—S(O)$_t$—C$_{1-6}$alkyl, —S(O)$_t$—NR$^a$R$^b$, C$_{1-6}$alkyl, C$_{2-6}$alkenyl, C$_{2-6}$alkynyl, C$_{3-6}$cycloalkyl, haloC$_{1-6}$alkyl, hydroxyC$_{1-6}$ alkyl, R$^a$R$^b$N—C$_{1-6}$alkyl-, C$_{1-6}$alkoxy, haloC$_{1-6}$alkoxy, hydroxy C$_{1-6}$alkoxy-, R$^a$R$^b$N—C$_{1-6}$alkoxy-, C$_{1-6}$alkoxyC$_{1-6}$alkyl, —C(O)NR$^a$R$^b$, —C(O)—C$_{1-6}$alkyl, —C(O)OH, and —C(O)O—C$_{1-6}$alkyl, phenyl, and a 5-6 membered monocyclic heteroaryl having one, two, or three heteroatoms selected from the group consisting of O, N, and S, wherein the phenyl or 5-6 membered monocyclic heteroaryl is optionally substituted with one, two or three substituents independently selected from the group consisting of: halo, —OH, —CN, —NO$_2$, Oxo, hydrazino, formyl, azido, silyl, siloxy, —S(O)$_q$—C$_{1-6}$alkyl, —NR$^a$R$^b$, —NR$^c$—S(O)$_t$—C$_{1-6}$alkyl, —S(O)$_t$—NR$^a$R$^b$ C$_{1-6}$alkyl, C$_{2-6}$alkenyl, C$_{2-6}$alkynyl, C$_{3-6}$cycloalkyl, haloC$_{1-6}$alkyl, hydroxyC$_{1-6}$alkyl, R$^a$R$^b$N—C$_{1-6}$alkyl-, C$_{1-6}$alkoxy, haloC$_{1-6}$alkoxy, hydroxyC$_{1-6}$alkoxy-, R$^a$R$^b$N—C$_{1-6}$alkoxy-, C$_{1-6}$alkoxy C$_{1-6}$alkyl, —C(O)NR$^a$R$^b$, —C(O)—C$_{1-6}$alkyl, —C(O)OH, and —C(O)O—C$_{1-6}$alkyl.

In certain embodiments, R$^3$ C$_{3-6}$cyclolkyl optionally substituted with one, two or three substituents independently selected from the group consisting of: halo, —OH, —CN, —NO$_2$, oxo, hydrazino, formyl, azido, silyl, siloxy, —S(O)$_q$—C$_{1-6}$alkyl, —NR$^a$R$^b$, —NR$^c$—S(O)$_t$—C$_{1-6}$alkyl, —S(O)$_t$—NR$^a$R$^b$, C$_{1-6}$alkyl, C$_{2-6}$alkenyl, C$_{2-6}$alkynyl, C$_{3-6}$cycloalkyl, haloC$_{1-6}$alkyl, hydroxyC$_{1-6}$ alkyl, R$^a$R$^b$N—C$_{1-6}$alkyl-, C$_{1-6}$alkoxy, haloC$_{1-6}$alkoxy, hydroxyC$_{1-6}$alkoxy-, R$^a$R$^b$N—C$_{1-6}$alkoxy-, C$_{1-6}$alkoxyC$_{1-6}$alkyl, —C(O)NR$^a$R$^b$, —C(O)—C$_{1-6}$alkyl, —C(O)OH, and —C(O)O—C$_{1-6}$alkyl, phenyl, and a 5-6 membered monocyclic heteroaryl having one, two, or three heteroatoms selected from the group consisting of O, N, and S, wherein the phenyl or 5-6 membered monocyclic heteroaryl is optionally substituted with one, two or three substituents independently selected from the group consisting of: halo, —OH, —CN, —NO$_2$, oxo, hydrazino, formyl, azido, silyl, siloxy, —S(O)$_q$—C$_{1-6}$alkyl, —NR$^a$R$^b$, —NR$^c$—S(O)$_t$—C$_{1-6}$alkyl, —S(O)$_t$—NR$^a$R$^b$ C$_{1-6}$alkyl, C$_{2-6}$alkenyl, C$_{2-6}$alkynyl, C$_{3-6}$cycloalkyl, haloC$_{1-6}$alkyl, hydroxyC$_{1-6}$alkyl, R$^a$R$^b$N—C$_{1-6}$alkyl-, C$_{1-6}$alkoxy, haloC$_{1-6}$alkoxy, hydroxyC$_{1-6}$alkoxy-, R$^a$R$^b$N—C$_{1-6}$alkoxy-, C$_{1-6}$ alkoxy C$_{1-6}$alkyl, —C(O)NR$^a$R$^b$, —C(O)—C$_{1-6}$alkyl, —C(O)OH, and —C(O)O—C$_{1-6}$alkyl;

wherein the 5-6 membered monocyclic heteroaryl having one, two, or three heteroatoms each selected from O, N, and S, is selected from the group consisting of: furanyl, thienyl, pyrrolyl, thiazolyl, oxazolyl, isothiazolyl, isoxazolyl, imidazolyl, pyrazolyl, 1H-1,2,3-triazolyl, 2H-1,2,3-triazolyl, 1,2,4-triazolyl, pyridinyl, pyridazinyl, pyrimidinyl, pyrazinyl, 1,3,5-triazinyl, 1,2,4-triazinyl, 1,2,3-triazinyl, 1,2,4-oxadiazolyl, 1,3,4-oxadiazolyl, 1,2,5-oxadiazolyl, 1,2,4-thiadiazolyl, 1,3,4-thiadiazolyl and 1,2,5-thiadiazolyl.

In certain embodiments, R$^3$ C$_{1-6}$alkyl optionally substituted with one, two or three substituents independently selected from the group consisting of: halo, —OH, —CN, —NO$_2$, oxo, hydrazino, formyl, azido, silyl, siloxy, —S(O)$_q$—C$_{1-6}$alkyl, —NR$^a$R$^b$, —NR$^c$—S(O)$_t$—C$_{1-6}$alkyl, —S(O)$_t$—NR$^a$R$^b$, C$_{1-6}$alkyl, C$_{2-6}$alkenyl, C$_{2-6}$alkynyl, C$_{3-6}$cycloalkyl, haloC$_{1-6}$alkyl, hydroxyC$_{1-6}$ alkyl, R$^a$R$^b$N—C$_{1-6}$alkyl-, C$_{1-6}$alkoxy, haloC$_{1-6}$alkoxy, hydroxy C$_{1-6}$alkoxy-, R$^a$R$^b$N—C$_{1-6}$alkoxy-, C$_{1-6}$alkoxyC$_{1-6}$alkyl, —C(O)NR$^a$R$^b$, —C(O)—C$_{1-6}$alkyl, —C(O)OH, and —C(O)O—C$_{1-6}$alkyl, phenyl, and a 5-6 membered monocyclic heteroaryl having one, two, or three heteroatoms selected from the group consisting of O, N, and S, wherein the phenyl or 5-6 membered monocyclic heteroaryl is optionally substituted with one, two or three substituents independently selected from the group consisting of: halo, —OH, —CN, —NO$_2$, oxo, hydrazino, formyl, azido, silyl, siloxy, —S(O)$_q$—C$_{1-6}$alkyl, —NR$^a$R$^b$, —NR$^c$—S(O)$_t$—C$_{1-6}$alkyl, —S(O)$_t$—NR$^a$R$^b$ C$_{1-6}$alkyl, C$_{2-6}$alkenyl, C$_{2-6}$alkynyl, C$_{3-6}$cycloalkyl, haloC$_{1-6}$alkyl, hydroxyC$_{1-6}$alkyl, R$^a$R$^b$N—C$_{1-6}$alkyl-, C$_{1-6}$alkoxy, haloC$_{1-6}$alkoxy, hydroxyC$_{1-6}$alkoxy-, R$^a$R$^b$N—C$_{1-6}$alkoxy-, C$_{1-6}$ alkoxy C$_{1-6}$alkyl, —C(O)NR$^a$R$^b$, —C(O)—C$_{1-6}$alkyl, —C(O)OH, and —C(O)O—C$_{1-6}$alkyl.

In certain embodiments, R$^3$ C$_{1-6}$alkyl optionally substituted with one, two or three substituents independently selected from the group consisting of: halo, —OH, —CN, —NO$_2$, oxo, hydrazino, formyl, azido, silyl, siloxy, —S(O)$_q$—C$_{1-6}$alkyl, —NR$^a$R$^b$, —NR$^c$—S(O)$_t$—C$_{1-6}$alkyl, —S(O)$_t$—NR$^a$R$^b$, C$_{1-6}$alkyl, C$_{2-6}$alkenyl, C$_{2-6}$alkynyl, C$_{3-6}$cycloalkyl, haloC$_{1-6}$alkyl, hydroxyC$_{1-6}$ alkyl, R$^a$R$^b$N—C$_{1-6}$alkyl-, C$_{1-6}$alkoxy, haloC$_{1-6}$alkoxy, hydroxyq C$_{1-6}$alkoxy-, R$^a$R$^b$N—C$_{1-6}$alkoxy-, C$_{1-6}$alkoxyC$_{1-6}$alkyl, —C(O)NR$^a$R$^b$, —C(O)—C$_{1-6}$alkyl, —C(O)OH, and —C(O)O—C$_{1-6}$alkyl, phenyl, and a 5-6 membered monocyclic heteroaryl having one, two, or three heteroatoms selected from the group consisting of O, N, and S, wherein the phenyl or 5-6 membered monocyclic heteroaryl is optionally substituted with one, two or three substituents independently selected from the group consisting of: halo, —OH, —CN, —NO$_2$, oxo, hydrazino, formyl, azido, silyl, siloxy, —S(O)$_q$—C$_{1-6}$alkyl, —NR$^a$R$^b$, —NR$^c$—S(O)$_t$—C$_{1-6}$alkyl, —S(O)$_t$—NR$^a$R$^b$ C$_{1-6}$alkyl, C$_{2-6}$alkenyl, C$_{2-6}$alkynyl, C$_{3-6}$cycloalkyl, haloC$_{1-6}$alkyl, hydroxyC$_{1-6}$alkyl, R$^a$R$^b$N—C$_{1-6}$alkyl-, C$_{1-6}$alkoxy, haloC$_{1-6}$alkoxy, hydroxyC$_{1-6}$alkoxy-, R$^a$R$^b$N—C$_{1-6}$alkoxy-, C$_{1-6}$alkoxy C$_{1-6}$alkyl, —C(O)NR$^a$R$^b$, —C(O)—C$_{1-6}$alkyl, —C(O)OH, and —C(O)O—C$_{1-6}$alkyl;

wherein the 5-6 membered monocyclic heteroaryl having one, two, or three heteroatoms each selected from O, N, and S, is selected from the group consisting of: furanyl, thienyl, pyrrolyl, thiazolyl, oxazolyl, isothiazolyl, isoxazolyl, imidazolyl, pyrazolyl, 1H-1,2,3-triazolyl, 2H-1,2,3-triazolyl, 1,2,4-triazolyl, pyridinyl, pyridazinyl, pyrimidinyl, pyrazinyl, 1,3,5-triazinyl, 1,2,4-triazinyl, 1,2,3-triazinyl, 1,2,4-oxadiazolyl, 1,3,4-oxadiazolyl, 1,2,5-oxadiazolyl, 1,2,4-thiadiazolyl, 1,3,4-thiadiazolyl and 1,2,5-thiadiazolyl.

In certain embodiments, R$^3$ is selected from the group consisting of:

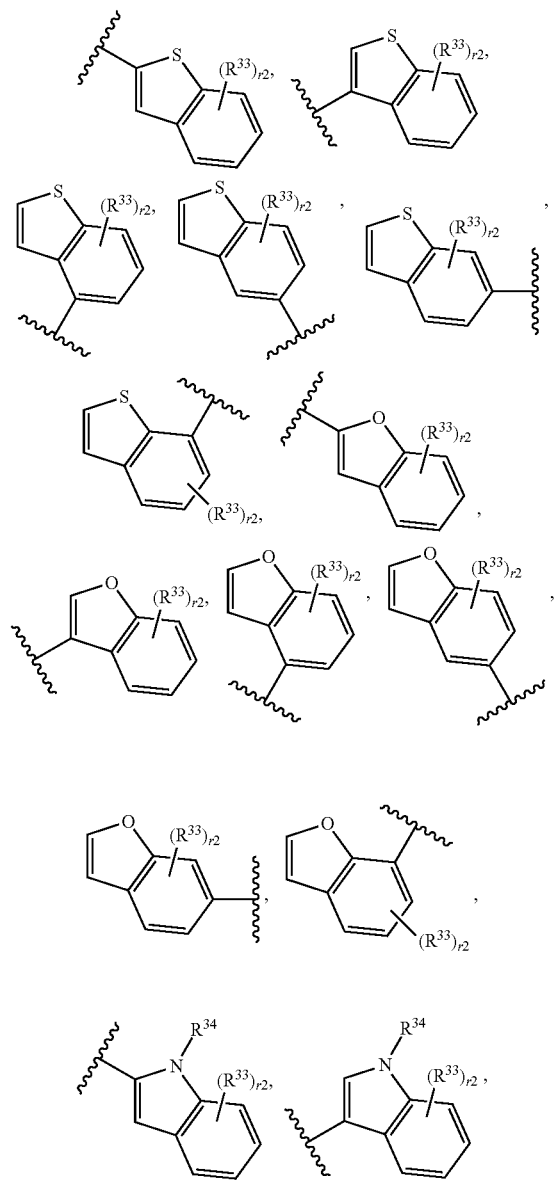

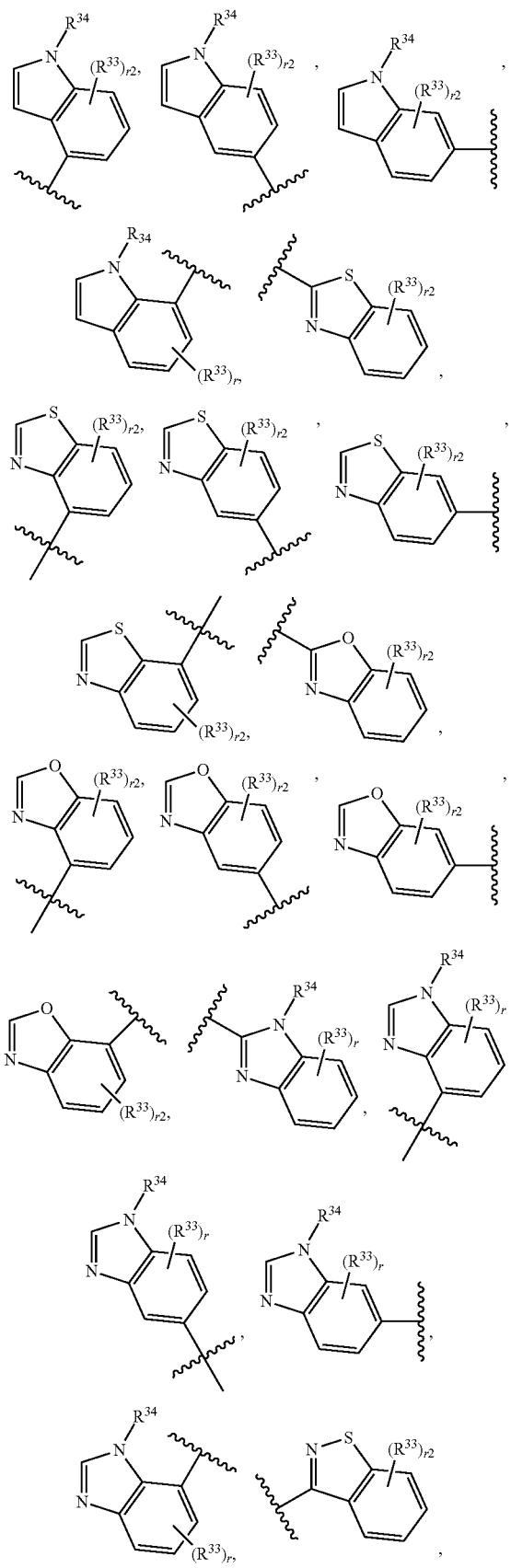

-continued

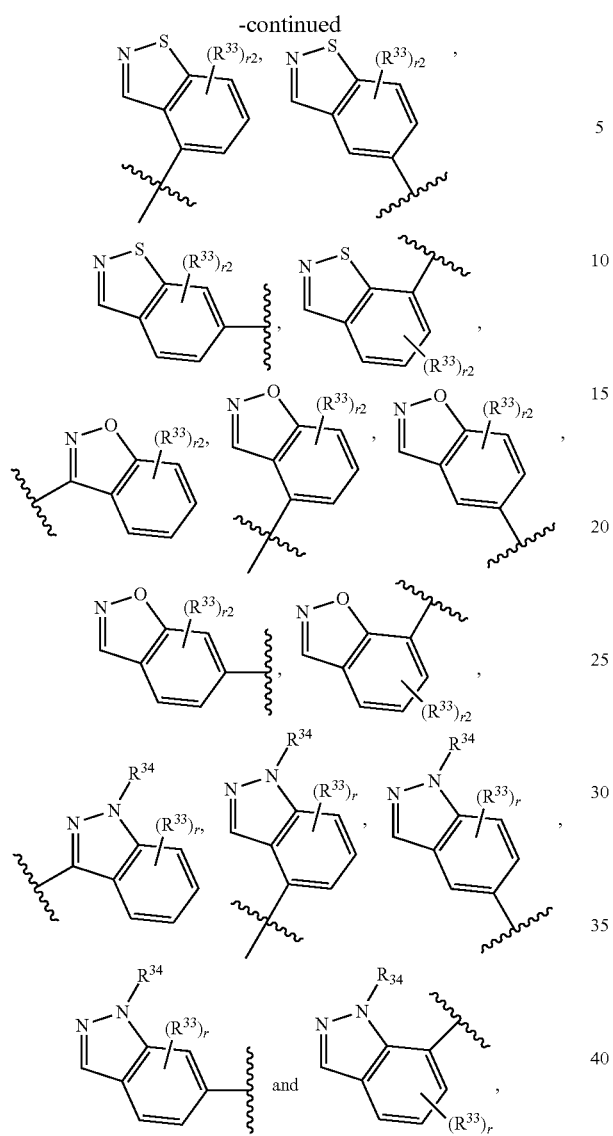

wherein:
R³³ is independently selected for each occurrence from the group consisting of: halo, —OH, —CN, —NO₂, Oxo, hydrazino, formyl, azido, silyl, siloxy, —S(O)$_q$—C$_{1-6}$alkyl, —NR$^a$R$^b$, —NR$^c$—S(O)$_t$—C$_{1-6}$alkyl, —S(O)$_t$—NR$^a$R$^b$, C$_{1-6}$alkyl, C$_{2-6}$alkenyl, C$_{2-6}$alkynyl, C$_{3-6}$cycloalkyl, haloC$_{1-6}$alkyl, hydroxyC$_{1-6}$alkyl, R$^a$R$^b$N—C$_{1-6}$alkyl-, C$_{1-6}$alkoxy, haloC$_{1-6}$alkoxy, hydroxyC$_{1-6}$alkoxy-, R$^a$R$^b$N—C$_{1-6}$alkoxy-, C$_{1-6}$alkoxyC$_{1-6}$alkyl, —C(O)NR$^a$R$^b$, —C(O)—C$_{1-6}$alkyl, —C(O)OH, and —C(O)O—C$_{1-6}$alkyl, phenyl, and a 5-6 membered monocyclic heteroaryl having one, two, or three heteroatoms selected from the group consisting of O, N, and S, wherein the phenyl or 5-6 membered monocyclic heteroaryl is optionally substituted with one, two or three substituents independently selected from the group consisting of: halo, —OH, —CN, —NO₂, oxo, hydrazino, formyl, azido, silyl, siloxy, —S(O)$_q$—C$_{1-6}$alkyl, —NR$^a$R$^b$, —NR$^c$—S(O)$_t$—C$_{1-6}$alkyl, —S(O)$_t$—NR$^a$R$^b$, C$_{1-6}$alkyl, C$_{2-6}$alkenyl, C$_{2-6}$alkynyl, C$_{3-6}$cycloalkyl, haloC$_{1-6}$alkyl, hydroxyC$_{1-6}$ alkyl, R$^a$R$^b$N—C$_{1-6}$alkyl-, C$_{1-6}$alkoxy, haloC$_{1-6}$alkoxy, hydroxyC$_{1-6}$alkoxy-, R$^a$R$^b$N—C$_{1-6}$alkoxy-C$_{1-6}$alkoxyC$_{1-6}$alkyl, —C(O)NR$^a$R$^b$, —C(O)—C$_{1-6}$alkyl, —C(O)OH, and —C(O)O—C$_{1-6}$alkyl;

R³⁴ is independently selected from the group consisting of hydrogen and C$_{1-4}$alkyl;

r is 0, 1 or 2; and r2 is 0, 1, 2 or 3;

with the provisos that:
when R³ is thiophen-2-yl or furan-2-yl, r2 is 1, 2 or 3;
when R³ is pyrazol-4-yl, in at least one instance, R³³ is other than C$_{1-6}$ alkyl; and
when R³ is phenyl, at least one of R³⁵, R³⁶ and R³⁷ is other than halo and C$_{1-6}$alkoxy.

In certain embodiments, R³ is selected from the group consisting of:

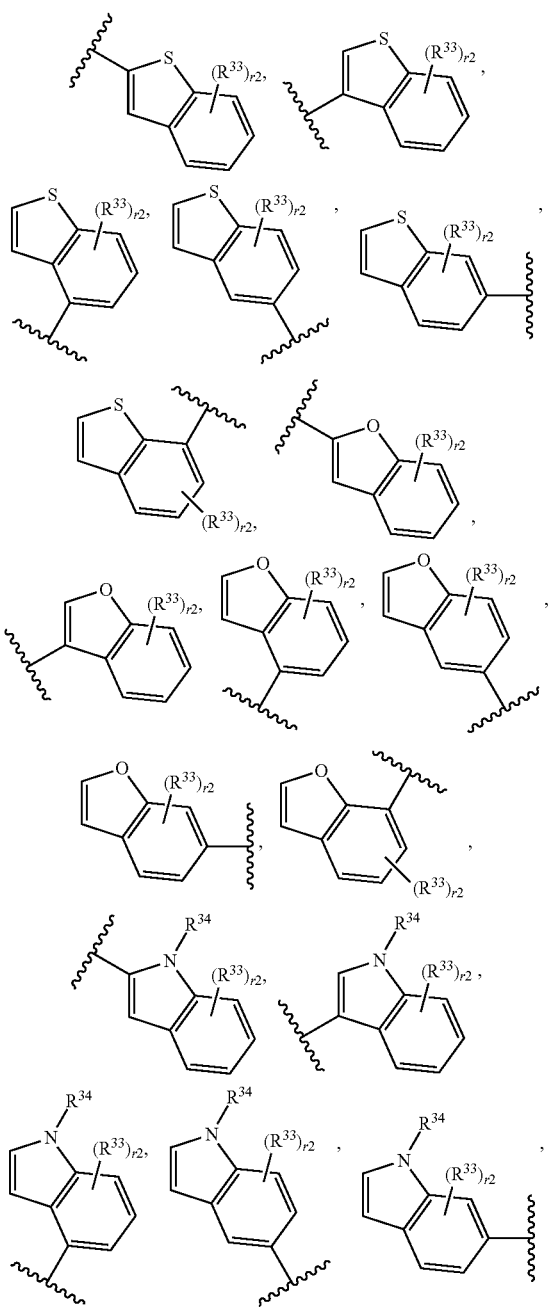

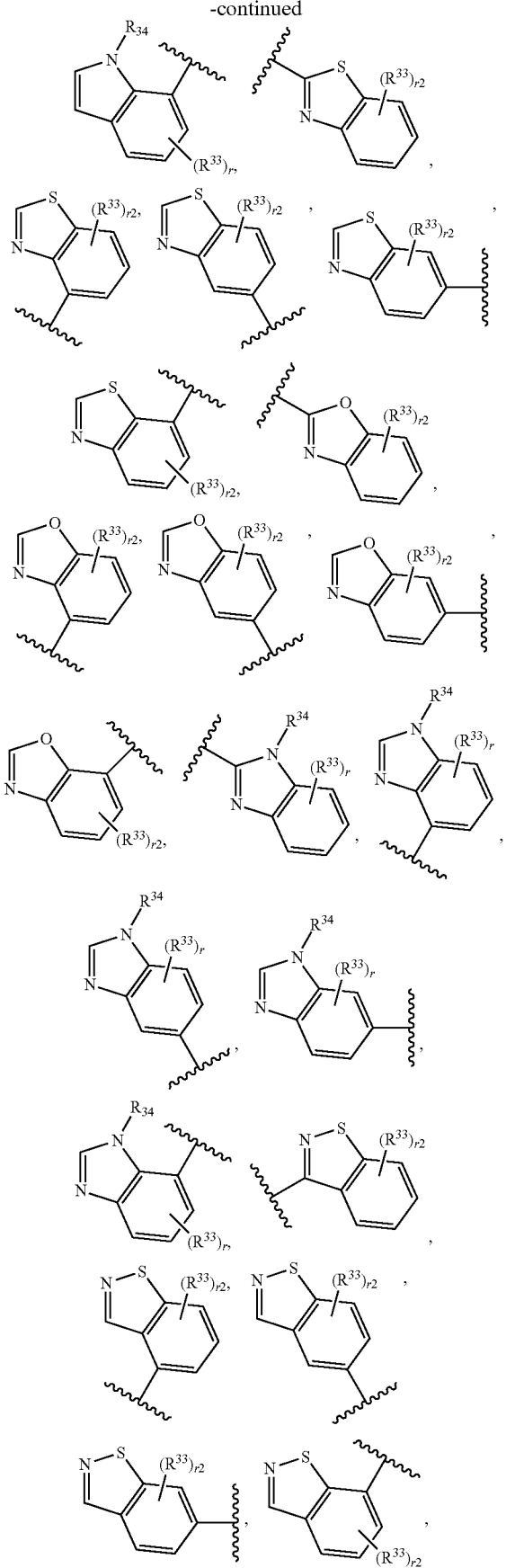
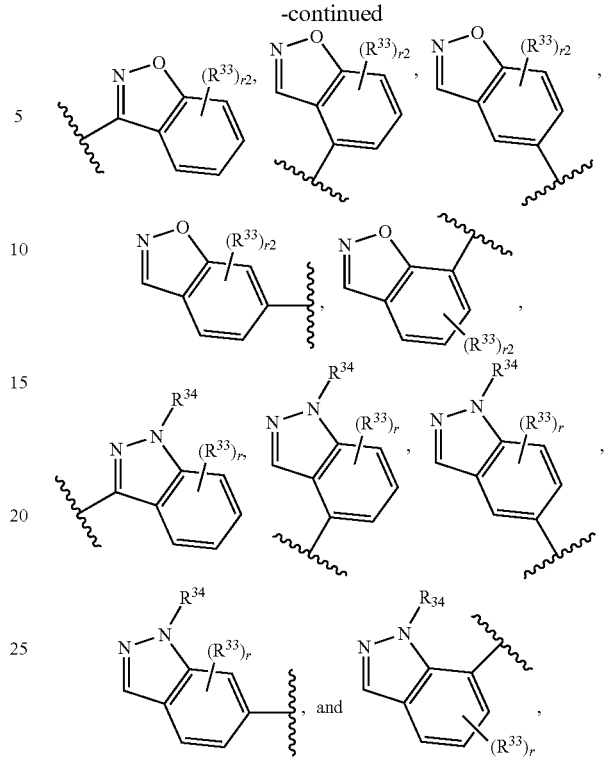

wherein:

R[33] is independently selected for each occurrence from the group consisting of: halo, —OH, —CN, —NO$_2$, oxo, hydrazino, formyl, azido, silyl, siloxy, —S(O)$_q$—C$_{1-6}$alkyl, —NR$^a$R$^b$, —NR$^c$—S(O)$_t$—C$_{1-6}$alkyl, —S(O)$_t$—NR$^a$R$^b$, C$_{1-6}$alkyl, C$_{2-6}$alkenyl, C$_{2-6}$alkynyl, C$_{3-6}$cycloalkyl, haloC$_{1-6}$alkyl, hydroxyC$_{1-6}$alkyl, R$^a$R$^b$N—C$_{1-6}$alkyl-, C$_{1-6}$alkoxy, haloC$_{1-6}$alkoxy, hydroxyC$_{1-6}$alkoxy-, R$^a$R$^b$N—C$_{1-6}$alkoxy-, C$_{1-6}$alkoxyC$_{1-6}$alkyl, —C(O)NR$^a$R$^b$, —C(O)—C$_{1-6}$alkyl, —C(O)OH, and —C(O)O—C$_{1-6}$alkyl, phenyl, and a 5-6 membered monocyclic heteroaryl having one, two, or three heteroatoms selected from the group consisting of O, N, and S, wherein the phenyl or 5-6 membered monocyclic heteroaryl is optionally substituted with one, two or three substituents independently selected from the group consisting of: halo, —OH, —CN, —NO$_2$, oxo, hydrazino, formyl, azido, silyl, siloxy, —S(O)$_q$—C$_{1-6}$alkyl, —NR$^a$R$^b$, —NR$^c$—S(O)$_t$—C$_{1-6}$alkyl, —S(O)$_t$—NR$^a$R$^b$, C$_{1-6}$alkyl, C$_{2-6}$alkenyl, C$_{2-6}$alkynyl, C$_{3-6}$cycloalkyl, haloC$_{1-6}$alkyl, hydroxyC$_{1-6}$ alkyl, R$^a$R$^b$N—C$_{1-6}$alkyl-, C$_{1-6}$alkoxy, haloC$_{1-6}$alkoxy, hydroxyC$_{1-6}$alkoxy-, R$^a$R$^b$N—C$_{1-6}$alkoxy-C$_{1-6}$alkoxyC$_{1-6}$alkyl, —C(O)NR$^a$R$^b$, —C(O)—C$_{1-6}$alkyl, —C(O)OH, and —C(O)O—C$_{1-6}$alkyl;

R[34] is independently selected from the group consisting of hydrogen and C$_{1-4}$alkyl;

r is 0, 1 or 2;

r2 is 0, 1, 2 or 3; and the 5-6 membered monocyclic heteroaryl having one, two, or three heteroatoms each selected from O, N, and S, is selected from the group consisting of: furanyl, thienyl, pyrrolyl, thiazolyl, oxazolyl, isothiazolyl, isoxazolyl, imidazolyl, pyrazolyl, 1H-1,2,3-triazolyl, 2H-1,2,3-triazolyl, 1,2,4-triazolyl, pyridinyl, pyridazinyl, pyrimidinyl, pyrazinyl, 1,3,5-triazinyl, 1,2,4-triazinyl, 1,2,3-triazinyl, 1,2,4-oxadiazolyl, 1,3,4-oxadiazolyl, 1,2,5-oxadiazolyl, 1,2,4-thiadiazolyl, 1,3,4-thiadiazolyl and 1,2,5-thiadiazolyl;

with the provisos that:
when R³ is thiophen-2-yl or furan-2-yl, r2 is 1, 2 or 3;
when R³ is pyrazol-4-yl, in at least one instance, R³³ is other than C₁₋₆ alkyl; and
when R³ is phenyl, at least one of R³⁵, R³⁶ and R³⁷ is other than halo and C₁₋₆alkoxy.

In certain embodiments, R³ is selected from the group consisting of:

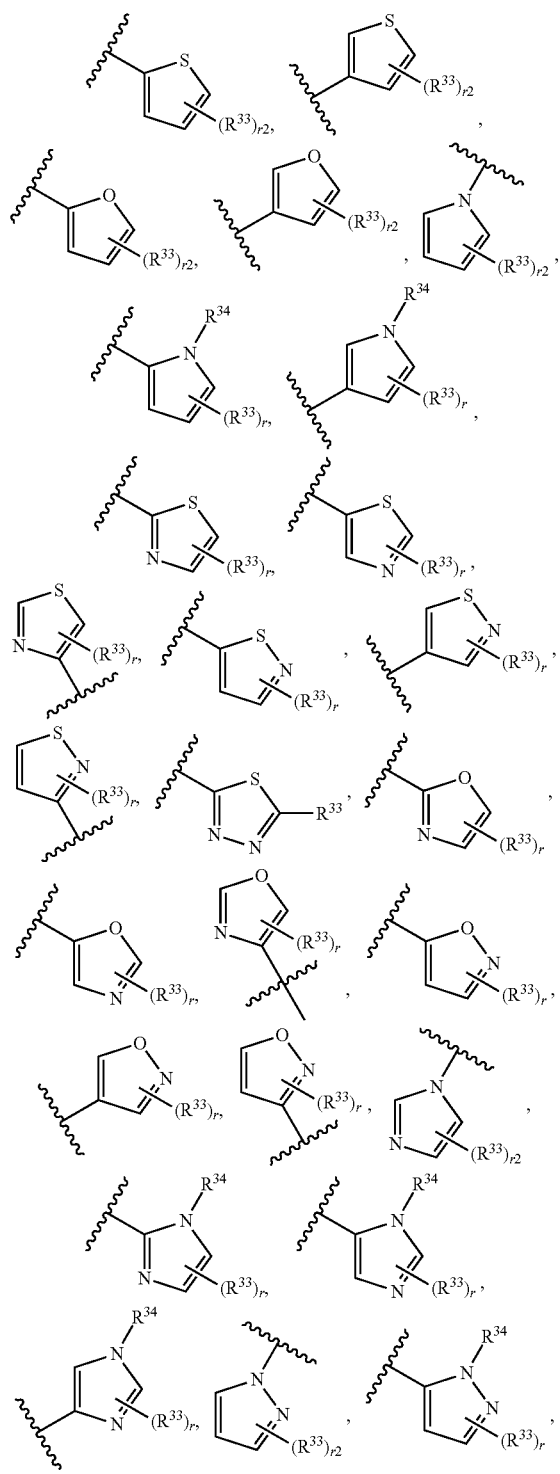

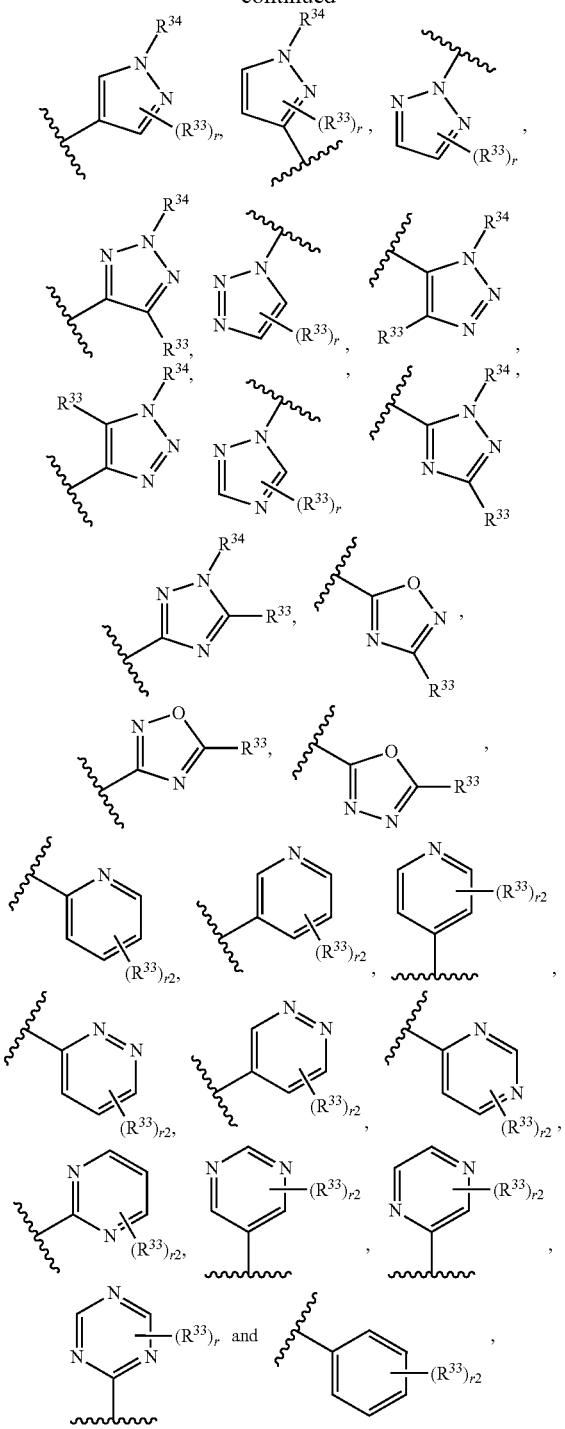

wherein:
R³³ is independently selected for each occurrence from the group consisting of: halo, —OH, —CN, —NO₂, Oxo, hydrazino, formyl, azido, silyl, siloxy, —S(O)$_q$—C₁₋₆alkyl, —NR$^a$R$^b$, —NR$^c$—S(O)$_t$—C₁₋₆alkyl, —S(O)$_t$—NR$^a$R$^b$, C₁₋₆alkyl, C₂₋₆alkenyl, C₂₋₆alkynyl, C₃₋₆cycloalkyl, haloC₁₋₆alkyl, hydroxyC₁₋₆alkyl, R$^a$R$^b$N—C₁₋₆alkyl-, C₁₋₆alkoxy, haloC₁₋₆alkoxy, hydroxyC₁₋₆alkoxy-, R$^a$R$^b$N—C₁₋₆alkoxy-, C₁₋₆alkoxyC₁₋₆alkyl, —C(O)NR$^a$R$^b$, —C(O)—C₁₋₆alkyl, —C(O)OH, and —C(O)O—C₁₋₆alkyl, phenyl, and a 5-6 membered monocyclic heteroaryl having one, two, or three heteroatoms selected from the group consisting of O, N, and S, wherein the phenyl or 5-6 membered monocyclic heteroaryl is optionally substituted with one, two or three substituents independently selected from the group consisting of: halo, —OH, —CN, —NO$_2$, oxo, hydrazino, formyl, azido, silyl, siloxy, —S(O)$_q$—C$_{1-6}$alkyl, —NR$^a$R$^b$, —NR$^c$—S(O)$_t$—C$_{1-6}$alkyl, —S(O)$_t$—NR$^a$R$^b$, C$_{1-6}$alkyl, C$_{2-6}$alkenyl, C$_{2-6}$alkynyl, C$_{3-6}$cycloalkyl, haloC$_{1-6}$alkyl, hydroxyC$_{1-6}$ alkyl, R$^a$R$^b$N—C$_{1-6}$alkyl-, C$_{1-6}$alkoxy, haloC$_{1-6}$alkoxy, hydroxyC$_{1-6}$alkoxy-, R$^a$R$^b$N—C$_{1-6}$alkoxy-, C$_{1-6}$alkoxyC$_{1-6}$alkyl, —C(O)NR$^a$R$^b$, —C(O)—C$_{1-6}$alkyl, —C(O)OH, and —C(O)O—C$_{1-6}$alkyl;

R$^{34}$ is independently selected from the group consisting of hydrogen and C$_{1-4}$alkyl;

r is 0, 1 or 2; and r2 is 0, 1, 2 or 3;

with the provisos that:

when R$^3$ is thiophen-2-yl or furan-2-yl, r2 is 1, 2 or 3;

when R$^3$ is pyrazol-4-yl, in at least one instance, R$^{33}$ is other than C$_{1-6}$ alkyl; and when R$^3$ is phenyl, at least one of R$^{35}$, R$^{36}$ and R$^{37}$ is other than halo and C$_{1-6}$alkoxy.

In certain embodiments, R$^3$ is selected from the group consisting of:

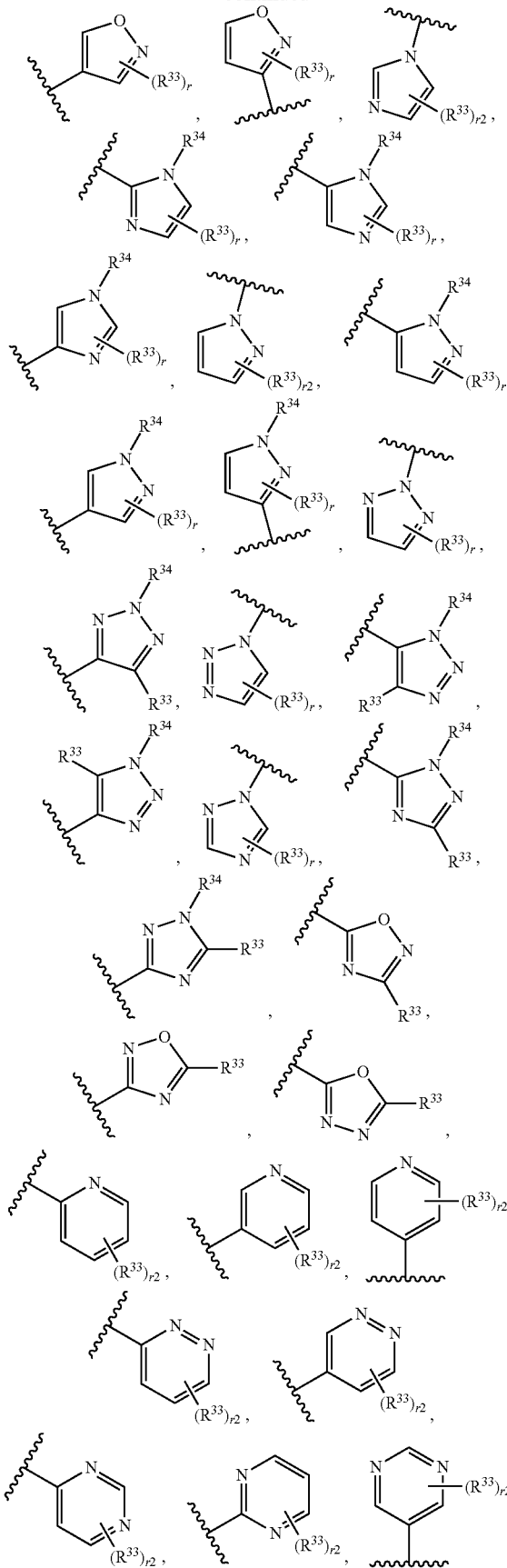

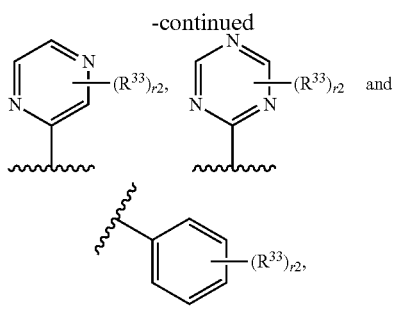
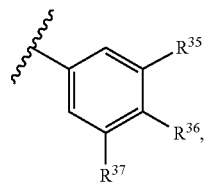

wherein:

$R^{33}$ is independently selected for each occurrence from the group consisting of: halo, —OH, —CN, —NO$_2$, oxo, hydrazino, formyl, azido, silyl, siloxy, —S(O)$_q$—C$_{1-6}$alkyl, —NR$^a$R$^b$, —NR$^c$—S(O)$_t$—C$_{1-6}$alkyl, —S(O)$_t$—NR$^a$R$^b$, C$_{1-6}$alkyl, C$_{2-6}$alkenyl, C$_{2-6}$alkynyl, C$_{3-6}$cycloalkyl, haloC$_{1-6}$alkyl, hydroxyC$_{1-6}$alkyl, R$^a$R$^b$N—C$_{1-6}$alkyl-, C$_{1-6}$alkoxy, haloC$_{1-6}$alkoxy, hydroxyC$_{1-6}$alkoxy-, R$^a$R$^b$N—C$_{1-6}$alkoxy-, C$_{1-6}$alkoxyC$_{1-6}$alkyl, —C(O)NR$^a$R$^b$, —C(O)—C$_{1-6}$alkyl, —C(O)OH, and —C(O)O—C$_{1-6}$alkyl, phenyl, and a 5-6 membered monocyclic heteroaryl having one, two, or three heteroatoms selected from the group consisting of O, N, and S, wherein the phenyl or 5-6 membered monocyclic heteroaryl is optionally substituted with one, two or three substituents independently selected from the group consisting of: halo, —OH, —CN, —NO$_2$, oxo, hydrazino, formyl, azido, silyl, siloxy, —S(O)$_q$—C$_{1-6}$alkyl, —NR$^a$R$^b$, —NR$^c$—S(O)$_t$—C$_{1-6}$alkyl, —S(O)$_t$—NR$^a$R$^b$, C$_{1-6}$alkyl, C$_{2-6}$alkenyl, C$_{2-6}$alkynyl, C$_{3-6}$cycloalkyl, haloC$_{1-6}$alkyl, hydroxyC$_{1-6}$ alkyl, R$^a$R$^b$N—C$_{1-6}$alkyl-, C$_{1-6}$alkoxy, haloC$_{1-6}$alkoxy, hydroxyC$_{1-6}$alkoxy-, R$^a$R$^b$N—C$_{1-6}$alkoxy-, C$_{1-6}$alkoxyC$_{1-6}$alkyl, —C(O)NR$^a$R$^b$, —C(O)—C$_{1-6}$alkyl, —C(O)OH, and —C(O)O—C$_{1-6}$alkyl;

$R^{34}$ is independently selected from the group consisting of hydrogen and C$_{1-4}$alkyl;

r is 0, 1 or 2;

r2 is 0, 1, 2 or 3; and the 5-6 membered monocyclic heteroaryl having one, two, or three heteroatoms each selected from O, N, and S, is selected from the group consisting of: furanyl, thienyl, pyrrolyl, thiazolyl, oxazolyl, isothiazolyl, isoxazolyl, imidazolyl, pyrazolyl, 1H-1,2,3-triazolyl, 2H-1,2,3-triazolyl, 1,2,4-triazolyl, pyridinyl, pyridazinyl, pyrimidinyl, pyrazinyl, 1,3,5-triazinyl, 1,2,4-triazinyl, 1,2,3-triazinyl, 1,2,4-oxadiazolyl, 1,3,4-oxadiazolyl, 1,2,5-oxadiazolyl, 1,2,4-thiadiazolyl, 1,3,4-thiadiazolyl and 1,2,5-thiadiazolyl;

with the provisos that:
when $R^3$ is thiophen-2-yl or furan-2-yl, r2 is 1, 2 or 3;
when $R^3$ is pyrazol-4-yl, in at least one instance, $R^{33}$ is other than C$_{1-6}$ alkyl; and
when $R^3$ is phenyl, at least one of $R^{35}$, $R^{36}$ and $R^{37}$ is other than halo and C$_{1-6}$alkoxy.

In certain embodiments, $R^3$ is

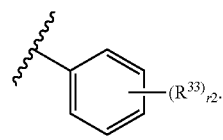

In certain embodiments, $R^3$ is

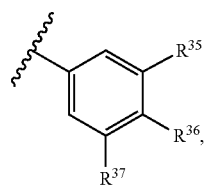

wherein:

$R^{35}$, $R^{36}$ and $R^{37}$ are independently selected from the group consisting of: hydrogen, halo, —OH, —CN, —NO$_2$, oxo, hydrazino, formyl, azido, silyl, siloxy, —S(O)$_q$—C$_{1-6}$alkyl, —NR$^a$R$^b$, —NR$^c$—S(O)$_t$—C$_{1-6}$alkyl, —S(O)$_t$—NR$^a$R$^b$, C$_{1-6}$alkyl, C$_{2-6}$alkenyl, C$_{2-6}$alkynyl, C$_{3-6}$cycloalkyl, haloC$_{1-6}$alkyl, hydroxyC$_{1-6}$alkyl, R$^a$R$^b$N—C$_{1-6}$alkyl-, C$_{1-6}$alkoxy, haloC$_{1-6}$alkoxy, hydroxyC$_{1-6}$alkoxy-, R$^a$R$^b$N—C$_{1-6}$alkoxy-, C$_{1-6}$alkoxyC$_{1-6}$alkyl, —C(O)NR$^a$R$^b$, —C(O)—C$_{1-6}$alkyl, —C(O)OH, and —C(O)O—C$_{1-6}$alkyl, phenyl, and a 5-6 membered monocyclic heteroaryl having one, two, or three heteroatoms selected from the group consisting of O, N, and S, wherein the phenyl or 5-6 membered monocyclic heteroaryl is optionally substituted with one, two or three substituents independently selected from the group consisting of: halo, —OH, —CN, —NO$_2$, oxo, hydrazino, formyl, azido, silyl, siloxy, —S(O)$_q$—C$_{1-6}$alkyl, —NR$^a$R$^b$, —NR$^c$—S(O)$_t$—C$_{1-6}$alkyl, —S(O)$_t$—NR$^a$R$^b$, C$_{1-6}$alkyl, C$_{2-6}$alkenyl, C$_{2-6}$alkynyl, C$_{3-6}$cycloalkyl, haloC$_{1-6}$alkyl, hydroxyC$_{1-6}$ alkyl, R$^a$R$^b$N—C$_{1-6}$alkyl-, C$_{1-6}$alkoxy, haloC$_{1-6}$alkoxy, hydroxyC$_{1-6}$alkoxy-, R$^a$R$^b$N—C$_{1-6}$alkoxy-, C$_{1-6}$alkoxyC$_{1-6}$alkyl, —C(O)NR$^a$R$^b$, —C(O)—C$_{1-6}$alkyl, —C(O)OH, and —C(O)O—C$_{1-6}$alkyl.

In certain embodiments, $R^3$ is

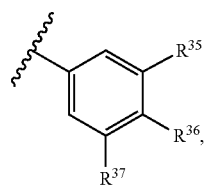

wherein:

$R^{35}$, $R^{36}$ and $R^{37}$ are independently selected from the group consisting of hydrogen, hydroxy, cyano, carboxy, carbamoyl, haloC$_{1-4}$alkyl, haloC$_{1-4}$alkoxy, carboxyC$_{1-4}$alkoxy, R$^a$R$^b$N—C$_{1-4}$alkoxy, C$_{1-4}$alkoxycarbonyl, thienyl, thiazolyl, pyrazolyl optionally substituted with C$_{1-4}$alkyl, and imidazolyl optionally substituted with C$_{1-4}$alkyl.

In certain embodiments, $R^3$ is

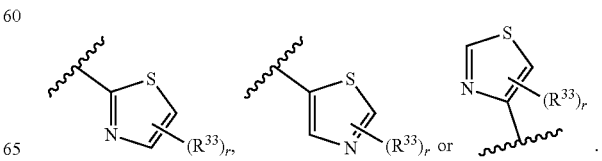

In certain embodiments, $R^3$ is

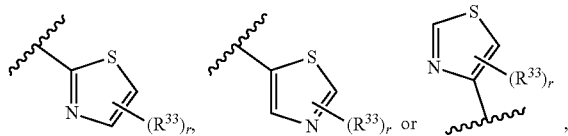

wherein:
$R^{33}$ is independently selected for each occurrence from the group consisting of: halo, $C_{1-4}$alkyl, halo$C_{1-4}$alkyl, $C_{1-4}$alkoxy, $R^aR^bN$—$C_{1-4}$alkoxy, benzyl, thienyl, thiazolyl, pyrazolyl optionally substituted with $C_{1-4}$alkyl, imidazolyl optionally substituted with $C_{1-4}$ alkyl, phenyl, pyridyl, and pyrimidinyl, wherein the phenyl, pyridyl and pyrimidinyl are optionally substituted with one or two substituents independently selected from the group consisting of halo, $C_{1-4}$alkyl, halo$C_{1-4}$alkyl, $C_{1-4}$alkoxy, and $C_{1-4}$alkylsulfonylamino.

In certain embodiments, $R^3$ is

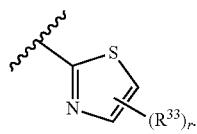

In certain embodiments, $R^3$ is

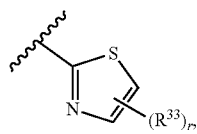

wherein:
$R^{33}$ is independently selected for each occurrence from the group consisting of: halo, $C_{1-4}$alkyl, halo$C_{1-4}$alkyl, $C_{1-4}$alkoxy, $R^aR^bN$—$C_{1-4}$alkoxy, benzyl, thienyl, thiazolyl, pyrazolyl optionally substituted with $C_{1-4}$alkyl, imidazolyl optionally substituted with $C_{1-4}$ alkyl, phenyl, pyridyl, and pyrimidinyl, wherein the phenyl, pyridyl and pyrimidinyl are optionally substituted with one or two substituents independently selected from the group consisting of halo, $C_{1-4}$alkyl, halo$C_{1-4}$alkyl, $C_{1-4}$alkoxy, and $C_{1-4}$alkylsulfonylamino.

In certain embodiments, $R^3$ is

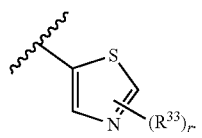

In certain embodiments, $R^3$ is

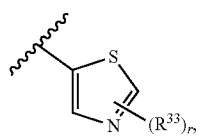

wherein:
$R^{33}$ is independently selected for each occurrence from the group consisting of: halo, $C_{1-4}$alkyl, halo$C_{1-4}$alkyl, $C_{1-4}$alkoxy, $R^aR^bN$—$C_{1-4}$alkoxy, benzyl, thienyl, thiazolyl, pyrazolyl optionally substituted with $C_{1-4}$alkyl, imidazolyl optionally substituted with $C_{1-4}$ alkyl, phenyl, pyridyl, and pyrimidinyl, wherein the phenyl, pyridyl and pyrimidinyl are optionally substituted with one or two substituents independently selected from the group consisting of halo, $C_{1-4}$alkyl, halo$C_{1-4}$alkyl, $C_{1-4}$alkoxy, and $C_{1-4}$alkylsulfonylamino.

In certain embodiments, $R^3$ is

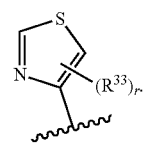

In certain embodiments, $R^3$ is

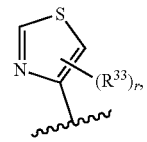

wherein:
$R^{33}$ is independently selected for each occurrence from the group consisting of: halo, $C_{1-4}$alkyl, halo$C_{1-4}$alkyl, $C_{1-4}$alkoxy, $R^aR^bN$—$C_{1-4}$alkoxy, benzyl, thienyl, thiazolyl, pyrazolyl optionally substituted with $C_{1-4}$alkyl, imidazolyl optionally substituted with $C_{1-4}$ alkyl, phenyl, pyridyl, and pyrimidinyl, wherein the phenyl, pyridyl and pyrimidinyl are optionally substituted with one or two substituents independently selected from the group consisting of halo, $C_{1-4}$alkyl, halo$C_{1-4}$alkyl, $C_{1-4}$alkoxy, and $C_{1-4}$alkylsulfonylamino.

In certain embodiments, $R^3$ is

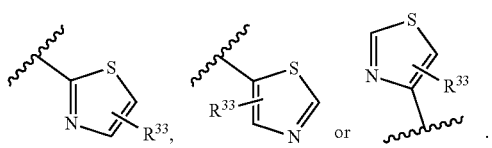

In certain embodiments, $R^3$ is

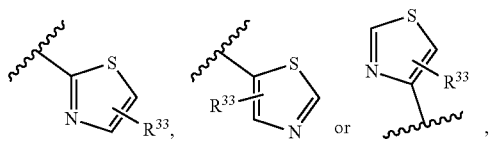

wherein:
$R^{33}$ is selected from the group consisting of: hydrogen, halo, $C_{1-4}$alkyl, halo$C_{1-4}$ alkyl, $C_{1-4}$alkoxy, $R^aR^bN$—$C_{1-4}$alkoxy, benzyl, thienyl, thiazolyl, pyrazolyl optionally substituted with $C_{1-4}$alkyl, imidazolyl optionally substituted with $C_{1-4}$alkyl, phenyl, pyridyl, and pyrimidinyl, wherein the phenyl, pyridyl and pyrimidinyl are optionally substituted with one or two substituents independently selected from the group consisting of halo, $C_{1-4}$alkyl, halo$C_{1-4}$alkyl, $C_{1-4}$alkoxy, and $C_{1-4}$alkylsulfonylamino.

In certain embodiments, $R^3$ is

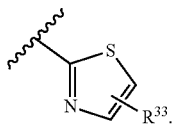

In certain embodiments, $R^3$ is

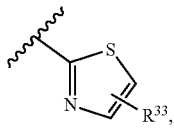

wherein
$R^{33}$ is selected from the group consisting of: hydrogen, halo, $C_{1-4}$alkyl, halo$C_{1-4}$ alkyl, $C_{1-4}$alkoxy, $R^aR^bN$—$C_{1-4}$alkoxy, benzyl, thienyl, thiazolyl, pyrazolyl optionally substituted with $C_{1-4}$alkyl, imidazolyl optionally substituted with $C_{1-4}$alkyl, phenyl, pyridyl, and pyrimidinyl, wherein the phenyl, pyridyl and pyrimidinyl are optionally substituted with one or two substituents independently selected from the group consisting of halo, $C_{1-4}$alkyl, halo$C_{1-4}$alkyl, $C_{1-4}$alkoxy, and $C_{1-4}$alkylsulfonylamino.

In certain embodiments, $R^3$ is

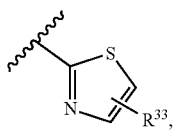

wherein:
$R^{33}$ is selected from the group consisting of: hydrogen, halo, $C_{1-4}$alkyl, halo$C_{1-4}$ alkyl, thienyl, thiazolyl, pyrazolyl, 1-methylpyrazolyl, pyridinyl optionally substituted with halo, and phenyl optionally substituted with one or two substituents independently selected from the group consisting of halo and $C_{1-4}$alkoxy.

In certain embodiments, $R^3$ is:

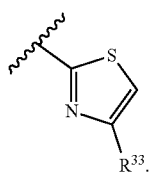

In certain embodiments, $R^3$ is

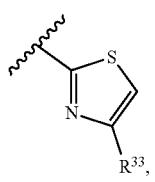

wherein:
$R^{33}$ is selected from the group consisting of: hydrogen, halo, $C_{1-4}$alkyl, halo$C_{1-4}$ alkyl, $C_{1-4}$alkoxy, $R^aR^bN$—$C_{1-4}$alkoxy, benzyl, thienyl, thiazolyl, pyrazolyl optionally substituted with $C_{1-4}$alkyl, imidazolyl optionally substituted with $C_{1-4}$alkyl, phenyl, pyridyl, and pyrimidinyl, wherein the phenyl, pyridyl and pyrimidinyl are optionally substituted with one or two substituents independently selected from the group consisting of halo, $C_{1-4}$alkyl, halo$C_{1-4}$alkyl, $C_{1-4}$alkoxy, and $C_{1-4}$alkylsulfonylamino.

In certain embodiments, $R^3$ is

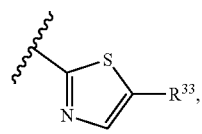

In certain embodiments, $R^3$ is:

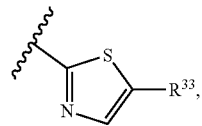

wherein:
$R^{33}$ is selected from the group consisting of: hydrogen, halo, $C_{1-4}$alkyl, halo$C_{1-4}$ alkyl, $C_{1-4}$alkoxy, $R^aR^bN$—$C_{1-4}$alkoxy, benzyl, thienyl, thiazolyl, pyrazolyl optionally substituted with $C_{1-4}$alkyl, imidazolyl optionally substituted with $C_{1-4}$alkyl, phenyl, pyridyl, and pyrimidinyl, wherein the phenyl, pyridyl and pyrimidinyl are optionally substituted with one or two substituents independently selected from the group consisting of halo, $C_{1-4}$alkyl, halo$C_{1-4}$alkyl, $C_{1-4}$alkoxy, and $C_{1-4}$alkylsulfonylamino.

In certain embodiments, $R^3$ is

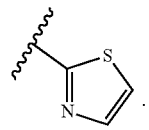

In certain embodiments, $R^3$ is

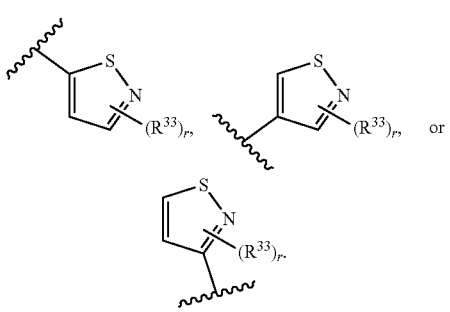

In certain embodiments, $R^3$ is

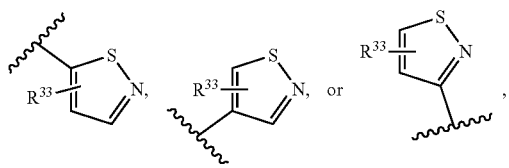

wherein:
$R^{33}$ is selected from the group consisting of hydrogen, methyl and halide.

In certain embodiments, $R^3$ is

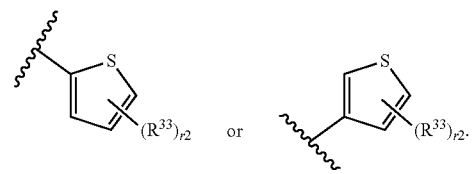

In certain embodiments, $R^3$ is:

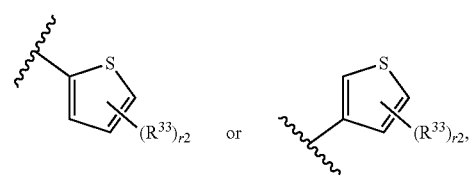

wherein:
$R^{33}$ is independently selected for each occurrence from the group consisting of: halo, $C_{1-4}$-alkyl, halo$C_{1-4}$alkyl, $C_{1-4}$alkoxy, $R^aR^bN$—$C_{1-4}$alkoxy, benzyl, thienyl, thiazolyl, pyrazolyl optionally substituted with $C_{1-4}$alkyl or hydroxy$C_{1-4}$alkyl, imidazolyl optionally substituted with $C_{1-4}$alkyl, phenyl, pyridyl, and pyrimidinyl, wherein the phenyl, pyridyl and pyrimidinyl are optionally substituted with one or two substituents independently selected from the group consisting of halo, $C_{1-4}$alkyl, halo$C_{1-4}$alkyl, $C_{1-4}$alkoxy, and $C_{1-4}$alkylsulfonylamino.

In certain embodiments, $R^3$ is

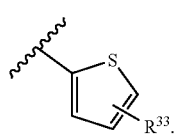

In certain embodiments, $R^3$ is

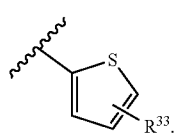

wherein:
$R^{33}$ is selected from the group consisting of: halo, $C_{1-4}$alkyl, halo$C_{1-4}$alkyl, $C_{1-4}$ alkoxy, $R^aR^bN$—$C_{1-4}$alkoxy, benzyl, thienyl, thiazolyl, pyrazolyl optionally substituted with $C_{1-4}$alkyl or hydroxy$C_{1-4}$alkyl, imidazolyl optionally substituted with $C_{1-4}$alkyl, phenyl, pyridyl, and pyrimidinyl, wherein the phenyl, pyridyl and pyrimidinyl are optionally substituted with one or two substituents independently selected from the group consisting of halo, $C_{1-4}$alkyl, halo$C_{1-4}$alkyl, $C_{1-4}$alkoxy, and $C_{1-4}$alkylsulfonylamino.

In certain embodiments, $R^3$ is

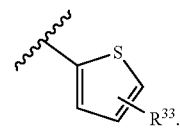

wherein:
$R^{33}$ is selected from the group consisting of: halo, $C_{1-4}$alkyl, $R^aR^bN$—$C_{1-4}$alkoxy, thienyl, pyrimidinyl, pyrazolyl, 1-methylpyrazolyl, benzyl, pyridinyl optionally substituted with halo or halo$C_{1-4}$alkyl, and phenyl optionally substituted with one or two substituents independently selected from the group consisting of halo, cyano, $C_{1-4}$alkoxy, halo$C_{1-4}$alkyl and $C_{1-4}$alkylsulfonylamino.

In certain embodiments, $R^3$ is

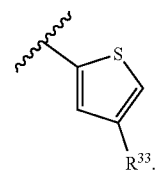

In certain embodiments, $R^3$ is

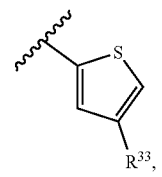

wherein:
$R^{33}$ is selected from the group consisting of: halo, $C_{1-4}$alkyl, halo$C_{1-4}$alkyl, $C_{1-4}$ alkoxy, $R^aR^bN$—$C_{1-4}$alkoxy, benzyl, thienyl, thiazolyl, pyrazolyl optionally substituted with $C_{1-4}$alkyl or hydroxy$C_{1-4}$alkyl, imidazolyl optionally substituted with $C_{1-4}$alkyl, phenyl, pyridyl, and pyrimidinyl, wherein the phenyl, pyridyl and pyrimidinyl are optionally substituted with one or two substituents independently selected from the group consisting of halo, $C_{1-4}$alkyl, halo$C_{1-4}$alkyl, $C_{1-4}$alkoxy, and $C_{1-4}$alkylsulfonylamino.

In certain embodiments, $R^3$ is

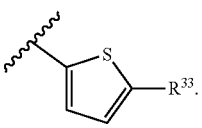

In certain embodiments, $R^3$ is

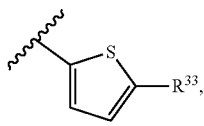

wherein:
$R^{33}$ is selected from the group consisting of: halo, $C_{1-4}$alkyl, haloC$_{1-4}$alkyl, $C_{1-4}$ alkoxy, $R^aR^bN$—$C_{1-4}$alkoxy, benzyl, thienyl, thiazolyl, pyrazolyl optionally substituted with $C_{1-4}$alkyl or hydroxyC$_{1-4}$alkyl, imidazolyl optionally substituted with $C_{1-4}$alkyl, phenyl, pyridyl, and pyrimidinyl, wherein the phenyl, pyridyl and pyrimidinyl are optionally substituted with one or two substituents independently selected from the group consisting of halo, $C_{1-4}$alkyl, haloC$_{1-4}$alkyl, $C_{1-4}$alkoxy, and $C_{1-4}$alkylsulfonylamino.

In certain embodiments, $R^3$ is

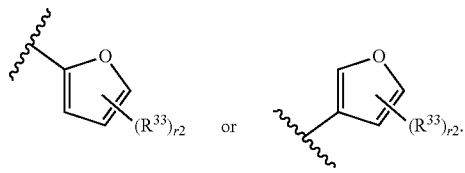

In certain embodiments,

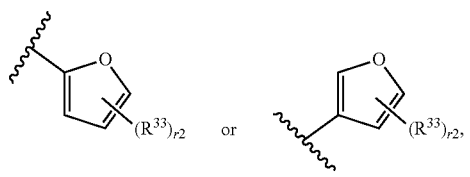

wherein
$R^{33}$ is independently selected for each occurrence from the group consisting of: halo, $C_{1-4}$ alkyl, haloC$_{1-4}$ alkyl, $C_{1-4}$ alkoxy, $R^aR^bN$—$C_{1-4}$ alkoxy, benzyl, thienyl, pyrazolyl optionally substituted with $C_{1-4}$alkyl, imidazolyl optionally substituted with $C_{1-4}$alkyl, phenyl, pyridyl, and pyrimidinyl, wherein the phenyl, pyridyl and pyrimidinyl are optionally substituted with one or two substituents independently selected from the group consisting of halo, $C_{1-4}$alkyl, haloC$_{1-4}$alkyl, $C_{1-4}$ alkoxy, and $C_{1-4}$ alkylsulfonylamino.

In certain embodiments, $R^3$ is

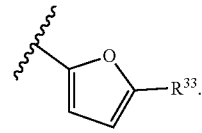

wherein:
$R^{33}$ is selected from the group consisting of: halo, $C_{1-4}$alkyl, haloC$_{1-4}$alkyl, $C_{1-4}$ alkoxy, $R^aR^bN$—$C_{1-4}$alkoxy, benzyl, thienyl, pyrazolyl optionally substituted with $C_{1-4}$alkyl, imidazolyl optionally substituted with $C_{1-4}$alkyl, phenyl, pyridyl, and pyrimidinyl, wherein the phenyl, pyridyl and pyrimidinyl are optionally substituted with one or two substituents independently selected from the group consisting of halo, $C_{1-4}$alkyl, haloC$_{1-4}$alkyl, $C_{1-4}$alkoxy, and $C_{1-4}$alkylsulfonylamino.

In certain embodiments, $R^3$ is

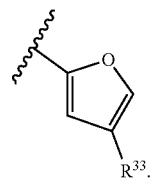

In certain embodiments, $R^3$ is

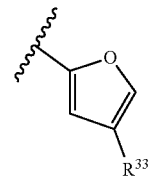

wherein:
$R^{33}$ is selected from the group consisting of halo, $C_{1-4}$alkyl, haloC$_{1-4}$alkyl, $C_{1-4}$ alkoxy, $R^aR^bN$—$C_{1-4}$alkoxy, benzyl, thienyl, thiazolyl, pyrazolyl optionally substituted with $C_{1-4}$alkyl, imidazolyl optionally substituted with $C_{1-4}$alkyl, phenyl, pyridyl, and pyrimidinyl, wherein the phenyl, pyridyl and pyrimidinyl are optionally substituted with one or two substituents independently selected from the group consisting of halo, $C_{1-4}$alkyl, haloC$_{1-4}$ alkyl, $C_{1-4}$alkoxy, and $C_{1-4}$alkylsulfonylamino.

In certain embodiments, $R^3$ is R

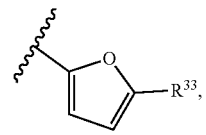

In certain embodiments, $R^3$ is

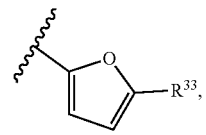

wherein:
$R^{33}$ is selected from the group consisting of: halo, $C_{1-4}$alkyl, haloC$_{1-4}$alkyl, $C_{1-4}$ alkoxy, $R^aR^bN$—$C_{1-4}$alkoxy, benzyl, thienyl, thiazolyl, pyrazolyl optionally substituted with $C_{1-4}$alkyl, imidazolyl optionally substituted with $C_{1-4}$alkyl, phenyl, pyridyl, and pyrimidinyl, wherein the phenyl, pyridyl and pyrimidinyl are optionally substituted with one or two substituents independently selected from the group consisting of halo, $C_{1-4}$alkyl, haloC$_{1-4}$ alkyl, $C_{1-4}$alkoxy, and $C_{1-4}$alkylsulfonylamino.

In certain embodiments, $R^{33}$ for each occurrence is selected from the group consisting of: halo, $C_{1-4}$alkyl, haloC$_{1-4}$alkyl, $C_{1-4}$alkoxy, hydroxyC$_{1-4}$alkoxy, $R^aR^bN$—$C_{1-4}$ alkoxy, benzyl, thienyl, thiazolyl, pyrazolyl, imidazolyl, phenyl, pyridyl, and pyrimidinyl, wherein the benzyl, thienyl, thiazolyl, pyrazolyl, imidazolyl, phenyl, pyridyl, and pyrimidinyl are optionally substituted with one or two substituents independently selected from the group consisting of halo, $C_{1-4}$alkyl, halo$C_{1-4}$alkyl, $C_{1-4}$alkoxy, and $C_{1-4}$alkylsulfonylamino.

In certain embodiments, $R^{33}$ for each occurrence is selected from the group consisting of: halo, $C_{1-4}$alkyl, halo$C_{1-4}$alkyl, $C_{1-4}$alkoxy, $R^aR^bN$—$C_{1-4}$alkoxy, benzyl, thienyl, thiazolyl, pyrazolyl optionally substituted with $C_{1-4}$alkyl or hydroxy$C_{1-4}$alkyl, imidazolyl optionally substituted with $C_{1-4}$alkyl, phenyl, pyridyl, and pyrimidinyl, wherein the phenyl, pyridyl and pyrimidinyl are optionally substituted with one or two substituents independently selected from the group consisting of halo, $C_{1-4}$alkyl, halo$C_{1-4}$alkyl, $C_{1-4}$alkoxy, and $C_{1-4}$ alkylsulfonylamino.

In certain embodiments, in one occurrence $R^{33}$ is pyrazolyl or imidazolyl optionally substituted with $C_{1-4}$alkyl.

In certain embodiments, $R^4$ is hydrogen, $C_{2-6}$alkenyl, $C_{2-6}$alkynyl or $C_{1-4}$alkyl optionally substituted with hydroxy, cyano, $C_{1-4}$alkoxy, halo$C_{1-4}$alkoxy, methylsulfonyl, diethylamino, carboxy, carbamoyl, benzyloxy, formyl, methoxyphenyl, pyrrolidinyl, morpholinyl, tetrahydrofuranyl or triazolyl.

In certain embodiments, $R^4$ is hydrogen or $C_{1-6}$alkyl optionally substituted with a substituent selected from the group consisting of $C_{1-6}$alkoxy, —$NR^aR^b$, $C_{2-6}$alkenyl, —OH, —COOH, and $C_{1-6}$haloalkoxy.

In certain embodiments, $R^4$ is $C_{1-6}$alkyl optionally substituted with a substituent selected from the group consisting of $C_{1-6}$alkoxy, —$NR^aR^b$, $C_{2-6}$alkenyl, —OH, —COOH, and $C_{1-6}$ haloalkoxy.

In certain embodiments, $R^4$ is —$CH_2CH_2OCH_3$.
In certain embodiments, $R^4$ is methyl.
In certain embodiments, $R^5$ is hydrogen, $C_{1-4}$alkyl, $C_{1-4}$alkoxy, or $R^aR^bN$—$C_{1-4}$ alkyl.
In certain embodiments, $R^5$ is hydrogen, methyl, methoxyethyl or dimethylaminoethyl.
In certain embodiments, $R^5$ is hydrogen or methyl.
In certain embodiments, $R^5$ is hydrogen.
In certain embodiments, $R^6$ is hydrogen or $C_{1-6}$alkyl;
In certain embodiments, $R^6$ is hydrogen.
In certain embodiments, $R^2$ and $R^6$ are hydrogen.
In certain embodiments, $R^2$ and $R^6$ are hydrogen and w is 2.
In certain embodiments, $R^2$, $R^5$ and $R^6$ are hydrogen.
In certain embodiments, $R^2$, $R^5$ and $R^6$ are hydrogen and w is 2.
In certain embodiments, $R^2$, $R^5$ and $R^6$ are hydrogen and $R^4$ is methyl.
In certain embodiments, $R^2$, $R^5$ and $R^6$ are hydrogen, $R^4$ is methyl, and w is 2.
In certain embodiments, $R^1$ is 3-chloro-4-fluourophenyl and each of $R^2$ and $R^6$ is hydrogen.
In certain embodiments, $R^1$ is 3-chloro-4-fluourophenyl, $R^2$ and $R^6$ are hydrogen, and w is 2.
In certain embodiments, $R^1$ is 3-chloro-4-fluourophenyl and each of $R^2$, $R^5$ and $R^6$ is hydrogen.
In certain embodiments, $R^1$ is 3-chloro-4-fluourophenyl; each of $R^2$, $R^5$ and $R^6$ is hydrogen; and w is 2.
In certain embodiments, $R^1$ is 3-chloro-4-fluourophenyl; each of $R^2$, $R^5$ and $R^6$ is hydrogen; and $R^4$ is methyl.
In certain embodiments, $R^1$ is 3-chloro-4-fluourophenyl; each of $R^2$, $R^5$ and $R^6$ is hydrogen, $R^4$ is methyl, and w is 2.

It will be appreciated that all chemically allowable combinations of the embodiments described above, and elsewhere in this disclosure, are envisioned as further embodiments of the invention.

II. Pharmaceutical Compositions and Kits

In another aspect, the disclosure provides pharmaceutical compositions comprising a compound of Formula I, or a pharmaceutically acceptable salt thereof, and a pharmaceutically acceptable excipient. In particular, the present disclosure provides pharmaceutical compositions comprising compounds as disclosed herein formulated together with one or more pharmaceutically acceptable carriers. These formulations include those suitable for oral, rectal, topical, buccal, parenteral (e.g., subcutaneous, intramuscular, intradermal, or intravenous), rectal, vaginal, or aerosol administration, although the most suitable form of administration in any given case will depend on the degree and severity of the condition being treated and on the nature of the particular compound being used. For example, disclosed compositions may be formulated as a unit dose, and/or may be formulated for oral or subcutaneous administration.

In another aspect, the disclosure provides a pharmaceutical composition comprises a compound of Table 2, or a pharmaceutically acceptable salt and/or stereoisomer thereof.

Exemplary pharmaceutical compositions of this disclosure may be used in the form of a pharmaceutical preparation, for example, in solid, semisolid or liquid form, which contains one or more of the compound of the disclosure, as an active ingredient, in admixture with an organic or inorganic carrier or excipient suitable for external, enteral or parenteral applications. The active ingredient may be compounded, for example, with the usual non-toxic, pharmaceutically acceptable carriers for tablets, pellets, capsules, suppositories, solutions, emulsions, suspensions, and any other form suitable for use. The active object compound is included in the pharmaceutical composition in an amount sufficient to produce the desired effect upon the process or condition of the disease.

For preparing solid compositions such as tablets, the principal active ingredient may be mixed with a pharmaceutical carrier, e.g., conventional tableting ingredients such as corn starch, lactose, sucrose, sorbitol, talc, stearic acid, magnesium stearate, dicalcium phosphate or gums, and other pharmaceutical diluents, e.g., water, to form a solid preformulation composition containing a homogeneous mixture of a compound of the disclosure, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules.

In solid dosage forms for oral administration (capsules, tablets, pills, dragees, powders, granules and the like), the subject composition is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the subject composition moistened with an inert liquid diluent. Tablets, and other solid dosage forms, such as dragees, capsules, pills and granules, may optionally be scored or prepared with coatings and shells, such as enteric coatings and other coatings well known in the pharmaceutical-formulating art.

Compositions for inhalation or insufflation include solutions and suspensions in pharmaceutically acceptable, aqueous or organic solvents, or mixtures thereof, and powders. Liquid dosage forms for oral administration include pharmaceutically acceptable emulsions, microemulsions, solutions, suspensions, syrups and elixirs. In addition to the subject composition, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, cyclodextrins and mixtures thereof.

Suspensions, in addition to the subject composition, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations for rectal or vaginal administration may be presented as a suppository, which may be prepared by mixing a subject composition with one or more suitable non-irritating excipients or carriers comprising, for example, cocoa butter, polyethylene glycol, a suppository wax or a salicylate, and which is solid at room temperature, but liquid at body temperature and, therefore, will melt in the body cavity and release the active agent.

Dosage forms for transdermal administration of a subject composition include powders, sprays, ointments, pastes, creams, lotions, gels, solutions, patches and inhalants. The active component may be mixed under sterile conditions with a pharmaceutically acceptable carrier, and with any preservatives, buffers, or propellants which may be required.

The ointments, pastes, creams and gels may contain, in addition to a subject composition, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays may contain, in addition to a subject composition, excipients such as lactose, talc, silicic acid, aluminum hydroxide, calcium silicates and polyamide powder, or mixtures of these substances. Sprays may additionally contain customary propellants, such as chlorofluorohydrocarbons and volatile unsubstituted hydrocarbons, such as butane and propane.

Compositions and compounds of the present disclosure may alternatively be administered by aerosol. This is accomplished by preparing an aqueous aerosol, liposomal preparation or solid particles containing the compound. A non-aqueous (e.g., fluorocarbon propellant) suspension could be used. Sonic nebulizers may be used because they minimize exposing the agent to shear, which may result in degradation of the compounds contained in the subject compositions. Ordinarily, an aqueous aerosol is made by formulating an aqueous solution or suspension of a subject composition together with conventional pharmaceutically acceptable carriers and stabilizers. The carriers and stabilizers vary with the requirements of the particular subject composition, but typically include non-ionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Pharmaceutical compositions of this disclosure suitable for parenteral administration comprise a subject composition in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and non-aqueous carriers which may be employed in the pharmaceutical compositions of the disclosure include water, ethanol, polyols (such as glycerol, propylene glycol, polyethylene glycol, and the like), and suitable mixtures thereof, vegetable oils, such as olive oil, and injectable organic esters, such as ethyl oleate and cyclodextrins. Proper fluidity may be maintained, for example, by the use of coating materials, such as lecithin, by the maintenance of the required particle size in the case of dispersions, and by the use of surfactants In another aspect, the disclosure provides enteral pharmaceutical formulations including a disclosed compound and an enteric material; and a pharmaceutically acceptable carrier or excipient thereof. Enteric materials refer to polymers that are substantially insoluble in the acidic environment of the stomach, and that are predominantly soluble in intestinal fluids at specific pHs. The small intestine is the part of the gastrointestinal tract (gut) between the stomach and the large intestine, and includes the duodenum, jejunum, and ileum. The pH of the duodenum is about 5.5, the pH of the jejunum is about 6.5 and the pH of the distal ileum is about 7.5. Accordingly, enteric materials are not soluble, for example, until a pH of about 5.0, of about 5.2, of about 5.4, of about 5.6, of about 5.8, of about 6.0, of about 6.2, of about 6.4, of about 6.6, of about 6.8, of about 7.0, of about 7.2, of about 7.4, of about 7.6, of about 7.8, of about 8.0, of about 8.2, of about 8.4, of about 8.6, of about 8.8, of about 9.0, of about 9.2, of about 9.4, of about 9.6, of about 9.8, or of about 10.0. Exemplary enteric materials include cellulose acetate phthalate (CAP), hydroxypropyl methylcellulose phthalate (HPMCP), polyvinyl acetate phthalate (PVAP), hydroxypropyl methylcellulose acetate succinate (HPMCAS), cellulose acetate trimellitate, hydroxypropyl methylcellulose succinate, cellulose acetate succinate, cellulose acetate hexahydrophthalate, cellulose propionate phthalate, cellulose acetate maleate, cellulose acetate butyrate, cellulose acetate propionate, copolymer of methylmethacrylic acid and methyl methacrylate, copolymer of methyl acrylate, methylmethacrylate and methacrylic acid, copolymer of methyl-vinyl ether and maleic anhydride (Gantrez ES series), ethyl methyacrylate-methylmethacrylate-chlorotrimethylammonium ethyl acrylate copolymer, natural resins such as zein, shellac and copal collophorium, and several commercially available enteric dispersion systems (e.g., Eudragit L30D55, Eudragit FS30D, Eudragit L100, Eudragit S100, Kollicoat EMM30D, Estacryl 30D, Coateric, and Aquateric). The solubility of each of the above materials is either known or is readily determinable in vitro. The foregoing is a list of possible materials, but one of skill in the art with the benefit of the disclosure would recognize that it is not comprehensive and that there are other enteric materials that would meet the objectives of the present disclosure.

Advantageously, the disclosure also provides kits for use by a e.g. a consumer in need of HBV infection treatment. Such kits include a suitable dosage form such as those described above and instructions describing the method of using such dosage form to mediate, reduce or prevent HBV infection. The instructions would direct the consumer or medical personnel to administer the dosage form according to administration modes known to those skilled in the art. Such kits could advantageously be packaged and sold in single or multiple kit units. An example of such a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process recesses are formed in the plastic foil. The recesses have the size and shape of the tablets or capsules to be packed. Next, the tablets or capsules are placed in the recesses and the sheet of relatively stiff material is sealed against the plastic foil at the face of the foil which is opposite from the direction in which the recesses were formed. As a result, the tablets or capsules are sealed in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed via said opening.

It may be desirable to provide a memory aid on the kit, e.g., in the form of numbers next to the tablets or capsules whereby the numbers correspond with the days of the regimen which the tablets or capsules so specified should be ingested. Another example of such a memory aid is a calendar printed on the card, e.g., as follows "First Week, Monday, Tuesday, . . . etc. . . . Second Week, Monday, Tuesday, . . . " etc. Other variations of memory aids will be readily apparent. A "daily dose" can be a single tablet or capsule or several pills or capsules to be taken on a given day. Also, a daily dose of a first compound can consist of one tablet or capsule while a daily dose of the second compound can consist of several tablets or capsules and vice versa. The memory aid should reflect this.

III. Methods

In a further aspect, a method for treating a hepatitis B infection in a patient in need thereof is provided, comprising administering to a subject or patient an effective amount of a disclosed compound, and/or administering a first disclosed compound and optionally, an additional, different disclosed compound(s). In another embodiment, a method for treating a hepatitis B infection in a patient in need thereof is provided, comprising administering to a subject or patient a therapeutically effective amount of a disclosed pharmaceutical composition or a pharmaceutical composition comprising a disclosed compound, or two or more disclosed compounds, and a pharmaceutically acceptable excipient.

For use in accordance with this aspect, the appropriate dosage is expected to vary depending on, for example, the particular compound employed, the mode of administration, and the nature and severity of the infection to be treated as well as the specific infection to be treated and is within the purview of the treating physician. Usually, an indicated administration dose may be in the range between about 0.1 to about 1000 µg/kg body weight. In some cases, the administration dose of the compound may be less than 400 µg/kg body weight. In other cases, the administration dose may be less than 200 µg/kg body weight. In yet other cases, the administration dose may be in the range between about 0.1 to about 100 µg/kg body weight. The dose may be conveniently administered once daily, or in divided doses up to, for example, four times a day or in sustained release form.

A compound of the present disclosure may be administered by any conventional route, in particular: enterally, topically, orally, nasally, e.g. in the form of tablets or capsules, via suppositories, or parenterally, e.g. in the form of injectable solutions or suspensions, for intravenous, intramuscular, sub-cutaneous, or intra-peritoneal injection. Suitable formulations and pharmaceutical compositions will include those formulated in a conventional manner using one or more physiologically acceptable carriers or excipients, and any of those known and commercially available and currently employed in the clinical setting. Thus, the compounds may be formulated for oral, buccal, topical, parenteral, rectal or transdermal administration or in a form suitable for administration by inhalation or insufflation (either orally or nasally).

For oral administration, pharmaceutical compositions may take the form of, for example, tablets or capsules prepared by conventional means with pharmaceutically acceptable excipients such as binding agents (e.g. pregelatinised maize starch, polyvinylpyrrolidone or hydroxypropyl methylcellulose); fillers (e.g. lactose, microcrystalline cellulose or calcium hydrogen phosphate); lubricants (e.g. magnesium stearate, talc or silica); disintegrants (e.g. potato starch or sodium starch glycollate); or wetting agents (e.g. sodium lauryl sulphate). Tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g. sorbitol syrup, cellulose derivatives or hydrogenated edible fats); emulsifying agents (e.g. lecithin or acacia); non-aqueous vehicles (e.g. almond oil, oily esters, ethyl alcohol or fractionated vegetable oils); and preservatives (e.g. methyl or propyl-p-hydroxybenzoates or sorbic acid). Preparations may also contain buffer salts, flavoring, coloring and sweetening agents as appropriate.

Preparations for oral administration may also be suitably formulated to give controlled-release or sustained release of the active compound(s) over an extended period. For buccal administration the compositions may take the form of tablets or lozenges formulated in a conventional manner known to the skilled artisan.

A disclosed compound may also be formulated for parenteral administration by injection e.g. by bolus injection or continuous infusion. Formulations for injection may be presented in unit dosage form e.g. in ampoules or in multi-dose containers, with an added preservative. The compositions may take such forms as suspensions, solutions or emulsions in oily or aqueous vehicles, and may contain additives such as suspending, stabilizing and/or dispersing agents. Alternatively, the compound may be in powder form for constitution with a suitable vehicle, e.g. sterile pyrogen-free water, before use. Compounds may also be formulated for rectal administration as suppositories or retention enemas, e.g. containing conventional suppository bases such as cocoa butter or other glycerides.

Also contemplated herein are methods and compositions that include a second active agent, or administering a second active agent. For example, in addition to being infected with HBV, a subject or patient can further have HBV infection-related co-morbidities, i.e., diseases and other adverse health conditions associated with, exacerbated by, or precipitated by being infected with HBV. Contemplated herein are disclosed compounds in combination with at least one other agent that has previously been shown to treat these HBV-infection-related conditions.

In some cases, a disclosed compound may be administered as part of a combination therapy in conjunction with one or more antivirals. Example antivirals include nucleoside analogs, interferon α, and other assembly effectors, for instance heteroaryldihydropyrimidines (HAPs) such as methyl 4-(2-chloro-4-fluorophenyl)-6-methyl-2-(pyridin-2-yl)-1,4-dihydropyrimidine-5-carboxylate (HAP-1). For example, provided herein is a method of treating a patient suffering from hepatitis B infection comprising administering to the patient a first amount of a disclosed compound and a second amount of an antiviral, or other anti HBV agent, for example a second amount of a second compound selected from the group consisting of: a HBV capsid assembly promoter (for example, GLS4, BAY 41-4109, AT-130, DVR-23 (e.g., as depicted below),

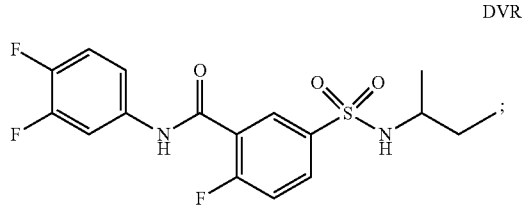

DVR-23

NVR 3-778, NVR1221 (by code); and N890 (as depicted below):

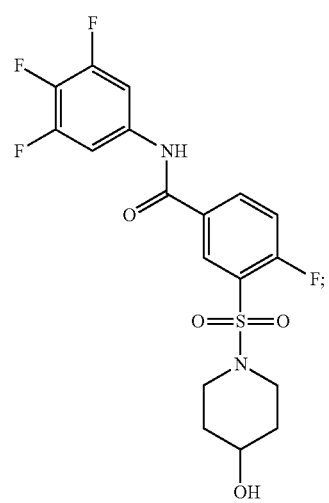 [SMILES: O=C(Nc1cc(F)c(F)c(F)c1)c1ccc(F)c(S(=O)(=O)N2CCC(O)CC2)c1]

other CpAMs such as those disclosed in the following patent applications hereby incorporated by reference: WO2014037480, WO2014184328, WO2013006394, WO2014089296, WO2014106019, WO2013102655, WO2014184350, WO2014184365, WO2014161888, WO2014131847, WO2014033176, WO2014033167, and WO2014033170; Nucleoside analogs interfering with viral polymerase, such as entecavir (Baraclude), Lamivudine, (Epivir-HBV), Telbivudine (Tyzeka, Sebivo), Adefovir dipivoxil (Hepsera), Tenofovir (Viread), Tenofovir alafenamide fumarate (TAF), prodrugs of tenofovir (e.g. AGX-1009), L-FMAU (Clevudine), LB80380 (Besifovir) and:

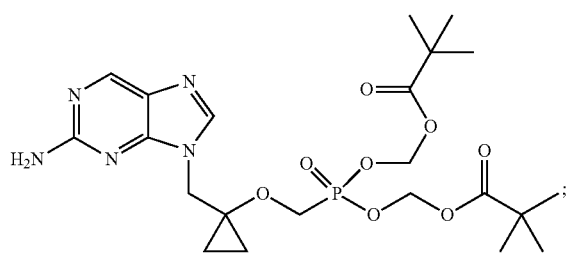 [SMILES: CC(C)(C)C(=O)OCOP(=O)(COC1(Cn2cnc3cnc(N)nc32)CC1)OCOC(=O)C(C)(C)C]

viral entry inhibitors such as Myrcludex B and related lipopeptide derivatives; HBsAg secretion inhibitors such as REP 9AC' and related nucleic acid-based amphipathic polymers, HBF-0529 (PBHBV-001), PBHBV-2-15 as depicted below:

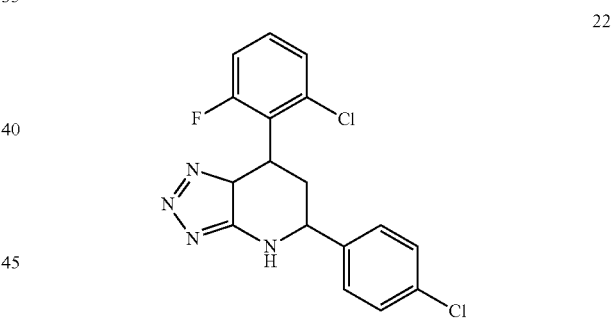

HBF-0529

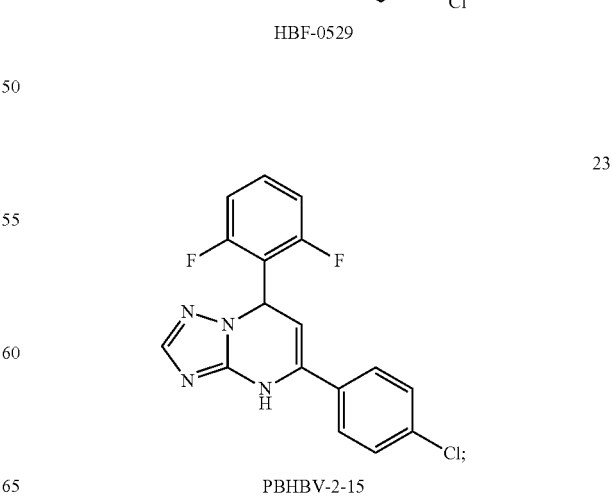

PBHBV-2-15 and BM601 as depicted below:

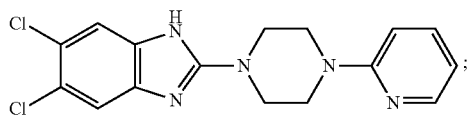 [SMILES: Clc1cc2nc(N3CCN(c4ccccn4)CC3)[nH]c2cc1Cl]

disruptors of nucleocapsid formation or integrity such as NZ-4/W28F:

NZ-4

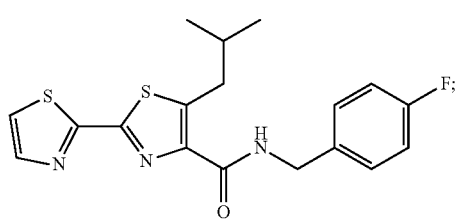

cccDNA formation inhibitors such as BSBI-25, CCC-0346, CCC-0975 (as depicted below):

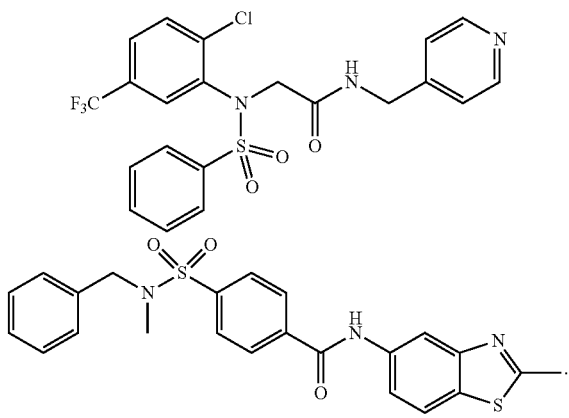

HBc directed transbodies such as those described in Wang Y, et al, Transbody against hepatitis B virus core protein inhibits hepatitis B virus replication in vitro, Int. Immunopharmacol (2014), located at //dx.doi.org/10.1016/j.intimp.2015.01.028; antiviral core protein mutant (such as Cp183-V124W and related mutations as described in WO/2013/010069, WO2014/074906, each incorporated by reference); inhibitors of HBx-interactions such as RNAi, antisense and nucleic acid based polymers targeting HBV RNA, e.g., RNAi (for example ALN-HBV, ARC-520, TKM-HBV, ddRNAi), antisense (ISIS-HBV), or nucleic acid based polymer: (REP 2139-Ca); immunostimulants such as Interferon alpha 2a (Roferon), Intron A (interferon alpha 2b), Pegasys (peginterferon alpha 2a), Pegylated IFN 2b, IFN lambda 1a and PEG IFN lambda 1a, Wellferon, Roferon, Infergen, lymphotoxin beta agonists such as CBE11 and BS1); Non-Interferon Immune enhancers such as Thymosin alpha-1 (Zadaxin) and Interleukin-7 (CYT107); TLR-7/9 agonists such as GS-9620, CYT003, Resiquimod; Cyclophilin Inhibitors such as NVP018; OCB-030; SCY-635; Alisporivir; NIM811 and related cyclosporine analogs; vaccines such as GS-4774, TG1050, Core antigen vaccine; SMAC mimetics such as birinapant and other IAP-antagonists; Epigenetic modulators such as KMT inhibitors (EZH1/2, G9a, SETD7, Suv39 inhibitors), PRMT inhibitors, HDAC inhibitors, SIRT agonists, HAT inhibitors, WD antagonists (e.g. OICR-9429), PARP inhibitors, APE inhibitors, DNMT inhibitors, LSD1 inhibitors, JMJD HDM inhibitors, and Bromodomain antagonists; kinase inhibitors such as TKB1 antagonists, PLK1 inhibitors, SRPK inhibitors, CDK2 inhibitors, ATM & ATR kinase inhibitors; STING Agonists; Ribavirin; N-acetyl cysteine; NOV-205 (BAM205); Nitazoxanide (Alinia), Tizoxanide; SB 9200 Small Molecule Nucleic Acid Hybrid (SMNH); DV-601; Arbidol; FXR agonists (such as GW 4064 and Fexaramin); antibodies, therapeutic proteins, gene therapy, and biologics directed against viral components or interacting host proteins.

In some embodiments, the disclosure provides a method of treating a hepatitis B infection in a patient in need thereof, comprising administering a first compound selected from any one of the disclosed compounds, and one or more other HBV agents each selected from the group consisting of HBV capsid assembly promoters, HBF viral polymerase interfering nucleosides, viral entry inhibitors, HBsAg secretion inhibitors, disruptors of nucleocapsid formation, cccDNA formation inhibitors, antiviral core protein mutant, HBc directed transbodies, RNAi targeting HBV RNA, immunostimulants, TLR-7/9 agonists, cyclophilin inhibitors, HBV vaccines, SMAC mimetics, epigenetic modulators, kinase inhibitors, and STING agonists. In some embodiments, the disclosure provides a method of treating a hepatitis B infection in a patient in need thereof, comprising administering an amount of a disclosed compound, and administering another HBV capsid assembly promoter.

In some embodiments, the first and second amounts together comprise a pharmaceutically effective amount. The first amount, the second amount, or both may be the same, more, or less than effective amounts of each compound administered as monotherapies. Therapeutically effective amounts of a disclosed compound and antiviral may be co-administered to the subject, i.e., administered to the subject simultaneously or separately, in any given order and by the same or different routes of administration. In some instances, it may be advantageous to initiate administration of a disclosed compound first, for example one or more days or weeks prior to initiation of administration of the antiviral. Moreover, additional drugs may be given in conjunction with the above combination therapy.

In another embodiment, a disclosed compound may be conjugated (e.g., covalently bound directly or through molecular linker to a free carbon, nitrogen (e.g. an amino group), or oxygen (e.g. an active ester) of a disclosed compound), with a detection moiety, for e.g., a fluorophore moiety (such a moiety may for example re-emit a certain light frequency upon binding to a virus and/or upon photon excitation). Contemplated fluorophores include AlexaFluor® 488 (Invitrogen) and BODIPY FL (Invitrogen), as well as fluorescein, rhodamine, cyanine, indocarbocyanine, anthraquinones, fluorescent proteins, aminocoumarin, methoxycoumarin, hydroxycoumarin, Cy2, Cy3, and the like. Such disclosed compounds conjugated to a detection moiety may be used in e.g. a method for detecting HBV or biological pathways of HBV infection, e.g., in vitro or in vivo; and/or methods of assessing new compounds for biological activity.

EXAMPLES

The compounds described herein can be prepared in a number of ways based on the teachings contained herein and synthetic procedures known in the art. In the description of the synthetic methods described below, it is to be understood that all proposed reaction conditions, including choice of solvent, reaction atmosphere, reaction temperature, duration of the experiment and workup procedures, can be chosen to be the conditions standard for that reaction, unless otherwise indicated. It is understood by one skilled in the art of organic synthesis that the functionality present on various portions of the molecule should be compatible with the reagents and reactions proposed. Substituents not compatible with the reaction conditions will be apparent to one skilled in the art, and alternate methods are therefore indicated. The starting materials for the examples are either commercially available or are readily prepared by standard methods from known materials.

At least some of the compounds identified as "intermediates" herein are contemplated as compounds of the disclosure.

Abbreviations

DCM Dichloromethane
EtOAC Ethyl acetate
MeOH Methanol
DMSO Dimethyl sulfoxide
NMO N-Methylmorpholine N-oxide
LiHMDS Lithium bis(trimethylsilyl)amide
p-TSA p-Toluenesulfonic acid
DMF N,N-Dimethylformamide
THF Tetrahydrofuran
TLC Thin-layer chromatography
LCMS Liquid chromatography-mass spectrometry
HPLC High performance liquid chromatography General Procedure for the Synthesis of 2,4-Diketoester:

To a stirred solution of corresponding acetyl compound (1 eq.) in dry THF (10V) at −78° C. under Ar atmosphere, LiHMDS (1M in THF, 1.3 eq.) was added and stirred at the same temperature for 1 h. To this solution, dimethyl oxalate (1.5 eq.) in dry THF (5V) was added drop wise at −78° C. and the resulting reaction mixture was stirred at room temperature for overnight. The progress of the reaction was monitored by TLC and LCMS. After completion, the reaction mixture was concentrated under reduced pressure. The residue was diluted with water; the precipitated solid was collected by filtration, washed with ethyl acetate followed by diethyl ether and dried under reduced pressure to afford desired compound (Note: The desired compound was isolated in enol form and used as such for the next step).

General Procedure for the Synthesis of Cyclic Sulphonamide:

Method A (HCl (g)/MeOH, Sealed Tube):

To a stirred solution of 2,4-diketoester (1 eq.) and sulfamide (1 eq.) in MeOH (10V), in sealed tube, HCl gas (generated by sodium chloride+$H_2SO_4$) was purged for 2 h at 0° C. The resulting reaction mixture was stirred at 80° C. for 24 h. The progress of the reaction was monitored by TLC and LCMS. After completion, the reaction mixture was cooled to 0° C., precipitated solid was filtered, washed with water followed by cold methanol and dried in vacuo to afford cyclic sulphonamide.

Method B (4N HCl in MeOH, RB Flask):

In a round bottom flask fitted with reflux condenser, 2,4-diketoester (1 eq.) and sulfamide (1 eq.) was taken in 4 N methanolic HCl (10V). The resulting reaction mixture was stirred at 60° C. for 16 h. The progress of the reaction was monitored by TLC and LCMS. After completion, the reaction mixture was cooled to 0° C., precipitated solid was filtered, washed with water followed by diethyl ether and dried in vacuo to afford cyclic sulphonamide.

General Procedure for Alkylation

Method A (Alkylation Using NaH/MeI)

To a stirred solution of cyclic sulphonamide (1 eq.) in dry DMF (8V) at 0° C. under Ar atmosphere, NaH (60% w/w in mineral oil, 1.5 eq.) was added and stirred at 0° C. for 45 min. To this solution, MeI (1.1 eq.) was added slowly and resulting reaction mixture was stirred at room temperature for 12 h. The progress of the reaction was monitored by TLC and LCMS. After completion, the reaction mixture was diluted with ice cold water; the obtained solid was collected by filtration. The solid was washed with diethyl ether and dried in vacuo to afford N-alkylated desired compound after silica gel column chromatography.

Method B (Alkylation Using Mitsunobu Reaction):

To a stirred solution of cyclic sulphonamide (1 eq.) in dry THF (4V) at 0° C. under Ar atmosphere, TPP (2 eq.) and methanol (10 eq.) was added and stirred at 0° C. for 45 min. To this solution, DEAD/DIAD (2 eq.) was added slowly and resulting reaction mixture (color change to dark brown) was heated at 60° C. for 16 h. The progress of the reaction was monitored by TLC and LCMS. After completion, the reaction mixture concentrated under vacuum, residue obtained was taken in diethyl ether, stirred for 30 min. and filtered. The solid obtained was further stirred in methanol for 30 min., filtered and dried in vacuo to afford N-alkylated desired compound (Note: a few compounds were further purified using silica gel column chromatography).

General Procedure for Amidation:

Method A ($AlMe_3$ Mediated Amidation):

To a stirred solution of corresponding anilines (3 eq.) in DCM/Toluene at 0° C. under Ar atmosphere, $AlMe_3$ (2M in toluene, 3 eq.) was added and the reaction mixture was stirred at 0° C. for 10 min and continued stirring at room temperature for 1 h. To this solution, corresponding ester compound (1 eq.) was added at 0° C. under Ar atmosphere and resulting reaction mixture was refluxed at 40° C. for overnight. The progress of the reaction was monitored by TLC and LCMS. After completion, the reaction mixture was cooled to 0° C.; quenched with 1N HCl solution slowly and extracted with DCM. The combined organic layers were collected, dried over anhydrous sodium sulphate and concentrated in vacuo. The crude compound was purified by silica gel column chromatography followed by trituration with diethyl ether to afford the compound HBV-CSU_Int. (Note: The reaction was heated at 110° C. for a few compounds wherein toluene was used as solvent).

Method B (Hydrolysis Followed by Acid-Amine Coupling Using HATU)

To a solution of corresponding ester compound (1 eq.) in 10V of $CH_3CN:H_2O$ (1:1) at 0° C. was added TEA (5 eq.) and the resulting reaction mixture was stirred at the same temperature till clear solution was observed (usually 4-6 h). The progress of reaction was monitored by TLC. After completion, the reaction mixture was concentrated under reduced pressure, and the residue obtained was acidified with 6N HCl and extracted with ethyl acetate. The combined organic layer was dried over anhydrous sodium sulphate, filtered and concentrated under reduced pressure to afford acid derivative which was used in the next step after trituration with di-ethyl ether. To a stirred solution of above acid compound (1 eq.) in DCM/DMF (10V) at 0° C. was added DIPEA (2 eq.), stirred for 15 min, followed by addition of HATU (2 eq.), again stirred for 15 min and then corresponding aniline (1.2 eq.) was added. The reaction mixture was then stirred at room temperature for overnight.

The progress of the reaction was monitored by TLC. After completion, the reaction mixture was diluted with ice cold water and extracted with DCM. The combined organic layers were dried over anhydrous sodium sulphate and concentrated under reduced pressure to afford a crude compound. The crude compound was taken in methanol (10V), stirred for 15 min., filtered and dried under reduced pressure to afford compound desired compound.

Method C (Hydrolysis Followed by Acid-Amine Coupling Using EDCI.HCl):

To a solution of corresponding ester compound (1 eq.) in 10V of $CH_3CN:H_2O$ (1:1) at 0° C. was added TEA (5 eq.) and the resulting reaction mixture was stirred at the same temperature till clear solution was observed (usually 4-6 h). The progress of reaction was monitored by TLC. After completion, the reaction mixture was concentrated under reduced pressure, and residue obtained was acidified with 6N HCl and extracted with ethyl acetate. The combined organic layer was dried over sodium sulphate, filtered and concentrated under reduced pressure to afford acid derivative which was used in the next step after trituration with di-ethyl ether. To a stirred solution of above acid compound (1 eq.) in DMF (10-25V) at 0° C. was added EDCI.HCl (1.5 eq.) and HOBt (1.5 eq.) with stirring for 15 min; followed by addition of DIPEA (3 eq.) then the corresponding aniline (1.2 eq.). The reaction mixture was then stirred at room temperature for overnight. The progress of the reaction was monitored by TLC. After completion, the reaction mixture was diluted with ice cold water and extracted with DCM. The combined organic layers were dried over anhydrous sodium sulphate and concentrated under reduced pressure to afford a crude compound. The crude compound was purified using silica gel column chromatography to afford compound HBV-CSU_Int.

General Procedure for Reduction:

To a stirred solution of compound HBV-CSU_Int (1 eq.) in EtOH at 0° C. under Ar atmosphere, $NaBH_4$ (2 eq.) was added and stirred at room temperature for 20 min. The progress of the reaction was monitored by TLC and LCMS. After completion, the reaction mixture was concentrated in vacuo, the residue obtained was diluted with water and extracted using ethyl acetate. The combined organic layers were collected, dried over anhydrous sodium sulphate, filtered, concentrated in vacuo and purified by silica gel column chromatography to afford the desired compound. Note: The regioselective alkylation and the cis stereochemistry were confirmed by NOE experiments for a few representative compounds.

General Method for Suzuki Coupling:

To a mixture of bromo compound (1 eq.), boronic acid/boronate ester (1 eq.) in 1,4-dioxane, 2M solution of potassium phosphate was added, purged with Ar atmosphere for 15 min, followed by the addition of tetrakistriphenyl phosphine palladium (0.06 eq.), and stirred at 90° C. for overnight. The progress of the reaction was monitored by TLC. After completion of the reaction, the reaction mixture was filtered through Celite and evaporated to dryness. The residue was taken in ethyl acetate, washed with water, followed by brine, dried over anhydrous sodium sulfate and evaporated under reduced pressure. The crude product was purified by column chromatography/preparative HPLC to afford the desired product.

General Method for Stille Coupling:

To a mixture of bromo compound (1 eq.) in toluene/dioxane, stannane reagent (1 eq.) was added and purged with Ar atmosphere for 15 min followed by the addition of tetrakistriphenyl phosphine palladium (0.06 eq.). The resulting reaction mixture was then stirred at 90° C. for overnight. The progress of the reaction was monitored by TLC. After completion of the reaction, the reaction mixture was filtered through Celite and evaporated to dryness. The residue was taken in ethyl acetate, washed with water, brine, dried over anhydrous sodium sulfate and evaporated under reduced pressure. The crude product was purified by column chromatography/preparative HPLC to afford the desired product. (Note: The reaction has been performed in acetonitrile solvent for some compounds wherein solubility of bromo compound is an issue).

General Method for Negishi Coupling:

To an Ar purged mixture of bromo compound (1 eq.) in 1,4-dioxane was added $PdCl_2(dppf)$. DCM (0.1 eq.) and reaction mixture was stirred for 10 min; then $Me_2Zn$ (2 eq.) was added and stirred at 90° C. for 6 h. The progress of the reaction was monitored by TLC. After completion of the reaction, the reaction mixture was quenched with methanol followed by water and then extracted using ethyl acetate. The combined organic layer was washed with brine, dried over anhydrous sodium sulfate and evaporated under reduced pressure to afford the crude product which was purified by column chromatography/preparative HPLC to afford the desired product as a solid.

Methods for Chiral Separation:
Method A
Column: YMC chiral Amylose-SA, 250 mm×20 mm, 5 micron
Mobile Phase:
A: n-Hexane+0.1% DEA
B: DCM:MeOH (1:1)
Isocratic: 30-90% B
Flow rate: 18 mL/Min
Method B
Column: DIACEL CHIRALPACK-IA, 250 mm×20 mm, 5 micron
Mobile Phase:
A: n-Hexane+0.1% DEA
B: DCM:MeOH (1:1)
Gradient: Hold 50% B till 4 min then 100% B at 5 min & hold up to 15 min
Flow rate: 18 mL/Min
Method C
Column: CHIRALPACK-IA, 250 mm×30 mm, 5 micron
Mobile Phase:
A: n-Hexane+0.1% DEA
B: DCM:MeOH (1:1)
Isocratic: 30-90% B
Flow rate: 30 mL/Min
The chiral purity was confirmed by using following methods:
Method A
Column: YMC chiral Amylose-SA, 250 mm×4.6 mm, 5 micron
Mobile Phase:
A: n-Hexane+0.1% DEA
B: DCM:MeOH (1:1)
Isocratic: 30-90% B
Flow rate: 1 mL/Min
Method B
Column: YMC chiral art cellulose-SC, 250 mm×4.6 mm, 5 micron
Mobile Phase:
A: n-Hexane+0.1% DEA
B: DCM:MeOH (1:1)
Isocratic: 30-90% B
Flow rate: 1 mL/Min Method C
Column: CHIRALPACK-IA, 250 mm×4.6 mm, 5 micron
Mobile Phase:
A: n-Hexane+0.1% DEA
B: DCM:MeOH (1:1)
Isocratic: 30-90% B
Flow rate: 30 mL/Min
The first eluting compound was labelled as HBV-CSU-XXX-ISO-I and second eluting compound was labelled as HBV-CSU-XXX-ISO-II.
Note: The mobile phases have been changed based on solubility and other issues encountered during prep-HPLC purification as well as analysis. In few cases additives like TFA and MeSO$_3$H were used. For few samples instead of Isocratic gradient elution method was adopted.

Scheme 1

General Synthetic Scheme for 5-(thiophen-2-yl)-1,2,6-thiadiazinane-3-carboxamide 1,1-dioxide Derivatives with N-alkyl & Aniline Variations Scheme 1:

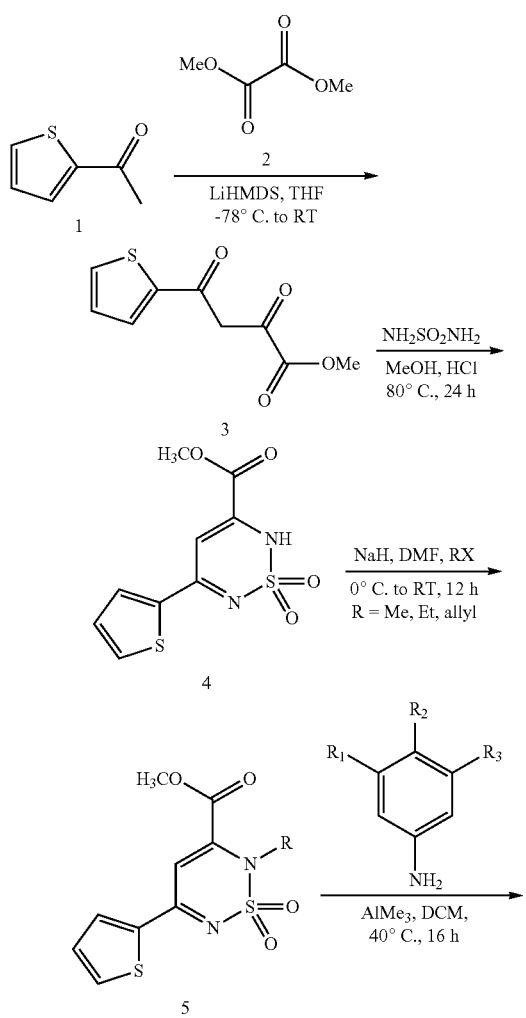

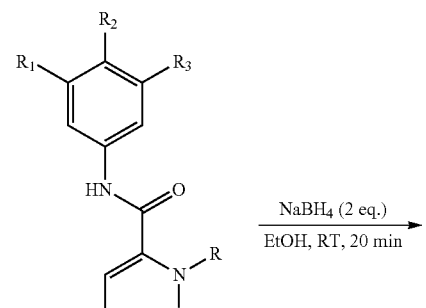

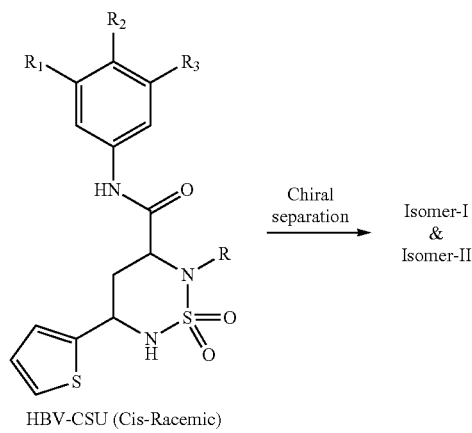

| Target | R variation | Aniline (R1/R2/R3 variation) |
|---|---|---|
| HBV-CSU-006 | Methyl | aniline |
| HBV-CSU-007 | Methyl | 4-F aniline |
| HBV-CSU-010 | Methyl | 3-Cl aniline |
| HBV-CSU-011 | Methyl | 3,4-diF aniline |
| HBV-CSU-012 | Methyl | 3-CF$_3$ aniline |

-continued

| Target | R variation | Aniline (R1/R2/R3 variation) |
|---|---|---|
| HBV-CSU-013 | Methyl | 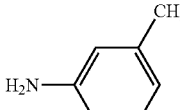 |
| HBV-CSU-014 | Methyl | 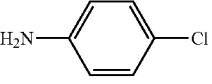 |
| HBV-CSU-015 | Methyl | 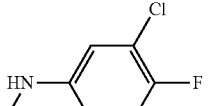 |
| HBV-CSU-016 | Methyl | 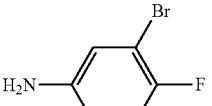 |
| HBV-CSU-017 | Methyl | 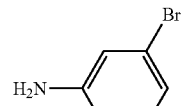 |
| HBV-CSU-018 | Methyl | 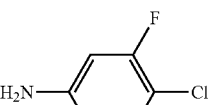 |
| HBV-CSU-019 | Methyl | 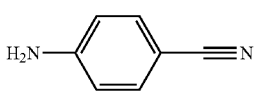 |
| HBV-CSU-020 | Methyl | 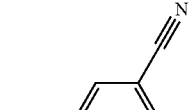 |
| HBV-CSU-024 | Ethyl | 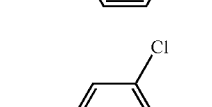 |
| HBV-CSU-036 | Methyl | 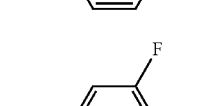 |
| HBV-CSU-040 | Allyl | 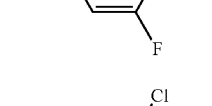 |

-continued

| Target | R variation | Aniline (R1/R2/R3 variation) |
|---|---|---|
| HBV-CSU-045 | Methyl | 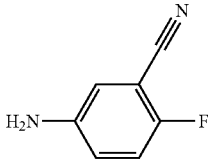 |
| HBV-CSU-046 | Methyl | 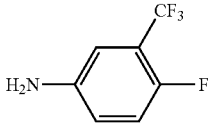 [SMILES: Nc1ccc(F)c(C(F)(F)F)c1] |
| HBV-CSU-047 | Methyl | 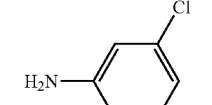 |
| HBV-CSU-048 | Methyl | 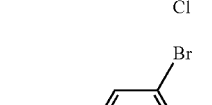 |
| HBV-CSU-049 | Methyl | 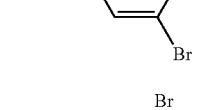 |
| HBV-CSU-023_Int-1 | Methyl | 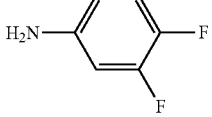 |

Synthesis of methyl 2,4-dioxo-4-(thiophen-2-yl)butanoate (3)

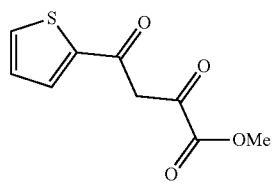 [SMILES: COC(=O)C(=O)CC(=O)c1cccs1]

Title compound was synthesized using general method for the synthesis of 2,4-diketoester described above to afford 26 g (77%, reaction scale is 20 g) as a yellow colored solid. TLC: 10% MeOH/DCM (R$_f$: 0.1); $^1$H NMR (DMSO-d$_6$, 400 MHz): δ 7.68 (d, J=5.2 Hz, 1H), 7.61 (d, J=4.4 Hz, 1H), 7.10 (t, J=5.2 Hz, 1H), 6.34 (s, 1H), 3.69 (s, 3H); LCMS Calculated for C$_9$H$_8$O$_4$S: 212.01; Observed: 212.95 (M+1)$^+$.

Synthesis of methyl 5-(thiophen-2-yl)-2H-1,2,6-thiadiazine-3-carboxylate 1,1-dioxide (4)

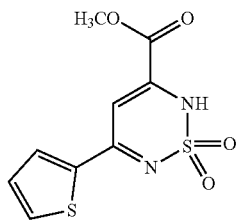 [SMILES: COC(=O)C1=CC(c2cccs2)=NS(=O)(=O)N1]

Title compound was synthesized using general method for the synthesis of cyclic sulfonamide described above to afford 8 g (62%, reaction scale is 10 g) as yellow colored solid. TLC: 20% MeOH/DCM ($R_f$: 0.1); $^1$H NMR (DMSO-$d_6$, 400 MHz): δ 11.50 (br.s, 1H), 8.06 (d, J=4.0 Hz, 1H), 7.93 (d, J=5.2 Hz, 1H), 7.23 (t, J=4.0 Hz, 1H), 6.99 (s, 1H), 3.87 (s, 3H); LCMS Calculated for $C_9H_8N_2O_4S_2$: 271.99; LCMS observed: 272.85 (M+1)$^+$.

Synthesis of methyl 2-methyl-5-(thiophen-2-yl)-2H-1,2,6-thiadiazine-3-carboxylate 1,1-dioxide (5)

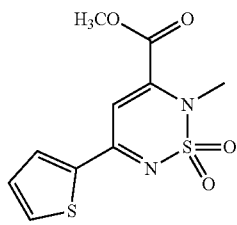 [SMILES: COC(=O)C1=CC(c2cccs2)=NS(=O)(=O)N1C]

Title compound was synthesized using general method A for alkylation described above to afford 4 g (77%, reaction scale is 5 g) as yellow colored solid. TLC: 40% EtOAc/hexanes ($R_f$: 0.4); $^1$H NMR (DMSO-$d_6$, 400 MHz): δ 8.23 (d, J=4.0 Hz, 1H), 8.10 (d, J=4.8 Hz, 1H), 7.32-7.30 (m, 2H), 3.94 (s, 3H), 3.50 (s, 3H); LCMS Calculated for $C_{10}H_{10}N_2O_4S_2$: 286.01; LCMS observed: 286.94 (M+1)$^+$.

Methyl 2-ethyl-5-(thiophen-2-yl)-2H-1,2,6-thiadiazine-3-carboxylate 1,1-dioxide (5)

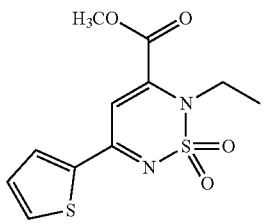 [SMILES: CCN1C(C(=O)OC)=CC(c2cccs2)=NS1(=O)=O]

Title compound was synthesized using general method A for alkylation described above to afford 0.2 g (crude) as a light yellow solid. TLC: 40% EtOAc/hexanes ($R_f$: 0.4); $^1$H NMR (DMSO-$d_6$, 400 MHz): δ 7.93 (d, J=4.0 Hz, 1H), 7.83 (d, J=4.8 Hz, 1H), 7.21-7.19 (m, 1H), 6.81 (s, 1H), 4.32-4.25 (m, 2H), 1.32 (t, J=6.8 Hz, 3H), 3H merged in solvent peak; LCMS Calculated for $C_{11}H_{12}N_2O_4S_2$: 300.02; LCMS observed: 300.90 (M+1)$^+$.

Methyl 2-allyl-5-(thiophen-2-yl)-2H-1,2,6-thiadiazine-3-carboxylate 1,1-dioxide (5)

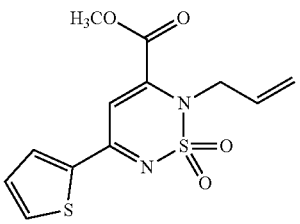 [SMILES: C=CCN1C(C(=O)OC)=CC(c2cccs2)=NS1(=O)=O]

Title compound was synthesized using general method A for alkylation described above to afford 0.13 g (45%, reaction scale is 0.25 g)) as a yellow solid. TLC: 50% EtOAc/hexanes ($R_f$: 0.3); $^1$H NMR (DMSO-$d_6$, 400 MHz): δ 8.26 (dd, J=3.9, 1.3 Hz, 1H), 8.16-8.06 (m, 1H), 7.41 (d, J=1.2 Hz, 1H), 7.34-7.31 (m, 1H), 5.97-5.90 (m, 1H), 5.34-5.18 (m, 2H), 4.59-4.50 (m, 2H), 3.92 (s, 3H); LCMS Calculated for $C_{12}H_{12}N_2O_4S_2$: 312.02; LCMS observed: 312.95 (M+1)$^+$.

2-Methyl-N-phenyl-5-(thiophen-2-yl)-2H-1,2,6-thiadiazine-3-carboxamide 1,1-dioxide (HBV-CSU-006_Int)

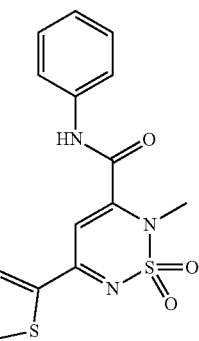

HBV-CSU-006_Int

The above titled compound has been synthesized by following the general procedure (Method A) described above for amidation by using corresponding 5 and corresponding amine (see Table 1 for analytical data).

N-(4-fluorophenyl)-2-methyl-5-(thiophen-2-yl)-2H-1,2,6-thiadiazine-3-carboxamide 1,1-dioxide (HBV-CSU-007_Int)

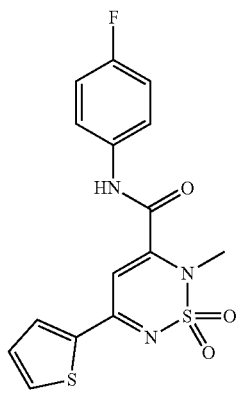

HBV-CSU-007_Int

The above titled compound has been synthesized by following the general procedure (Method A) described above for amidation by using corresponding 5 and corresponding amine (see Table 1 for analytical data).

N-(3-chlorophenyl)-2-methyl-5-(thiophen-2-yl)-2H-1,2,6-thiadiazine-3-carboxamide 1,1-dioxide (HBV-CSU-010_Int)

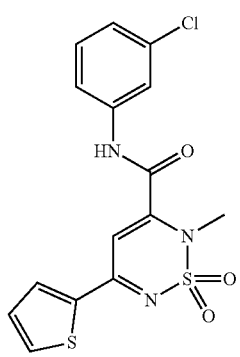

HBV-CSU-010_Int

The above titled compound has been synthesized by following the general procedure (Method A) described above for amidation by using corresponding 5 and corresponding amine (see Table 1 for analytical data).

N-(3,4-difluorophenyl)-2-methyl-5-(thiophen-2-yl)-2H-1,2,6-thiadiazine-3-carboxamide 1,1-dioxide (HBV-CSU-011_Int)

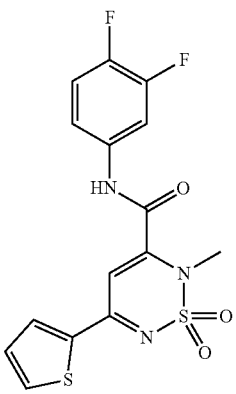

HBV-CSU-011_Int

The above titled compound has been synthesized by following the general procedure (Method A) described above for amidation by using corresponding 5 and corresponding amine (see Table 1 for analytical data).

2-Methyl-5-(thiophen-2-yl)-N-(3-(trifluoromethyl)phenyl)-2H-1,2,6-thiadiazine-3-carboxamide 1,1-dioxide (HBV-CSU-012_Int)

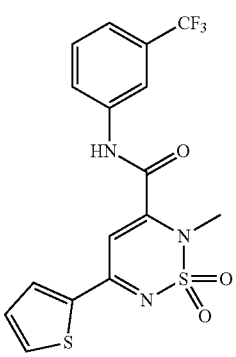

HBV-CSU-012_Int

The above titled compound has been synthesized by following the general procedure (Method A) described above for amidation by using corresponding 5 and corresponding amine (see Table 1 for analytical data).

2-Methyl-5-(thiophen-2-yl)-N-(m-tolyl)-2H-1,2,6-thiadiazine-3-carboxamide 1,1-dioxide (HBV-CSU-013_Int)

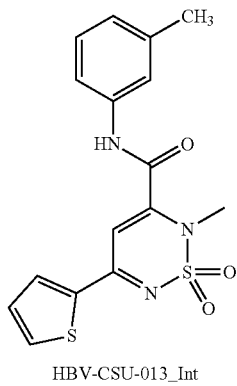 [SMILES: Cc1cccc(NC(=O)C2=CC(c3cccs3)=NS(=O)(=O)N2C)c1]

HBV-CSU-013_Int

The above titled compound has been synthesized by following the general procedure (Method A) described above for amidation by using corresponding 5 and corresponding amine (see Table 1 for analytical data).

N-(4-chlorophenyl)-2-methyl-5-(thiophen-2-yl)-2H-1,2,6-thiadiazine-3-carboxamide 1,1-dioxide (HBV-CSU-014_Int)

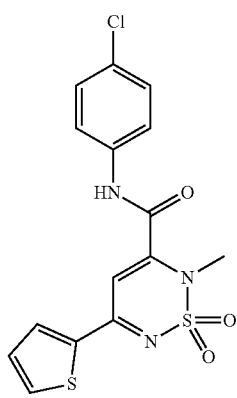

HBV-CSU-014_Int

The above titled compound has been synthesized by following the general procedure (Method A) described above for amidation by using corresponding 5 and corresponding amine (see Table 1 for analytical data).

N-(3-chloro-4-fluorophenyl)-N,2-dimethyl-5-(thiophen-2-yl)-2H-1,2,6-thiadiazine-3-carboxamide 1,1-dioxide (HBV-CSU-015_Int)

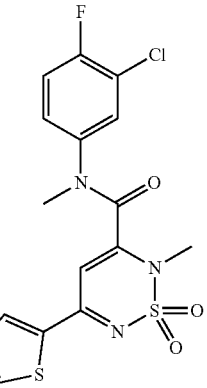

HBV-CSU-015_Int

The above titled compound has been synthesized by following the general procedure (Method A) described above for amidation by using corresponding 5 and corresponding amine (see Table 1 for analytical data).

N-(3-bromo-4-fluorophenyl)-2-methyl-5-(thiophen-2-yl)-2H-1,2,6-thiadiazine-3-carboxamide 1,1-dioxide (HBV-CSU-016_Int)

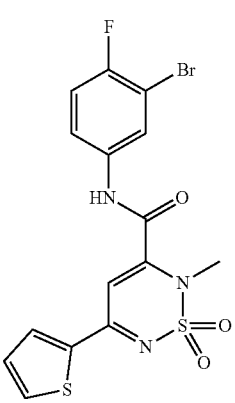

HBV-CSU-016_Int

The above titled compound has been synthesized by following the general procedure (Method A) described above for amidation by using corresponding 5 and corresponding amine (see Table 1 for analytical data).

N-(3-bromophenyl)-2-methyl-5-(thiophen-2-yl)-2H-1,2,6-thiadiazine-3-carboxamide 1,1-dioxide (HBV-CSU-017_Int)

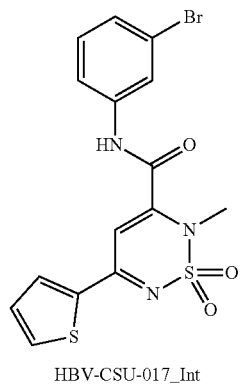 [SMILES: CN1C(C(=O)Nc2cccc(Br)c2)=CC(c2cccs2)=NS1(=O)=O]

HBV-CSU-017_Int

The above titled compound has been synthesized by following the general procedure (Method A) described above for amidation by using corresponding 5 and corresponding amine (see Table 1 for analytical data).

N-(4-chloro-3-fluorophenyl)-2-methyl-5-(thiophen-2-yl)-2H-1,2,6-thiadiazine-3-carboxamide 1,1-dioxide (HBV-CSU-018_Int)

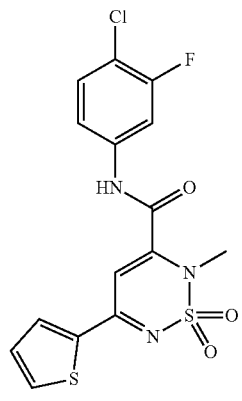

HBV-CSU-018_Int

The above titled compound has been synthesized by following the general procedure (Method A) described above for amidation by using corresponding 5 and corresponding amine (see Table 1 for analytical data).

N-(4-Cyanophenyl)-2-methyl-5-(thiophen-2-yl)-2H-1,2,6-thiadiazine-3-carboxamide 1,1-dioxide (HBV-CSU-019_Int)

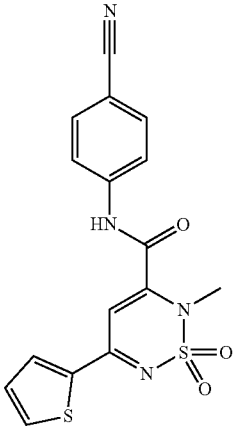

HBV-CSU-019_Int

The above titled compound has been synthesized by following the general procedure (Method A) described above for amidation by using corresponding 5 and corresponding amine (see Table 1 for analytical data).

N-(3-Cyanophenyl)-2-methyl-5-(thiophen-2-yl)-2H-1,2,6-thiadiazine-3-carboxamide 1,1-dioxide (HBV-CSU-020_Int)

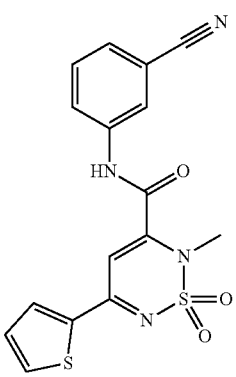

HBV-CSU-020_Int

The above titled compound has been synthesized by following the general procedure (Method A) described above for amidation by using corresponding 5 and corresponding amine (see Table 1 for analytical data).

71

N-(3-Chloro-4-fluorophenyl)-2-methyl-5-(thiophen-2-yl)-2H-1,2,6-thiadiazine-3-carboxamide 1,1-dioxide (HBV-CSU-023_Int)

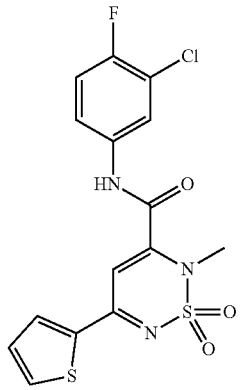

HBV-CSU-023_Int

The above titled compound has been synthesized by following the general procedure (Method A) described above for amidation by using corresponding 5 and corresponding amine (see Table 1 for analytical data).

N-(3-chloro-4-fluorophenyl)-2-ethyl-5-(thiophen-2-yl)-2H-1,2,6-thiadiazine-3-carboxamide 1,1-dioxide (HBV-CSU-024_Int)

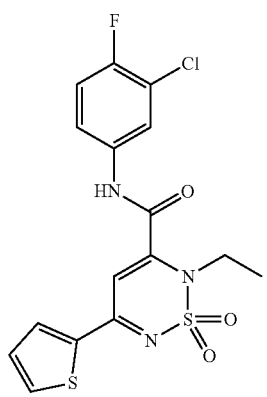

HBV-CSU-024_Int

The above titled compound has been synthesized by following the general procedure (Method A) described above for amidation by using corresponding 5 and corresponding amine (see Table 1 for analytical data).

72

2-Methyl-5-(thiophen-2-yl)-N-(3,4,5-trifluorophenyl)-2H-1,2,6-thiadiazine-3-carboxamide 1,1-dioxide (HBV-CSU-036_Int)

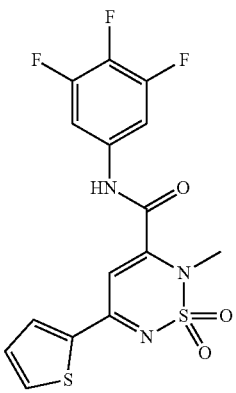

HBV-CSU-036_Int

The above titled compound has been synthesized by following the general procedure (Method A) described above for amidation by using corresponding 5 and corresponding amine (see Table 1 for analytical data).

2-Allyl-N-(3-chloro-4-fluorophenyl)-5-(thiophen-2-yl)-2H-1,2,6-thiadiazine-3-carboxamide 1,1-dioxide (HBV-CSU-040_Int)

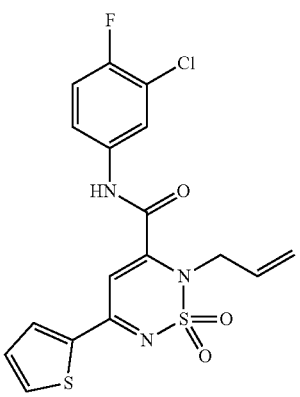

HBV-CSU-040_Int

The above titled compound has been synthesized by following the general procedure (Method A) described above for amidation by using corresponding 5 and corresponding amine (see Table 1 for analytical data).

N-(3-Cyano-4-fluorophenyl)-2-methyl-5-(thiophen-2-yl)-2H-1,2,6-thiadiazine-3-carboxamide 1,1-dioxide (HBV-CSU-045_Int)

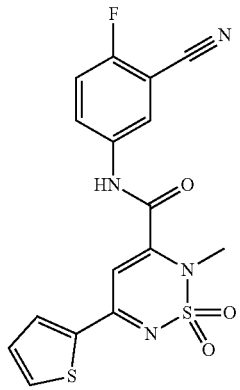

HBV-CSU-045_Int

The above titled compound has been synthesized by following the general procedure (Method A) described above for amidation by using corresponding 5 and corresponding amine (see Table 1 for analytical data).

N-(4-Fluoro-3-(trifluoromethyl)phenyl)-2-methyl-5-(thiophen-2-yl)-2H-1,2,6-thiadiazine-3-carboxamide 1,1-dioxide (HBV-CSU-046_Int)

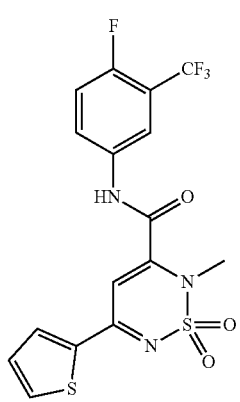

HBV-CSU-046_Int

The above titled compound has been synthesized by following the general procedure (Method A) described above for amidation by using corresponding 5 and corresponding amine (see Table 1 for analytical data).

N-(3,5-Dichlorophenyl)-2-methyl-5-(thiophen-2-yl)-2H-1,2,6-thiadiazine-3-carboxamide 1,1-dioxide (HBV-CSU-047_Int)

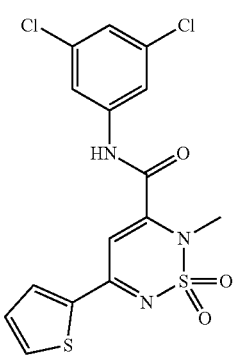

HBV-CSU-047_Int

The above titled compound has been synthesized by following the general procedure (Method A) described above for amidation by using corresponding 5 and corresponding amine (see Table 1 for analytical data).

N-(3,5-Dibromophenyl)-2-methyl-5-(thiophen-2-yl)-2H-1,2,6-thiadiazine-3-carboxamide 1,1-dioxide (HBV-CSU-048_Int)

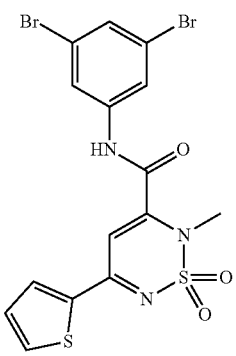

HBV-CSU-048_Int

The above titled compound has been synthesized by following the general procedure (Method A) described above for amidation by using corresponding 5 and corresponding amine (see Table 1 for analytical data).

75

N-(3-Bromo-4,5-difluorophenyl)-2-methyl-5-(thiophen-2-yl)-2H-1,2,6-thiadiazine-3-carboxamide 1,1-dioxide (HBV-CSU-049_Int)

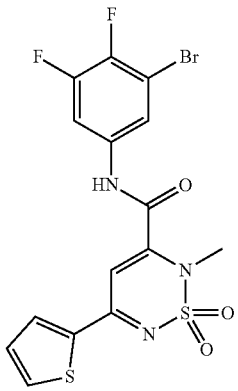

HBV-CSU-049_Int

The above titled compound has been synthesized by following the general procedure (Method A) described above for amidation by using corresponding 5 and corresponding amine (see Table 1 for analytical data).

Cis-2-Methyl-N-phenyl-5-(thiophen-2-yl)-1,2,6-thiadiazinane-3-carboxamide 1,1-dioxide (HBV-CSU-006)

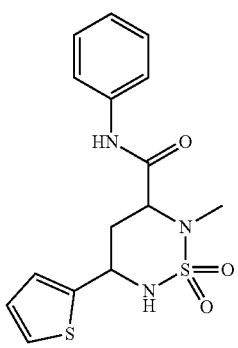

HBV-CSU-006

The above titled compound has been synthesized by following the general procedure described above for reduction by using corresponding HBV-CSU-006_Int (see Table 2 for analytical data).

76

Cis-N-(4-Fluorophenyl)-2-methyl-5-(thiophen-2-yl)-1,2,6-thiadiazinane-3-carboxamide 1,1-dioxide (HBV-CSU-007)

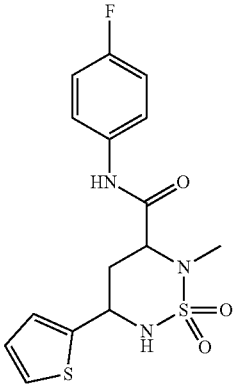

HBV-CSU-007

The above titled compound has been synthesized by following the general procedure described above for reduction by using corresponding HBV-CSU-007_Int (see Table 2 for analytical data).

Cis-N-(3-chlorophenyl)-2-methyl-5-(thiophen-2-yl)-1,2,6-thiadiazinane-3-carboxamide 1,1-dioxide (HBV-CSU-010 & HBV-CSU-010-ISO-I)

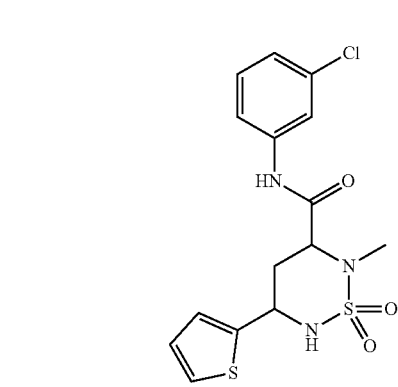

HBV-CSU-010

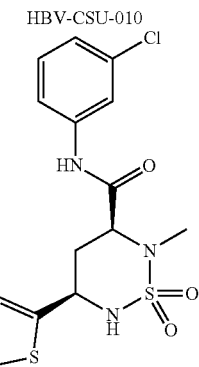

HBV-CSU-010-ISO-I

The above titled compound has been synthesized by following the general procedure described above for reduction by using corresponding HBV-CSU-010_Int (see Table 2 for analytical data).

Cis-N-(3,4-difluorophenyl)-2-methyl-5-(thiophen-2-yl)-1,2,6-thiadiazinane-3-carboxamide 1,1-dioxide (HBV-CSU-011)

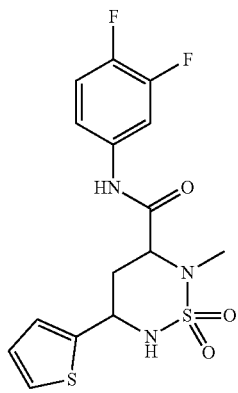

HBV-CSU-011

The above titled compound has been synthesized by following the general procedure described above for reduction by using corresponding HBV-CSU-011_Int (see Table 2 for analytical data).

Cis-2-Methyl-5-(thiophen-2-yl)-N-(3-(trifluoromethyl)phenyl)-1,2,6-thiadiazinane-3-carboxamide 1,1-dioxide (HBV-CSU-012)

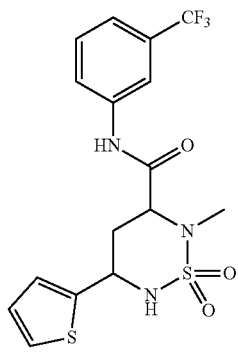

HBV-CSU-012

The above titled compound has been synthesized by following the general procedure described above for reduction by using corresponding HBV-CSU-012_Int (see Table 2 for analytical data).

Cis-2-Methyl-5-(thiophen-2-yl)-N-(m-tolyl)-1,2,6-thiadiazinane-3-carboxamide 1,1-dioxide (HBV-CSU-013)

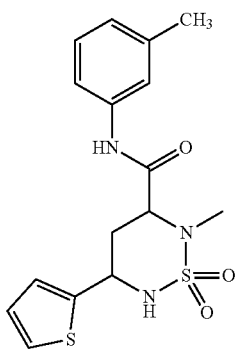

HBV-CSU-013

The above titled compound has been synthesized by following the general procedure described above for reduction by using corresponding HBV-CSU-013_Int (see Table 2 for analytical data).

Cis-N-(4-chlorophenyl)-2-methyl-5-(thiophen-2-yl)-1,2,6-thiadiazinane-3-carboxamide 1,1-dioxide (HBV-CSU-014)

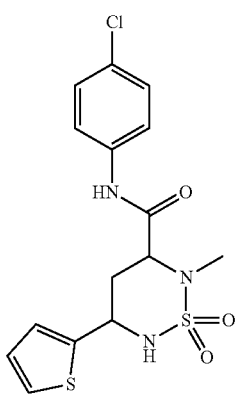

HBV-CSU-014

The above titled compound has been synthesized by following the general procedure described above for reduction by using corresponding HBV-CSU-014_Int (see Table 2 for analytical data).

Cis-N-(3-Chloro-4-fluorophenyl)-N-2-dimethyl-5-(thiophen-2-yl)-1,2,6-thiadiazinane-3-carboxamide 1,1-dioxide (HBV-CSU-015)

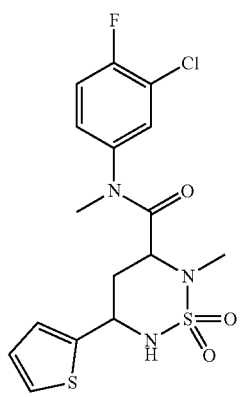

HBV-CSU-015

The above titled compound has been synthesized by following the general procedure described above for reduction by using corresponding HBV-CSU-015_Int (see Table 2 for analytical data).

Cis-N-(3-Bromo-4-fluorophenyl)-2-methyl-5-(thiophen-2-yl)-1,2,6-thiadiazinane-3-carboxamide 1,1-dioxide (HBV-CSU-016 & HBV-CSU-016-ISO-I)

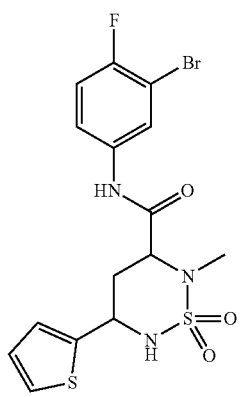

HBV-CSU-016

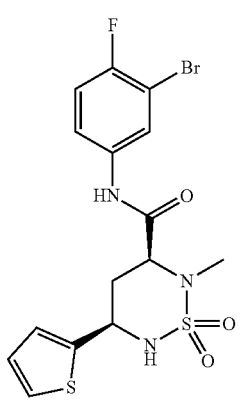

HBV-CSU-016-ISO-I

The above titled compounds have been synthesized by following the general procedure described above for reduction by using corresponding HBV-CSU-016_Int (see Table 2 for analytical data).

Cis-N-(3-Bromophenyl)-2-methyl-5-(thiophen-2-yl)-1,2,6-thiadiazinane-3-carboxamide 1,1-dioxide (HBV-CSU-017 & HBV-CSU-017-ISO-I)

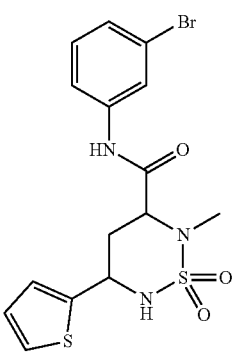

HBV-CSU-017

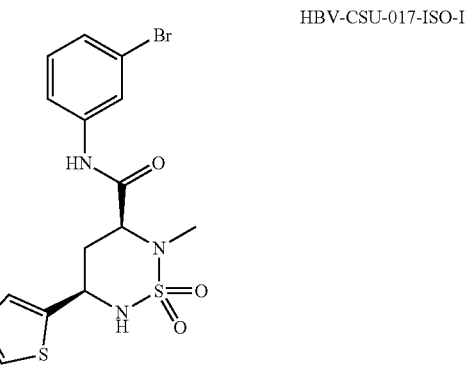

HBV-CSU-017-ISO-I

The above titled compounds have been synthesized by following the general procedure described above for reduction by using corresponding HBV-CSU-017_Int (see Table 2 for analytical data).

Cis-N-(4-Chloro-3-fluorophenyl)-2-methyl-5-(thiophen-2-yl)-1,2,6-thiadiazinane-3-carboxamide 1,1-dioxide (HBV-CSU-018)

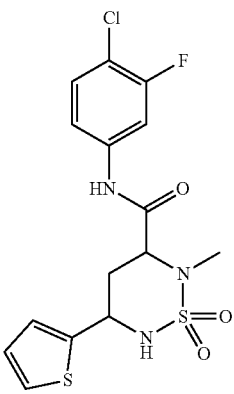

HBV-CSU-018

The above titled compound has been synthesized by following the general procedure described above for reduction by using corresponding HBV-CSU-018_Int (see Table 2 for analytical data).

Cis-N-(4-cyanophenyl)-2-methyl-5-(thiophen-2-yl)-1,2,6-thiadiazinane-3-carboxamide 1,1-dioxide (HBV-CSU-019)

HBV-CSU-019

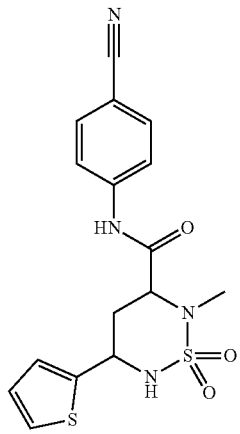

The above titled compound has been synthesized by following the general procedure described above for reduction by using corresponding HBV-CSU-019_Int (see Table 2 for analytical data).

Cis-N-(3-cyanophenyl)-2-methyl-5-(thiophen-2-yl)-1,2,6-thiadiazinane-3-carboxamide 1,1-dioxide (HBV-CSU-020 & HBV-CSU-020-ISO-I)

HBV-CSU-020

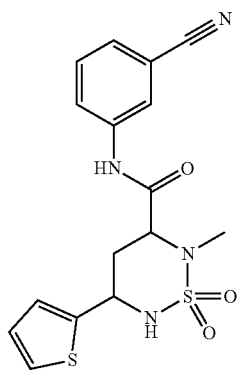

HBV-CSU-020-ISO-I

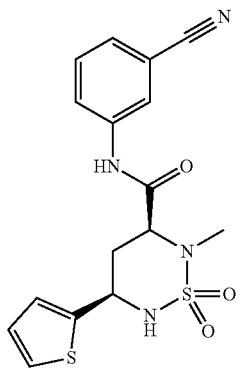

The above titled compounds have been synthesized by following the general procedure described above for reduction by using corresponding HBV-CSU-020_Int (see Table 2 for analytical data).

Cis-N-(3-chloro-4-fluorophenyl)-2-ethyl-5-(thiophen-2-yl)-1,2,6-thiadiazinane-3-carboxamide 1,1-dioxide (HBV-CSU-024)

HBV-CSU-024

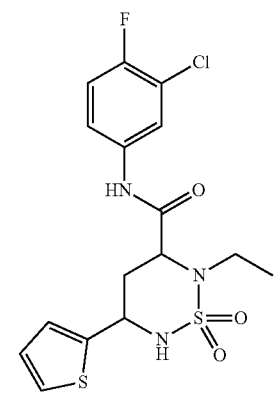

The above titled compound has been synthesized by following the general procedure described above for reduction by using corresponding HBV-CSU-24_Int (see Table 2 for analytical data).

Cis-2-Methyl-5-(thiophen-2-yl)-N-(3,4,5-trifluorophenyl)-1,2,6-thiadiazinane-3-carboxamide 1,1-dioxide (HBV-CSU-036)

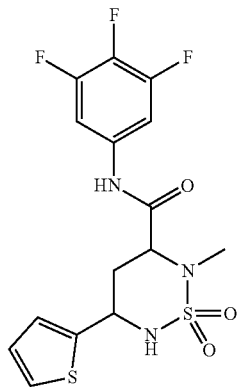

HBV-CSU-036

The above titled compound has been synthesized by following the general procedure described above for reduction by using corresponding HBV-CSU-36_Int (see Table 2 for analytical data).

Cis-2-Allyl-N-(3-chloro-4-fluorophenyl)-5-(thiophen-2-yl)-1,2,6-thiadiazinane-3-carboxamide 1,1-dioxide (HBV-CSU-040)

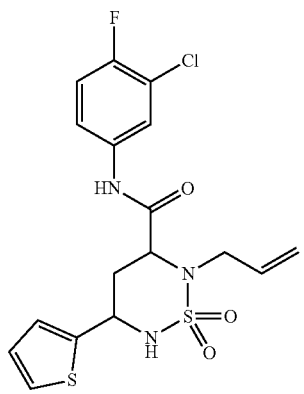

HBV-CSU-040

The above titled compound has been synthesized by following the general procedure described above for reduction by using corresponding HBV-CSU-40_Int (see Table 2 for analytical data).

Cis-N-(3-cyano-4-fluorophenyl)-2-methyl-5-(thiophen-2-yl)-1,2,6-thiadiazinane-3-carboxamide 1,1-dioxide (HBV-CSU-045 & HBV-CSU-045-ISO-I)

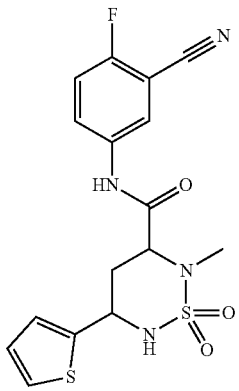

HBV-CSU-045

HBV-CSU-045-ISO-I

The above titled compounds have been synthesized by following the general procedure described above for reduction by using corresponding HBV-CSU-45_Int (see Table 2 for analytical data).

Cis-N-(4-Fluoro-3-(trifluoromethyl)phenyl)-2-methyl-5-(thiophen-2-yl)-1,2,6-thiadiazinane-3-carboxamide 1,1-dioxide (HBV-CSU-046-ISO-I)

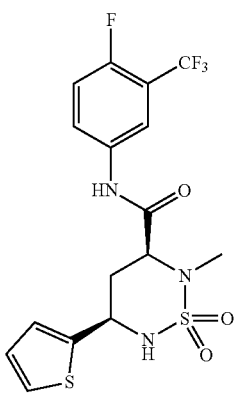

HBV-CSU-046-ISO-I

The above titled compound has been synthesized by following the general procedure described above for reduction by using corresponding HBV-CSU-46_Int (see Table 2 for analytical data).

Cis-N-(3,5-Dichlorophenyl)-2-methyl-5-(thiophen-2-yl)-1,2,6-thiadiazinane-3-carboxamide 1,1-dioxide (HBV-CSU-047-ISO-I)

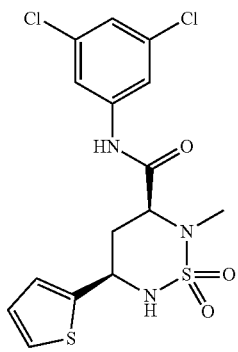

HBV-CSU-047-ISO-I

The above titled compound had been synthesized by following the general procedure described above for reduction by using corresponding HBV-CSU-47_Int (see Table 2 for analytical data).

Cis-N-(3,5-Dibromophenyl)-2-methyl-5-(thiophen-2-yl)-1,2,6-thiadiazinane-3-carboxamide 1,1-dioxide (HBV-CSU-048-ISO-I)

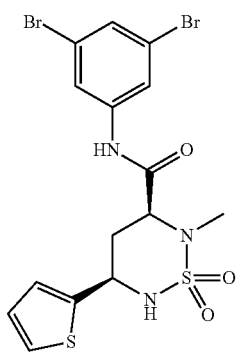

HBV-CSU-048-ISO-I

The above titled compound had been synthesized by following the general procedure described above for reduction by using corresponding HBV-CSU-48_Int (see Table 2 for analytical data).

Cis-N-(3-Bromo-4,5-difluorophenyl)-2-methyl-5-(thiophen-2-yl)-1,2,6-thiadiazinane-3-carboxamide 1,1-dioxide (HBV-CSU-049-ISO-I)

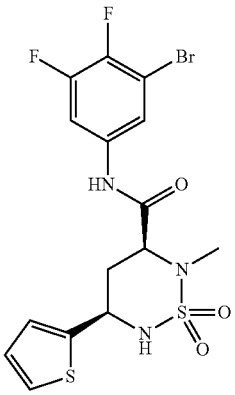

HBV-CSU-049-ISO-I

The above titled compound has been synthesized by following the general procedure described above for reduction by using corresponding HBV-CSU-49_Int (see Table 2 for analytical data).

Scheme 2

General Synthetic Scheme for 5-(thiophen-2-yl)-1,2,6-thiadiazinane-3-carboxamide 1,1-dioxide Derivatives with N-alkyl Variations at C-6

Scheme 2

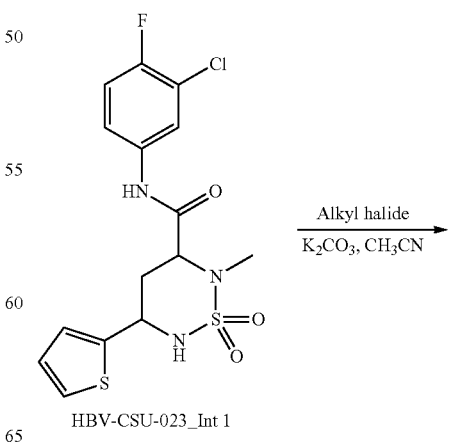

HBV-CSU-023_Int 1

87

-continued

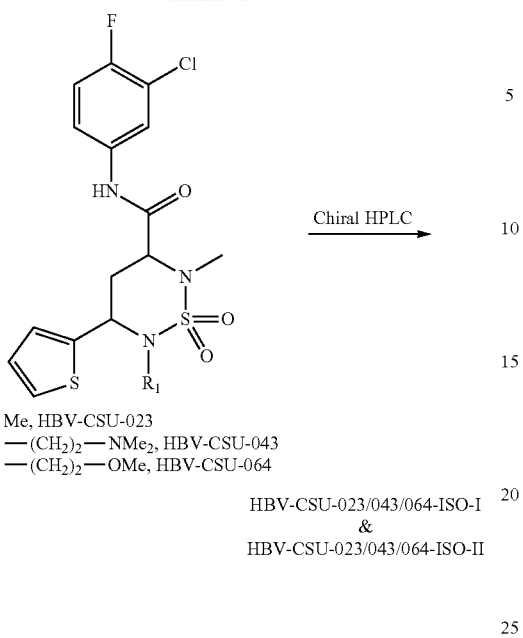

R₁ = Me, HBV-CSU-023
R₁ = —(CH₂)₂—NMe₂, HBV-CSU-043
R₁ = —(CH₂)₂—OMe, HBV-CSU-064

Chiral HPLC →

HBV-CSU-023/043/064-ISO-I
&
HBV-CSU-023/043/064-ISO-II

Cis-N-(3-Chloro-4-fluorophenyl)-2,6-dimethyl-5-(thiophen-2-yl)-1,2,6-thiadiazinane-3-carboxamide 1,1-dioxide (HBV-CSU-023)

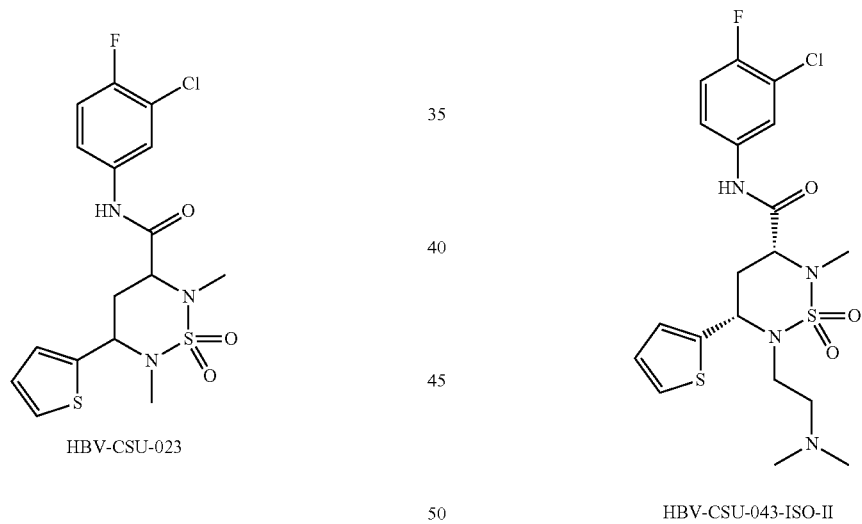

HBV-CSU-023

88

Cis-N-(3-chloro-4-fluorophenyl)-6-(2-(dimethylamino)ethyl)-2-methyl-5-(thiophen-2-yl)-1,2,6-thiadiazinane-3-carboxamide 1,1-dioxide (HBV-CSU-043-ISO-I & ISO-II)

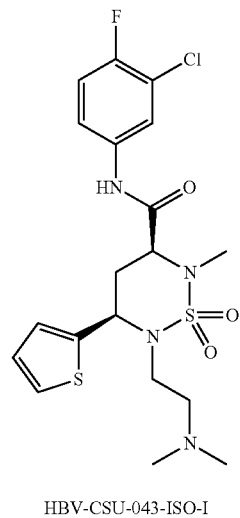

HBV-CSU-043-ISO-I

HBV-CSU-043-ISO-II

To a stirred solution of compound HBV-CSU-023_Int 1 (0.15 g, 0.372 mmol) in acetonitrile (3 mL) at 0° C., K₂CO₃ (0.154 g, 1.16 mmol) was added and stirred at room temperature for 10 min. To this solution, MeI (0.063 g, 0.446 mmol) was added. The reaction mixture was stirred at room temperature for 12 h. The progress of the reaction was monitored by TLC and LCMS. After completion, the reaction mixture was diluted with water and extracted using ethyl acetate. The combined organic layers were washed with brine, dried over anhydrous sodium sulphate and concentrated in vacuo. The crude compound was purified by silica gel column chromatography to afford the desired compound (see Table 2 for analytical data).

To a stirred solution of compound HBV-CSU-023_Int I (0.25 g, 0.621 mmol) in acetonitrile (10 mL), K₂CO₃ (0.257 g, 1.86 mmol) and 2-chloro-N,N-dimethylethan-1-amine hydrochloride (0.107 g, 0.745 mmol) were added and stirred at room temperature for 12 h. The progress of the reaction was monitored by TLC and LCMS. After completion, the reaction mixture was concentrated in vacuo and the crude compound obtained was purified by chiral preparative HPLC to afford the desired compound (25 mg, 8.41%) as a white solid. TLC: 40% EtOAc/hexanes (R$_f$: 0.1); (see Table 2 for analytical data).

Cis-N-(3-Chloro-4-fluorophenyl)-6-(2-methoxy-ethyl)-2-methyl-5-(thiophen-2-yl)-1,2,6-thiadiazi-nane-3-carboxamide 1,1-dioxide (HBV-CSU-064)

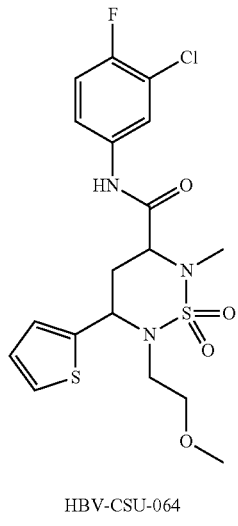 [SMILES: COCCN1C(c2cccs2)CC(C(=O)Nc2ccc(F)c(Cl)c2)N(C)S1(=O)=O ; "HBV-CSU-064"]

HBV-CSU-064

To a stirred solution of compound HBV-CSU-023_Int 1 (0.05 g, 0.123 mmol.) in acetonitrile (3 mL) at 0° C., K₂CO₃ (0.051 g, 0.371 mmol) was added and stirred at room temperature for 10 min. To this solution, 1-bromo-2-methoxyethane (0.034 g, 0.247 mmol) was added. The reaction mixture was stirred at room temperature for 12 h. The progress of the reaction was monitored by TLC and LCMS. After completion, the reaction mixture was diluted with water and extracted with ethyl acetate. The combined organic layers were washed with brine, dried over anhydrous sodium sulphate and concentrated in vacuo. The crude compound was purified by silica gel column chromatography to afford the desired compound (see Table 2 for analytical data).

Scheme 3

Synthesis of Cis-N-(3-chloro-4-fluorophenyl)-2-(2-methoxyethyl)-5-(thiophen-2-yl)-1,2,6-thiadiazi-nane-3-carboxamide 1,1-dioxide (HBV-CSU-25, HBV-CSU-025-ISO-I &II) & Cis-N-(3-chloro-4-fluorophenyl)-6-(2-methoxyethyl)-5-(thiophen-2-yl)-1,2,6-thiadiazinane-3-carboxamide 1,1-dioxide (HBV-CSU-044-ISO-I &II)

Scheme 3

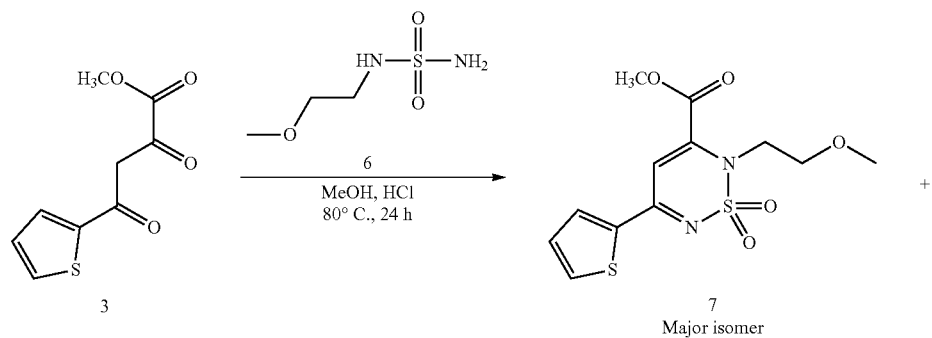

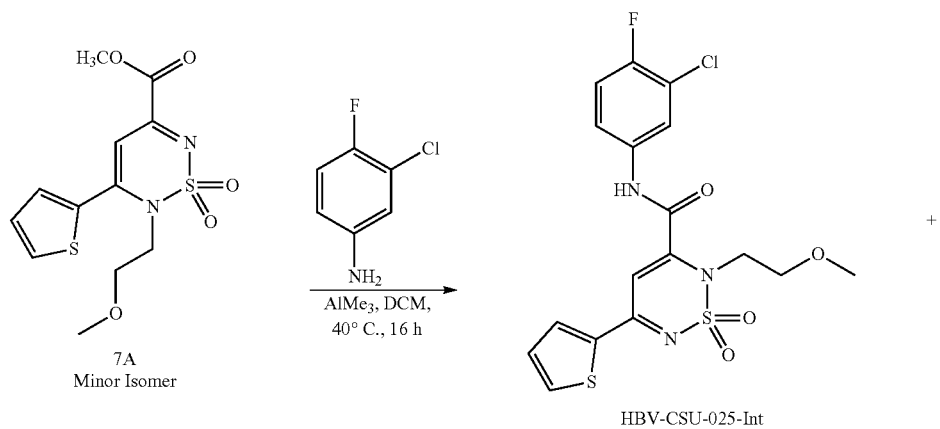

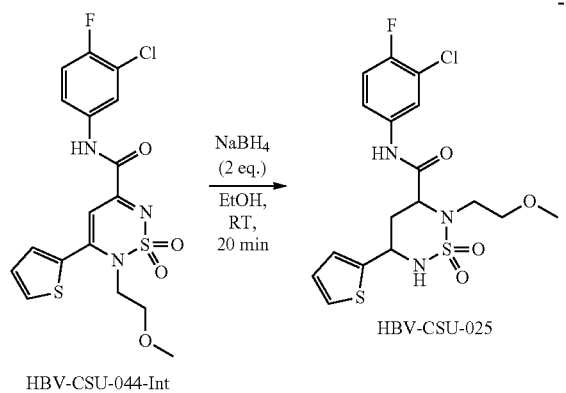

HBV-CSU-044-Int

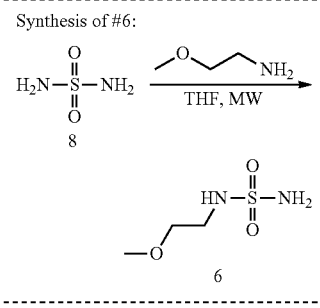

Synthesis of #6:

Chiral HPLC → HBV-CSU-025-ISO-I + HBV-CSU-025-ISO-II

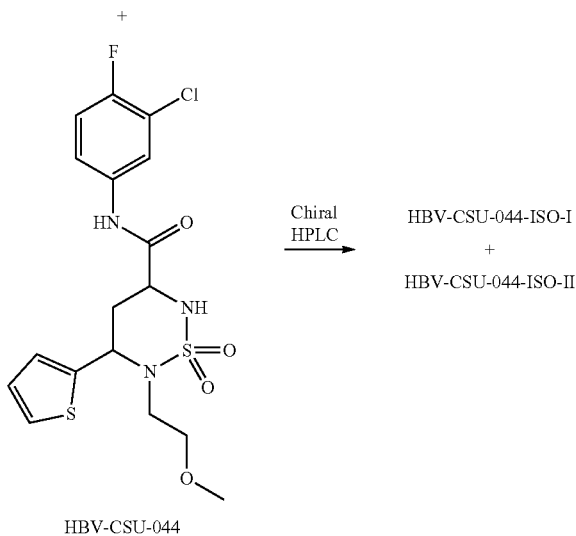

HBV-CSU-044

Chiral HPLC → HBV-CSU-044-ISO-I + HBV-CSU-044-ISO-II

Methyl 2-(2-methoxyethyl)-5-(thiophen-2-yl)-2H-1,2,6-thiadiazine-3-carboxylate 1,1-dioxide (7) and methyl 2-(2-methoxyethyl)-3-(thiophen-2-yl)-2H-1,2,6-thiadiazine-5-carboxylate 1,1-dioxide (7A)

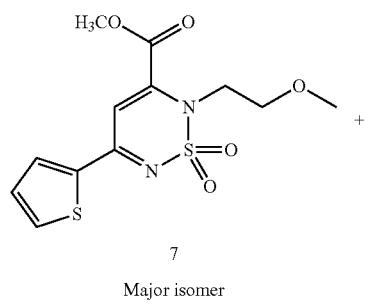

7

Major isomer

-continued

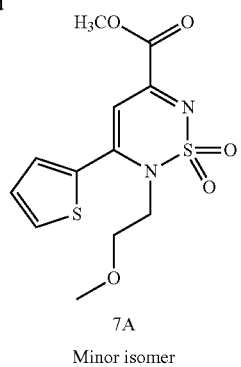

7A

Minor isomer

To a stirred solution of compound 3 (5 g, 23.58 mmol) and compound 6 (3.6 g, 23.58 mmol) in MeOH (40 mL), in sealed tube, HCl gas (generated by sodium chloride+$H_2SO_4$) was purged for 2 h at 0° C. The resulting reaction mixture was stirred at 80° C. for 24 h. The progress of the reaction was monitored by TLC and LCMS. After completion, the reaction mixture was concentrated under reduced pressure. The crude compound was purified by silica gel column chromatography using 15% EtOAc/hexane to afford mixture of compounds 7 and 7A (1 g, 13%) as a white solid TLC: 40% EtOAc/hexanes ($R_f$: 0.6); LCMS Calculated for $C_9H_5N_2O_4S_2$: 330.03; LCMS observed: 330.95 (M+1)$^+$.

N-(3-Chloro-4-fluorophenyl)-2-(2-methoxyethyl)-5-(thiophen-2-yl)-2H-1,2,6-thiadiazine-3-carboxamide 1,1-dioxide (HBV-CSU-025_Int) and N-(3-chloro-4-fluorophenyl)-2-(2-methoxyethyl)-3-(thiophen-2-yl)-2H-1,2,6-thiadiazine-5-carboxamide 1,1-dioxide (HBV-CSU-044_Int)

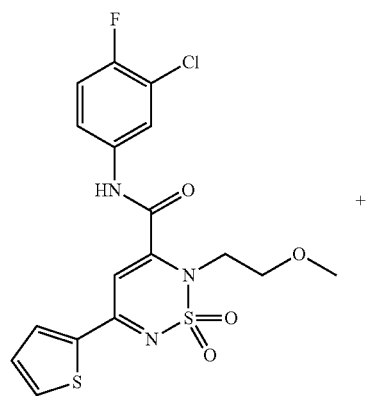

HBV-CSU-025-Int

+

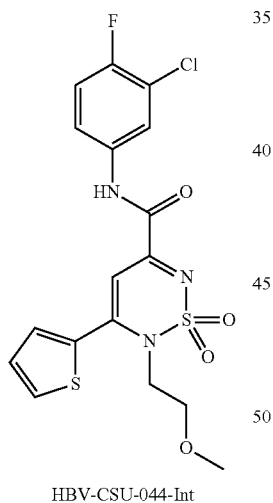

HBV-CSU-044-Int

The above titled compounds have been isolated as inseparable mixture of compounds by following the general procedure (Method A) described above for amidation by using corresponding 7/7A and corresponding amine. The desired product formation was confirmed by LCMS. LCMS Calculated for $C_{17}H_{15}ClFN_3O_4S_2$: 443.02; LCMS observed: 444.04 (M+1)$^+$.

N-(2-methoxyethyl)sulfamide (6)

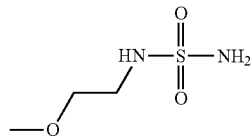

To a stirred solution of Sulfamide (1 g, 10.42 mmol) in THF (5 mL), 2-methoxyethan-1-amine (0.78 g, 10.41 mmol) was added and the reaction mixture was stirred at 100° C. in microwave for 30 min. The progress of the reaction was monitored by TLC and LCMS. After completion, the reaction mixture was concentrated in vacuo. The crude compound was purified by silica gel column chromatography to afford the compound 6 (6.05 g, 75.43%) as a colorless oil. TLC: 5% MeOH/DCM ($R_f$: 0.5); $^1$H NMR (DMSO-$d_6$, 400 MHz): δ 6.48 (br. s, 3H), 3.40-3.32 (m, 2H), 3.23 (s, 3H), 3.02-2.99 (m, 2H).

Cis-N-(3-chloro-4-fluorophenyl)-2-(2-methoxyethyl)-5-(thiophen-2-yl)-1,2,6-thiadiazinane-3-carboxamide 1,1-dioxide (HBV-CSU-025, HBV-CSU-025-ISO-I & HBV-CSU-025-ISO-II)

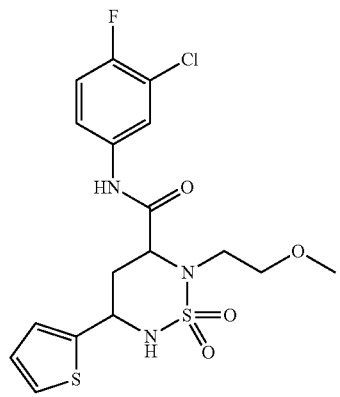

HBV-CSU-025

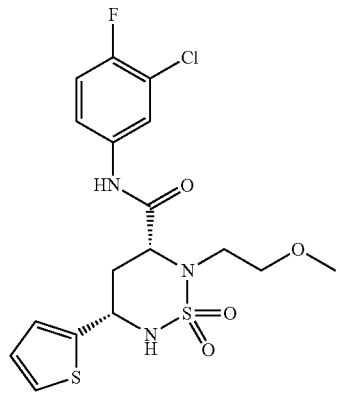

HBV-CSU-025-ISO-I

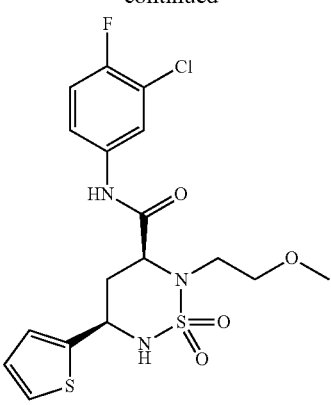

HBV-CSU-025-ISO-II

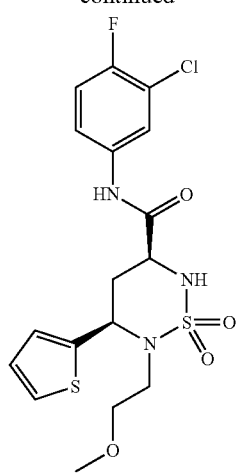

HBV-CSU-044-ISO-II

The above titled compounds have been synthesized by following the general procedure described above for reduction by using corresponding inseparable mixture of HBV-CSU-025_Int/HBV-CSU-044_Int. The regio-isomers were separated using prep-HPLC and then subjected to chiral HPLC separation (see Table 2 for analytical data).

Cis-N-(3-Chloro-4-fluorophenyl)-6-(2-methoxyethyl)-5-(thiophen-2-yl)-1,2,6-thiadiazinane-3-carboxamide 1,1-dioxide (HBV-CSU-044-ISO-I & HBV-CSU-044-ISO-II)

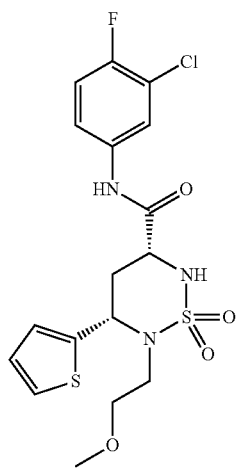

HBV-CSU-044-ISO-I

The above titled compound has been synthesized by following the general procedure described above for reduction by using inseparable mixture of HBV-CSU-025_Int/HBV-CSU-044_Int. The regio-isomers were separated using prep-HPLC and then subjected to chiral HPLC separation (see Table 2 for analytical data).

Scheme 4

General Synthetic Scheme for 5-(thiazol-2-yl)-1,2,6-thiadiazinane-3-carboxamide 1,1-dioxide Derivatives with N-alkyl Variations at C-6

Scheme 4

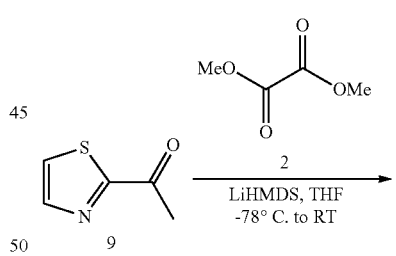

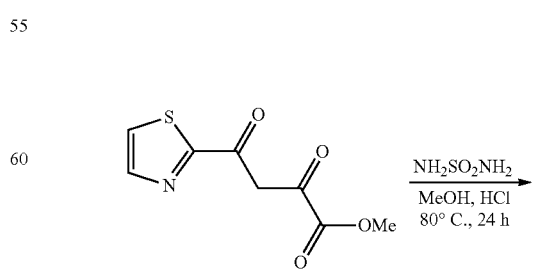

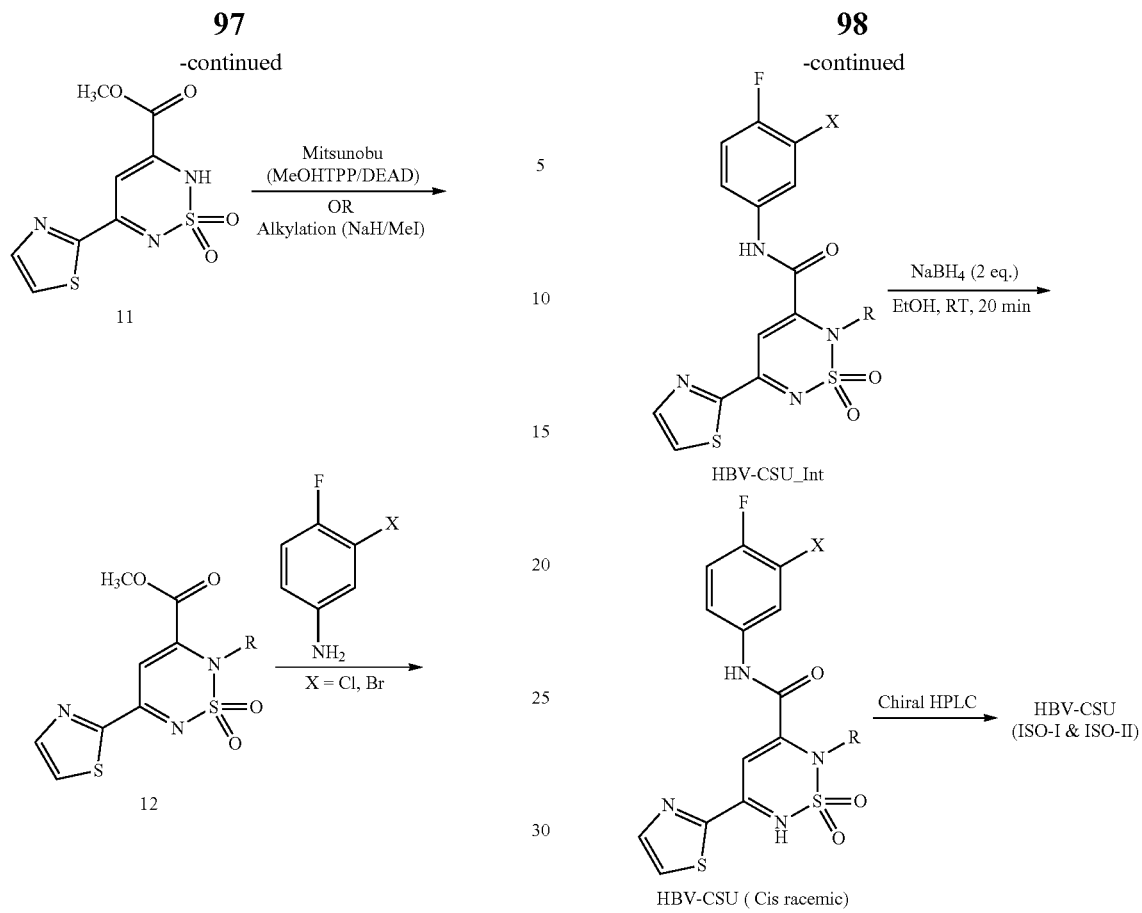
| Target | R variation | Aniline (X = Br/Cl) | Step 3 | Step 4 |
| --- | --- | --- | --- | --- |
| HBV-CSU-027 | Methyl | 3-Cl, 4-F aniline | Alkylation (Method A) | Amidation (Method A) |
| HBV-CSU-058 | -CH(CH₃)CH₂CH₂OMe | 3-Cl, 4-F aniline | Alkylation (Method A) | Amidation (Method A) |
| HBV-CSU-059 | -CH(CH₃)CH₂CH₂OMe | 3-Br, 4-F aniline | Alkylation (Method A) | Amidation (Method A) |
| HBV-CSU-060 | Methyl | 3-Br, 4-F aniline | Alkylation (Method A) | Amidation (Method A) |

-continued

| Target | R variation | Aniline (X = Br/Cl) | Step 3 | Step 4 |
|---|---|---|---|---|
| HBV-CSU-071 | (CH2CH2-O-tBu) | 3-Cl-4-F-aniline | Mitsunobu (Method B) | Amidation (Method C) |
| HBV-CSU-072 | (CH2CH2-O-CF3) | 3-Cl-4-F-aniline | Mitsunobu (Method B) | Amidation (Method B) |
| HBV-CSU-077 | (CH2CH2CH2-OMe) | 3-Cl-4-F-aniline | Mitsunobu (Method B) | Amidation (Method B) |
| HBV-CSU-079 | (CH2-tetrahydrofuran-2-yl) | 3-Cl-4-F-aniline | Mitsunobu (Method B) | Amidation (Method A) |
| HBV-CSU-082 | (CH2CH2CH2-morpholinyl) | 3-Cl-4-F-aniline | Mitsunobu (Method B) | Amidation (Method C) |
| HBV-CSU-083 | (CH2CH2-C(CH3)2-OMe) | 3-Cl-4-F-aniline | Mitsunobu (Method B) | Amidation (Method B) |
| HBV-CSU-089 | (CH2-C≡CH) | 3-Cl-4-F-aniline | Mitsunobu (Method B) | Amidation (Method B) |
| HBV-CSU-090 | (CH2CH2CH2-C≡CH) | 3-Cl-4-F-aniline | Mitsunobu (Method B) | Amidation (Method A) |
| HBV-CSU-094 | (CH2CH2-CH=CH2) | 3-Cl-4-F-aniline | Mitsunobu (Method B) | Amidation (Method B) |
| HBV-CSU-095 | (CH2CH2-OBn) | 3-Cl-4-F-aniline | Mitsunobu (Method B) | Amidation (Method B) |

| Target | R variation | Aniline (X = Br/Cl) | Step 3 | Step 4 |
|---|---|---|---|---|
| HBV-CSU-108 | PMB | 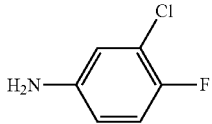 | Mitsunobu (Method B) | Amidation (Method B) |
| HBV-CSU-109 | 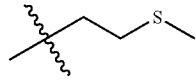 [SMILES: *CCOC] | 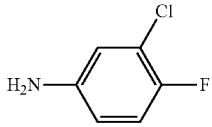 | Mitsunobu (Method B) | Amidation (Method C) |
| HBV-CSU-142 | 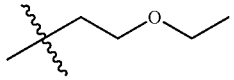 | 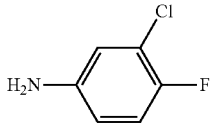 | Mitsunobu (Method B) | Amidation (Method C) |
| HBV-CSU-143 | 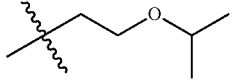 [SMILES: *CCOC(C)C] | 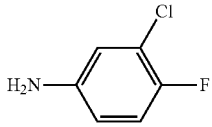 | Mitsunobu (Method B) | Amidation (Method C) |

Methyl 2,4-dioxo-4-(thiazol-2-yl)butanoate (10)

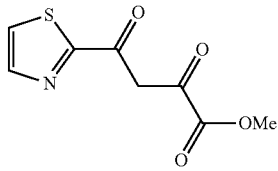 [SMILES: COC(=O)C(=O)CC(=O)c1nccs1]

Title compound was synthesized using general method for the synthesis of 2,4-diketoester described above to afford 11 g (66%, reaction scale is 10 g) as a yellow colored solid. TLC: 5% MeOH/DCM ($R_f$: 0.2); $^1$H NMR (DMSO-$d_6$, 400 MHz): δ 7.92-7.82 (m, 2H), 6.72 (s, 1H), 3.68 (s, 3H); LCMS Calculated for $C_8H_7NO_4S$: 213.01; Observed: 213.97 $(M+1)^+$.

Methyl 5-(thiazol-2-yl)-2H-1,2,6-thiadiazine-3-carboxylate 1,1-dioxide (11)

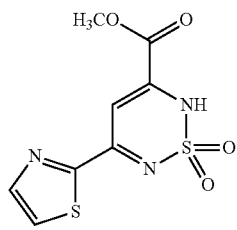 [SMILES: COC(=O)C1=CC(c2nccs2)=NS(=O)(=O)N1]

Title compound was synthesized using general method for the synthesis of cyclic sulfonamide described above to afford 4 g (45%, reaction scale is 7 g) as a light yellow colored solid. TLC: 10% MeOH/DCM ($R_f$: 0.1); $^1$H NMR (DMSO-$d_6$, 400 MHz) δ 11.13 (br. s, 1H), 7.99 (d, J=3.2 Hz, 1H), 7.93 (d, J=3.2 Hz, 1H), 6.96 (s, 1H), 3.80 (s, 3H); LCMS observed for $C_8H_7N_3O_4S_2$: 273.85 $(M+1)^+$.

Methyl 2-methyl-5-(thiazol-2-yl)-2H-1,2,6-thiadiazine-3-carboxylate 1,1-dioxide (12)

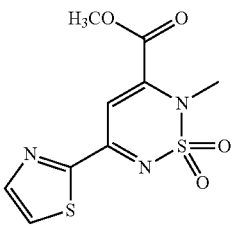 [SMILES: COC(=O)C1=CC(c2nccs2)=NS(=O)(=O)N1C]

Title compound was synthesized using general method A for alkylation described above to afford 1.3 g (80%, reaction scale is 1.5 g) as yellow colored solid. TLC: 50% EtOAc/hexanes ($R_f$: 0.4); $^1$H-NMR (DMSO-$d_6$, 400 MHz): δ 8.25 (d, J=2.8 Hz, 1H), 8.19 (d, J=2.8 Hz, 1H), 7.43 (s, 1H), 3.91 (s, 3H), 3.56 (s, 3H); LCMS observed for $C_9H_9N_3O_4S_2$: 287.00, Observed: 287.90 $(M+1)^+$.

Methyl 2-(2-methoxyethyl)-5-(thiazol-2-yl)-2H-1,2,6-thiadiazine-3-carboxylate 1,1-dioxide (12)

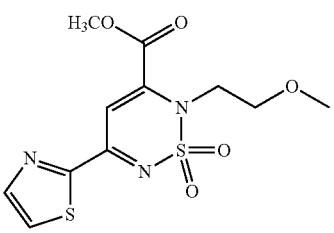 [SMILES: COCCN1C(C(=O)OC)=CC(c2nccs2)=NS1(=O)=O]

Title compound was synthesized using general method C for alkylation described above to afford 1.1 g (45.3%, reaction scale is 2 g). LCMS observed for $C_{11}H_{13}N_3O_5S_2$: 331.03, Observed: 332 (M+1)$^+$.

Methyl 2-(2-(tert-butoxy)ethyl)-5-(thiazol-2-yl)-2H-1,2,6-thiadiazine-3-carboxylate 1,1-dioxide (12)

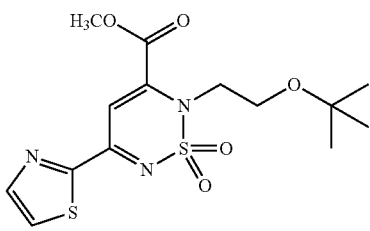 [SMILES: COC(=O)C1=CC(c2nccs2)=NS(=O)(=O)N1CCOC(C)(C)C]

Title compound was synthesized using general method B for alkylation described above to afford 2.5 g (61%, reaction scale is 3 g). $^1$H NMR (DMSO-d$_6$, 500 MHz): δ 8.30 (d, J=2.9 Hz, 1H), 8.25 (d, J=2.9 Hz, 1H), 7.49 (s, 1H), 4.29 (t, J=4.9 Hz, 2H), 3.92 (s, 3H), 3.38 (t, J=4.9 Hz, 2H), 0.94 (s, 9H).

Methyl 5-(thiazol-2-yl)-2-(2-(trifluoromethoxy)ethyl)-2H-1,2,6-thiadiazine-3-carboxylate 1,1-dioxide (12)

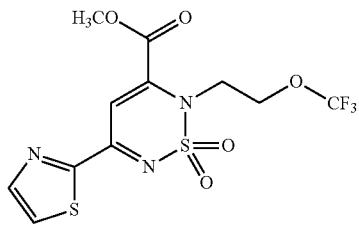 [SMILES: COC(=O)C1=CC(c2nccs2)=NS(=O)(=O)N1CCOC(F)(F)F]

Title compound was synthesized using general method B for alkylation described above to afford 0.7 g (crude, reaction scale is 0.5 g). LCMS observed for $C_{11}H_{10}F_3N_3O_5S_2$: 385.00, Observed: 385.95 (M+1)$^+$.

Methyl 2-allyl-5-(thiazol-2-yl)-2H-1,2,6-thiadiazine-3-carboxylate 1,1-dioxide (12)

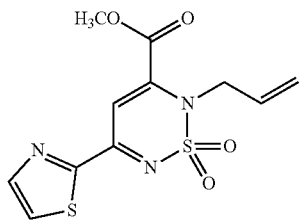 [SMILES: C=CCN1C(C(=O)OC)=CC(c2nccs2)=NS1(=O)=O]

Title compound was synthesized using general method A for alkylation described above to afford 0.85 g (74.56%, reaction scale is 1 g/trans-esterified product also observed which was carried forward as mixture to next step); LCMS observed for $C_{11}H_{11}N_3O_4S_2$: 313.02, Observed: 313.6 (M+1)$^+$.

Methyl 2-(prop-2-yn-1-yl)-5-(thiazol-2-yl)-2H-1,2,6-thiadiazine-3-carboxylate 1,1-dioxide (12)

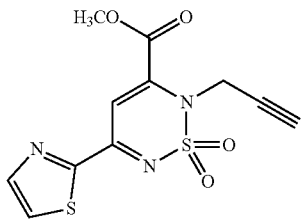 [SMILES: C#CCN1C(C(=O)OC)=CC(c2nccs2)=NS1(=O)=O]

Title compound was synthesized using general method B for alkylation described above to afford 0.75 g (66.37%, reaction scale is 1 g); LCMS observed for $C_{11}H_9N_3O_4S_2$: 311.00, Observed: 311.95 (M+1)$^-$.

Methyl 2-(3-methoxypropyl)-5-(thiazol-2-yl)-2H-1,2,6-thiadiazine-3-carboxylate 1,1-dioxide (12)

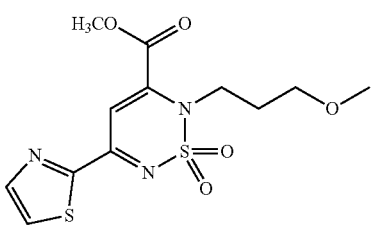 [SMILES: COCCCN1C(C(=O)OC)=CC(c2nccs2)=NS1(=O)=O]

Title compound was synthesized using general method B for alkylation described above to afford 1.5 g (59.28%, reaction scale is 2 g); LCMS observed for $C_{12}H_{15}N_3O_5S_2$: 345.05, Observed: 346 (M+1)$^+$.

Methyl 2-((tetrahydrofuran-2-yl)methyl)-5-(thiazol-2-yl)-2H-1,2,6-thiadiazine-3-carboxylate 1,1-dioxide (12)

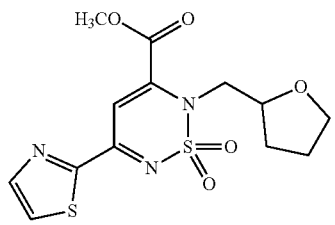 [SMILES: COC(=O)C1=CC(c2nccs2)=NS(=O)(=O)N1CC1CCCO1]

Title compound was synthesized using general method B for alkylation described above to afford 0.4 g (61%, reaction scale is 0.5 g). $^1$H NMR (500 MHz, DMSO-d$_6$): δ 8.31 (d, J=2.9 Hz, 1H), 8.25 (d, J=2.9 Hz, 1H), 7.48 (s, 1H), 4.32-4.27 (m, 1H), 4.24-4.14 (m, 1H), 3.99-3.93 (m, 1H), 3.93 (s, 3H), 3.61-3.54 (m, 1H), 3.47-3.41 (m, 1H), 1.96-1.85 (m, 1H), 1.78-1.58 (m, 2H), 1.51-1.42 (m, 1H).

Methyl 2-(2-morpholinoethyl)-5-(thiazol-2-yl)-2H-1,2,6-thiadiazine-3-carboxylate 1,1-dioxide (12)

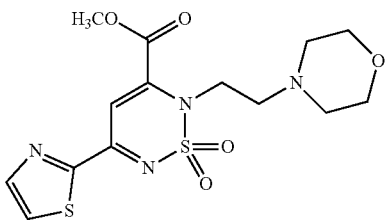 [SMILES: COC(=O)C1=CC(c2nccs2)=NS(=O)(=O)N1CCN1CCOCC1]

Title compound was synthesized using general method B for alkylation described above to afford 150 mg (crude, reaction scale is 1.5 g). LCMS observed for $C_{14}H_{18}N_4O_5S_2$: 386.07, Observed: 387.20 (M+1)$^+$.

Methyl 2-(3-methoxy-3-methylbutyl)-5-(thiazol-2-yl)-2H-1,2,6-thiadiazine-3-carboxylate 1,1-dioxide (12)

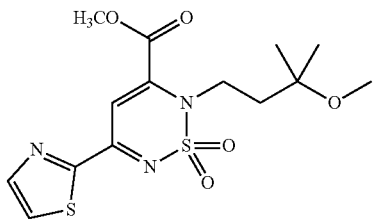 [SMILES: COC(=O)C1=CC(c2nccs2)=NS(=O)(=O)N1CCC(C)(C)OC]

Title compound was synthesized using general method B for alkylation described above to afford 1.5 g (55%, reaction scale is 1.73 g). 1H NMR (400 MHz, DMSO-d$_6$): δ 8.30 (d, J=3.0 Hz, 1H), 8.24 (d, J=3.0 Hz, 1H), 7.49 (s, 1H), 4.04-3.98 (m, 2H), 3.95 (s, 3H), 3.08 (s, 3H), 2.03-1.96 (m, 2H), 1.12 (s, 6H).

Methyl 2-(but-3-yn-1-yl)-5-(thiazol-2-yl)-2H-1,2,6-thiadiazine-3-carboxylate 1,1-dioxide (12)

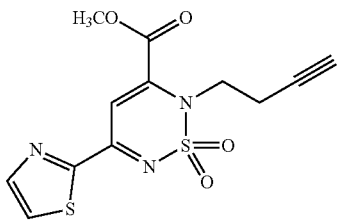 [SMILES: C#CCCN1C(C(=O)OC)=CC(c2nccs2)=NS1(=O)=O]

Title compound was synthesized using general method B for alkylation described above to afford 310 mg (26%, reaction scale is 1 g). $^1$H-NMR (DMSO-d$_6$, 400 MHz): δ 8.32 (d, J=3.1 Hz, 1H), 8.25 (d, J=3.0 Hz, 1H), 7.56 (s, 1H), 4.21 (t, J=7.0 Hz, 2H), 3.96 (s, 3H), 3.00 (t, J=2.6 Hz, 1H), 2.65 (td, J=7.0, 2.6 Hz, 2H); LCMS observed for $C_{12}H_{11}N_3O_4S_2$: 325.02, Observed: 326.10 (M+1)$^+$.

Methyl 2-(2-(benzyloxy)ethyl)-5-(thiazol-2-yl)-2H-1,2,6-thiadiazine-3-carboxylate 1,1-dioxide (12)

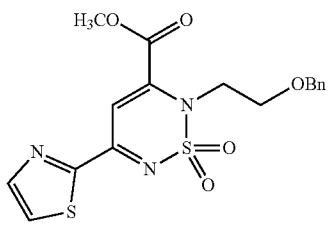 [SMILES: COC(=O)C1=CC(c2nccs2)=NS(=O)(=O)N1CCOCc1ccccc1]

Title compound was synthesized using general method B for alkylation described above to afford 780 mg (17.7%, reaction scale is 2 g); LCMS observed for $C_{17}H_{17}N_3O_5S_2$: 407.06, Observed: 408.05 (M+1)$^+$.

Methyl 2-(4-methoxybenzyl)-5-(thiazol-2-yl)-2H-1,2,6-thiadiazine-3-carboxylate 1,1-dioxide (12)

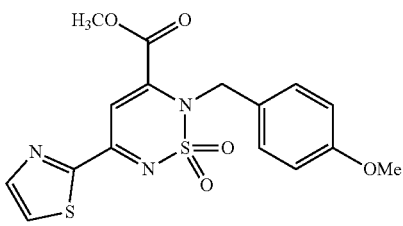 [SMILES: COC(=O)C1=CC(c2nccs2)=NS(=O)(=O)N1Cc1ccc(OC)cc1]

Title compound was synthesized using general method B for alkylation described above to afford 900 mg (24.32%, reaction scale is 2 g). $^1$H-NMR (DMSO-d$_6$, 400 MHz): δ 8.32 (d, J=2.8 Hz, 1H), 8.24 (d, J=2.8 Hz, 1H), 7.49 (s, 1H), 7.19 (d, J=8.8 Hz, 1H), 6.91 (d, J=8.4 Hz, 1H), 5.16 (s, 2H), 3.85 (s, 3H), 3.72 (s, 3H).

Methyl 2-(2-(methylthio)ethyl)-5-(thiazol-2-yl)-2H-1,2,6-thiadiazine-3-carboxylate 1,1-dioxide (12)

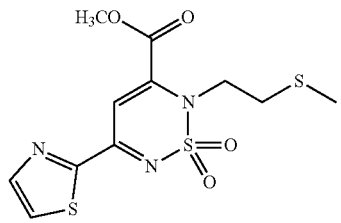 [SMILES: COC(=O)C1=CC(c2nccs2)=NS(=O)(=O)N1CCSC]

Title compound was synthesized using general method B for alkylation described above to afford 1.5 g (60%, reaction scale is 2 g). $^1$H-NMR (DMSO-d$_6$, 400 MHz): 8.31 (d, J=3.1 Hz, 1H), 8.25 (d, J=2.9 Hz, 1H), 7.55 (s, 1H), 4.23 (t, J=7.0 Hz, 2H), 3.96 (s, 3H), 2.83 (t, J=7.0 Hz, 2H), 2.04 (s, 3H); LCMS observed for $C_{11}H_{13}N_3O_4S_3$: 347.01, Observed: 347.10 (M+1)$^+$.

Methyl 2-(2-ethoxyethyl)-5-(thiazol-2-yl)-2H-1,2,6-thiadiazine-3-carboxylate 1,1-dioxide (12)

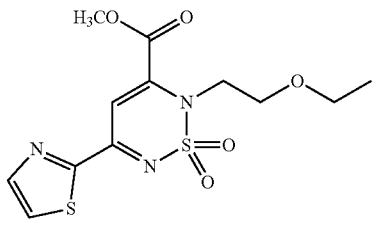 [SMILES: CCOCCN1C(C(=O)OC)=CC(c2nccs2)=NS1(=O)=O]

Title compound was synthesized using general method B for alkylation described above to afford 1.3 g (52%, reaction scale is 2 g). $^1$H-NMR (DMSO-$d_6$, 400 MHz): δ 8.31 (d, J=3.1 Hz, 1H), 8.25 (d, J=3.1 Hz, 1H), 7.47 (s, 1H), 4.29 (t, J=5.0 Hz, 2H), 3.93 (s, 3H), 3.49 (t, J=5.0 Hz, 2H), 3.30 (q, J=7.4 Hz, 2H), 0.97 (t, J=7.0 Hz, 3H); LCMS observed for $C_{12}H_{15}N_3O_5S_2$: 345.05, Observed: 346.10 (M+1)$^+$.

Methyl 2-(2-isopropoxyethyl)-5-(thiazol-2-yl)-2H-1,2,6-thiadiazine-3-carboxylate 1,1-dioxide (12)

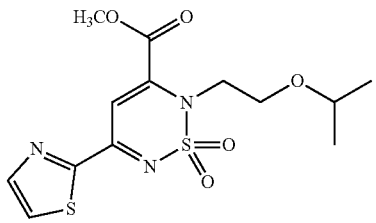 [SMILES: COC(=O)C1=CC(c2nccs2)=NS(=O)(=O)N1CCOC(C)C]

Title compound was synthesized using general method B for alkylation described above to afford 1.3 g (66%, reaction scale is 1.5 g). $^1$H-NMR (DMSO-$d_6$, 400 MHz): δ 8.31 (d, J=3.0 Hz, 1H), 8.25 (d, J=3.1 Hz, 1H), 7.49 (s, 1H), 4.29 (t, J=5.0 Hz, 2H), 3.93 (s, 3H), 3.46 (t, J=5.0 Hz, 2H), 3.43-3.35 (m, 1H), 0.92 (d, J=6.0 Hz, 6H); LCMS observed for $C_{13}H_{17}N_3O_5S_2$: 359.06, Observed: 359.90 (M+1)$^+$.

N-(3-Chloro-4-fluorophenyl)-2-methyl-5-(thiazol-2-yl)-2H-1,2,6-thiadiazine-3-carboxamide 1,1-dioxide (HBV-CSU-027_Int)

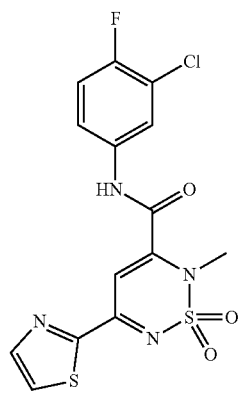

HBV-CSU-027-Int

The above titled compounds have been synthesized by following the general procedure (Method A) described above for amidation by using corresponding 12 and corresponding amine. The desired product formation was confirmed by LCMS and the crude intermediate carried forward to the next step. LCMS observed for $C_{14}H_{10}ClFN_4O_3S_2$: 399.99, Observed: 400.90 (M+1)$^+$.

N-(3-chloro-4-fluorophenyl)-2-(2-methoxyethyl)-5-(thiazol-2-yl)-2H-1,2,6-thiadiazine-3-carboxamide 1,1-dioxide (HBV-CSU-058_Int)

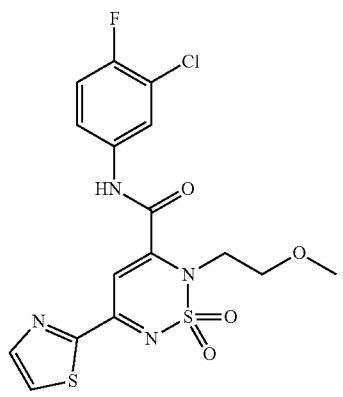

HBV-CSU-058-Int

The above titled compound has been synthesized by following the general procedure (Method A) described above for amidation by using corresponding 12 and corresponding amine (see Table 1 for analytical data).

N-(3-Bromo-4-fluorophenyl)-2-(2-methoxyethyl)-5-(thiazol-2-yl)-2H-1,2,6-thiadiazine-3-carboxamide 1,1-dioxide (HBV-CSU-059_Int)

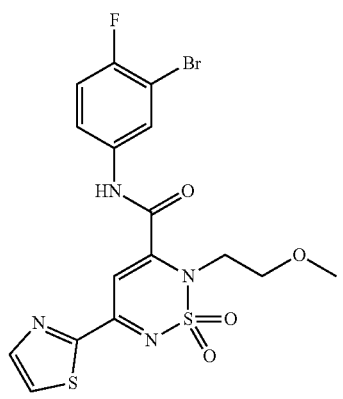

HBV-CSU-059-Int

The above titled compound has been synthesized by following the general procedure (Method A) described above for amidation by using corresponding 12 and corresponding amine (see Table 1 for analytical data).

109

N-(3-Bromo-4-fluorophenyl)-2-methyl-5-(thiazol-2-yl)-2H-1,2,6-thiadiazine-3-carboxamide 1,1-dioxide (HBV-CSU-060_Int)

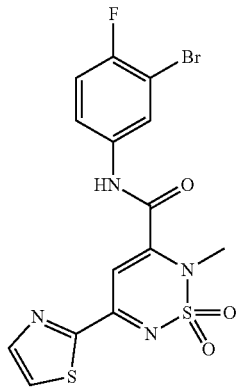

HBV-CSU-060-Int

The above titled compound has been synthesized by following the general procedure (Method A) described above for amidation by using corresponding 12 and corresponding amine (see Table 1 for analytical data).

2-(tert-Butoxy)ethyl)-N-(3-chloro-4-fluorophenyl)-5-(thiazol-2-yl)-2H-1,2,6-thiadiazine-3-carboxamide 1,1-dioxide (HBV-CSU-071_Int)

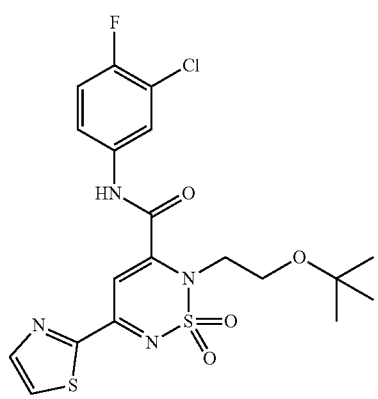

HBV-CSU-071-Int

The above titled compound has been synthesized by following the general procedure (Method C) described above for amidation by using corresponding 12 and corresponding amine see Table 1 for analytical data).

110

N-(3-Chloro-4-fluorophenyl)-5-(thiazol-2-yl)-2-(2-(trifluoromethoxy)ethyl)-2H-1,2,6-thiadiazine-3-carboxamide 1,1-dioxide (HBV-CSU-072_Int)

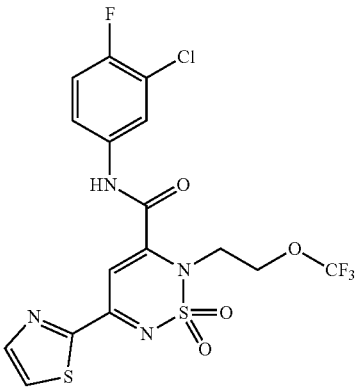

HBV-CSU-072-Int

The above titled compound has been synthesized by following the general procedure (Method B) described above for amidation by using corresponding 12 and corresponding amine (see Table 1 for analytical data).

N-(3-Chloro-4-fluorophenyl)-2-(3-methoxypropyl)-5-(thiazol-2-yl)-2H-1,2,6-thiadiazine-3-carboxamide 1,1-dioxide (HBV-CSU-077_Int)

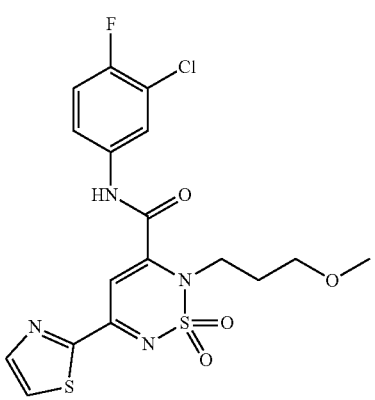

HBV-CSU-077-Int

The above titled compound has been synthesized by following the general procedure (Method B) described above for amidation by using corresponding 12 and corresponding amine (see Table 1 for analytical data).

111

N-(3-Chloro-4-fluorophenyl)-2-((tetrahydrofuran-2-yl)methyl)-5-(thiazol-2-yl)-2H-1,2,6-thiadiazine-3-carboxamide 1,1-dioxide (HBV-CSU-079_Int)

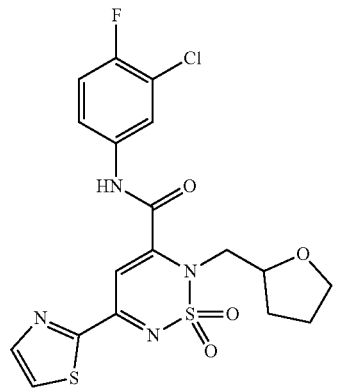

HBV-CSU-079-Int

The above titled compound has been synthesized by following the general procedure (Method A) described above for amidation by using corresponding 12 and corresponding amine (see Table 1 for analytical data).

N-(3-chloro-4-fluorophenyl)-2-(2-morpholinoethyl)-5-(thiazol-2-yl)-2H-1,2,6-thiadiazine-3-carboxamide 1,1-dioxide (HBV-CSU-082_Int)

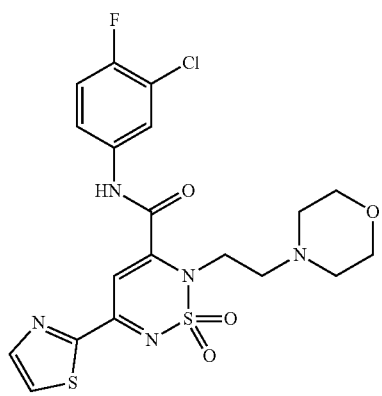

HBV-CSU-082-Int

The above titled compound has been synthesized by following the general procedure (Method C) described above for amidation by using corresponding 12 and corresponding amine (see Table 1 for analytical data).

112

N-(3-chloro-4-fluorophenyl)-2-(3-methoxy-3-methylbutyl)-5-(thiazol-2-yl)-2H-1,2,6-thiadiazine-3-carboxamide 1,1-dioxide (HBV-CSU-083_Int)

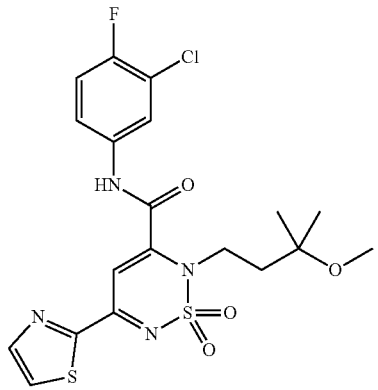

HBV-CSU-083-Int

The above titled compound has been synthesized by following the general procedure (Method B) described above for amidation by using corresponding 12 and corresponding amine (see Table 1 for analytical data).

N-(3-Chloro-4-fluorophenyl)-2-(prop-2-yn-1-yl)-5-(thiazol-2-yl)-2H-1,2,6-thiadiazine-3-carboxamide 1,1-dioxide (HBV-CSU-089_Int)

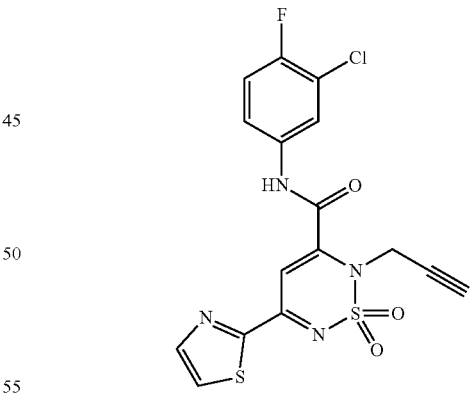

HBV-CSU-089-Int

The above titled compound has been synthesized by following the general procedure (Method B) described above for amidation by using corresponding 12 and corresponding amine (see Table 1 for analytical data).

113

2-(But-3-yn-1-yl)-N-(3-chloro-4-fluorophenyl)-5-(thiazol-2-yl)-2H-1,2,6-thiadiazine-3-carboxamide 1,1-dioxide (HBV-CSU-090_Int)

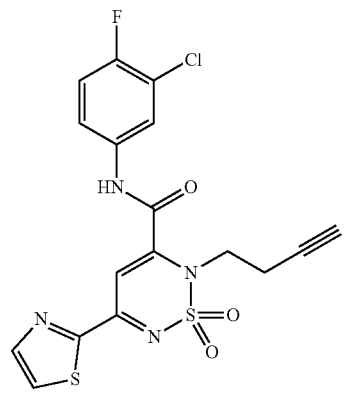

HBV-CSU-090-Int

The above titled compound has been synthesized by following the general procedure (Method A) described above for amidation by using corresponding 12 and corresponding amine (see Table 1 for analytical data).

2-Allyl-N-(3-chloro-4-fluorophenyl)-5-(thiazol-2-yl)-2H-1,2,6-thiadiazine-3-carboxamide 1,1-dioxide (HBV-CSU-094_Int)

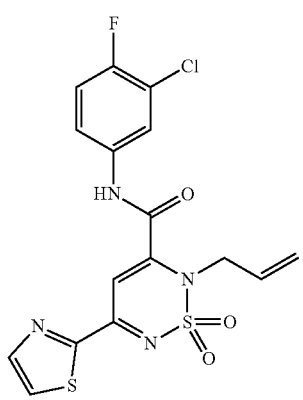

HBV-CSU-094-Int

The above titled compound has been synthesized by following the general procedure (Method A) described above for amidation by using corresponding 12 and corresponding amine (see Table 1 for analytical data).

114

2-(2-(Benzyloxy)ethyl)-N-(3-chloro-4-fluorophenyl)-5-(thiazol-2-yl)-2H-1,2,6-thiadiazine-3-carboxamide 1,1-dioxide (HBV-CSU-095_Int)

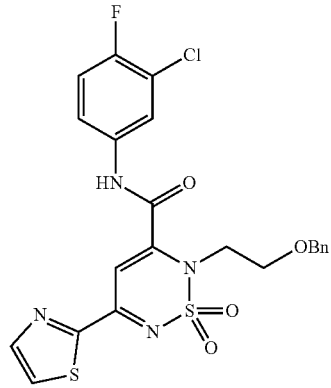

HBV-CSU-095-Int

The above titled compound has been synthesized by following the general procedure (Method B) described above for amidation by using corresponding 12 and corresponding amine (see Table 1 for analytical data).

N-(3-Chloro-4-fluorophenyl)-2-(4-methoxybenzyl)-5-(thiazol-2-yl)-2H-1,2,6-thiadiazine-3-carboxamide 1,1-dioxide (HBV-CSU-108_Int)

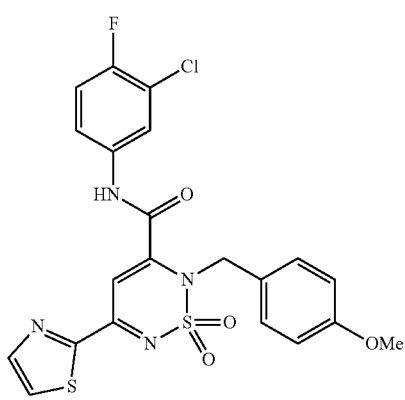

HBV-CSU-108-Int

The above titled compound has been synthesized by following the general procedure (Method B) described above for amidation by using corresponding 12 and corresponding amine (see Table 1 for analytical data).

115
N-(3-Chloro-4-fluorophenyl)-2-(2-(methylthio)ethyl)-5-(thiazol-2-yl)-2H-1,2,6-thiadiazine-3-carboxamide 1,1-dioxide (HBV-CSU-109_Int)

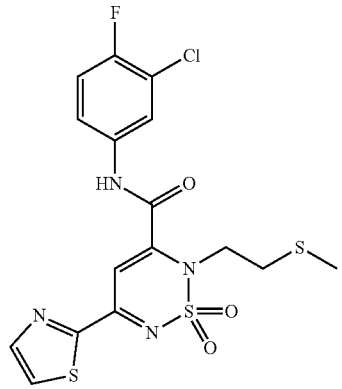

HBV-CSU-109-Int

The above titled compound has been synthesized by following the general procedure (Method C) described above for amidation by using corresponding 12 and corresponding amine (see Table 1 for analytical data).

N-(3-chloro-4-fluorophenyl)-2-(2-ethoxyethyl)-5-(thiazol-2-yl)-2H-1,2,6-thiadiazine-3-carboxamide 1,1-dioxide (HBV-CSU-142_Int)

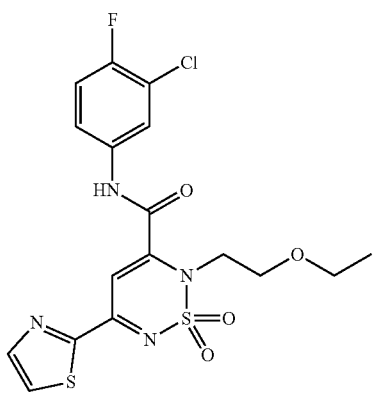

HBV-CSU-142-Int

The above titled compound has been synthesized by following the general procedure (Method C) described above for amidation by using corresponding 12 and corresponding amine (see Table 1 for analytical data).

116
N-(3-chloro-4-fluorophenyl)-2-(2-isopropoxyethyl)-5-(thiazol-2-yl)-2H-1,2,6-thiadiazine-3-carboxamide 1,1-dioxide (HBV-CSU-143_Int)

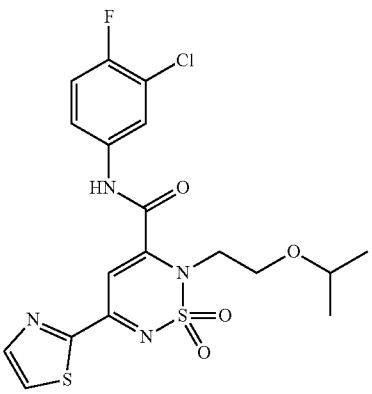

HBV-CSU-143-Int

The above titled compound has been synthesized by following the general procedure (Method C) described above for amidation by using corresponding 12 and corresponding amine (see Table 1 for analytical data).

Cis-N-(3-chloro-4-fluorophenyl)-2-methyl-5-(thiazol-2-yl)-1,2,6-thiadiazinane-3-carboxamide 1,1-dioxide (HBV-CSU-027, HBV-CSU-027-ISO-I & HBV-CSU-027-ISO-II)

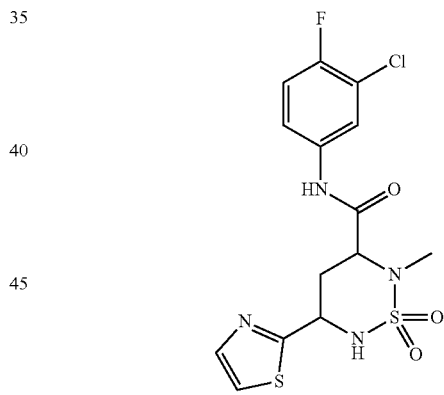

HBV-CSU-027

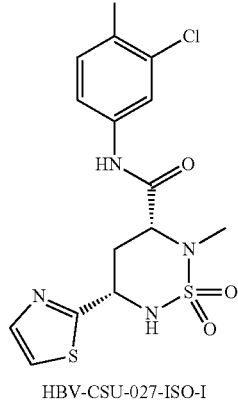

HBV-CSU-027-ISO-I

117

-continued

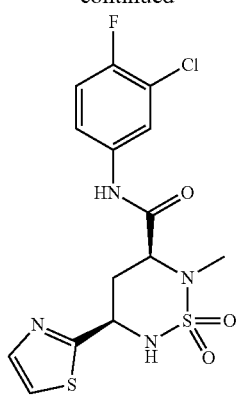

HBV-CSU-027-ISO-II

The above titled compounds have been synthesized by following the general procedure described above for reduction by using corresponding HBV-CSU-027_Int (see Table 2 for analytical data).

Cis-N-(3-chloro-4-fluorophenyl)-2-(2-methoxy-ethyl)-5-(thiazol-2-yl)-1,2,6-thiadiazinane-3-carboxamide 1,1-dioxide (HBV-CSU-058, HBV-CSU-058-ISO-I & HBV-CSU-058-ISO-II)

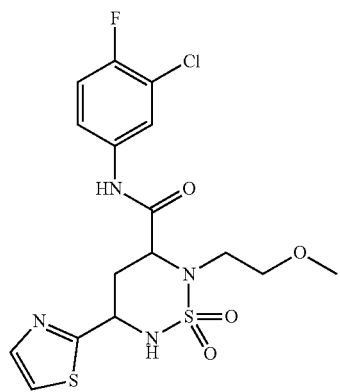

HBV-CSU-058

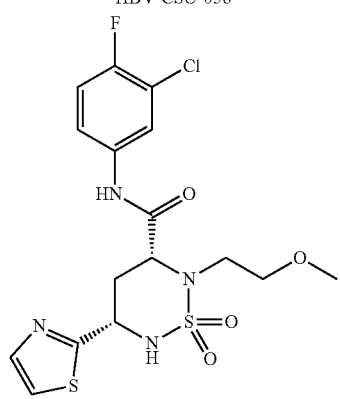

HBV-CSU-058-ISO-I

118

-continued

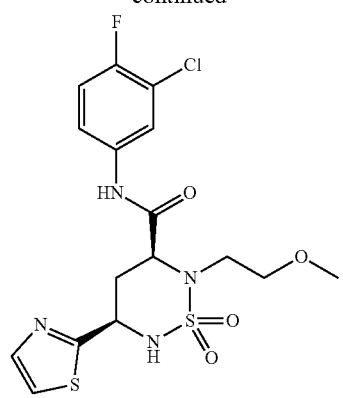

HBV-CSU-058-ISO-II

The above titled compounds have been synthesized by following the general procedure described above for reduction by using corresponding HBV-CSU-058_Int (see Table 2 for analytical data).

Cis-N-(3-bromo-4-fluorophenyl)-2-(2-methoxy-ethyl)-5-(thiazol-2-yl)-1,2,6-thiadiazinane-3-carboxamide 1,1-dioxide (HBV-CSU-059, HBV-CSU-059-ISO-I & HBV-CSU-059-ISO-II)

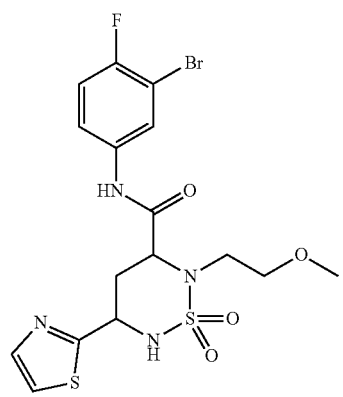

HBV-CSU-059

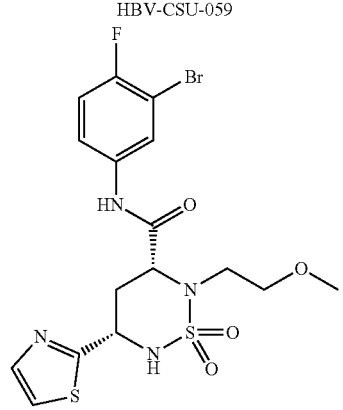

HBV-CSU-059-ISO-I

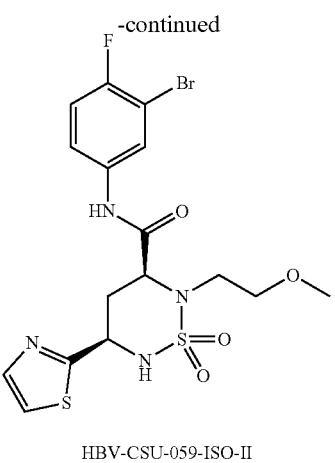

HBV-CSU-059-ISO-II

The above titled compounds have been synthesized by following the general procedure described above for reduction by using corresponding HBV-CSU-059_Int (see Table 2 for analytical data).

Cis-N-(3-bromo-4-fluorophenyl)-2-methyl-5-(thiazol-2-yl)-1,2,6-thiadiazinane-3-carboxamide 1,1-dioxide (HBV-CSU-060-ISO-I & HBV-CSU-060-ISO-II)

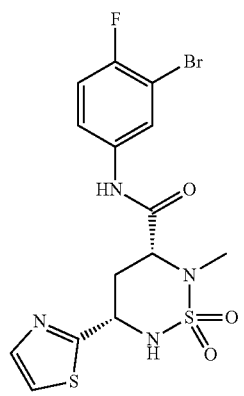

HBV-CSU-060-Isomer I

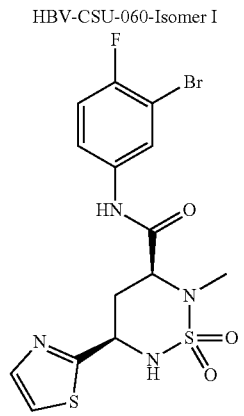

HBV-CSU-060-Isomer II

The above titled compounds have been synthesized by following the general procedure described above for reduction by using corresponding HBV-CSU-060_Int. The chiral HPLC separation provided desired compound (see Table 2 for analytical data).

Cis-2-(2-(tert-Butoxy)ethyl)-N-(3-chloro-4-fluorophenyl)-5-(thiazol-2-yl)-1,2,6-thiadiazinane-3-carboxamide 1,1-dioxide (HBV-CSU-071, HBV-CSU-071-ISO-I & HBV-CSU-071-ISO-II))

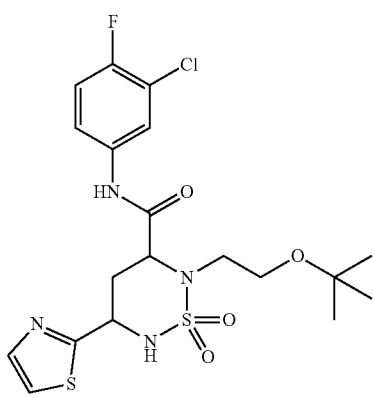

HBV-CSU-071

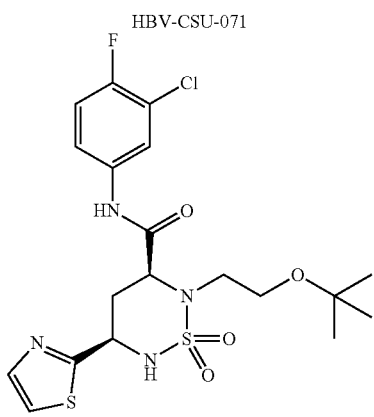

HBV-CSU-071-ISO-I

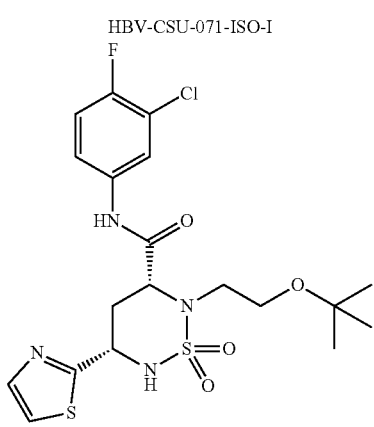

HBV-CSU-071-ISO-II

The above titled compounds have been synthesized by following the general procedure described above for reduction by using corresponding HBV-CSU-071_Int (see Table 2 for analytical data).

121

Cis-N-(3-Chloro-4-fluorophenyl)-5-(thiazol-2-yl)-2-(2-(trifluoromethoxy)ethyl)-1,2,6-thiadiazinane-3-carboxamide 1,1-dioxide (HBV-CSU-072, HBV-CSU-072-ISO-I & HBV-CSU-072-ISO-II)

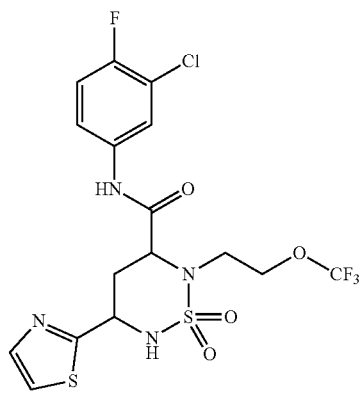

HBV-CSU-072

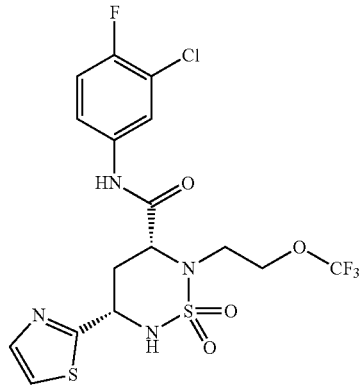

HBV-CSU-072-ISO-I

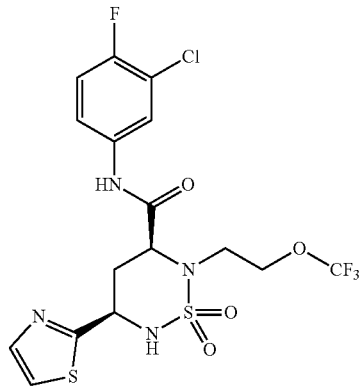

HBV-CSU-072-ISO-II

The above titled compounds have been synthesized by following the general procedure described above for reduction by using corresponding HBV-CSU-072_Int (see Table 2 for analytical data).

122

Cis-N-(3-Chloro-4-fluorophenyl)-2-(3-methoxypropyl)-5-(thiazol-2-yl)-1,2,6-thiadiazinane-3-carboxamide 1,1-dioxide (HBV-CSU-077-ISO-I & HBV-CSU-077-ISO-II)

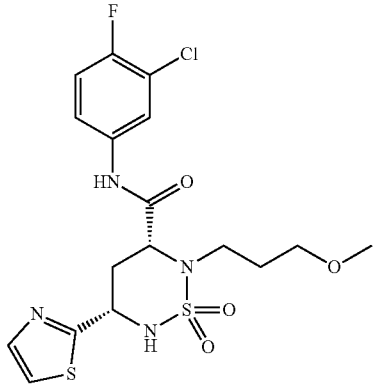

HBV-CSU-077-ISO-I

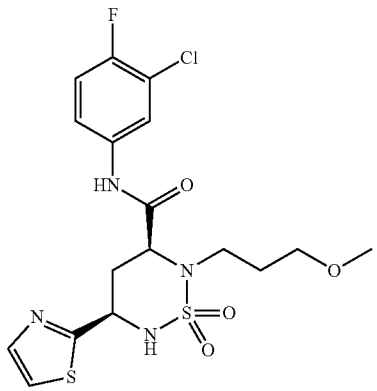

HBV-CSU-077-ISO-II

The above titled compounds have been synthesized by following the general procedure described above for reduction by using corresponding HBV-CSU-077_Int (see Table 2 for analytical data).

Cis-N-(3-Chloro-4-fluorophenyl)-2-((tetrahydrofuran-2-yl)methyl)-5-(thiazol-2-yl)-1,2,6-thiadiazinane-3-carboxamide 1,1-dioxide (HBV-CSU-079-Rac-A & HBV-CSU-079-Rac-B)

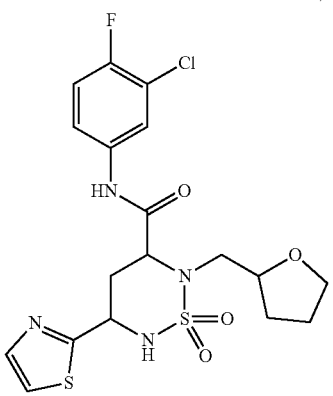

HBV-CSU-079-Rac-A

123

-continued

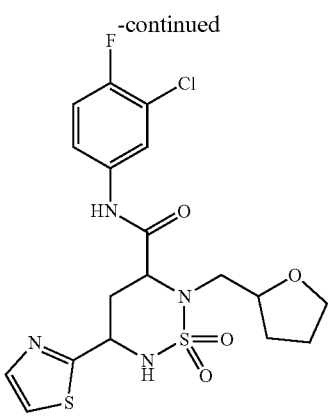

HBV-CSU-079-Rac-B

The above titled compounds have been synthesized by following the general procedure described above for reduction by using corresponding HBV-CSU-079_Int (see Table 2 for analytical data).

Cis-N-(3-Chloro-4-fluorophenyl)-2-(2-morpholinoethyl)-5-(thiazol-2-yl)-1,2,6-thiadiazinane-3-carboxamide 1,1-dioxide (HBV-CSU-082)

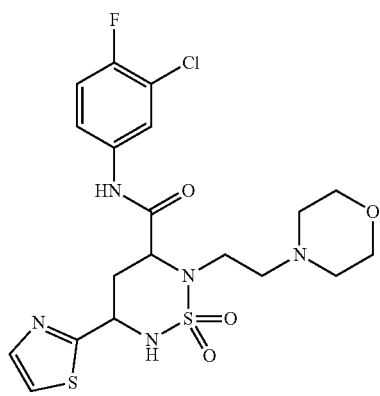

HBV-CSU-082

The above titled compounds have been synthesized by following the general procedure described above for reduction by using corresponding HBV-CSU-082_Int (see Table 2 for analytical data).

124

Cis-N-(3-Chloro-4-fluorophenyl)-2-(3-methoxy-3-methylbutyl)-5-(thiazol-2-yl)-1,2,6-thiadiazinane-3-carboxamide 1,1-dioxide (HBV-CSU-083, HBV-CSU-083-ISO-I & HBV-CSU-083-ISO-II)

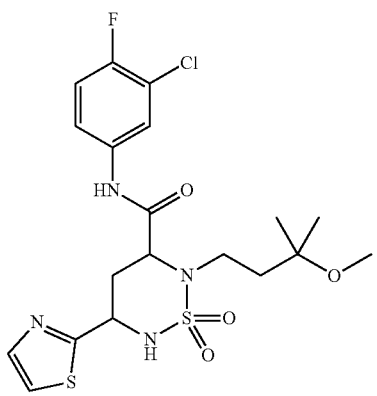

HBV-CSU-083

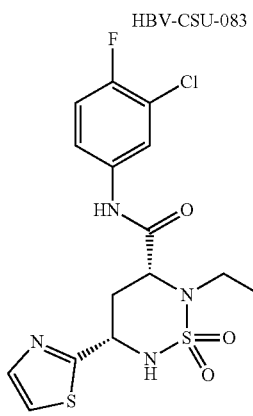

HBV-CSU-083-ISO-I

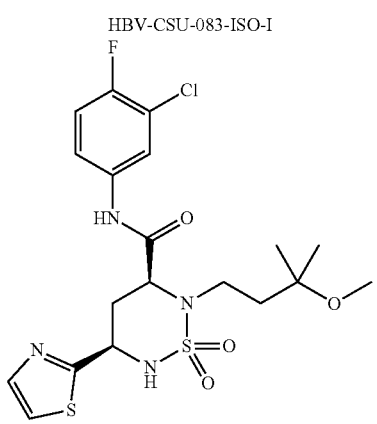

HBV-CSU-083-ISO-II

The above titled compounds have been synthesized by following the general procedure described above for reduction by using corresponding HBV-CSU-083_Int (see Table 2 for analytical data).

Cis-N-(3-chloro-4-fluorophenyl)-2-(prop-2-yn-1-yl)-5-(thiazol-2-yl)-1,2,6-thiadiazinane-3-carboxamide 1,1-dioxide (HBV-CSU-089-ISO-I & HBV-CSU-089-ISO-II)

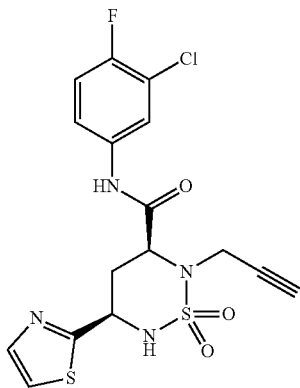

HBV-CSU-089-ISO-I

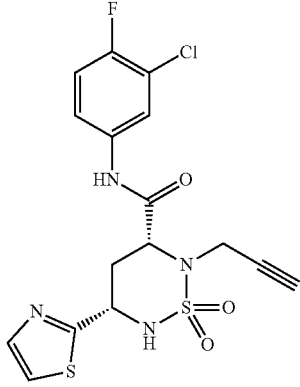

HBV-CSU-089-ISO-II

The above titled compounds have been synthesized by following the general procedure described above for reduction by using corresponding HBV-CSU-089_Int (see Table 2 for analytical data).

Cis-2-(But-3-yn-1-yl)-N-(3-chloro-4-fluorophenyl)-5-(thiazol-2-yl)-1,2,6-thiadiazinane-3-carboxamide 1,1-dioxide (HBV-CSU-090, HBV-CSU-090-ISO-I, HBV-CSU-090-ISO-II)

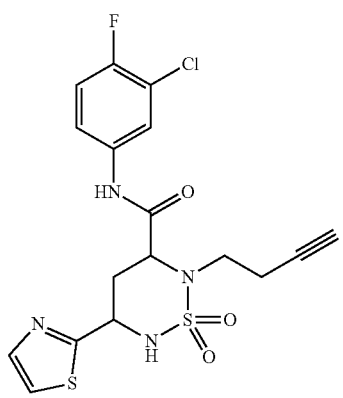

HBV-CSU-090

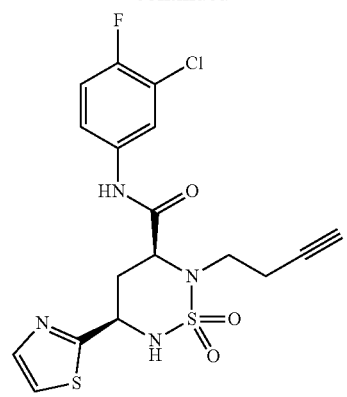

HBV-CSU-090-ISO-I

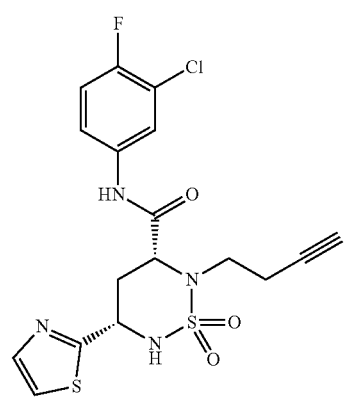

HBV-CSU-090-ISO-II

The above titled compounds have been synthesized by following the general procedure described above for reduction by using corresponding HBV-CSU-090_Int (see Table 2 for analytical data).

Cis-2-Allyl-N-(3-chloro-4-fluorophenyl)-5-(thiazol-2-yl)-1,2,6-thiadiazinane-3-carboxamide 1,1-dioxide (HBV-CSU-094-ISO-I & HBV-CSU-094-ISO-II)

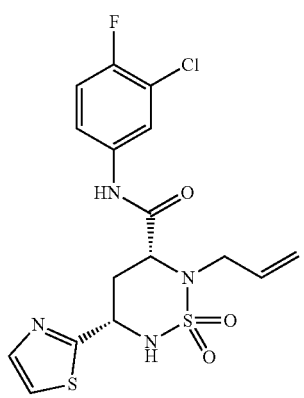

HBV-CSU-094-ISO-I

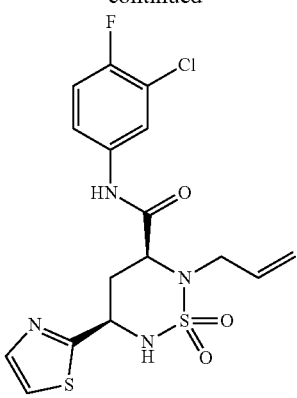

HBV-CSU-094-ISO-II

The above titled compounds have been synthesized by following the general procedure described above for reduction by using corresponding HBV-CSU-094_Int (see Table 2 for analytical data).

Cis-2-(2-(benzyloxy)ethyl)-N-(3-chloro-4-fluorophenyl)-5-(thiazol-2-yl)-1,2,6-thiadiazinane-3-carboxamide 1,1-dioxide (HBV-CSU-095, HBV-CSU-095-ISO-I & HBV-CSU-095-ISO-II)

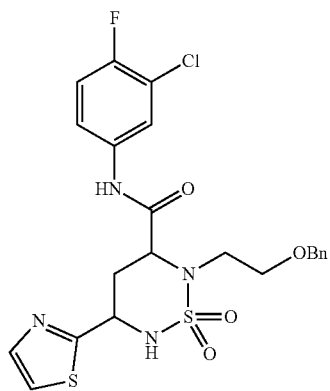

HBV-CSU-095


HBV-CSU-095-ISO-I

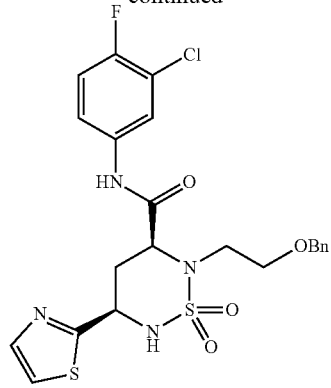

HBV-CSU-095-ISO-II

The above titled compounds have been synthesized by following the general procedure described above for reduction by using corresponding HBV-CSU-095_Int (see Table 2 for analytical data).

Cis-N-(3-chloro-4-fluorophenyl)-2-(4-methoxybenzyl)-5-(thiazol-2-yl)-1,2,6-thiadiazinane-3-carboxamide 1,1-dioxide (HBV-CSU-108)

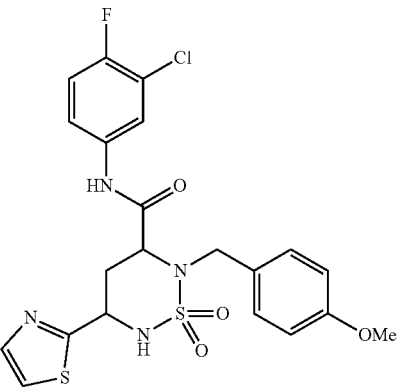

HBV-CSU-108

The above titled compound has been synthesized by following the general procedure described above for reduction by using corresponding HBV-CSU-108_Int (see Table 2 for analytical data).

129

Cis-N-(3-Chloro-4-fluorophenyl)-2-(2-(methylthio)ethyl)-5-(thiazol-2-yl)-1,2,6-thiadiazinane-3-carboxamide 1,1-dioxide (HBV-CSU-109, HBV-CSU-109-ISO-I & HBV-CSU-109-ISO-II)

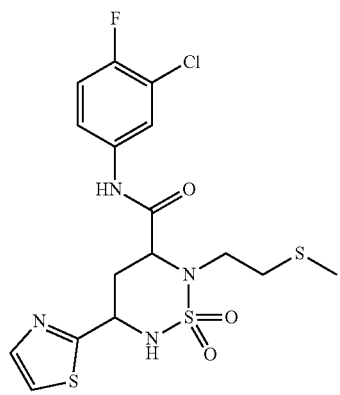

HBV-CSU-109

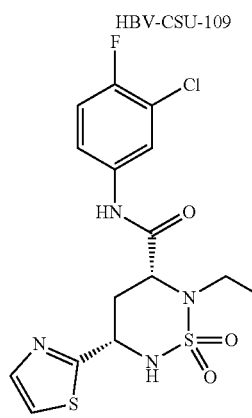

HBV-CSU-109-ISO-I

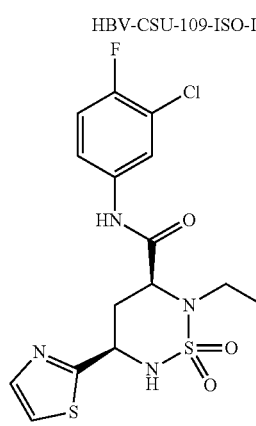

HBV-CSU-109-ISO-II

The above titled compound has been synthesized by following the general procedure described above for reduction by using corresponding HBV-CSU-109_Int (see Table 2 for analytical data).

130

Cis-N-(3-Chloro-4-fluorophenyl)-2-(2-ethoxyethyl)-5-(thiazol-2-yl)-1,2,6-thiadiazinane-3-carboxamide 1,1-dioxide (HBV-CSU-142, HBV-CSU-142-ISO-I & HBV-CSU-142-ISO-II)

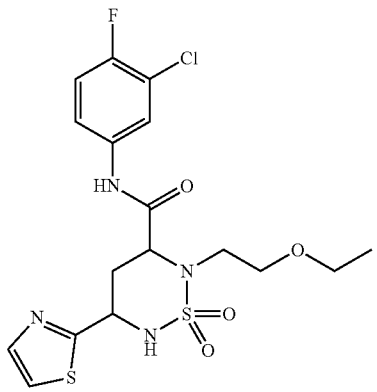

HBV-CSU-142

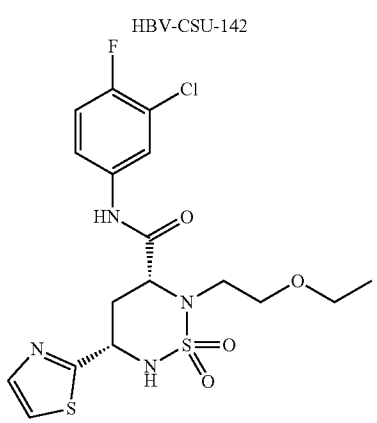

HBV-CSU-142-ISO-I

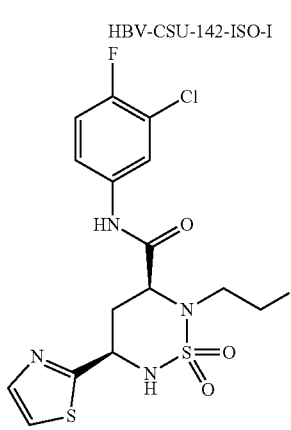

HBV-CSU-142-ISO-II

The above titled compound has been synthesized by following the general procedure described above for reduction by using corresponding HBV-CSU-142_Int (see Table 2 for analytical data).

Cis-N-(3-Chloro-4-fluorophenyl)-2-(2-isopropoxy-ethyl)-5-(thiazol-2-yl)-1,2,6-thiadiazinane-3-carboxamide 1,1-dioxide (HBV-CSU-143)

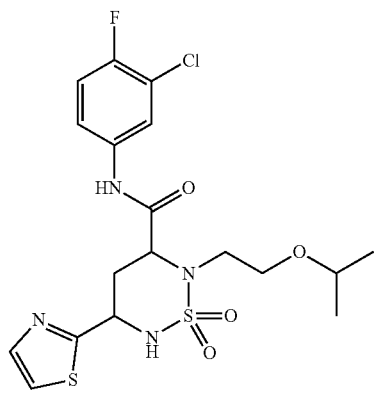

HBV-CSU-143

The above titled compound has been synthesized by following the general procedure described above for reduction by using corresponding HBV-CSU-143_Int (see Table 2 for analytical data).

Scheme 5

Synthesis of Cis-N-(3-chloro-4-fluorophenyl)-5-(5-fluorothiophen-2-yl)-2-methyl-1,2,6-thiadiazinane-3-carboxamide 1,1-dioxide (HBV-CSU-029-ISO-I)

Scheme 5

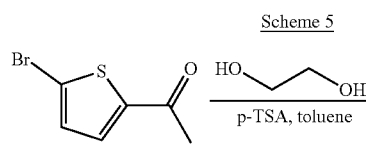

13

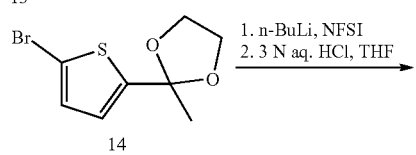

14

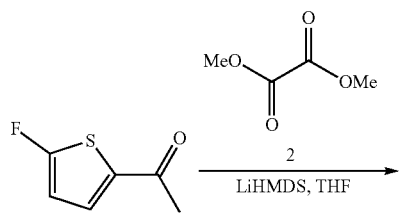

15

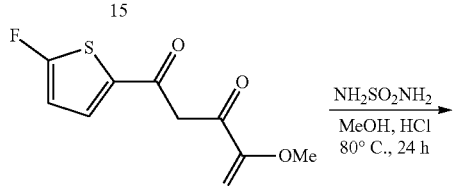

16

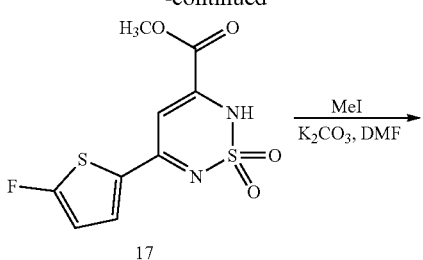

17

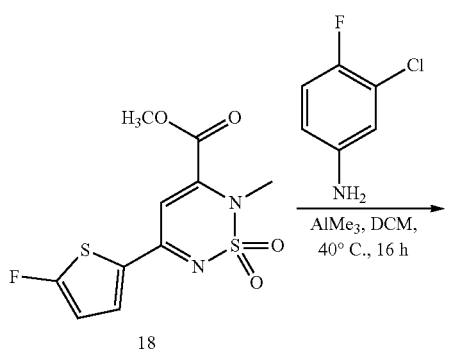

18

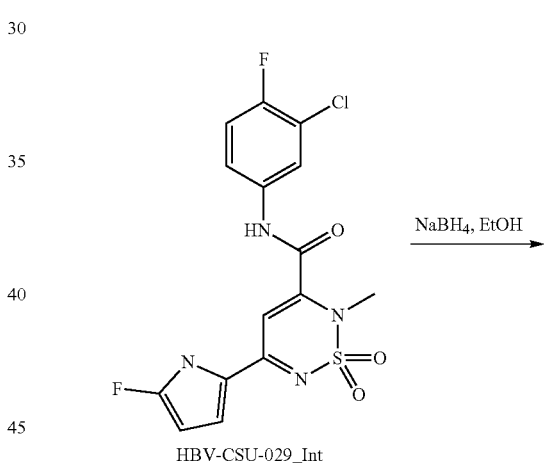

HBV-CSU-029_Int

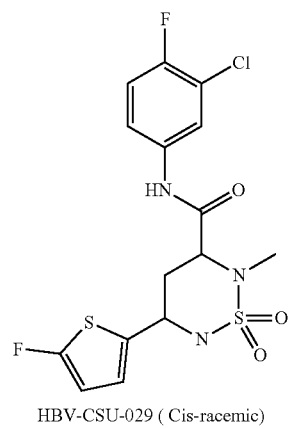

HBV-CSU-029 (Cis-racemic)

2-(5-Bromothiophen-2-yl)-2-methyl-1,3-dioxolane (14)

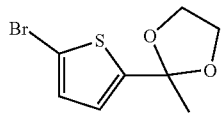

To a stirred solution of compound 13 (5 g, 24.39 mmol) in toluene (50 mL), p-TSA (0.413 g, 2.43 mmol) and ethane-1,2-diol (6.04 g, 97.56 mmol) were added and the reaction was refluxed for 24 h using Dean Stark apparatus. The progress of the reaction was monitored by TLC and LCMS. After completion, the reaction mixture was diluted with water and extracted with ethyl acetate. The combined organic layers were washed with water and brine; dried over anhydrous sodium sulphate and concentrated in vacuo. The crude compound was purified by silica gel column chromatography to afford the title compound 14 (2.7 g, 44.33%) as a white solid. TLC: 40% EtOAc/hexanes ($R_f$: 0.6); $^1$H NMR (CDCl$_3$, 400 MHz): δ 6.92 (d, J=3.2 Hz, 1H), 6.80 (d, J=4.0 Hz, 1H), 4.08-3.95 (m, 4H), 7.78 (s, 3H).

1-(5-Fluorothiophen-2-yl)ethan-1-one (15)

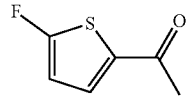

To a stirred solution of compound 14 (5 g, 20 mmol) in dry THF (50 mL) at −78° C. under Ar atmosphere, n-BuLi (2.5 M, 13.04 mL, 30 mmol) was added dropwise and stirred at same temperature for 45 min. To this solution, NFSI dissolved in dry THF (10 mL) (8.19 g, 26 mmol) was added at −78° C. slowly. The resulting reaction mixture was stirred at room temperature for 12 h. The progress of the reaction was monitored by TLC. After completion, the reaction mixture was quenched with sat. NH$_4$Cl solution and extracted with diethyl ether. The combined organic layers were washed with water and brine; dried over anhydrous sodium sulphate and concentrated in vacuo. The crude compound was purified by silica gel column chromatography using 2% EtOAc/hexane to afford fluoro-substituted compound (2.7 g). To a stirred solution above, the fluoro-substituted compound (2.7 g, 14.36 mmol) in THF (20 mL), 3N HCl (10 mL) was added and stirred at room temperature for 3 h. The progress of the reaction was monitored by TLC. After completion, the reaction mixture was diluted with water and extracted with ethyl acetate. The combined organic layers were washed with water and brine; dried over anhydrous sodium sulphate and concentrated in vacuo to afford the title compound 15 (2.2 g, crude) as a light brown oil. TLC: 10% EtOAc/hexane ($R_f$: 0.4); $^1$H NMR (DMSO-d$_6$, 400 MHz): δ 7.40 (d, J=4.0 Hz, 1H), 6.55 (dd, J=4.0, 1.2 Hz, 1H), 2.51 (s, 3H).

Methyl 4-(5-fluorothiophen-2-yl)-2,4-dioxobutanoate (16)

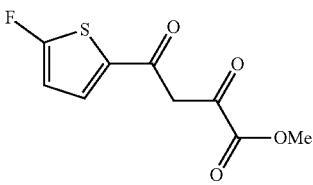 [SMILES: COC(=O)C(=O)CC(=O)c1ccc(F)s1]

To a stirred solution of Compound 15 (2.3 g, 15.97 mmol) in dry THF (20 mL) at −78° C. under Ar atmosphere, LiHMDS (1M in THF, 20.76 mL, 20.76 mmol) was added and stirred at the same temperature for 1 h. To this solution, Compound 2 (2.45 g, 20.76 mmol) in dry THF (10 mL) was added drop wise at −78° C. The resulting reaction mixture was stirred at room temperature for overnight. The progress of the reaction was monitored by TLC and LCMS. After completion, the reaction mixture was concentrated under reduced pressure. The residue was diluted with water; the precipitated solid was collected by filtration, washed with ethyl acetate followed by diethyl ether and dried under reduced pressure to afford compound 16 (2.7 g, 62.64%) as yellow solid. (Note: 16 was isolated in enol form and used as such for the next step). TLC: 10% MeOH in DCM ($R_f$: 0.1); LCMS Calculated for C$_9$H$_7$FO$_4$S: 230.0; Observed: 230.88 (M+1)$^+$.

Methyl 5-(5-fluorothiophen-2-yl)-2H-1,2,6-thiadiazine-3-carboxylate 1,1-dioxide (17)

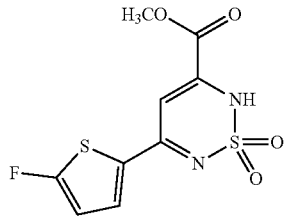 [SMILES: COC(=O)C1=CC(c2ccc(F)s2)=NS(=O)(=O)N1]

To a stirred solution of compound 16 (2.5 g, 10.86 mmol) and sulfamide (1.25 g, 10.86 mmol) in MeOH (30 mL), in sealed tube, HCl gas (generated by sodium chloride+H$_2$SO$_4$) was purged for 2 h at 0° C. The resulting reaction mixture was stirred at 80° C. for 24 h. The progress of the reaction was monitored by TLC and LCMS. After completion, the reaction mixture was cooled to 0° C. and filtered. The solid was washed with cold methanol and dried in vacuo to afford compound 17 (1.8 g, 57.14%) LCMS Calculated for C$_9$H$_7$FN$_2$O$_4$S$_2$: 289.98; LCMS observed: 290.94 (M+1)$^+$.

Methyl 5-(5-fluorothiophen-2-yl)-2-methyl-2H-1,2,6-thiadiazine-3-carboxylate 1,1-dioxide (18)

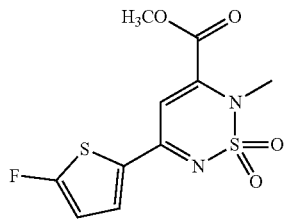 [SMILES: COC(=O)C1=CC(c2ccc(F)s2)=NS(=O)(=O)N1C]

To a stirred solution of compound 17 (1.2 g, 4.14 mmol.) in DMF (10 mL) at 0° C., K$_2$CO$_3$ (1.8 g, 12.41 mmol) was added and stirred at room temperature for 10 min. To this solution, MeI (1.22 g, 8.28 mmol) was added. The reaction mixture was stirred at room temperature for 12 h. The progress of the reaction was monitored by TLC and LCMS. After completion, the reaction mixture was diluted with water and extracted with ethyl acetate. The combined organic layers were washed with water and brine; dried over anhydrous sodium sulphate and concentrated in vacuo. The crude compound was purified by silica gel column chromatography to afford the compound 18 (0.4 g, 32%) as brown colored solid. TLC: 40% EtOAc/hexanes ($R_f$: 0.7); $^1$H NMR (DMSO-d$_6$, 400 MHz): δ 8.13-8.11 (m, 1H), 7.33 (s, 1H), 7.05-7.04 (m, 1H), 3.94 (s, 3H), 3.49 (s, 3H); LCMS Calculated for $C_{10}H_9FN_2O_4S_2$: 304.00; LCMS observed: 304.85 (M+1)$^+$.

N-(3-chloro-4-fluorophenyl)-5-(5-fluorothiophen-2-yl)-2-methyl-2H-1,2,6-thiadiazine-3-carboxamide 1,1-dioxide (HBV-CSU-029_Int)

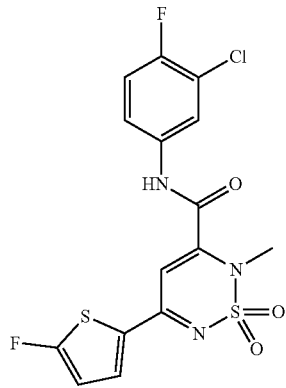

HBV-CSU-029_Int

To a stirred solution of compound 18 (0.287 g, 1.97 mmol) in DCM (10 mL) at 0° C. under Ar atmosphere, AlMe$_3$ (2M in toluene, 0.986 mL, 1.97 mmol) was added and the reaction mixture was stirred at 0° C. for 10 min and continued stirring at room temperature for 1 h. To this solution, aniline (0.2 g, 0.657 mmol) was added at 0° C. under Ar atmosphere and resulting reaction mixture was refluxed at 40° C. for overnight. The progress of the reaction was monitored by TLC and LCMS. After completion, the reaction mixture was cooled to 0° C., quenched with 1N HCl solution slowly, and extracted with DCM. The combined organic layers were collected, dried over anhydrous sodium sulphate, and concentrated in vacuo. The crude compound was purified by silica gel column chromatography followed by trituration with diethyl ether to afford the compound HBV-CSU-029_Int. (see Table 1 for analytical data).

Cis-N-(3-chloro-4-fluorophenyl)-5-(5-fluorothiophen-2-yl)-2-methyl-1,2,6-thiadiazinane-3-carboxamide 1,1-dioxide (HBV-CSU-029-ISO-I)

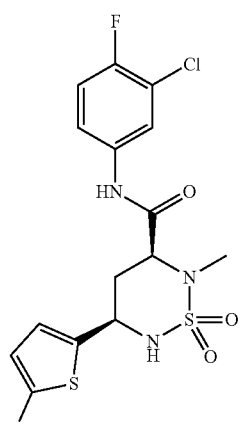

HBV-CSU-029-ISO-I

The above titled compound has been synthesized by following the general procedure described above for reduction by using corresponding HBV-CSU-029_Int. The chiral HPLC separation provided desired compound (see Table 2 for analytical data).

Scheme 6

General Synthetic Scheme for 5-(Phenyl/Pyridyl)-1,2,6-thiadiazinane-3-carboxamide 1,1-dioxide Derivatives with Substituted Phenyl/Pyridyl, N-2 alkyl & Aniline Variations

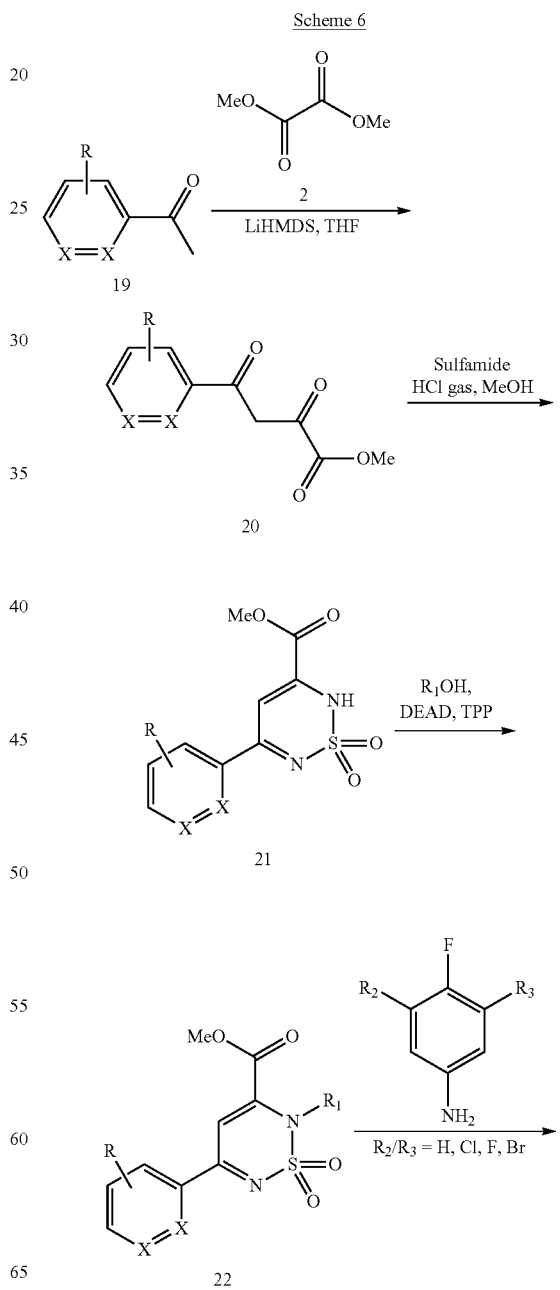

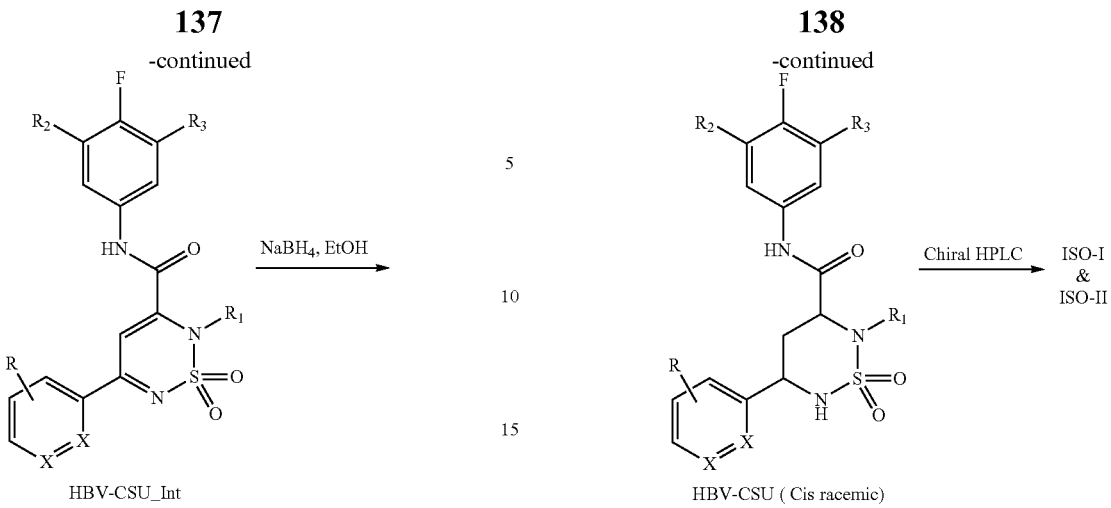

| Target | #28 (R variation) | N-Alkyl (R₁ Variation) | Aniline (R₂/R₃ variation) |
|---|---|---|---|
| HBV-CSU-031 | 2-acetylpyridine | Methyl | 3-chloro-4-fluoroaniline |
| HBV-CSU-032 | 5-fluoro-2-acetylpyridine | Methyl | 3-chloro-4-fluoroaniline |
| HBV-CSU-033 | 3-acetylpyridine | Methyl | 3-chloro-4-fluoroaniline |
| HBV-CSU-112 | 4'-fluoroacetophenone | Methyl | 3-chloro-4-fluoroaniline |
| HBV-CSU-113 | acetophenone | Methyl | 3-chloro-4-fluoroaniline |
| HBV-CSU-200 | 4'-methoxyacetophenone | Methyl | 3-chloro-4-fluoroaniline |
| HBV-CSU-202 | 4'-bromoacetophenone | Methyl | 3-chloro-4-fluoroaniline |

-continued

| Target | #28 (R variation) | N-Alkyl (R₁ Variation) | Aniline (R₂/R₃ variation) |
|---|---|---|---|
| HBV-CSU-204 | 3-methoxyacetophenone | Methyl | 3-chloro-4-fluoroaniline |
| HBV-CSU-210 | 4-fluoroacetophenone | 3-methoxypropyl | 3-chloro-4-fluoroaniline |
| HBV-CSU-211 | 4-fluoroacetophenone | Methyl | 3-bromo-4-fluoroaniline |
| HBV-CSU-212 | 4-fluoroacetophenone | Methyl | 3,4,5-trifluoroaniline |
| HBV-CSU-215 | 2-methoxyacetophenone | Methyl | 3-chloro-4-fluoroaniline |
| HBV-CSU-217 | 4-(trifluoromethyl)acetophenone | Methyl | 3-chloro-4-fluoroaniline |
| HBV-CSU-230 | 3,4-difluoroacetophenone | Methyl | 3-chloro-4-fluoroaniline |
| HBV-CSU-231 | 3-fluoroacetophenone | Methyl | 3-chloro-4-fluoroaniline |
| HBV-CSU-232 | 4-(trifluoromethoxy)acetophenone | Methyl | 3-chloro-4-fluoroaniline |
| HBV-CSU-259 | 3-(trifluoromethyl)acetophenone | Methyl | 3-chloro-4-fluoroaniline |

-continued

| Target | #28 (R variation) | N-Alkyl (R₁ Variation) | Aniline (R₂/R₃ variation) |
|---|---|---|---|
| HBV-CSU-261 | 3-chlorophenyl methyl ketone | Methyl | 3-chloro-4-fluoroaniline |
| HBV-CSU-262 | 3-(trifluoromethoxy)phenyl methyl ketone | Methyl | 3-chloro-4-fluoroaniline |
| HBV-CSU-263 | 4-(difluoromethoxy)phenyl methyl ketone | Methyl | 3-chloro-4-fluoroaniline |
| HBV-CSU-264 | 3-(difluoromethoxy)phenyl methyl ketone | Methyl | 3-chloro-4-fluoroaniline |
| HBV-CSU-265 | 4-chlorophenyl methyl ketone | Methyl | 3-chloro-4-fluoroaniline |
| HBV-CSU-283 | 4-bromo-3-fluorophenyl methyl ketone | Methyl | 3-chloro-4-fluoroaniline |

Synthesis of methyl 2,4-dioxo-4-(pyridin-2-yl)butanoate (20)

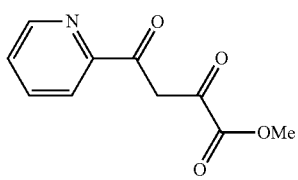 [SMILES: COC(=O)C(=O)CC(=O)c1ccccn1]

Title compound was synthesized using general method for the synthesis of 2,4-diketoester described above to afford 3.2 g (37.47%, reaction scale is 5 g); LCMS Calculated for $C_{10}H_9NO_4$: 207.05; Observed: 208.00 $(M+1)^+$.

Synthesis of methyl 4-(5-fluoropyridin-2-yl)-2,4-dioxobutanoate (20)

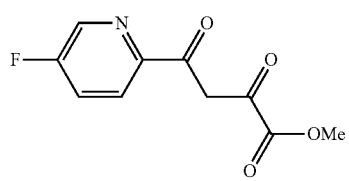 [SMILES: COC(=O)C(=O)CC(=O)c1ccc(F)cn1]

Title compound was synthesized using general method for the synthesis of 2,4-diketoester described above to afford 2.5 g (96.15%, reaction scale is 1.6 g); LCMS Calculated for $C_{10}H_8FNO_4$: 225.04; Observed: 225.90 $(M+1)^+$.

Synthesis of methyl 2,4-dioxo-4-(pyridin-3-yl)butanoate (20)

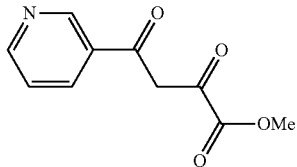 [SMILES: COC(=O)C(=O)CC(=O)c1cccnc1]

Title compound was synthesized using general method for the synthesis of 2,4-diketoester described above to afford 2 g (23.52%, reaction scale is 5 g); LCMS Calculated for $C_{10}H_9NO_4$: 207.05; Observed: 207.95 $(M+1)^+$.

Synthesis of methyl 4-(4-fluorophenyl)-2,4-dioxobutanoate (20)

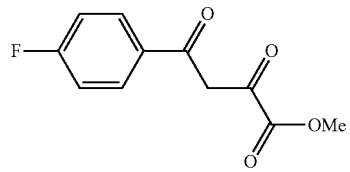

Title compound was synthesized using general method for the synthesis of 2,4-diketoester described above to afford 13.84 g (85.0%, reaction scale is 10 g); LCMS Calculated for $C_{11}H_9FO_4$: 224.05; Observed: 225.00 $(M+1)^+$.

Synthesis of methyl 2,4-dioxo-4-phenylbutanoate (20)

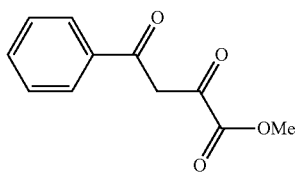 [SMILES: COC(=O)C(=O)CC(=O)c1ccccc1]

Title compound was synthesized using general method for the synthesis of 2,4-diketoester described above to afford 17.24 g (66%, reaction scale is 15 g); LCMS Calculated for $C_{11}H_{10}O_4$: 206.06; Observed: 207.10 $(M+1)^+$.

Synthesis of methyl 4-(4-methoxyphenyl)-2,4-dioxobutanoate (20)

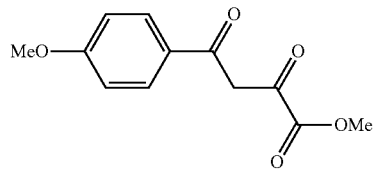 [SMILES: COC(=O)C(=O)CC(=O)c1ccc(OC)cc1]

Title compound was synthesized using general method for the synthesis of 2,4-diketoester described above to afford 27 g (crude, reaction scale is 15 g); LCMS Calculated for $C_{12}H_{12}O_5$: 236.07; Observed: 237.00 $(M+1)^+$.

Synthesis of methyl 4-(4-bromophenyl)-2,4-dioxobutanoate (20)

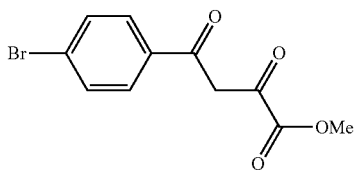

Title compound was synthesized using general method for the synthesis of 2,4-diketoester described above to afford 33 g (92.18%, reaction scale is 25 g); LCMS Calculated for $C_{11}H_9BrO_4$: 283.97; Observed: 286.95 $(M+2)^+$.

Synthesis of methyl 4-(3-methoxyphenyl)-2,4-dioxobutanoate (20)

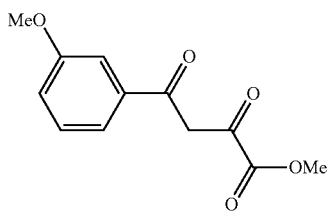 [SMILES: COC(=O)C(=O)CC(=O)c1cccc(OC)c1]

Title compound was synthesized using general method for the synthesis of 2,4-diketoester described above to afford 28.3 g (Crude, reaction scale is 25 g); LCMS Calculated for $C_{12}H_{12}O_5$: 236.07; Observed: 236.95 $(M+1)^+$.

Synthesis of methyl 4-(2-methoxyphenyl)-2,4-dioxobutanoate (20)

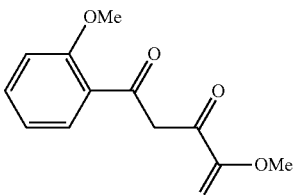

Title compound was synthesized using general method for the synthesis of 2,4-diketoester described above to afford 28 g (70.93%, reaction scale is 25 g); LCMS Calculated for $C_{12}H_{12}O_5$: 236.07; Observed: 237.00 $(M+1)^+$.

Synthesis of methyl 2,4-dioxo-4-(4-(trifluoromethyl)phenyl)butanoate (20)

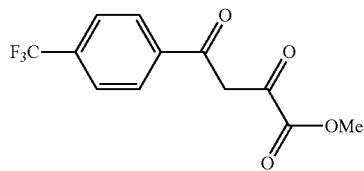 [SMILES: COC(=O)C(=O)CC(=O)c1ccc(C(F)(F)F)cc1]

Title compound was synthesized using general method for the synthesis of 2,4-diketoester described above to afford 34 g (93.32%, reaction scale is 25 g); LCMS Calculated for $C_{12}H_9F_3O_4$: 274.05; Observed: 275.05 (M+1)$^+$.

Synthesis of methyl 4-(3,4-difluorophenyl)-2,4-dioxobutanoate (20)

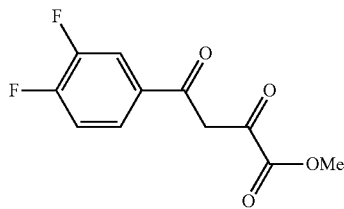 [SMILES: COC(=O)C(=O)CC(=O)c1ccc(F)c(F)c1]

Title compound was synthesized using general method for the synthesis of 2,4-diketoester described above to afford 30 g (77.41%, reaction scale is 25 g); LCMS Calculated for $C_{11}H_8F_2O_4$: 242.04; Observed: 242.95 (M+1)$^+$.

Synthesis of methyl 4-(3-fluorophenyl)-2,4-dioxobutanoate (20)

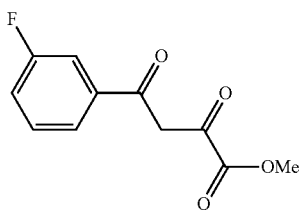 [SMILES: COC(=O)C(=O)CC(=O)c1cccc(F)c1]

Title compound was synthesized using general method for the synthesis of 2,4-diketoester described above to afford 30 g (73.65%, reaction scale is 25 g); LCMS Calculated for $C_{11}H_9FO_4$: 224.05; Observed: 225.00 (M+1)$^+$.

Synthesis of methyl 2,4-dioxo-4-(4-(trifluoromethoxy)phenyl)butanoate (20)

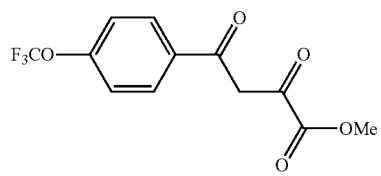 [SMILES: COC(=O)C(=O)CC(=O)c1ccc(OC(F)(F)F)cc1]

Title compound was synthesized using general method for the synthesis of 2,4-diketoester described above to afford 70 g (98.92%, reaction scale is 50 g); LCMS Calculated for $C_{12}H_9F_3O_5$: 290.04; Observed: 288.75 (M−1)$^-$.

Synthesis of methyl 2,4-dioxo-4-(3-(trifluoromethyl)phenyl)butanoate (20)

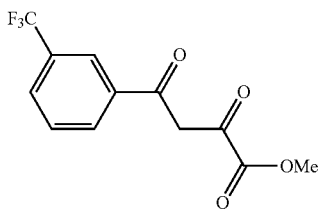 [SMILES: COC(=O)C(=O)CC(=O)c1cccc(C(F)(F)F)c1]

Title compound was synthesized using general method for the synthesis of 2,4-diketoester described above to afford 25 g (68.60%, reaction scale is 25 g).

Synthesis of methyl 4-(3-chlorophenyl)-2,4-dioxobutanoate (20)

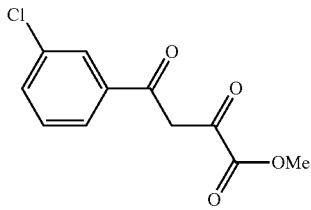 [SMILES: COC(=O)C(=O)CC(=O)c1cccc(Cl)c1]

Title compound was synthesized using general method for the synthesis of 2,4-diketoester described above to afford 18 g (96%, reaction scale is 12 g); LCMS Calculated for $C_{11}H_9ClO_4$: 240.02; Observed: 240.90 (M+1)$^+$.

Synthesis of methyl 2,4-dioxo-4-(3-(trifluoromethoxy)phenyl)butanoate (20)

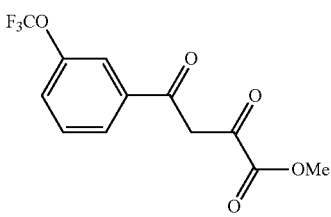 [SMILES: COC(=O)C(=O)CC(=O)c1cccc(OC(F)(F)F)c1]

Title compound was synthesized using general method for the synthesis of 2,4-diketoester described above to afford 15 g (crude, reaction scale is 10 g); LCMS Calculated for $C_{12}H_9F_3O_5$: 290.04; Observed: 291.25 (M+1)$^+$.

Synthesis of methyl 4-(4-(difluoromethoxy)phenyl)-2,4-dioxobutanoate (20)

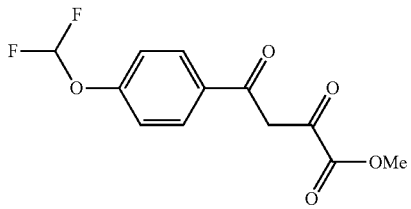 [SMILES: COC(=O)C(=O)CC(=O)c1ccc(OC(F)F)cc1]

Title compound was synthesized using general method for the synthesis of 2,4-diketoester described above to afford 12 g (crude, reaction scale is 10 g); LCMS Calculated for $C_{12}H_{10}F_2O_5$: 272.05; Observed: 272.95 (M+1)[+].

Synthesis of methyl 4-(3-(difluoromethoxy)phenyl)-2,4-dioxobutanoate (20)

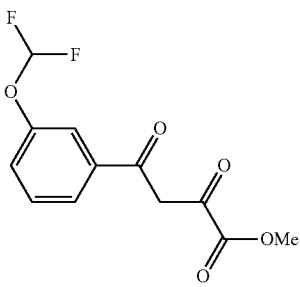 [SMILES: COC(=O)C(=O)CC(=O)c1cccc(OC(F)F)c1]

Title compound was synthesized using general method for the synthesis of 2,4-diketoester described above to afford 6.12 g (81.92%, reaction scale is 5 g); LCMS Calculated for $C_{12}H_{10}F_2O_5$: 272.05; Observed: 272.85 (M+1)[+].

Synthesis of methyl 4-(4-chlorophenyl)-2,4-dioxobutanoate (20)

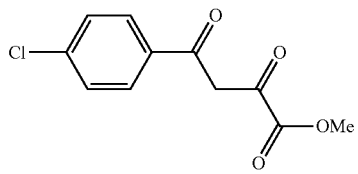 [SMILES: COC(=O)C(=O)CC(=O)c1ccc(Cl)cc1]

Title compound was synthesized using general method for the synthesis of 2,4-diketoester described above to afford 32 g (82.13%, reaction scale is 25 g); LCMS Calculated for $C_{11}H_9ClO_4$: 240.02; Observed: 240.90 (M+1)[+].

Synthesis of methyl 4-(4-bromo-3-fluorophenyl)-2,4-dioxobutanoate (20)

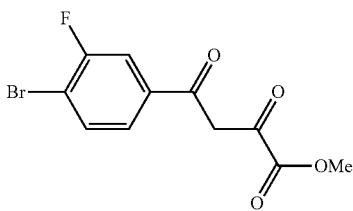 [SMILES: COC(=O)C(=O)CC(=O)c1ccc(Br)c(F)c1]

Title compound was synthesized using general method for the synthesis of 2,4-diketoester described above to afford 8 g (60.28%, reaction scale is 9.5 g); LCMS Calculated for $C_{11}H_8BrFO_4$: 301.96; Observed: 303.85 (M+2)[+].

Synthesis of methyl 5-(pyridin-2-yl)-2H-1,2,6-thiadiazine-3-carboxylate 1,1-dioxide (21)

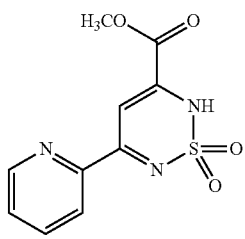 [SMILES: COC(=O)C1=CC(c2ccccn2)=NS(=O)(=O)N1]

Title compound was synthesized using general method A for the synthesis of cyclic sulfonamide described above to afford 1 g (19.68%, reaction scale is 3 g); LCMS Calculated for $C_{10}H_9N_3O_4S$: 267.03; LCMS observed: 268.15 (M+1)[+].

Synthesis of methyl 5-(5-fluoropyridin-2-yl)-2H-1,2,6-thiadiazine-3-carboxylate 1,1-dioxide (21)

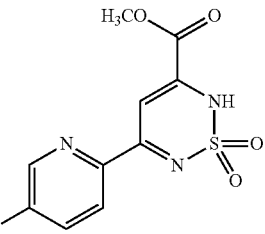

Title compound was synthesized using general method A for the synthesis of cyclic sulfonamide described above to afford 2.5 g (80.64%, reaction scale is 2.5 g); LCMS Calculated for $C_{10}H_8FN_3O_4S$: 285.02; LCMS observed: 286.15 (M+1)[+].

Synthesis of methyl 5-(pyridin-3-yl)-2H-1,2,6-thiadiazine-3-carboxylate 1,1-dioxide (21)

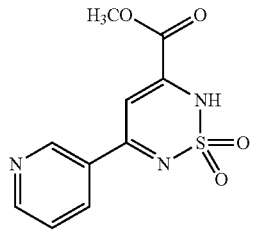 [SMILES: COC(=O)C1=CC(c2cccnc2)=NS(=O)(=O)N1]

Title compound was synthesized using general method A for the synthesis of cyclic sulfonamide described above to afford 3 g (46.58%, reaction scale is 5 g); LCMS Calculated for $C_{10}H_9N_3O_4S$: 267.03; LCMS observed: 267.95 $(M+1)^+$.

Synthesis of methyl 5-(4-fluorophenyl)-2H-1,2,6-thiadiazine-3-carboxylate 1,1-dioxide (21)

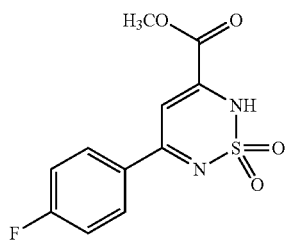 [SMILES: COC(=O)C1=CC(c2ccc(F)cc2)=NS(=O)(=O)N1]

Title compound was synthesized using general method A for the synthesis of cyclic sulfonamide described above to afford 10.52 g (64%, reaction scale is 13 g); LCMS Calculated for $C_{11}H_9FN_2O_4S$: 284.03; LCMS observed: 285.15 $(M+1)^+$.

Synthesis of methyl 5-phenyl-2H-1,2,6-thiadiazine-3-carboxylate 1,1-dioxide (21)

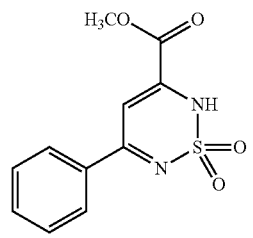 [SMILES: COC(=O)C1=CC(c2ccccc2)=NS(=O)(=O)N1]

Title compound was synthesized using general method for the synthesis of cyclic sulfonamide described above to afford 15.2 g (74%, reaction scale is 16 g); LCMS Calculated for $C_{11}H_{10}N_2O_4S$: 266.04; LCMS observed: 267.10 $(M+1)^+$.

Synthesis of methyl 5-(4-methoxyphenyl)-2H-1,2,6-thiadiazine-3-carboxylate 1,1-dioxide (21)

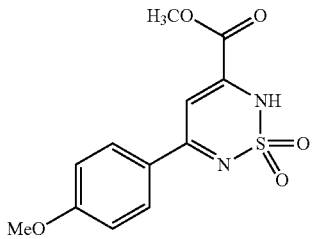 [SMILES: COC(=O)C1=CC(c2ccc(OC)cc2)=NS(=O)(=O)N1]

Title compound was synthesized using general method A for the synthesis of cyclic sulfonamide described above to afford 20 g (59.1%, reaction scale is 27 g); LCMS Calculated for $C_{12}H_{12}N_2O_5S$: 296.05; LCMS observed: 296.95 $(M+1)^+$.

Synthesis of methyl 5-(4-bromophenyl)-2H-1,2,6-thiadiazine-3-carboxylate 1,1-dioxide (21)

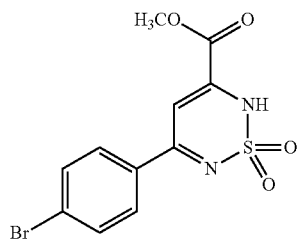

Title compound was synthesized using general method for the synthesis of cyclic sulfonamide described above to afford 33 g (68.39%, reaction scale is 40 g); LCMS Calculated for $C_{11}H_9BrN_2O_4S$: 343.95; LCMS observed: 346.95 $(M+2)^+$.

Synthesis of methyl 5-(3-methoxyphenyl)-2H-1,2,6-thiadiazine-3-carboxylate 1,1-dioxide (21)

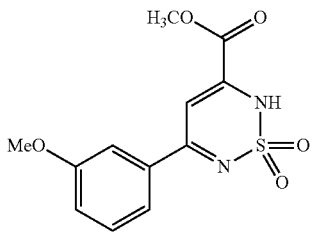 [SMILES: COC(=O)C1=CC(c2cccc(OC)c2)=NS(=O)(=O)N1]

Title compound was synthesized using general method for the synthesis of cyclic sulfonamide described above to afford 18 g (51%, reaction scale is 28 g); LCMS Calculated for $C_{12}H_{12}N_2O_5S$: 296.05; LCMS observed: 297.00 $(M+1)^+$.

151

Synthesis of methyl 5-(2-methoxyphenyl)-2H-1,2,6-thiadiazine-3-carboxylate 1,1-dioxide (21)

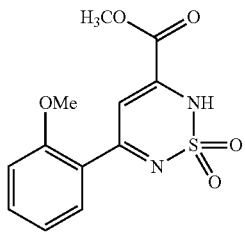 [SMILES: COC(=O)C1=CC(c2ccccc2OC)=NS(=O)(=O)N1]

Title compound was synthesized using general method B for the synthesis of cyclic sulfonamide described above to afford 24 g (68.31%, reaction scale is 28 g; LCMS Calculated for $C_{12}H_{12}N_2O_5S$: 296.05; LCMS observed: 296.95 $(M+1)^+$.

Synthesis of methyl 5-(4-(trifluoromethyl)phenyl)-2H-1,2,6-thiadiazine-3-carboxylate 1,1-dioxide (21)

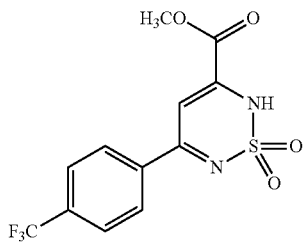

Title compound was synthesized using general method for the synthesis of cyclic sulfonamide described above to afford 35 g (71.79%, reaction scale is 40 g); LCMS Calculated for $C_{12}H_9F_3N_2O_4S$: 334.02; LCMS observed: 334.95 $(M+1)^+$.

Synthesis of methyl 5-(3,4-difluorophenyl)-2H-1,2,6-thiadiazine-3-carboxylate 1,1-dioxide (21)

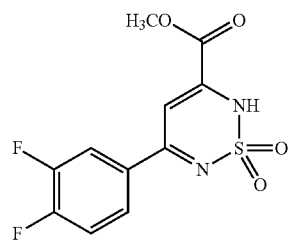 [SMILES: COC(=O)C1=CC(c2ccc(F)c(F)c2)=NS(=O)(=O)N1]

Title compound was synthesized using general method B for the synthesis of cyclic sulfonamide described above to afford 20 g (53.43%, reaction scale is 30 g); LCMS Calculated for $C_{11}H_8F_2N_2O_4S$: 302.02; LCMS observed: 302.95 $(M+1)^+$.

152

Synthesis of methyl 5-(3-fluorophenyl)-2H-1,2,6-thiadiazine-3-carboxylate 1,1-dioxide (21)

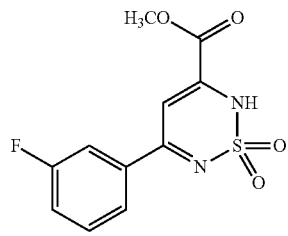 [SMILES: COC(=O)C1=CC(c2cccc(F)c2)=NS(=O)(=O)N1]

Title compound was synthesized using general method B for the synthesis of cyclic sulfonamide described above to afford 25 g (66.03%, reaction scale is 30 g); LCMS Calculated for $C_{11}H_9FN_2O_4S$: 284.03; LCMS observed: 284.95 $(M+1)^+$.

Synthesis of methyl 5-(4-(trifluoromethoxy)phenyl)-2H-1,2,6-thiadiazine-3-carboxylate 1,1-dioxide (21)

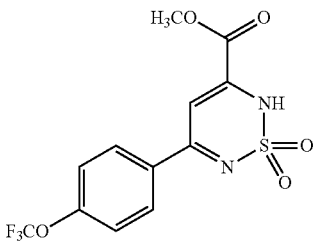

Title compound was synthesized using general method for the synthesis of cyclic sulfonamide described above to afford 48 g (67.61%, reaction scale is 60 g); LCMS Calculated for $C_{12}H_9F_3N_2O_5S$: 350.02; LCMS observed: 350.95 $(M+1)^+$.

Synthesis of methyl 5-(3-(trifluoromethyl)phenyl)-2H-1,2,6-thiadiazine-3-carboxylate 1,1-dioxide (21)

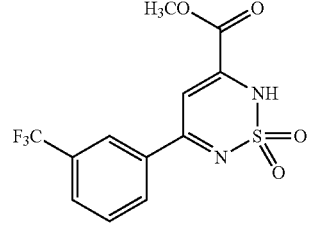

Title compound was synthesized using general method for the synthesis of cyclic sulfonamide described above to afford 10 g (32.81%, reaction scale is 25 g); LCMS Calculated for $C_{12}H_9F_3N_2O_4S$: 334.02; LCMS observed: 335.05 $(M+1)^+$.

Synthesis of methyl 5-(3-chlorophenyl)-2H-1,2,6-thiadiazine-3-carboxylate 1,1-dioxide (21)

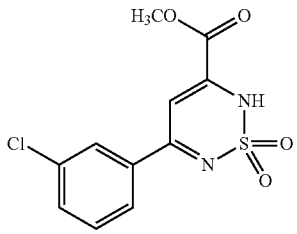 [SMILES: COC(=O)C1=CC(c2cccc(Cl)c2)=NS(=O)(=O)N1]

Title compound was synthesized using general method for the synthesis of cyclic sulfonamide described above to afford 12 g (53.3%, reaction scale is 18 g); LCMS Calculated for $C_{11}H_9ClN_2O_4S$: 300.00; LCMS observed: 300.90 $(M+1)^+$.

Synthesis of methyl 5-(3-(trifluoromethoxy)phenyl)-2H-1,2,6-thiadiazine-3-carboxylate 1,1-dioxide (21)

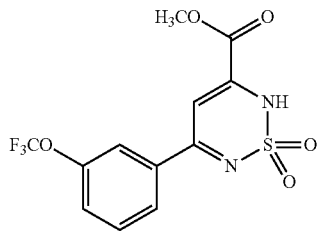 [SMILES: COC(=O)C1=CC(c2cccc(OC(F)(F)F)c2)=NS(=O)(=O)N1]

Title compound was synthesized using general method for the synthesis of cyclic sulfonamide described above to afford 13 g (crude, reaction scale is 15 g); LCMS Calculated for $C_{12}H_9F_3N_2O_5S$: 350.02; LCMS observed: 352 $(M+1)^+$.

Synthesis of methyl 5-(4-(difluoromethoxy)phenyl)-2H-1,2,6-thiadiazine-3-carboxylate 1,1-dioxide (21)

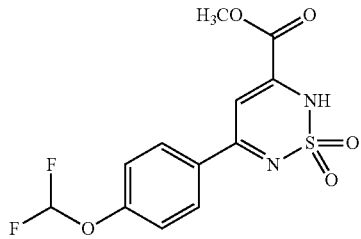 [SMILES: COC(=O)C1=CC(c2ccc(OC(F)F)cc2)=NS(=O)(=O)N1]

Title compound was synthesized using general method for the synthesis of cyclic sulfonamide described above to afford 9 g (crude, reaction scale is 12 g); LCMS Calculated for $C_{12}H_{10}F_2N_2O_5S$: 332.03; LCMS observed: 333 $(M+1)^+$.

Synthesis of methyl 5-(3-(difluoromethoxy)phenyl)-2H-1,2,6-thiadiazine-3-carboxylate 1,1-dioxide (21)

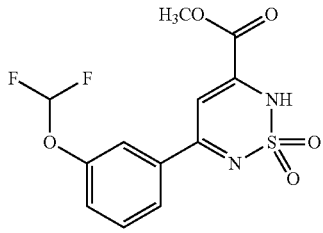 [SMILES: COC(=O)C1=CC(c2cccc(OC(F)F)c2)=NS(=O)(=O)N1]

Title compound was synthesized using general method for the synthesis of cyclic sulfonamide described above to afford 5.10 g (69.76%, reaction scale is 6 g); LCMS Calculated for $C_{12}H_{10}F_2N_2O_5S$: 332.03; LCMS observed: 333 $(M+1)^+$.

Synthesis of methyl 5-(4-chlorophenyl)-2H-1,2,6-thiadiazine-3-carboxylate 1,1-dioxide (21)

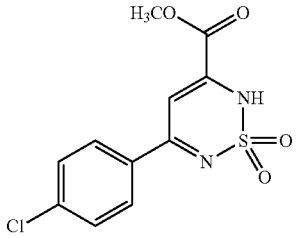 [SMILES: COC(=O)C1=CC(c2ccc(Cl)cc2)=NS(=O)(=O)N1]

Title compound was synthesized using general method for the synthesis of cyclic sulfonamide described above to afford 35 g (87%, reaction scale is 32 g); LCMS Calculated for $C_{11}H_9ClN_2O_4S$: 300.00; LCMS observed: 300.95 $(M+1)^+$.

Synthesis of methyl 5-(4-bromo-3-fluorophenyl)-2H-1,2,6-thiadiazine-3-carboxylate 1,1-dioxide (21)

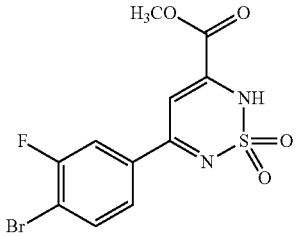

Title compound was synthesized using general method for the synthesis of cyclic sulfonamide described above to afford 7.6 g (79%, reaction scale is 8 g); LCMS Calculated for $C_{11}H_8BrFN_2O_4S$: 361.94; LCMS observed: 364.95 $(M+2)^+$.

Synthesis of methyl 2-methyl-5-(pyridin-2-yl)-2H-1,2,6-thiadiazine-3-carboxylate 1,1-dioxide (22)

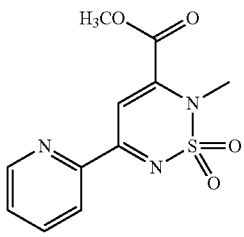 [SMILES: COC(=O)C1=CC(c2ccccn2)=NS(=O)(=O)N1C]

Title compound was synthesized using general method A for alkylation described above to afford 0.8 g (76.04%, reaction scale is 1 g); LCMS Calculated for $C_{11}H_{11}N_3O_4S$: 281.05; LCMS observed: 282.20 (M+1)$^+$.

Synthesis of methyl 5-(5-fluoropyridin-2-yl)-2-methyl-2H-1,2,6-thiadiazine-3-carboxylate 1,1-dioxide (22)

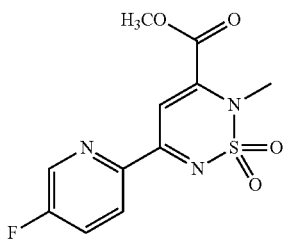 [SMILES: COC(=O)C1=CC(c2ccc(F)cn2)=NS(=O)(=O)N1C]

Title compound was synthesized using general method B for alkylation described above to afford 1 g (95.32%, reaction scale is 1 g); LCMS Calculated for $C_{11}H_{10}FN_3O_4S$: 299.04; LCMS observed: 299.95 (M+1)$^+$.

Synthesis of methyl 2-methyl-5-(pyridin-3-yl)-2H-1,2,6-thiadiazine-3-carboxylate 1,1-dioxide (22)

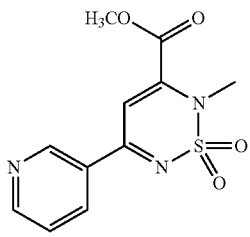 [SMILES: COC(=O)C1=CC(c2cccnc2)=NS(=O)(=O)N1C]

Title compound was synthesized using general method B for alkylation described above to afford 1.6 g (50.6%, reaction scale is 3 g); LCMS Calculated for $C_{11}H_{11}N_3O_4S$: 281.05; LCMS observed: 282.20 (M+1)$^+$.

Synthesis of methyl 5-(4-fluorophenyl)-2-methyl-2H-1,2,6-thiadiazine-3-carboxylate 1,1-dioxide (22)

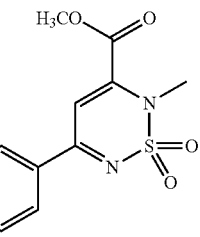

Title compound was synthesized using general method B for alkylation described above to afford 0.5 g (95%, reaction scale is 0.5 g); LCMS Calculated for $C_{12}H_{11}FN_2O_4S$: 298.04; LCMS observed: 299.10 (M+1)$^+$.

Synthesis of methyl 5-(4-fluorophenyl)-2-(2-methoxyethyl)-2H-1,2,6-thiadiazine-3-carboxylate 1,1-dioxide (22)

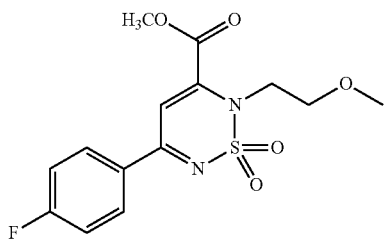 [SMILES: COCCN1C(C(=O)OC)=CC(c2ccc(F)cc2)=NS1(=O)=O]

Title compound was synthesized using general method B for alkylation described above to afford 0.8 g (crude, reaction scale is 1 g); {Note: Isolated as a mixture of desired product and major trans-esterified side product. This mixture was carried forward in the next reaction (ester hydrolysis) without any separation). LCMS Calculated for $C_{14}H_{15}FN_2O_5S$: 342.07; LCMS observed: 343.20 (M+1)$^+$.

Synthesis of methyl 2-methyl-5-phenyl-2H-1,2,6-thiadiazine-3-carboxylate 1,1-dioxide (22)

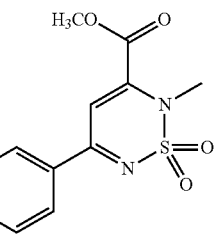

Title compound was synthesized using general method B for alkylation described above to afford 2.4 g (46%, reaction scale is 5 g); LCMS Calculated for $C_{12}H_{12}N_2O_4S$: 280.05; LCMS observed: 281.15 (M+1)$^+$.

Synthesis of methyl 5-(4-methoxyphenyl)-2-methyl-2H-1,2,6-thiadiazine-3-carboxylate 1,1-dioxide (22)

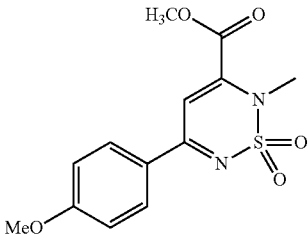 [SMILES: COC(=O)C1=CC(c2ccc(OC)cc2)=NS(=O)(=O)N1C]

Title compound was synthesized using general method B for alkylation described above to afford 5 g (95.9%, reaction scale is 5 g); LCMS Calculated for $C_{13}H_{14}N_2O_5S$: 310.06; LCMS observed: 310.95 (M+1)$^+$.

Synthesis of methyl 5-(4-bromophenyl)-2-methyl-2H-1,2,6-thiadiazine-3-carboxylate 1,1-dioxide (22)

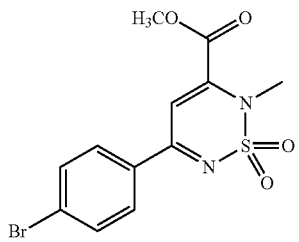

Title compound was synthesized using general method B for alkylation described above to afford 28 g (89.45%, reaction scale is 30 g); LCMS Calculated for $C_{12}H_{11}BrN_2O_4S$: 357.96; LCMS observed: 360.95 (M+1)$^+$.

Synthesis of methyl 5-(3-methoxyphenyl)-2-methyl-2H-1,2,6-thiadiazine-3-carboxylate 1,1-dioxide (22)

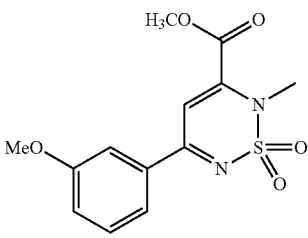 [SMILES: COC(=O)C1=CC(c2cccc(OC)c2)=NS(=O)(=O)N1C]

Title compound was synthesized using general method B for alkylation described above to afford 4.8 g (92%, reaction scale is 5 g); LCMS Calculated for $C_{13}H_{14}N_2O_5S$: 310.06; LCMS observed: 310.90 (M+1)$^+$.

Synthesis of methyl 5-(2-methoxyphenyl)-2-methyl-2H-1,2,6-thiadiazine-3-carboxylate 1,1-dioxide (22)

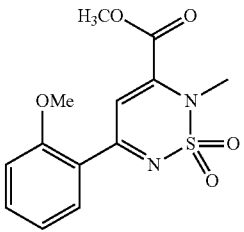 [SMILES: COC(=O)C1=CC(c2ccccc2OC)=NS(=O)(=O)N1C]

Title compound was synthesized using general method B for alkylation described above to afford 18 g (95.49%, reaction scale is 18 g); LCMS Calculated for $C_{13}H_{14}N_2O_5S$: 310.06; LCMS observed: 311.00 (M+1)$^+$.

Synthesis of methyl 2-methyl-5-(4-(trifluoromethyl)phenyl)-2H-1,2,6-thiadiazine-3-carboxylate 1,1-dioxide (22)

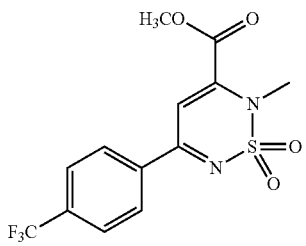 [SMILES: COC(=O)C1=CC(c2ccc(C(F)(F)F)cc2)=NS(=O)(=O)N1C]

Title compound was synthesized using general method B for alkylation described above to afford 5 g (99.9%, reaction scale is 5 g); LCMS Calculated for $C_{13}H_1F_3N_2O_4S$: 348.04; LCMS observed: 348.90 (M+1)$^+$.

Synthesis of methyl 5-(3,4-difluorophenyl)-2-methyl-2H-1,2,6-thiadiazine-3-carboxylate 1,1-dioxide (22)

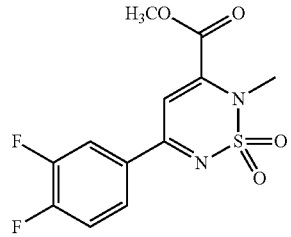 [SMILES: COC(=O)C1=CC(c2ccc(F)c(F)c2)=NS(=O)(=O)N1C]

Title compound was synthesized using general method B for alkylation described above to afford 4 g (76.48%, reaction scale is 5 g); LCMS Calculated for $C_{12}H_{10}F_2N_2O_4S$: 316.03; LCMS observed: 317.00 (M+1)$^+$.

Synthesis of methyl 5-(3-fluorophenyl)-2-methyl-2H-1,2,6-thiadiazine-3-carboxylate 1,1-dioxide (22)

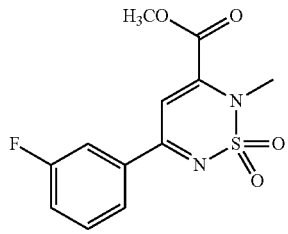 [SMILES: COC(=O)C1=CC(c2cccc(F)c2)=NS(=O)(=O)N1C]

Title compound was synthesized using general method B for alkylation described above to afford 7 g (66.73%, reaction scale is 10 g); LCMS Calculated for $C_{12}H_{11}FN_2O_4S$: 298.04; LCMS observed: 299.00 (M+1)$^+$.

Synthesis of methyl 2-methyl-5-(4-(trifluoromethoxy)phenyl)-2H-1,2,6-thiadiazine-3-carboxylate 1,1-dioxide (22)

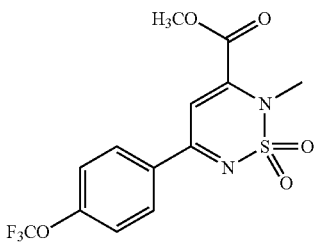 [SMILES: COC(=O)C1=CC(c2ccc(OC(F)(F)F)cc2)=NS(=O)(=O)N1C]

Title compound was synthesized using general method B for alkylation described above to afford 13.1 g (84.08%, reaction scale is 15 g); LCMS Calculated for $C_{13}H_1F_3N_2O_4S$: 364.03; LCMS observed: 364.90 (M+1)$^+$.

Synthesis of methyl 2-methyl-5-(3-(trifluoromethyl)phenyl)-2H-1,2,6-thiadiazine-3-carboxylate 1,1-dioxide (22)

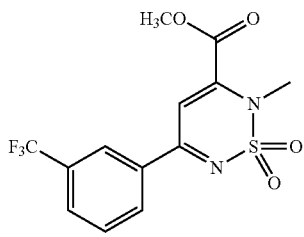 [SMILES: COC(=O)C1=CC(c2cccc(C(F)(F)F)c2)=NS(=O)(=O)N1C]

Title compound was synthesized using general method B for alkylation described above to afford 7 g (67.24%, reaction scale is 10 g); LCMS Calculated for $C_{13}H_1F_3N_2O_4S$: 348.04; LCMS observed: 349.15 (M+1)$^+$.

Synthesis of methyl 5-(3-chlorophenyl)-2-methyl-2H-1,2,6-thiadiazine-3-carboxylate 1,1-dioxide (22)

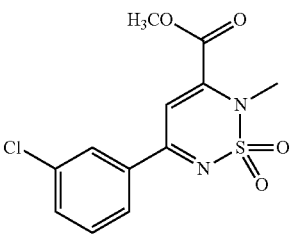 [SMILES: COC(=O)C1=CC(c2cccc(Cl)c2)=NS(=O)(=O)N1C]

Title compound was synthesized using general method B for alkylation described above to afford 3.6 g (69%, reaction scale is 5 g); LCMS Calculated for $C_{12}H_{11}ClN_2O_4S$: 314.01; LCMS observed: 314.95 (M+1)$^+$.

Synthesis of methyl 2-methyl-5-(3-(trifluoromethoxy)phenyl)-2H-1,2,6-thiadiazine-3-carboxylate 1,1-dioxide (22)

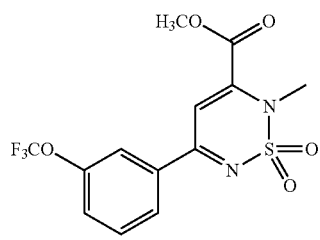 [SMILES: COC(=O)C1=CC(c2cccc(OC(F)(F)F)c2)=NS(=O)(=O)N1C]

Title compound was synthesized using general method B for alkylation described above to afford 5 g (96.15%, reaction scale is 5 g); LCMS Calculated for $C_{13}H_1F_3N_2O_5S$: 364.03; LCMS observed: 365.05 (M+1)$^+$.

Synthesis of methyl 5-(4-(difluoromethoxy)phenyl)-2-methyl-2H-1,2,6-thiadiazine-3-carboxylate 1,1-dioxide (22)

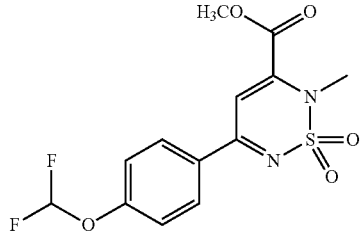 [SMILES: COC(=O)C1=CC(c2ccc(OC(F)F)cc2)=NS(=O)(=O)N1C]

Title compound was synthesized using general method B for alkylation described above to afford 5 g (95.96%, reaction scale is 5 g); LCMS Calculated for $C_{13}H_{12}F_2N_2O_5S$: 346.04; LCMS observed: 347.05 (M+1)$^+$.

161

Synthesis of methyl 5-(3-(difluoromethoxy)phenyl)-2-methyl-2H-1,2,6-thiadiazine-3-carboxylate 1,1-dioxide (22)

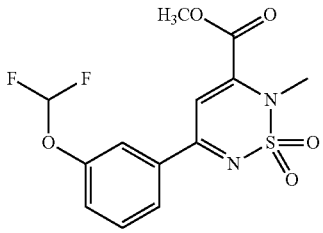 [SMILES: COC(=O)C1=CC(c2cccc(OC(F)F)c2)=NS(=O)(=O)N1C]

Title compound was synthesized using general method B for alkylation described above to afford 3 g (96.77%, reaction scale is 3 g); LCMS Calculated for $C_{13}H_{12}F_2N_2O_5S$: 346.04; LCMS observed: 347.05 $(M+1)^+$.

Synthesis of methyl 5-(4-chlorophenyl)-2-methyl-2H-1,2,6-thiadiazine-3-carboxylate 1,1-dioxide (22)

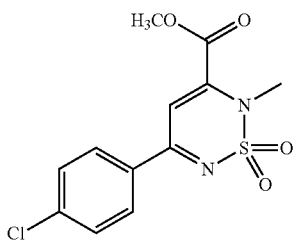 [SMILES: COC(=O)C1=CC(c2ccc(Cl)cc2)=NS(=O)(=O)N1C]

Title compound was synthesized using general method B for alkylation described above to afford 9.0 g (86%, reaction scale is 10 g); LCMS Calculated for $C_{12}H_{11}ClN_2O_4S$: 314.01; LCMS observed: 314.90 $(M+1)^+$.

Synthesis of methyl 5-(4-bromo-3-fluorophenyl)-2-methyl-2H-1,2,6-thiadiazine-3-carboxylate 1,1-dioxide (22)

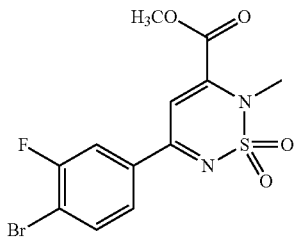 [SMILES: COC(=O)C1=CC(c2ccc(Br)c(F)c2)=NS(=O)(=O)N1C]

Title compound was synthesized using general method B for alkylation described above to afford 2.2 g (70.7%, reaction scale is 3 g); LCMS Calculated for $C_{12}H_{10}BrFN_2O_4S$: 375.95; LCMS observed: 378.95 $(M+2)^+$.

162

N-(3-Chloro-4-fluorophenyl)-2-methyl-5-(pyridin-2-yl)-2H-1,2,6-thiadiazine-3-carboxamide 1,1-dioxide (HBV-CSU-031_Int)

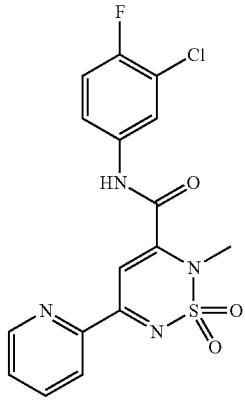

HBV-CSU-031_Int

The above titled compound has been synthesized by following the general procedure (Method A) described above for amidation by using corresponding Compound 22 and corresponding amine (see Table 1 for analytical data).

N-(3-Chloro-4-fluorophenyl)-5-(5-fluoropyridin-2-yl)-2-methyl-2H-1,2,6-thiadiazine-3-carboxamide 1,1-dioxide (HBV-CSU-032_Int)

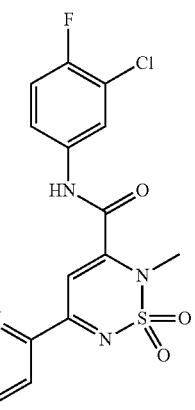

HBV-CSU-032_Int

The above titled compound has been synthesized by following the general procedure (Method A) described above for amidation by using Compound 22 and corresponding amine (see Table 1 for analytical data).

163
N-(3-Chloro-4-fluorophenyl)-2-methyl-5-(pyridin-3-yl)-2H-1,2,6-thiadiazine-3-carboxamide 1,1-dioxide (HBV-CSU-033_Int)

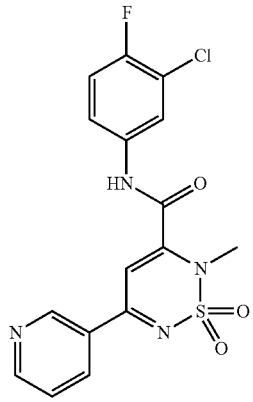

HBV-CSU-033_Int

The above titled compound has been synthesized by following the general procedure (Method A) described above for amidation by using corresponding Compound 22 and corresponding amine (see Table 1 for analytical data).

N-(3-chloro-4-fluorophenyl)-5-(4-fluorophenyl)-2-methyl-2H-1,2,6-thiadiazine-3-carboxamide 1,1-dioxide (HBV-CSU-112_Int)

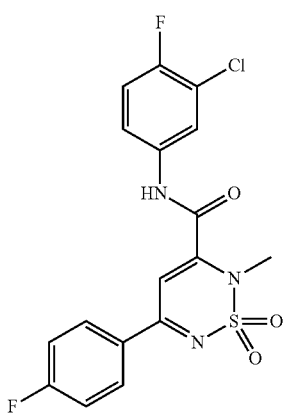

HBV-CSU-112_Int

The above titled compound has been synthesized by following the general procedure (Method B) described above for amidation by using corresponding Compound 22 and corresponding amine. The crude intermediate confirmed by LCMS and carried forward to the next step.

164
N-(3-chloro-4-fluorophenyl)-2-methyl-5-phenyl-2H-1,2,6-thiadiazine-3-carboxamide 1,1-dioxide (HBV-CSU-113_Int)

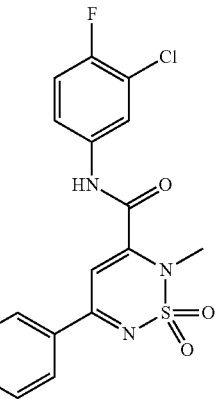

HBV-CSU-113_Int

The above titled compound has been synthesized by following the general procedure (Method B) described above for amidation by using corresponding Compound 22 and corresponding amine (see Table 1 for analytical data).

N-(3-chloro-4-fluorophenyl)-5-(4-methoxyphenyl)-2-methyl-2H-1,2,6-thiadiazine-3-carboxamide 1,1-dioxide (HBV-CSU-200_Int)

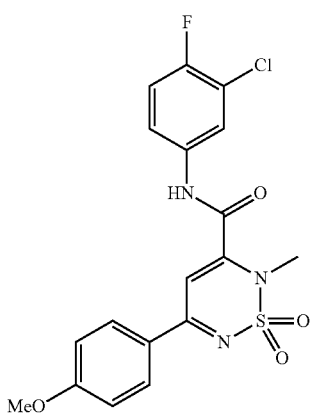

HBV-CSU-200_Int

The above titled compound has been synthesized by following the general procedure (Method B) described above for amidation by using corresponding Compound 22 and corresponding amine (see Table 1 for analytical data).

5-(4-Bromophenyl)-N-(3-chloro-4-fluorophenyl)-2-methyl-2H-1,2,6-thiadiazine-3-carboxamide 1,1-dioxide (HBV-CSU-202_Int)

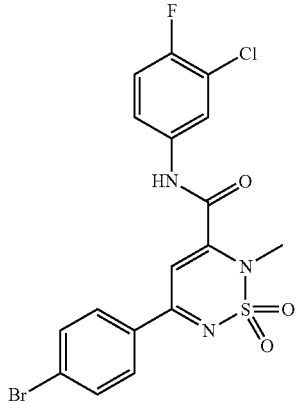

HBV-CSU-202_Int

The above titled compound has been synthesized by following the general procedure (Method B) described above for amidation by using corresponding Compound 22 and corresponding amine (see Table 1 for analytical data).

N-(3-chloro-4-fluorophenyl)-5-(3-methoxyphenyl)-2-methyl-2H-1,2,6-thiadiazine-3-carboxamide 1,1-dioxide (HBV-CSU-204_Int)

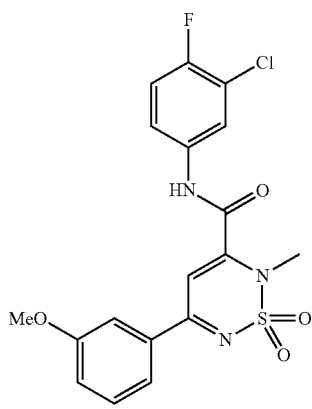

HBV-CSU-204_Int

The above titled compound has been synthesized by following the general procedure (Method B) described above for amidation by using corresponding Compound 22 and corresponding amine (see Table 1 for analytical data).

N-(3-chloro-4-fluorophenyl)-5-(4-fluorophenyl)-2-(2-methoxyethyl)-2H-1,2,6-thiadiazine-3-carboxamide 1,1-dioxide (HBV-CSU-210_Int)

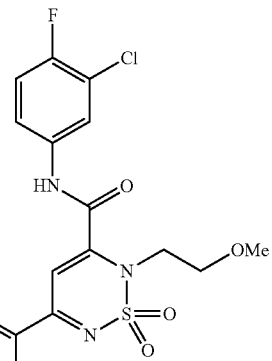

HBV-CSU-210_Int

The above titled compound has been synthesized by following the general procedure (Method B) described above for amidation by using corresponding Compound 22 and corresponding amine. The reaction was monitored by LCMS and the crude intermediate carried forward to the next step.

N-(3-Bromo-4-fluorophenyl)-5-(4-fluorophenyl)-2-methyl-2H-1,2,6-thiadiazine-3-carboxamide 1,1-dioxide (HBV-CSU-211_Int)

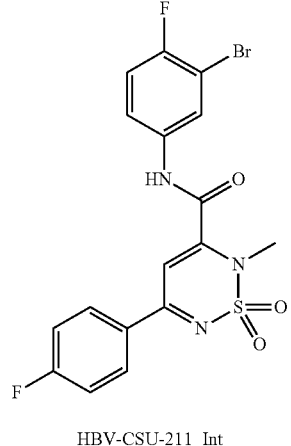

HBV-CSU-211_Int

The above titled compound has been synthesized by following the general procedure (Method B) described above for amidation by using corresponding Compound 22 and corresponding amine (see Table 1 for analytical data).

167

5-(4-Fluorophenyl)-2-methyl-N-(3,4,5-trifluorophenyl)-2H-1,2,6-thiadiazine-3-carboxamide 1,1-dioxide (HBV-CSU-212_Int)

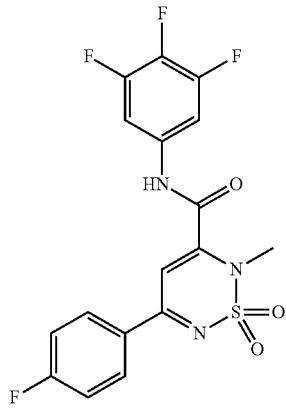

HBV-CSU-212_Int

The above titled compound has been synthesized by following the general procedure (Method B) described above for amidation by using corresponding Compound 22 and corresponding amine (see Table 1 for analytical data).

N-(3-chloro-4-fluorophenyl)-5-(2-methoxyphenyl)-2-methyl-2H-1,2,6-thiadiazine-3-carboxamide 1,1-dioxide (HBV-CSU-215_Int)

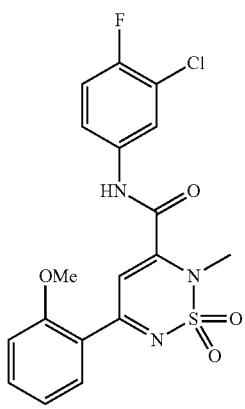

HBV-CSU-215_Int

The above titled compound has been synthesized by following the general procedure (Method B) described above for amidation by using corresponding Compound 22 and corresponding amine (see Table 1 for analytical data).

168

N-(3-Chloro-4-fluorophenyl)-2-methyl-5-(4-(trifluoromethyl)phenyl)-2H-1,2,6-thiadiazine-3-carboxamide 1,1-dioxide (HBV-CSU-217_Int)

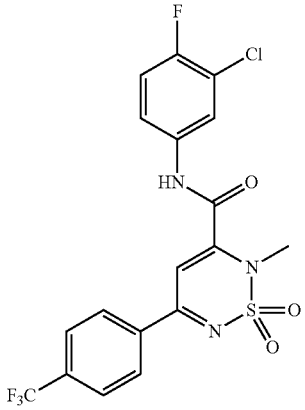

HBV-CSU-217_Int

The above titled compound has been synthesized by following the general procedure (Method B) described above for amidation by using corresponding Compound 22 and corresponding amine (see Table 1 for analytical data).

N-(3-Chloro-4-fluorophenyl)-5-(3,4-difluorophenyl)-2-methyl-2H-1,2,6-thiadiazine-3-carboxamide 1,1-dioxide (HBV-CSU-230_Int)

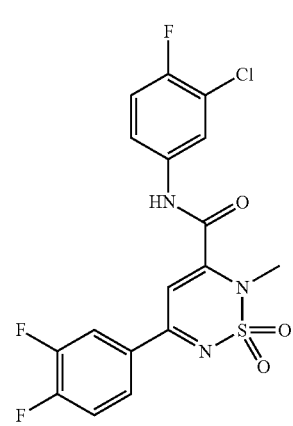

HBV-CSU-230_Int

The above titled compound has been synthesized by following the general procedure (Method B) described above for amidation by using corresponding Compound 22 and corresponding amine (see Table 1 for analytical data).

169

N-(3-Chloro-4-fluorophenyl)-5-(3-fluorophenyl)-2-methyl-2H-1,2,6-thiadiazine-3-carboxamide 1,1-dioxide (HBV-CSU-231_Int)

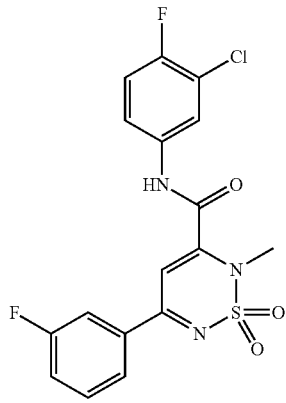

HBV-CSU-231_Int

The above titled compound has been synthesized by following the general procedure (Method B) described above for amidation by using corresponding Compound 22 and corresponding amine. The crude intermediate confirmed by LCMS and carried forward to the next step.

N-(3-Chloro-4-fluorophenyl)-2-methyl-5-(4-(trifluoromethoxy)phenyl)-2H-1,2,6-thiadiazine-3-carboxamide 1,1-dioxide (HBV-CSU-232_Int)

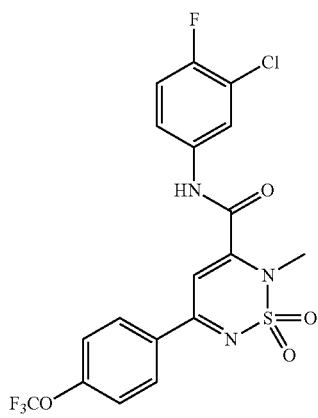

HBV-CSU-232_Int

The above titled compound has been synthesized by following the general procedure (Method B) described above for amidation by using corresponding Compound 22 and corresponding amine (see Table 1 for analytical data).

170

N-(3-chloro-4-fluorophenyl)-2-methyl-5-(3-(trifluoromethyl)phenyl)-2H-1,2,6-thiadiazine-3-carboxamide 1,1-dioxide (HBV-CSU-259_Int)

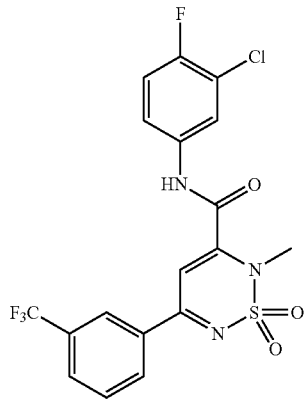

HBV-CSU-259_Int

The above titled compound has been synthesized by following the general procedure (Method B) described above for amidation by using corresponding Compound 22 and corresponding amine (see Table 1 for analytical data).

N-(3-Chloro-4-fluorophenyl)-5-(3-chlorophenyl)-2-methyl-2H-1,2,6-thiadiazine-3-carboxamide 1,1-dioxide (HBV-CSU-261_Int)

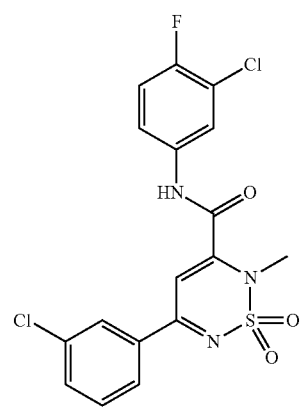

HBV-CSU-261_Int

The above titled compound has been synthesized by following the general procedure (Method B) described above for amidation by using corresponding Compound 22 and corresponding amine (see Table 1 for analytical data).

171

N-(3-Chloro-4-fluorophenyl)-2-methyl-5-(3-(trifluoromethoxy)phenyl)-2H-1,2,6-thiadiazine-3-carboxamide 1,1-dioxide (HBV-CSU-262_Int)

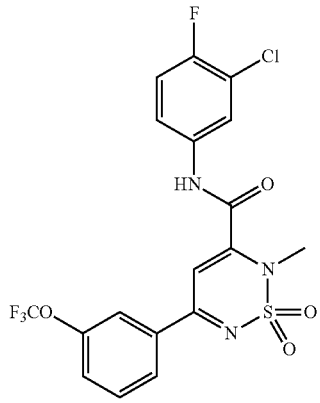

HBV-CSU-262_Int

The above titled compound has been synthesized by following the general procedure (Method B) described above for amidation by using corresponding Compound 22 and corresponding amine (see Table 1 for analytical data).

N-(3-Chloro-4-fluorophenyl)-5-(4-(difluoromethoxy)phenyl)-2-methyl-2H-1,2,6-thiadiazine-3-carboxamide 1,1-dioxide (HBV-CSU-263_Int)

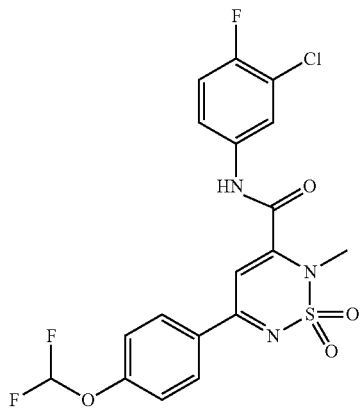

HBV-CSU-263_Int

The above titled compound has been synthesized by following the general procedure (Method B) described above for amidation by using corresponding Compound 22 and corresponding amine (see Table 1 for analytical data).

172

N-(3-chloro-4-fluorophenyl)-5-(3-(difluoromethoxy)phenyl)-2-methyl-2H-1,2,6-thiadiazine-3-carboxamide 1,1-dioxide (HBV-CSU-264_Int)

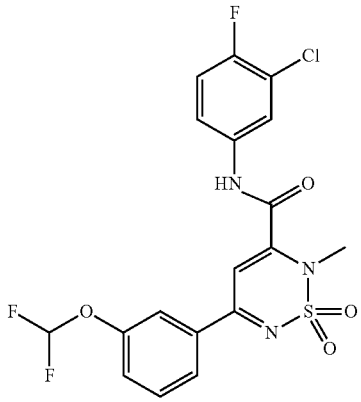

HBV-CSU-264_Int

The above titled compound has been synthesized by following the general procedure (Method B) described above for amidation by using corresponding Compound 22 and corresponding amine (see Table 1 for analytical data).

N-(3-Chloro-4-fluorophenyl)-5-(4-chlorophenyl)-2-methyl-2H-1,2,6-thiadiazine-3-carboxamide 1,1-dioxide (HBV-CSU-265_Int)

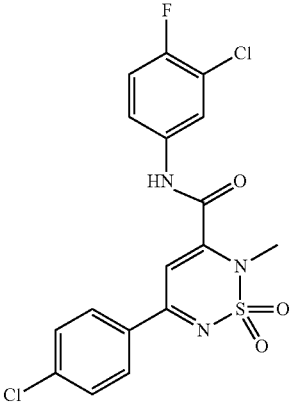

HBV-CSU-265_Int

The above titled compound has been synthesized by following the general procedure (Method B) described above for amidation by using corresponding Compound 22 and corresponding amine (see Table 1 for analytical data).

5-(4-Bromo-3-fluorophenyl)-N-(3-chloro-4-fluorophenyl)-2-methyl-2H-1,2,6-thiadiazine-3-carboxamide 1,1-dioxide (HBV-CSU-283_Int)

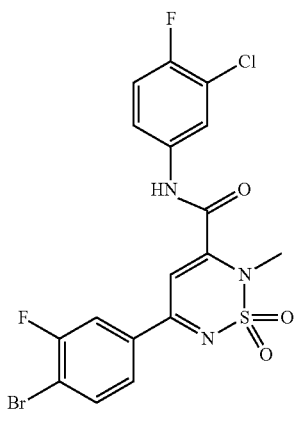

HBV-CSU-283_Int

The above titled compound has been synthesized by following the general procedure (Method B) described above for amidation by using corresponding Compound 22 and corresponding amine (see Table 1 for analytical data).

Cis-N-(3-Chloro-4-fluorophenyl)-2-methyl-5-(pyridin-2-yl)-1,2,6-thiadiazinane-3-carboxamide 1,1-dioxide (HBV-CSU-031, HBV-CSU-031-ISO-I & HBV-CSU-031-ISO-II)

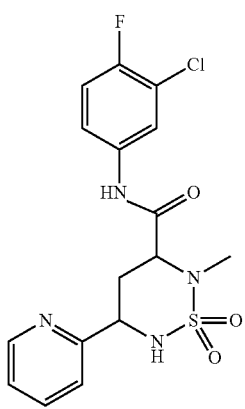

HBV-CSU-031

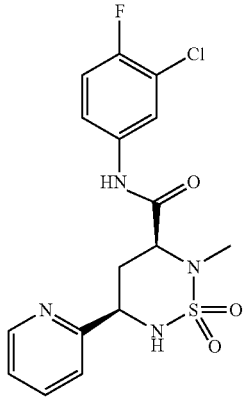

HBV-CSU-031-ISO-I

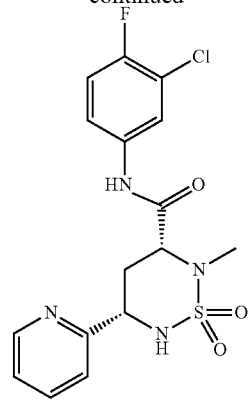

HBV-CSU-031-ISO-II

The above titled compounds have been synthesized by following the general procedure described above for reduction by using corresponding HBV-CSU-031_Int (see Table 2 for analytical data).

Cis-N-(3-Chloro-4-fluorophenyl)-5-(5-fluoropyridin-2-yl)-2-methyl-1,2,6-thiadiazinane-3-carboxamide 1,1-dioxide (HBV-CSU-032, HBV-CSU-032-ISO-I & HBV-CSU-032-ISO-II)

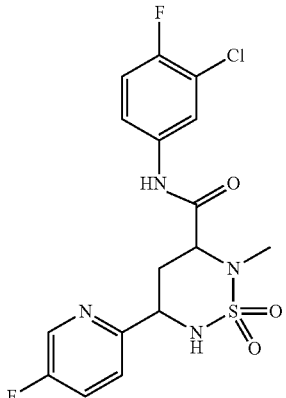

HBV-CSU-032

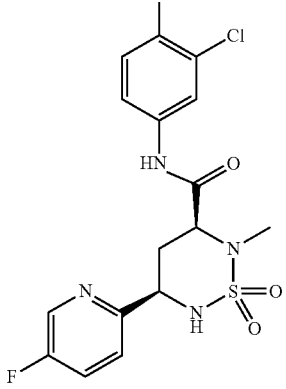

HBV-CSU-032-ISO-I

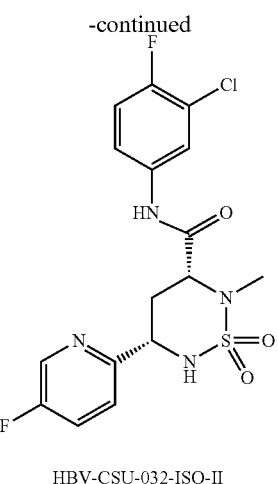

HBV-CSU-032-ISO-II

The above titled compounds have been synthesized by following the general procedure described above for reduction by using corresponding HBV-CSU-032_Int (see Table 2 for analytical data).

Cis-N-(3-Chloro-4-fluorophenyl)-2-methyl-5-(pyridin-3-yl)-1,2,6-thiadiazinane-3-carboxamide 1,1-dioxide (HBV-CSU-033)

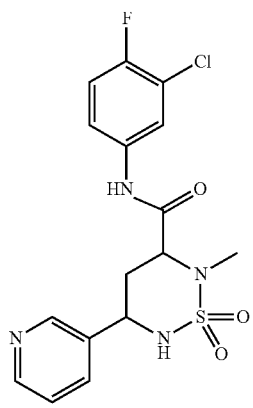

HBV-CSU-033

The above titled compound has been synthesized by following the general procedure described above for reduction by using corresponding HBV-CSU-033_Int (see Table 2 for analytical data).

Cis-N-(3-Chloro-4-fluorophenyl)-5-(4-fluorophenyl)-2-methyl-1,2,6-thiadiazinane-3-carboxamide 1,1-dioxide (HBV-CSU-112, HBV-CSU-112-ISO-I & HBV-CSU-112-ISO-II)

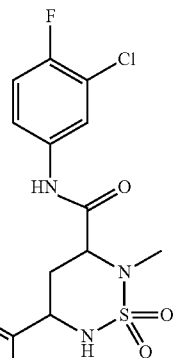

HBV-CSU-112

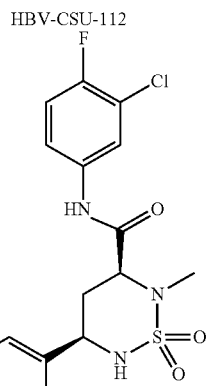

HBV-CSU-112-ISO-I

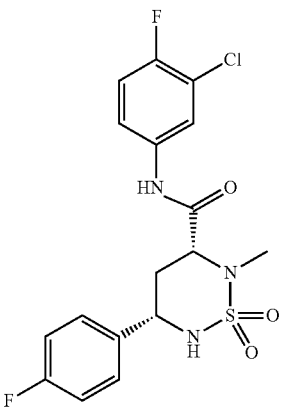

HBV-CSU-112-ISO-II

The above titled compounds have been synthesized by following the general procedure described above for reduction by using corresponding HBV-CSU-112_Int (see Table 2 for analytical data).

Cis-N-(3-chloro-4-fluorophenyl)-2-methyl-5-phenyl-1,2,6-thiadiazinane-3-carboxamide 1,1-dioxide (HBV-CSU-113-ISO-I & HBV-CSU-113-ISO-II)

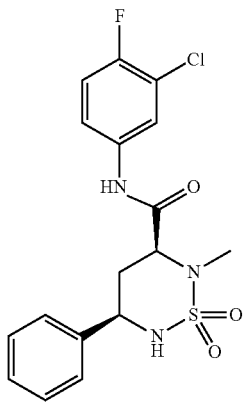

HBV-CSU-113-ISO-I

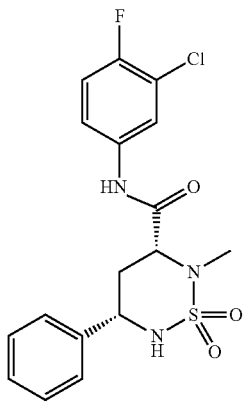

HBV-CSU-113-ISO-II

The above titled compounds have been synthesized by following the general procedure described above for reduction by using corresponding HBV-CSU-113_Int (see Table 2 for analytical data).

Cis-N-(3-Chloro-4-fluorophenyl)-5-(4-methoxyphenyl)-2-methyl-1,2,6-thiadiazinane-3-carboxamide 1,1-dioxide (HBV-CSU-200)

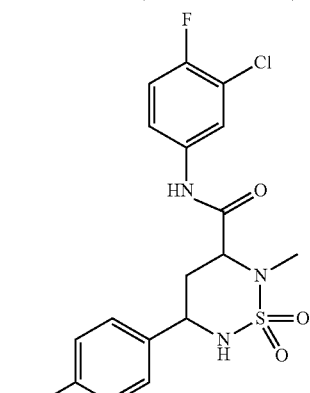

HBV-CSU-200

The above titled compounds have been synthesized by following the general procedure described above for reduction by using corresponding HBV-CSU-200_Int (see Table 2 for analytical data).

Cis-5-(4-Bromophenyl)-N-(3-chloro-4-fluorophenyl)-2-methyl-1,2,6-thiadiazinane-3-carboxamide 1,1-dioxide (HBV-CSU-202)

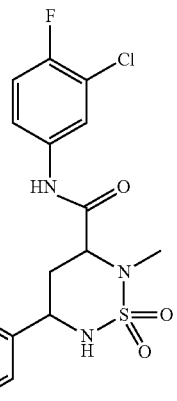

HBV-CSU-202

The above titled compounds have been synthesized by following the general procedure described above for reduction by using corresponding HBV-CSU-202_Int (see Table 2 for analytical data).

Cis-N-(3-Chloro-4-fluorophenyl)-5-(3-methoxyphenyl)-2-methyl-1,2,6-thiadiazinane-3-carboxamide 1,1-dioxide (HBV-CSU-204)

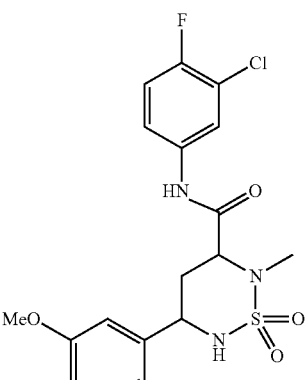

HBV-CSU-204

The above titled compounds have been synthesized by following the general procedure described above for reduction by using corresponding HBV-CSU-204_Int (see Table 2 for analytical data).

179

Cis-N-(3-Chloro-4-fluorophenyl)-5-(4-fluorophenyl)-2-(2-methoxyethyl)-1,2,6-thiadiazinane-3-carboxamide 1,1-dioxide (HBV-CSU-210, HBV-CSU-210-ISO-I & HBV-CSU-210-ISO-II)

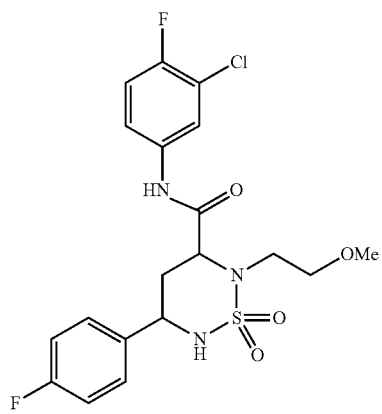
HBV-CSU-210

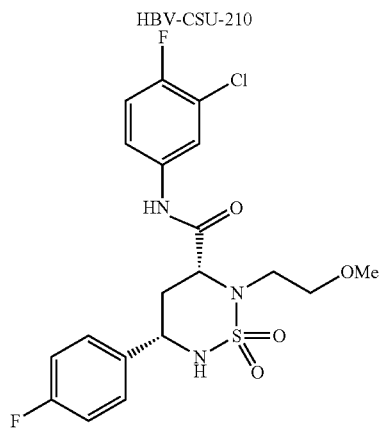
HBV-CSU-210-ISO-I

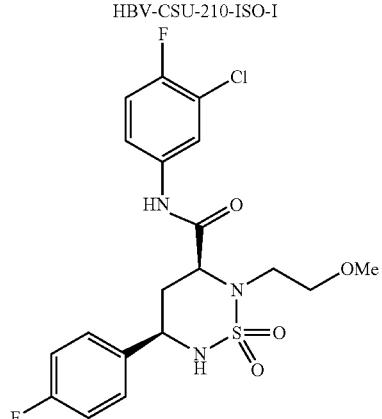
HBV-CSU-210-ISO-II

180

Cis-N-(3-Bromo-4-fluorophenyl)-5-(4-fluorophenyl)-2-methyl-1,2,6-thiadiazinane-3-carboxamide 1,1-dioxide (HBV-CSU-211, HBV-CSU-211-ISO-I & HBV-CSU-211-ISO-II)

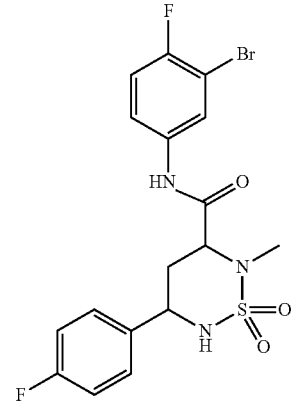
HBV-CSU-211

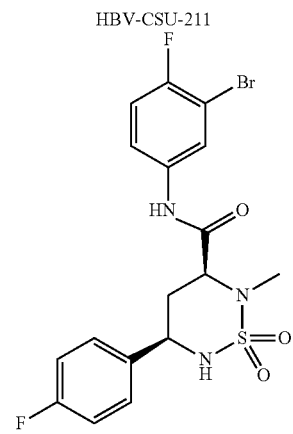
HBV-CSU-211-ISO-I

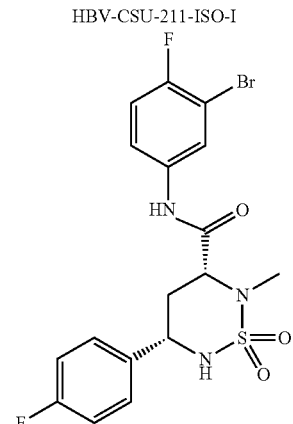
HBV-CSU-211-ISO-II

The above titled compounds have been synthesized by following the general procedure described above for reduction by using corresponding HBV-CSU-210_Int (see Table 2 for analytical data).

The above titled compounds have been synthesized by following the general procedure described above for reduction by using corresponding HBV-CSU-211_Int (see Table 2 for analytical data).

181

Cis-5-(4-Fluorophenyl)-2-methyl-N-(3,4,5-trifluorophenyl)-1,2,6-thiadiazinane-3-carboxamide 1,1-dioxide (HBV-CSU-212, HBV-CSU-212-ISO-I & HBV-CSU-212-ISO-II)

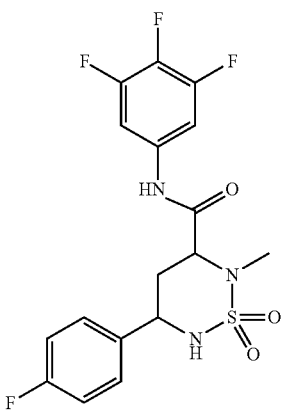

HBV-CSU-212

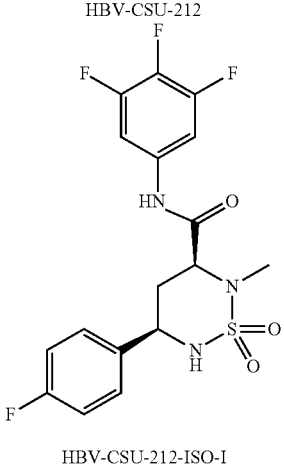

HBV-CSU-212-ISO-I

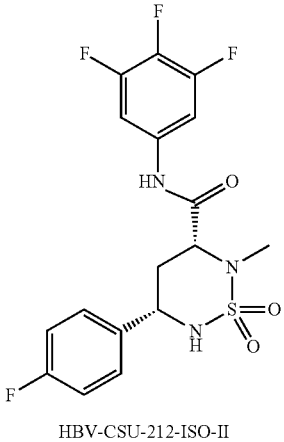

HBV-CSU-212-ISO-II

The above titled compounds have been synthesized by following the general procedure described above for reduction by using corresponding HBV-CSU-212_Int (see Table 2 for analytical data).

182

Cis-N-(3-Chloro-4-fluorophenyl)-5-(2-methoxyphenyl)-2-methyl-2H-1,2,6-thiadiazine-3-carboxamide 1,1-dioxide (HBV-CSU-215)

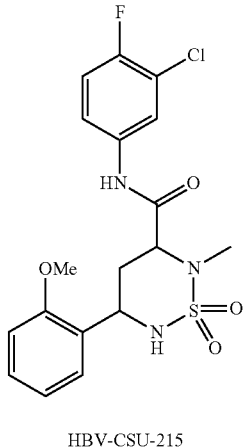

HBV-CSU-215

The above titled compound has been synthesized by following the general procedure described above for reduction by using corresponding HBV-CSU-215_Int (see Table 2 for analytical data).

Cis-N-(3-Chloro-4-fluorophenyl)-2-methyl-5-(4-(trifluoromethyl)phenyl)-1,2,6-thiadiazinane-3-carboxamide 1,1-dioxide (HBV-CSU-217, HBV-CSU-217-ISO-I & HBV-CSU-217-ISO-II)

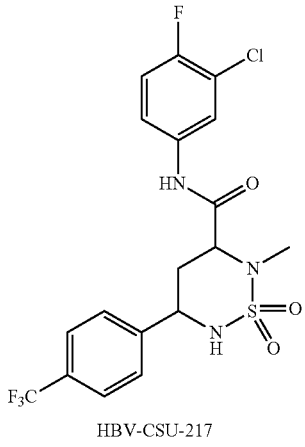

HBV-CSU-217

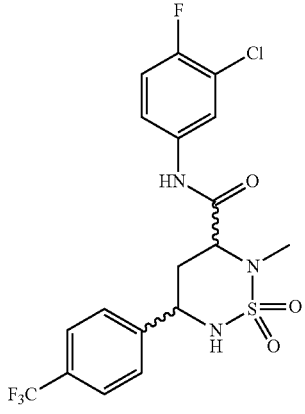

HBV-CSU-217-ISO-I

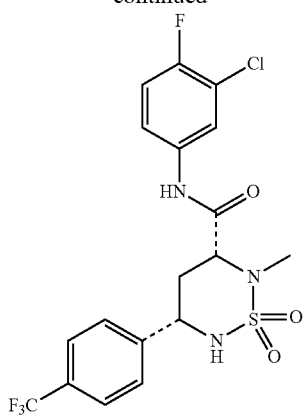

HBV-CSU-217-ISO-II

The above titled compounds have been synthesized by following the general procedure described above for reduction by using corresponding HBV-CSU-217_Int (see Table 2 for analytical data).

Cis-N-(3-Chloro-4-fluorophenyl)-5-(3,4-difluorophenyl)-2-methyl-1,2,6-thiadiazinane-3-carboxamide 1,1-dioxide (HBV-CSU-230, HBV-CSU-230-ISO-I & HBV-CSU-230-ISO-II)

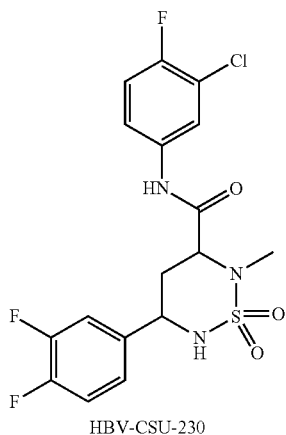

HBV-CSU-230

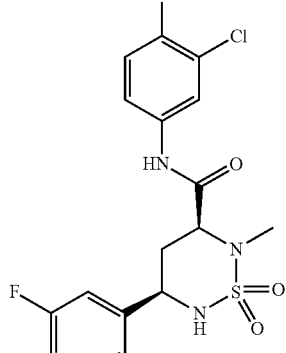

HBV-CSU-230-ISO-I

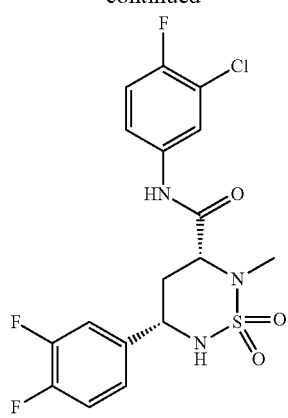

HBV-CSU-230-ISO-II

The above titled compounds have been synthesized by following the general procedure described above for reduction by using corresponding HBV-CSU-230_Int (see Table 2 for analytical data).

Cis-N-(3-Chloro-4-fluorophenyl)-5-(3-fluorophenyl)-2-methyl-1,2,6-thiadiazinane-3-carboxamide 1,1-dioxide (HBV-CSU-231, HBV-CSU-231-ISO-I & HBV-CSU-231-ISO-II)

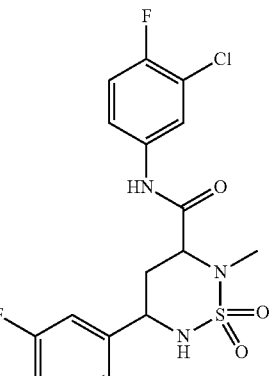

HBV-CSU-231

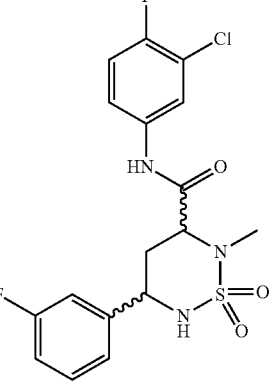

HBV-CSU-231-ISO-I

-continued

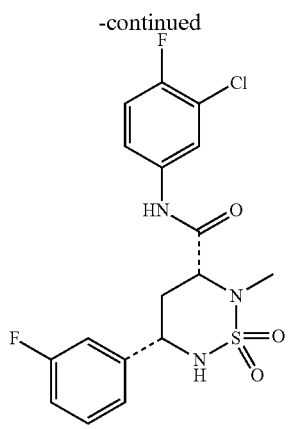

HBV-CSU-231-ISO-II

The above titled compounds have been synthesized by following the general procedure described above for reduction by using corresponding HBV-CSU-231_Int (see Table 2 for analytical data).

Cis-N-(3-Chloro-4-fluorophenyl)-2-methyl-5-(4-(trifluoromethoxy)phenyl)-1,2,6-thiadiazinane-3-carboxamide 1,1-dioxide (HBV-CSU-232)

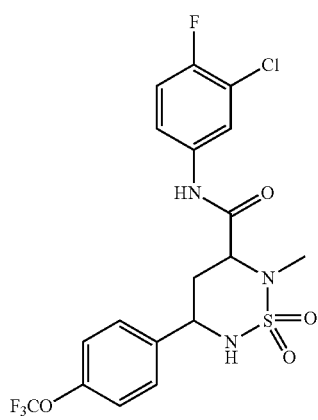

HBV-CSU-232

The above titled compound has been synthesized by following the general procedure described above for reduction by using corresponding HBV-CSU-232_Int (see Table 2 for analytical data).

Cis-N-(3-chloro-4-fluorophenyl)-2-methyl-5-(3-(trifluoromethyl)phenyl)-1,2,6-thiadiazinane-3-carboxamide 1,1-dioxide (HBV-CSU-259, HBV-CSU-259-ISO-I & HBV-CSU-259-ISO-II)

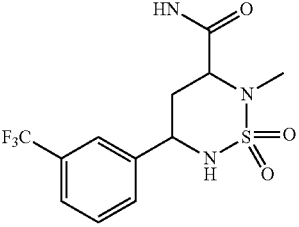

HBV-CSU-259

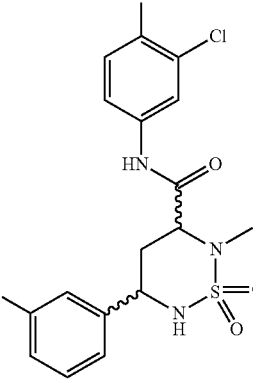

HBV-CSU-259-ISO-I

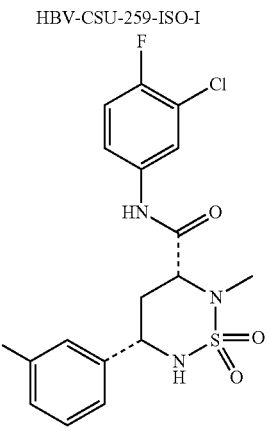

HBV-CSU-259-ISO-II

The above titled compounds have been synthesized by following the general procedure described above for reduction by using corresponding HBV-CSU-259_Int (see Table 2 for analytical data).

187

Cis-N-(3-Chloro-4-fluorophenyl)-5-(3-chlorophenyl)-2-methyl-1,2,6-thiadiazinane-3-carboxamide 1,1-dioxide (HBV-CSU-261, HBV-CSU-261-ISO-I & HBV-CSU-261-ISO-II)

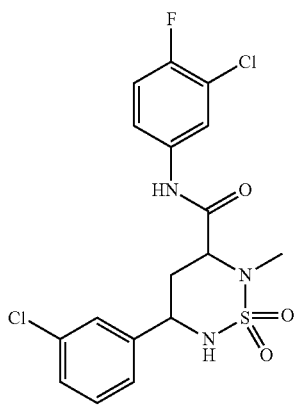

HBV-CSU-261

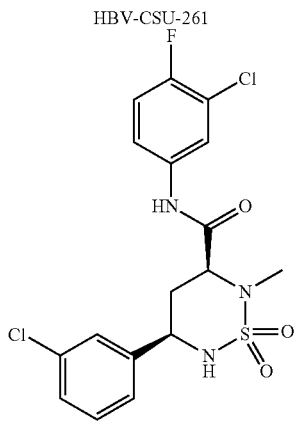

HBV-CSU-261-ISO-I

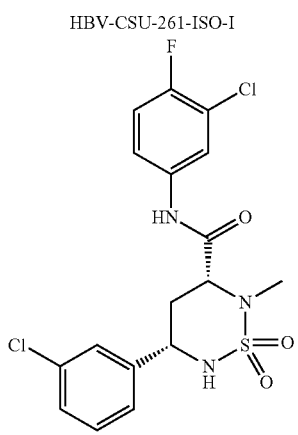

HBV-CSU-261-ISO-II

The above titled compounds have been synthesized by following the general procedure described above for reduction by using corresponding HBV-CSU-261_Int (see Table 2 for analytical data).

188

Cis-N-(3-Chloro-4-fluorophenyl)-2-methyl-5-(3-(trifluoromethoxy)phenyl)-1,2,6-thiadiazinane-3-carboxamide 1,1-dioxide (HBV-CSU-262, HBV-CSU-262-ISO-I & HBV-CSU-262-ISO-II)

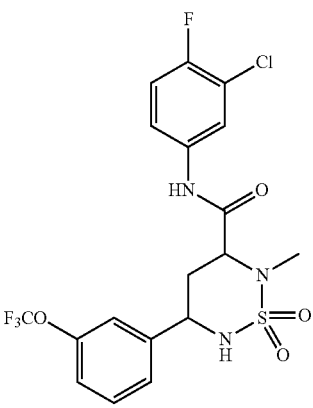

HBV-CSU-262

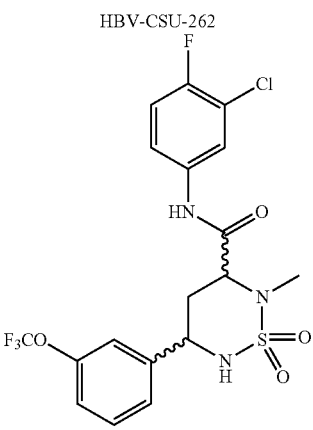

HBV-CSU-262-ISO-I

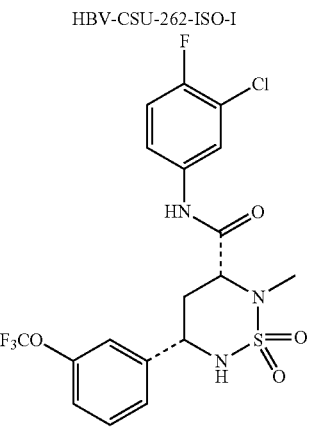

HBV-CSU-262-ISO-II

The above titled compounds have been synthesized by following the general procedure described above for reduction by using corresponding HBV-CSU-262_Int (see Table 2 for analytical data).

189

Cis-N-(3-Chloro-4-fluorophenyl)-5-(4-(difluoromethoxy)phenyl)-2-methyl-1,2,6-thiadiazinane-3-carboxamide 1,1-dioxide (HBV-CSU-263, HBV-CSU-263-ISO-I & HBV-CSU-263-ISO-II)

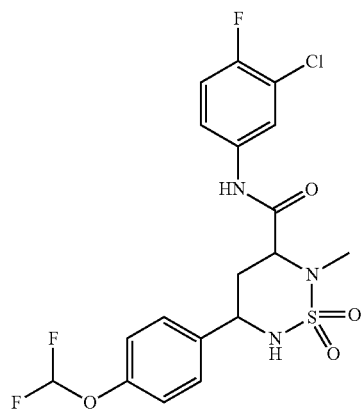
HBV-CSU-263

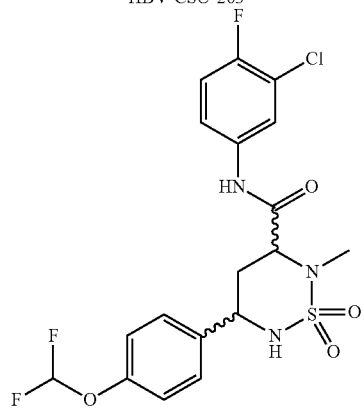
HBV-CSU-263-ISO-I

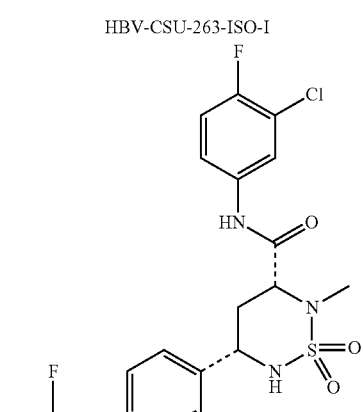
HBV-CSU-263-ISO-II

The above titled compounds have been synthesized by following the general procedure described above for reduction by using corresponding HBV-CSU-263_Int (see Table 2 for analytical data).

190

Cis-N-(3-chloro-4-fluorophenyl)-5-(3-(difluoromethoxy)phenyl)-2-methyl-1,2,6-thiadiazinane-3-carboxamide 1,1-dioxide (HBV-CSU-264, HBV-CSU-264-ISO-I & HBV-CSU-264-ISO-II)

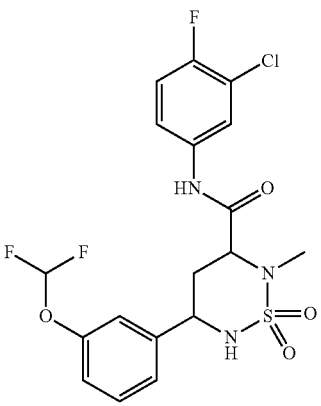
HBV-CSU-264

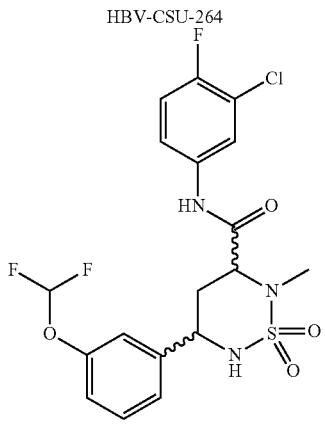
HBV-CSU-264-ISO-I

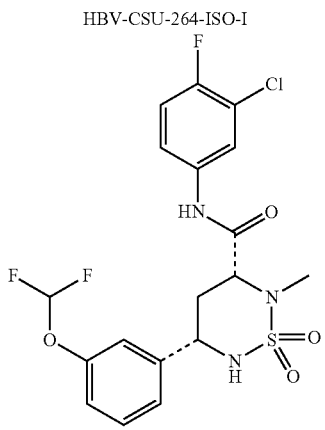
HBV-CSU-264-ISO-II

The above titled compounds have been synthesized by following the general procedure described above for reduction by using corresponding HBV-CSU-264_Int (see Table 2 for analytical data).

191

Cis-N-(3-Chloro-4-fluorophenyl)-5-(4-chlorophenyl)-2-methyl-1,2,6-thiadiazinane-3-carboxamide 1,1-dioxide (HBV-CSU-265)

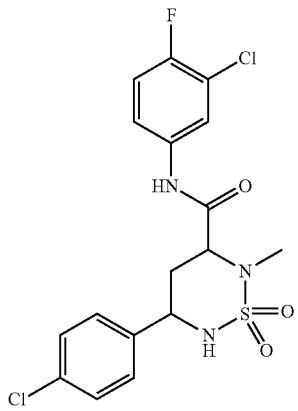

HBV-CSU-265

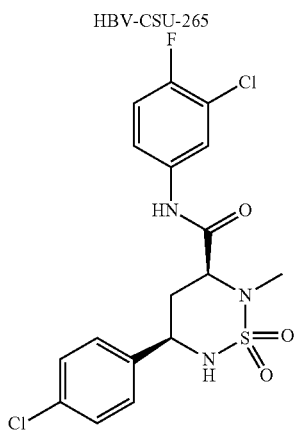

HBV-CSU-265-ISO-I

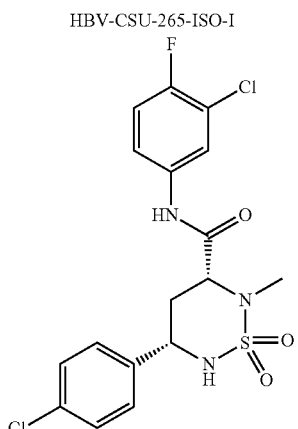

HBV-CSU-265-ISO-II

The above titled compounds have been synthesized by following the general procedure described above for reduction by using corresponding HBV-CSU-265_Int (see Table 2 for analytical data).

192

Cis-5-(4-Bromo-3-fluorophenyl)-N-(3-chloro-4-fluorophenyl)-2-methyl-1,2,6-thiadiazinane-3-carboxamide 1,1-dioxide (HBV-CSU-283)

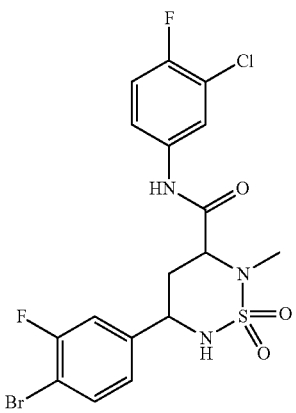

HBV-CSU-283

The above titled compounds have been synthesized by following the general procedure described above for reduction by using corresponding HBV-CSU-283_Int (see Table 2 for analytical data).

Scheme 7

Synthesis of Cis-N-(3-chloro-4-fluorophenyl)-2-(2-hydroxyethyl)-5-(thiophen-2-yl)-1,2,6-thiadiazinane-3-carboxamide 1,1-dioxide (HBV-CSU-041)

Scheme 7:

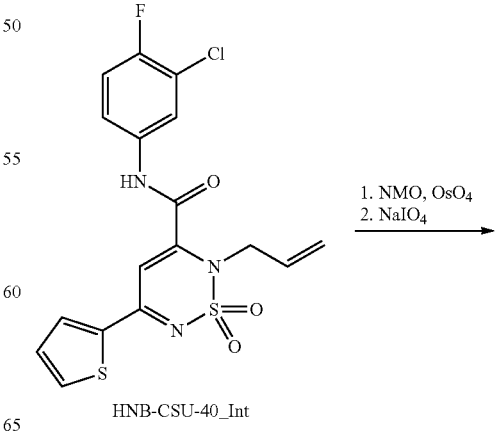

HNB-CSU-40_Int

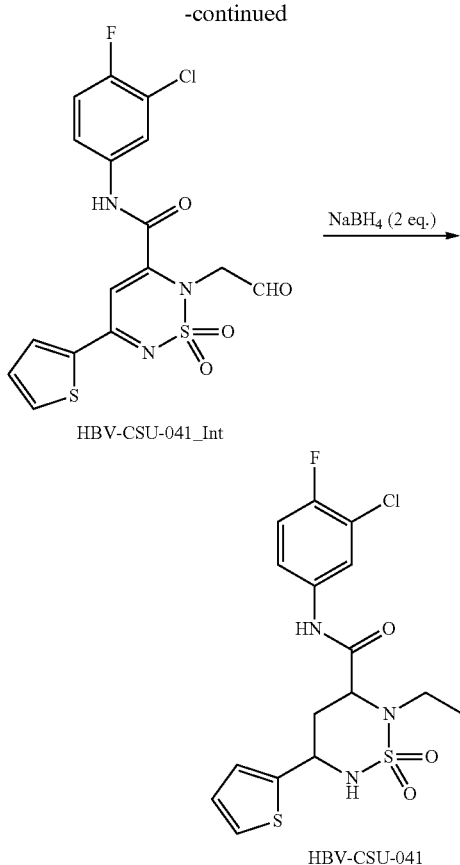

HBV-CSU-041_Int

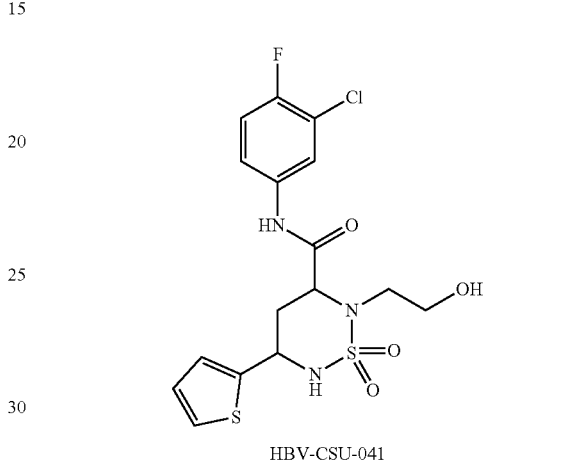

HBV-CSU-041

N-(3-chloro-4-fluorophenyl)-2-(2-oxoethyl)-5-(thiophen-2-yl)-2H-1,2,6-thiadiazine-3-carboxamide 1,1-dioxide (HBV-CSU-041_Int)

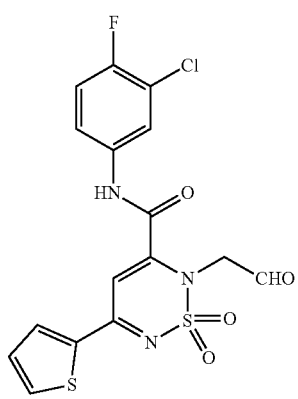 [SMILES: O=CCN1C(C(=O)Nc2ccc(F)c(Cl)c2)=CC(c2cccs2)=NS1(=O)=O]

To a stirred solution of HNB-CSU-40_Int (0.2 g, 0.47 mmol) in DCM (10 mL) at 0° C., NMO (0.169 g, 1.41 mmol) was added and stirred for 10 min. To this solution, OsO$_4$ in butanol (0.035 g, 0.141 mmol) was added at 0° C. and stirred at room temperature for 1 h. After completion, the reaction mixture was concentrated under reduced pressure. The crude residue obtained was dissolved in 10 mL of THF:H$_2$O (1:1) mixture, NaIO$_4$ (0.278 g, 1.41 mmol) was added and the reaction mixture was stirred at room temperature for 3 h. The progress of the reaction was monitored by TLC and LCMS. After completion, the reaction mixture was concentrated under reduced pressure and the crude compound obtained was purified by silica gel column chromatography using 15% EtOAc/hexane to afford the desired compound (0.1 g, 49.75%) as an off-white solid. TLC for aldehyde: 40% EtOAc/hexanes (R$_f$: 0.3); The reaction monitored by TLC (DNP stain) and the crude intermediate was carried forward to the next step without any purification.

Cis-N-(3-Chloro-4-fluorophenyl)-2-(2-hydroxyethyl)-5-(thiophen-2-yl)-1,2,6-thiadiazinane-3-carboxamide 1,1-dioxide (HBV-CSU-041)

HBV-CSU-041

The above titled compound has been synthesized by following the general procedure described above for reduction by using HBV-CSU-041_Int (see Table 2 for analytical data).

Scheme 8

Synthesis of Cis-N-(3-chloro-4-fluorophenyl)-2,5-dimethyl-1,2,6-thiadiazinane-3-carboxamide 1,1-dioxide (HBV-CSU-050-ISO-I & HBV-CSU-050-ISO-II)

Scheme 8:

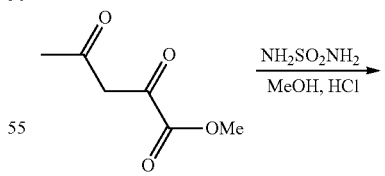

23

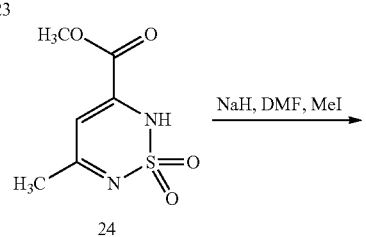

24

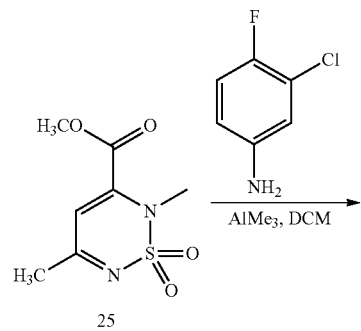

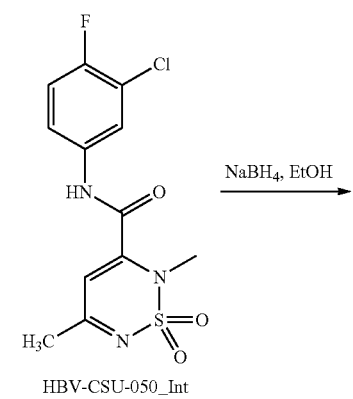

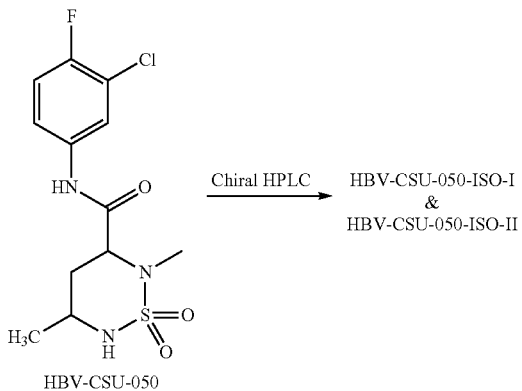

Synthesis of methyl
5-methyl-2H-1,2,6-thiadiazine-3-carboxylate
1,1-dioxide (24)

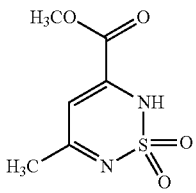

Title compound was synthesized using general method for the synthesis of cyclic sulfonamide described above to afford 5.95 g (84.03%, reaction scale is 5 g); LCMS Calculated for $C_6H_8N_2O_4S$: 204.02; LCMS observed: 204.85 (M+1)$^+$.

Synthesis of methyl
2,5-dimethyl-2H-1,2,6-thiadiazine-3-carboxylate
1,1-dioxide (25)

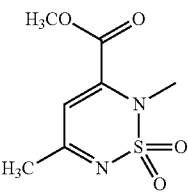

Title compound was synthesized using general method A for alkylation described above to afford 3.57 g (83.6%, reaction scale is 4 g); LCMS Calculated for $C_7H_{10}N_2O_4S$: 218.04; LCMS observed: 218.90 (M+1)$^+$.

Synthesis of N-(3-chloro-4-fluorophenyl)-2,5-dimethyl-2H-1,2,6-thiadiazine-3-carboxamide 1,1-dioxide (HBV-CSU-050_Int)

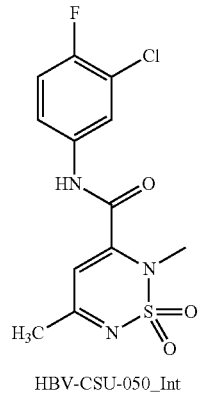

HBV-CSU-050_Int

The above titled compound has been synthesized by following the general procedure (Method B) described above for amidation by using Compound 25 and corresponding amine (see Table 1 for analytical data).

Cis-N-(3-chloro-4-fluorophenyl)-2,5-dimethyl-1,2,6-thiadiazinane-3-carboxamide 1,1-dioxide (HBV-CSU-050-ISO-I & HBV-CSU-050-ISO-II)

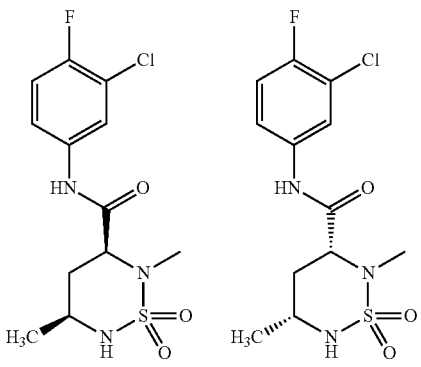

HBV-CSU-050-ISO-I          HBV-CSU-050-ISO-II

The above titled compounds have been synthesized by following the general procedure described above for reduction by using corresponding HBV-CSU-050_Int (see Table 2 for analytical data).

Scheme 9

Synthetic scheme for Cis-N-(3-chloro-4-fluorophenyl)-2-methyl-5-(1-methyl-1H-pyrazol-5-yl)-1,2,6-thiadiazinane-3-carboxamide 1,1-dioxide (HBV-CSU-054, HBV-CSU-054-ISO-I & HBV-CSU-054-ISO-II)

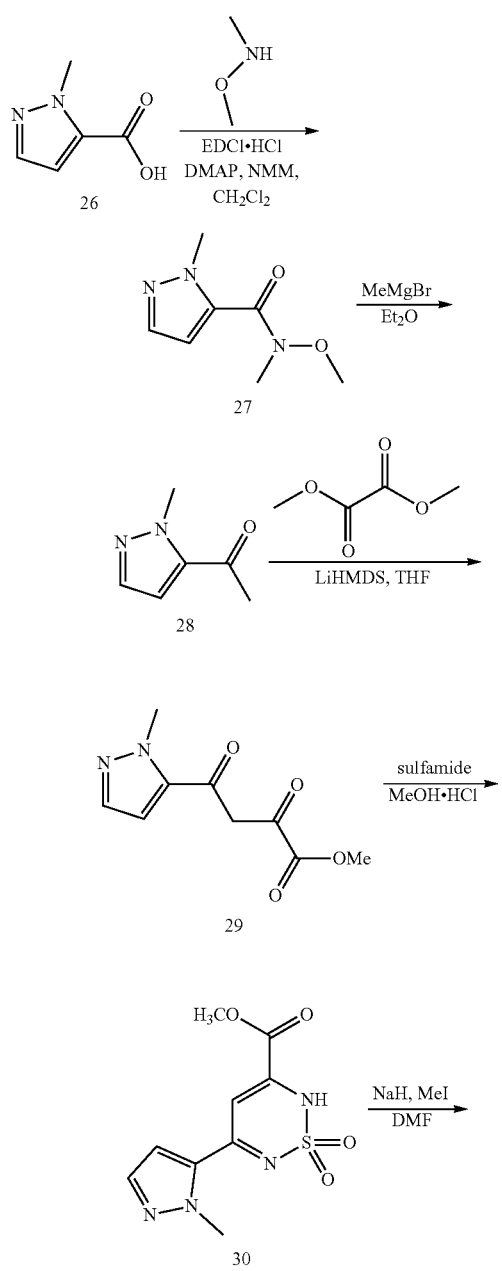

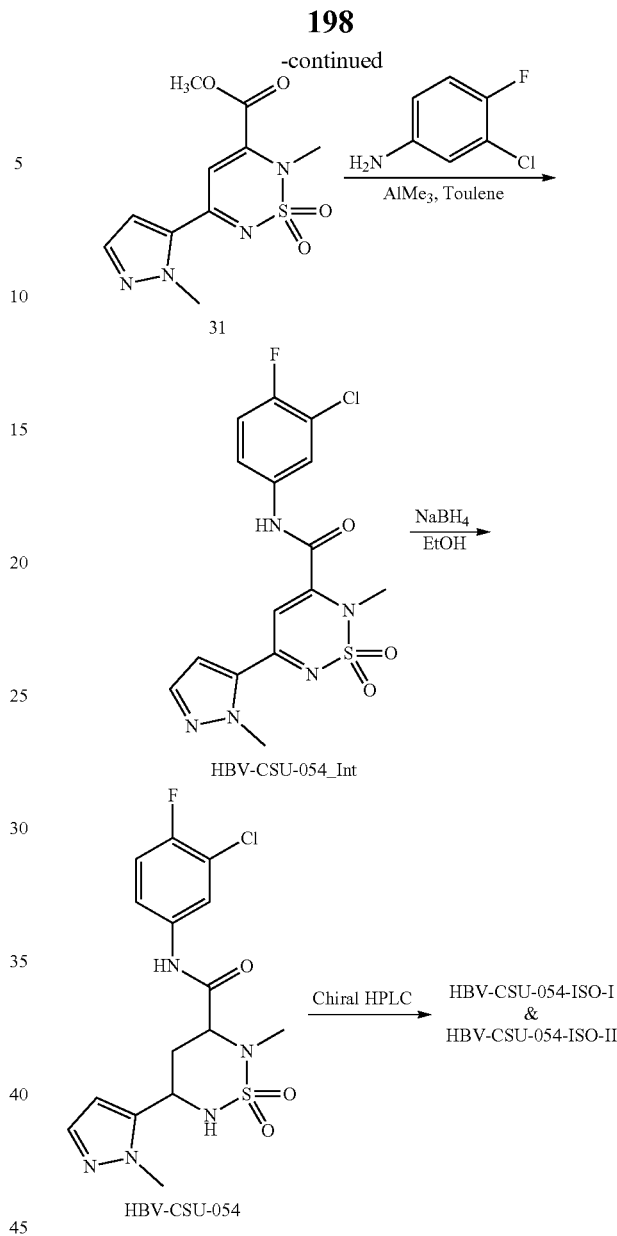

Synthesis of N-methoxy-N, 1-dimethyl-1H-pyrazole-5-carboxamide (27)

To a stirred solution of compound 26 (12 g, 95.23 mmol) in $CH_2Cl_2$ (600 mL) under inert atmosphere were added N,O-dimethylhydroxylamine hydrochloride (10.26 g, 104.76 mmol), EDCI.HCl (19.2 g, 100.00 mmol), DMAP (12.8 g, 104.91 mmol), and N-methylmorpholine (12.8 mL, 11.54 mmol) at 0° C., followed by warming to room temperature and stirring for 16 h. The reaction was monitored by TLC. After completion of the reaction, the reaction mixture was poured into ice-cold water and extracted using EtOAc. The combined organic extracts were dried over anhydrous sodium sulfate, filtered and concentrated in vacuo to obtain the crude. The crude was purified through silica gel flash column chromatography using 10% EtOAc/hexanes to afford compound 27 (12 g, 75%) as brown liquid. TLC: 20% EtOAc/hexanes (R$_f$: 0.8); $^1$H NMR (400 MHz, CDCl$_3$): δ 7.48 (d, J=2.0 Hz, 1H), 6.77 (d, J=2.0 Hz, 1H), 4.13 (s, 3H), 3.66 (s, 3H), 3.36 (s, 3H); LCMS Calculated for C$_7$H$_{11}$N$_3$O$_2$: 169.09; Observed: 169.9 (M+1)$^+$.

Synthesis of 1-(1-methyl-1H-pyrazol-5-yl) ethan-1-one (28)

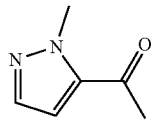

To a stirred solution of compound 27 (6 g, 35.50 mmol) in anhydrous diethyl ether (75 mL) under inert atmosphere was added methyl magnesium bromide (23.6 mL, 71.00 mmol, 3 M sol. in diethyl ether) dropwise for 15 min at −40° C., followed by warming to room temperature and stirring for 16 h. The reaction was monitored by TLC. After completion of the reaction, the reaction mixture was quenched with saturated ammonium chloride solution (50 mL) and extracted with diethyl ether. The combined organic extracts were dried over anhydrous sodium sulfate, filtered and concentrated in vacuo to afford compound 28 (5 g, crude) as pale brown liquid. TLC: 20% EtOAc/hexanes (R$_f$: 0.4); $^1$H NMR (400 MHz, CDCl$_3$): δ 7.46 (d, J=2.0 Hz, 1H), 6.83 (d, J=2.1 Hz, 1H), 4.16 (s, 3H), 2.52 (s, 3H); LCMS Calculated for C$_6$H$_8$N$_2$O: 124.06; Observed: 124.9 (M+1)$^+$.

Synthesis of methyl 4-(1-methyl-1H-pyrazol-5-yl)-2,4-dioxobutanoate (29)

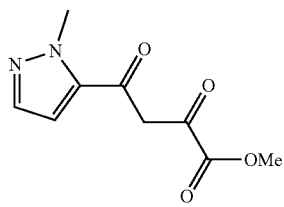

Title compound was synthesized using general method for the synthesis of 2,4-diketoester described above to afford 7 g (94%, over 2 steps, reaction scale is 5 g) as pale yellow solid. TLC: 20% EtOAc/hexanes (R$_f$: 0.3); $^1$H NMR (400 MHz, DMSO-d$_6$): δ 13.33 (br.s, 1H), 7.59 (d, J=1.8 Hz, 1H), 7.38 (br.s, 1H), 6.93 (s, 1H), 4.13 (s, 3H), 3.85 (s, 3H); LCMS Calculated for C$_9$H$_{10}$N$_2$O$_4$: 210.06; Observed: 210.9 (M)$^+$.

Synthesis of methyl 5-(1-methyl-1H-pyrazol-5-yl)-2H-1,2,6-thiadiazine-3-carboxylate 1,1-dioxide (30)

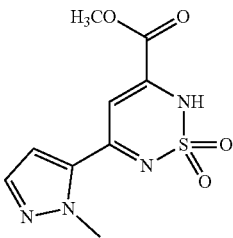 [SMILES: COC(=O)C1=CC(c2ccnn2C)=NS(=O)(=O)N1]

Title compound was synthesized using general method A for the synthesis of cyclic sulfonamide described above to afford 2 g (44%, reaction scale is 3.5 g) as pale yellow solid. TLC: 5% MeOH/CH$_2$Cl$_2$ (R$_f$: 0.2); $^1$H NMR (400 MHz, DMSO-d$_6$): δ 7.49 (d, J=2.0 Hz, 1H), 6.86 (d, J=2.0 Hz, 1H), 6.55 (s, 1H), 4.11 (s, 3H), 3.81 (s, 3H).

Synthesis of methyl 2-methyl-5-(1-methyl-1H-pyrazol-5-yl)-2H-1,2,6-thiadiazine-3-carboxylate 1,1-dioxide (31)

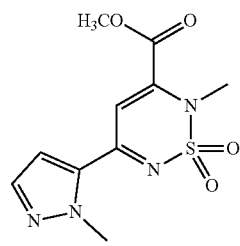 [SMILES: COC(=O)C1=CC(c2ccnn2C)=NS(=O)(=O)N1C]

Title compound was synthesized using general method A for alkylation described above to afford 50 mg (12%, reaction scale is 400 mg) as an off-white solid. TLC: 5% MeOH/CH$_2$Cl$_2$ (R$_f$: 0.4); $^1$H NMR (400 MHz, DMSO-d$_6$): δ 7.64 (d, J=2.1 Hz, 1H), 7.33 (d, J=2.3 Hz, 1H), 7.17 (s, 1H), 4.16 (s, 3H), 3.94 (s, 3H), 3.53 (s, 3H); LCMS Calculated for C$_{10}$H$_{12}$N$_4$O$_4$S: 284.06; Observed: 285.1 (M+1)$^+$.

Synthesis of N-(3-chloro-4-fluorophenyl)-2-methyl-5-(1-methyl-1H-pyrazol-5-yl)-2H-1,2,6-thiadiazine-3-carboxamide 1,1-dioxide (HBV-CSU-054_Int)

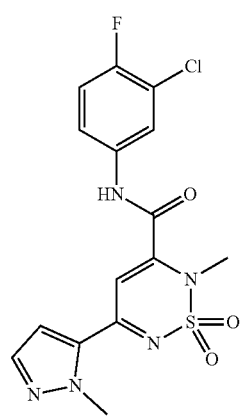

HBV-CSU-054_Int

The above titled compound has been synthesized by following the general procedure (Method A) described above for amidation by using corresponding 31 and corresponding amine (see Table 1 for analytical data).

Cis-N-(3-Chloro-4-fluorophenyl)-2-methyl-5-(1-methyl-1H-pyrazol-5-yl)-1,2,6-thiadiazinane-3-carboxamide 1,1-dioxide (HBV-CSU-054, HBV-CSU-054-ISO-I & HBV-CSU-054-ISO-II)

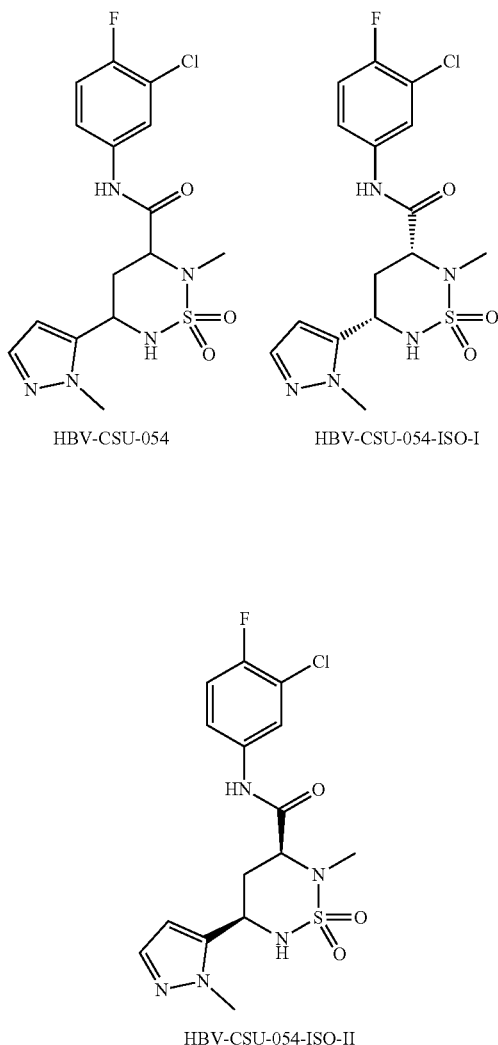

The above titled compounds have been synthesized by following the general procedure described above for reduction by using corresponding HBV-CSU-054_Int (see Table 2 for analytical data).

Scheme 10

Synthetic scheme for Cis-N-(3-Chloro-4-fluorophenyl)-5-(isoxazol-3-yl)-2-methyl-1,2,6-thiadiazinane-3-carboxamide 1,1-dioxide (HBV-CSU-055, HBV-CSU-055-ISO-I & HBV-CSU-055-II)

Scheme 10:

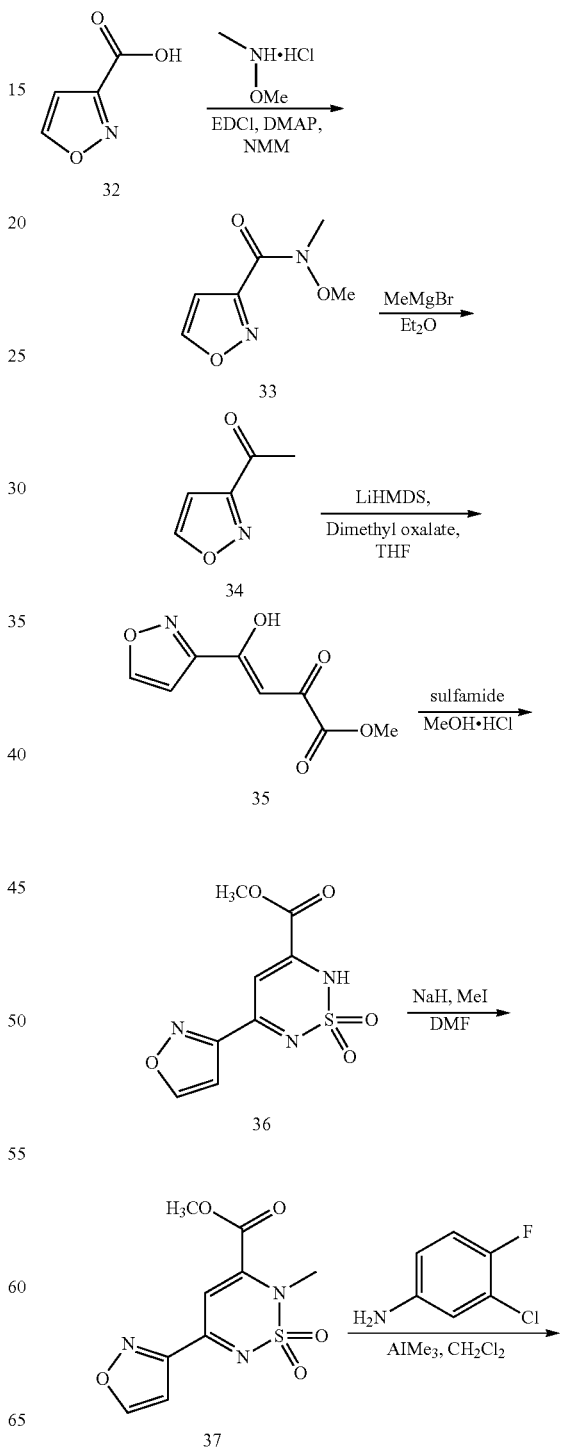

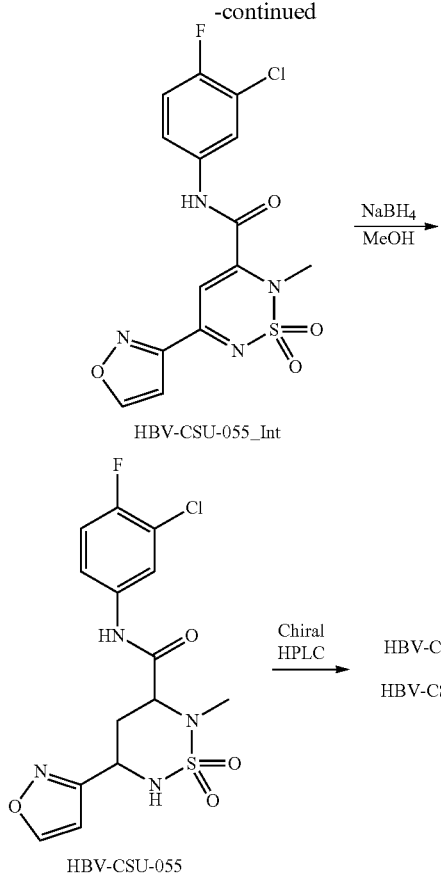

HBV-CSU-055_Int

HBV-CSU-055-ISO-I
+
HBV-CSU-055-ISO-II

HBV-CSU-055

Synthesis of
N-methoxy-N-methylisoxazole-3-carboxamide (33)

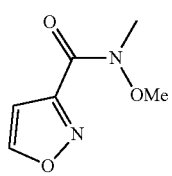

To a stirred solution isoxazole-3-carboxylic acid 32 (7 g, 61.94 mmol) in CH$_2$Cl$_2$ (200 mL) under inert atmosphere were added N, O-dimethylhydroxylamine hydrochloride (6.64 g, 68.14 mmol), EDCI.HCl (13 g, 68.14 mmol), DMAP (7.6 g, 61.94 mmol), and N-methylmorpholine (9.5 mL, 92.92 mmol) at 0° C., followed by warming to room temperature and stirred for 16 h. The reaction was monitored by TLC. After completion of the reaction, the reaction mixture was poured into ice-cold water, extracted with CH$_2$Cl$_2$. The combined organic extracts were washed with 2 N HCl, dried over anhydrous sodium sulfate, filtered and concentrated in vacuo to obtain the crude. The crude was purified through silica gel column chromatography using 3% MeOH/CH$_2$Cl$_2$ to afford compound 33 (6 g, 63%) as brown liquid. TLC: 5% MeOH/CH$_2$Cl$_2$ (R$_f$: 0.8); $^1$H NMR (400 MHz, DMSO-d$_6$): δ 9.08 (d, J=1.6 Hz, 1H), 6.86 (d, J=1.3 Hz, 1H), 3.68 (s, 3H), 3.31 (s, 3H).

Synthesis of 1-(isoxazol-3-yl) ethan-1-one (34)

To a stirred solution of compound 33 (6 g, 38.46 mmol) in dry diethyl ether (100 mL) under inert atmosphere was added methyl magnesium bromide (12.8 mL, 38.46 mmol, 3 M sol. in diethyl ether) dropwise for 10 min at −40° C., followed by warming to 0° C. and stirred for 2 h. The reaction was monitored by TLC. After completion of the reaction, the reaction mixture was quenched with saturated ammonium chloride solution at 0° C. and stirred for 15 min, then extracted with diethyl ether. The combined organic extracts were dried over anhydrous sodium sulfate, filtered and concentrated in vacuo to afford compound 34 (3 g, 70%) as pale brown liquid. TLC: 20% EtOAc/hexanes (R$_f$: 0.8); $^1$H NMR (400 MHz, DMSO-d$_6$): δ 9.13 (d, J=1.8 Hz, 1H), 6.92 (d, J=1.8 Hz, 1H), 2.60 (s, 3H).

Synthesis of methyl (E/Z)-4-hydroxy-4-(isoxazol-3-yl)-2-oxobut-3-enoate (35)

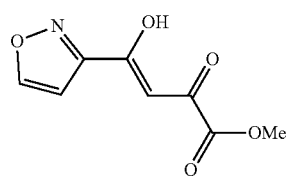 [SMILES: COC(=O)C(=O)/C=C(\O)c1ccon1]

Title compound was synthesized using general method for the synthesis of 2,4-diketoester described above to afford 2 g (38, reaction scale is 3 g) as off-white sticky solid. TLC: 5% MeOH/CH$_2$Cl$_2$ (R$_f$: 0.4); $^1$H NMR (400 MHz, DMSO-d$_6$): δ 9.19 (d, J=1.5 Hz, 1H), 7.08 (s, 1H), 5.24 (br. s, 2H), 3.85 (s, 3H).

Synthesis of methyl 5-(isoxazol-3-yl)-2H-1,2,6-thiadiazine-3-carboxylate 1,1-dioxide (36)

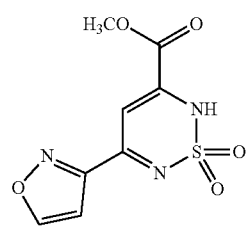 [SMILES: COC(=O)C1=CC(c2ccon2)=NS(=O)(=O)N1]

Title compound was synthesized using general method A for the synthesis of cyclic sulfonamide described above to afford 1.2 g (crude, reaction scale is 1 g) as off-white solid. TLC: 5% MeOH/CH$_2$Cl$_2$ (R$_f$: 0.4). The crude material was used as such in the next reaction without further characterization.

Synthesis of methyl 5-(isoxazol-3-yl)-2-methyl-2H-1,2,6-thiadiazine-3-carboxylate 1,1-dioxide (37)

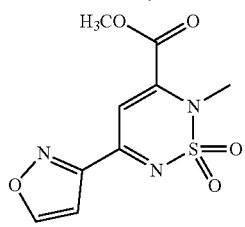

Title compound was synthesized using general method A for alkylation described above to afford 350 mg (26%, reaction scale is 1.2 g) as an off-white solid. TLC: 10% MeOH/CH$_2$Cl$_2$ (R$_f$: 0.4); $^1$H NMR (500 MHz, DMSO-d$_6$): δ 9.26 (s, 1H), 7.27 (s, 1H), 7.21 (s, 1H), 3.94 (s, 3H), 3.60 (s, 3H).

Synthesis of N-(3-chloro-4-fluorophenyl)-5-(isoxazol-3-yl)-2-methyl-2H-1,2,6-thiadiazine-3-carboxamide 1,1-dioxide (HBV-CSU-055_Int)

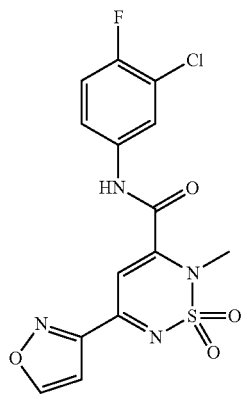

HBV-CSU-055_Int

The above titled compound has been synthesized by following the general procedure (Method A) described above for amidation by using corresponding 37 and corresponding amine (see Table 1 for analytical data).

Cis-N-(3-chloro-4-fluorophenyl)-5-(isoxazol-3-yl)-2-methyl-1,2,6-thiadiazinane-3-carboxamide 1,1-dioxide (HBV-CSU-055, HBV-CSU-055-ISO-I & HBV-CSU-055-II)

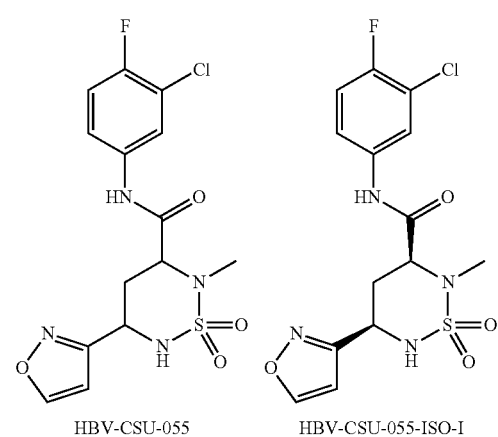

HBV-CSU-055   HBV-CSU-055-ISO-I

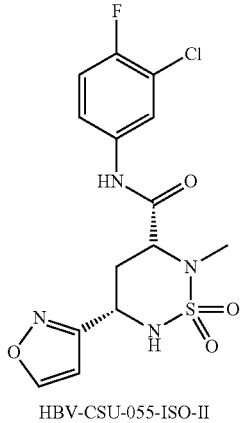

HBV-CSU-055-ISO-II

The above titled compounds have been synthesized by following the general procedure described above for reduction by using corresponding HBV-CSU-055_Int (see Table 2 for analytical data).

Scheme 11

Synthetic scheme for Cis-N-(3-chloro-4-fluorophenyl)-5-(isothiazol-3-yl)-2-methyl-1,2,6-thiadiazinane-3-carboxamide 1,1-dioxide (HBV-CSU-056, HBV-CSU-056-ISO-I & HBV-CSU-056-ISO-II)

Scheme 11:

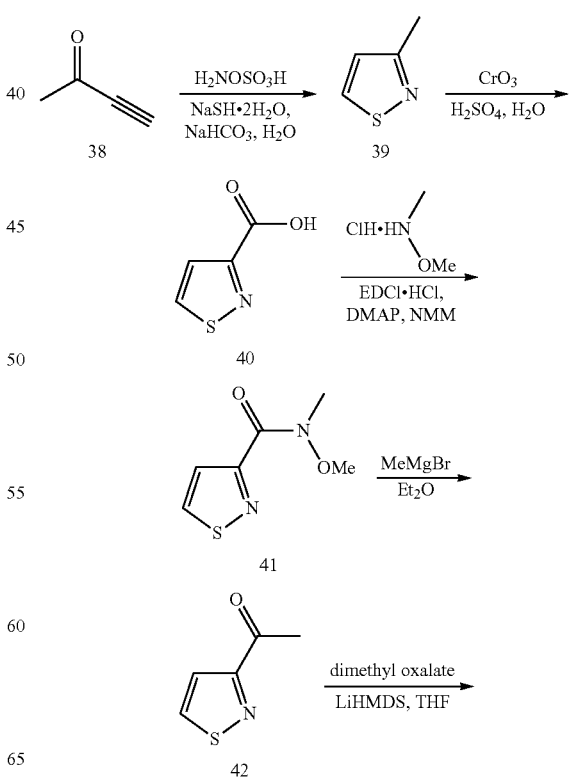

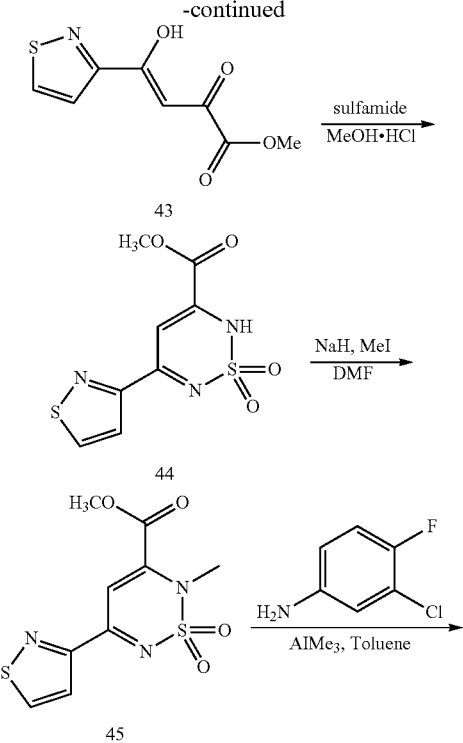

Synthesis of 3-methylisothiazole (39)

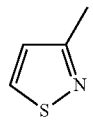

To a stirred solution of but-3-yn-2-one 38 (17 g, 249.70 mmol) in H$_2$O (100 mL) was added hydroxylamine-O-sulfonic acid (29.1 g, 257.23 mmol) at 0° C. and stirred for 30 min. To this was added sodium bicarbonate (23.72 g, 281.9 mmol) portion wise for 20 min at 0° C., followed by dropwise addition of sodium hydrogen sulfide dihydrate (26 g, 282.2 mmol) in H$_2$O (170 mL) at 0° C. for 15 min, then warming to room temperature and stirring for 16 h. The reaction was monitored by TLC. After completion of the reaction, the reaction mixture was diluted with water and extracted with diethyl ether. The combined organic extracts were dried over anhydrous sodium sulfate and concentrated in vacuo at 20° C. to afford compound 39 (10 g, 40%) as colorless syrup. TLC: 15% EtOAc/hexanes (R$_f$: 0.5); $^1$H-NMR (DMSO-d$_6$, 400 MHz): δ 8.96 (d, J=4.5 Hz, 1H), 7.20 (d, J=4.5 Hz, 1H), 2.45 (s, 3H).

Synthesis of isothiazole-3-carboxylic acid (40)

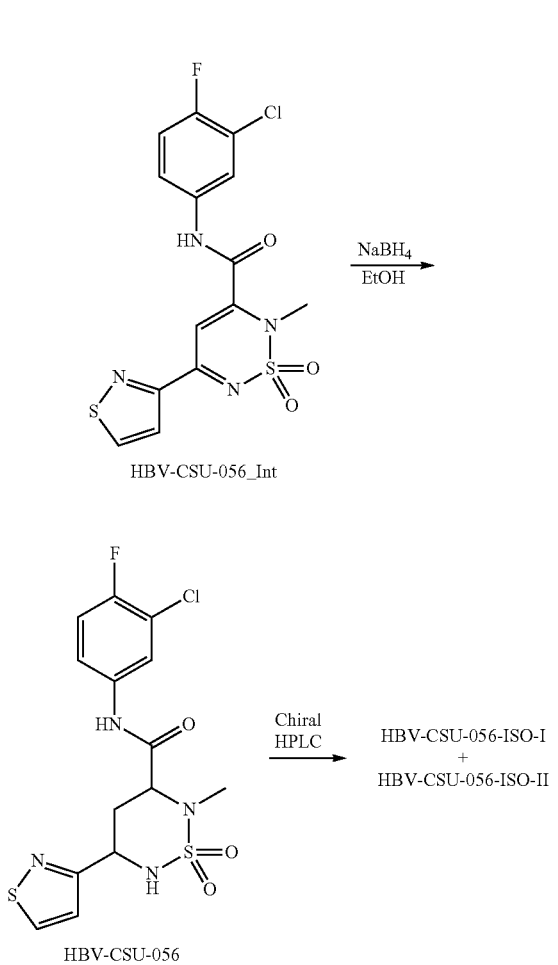

To a stirred solution of compound 39 (10 g, 100.85 mmol) in concentrated sulfuric acid (300 mL) under inert atmosphere was added chromium (VI) oxide (30.25 g, 302.57 mmol) portion wise at 0° C., followed by warming to room temperature and stirring for 16 h. The reaction was monitored by TLC. After completion of the reaction, the reaction mixture was quenched with ice-cold water (3 L) slowly and extracted with diethyl ether (10×600 mL). The combined organic extracts were dried over anhydrous sodium sulfate, filtered and concentrated in vacuo to afford crude compound 40 (3 g, 23%) as white solid. TLC: 20% EtOAc/hexanes (R$_f$: 0.1). $^1$H-NMR (DMSO-d$_6$, 400 MHz): δ 10.95 (br.s, 1H), 9.16 (d, J=4.6 Hz, 1H), 7.80 (d, J=4.6 Hz, 1H); LCMS Calculated for C$_4$H$_3$NO$_2$S: 128.99; Observed: 130.4 (M+1)$^+$.

Synthesis of N-methoxy-N-methylisothiazole-3-carboxamide (41)

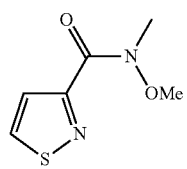

To a stirred solution compound 40 (3 g, 23.25 mmol) in CH$_2$Cl$_2$ (60 mL) under inert atmosphere were added EDCI.HCl (4.9 g, 25.58 mmol), DMAP (2.8 g, 23.25 mmol), N-methylmorpholine (7.65 mL, 69.76 mmol) and N, O-dimethylhydroxylamine hydrochloride (2.72 g, 27.90 mmol) at 0° C., followed by warming to room temperature and stirring for 16 h. The reaction was monitored by TLC. After completion of the reaction, the reaction mixture was diluted with ice-cold water and extracted with CH$_2$Cl$_2$. The combined organic extracts were dried over anhydrous sodium sulfate, filtered and concentrated in vacuo to obtain the crude. The crude was purified through silica gel flash column chromatography using 40-45% EtOAc/hexanes to afford compound 41 (2.5 g, 63%) as brown syrup. TLC: 40% EtOAc/hexanes (R$_f$: 0.5); $^1$H NMR (400 MHz, DMSO-d$_6$): δ 9.15 (d, J=4.8 Hz, 1H), 7.63 (d, J=4.4 Hz, 1H), 3.69 (s, 3H), 3.33 (s, 3H); LCMS Calculated for C$_6$H$_7$NOS: 141.02; Observed: 142.0 (M+1)$^+$. LC-MS: 98.67%; 172.9 (M+1)$^+$.

Synthesis of 1-(isothiazol-3-yl) ethan-1-one (42)

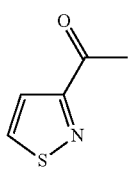

To a stirred solution of compound 41 (2.5 g, 14.53 mmol) in anhydrous diethyl ether (25 mL) under inert atmosphere was added methyl magnesium bromide (58 mL, 58.13 mmol, 3 M sol. in diethyl ether) dropwise for 20 min at −40° C., followed by warming to 0° C. and stirring for 2 h. The reaction was monitored by TLC. After completion of the reaction, the reaction mixture was quenched with saturated ammonium chloride solution at 0° C. and extracted with diethyl ether. The combined organic extracts were dried over anhydrous sodium sulfate, filtered and concentrated in vacuo below 20° C. to afford crude compound 42 (1.8 g, 98%) as yellow liquid. TLC: 30% EtOAc/hexanes (R$_f$: 0.8); $^1$H NMR (500 MHz, DMSO-d$_6$): δ 9.15 (d, J=4.5 Hz, 1H), 7.80 (d, J=4.5 Hz, 1H), 2.62 (s, 3H); LCMS Calculated for C$_5$H$_5$NOS: 127.01; Observed: 128.4 (M+1)$^+$.

Synthesis of methyl (E/Z)-4-hydroxy-4-(isothiazol-3-yl)-2-oxobut-3-enoate (43)

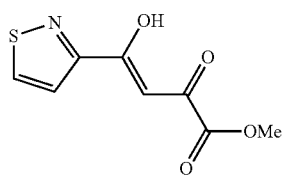 [SMILES: COC(=O)C(=O)/C=C(\O)c1ccsn1]

Title compound was synthesized using general method for the synthesis of 2,4-diketoester described above to afford 1.5 g (50%, reaction scale is 1.8 g) as yellow solid. TLC: 5% MeOH/CH$_2$Cl$_2$ (R$_f$: 0.4); $^1$H NMR (400 MHz, DMSO-d$_6$): δ 9.24 (d, J=4.6 Hz, 1H), 7.95 (d, J=4.4 Hz, 1H), 7.27-7.24 (m, 1H), 3.86 (s, 3H); LCMS Calculated for C$_8$H$_7$NO$_4$S: 213.01; Observed: 214.2 (M+1)$^+$.

Synthesis of methyl 5-(isothiazol-3-yl)-2H-1,2,6-thiadiazine-3-carboxylate 1,1-dioxide (44)

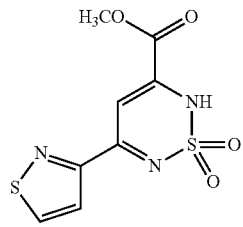 [SMILES: COC(=O)C1=CC(c2ccsn2)=NS(=O)(=O)N1]

Title compound was synthesized using general method A for the synthesis of cyclic sulfonamide described above to afford 1.2 g (63%, reaction scale is 1.5 g) as off-white solid. TLC: 5% MeOH/CH$_2$Cl$_2$ (R$_f$: 0.1); $^1$H NMR (400 MHz, DMSO-d$_6$): δ 9.16 (d, J=4.6 Hz, 1H), 7.90 (d, J=4.6 Hz, 1H), 7.06 (s, 1H), 3.83 (s, 3H); LCMS Calculated for C$_8$H$_7$N$_3$O$_4$S$_2$: 272.99; LCMS observed: 271.9 (M−1)$^-$.

Synthesis of methyl 5-(isothiazol-3-yl)-2-methyl-2H-1,2,6-thiadiazine-3-carboxylate 1,1-dioxide (45)

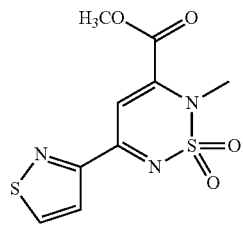 [SMILES: COC(=O)C1=CC(c2ccsn2)=NS(=O)(=O)N1C]

Title compound was synthesized using general method A for alkylation described above to afford 450 mg (61%, reaction scale is 700 mg) as an off-white solid. TLC: 40% EtOAc/hexanes (R$_f$: 0.6); 1H NMR (400 MHz, DMSO-d$_6$): δ 9.28 (d, J=4.8 Hz, 1H), 8.04 (d, J=4.8 Hz, 1H), 7.50 (s, 1H), 3.94 (s, 3H), 3.58 (s, 3H).

Synthesis of N-(3-chloro-4-fluorophenyl)-5-(isothiazol-3-yl)-2-methyl-2H-1,2,6-thiadiazine-3-carboxamide 1,1-dioxide (HBV-CSU-056_Int)

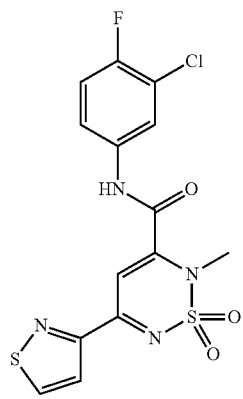

HBV-CSU-056_Int

The above titled compound has been synthesized by following the general procedure (Method A) described above for amidation by using corresponding 45 and corresponding amine (see Table 1 for analytical data).

Cis-N-(3-chloro-4-fluorophenyl)-5-(isothiazol-3-yl)-2-methyl-1,2,6-thiadiazinane-3-carboxamide 1,1-dioxide (HBV-CSU-056, HBV-CSU-056-ISO-I & HBV-CSU-056-ISO-II)

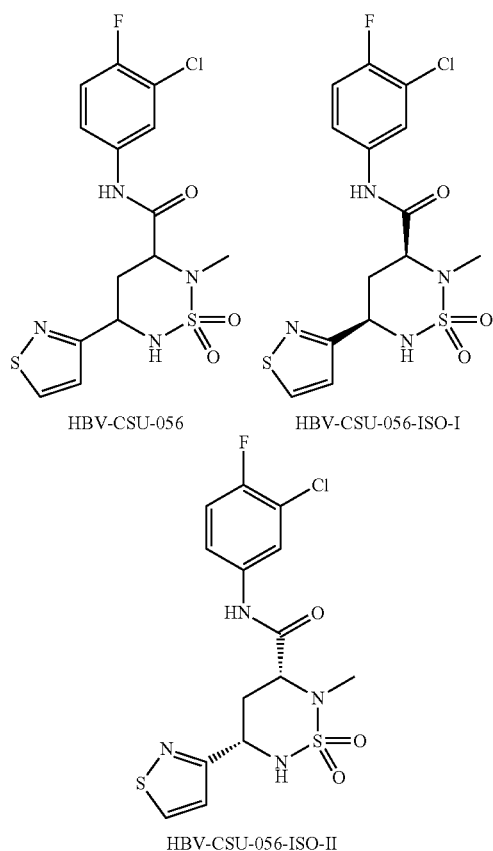

HBV-CSU-056

HBV-CSU-056-ISO-I

HBV-CSU-056-ISO-II

The above titled compounds have been synthesized by following the general procedure described above for reduction by using corresponding HBV-CSU-055_Int (see Table 2 for analytical data).

Scheme 12

Synthetic scheme for Cis-N-(3-chloro-4-fluorophenyl)-5-(isothiazol-5-yl)-2-methyl-1,2,6-thiadiazinane-3-carboxamide 1,1-dioxide (HBV-CSU-057, HBV-CSU-057-ISO-I & HBV-CSU-057-ISO-II)

Scheme 12:

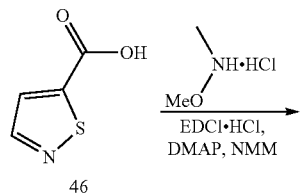

46

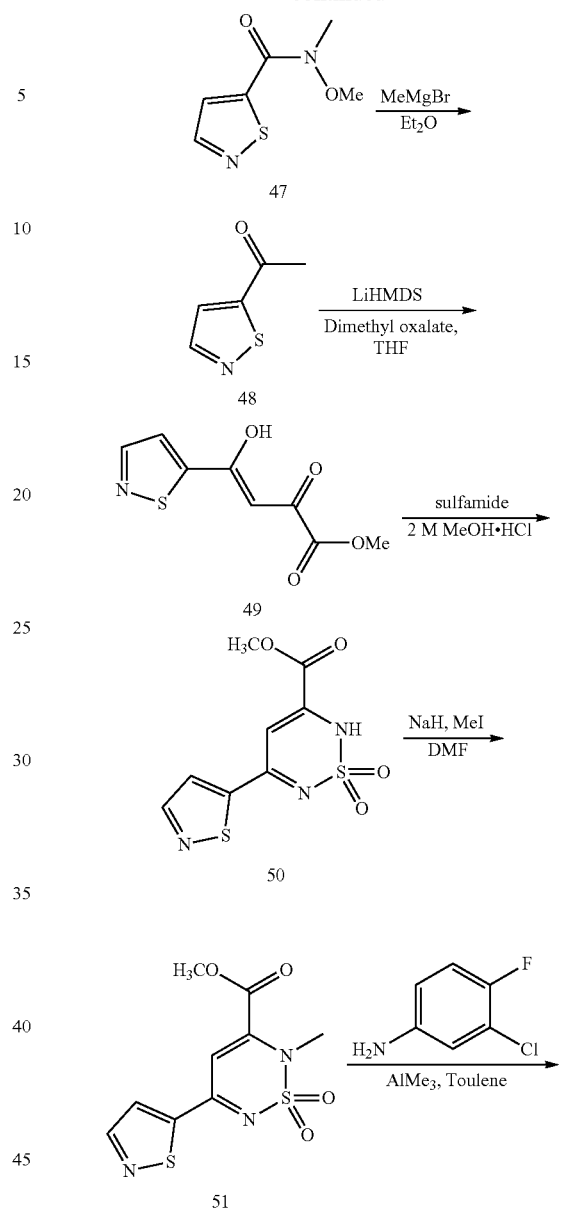

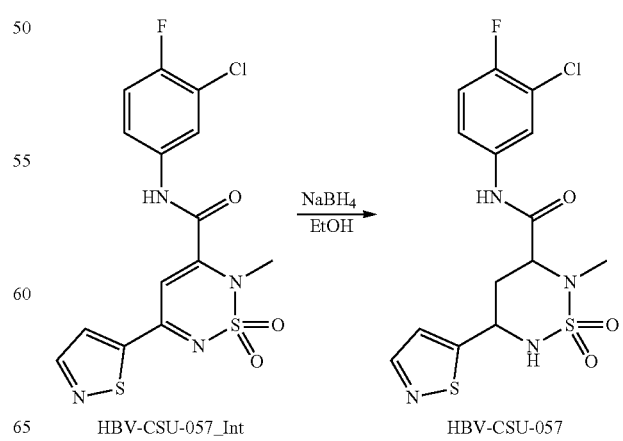

HBV-CSU-057_Int

HBV-CSU-057

Synthesis of N-methoxy-N-methylisothiazole-5-carboxamide (47)

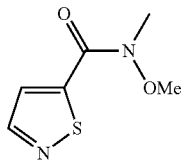

To a stirred solution isothiazole-5-carboxylic acid 46 (1.75 g, 13.56 mmol) in CH$_2$Cl$_2$ (50 mL) under inert atmosphere were added N, O-dimethylhydroxylamine (1.45 g, 14.92 mmol), EDCI.HCl (2.85 g, 14.92 mmol), DMAP (1.66 g, 13.56 mmol) and N-methylmorpholine (4.1 mL, 40.69 mmol) at 0° C., followed by warming to room temperature and stirring for 16 h. The reaction was monitored by TLC. After completion of the reaction, the reaction mixture was poured into ice-cold water, extracted with CH$_2$Cl$_2$. The combined organic extracts were dried over sodium sulfate, filtered and concentrated in vacuo to obtain the crude. The crude was purified through silica gel column chromatography using 2% MeOH/CH$_2$Cl$_2$ to afford compound 47 (1.2 g, 52%) as brown syrup. TLC: 5% MeOH/CH$_2$Cl$_2$ (R$_f$: 0.2); $^1$H NMR (400 MHz, DMSO-d$_6$): δ 8.64 (d, J=1.8 Hz, 1H), 7.96 (d, J=1.8 Hz, 1H), 3.82 (s, 3H), 3.33 (s, 3H); LCMS Calculated for C$_6$H$_8$N$_2$O$_2$S: 172.03; Observed: 173.1 (M+1)$^+$.

Synthesis of 1-(isothiazol-5-yl) ethan-1-one (48)

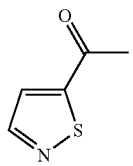

To a stirred solution of compound 47 (1.2 g, 6.97 mmol) in anhydrous diethyl ether (30 mL) under inert atmosphere was added methyl magnesium bromide (6.97 mL, 20.93 mmol, 3 M sol. in diethyl ether) dropwise for 10 min at −40° C., followed by warming to 0° C. and stirring for 2 h. The reaction was monitored by TLC. After completion of the reaction, the reaction mixture was quenched with saturated ammonium chloride solution and extracted with diethyl ether. The combined organic extracts were dried over sodium sulfate, filtered and concentrated in vacuo to afford compound 48 (800 mg, crude) as yellow liquid. TLC: 20% EtOAc/hexanes (R$_f$: 0.8); $^1$H NMR (400 MHz, DMSO-d$_6$): δ 8.75 (d, J=1.9 Hz, 1H), 8.04 (d, J=1.8 Hz, 1H), 2.64 (s, 3H).

Synthesis of methyl (E/Z)-4-hydroxy-4-(isothiazol-5-yl)-2-oxobut-3-enoate (49)

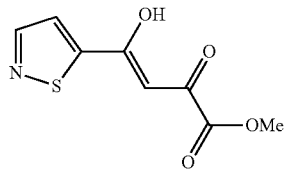 [SMILES: COC(=O)C(=O)/C=C(\O)c1ccns1]

Title compound was synthesized using general method for the synthesis of 2,4-diketoester described above to afford 600 mg (45%, reaction scale is 800 mg) as a yellow solid. TLC: 5% MeOH/CH$_2$Cl$_2$(R$_f$: 0.4); $^1$H NMR (400 MHz, DMSO-d$_6$): δ 8.78 (d, J=1.9 Hz, 1H), 8.29 (br.s, 1H), 6.98 (br.s, 1H), 3.86 (s, 3H).

Synthesis of methyl 5-(isothiazol-5-yl)-2H-1,2,6-thiadiazine-3-carboxylate 1,1-dioxide (50)

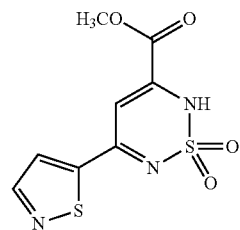 [SMILES: COC(=O)C1=CC(c2ccns2)=NS(=O)(=O)N1]

Title compound was synthesized using general method A for the synthesis of cyclic sulfonamide described above to afford 300 mg (36%, reaction scale is 650 mg) as yellow solid. TLC: 10% MeOH/CH$_2$Cl$_2$ (R$_f$: 0.1); $^1$H NMR (400 MHz, DMSO-d$_6$): δ 8.59 (d, J=1.9 Hz, 1H), 7.93 (d, J=1.9 Hz, 1H), 6.73 (br.s, 1H), 6.60 (s, 1H), 3.80 (s, 3H); LCMS Calculated for C$_{13}$H$_{10}$N$_4$O$_4$S$_2$: 272.99; LCMS observed: 274.2 (M+1)$^+$.

Synthesis of methyl 5-(isothiazol-5-yl)-2H-1,2,6-thiadiazine-3-carboxylate 1,1-dioxide (51)

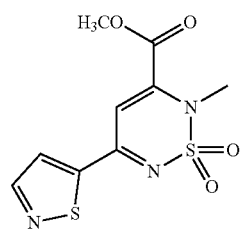 [SMILES: COC(=O)C1=CC(c2ccns2)=NS(=O)(=O)N1C]

Title compound was synthesized using general method A for alkylation described above to afford 85 mg (32%, reaction scale is 250 mg) as an off-white solid. TLC: 30% EtOAc/hexanes (R$_f$: 0.48; $^1$H NMR (400 MHz, DMSO-d$_6$): δ 8.80 (d, J=1.9 Hz, 1H), 8.37 (d, J=1.9 Hz, 1H), 7.37 (s, 1H), 3.96 (s, 3H), 3.58 (s, 3H); LCMS Calculated for C$_{13}$H$_{10}$N$_4$O$_4$S$_2$: 287.00; LCMS observed: 288.1 (M+1)$^+$.

215

Synthesis of N-(3-chloro-4-fluorophenyl)-5-(isothiazol-5-yl)-2-methyl-2H-1,2,6-thiadiazine-3-carboxamide 1,1-dioxide (HBV-CSU-057_Int)

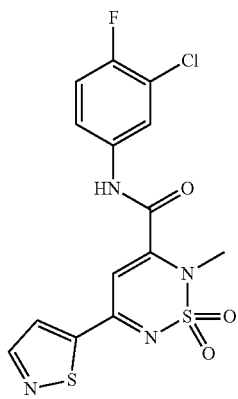 [SMILES: CN1C(C(=O)Nc2ccc(F)c(Cl)c2)=CC(c2ccns2)=NS1(=O)=O]

The above titled compound has been synthesized by following the general procedure (Method A) described above for amidation by using corresponding 51 and corresponding amine (see Table 1 for analytical data).

Cis-N-(3-chloro-4-fluorophenyl)-5-(isothiazol-5-yl)-2-methyl-1,2,6-thiadiazinane-3-carboxamide 1,1-dioxide (HBV-CSU-057)

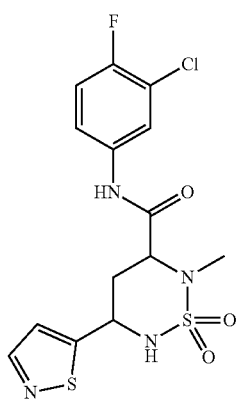 [SMILES: CN1C(C(=O)Nc2ccc(F)c(Cl)c2)CC(c2ccns2)NS1(=O)=O]

The above titled compounds have been synthesized by following the general procedure described above for reduction by using corresponding HBV-CSU-057_Int (see Table 2 for analytical data).

216

Scheme 13

Synthesis of Cis-N-(3-chloro-4-fluorophenyl)-2-(2-(methylsulfonyl)ethyl)-5-(thiazol-2-yl)-1,2,6-thiadiazinane-3-carboxamide 1,1-dioxide (HBV-CSU-73, HBV-CSU-73-ISO-I & HBV-CSU-73-ISO-II)

Scheme 13:

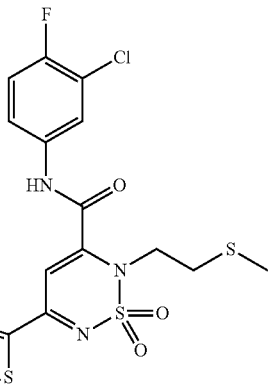

HBV-CSU-109_Int $\xrightarrow{\text{RuCl}_3, \text{NaIO}_4}{\text{DCE: CH}_3\text{CN: H}_2\text{O}}$

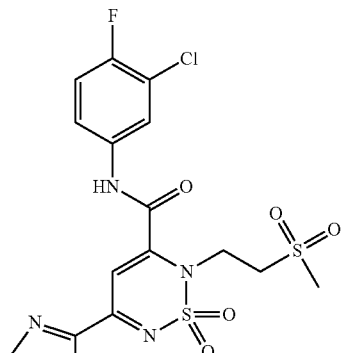

HBV-CSU-073_Int $\xrightarrow{\text{NaBH}_4}{\text{EtOH}}$

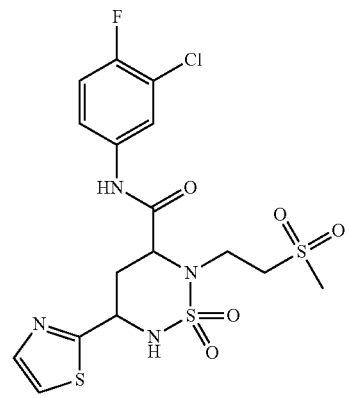

HBV-CSU-073

$\xrightarrow{\text{Chiral HPLC}}$

HBV-CSU-073-ISO-I
+
HBV-CSU-073-ISO-II

217

Synthesis of N-(3-chloro-4-fluorophenyl)-2-(2-(methylsulfonyl)ethyl)-5-(thiazol-2-yl)-2H-1,2,6-thiadiazine-3-carboxamide 1,1-dioxide (HBV-CSU-073_Int)

To a stirred solution of HBV-CSU-109_Int (1 g, 2.17 mmol) in 1,2-dichloro ethane:CH$_3$CN:H$_2$O (1:1:2, 20 mL) were added sodium metaperiodate (1.3 g, 6.07 mmol) and ruthenium chloride (22.54 mg, 0.10 mmol) at room temperature and stirred for 3 h. The reaction was monitored by TLC. After completion, the volatiles were removed in vacuo. The residue was diluted with water and extracted using EtOAc. The combined organic extracts were dried over anhydrous sodium sulfate, filtered and concentrated in vacuo to obtain the crude. The crude was purified through silica gel column chromatography using 1% MeOH/CH$_2$Cl$_2$. The obtained solid was washed with diethyl ether and dried in vacuo to afford HBV-CSU-073_Int (560 mg, 53%) as an off-white solid. TLC: 5% MeOH/CH$_2$Cl$_2$ (R$_f$: 0.5) (see Table 1 for analytical data).

Cis-N-(3-Chloro-4-fluorophenyl)-2-(2-(methylsulfonyl)ethyl)-5-(thiazol-2-yl)-1,2,6-thiadiazinane-3-carboxamide 1,1-dioxide (HBV-CSU-073

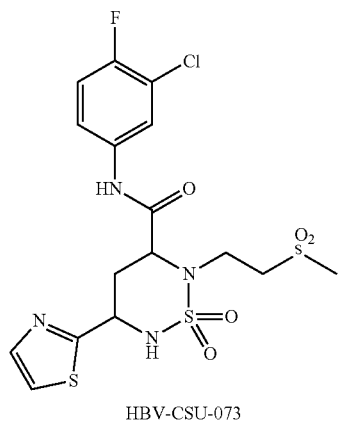 [SMILES: CS(=O)(=O)CCN1C(C(=O)Nc2ccc(F)c(Cl)c2)CC(c2nccs2)NS1(=O)=O ; "HBV-CSU-073"]

HBV-CSU-073

The above titled compound has been synthesized by following the general procedure described above for reduction by using corresponding HBV-CSU-073_Int (see Table 2 for analytical data).

218

Scheme 14

Synthesis of Cis-N-(3-Chloro-4-fluorophenyl)-2-(2-(dimethylamino)ethyl)-5-(thiazol-2-yl)-1,2,6-thiadiazinane-3-carboxamide 1,1-dioxide (HBV-CSU-074) & Cis-N-(3-Chloro-4-fluorophenyl)-5-(thiazol-2-yl)-1,2,6-thiadiazinane-3-carboxamide 1,1-dioxide (HBV-CSU-096)

Scheme 14:

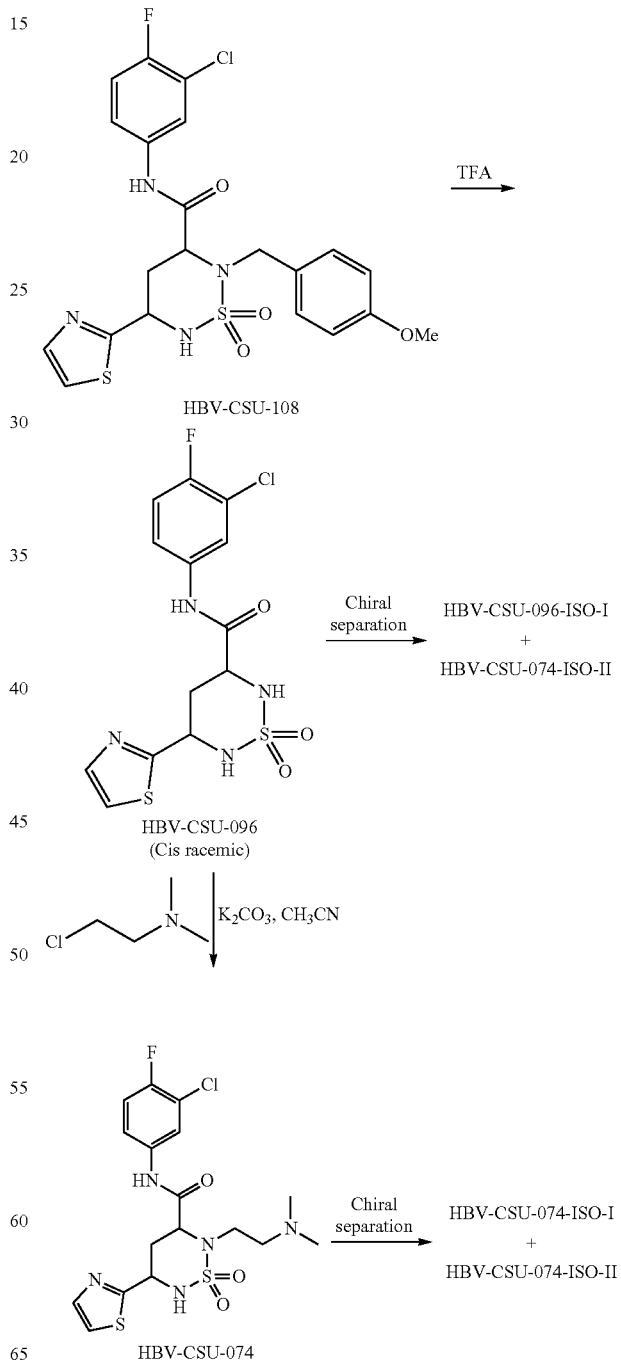

219

Cis-N-(3-Chloro-4-fluorophenyl)-2-(2-(dimethyl-amino)ethyl)-5-(thiazol-2-yl)-1,2,6-thiadiazinane-3-carboxamide 1,1-dioxide (HBV-CSU-074)

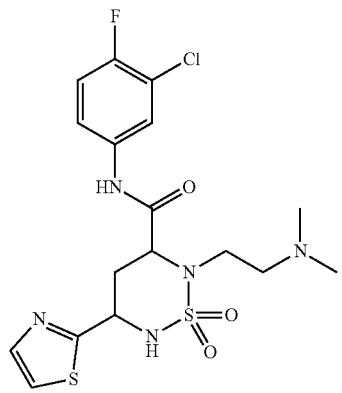 [SMILES: CN(C)CCN1C(C(=O)Nc2ccc(F)c(Cl)c2)CC(c2nccs2)NS1(=O)=O]

To a stirred solution of HBV-CSU-096 (20 mg, 0.051 mmol.) in $CH_3CN$ (0.5 mL) at 0° C., $K_2CO_3$ (14 mg, 0.102 mmol) and 2-chloro-N,N-dimethylethan-1-amine hydrochloride (7 mg, 0.051 mmol) were added. The reaction mixture was stirred at room temperature for 12 h. The progress of the reaction was monitored by TLC and LCMS. After completion, the reaction mixture was diluted with ice cold water. The obtained solid was filtered and the filtrate was extracted with ethyl acetate. The combined organic layers were washed with water and brine; dried over anhydrous sodium sulphate and concentrated in vacuo. The crude compound was purified by silica gel column chromatography to afford the compound HBV-CSU-074 (see Table 2 for analytical data).

Cis-N-(3-Chloro-4-fluorophenyl)-5-(thiazol-2-yl)-1,2,6-thiadiazinane-3-carboxamide 1,1-dioxide (HBV-CSU-096, HBV-CSU-096-ISO-I & HBV-CSU-096-ISO-II)

220

-continued

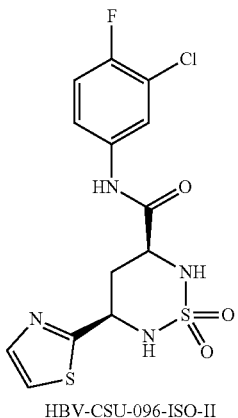

HBV-CSU-096-ISO-II

To a stirred solution of compound HBV-CSU-108 (0.14 g, 0.274 mmol) in DCM (1 mL) at 0° C., TFA (5 mL) was added and stirred at room temperature for 30 h. The progress of the reaction was monitored by TLC and LCMS. After completion, the reaction mixture was concentrated under reduced pressure. The crude compound was purified by silica gel column chromatography to afford the desired compound as HBV-CSU-096 (80 mg, 76%) as an off white solid. TLC: 40% EtOAc/hexanes ($R_f$: 0.3) (see Table 2 for analytical data).

Scheme 15

Synthesis of Cis-N-(3-Chloro-4-fluorophenyl)-2-(3-hydroxypropyl)-5-(thiazol-2-yl)-1,2,6-thiadiazinane-3-carboxamide 1,1-dioxide (HBV-CSU-078, HBV-CSU-078-ISO-I & HBV-CSU-078-ISO-II)

Scheme 15:

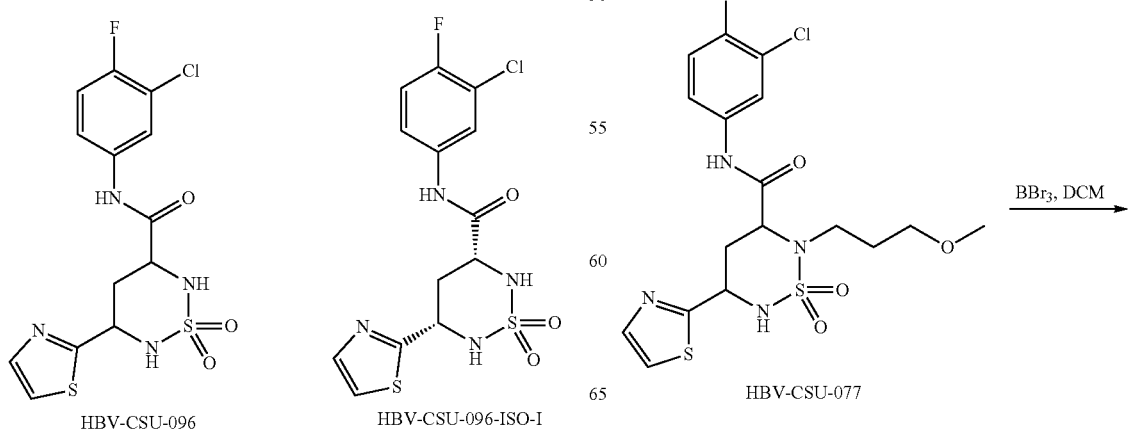

221
-continued

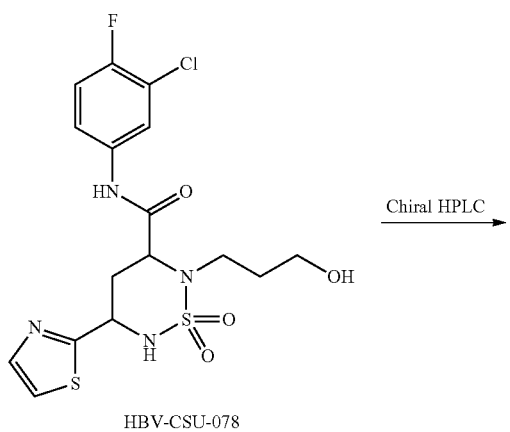

HBV-CSU-078

→ Chiral HPLC →

HBV-CSU-078-Isomer I
+
HBV-CSU-078-Isomer II

To a stirred solution of compound HBV-CSU-077 (50 mg, 0.108 mmol) in DCM (5 mL) at −40° C., BBr$_3$ (0.054 g, 0.216 mmol) was added and stirred at room temperature for 4 h. The progress of the reaction was monitored by TLC and LCMS. After completion, the reaction mixture was quenched with sat. NaHCO$_3$ solution and extracted with DCM. The combined organic layers were dried over anhydrous sodium sulphate and concentrated under reduced pressure. The crude compound was purified by silica gel column chromatography to afford the desired compound as HBV-CSU-078 (0.042 g, 88%) as a white solid TLC: 40% EtOAc/hexanes (R$_f$: 0.1) (see Table 2 for analytical data).

Scheme 16

Synthesis of Cis-N-(3-chloro-4-fluorophenyl)-2-(2-(methylsulfonyl)ethyl)-5-(thiazol-2-yl)-1,2,6-thiadiazinane-3-carboxamide 1,1-dioxide (HBV-CSU-092, HBV-CSU-092-ISO-I & HBV-CSU-092-ISO-II)

Scheme 16:

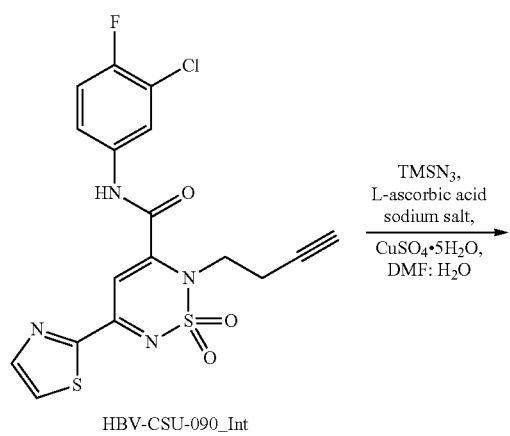

HBV-CSU-090_Int

222
-continued

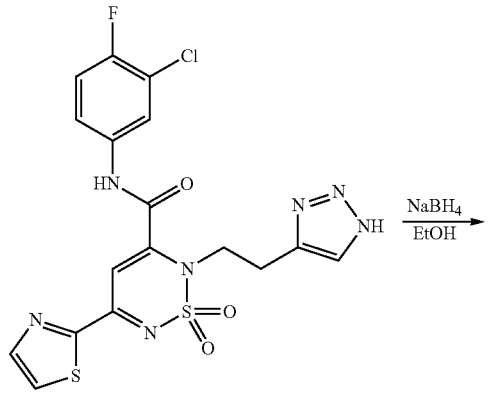

HBV-CSU-092_Int

→ NaBH$_4$ / EtOH →

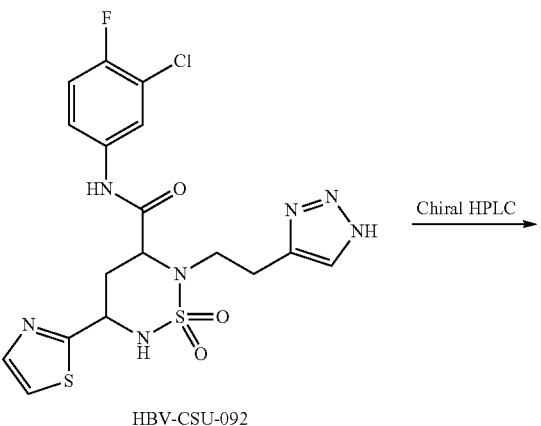

HBV-CSU-092

→ Chiral HPLC →

HBV-CSU-092-Isomer I
+
HBV-CSU-092-Isomer II 2-(2-(1H-1,2,3-Triazol-4-yl)ethyl)-N-(3-chloro-4-fluorophenyl)-5-(thiazol-2-yl)-2H-1,2,6-thiadiazine-3-carboxamide 1,1-dioxide (HBV-CSU-092_Int)

To a stirred solution of HBV-CSU-090_Int (300 mg, 0.68 mmol) in a mixture of DMF:H$_2$O (3:1, 8 mL) were added copper (II) sulfate pentahydrate (17 mg, 0.068 mmol) and L-ascorbic acid sodium salt (543 mg, 2.73 mmol) and azidotrimethylsilane (0.14 mL, 1.02 mmol) in 10° C., followed by warming to room temperature and stirring for 36 h. The reaction was monitored by TLC. After completion of the reaction, the reaction mixture was diluted with water and extracted using EtOAc. The combined organic extracts were dried over anhydrous sodium sulfate, filtered and concentrated in vacuo to obtain the crude. The crude was purified through silica gel flash column chromatography 1-2% MeOH/CH$_2$Cl$_2$ to afford HBV-CSU-092_Int (80 mg, 24%) as an off-white solid. TLC: 40% EtOAc/hexanes (R$_f$: 0.3) (see Table 1 for analytical data).

Cis-2-(2-(1H-1,2,3-Triazol-4-yl)ethyl)-N-(3-chloro-4-fluorophenyl)-5-(thiazol-2-yl)-1,2,6-thiadiazinane-3-carboxamide 1,1-dioxide (HBV-CSU-092, HBV-CSU-092-ISO-I, HBV-CSU-092-ISO-II)

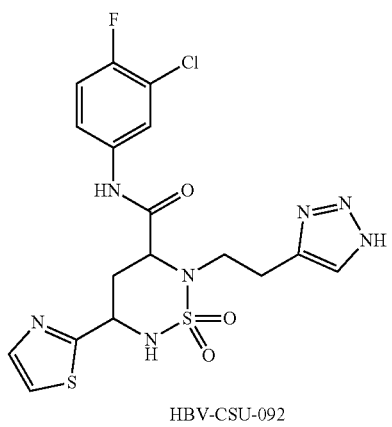

HBV-CSU-092

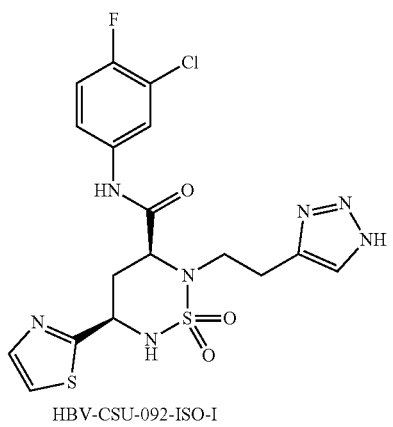

HBV-CSU-092-ISO-I

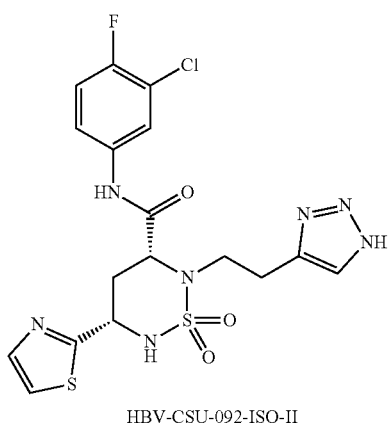

HBV-CSU-092-ISO-II

The above titled compounds have been synthesized by following the general procedure described above for reduction by using corresponding HBV-CSU-092_Int (see Table 2 for analytical data).

Scheme 17

Cis-N-(3-Chloro-4-fluorophenyl)-2-(cyanomethyl)-5-(thiazol-2-yl)-1,2,6-thiadiazinane-3-carboxamide 1,1-dioxide (HBV-CSU-093)/Cis-2-(3-((3-Chloro-4-fluorophenyl)carbamoyl)-1,1-dioxido-5-(thiazol-2-yl)-1,2,6-thiadiazinan-2-yl)acetic acid (HBV-CSU-110) & Cis-2-(3-((3-Chloro-4-fluorophenyl)carbamoyl)-1,1-dioxido-5-(thiazol-2-yl)-1,2,6-thiadiazinan-2-yl)acetic acid (HBV-CSU-111)

Scheme 17:

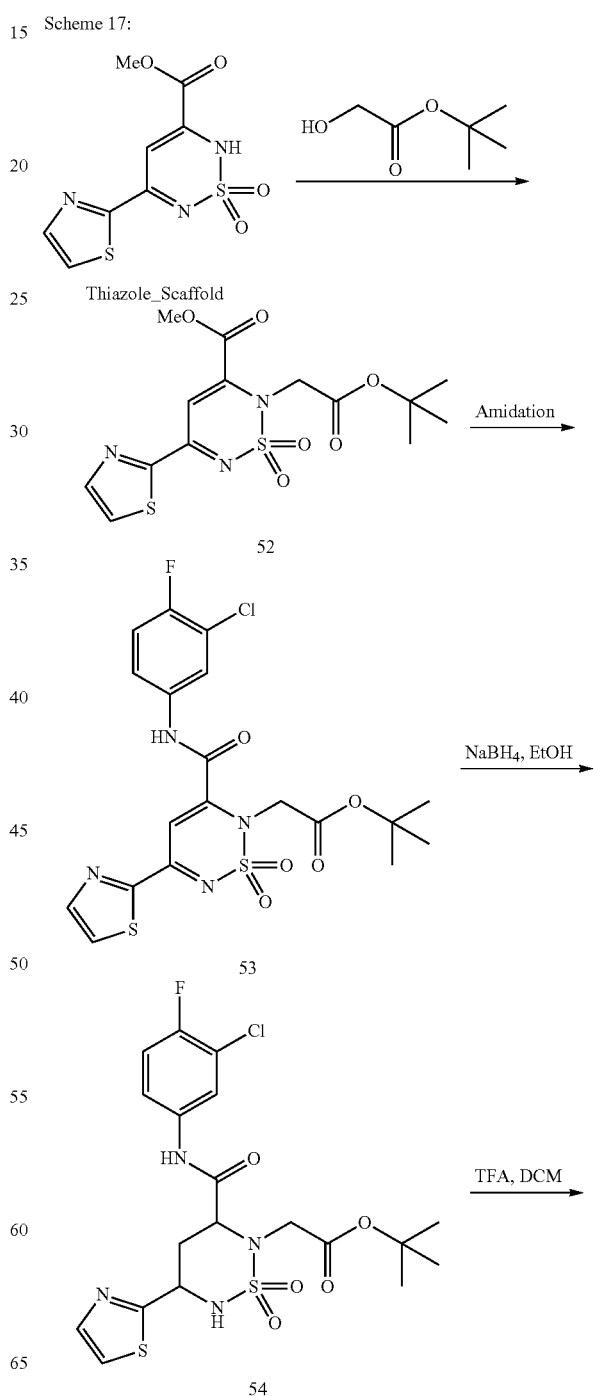

-continued

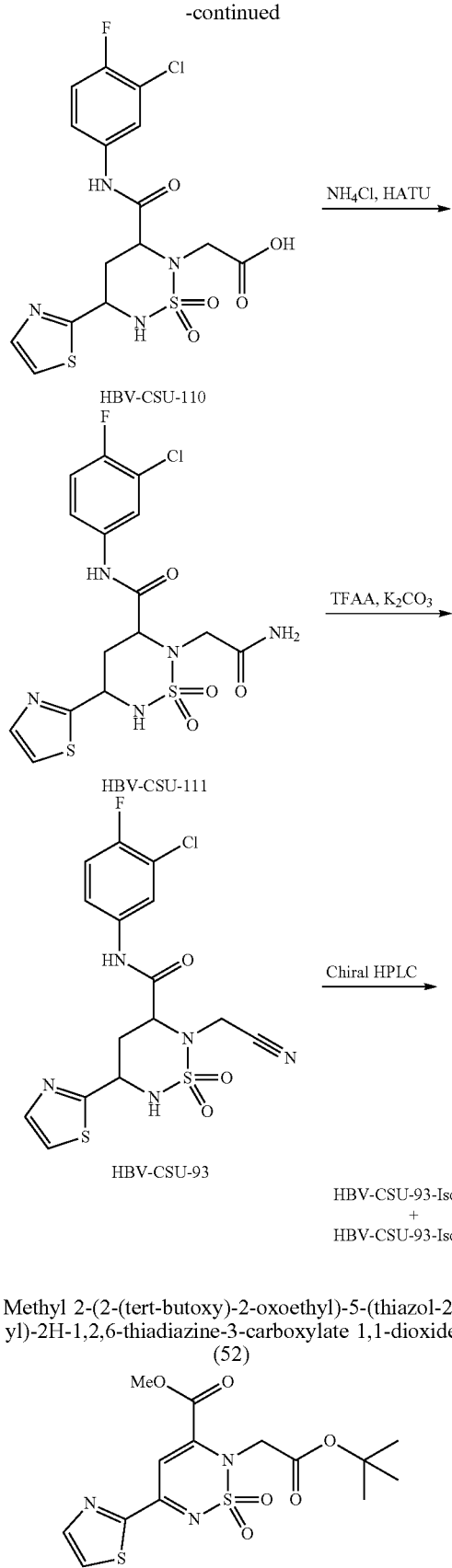

HBV-CSU-110

NH₄Cl, HATU →

HBV-CSU-111

TFAA, K₂CO₃ →

HBV-CSU-93

Chiral HPLC →

HBV-CSU-93-Isomer I
+
HBV-CSU-93-Isomer I

Methyl 2-(2-(tert-butoxy)-2-oxoethyl)-5-(thiazol-2-yl)-2H-1,2,6-thiadiazine-3-carboxylate 1,1-dioxide (52)

Title compound was synthesized using general method B for alkylation described above to afford 6 g (84.74%, reaction scale is 5 g); LCMS Calculated for $C_{14}H_{17}N_3O_6S_2$: 387.06; LCMS observed: 332.15 (M−55)⁺.

Synthesis of tert-butyl 2-(3-((3-chloro-4-fluorophenyl) carbamoyl)-1,1-dioxido-5-(thiazol-2-yl)-2H-1,2,6-thiadiazin-2-yl)acetate (53)


The above titled compound has been synthesized by following the general procedure (Method B) described above for amidation by using corresponding Compound 52 and corresponding amine. The ¹H NMR hints for the desired alkylation (Note: the NMR indicated contamination with a hydrazide side product).

tert-Butyl 2-(3-((3-chloro-4-fluorophenyl)carbamoyl)-1,1-dioxido-5-(thiazol-2-yl)-1,2,6-thiadiazinan-2-yl)acetate (54)

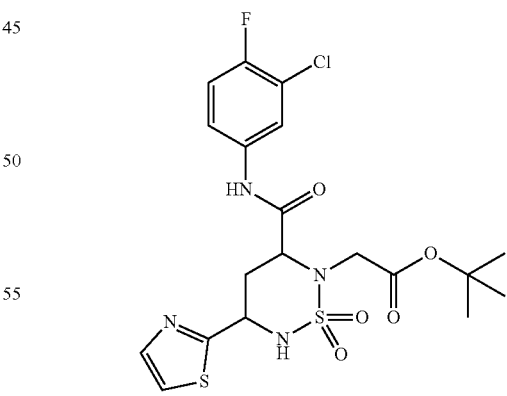

The above titled compounds have been synthesized by following the general procedure described above for reduction by using corresponding Compound 53. The crude material was directly used in the next step.

Cis-N-(3-Chloro-4-fluorophenyl)-2-(cyanomethyl)-5-(thiazol-2-yl)-1,2,6-thiadiazinane-3-carboxamide 1,1-dioxide (HBV-CSU-093, HBV-CSU-093-ISO-I & HBV-CSU-093-ISO-II)

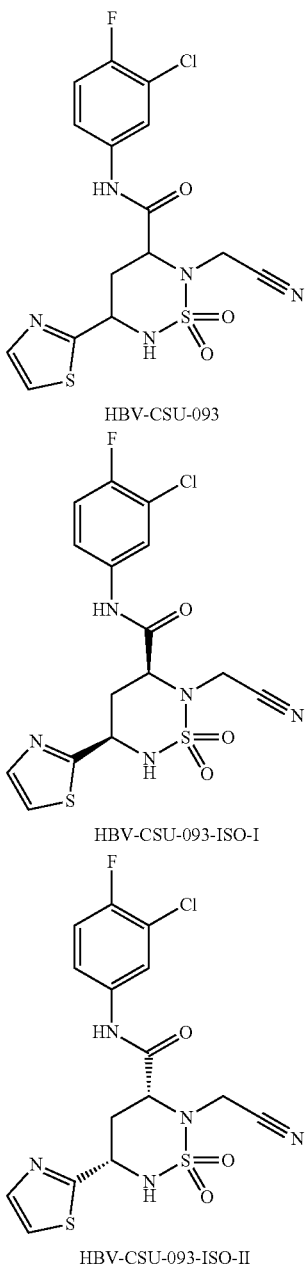

Cis-2-(3-((3-Chloro-4-fluorophenyl)carbamoyl)-1,1-dioxido-5-(thiazol-2-yl)-1,2,6-thiadiazinan-2-yl)acetic acid (HBV-CSU-110)

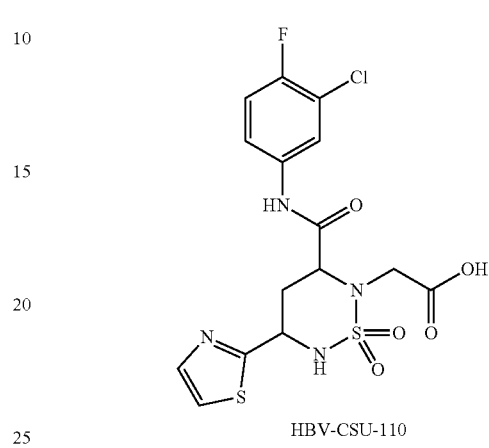

To a stirred solution of compound 54 (0.9 g, 1.78 mmol) in DCM (5 mL) at 0° C., TFA (15 mL) was added and stirred at room temperature for 6 h. The progress of the reaction was monitored by TLC and LCMS. After completion, the reaction mixture was concentrated under reduced pressure. The crude compound was washed with diethyl ether and purified by prep. HPLC to afford the desired compound HBV-CSU-110 (30 mg, 23%) as a white solid. TLC: 40% EtOAc/hexanes ($R_f$: 0.1) (see Table 2 for analytical data).

Cis-2-(3-((3-Chloro-4-fluorophenyl)carbamoyl)-1,1-dioxido-5-(thiazol-2-yl)-1,2,6-thiadiazinan-2-yl)acetic acid (HBV-CSU-111)

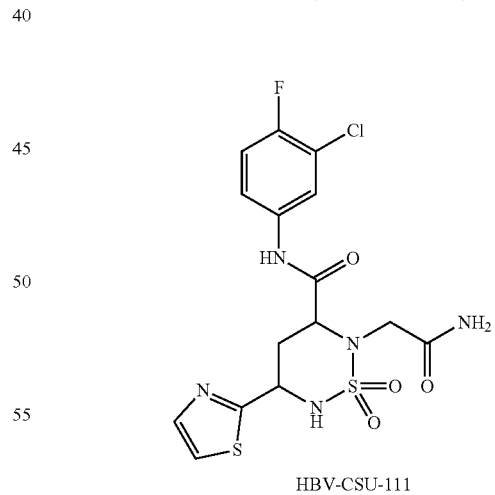

To a stirred solution of HBV-CSU-111 (50 mg, 0.111 mmol) in DCM (2 mL) at 0° C., TFAA (0.046 mL, 0.33 mmol) was added and stirred at same temperature for 20 min. The progress of the reaction was monitored by TLC and LCMS. After completion, the reaction mixture was concentrated under reduced pressure; water was added and extracted with DCM. The combined organic extracts were dried over anhydrous sodium sulphate, filtered, concentrated under vacuo to afford solid material which was triturated with diethyl ether to afford the desired compound HBV-CSU-093 (0.11 g, 38.32%) as a white solid. TLC: 5% MeOH/DCM ($R_f$: 0.2) (see Table 2 for analytical data).

To a stirred solution of compound HBV-CSU-110 (0.16 g, 0.357 mmol) in DMF (10 mL) at 0° C., DIPEA (0.138 g, 1.07 mmol) and HATU (0.176 g, 0.464 mmol) were added and stirred for 15 min. To this solution, NH$_4$Cl (0.056 g, 1.07 mmol) was added. The reaction mixture was stirred at room temperature for overnight. The progress of the reaction was monitored by TLC. After completion, the reaction mixture was diluted with ice cold water and extracted with DCM.

The combined organic layers were dried over anhydrous sodium sulphate and concentrated under reduced pressure to afford a crude compound. The crude compound was purified by silica gel column chromatography to afford the desired compound as HBV-CSU-111 (0.1 g, 63%) as a white solid. TLC: 10% MeOH/DCM ($R_f$: 0.3) (see Table 2 for analytical data).

Scheme 18

Synthesis of Cis-N-(3-Chloro-4-fluorophenyl)-2-(2-hydroxyethyl)-5-(thiazol-2-yl)-1,2,6-thiadiazinane-3-carboxamide 1,1-dioxide (HBV-CSU-097, HBV-CSU-097-ISO-I & HBV-CSU-097-ISO-II)

Scheme 19

Synthesis of Cis-N-(3-Chloro-4-fluorophenyl)-2-(3-(diethylamino)propyl)-5-(thiazol-2-yl)-1,2,6-thiadiazinane-3-carboxamide 1,1-dioxide (HBV-CSU-101)/Cis-N-(3-Chloro-4-fluorophenyl)-2-(3-(pyrrolidin-1-yl)propyl)-5-(thiazol-2-yl)-1,2,6-thiadiazinane-3-carboxamide 1,1-dioxide (HBV-CSU-102) & Cis-N-(3-Chloro-4-fluorophenyl)-2-(3-morpholinopropyl)-5-(thiazol-2-yl)-1,2,6-thiadiazinane-3-carboxamide 1,1-dioxide (HBV-CSU-103)

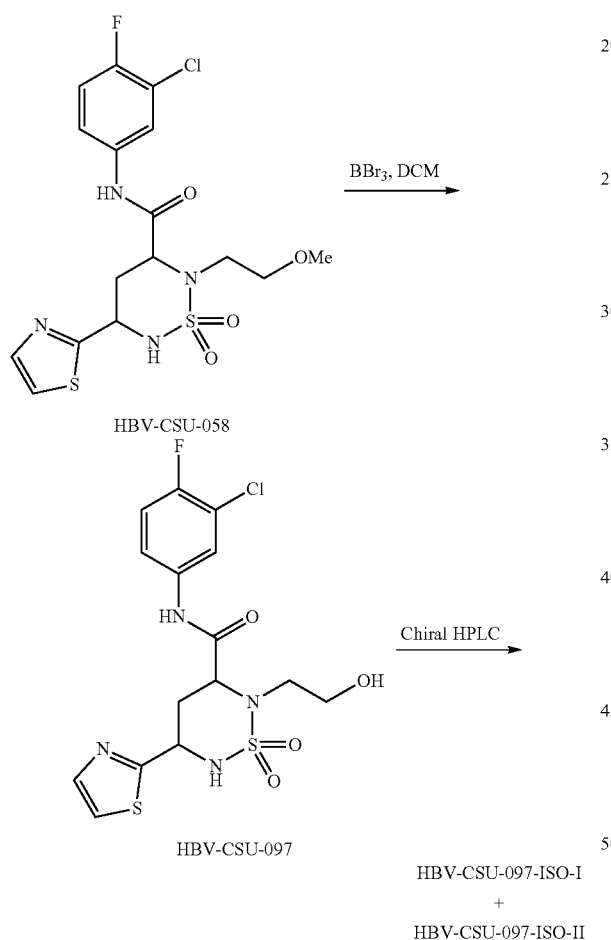

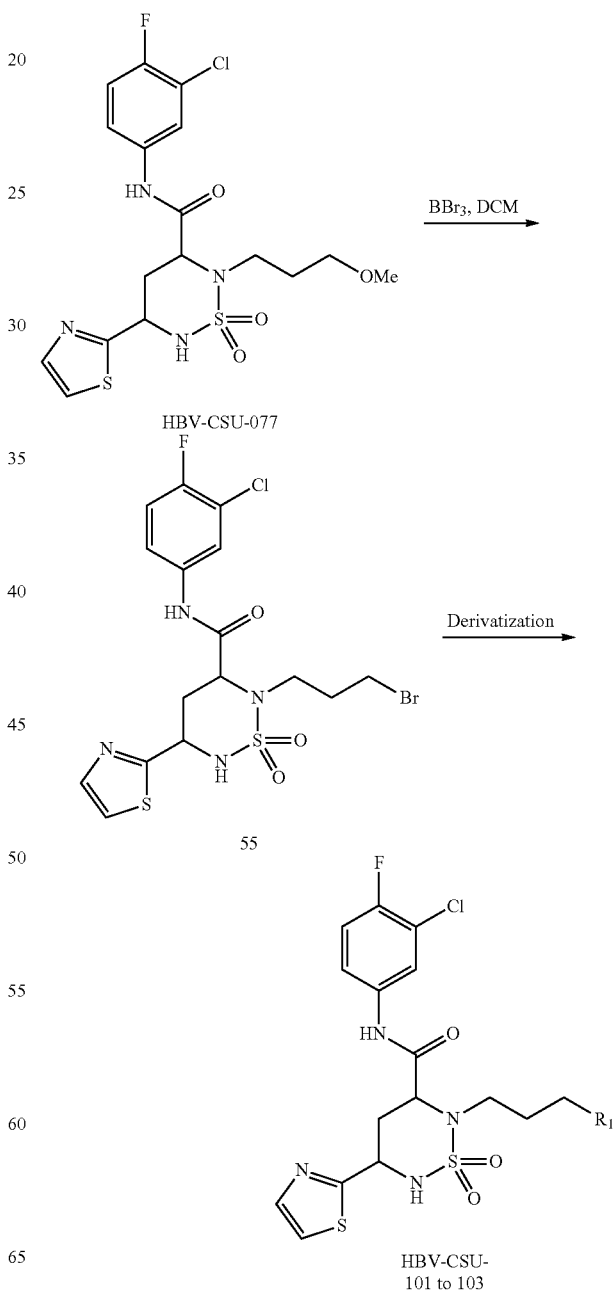

To a stirred solution of HBV-CSU-058 (0.25 g, 0.558 mmol) in DCM (10 mL) at −40° C., BBr$_3$ (0.104 mL, 1.11 mmol) was added and stirred at room temperature for 4 h. The progress of the reaction was monitored by TLC and LCMS. After completion, the reaction mixture was quenched with sat. NaHCO$_3$ solution and extracted with DCM. The combined organic layers were dried over anhydrous sodium sulphate and concentrated under reduced pressure. The crude compound was purified by silica gel column chromatography to afford the desired compound as HBV-CSU-097 (0.06 g, 24.79%) as an off white solid. TLC: 5% MeOH/DCM ($R_f$: 0.2) (see Table 2 for analytical data).

R1 = 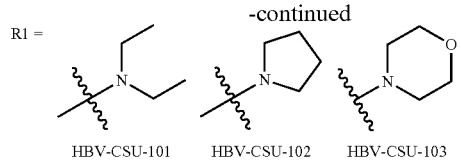

2-(3-Bromopropyl)-N-(3-chloro-4-fluorophenyl)-5-(thiazol-2-yl)-1,2,6-thiadiazinane-3-carboxamide 1,1-dioxide (55)

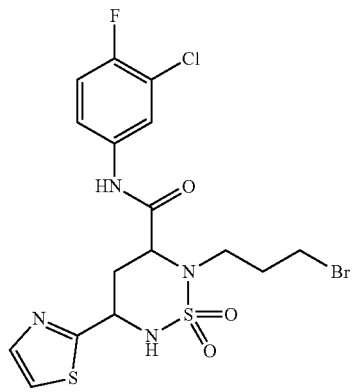 [SMILES: O=C(Nc1ccc(F)c(Cl)c1)C1CC(c2nccs2)NS(=O)(=O)N1CCCBr]

To a stirred solution of HBV-CSU-077 (2 g, 4.31 mmol) in DCM (20 mL) at −40° C. under Ar atmosphere, BBr$_3$ (2.02 mL, 21.59 mmol) was added drop wise. The resulting reaction mixture was stirred at room temperature for 5 h. The progress of the reaction was monitored by TLC and LCMS. After completion, the reaction mixture was quenched with sat. NaHCO$_3$ solution and extracted with DCM. The combined organic layers were washed with water and brine, dried over anhydrous sodium sulphate, and concentrated in vacuo. The crude compound was purified by silica gel column chromatography using 2% MeOH/DCM to afford compound 55 (1.35 g, 61.08%) as a brown colored oil. LCMS Calculated for $C_{16}H_{17}BrClFN_4O_3S_2$: 509.16; Observed: 513.35 (M+4)$^+$.

Cis-N-(3-Chloro-4-fluorophenyl)-2-(3-(diethylamino)propyl)-5-(thiazol-2-yl)-1,2,6-thiadiazinane-3-carboxamide 1,1-dioxide (HBV-CSU-101-ISO-I & HBV-CSU-101-ISO-II)

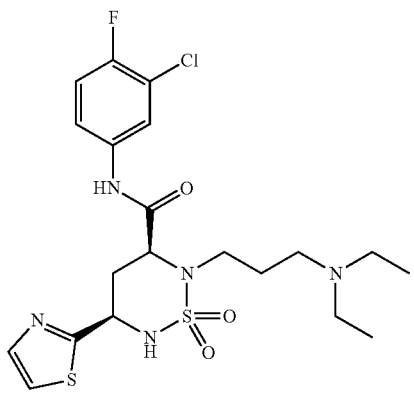

To a stirred solution of compound 55 (0.3 g, 0.585 mmol.) in DMF (5 mL) at 0° C., K$_2$CO$_3$ (0.161 g, 1.17 mmol) and diethylamine (0.042 g, 0.585 mmol) were added. The reaction mixture was stirred at room temperature for 12 h. The progress of the reaction was monitored by TLC and LCMS. After completion, the reaction mixture was diluted with ice cold water. The obtained solid was filtered and the filtrate was extracted with ethyl acetate. The combined organic layers were washed with water and brine; dried over anhydrous sodium sulphate, and concentrated in vacuo. The crude compound was purified by prep. HPLC to afford the compound HBV-CSU-101 (0.26 g, 75.80%) as a white solid. (see Table 2 for analytical data).

Cis-N-(3-Chloro-4-fluorophenyl)-2-(3-(pyrrolidin-1-yl)propyl)-5-(thiazol-2-yl)-1,2,6-thiadiazinane-3-carboxamide 1,1-dioxide (HBV-CSU-102, HBV-CSU-102-ISO-I & HBV-CSU-102-ISO-II)

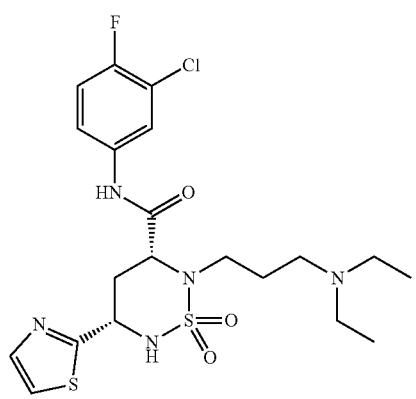

HBV-CSU-101-ISO-I

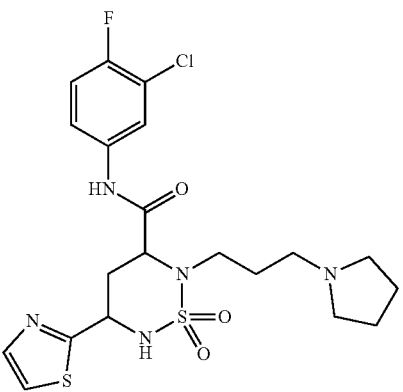

HBV-CSU-102

233

-continued

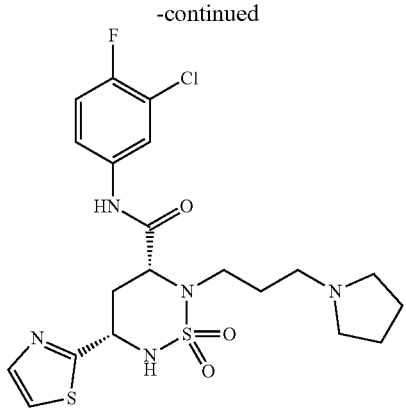

HBV-CSU-102-ISO-I

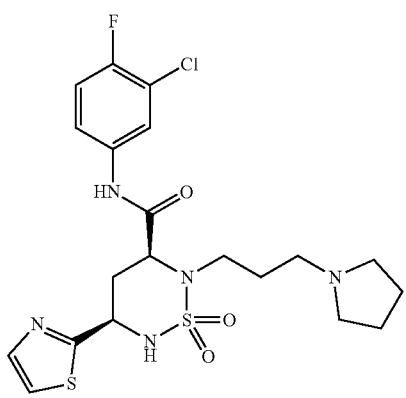

HBV-CSU-102-ISO-II

To a stirred solution of compound 55 (0.5 g, 0.976 mmol.) in DMF (5 mL) at 0° C., K₂CO₃ (0.404 g, 2.92 mmol) and pyrrolidine (0.138 g, 1.95 mmol) were added. The reaction mixture was stirred at room temperature for 12 h. The progress of the reaction was monitored by TLC and LCMS. After completion, the reaction mixture was diluted with ice cold water. The obtained solid was filtered and the filtrate was extracted with ethyl acetate. The combined organic layers were washed with water and brine, dried over anhydrous sodium sulphate, and concentrated in vacuo. The crude compound was purified by prep. HPLC to afford the compound HBV-CSU-102 (Cis isomer) (0.12 g, 24.53%) as a white solid. TLC: 5% MeOH/DCM ($R_f$: 0.1) (see Table 2 for analytical data).

234

Cis-N-(3-Chloro-4-fluorophenyl)-2-(3-morpholinopropyl)-5-(thiazol-2-yl)-1,2,6-thiadiazinane-3-carboxamide 1,1-dioxide (HBV-CSU-103)

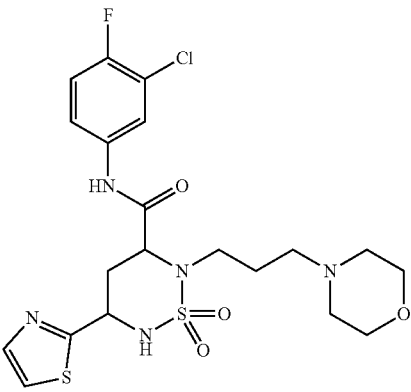

HBV-CSU-102

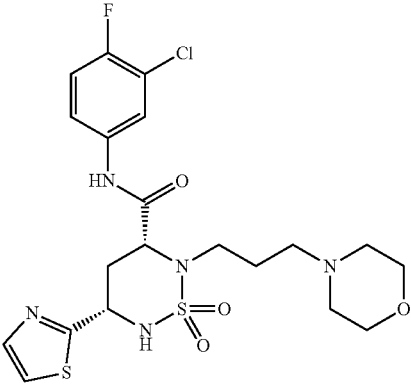

HBV-CSU-103-ISO-I

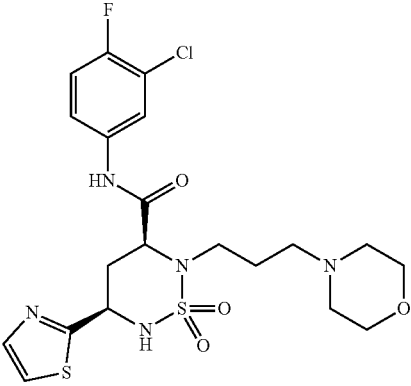

HBV-CSU-103-ISO-II

To a stirred solution of compound 55 (0.5 g, 0.976 mmol.) in DMF (5 mL) at 0° C., K₂CO₃ (0.404 g, 2.92 mmol) and morpholine (0.169 g, 1.95 mmol) were added. The reaction mixture was stirred at room temperature for 12 h. The progress of the reaction was monitored by TLC and LCMS. After completion, the reaction mixture was diluted with ice cold water. The obtained solid was filtered and the filtrate was extracted with ethyl acetate. The combined organic layers were washed with water and brine, dried over anhydrous sodium sulphate, and concentrated in vacuo. The crude compound was purified by prep. HPLC to afford the compound HBV-CSU-103 (0.16 g, 31.74%) as a white solid. TLC: 5% MeOH/DCM (R$^f$: 0.1) (see Table 2 for analytical data).
Scheme 20
General Synthetic Scheme for 5-(thiophen-2-yl)-1,2,6-thiadiazinane-3-carboxamide 1,1-dioxide Derivatives with 5-Substituted Thiophene & Aniline Variations
Scheme 20
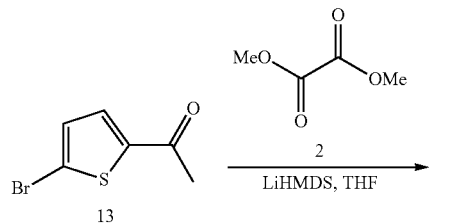
13
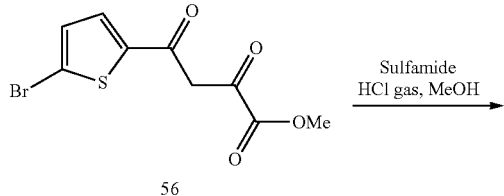
56
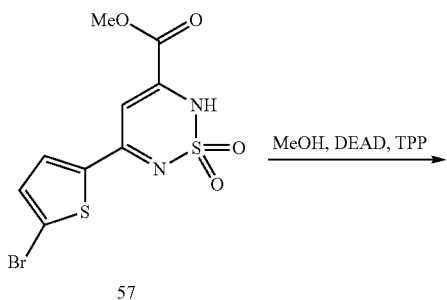
57
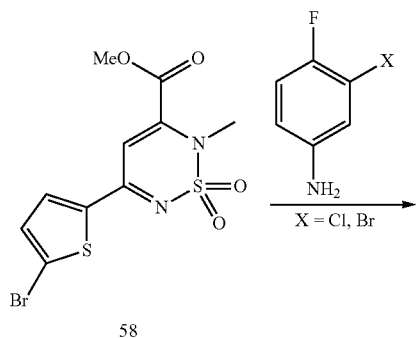
58
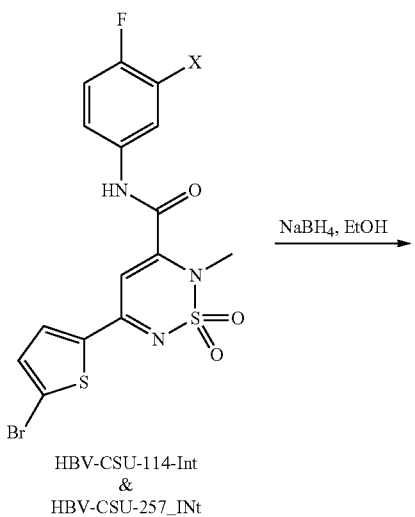
HBV-CSU-114-Int
&
HBV-CSU-257_INt
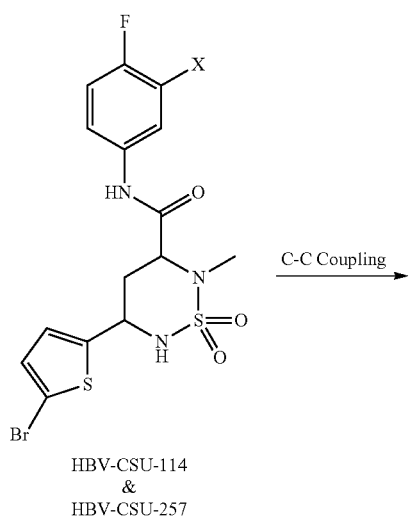
HBV-CSU-114
&
HBV-CSU-257
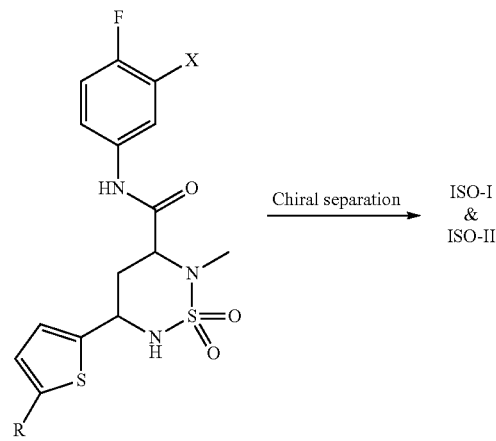

| Target | Coupling reaction | Aniline (X = Cl, Br) | #2 (R variation) |
|---|---|---|---|
| HBV-CSU-114 | — | X = Cl | Br |
| HBV-CSU-115 | Negishi coupling | X = Cl | Methyl |
| HBV-CSU-116 | Suzuki coupling | X = Cl | 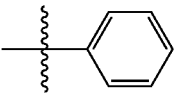 |
| HBV-CSU-117 | Suzuki coupling | X = Cl | 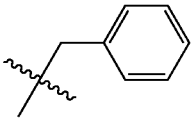 [SMILES: *Cc1ccccc1] |
| HBV-CSU-156 | Suzuki coupling | X = Cl | 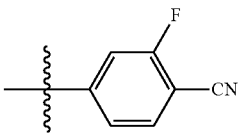 [SMILES: *c1ccc(C#N)c(F)c1] |
| HBV-CSU-157 | Suzuki coupling | X = Cl | 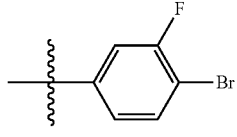 [SMILES: *c1ccc(Br)c(F)c1] |
| HBV-CSU-158 | Suzuki coupling | X = Cl | 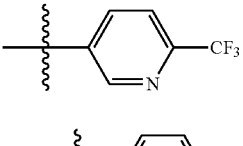 |
| HBV-CSU-159 | Suzuki coupling | X = Cl | 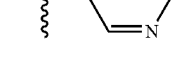 |
| HBV-CSU-160 | Stille coupling | X = Cl | 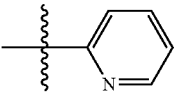 |
| HBV-CSU-161 | Suzuki coupling | X = Cl | 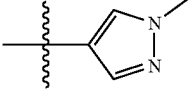 |
| HBV-CSU-162 | Suzuki coupling | X = Cl | 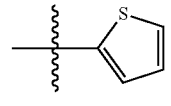 [SMILES: *c1cccs1] |
| HBV-CSU-163 | Suzuki coupling | X = Cl | 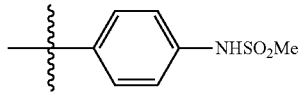 |
| HBV-CSU-188 | Displacement | X = Cl | 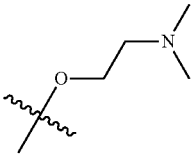 [SMILES: *OCCN(C)C] |
| HBV-CSU-257 | — | X = Br | Br |

-continued
| Target | Coupling reaction | Aniline (X = Cl, Br) | #2 (R variation) |
|---|---|---|---|
| HBV-CSU-271 | Suzuki coupling | X = Cl | 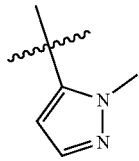 [SMILES: *c1ccnn1C] |
| HBV-CSU-272 | Stille coupling | X = Cl | 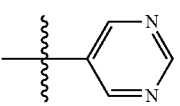 [SMILES: *c1cncnc1] |
| HBV-CSU-291 | Suzuki coupling | X = Cl | 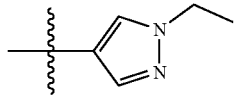 [SMILES: *c1cnn(CC)c1] |
| HBV-CSU-292 | Suzuki coupling | X = Cl | 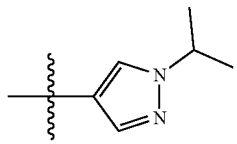 [SMILES: *c1cnn(C(C)C)c1] |
| HBV-CSU-293 | Suzuki coupling | X = Cl | 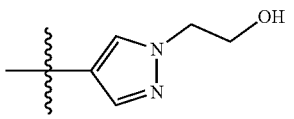 [SMILES: *c1cnn(CCO)c1] |
| HBV-CSU-312 | Suzuki coupling | X = Cl | 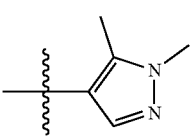 [SMILES: *c1cnn(C)c1C] |
| HBV-CSU-313 | Suzuki coupling | X = Cl | 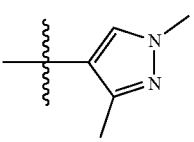 [SMILES: *c1cn(C)nc1C] |
| HBV-CSU-314 | Suzuki coupling | X = Cl | 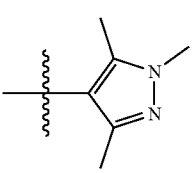 |
| HBV-CSU-321 | Suzuki coupling | X = Cl | 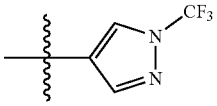 [SMILES: *c1cnn(C(F)(F)F)c1] |

Synthesis of methyl 4-(5-bromothiophen-2-yl)-2,4-dioxobutanoate (56)

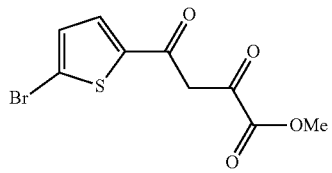 [SMILES: COC(=O)C(=O)CC(=O)c1ccc(Br)s1]

Title compound was synthesized using general method for the synthesis of 2,4-diketoester described above to afford 115 g (81%, reaction scale is 100 g) as a brown solid. TLC: 10% MeOH/DCM ($R_f$: 0.1); $^1$H NMR (DMSO-$d_6$, 400 MHz): δ 8.12 (d, J=4.0 Hz, 1H), 7.45 (d, J=4.0 Hz, 1H), 7.03 (br.s, 1H), 3.84 (s, 3H); {Note: Enol form observed by $^1$H NMR and peak for enolic alcohol was not observed}. LCMS Calculated for $C_9H_7BrO_4S$: 289.92; Observed: 290.95 $(M+1)^+$.

Synthesis of methyl 5-(5-bromothiophen-2-yl)-2H-1,2,6-thiadiazine-3-carboxylate 1,1-dioxide (57)

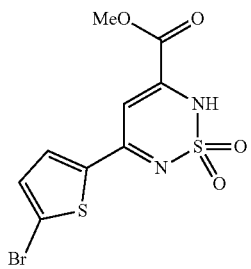 [SMILES: COC(=O)C1=CC(c2ccc(Br)s2)=NS(=O)(=O)N1]

Title compound was synthesized using general method B for the synthesis of cyclic sulfonamide described above to afford 100 g (72%, reaction scale is 115 g) as a brown colored solid. TLC: 20% MeOH/DCM ($R_f$: 0.1); $^1$H NMR (DMSO-$d_6$, 400 MHz): δ 7.85 (d, J=4.0 Hz, 1H), 7.33 (d, J=4.0 Hz, 1H), 6.87 (s 1H), 3.84 (s, 3H); LCMS Calculated for $C_9H_7BrN_2O_4S_2$: 349.90; LCMS observed: 352.90 $(M+2)^+$.

Synthesis of methyl 5-(5-bromothiophen-2-yl)-2-methyl-2H-1,2,6-thiadiazine-3-carboxylate 1,1-dioxide (58)

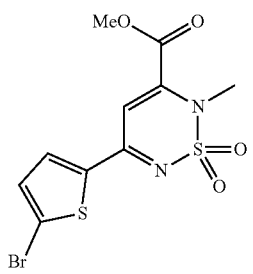 [SMILES: COC(=O)C1=CC(c2ccc(Br)s2)=NS(=O)(=O)N1C]

Title compound was synthesized using general method A for alkylation described above to afford 65 g (62%, reaction scale is 100 g) as a brown solid. TLC: 40% EtOAc/hexanes ($R_f$: 0.4); $^1$H NMR (DMSO-$d_6$, 400 MHz): δ 8.11 (d, J=4.0 Hz, 1H), 7.48 (d, J=4.0 Hz, 1H), 7.31 (s 1H), 3.93 (s, 3H), 3.50 (s, 3H); LCMS Calculated for $C_{10}H_9BrN_2O_4S_2$: 363.92; LCMS observed: 366.90 $(M+2)^+$.

5-(5-Bromothiophen-2-yl)-N-(3-chloro-4-fluorophenyl)-2-methyl-2H-1,2,6-thiadiazine-3-carboxamide 1,1-dioxide (HBV-CSU-0114-Int)

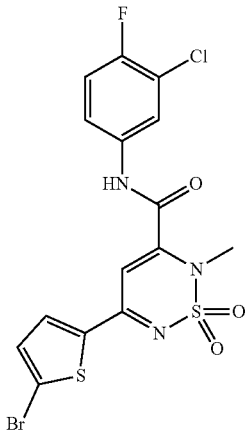

The above titled compound has been synthesized by following the general procedure (Method B) described above for amidation by using Compound 58 and corresponding amine (see Table 1 for analytical data).

N-(3-Bromo-4-fluorophenyl)-5-(5-bromothiophen-2-yl)-2-methyl-2H-1,2,6-thiadiazine-3-carboxamide 1,1-dioxide (HBV-CSU-257_Int)

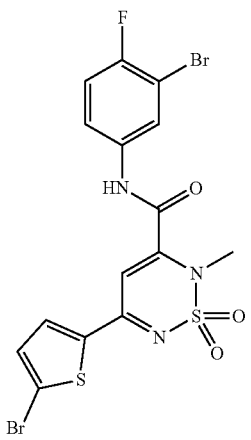 [SMILES: CN1C(C(=O)Nc2ccc(F)c(Br)c2)=CC(c2ccc(Br)s2)=NS1(=O)=O]

The above titled compound has been synthesized by following the general procedure (Method B) described above for amidation by using Compound 58 and corresponding amine. The crude intermediate confirmed by LCMS and carried forward to the next step.

243

5-(5-Bromothiophen-2-yl)-N-(3-chloro-4-fluorophenyl)-2-methyl-1,2,6-thiadiazinane-3-carboxamide 1,1-dioxide (HBV-CSU-114, HBV-CSU-114-ISO-I & HBV-CSU-114-ISO-II)

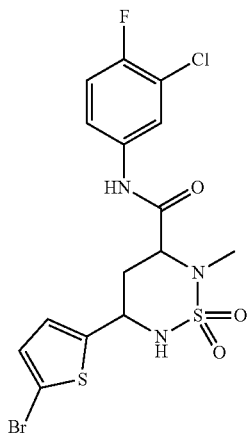 [SMILES: CN1C(C(=O)Nc2ccc(F)c(Br)c2)CC(c2ccc(Br)s2)NS1(=O)=O]

HBV-CSU-114

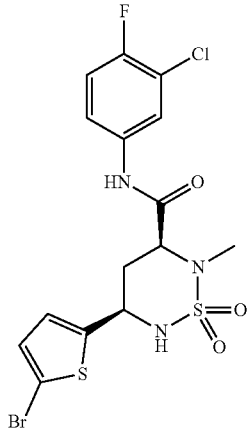

HBV-CSU-114-ISO-I

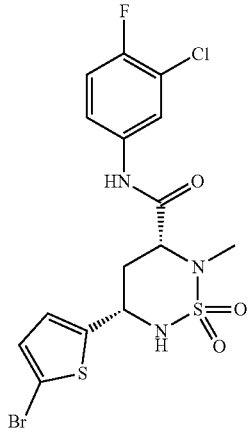

HBV-CSU-114-ISO-II

The above titled compounds have been synthesized by following the general procedure described above for reduction by using corresponding HBV-CSU-0114-Int (see Table 2 for analytical data).

244

Cis-N-(3-chloro-4-fluorophenyl)-2-methyl-5-(5-methylthiophen-2-yl)-1,2,6-thiadiazinane-3-carboxamide 1,1-dioxide (HBV-CSU-115, HBV-CSU-115-ISO-I & HBV-CSU-115-ISO-II)

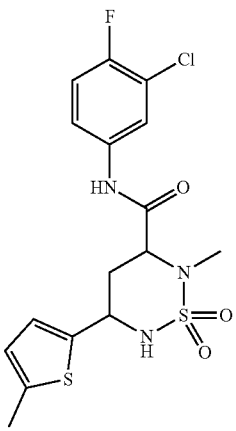

HBV-CSU-115

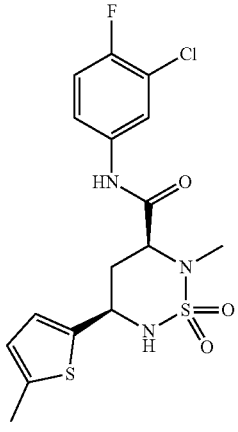

HBV-CSU-115-ISO-I

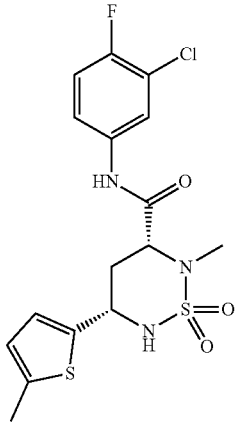

HBV-CSU-115-ISO-II

The above titled compounds have been synthesized by following the general procedure described above for Negishi coupling by using HBV-CSU-114 and dimethyl zinc (see Table 2 for analytical data).

245

Cis-N-(3-chloro-4-fluorophenyl)-2-methyl-5-(5-phenylthiophen-2-yl)-1,2,6-thiadiazinane-3-carboxamide 1,1-dioxide (HBV-CSU-116-ISO-I & HBV-CSU-116-ISO-II)

246

Cis-(5-benzylthiophen-2-yl)-N-(3-chloro-4-fluorophenyl)-2-methyl-1,2,6-thiadiazinane-3-carboxamide 1,1-dioxide (HBV-CSU-117, HBV-CSU-117-ISO-I & HBV-CSU-117-ISO-II)

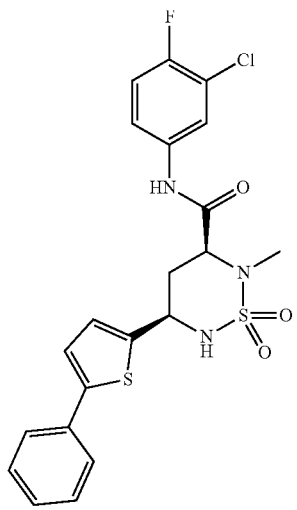

HBV-CSU-116-ISO-I

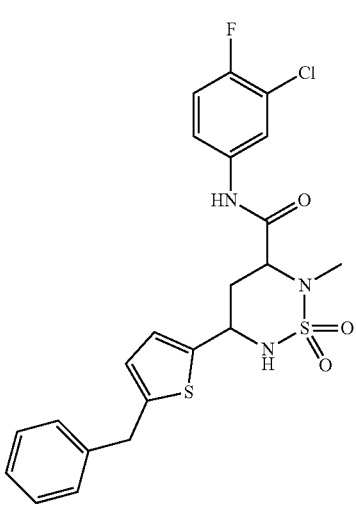

HBV-CSU-117

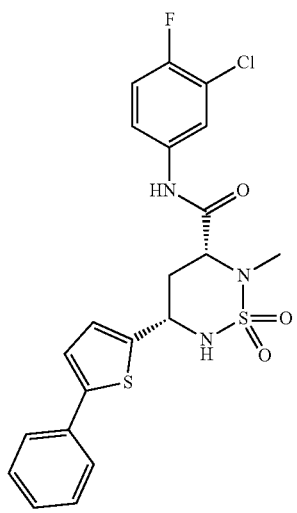

HBV-CSU-116-ISO-II

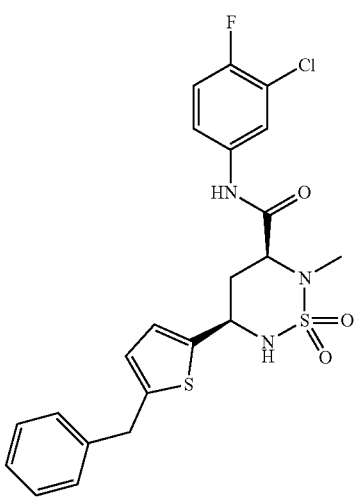

HBV-CSU-117-ISO-I

The above titled compounds have been synthesized by following the general procedure described above for Suzuki coupling by using HBV-CSU-114 and corresponding boronic acid (see Table 2 for analytical data).

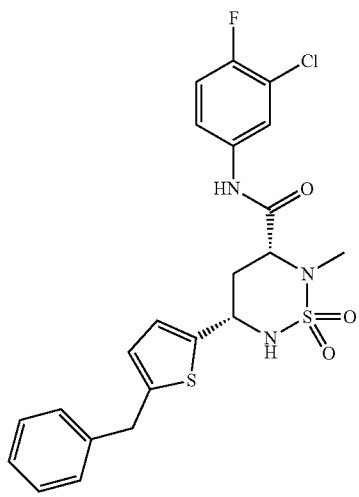

HBV-CSU-117-ISO-II

The above titled compounds have been synthesized by following the general procedure described above for Suzuki coupling by using HBV-CSU-114 and corresponding boronic acid (see Table 2 for analytical data).

Cis-N-(3-chloro-4-fluorophenyl)-5-(5-(4-cyano-3-fluorophenyl)thiophen-2-yl)-2-methyl-1,2,6-thiadiazinane-3-carboxamide 1,1-dioxide (HBV-CSU-156, HBV-CSU-156-ISO-I & HBV-CSU-156-ISO-II)

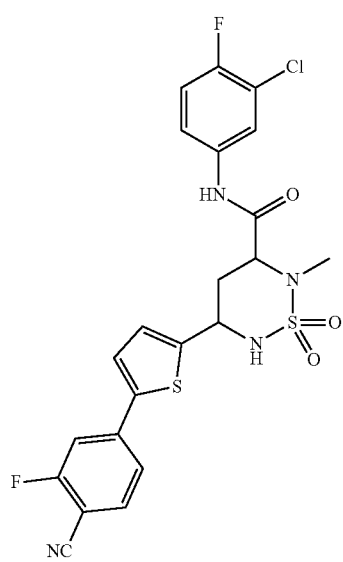

HBV-CSU-156

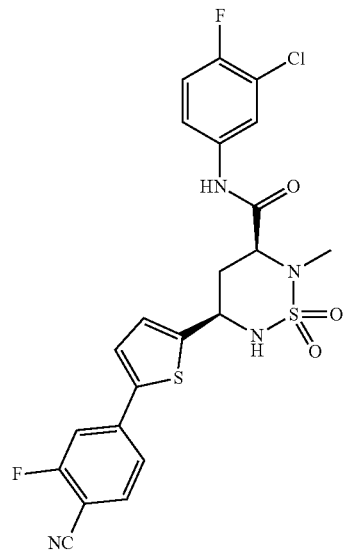

HBV-CSU-156-ISO-I

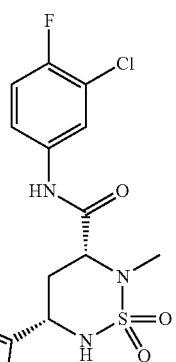

HBV-CSU-156-ISO-II

The above titled compounds have been synthesized by following the general procedure described above for Suzuki coupling by using HBV-CSU-114 and corresponding boronic acid (see Table 2 for analytical data).

Cis-N-(3-chloro-4-fluorophenyl)-5-(5-(4-bromo-3-fluorophenyl)thiophen-2-yl)-2-methyl-1,2,6-thiadiazinane-3-carboxamide 1,1-dioxide (HBV-CSU-157)

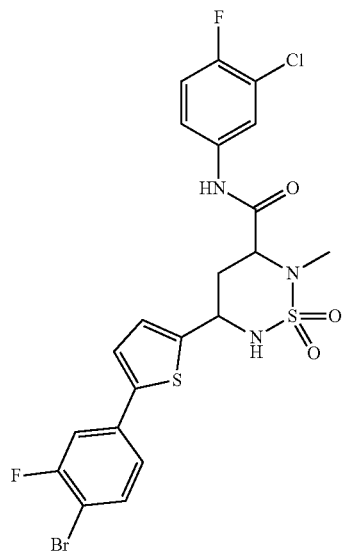

HBV-CSU-157

The above titled compound has been synthesized by following the general procedure described above for Suzuki coupling by using HBV-CSU-114 and corresponding boronic acid (see Table 2 for analytical data).

Cis-N-(3-chloro-4-fluorophenyl)-2-methyl-5-(5-(6-(trifluoromethyl)pyridin-3-yl)thiophen-2-yl)-1,2,6-thiadiazinane-3-carboxamide 1,1-dioxide (HBV-CSU-158, HBV-CSU-158-ISO-I & HBV-CSU-158-ISO-II)

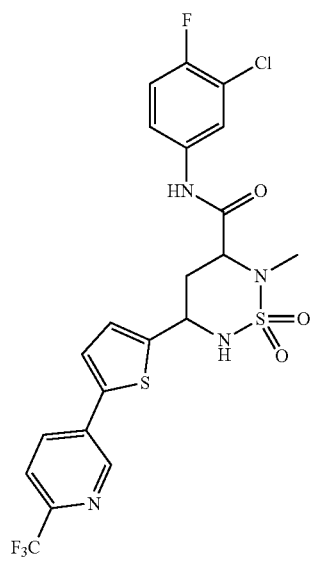

HBV-CSU-158

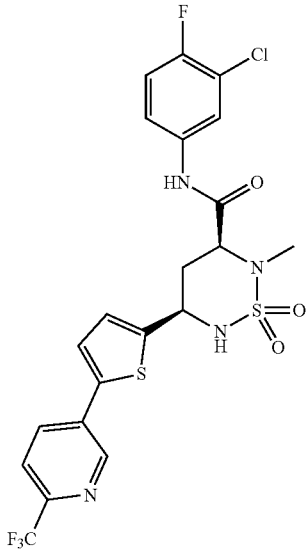

HBV-CSU-158-ISO-I

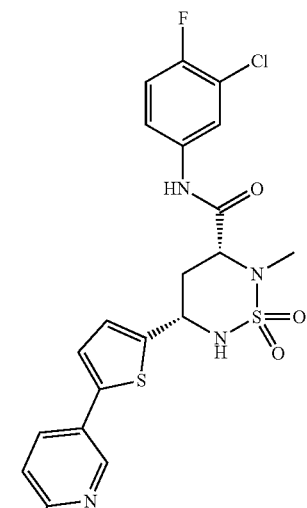

HBV-CSU-158-ISO-II

The above titled compounds have been synthesized by following the general procedure described above for Suzuki coupling by using HBV-CSU-114 and corresponding boronic acid (see Table 2 for analytical data).

251

Cis-N-(3-chloro-4-fluorophenyl)-2-methyl-5-(5-(pyridin-3-yl)thiophen-2-yl)-1,2,6-thiadiazinane-3-carboxamide 1,1-dioxide (HBV-CSU-159, HBV-CSU-159-ISO-I & HBV-CSU-159-ISO-II)

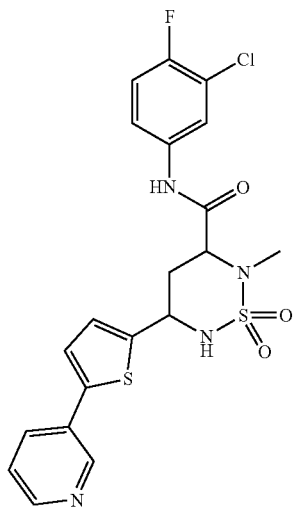

HBV-CSU-159

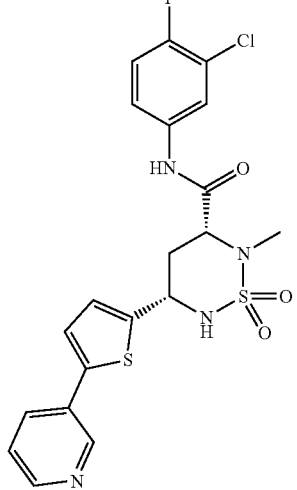

HBV-CSU-159-ISO-I


HBV-CSU-159-ISO-II

252

The above titled compounds have been synthesized by following the general procedure described above for Suzuki coupling by using HBV-CSU-114 and corresponding boronic acid (see Table 2 for analytical data).

Cis-N-(3-chloro-4-fluorophenyl)-2-methyl-5-(5-(pyridin-2-yl)thiophen-2-yl)-1,2,6-thiadiazinane-3-carboxamide 1,1-dioxide (HBV-CSU-160, HBV-CSU-160-ISO-I & HBV-CSU-160-ISO-II)

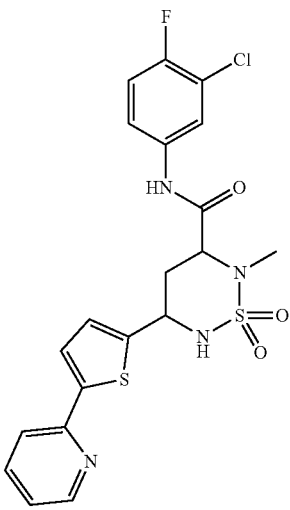

HBV-CSU-160

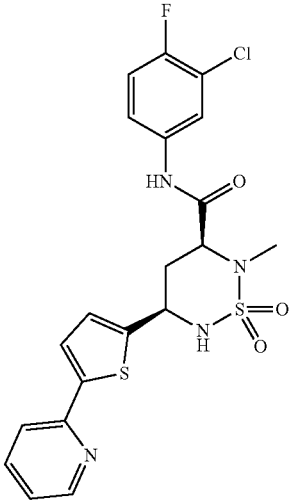

HBV-CSU-160-ISO-I

253

-continued

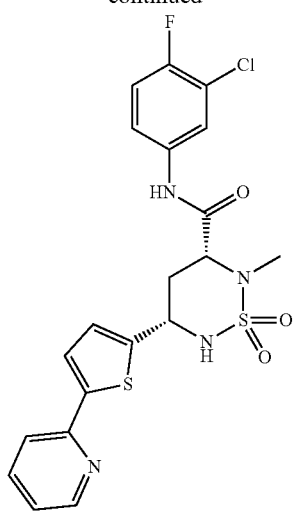

HBV-CSU-160-ISO-II

The above titled compounds have been synthesized by following the general procedure described above for Stille coupling by using HBV-CSU-114 and corresponding stannane (see Table 2 for analytical data).

Cis-N-(3-chloro-4-fluorophenyl)-2-methyl-5-(5-(1-methyl-1H-pyrazol-4-yl)thiophen-2-yl)-1,2,6-thiadiazinane-3-carboxamide 1,1-dioxide (HBV-CSU-161, HBV-CSU-161-ISO-I & HBV-CSU-161-ISO-II)

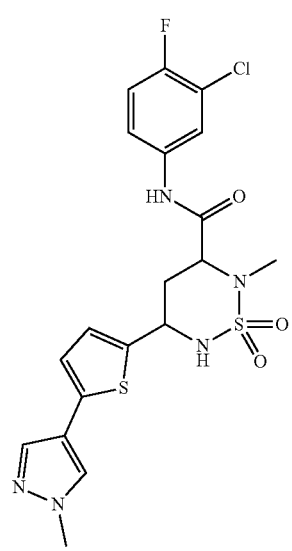

HBV-CSU-161

254

-continued

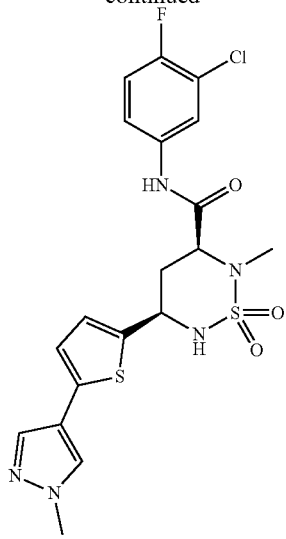

HBV-CSU-161-ISO-I

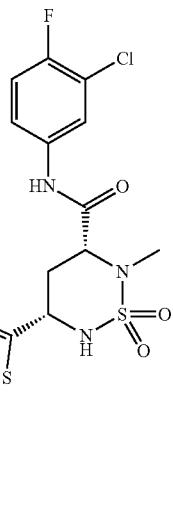

HBV-CSU-161-ISO-II

The above titled compounds have been synthesized by following the general procedure described above for Suzuki coupling by using HBV-CSU-114 and corresponding boronic acid (see Table 2 for analytical data).

255

Cis-N-5-([2,2'-bithiophen]-5-yl)-N-(3-chloro-4-fluorophenyl)-2-methyl-1,2,6-thiadiazinane-3-carboxamide 1,1-dioxide (HBV-CSU-162, HBV-CSU-162-ISO-I & HBV-CSU-162-ISO-II)

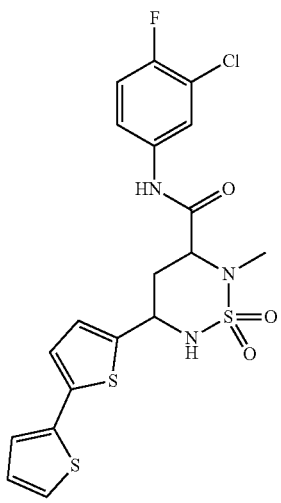

HBV-CSU-162

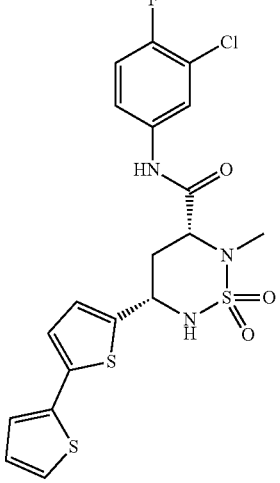

HBV-CSU-162-ISO-II

The above titled compounds have been synthesized by following the general procedure described above for Suzuki coupling by using HBV-CSU-114 and corresponding boronic acid (see Table 2 for analytical data).

Cis-N-(3-chloro-4-fluorophenyl)-2-methyl-5-(5-(4-(methylsulfonamido)phenyl)thiophen-2-yl)-1,2,6-thiadiazinane-3-carboxamide 1,1-dioxide (HBV-CSU-163, HBV-CSU-163-ISO-I & HBV-CSU-163-ISO-II)

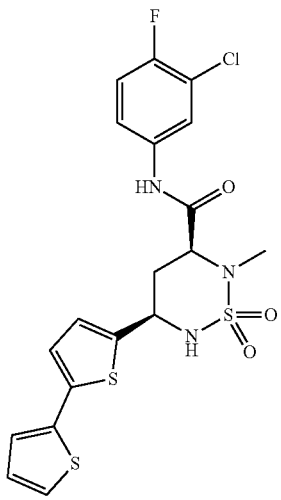

HBV-CSU-162-ISO-I

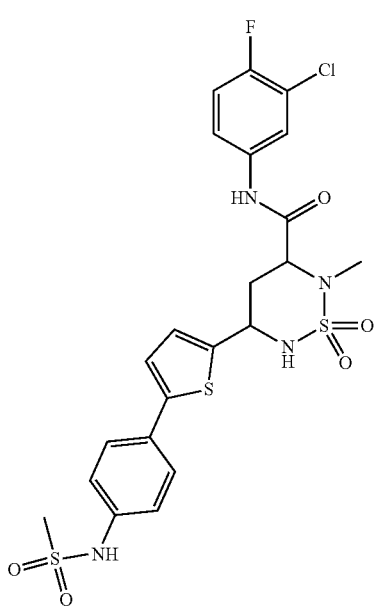

HBV-CSU-163

257

-continued

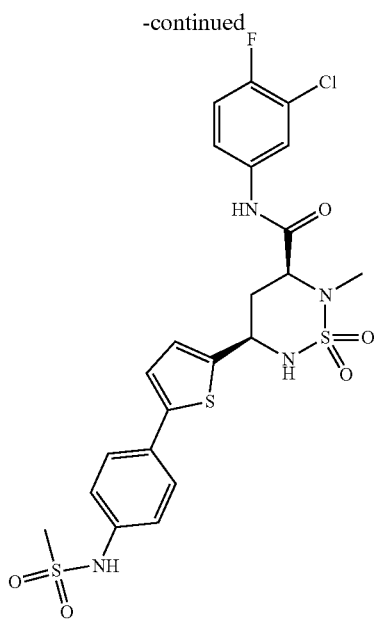

HBV-CSU-163-ISO-I

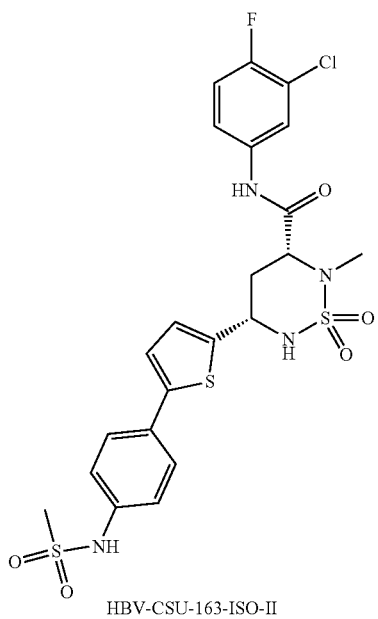

HBV-CSU-163-ISO-II

The above titled compounds have been synthesized by following the general procedure described above for Suzuki coupling by using HBV-CSU-114 and corresponding boronic acid (see Table 2 for analytical data).

258

Cis-N-(3-chloro-4-fluorophenyl)-5-(5-(2-(dimethyl-amino)ethoxy)thiophen-2-yl)-2-methyl-1,2,6-thiadi-azinane-3-carboxamide 1,1-dioxide (HBV-CSU-188)

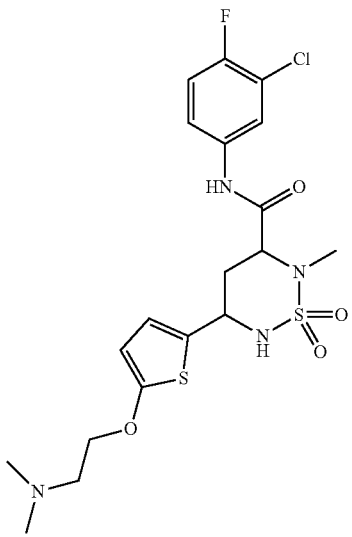

HBV-CSU-188

In a sealed tube, dimethyl amino ethanol (462 mg, 5.188 mmol) was taken in THF (10 mL), sodium metal (114.8 mg, 5.188 mmol) was added at 0° C. and stirred at room temperature for 30 min. To this reaction mixture, HBV-CSU-114 (500 mg, 1.0374 mmol) and CuBr (14.8 mg, 0.1037 mmol) were added and heated to 100° C. for overnight. The progress of reaction was monitored by TLC. After completion, the reaction mixture was quenched with saturated ammonium chloride and extracted with ethyl acetate. The combined organic layer was dried over anhydrous sodium sulphate, filtered and concerted under reduced pressure to afford the crude product which was purified by column chromatography to give of desired pure compound (12 mg, 2%) as a solid (see Table 2 for analytical data).

Cis-N-(3-Bromo-4-fluorophenyl)-5-(5-bromothio-phen-2-yl)-2-methyl-1,2,6-thiadiazinane-3-carbox-amide 1,1-dioxide (HBV-CSU-257)

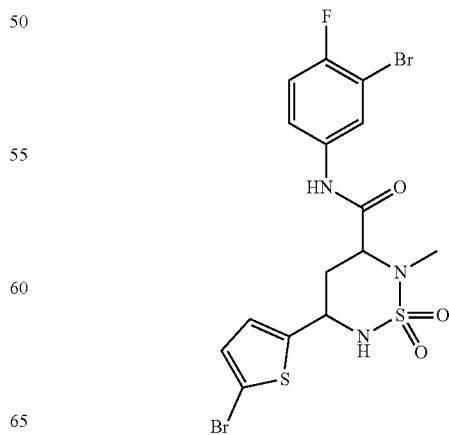

The above titled compound has been synthesized by following the general procedure described above for reduction by using HBV-CSU-257-Int-1 (see Table 2 for analytical data).

Cis-N-(3-chloro-4-fluorophenyl)-2-methyl-5-(5-(1-methyl-1H-pyrazol-5-yl)thiophen-2-yl)-1,2,6-thiadiazinane-3-carboxamide 1,1-dioxide (HBV-CSU-271, HBV-CSU-271-ISO-I & HBV-CSU-271-ISO-II)

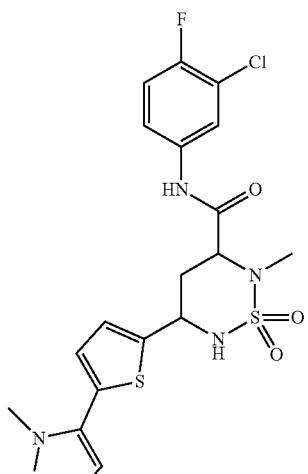

HBV-CSU-271

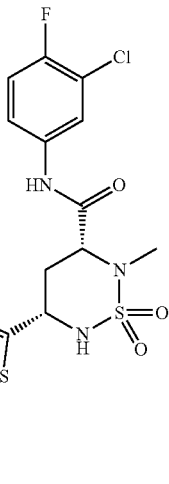

HBV-CSU-271-ISO-II

The above titled compounds have been synthesized by following the general procedure described above for Stille coupling by using HBV-CSU-114 and corresponding boronic acid (see Table 2 for analytical data).

Cis-N-(3-chloro-4-fluorophenyl)-2-methyl-5-(5-(pyrimidin-5-yl)thiophen-2-yl)-1,2,6-thiadiazinane-3-carboxamide 1,1-dioxide (HBV-CSU-272, HBV-CSU-272-ISO-I & HBV-CSU-272-ISO-II)

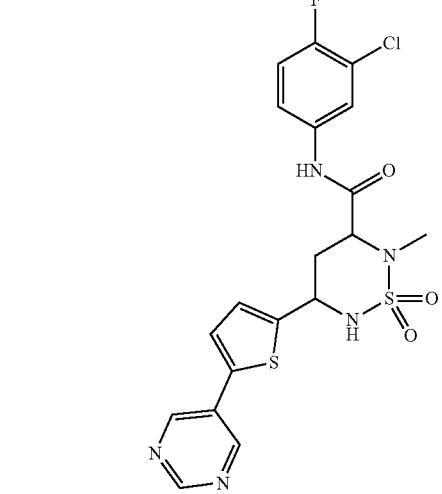

HBV-CSU-272

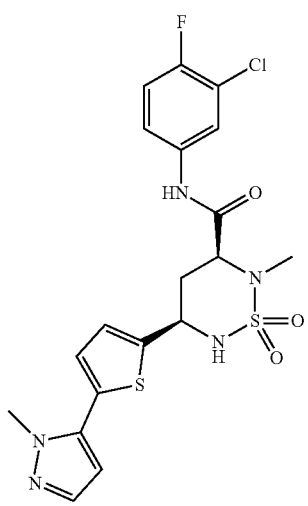

HBV-CSU-271-ISO-I

261

-continued

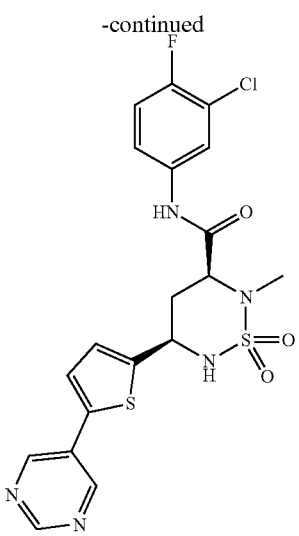

HBV-CSU-272-ISO-I

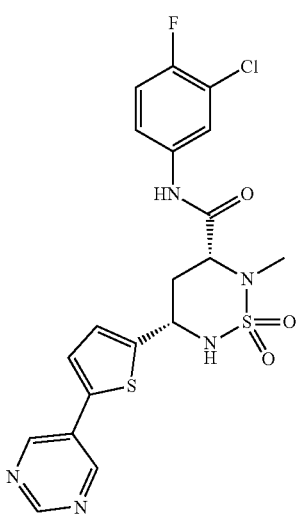

HBV-CSU-272-ISO-II

The above titled compounds have been synthesized by following the general procedure described above for Stille coupling by using HBV-CSU-114 and corresponding boronic acid (see Table 2 for analytical data).

262

Cis-N-(3-chloro-4-fluorophenyl)-5-(5-(1-ethyl-1H-pyrazol-4-yl)thiophen-2-yl)-2-methyl-1,2,6-thiadiazinane-3-carboxamide 1,1-dioxide (HBV-CSU-291, HBV-CSU-291-ISO-I & HBV-CSU-291-ISO-II)

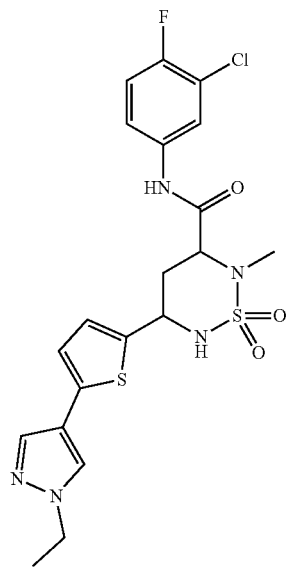

HBV-CSU-291

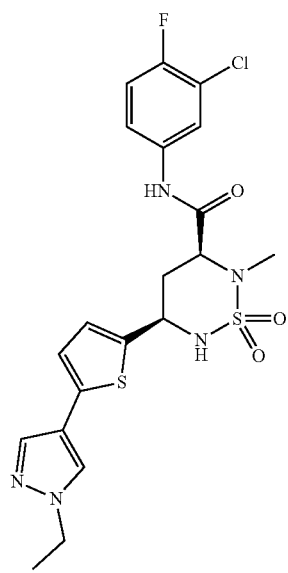

HBV-CSU-291-ISO-I


HBV-CSU-291-ISO-II

The above titled compounds have been synthesized by following the general procedure described above for Stille coupling by using HBV-CSU-114 and corresponding boronic acid (see Table 2 for analytical data).

Cis-N-(3-chloro-4-fluorophenyl)-5-(5-(1-isopropyl-1H-pyrazol-4-yl)thiophen-2-yl)-2-methyl-1,2,6-thiadiazinane-3-carboxamide 1,1-dioxide (HBV-CSU-292, HBV-CSU-292-ISO-I & HBV-CSU-292-ISO-II)

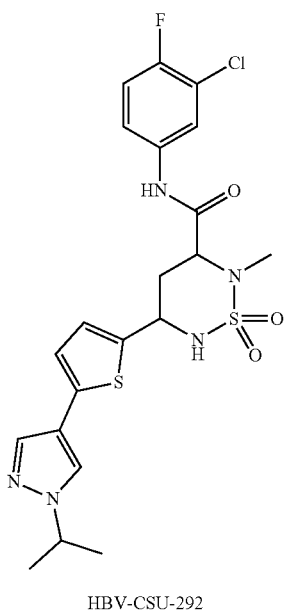

HBV-CSU-292

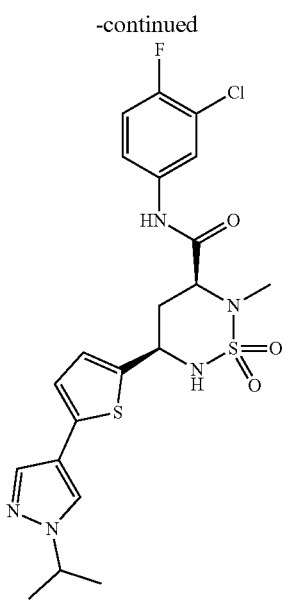

HBV-CSU-292-ISO-I

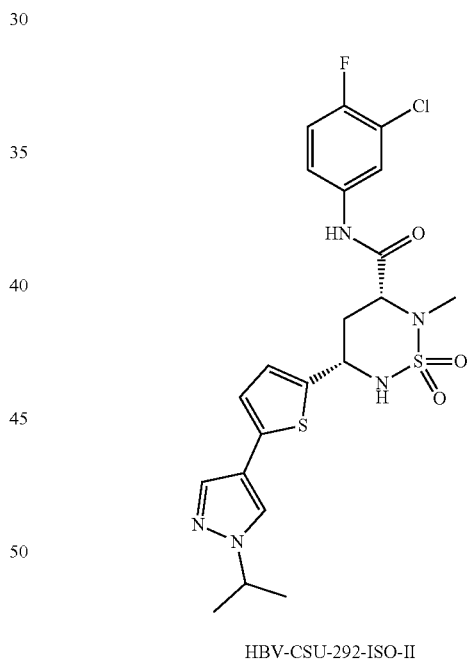

HBV-CSU-292-ISO-II

The above titled compounds have been synthesized by following the general procedure described above for Stille coupling by using HBV-CSU-114 and corresponding boronic acid (see Table 2 for analytical data).

Cis-N-(3-chloro-4-fluorophenyl)-5-(5-(1-(2-hydroxyethyl)-1H-pyrazol-4-yl)thiophen-2-yl)-2-methyl-1,2,6-thiadiazinane-3-carboxamide 1,1-dioxide (HBV-CSU-293, HBV-CSU-293-ISO-I & HBV-CSU-293-ISO-II)

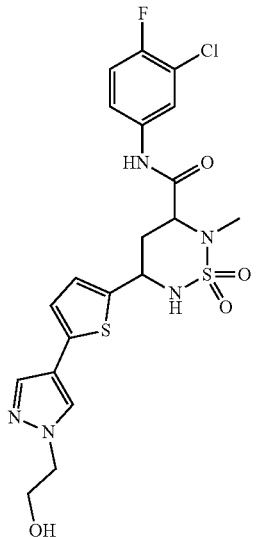

HBV-CSU-293

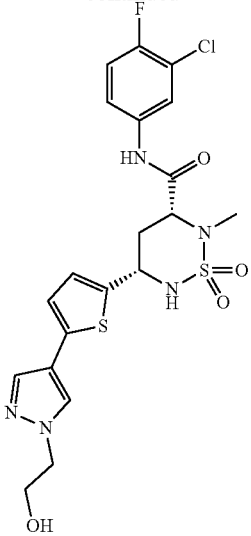

HBV-CSU-293-ISO-II

The above titled compounds have been synthesized by following the general procedure described above for Stille coupling by using HBV-CSU-114 and corresponding boronic acid (see Table 2 for analytical data).

Cis-N-(3-chloro-4-fluorophenyl)-5-(5-(1,5-dimethyl-1H-pyrazol-4-yl)thiophen-2-yl)-2-methyl-1,2,6-thiadiazinane-3-carboxamide 1,1-dioxide (HBV-CSU-312, HBV-CSU-312-ISO-I & HBV-CSU-312-ISO-II)

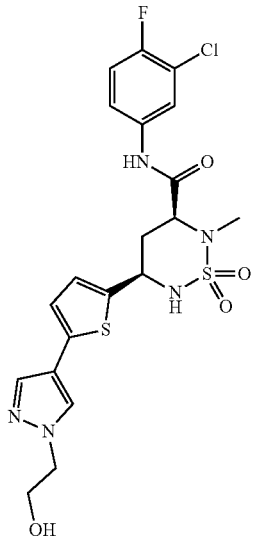

HBV-CSU-293-ISO-I

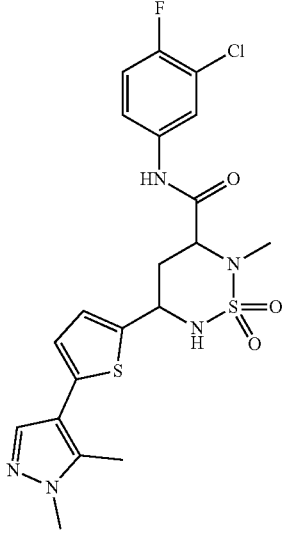

HBV-CSU-312

267

-continued

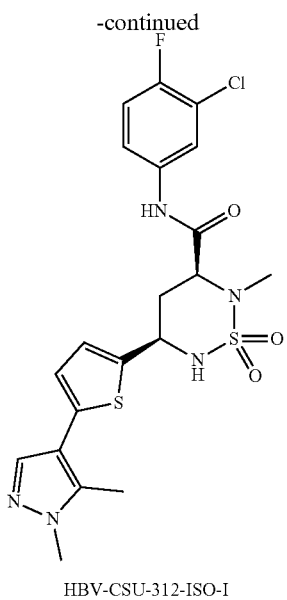

HBV-CSU-312-ISO-I

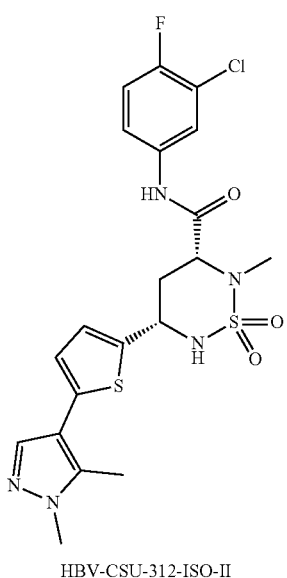

HBV-CSU-312-ISO-II

The above titled compounds have been synthesized by following the general procedure described above for Stille coupling by using HBV-CSU-114 and corresponding boronic acid (see Table 2 for analytical data).

268

Cis-N-(3-chloro-4-fluorophenyl)-5-(5-(1,3-dimethyl-1H-pyrazol-4-yl)thiophen-2-yl)-2-methyl-1,2,6-thiadiazinane-3-carboxamide 1,1-dioxide (HBV-CSU-313, HBV-CSU-313-ISO-I & HBV-CSU-313-ISO-II)

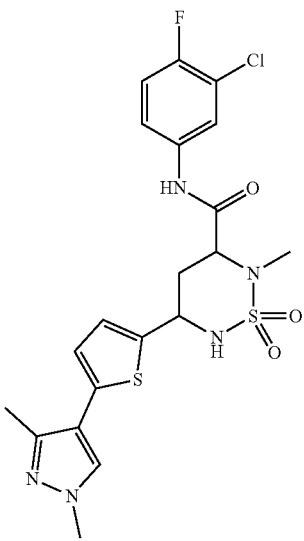

HBV-CSU-313

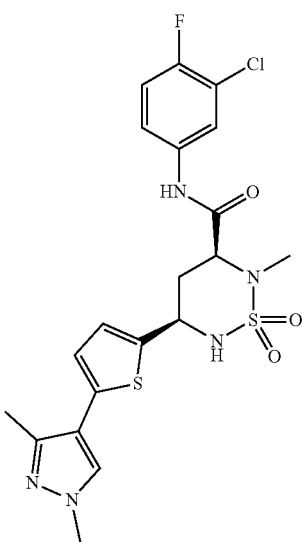

HBV-CSU-313-ISO-I

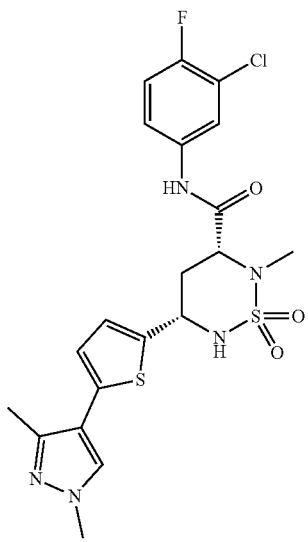

HBV-CSU-313-ISO-II

The above titled compounds have been synthesized by following the general procedure described above for Stille coupling by using HBV-CSU-114 and corresponding boronic acid (see Table 2 for analytical data).

Cis-N-(3-chloro-4-fluorophenyl)-2-methyl-5-(5-(1,3,5-trimethyl-1H-pyrazol-4-yl)thiophen-2-yl)-1,2,6-thiadiazinane-3-carboxamide 1,1-dioxide (HBV-CSU-314-ISO-I & HBV-CSU-314-ISO-II)

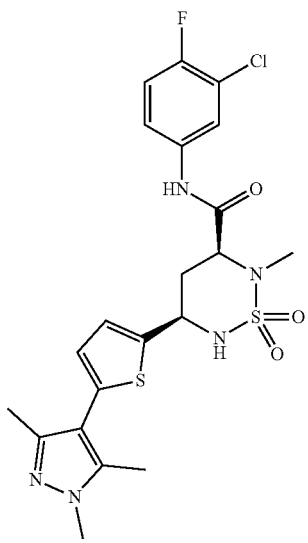

HBV-CSU-314-ISO-I

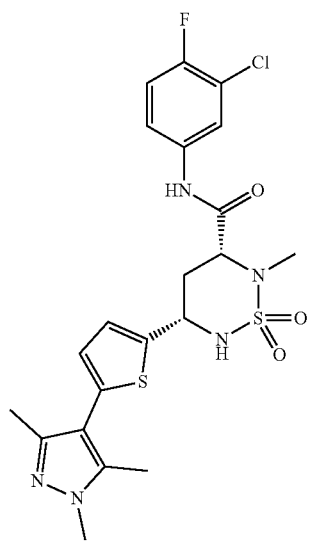

HBV-CSU-314-ISO-II

The above titled compounds have been synthesized by following the general procedure described above for Stille coupling by using HBV-CSU-114 and corresponding boronic acid (see Table 2 for analytical data).

Cis-N-(3-Chloro-4-fluorophenyl)-2-methyl-5-(5-(1-(trifluoromethyl)-1H-pyrazol-4-yl)thiophen-2-yl)-1,2,6-thiadiazinane-3-carboxamide 1,1-dioxide (HBV-CSU-321-ISO-I & HBV-CSU-321-ISO-II)

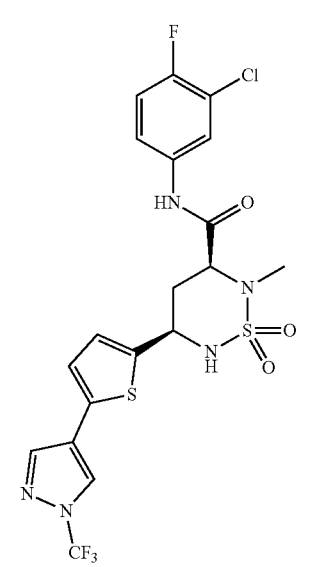

HBV-CSU-321-ISO-I

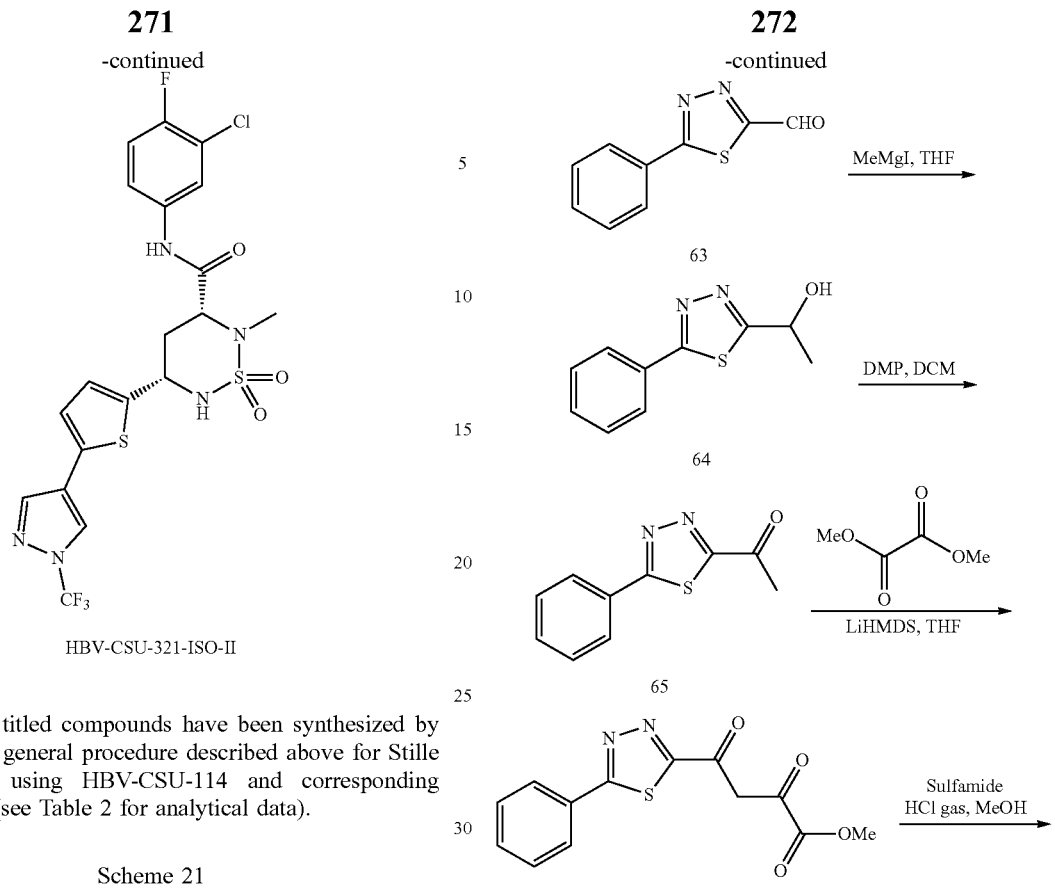

HBV-CSU-321-ISO-II

The above titled compounds have been synthesized by following the general procedure described above for Stille coupling by using HBV-CSU-114 and corresponding boronic acid (see Table 2 for analytical data).

Scheme 21

Synthesis of Cis-N-(3-chloro-4-fluorophenyl)-2-methyl-5-(5-phenyl-1,3,4-thiadiazol-2-yl)-1,2,6-thiadiazinane-3-carboxamide 1,1-dioxide (HBV-CSU-120, HBV-CSU-120-ISO-I & HBV-CSU-120-ISO-II)

Scheme 21:

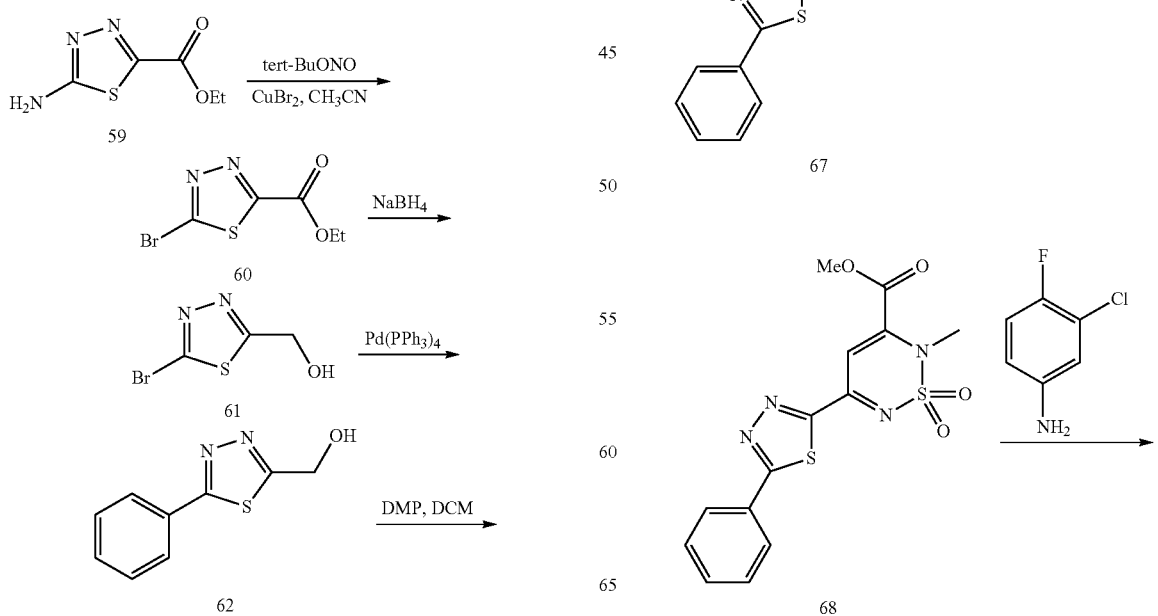

-continued

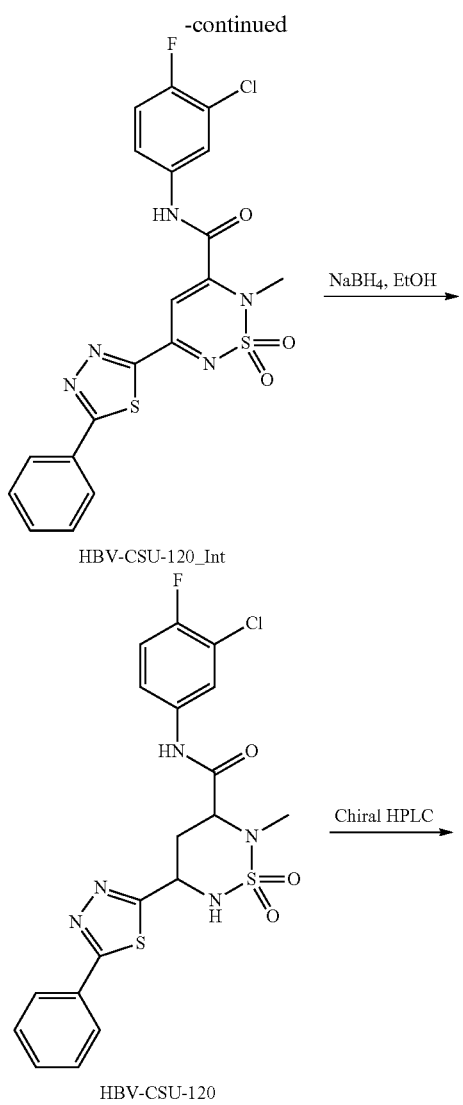

HBV-CSU-120_Int

↓ NaBH₄, EtOH

HBV-CSU-120

→ Chiral HPLC

HBV-CSU-120-ISO-I
+
HBV-CSU-120-ISO-II

Synthesis of ethyl
5-bromo-1,3,4-thiadiazole-2-carboxylate (60)

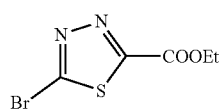

To a stirred solution of compound 59 (21 g, 121.38 mmol) in ACN (400 mL), CuBr₂ (53.3 g, 239.01 mmol) was added and stirred at room temperature for 15 min. To this solution, tert-butyl nitrite (24.65 g, 239.04 mmol) was added drop wise over a period of 20 min. The resulting reaction mixture was stirred at room temperature for 30 min. and then heated at 60° C. for 30 min. The progress of the reaction was monitored by TLC. After completion, the reaction mixture was diluted with water; ethyl acetate and filtered through Celite bed. The organic layer was separated; washed with brine; dried over anhydrous sodium sulfate, filtered and concentrated in vacuo to afford the title compound 60 (25 g, 87.40%) as a yellow solid. TLC: 20% EtOAc/hexane ($R_f$: 0.7); ¹H NMR (400 MHz, DMSO-$d_6$): δ 4.45-4.40 (m, 2H), 1.34 (t, J=6.8 Hz, 3H).

Synthesis of
(5-bromo-1,3,4-thiadiazol-2-yl)methanol (61)

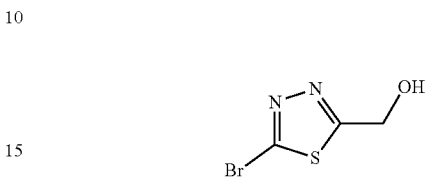

To a stirred solution of compound 60 (25 g, 105.96 mmol) in MeOH (250 mL) at 0° C., NaBH₄ (12 g, 317.20 mmol) was added portion wise and stirred at room temperature for 16 h. The progress of the reaction was monitored by TLC. After completion, the reaction mixture was quenched with acetic acid (5 mL); diluted with water and extracted with ethyl acetate. The combined organic layers were washed with sat. NaHCO₃ solution; dried over anhydrous sodium sulfate, filtered and concentrated in vacuo to obtain crude. The crude was purified through silica gel column chromatography using 15% EtOAc/hexanes to afford compound 61 (15 g, 73%) as yellow solid. TLC: 40% EtOAc/hexanes ($R_f$: 0.3); ¹H NMR (400 MHz, DMSO-$d_6$): δ 6.39 (t, J=6.0 Hz, 1H), 4.85-4.83 (s, 2H); LCMS Calculated for $C_3H_3BrN_2OS$: 193.91; Observed: 194.90 (M+1)⁺.

Synthesis of
(5-phenyl-1,3,4-thiadiazol-2-yl)methanol (62)

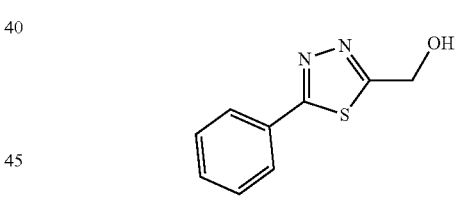

To a mixture of bromo compound 61 (3 g, 15.54 mmol) and phenylboronic acid (2.27 g, 18.65 mmol) in toluene: EtOH (1:1, 160 mL) mixture, 2M Na₂CO₃ solution (4.92 g, 46.41 mmol) was added and purged with Ar for 30 min. To this solution, Pd(PPh₃)₄ (0.890 g, 0.77 mmol) was added and the reaction mixture was stirred at 100° C. for 3 h. The progress of the reaction was monitored by TLC. After completion, the reaction mixture was filtered through Celite bed and filtrate was concentrated in vacuo. The residue was diluted with water and extracted with ethyl acetate. The combined organic layers were washed brine; dried over anhydrous sodium sulfate, filtered and concentrated in vacuo to obtain crude. The crude was purified through silica gel column chromatography using 15% EtOAc/hexanes to afford compound 62 as yellow solid. Same reaction was carried out on 2×3 g scale to afford 11 g of desired compound. TLC: 50% EtOAc/hexanes ($R_f$: 0.5); LCMS Calculated for $C_9H_8N_2OS$: 192.04; Observed: 192.95 (M+1)⁺.

Synthesis of 5-phenyl-1,3,4-thiadiazole-2-carbaldehyde (63)

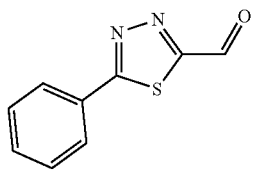 [SMILES: O=Cc1nnc(-c2ccccc2)s1]

To a stirred solution of compound 62 (11 g, 57.29 mmol) in DCM (330 mL), Dess-Martin periodinane (36.47 g, 85.98 mmol) was added. The resulting reaction mixture was stirred at room temperature for 3 h. The reaction was monitored by TLC. After completion of the reaction, the reaction mixture was quenched by adding sat. NaHCO$_3$ solution; sat. sodium thiosulphate solution and extracted with ethyl acetate. The combined organic extracts were dried over anhydrous sodium sulfate, filtered and concentrated in vacuo to obtain the crude. The crude was purified through silica gel column chromatography using 5% EtOAc/hexanes to afford compound 63 (8 g, 73.5%) as an off white solid. TLC: 50% EtOAc/hexanes (R$_f$: 0.4); $^1$H NMR (400 MHz, DMSO-d$_6$): δ 10.18 (s, 1H), 8.12-8.10 (m, 1H), 7.67-7.55 (m, 4H).

Synthesis of 1-(5-phenyl-1,3,4-thiadiazol-2-yl)ethan-1-ol (64)

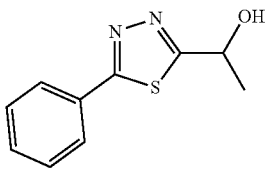

To a stirred solution of compound 63 (8 g, 42.10 mmol) in dry THF (80 mL) at 0° C., under inert atmosphere, methyl magnesium iodide (3M, 42 mL, 126.70 mmol) was added dropwise. The resulting reaction mixture was stirred at room temperature for 2 h. The reaction was monitored by TLC. After completion of the reaction, the reaction mixture was quenched with saturated ammonium chloride solution and extracted with ethyl acetate. The combined organic extracts were dried over anhydrous sodium sulfate, filtered and concentrated in vacuo to obtain the crude. The crude was purified through silica gel column chromatography using 20% EtOAc/hexanes to afford compound 64 (0.5 g, 76.53%) as white solid. TLC: 40% EtOAc/hexanes (R$_f$: 0.2); $^1$H NMR (400 MHz, DMSO-d$_6$): δ 7.97-7.95 (m, 2H), 7.56-7.54 (m, 3H), 6.41 (d, J=4.8 Hz, 1H), 5.15-5.12 (m, 1H), 1.50-1.40 (m, 3H); LCMS Calculated for C$_{10}$H$_{10}$N$_2$OS: 206.05; Observed: 206.90 (M+1)$^+$.

Synthesis of 1-(5-phenyl-1,3,4-thiadiazol-2-yl)ethan-1-one (65)

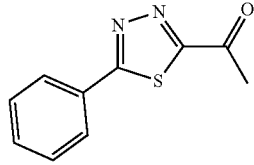

To a stirred solution of compound 64 (7 g, 33.98 mmol) in DCM (70 mL), Dess-Martin periodinane (27.37 g, 64.56 mmol) was added. The resulting reaction mixture was stirred at room temperature for 3 h. The reaction was monitored by TLC. After completion of the reaction, the reaction mixture was quenched by adding sat. NaHCO$_3$ solution; sat. sodium thiosulphate solution and extracted with ethyl acetate. The combined organic extracts were dried over anhydrous sodium sulfate, filtered and concentrated in vacuo to obtain the crude. The crude was purified through silica gel column chromatography using 5% EtOAc/hexanes to afford compound 65 (3.2 g, 43.24%) as an off white solid. TLC: 20% EtOAc/hexanes (R$_f$: 0.4); $^1$H NMR (400 MHz, DMSO-d$_6$): δ 8.08-8.05 (m, 2H), 7.62-7.54 (m, 3H), 2.73 (m, 3H); LCMS Calculated for C$_{10}$H$_8$N$_2$OS: 204.04; Observed: 204.95 (M+1)$^+$.

Synthesis of methyl 2,4-dioxo-4-(5-phenyl-1,3,4-thiadiazol-2-yl)butanoate (66)

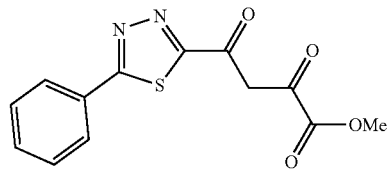 [SMILES: COC(=O)C(=O)CC(=O)c1nnc(-c2ccccc2)s1]

Title compound was synthesized using general method for the synthesis of 2,4-diketoester described above to afford 4.44 g (crude, reaction scale is 3.13 g) as a light brown solid. TLC: 40% EtOAc/hexanes (R$_f$: 0.1); LCMS Calculated for C$_{13}$H$_{10}$N$_2$O$_4$S: 290.04; Observed: 290.95 (M+1)$^+$.

Synthesis of methyl 5-(5-phenyl-1,3,4-thiadiazol-2-yl)-2H-1,2,6-thiadiazine-3-carboxylate 1,1-dioxide (67)

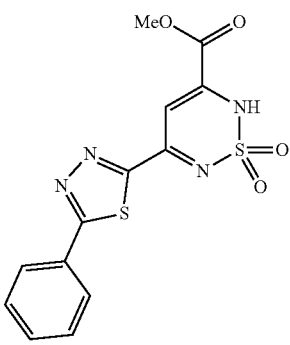 [SMILES: COC(=O)C1=CC(c2nnc(-c3ccccc3)s2)=NS(=O)(=O)N1]

Title compound was synthesized using general method B for the synthesis of cyclic sulfonamide described above to afford 1.2 g (24.89%, reaction scale is 4 g) as a light brown solid. $^1$H NMR (DMSO-d$_6$, 400 MHz): δ 8.07-8.04 (m, 2H), 7.61-7.55 (m, 3H), 6.93 (s, 1H), 3.82 (s, 3H); LCMS Calculated for C$_{13}$H$_{10}$N$_4$O$_4$S$_2$: 350.01; LCMS observed: 351 (M+1)$^+$.

Synthesis of methyl 2-methyl-5-(5-phenyl-1,3,4-thiadiazol-2-yl)-2H-1,2,6-thiadiazine-3-carboxylate 1,1-dioxide (68)

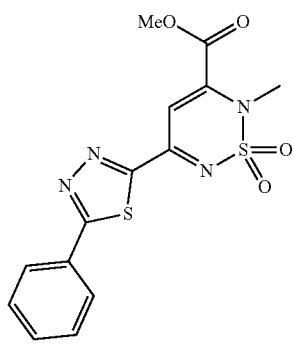 [SMILES: COC(=O)C1=CC(c2nnc(-c3ccccc3)s2)=NS(=O)(=O)N1C]

Title compound was synthesized using general method B for alkylation described above to afford 1 g (96.15%, reaction scale is 1 g) as a light yellow solid. TLC: 40% EtOAc/hexanes (R$_f$: 0.3).

Synthesis of N-(3-chloro-4-fluorophenyl)-2-methyl-5-(5-phenyl-1,3,4-thiadiazol-2-yl)-2H-1,2,6-thiadiazine-3-carboxamide 1,1-dioxide (HBV-CSU-120_Int)

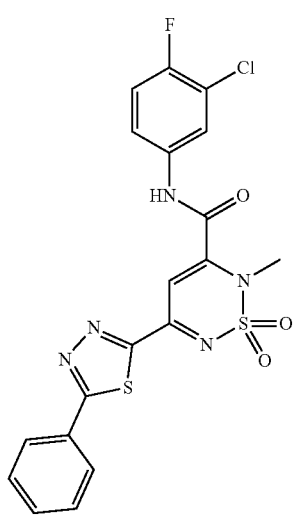 [SMILES: CN1C(C(=O)Nc2ccc(F)c(Cl)c2)=CC(c2nnc(-c3ccccc3)s2)=NS1(=O)=O]

The above titled compound has been synthesized by following the general procedure (Method A) described above for amidation by using compound 68 and corresponding amine (see Table 1 for analytical data).

Cis-N-(3-Chloro-4-fluorophenyl)-2-methyl-5-(5-phenyl-1,3,4-thiadiazol-2-yl)-1,2,6-thiadiazinane-3-carboxamide 1,1-dioxide (HBV-CSU-120, HBV-CSU-120-ISO-I & HBV-CSU-120-ISO-II)

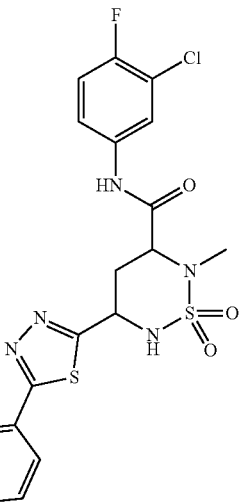

HBV-CSU-120

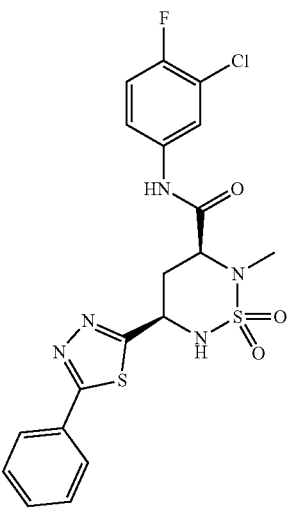

HBV-CSU-120-ISO-I

-continued

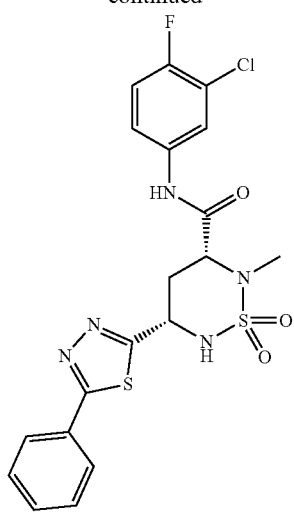

HBV-CSU-120-ISO-II

The above titled compounds have been synthesized by following the general procedure described above for reduction by using corresponding HBV-CSU-120_Int (see Table 2 for analytical data).

Scheme 22

General Synthetic Scheme for 5-(thiazol-2-yl)-1,2,6-thiadiazinane-3-carboxamide 1,1-dioxide Derivatives with 5-Substituted Thiazole Variations Scheme 22:

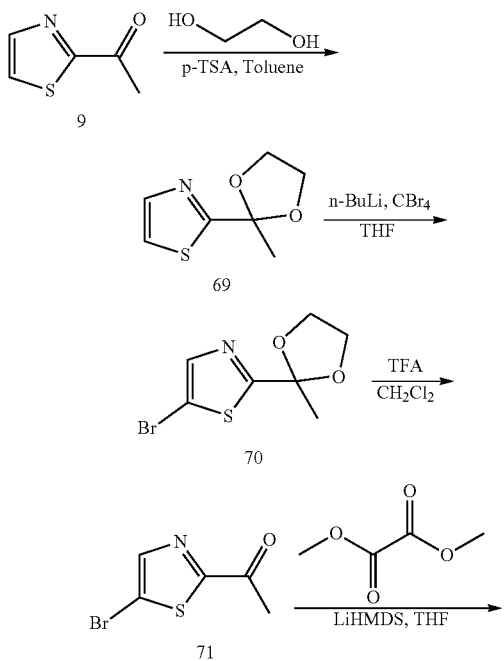

-continued


72

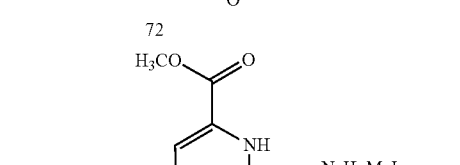

73

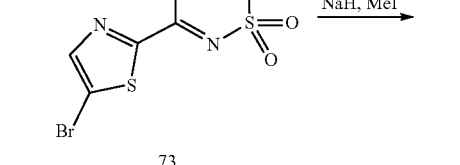

74

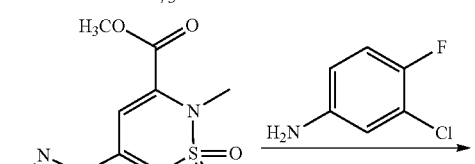

HBV-CSU-122-Int

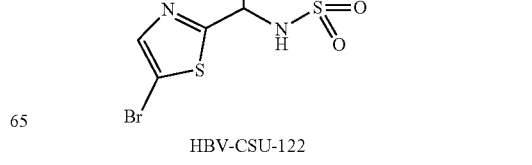

HBV-CSU-122

-continued

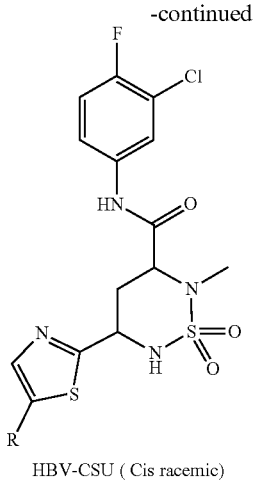

HBV-CSU (Cis racemic) →(Chiral separation) ISO-I & ISO-II

| Target | Coupling reaction | #2 (R variation) |
|---|---|---|
| HBV-CSU-122 | — | Br |
| HBV-CSU-124 | Suzuki coupling | phenyl |
| HBV-CSU-173 | Suzuki coupling | 2-fluoro-4-bromophenyl |
| HBV-CSU-175 | Suzuki coupling | pyridin-3-yl |
| HBV-CSU-176 | Stille coupling | pyridin-2-yl |
| HBV-CSU-177 | Suzuki coupling | 1-methyl-1H-pyrazol-4-yl |
| HBV-CSU-178 | Suzuki coupling | thiophen-2-yl |
| HBV-CSU-179 | Suzuki coupling | 4-(methylsulfonylamino)phenyl |
| HBV-CSU-248 | Suzuki coupling | 4-fluorophenyl |
| HBV-CSU-250 | Suzuki coupling | 4-methoxyphenyl |

-continued

| Target | Coupling reaction | #2 (R variation) |
|---|---|---|
| HBV-CSU-252 | Stille coupling | 5-fluoropyridin-2-yl |
| HBV-CSU-254 | Suzuki coupling | 1H-pyrazol-4-yl |
| HBV-CSU-276 | Stille coupling | 1-methyl-1H-imidazol-2-yl |
| HBV-CSU-277 | Stille coupling | 1-methyl-1H-imidazol-5-yl |
| HBV-CSU-278 | Stille coupling | thiazol-5-yl |
| HBV-CSU-280 | Suzuki coupling | 1-methyl-1H-pyrazol-3-yl |
| HBV-CSU-281 | Suzuki coupling | 1-methyl-1H-pyrazol-5-yl |

Synthesis of 2-(2-methyl-1,3-dioxolan-2-yl)thiazole (69)

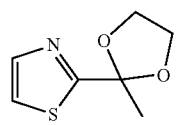

To a stirred solution of 1-(thiazol-2-yl) ethan-1-one 9 (13 g, 102.36 mmol) in Toluene (250 mL) under inert atmosphere were added ethane-1,2-diol (5.71 mL, 153.54 mmol) and p-toluene sulfonic acid (1.16 g, 6.14 mmol) at room temperature, followed by heating to 120° C. using a dean stark apparatus, and stirring for 24 h. The reaction was monitored by TLC. After completion, volatiles were removed in vacuo to obtain the crude. The crude was diluted with $CH_2Cl_2$ (300 mL) and washed with 10% $NaHCO_3$ solution (100 mL). The organic extract was dried over anhydrous sodium sulfate and concentrated in vacuo to afford compound 69 (13 g, 74%) as a yellow liquid. TLC: 10% EtOAc/hexanes ($R_f$: 0.5); $^1$H NMR (DMSO-$d_6$, 400 MHz): δ 7.80 (d, J=3.1 Hz, 1H), 7.71 (d, J=3.2 Hz, 1H), 4.08-4.01 (m, 2H), 4.00-3.93 (m, 2H), 1.71 (s, 3H); LCMS Calculated for $C_7H_9NO_2S$: 171.04; Observed: 171.8 $(M+1)^+$.

Synthesis of 5-bromo-2-(2-methyl-1,3-dioxolan-2-yl)thiazole (70)

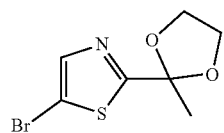

To a stirred solution of compound 69 (17 g, 99.41 mmol) in anhydrous THF (275 mL) under inert atmosphere was added n-butyl lithium (39.7 mL, 99.4 mmol) dropwise for 15 min at −78° C. and, followed by stirring for 1 h. To this was added carbon tetra bromide (33 g, 99.4 mmol) in anhydrous THF (75 mL) dropwise for 20 min at −78° C., followed by warming to 0° C. and stirring for 30 min. The reaction was monitored by TLC. After completion of the reaction, the reaction mixture was quenched with saturated ammonium chloride solution (50 mL) and extracted with EtOAc (3×500 mL). The combined organic extracts were dried over anhydrous sodium sulfate, filtered and concentrated in vacuo to obtain the crude. The crude was purified through silica gel column chromatography using 3% EtOAc/hexanes to afford compound 70 (15 g, 60%) as brown liquid. TLC: 10% EtOAc/hexanes ($R_f$: 0.8); $^1$H NMR (DMSO-$d_6$, 400 MHz): δ 7.88 (s, 1H), 4.07-4.01 (m, 2H), 4.00-3.93 (m, 2H), 1.68 (s, 3H); LCMS Calculated for $C_7H_4BrNO_2S$: 248.95; Observed: 249.8 (M+1)$^+$.

Synthesis of 1-(5-bromothiazol-2-yl) ethan-1-one (71)

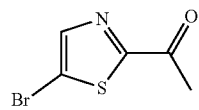

To a stirred solution of compound 70 (15 g, 60.24 mmol) in a mixture of $CH_2Cl_2$ (150 mL) and $H_2O$ (5 mL) was added trifluoroacetic anhydride (150 mL, 10 V) at 0° C., followed by warming to room temperature and stirring for 36 h. The reaction was monitored by TLC. After completion of the reaction, the volatiles were removed in vacuo. The crude was diluted with $CH_2Cl_2$ (500 mL) then washed with 10% aqueous $NaHCO_3$ solution (150 mL). The organic extract was dried over anhydrous sodium sulfate, filtered, and concentrated in vacuo to obtain the crude compound 71 (10.5 g, 85%) as brown solid. TLC: 10% EtOAc/hexanes ($R_f$: 0.8); $^1$H-NMR (DMSO-$d_6$, 400 MHz): δ 8.21 (s, 1H), 2.60 (s, 3H); LCMS Calculated for $C_5H_4BrNOS$: 204.92; Observed: 208.0 (M+2)$^+$.

Synthesis of methyl 4-(5-bromothiazol-2-yl)-2,4-dioxobutanoate (72)

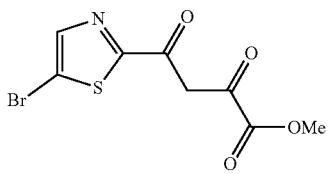 [SMILES: COC(=O)C(=O)CC(=O)c1ncc(Br)s1]

Title compound was synthesized using general method for the synthesis of 2,4-diketoester described above to afford 7.5 g (50%, reaction scale is 10.5 g) as off-white solid. TLC: 5% MeOH/$CH_2Cl_2$ ($R_f$: 0.4); $^1$H NMR (400 MHz, DMSO-$d_6$): δ 8.27 (s, 1H), 7.00 (br.s, 1H), 3.84 (s, 3H); LCMS Calculated for $C_8H_6BrNO_4S$: 290.92; Observed: 294.0 (M+2)$^+$.

Synthesis of methyl 5-(5-bromothiazol-2-yl)-2H-1,2,6-thiadiazine-3-carboxylate 1,1-dioxide (73)

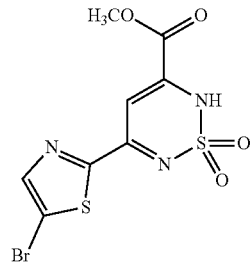 [SMILES: COC(=O)C1=CC(c2ncc(Br)s2)=NS(=O)(=O)N1]

Title compound was synthesized using general method for the synthesis of cyclic sulfonamide described above to afford 4 g (44%, reaction scale is 7.5 g) as pale brown solid. TLC: 10% MeOH/$CH_2Cl_2$ ($R_f$: 0.3); $^1$H NMR (400 MHz, DMSO-$d_6$): δ 8.02 (s, 1H), 6.77 (s, 1H), 3.79 (s, 3H); LCMS Calculated for $C_8H_6BrN_3O_4S_2$: 350.90; Observed: 349.8 (M−1)$^+$.

Synthesis of methyl 5-(5-bromothiazol-2-yl)-2-methyl-2H-1,2,6-thiadiazine-3-carboxylate 1,1-dioxide (74)

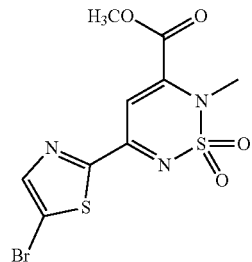 [SMILES: COC(=O)C1=CC(c2ncc(Br)s2)=NS(=O)(=O)N1C]

Title compound was synthesized using general procedure for alkylation (Method A) described above to afford 2 g (48%, reaction scale is 4 g) as an off-white solid. TLC: 30% EtOAc/hexanes ($R_f$: 0.8); $^1$H NMR (500 MHz, DMSO-$d_6$): δ 8.34 (s, 1H), 7.37 (s, 1H), 3.94 (s, 3H), 3.59 (s, 3H).

Synthesis of 5-(5-bromothiazol-2-yl)-N-(3-chloro-4-fluorophenyl)-2-methyl-2H-1,2,6-thiadiazine-3-carboxamide 1,1-dioxide (HBV-CSU-122_Int/HBV-CSU-435)

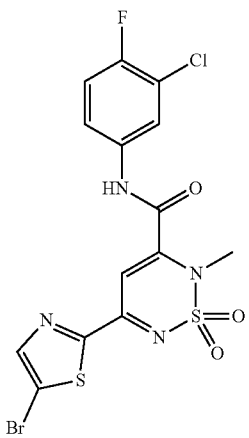

HBV-CSU-122-Int

The above titled compound has been synthesized by following the general procedure (Method B) described above for amidation by using Compound 74 and corresponding amine (see Table 1 for analytical data).

Cis-5-(5-bromothiazol-2-yl)-N-(3-chloro-4-fluorophenyl)-2-methyl-1,2,6-thiadiazinane-3-carboxamide 1,1-dioxide (HBV-CSU-122, HBV-CSU-122-ISO-I & HBV-CSU-122-ISO-II)

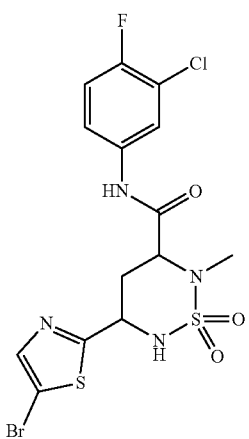

HBV-CSU-122

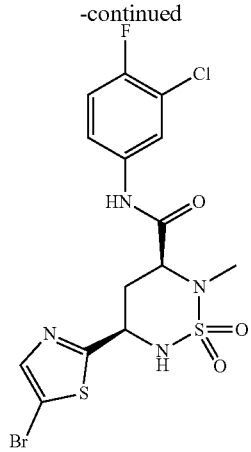

HBV-CSU-122-ISO-I

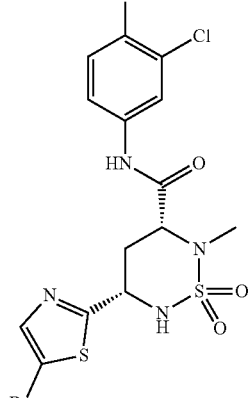

HBV-CSU-122-ISO-II

The above titled compounds have been synthesized by following the general procedure described above for reduction by using corresponding HBV-CSU-222_Int/HBV-CSU-435 (see Table 2 for analytical data).

Cis-5-(5-Bromothiazol-2-yl)-N-(3-chloro-4-fluorophenyl)-2-methyl-1,2,6-thiadiazinane-3-carboxamide 1,1-dioxide (HBV-CSU-124, HBV-CSU-124-I & HBV-CSU-124-II)

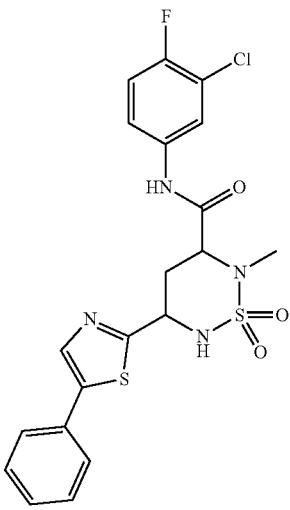

HBV-CSU-124

287

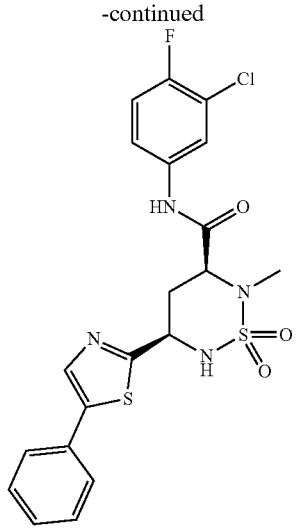

HBV-CSU-124-ISO-I

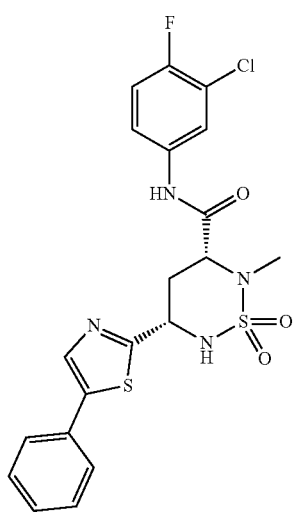

HBV-CSU-124-ISO-II

The above titled compounds have been synthesized by following the general procedure described above for Suzuki coupling by using HBV-CSU-122 and corresponding boronic acid (see Table 2 for analytical data).

288

Cis-5-(5-(4-Bromo-3-fluorophenyl)thiazol-2-yl)-N-(3-chloro-4-fluorophenyl)-2-methyl-1,2,6-thiadiazinane-3-carboxamide 1,1-dioxide (HBV-CSU-173, HBV-CSU-173-ISO-I & HBV-CSU-173-ISO-II)

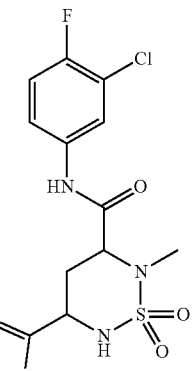

HBV-CSU-173

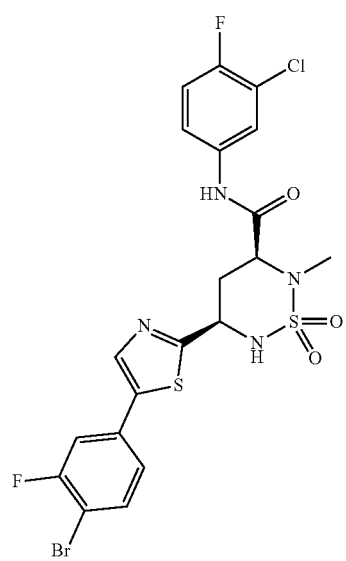

HBV-CSU-173-ISO-I

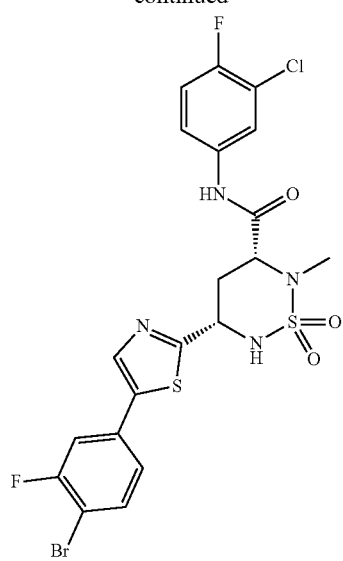

HBV-CSU-173-ISO-II

The above titled compounds have been synthesized by following the general procedure described above for Suzuki coupling by using HBV-CSU-122 and corresponding boronic acid (see Table 2 for analytical data).

Cis-N-(3-Chloro-4-fluorophenyl)-2-methyl-5-(5-(pyridin-3-yl)thiazol-2-yl)-1,2,6-thiadiazinane-3-carboxamide 1,1-dioxide (HBV-CSU-175, HBV-CSU-175-ISO-I & HBV-CSU-175-ISO-II)

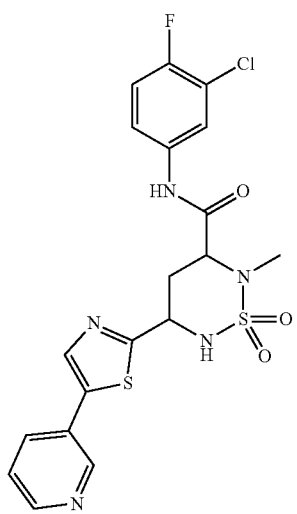

HBV-CSU-175

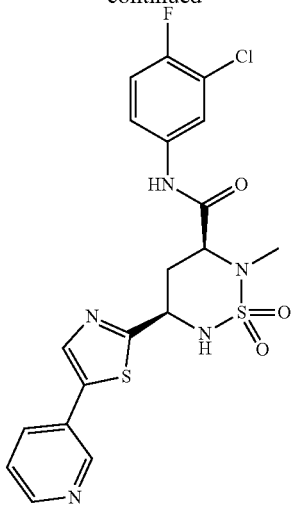

HBV-CSU-175-ISO-I

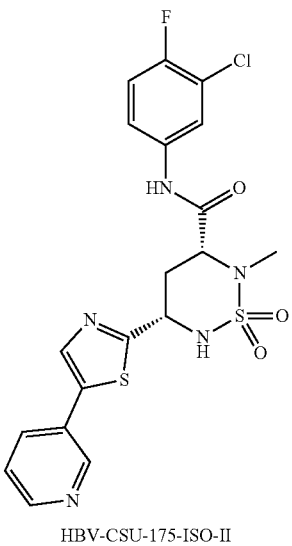

HBV-CSU-175-ISO-II

The above titled compounds have been synthesized by following the general procedure described above for Suzuki coupling by using HBV-CSU-122 and corresponding boronic acid (see Table 2 for analytical data).

291

Cis-N-(3-chloro-4-fluorophenyl)-2-methyl-5-(5-(pyridin-2-yl)thiazol-2-yl)-1,2,6-thiadiazinane-3-carboxamide 1,1-dioxide (HBV-CSU-176, HBV-CSU-176-ISO-I & HBV-CSU-176-ISO-II)

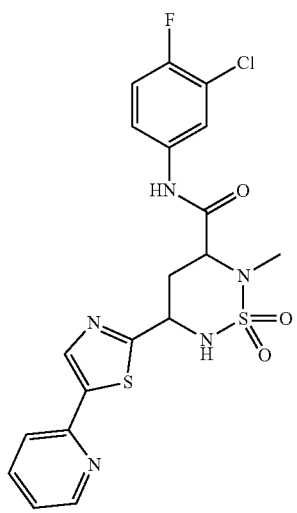

HBV-CSU-176

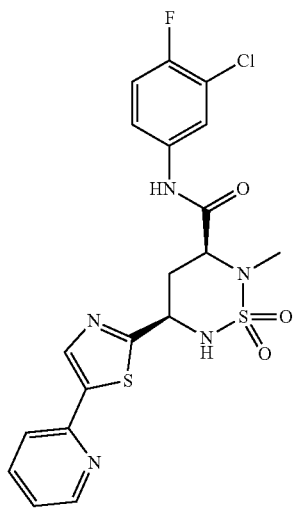

HBV-CSU-176-ISO-I

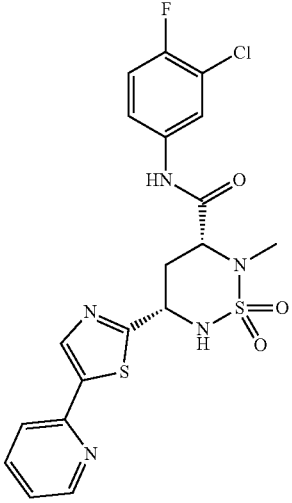

HBV-CSU-176-ISO-II

The above titled compounds have been synthesized by following the general procedure described above for Stille coupling by using HBV-CSU-122 and corresponding stannane (see Table 2 for analytical data).

Note: Stannane reagent was synthesized as per following protocol:

To a stirred solution of 2-bromopyridine (1 g, 6.32 mmol) in anhydrous THF (10 mL) under inert atmosphere was added n-butyl lithium (4.2 mL, 6.32 mmol, 1.6 M solution in hexanes) at −78° C. followed by stirring for 1 h. To this was added tributyltin chloride (1.71 mL, 6.32 mmol) drop wise for 10 min at −78° C., which was then stirred at the same temperature for 2 h, then warmed to room temperature and stirred for 2 h. The reaction was monitored by TLC. After completion of the reaction, the reaction mixture was quenched with saturated ammonium chloride (30 mL) and extracted with EtOAc (3×50 mL). The combined organic extracts were dried over anhydrous sodium sulfate, filtered and concentrated in vacuo to obtain the crude stannane compound (2 g) as yellow syrup. The crude was carried forward for next step without further purification. TLC: 10% EtOAc/hexanes ($R_f$: 0.5).

293

Cis-N-(3-Chloro-4-fluorophenyl)-2-methyl-5-(5-(1-methyl-1H-pyrazol-4-yl)thiazol-2-yl)-1,2,6-thiadiazinane-3-carboxamide 1,1-dioxide (HBV-CSU-177, HBV-CSU-177-ISO-I & HBV-CSU-177-ISO-II)

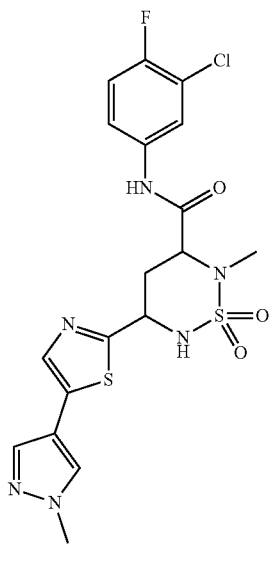

HBV-CSU-177

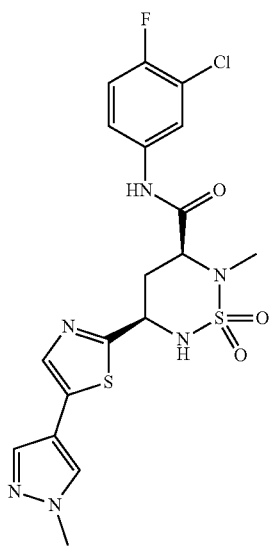

HBV-CSU-177-ISO-I

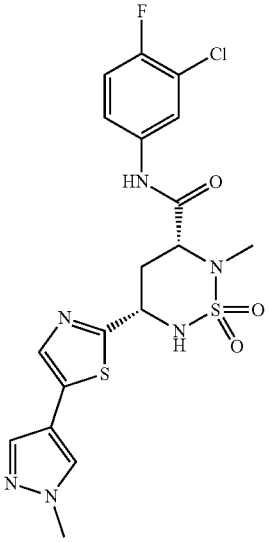

HBV-CSU-177-ISO-II

The above titled compounds have been synthesized by following the general procedure described above for Suzuki coupling by using HBV-CSU-122 and corresponding boronic acid (see Table 2 for analytical data).

Cis-N-(3-Chloro-4-fluorophenyl)-2-methyl-5-(5-(thiophen-2-yl)thiazol-2-yl)-1,2,6-thiadiazinane-3-carboxamide 1,1-dioxide (HBV-CSU-178, HBV-CSU-178-ISO-I & HBV-CSU-178-ISO-II)

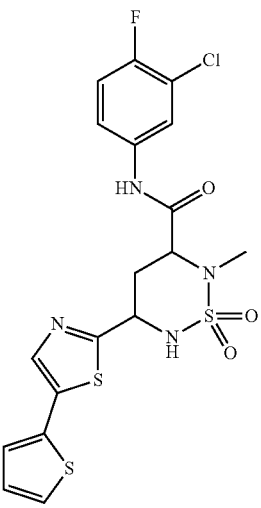

HBV-CSU-178

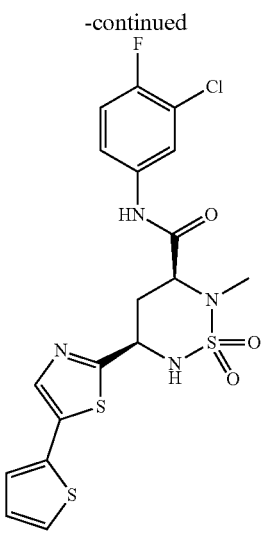

HBV-CSU-178-ISO-I

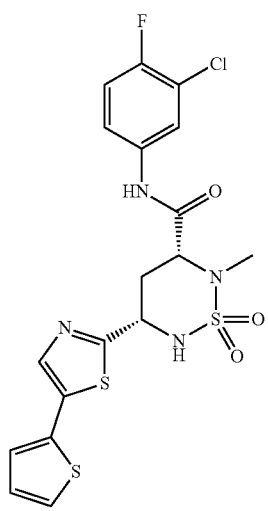

HBV-CSU-178-ISO-II

The above titled compounds have been synthesized by following the general procedure described above for Suzuki coupling by using HBV-CSU-122 and corresponding boronic acid (see Table 2 for analytical data).

Cis-N-(3-Chloro-4-fluorophenyl)-2-methyl-5-(5-(4-(methylsulfonamido)phenyl)thiazol-2-yl)-1,2,6-thiadiazinane-3-carboxamide 1,1-dioxide (HBV-CSU-179, HBV-CSU-179-ISO-I & HBV-CSU-179-ISO-II)

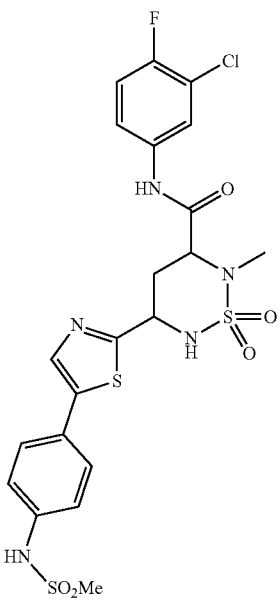

HBV-CSU-178

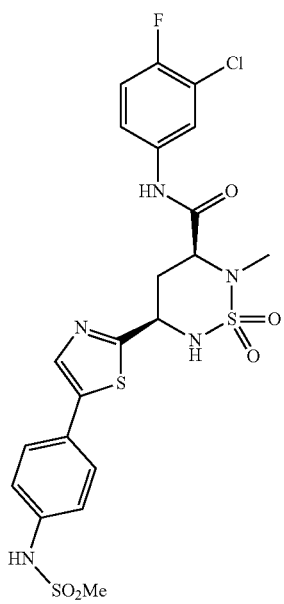

HBV-CSU-178-ISO-I

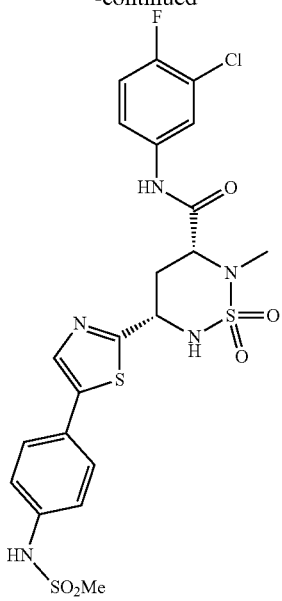

HBV-CSU-178-ISO-II

The above titled compounds have been synthesized by following the general procedure described above for Suzuki coupling by using HBV-CSU-122 and corresponding boronic acid (see Table 2 for analytical data).

Cis-N-(3-Chloro-4-fluorophenyl)-5-(5-(4-fluorophenyl)thiazol-2-yl)-2-methyl-1,2,6-thiadiazinane-3-carboxamide 1,1-dioxide (HBV-CSU-248, HBV-CSU-248-ISO-I & HBV-CSU-248-ISO-II)

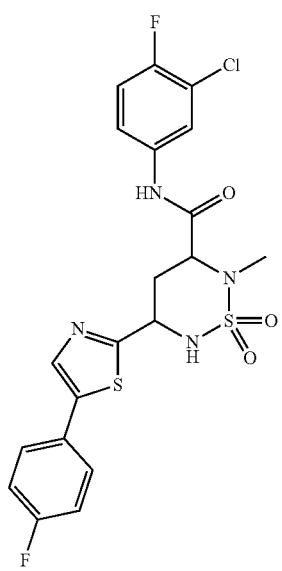

HBV-CSU-248

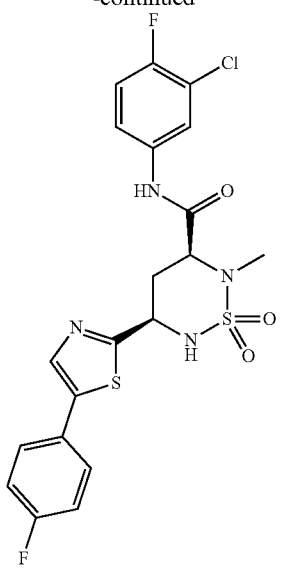

HBV-CSU-248-ISO-I

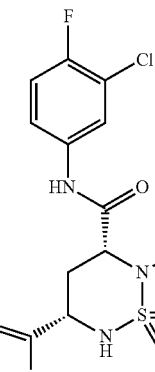

HBV-CSU-248-ISO-II

The above titled compounds have been synthesized by following the general procedure described above for Suzuki coupling by using HBV-CSU-122 and corresponding boronic acid (see Table 2 for analytical data).

299

Cis-N-(3-Chloro-4-fluorophenyl)-5-(5-(4-methoxyphenyl)thiazol-2-yl)-2-methyl-1,2,6-thiadiazinane-3-carboxamide 1,1-dioxide (HBV-CSU-250, HBV-CSU-250-ISO-I & HBV-CSU-250-ISO-II)

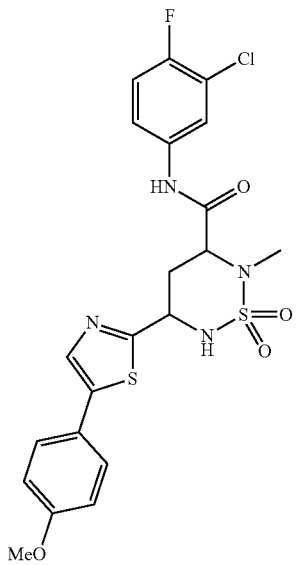

HBV-CSU-250

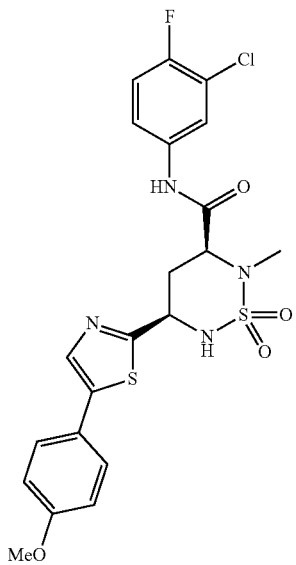

HBV-CSU-250-ISO-I

300

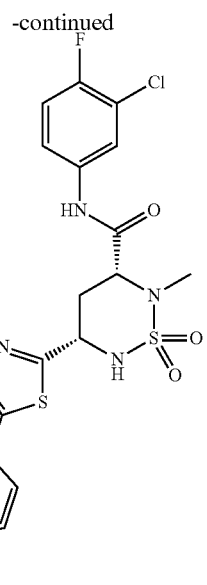

HBV-CSU-ISO-250-II

The above titled compounds have been synthesized by following the general procedure described above for Suzuki coupling by using HBV-CSU-122 and corresponding boronic acid (see Table 2 for analytical data).

Cis-N-(3-Chloro-4-fluorophenyl)-5-(5-(5-fluoropyridin-2-yl)thiazol-2-yl)-2-methyl-1,2,6-thiadiazinane-3-carboxamide 1,1-dioxide (HBV-CSU-252, HBV-CSU-252-ISO-I & HBV-CSU-252-ISO-II)

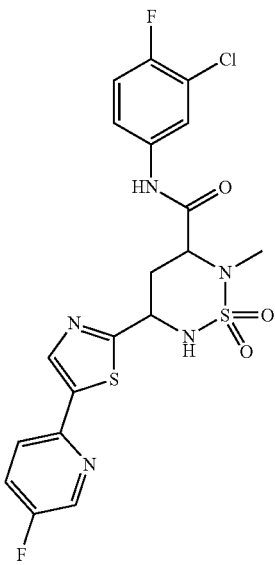

HBV-CSU-252

-continued

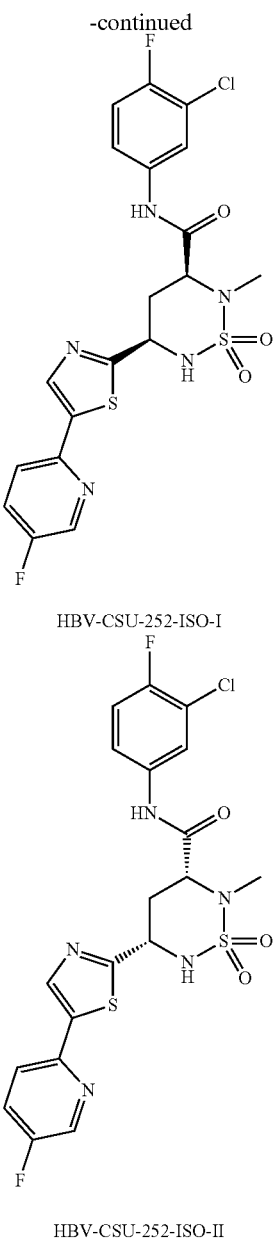

HBV-CSU-252-ISO-I

HBV-CSU-252-ISO-II

The above titled compounds have been synthesized by following the general procedure described above for Stille coupling by using HBV-CSU-122 and corresponding stannane (see Table 2 for analytical data).

Note: Stannane reagent was synthesized as per following protocol:

To a stirred solution of 2-bromo-5-fluoropyridine (300 mg, 1.71 mmol) in anhydrous Toluene (10 mL) under inert atmosphere was added n-butyl lithium (1.28 mL, 2.05 mmol, 1.6 M solution in hexanes) at −78° C. and stirred for 1 h. To this was added tributyltin chloride (0.55 mL, 2.05 mmol) drop wise for 5 min at −78° C., which was warmed to 0° C. and stirred for 1.5 h. The reaction was monitored by TLC. After completion of the reaction, the reaction mixture was quenched with saturated ammonium chloride (30 mL) and extracted with EtOAc (3×50 mL). The combined organic extracts were washed with water (75 mL), brine (75 mL), then dried over anhydrous sodium sulfate, filtered, and concentrated in vacuo to obtain the crude stannane compound (1 g) as a colorless liquid. The crude was carried forward for next step without further purification. TLC: 5% EtOAc/hexanes (R$_f$: 0.8)

5   Cis-5-(5-(1H-pyrazol-4-yl)thiazol-2-yl)-N-(3-chloro-4-fluorophenyl)-2-methyl-1,2,6-thiadiazinane-3-carboxamide 1,1-dioxide (HBV-CSU-254, HBV-CSU-254-ISO-I & HBV-CSU-254-ISO-II)

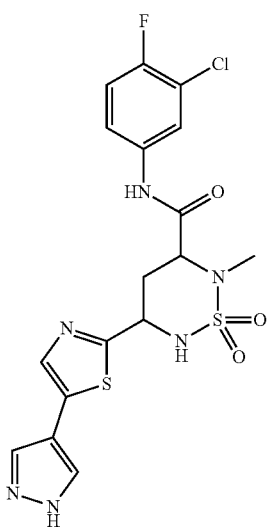

HBV-CSU-254

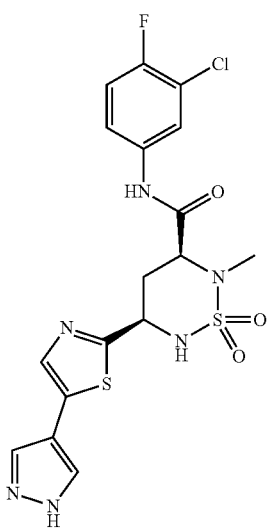

HBV-CSU-254-ISO-I

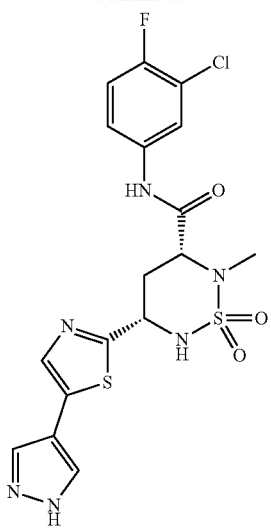

HBV-CSU-254-ISO-II

The above titled compounds have been synthesized by following the general procedure described above for Suzuki coupling by using HBV-CSU-122 and corresponding boronic acid (see Table 2 for analytical data).

Cis-N-(3-Chloro-4-fluorophenyl)-2-methyl-5-(5-(1-methyl-1H-imidazol-4-yl)thiazol-2-yl)-1,2,6-thiadiazinane-3-carboxamide 1,1-dioxide (HBV-CSU-276, HBV-CSU-276-ISO-I & HBV-CSU-276-ISO-II)

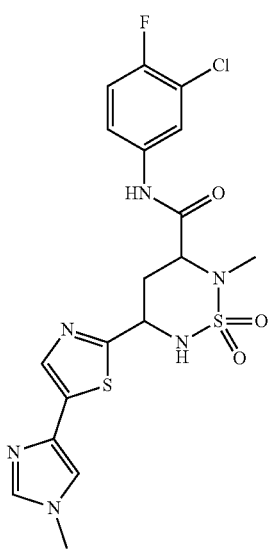

HBV-CSU-276

HBV-CSU-276-ISO-I

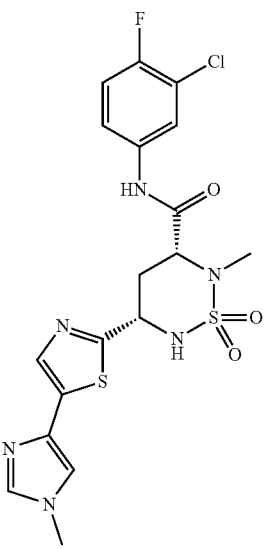

HBV-CSU-276-ISO-II

The above titled compounds have been synthesized by following the general procedure described above for Stille coupling by using HBV-CSU-122 and corresponding boronic acid (see Table 2 for analytical data).

Cis-N-(3-Chloro-4-fluorophenyl)-2-methyl-5-(5-(1-methyl-1H-imidazol-5-yl)thiazol-2-yl)-1,2,6-thiadiazinane-3-carboxamide 1,1-dioxide (HBV-CSU-277, HBV-CSU-277-ISO-I & HBV-CSU-277-ISO-II)

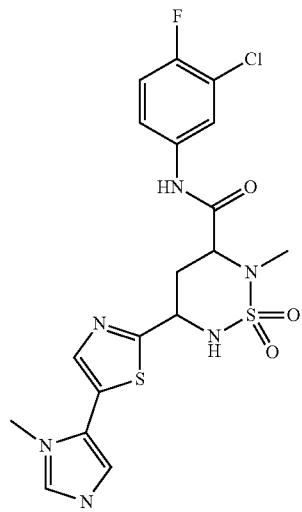

HBV-CSU-277

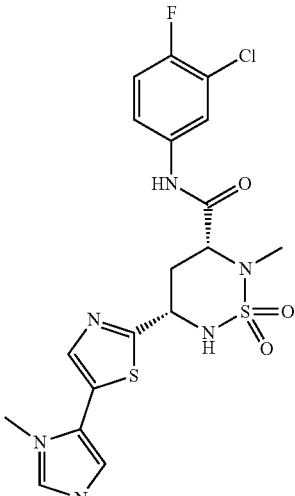

HBV-CSU-277-ISO-II

The above titled compounds have been synthesized by following the general procedure described above for Stille coupling by using HBV-CSU-122 and corresponding boronic acid (see Table 2 for analytical data).

Cis-5-([5,5'-Bithiazol]-2-yl)-N-(3-chloro-4-fluorophenyl)-2-methyl-1,2,6-thiadiazinane-3-carboxamide 1,1-dioxide (HBV-CSU-278, HBV-CSU-278-ISO-I & HBV-CSU-278-ISO-II)

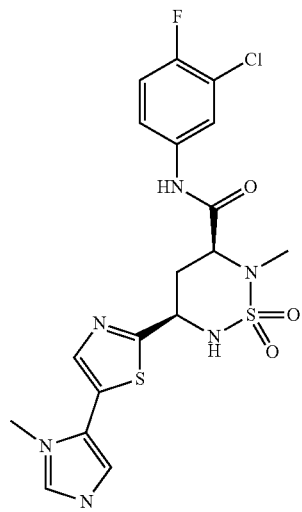

HBV-CSU-277-ISO-I

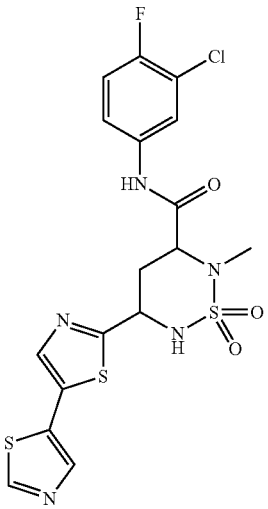

HBV-CSU-278

307

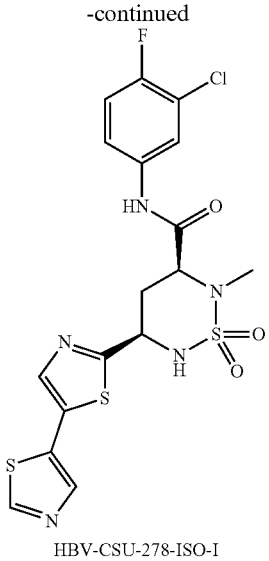

HBV-CSU-278-ISO-I

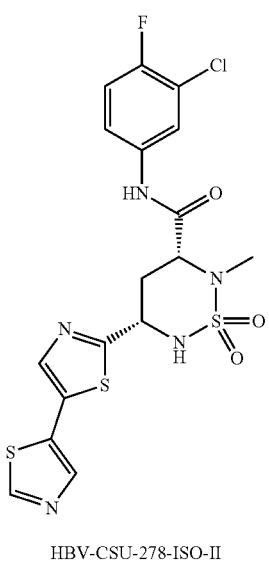

HBV-CSU-278-ISO-II

The above titled compounds have been synthesized by following the general procedure described above for Stille coupling by using HBV-CSU-122 and corresponding boronic acid (see Table 2 for analytical data).

308

Cis-N-(3-Chloro-4-fluorophenyl)-2-methyl-5-(5-(1-methyl-1H-pyrazol-3-yl)thiazol-2-yl)-1,2,6-thiadiazinane-3-carboxamide 1,1-dioxide (HBV-CSU-280, HBV-CSU-280-ISO-I & HBV-CSU-280-ISO-II)

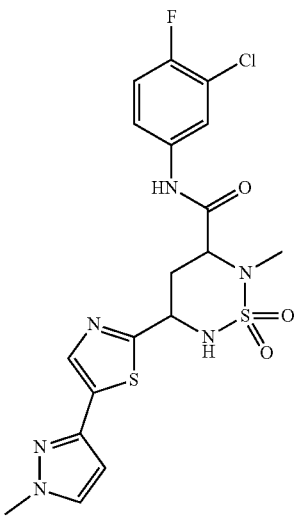

HBV-CSU-280

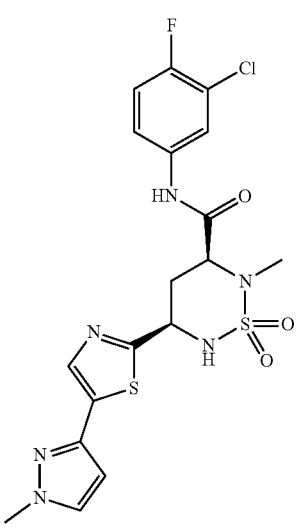

HBV-CSU-280-ISO-I

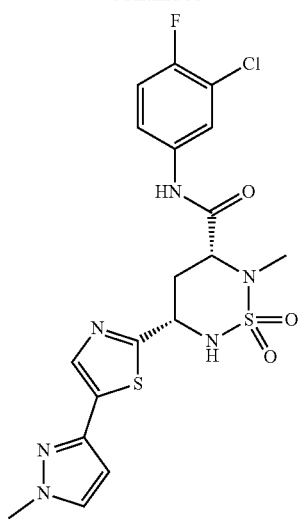

HBV-CSU-280-ISO-II

The above titled compounds have been synthesized by following the general procedure described above for Suzuki coupling by using HBV-CSU-122 and corresponding boronic acid (see Table 2 for analytical data).

Cis-N-(3-Chloro-4-fluorophenyl)-2-methyl-5-(5-(1-methyl-1H-pyrazol-5-yl)thiazol-2-yl)-1,2,6-thiadiazinane-3-carboxamide 1,1-dioxide (HBV-CSU-281, HBV-CSU-281-ISO-I & HBV-CSU-281-ISO-II)

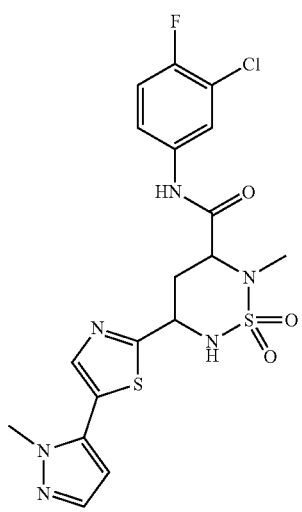

HBV-CSU-281

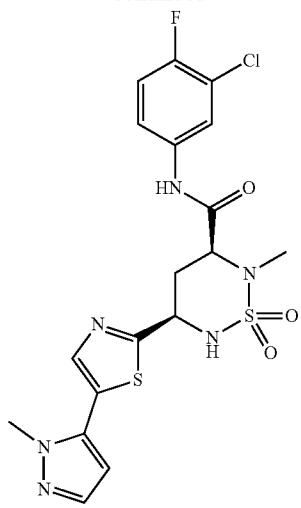

HBV-CSU-281-ISO-I

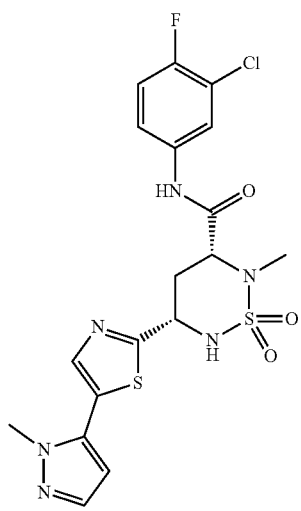

HBV-CSU-281-ISO-II

The above titled compounds have been synthesized by following the general procedure described above for Suzuki coupling by using HBV-CSU-122 and corresponding boronic acid (see Table 2 for analytical data).

Scheme 23

Synthesis of Cis-5-(5-bromothiazol-2-yl)-N-(3-chloro-4-fluorophenyl)-2-methyl-1,2,6-thiadiazinane-3-carboxamide 1,1-dioxide (HBV-CSU-123, HBV-CSU-123-ISO-I & HBV-CSU-123-ISO-II)

Scheme 23:

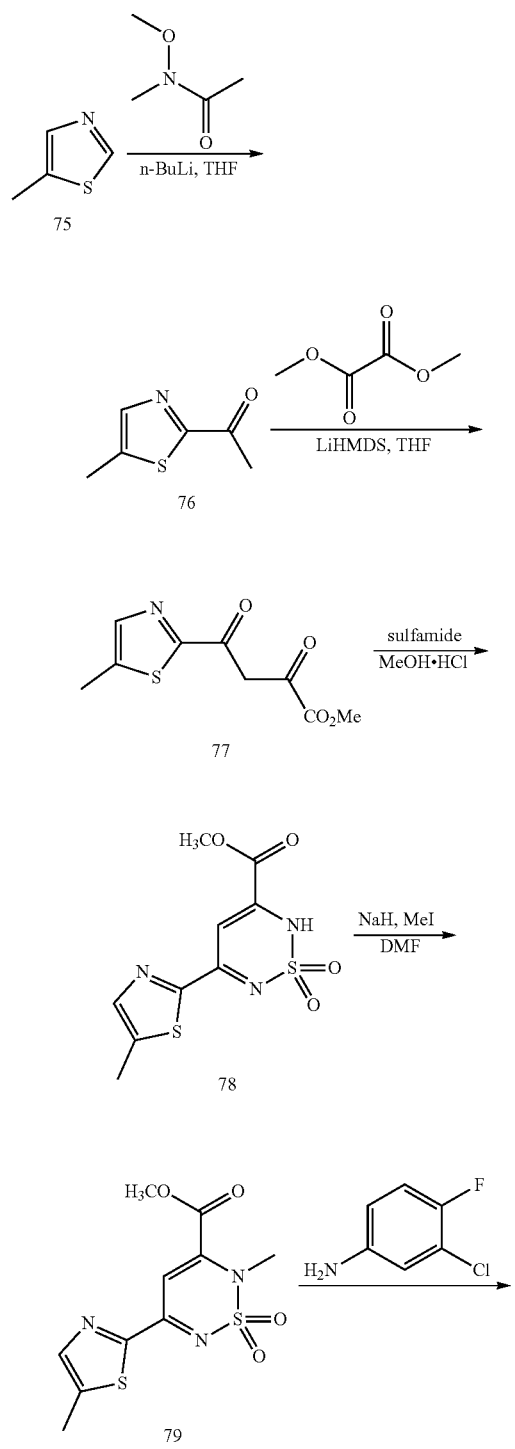

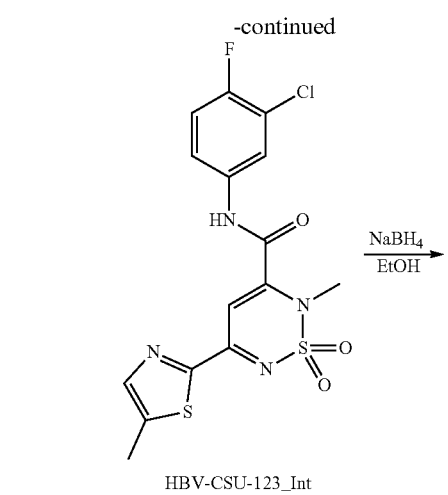

HBV-CSU-123_Int

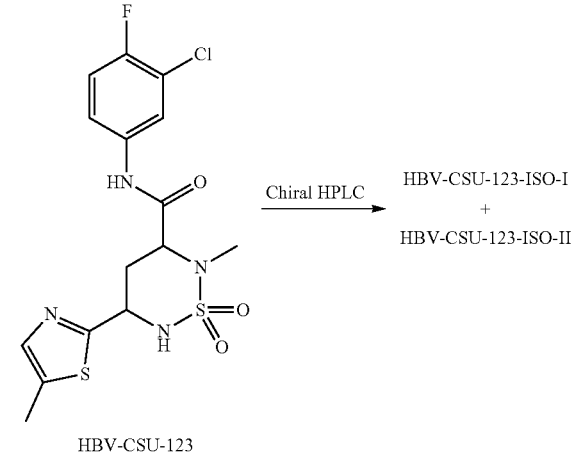 [SMILES: Cc1cnc(C2CC(C(=O)Nc3ccc(F)c(Cl)c3)N(C)S(=O)(=O)N2)s1 ; "HBV-CSU-123"]

HBV-CSU-123

Synthesis of 1-(5-methylthiazol-2-yl) ethan-1-one (76)

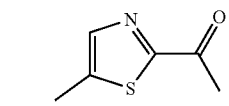

To a stirred solution of 5-methylthiazole 75 (9 g, 90.90 mmol) in anhydrous THF (200 mL) under inert atmosphere was added n-butyl lithium (40 mL, 99.99 mmol) dropwise for 30 min at −78° C. To this was added N-methoxy-N-methylacetamide (11.24 mL, 109.1 mmol) dropwise for 20 min at −78° C., followed by warming to 0° C. and stirring for 16 min. The reaction was monitored by TLC. After completion of the reaction, the reaction mixture was quenched with saturated ammonium chloride solution and extracted using EtOAc. The combined organic extracts were dried over anhydrous sodium sulfate, filtered and concentrated in vacuo to obtain the crude. The crude was purified through silica gel column chromatography using 3% EtOAc/hexanes to afford compound 76 (12 g, 94%) as pale yellow liquid. TLC: 10% EtOAc/hexanes ($R_f$: 0.5); $^1$H NMR (DMSO-$d_6$, 400 MHz): δ 7.83 (s, 1H), 2.58 (s, 3H), 2.54 (s, 3H).

Synthesis of methyl 4-(5-methylthiazol-2-yl)-2,4-dioxobutanoate (77)

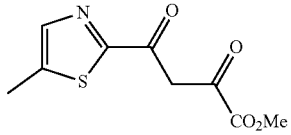

Title compound was synthesized using general method for the synthesis of 2,4-diketoester described above to afford 14 g (73%, reaction scale is 12 g) as yellow solid. TLC: 5% MeOH/CH$_2$Cl$_2$(R$_f$: 0.2); $^1$H NMR (400 MHz, DMSO-d$_6$): δ 7.86 (br.s, 1H), 6.99 (br.s, 1H), 3.82 (s, 3H), 2.56 (s, 3H); LCMS Calculated for C$_9$H$_9$NO$_4$S: 227.03; Observed: 228.1 (M+1)$^+$.

Synthesis of methyl 5-(5-methylthiazol-2-yl)-2H-1,2,6-thiadiazine-3-carboxylate 1,1-dioxide (78)

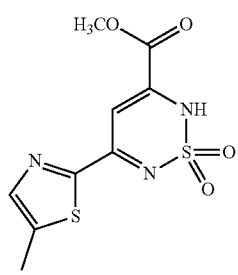 [SMILES: COC(=O)C1=CC(c2ncc(C)s2)=NS(=O)(=O)N1]

Title compound was synthesized using general method A for the synthesis of cyclic sulfonamide described above to afford 1.9 g (38%, reaction scale is 4 g) as an off-white solid (1.9 g, 38%). TLC: 10% MeOH/CH$_2$Cl$_2$ (R$_f$: 0.1); $^1$H NMR (400 MHz, DMSO-d$_6$): δ 7.66 (s, 1H), 6.85 (s, 1H), 6.07 (br.s, 1H), 3.79 (s, 3H), 2.50 (s, 3H); LCMS Calculated for C$_9$H$_9$N$_3$O$_4$S$_2$: 287.00; Observed: 288.1 (M+1)$^+$.

Synthesis of methyl 2-methyl-5-(5-methylthiazol-2-yl)-2H-1,2,6-thiadiazine-3-carboxylate 1,1-dioxide (79)

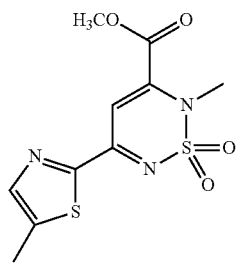 [SMILES: COC(=O)C1=CC(c2ncc(C)s2)=NS(=O)(=O)N1C]

Title compound was synthesized using general method A for alkylation described above to afford 250 mg (48%, reaction scale is 500 mg) as an off-white solid. TLC: 40% EtOAc/hexanes (R$_f$: 0.4); $^1$H NMR (400 MHz, DMSO-d$_6$): δ 7.96 (s, 1H), 7.41 (s, 1H), 3.94 (s, 3H), 3.57 (s, 3H), 2.60 (s, 3H); LCMS Calculated for C$_{10}$H$_{11}$N$_3$O$_4$S$_2$: 301.02; Observed: 302.1 (M+1)$^+$.

Synthesis of N-(3-chloro-4-fluorophenyl)-2-methyl-5-(5-methylthiazol-2-yl)-2H-1,2,6-thiadiazine-3-carboxamide 1,1-dioxide (HBV-CSU-123_Int)

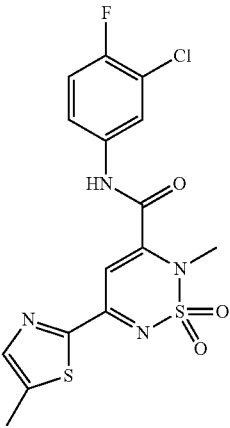

HBV-CSU-123_Int

The above titled compound has been synthesized by following the general procedure (Method B) described above for amidation by using corresponding 79 and corresponding amine (see Table 1 for analytical data).

Cis-5-(5-Bromothiazol-2-yl)-N-(3-chloro-4-fluorophenyl)-2-methyl-1,2,6-thiadiazinane-3-carboxamide 1,1-dioxide (HBV-CSU-123, HBV-CSU-123-ISO-I & HBV-CSU-123-ISO-II)

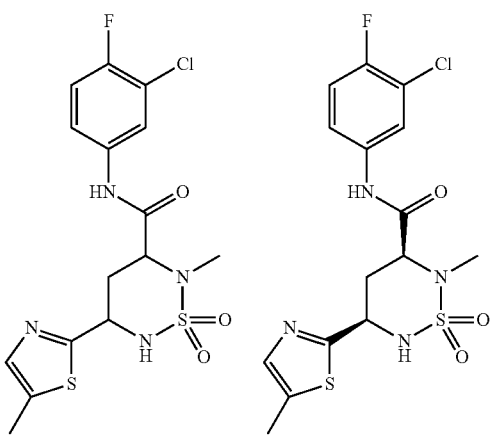

HBV-CSU-123          HBV-CSU-123-ISO-I

315

-continued

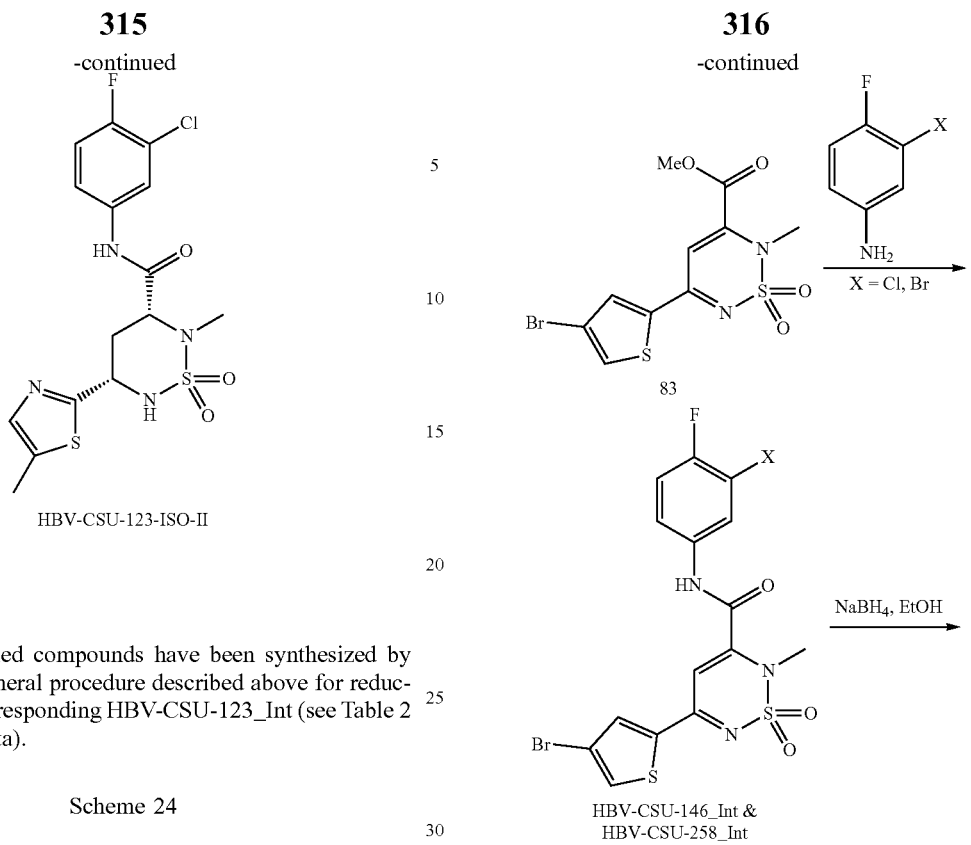

HBV-CSU-123-ISO-II

The above titled compounds have been synthesized by following the general procedure described above for reduction by using corresponding HBV-CSU-123_Int (see Table 2 for analytical data).

Scheme 24

General Synthetic Scheme for 5-(thiophen-2-yl)-1,2,6-thiadiazinane-3-carboxamide 1,1-dioxide Derivatives with 4-Substituted Thiophene & Aniline Variations Scheme 24:

316

-continued

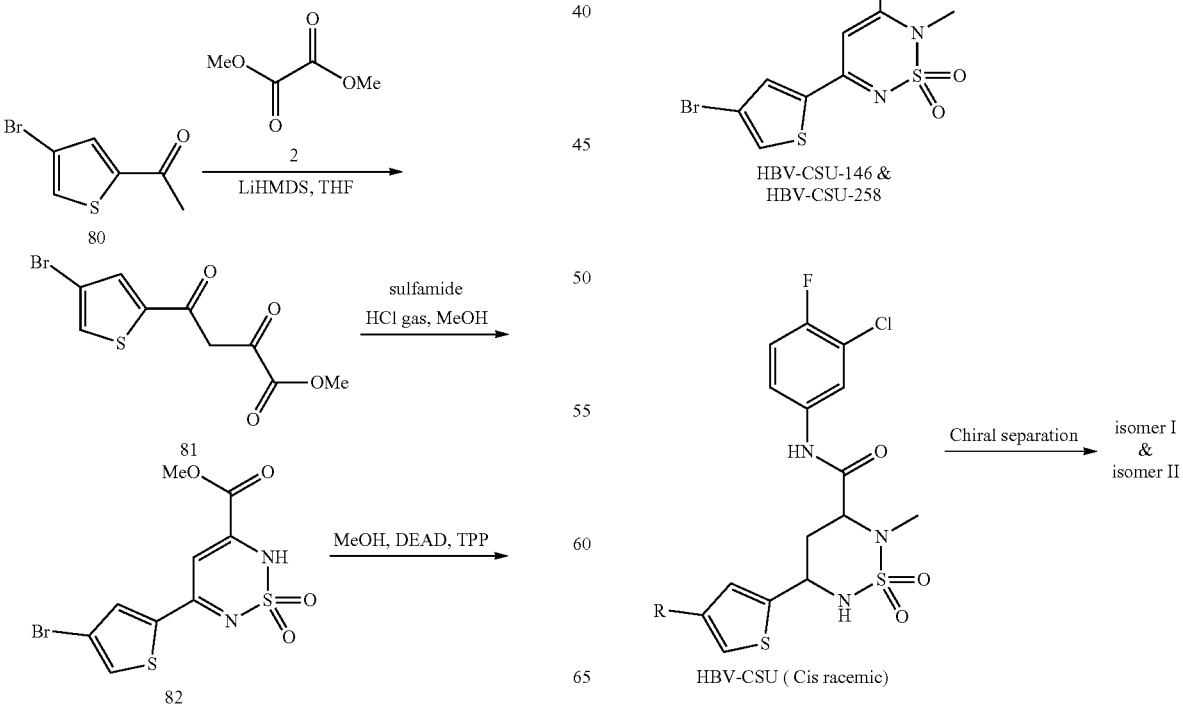

| Target | Coupling reaction | Aniline (X = Cl/Br) | #2 (R variation) |
|---|---|---|---|
| HBV-CSU-146 | — | X = Cl | Br |
| HBV-CSU-147 | Negishi coupling | X = Cl | Methyl |
| HBV-CSU-148 | Suzuki coupling | X = Cl | 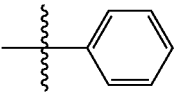 |
| HBV-CSU-149 | Suzuki coupling | X = Cl | 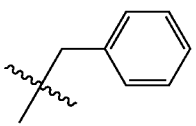 |
| HBV-CSU-164 | Suzuki coupling | X = Cl | 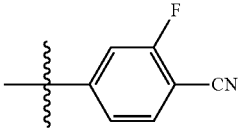 [SMILES: *c1ccc(C#N)c(F)c1] |
| HBV-CSU-165 | Suzuki coupling | X = Cl | 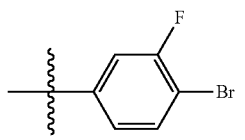 [SMILES: *c1ccc(Br)c(F)c1] |
| HBV-CSU-166 | Suzuki coupling | X = Cl | 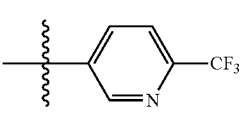 [SMILES: *c1ccc(C(F)(F)F)nc1] |
| HBV-CSU-167 | Suzuki coupling | X = Cl | 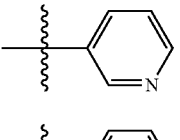 |
| HBV-CSU-168 | Stille coupling | X = Cl | 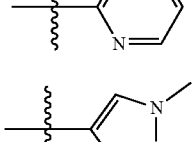 |
| HBV-CSU-169 | Suzuki coupling | X = Cl | 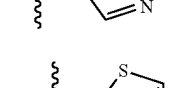 |
| HBV-CSU-170 | Suzuki coupling | X = Cl |  |
| HBV-CSU-171 | Suzuki coupling | X = Cl | 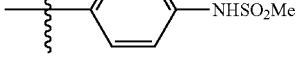 |
| HBV-CSU-243 | Stille coupling | X = Cl | 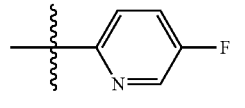 |
| HBV-CSU-258 | — | X = Br | Br |
| HBV-CSU-289 | Suzuki coupling | X = Cl | 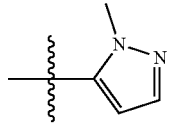 |

-continued

| Target | Coupling reaction | Aniline (X = Cl/Br) | #2 (R variation) |
|---|---|---|---|
| HBV-CSU-290 | Suzuki coupling | X = Cl | 5-pyrimidinyl |
| HBV-CSU-294 | Suzuki coupling | X = Cl | 1-ethyl-1H-pyrazol-4-yl |
| HBV-CSU-295 | Suzuki coupling | X = Cl | 1-isopropyl-1H-pyrazol-4-yl |
| HBV-CSU-296 | Suzuki coupling | X = Cl | 1-(2-hydroxyethyl)-1H-pyrazol-4-yl |
| HBV-CSU-315 | Suzuki coupling | X = Cl | 1,5-dimethyl-1H-pyrazol-4-yl |
| HBV-CSU-316 | Suzuki coupling | X = Cl | 1,3-dimethyl-1H-pyrazol-4-yl |
| HBV-CSU-317 | Suzuki coupling | X = Cl | 1,3,5-trimethyl-1H-pyrazol-4-yl |
| HBV-CSU-325 | Suzuki coupling | X = Cl | 1-(trifluoromethyl)-1H-pyrazol-4-yl |

Synthesis of methyl 4-(4-bromothiophen-2-yl)-2,4-dioxobutanoate (81)

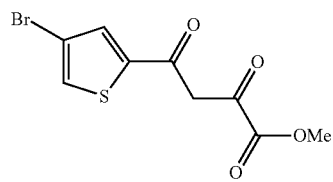 [SMILES: COC(=O)C(=O)CC(=O)c1cc(Br)cs1]

Title compound was synthesized using general method for the synthesis of 2,4-diketoester described above to afford 30 g (84.57%, reaction scale is 25 g); LCMS Calculated for $C_9H_7BrO_4S$: 289.92; Observed: 292.80 $(M+2)^+$.

Synthesis of methyl 5-(4-bromothiophen-2-yl)-2H-1,2,6-thiadiazine-3-carboxylate 1,1-dioxide (82)

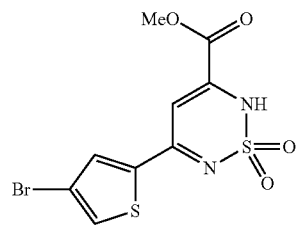 [SMILES: COC(=O)C1=CC(c2cc(Br)cs2)=NS(=O)(=O)N1]

Title compound was synthesized using general method for the synthesis of cyclic sulfonamide described above to afford 15 g (41.60%, reaction scale is 30 g); LCMS Calculated for $C_9H_7BrN_2O_4S_2$: 349.90; LCMS observed: 353.05 $(M+2)^+$.

Synthesis of methyl 5-(4-bromothiophen-2-yl)-2-methyl-2H-1,2,6-thiadiazine-3-carboxylate 1,1-dioxide (83)

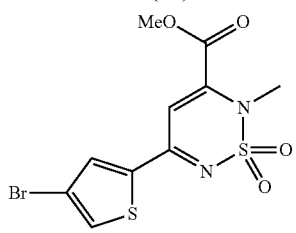

Title compound was synthesized using general method B for alkylation described above to afford 9 g (57.58%, reaction scale is 5 g); LCMS Calculated for $C_{10}H_9BrN_2O_4S_2$: 363.92; LCMS observed: 367.10 $(M+2)^+$.

5-(4-Bromothiophen-2-yl)-N-(3-chloro-4-fluorophenyl)-2-methyl-2H-1,2,6-thiadiazine-3-carboxamide 1,1-dioxide (HBV-CSU-146_Int)

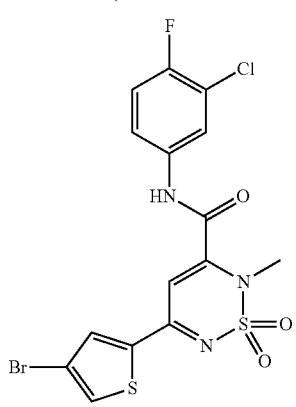

The above titled compound has been synthesized by following the general procedure (Method B) described above for amidation by using Compound 83 and corresponding amine (see Table 1 for analytical data).

N-(3-Bromo-4-fluorophenyl)-5-(4-bromothiophen-2-yl)-2-methyl-2H-1,2,6-thiadiazine-3-carboxamide 1,1-dioxide (HBV-CSU-258_Int)

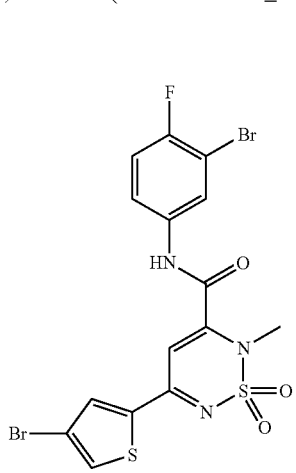

The above titled compound has been synthesized by following the general procedure (Method B) described above for amidation by using Compound 90 and corresponding amine. The crude intermediate confirmed by LCMS and carried forward to the next step.

5-(4-Bromothiophen-2-yl)-N-(3-chloro-4-fluorophenyl)-2-methyl-1,2,6-thiadiazinane-3-carboxamide 1,1-dioxide (HBV-CSU-146, HBV-CSU-146-ISO-I & HBV-CSU-146-ISO-II)

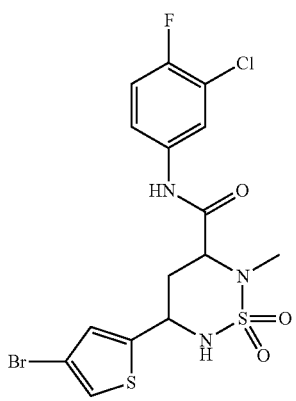 [SMILES: CN1C(C(=O)Nc2ccc(F)c(Cl)c2)=CC(c2cc(Br)cs2)=NS1(=O)=O]

HBV-CSU-146

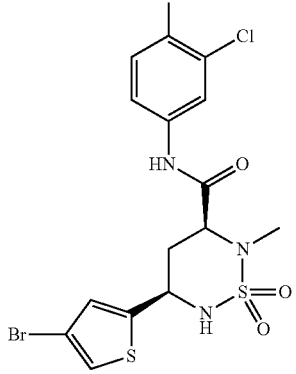

HBV-CSU-146-ISO-I

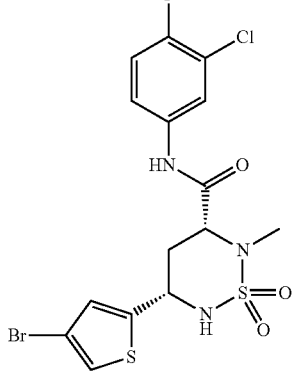

HBV-CSU-146-ISO-II

The above titled compounds have been synthesized by following the general procedure described above for reduction by using corresponding HBV-CSU-146_Int (see Table 2 for analytical data).

Cis-N-(3-chloro-4-fluorophenyl)-2-methyl-5-(4-methylthiophen-2-yl)-1,2,6-thiadiazinane-3-carboxamide 1,1-dioxide (HBV-CSU-147, HBV-CSU-147-ISO-I & HBV-CSU-147-ISO-II)

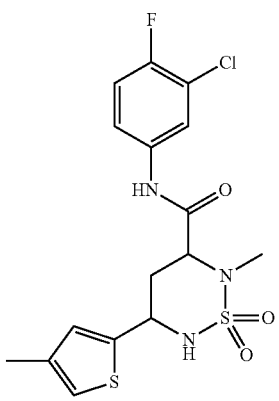

HBV-CSU-147

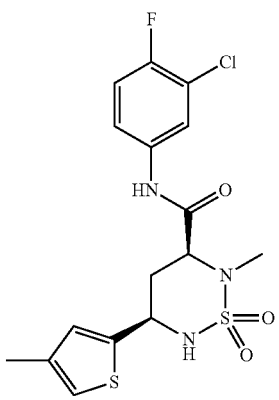

HBV-CSU-147-ISO-I

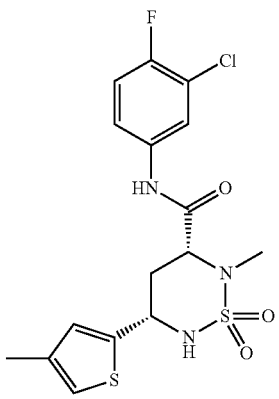

HBV-CSU-147-ISO-II

The above titled compounds have been synthesized by following the general procedure described above for Suzuki coupling by using HBV-CSU-146 and dimethyl zinc (see Table 2 for analytical data).

Cis-N-(3-chloro-4-fluorophenyl)-2-methyl-5-(4-phenylthiophen-2-yl)-1,2,6-thiadiazinane-3-carboxamide 1,1-dioxide (HBV-CSU-148-ISO-I & HBV-CSU-148-ISO-II)

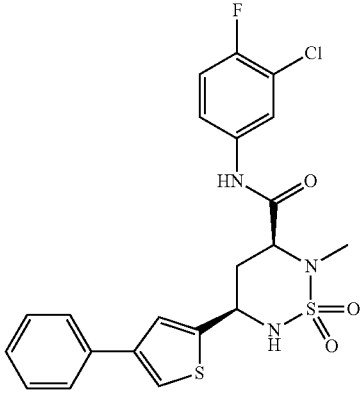

HBV-CSU-148-ISO-I

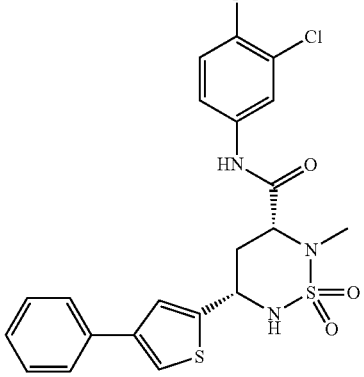

HBV-CSU-148-ISO-II

The above titled compounds have been synthesized by following the general procedure described above for Suzuki coupling by using HBV-CSU-146 and corresponding boronic acid (see Table 2 for analytical data).

Cis-(4-benzylthiophen-2-yl)-N-(3-chloro-4-fluorophenyl)-2-methyl-1,2,6-thiadiazinane-3-carboxamide 1,1-dioxide (HBV-CSU-149-ISO-I & HBV-CSU-149-ISO-II)

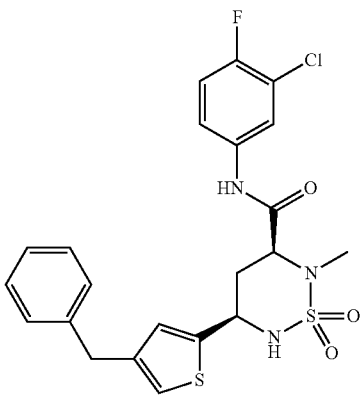

HBV-CSU-149-ISO-I

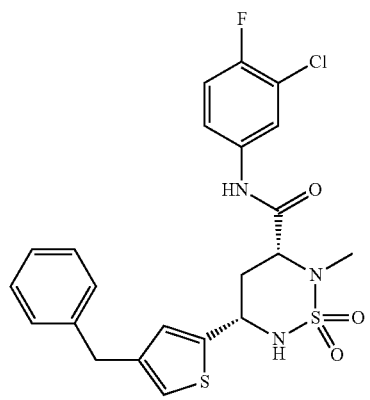

HBV-CSU-149-ISO-II

The above titled compounds have been synthesized by following the general procedure described above for Suzuki coupling by using HBV-CSU-146 and corresponding boronic acid (see Table 2 for analytical data).

Cis-N-(3-chloro-4-fluorophenyl)-5-(4-(4-cyano-3-fluorophenyl)thiophen-2-yl)-2-methyl-1,2,6-thiadiazinane-3-carboxamide 1,1-dioxide (HBV-CSU-164, HBV-CSU-164-ISO-I & HBV-CSU-164-ISO-II)

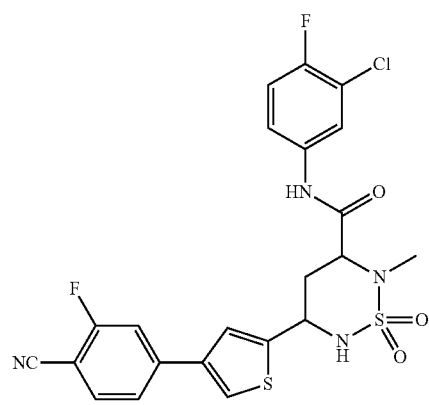

HBV-CSU-164

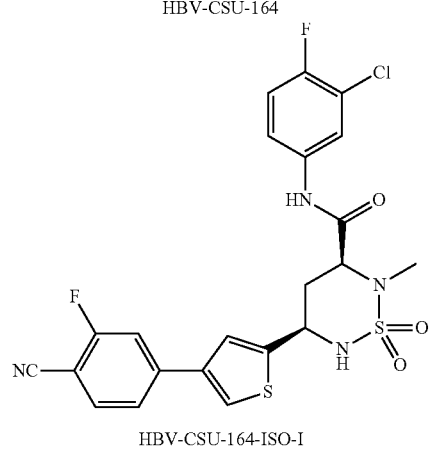

HBV-CSU-164-ISO-I

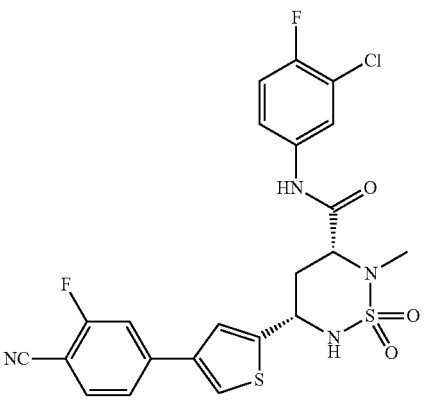

HBV-CSU-164-ISO-II

The above titled compounds have been synthesized by following the general procedure described above for Suzuki coupling by using HBV-CSU-146 and corresponding boronic acid (see Table 2 for analytical data).

Cis-N-(3-chloro-4-fluorophenyl)-5-(4-(4-bromo-3-fluorophenyl)thiophen-2-yl)-2-methyl-1,2,6-thiadiazinane-3-carboxamide 1,1-dioxide (HBV-CSU-165)

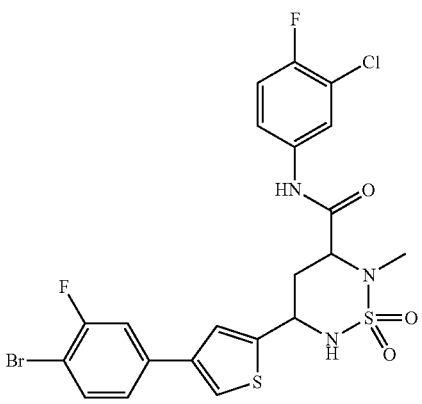

HBV-CSU-165

The above titled compound has been synthesized by following the general procedure described above for Suzuki coupling by using HBV-CSU-146 and corresponding boronic acid (see Table 2 for analytical data).

Cis-N-(3-chloro-4-fluorophenyl)-2-methyl-5-(4-(6-(trifluoromethyl)pyridin-3-yl)thiophen-2-yl)-1,2,6-thiadiazinane-3-carboxamide 1,1-dioxide (HBV-CSU-166, HBV-CSU-166-ISO-I & HBV-CSU-166-ISO-II)

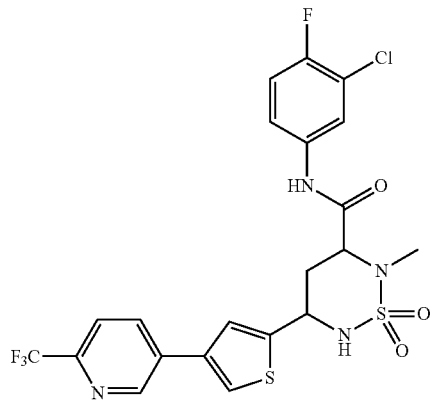

HBV-CSU-166


HBV-CSU-166-ISO-I

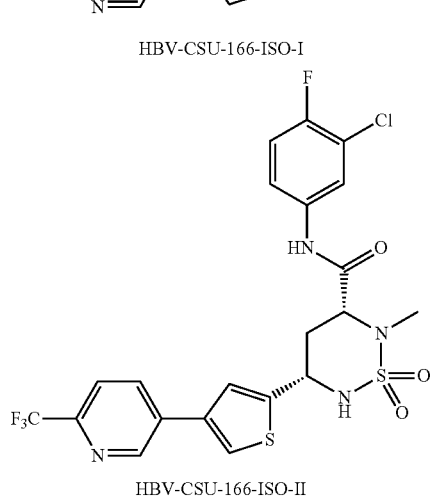

HBV-CSU-166-ISO-II

The above titled compounds have been synthesized by following the general procedure described above for Suzuki coupling by using HBV-CSU-146 and corresponding boronic acid (see Table 2 for analytical data).

Cis-N-(3-chloro-4-fluorophenyl)-2-methyl-5-(4-(pyridin-3-yl)thiophen-2-yl)-1,2,6-thiadiazinane-3-carboxamide 1,1-dioxide (HBV-CSU-167-ISO-I & HBV-CSU-167-ISO-II)

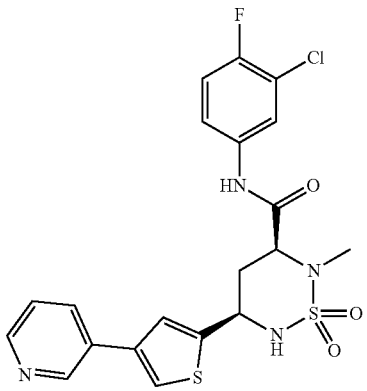

HBV-CSU-167-ISO-I

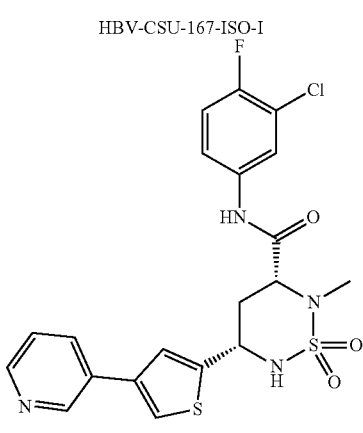

HBV-CSU-167-ISO-II

The above titled compounds have been synthesized by following the general procedure described above for Suzuki coupling by using HBV-CSU-146 and corresponding boronic acid (see Table 2 for analytical data).

Cis-N-(3-chloro-4-fluorophenyl)-2-methyl-5-(4-(pyridin-2-yl)thiophen-2-yl)-1,2,6-thiadiazinane-3-carboxamide 1,1-dioxide (HBV-CSU-168, HBV-CSU-168-ISO-I & HBV-CSU-168-ISO-II)

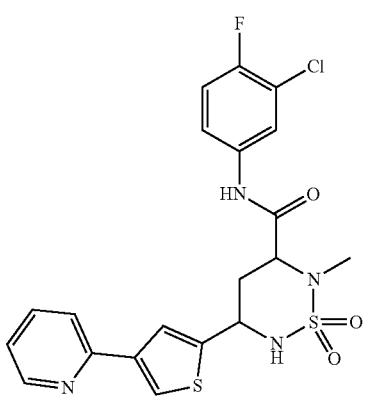

HBV-CSU-168

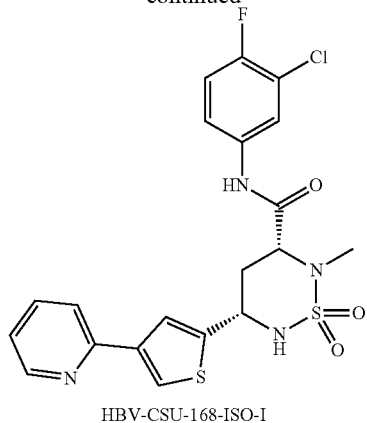

HBV-CSU-168-ISO-I

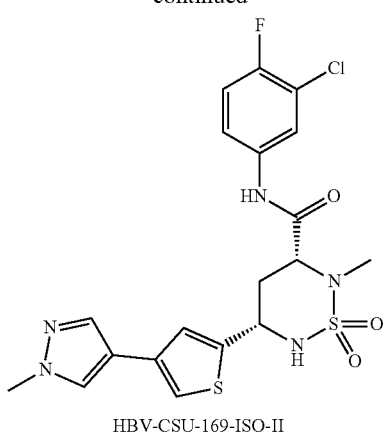

HBV-CSU-169-ISO-II

The above titled compounds have been synthesized by following the general procedure described above for Suzuki coupling by using HBV-CSU-146 and corresponding boronic acid (see Table 2 for analytical data).

Cis-N-4-([2,2'-bithiophen]-5-yl)-N-(3-chloro-4-fluorophenyl)-2-methyl-1,2,6-thiadiazinane-3-carboxamide 1,1-dioxide (HBV-CSU-170, HBV-CSU-170-ISO-I & HBV-CSU-170-ISO-II)

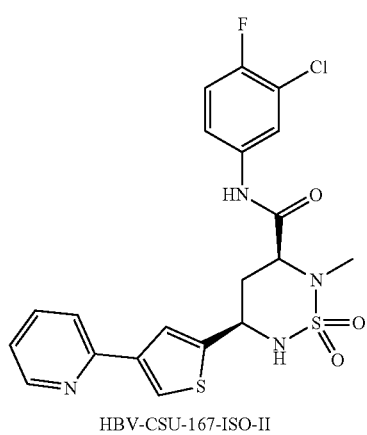

HBV-CSU-167-ISO-II

The above titled compounds have been synthesized by following the general procedure described above for Suzuki coupling by using HBV-CSU-146 and corresponding boronic acid (see Table 2 for analytical data).

Cis-N-(3-chloro-4-fluorophenyl)-2-methyl-5-(4-(1-methyl-1H-pyrazol-4-yl)thiophen-2-yl)-1,2,6-thiadiazinane-3-carboxamide 1,1-dioxide (HBV-CSU-169-ISO-I & HBV-CSU-169-ISO-II)

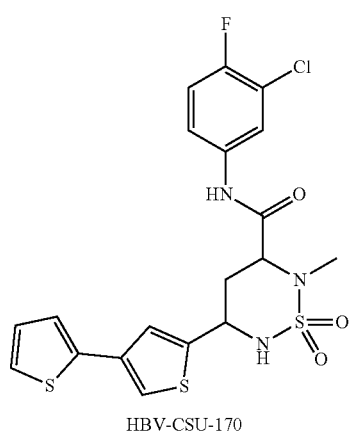

HBV-CSU-170

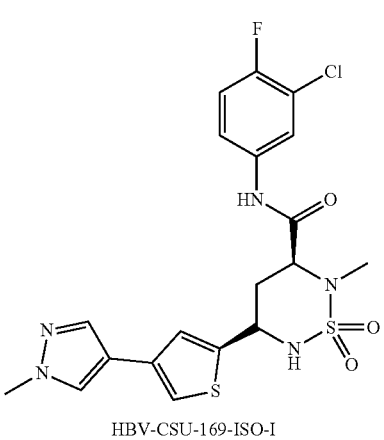

HBV-CSU-169-ISO-I

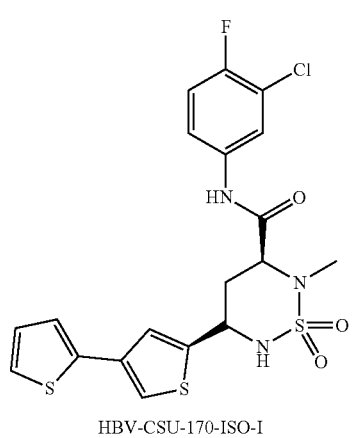

HBV-CSU-170-ISO-I

331

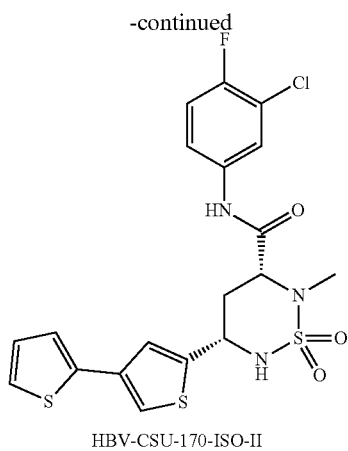

HBV-CSU-170-ISO-II

The above titled compounds have been synthesized by following the general procedure described above for Suzuki coupling by using HBV-CSU-146 and corresponding boronic acid (see Table 2 for analytical data).

Cis-N-(3-chloro-4-fluorophenyl)-2-methyl-5-(4-(4-(methylsulfonamido)phenyl)thiophen-2-yl)-1,2,6-thiadiazinane-3-carboxamide 1,1-dioxide (HBV-CSU-171)

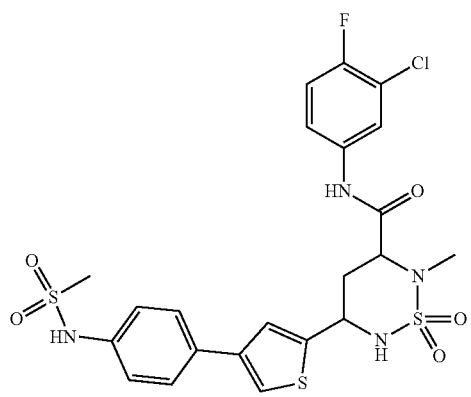

HBV-CSU-171

The above titled compound has been synthesized by following the general procedure described above for Suzuki coupling by using HBV-CSU-146 and corresponding boronic acid (see Table 2 for analytical data).

332

Cis-N-(3-chloro-4-fluorophenyl)-5-(4-(5-fluoropyridin-2-yl)thiophen-2-yl)-2-methyl-1,2,6-thiadiazinane-3-carboxamide 1,1-dioxide (HBV-CSU-243, HBV-CSU-243-ISO-I & HBV-CSU-243-ISO-II)

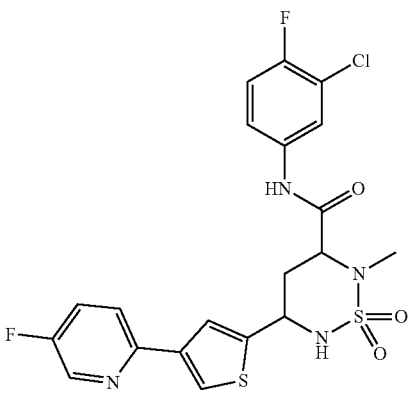

HBV-CSU-243

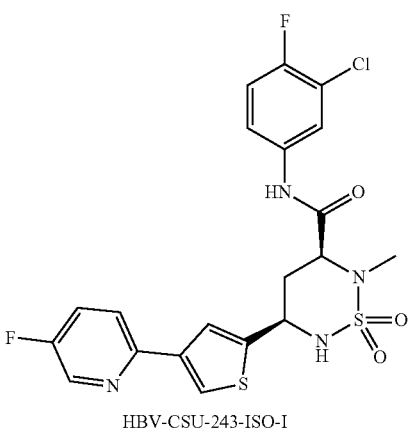

HBV-CSU-243-ISO-I

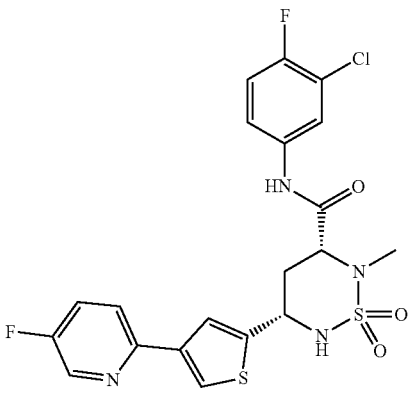

HBV-CSU-243-ISO-II

The above titled compound has been synthesized by following the general procedure described above for Suzuki coupling by using HBV-CSU-146 and corresponding boronic acid (see Table 2 for analytical data).

333

Cis-N-(3-Bromo-4-fluorophenyl)-5-(4-bromothiophen-2-yl)-2-methyl-1,2,6-thiadiazinane-3-carboxamide 1,1-dioxide (HBV-CSU-258)

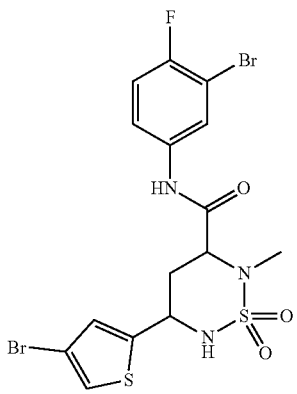 [SMILES: CN1C(C(=O)Nc2ccc(F)c(Br)c2)CC(c2cc(Br)cs2)NS1(=O)=O]

The above titled compounds have been synthesized by following the general procedure described above for reduction by using HBV-CSU-258-Int-1 (see Table 2 for analytical data).

Cis-N-(3-chloro-4-fluorophenyl)-2-methyl-5-(4-(1-methyl-1H-pyrazol-5-yl)thiophen-2-yl)-1,2,6-thiadiazinane-3-carboxamide 1,1-dioxide (HBV-CSU-289, HBV-CSU-289-ISO-I & HBV-CSU-289-ISO-II)

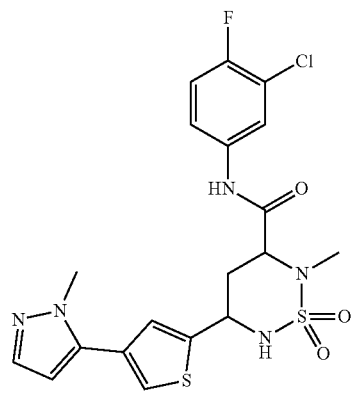

HBV-CSU-289

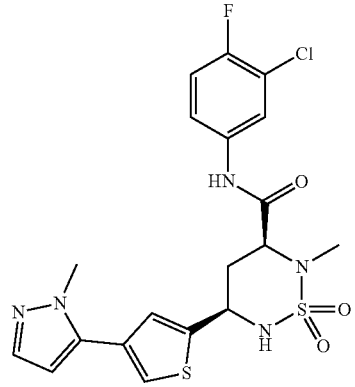

HBV-CSU-289-ISO-I

334

-continued

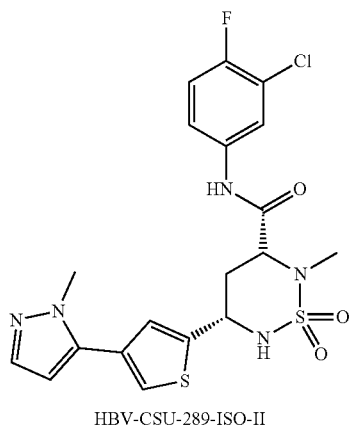

HBV-CSU-289-ISO-II

The above titled compound has been synthesized by following the general procedure described above for Suzuki coupling by using HBV-CSU-146 and corresponding boronic acid (see Table 2 for analytical data).

Cis-N-(3-chloro-4-fluorophenyl)-2-methyl-5-(4-(pyrimidin-5-yl)thiophen-2-yl)-1,2,6-thiadiazinane-3-carboxamide 1,1-dioxide (HBV-CSU-290, HBV-CSU-290-ISO-I & HBV-CSU-290-ISO-II)

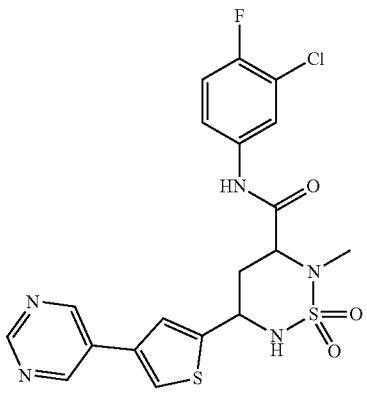

HBV-CSU-290

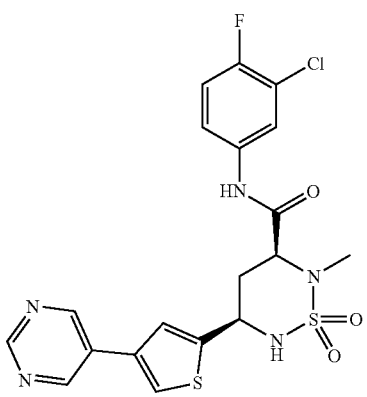

HBV-CSU-290-ISO-I

-continued

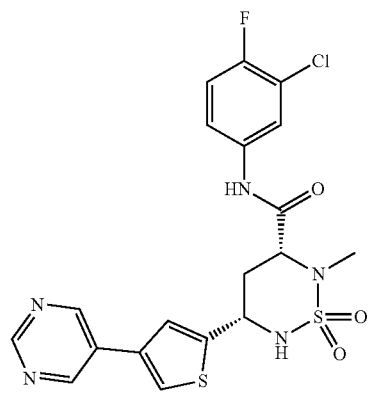
HBV-CSU-290-ISO-II

The above titled compound has been synthesized by following the general procedure described above for Suzuki coupling by using HBV-CSU-146 and corresponding boronic acid (see Table 2 for analytical data).

Cis-N-(3-chloro-4-fluorophenyl)-5-(4-(1-ethyl-1H-pyrazol-4-yl)thiophen-2-yl)-2-methyl-1,2,6-thiadiazinane-3-carboxamide 1,1-dioxide (HBV-CSU-294, HBV-CSU-294-ISO-I & HBV-CSU-294-ISO-II)

-continued

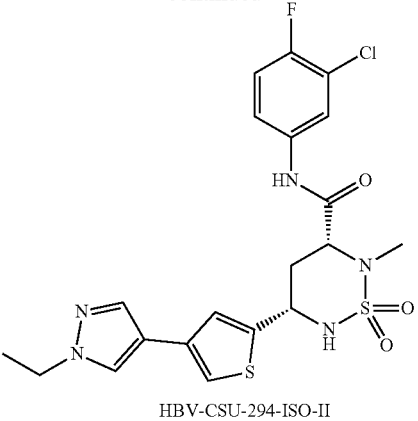
HBV-CSU-294-ISO-II

The above titled compound has been synthesized by following the general procedure described above for Suzuki coupling by using HBV-CSU-146 and corresponding boronic acid (see Table 2 for analytical data).

Cis-N-(3-chloro-4-fluorophenyl)-5-(4-(1-isopropyl-1H-pyrazol-4-yl)thiophen-2-yl)-2-methyl-1,2,6-thiadiazinane-3-carboxamide 1,1-dioxide (HBV-CSU-295, HBV-CSU-295-ISO-I & HBV-CSU-295-ISO-II)

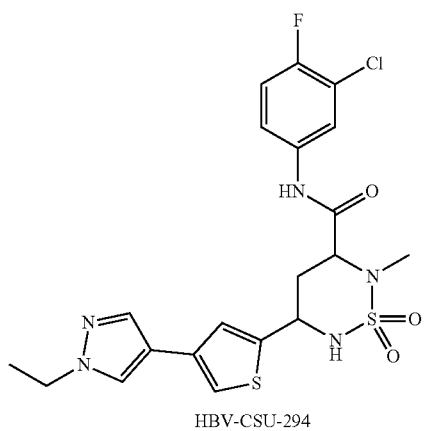
HBV-CSU-294

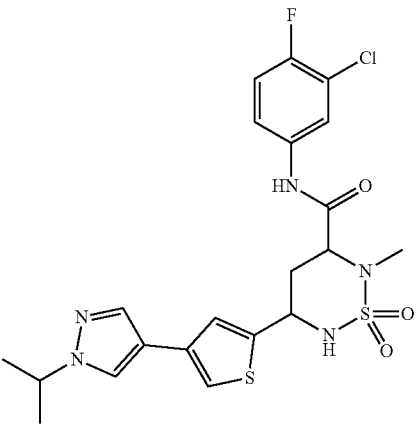
HBV-CSU-295

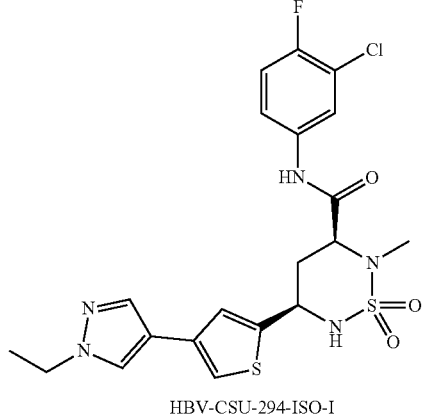
HBV-CSU-294-ISO-I

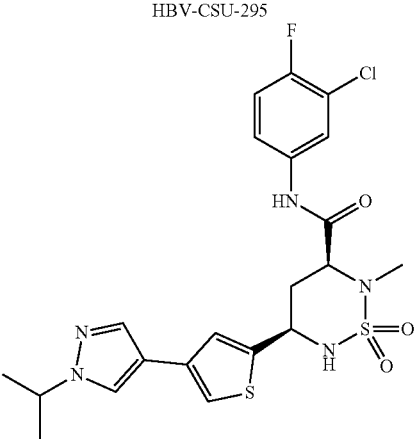
HBV-CSU-295-ISO-I

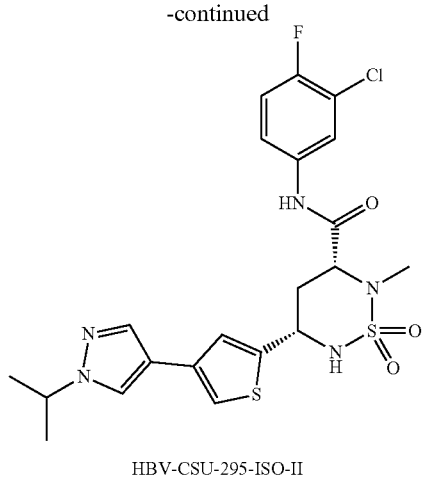

HBV-CSU-295-ISO-II

The above titled compound has been synthesized by following the general procedure described above for Suzuki coupling by using HBV-CSU-146 and corresponding boronic acid (see Table 2 for analytical data).

Cis-N-(3-chloro-4-fluorophenyl)-5-(4-(1-(2-hydroxyethyl)-1H-pyrazol-4-yl)thiophen-2-yl)-2-methyl-1,2,6-thiadiazinane-3-carboxamide 1,1-dioxide (HBV-CSU-296, HBV-CSU-296-ISO-I & HBV-CSU-296-ISO-II)

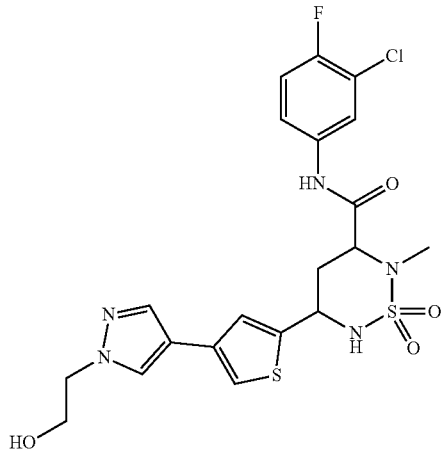

HBV-CSU-296

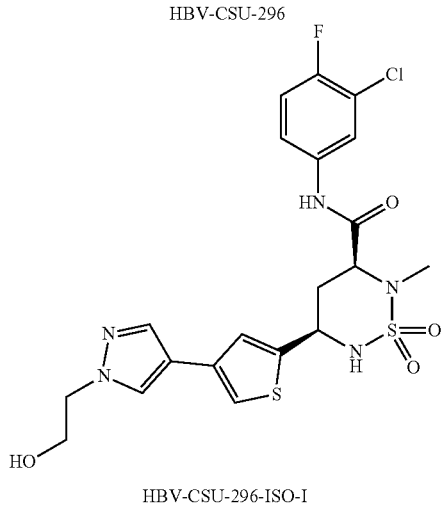

HBV-CSU-296-ISO-I

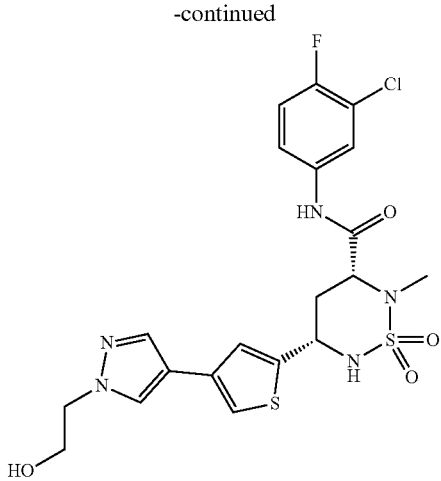

HBV-CSU-296-ISO-II

The above titled compound has been synthesized by following the general procedure described above for Suzuki coupling by using HBV-CSU-146 and corresponding boronic acid (see Table 2 for analytical data).

Cis-N-(3-chloro-4-fluorophenyl)-5-(4-(1,5-dimethyl-1H-pyrazol-4-yl)thiophen-2-yl)-2-methyl-1,2,6-thiadiazinane-3-carboxamide 1,1-dioxide (HBV-CSU-315, HBV-CSU-315-ISO-I & HBV-CSU-315-ISO-II)

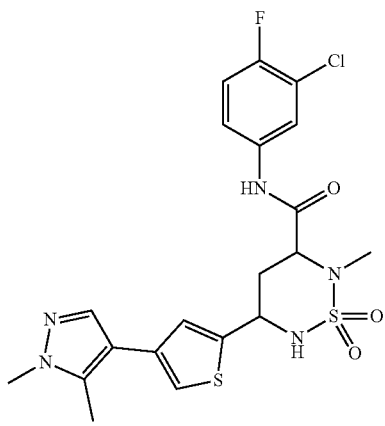

HBV-CSU-315

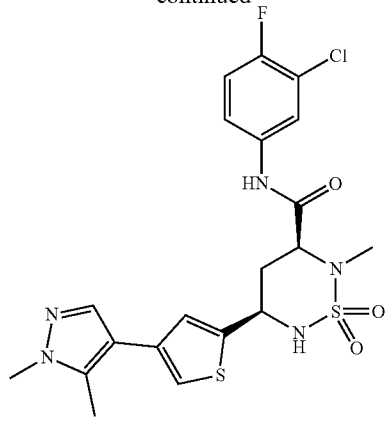

HBV-CSU-315-ISO-I

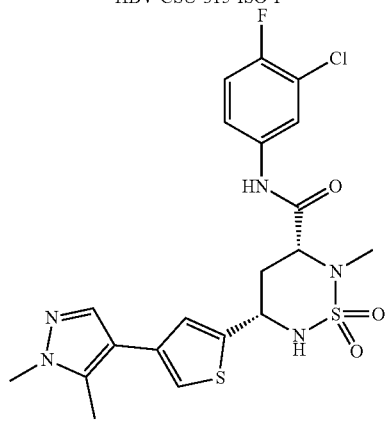

HBV-CSU-315-ISO-II

The above titled compound has been synthesized by following the general procedure described above for Suzuki coupling by using HBV-CSU-146 and corresponding boronic acid (see Table 2 for analytical data).

Cis-N-(3-chloro-4-fluorophenyl)-5-(4-(1,3-dimethyl-1H-pyrazol-4-yl)thiophen-2-yl)-2-methyl-1,2,6-thiadiazinane-3-carboxamide 1,1-dioxide (HBV-CSU-316, HBV-CSU-316-ISO-I & HBV-CSU-316-ISO-II)

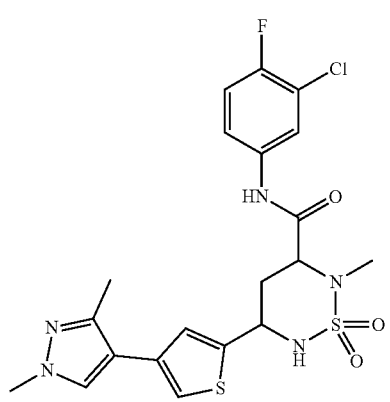

HBV-CSU-316

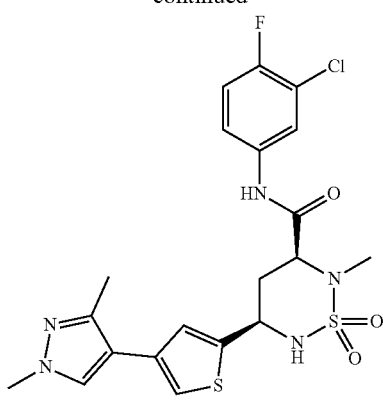

HBV-CSU-316-ISO-I

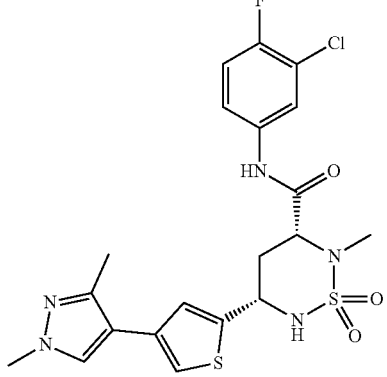

HBV-CSU-316-ISO-II

The above titled compound has been synthesized by following the general procedure described above for Suzuki coupling by using HBV-CSU-146 and corresponding boronic acid (see Table 2 for analytical data).

Cis-N-(3-chloro-4-fluorophenyl)-2-methyl-5-(4-(1,3,5-trimethyl-1H-pyrazol-4-yl)thiophen-2-yl)-1,2,6-thiadiazinane-3-carboxamide 1,1-dioxide (HBV-CSU-317, HBV-CSU-317-ISO-I & HBV-CSU-317-ISO-II)

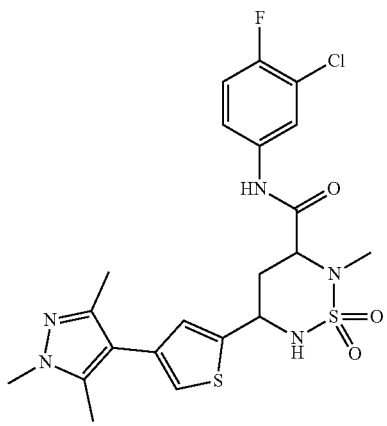

HBV-CSU-317


HBV-CSU-317-ISO-I

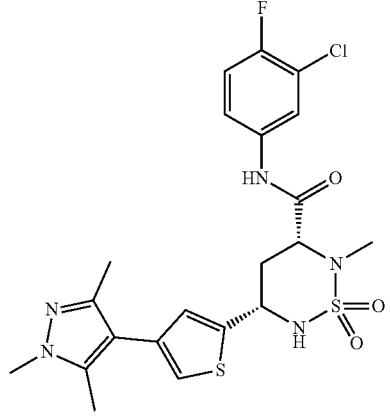

HBV-CSU-317-ISO-II

The above titled compound has been synthesized by following the general procedure described above for Suzuki coupling by using HBV-CSU-146 and corresponding boronic acid (see Table 2 for analytical data).

Cis-N-(3-Chloro-4-fluorophenyl)-2-methyl-5-(4-(1-(trifluoromethyl)-1H-pyrazol-4-yl)thiophen-2-yl)-1,2,6-thiadiazinane-3-carboxamide 1,1-dioxide (HBV-CSU-325-ISO-I & HBV-CSU-325-ISO-II)

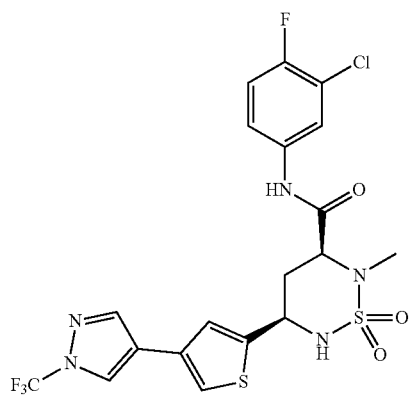

HBV-CSU-325-ISO-I

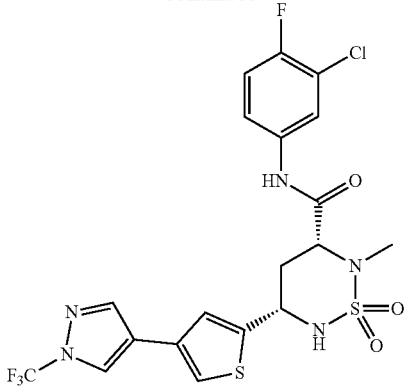

HBV-CSU-325-ISO-II

The above titled compounds have been synthesized by following the general procedure described above for Stille coupling by using HBV-CSU-146 and corresponding boronic acid (see Table 2 for analytical data).

Scheme 25

Synthesis of 5-(4-bromothiazol-2-yl)-N-(3-chloro-4-fluorophenyl)-2-methyl-1,2,6-thiadiazinane-3-carboxamide 1,1-dioxide (HBV-CSU-150)

Scheme 25:

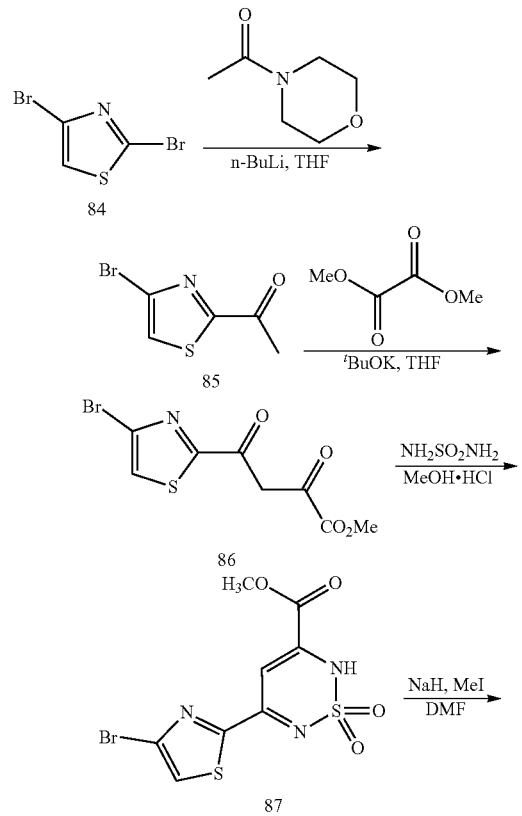

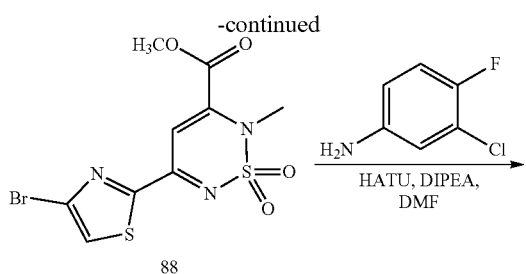

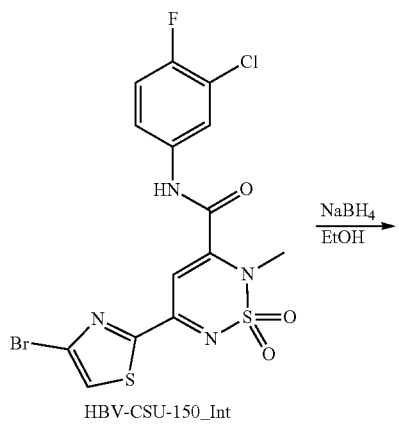

HBV-CSU-150_Int

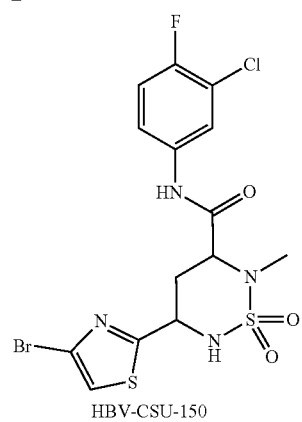

HBV-CSU-150

Synthesis of 1-(4-bromothiazol-2-yl) ethan-1-one (85)

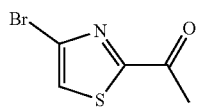

To a stirring solution of 2,4-dibromothiazole 84 (50 g, 205.82 mmol) in anhydrous THF (500 mL) under inert atmosphere was added n-butyllithium (193 mL, 308.74 mmol) dropwise for 30 min at −40° C. and stirred for 1 h at the same temperature. To this was added 1-morpholino-ethan-1-one (32 g, 248 mmol) in anhydrous THF (100 mL) dropwise for 20 min at −40° C. and stirred for 3 h. The reaction was monitored by TLC; after completion of the reaction, the reaction mixture was quenched with saturated ammonium chloride solution and extracted using EtOAc. The combined organic extracts were dried over anhydrous sodium sulfate, filtered and concentrated in vacuo to obtain the crude. The crude was purified through silica gel column chromatography using 1-2% EtOAc/hexanes to afford compound 85 (14 g, 33%) as an off-white solid. TLC: 10% EtOAc/hexanes ($R_f$: 0.8); $^1$H NMR (DMSO-$d_6$, 400 MHz): δ 8.33 (s, 1H), 2.62 (s, 3H); LCMS Calculated for $C_5H_4BrNOS$: 204.92; LCMS observed: 208.0 $(M+2)^+$.

Synthesis of methyl 4-(4-bromothiazol-2-yl)-2,4-dioxobutanoate (86)

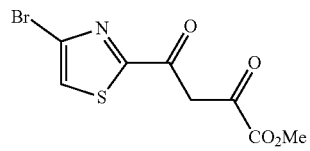

To a stirring solution of 1-(4-bromothiazol-2-yl) ethan-1-one 85 (10 g, 48.53 mmol) in anhydrous THF (200 mL) under inert atmosphere was added potassium tert-butoxide (122 mL, 121.94 mmol, 1 M sol. in THF) dropwise for 25 min at −78° C. and stirred at the same temperature for 1 h. To this was added dimethyl oxalate (8.6 g, 72.81 mmol) drop wise for 20 min at −78° C.; warmed to room temperature and stirred for 16 h. The reaction was monitored by TLC; after completion of the reaction, the pH of the reaction mixture was quenched with 1N aq. HCl and extracted using diethyl ether. The combined organic extracts were dried over anhydrous sodium sulfate and concentrated in vacuo to obtain the crude. The crude was purified through silica gel column chromatography using 1.5-2% MeOH/$CH_2Cl_2$ to afford compound 86 (2 g, 14%) as yellow solid. TLC: 70% EtOAc/hexanes ($R_f$: 0.4); $^1$H-NMR (DMSO-$d_6$, 400 MHz): δ 8.33 (s, 1H), 2.62 (s, 3H); LCMS Calculated for $C_8H_6BrNO_4S$: 290.92; LCMS observed: 292.0 $(M+1)^+$.

Synthesis of methyl 5-(4-bromothiazol-2-yl)-2H-1,2,6-thiadiazine-3-carboxylate 1,1-dioxide (87)

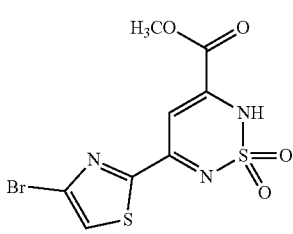 [SMILES: COC(=O)C1=CC(c2nc(Br)cs2)=NS(=O)(=O)N1]

Title compound was synthesized using general method A for cyclisation described above to afford 800 mg (33%, reaction scale is 2 g) as a brown solid. TLC: 10% MeOH/DCM ($R_f$: 0.1); $^1$H NMR (DMSO-$d_6$, 400 MHz): δ 7.99 (s, 1H), 6.78 (s, 1H), 3.80 (s, 3H); LCMS Calculated for $C_8H_6BrN_3O_4S_2$: 350.90; LCMS observed: 351.90 $(M+1)^+$.

345

Synthesis of methyl 5-(4-bromothiazol-2-yl)-2-methyl-2H-1,2,6-thiadiazine-3-carboxylate 1,1-dioxide (88)

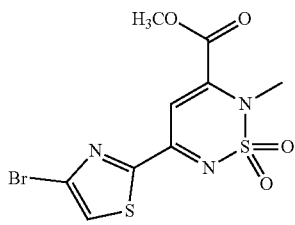 [SMILES: COC(=O)C1=CC(c2nc(Br)cs2)=NS(=O)(=O)N1C]

Title compound was synthesized using general method A for alkylation described above to afford 350 mg (42%, reaction scale is 800 mg) as an off-white solid. TLC: 10% MeOH/DCM ($R_f$: 0.4); $^1$H NMR (DMSO-$d_6$, 400 MHz): δ 8.40 (s, 1H), 7.35 (s, 1H), 3.96 (s, 3H), 3.61 (s, 3H); LCMS Calculated for $C_9H_8BrN_3O_4S_2$: 364.91; LCMS observed: 368.0 (M+2)$^+$.

Synthesis of 5-(4-bromothiazol-2-yl)-N-(3-chloro-4-fluorophenyl)-2-methyl-2H-1,2,6-thiadiazine-3-carboxamide 1,1-dioxide (HBV-CSU-150_Int)

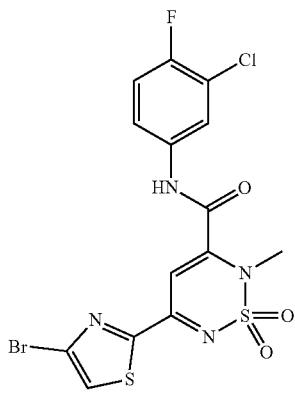 [SMILES: CN1C(C(=O)Nc2ccc(F)c(Cl)c2)=CC(c2nc(Br)cs2)=NS1(=O)=O]

The above titled compound has been synthesized by following the general procedure (Method B) described above for amidation by using corresponding 88 and corresponding amine (see Table 1 for analytical data).

Cis-5-(4-Bromothiazol-2-yl)-N-(3-chloro-4-fluorophenyl)-2-methyl-1,2,6-thiadiazinane-3-carboxamide 1,1-dioxide (HBV-CSU-150)

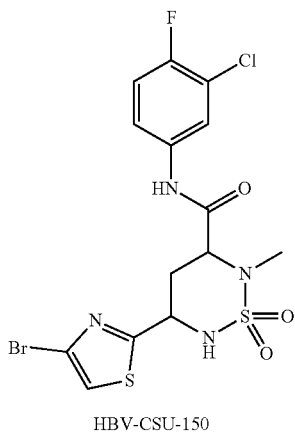

HBV-CSU-150

346

The above titled compound has been synthesized by following the general procedure described above for reduction by using corresponding HBV-CSU-0150_Int (see Table 2 for analytical data).

Scheme 26

Synthesis of Cis-N-(3-Chloro-4-fluorophenyl)-5-(4-hydroxyphenyl)-2-methyl-1,2,6-thiadiazinane-3-carboxamide 1,1-dioxide (HBV-CSU-201) & N-(3-chloro-4-fluorophenyl)-5-(4-(3-(dimethylamino)propoxy)phenyl)-2-methyl-1,2,6-thiadiazinane-3-carboxamide 1,1-dioxide (HBV-CSU-208, HBV-CSU-208-ISO-I & HBV-CSU-208-ISO-II)

Scheme 26:

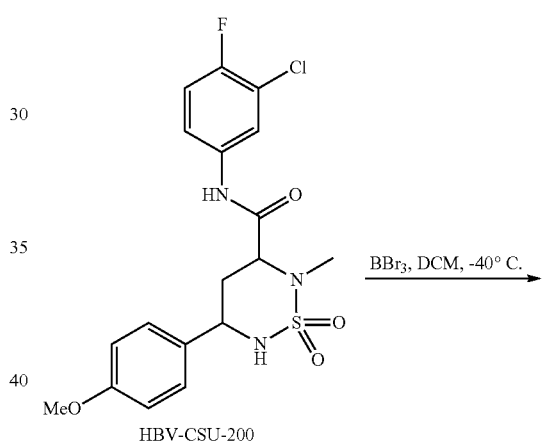

HBV-CSU-200

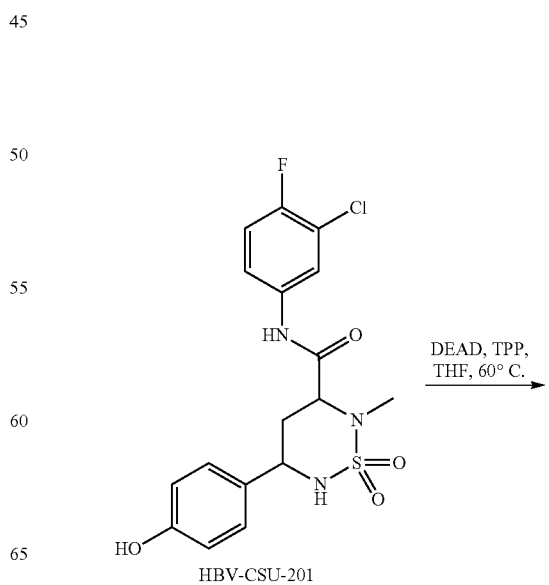

HBV-CSU-201

347

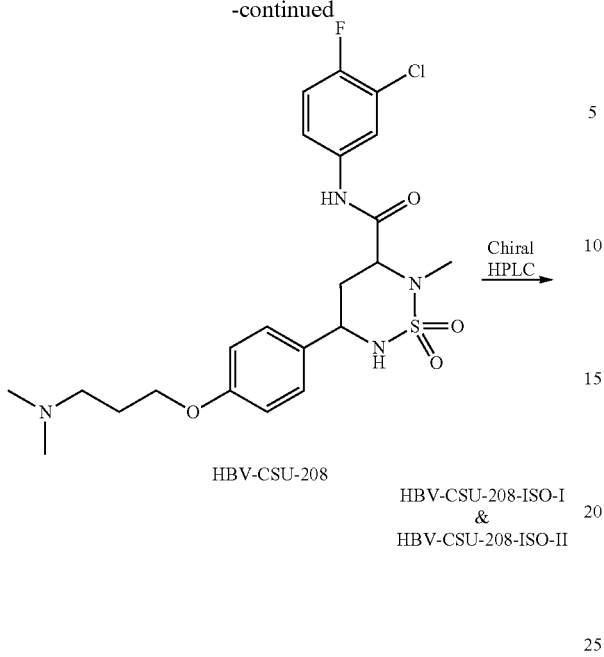

Cis-N-(3-Chloro-4-fluorophenyl)-5-(4-hydroxyphenyl)-2-methyl-1,2,6-thiadiazinane-3-carboxamide 1,1-dioxide (HBV-CSU-201)

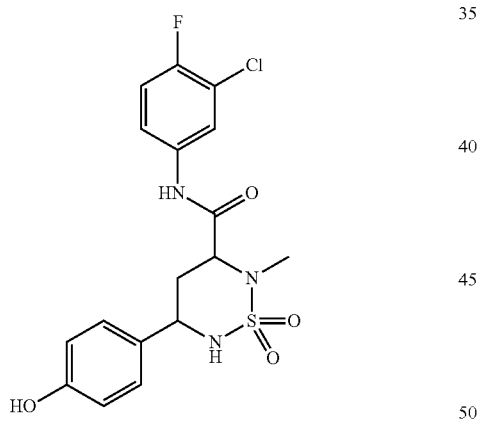

To a stirred solution of compound HBV-CSU-200 (50 mg, 0.116 mmol) in DCM (2 mL) at −40° C., BBr$_3$ (0.025 mL, 0.233 mmol) was added and stirred at room temperature for 4 h. The progress of the reaction was monitored by TLC and LCMS. After completion, the reaction mixture was quenched with sat. NaHCO$_3$ solution and extracted with DCM. The combined organic layers were dried over anhydrous sodium sulphate and concentrated under reduced pressure. The crude compound was purified by silica gel column chromatography to afford the desired compound as HBV-CSU-201 (20 mg, 41.66%) as a white solid (see Table 2 for analytical data).

348

Cis-N-(3-chloro-4-fluorophenyl)-5-(4-(3-(dimethylamino)propoxy)phenyl)-2-methyl-1,2,6-thiadiazinane-3-carboxamide 1,1-dioxide (HBV-CSU-208, HBV-CSU-208-ISO-I & HBV-CSU-208-ISO-II)

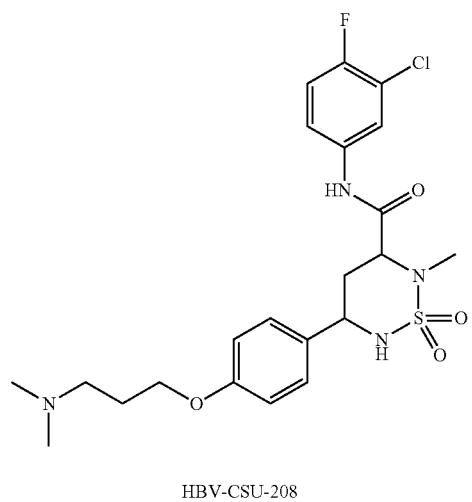

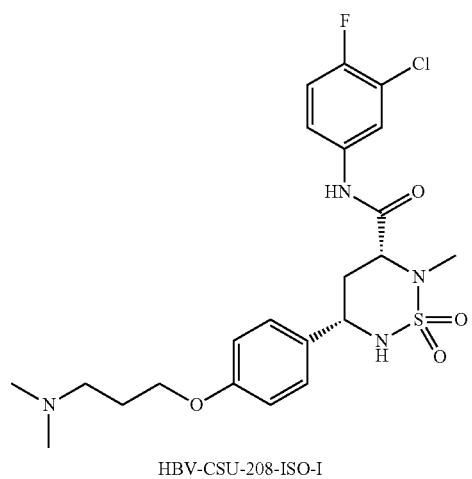

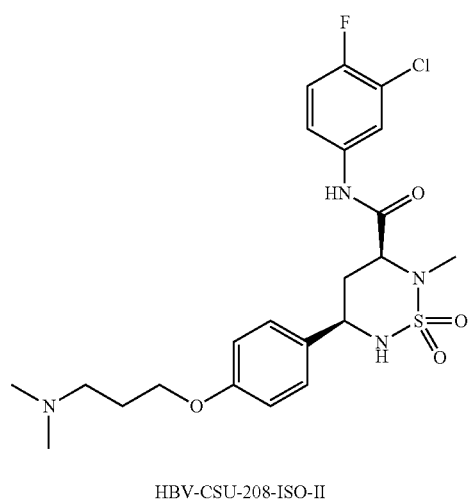

Title compound was synthesized using general method B for alkylation described above to afford 150 mg (35.62%,

Scheme 27

Synthesis of Cis-N-(3-chloro-4-fluorophenyl)-5-(3-hydroxyphenyl)-2-methyl-1,2,6-thiadiazinane-3-carboxamide 1,1-dioxide (HBV-CSU-205) & N-(3-Chloro-4-fluorophenyl)-5-(3-(3-(dimethylamino)propoxy)phenyl)-2-methyl-1,2,6-thiadiazinane-3-carboxamide 1,1-dioxide (HBV-CSU-209)

Scheme 27:

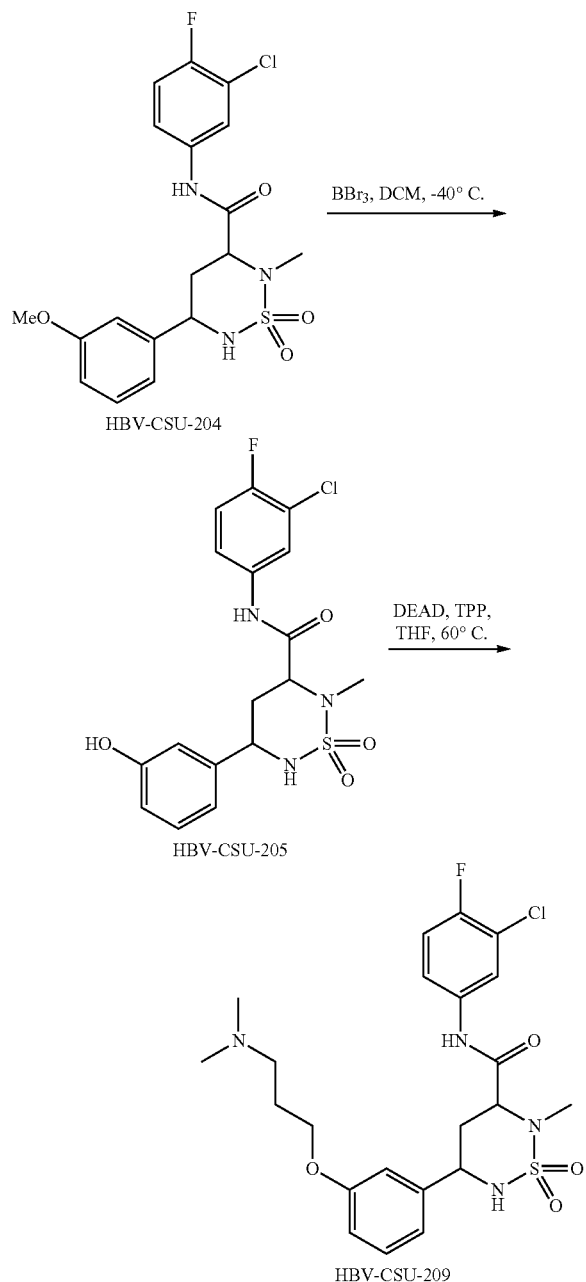

reaction scale is 350 mg) as an off white solid. TLC: 10% MeOH/DCM ($R_f$: 0.2) (see Table 2 for analytical data).

Cis-N-(3-chloro-4-fluorophenyl)-5-(3-hydroxyphenyl)-2-methyl-1,2,6-thiadiazinane-3-carboxamide 1,1-dioxide (HBV-CSU-205)

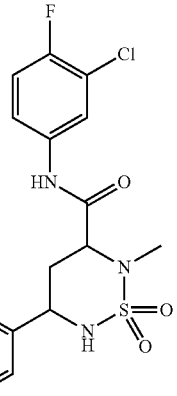

To a stirred solution of compound HBV-CSU-204 (0.71 g, 1.66 mmol) in DCM (7 mL) at −40° C., BBr$_3$ (7 mL) was added and stirred at room temperature for 4 h. The progress of the reaction was monitored by TLC and LCMS. After completion, the reaction mixture was quenched with sat. NaHCO$_3$ solution and extracted with DCM. The combined organic layers were dried over anhydrous sodium sulphate and concentrated under reduced pressure. The crude compound was purified by silica gel column chromatography to afford the desired compound as HBV-CSU-205 (0.6 g, 89.15%) as a white solid. TLC: 50% EtOAc/hexanes ($R_f$: 0.3) (see Table 2 for analytical data).

Cis-N-(3-Chloro-4-fluorophenyl)-5-(3-(3-(dimethylamino)propoxy)phenyl)-2-methyl-1,2,6-thiadiazinane-3-carboxamide 1,1-dioxide (HBV-CSU-209)

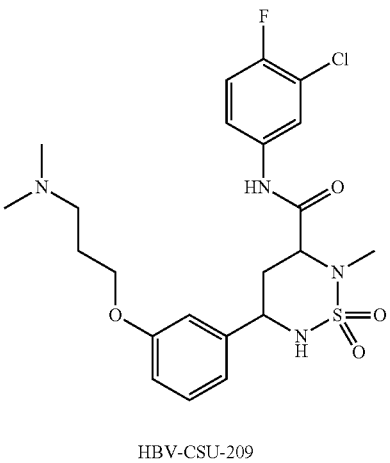 [SMILES: CN(C)CCCOc1cccc(C2CC(C(=O)Nc3ccc(F)c(Cl)c3)N(C)S(=O)(=O)N2)c1 ; "HBV-CSU-209"]

Title compound was synthesized using general method B for alkylation described above (see Table 2 for analytical data).

Scheme 28
Synthesis of N-(3-chloro-4-fluorophenyl)-5-(4-cyanophenyl)-2-methyl-1,2,6-thiadiazinane-3-carboxamide 1,1-dioxide (HBV-CSU-213) & 5-(4-Carbamoylphenyl)-N-(3-chloro-4-fluorophenyl)-2-methyl-1,2,6-thiadiazinane-3-carboxamide 1,1-dioxide (HBV-CSU-214)
Scheme 28:
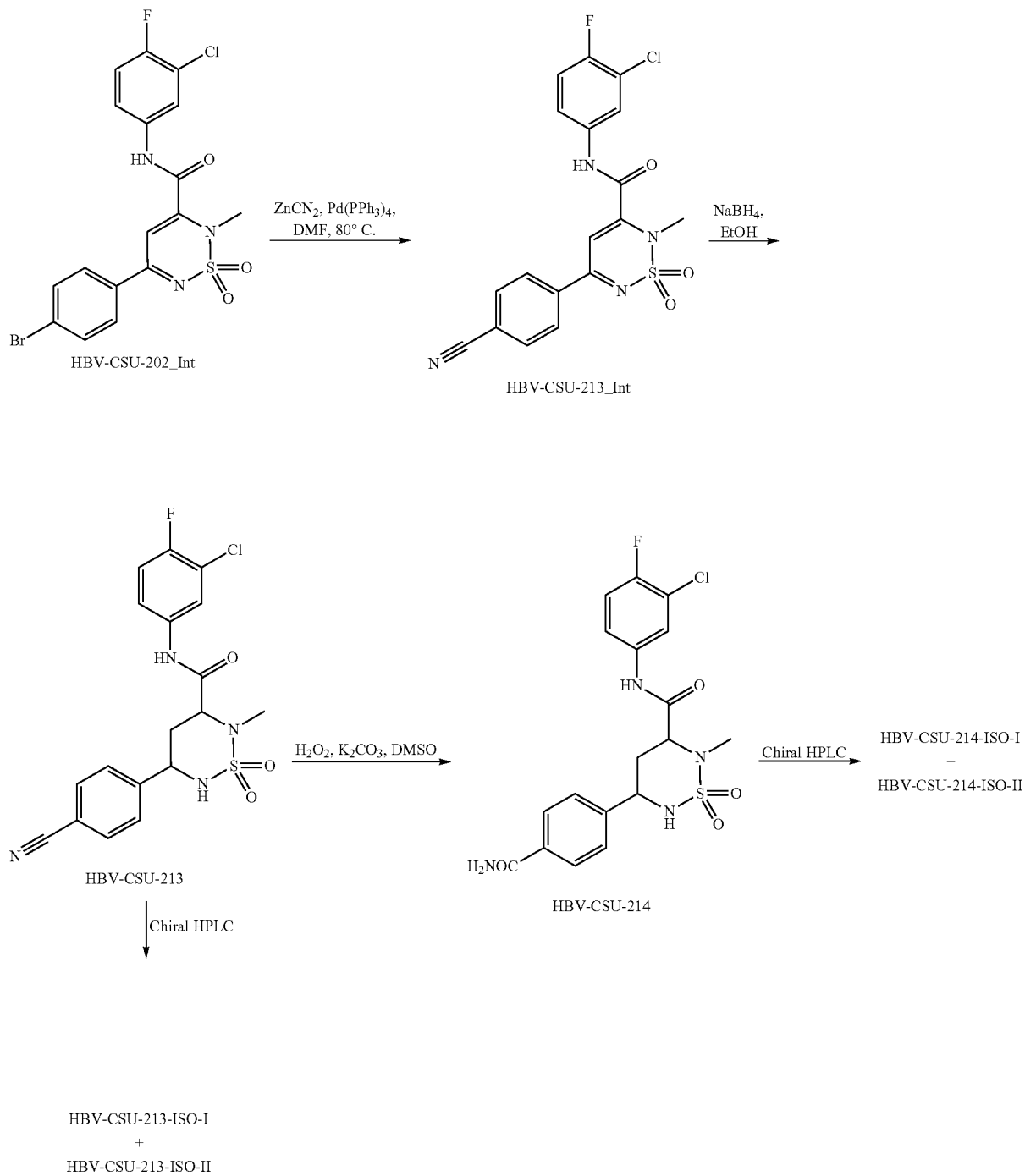

5-(4-Carbamoylphenyl)-N-(3-chloro-4-fluorophenyl)-2-methyl-1,2,6-thiadiazinane-3-carboxamide 1,1-dioxide (HBV-CSU-213_Int)

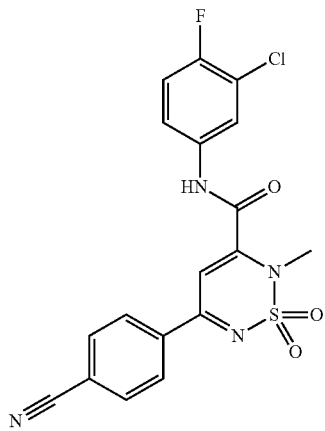

HBV-CSU-213_Int

To a mixture of bromo compound (200 mg, 0.423 mmol) in DMF, tetrakistriphenyl phosphine palladium (48.8 mg, 0.0423 mmol) was added and purged with Ar for 15 min. To this solution, $ZnCN_2$ (99.52 mg, 0.847 mmol) was added and purged with Ar for another 15 min. The resulting reaction mixture was then stirred at 80° C. for overnight. The progress of the reaction was monitored by TLC. After completion of the reaction, the reaction mixture was filtered through Celite and evaporated to dryness. The residue was taken in ethyl acetate, washed with water, brine, dried over anhydrous sodium sulfate and evaporated under reduced pressure. The crude product was purified by column chromatography to afford HBV-CSU-213_Int (100 mg, 56.5%) as an orange liquid. TLC: 40% EtOAc/hexane ($R_f$: 0.3) (see Table 1 for analytical data).

Cis-N-(3-chloro-4-fluorophenyl)-5-(4-cyanophenyl)-2-methyl-1,2,6-thiadiazinane-3-carboxamide 1,1-dioxide (HBV-CSU-213)

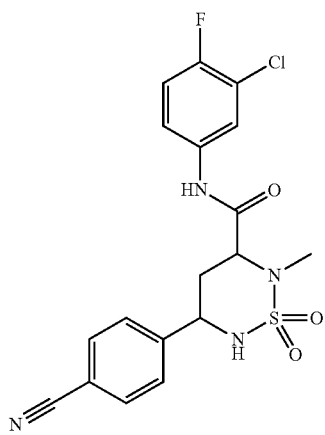

HBV-CSU-213

The above titled compound has been synthesized by following the general procedure described above for reduction by using HBV-CSU-213_Int (see Table 2 for analytical data).

Cis-5-(4-Carbamoylphenyl)-N-(3-chloro-4-fluorophenyl)-2-methyl-1,2,6-thiadiazinane-3-carboxamide 1,1-dioxide (HBV-CSU-214, HBV-CSU-214-ISO-I & HBV-CSU-214-ISO-II)

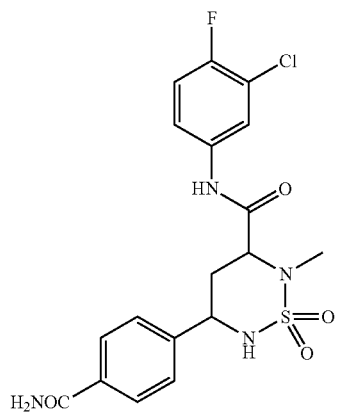

HBV-CSU-214

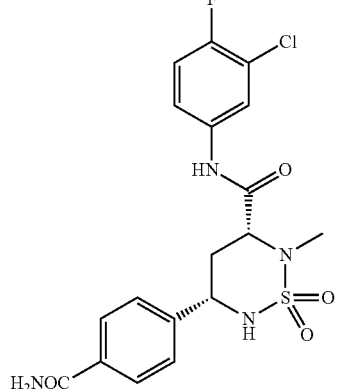

HBV-CSU-214-ISO-I

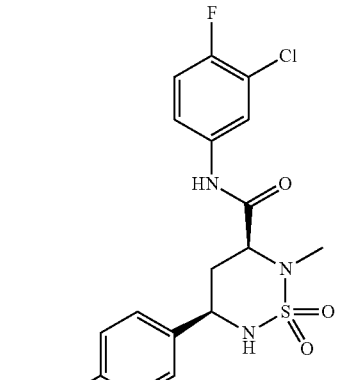

HBV-CSU-214-ISO-II

To a stirred solution of compound HBV-CSU-213 (0.3 g, 0.709 mmol) in DMSO (15 mL) at 0° C., $K_2CO_3$ (0.196 g, 1.42 mmol) and H₂O₂ (30% in water 0.241 mL, 2.13 mmol) were added and stirred at room temperature for 2 h. The progress of the reaction was monitored by TLC and LCMS. After completion, the reaction mixture was quenched with ice cold water. The precipitated solid was collected by filtration; washed with water and dried under reduced pressure to afford the desired compound as HBV-CSU-214 (0.1 g, 32.15%) as a white solid. TLC: 5% MeOH/DCM (R$_f$: 0.4) (see Table 2 for analytical data).

Scheme 29

Synthesis of 2-(4-(5-((3-Chloro-4-fluorophenyl)carbamoyl)-6-methyl-1,1-dioxido-1,2,6-thiadiazinan-3-yl)phenoxy)acetic acid (HBV-CSU-216, HBV-CSU-216-ISO-I & HBV-CSU-216-ISO-II)

Scheme 29:

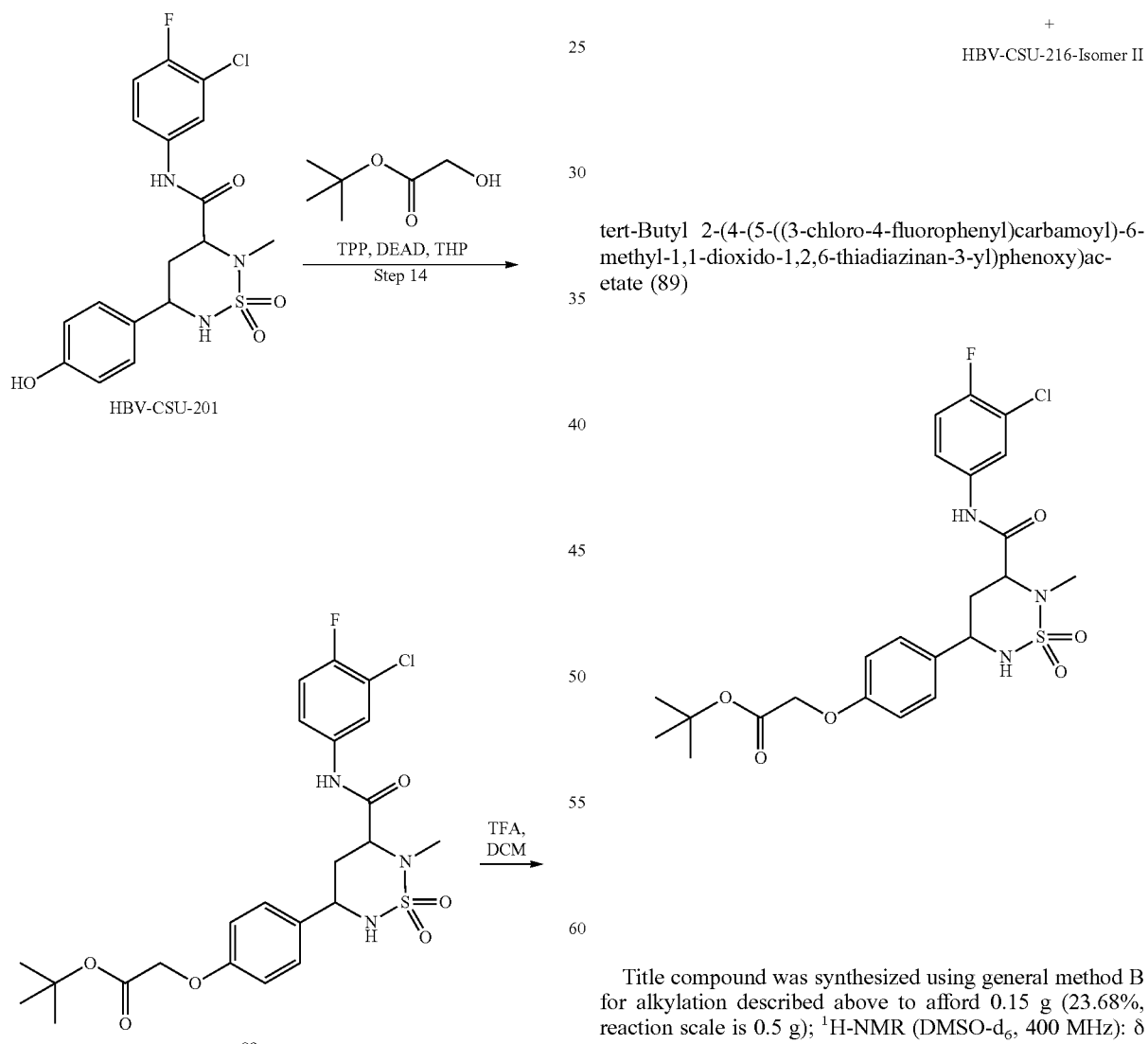

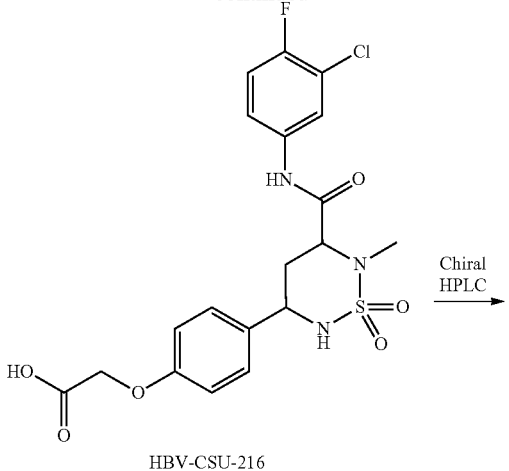

HBV-CSU-216-Isomer I
+
HBV-CSU-216-Isomer II tert-Butyl 2-(4-(5-((3-chloro-4-fluorophenyl)carbamoyl)-6-methyl-1,1-dioxido-1,2,6-thiadiazinan-3-yl)phenoxy)acetate (89)

Title compound was synthesized using general method B for alkylation described above to afford 0.15 g (23.68%, reaction scale is 0.5 g); ¹H-NMR (DMSO-d₆, 400 MHz): δ 10.53 (s, 1H), 7.96-7.94 (m, 1H), 7.56-7.35 (m, 5H), 6.88 (d, J=8.8 Hz, 2H), 4.65 (s, 2H), 4.54-4.49 (m, 1H), 4.26-4.19 (m, 1H), 2.63 (s, 3H), 2.09-2.01 (m, 2H), 1.42 (s, 9H).

357

Cis-2-(4-(5-((3-Chloro-4-fluorophenyl) carbamoyl)-6-methyl-1,1-dioxido-1,2,6-thiadiazinan-3-yl)phenoxy)acetic acid (HBV-CSU-216, HBV-CSU-216-ISO-I & HBV-CSU-216-ISO-II)

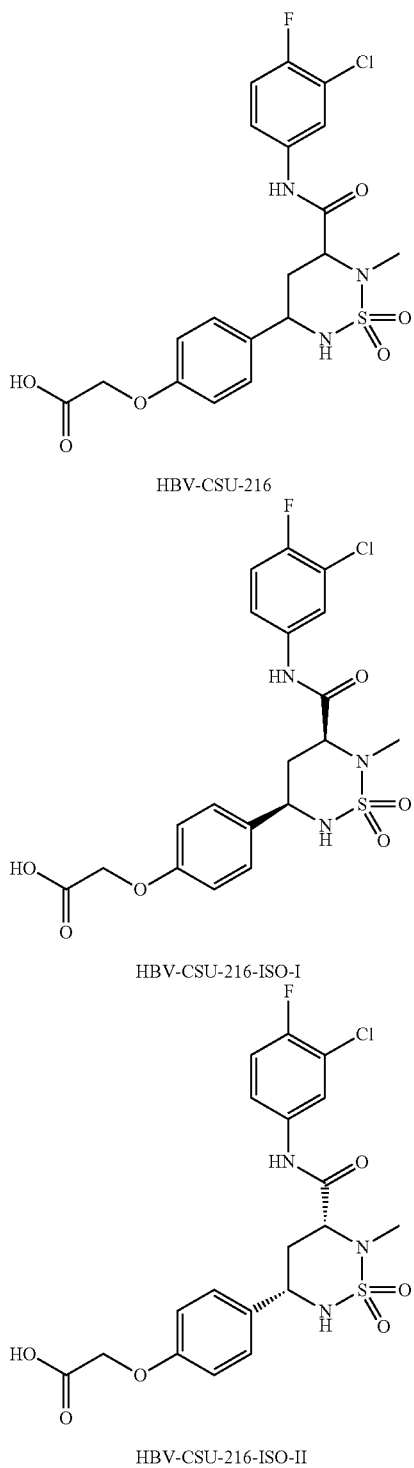

HBV-CSU-216

HBV-CSU-216-ISO-I

HBV-CSU-216-ISO-II

To a stirred solution of compound 89 (50 mg, 0.246 mmol) in DCM (5 mL) at 0° C., TFA (0.083 mL, 0.739 mmol) was added and stirred at room temperature for 2 h. The progress of the reaction was monitored by TLC and

358

LCMS. After completion, the reaction mixture was concentrated and co-evaporated with DCM twice and the residue obtained was triturated with di-ethyl ether to afford the desired compound as HBV-CSU-216 (90 mg, 78%) as an off white solid. TLC: 40% EtOAc/hexanes ($R_f$: 0.3) (see Table 2 for analytical data).

Scheme 30

Synthesis of Cis-4-(5-((3-Chloro-4-fluorophenyl) carbamoyl)-6-methyl-1,1-dioxido-1,2,6-thiadiazinan-3-yl)benzoic acid (HBV-CSU-218, HBV-CSU-218-ISO-I & HBV-CSU-218-ISO-II) and Cis-methyl 4-(5-((3-chloro-4-fluorophenyl)carbamoyl)-6-methyl-1,1-dioxido-1,2,6-thiadiazinan-3-yl) benzoate (HBV-CSU-256)

Scheme 30:

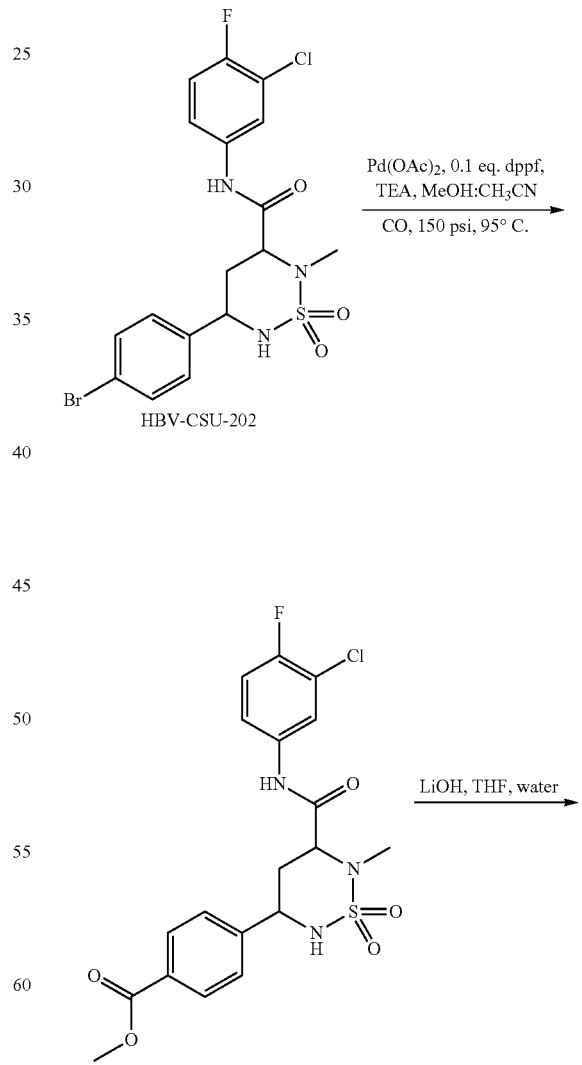

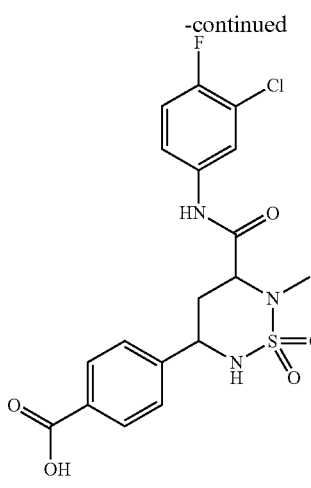

HBV-CSU-218

→ Chiral HPLC →

HBV-CSU-218-isomer I
+
HBV-CSU-218-isomer II

Cis-methyl 4-(5-((3-chloro-4-fluorophenyl)carbamoyl)-6-methyl-1,1-dioxido-1,2,6-thiadiazinan-3-yl)benzoate (HBV-CSU-256)

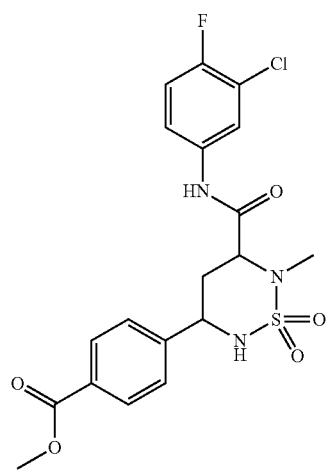

HBV-CSU-256

To a stirred solution of compound HBV-CSU-202 (0.5 g, 1.04 mmol) in MeOH:ACN (4:1, 2.5 mL) mixture under Ar atmosphere in an autoclave, TEA (0.05 mL, 0.312 mmol) and dppf (0.058 g, 0.104 mmol) were added and purged with Ar for 30 min. To this solution, Pd(OAc)$_2$ (0.023 g, 0.104 mmol) was added and again purged with carbon monoxide. The resulting reaction mixture was heated in autoclave at 100° C. for 150 psi pressure for 6 h. The progress of the reaction was monitored by TLC. After completion, the reaction mixture was filtered through a pad of celite and filtrate was concentrated in vacuo. The residue was diluted with water (100 mL) and extracted with ethyl acetate (2×100 mL). The combined organic layers were dried over anhydrous sodium sulfate, filtered and concentrated in vacuo to obtain the crude. The crude was purified through silica gel column chromatography using 10% EtOAc/hexane to afford compound HBV-CSU-256 (0.03 g, 6.3%) as a white solid. TLC: 40% EtOAc/hexane (R$_f$: 0.3) (see Table 2 for analytical data).

Cis-4-(5-((3-Chloro-4-fluorophenyl)carbamoyl)-6-methyl-1,1-dioxido-1,2,6-thiadiazinan-3-yl)benzoic acid (HBV-CSU-218, HBV-CSU-218-ISO-I & HBV-CSU-218-ISO-II)

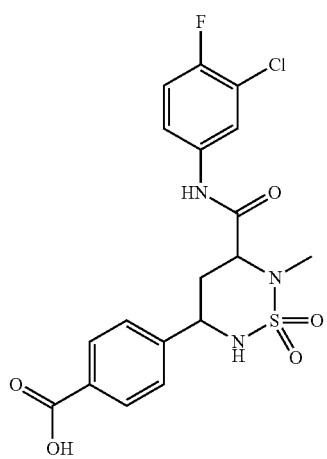

HBV-CSU-218

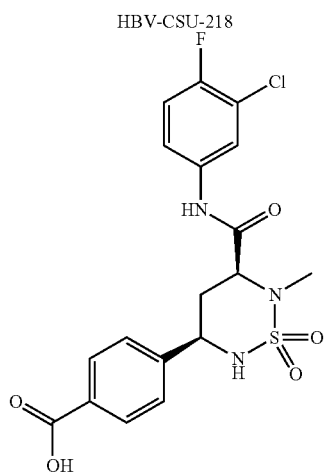

HBV-CSU-218-ISO-I

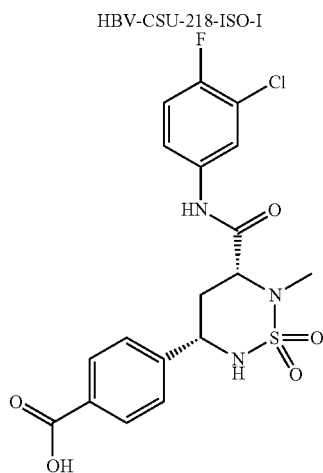

HBV-CSU-218-ISO-II

To a stirred solution of HBV-CSU-256 (0.25 g, 0.549 mmol) in THF:H₂O (1:1, 10 mL) mixture, aqueous LiOH (0.23 g, 5.49 mmol) was added and stirred at room temperature for 4 h. The progress of the reaction was monitored by TLC. After completion, the volatiles were removed in vacuo. The residue was acidified with 1N HCl to pH-3 and extracted with ethyl acetate. The combined organic layers were dried over anhydrous sodium sulfate, filtered and concentrated in vacuo to afford the desired compound HBV-CSU-218 (0.1 g, 41.49%) as a white solid. TLC: 40% EtOAc/hexane ($R_f$: 0.1) (see Table 2 for analytical data).

Scheme 31

General Synthetic Scheme for 5-(thiophen-2-yl)-1,2,6-thiadiazinane-3-carboxamide 1,1-dioxide Derivatives with 5-Substituted Thiophene Variations (Reverse Suzuki Approach)

Scheme 31:

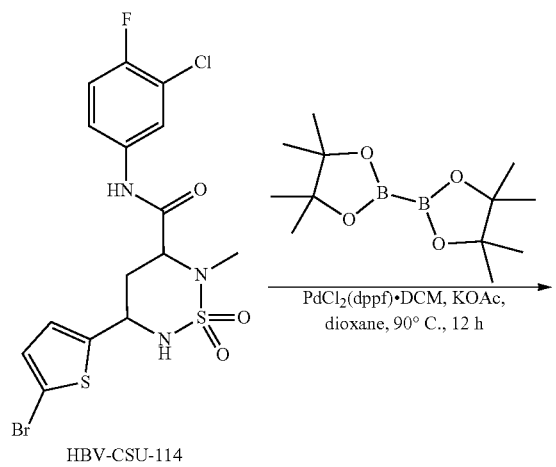

HBV-CSU-114

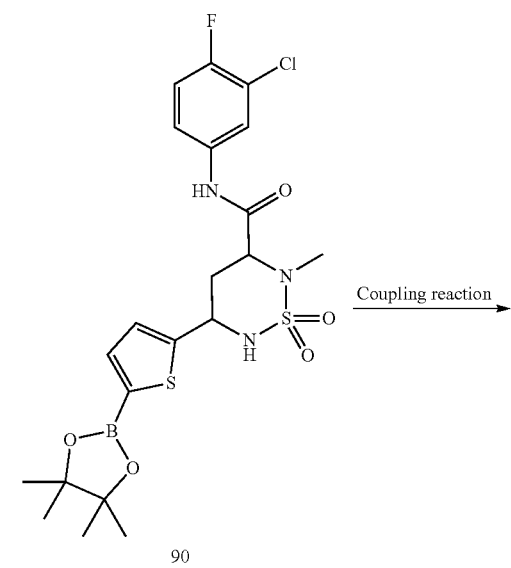

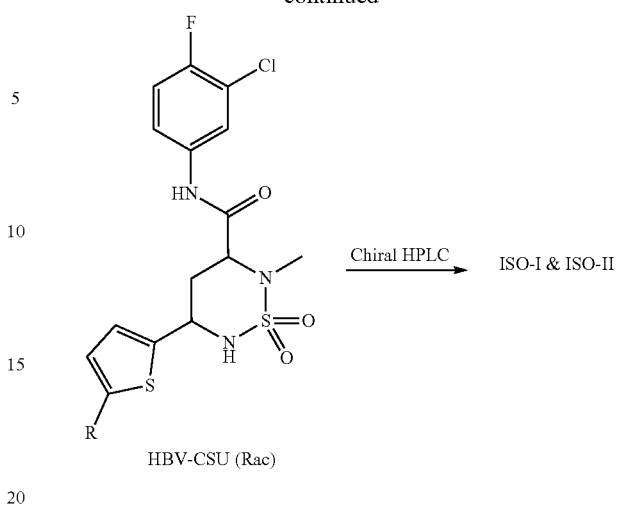

HBV-CSU (Rac)

| Target | Coupling reaction | #2 (R variation) |
| --- | --- | --- |
| HBV-CSU-219 | — | —CF3 |
| HBV-CSU-242 | Suzuki coupling | 2-(5-fluoropyridinyl) |
| HBV-CSU-266 | Suzuki coupling | 1-methylimidazol-2-yl |
| HBV-CSU-267 | Suzuki coupling | 1-methylimidazol-5-yl |
| HBV-CSU-268 | Suzuki coupling | thiazol-5-yl |
| HBV-CSU-270 | Suzuki coupling | 1-methylpyrazol-3-yl |
| HBV-CSU-322 | Suzuki coupling | 1-methyl-1,2,4-triazol-3-yl |
| HBV-CSU-323 | Suzuki coupling | 1-methyl-1,2,4-triazol-5-yl |

363

Synthesis of N-(3-chloro-4-fluorophenyl)-2-methyl-5-(5-(4,4,5,5-tetramethyl-1,3,2-dioxaborolan-2-yl)thiophen-2-yl)-1,2,6-thiadiazinane-3-carboxamide 1,1-dioxide (90)

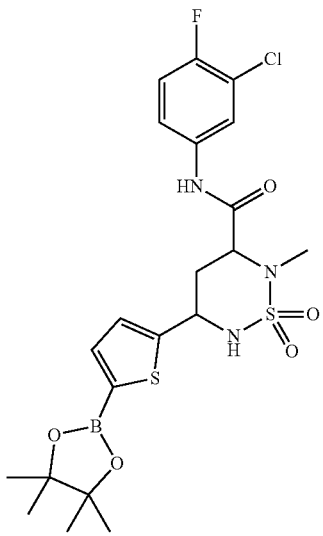 [SMILES: CN1C(C(=O)Nc2ccc(F)c(Cl)c2)CC(c2ccc(B3OC(C)(C)C(C)(C)O3)s2)NS1(=O)=O]

To a mixture of bromo compound HBV-CSU-114 (2 g, 4.143 mmol) and Bis(pinacolato)diboron (2.63 g, 10.35 mmol) in 1,4-dioxane (20 mL), potassium acetate (2.03 g, 20.71 mmol) was added and purged with Ar for 15 min. To this solution, PdCl$_2$(dppf).CH$_2$Cl$_2$ (0.101 g, 0.124 mmol) was added and the reaction mixture was stirred at 90° C. for overnight. The progress of the reaction was monitored by TLC. After completion of the reaction, the reaction mixture was filtered through Celite, evaporated to dryness to afford the desired Boronate ester as crude product 90 (2.35 g, crude) and used as such for the next step without further purification. TLC: 40% EtOAc/hexanes (R$_f$: 0.2); LCMS Calculated for C$_{21}$H$_{26}$BClFN$_3$O$_5$S$_2$: 529.11; Observed: 447.95 (M+1)$^+$ for boronic acid.

Cis-N-(3-Chloro-4-fluorophenyl)-2-methyl-5-(5-(trifluoromethyl)thiophen-2-yl)-1,2,6-thiadiazinane-3-carboxamide 1,1-dioxide (HBV-CSU-219, HBV-CSU-219-ISO-I & HBV-CSU-219-II)

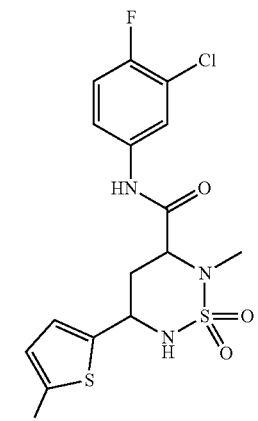

HBV-CSU-219

364

-continued

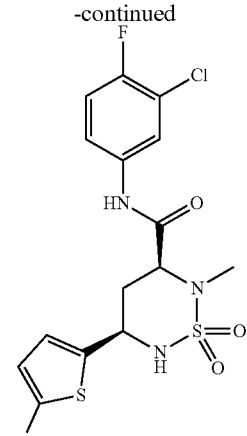

HBV-CSU-219-Isomer I

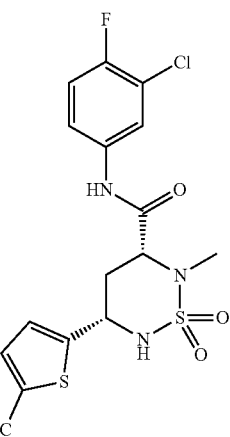

HBV-CSU-219-Isomer II

To a stirred solution of compound 90 (0.25 g, 0.472 mmol) and NaSO$_2$CF$_3$ (0.221 g, 1.417 mmol) in MeOH:DCM:H$_2$O (1:1:0.8, 5.6 mL) mixture at 0° C., CuCl (0.046 g, 0.472 mmol) was added and stirred for 10 min. To this solution, TBHP (70% aq., 0.303 mL, 2.36 mmol) was added slowly. The resulting reaction mixture was stirred at room temperature for overnight. The reaction was monitored by TLC. After completion, the reaction mixture was concentrated under reduced pressure and the crude compound obtained was purified by silica gel column chromatography using 15% EtOAc/hexane to afford the title compound HBV-CSU-219 (0.08 g, 36.03%) as an off-white solid. TLC: 40% EtOAc/hexanes (R$_f$: 0.5); (see Table 2 for analytical data).

365

Cis-N-(3-chloro-4-fluorophenyl)-5-(5-(5-fluoropyridin-2-yl)thiophen-2-yl)-2-methyl-1,2,6-thiadiazinane-3-carboxamide 1,1-dioxide (HBV-CSU-242 HBV-CSU-242-ISO-I & HBV-CSU-242-ISO-II)

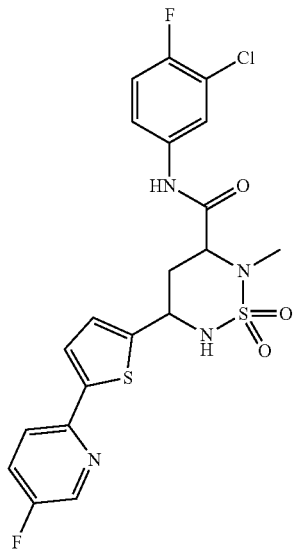

HBV-CSU-242

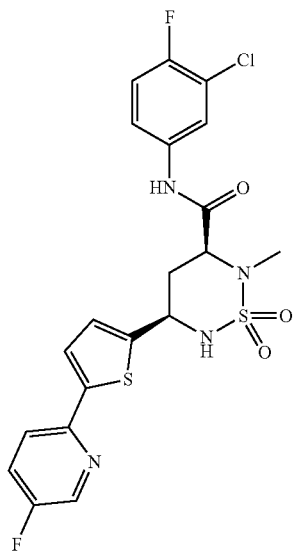

HBV-CSU-242-ISO-I

366

-continued

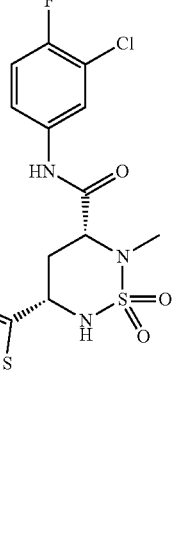

HBV-CSU-242-ISO-II

The above titled compounds have been synthesized by following the general procedure described above for Suzuki coupling by using compound 90 and corresponding bromo compound (see Table 2 for analytical data).

Cis-N-(3-Chloro-4-fluorophenyl)-2-methyl-5-(5-(1-methyl-1H-imidazol-4-yl)thiophen-2-yl)-1,2,6-thiadiazinane-3-carboxamide 1,1-dioxide (HBV-CSU-266, HBV-CSU-266-ISO-I & HBV-CSU-266-II)

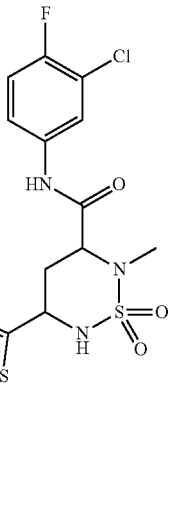

HBV-CSU-266

367

-continued

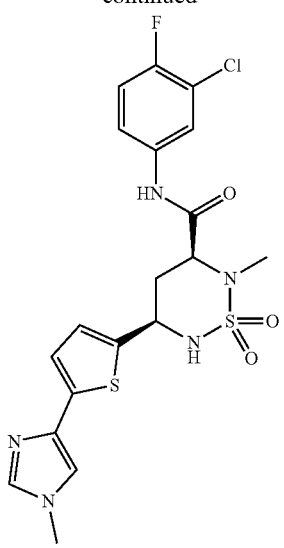

HBV-CSU-266-ISO-I

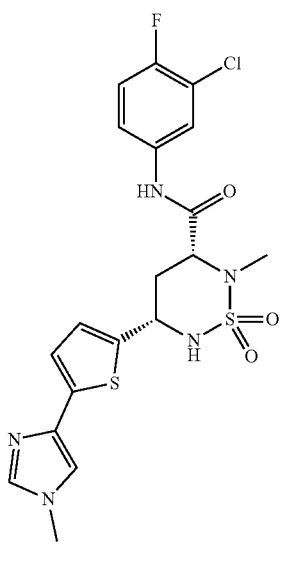

HBV-CSU-266-ISO-II

The above titled compounds have been synthesized by following the general procedure described above for Suzuki coupling by using compound 90 and corresponding bromo compound (see Table 2 for analytical data).

368

Cis-N-(3-Chloro-4-fluorophenyl)-2-methyl-5-(5-(1-methyl-1H-imidazol-5-yl)thiophen-2-yl)-1,2,6-thiadiazinane-3-carboxamide 1,1-dioxide (HBV-CSU-267, HBV-CSU-267-ISO-I & HBV-CSU-267-II)

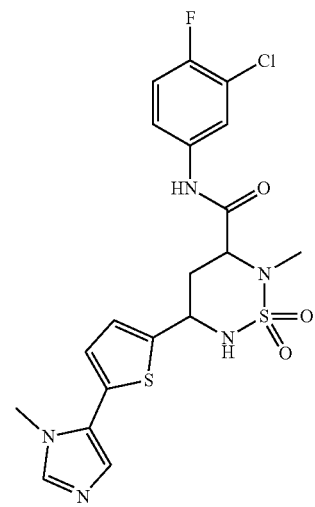

HBV-CSU-267

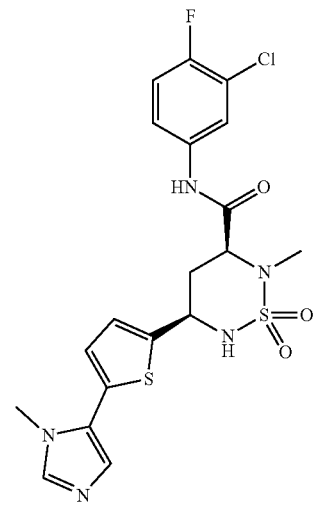

HBV-CSU-267-ISO-I

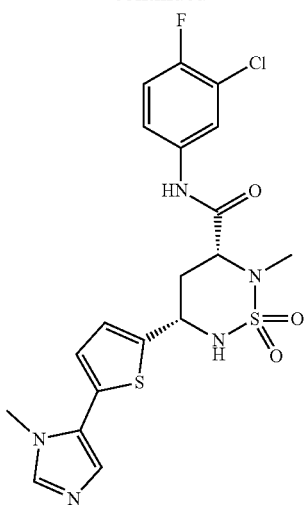

HBV-CSU-267-ISO-II

The above titled compounds have been synthesized by following the general procedure described above for Suzuki coupling by using compound 90 and corresponding bromo compound (see Table 2 for analytical data).

Cis-N-(3-Chloro-4-fluorophenyl)-2-methyl-5-(5-(thiazol-5-yl)thiophen-2-yl)-1,2,6-thiadiazinane-3-carboxamide 1,1-dioxide (HBV-CSU-268, HBV-CSU-268-ISO-I & HBV-CSU-268-II)

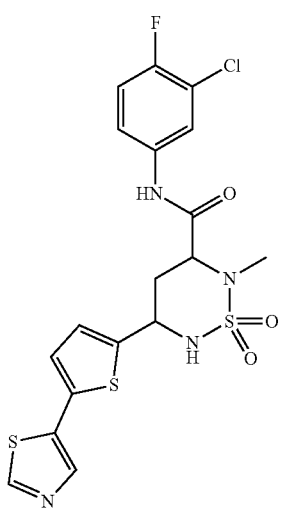

HBV-CSU-268

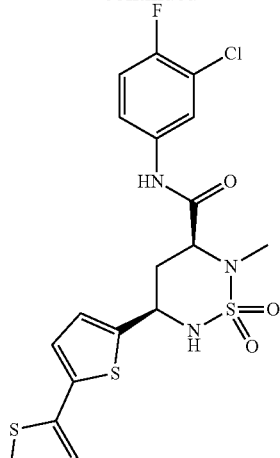

HBV-CSU-268-ISO-I

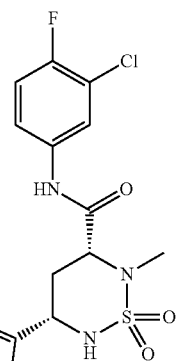

HBV-CSU-268-ISO-II

The above titled compounds have been synthesized by following the general procedure described above for Suzuki coupling by using compound 90 and corresponding bromo compound (see Table 2 for analytical data).

371

Cis-N-(3-Chloro-4-fluorophenyl)-2-methyl-5-(5-(1-methyl-1H-pyrazol-3-yl)thiophen-2-yl)-1,2,6-thiadiazinane-3-carboxamide 1,1-dioxide (HBV-CSU-270, HBV-CSU-270-ISO-I & HBV-CSU-270-ISO-II)

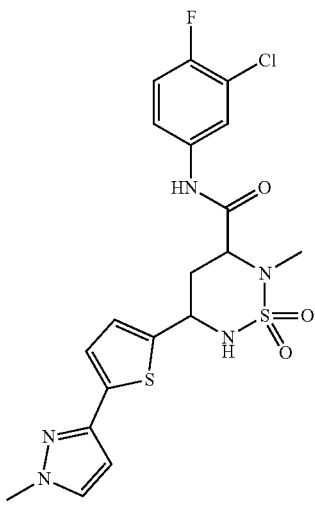

HBV-CSU-270

372

-continued

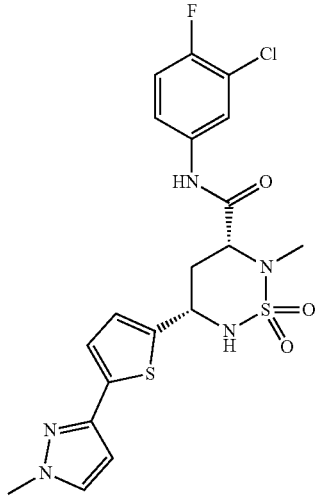

HBV-CSU-270-ISO-II

The above titled compounds have been synthesized by following the general procedure described above for Suzuki coupling by using compound 90 and corresponding bromo compound (see Table 2 for analytical data).

Cis-N-(3-Chloro-4-fluorophenyl)-2-methyl-5-(5-(1-methyl-1H-1,2,4-triazol-3-yl)thiophen-2-yl)-1,2,6-thiadiazinane-3-carboxamide 1,1-dioxide (HBV-CSU-322-ISO-I & HBV-CSU-322-ISO-II)

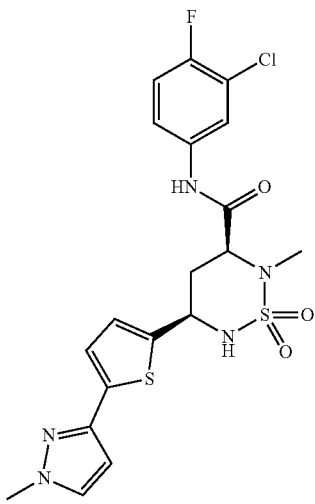

HBV-CSU-270-ISO-I

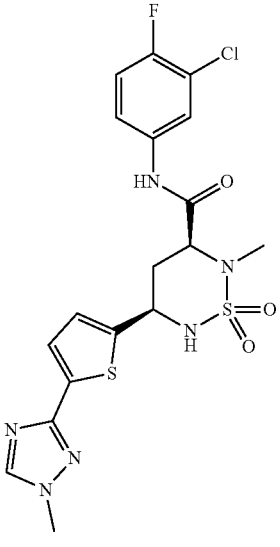

HBV-CSU-322-Isomer I

-continued

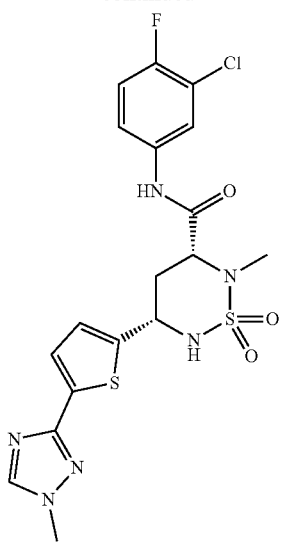

HBV-CSU-322-Isomer II

The above titled compounds have been synthesized by following the general procedure described above for Suzuki coupling by using compound 90 and corresponding bromo compound (see Table 2 for analytical data).

Cis-N-(3-Chloro-4-fluorophenyl)-2-methyl-5-(5-(1-methyl-1H-1,2,4-triazol-5-yl)thiophen-2-yl)-1,2,6-thiadiazinane-3-carboxamide 1,1-dioxide (HBV-CSU-323-ISO-I & HBV-CSU-323-ISO-II)

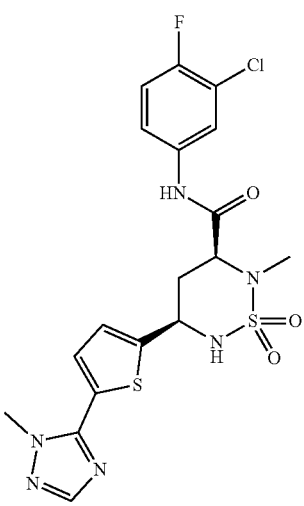

HBV-CSU-323-ISO-I

-continued

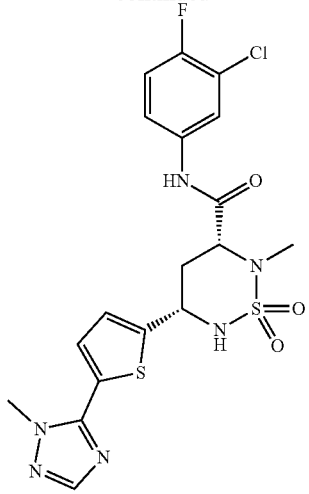

HBV-CSU-323-ISO-II

The above titled compounds have been synthesized by following the general procedure described above for Suzuki coupling by using compound 90 and corresponding bromo compound (see Table 2 for analytical data).

Scheme 32

Synthesis of N-(3-chloro-4-fluorophenyl)-5-(3-chloro-4-hydroxyphenyl)-2-methyl-1,2,6-thiadiazinane-3-carboxamide 1,1-dioxide (HBV-CSU-220) & N-(3-Chloro-4-fluorophenyl)-5-(3,5-dichloro-4-hydroxyphenyl)-2-methyl-1,2,6-thiadiazinane-3-carboxamide 1,1-dioxide (HBV-CSU-260)

Scheme 32:

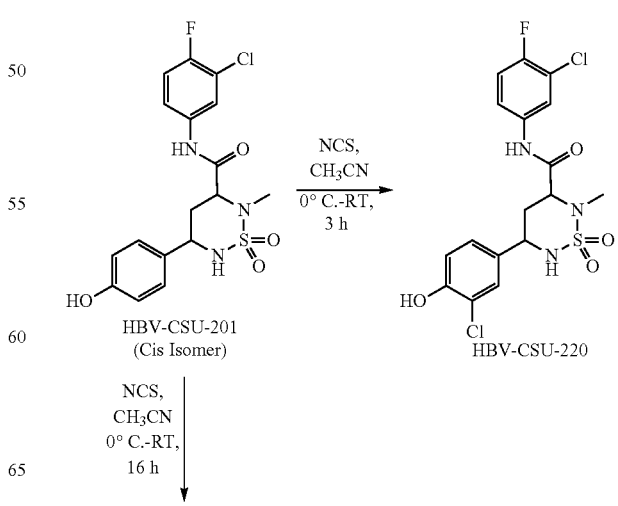

375

-continued

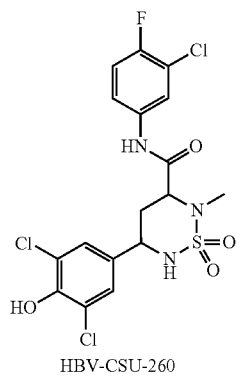

HBV-CSU-260

Cis-N-(3-chloro-4-fluorophenyl)-5-(3-chloro-4-hydroxyphenyl)-2-methyl-1,2,6-thiadiazinane-3-carboxamide 1,1-dioxide (HBV-CSU-220)

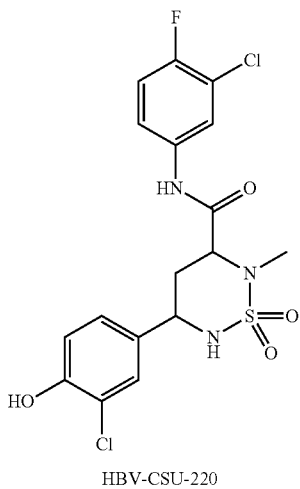

HBV-CSU-220

To a stirred solution of compound HBV-CSU-201 (200 mg, 0.483 mmol) in acetonitrile at 0° C., NCS (65 mg, 0.483 mmol) was added and stirred at room temperature for 3 h. The progress of the reaction was monitored by TLC and LCMS. After completion, the reaction mixture was concentrated and the crude compound was purified by silica gel column chromatography to afford the desired compound as HBV-CSU-220 (150 mg, 69.4%) as a white solid (see Table 2 for analytical data).

376

Cis-N-(3-Chloro-4-fluorophenyl)-5-(3,5-dichloro-4-hydroxyphenyl)-2-methyl-1,2,6-thiadiazinane-3-carboxamide 1,1-dioxide (HBV-CSU-260)

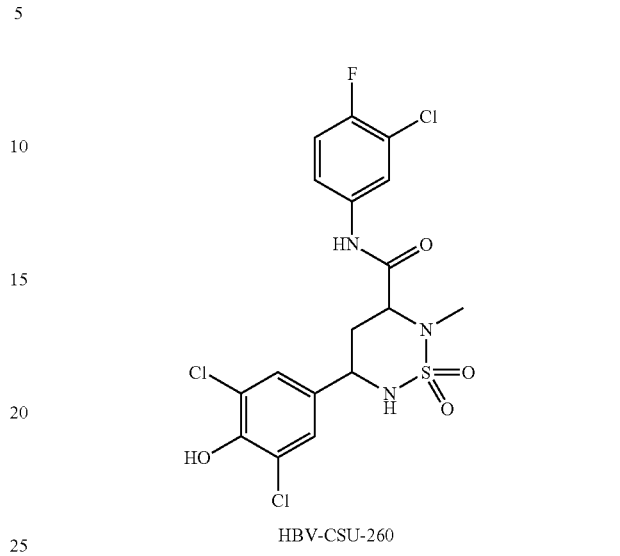

HBV-CSU-260

To a stirred solution of compound HBV-CSU-201 (200 mg, 0.483 mmol) in acetonitrile at 0° C., NCS (77 mg, 0.579 mmol) was added and stirred at room temperature for 16 h. The progress of the reaction was monitored by TLC and LCMS. After completion, the reaction mixture was concentrated and the crude compound was purified by silica gel column chromatography to afford the desired compound as HBV-CSU-260 (80 mg, 34.33%) as a white solid (see Table 2 for analytical data).

Scheme 33

Synthesis of Cis-N-(3-chloro-4-fluorophenyl)-5-(4-cyano-3-fluorophenyl)-2-methyl-1,2,6-thiadiazinane-3-carboxamide 1,1-dioxide (HBV-CSU-221, HBV-CSU-221-ISO-I & HBV-CSU-221-ISO-II)

Scheme 33:

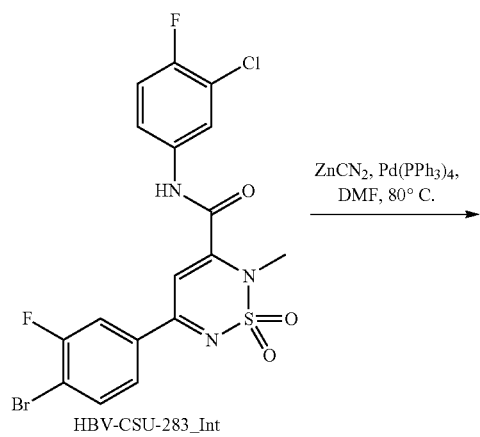

HBV-CSU-283_Int

-continued

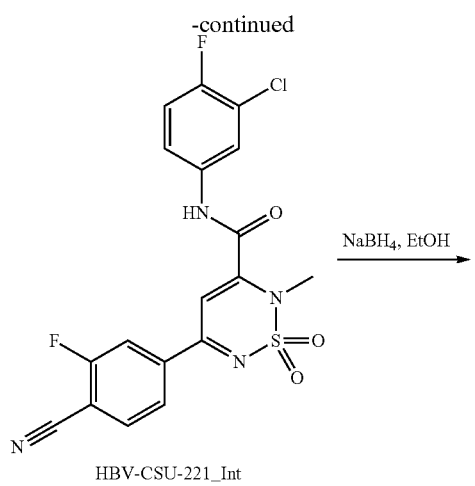

HBV-CSU-221_Int

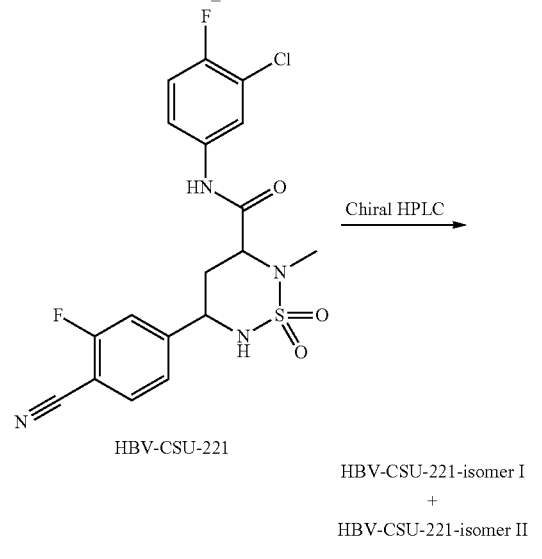

HBV-CSU-221

N-(3-Chloro-4-fluorophenyl)-5-(4-cyano-3-fluorophenyl)-2-methyl-2H-1,2,6-thiadiazine-3-carboxamide 1,1-dioxide (HBV-CSU-221_Int)

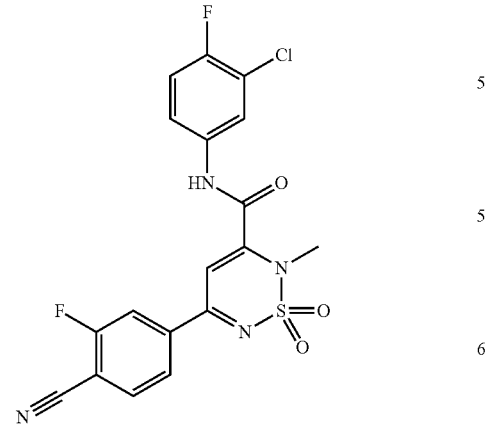

To a mixture of bromo compound (0.5 g, 1.02 mmol) in DMF (5 mL), tetrakistriphenyl phosphine palladium (0.118 g, 0.102 mmol) was added and purged with Ar for 15 min. To this solution, ZnCN$_2$ (0.239 g, 2.04 mmol) was added and purged with Ar for another 15 min. The resulting reaction mixture was then stirred at 80° C. for overnight. The progress of the reaction was monitored by TLC. After completion of the reaction, the reaction mixture was filtered through Celite and evaporated to dryness. The residue was taken in ethyl acetate, washed with water, brine, then dried over anhydrous sodium sulfate and evaporated under reduced pressure. The crude product was purified by column chromatography to afford HBV-CSU-221_Int (0.3 g, 67.41%) as an orange liquid. TLC: 40% EtOAc/hexane (R$_f$: 0.3) (see Table 1 for analytical data).

Cis-N-(3-chloro-4-fluorophenyl)-5-(4-cyano-3-fluorophenyl)-2-methyl-1,2,6-thiadiazinane-3-carboxamide 1,1-dioxide (HBV-CSU-221, HBV-CSU-221-ISO-I & HBV-CSU-221-ISO-II)

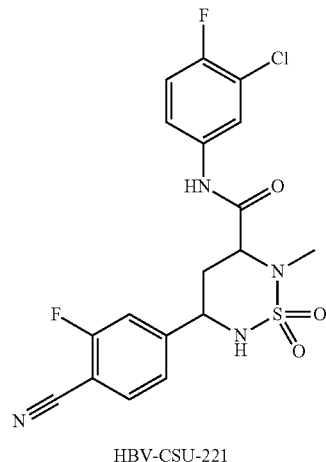

HBV-CSU-221

HBV-CSU-221-isomer I
+
HBV-CSU-221-isomer II

HBV-CSU-221-ISO-I

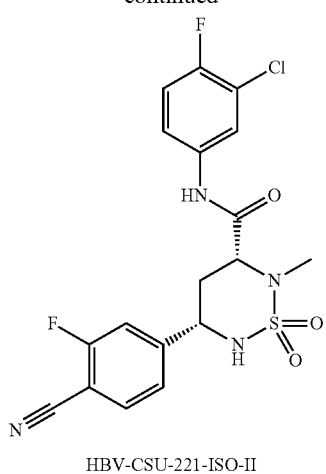

HBV-CSU-221-ISO-II

The above titled compounds have been synthesized by following the general procedure described above for reduction by using corresponding HBV-CSU-221_Int (see Table 2 for analytical data).

Scheme 34

Synthesis of Cis-N-(3-chloro-4-fluorophenyl)-5-cyclopentyl-2-methyl-1,2,6-thiadiazinane-3-carboxamide 1,1-dioxide (HBV-CSU-222, HBV-CSU-222-ISO-I & HBV-CSU-222-ISO-II)

Scheme 34:

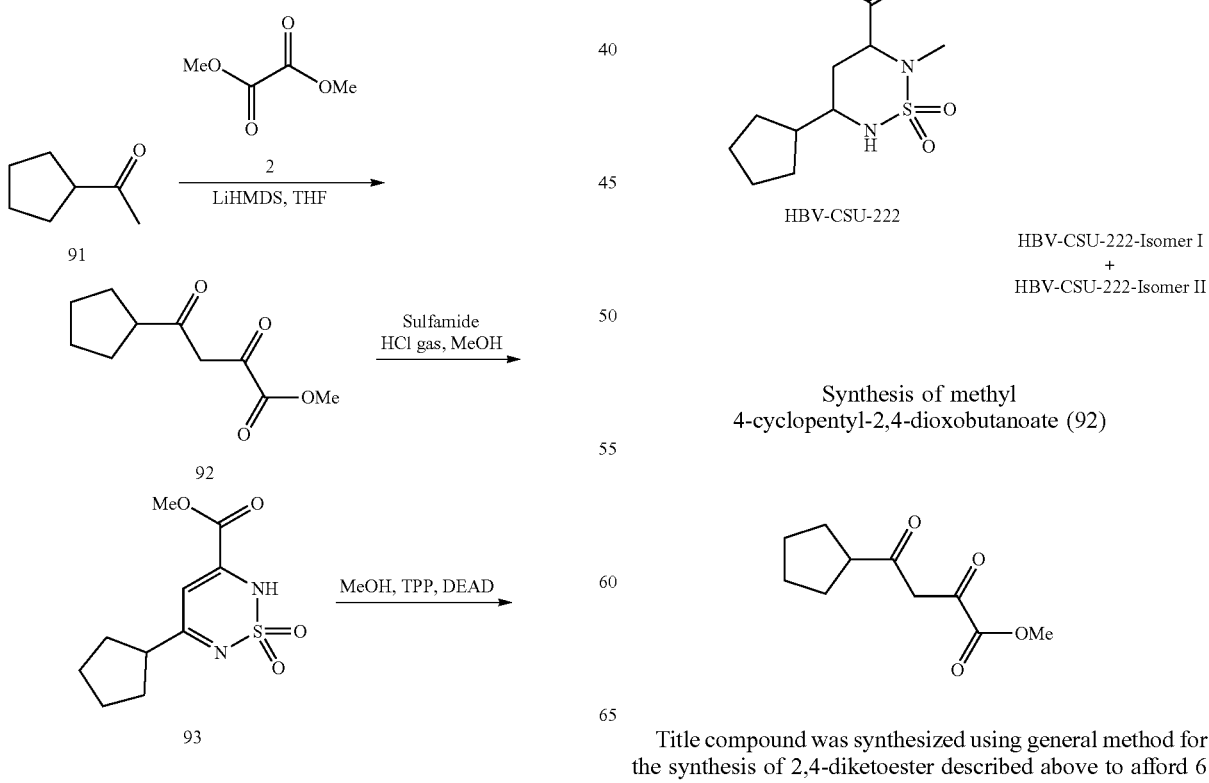

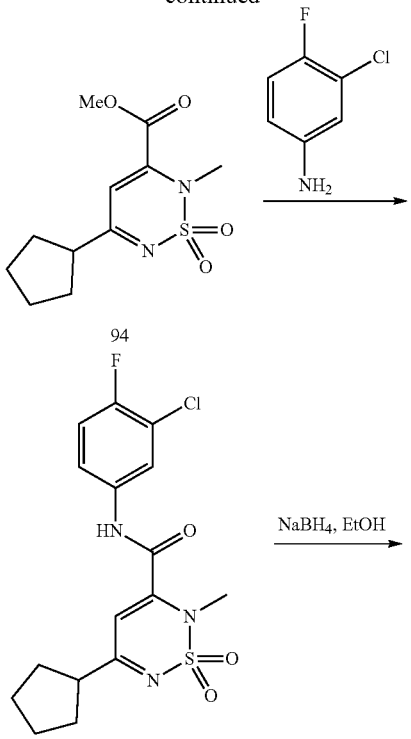

HBV-CSU-222-Isomer I
+
HBV-CSU-222-Isomer II

Synthesis of methyl 4-cyclopentyl-2,4-dioxobutanoate (92)

Title compound was synthesized using general method for the synthesis of 2,4-diketoester described above to afford 6 g (97%, reaction scale is 3.5 g); LCMS Calculated for $C_{10}H_{14}O_4$: 198.05; Observed: 198.95 $(M+1)^+$.

Synthesis of methyl 5-cyclopentyl-2H-1,2,6-thiadiazine-3-carboxylate 1,1-dioxide (93)

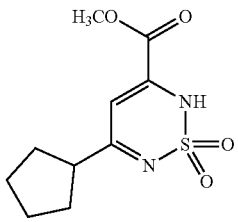 [SMILES: COC(=O)C1=CC(C2CCCC2)=NS(=O)(=O)N1]

Title compound was synthesized using general method for the synthesis of cyclic sulfonamide described above to afford 5 g (64%, reaction scale is 6 g); LCMS Calculated for $C_{10}H_{14}N_2O_4S$: 258.07; LCMS observed: 259 $(M+1)^+$.

Synthesis of methyl 5-cyclopentyl-2-methyl-2H-1,2,6-thiadiazine-3-carboxylate 1,1-dioxide (94)

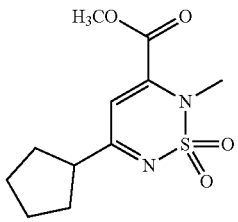 [SMILES: COC(=O)C1=CC(C2CCCC2)=NS(=O)(=O)N1C]

Title compound was synthesized using general procedure for alkylation (Method B) described above to afford 4.5 g (85%, reaction scale is 5 g); LCMS Calculated for $C_{11}H_{16}N_2O_4S$: 272.08; LCMS observed: 273 $(M+1)^+$.

Synthesis of N-(3-chloro-4-fluorophenyl)-5-cyclopentyl-2-methyl-2H-1,2,6-thiadiazine-3-carboxamide 1,1-dioxide (HBV-CSU-222_Int)

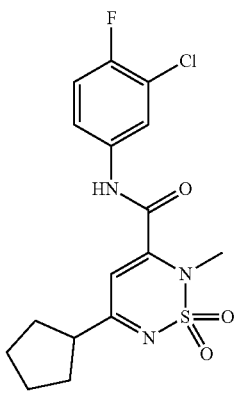

HBV-CSU-222_Int

The above titled compound has been synthesized by following the general procedure (Method B) described above for amidation by using corresponding Compound 94 and corresponding amine (see Table 1 for analytical data).

Cis-N-(3-chloro-4-fluorophenyl)-5-cyclopentyl-2-methyl-1,2,6-thiadiazinane-3-carboxamide 1,1-dioxide (HBV-CSU-222, HBV-CSU-222-ISO-I & HBV-CSU-222-ISO-II)

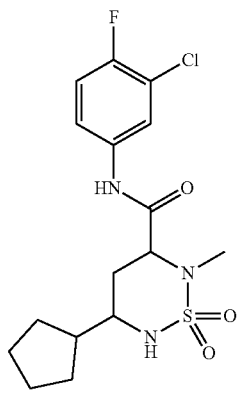

HBV-CSU-222

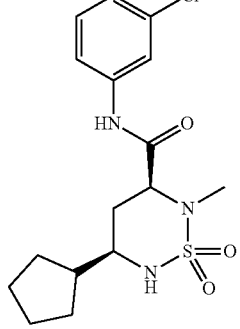

HBV-CSU-222-ISO-I

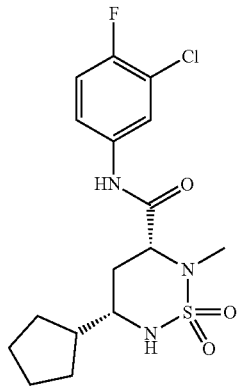

HBV-CSU-222-ISO-II

The above titled compounds have been synthesized by following the general procedure described above for reduction by using corresponding HBV-CSU-222_Int (see Table 2 for analytical data).

383
Scheme 35
Synthetic scheme for N-(3-chloro-4-fluorophenyl)-2-methyl-5-(2-methylthiazol-5-yl)-1,2,6-thiadiazinane-3-carboxamide 1,1-dioxide (HBV-CSU-224, HBV-CSU-224-ISO-I & HBV-CSU-224-ISO-II)
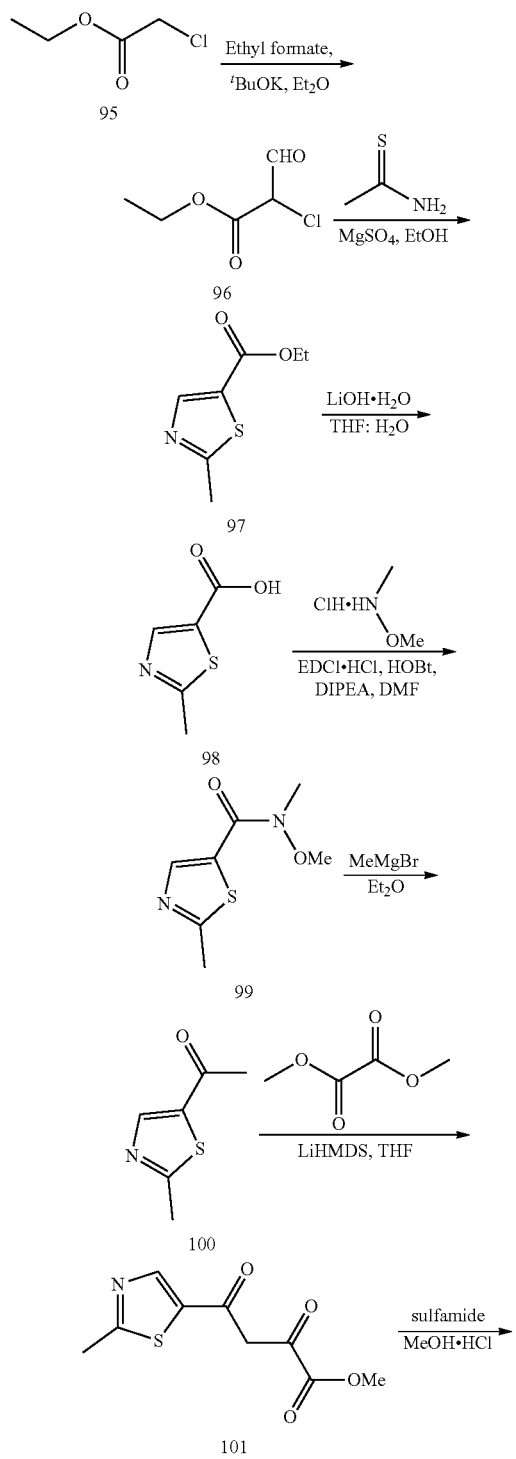
384
-continued
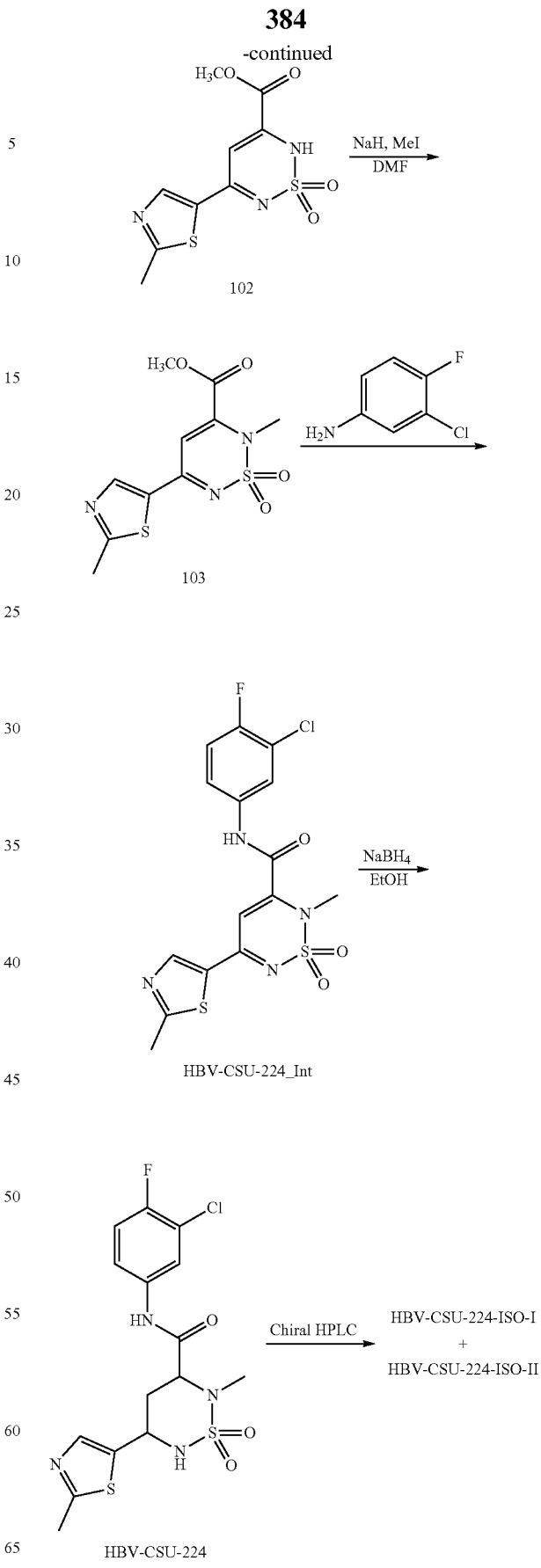

Synthesis of ethyl 2-chloro-3-oxopropanoate (96)

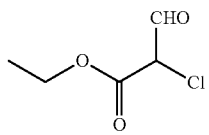

To a stirred solution of ethyl 2-chloroacetate 95 (5 g, 40.98 mmol) and ethyl formate (3.33 mL, 40.98 mmol) in diisopropyl ether (50 mL) under Ar atmosphere was added potassium tert-butoxide (45 mL, 45.08 mmol, 1 M sol. in THF) portion wise for 20 min at 0° C., followed by warming to room temperature and stirring for 24 h. The reaction was monitored by TLC. After completion of the reaction, the pH of the reaction mixture was adjusted to ~6 using 6 N HCl and extracted using diethyl ether. The combined organic extracts were dried over anhydrous sodium sulfate and concentrated in vacuo to afford compound 96 (5.6 g, 91%) as thick syrup. TLC: 40% EtOAc/hexanes ($R_f$: 0.7); $^1$H-NMR (DMSO-$d_6$, 400 MHz): δ 11.75 (br.s, 1H), 4.14 (q, J=7.0 Hz, 2H), 4.05 (s, 1H), 1.21 (t, J=7.1 Hz, 3H).

Synthesis of ethyl 2-methylthiazole-5-carboxylate (97)

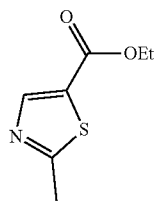

To a stirring solution of compound 96 (110 g, 733.33 mmol) in ethanol (1.2 L) under Ar atmosphere were added ethanethioamide (54.99 g, 733.33 mmol) and anhydrous magnesium sulfate (55 mg, 454.66 mmol) at room temperature, followed by heating to 80° C. for 16 h. The reaction was monitored by TLC. After completion of the reaction, the volatiles were removed in vacuo. The residue was diluted with water and extracted using EtOAc. The organic extract was dried over anhydrous sodium sulfate, filtered and concentrated in vacuo to obtain the crude. The crude was purified through silica gel column chromatography using 10% EtOAc/hexanes to afford compound 97 (41 g, 33%) as thick syrup. TLC: 20% EtOAc/hexanes ($R_f$: 0.3); $^1$H NMR (400 MHz, DMSO-$d_6$): δ 8.26 (s, 1H), 4.29 (q, J=7.2 Hz, 2H), 2.71 (s, 3H), 1.29 (t, J=7.1 Hz, 3H); LCMS Calculated for $C_7H_9NO_2S$: 171.04; Observed: 172.1 (M+1)$^+$.

Synthesis of 2-methylthiazole-5-carboxylic acid (98)

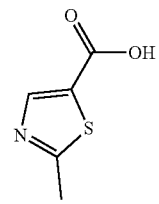

To a stirred solution of compound 97 (41 g, 239.76 mmol) in THF:H$_2$O (7:1, 400 mL) was added lithium hydroxide monohydrate (29.49 g, 719.29 mmol) at room temperature and stirred for 16 h. The reaction was monitored by TLC. After completion of the reaction, the volatiles were removed in vacuo. The residue was diluted with water and acidified with 2 N HCl to pH~2 and extracted using EtOAc. The combined organic extracts were dried over anhydrous sodium sulfate, filtered and concentrated in vacuo to afford compound 98 (14 g, 41%) as an off-white solid. TLC: 20% EtOAc/hexanes ($R_f$: 0.1); $^1$H NMR (DMSO-$d_6$, 400 MHz): δ 13.29 (br.s, 1H), 8.16 (s, 1H), 2.69 (s, 3H); LCMS Calculated for $C_5H_5NO_2S$: 143.00; Observed: 144.1 (M+1)$^+$.

Synthesis of N-methoxy-N, 2-dimethylthiazole-5-carboxamide (99)

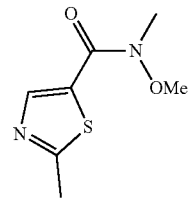

To a stirred solution compound 98 (19 g, 132.86 mmol) in DMF (300 mL) under inert atmosphere were added EDCI.HCl (38.06 g, 199.26 mmol), HOBt (26.9 g, 199.25 mmol) N, O-dimethylhydroxylamine hydrochloride (15.3 g, 158.54 mmol) and diisopropylethylamine (69.48 mL, 398.44 mmol) at 0° C., followed by warming to room temperature and stirred for 16 h. The reaction was monitored by TLC. After completion of the reaction, the reaction mixture was diluted with ice-cold water and extracted using EtOAc. The combined organic extracts were dried over anhydrous sodium sulfate, filtered and concentrated in vacuo to obtain the crude. The crude was purified through silica gel flash column chromatography using 50% EtOAc/hexanes to afford compound 99 (13 g, 53%) as thick syrup. TLC: 10% MeOH/CH$_2$Cl$_2$ ($R_f$: 0.7); $^1$H NMR (500 MHz, DMSO-$d_6$): δ 8.26 (s, 1H), 3.75 (s, 3H), 3.27 (s, 3H), 2.68 (s, 3H); LCMS Calculated for $C_7H_{10}N_2O_2S$: 186.05; Observed: 187.1 (M+1)$^+$.

Synthesis of 1-(2-methylthiazol-5-yl) ethan-1-one (100)

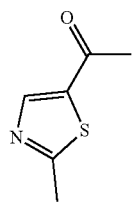

To a stirring solution of compound 99 (13 g, 69.89 mmol) in dry diethyl ether (200 mL) under inert atmosphere was added methyl magnesium bromide (69.8 mL, 209.67 mmol, 3 M sol. in diethyl ether) dropwise for 25 min at −40° C., following by warming to room temperature and stirring for 16 h. The reaction was monitored by TLC. After completion of the reaction, the reaction mixture was quenched with saturated ammonium chloride solution at 0° C. and extracted using diethyl ether. The combined organic extracts were dried over anhydrous sodium sulfate, filtered and concentrated in vacuo to obtain the crude. The crude was purified through silica gel flash column chromatography using 20% EtOAc/hexanes to afford compound 100 (5.62 g, 57%) as yellow solid. TLC: 20% EtOAc/hexanes ($R_f$: 0.3); $^1$H NMR (400 MHz, DMSO-$d_6$): δ 8.45 (s, 1H), 2.71 (s, 3H), 2.54 (s, 3H); LCMS Calculated for $C_6H_7NOS$: 141.02; Observed: 142.0 (M+1)$^+$.

Synthesis of methyl 4-(2-methylthiazol-5-yl)-2,4-dioxobutanoate (101)

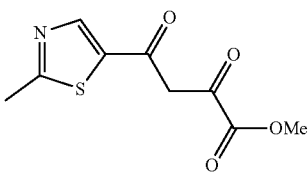

Title compound was synthesized using general method for the synthesis of 2,4-diketoester described above to afford 9.01 g (99%, reaction scale is 5.62 g) as off-white sticky solid. TLC: 5% MeOH/CH$_2$Cl$_2$ ($R_f$: 0.4); LCMS Calculated for $C_9H_9NO_4S$: 227.03; Observed: 228.1 (M+1)$^+$.

Synthesis of methyl 5-(2-methylthiazol-5-yl)-2H-1,2,6-thiadiazine-3-carboxylate 1,1-dioxide (102)

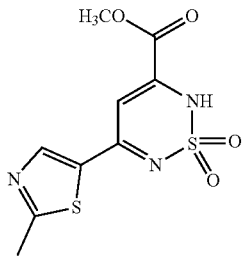 [SMILES: COC(=O)C1=CC(c2cnc(C)s2)=NS(=O)(=O)N1]

Title compound was synthesized using general method A for the synthesis of cyclic sulfonamide described above to afford 1.2 g (crude reaction scale is 1.2 g) as a light brown solid. TLC: 20% MeOH/CH$_2$Cl$_2$ ($R_f$: 0.2); LCMS Calculated for $C_{13}H_{10}N_4O_4S_2$: 287.00; LCMS observed: 288.1 (M+1)$^+$.

Synthesis of methyl 2-methyl-5-(2-methylthiazol-5-yl)-2H-1,2,6-thiadiazine-3-carboxylate 1,1-dioxide (103)

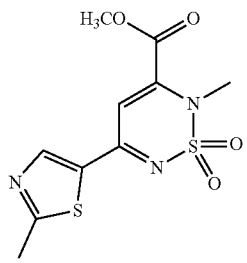 [SMILES: COC(=O)C1=CC(c2cnc(C)s2)=NS(=O)(=O)N1C]

Title compound was synthesized using general method A for alkylation described above to afford 100 mg (8%, over two steps, reaction scale is 1 g) as yellow solid. TLC: 40% EtOAc/hexanes ($R_f$: 0.3); $^1$H NMR (400 MHz, DMSO-$d_6$): δ 8.77 (s, 1H), 7.36 (s, 1H), 3.94 (s, 3H), 3.51 (s, 3H), 2.76 (s, 3H); LCMS Calculated for $C_{10}H_{11}N_3O_4S_2$: 301.02; Observed: 302.1 (M+1)$^+$.

Synthesis of N-(3-chloro-4-fluorophenyl)-2-methyl-5-(2-methylthiazol-5-yl)-2H-1,2,6-thiadiazine-3-carboxamide 1,1-dioxide (HBV-CSU-224_Int)

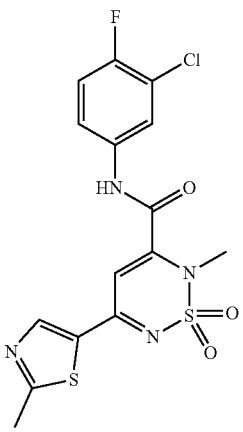

HBV-CSU-224_Int

The above titled compound has been synthesized by following the general procedure (Method B) described above for amidation by using corresponding 103 and corresponding amine (see Table 1 for analytical data).

389

Cis-N-(3-Chloro-4-fluorophenyl)-2-methyl-5-(2-methylthiazol-5-yl)-1,2,6-thiadiazinane-3-carboxamide 1,1-dioxide (HBV-CSU-224, HBV-CSU-224-ISO-I & HBV-CSU-224-ISO-II)

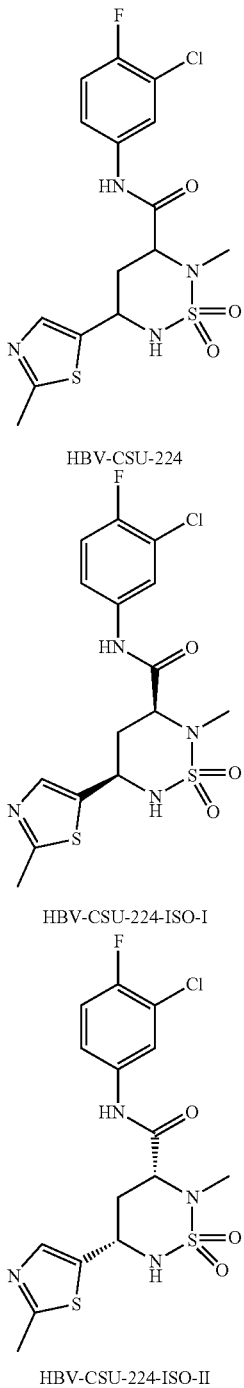

HBV-CSU-224

HBV-CSU-224-ISO-I

HBV-CSU-224-ISO-II

The above titled compounds have been synthesized by following the general procedure described above for reduction by using corresponding HBV-CSU-224_Int (see Table 2 for analytical data).

390

Scheme 36

Synthetic scheme for N-(3-chloro-4-fluorophenyl)-2-methyl-5-(2-methylthiazol-5-yl)-1,2,6-thiadiazinane-3-carboxamide 1,1-dioxide (HBV-CSU-226)

Scheme 36:

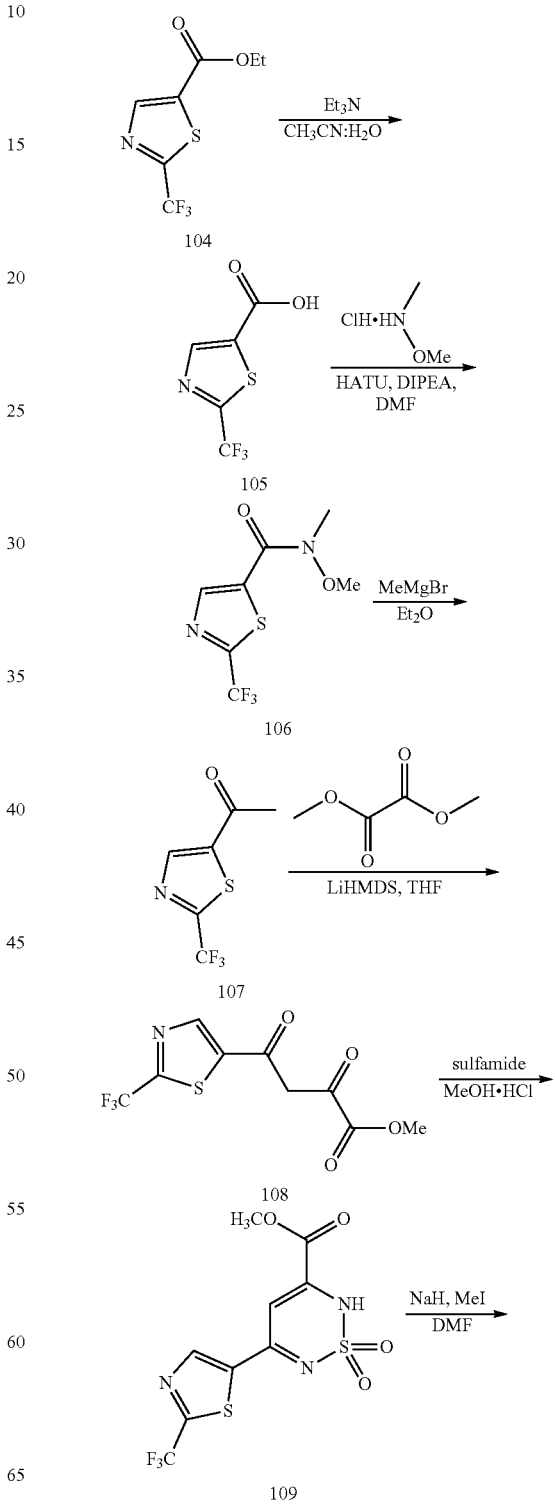

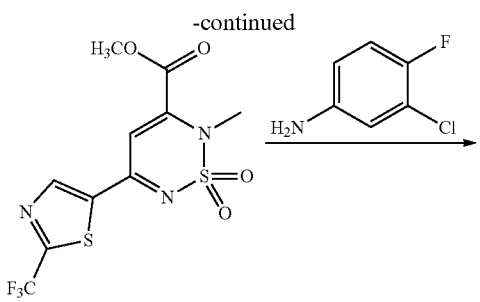

110

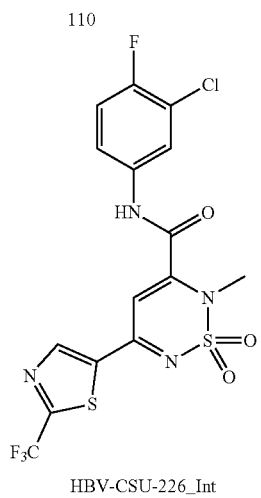

HBV-CSU-226_Int

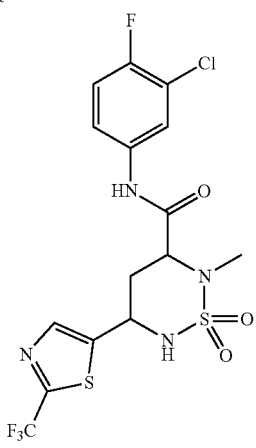

HBV-CSU-226

Synthesis of N-methoxy-N-methyl-2-(trifluoromethyl)thiazole-5-carboxamide (106)

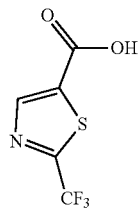

To a stirred solution of ethyl 2-(trifluoromethyl)thiazole-5-carboxylate 104 (1 g, 4.44 mmol) in CH$_3$CN:H$_2$O (1:1, 20 mL) was added triethylamine (3.2 mL, 22.22 mml) at 0° C.; warmed to room temperature and stirred for 16 h. The reaction was monitored by TLC. After completion of the reaction, the volatiles were removed in vacuo and further dried by azeotropic distillation using toluene to afford compound 105 (900 mg, crude) as pale yellow solid. TLC: 50% EtOAc/hexanes (R$_f$: 0.1); $^1$H NMR (DMSO-d$_6$, 400 MHz): δ10.66 (br.s, 1H), 8.18 (s, 1H).

Synthesis of N-methyl-N-methyl-2-(trifluoromethyl)thiazole-5-carboxamide (106)

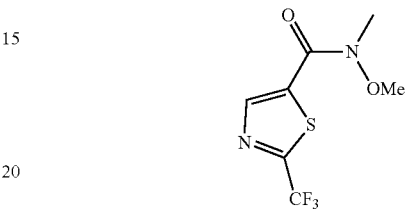

To a stirred solution compound 105 (900 mg, crude) in DMF (15 mL) under inert atmosphere were added N,O-dimethylhydroxylamine hydrochloride (537 mg, 5.47 mmol), HATU (3.47 g, 9.13 mmol) and diisopropylethylamine (2.38 mL, 13.66 mmol) at 0° C., followed by warming to room temperature and stirring for 16 h. The reaction was monitored by TLC. After completion of the reaction, the reaction mixture was poured into ice-cold water and extracted using CH$_2$Cl$_2$. The combined organic extracts were washed with 2 N HCl, dried over anhydrous sodium sulfate, filtered and concentrated in vacuo to obtain the crude. The crude was purified through silica gel column chromatography using 20% EtOAc/hexanes to afford compound 106 (600 mg, 60% over 2 steps) as brown liquid. TLC: 30% EtOAc/hexanes (R$_f$: 0.7); $^1$H NMR (500 MHz, DMSO-d$_6$): δ 8.67 (s, 1H), 3.83 (s, 3H), 3.34 (s, 3H); LCMS Calculated for C$_7$H$_7$F$_3$N$_2$O$_2$S: 240.02; Observed: 241.1 (M+1)$^+$.

Synthesis of 1-(2-(trifluoromethyl)thiazol-5-yl)ethan-1-one (107)

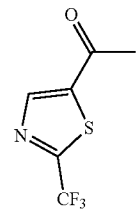

To a stirred solution of compound 106 (1.05 g, 4.37 mmol) in anhydrous diethyl ether (20 mL) under inert atmosphere was added methyl magnesium bromide (3.7 mL, 10.93 mmol, 3 M sol. in diethyl ether) dropwise for 10 min at −40° C. and stirred at the same temperature for 3 h. The reaction was monitored by TLC. After completion of the reaction, the reaction mixture was quenched with ice-cold water at 0° C. and extracted using diethyl ether. The combined organic extracts were dried over anhydrous sodium sulfate, filtered and concentrated in vacuo to afford compound 107 (450 mg, crude) as pale yellow solid. TLC: 30% EtOAc/hexanes (R$_f$: 0.9); $^1$H NMR (400 MHz, DMSO-d$_6$): δ 8.89 (s, 1H), 2.67 (s, 3H).

Synthesis of methyl 2,4-dioxo-4-(2-(trifluoromethyl)thiazol-5-yl) butanoate (108)

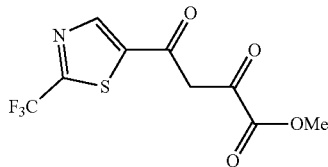 [SMILES: COC(=O)C(=O)CC(=O)c1cnc(C(F)(F)F)s1]

Title compound was synthesized using general method for the synthesis of 2,4-diketoester described above to afford 400 mg (36%, over 2 steps, reaction scale is 450 mg) as an off-white solid. TLC: 2% MeOH/CH$_2$Cl$_2$ (R$_f$: 0.4); $^1$H NMR (400 MHz, DMSO-d$_6$): δ 9.13 (br.s, 1H), 7.07 (br.s, 1H), 3.86 (s, 3H); LCMS Calculated for C$_9$H$_6$F$_3$NO$_4$S: 281.00; Observed: 279.9 (M+1)$^+$.

Synthesis of methyl 5-(2-(trifluoromethyl)thiazol-5-yl)-2H-1,2,6-thiadiazine-3-carboxylate 1,1-dioxide (109)

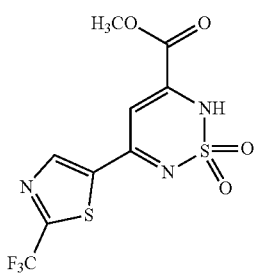

Title compound was synthesized using general method A for the synthesis of cyclic sulfonamide described above to afford 400 mg (83%, reaction scale is 400 mg) as an off-white solid. TLC: 6% MeOH/CH$_2$Cl$_2$ (R$_f$: 0.1); $^1$H NMR (400 MHz, DMSO-d$_6$): δ 8.75 (s, 1H), 8.39 (br.s, 1H), 6.71 (s, 1H), 3.80 (s, 3H).

Synthesis of methyl 2-methyl-5-(2-(trifluoromethyl)thiazol-5-yl)-2H-1,2,6-thiadiazine-3-carboxylate 1,1-dioxide (110)

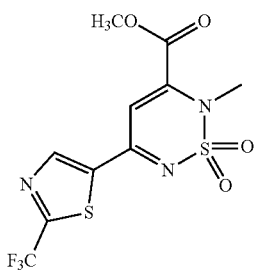

Title compound was synthesized using general method A for alkylation described above to afford 340 mg (83%, reaction scale is 400 mg) as an off-white solid. TLC: 5% MeOH/CH$_2$Cl$_2$ (R$_f$: 0.6); $^1$H NMR (400 MHz, DMSO-d$_6$): δ 9.19 (s, 1H), 7.49 (s, 1H), 3.97 (s, 3H), 3.58 (s, 3H).

Synthesis of N-(3-chloro-4-fluorophenyl)-2-methyl-5-(2-(trifluoromethyl)thiazol-5-yl)-2H-1,2,6-thiadiazine-3-carboxamide 1,1-dioxide (HBV-CSU-226_Int)

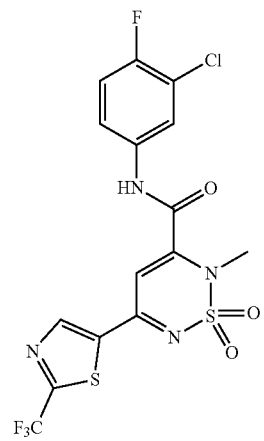

HBV-CSU-226_int

The above titled compound has been synthesized by following the general procedure (Method B) described above for amidation by using corresponding 110 and corresponding amine (see Table 1 for analytical data).

Cis-N-(3-chloro-4-fluorophenyl)-2-methyl-5-(2-(trifluoromethyl)thiazol-5-yl)-1,2,6-thiadiazinane-3-carboxamide 1,1-dioxide (HBV-CSU-226)

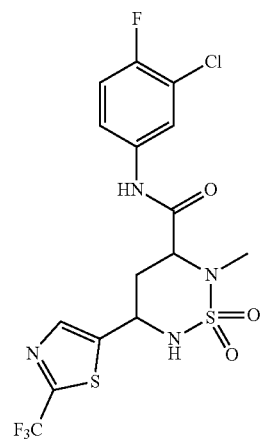

HBV-CSU-226

The above titled compound has been synthesized by following the general procedure described above for reduction by using corresponding HBV-CSU-226_Int (see Table 2 for analytical data).

Scheme 37
Synthesis of Cis-3-chloro-4-fluorophenyl)-2-methyl-5-(2-phenylthiazol-5-yl)-1,2,6-thiadiazinane-3-carboxamide 1,1-dioxide (HBV-CSU-235, HBV-CSU-235-ISO-I & HBV-CSU-235-ISO-II)
Scheme 37:
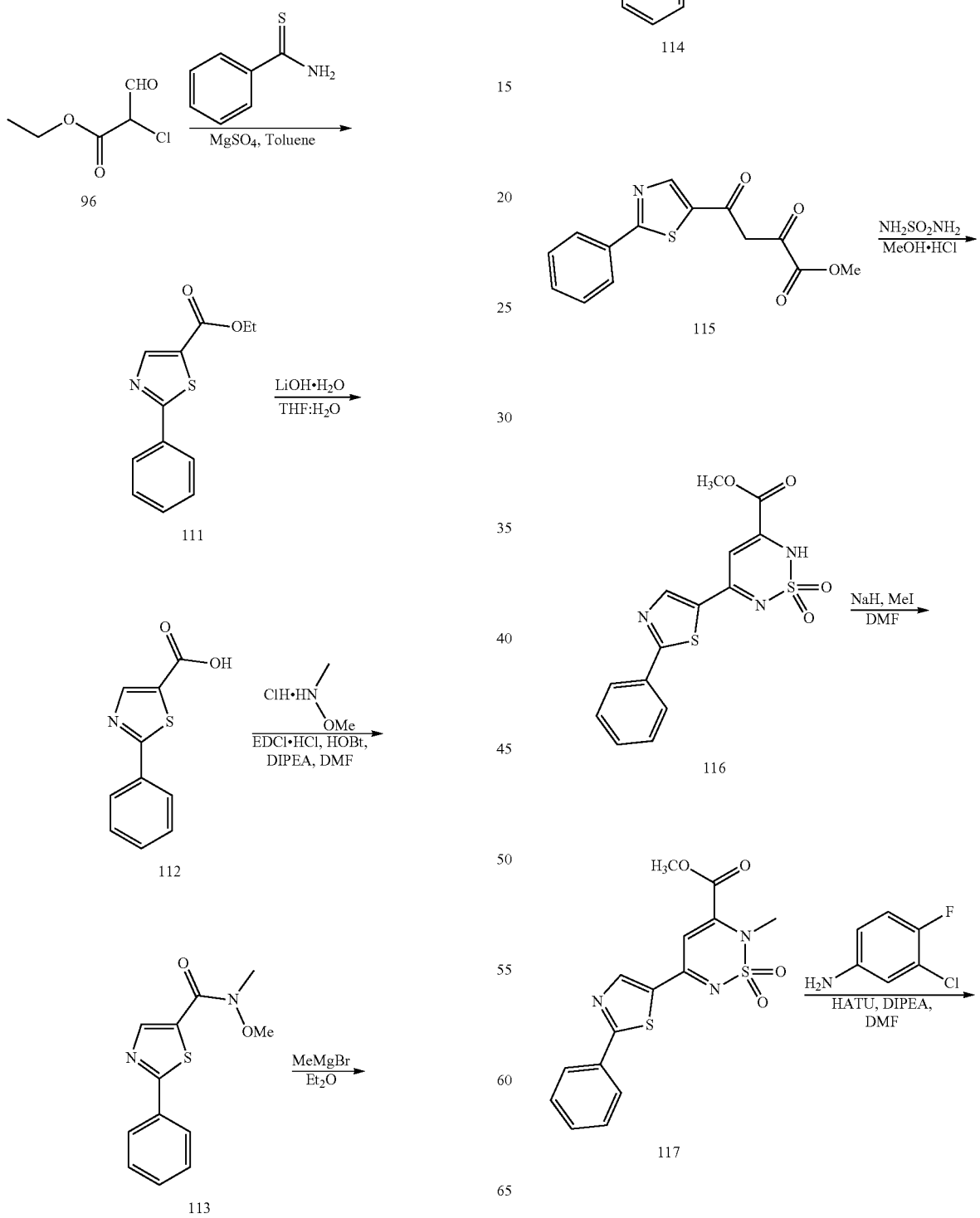

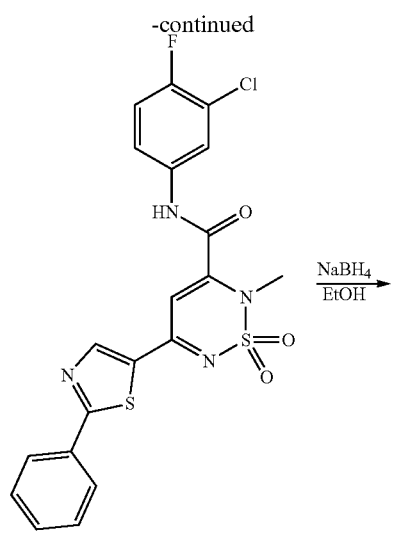

HBV-CSU-235_Int

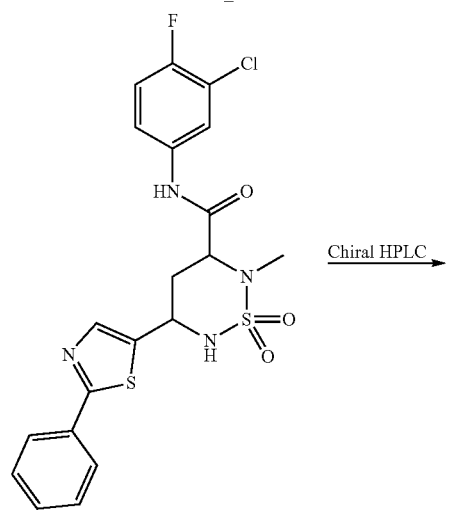

HBV-CSU-235

HBV-CSU-235-ISO-I

+

HBV-CSU-235-ISO-II

Synthesis of ethyl 2-phenylthiazole-5-carboxylate (111)

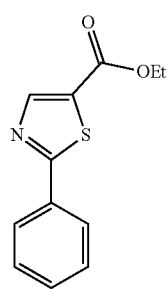 [SMILES: CCOC(=O)c1cnc(-c2ccccc2)s1]

To a stirring solution of benzothioamide (25 g, 182.48 mmol) in toluene (250 mL) under inert atmosphere were added ethyl 2-chloro-3-oxopropanoate 96 (41.15 g, 274.34 mmol), anhydrous magnesium sulfate (65.85 g, 547.44 mmol) at room temperature and heated to 90° C. and stirred for 16 h. The reaction was monitored by TLC; after completion of the reaction, the reaction mixture was diluted with water and extracted with EtOAc. The combined organic extracts were dried over anhydrous sodium sulfate, filtered and concentrated in vacuo to obtain the crude. The crude was purified through silica gel column chromatography using 10% EtOAc/hexanes to afford compound 111 (15 g, 35%) as pale yellow solid. TLC: 20% EtOAc/hexanes ($R_f$: 0.8); $^1$H NMR (400 MHz, DMSO-$d_6$): δ 8.49 (s, 1H), 8.04-8.01 (m, 2H), 7.58-7.51 (m, 3H), 4.34 (q, J=7.2 Hz, 2H), 1.32 (t, J=7.1 Hz, 3H); LCMS Calculated for $C_{12}H_{11}NO_2S$: 233.05; LCMS observed: 234.1 (M+1)$^+$.

Synthesis of 2-phenylthiazole-5-carboxylic acid (112)

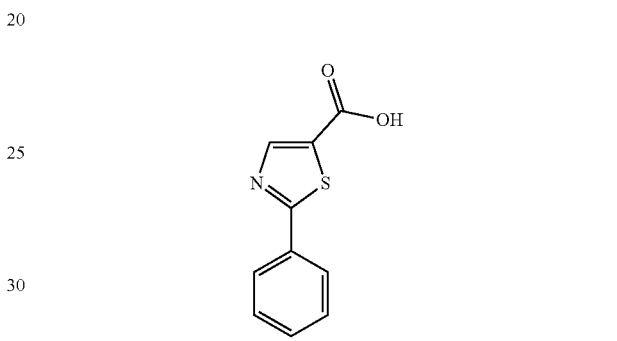

To a stirring solution of compound 111 (1 g, 4.28 mmol) in THF:H$_2$O (1:1, 20 mL) was added lithium hydroxide monohydrate (515 mg, 21.45 mmol) at room temperature and stirred for 6 h. The reaction was monitored by TLC; after completion of the reaction, the volatiles were removed in vacuo and the pH of the aqueous layer was neutralized with 1 N aqueous HCl. The precipitated solid was filtered and dried in vacuo to afford compound 112 (600 mg, 68%) as pale yellow solid. TLC: 30% EtOAc/hexanes ($R_f$: 0.1); $^1$H NMR (DMSO-$d_6$, 400 MHz): δ 7.93 (s, 1H), 7.92-7.88 (m, 2H), 7.51-7.43 (m, 3H); LCMS Calculated for $C_{10}H_7NO_2S$: 205.02; LCMS observed: 206.1 (M+1)$^+$.

Synthesis of N-methoxy-N-methyl-2-phenylthiazole-5-carboxamide (113)

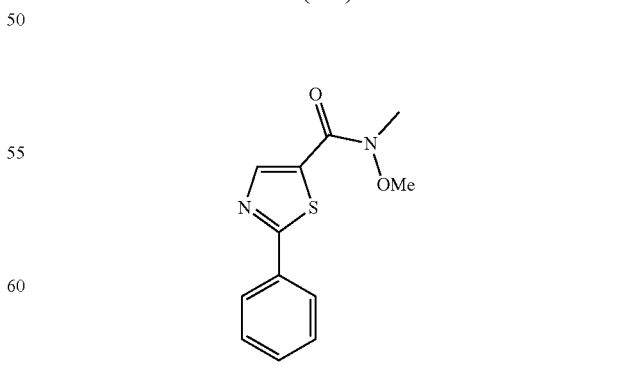

To a stirring solution of compound 112 (10 g, 48.72 mmol) in DMF (150 mL) under inert atmosphere were added N,O-dimethylhydroxylamine hydrochloride (5.73 g, 58.46 mmol), EDCl.HCl (14 g, 73.17 mmol), HOBt (6.68 g, 48.787 mmol), N, N-diisopropylethylamine (25.5 mL, 146.73 mmol) at 0° C.; warmed to room temperature and stirred for 16 h. The reaction was monitored by TLC; after completion of the reaction, the reaction mixture was diluted with ice-cold water (500 mL) and extracted using EtOAc. The combined organic extracts were dried over anhydrous sodium sulfate, filtered and concentrated in vacuo to obtain the crude. The crude was purified through silica gel flash column chromatography using 20% EtOAc/hexanes to afford compound 113 (9.6 g, 79%) as pale yellow liquid. TLC: 30% EtOAc/hexanes ($R_f$: 0.8); $^1$H NMR (500 MHz, DMSO-$d_6$): δ 8.50 (s, 1H), 8.07-7.99 (m, 2H), 7.57-7.53 (m, 3H), 3.82 (s, 3H), 3.32 (s, 3H); LCMS Calculated for $C_{12}H_{12}N_2O_2S$: 248.06; LCMS observed: 249.1 (M+1)$^+$.

Synthesis of 1-(2-phenylthiazol-5-yl) ethan-1-one (114)

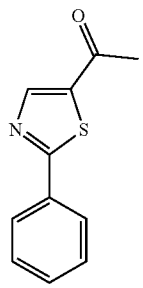

To a stirring solution of compound 113 (1 g, 4.03 mmol) in anhydrous diethyl ether (10 mL) under inert atmosphere was added methyl magnesium bromide (3.36 mL, 10.08 mmol, 3 M sol. in diethyl ether) dropwise for 10 min at −40° C.; warmed to room temperature and stirred for 3 h. The reaction was monitored by TLC; after completion of the reaction, the reaction mixture was quenched with saturated ammonium chloride solution (50 mL) at 0° C. and extracted using EtOAc. The combined organic extracts were dried over anhydrous sodium sulfate, filtered and concentrated in vacuo to obtain the crude. The crude was purified through silica gel flash column chromatography using 20% EtOAc/hexanes to afford compound 114 (600 mg, 74%) as pale yellow liquid. TLC: 20% EtOAc/hexanes ($R_f$: 0.7); $^1$H NMR (500 MHz, DMSO-$d_6$): δ 8.70 (s, 1H), 8.04 (dd, J=7.8, 1.4 Hz, 2H), 7.61-7.52 (m, 3H), 2.61 (s, 3H); LCMS Calculated for $C_{11}H_9NOS$: 203.04; LCMS observed: 204.1 (M+1)$^+$.

Synthesis of methyl 2,4-dioxo-4-(2-phenylthiazol-5-yl) butanoate (115)

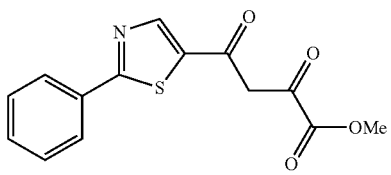 [SMILES: COC(=O)C(=O)CC(=O)c1cnc(-c2ccccc2)s1]

Title compound was synthesized using general method for the synthesis of 2,4-diketoester described above to afford 6.6 g (86%, reaction scale is 5.4 g) as a yellow colored solid. TLC: 5% MeOH/DCM ($R_f$: 0.6); $^1$H NMR (DMSO-$d_6$, 400 MHz): δ 0.92 (br.s, 1H), 8.04-7.98 (m, 2H), 7.57-7.47 (m, 3H), 7.05 (br.s, 1H), 3.80 (s, 3H); LCMS Calculated for $C_{14}H_{11}NO_4S$: 289.04; LCMS observed: 290.1 (M+1)$^+$.

Synthesis of methyl 5-(2-phenylthiazol-5-yl)-2H-1,2,6-thiadiazine-3-carboxylate 1,1-dioxide (116)

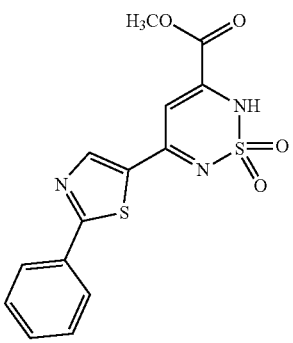 [SMILES: COC(=O)C1=CC(c2cnc(-c3ccccc3)s2)=NS(=O)(=O)N1]

Title compound was synthesized using general method A for cyclisation described above to afford 3.2 g (41%, reaction scale is 6.5 g) as a pale yellow solid. TLC: 5% MeOH/DCM ($R_f$: 0.1); $^1$H NMR (DMSO-$d_6$, 400 MHz): δ 8.66 (s, 1H), 8.03 (dd, J=6.4, 2.9 Hz, 2H), 7.58-7.50 (m, 3H), 6.85 (br.s, 1H), 3.84 (s, 3H); LCMS Calculated for $C_{14}H_{11}N_3O_4S_2$: 349.02; LCMS observed: 350.1 (M+1)$^+$.

Synthesis of methyl 2-methyl-5-(2-phenylthiazol-5-yl)-2H-1,2,6-thiadiazine-3-carboxylate 1,1-dioxide (117)

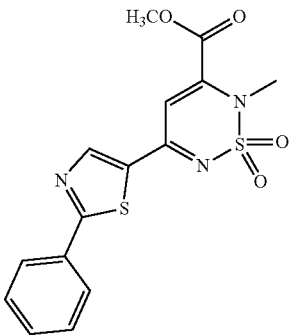 [SMILES: COC(=O)C1=CC(c2cnc(-c3ccccc3)s2)=NS(=O)(=O)N1C]

Title compound was synthesized using general method A for alkylation described above to afford 1.6 g (48% yield, reaction scale was 3.2 g) as an off-white solid. TLC: 30% EtOAc/hexanes ($R_f$: 0.8); $^1$H NMR (DMSO-$d_6$, 400 MHz): δ 9.01 (s, 1H), 8.09 (d, J=6.7 Hz, 2H), 7.64-7.54 (m, 3H), 7.44 (s, 1H), 3.96 (s, 3H), 3.54 (s, 3H); LCMS Calculated for $C_{15}H_{13}N_3O_4S_2$: 363.03; LCMS observed: 364.1 (M+1)$^+$.

401

Synthesis of N-(3-chloro-4-fluorophenyl)-2-methyl-5-(2-phenylthiazol-5-yl)-2H-1,2,6-thiadiazine-3-carboxamide 1,1-dioxide (HBV-CSU-235_Int)

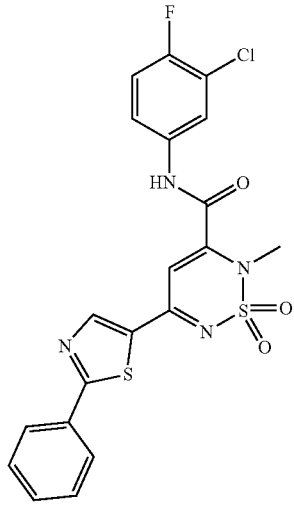 [SMILES: CN1C(C(=O)Nc2ccc(F)c(Cl)c2)=CC(c2cnc(-c3ccccc3)s2)=NS1(=O)=O]

The above titled compound has been synthesized by following the general procedure (Method B) described above for amidation by using corresponding 117 and corresponding amine (see Table 1 for analytical data).

N-(3-Chloro-4-fluorophenyl)-2-methyl-5-(2-phenylthiazol-5-yl)-1,2,6-thiadiazinane-3-carboxamide 1,1-dioxide (HBV-CSU-235, HBV-CSU-235-ISO-I & HBV-CSU-235-ISO-II)

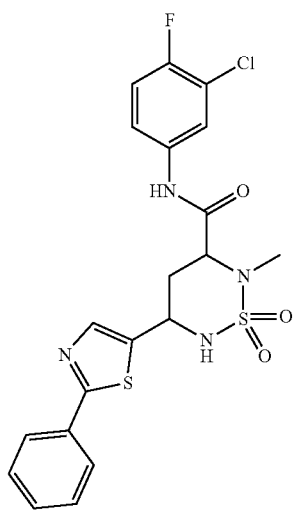

HBV-CSU-235

402

-continued

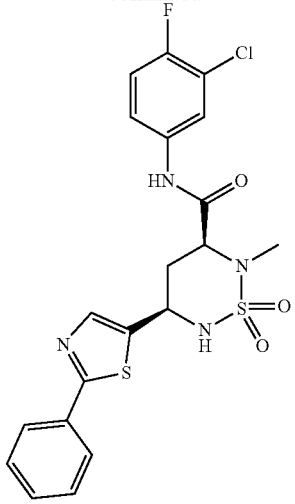

HBV-CSU-235-ISO-I

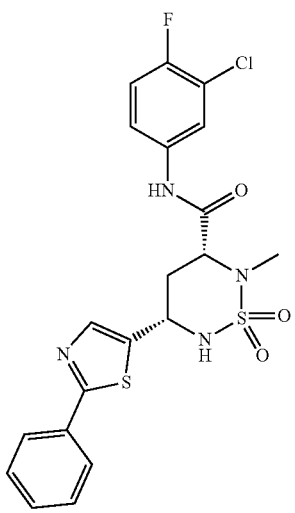

HBV-CSU-235-ISO-II

The above titled compounds have been synthesized by following the general procedure described above for reduction by using corresponding HBV-CSU-235_Int (see Table 2 for analytical data).

403

Scheme 38

Synthesis of Cis-N-(3-Chloro-4-fluorophenyl)-2-methyl-5-(4-(1-methyl-1H-pyrazol-4-yl)phenyl)-1,2,6-thiadiazinane-3-carboxamide 1,1-dioxide (HBV-CSU-246, HBV-CSU-246-ISO-I & HBV-CSU-246-ISO-II)

Scheme 38:

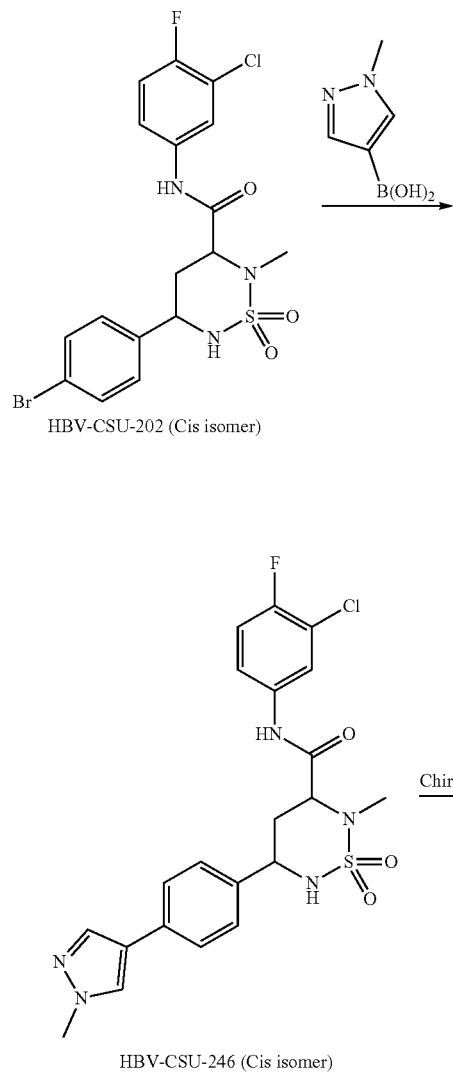

404

Scheme 39

Synthesis of N-(3-Chloro-4-fluorophenyl)-2-methyl-5-(3-(1-methyl-1H-pyrazol-4-yl)phenyl)-1,2,6-thiadiazinane-3-carboxamide 1,1-dioxide (HBV-CSU-247, HBV-CSU-247-ISO-I, HBV-CSU-247-ISO-II)

Scheme 39:

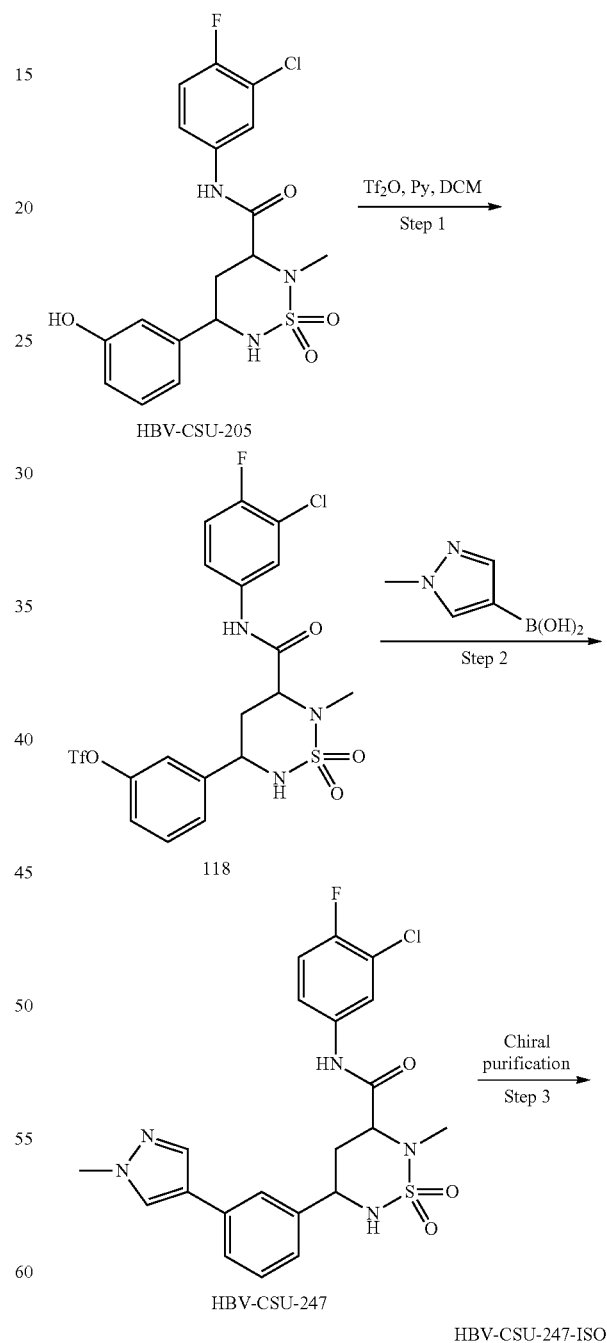

The above titled compounds have been synthesized by following the general procedure described above for Suzuki coupling by using HBV-CSU-202 and corresponding boronic acid (see Table 2 for analytical data).

3-(5-((3-Chloro-4-fluorophenyl) carbamoyl)-6-methyl-1,1-dioxido-1,2,6-thiadiazinan-3-yl)phenyl trifluoromethanesulfonate (118)

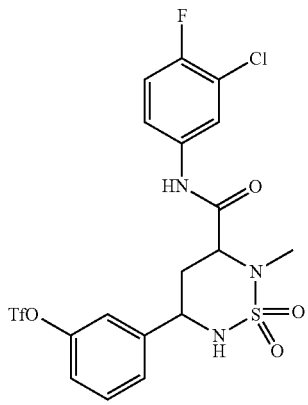 [SMILES: CN1C(C(=O)Nc2ccc(F)c(Cl)c2)CC(c2cccc(OS(=O)(=O)C(F)(F)F)c2)NS1(=O)=O]

To a stirred solution of compound HBV-CSU-205 (0.4 g, 0.968 mmol) in DCM at 0° C., pyridine (0.153 g, 1.93 mmol) was added drop wise and stirred at same temperature for 10 minutes. To this solution, triflic anhydride (0.327 mL 1.93 mmol) was added drop wise at 0° C. The resulting reaction mixture was stirred at room temperature for 4 h. The progress of the reaction was monitored by TLC and LCMS. After completion, the reaction mass was concentrated under reduced pressure. The residue was quenched with 10% dil. HCl, washed with sat. NaHCO$_3$, brine, and dried in vacuo. The crude compound was purified by silica gel column chromatography to afford the desired compound 118 (0.17 g, 32.25%) as a white solid TLC: 40% EtOAc/hexanes (R$_f$: 0.4)

Cis-N-(3-chloro-4-fluorophenyl)-2-methyl-5-(3-(1-methyl-1H-pyrazol-4-yl)phenyl)-1,2,6-thiadiazinane-3-carboxamide 1,1-dioxide (HBV-CSU-247, HBV-CSU-247-ISO-I, HBV-CSU-247-ISO-II)

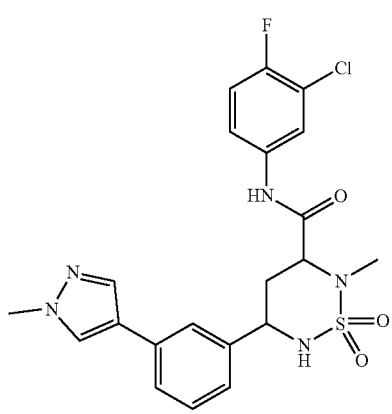

HBV-CSU-247

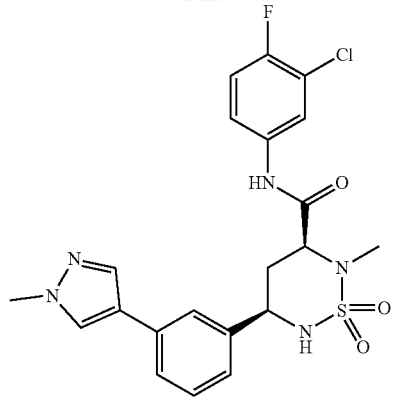

HBV-CSU-247-ISO-I

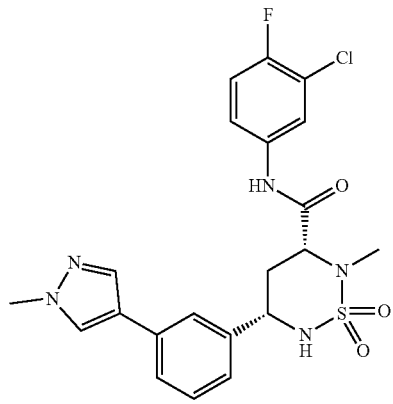

HBV-CSU-247-ISO-II

The above titled compound has been synthesized by following the general procedure described above for Suzuki coupling by using compound 118 and corresponding boronic acid (see Table 2 for analytical data).

Scheme 40

Synthesis of N-(3-Chloro-4-fluorophenyl)-2-methyl-5-(5-(oxazol-5-yl)thiophen-2-yl)-1,2,6-thiadiazinane-3-carboxamide 1,1-dioxide (HBV-CSU-269, HBV-CSU-269-ISO-I & HBV-CSU-269-II)

Scheme 40:

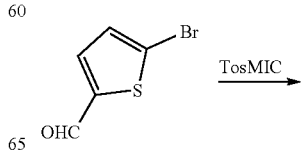

119

407
-continued
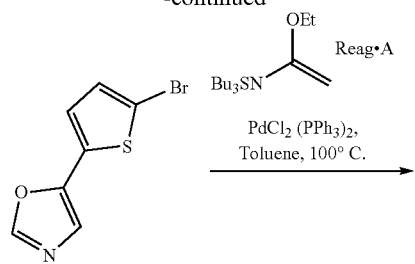
120
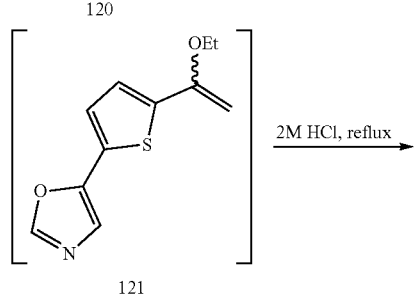
121
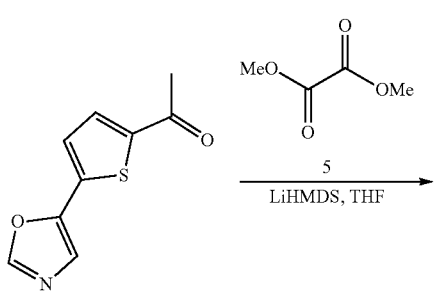
122
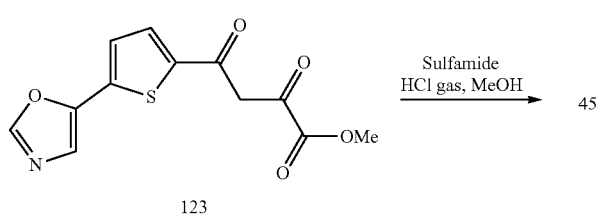
123
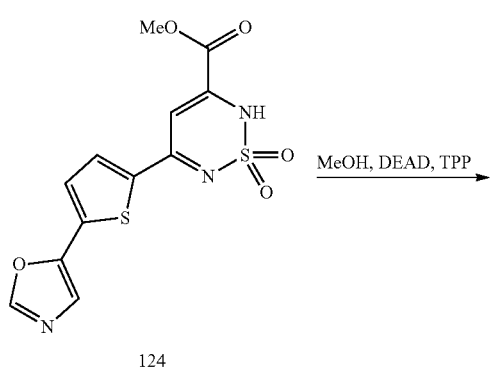
124
408
-continued
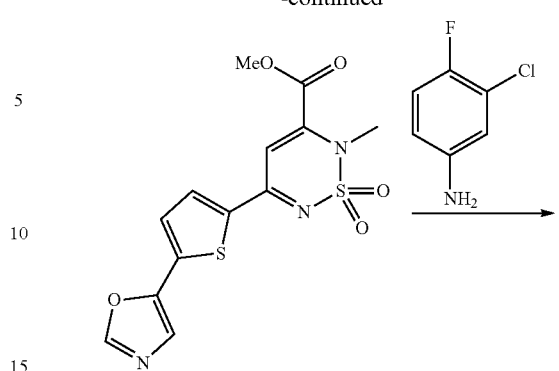
125
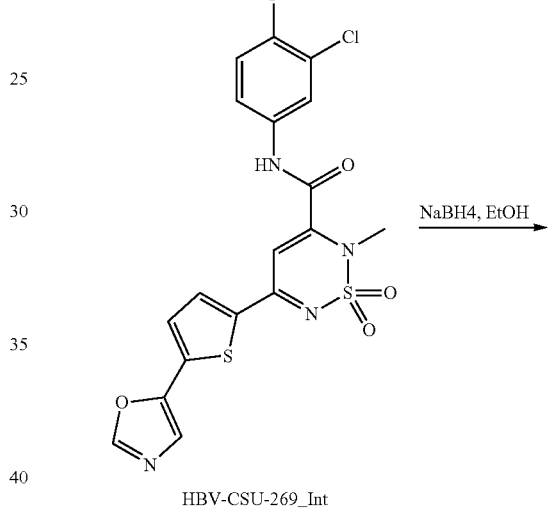
HBV-CSU-269_Int
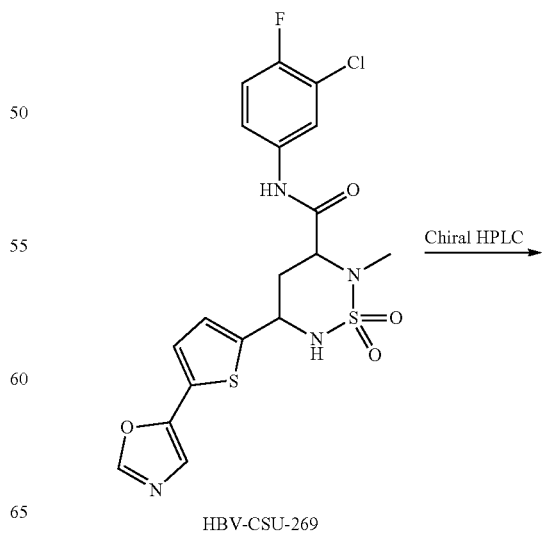
HBV-CSU-269

-continued

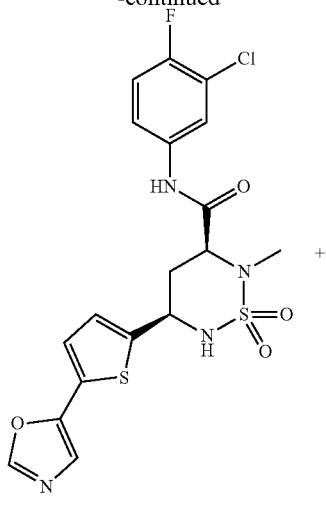

HBV-CSU-269-ISO-I

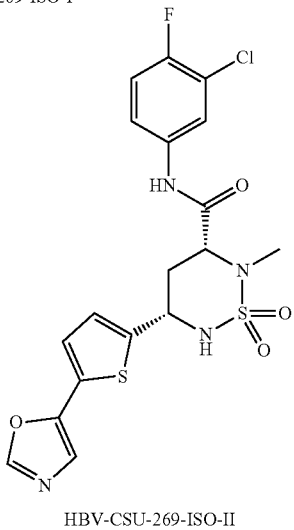

HBV-CSU-269-ISO-II

Synthesis of 5-(5-bromothiophen-2-yl)oxazole (120)

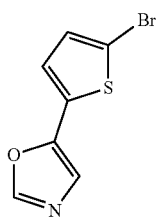 [SMILES: Brc1ccc(-c2cnco2)s1]

To a stirred solution of compound 119 (10 g, 52.36 mmol) and TosMIC (11.24 g, 57.59 mmol) in MeOH (300 mL), K$_2$CO$_3$ (7.91 g, 57.59 mmol) was added and reaction mixture was refluxed for 4 h. The progress of the reaction was monitored by TLC. After completion, the reaction mixture was concentrated in vacuo to obtain the crude. The crude was purified through silica gel column chromatography using 12% EtOAc/hexane to afford the title compound 120 (8.23 g, 62.50%) as a light yellow solid. TLC: 20% EtOAc/hexane (R$_f$: 0.3); $^1$H NMR (DMSO-d$_6$, 400 MHz): δ 8.42 (s, 1H), 7.54 (s, 1H), 7.31-7.28 (m, 2H); LCMS Calculated for C$_7$H$_4$BrNOS: 228.92: Observed: 229.75 (M+1)$^+$.

Synthesis of 1-(5-(oxazol-5-yl)thiophen-2-yl)ethan-1-one (122)

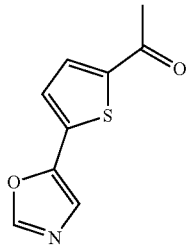

To a stirred solution of bromo compound 120 (7.6 g, 33.18 mmol) in toluene (150 mL), tributyl(1-ethoxyvinyl) stannane (17.97 g, 49.78 mmol) was added and purged with Ar for 15 min. To this solution, Pd(PPh$_3$)$_2$Cl$_2$ (1.16 g, 1.16 mmol) was added and the reaction mixture was stirred at 100° C. for overnight. The progress of the reaction was monitored by TLC. After completion, the intermediate compound 121 was treated with 2M HCl (60 mL) at reflux temperature for 3 h. The progress of the reaction was monitored by TLC. After completion, the reaction mixture was concentrated in vacuo to obtain the crude which was purified through silica gel column chromatography using 15% EtOAc/hexane to afford the title compound 122 (4.75 g, 74.45%) as a light yellow solid. TLC: 30% EtOAc/hexane (R$_f$: 0.2) 1H NMR (DMSO-d$_6$, 400 MHz): δ 8.52 (s, 1H), 7.97 (d, J=3.6 HZ, 1H), 7.78 (s, 1H), 7.59 (d, J=4.0 HZ, 1H), 2.56 (s, 3H); LCMS Calculated for C$_9$H$_7$NO$_2$S: 193.02: Observed: 194 (M+1)$^+$.

Synthesis of methyl 4-(5-(oxazol-5-yl)thiophen-2-yl)-2,4-dioxobutanoate (123)

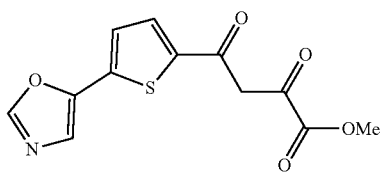 [SMILES: COC(=O)C(=O)CC(=O)c1ccc(-c2cnco2)s1]

Title compound was synthesized using general method for the synthesis of 2,4-diketoester described above to afford 5.5 g (84%, reaction scale is 4.5 g) as a yellow solid. 30% EtOAc/hexane (R$_f$: 0.1); LCMS Calculated for C$_{12}$H$_9$NO$_5$S: 279.02; Observed: 280 (M+1).

411

Synthesis of methyl 5-(5-(oxazol-5-yl)thiophen-2-yl)-2H-1,2,6-thiadiazine-3-carboxylate 1,1-dioxide (124)

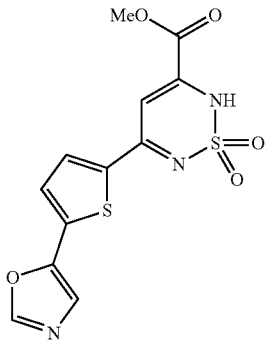 [SMILES: COC(=O)C1=CC(c2ccc(-c3cnco3)s2)=NS(=O)(=O)N1]

Title compound was synthesized using general method B for the synthesis of cyclic sulfonamide described above to afford 4 g (59.90%, reaction scale is 5.5 g) as brown solid. TLC: 5% MeOH/DCM ($R_f$: 0.1); $^1$H NMR (DMSO-$d_6$, 400 MHz): δ 8.49 (s, 1H), 7.94 (d, J=4.0 Hz, 1H), 7.70 (s, 1H), 7.52 (d, J=4.0 Hz, 1H), 6.80 (s, 1H), 3.83 (s, 3H); LCMS Calculated for $C_{12}H_9N_3O_5S_2$: 339.00; LCMS observed: 340.05 (M+1)$^+$.

Synthesis of methyl 2-methyl-5-(5-(oxazol-5-yl)thiophen-2-yl)-2H-1,2,6-thiadiazine-3-carboxylate 1,1-dioxide (125)

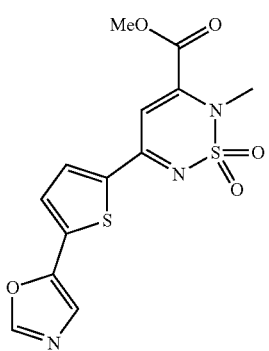 [SMILES: COC(=O)C1=CC(c2ccc(-c3cnco3)s2)=NS(=O)(=O)N1C]

Title compound was synthesized using general method B for alkylation described above to afford 2.3 g (49.14%, reaction scale is 4.5 g) as a light brown solid. TLC: 10% MeOH/DCM ($R_f$: 0.1); $^1$H NMR (DMSO-$d_6$, 400 MHz): δ 8.57 (s, 1H), 8.31 (d, J=4.0 Hz, 1H), 7.85 (s, 1H), 7.67 (d, J=4.4 Hz, 1H), 7.36 (s 1H), 3.94 (s, 3H), 3.51 (s, 3H); LCMS Calculated for $C_{13}H_{11}N_3O_5S_2$: 353.01; LCMS observed: 354.02 (M+1)$^+$.

412

Synthesis of N-(3-chloro-4-fluorophenyl)-2-methyl-5-(5-(oxazol-5-yl)thiophen-2-yl)-2H-1,2,6-thiadiazine-3-carboxamide 1,1-dioxide (HBV-CSU-269_Int)

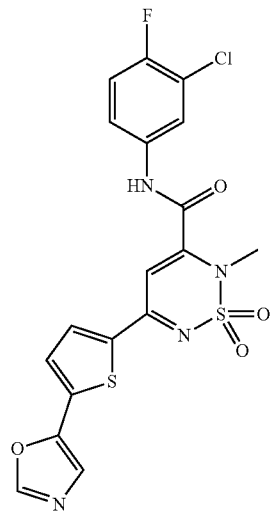 [SMILES: CN1C(C(=O)Nc2ccc(F)c(Cl)c2)=CC(c2ccc(-c3cnco3)s2)=NS1(=O)=O]

The above titled compound has been synthesized by following the general procedure (Method A) described above for amidation by using corresponding 125 and corresponding amine (see Table 1 for analytical data).

Cis-N-(3-Chloro-4-fluorophenyl)-2-methyl-5-(5-(oxazol-5-yl)thiophen-2-yl)-1,2,6-thiadiazinane-3-carboxamide 1,1-dioxide (HBV-CSU-269, HBV-CSU-269-ISO-I & HBV-CSU-269-II)

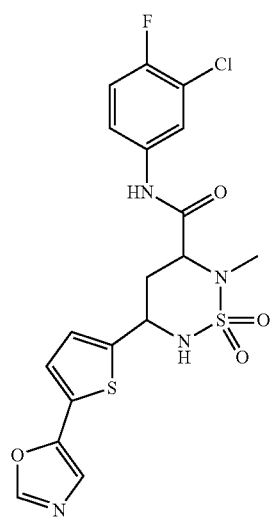

HBV-CSU-269

-continued
HBV-CSU-269-ISO-I
HBV-CSU-269-ISO-II
The above titled compounds have been synthesized by following the general procedure described above for reduction by using corresponding HBV-CSU-269_Int (see Table 2 for analytical data).
Scheme 41
Synthesis of Cis-5-(benzo[d]thiazol-6-yl)-N-(3-chloro-4-fluorophenyl)-2-methyl-1,2,6-thiadiazinane-3-carboxamide 1,1-dioxide (HBV-CSU-273)
Scheme 41:
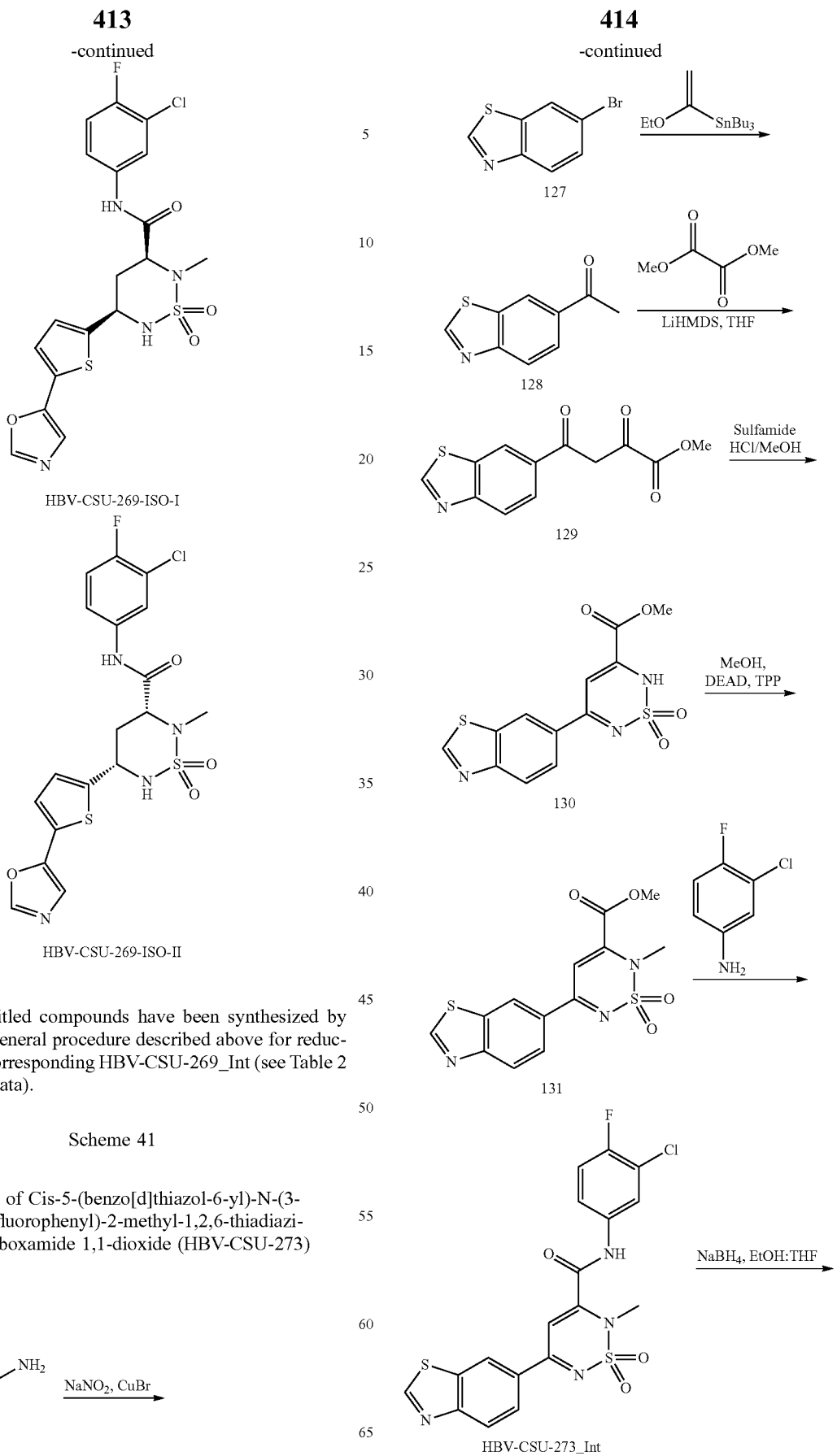

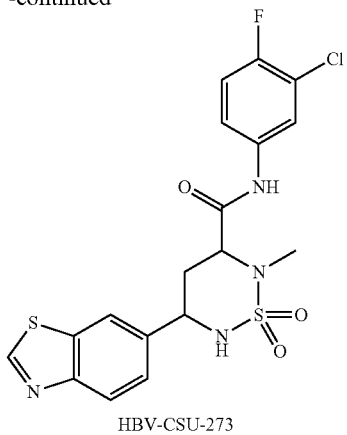

HBV-CSU-273

Synthesis of 6-bromobenzo[d]thiazole (127)

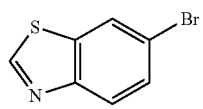

Titled compound was prepared using the reported method in Organic Letters, 9(18), 3623-3625; 2007.

Synthesis of 6-bromobenzo[d]thiazole (128)

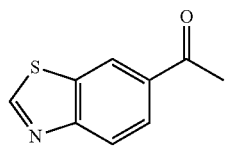

To a mixture of bromo compound 127 (7 g, 32.17 mmol) in toluene (70 mL), tributyl(1-ethoxyvinyl)stannane (11.40 g, 35.98 mmol) was added, purged with Ar for 15 min followed by the addition of PdCl$_2$ (PPh$_3$)$_2$ (2.29 g, 3.27 mmol) and then the resulting reaction mixture was stirred at 90° C. for overnight. The progress of the reaction was monitored by TLC. After completion, the reaction mixture was concentrated in vacuo, the residue obtained was treated with 6N HCl at room temperature for 1 h. After completion, the reaction mixture was concentrated in vacuo, neutralized with aq. NaHCO$_3$ solution, extracted with ethyl acetate. The combined organic extracts were dried over anhydrous sodium sulfate, filtered and concentrated in vacuo to to afford compound 128 (4 g, 69%) as an off-white solid. TLC: 20% EtOAc/hexanes (R$_1$ 0.2); H NMR (DMSO-d$_6$, 400 MHz): δ 9.18 (s, 1H), 8.62 (s, 1H), 8.20 (d, J=8.8 Hz, 1H), 8.12 (d, J=8.8 Hz, 1H), 2.72 (s, 3H); LCMS Calculated for C$_9$H$_7$NOS: 177.02; LCMS observed: 178 (M+1)$^+$.

Synthesis of methyl 4-(benzo[d]thiazol-6-yl)-2,4-dioxobutanoate (129)

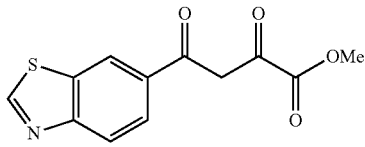 [SMILES: COC(=O)C(=O)CC(=O)c1ccc2ncsc2c1]

Title compound was synthesized using general method for the synthesis of 2,4-diketoester described above to afford 5 g of Compound 129 (84%, reaction scale is 4 g) as a brown solid. TLC: 40% EtOAc/hexanes (R$_f$: 0.2).

Synthesis of methyl 5-(benzo[d]thiazol-6-yl)-2H-1,2,6-thiadiazine-3-carboxylate 1,1-dioxide (130)

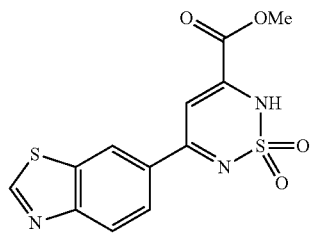 [SMILES: COC(=O)C1=CC(c2ccc3ncsc3c2)=NS(=O)(=O)N1]

Title compound was synthesized using general method A for cyclisation described above to afford 0.5 g of Compound 130 (10%, reaction scale is 4 g) as a brown solid. TLC: 20% MeOH/DCM (R$_f$: 0.1); $^1$H NMR (DMSO-d$_6$, 400 MHz): δ 9.51 (s, 1H), 8.83 (s, 1H), 8.16-8.06 (m, 2H), 6.88 (s, 1H), 3.84 (s, 3H); LCMS Calculated for C$_{12}$H$_9$N$_3$O$_4$S$_2$: 323.00; LCMS observed: 324 (M+1)$^+$.

Synthesis of methyl 5-(benzo[d]thiazol-6-yl)-2-methyl-2H-1,2,6-thiadiazine-3-carboxylate 1,1-dioxide (131)

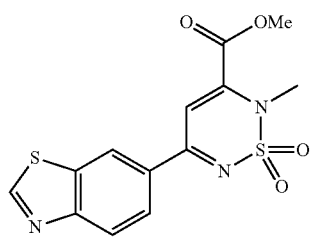 [SMILES: COC(=O)C1=CC(c2ccc3ncsc3c2)=NS(=O)(=O)N1C]

Title compound was synthesized using general method B for alkylation described above to afford 0.4 g of Compound 131 (76% yield, reaction scale was 0.5 g) as a brown solid. TLC: 40% EtOAc/hexanes (R$_f$: 0.3); $^1$H NMR (CDCl3, 400 MHz): δ 9.20 (s, 1H), 8.75 (s, 1H), 8.25 (d, J=8.8 Hz, 1H), 8.16 (d, J=8.8 Hz, 1H), 7.25 (s, 1H), 4.04 (s, 3H), 3.72 (s, 3H); LCMS Calculated for C$_{13}$H$_{11}$N$_3$O$_4$S$_2$: 337.02; LCMS observed: 338 (M+1)$^+$.

417

Synthesis of 5-(benzo[d]thiazol-6-yl)-N-(3-chloro-4-fluorophenyl)-2-methyl-2H-1,2,6-thiadiazine-3-carboxamide 1,1-dioxide (HBV-CSU-273_Int)

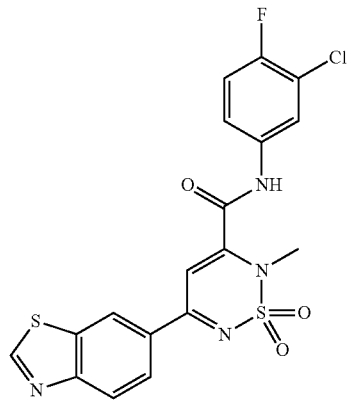 [SMILES: CN1C(C(=O)Nc2ccc(F)c(Cl)c2)=CC(c2ccc3ncsc3c2)=NS1(=O)=O]

The above titled compound has been synthesized by following the general procedure (Method B) described above for amidation by using corresponding 131 and corresponding amine (see Table 1 for analytical data).

Synthesis of Cis-5-(benzo[d]thiazol-6-yl)-N-(3-chloro-4-fluorophenyl)-2-methyl-1,2,6-thiadiazinane-3-carboxamide 1,1-dioxide (HBV-CSU-273)

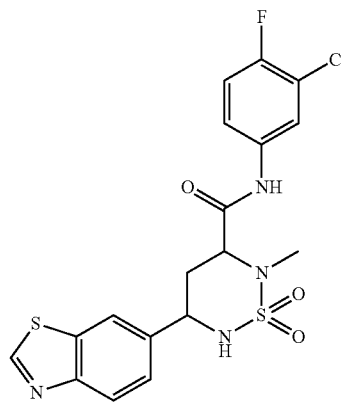

The above titled compounds have been synthesized by following the general procedure described above for reduction by using corresponding HBV-CSU-273_Int (see Table 2 for analytical data).

418

Scheme 42

General Synthetic Scheme for 5-(thiophen-2-yl)-1,2,6-thiadiazinane-3-carboxamide 1,1-dioxide Derivatives with 4-Substituted Thiophene Scheme 42:

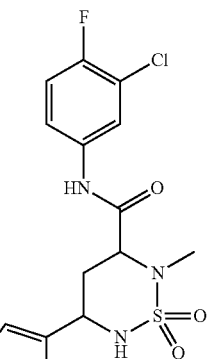

HBV-CSU-146

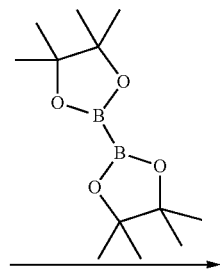

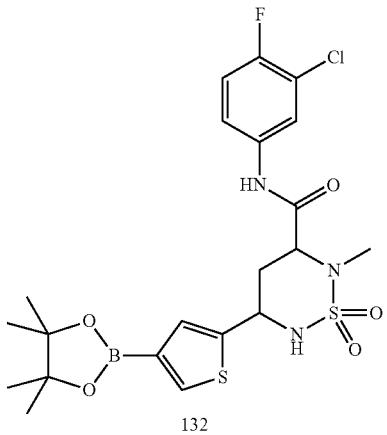

132

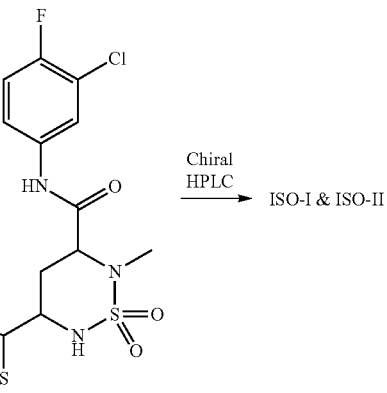

HBV-CSU_Int

| Target | R variation |
|---|---|
| HBV-CSU-284 | [N-methylimidazol-4-yl] |
| HBV-CSU-285 | [1-methylimidazol-5-yl] |
| HBV-CSU-286 | [isothiazol-5-yl] |
| HBV-CSU-288 | [1-methylpyrazol-3-yl] |
| HBV-CSU-326 | [1-methyl-1,2,4-triazol-3-yl] |
| HBV-CSU-327 | [2-methyl-2H-1,2,4-triazol-3-yl] |

Synthesis of N-(3-chloro-4-fluorophenyl)-2-methyl-5-(4-(4,4,5,5-tetramethyl-1,3,2-dioxaborolan-2-yl)thiophen-2-yl)-1,2,6-thiadiazinane-3-carboxamide 1,1-dioxide (132)

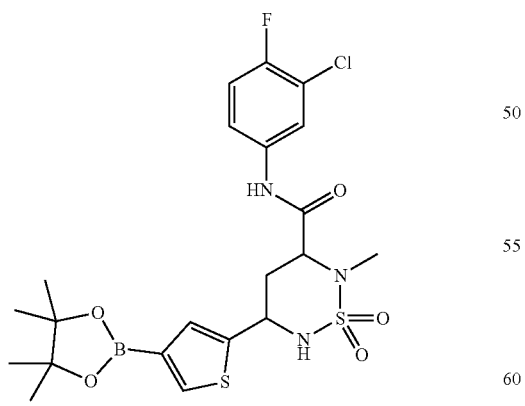

To a mixture of bromo compound HBV-CSU-146 (3 g, 6.21 mmol) and Bis(pinacolato)diboron (3.95 g, 15.53 mmol) in 1,4-dioxane (30 mL), potassium acetate (3.04 g, 31.05 mmol) was added and purged with Ar for 15 min. To this solution, 1,1'-Bis(diphenylphosphino) ferrocene palladium(II)dichloride dichloromethane adduct (PdCl$_2$(dppf).CH$_2$Cl$_2$) (0.152 g, 0.186 mmol) was added and the reaction mixture was stirred at 90° C. for overnight. The progress of the reaction was monitored by TLC. After completion of the reaction, the reaction mixture was filtered through Celite, evaporated to dryness to afford the desired Boronate ester as crude product 132 (2.35 g, crude) and used as such for the next step without further purification. TLC: 40% EtOAc/hexanes (R$_f$: 0.2); LCMS Calculated for C$_{21}$H$_{26}$BClFN$_3$O$_5$S$_2$: 529.11; Observed: 448.05 (M+1)$^+$ for boronic acid.

Cis-N-(3-Chloro-4-fluorophenyl)-2-methyl-5-(5-(1-methyl-1H-imidazol-4-yl)thiophen-2-yl)-1,2,6-thiadiazinane-3-carboxamide 1,1-dioxide (HBV-CSU-284, HBV-CSU-284-ISO-I & HBV-CSU-284-II)

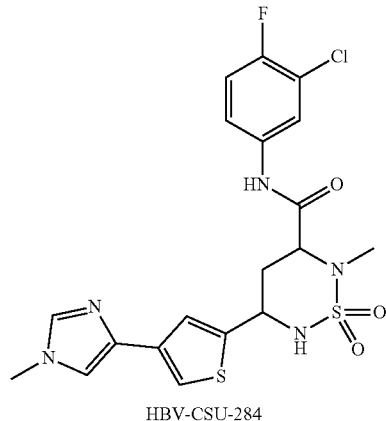

HBV-CSU-284

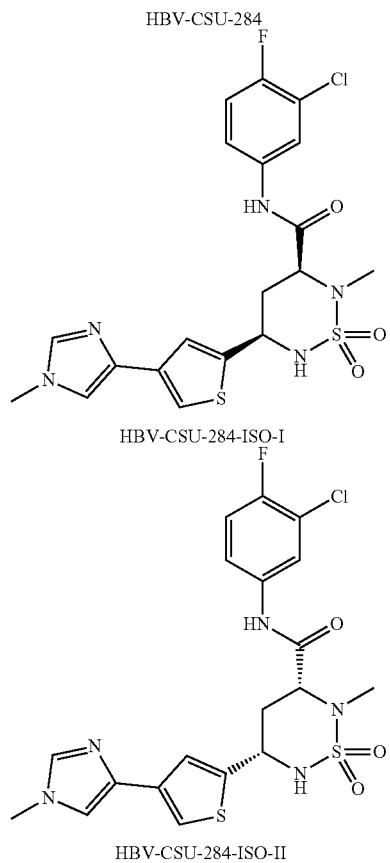

HBV-CSU-284-ISO-I

HBV-CSU-284-ISO-II

421

The above titled compounds have been synthesized by following the general procedure described above for Suzuki coupling by using compound 132 and corresponding bromo compound (see Table 2 for analytical data).

Cis-N-(3-Chloro-4-fluorophenyl)-2-methyl-5-(4-(1-methyl-1H-imidazol-5-yl)thiophen-2-yl)-1,2,6-thiadiazinane-3-carboxamide 1,1-dioxide (HBV-CSU-285, HBV-CSU-285-ISO-I & HBV-CSU-285-ISO-II)

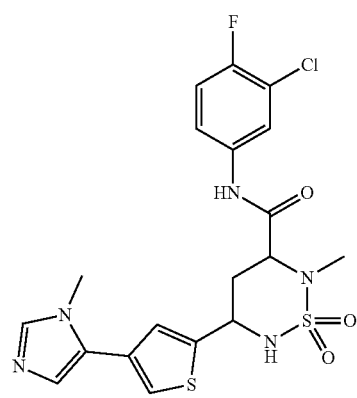
HBV-CSU-285

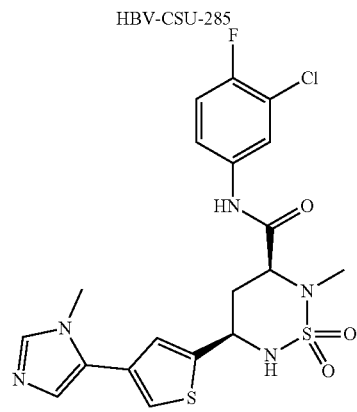
HBV-CSU-285-ISO-I

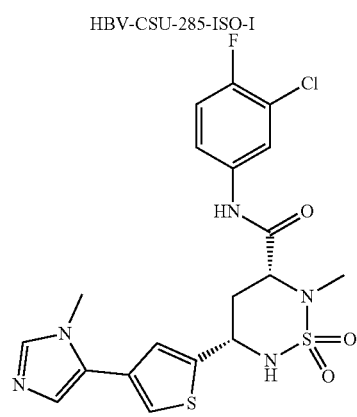
HBV-CSU-285-ISO-II

The above titled compounds have been synthesized by following the general procedure described above for Suzuki coupling by using compound 132 and corresponding bromo compound (see Table 2 for analytical data).

422

Cis-N-(3-Chloro-4-fluorophenyl)-2-methyl-5-(4-(thiazol-5-yl)thiophen-2-yl)-1,2,6-thiadiazinane-3-carboxamide 1,1-dioxide (HBV-CSU-286, HBV-CSU-286-ISO-I & HBV-CSU-286-II)

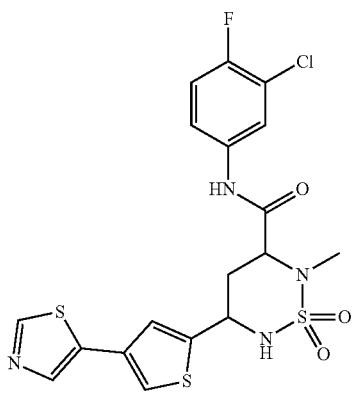
HBV-CSU-286

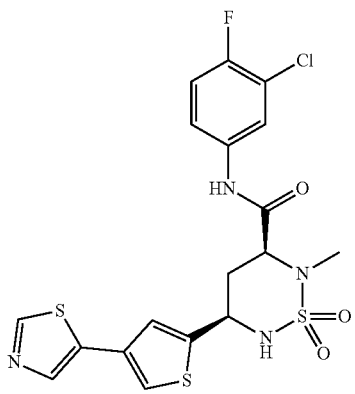
HBV-CSU-286-ISO-I

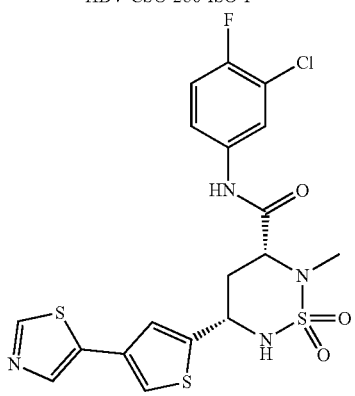
HBV-CSU-286-ISO-II

The above titled compounds have been synthesized by following the general procedure described above for Suzuki coupling by using compound 132 and corresponding bromo compound (see Table 2 for analytical data).

423

Cis-N-(3-Chloro-4-fluorophenyl)-2-methyl-5-(4-(1-methyl-1H-pyrazol-3-yl)thiophen-2-yl)-1,2,6-thiadiazinane-3-carboxamide 1,1-dioxide (HBV-CSU-288, HBV-CSU-288-ISO-I & HBV-CSU-288-II)

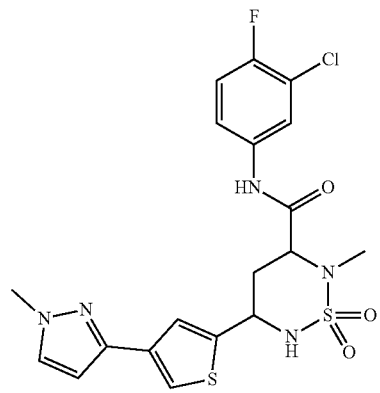

HBV-CSU-288

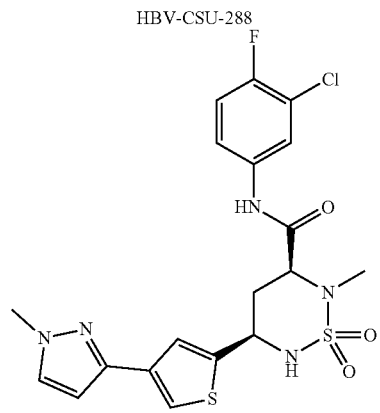

HBV-CSU-288-ISO-I

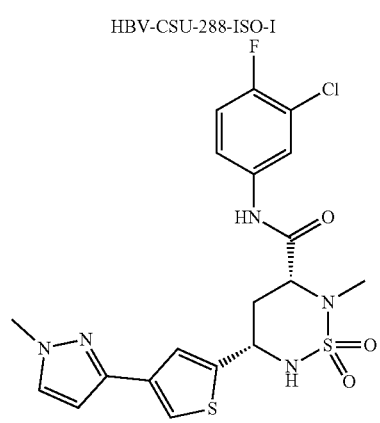

HBV-CSU-288-ISO-II

The above titled compounds have been synthesized by following the general procedure described above for Suzuki coupling by using compound 132 and corresponding bromo compound (see Table 2 for analytical data).

424

Cis-N-(3-chloro-4-fluorophenyl)-2-methyl-5-(4-(1-methyl-1H-1,2,4-triazol-3-yl)thiophen-2-yl)-1,2,6-thiadiazinane-3-carboxamide 1,1-dioxide (HBV-CSU-326-ISO-I & HBV-CSU-326-II)

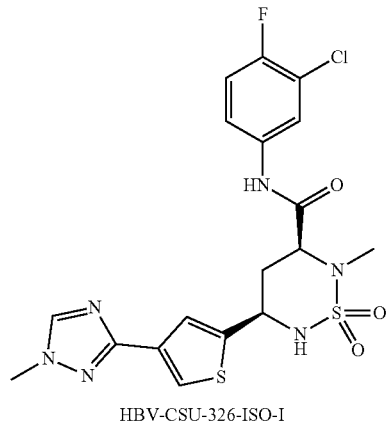

HBV-CSU-326-ISO-I

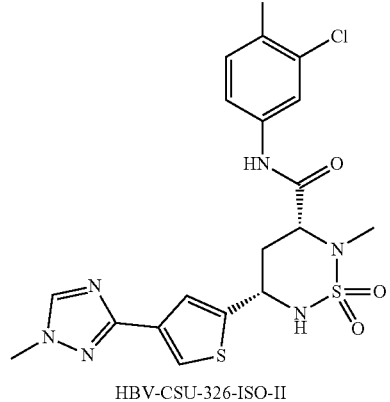

HBV-CSU-326-ISO-II

The above titled compounds have been synthesized by following the general procedure described above for Suzuki coupling by using compound 132 and corresponding bromo compound (see Table 2 for analytical data).

Cis-N-(3-Chloro-4-fluorophenyl)-2-methyl-5-(4-(1-methyl-1H-1,2,4-triazol-5-yl)thiophen-2-yl)-1,2,6-thiadiazinane-3-carboxamide 1,1-dioxide (HBV-CSU-327-ISO-I & HBV-CSU-327-II)

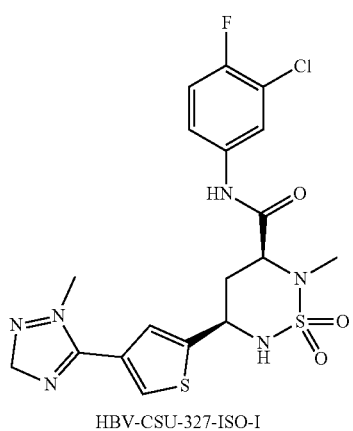

HBV-CSU-327-ISO-I

425
-continued

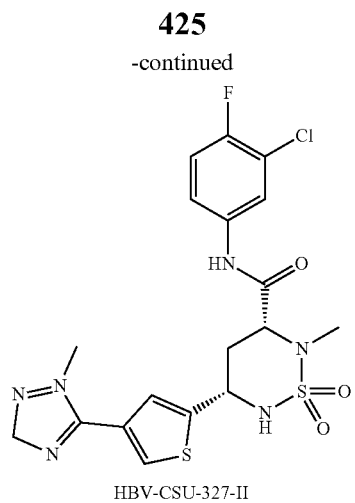
HBV-CSU-327-II

The above titled compounds have been synthesized by following the general procedure described above for Suzuki coupling by using compound 132 and corresponding bromo compound (see Table 2 for analytical data).

Scheme 43

Synthesis of N-(3-chloro-4-fluorophenyl)-2-methyl-5-(4-methyl-5-(1-methyl-1H-pyrazol-4-yl)thiophen-2-yl)-1,2,6-thiadiazinane-3-carboxamide 1,1-dioxide (HBV-CSU-300, HBV-CSU-300-ISO-I & HBV-CSU-300-ISO-I) and 5-(5-bromo-4-methylthiophen-2-yl)-N-(3-chloro-4-fluorophenyl)-2-methyl-1,2,6-thiadiazinane-3-carboxamide 1,1-dioxide (HBV-CSU-335)

Scheme 43:

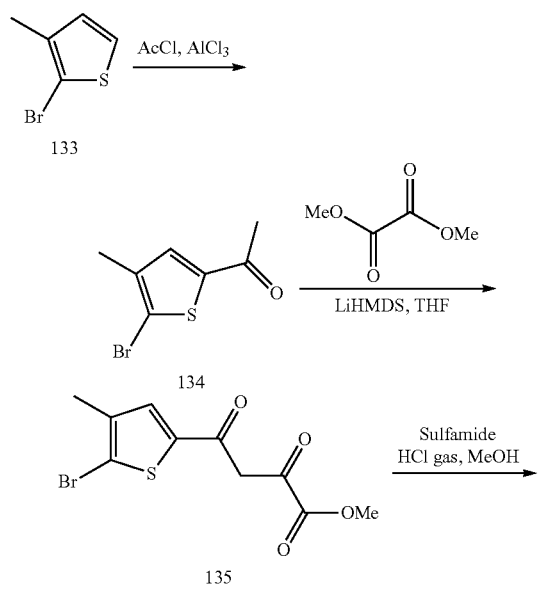

426
-continued

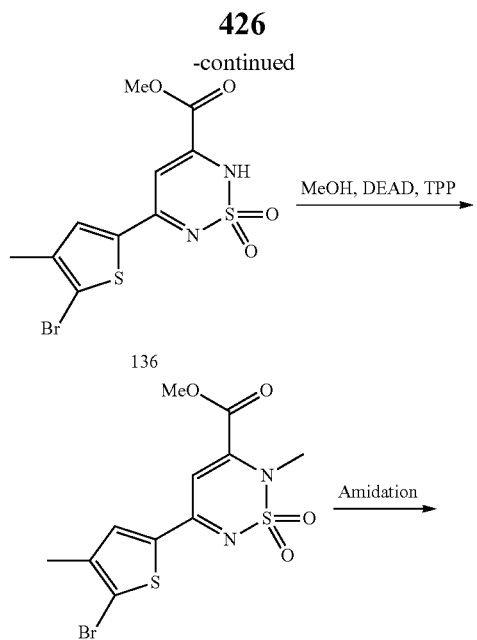

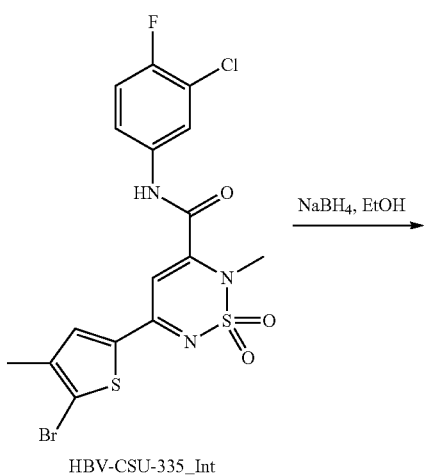

427
-continued

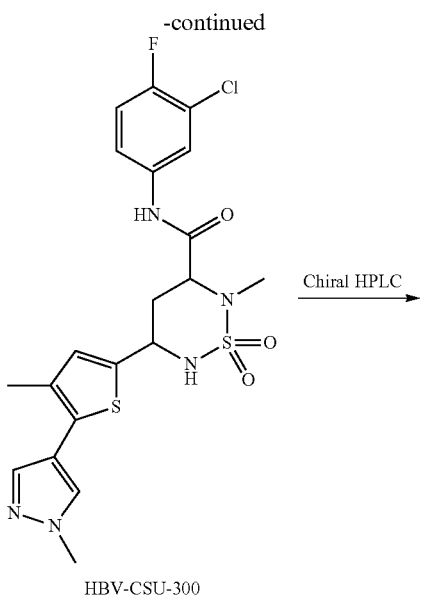

HBV-CSU-300

⟶ Chiral HPLC

HBV-CSU-300-ISO-I
+
HBV-CSU-300-ISO-II

Synthesis of 1-(5-bromo-4-methylthiophen-2-yl)ethan-1-one (134)

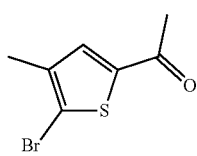

To a stirred solution of compound 133 (10 g, 56.49 mmol) in DCM (100 mL) at 0° C., AlCl$_3$ (9.3 g, 70.62 mmol) was added and stirred for 10 min. To this solution, acetyl chloride (4.85 g, 61.51 mmol) was added at the same temperature and the resulting reaction mixture was stirred at room temperature for 16 h. The progress of the reaction was monitored by TLC. After completion, the reaction mixture was cooled to 0° C.; quenched by adding ice cold water, basified using sat. NaHCO$_3$ solution and then extracted using DCM. The combined organic layers were collected, dried over anhydrous sodium sulphate, filtered and concentrated in vacuo to afford the crude compound. The crude compound was purified by silica gel column chromatography using 5% EtOAc/hexane to afford the title compound 134 (12 g, 97%) as a brown solid. TLC: 10% EtOAc/hexane (R$_f$: 0.4); LCMS Calculated for C$_7$H$_7$BrOS: 217.94; Observed: 218.80 (M)$^+$.

428
Synthesis of methyl 4-(5-bromo-4-methylthiophen-2-yl)-2,4-dioxobutanoate (135)

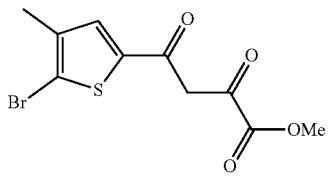 [SMILES: COC(=O)C(=O)CC(=O)c1cc(C)c(Br)s1]

Title compound was synthesized using general method for the synthesis of 2,4-diketoester described above to afford 15 g (90.09%, reaction scale is 12 g) as a brown solid. TLC: 20% EtOAc/hexane (R$_f$: 0.1). The crude material was used as such in the next reaction without further characterization.

Synthesis methyl 5-(5-bromo-4-methylthiophen-2-yl)-2H-1,2,6-thiadiazine-3-carboxylate 1,1-dioxide (136)

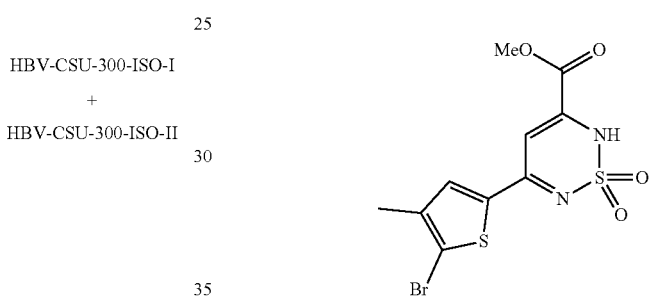

Title compound was synthesized using general method B for the synthesis of cyclic sulfonamide described above to afford 13 g of compound 136 (72.22%, reaction scale is 15 g) as yellow solid. TLC: 50% EtOAc/hexane (R$_f$: 0.1); LCMS Calculated for C$_{10}$H$_9$BrN$_2$O$_4$S$_2$: 363.92; LCMS observed: 366.90 (M+2)$^+$.

Synthesis of methyl 5-(5-bromo-4-methylthiophen-2-yl)-2-methyl-2H-1,2,6-thiadiazine-3-carboxylate 1,1-dioxide (137)

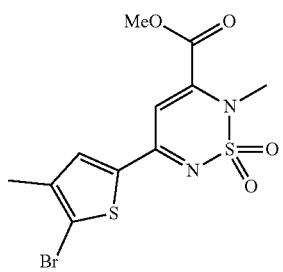 [SMILES: COC(=O)C1=CC(c2cc(C)c(Br)s2)=NS(=O)(=O)N1C]

Title compound was synthesized using general method B for alkylation described above to afford 10 g of compound 137 (75%, reaction scale is 13 g) as a yellow solid. TLC: 40% EtOAc/hexanes (R$_f$: 0.3); LCMS Calculated for C$_{11}$H$_{11}$BrIN$_2$O$_4$S$_2$:377.93; LCMS observed: 381.25 (M+2)$^+$.

Synthesis of 5-(5-bromo-4-methylthiophen-2-yl)-N-(3-chloro-4-fluorophenyl)-2-methyl-2H-1,2,6-thiadiazine-3-carboxamide 1,1-dioxide (HBV-CSU-335_Int)

Cis-N-(3-Chloro-4-fluorophenyl)-5-(4-methyl-5-(1-methyl-1H-pyrazol-4-yl)thiophen-2-yl)-2-methyl-1,2,6-thiadiazinane-3-carboxamide 1,1-dioxide (HBV-CSU-300, HBV-CSU-300-ISO-I & HBV-CSU-300-ISO-II)

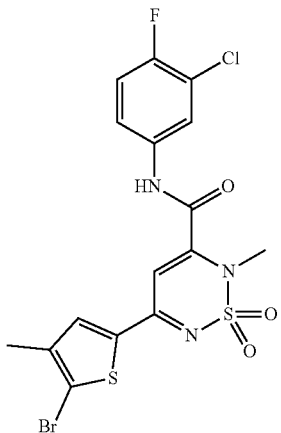 [SMILES: Cc1cc(C2=NS(=O)(=O)N(C)C(C(=O)Nc3ccc(F)c(Cl)c3)=C2)sc1Br]

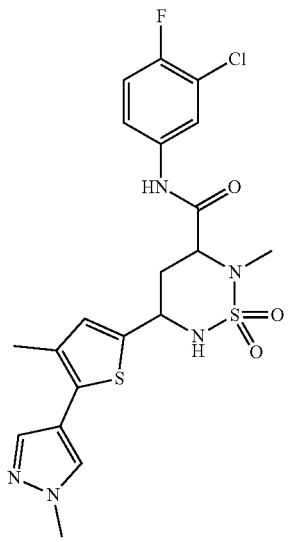

HBV-CSU-300

The above titled compound has been synthesized by following the general procedure (Method B) described above for amidation by using compound 137 and corresponding amine (see Table 1 for analytical data).

Cis-5-(5-bromo-4-methylthiophen-2-yl)-N-(3-chloro-4-fluorophenyl)-2-methyl-1,2,6-thiadiazinane-3-carboxamide 1,1-dioxide (HBV-CSU-335)

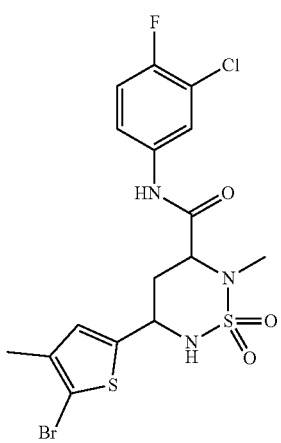 [SMILES: Cc1cc(C2CC(C(=O)Nc3ccc(F)c(Cl)c3)N(C)S(=O)(=O)N2)sc1Br]

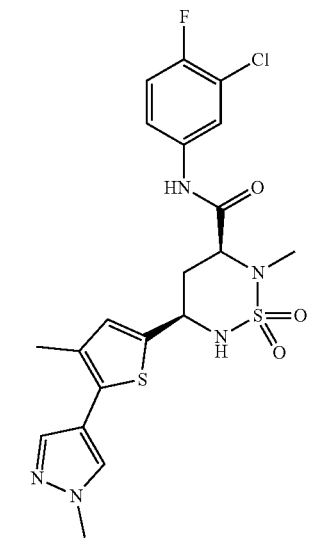

HBV-CSU-300-ISO-I

The above titled compounds have been synthesized by following the general procedure described above for reduction by using corresponding HBV-CSU-335_Int (see Table 2 for analytical data).

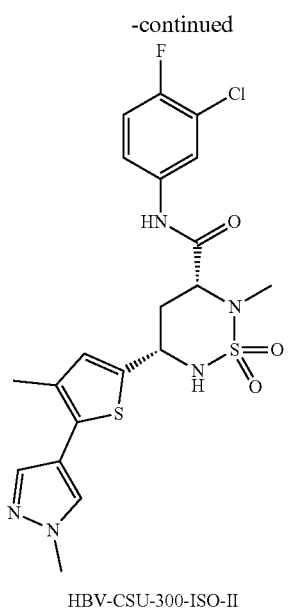

HBV-CSU-300-ISO-II

The above titled compounds have been synthesized by following the general procedure described above for Suzuki coupling by using HBV-CSU-335 and corresponding bromo compound (see Table 2 for analytical data).

Scheme 44

Synthesis of N-(3-chloro-4-fluorophenyl)-5-(4-chloro-5-(1-methyl-1H-pyrazol-4-yl)thiophen-2-yl)-2-methyl-1,2,6-thiadiazinane-3-carboxamide 1,1-dioxide (HBV-CSU-302, HBV-CSU-302-ISO-I & HBV-CSU-302-ISO-II)

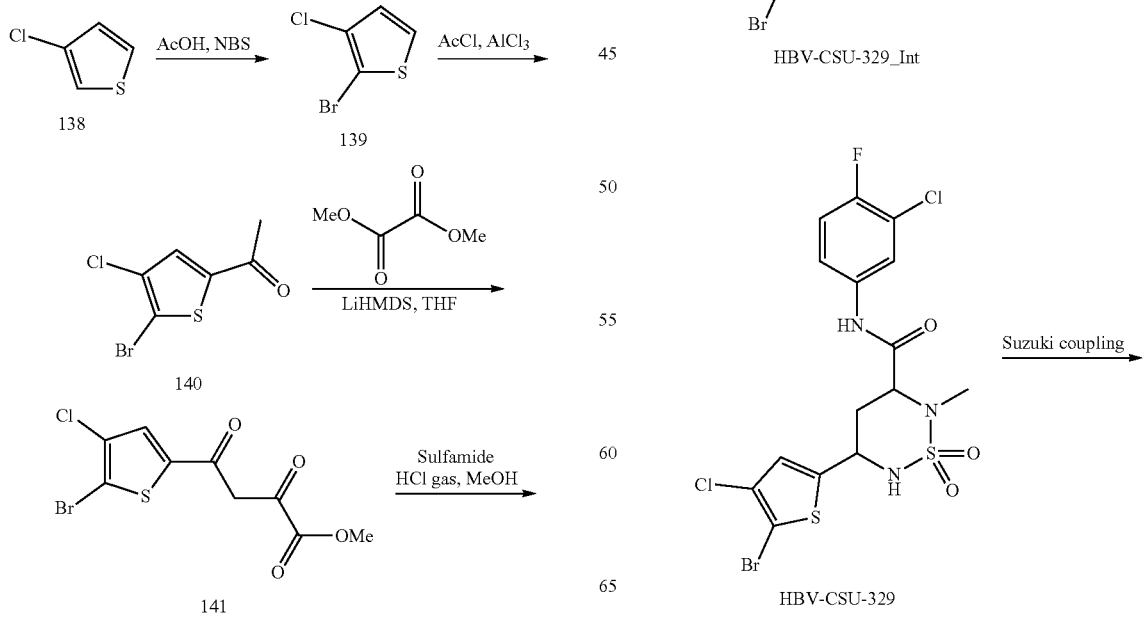

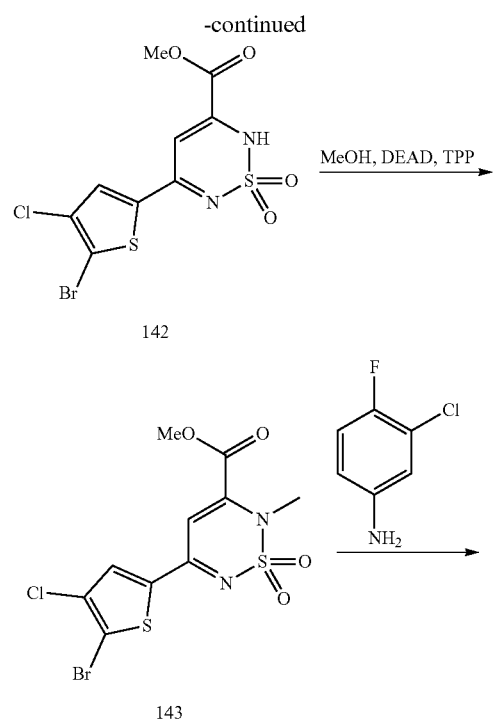

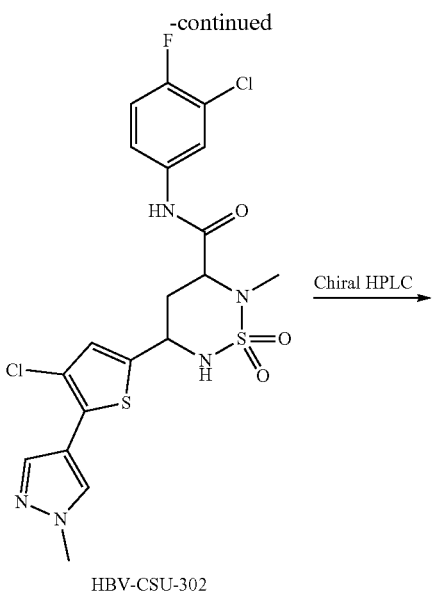

HBV-CSU-302

HBV-CSU-302-ISO-I
+
HBV-CSU-302-ISO-II

Synthesis of 2-bromo-3-chlorothiophene (139)

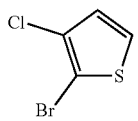

To a stirred solution of compound 138 (5 g, 42.37 mmol) in CCl$_4$ (30 mL) at 0° C., Br$_2$ (6.4 g, 40.25 mmol) was added drop wise. The resulting reaction mixture was stirred room temperature for 12 h. The progress of the reaction was monitored by TLC. After completion, the reaction mixture was cooled to 0° C.; quenched by adding aq. Sodium thiosulphate and 50% NaOH solution and extracted with DCM. The combined organic layers were collected, dried over anhydrous sodium sulphate and concentrated in vacuo to afford the title compound 139 (6 g, 71.94%) as a colorless liquid and used as such for the next step without further purification TLC: hexane (R$_f$: 0.4); $^1$H NMR (DMSO-d$_6$, 400 MHz): δ 7.75 (d, J=5.6 Hz, 1H), 7.11 (d, J=6.0 Hz, 1H).

Synthesis of 1-(5-bromo-4-chlorothiophen-2-yl)ethan-1-one (140)

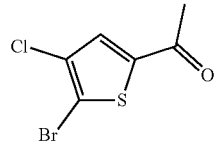

To a stirred solution of compound 139 (6 g, 30.45 mmol) in DCM (300 mL) at 0° C., AlCl$_3$ (4.41 g, 33.16 mmol) was added and stirred for 10 min. To this solution, acetyl chloride (2.96 g, 38.07 mmol) was added at same temperature. The resulting reaction mixture was stirred room temperature for 16 h. The progress of the reaction was monitored by TLC. After completion, the reaction mixture was cooled to 0° C.; quenched by adding ice cold water; sat. NaHCO$_3$ solution and extracted using DCM. The combined organic layers were collected, dried over anhydrous sodium sulphate, filtered and concentrated in vacuo to afford the crude. The crude was purified by silica gel column chromatography using 10% EtOAc/hexane to afford the title compound 140 (5.5 g, 75.34%) as a brown solid TLC: 5% EtOAc/hexane (R$_f$: 0.3) $^1$H NMR (DMSO-d$_6$, 400 MHz): δ 8.06 (s, 1H), 2.52 (s, 3H). LCMS Calculated for C$_6$H$_4$BrClOS: 237.89; Observed: 240.85 (M+2)$^+$.

Synthesis of methyl 4-(5-bromo-4-chlorothiophen-2-yl)-2,4-dioxobutanoate (141)

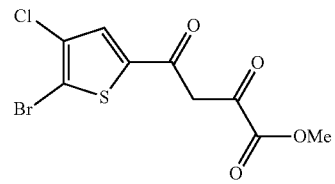 [SMILES: COC(=O)C(=O)CC(=O)c1cc(Cl)c(Br)s1]

Title compound was synthesized using general method for the synthesis of 2,4-diketoester described above to afford 10 g of compound 141 (crude, reaction scale is 5.5 g) as a brown solid TLC: 10% MeOH/DCM (R$_f$: 0.1). The crude material was used as such in the next reaction without further characterization.

Synthesis methyl 5-(5-bromo-4-chlorothiophen-2-yl)-2H-1,2,6-thiadiazine-3-carboxylate 1,1-dioxide (142)

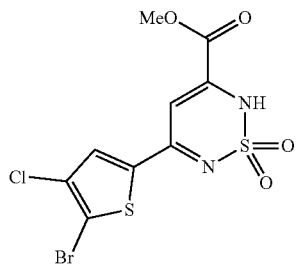 [SMILES: COC(=O)C1=CC(c2cc(Cl)c(Br)s2)=NS(=O)(=O)N1]

Title compound was synthesized using general method B for the synthesis of cyclic sulfonamide described above to afford 7 g of compound 142 (58%, reaction scale is 10 g) as yellow solid. TLC: 20% EtOAc/hexane (R$_f$: 0.1); $^1$H NMR (DMSO-d$_6$, 400 MHz): δ 7.96 (s, 1H), 6.72 (s, 1H), 3.81 (s, 3H); LCMS Calculated for C$_9$H$_6$BrClN$_2$O$_4$S$_2$: 383.86; LCMS observed: 386.90 (M+2)$^+$.

435

Synthesis of methyl 5-(5-bromo-4-chlorothiophen-2-yl)-2-methyl-2H-1,2,6-thiadiazine-3-carboxylate 1,1-dioxide (143)

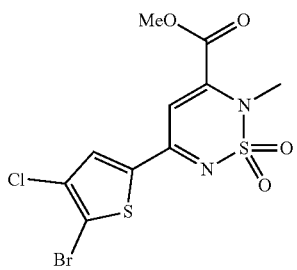 [SMILES: COC(=O)C1=CC(c2cc(Cl)c(Br)s2)=NS(=O)(=O)N1C]

Title compound was synthesized using general method B for alkylation described above to afford 9 g of compound 143 (crude, reaction scale is 7 g) as a yellow solid. TLC: 40% EtOAc/hexanes ($R_f$: 0.4); $^1$H NMR (DMSO-$d_6$, 400 MHz): δ 8.41 (s 1H), 7.37 (s, 1H), 3.94 (s, 3H), 3.53 (s, 3H); LCMS Calculated for $C_{10}H_8BrClN_2O_4S_2$: 397.88; LCMS observed: 401.25 (M+2)$^+$.

Synthesis of 5-(5-bromo-4-chlorothiophen-2-yl)-N-(3-chloro-4-fluorophenyl)-2-methyl-2H-1,2,6-thiadiazine-3-carboxamide 1,1-dioxide (HBV-CSU-329_Int)

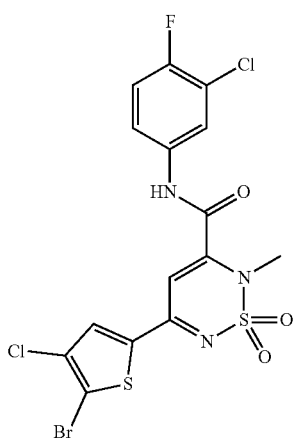 [SMILES: CN1C(C(=O)Nc2ccc(F)c(Cl)c2)=CC(c2cc(Cl)c(Br)s2)=NS1(=O)=O]

The above titled compound has been synthesized by following the general procedure (Method A) described above for amidation by using compound 143 and corresponding amine (see Table 1 for analytical data).

436

Cis-5-(5-bromo-4-chlorothiophen-2-yl)-N-(3-chloro-4-fluorophenyl)-2-methyl-1,2,6-thiadiazinane-3-carboxamide 1,1-dioxide (HBV-CSU-329)

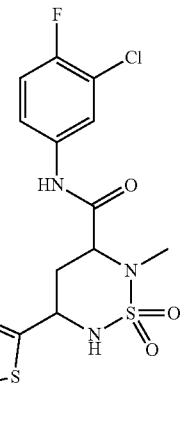

The above titled compounds have been synthesized by following the general procedure described above for reduction by using corresponding HBV-CSU-329_Int (see Table 2 for analytical data).

Cis-N-(3-Chloro-4-fluorophenyl)-5-(4-chloro-5-(1-methyl-1H-pyrazol-4-yl)thiophen-2-yl)-2-methyl-1,2,6-thiadiazinane-3-carboxamide 1,1-dioxide (HBV-CSU-302, HBV-CSU-302-ISO-I & HBV-CSU-302-ISO-II)

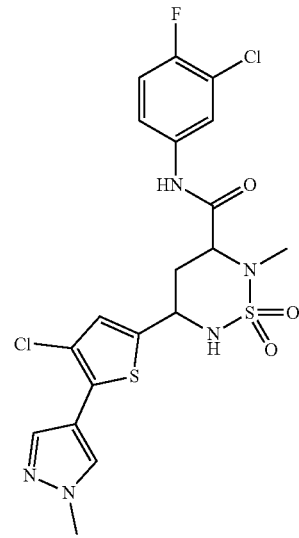

HBV-CSU-302

437
-continued

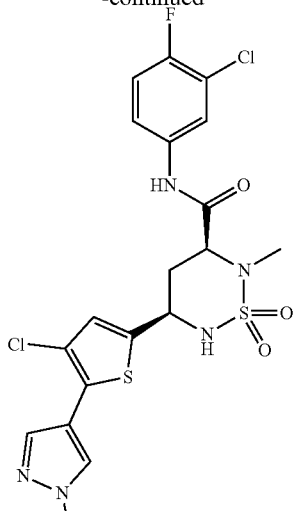

HBV-CSU-302-ISO-I

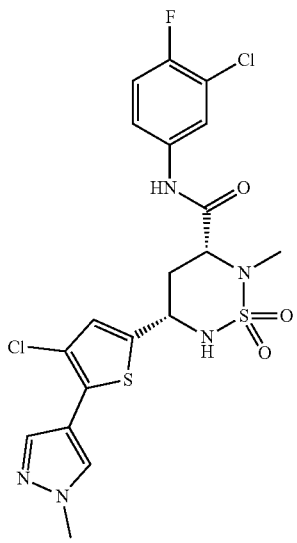

HBV-CSU-302-ISO-II

The above titled compounds have been synthesized by following the general procedure described above for Suzuki coupling by using HBV-CSU-329 and corresponding bromo compound (see Table 2 for analytical data).

438

Scheme 45

Synthesis of Cis-3-chloro-4-fluorophenyl)-2-methyl-5-(5-phenyl-1,3,4-thiadiazol-2-yl)-1,2,6-thiadiazinane-3-carboxamide 1,1-dioxide (HBV-CSU-304, HBV-CSU-304-ISO-I & HBV-CSU-304-ISO-II)

Scheme 45:

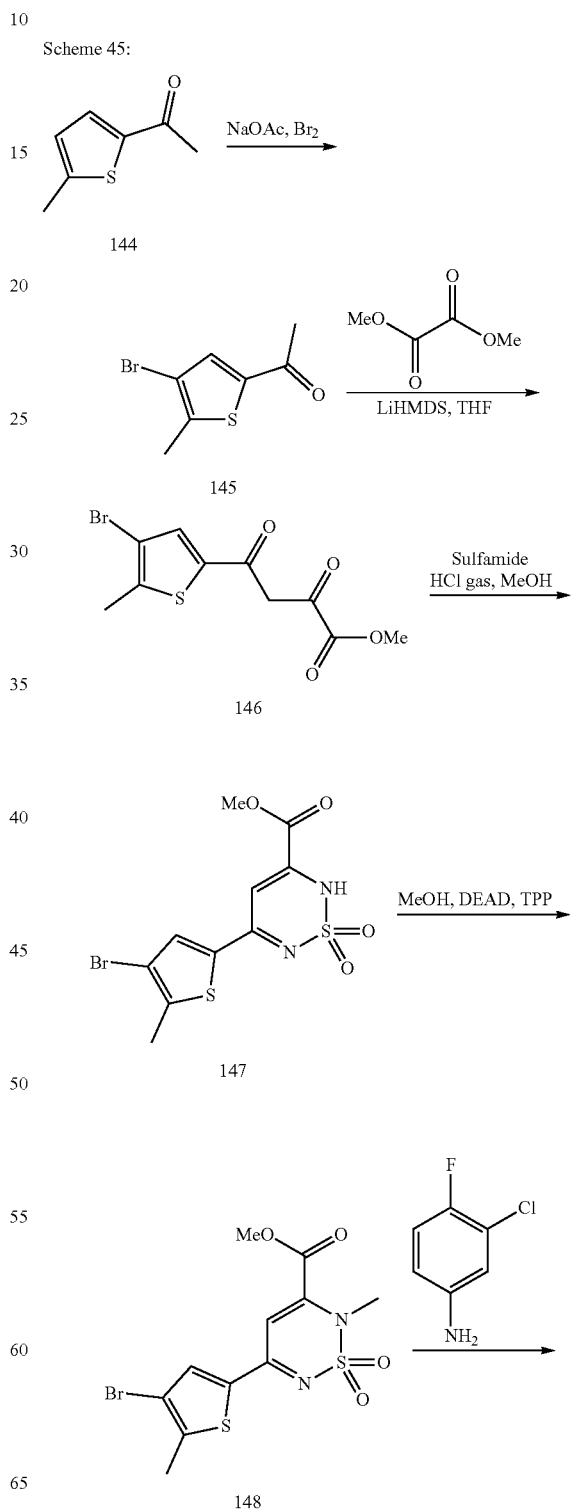

-continued

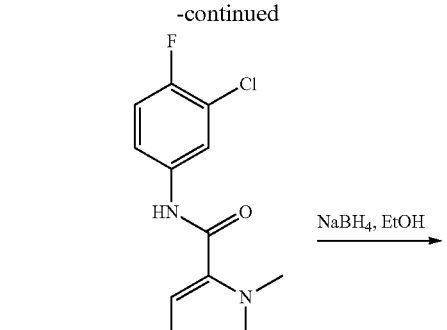

HBV-CSU-304_Int

↓ NaBH₄, EtOH

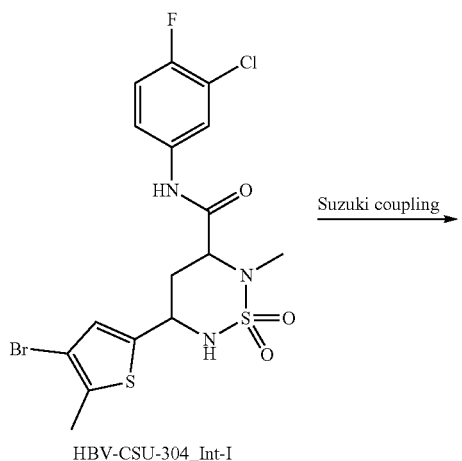

HBV-CSU-304_Int-I

↓ Suzuki coupling

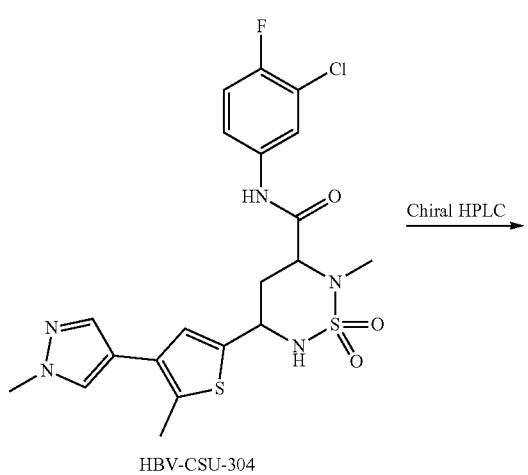

HBV-CSU-304

↓ Chiral HPLC

HBV-CSU-304-ISO-I

+

HBV-CSU-304-ISO-II

Synthesis of 1-(4-bromo-5-methylthiophen-2-yl) ethan-1-one (145)

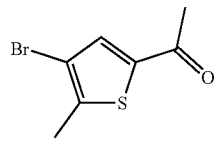

To a stirred solution of compound 144 (5 g, 35.71 mmol) and NaOAc (3.22 g, 39.28 mmol) in water (300 mL), Br₂ (5.7 g, 35.71 mmol) was added drop wise at 0° C. The resulting reaction mixture was stirred at room temperature for 2 h. The progress of the reaction was monitored by TLC and LCMS. After completion, the reaction mixture was cooled to 0° C.; quenched by using aq. Sodium thiosulphate and extracted using ethyl acetate. The combined organic layers were collected, dried over anhydrous sodium sulphate, filtered and concentrated in vacuo to afford the title compound 145 (7.5 g, 96.77%) as a brown solid and used as such for the next step without further purification TLC: 40% EtOAc/hexane ($R_f$: 0.5); ¹H NMR (DMSO-d₆, 400 MHz): δ 7.88 (s, 1H), 2.46 (s, 3H), 2.38 (s, 3H); LCMS Calculated for C7H7BrOS: 217.94; Observed: 218.95 (M+1)⁺.

Synthesis of methyl 4-(4-bromo-5-methylthiophen-2-yl)-2,4-dioxobutanoate (146)

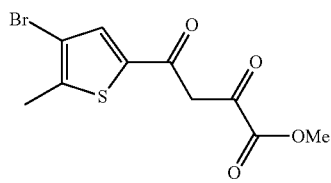 [SMILES: COC(=O)C(=O)CC(=O)c1cc(Br)c(C)s1]

Title compound was synthesized using general method for the synthesis of 2,4-diketoester described above to afford 6 g of compound 146 (57.30%, reaction scale is 7.5 g) as a brown solid. TLC: 40% EtOAc/hexane ($R_f$: 0.3). The crude material was used as such in the next reaction without further characterization.

Synthesis of methyl 5-(4-bromo-5-methylthiophen-2-yl)-2H-1,2,6-thiadiazine-3-carboxylate 1,1-dioxide (147)

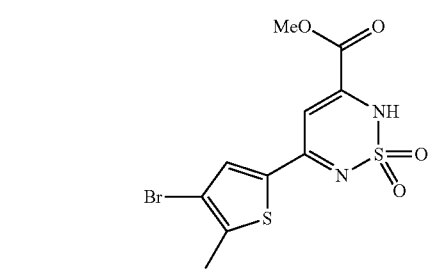 [SMILES: COC(=O)C1=CC(c2cc(Br)c(C)s2)=NS(=O)(=O)N1]

Title compound was synthesized using general method B for the synthesis of cyclic sulfonamide described above to afford 8.9 g of compound 147 (crude, reaction scale is 6 g) as yellow solid. TLC: 40% EtOAc/hexane ($R_f$: 0.2); $^1$H NMR (DMSO-d$_6$, 400 MHz): 8.01 (s, 1H), 6.92 (s, 1H), 3.84 (s, 3H), 2.42 (s, 3H); LCMS Calculated for $C_{10}H_9BrN_2O_4S_2$: 363.92; LCMS observed: 366.95 (M+2)$^+$.

Synthesis of methyl 5-(4-bromo-5-methylthiophen-2-yl)-2-methyl-2H-1,2,6-thiadiazine-3-carboxylate 1,1-dioxide (148)

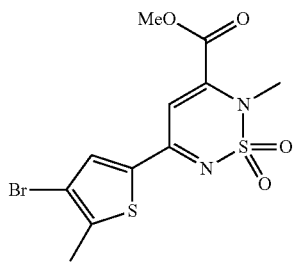 [SMILES: COC(=O)C1=CC(c2cc(Br)c(C)s2)=NS(=O)(=O)N1C]

Title compound was synthesized using general method B for alkylation described above to afford 7 g of compound 148 (79.54%, reaction scale is 8.5 g) as a yellow solid. TLC: 40% EtOAc/hexanes ($R_f$: 0.3); $^1$H NMR (DMSO-d$_6$, 400 MHz): δ 8.30 (s, 1H), 7.34 (s, 1H), 3.93 (s, 3H), 3.51 (s, 3H), 2.47 (s, 3H); LCMS Calculated for $C_{11}H_{11}BrN_2O_4S_2$: 377.93; LCMS observed: 380.95 (M+2)$^+$.

Synthesis of 5-(4-bromo-5-methylthiophen-2-yl)-N-(3-chloro-4-fluorophenyl)-2-methyl-2H-1,2,6-thiadiazine-3-carboxamide 1,1-dioxide (HBV-CSU-304_Int)

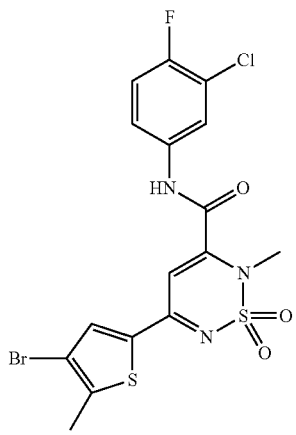

The above titled compound has been synthesized by following the general procedure (Method A) described above for amidation by using corresponding 148 and corresponding amine (see Table 1 for analytical data).

Synthesis of 5-(4-bromo-5-methylthiophen-2-yl)-N-(3-chloro-4-fluorophenyl)-2-methyl-1,2,6-thiadiazinane-3-carboxamide 1,1-dioxide (HBV-CSU-304_Int-I)

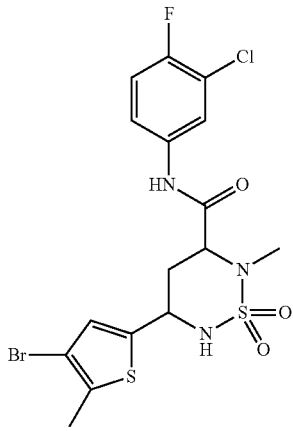 [SMILES: Cc1sc(C2CC(C(=O)Nc3ccc(F)c(Cl)c3)N(C)S(=O)(=O)N2)cc1Br]

The above titled compounds have been synthesized by following the general procedure described above for reduction by using corresponding HBV-CSU-304_Int-I (see Table 2 for analytical data).

Cis-N-(3-Chloro-4-fluorophenyl)-2-methyl-5-(5-methyl-4-(1-methyl-1H-pyrazol-4-yl)thiophen-2-yl)-1,2,6-thiadiazinane-3-carboxamide 1,1-dioxide (HBV-CSU-304, HBV-CSU-304-ISO-I & HBV-CSU-304-ISO-II)

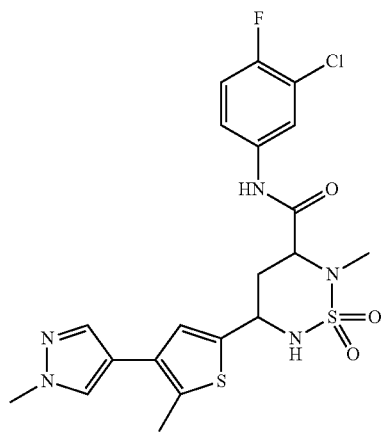

HBV-CSU-304

HBV-CSU-304-ISO-I

HBV-CSU-304-ISO-II

The above titled compounds have been synthesized by following the general procedure described above for Suzuki coupling by using HBV-CSU-304_Int-I and corresponding bromo compound (see Table 2 for analytical data).

Scheme 46

Synthesis of Cis-N-(3-chloro-4-fluorophenyl)-5-(5-ethyl-4-(1-methyl-1H-pyrazol-4-yl)thiophen-2-yl)-2-methyl-1,2,6-thiadiazinane-3-carboxamide 1,1-dioxide (HBV-CSU-305, HBV-CSU-305-ISO-I & HBV-CSU-305-ISO-II) and Cis-5-(4-bromo-5-ethylthiophen-2-yl)-N-(3-chloro-4-fluorophenyl)-2-methyl-1,2,6-thiadiazinane-3-carboxamide 1,1-dioxide (HBV-CSU-334)

Scheme 46:

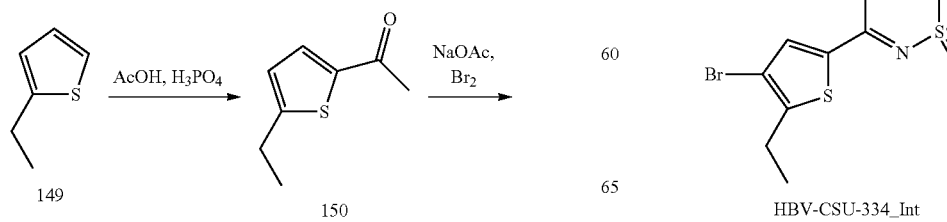

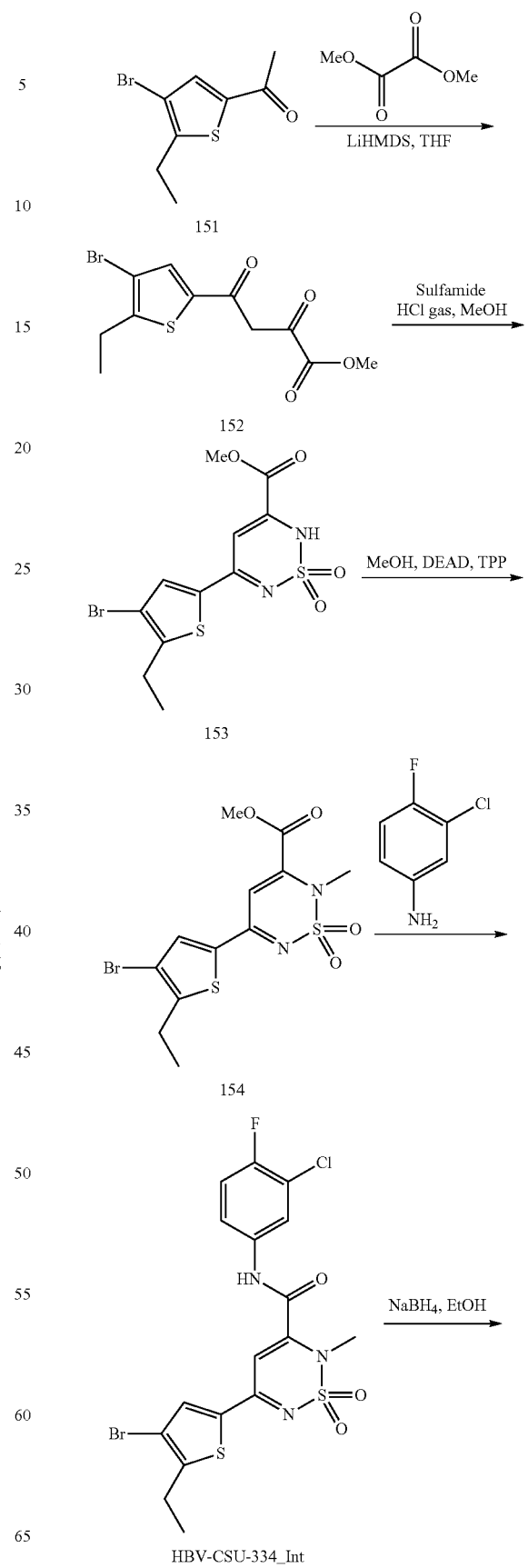

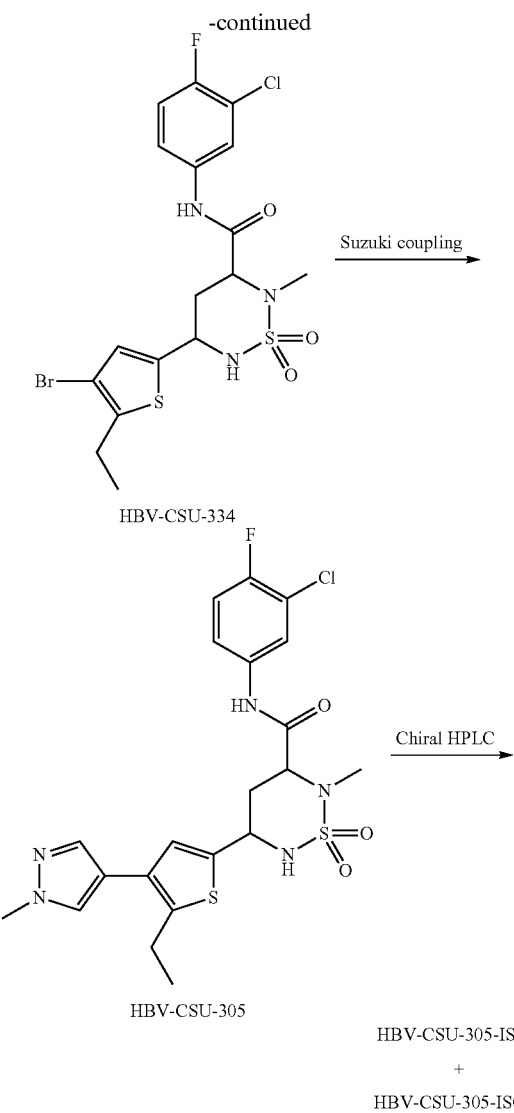

HBV-CSU-334

Suzuki coupling →

HBV-CSU-305

Chiral HPLC →

HBV-CSU-305-ISO-I
+
HBV-CSU-305-ISO-II

Synthesis of 1-(5-ethylthiophen-2-yl)ethan-1-one (150)

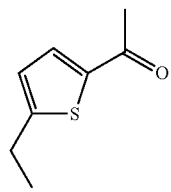

To a stirred solution of compound 149 (10 g, 89.13 mmol) in acetic anhydride (9.27 mL, 98.04 mmol) under inert atmosphere was added H$_3$PO$_4$ (0.464 mL, 8.913 mmol) portion wise at room temperature. The reaction was stirred at 100° C. for 1 h. The reaction was monitored by TLC. After completion of the reaction, the reaction mixture was poured on ice-cold slowly and extracted with ethyl acetate. The combined organic extracts were dried over anhydrous sodium sulfate, filtered and concentrated in vacuo to afford crude compound 150 (12 g, crude) as brown liquid. TLC: 40% EtOAc/hexanes (R$_f$: 0.5). $^1$H-NMR (DMSO-d$_6$, 400 MHz): δ 7.77 (d, J=4.6 Hz, 1H), 6.98 (d, J=3.6 Hz, 1H), 2.88-2.82 (m, 2H), 2.47 (s, 3H), 1.25 (t, J=7.2 Hz, 3H); LCMS Calculated for C$_8$H$_{10}$OS: 154.05; Observed: 155 (M+1)$^+$.

Synthesis of 1-(4-bromo-5-methylthiophen-2-yl)ethan-1-one (151)

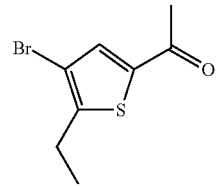

To a stirred solution of compound 150 (14 g, 90.90 mmol) and NaOAc (8.20 g, 99.99 mmol) in water (100 mL), Br$_2$ (4.69 mL, 90.90 mmol) was added drop wise at 0° C. The resulting reaction mixture was stirred at room temperature for 2 h. The progress of the reaction was monitored by TLC and LCMS. After completion, the reaction mixture was cooled to 0° C.; quenched by using aq. Sodium thiosulphate and extracted using ethyl acetate. The combined organic layers were collected, dried over anhydrous sodium sulphate, filtered and concentrated in vacuo to afford the title compound 151 (24 g, crude) as a brown sticky solid and used as such for the next step without further purification TLC: 40% EtOAc/hexane (R$_f$: 0.6); $^1$H-NMR (DMSO-d$_6$, 400 MHz): δ 7.90 (s, 1H), 2.81-2.73 (m, 5H), 1.21-1.15 (m, 3H); LCMS Calculated for C$_8$H$_9$BrOS: 231.96; Observed: 232.90 (M+1)$^+$.

Synthesis of methyl 4-(4-bromo-5-ethylthiophen-2-yl)-2,4-dioxobutanoate (152)

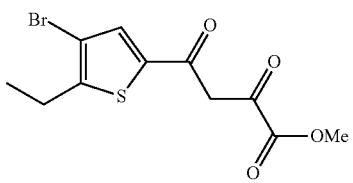 [SMILES: CCc1sc(C(=O)CC(=O)C(=O)OC)cc1Br]

Title compound was synthesized using general method for the synthesis of 2,4-diketoester described above to afford 12 g of compound 152 (crude, reaction scale is 24 g) as a light yellow solid. TLC: 40% EtOAc/hexane (R$_f$: 0.2). The crude material was used as such in the next reaction without further characterization.

447

Synthesis of methyl 5-(4-bromo-5-ethylthiophen-2-yl)-2H-1,2,6-thiadiazine-3-carboxylate 1,1-dioxide (153)

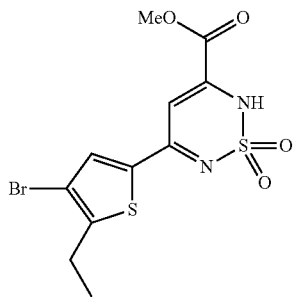 [SMILES: CCc1sc(C2=NS(=O)(=O)NC(C(=O)OC)=C2)cc1Br]

Title compound was synthesized using general method B for the synthesis of cyclic sulfonamide described above to afford 12 g of compound 153 (crude, reaction scale is 12 g) as a brown sticky solid. TLC: 40% EtOAc/hexane ($R_f$: 0.2); $^1$H NMR (DMSO-$d_6$, 400 MHz): 8.03 (s, 1H), 6.94 (s, 1H), 6.32 (br.s, 1H), 3.85 (s, 3H), 2.83-2.81 (m, 2H), 1.24 (t, J=7.2 Hz, 3H); LCMS Calculated for $C_{11}H_{11}BrN_2O_4S_2$: 377.93; LCMS observed: 380.90 $(M+2)^+$.

Synthesis of methyl 5-(4-bromo-5-ethylthiophen-2-yl)-2-methyl-2H-1,2,6-thiadiazine-3-carboxylate 1,1-dioxide (154)

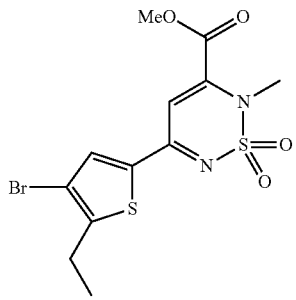 [SMILES: CCc1sc(C2=NS(=O)(=O)N(C)C(C(=O)OC)=C2)cc1Br]

Title compound was synthesized using general method B for alkylation described above to afford 7.6 g of compound 154 (61.09%, reaction scale is 12 g) as a yellow solid. TLC: 40% EtOAc/hexanes ($R_f$: 0.4); $^1$H NMR (DMSO-$d_6$, 400 MHz): 8.31 (s, 1H), 7.35 (s, 1H), 3.94 (s, 3H), 3.51 (s, 3H), 2.87-2.81 (m, 2H), 1.24 (t, J=7.2 Hz, 3H), LCMS Calculated for $C_{12}H_{13}BrN_2O_4S_2$: 391.95; LCMS observed: 395 $(M+2)^+$.

448

Synthesis of 5-(4-bromo-5-ethylthiophen-2-yl)-N-(3-chloro-4-fluorophenyl)-2-methyl-2H-1,2,6-thiadiazine-3-carboxamide 1,1-dioxide (HBV-CSU-334_Int)

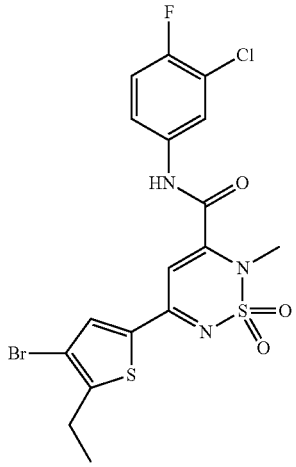 [SMILES: CCc1sc(C2=NS(=O)(=O)N(C)C(C(=O)Nc3ccc(F)c(Cl)c3)=C2)cc1Br]

The above titled compound has been synthesized by following the general procedure (Method B) described above for amidation by using corresponding 154 and corresponding amine (see Table 1 for analytical data).

Synthesis of 5-(4-bromo-5-ethylthiophen-2-yl)-N-(3-chloro-4-fluorophenyl)-2-methyl-1,2,6-thiadiazinane-3-carboxamide 1,1-dioxide (HBV-CSU-334)

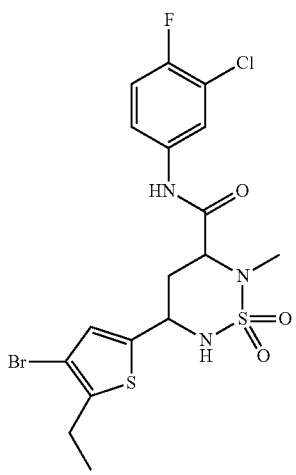 [SMILES: CCc1sc(C2CC(C(=O)Nc3ccc(F)c(Cl)c3)N(C)S(=O)(=O)N2)cc1Br]

The above titled compounds have been synthesized by following the general procedure described above for reduction by using corresponding HBV-CSU-334_Int-I (see Table 2 for analytical data).

449

Cis-N-(3-Chloro-4-fluorophenyl)-5-(5-ethyl-4-(1-methyl-1H-pyrazol-4-yl)thiophen-2-yl)-2-methyl-1,2,6-thiadiazinane-3-carboxamide 1,1-dioxide (HBV-CSU-305, HBV-CSU-305-ISO-I & HBV-CSU-305-ISO-II)

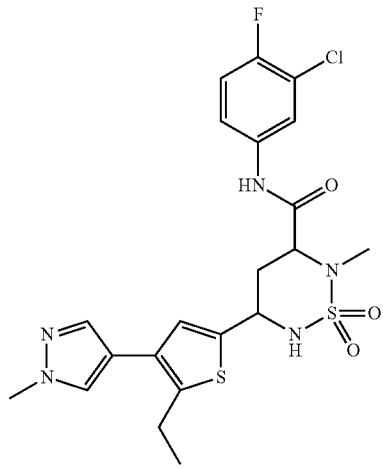

HBV-CSU-305

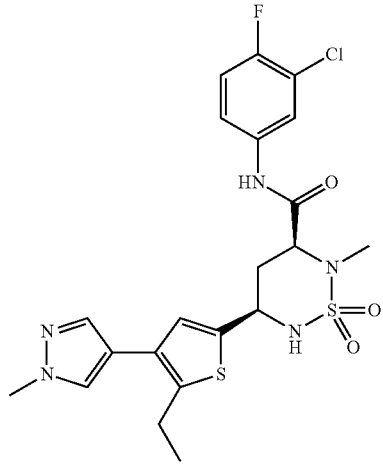

HBV-CSU-305-ISO-I

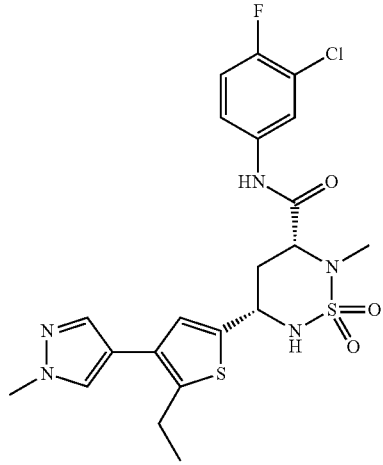

HBV-CSU-305-ISO-II

The above titled compounds have been synthesized by following the general procedure described above for Suzuki coupling by using HBV-CSU-334 and corresponding bromo compound (see Table 2 for analytical data).

450

Scheme 47

Synthesis of 5-(5-chloro-4-(1-methyl-1H-pyrazol-4-yl)thiophen-2-yl)-N-(3-chloro-4-fluorophenyl)-2-methyl-1,2,6-thiadiazinane-3-carboxamide 1,1-dioxide (HBV-CSU-306, HBV-CSU-306-ISO-I & HBV-CSU-306-ISO-II) and 5-(4-bromo-5-chlorothiophen-2-yl)-N-(3-chloro-4-fluorophenyl)-2-methyl-1,2,6-thiadiazinane-3-carboxamide 1,1-dioxide (HBV-CSU-330)

Scheme 47:

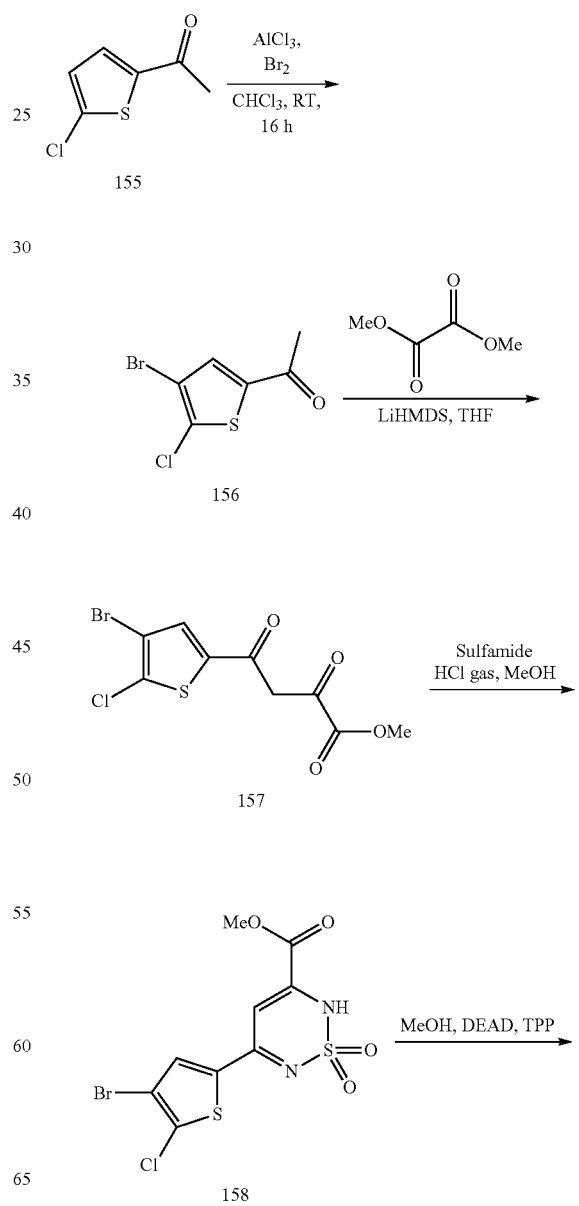

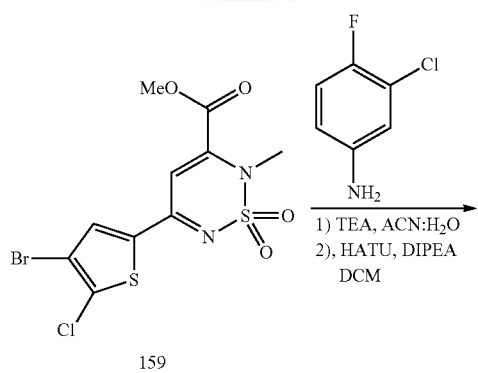

159

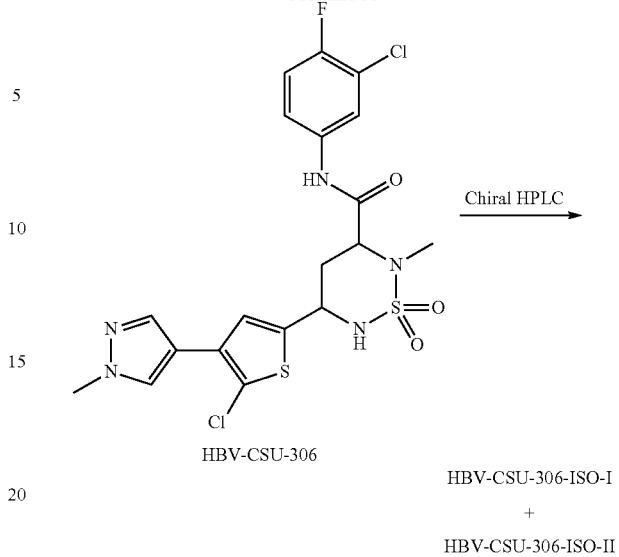

HBV-CSU-306

HBV-CSU-306-ISO-I
+
HBV-CSU-306-ISO-II

Synthesis of 1-(4-bromo-5-chlorothiophen-2-yl)ethan-1-one (156)

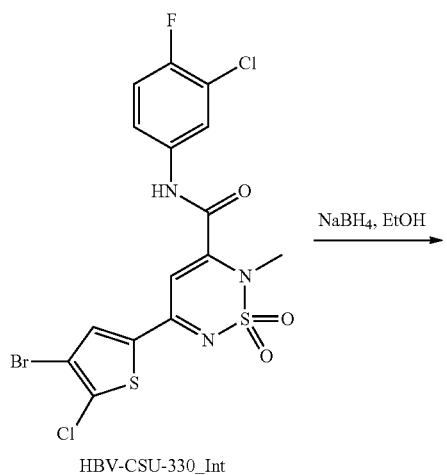

HBV-CSU-330_Int

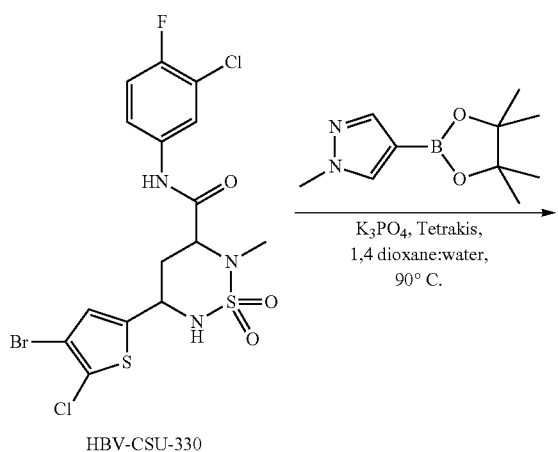

HBV-CSU-330

To a stirred solution of compound 155 (20 g, 124.51 mmol) in $CHCl_3$ (300 mL) at 0° C., $AlCl_3$ (48.14 g, 361.07 mmol) was added and stirred at same temperature for 10 min. To this solution, $Br_2$ (7.06 mL, 136.96 mmol) was added drop wise at 0° C. The resulting reaction mixture was stirred room temperature for 16 h. The progress of the reaction was monitored by TLC and LCMS. After completion, the reaction mixture was cooled to 0° C.; quenched by using aq. Sodium thiosulphate and extracted with ethyl acetate. The combined organic layers were collected, dried over anhydrous sodium sulphate and concentrated in vacuo to afford the title compound 156 (25 g, crude) as a yellow colored liquid and used as such for the next step without further purification. TLC: 40% EtOAc/hexane ($R_f$: 0.6); $^1H$ NMR (DMSO-$d_6$, 400 MHz): δ 7.50 (s, 1H), 2.51 (s, 3H).

Synthesis of methyl 4-(4-bromo-5-chlorothiophen-2-yl)-2,4-dioxobutanoate (157)

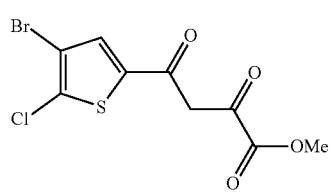 [SMILES: COC(=O)C(=O)CC(=O)c1cc(Br)c(Cl)s1]

Title compound was synthesized using general method for the synthesis of 2,4-diketoester described above to afford 22 g of compound 157 (crude, reaction scale is 32 g) as a brown colored liquid. TLC: 40% EtOAc/hexane ($R_f$: 0.3). The crude material was used as such in the next reaction without further characterization.

Synthesis of methyl 5-(4-bromo-5-chlorothiophen-2-yl)-2H-1,2,6-thiadiazine-3-carboxylate 1,1-dioxide (158)

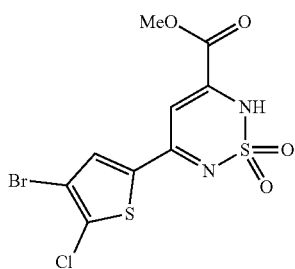

Title compound was synthesized using general method B for the synthesis of cyclic sulfonamide described above to afford 20 g of compound 158 (crude, reaction scale is 22 g) as light black solid. TLC: 40% EtOAc/hexane ($R_f$: 0.2); $^1$H NMR (DMSO-$d_6$, 400 MHz): δ 8.00 (s, 1H), 6.75 (s, 1H), 3.81 (s, 3H).

Synthesis of methyl 5-(4-bromo-5-chlorothiophen-2-yl)-2-methyl-2H-1,2,6-thiadiazine-3-carboxylate 1,1-dioxide (159)

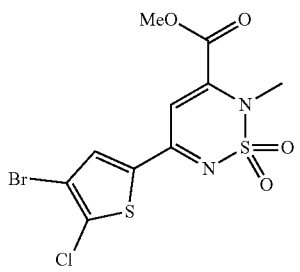 [SMILES: COC(=O)C1=CC(c2cc(Br)c(Cl)s2)=NS(=O)(=O)N1C]

Title compound was synthesized using general method B for alkylation described above to afford 10 g of compound 159 (96%, reaction scale is 10 g) as a yellow solid. TLC: 40% EtOAc/hexanes ($R_f$: 0.4); $^1$H NMR (DMSO-$d_6$, 400 MHz): δ 8.46 (s 1H), 7.39 (s, 1H), 3.94 (s, 3H), 3.53 (s, 3H); LCMS Calculated for $C_{10}H_8BrClN_2O_4S_2$: 397.88; LCMS observed: 400.90 (M+2)$^+$.

Synthesis of 5-(4-bromo-5-chlorothiophen-2-yl)-N-(3-chloro-4-fluorophenyl)-2-methyl-2H-1,2,6-thiadiazine-3-carboxamide 1,1-dioxide (HBV-CSU-330_Int)

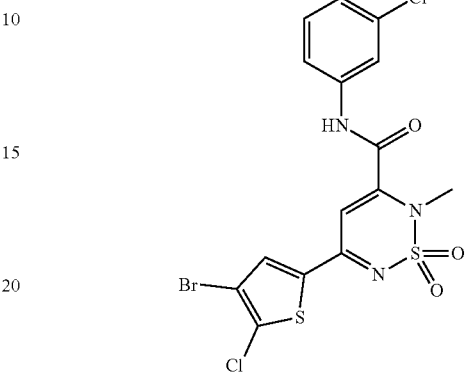

The above titled compound has been synthesized by following the general procedure (Method A) described above for amidation by using corresponding 159 and corresponding amine (see Table 1 for analytical data).

Cis-5-(4-bromo-5-chlorothiophen-2-yl)-N-(3-chloro-4-fluorophenyl)-2-methyl-1,2,6-thiadiazinane-3-carboxamide 1,1-dioxide (HBV-CSU-330)

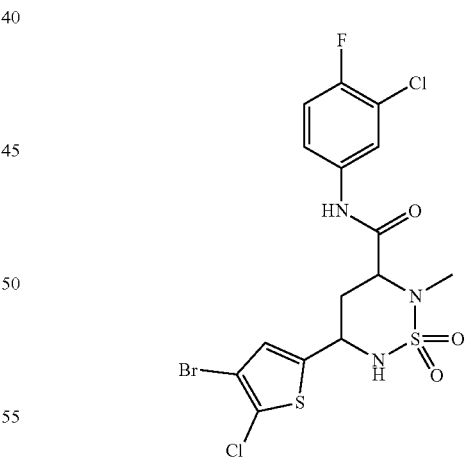

The above titled compounds have been synthesized by following the general procedure described above for reduction by using corresponding HBV-CSU-330_Int-I (see Table 2 for analytical data).

455

Cis-5-(5-chloro-4-(1-methyl-1-pyrazol-4-yl)thiophen-2-yl)-N-(3-chloro-4-fluorophenyl)-2-methyl-1,2,6-thiadiazinane-3-carboxamide 1,1-dioxide (HBV-CSU-306, HBV-CSU-306-ISO-I & HBV-CSU-306-ISO-II)

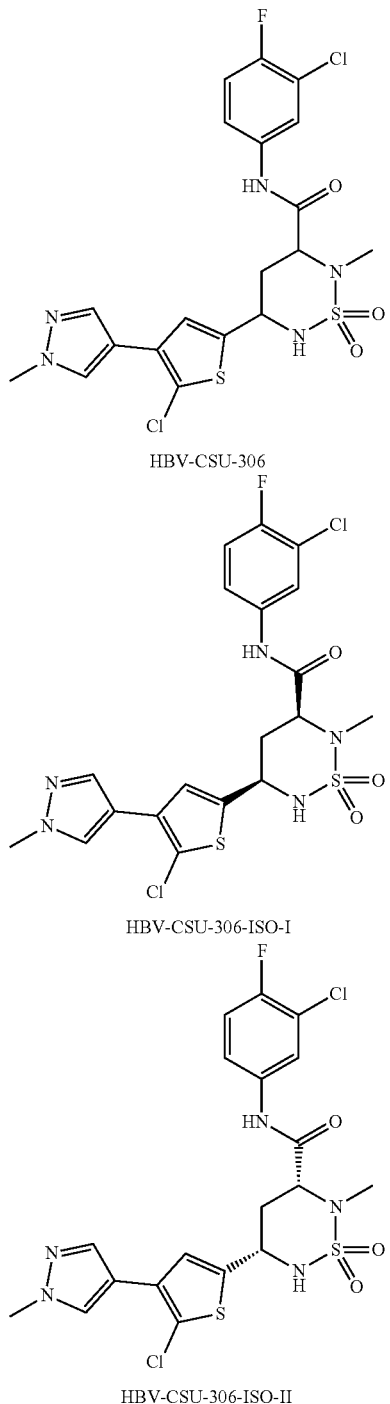

HBV-CSU-306

HBV-CSU-306-ISO-I

HBV-CSU-306-ISO-II

The above titled compounds have been synthesized by following the general procedure described above for Suzuki coupling by using HBV-CSU-330 and corresponding bromo compound (see Table 2 for analytical data).

456

Scheme 48

Synthesis of Cis-N-(3-chloro-4-fluorophenyl)-2-methyl-5-(5-(4-methyl-4H-1,2,4-triazol-3-yl)thiophen-2-yl)-1,2,6-thiadiazinane-3-carboxamide 1,1-dioxide (HBV-CSU-324, HBV-CSU-324-ISO-I & HBV-CSU-324-ISO-II)

Scheme 48:

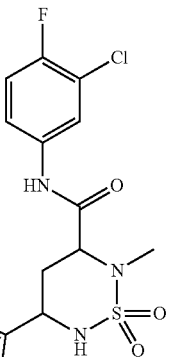

HBV-CSU-114

Pd(OAc)$_2$, dppf, TEA
CO (150 psi) MeOH,
CH$_3$CN, 100° C.

→

160

LiOH, THF, Water
RT, 2 h

→

161

EDC—HCl, HOBt, DMF,
RT, 12 h

→

-continued

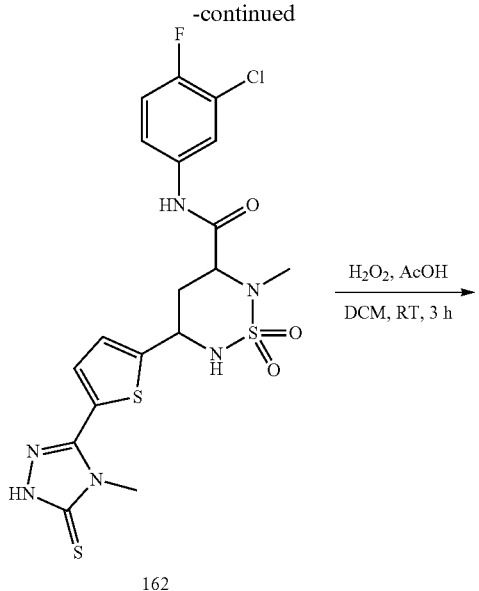

162

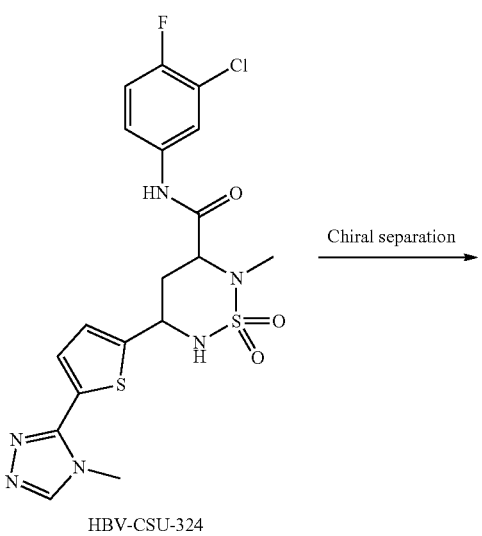

HBV-CSU-324

Chiral separation →

HBV-CSU-324-ISO-I
+
HBV-CSU-324-ISO-II

H₂O₂, AcOH
DCM, RT, 3 h →

Synthesis of methyl 5-(5-((3-chloro-4-fluorophenyl)carbamoyl)-6-methyl-1,1-dioxido-1,2,6-thiadiazinan-3-yl)thiophene-2-carboxylate (160)

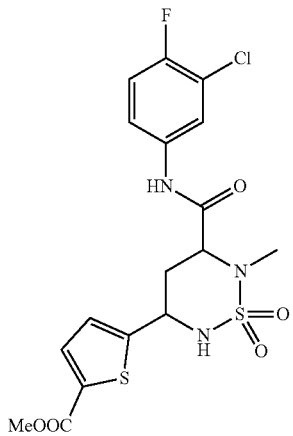 [SMILES: COC(=O)c1ccc(C2CC(C(=O)Nc3ccc(F)c(Cl)c3)N(C)S(=O)(=O)N2)s1]

To a stirred solution of compound HBV-CSU-114 (5 g, 10.33 mmol) in MeOH:ACN (50 mL:12.5 mL) mixture under Ar atmosphere in an autoclave, TEA (3.13 g, 30.99 mmol) and dppf (0.57 g, 1.03 mmol) were added and purged with Ar for 15 min. To this, Pd(OAc)$_2$ (0.231 g, 1.03 mmol) was added and again purged with carbon monoxide and the resulting reaction mixture was heated in autoclave at 100° C. for 150 psi pressure for 6 h. The progress of the reaction was monitored by TLC. After completion, the reaction mixture was filtered through a pad of Celite and filtrate was concentrated in vacuo. The residue obtained was diluted with water and extracted using ethyl acetate. The combined organic layers were dried over anhydrous sodium sulfate, filtered and concentrated in vacuo to obtain the crude. The crude was purified through silica gel column chromatography using 30% EtOAc/hexane to afford the title compound 160 (2.5 g, 51.02%) as a brown solid. TLC: 40% EtOAc/hexane (R$_f$: 0.3); $^1$H-NMR (DMSO-d$_6$, 400 MHz): δ 10.60 (s, 1H), 7.98-7.96 (m, 1H), 7.84-7.81 (m, 1H), 7.71 (d, J=4 Hz, 1H), 7.57-7.53 (m, 1H), 7.41 (t, J=9.2 Hz, 1H), 7.25 (d, J=4 Hz, 1H), 4.88-4.83 (m, 1H), 4.33-4.30 (m, 1H), 3.82 (s, 3H), 2.62 (s, 3H), 2.30-1.98 (m, 2H). LCMS Calculated for C$_{17}$H$_{17}$ClFN$_3$O$_5$S$_2$: 461.03; LCMS observed: 462.15 (M+1)$^+$.

Synthesis of 5-(5-((3-chloro-4-fluorophenyl)carbamoyl)-6-methyl-1,1-dioxido-1,2,6-thiadiazinan-3-yl)thiophene-2-carboxylic acid (161)

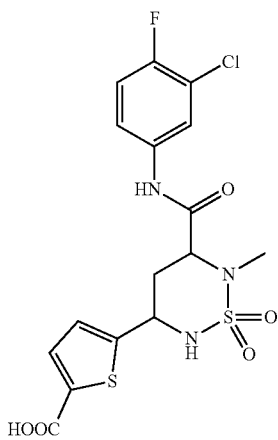 [SMILES: CN1C(C(=O)Nc2ccc(F)c(Cl)c2)CC(c2ccc(C(=O)O)s2)NS1(=O)=O]

To a stirred solution of compound 160 (1 g, 2.10 mmol) in THF (15 mL), aq. LiOH (0.22 g, 5.26 mmol, dissolved in 15 mL water) was added. The resulting reaction mixture was stirred at room temperature for 2 h. The reaction was monitored by TLC. After completion of the reaction, the volatiles were removed in vacuo. The residue was diluted with water and acidified with 2 N HCl to pH-2 and extracted with ethyl acetate. The combined organic extracts were dried over anhydrous sodium sulfate, filtered and concentrated in vacuo to afford compound 161 (0.6 g, 61.8%) as a white solid. TLC: 50% EtOAc/hexanes ($R_f$: 0.1); LCMS Calculated for $C_{16}H_{15}ClFN_3O_5S_2$: 447.01; LCMS observed: 448.05 $(M+1)^+$.

Synthesis of N-(3-chloro-4-fluorophenyl)-2-methyl-5-(5-(4-methyl-5-thioxo-4,5-dihydro-1H-1,2,4-triazol-3-yl)thiophen-2-yl)-1,2,6-thiadiazinane-3-carboxamide 1,1-dioxide (162)

To a stirred solution compound 161 (0.6 g, 1.34 mmol) and N-methylhydrazinecarbothioamide (0.155 g, 1.47 mmol) in DMF (15 mL) under inert atmosphere, EDCI.HCl (38.06 g, 199.26 mmol) and HOBt (26.9 g, 199.25 mmol) were added. The reaction mixture was stirred at room temperature for 18 h. The reaction was monitored by TLC. After completion of the reaction, the reaction mixture was diluted with water and extracted with ethyl acetate. The combined organic extracts were dried over anhydrous sodium sulfate, filtered and concentrated in vacuo to obtain 0.71 g of crude compound which was used in the next step. The crude compound was dissolved in 5% NaOH solution and heated at 60° C. for 16 h. After completion, the reaction mixture was cooled to at 0° C.; acidified with 1 N HCl to pH~6 and extracted with ethyl acetate. The combined organic extracts were dried over anhydrous sodium sulfate, filtered and concentrated in vacuo to afford the crude. The crude compound was purified by silica gel column chromatography using 50% EtOAc/hexanes to afford compound 162 (0.21 g, 27%) as an off white solid. TLC: 80% EtOAc/hexanes ($R_f$: 0.7);

$^1$H-NMR (DMSO-$d_6$, 400 MHz): δ 13.98 (s, 1H), 10.62 (s, 1H), 7.99-7.97 (m, 1H), 7.85-7.83 (m, 1H), 7.64-7.54 (m, 2H), 7.41 (t, J=8.8 Hz, 1H), 7.30-7.29 (m, 1H), 4.90-4.85 (m, 1H), 4.35-4.32 (m, 1H), 3.67 (s, 3H), 2.63 (s, 3H), 2.33-1.99 (m, 2H). LCMS Calculated for $C_{18}H_{18}ClFN_6O_3S_3$: 516.03; LCMS observed: 517.05 $(M+1)^+$.

Cis-N-(3-Chloro-4-fluorophenyl)-2-methyl-5-(5-(4-methyl-4H-1,2,4-triazol-3-yl)thiophen-2-yl)-1,2,6-thiadiazinane-3-carboxamide 1,1-dioxide (HBV-CSU-324, HBV-CSU-324-ISO-I & HBV-CSU-324-ISO-II)

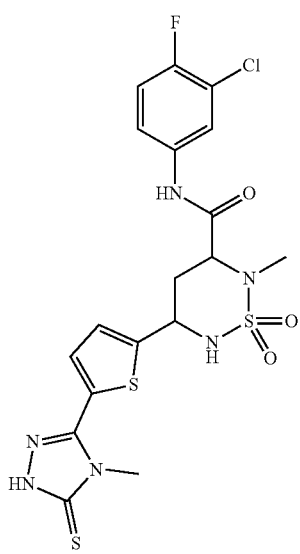 [SMILES: CN1C(C(=O)Nc2ccc(F)c(Cl)c2)CC(c2ccc(-c3n[nH]c(=S)n3C)s2)NS1(=O)=O]

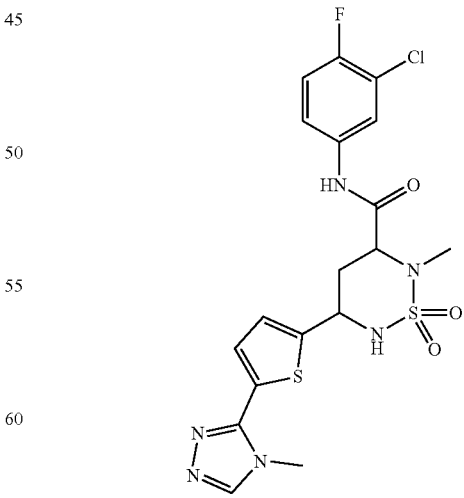

HBV-CSU-324

461

-continued

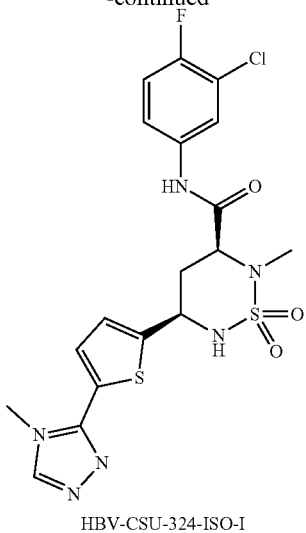

HBV-CSU-324-ISO-I

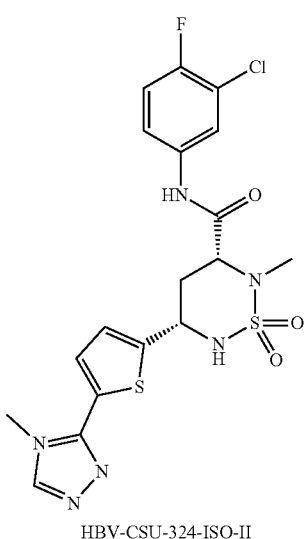

HBV-CSU-324-ISO-II

To a stirred solution compound 162 (0.2 g, 0.387 mmol) in DCM (2 mL) at 0° C., $H_2O_2$ (0.028 g, 0.85 mmol) and acetic acid (0.5 mL) were added. The reaction mixture was stirred at room temperature for 3 h. The reaction was monitored by TLC. After completion of the reaction, the reaction mixture was basified with 2N NaOH to pH-10 and extracted with DCM. The combined organic extracts were dried over anhydrous sodium sulfate, filtered and concentrated in vacuo to afford the crude. The crude compound was purified by silica gel column chromatography using 50% EtOAc/hexanes to afford compound HBV-CSU-324 (0.11 g, 59%) as a white solid. TLC: 80% EtOAc/hexanes ($R_f$: 0.2); (see Table 2 for analytical data).

462

Scheme 49

Synthesis of N-(3-Chloro-4-fluorophenyl)-2-methyl-5-(4-(4-methyl-4H-1,2,4-triazol-3-yl)thiophen-2-yl)-1,2,6-thiadiazinane-3-carboxamide 1,1-dioxide (HBV-CSU-328, HBV-CSU-328-ISO-I & HBV-CSU-328-ISO-II)

Scheme 49:

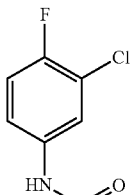

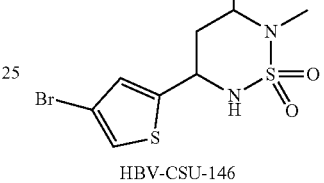

HBV-CSU-146

$\xrightarrow{\text{Pd(OAc)}_2\text{, dppf, TEA} \\ \text{CO (150 psi) MeOH,} \\ \text{CH}_3\text{CN, 100° C.}}$

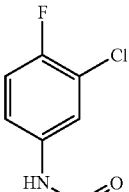

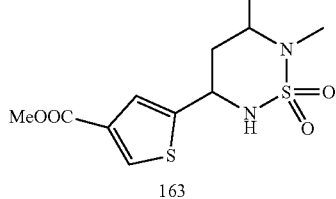

163

$\xrightarrow{\text{LiOH, THF, Water} \\ \text{RT, 2 h}}$

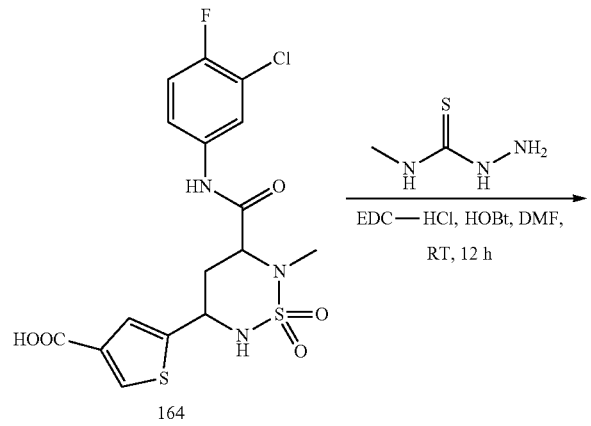

164

$\xrightarrow{\text{EDC—HCl, HOBt, DMF,} \\ \text{RT, 12 h}}$

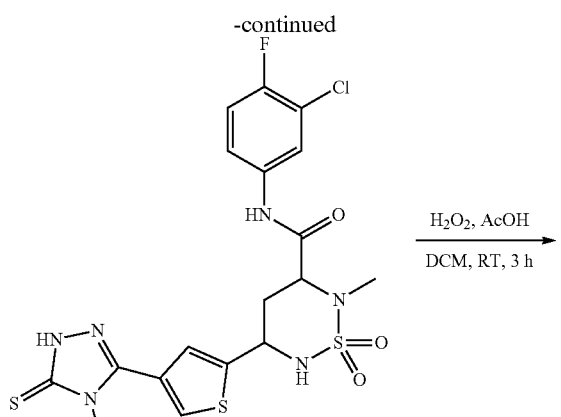

165

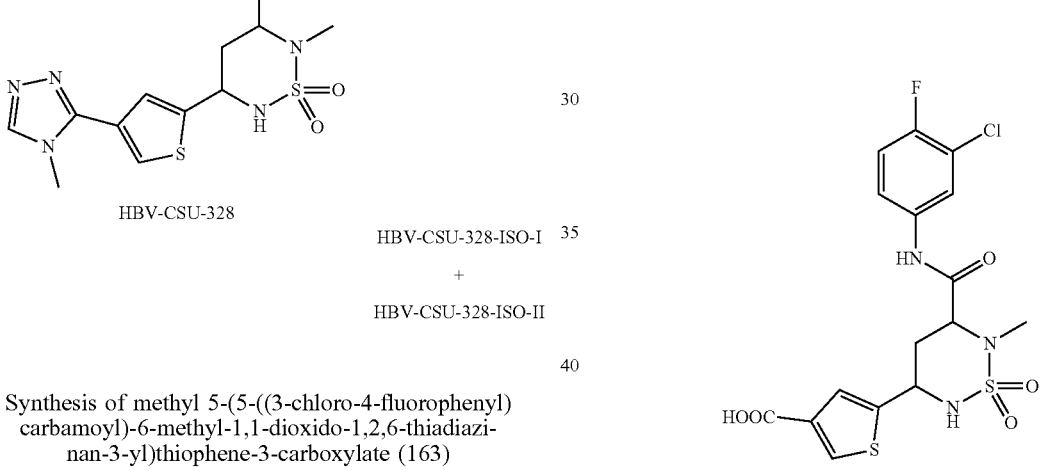

HBV-CSU-328

HBV-CSU-328-ISO-I
+
HBV-CSU-328-ISO-II

Synthesis of methyl 5-(5-((3-chloro-4-fluorophenyl)carbamoyl)-6-methyl-1,1-dioxido-1,2,6-thiadiazinan-3-yl)thiophene-3-carboxylate (163)

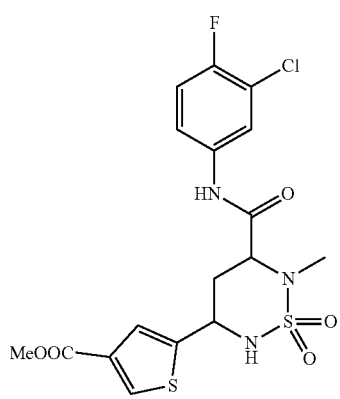 [SMILES: COC(=O)c1csc(C2CC(C(=O)Nc3ccc(F)c(Cl)c3)N(C)S(=O)(=O)N2)c1]

To a stirred solution of compound HBV-CSU-146 (5 g, 10.33 mmol) in MeOH:ACN (50 mL:12.5 mL) mixture under Ar atmosphere in an autoclave, TEA (3.13 g, 30.99 mmol) and dppf (0.57 g, 1.03 mmol) were added and purged with Ar for 15 min. To this, Pd(OAc)$_2$ (0.231 g, 1.03 mmol) was added and again purged with carbon monoxide and the resulting reaction mixture was heated in autoclave at 100° C. for 150 psi pressure for 6 h. The progress of the reaction was monitored by TLC. After completion, the reaction mixture was filtered through a pad of Celite and filtrate was concentrated in vacuo. The residue obtained was diluted with water and extracted using ethyl acetate. The combined organic layers were dried over anhydrous sodium sulfate, filtered and concentrated in vacuo to obtain the crude. The crude was purified through silica gel column chromatography using 30% EtOAc/hexane to afford the title compound 163 (3 g, 63.8%) as a brown solid. TLC: 40% EtOAc/hexane (R$_f$: 0.2); $^1$H-NMR (DMSO-d$_6$, 400 MHz): δ 10.57 (s, 1H), 8.37 (s, 1H), 7.97-7.95 (m, 1H), 7.75-7.72 (m, 1H), 7.57-7.53 (m, 1H), 7.46 (s, 1H), 7.40 (t, J=8.8 Hz, 1H), 4.83-4.77 (m, 1H), 4.32-4.28 (m, 1H), 3.78 (s, 3H), 2.63 (s, 3H), 2.30-2.27 (m, 1H), 2.16-1.97 (m, 1H); LCMS Calculated for C$_{17}$H$_{17}$ClFN$_3$O$_5$S$_2$: 461.03; LCMS observed: 462 (M+1)$^+$.

Synthesis of 5-(5-((3-chloro-4-fluorophenyl)carbamoyl)-6-methyl-1,1-dioxido-1,2,6-thiadiazinan-3-yl)thiophene-3-carboxylic acid (164)

To a stirred solution of compound 163 (1 g, 2.16 mmol) in THF (10 mL), aq. LiOH (0.18 g, 5.4 mmol, dissolved in 10 mL water) was added. The resulting reaction mixture was stirred at room temperature for 2 h. The reaction was monitored by TLC. After completion of the reaction, the volatiles were removed in vacuo. The residue was diluted with water and acidified with 2 N HCl to pH-2 and extracted with ethyl acetate. The combined organic extracts were dried over anhydrous sodium sulfate, filtered and concentrated in vacuo to afford compound 164 (0.9 g, 93.7%) as a white solid. TLC: 40% EtOAc/hexanes (R$_f$: 0.1); LCMS Calculated for C$_{16}$H$_{15}$ClFN$_3$O$_5$S$_2$: 447.01; LCMS observed: 448 (M+1)$^+$.

465

Synthesis of N-(3-chloro-4-fluorophenyl)-2-methyl-5-(4-(4-methyl-5-thioxo-4,5-dihydro-1H-1,2,4-triazol-3-yl)thiophen-2-yl)-1,2,6-thiadiazinane-3-carboxamide 1,1-dioxide (165)

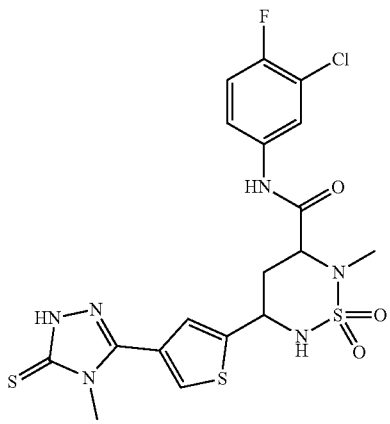 [SMILES: CN1C(C(=O)Nc2ccc(F)c(Cl)c2)CC(c2cc(-c3n[nH]c(=S)n3C)cs2)NS1(=O)=O]

To a stirred solution compound 164 (0.9 g, 2.01 mmol) and N-methylhydrazinecarbothioamide (0.22 g, 2.21 mmol) in DMF (10 mL) under inert atmosphere, EDCI.HCl (0.41 g, 2.21 mmol) and HOBt (0.28 g, 2.21 mmol) were added. The reaction mixture was stirred at room temperature for 18 h. The reaction was monitored by TLC. After completion of the reaction, the reaction mixture was diluted with water and extracted with ethyl acetate. The combined organic extracts were dried over anhydrous sodium sulfate, filtered and concentrated in vacuo to obtain crude compound which was used in the next step. The crude compound was dissolved in 5% NaOH solution and heated at 60° C. for 16 h. After completion, the reaction mixture was cooled to at 0° C.; acidified with 1 N HCl to pH~6 and extracted with ethyl acetate. The combined organic extracts were dried over anhydrous sodium sulfate, filtered and concentrated in vacuo to afford the crude. The crude compound was purified by silica gel column chromatography using 20% EtOAc/hexanes to afford compound 165 (0.2 g, 18.18%) as an off white solid. TLC: 70% EtOAc/hexanes ($R_f$: 0.7);

LCMS Calculated for $C_{18}H_{18}ClFN_6O_3S_3$: 516.03; LCMS observed: 517 (M+1)$^+$.

Cis-N-(3-chloro-4-fluorophenyl)-2-methyl-5-(4-(4-methyl-4H-1,2,4-triazol-3-yl)thiophen-2-yl)-1,2,6-thiadiazinane-3-carboxamide 1,1-dioxide (HBV-CSU-328, HBV-CSU-328-ISO-I & HBV-CSU-328-ISO-II)

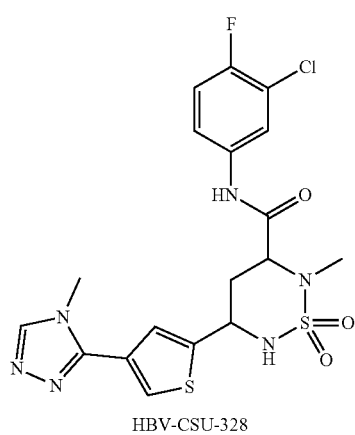

HBV-CSU-328

466

-continued

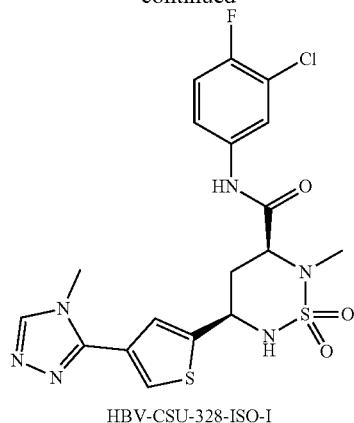

HBV-CSU-328-ISO-I

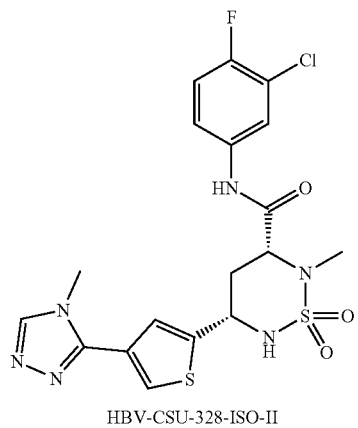

HBV-CSU-328-ISO-II

To a stirred solution compound 165 (0.2 g, 0.387 mmol) in DCM (10 mL) at 0° C., $H_2O_2$ (0.029 g, 0.85 mmol) and acetic acid (0.5 mL) were added. The reaction mixture was stirred at room temperature for 3 h. The reaction was monitored by TLC. After completion of the reaction, the reaction mixture was basified with 2N NaOH to pH-10 and extracted with DCM. The combined organic extracts were dried over anhydrous sodium sulfate, filtered and concentrated in vacuo to afford the crude. The crude compound was purified by silica gel column chromatography using 50% EtOAc/hexanes to afford compound HBV-CSU-328 (0.1 g, 53.9%) as an off white solid. TLC: 5% MeOH/DCM ($R_f$: 0.1); (see Table 2 for analytical data).

Scheme 50

Synthesis of 5-(5-(1H-imidazol-4-yl)thiophen-2-yl)-N-(3-chloro-4-fluorophenyl)-2-methyl-1,2,6-thiadiazinane-3-carboxamide 1,1-dioxide (HBV-CSU-331-ISO-I & HBV-CSU-331-ISO-II)

Scheme 50:

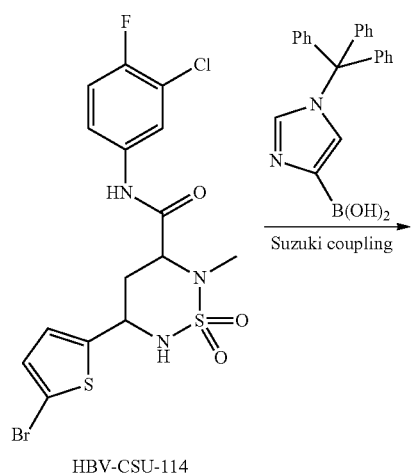

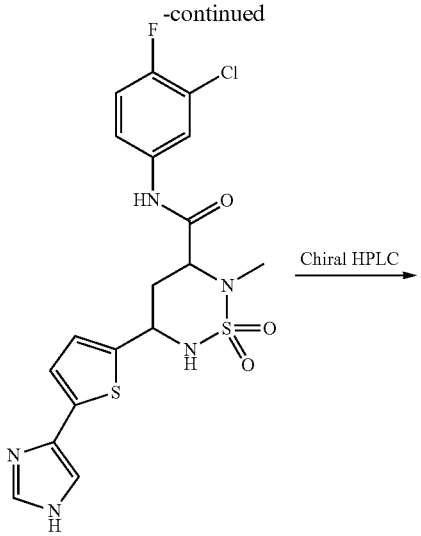

Synthesis of N-(3-chloro-4-fluorophenyl)-2-methyl-5-(5-(1-trityl-1H-imidazol-4-yl)thiophen-2-yl)-1,2,6-thiadiazinane-3-carboxamide 1,1-dioxide (166)

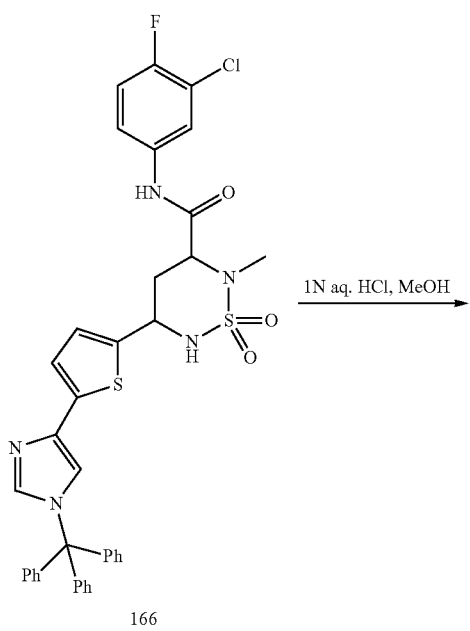

The above titled compounds have been synthesized by following the general procedure described above for Suzuki coupling by using HBV-CSU-114 and (1-trityl-1H-imidazol-4-yl)boronic acid to afford compound 166 (0.75 g, 34.69%). TLC: 50% EtOAc/Hexane ($R_f$: 0.3); New spot isolated after column purification and used as such in the next reaction without characterization.

469

Synthesis of Cis-5-(5-(1H-imidazol-4-yl)thiophen-2-yl)-N-(3-chloro-4-fluorophenyl)-2-methyl-1,2,6-thiadiazinane-3-carboxamide 1,1-dioxide (HBV-CSU-331-ISO-I & HBV-CSU-331-ISO-II)

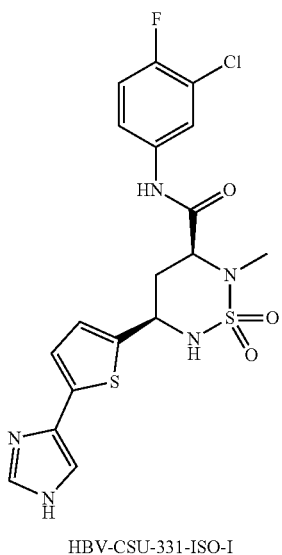

HBV-CSU-331-ISO-I

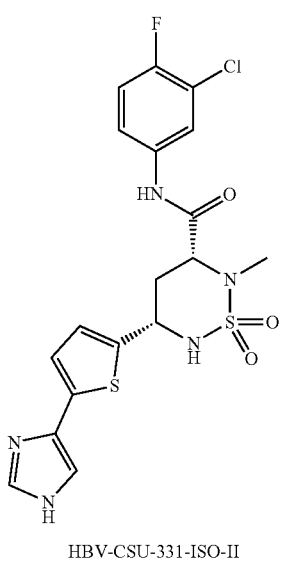

HBV-CSU-331-ISO-II

To a stirred solution of compound 166 (0.6 g, 0.842 mmol) in MeOH (10 mL), 1N HCl (10 mL) was added and refluxed for 1 h. The reaction was monitored by TLC. After completion, the reaction mixture was poured into ice cold water; basified with 10% NaHCO3 solution and extracted with ethyl acetate. The combined organic extracts were dried over anhydrous sodium sulfate, filtered and concentrated in vacuo to afford the crude. The crude compound was purified by silica gel column chromatography to afford compound HBV-CSU-331 (0.1 g, 25.64%)
(See Table 2 for analytical data).

470

Scheme 51

Synthesis of Cis-5-(5-(1H-imidazol-4-yl)thiophen-2-yl)-N-(3-chloro-4-fluorophenyl)-2-methyl-1,2,6-thiadiazinane-3-carboxamide 1,1-dioxide (HBV-CSU-333-ISO-I & HBV-CSU-333-ISO-II)

Scheme 51:

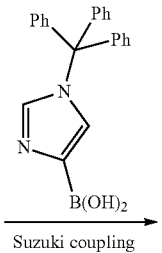

HBV-CSU-122

Suzuki coupling

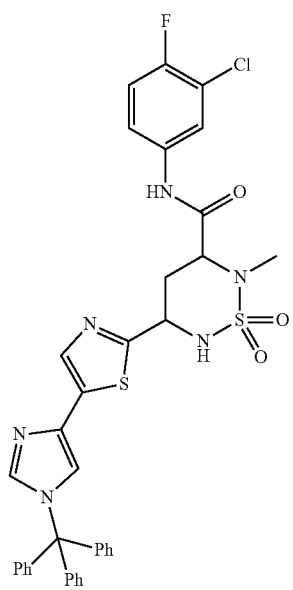

167

1N aq. HCl, MeOH

-continued

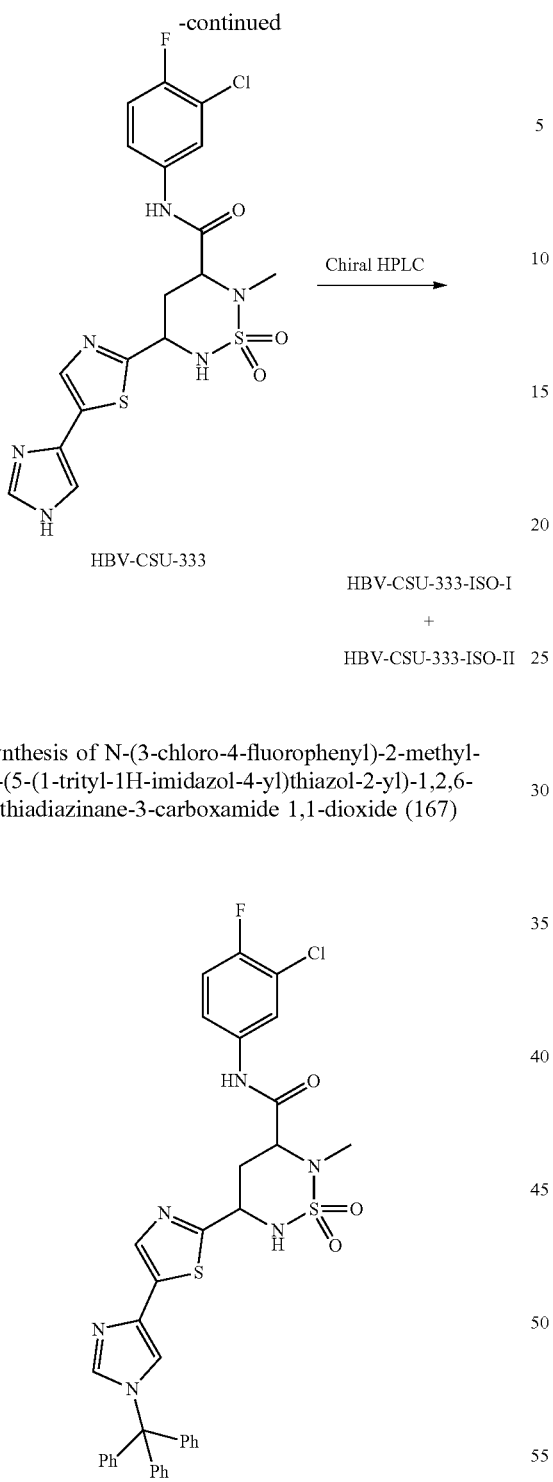

HBV-CSU-333

Chiral HPLC →

HBV-CSU-333-ISO-I
+
HBV-CSU-333-ISO-II

Synthesis of N-(3-chloro-4-fluorophenyl)-2-methyl-5-(5-(1-trityl-1H-imidazol-4-yl)thiazol-2-yl)-1,2,6-thiadiazinane-3-carboxamide 1,1-dioxide (167)

To a mixture of compound HBV-CSU-122 (1 g, 2.06 mmol) and (1-trityl-1H-imidazol-4-yl)boronic acid (1.4 g, 4.12 mmol) in THF:H$_2$O (10 mL:2 mL) mixture, NaHCO$_3$ (0.51 g, 6.18 mmol) was added, purged with Ar for 15 min, followed by the addition of Pd (dppf)Cl$_2$ (0.15 g, 0.206 mmol) and stirred at 100° C. for 16 h. The progress of the reaction was monitored by TLC. After completion, the reaction mixture was diluted with water and extracted with ethyl acetate. The combined organic layers were washed with 1N HCl, brine, dried over anhydrous sodium sulfate and evaporated under reduced pressure to afford the title compound 167 (0.75 g, 54%) as an off white solid. TLC: 30% EtOAc/hexanes (R$_f$: 0.2); New spot isolated after column purification and used as such in the next reaction without characterization.

Synthesis of 5-(5-(1H-imidazol-4-yl)thiazol-2-yl)-N-(3-chloro-4-fluorophenyl)-2-methyl-1,2,6-thiadiazinane-3-carboxamide 1,1-dioxide (HBV-CSU-333-ISO-I & HBV-CSU-333-ISO-II)

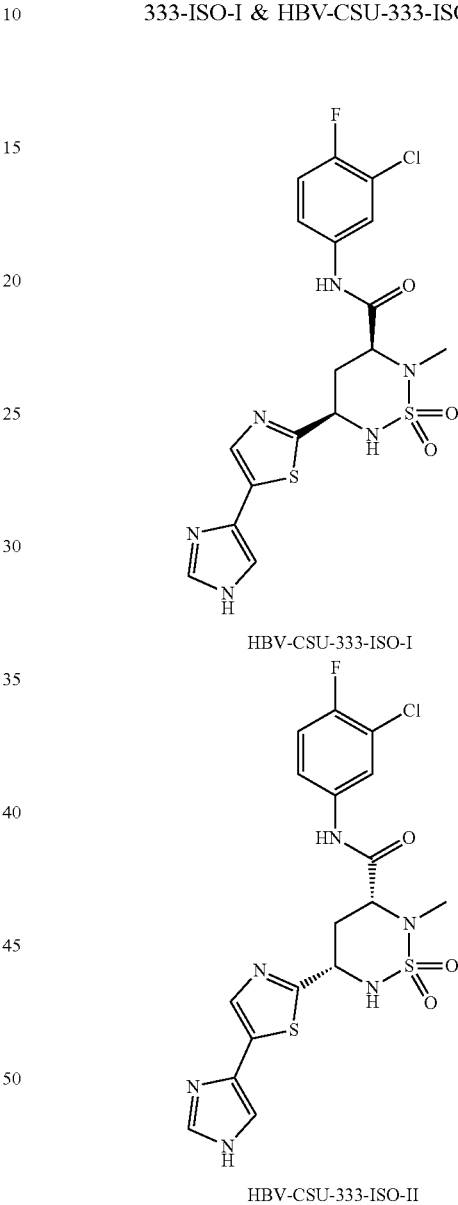

HBV-CSU-333-ISO-I

HBV-CSU-333-ISO-II

To a stirred solution of compound 167 (0.75 g, 1.05 mmol) in MeOH (5 mL) at 0° C., 1N HCl (5 mL) was added. The reaction mixture was stirred at 70° C. for 1 h. The reaction was monitored by TLC. After completion, the reaction mixture was diluted with water; basified with sat. NaHCO$_3$ solution and extracted with ethyl acetate. The combined organic layers were washed with brine, dried over anhydrous sodium sulfate and evaporated under reduced pressure. The crude compound was purified by prep. HPLC to afford the desired compound. (see Table 2 for analytical data).

Scheme 52
Synthesis of Cis-5-(5-Bromothiazol-2-yl)-N-(3-chloro-4-fluorophenyl)-2-(methyl-d₃)-1,2,6-thiadiazinane-3-carboxamide 1,1-dioxide (HBV-CSU-336, HBV-CSU-336-ISO-I & HBV-CSU-336-ISO-II)

Scheme 52:

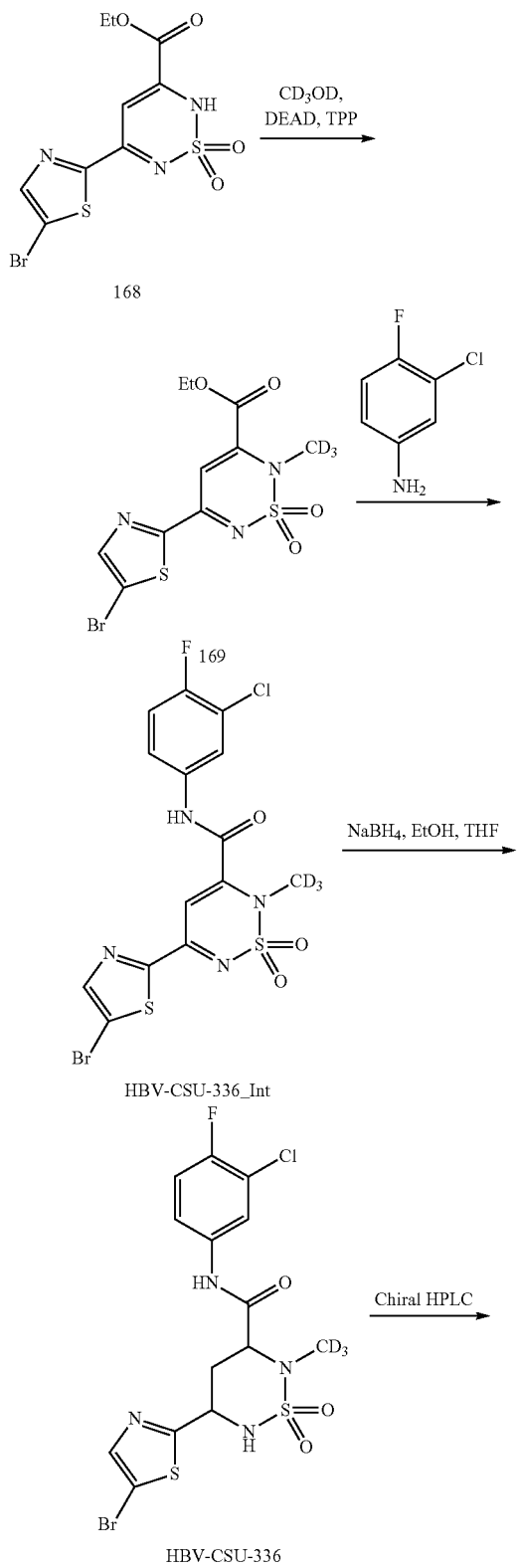

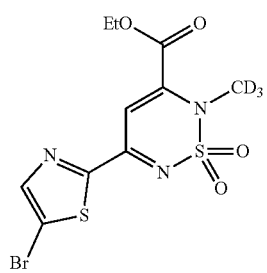 [SMILES: [2H]C([2H])([2H])N1C(C(=O)OCC)=CC(c2ncc(Br)s2)=NS1(=O)=O]

Synthesis of ethyl 5-(5-Bromothiazol-2-yl)-2-(methyl-d₃)-2H-1,2,6-thiadiazine-3-carboxylate 1,1-dioxide (169)

Title compound was synthesized using general method B for alkylation described above to afford 4.82 g of Compound 169 (71%, reaction scale is 6.45 g) as a brown solid. TLC: 50% EtOAc/hexanes ($R_f$: 0.6); LCMS Calculated for $C_{10}H_7D_3BrN_3O_4S_2$: 381.95; LCMS observed: 385 (M+2)⁺.

Synthesis of 5-(5-Bromothiazol-2-yl)-N-(3-chloro-4-fluorophenyl)-2-(methyl-d₃)-2H-1,2,6-thiadiazine-3-carboxamide 1,1-dioxide (HBV-CSU-336_Int)

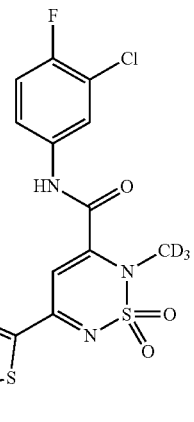

The above titled compound has been synthesized by following the general procedure (Method B) described above for amidation by using Compound 169 and corresponding amine (see Table 1 for analytical data).

475

Synthesis of 5-(5-Bromothiazol-2-yl)-N-(3-chloro-4-fluorophenyl)-2-(methyl-d₃)-1,2,6-thiadiazinane-3-carboxamide 1,1-dioxide (HBV-CSU-336, HBV-CSU-336-ISO-I & HBV-CSU-336-ISO-II

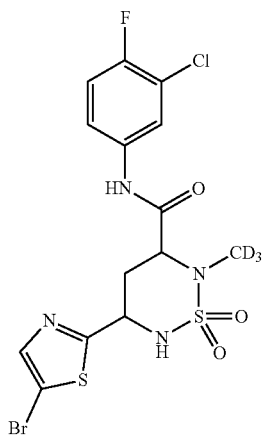

HBV-CSU-336

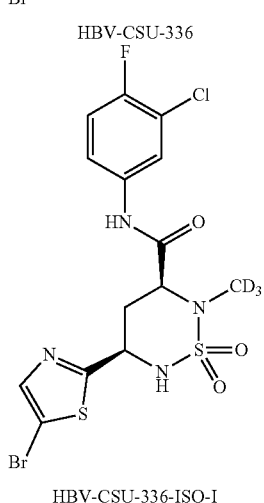

HBV-CSU-336-ISO-I

476

-continued

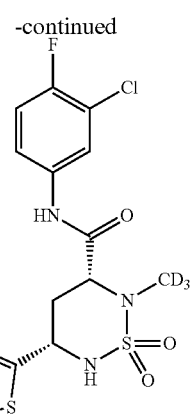

HBV-CSU-336-ISO-II

The above titled compounds have been synthesized by following the general procedure described above for reduction by using corresponding HBV-CSU-336_Int (see Table 2 for analytical data).

Scheme 53

Synthesis of N-(3-chloro-4-fluorophenyl)-2-(methyl-d₃)-5-(5-(1-(methyl-d₃)-1H-imidazol-4-yl)thiazol-2-yl)-1,2,6-thiadiazinane-3-carboxamide 1,1-dioxide (HBV-CSU-337-ISO-I & HBV-CSU-337-ISO-II) and N-(3-chloro-4-fluorophenyl)-2-(methyl-d₃)-5-(5-(1-methyl-1H-imidazol-4-yl)thiazol-2-yl)-1,2,6-thiadiazinane-3-carboxamide 1,1-dioxide (HBV-CSU-338-ISO-I & HBV-CSU-338-ISO-II)

Scheme 53:

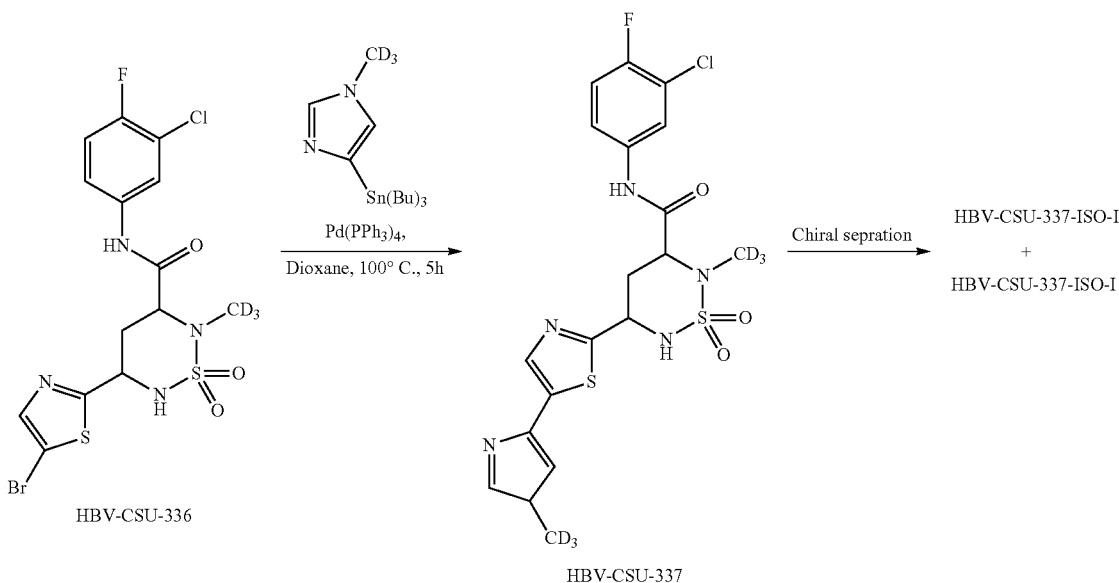

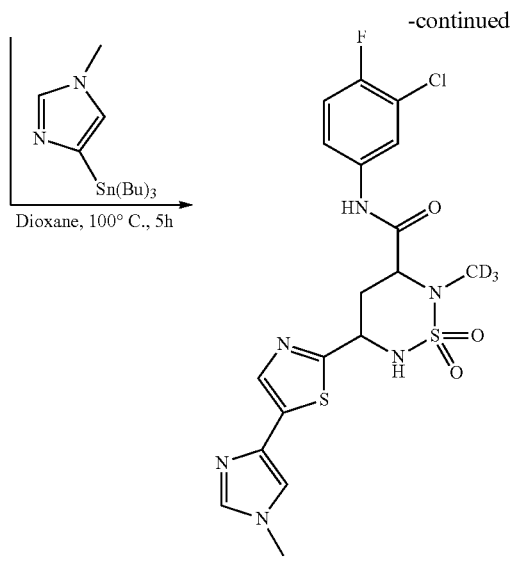

HBV-CSU-338

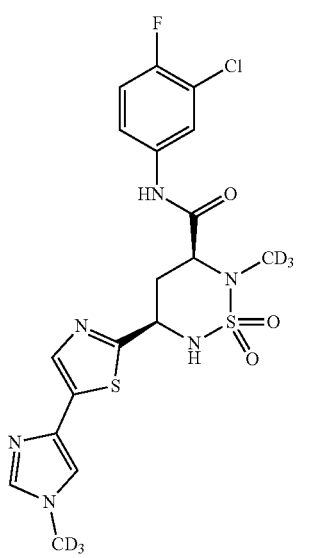

Cis-N-(3-Chloro-4-fluorophenyl)-2-(methyl-d₃)-5-(5-(1-(methyl-d₃)-1H-imidazol-4-yl)thiazol-2-yl)-1,2,6-thiadiazinane-3-carboxamide 1,1-dioxide (HBV-CSU-337-ISO-I & HBV-CSU-337-ISO-II)

HBV-CSU-337-ISO-I

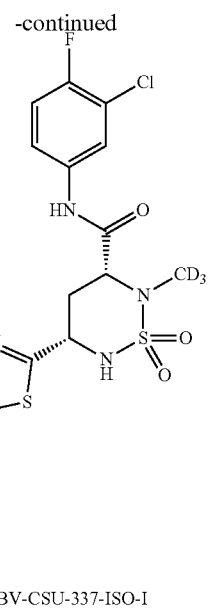

HBV-CSU-337-ISO-I

The above titled compounds have been synthesized by following the general procedure described above for Stille coupling by using HBV-CSU-336 and corresponding stannane (see Table 2 for analytical data).

479

Cis-N-(3-Chloro-4-fluorophenyl)-2-(methyl-d₃)-5-(5-(1-methyl-1H-imidazol-4-yl)thiazol-2-yl)-1,2,6-thiadiazinane-3-carboxamide 1,1-dioxide (HBV-CSU-338-ISO-I & HBV-CSU-338-ISO-II)

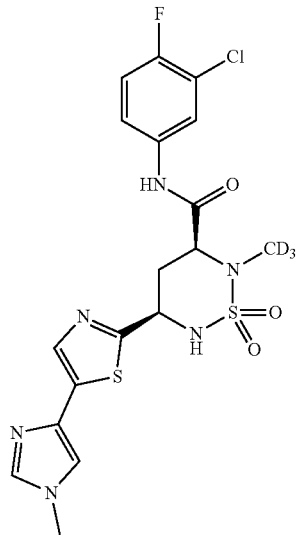

HBV-CSU-338-ISO-I

480

-continued

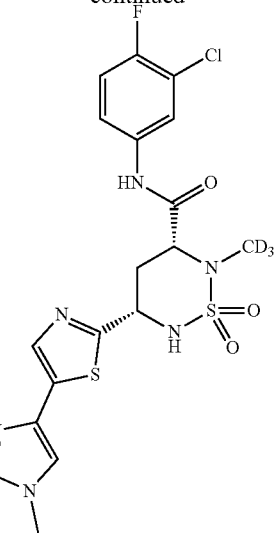

HBV-CSU-338-ISO-II

The above titled compounds have been synthesized by following the general procedure described above for Stille coupling by using HBV-CSU-336 and corresponding stannane (see Table 2 for analytical data).

Scheme 54

Synthesis of Cis-N-(3-Chloro-4-fluorophenyl)-2-(methyl-d₃)-5-(5-(1-(methyl-d₃)-1H-imidazol-4-yl)thiazol-2-yl)-1,2,6-thiadiazinane-3,4,5-d₃-3-carboxamide 1,1-dioxide and Cis-N-(3-Chloro-4-fluorophenyl)-2-(methyl-d₃)-5-(5-(1-methyl-1H-imidazol-4-yl)thiazol-2-yl)-1,2,6-thiadiazinane-3,4,5-d₃-3-carboxamide 1,1-dioxide (HBV-CSU-340-ISO-I & HBV-CSU-340-ISO-II)

Scheme 54:

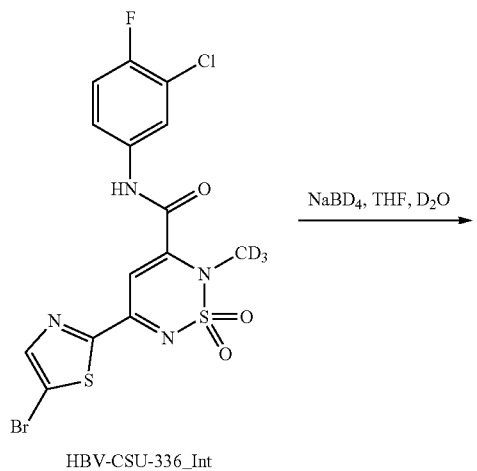

HBV-CSU-336_Int

NaBD₄, THF, D₂O →

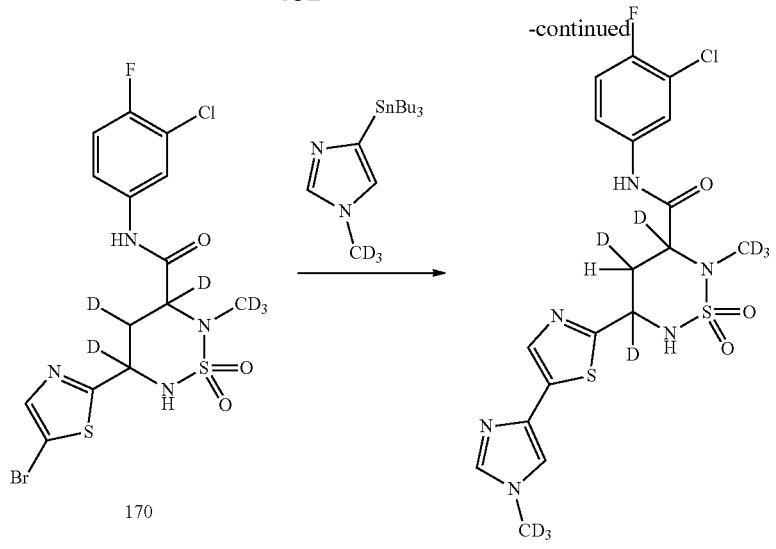

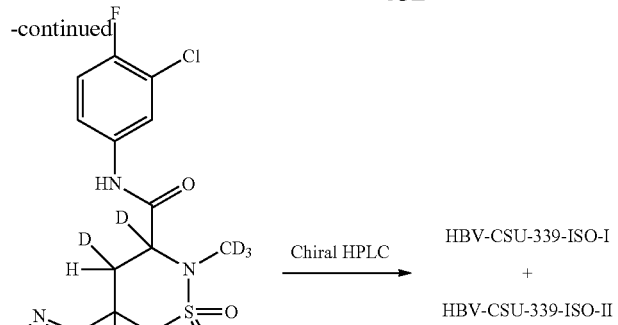

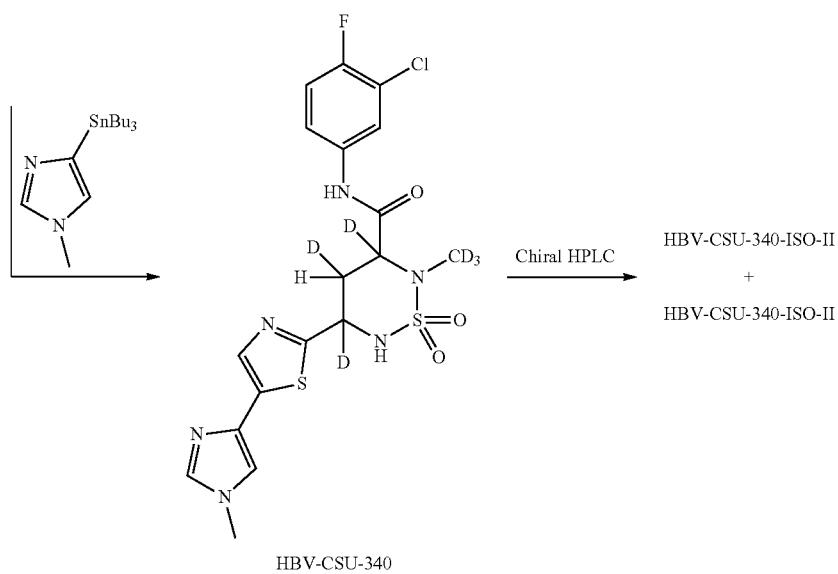

Synthesis of 5-(5-Bromothiazol-2-yl)-N-(3-chloro-4-fluorophenyl)-2-(methyl-d₃)-1,2,6-thiadiazinane-3,4,5-d₃-3-carboxamide 1,1-dioxide (170)

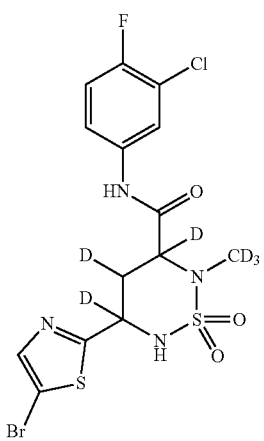 [SMILES: [2H]C1C([2H])(c2ncc(Br)s2)NS(=O)(=O)N(C([2H])([2H])[2H])C1([2H])C(=O)Nc1ccc(F)c(Cl)c1]

To a stirred solution of compound HBV-CSU-336_Int (1 g, 2.07 mmol) in THF:D$_2$O (1:1, 10 mL) mixture at 0° C. under Ar atmosphere, NaBD$_4$ (0.173 g, 4.14 mmol) was added and stirred at room temperature for 2 h. The progress of the reaction was monitored by TLC and LCMS. After completion, the reaction mixture was concentrated in vacuo. The crude compound was purified by silica gel column chromatography using 5% MeOH/DCM to afford compound 170 (0.9 g, 88.75%) as a yellow solid. TLC: 30% EtOAc/hexanes (R$_f$: 0.2); $^1$H-NMR (DMSO-d$_6$, 400 MHz): δ 10.59 (s, 1H), 7.98-7.93 (m, 2H), 7.90 (s, 1H), 7.58-7.54 (m, 1H), 7.40 (t, J=8.8 Hz, 1H), 2.12 (s, 1H). LCMS Calculated for C$_{14}$H$_7$D$_6$BrClFN$_4$O$_3$S$_2$: 487.97; LCMS observed: 491.1 (M+1)$^+$.

483

Cis-N-(3-Chloro-4-fluorophenyl)-2-(methyl-d₃)-5-(5-(1-(methyl-d₃)-1H-imidazol-4-yl)thiazol-2-yl)-1,2,6-thiadiazinane-3,4,5-d₃-3-carboxamide 1,1-dioxide (HBV-CSU-339-ISO-I & HBV-CSU-339-ISO-II)

484

Cis-N-(3-Chloro-4-fluorophenyl)-2-(methyl-d₃)-5-(5-(1-methyl-1H-imidazol-4-yl)thiazol-2-yl)-1,2,6-thiadiazinane-3,4,5-d₃-3-carboxamide 1,1-dioxide (HBV-CSU-340-ISO-I & HBV-CSU-340-ISO-II)

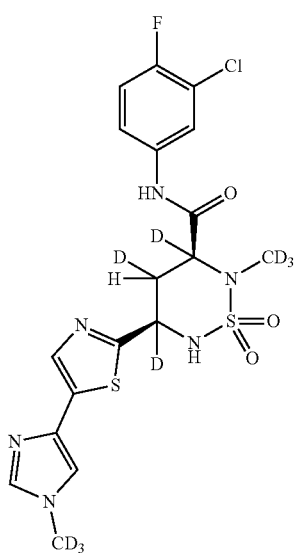

HBV-CSU-339-ISO-I

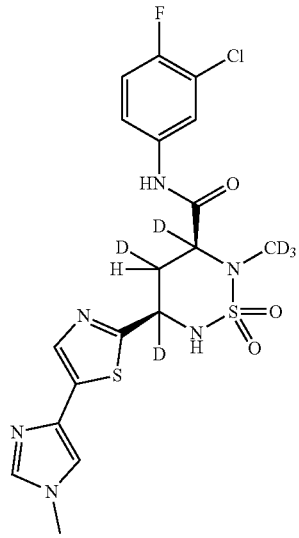

HBV-CSU-340-ISO-I

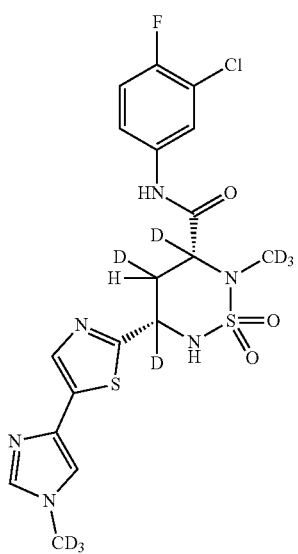

HBV-CSU-339-ISO-II

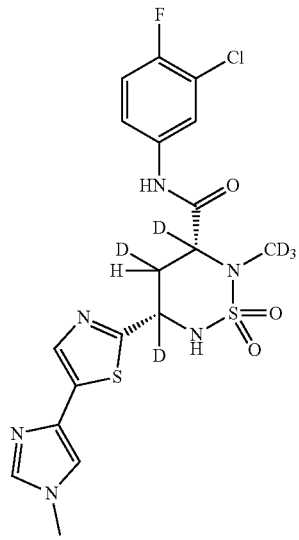

HBV-CSU-340-ISO-II

The above titled compounds have been synthesized by following the general procedure described above for Stille coupling by using Compound 170 and corresponding stannane (see Table 2 for analytical data).

The above titled compounds have been synthesized by following the general procedure described above for Stille coupling by using Compound 170 and corresponding stannane (see Table 2 for analytical data).

Scheme 55

Synthesis of Cis-N-(3-Chloro-4-fluorophenyl)-2-methyl-5-(5-(1-(methyl-d₃)-1H-imidazol-4-yl)thiazol-2-yl)-1,2,6-thiadiazinane-3,4,5-d₃-3-carboxamide 1,1-dioxide (HBV-CSU-341-ISO-I & HBV-CSU-341-ISO-II)

Scheme 55:

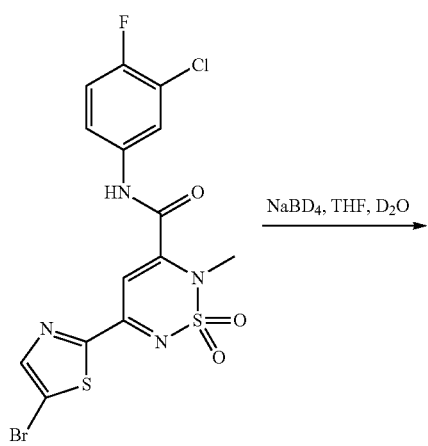

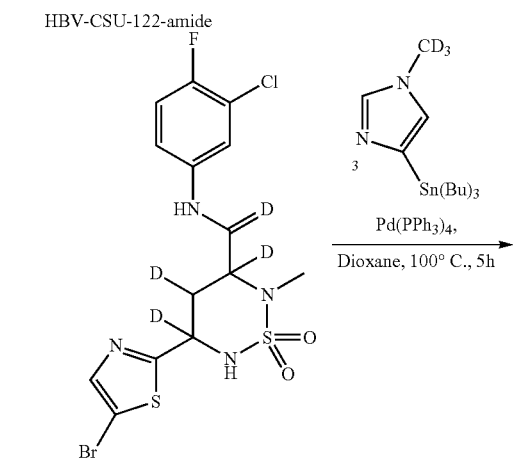

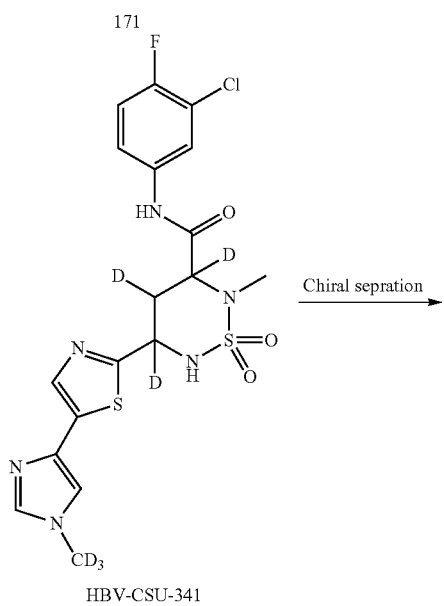

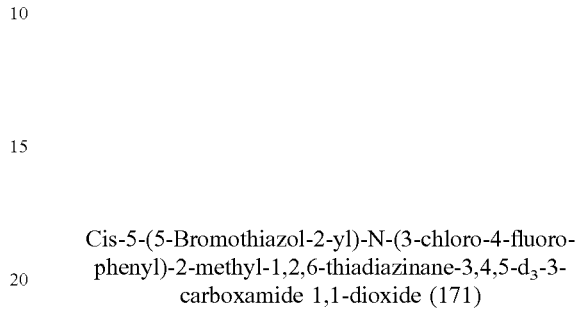

Cis-5-(5-Bromothiazol-2-yl)-N-(3-chloro-4-fluorophenyl)-2-methyl-1,2,6-thiadiazinane-3,4,5-d₃-3-carboxamide 1,1-dioxide (171)

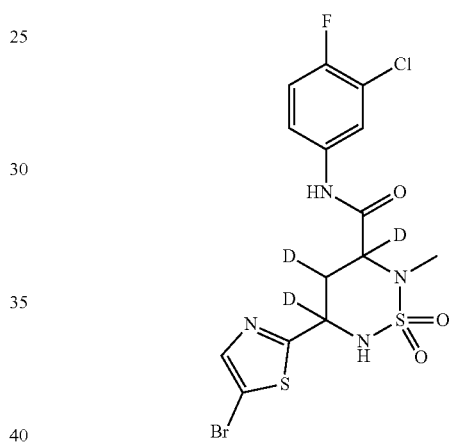

To a stirred solution of compound HBV-CSU-122-amide (1.2 g, 2.5 mmol) in THF:D₂O (1:1, 10 mL) mixture at 0° C. under Ar atmosphere, NaBD₄ (0.209 g, 5 mmol) was added and stirred at room temperature for 45 min. The progress of the reaction was monitored by TLC and LCMS. After completion, the reaction mixture was concentrated in vacuo. The crude compound was purified by silica gel column chromatography using 100% EtOAc/hexanes to afford compound 171 (1.1 g, 90.9%) as a light yellow solid. TLC: 40% EtOAc/hexanes ($R_f$: 0.5); ¹H-NMR (DMSO-d₆, 400 MHz): δ 10.58 (s, 1H), 7.97-7.94 (m, 2H), 7.89 (s, 1H), 7.57-7.54 (m, 1H), 7.40 (t, J=8.8 Hz, 1H), 2.63 (s, 3H), 2.12 (s, 1H); LCMS Calculated for $C_{14}H_{10}D_3BrClFN_4O_3S_2$: 484.95; LCMS observed: 488 (M+2)⁺.

487

Cis-N-(3-Chloro-4-fluorophenyl)-2-methyl-5-(5-(1-(methyl-d$_3$)-1H-imidazol-4-yl)thiazol-2-yl)-1,2,6-thiadiazinane-3,4,5-d$_3$-3-carboxamide 1,1-dioxide (HBV-CSU-341-ISO-I & HBV-CSU-341-ISO-II)

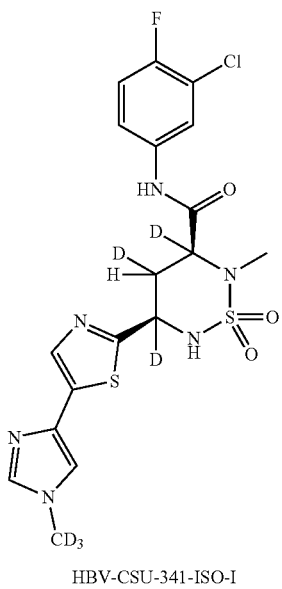

HBV-CSU-341-ISO-I

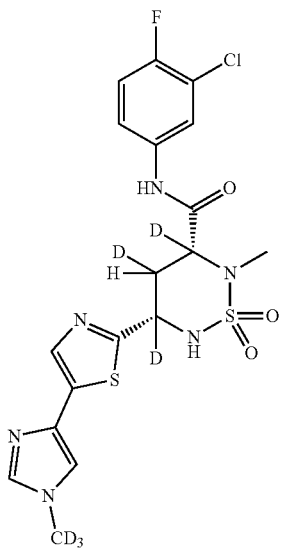

HBV-CSU-341-ISO-II

The above titled compounds have been synthesized by following the general procedure described above for Stille coupling by using Compound 171 and corresponding stannane (see Table 2 for analytical data).

488

Scheme 56

Synthesis of Cis-N-(3-chloro-4-fluorophenyl)-2-methyl-5-(1-methyl-1H-benzo[d]imidazol-5-yl)-1,2,6-thiadiazinane-3-carboxamide 1,1-dioxide (HBV-360, HBV-CSU-360-ISO-I & HBV-CSU-360-ISO-II)

Scheme 56:

489
-continued

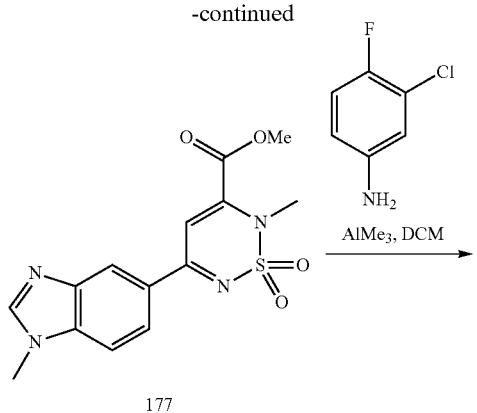

177

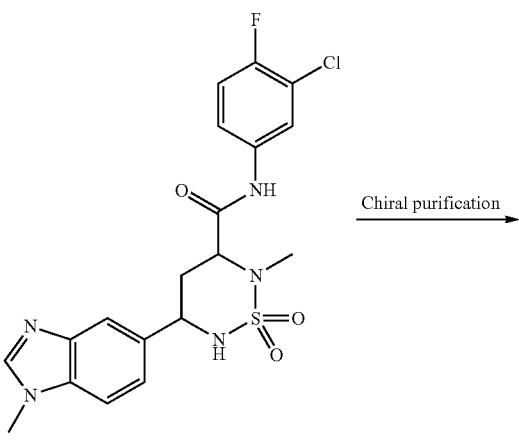

HBV-CSU-360_Int

NaBH₄, EtOH
⟶

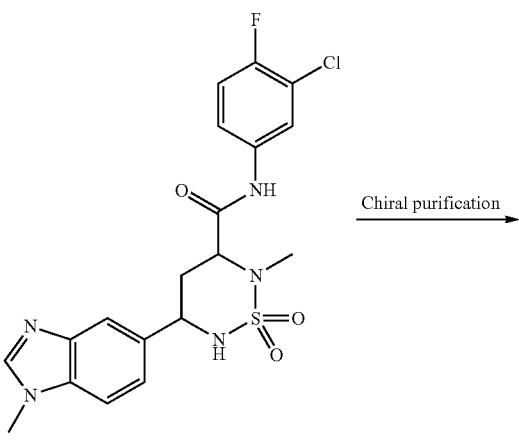

HBV-CSU-360

Chiral purification
⟶

HBV-CSU-360-ISO-I
+
HBV-CSU-360-ISO-II

490

Synthesis of N-methoxy-N, 1-dimethyl-1H-benzo[d]imidazole-5-carboxamide (173)

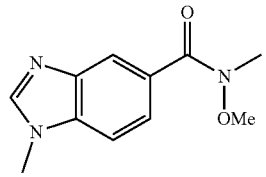 [SMILES: CON(C)C(=O)c1ccc2c(c1)ncn2C]

To a stirred solution acid compound 172 (6.7 g, 38.06 mmol) and N,O-dimethylhydroxylamine (5.57 g, 57.09 mmol) in DCM (70 mL) at 0° C. was added DIPEA (13.53 mL, 76.13 mmol), stirred for 15 min, followed by addition of HATU (21.69 g, 57.09 mmol), again stirred for 15 min. The reaction mixture was then stirred at room temperature for overnight. The progress of the reaction was monitored by TLC. After completion, the reaction mixture was diluted with ice cold water and extracted with DCM. The combined organic layers were dried over anhydrous sodium sulphate and concentrated under reduced pressure to afford a crude compound. The crude compound was purified by silica gel column chromatography using 2% MeOH/DCM to afford the title compound 173 (8.1 g, 98.78%) as a brown liquid. TLC: 5% MeOH/DCM ($R_f$: 0.3). ¹H LCMS Calculated for $C_{11}H_{13}N_3O_2$: 219.10; LCMS observed: 219.95 (M+1)⁺.

Synthesis of 1-(1-methyl-1H-benzo[d]imidazol-5-yl)ethan-1-one (174)

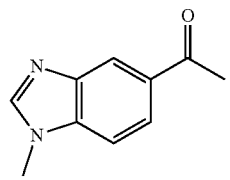

To a stirred solution of compound 173 (8.1 g, 36.95 mmol) in anhydrous THF (80 mL) under inert atmosphere was added methyl magnesium bromide (24.77 mL, 73.97 mmol, 3 M sol. in diethyl ether) dropwise for 15 min at 0° C., followed by warming to room temperature and stirring for 3 h. The reaction was monitored by TLC. After completion of the reaction, the reaction mixture was quenched with saturated ammonium chloride solution (50 mL) and extracted with ethyl acetate. The combined organic layers were dried over anhydrous sodium sulfate, filtered and concentrated in vacuo. The crude compound was purified by silica gel column chromatography using 2% MeOH/DCM to afford the title compound 174 (5.65 g, 87.59%) as an off white solid. TLC: 5% MeOH/DCM ($R_f$: 0.4); ¹H NMR (400 MHz, DMSO-d₆): δ 8.34-8.32 (m, 2H), 7.90 (d, J=8.4 Hz, 1H), 7.66 (d, J=8.8 Hz, 1H), 3.87 (s, 3H), 2.64 (s, 3H); LCMS Calculated for $C_{10}H_{10}N_2O$: 174.08; Observed: 175.10 (M+1)⁺.

Synthesis of methyl 4-(1-methyl-1H-benzo[d]imidazol-5-yl)-2,4-dioxobutanoate (175)

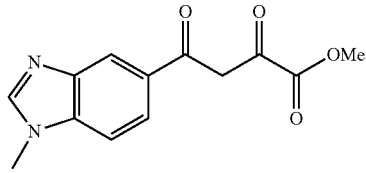 [SMILES: COC(=O)C(=O)CC(=O)c1ccc2c(c1)ncn2C]

Title compound was synthesized using general method for the synthesis of 2,4-diketoester described above to afford 3.8 g of Compound 175 (crude, reaction scale is 5 g) as a brown solid. TLC: 80% EtOAc/hexane ($R_f$: 0.1); LCMS Calculated for $C_{13}H_{12}N_2O_4$: 260.08; Observed: 261 (M+1)$^+$.

Synthesis of methyl 5-(1-methyl-1H-benzo[d]imidazol-5-yl)-2H-1,2,6-thiadiazine-3-carboxylate 1,1-dioxide (176)

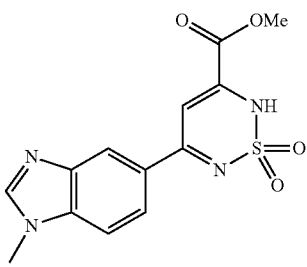 [SMILES: COC(=O)C1=CC(c2ccc3c(c2)ncn3C)=NS(=O)(=O)N1]

Title compound was synthesized using general method B for the synthesis of cyclic sulfonamide described above to afford 2 g of Compound 176 (42.82%, reaction scale is 3.8 g) as a yellow solid. TLC: 5% MeOH/DCM ($R_f$: 0.1; LCMS observed for $C_{13}H_{12}N_4O_4S$: 320.06 (M+1)$^+$. Observed: 320.95 (M+1)$^+$.

Synthesis of methyl 2-methyl-5-(1-methyl-1H-benzo[d]imidazol-5-yl)-2H-1,2,6-thiadiazine-3-carboxylate 1,1-dioxide (177)

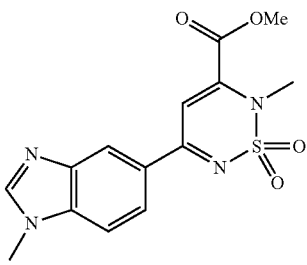 [SMILES: COC(=O)C1=CC(c2ccc3c(c2)ncn3C)=NS(=O)(=O)N1C]

Title compound was synthesized using general method B for alkylation described above to afford 1.3 g of Compound 177 (crude, reaction scale is 1.8 g); TLC: 5% MeOH/DCM ($R_f$: 0.2); LCMS Calculated for $C_{14}H_{14}N_4O_4S$: 334.07; LCMS observed: 335 (M+1)$^+$.

Synthesis of N-(3-chloro-4-fluorophenyl)-2-methyl-5-(1-methyl-1H-benzo[d]imidazol-5-yl)-2H-1,2,6-thiadiazine-3-carboxamide 1,1-dioxide (HBV-CSU-360_Int)

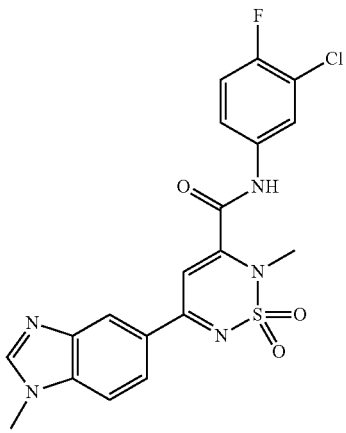 [SMILES: CN1C(C(=O)Nc2ccc(F)c(Cl)c2)=CC(c2ccc3c(c2)ncn3C)=NS1(=O)=O]

The above titled compound has been synthesized by following the general procedure (Method A) described above for amidation by using Compound 177 and corresponding amine (see Table 1 for analytical data).

Synthesis of Cis-N-(3-chloro-4-fluorophenyl)-2-methyl-5-(1-methyl-1H-benzo[d]imidazol-5-yl)-1,2,6-thiadiazinane-3-carboxamide 1,1-dioxide (HBV-360, HBV-CSU-360-ISO-I & HBV-CSU-360-ISO-II)

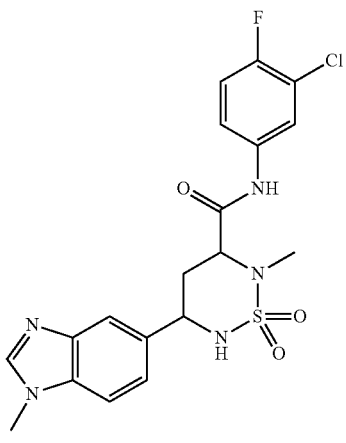

HBV-CSU-360

493

-continued

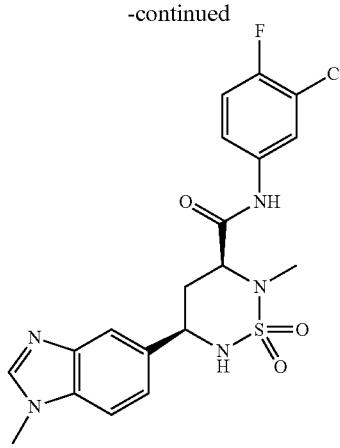

HBV-CSU-360-ISO-I

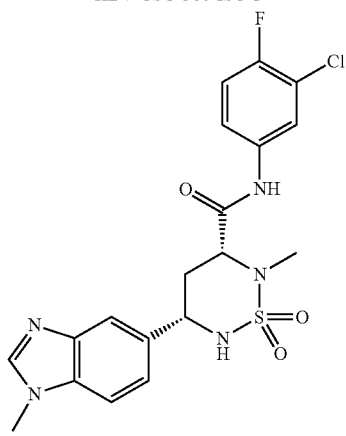

HBV-CSU-360-ISO-II

The above titled compounds have been synthesized by following the general procedure described above for reduction by using corresponding HBV-CSU-360_Int (see Table 2 for analytical data).

Scheme 57

Synthesis of Cis-5-(benzo[d]thiazol-5-yl)-N-(3-chloro-4-fluorophenyl)-2-methyl-1,2,6-thiadiazinane-3-carboxamide 1,1-dioxide (HBV-CSU-361)

Scheme 57:

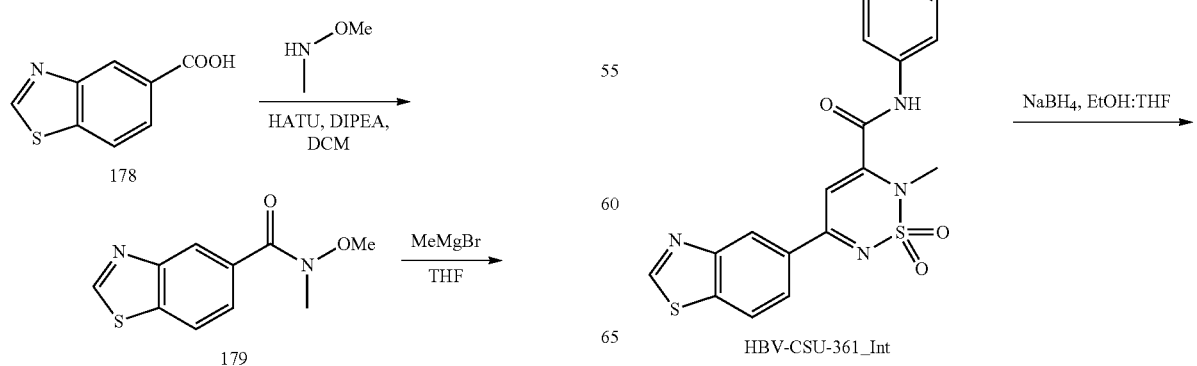

494

-continued

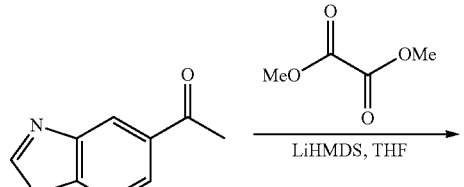

180

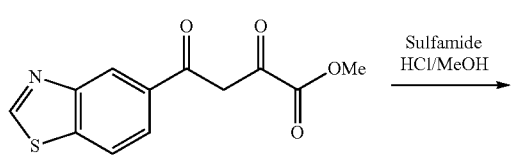

181

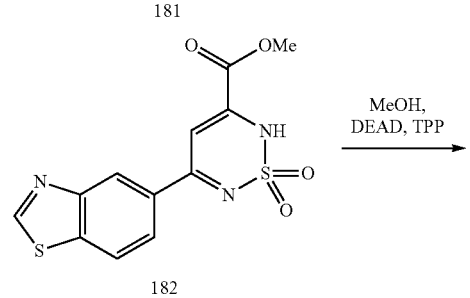

182

183

HBV-CSU-361_Int

-continued

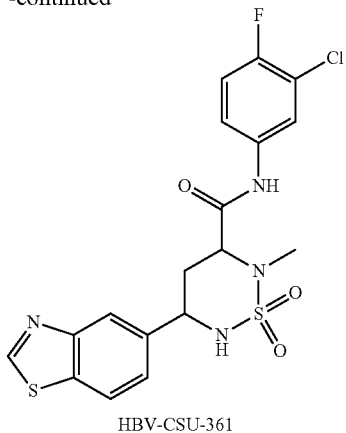

HBV-CSU-361

Synthesis of N-methoxy-N-methylbenzo[d]thiazole-5-carboxamide (179)

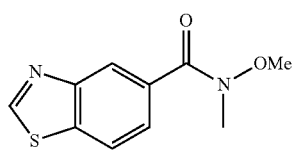

To a stirred solution of compound 178 (4 g, 22.32 mmol) in DCM (50 mL) at 0° C., DIPEA (7.77 mL, 44.64 mmol) and HATU (12.72 g, 33.48 mmol) were added and stirred for 15 min. To this solution, N,O-dimethylhydroxylamine hydrochloride (3.26 g, 33.48 mmol) was added. The reaction mixture was stirred at room temperature for 16 h. The progress of the reaction was monitored by TLC. After completion, the reaction mixture was diluted with ice cold water and extracted with DCM. The combined organic layers were dried over anhydrous sodium sulphate and concentrated under reduced pressure to afford a crude compound. The crude compound was purified by silica gel column chromatography using 50% EtOAc/hexane to afford the title compound 179 (3.7 g, 60.48%) as a white solid. TLC: 60% EtOAc/hexane ($R_f$: 0.3). LCMS Calculated for $C_{10}H_{10}N_2O_2S$: 222.05; LCMS observed: 222.95 (M+1)$^+$.

Synthesis of 1-(benzo[d]thiazol-5-yl)ethan-1-one (180)

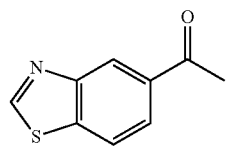

To a stirred solution of compound 179 (3.7 g, 16.6 mmol) in anhydrous THF (40 mL) under inert atmosphere was added methyl magnesium bromide (11.09 mL, 33.3 mmol, 3 M sol. in diethyl ether) dropwise for 15 min at 0° C., followed by warming to room temperature and stirring for 2 h. The reaction was monitored by TLC. After completion of the reaction, the reaction mixture was quenched with satu- rated ammonium chloride solution and extracted with ethyl acetate. The combined organic layers were dried over anhydrous sodium sulfate, filtered and concentrated in vacuo to afford the title compound 180 (2.4 g, 81.35%) as yellow solid. TLC: 30% EtOAc/hexane ($R_f$: 0.4). LCMS Calculated for $C_9H_7NOS$:177.02; Observed: 177.90 (M+1)$^+$.

Synthesis of methyl 4-(benzo[d]thiazol-5-yl)-2,4-dioxobutanoate (181)

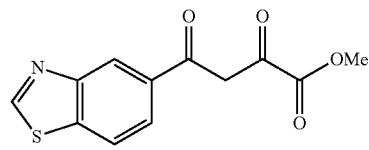 [SMILES: COC(=O)C(=O)CC(=O)c1ccc2scnc2c1]

Title compound was synthesized using general method for the synthesis of 2,4-diketoester described above to afford 3 g of Compound 181 (crude, reaction scale is 2.3 g); TLC: 30% EtOAc/hexane ($R_f$: 0.1); LCMS Calculated for $C_{12}H_9NO_4S$: 263.03; Observed: 263.95 (M+1)$^+$.

Synthesis of methyl 5-(benzo[d]thiazol-5-yl)-2H-1,2,6-thiadiazine-3-carboxylate 1,1-dioxide (182)

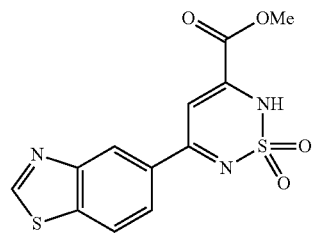 [SMILES: COC(=O)C1=CC(c2ccc3scnc3c2)=NS(=O)(=O)N1]

Title compound was synthesized using general method B for cyclisation described above to afford 0.5 g of Compound 182 (13.57%, reaction scale is 3 g) as a yellow solid. TLC: 10% MeOH/DCM ($R_f$: 0.2); $^1$H NMR (DMSO-$d_6$, 400 MHz): δ 9.49 (s, 1H), 8.62 (s, 1H), 8.28 (d, J=8.4 Hz, 1H), 8.06 (d, J=8.4 Hz, 1H), 6.94 (s, 1H), 3.86 (s, 3H); LCMS Calculated for $C_{12}H_9N_3O_4S_2$: 323.00; LCMS observed: 323.9 (M+1)$^+$.

Synthesis of methyl 5-(benzo[d]thiazol-5-yl)-2-methyl-2H-1,2,6-thiadiazine-3-carboxylate 1,1-dioxide (183)

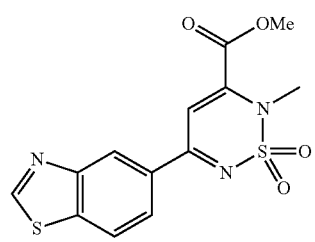 [SMILES: COC(=O)C1=CC(c2ccc3scnc3c2)=NS(=O)(=O)N1C]

Title compound was synthesized using general method B for alkylation described above to afford 0.3 g of Compound 183 (58%, reaction scale is 0.5 g) as a yellow solid. TLC: 30% EtOAc/hexane ($R_f$: 0.1); LCMS Calculated for $C_{13}H_1N_3O_4S_2$: 337.02; LCMS observed: 338 $(M+1)^+$.

Synthesis of 5-(benzo[d]thiazol-5-yl)-N-(3-chloro-4-fluorophenyl)-2-methyl-2H-1,2,6-thiadiazine-3-carboxamide 1,1-dioxide (HBV-CSU-361_Int)

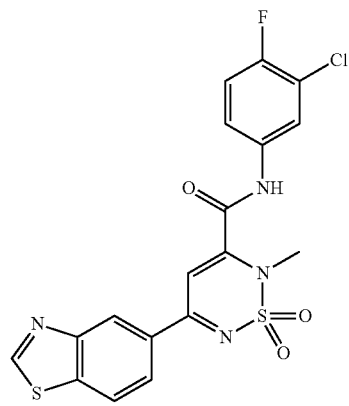 [SMILES: CN1C(C(=O)Nc2ccc(F)c(Cl)c2)=CC(c2ccc3scnc3c2)=NS1(=O)=O]

The above titled compound has been synthesized by following the general procedure (Method B) described above for amidation by using Compound 183 and corresponding amine (see Table 1 for analytical data).

Synthesis of Cis-5-(benzo[d]thiazol-5-yl)-N-(3-chloro-4-fluorophenyl)-2-methyl-1,2,6-thiadiazinane-3-carboxamide 1,1-dioxide (HBV-CSU-361)

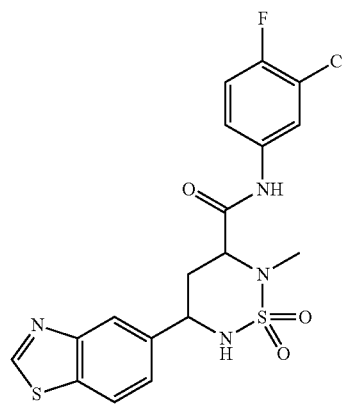

The above titled compounds have been synthesized by following the general procedure described above for reduction by using corresponding HBV-CSU-361_Int (see Table 2 for analytical data).

Synthesis of Cis-5-(benzo[d]thiazol-2-yl)-N-(3-chloro-4-fluorophenyl)-2-methyl-1,2,6-thiadiazinane-3-carboxamide 1,1-dioxide (HBV-CSU-364)

Scheme 58:

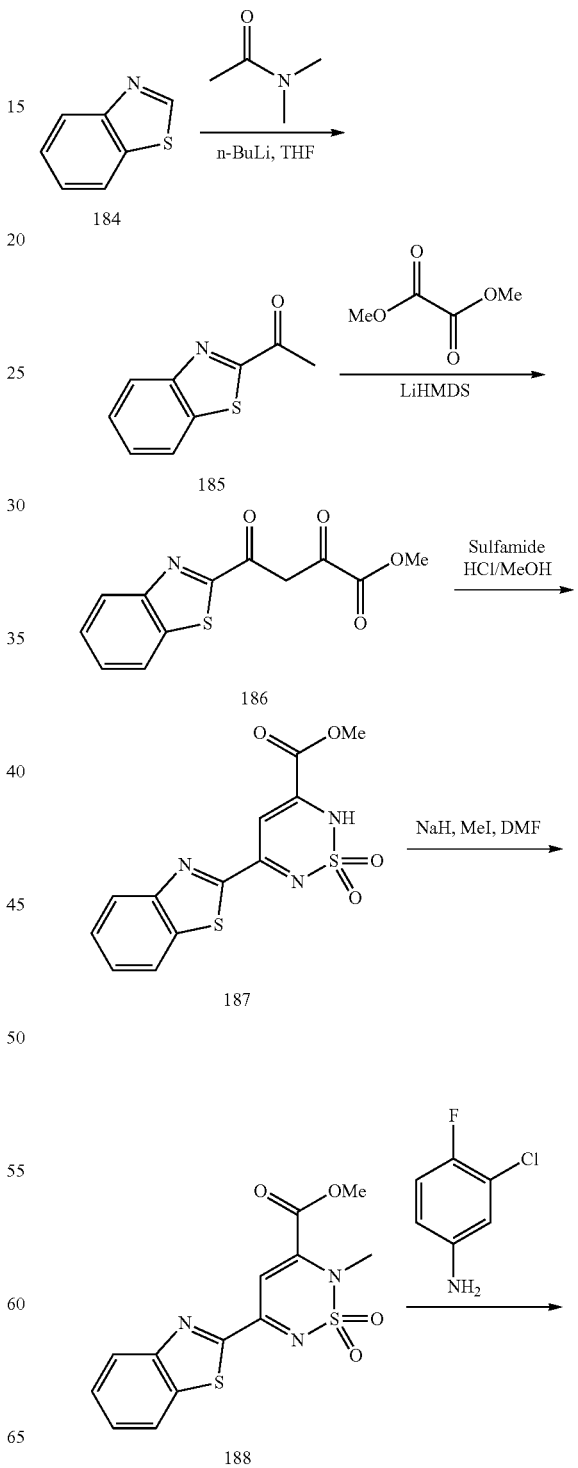

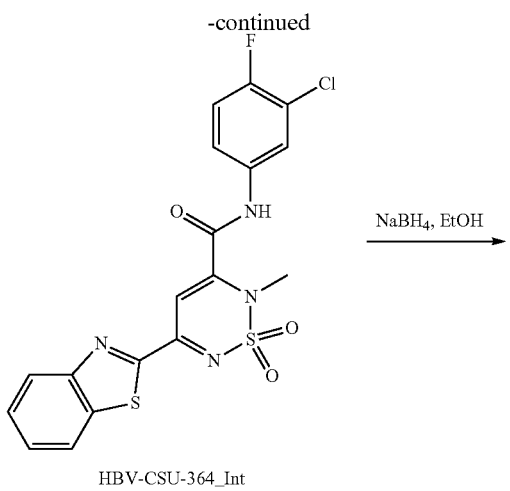

HBV-CSU-364_Int

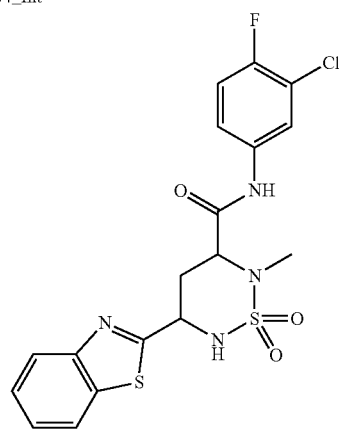

HBV-CSU-364

Synthesis of 1-(benzo[d]thiazol-2-yl)ethan-1-one (185)

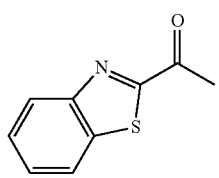

To a stirred solution of compound 184 (10 g, 74.07 mmol) in anhydrous THF (100 mL) under inert atmosphere was added n-butyl lithium (32.5 mL, 81.48 mmol, 2.5 M in hexane) dropwise for 15 min at −78° C. and, followed by stirring for 1 h. To this was added N,N-dimethylacetamide (6.44 g, 74.07 mmol) at −78° C. and stirred for 1 h. Then Conc. HCl (15 mL) was added at to 0° C. and stirring for 2 h. The reaction was monitored by TLC. After completion of the reaction, the reaction mixture was poured on water and extracted with EtOAc (3×100 mL). The combined organic extracts were dried over anhydrous sodium sulfate, filtered and concentrated in vacuo to obtain the crude. The crude was purified through silica gel column chromatography using 4% EtOAc/hexanes to afford compound 185 (3.1 g, 23.64%) as a off white solid. TLC: 10% EtOAc/hexanes (R$_f$: 0.3); $^1$H NMR (DMSO-d$_6$, 400 MHz): δ 8.26-8.23 (m, 2H), 7.69-7.61 (m, 2H), 2.76 (s, 3H); LCMS Calculated for C$_9$H$_7$NOS: 177.02; Observed: 178 (M+1)$^+$.

Synthesis of methyl 4-(benzo[d]thiazol-2-yl)-2,4-dioxobutanoate (186)

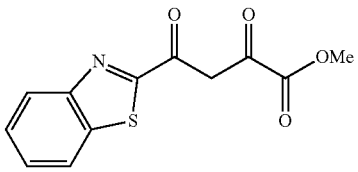 [SMILES: COC(=O)C(=O)CC(=O)c1nc2ccccc2s1]

Title compound was synthesized using general method for the synthesis of 2,4-diketoester described above to afford 2.7 g of Compound 186 (crude, reaction scale is 3 g); LCMS Calculated for C$_{12}$H$_9$NO$_4$S: 263.03; Observed: 264.1 (M+1)$^+$.

Synthesis of methyl 5-(benzo[d]thiazol-2-yl)-2H-1,2,6-thiadiazine-3-carboxylate 1,1-dioxide (187)

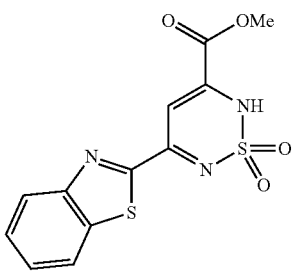 [SMILES: COC(=O)C1=CC(c2nc3ccccc3s2)=NS(=O)(=O)N1]

Title compound was synthesized using general method B for cyclisation described above to afford 0.53 g of Compound 187 (28.80%, reaction scale is 1.5 g) as an off white solid. 50% EtOAc/hexanes (R$_f$: 0.1); LCMS Calculated for C$_{12}$H$_9$N$_3$O$_4$S$_2$: 323.00; LCMS observed: 324 (M+1)$^+$.

Synthesis of methyl 5-(benzo[d]thiazol-2-yl)-2-methyl-2H-1,2,6-thiadiazine-3-carboxylate 1,1-dioxide (188)

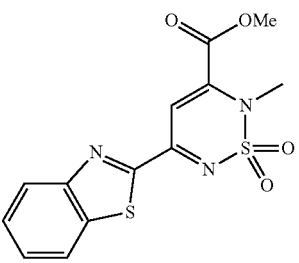 [SMILES: COC(=O)C1=CC(c2nc3ccccc3s2)=NS(=O)(=O)N1C]

Title compound was synthesized using general method A for alkylation described above to afford 0.37 g of Compound 188 (59%, reaction scale is 0.6 g) as an off white solid. TLC: 20% EtOAc/hexanes (R$_f$: 0.5); LCMS Calculated for C$_{13}$H$_{11}$N$_3$O$_4$S$_2$: 337.02; LCMS observed: 338.05 (M+1)$^+$.

Synthesis of 5-(benzo[d]thiazol-2-yl)-N-(3-chloro-4-fluorophenyl)-2-methyl-2H-1,2,6-thiadiazine-3-carboxamide 1,1-dioxide (HBV-CSU-364_Int)

Scheme 59

Synthesis of Cis-N-(3-chloro-4-fluorophenyl)-2-methyl-5-(1-methyl-1H-benzo[d]imidazol-2-yl)-1,2,6-thiadiazinane-3-carboxamide 1,1-dioxide (HBV-CSU-368)

Scheme 59:

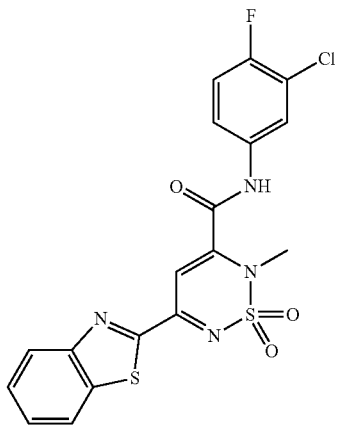 [SMILES: CN1C(C(=O)Nc2ccc(F)c(Cl)c2)=CC(c2nc3ccccc3s2)=NS1(=O)=O]

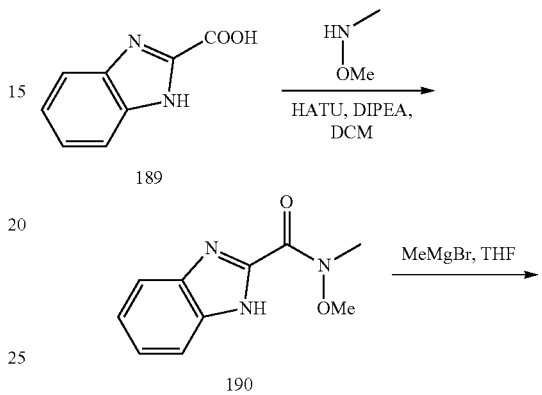

The above titled compound has been synthesized by following the general procedure (Method A) described above for amidation by using Compound 188 and corresponding amine (see Table 1 for analytical data).

Synthesis of Cis-5-(benzo[d]thiazol-2-yl)-N-(3-chloro-4-fluorophenyl)-2-methyl-1,2,6-thiadiazinane-3-carboxamide 1,1-dioxide (HBV-CSU-364)

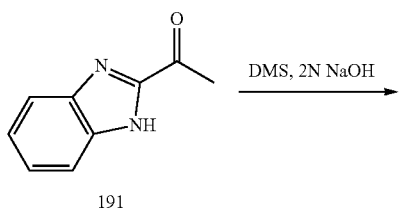

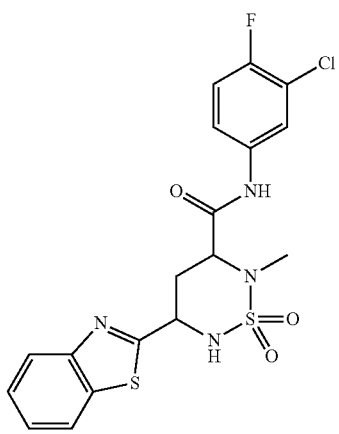 [SMILES: CN1C(C(=O)Nc2ccc(F)c(Cl)c2)CC(c2nc3ccccc3s2)NS1(=O)=O]

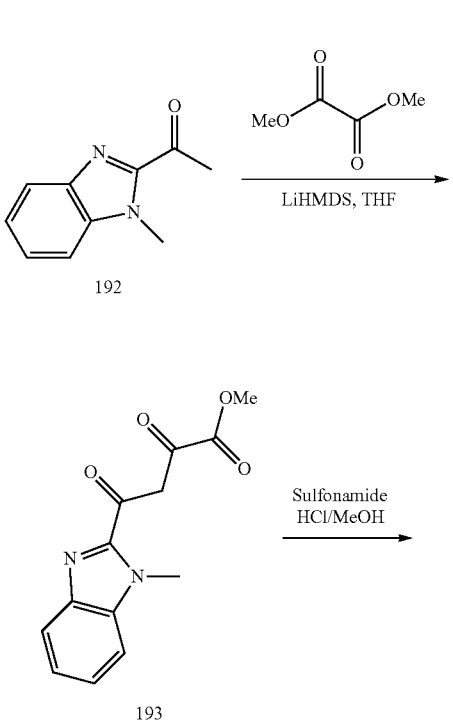

The above titled compounds have been synthesized by following the general procedure described above for reduction by using corresponding HBV-CSU-364_Int (see Table 2 for analytical data).

-continued

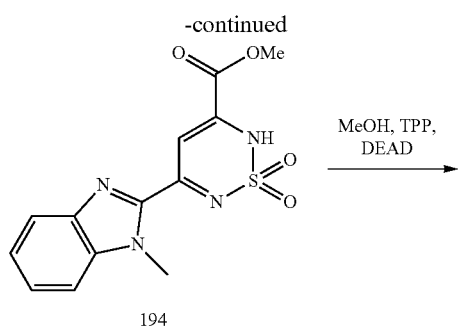

194

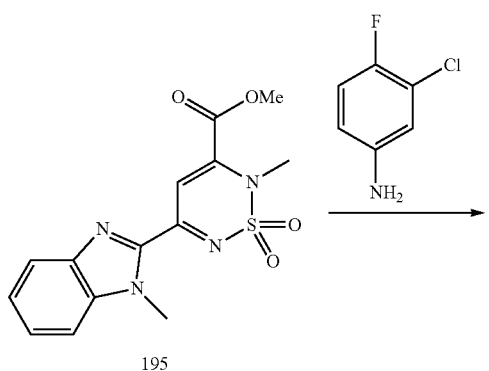

195

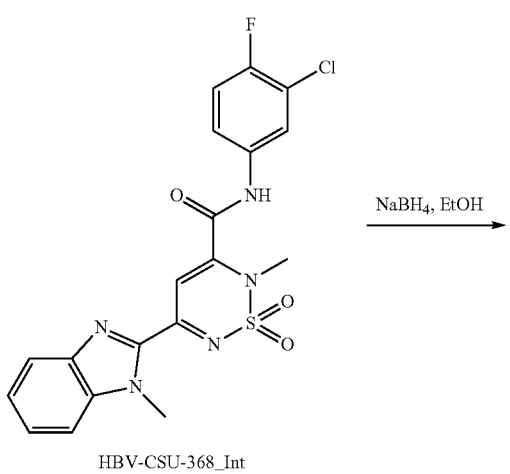

HBV-CSU-368_Int

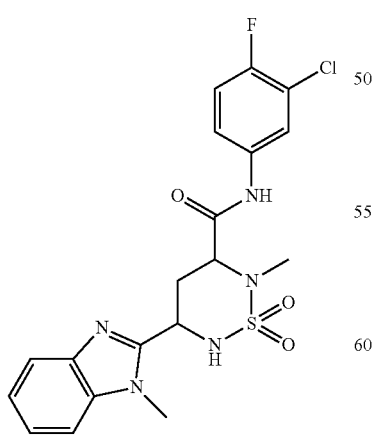

HBV-CSU-368

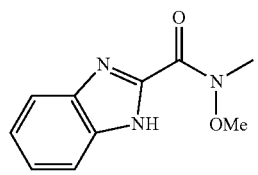

Synthesis of N-methoxy-N-methyl-1H-benzo[d]imidazole-2-carboxamide (190)

To a stirred solution of compound 189 (24 g, 148 mmol) in DCM (250 mL) under inert atmosphere, DIPEA (51.58 mL, 296 mmol) and HATU (84.39 g, 222 mmol) were added. To this solution, N,O-dimethylhydroxylamine hydrochloride (21.66 g, 222 mmol) was added and stirred at room temperature for 16 h. The progress of the reaction was monitored by TLC. After completion of the reaction, the reaction mixture was poured into ice-cold water and extracted using DCM. The combined organic extracts were washed with brine, dried over anhydrous sodium sulfate, filtered and concentrated in vacuo to obtain the crude. The crude was purified through silica gel column chromatography using 50% EtOAc/hexanes to afford compound 190 (15 g, 49.40%) as a white solid. TLC: 5% MeOH/DCM ($R_f$: 0.5); $^1$H NMR (400 MHz, DMSO-$d_6$): δ 13.19 (s, 1H), 7.84 (d, J=8.4 Hz, 1H), 7.54 (d, J=7.6 Hz, 1H), 7.34-7.24 (m, 2H), 3.83 (s, 6H); LCMS Calculated for $C_{10}H_{11}N_3O_2$: 205.09; Observed: 206 (M+1)$^+$.

Synthesis of 1-(1H-benzo[d]imidazol-2-yl)ethan-1-one (191)

To a stirred solution of compound 190 (15 g, 73.13 mmol) in anhydrous THF (200 mL) under inert atmosphere was added methyl magnesium bromide (48.75 mL, 146.3 mmol, 3 M sol. in diethyl ether) dropwise for 15 min at 0° C. The reaction mixture was stirred at 0° C. for 2 h. The progress of the reaction was monitored by TLC. After completion of the reaction, the reaction mixture was quenched with saturated ammonium chloride solution and extracted with ethyl acetate The combined organic extracts were dried over anhydrous sodium sulfate, filtered and concentrated in vacuo to afford compound 191 (7 g, 60%) as a yellow solid. TLC: 30% EtOAc/hexanes ($R_f$: 0.5); $^1$H NMR (400 MHz, DMSO-$d_6$): δ δ 13.28 (s, 1H), 7.82-7.80 (m, 1H), 7.55-7.53 (m, 1H), 7.35-7.30 (m, 2H), 2.69 (s, 3H); LCMS Calculated for $C_9H_8N_2O$: 160.06; Observed: 160.95 (M+1)$^+$.

Synthesis of 1-(1-methyl-1H-benzo[d]imidazol-2-yl)ethan-1-one (192)

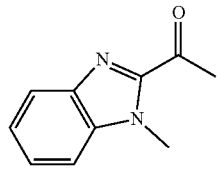

To a stirred solution of compound 191 (5.5 g, 34.37 mmol) in 2N NaOH (165 mL) at 0° C., dimethyl sulfate (5.63 g, 44.68 mmol) was added and reaction was stirred the at room temperature for 1 h. The progress of the reaction was monitored by TLC. After completion, the reaction mixture was acidified with 1N HCl and and extracted with ethyl acetate. The combined organic extracts were dried over anhydrous sodium sulfate, filtered and concentrated in vacuo to afford compound 192 (4 g, 66.88%) as a off white solid. TLC: 20% EtOAc/hexanes ($R_f$: 0.7); $^1$H NMR (400 MHz, DMSO-$d_6$): δ 7.82 (d, J=8.4 Hz, 1H), 7.21 (d, J=8.4 Hz, 1H), 7.45 (t, J=8.0 Hz, 1H), 7.35 (d, J=7.6 Hz, 1H), 4.07 (s, 3H), 2.73 (s, 3H); LCMS Calculated for $C_{10}H_{10}N_2O$: 174.08; Observed: 174.90 (M+1)$^+$.

Synthesis of methyl 4-(1-methyl-1H-benzo[d]imidazol-2-yl)-2,4-dioxobutanoate (193)

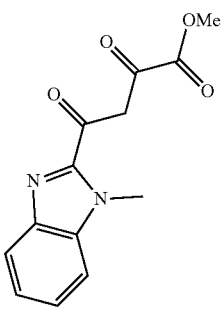 [SMILES: COC(=O)C(=O)CC(=O)c1nc2ccccc2n1C]

Title compound was synthesized using general method for the synthesis of 2,4-diketoester described above to afford 3.3 g (51%, reaction scale is 4 g); TLC: 5% MeOH/DCM ($R_f$: 0.1); $^1$LCMS Calculated for $C_{13}H_{12}N_2O_4$: 260.08; Observed: 260.8 (M+1)$^+$.

Synthesis of methyl 5-(1-methyl-1H-benzo[d]imidazol-2-yl)-2H-1,2,6-thiadiazine-3-carboxylate 1,1-dioxide (194)

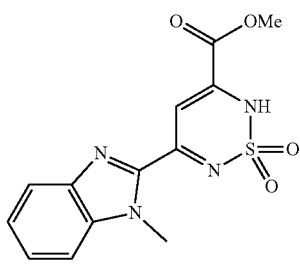 [SMILES: COC(=O)C1=CC(c2nc3ccccc3n2C)=NS(=O)(=O)N1]

Title compound was synthesized using general method B for cyclisation described above to afford 2.1 g of Compound 194 (52%, reaction scale is 3.3 g) as an off white solid. TLC: 10% MeOH/DCM ($R_f$: 0.1); $^1$H NMR (400 MHz, DMSO-$d_6$): δ 7.97 (d, J=7.6 Hz, 1H), 7.82-7.78 (m, 1H), 7.63-7.60 (m, 2H), 7.30-7.04 (m, 1H), 6.85 (s, 1H), 4.28 (s, 3H), 3.84 (s, 3H); LCMS Calculated for $C_{13}H_{12}N_4O_4S$: 320.06; LCMS observed: 320.95 (M+1)$^+$.

Synthesis of methyl 2-methyl-5-(1-methyl-1H-benzo[d]imidazol-2-yl)-2H-1,2,6-thiadiazine-3-carboxylate 1,1-dioxide (195)

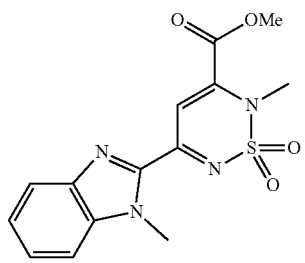 [SMILES: COC(=O)C1=CC(c2nc3ccccc3n2C)=NS(=O)(=O)N1C]

Title compound was synthesized using general method B for alkylation described above to afford 1.1 g of Compound 195 (51%, reaction scale is 2.1 g) as a yellow solid. TLC: 5% MeOH/DCM ($R_f$: 0.5); NMR (400 MHz, DMSO-$d_6$): δ 7.85 (d, J=8.0 Hz, 1H), 7.76 (d, J=8.4 Hz, 1H), 7.73 (s, 1H), 7.49 (t, J=8.4 Hz, 1H), 7.38 (t, J=8.4 Hz, 1H), 4.21 (s, 3H), 3.97 (s, 3H), 3.60 (s, 3H); LCMS Calculated for $C_{14}H_{14}N_4O_4S$: 334.07; LCMS observed: 334.95 (M+1)$^+$.

Synthesis of N-(3-chloro-4-fluorophenyl)-2-methyl-5-(1-methyl-1H-benzo[d]imidazol-2-yl)-2H-1,2,6-thiadiazine-3-carboxamide 1,1-dioxide (HBV-CSU-368_Int)

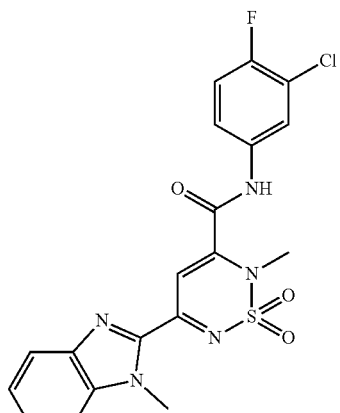

The above titled compound has been synthesized by following the general procedure (Method B) described above for amidation by using Compound 195 and corresponding amine (see Table 1 for analytical data).

507

Synthesis of Cis-N-(3-chloro-4-fluorophenyl)-2-methyl-5-(1-methyl-1H-benzo[d]imidazol-2-yl)-1,2,6-thiadiazinane-3-carboxamide 1,1-dioxide (HBV-CSU-368)

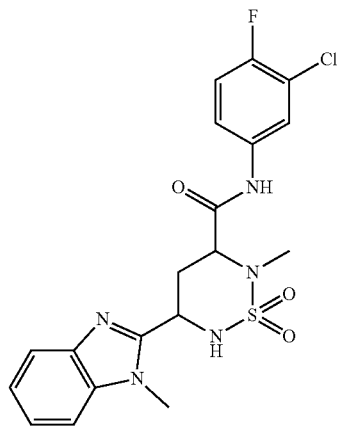 [SMILES: CN1C(C(=O)Nc2ccc(F)c(Cl)c2)CC(c2nc3ccccc3n2C)NS1(=O)=O]

The above titled compounds have been synthesized by following the general procedure described above for reduction by using corresponding HBV-CSU-368_Int (see Table 2 for analytical data).

Scheme 60

Synthesis of (3S,5R)—N-(3-bromo-4-fluorophenyl)-2-methyl-5-(5-(1-methyl-1H-imidazol-4-yl)thiazol-2-yl)-1,2,6-thiadiazinane-3-carboxamide 1,1-dioxide (HBV-CSU-369) and (3S,5R)—N-(3-bromo-4-fluorophenyl)-5-(5-bromothiazol-2-yl)-2-methyl-1,2,6-thiadiazinane-3-carboxamide 1,1-dioxide (HBV-CSU-383)

Scheme 60:

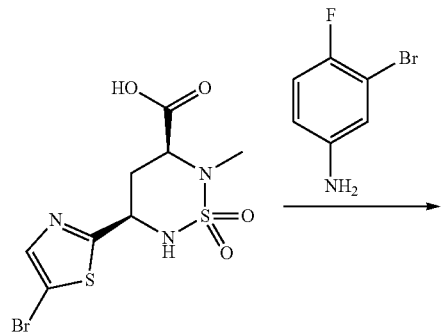

196

508

-continued

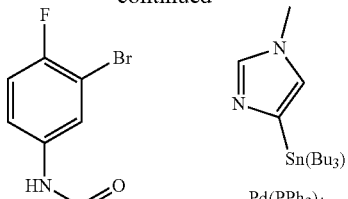

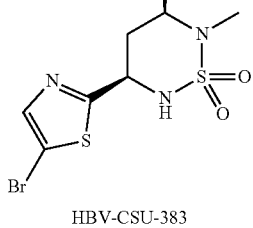

HBV-CSU-383

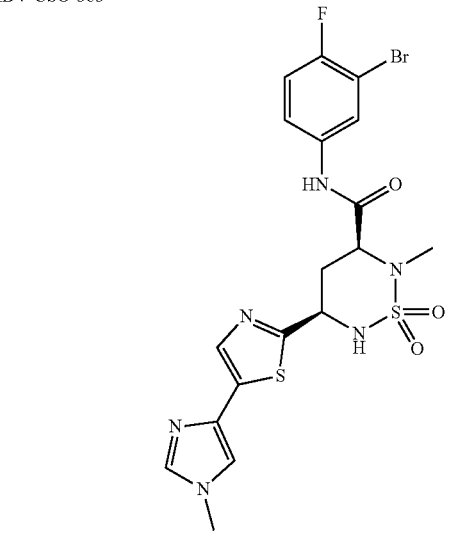

HBV-CSU-369

Synthesis of (3S,5R)—N-(3-bromo-4-fluorophenyl)-5-(5-bromothiazol-2-yl)-2-methyl-1,2,6-thiadiazinane-3-carboxamide 1,1-dioxide (HBV-CSU-383)

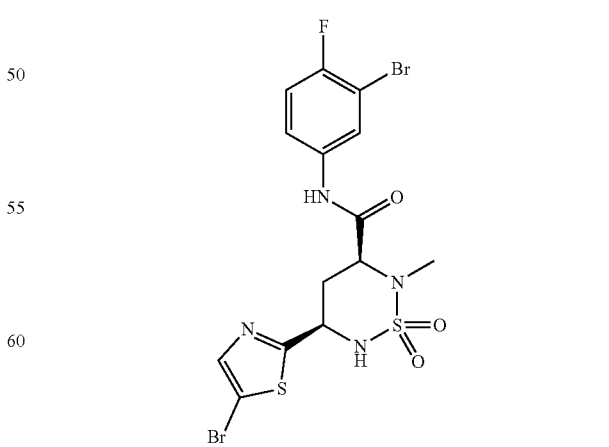

The above titled compound has been synthesized by following the general procedure (Method A, amide coupling) described above for amidation by using Compound 196 and corresponding amine (see Table 1 for analytical data).

Synthesis of (3S,5R)—N-(3-bromo-4-fluorophenyl)-2-methyl-5-(5-(1-methyl-1H-imidazol-4-yl)thiazol-2-yl)-1,2,6-thiadiazinane-3-carboxamide 1,1-dioxide (HBV-CSU-369)

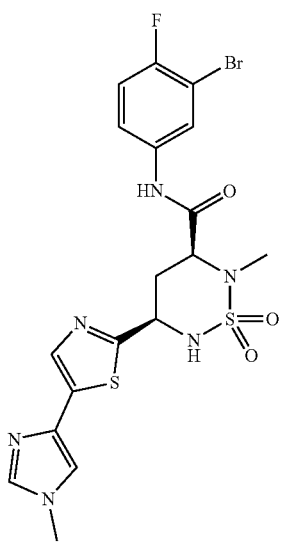 [SMILES: CN1[C@H](C(=O)Nc2ccc(F)c(Br)c2)C[C@H](c2ncc(-c3cn(C)cn3)s2)NS1(=O)=O]

The above titled compounds have been synthesized by following the general procedure described above for Stille coupling by using HBV-CSU-383 and corresponding stannane (see Table 2 for analytical data).

Scheme 61

Synthesis of Cis-5-(5-bromothiophen-2-yl)-N-(3-chloro-4-fluorophenyl)-2-(methyl-d₃)-1,2,6-thiadiazinane-3-carboxamide 1,1-dioxide (HBV-CSU-370, HBV-CSU-370-ISO-I & HBV-CSU-370-ISO-II)

Scheme 61:

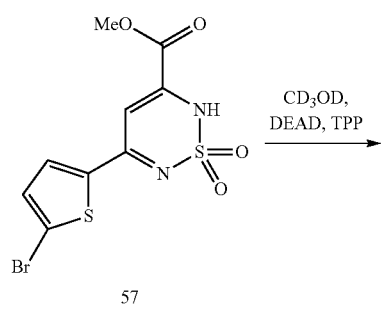

57

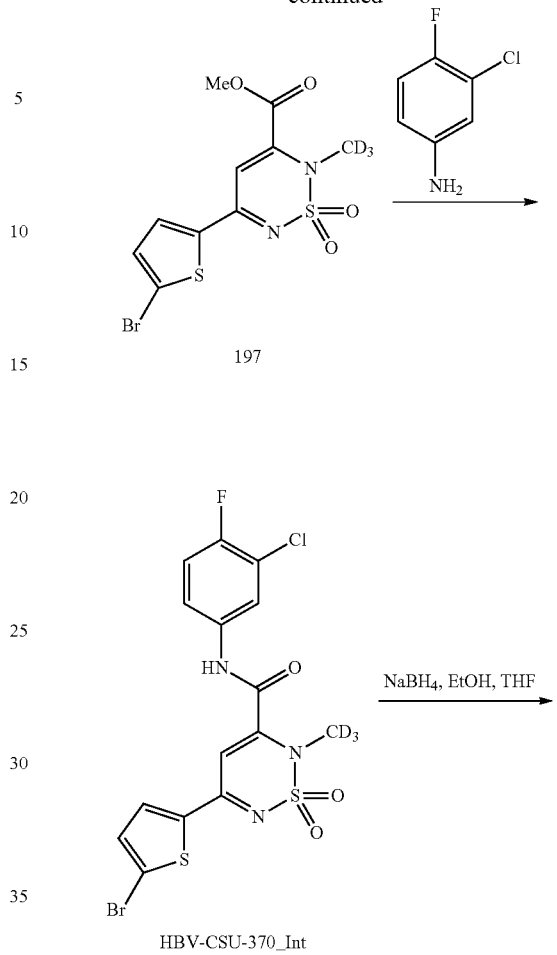

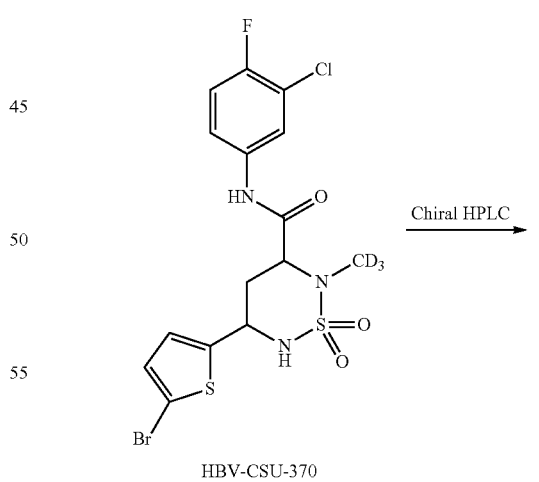

HBV-CSU-370-ISO-I
+
HBV-CSU-370-ISO-II

511

Synthesis of Methyl 5-(5-bromothiophen-2-yl)-2-(methyl-d3)-2H-1,2,6-thiadiazine-3-carboxylate 1,1-dioxide (197)

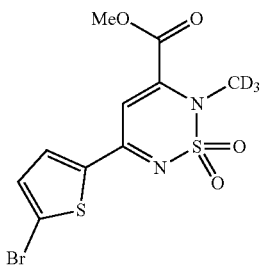 [SMILES: [2H]C([2H])([2H])N1C(C(=O)OC)=CC(c2ccc(Br)s2)=NS1(=O)=O]

Title compound was synthesized using general method B for alkylation described above to afford 15 g of Compound 197 (71.53%, reaction scale is 20 g) as a brown solid. TLC: 10% MeOH/DCM ($R_f$: 0.6); LCMS Calculated for $C_{10}H_6D_3BrN_2O_4S_2$: 366.94; LCMS observed: 373 (M+2)$^+$.

Synthesis of 5-(5-bromothiazol-2-yl)-N-(3-chloro-4-fluorophenyl)-2-(methyl-d$_3$)-2H-1,2,6-thiadiazine-3-carboxamide 1,1-dioxide (HBV-CSU-370_Int)

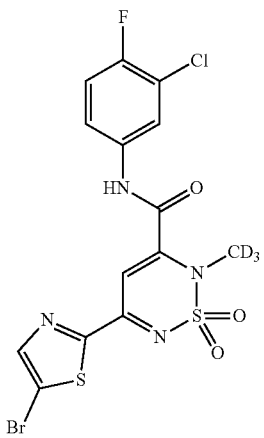 [SMILES: [2H]C([2H])([2H])N1C(C(=O)Nc2ccc(F)c(Cl)c2)=CC(c2ncc(Br)s2)=NS1(=O)=O]

The above titled compound has been synthesized by following the general procedure (Method B) described above for amidation by using Compound 197 and corresponding amine (see Table 1 for analytical data).

512

Synthesis of Cis-5-(5-bromothiophen-2-yl)-N-(3-chloro-4-fluorophenyl)-2-(methyl-d$_3$)-1,2,6-thiadiazinane-3-carboxamide 1,1-dioxide (HBV-CSU-370, HBV-CSU-370-ISO-I & HBV-CSU-370-ISO-I)

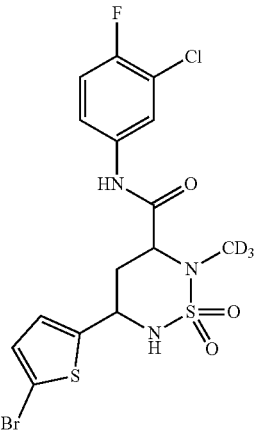

HBV-CSU-370

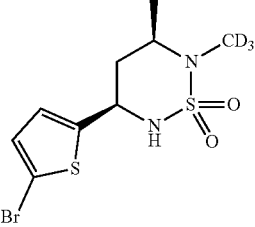

HBV-CSU-370-ISO-I

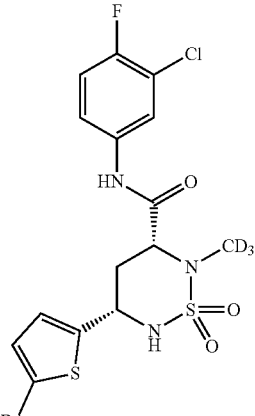

HBV-CSU-370-ISO-II

The above titled compounds have been synthesized by following the general procedure described above for reduction by using corresponding HBV-CSU-370_Int (see Table 2 for analytical data).

Scheme 62
Synthesis of Cis-N-(3-Chloro-4-fluorophenyl)-2-methyl-5-(5-(1-(methyl-d₃)-1H-imidazol-4-yl)thiazol-2-yl)-1,2,6-thiadiazinane-3,4,5-d₃-3-carboxamide 1,1-dioxide (HBV-CSU-371, HBV-CSU-371-ISO-I & HBV-CSU-371-ISO-I)
Scheme 62:
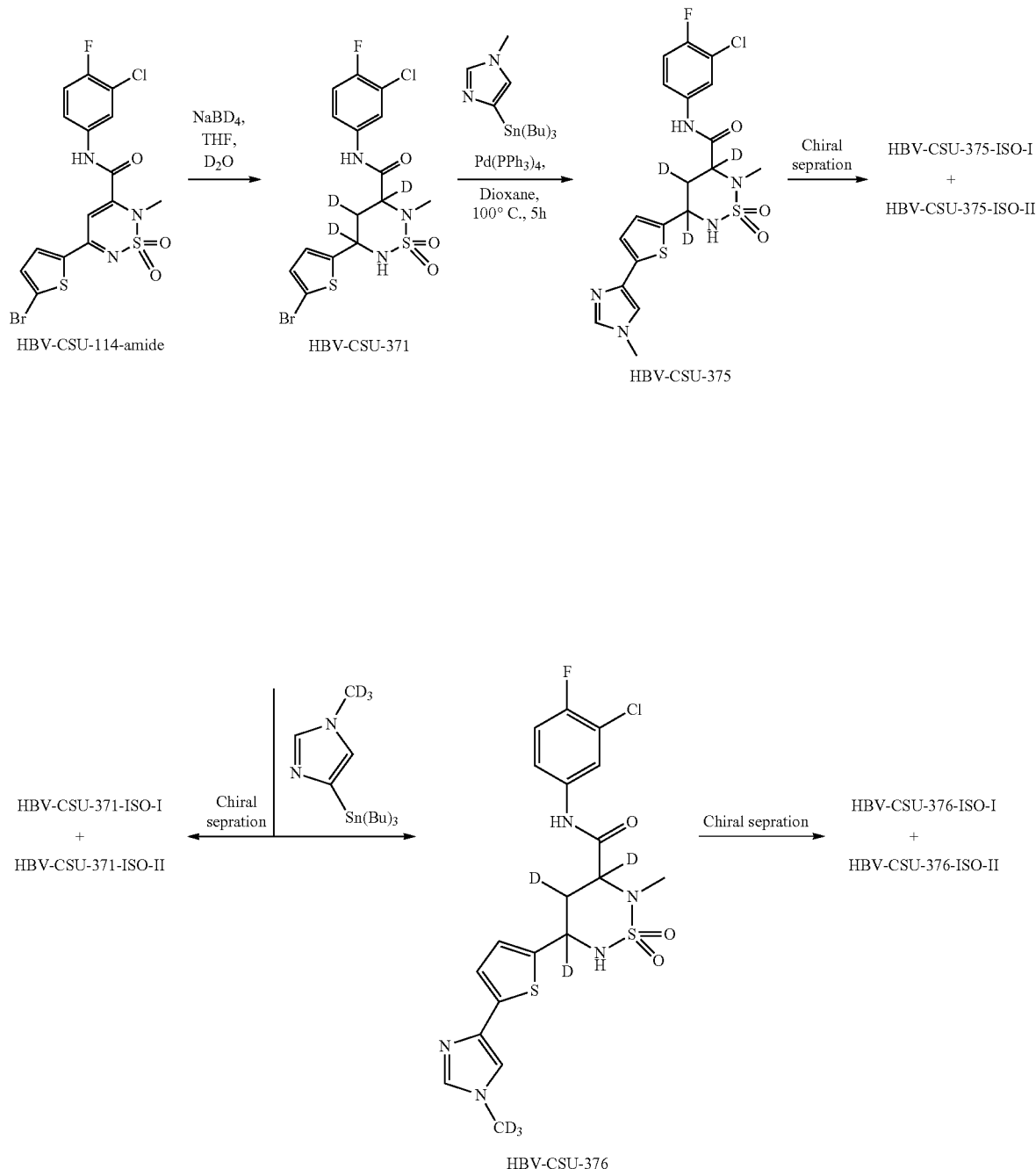

Cis-5-(5-Bromothiophen-2-yl)-N-(3-chloro-4-fluorophenyl)-2-methyl-1,2,6-thiadiazinane-3,4,5-d₃-3-carboxamide 1,1-dioxide (HBV-CSU-371, HBV-CSU-371-ISO-I & HBV-CSU-371-ISO-I)

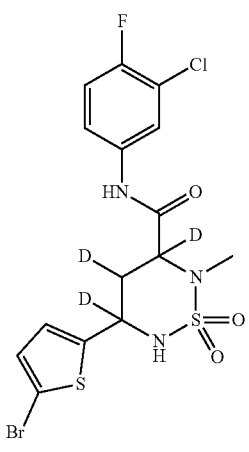

HBV-CSU-371

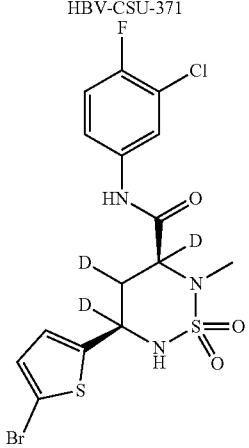

HBV-CSU-371-ISO-I

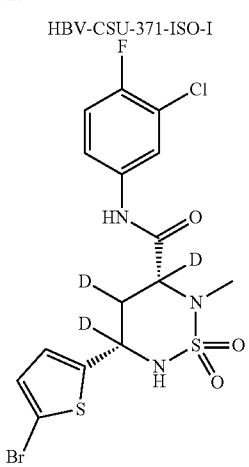

HBV-CSU-371-ISO-II

To a stirred solution of compound HBV-CSU-114-amide (3 g, 6.25 mmol) in THF:D₂O (1:1, 30 mL) mixture at 0° C. under Ar atmosphere, NaBD₄ (0.523 g, 12.5 mmol) was added and stirred at room temperature for 30 min. The progress of the reaction was monitored by TLC and LCMS. After completion, the reaction mixture was concentrated in vacuo. The crude compound was purified by silica gel column chromatography to afford compound HBV-CSU-371 (2 g, 66.6%) as a white solid. TLC: 50% EtOAc/hexanes (R$_f$: 0.3); Cis-N-(3-Chloro-4-fluorophenyl)-2-methyl-5-(5-(1-methyl-1H-imidazol-4-yl)thiophen-2-yl)-1,2,6-thiadiazinane-3,4,5-d₃-3-carboxamide 1,1-dioxide (HBV-CSU-375, HBV-CSU-375-ISO-I & HBV-CSU-375-ISO-I)

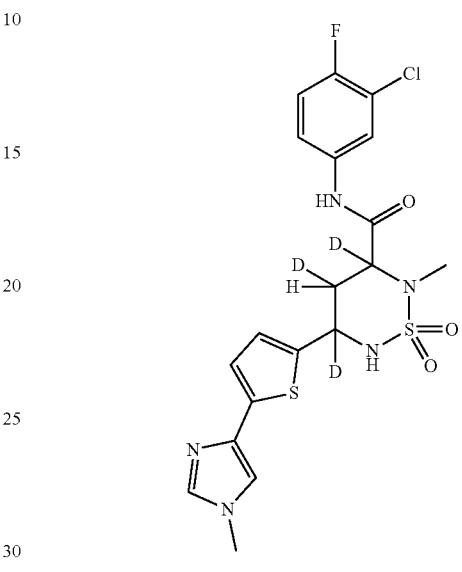

HBV-CSU-375

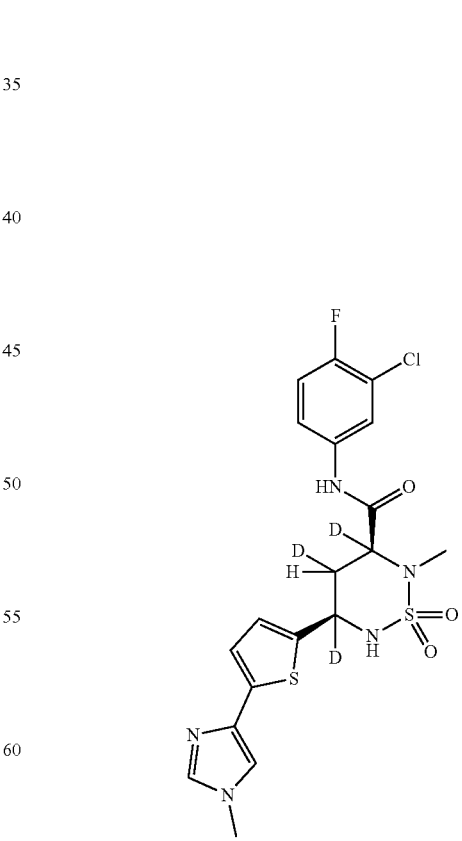

HBV-CSU-375-ISO-I

517

-continued

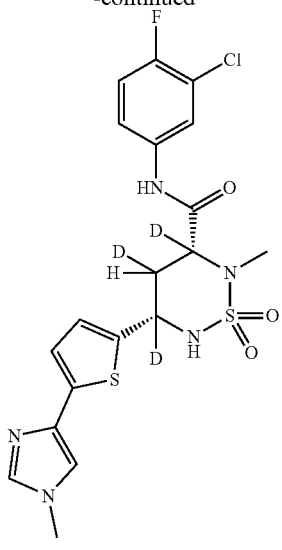

HBV-CSU-375-ISO-II

The above titled compounds have been synthesized by following the general procedure described above for Stille coupling by using HBV-CSU-371 and corresponding stannane (see Table 2 for analytical data).

Cis-N-(3-Chloro-4-fluorophenyl)-2-methyl-5-(5-(1-(methyl-d$_3$)-1H-imidazol-4-yl)thiophen-2-yl)-1,2,6-thiadiazinane-3,4,5-d$_3$-3-carboxamide 1,1-dioxide (HBV-CSU-376, HBV-CSU-376-ISO-I & HBV-CSU-376-ISO-I)

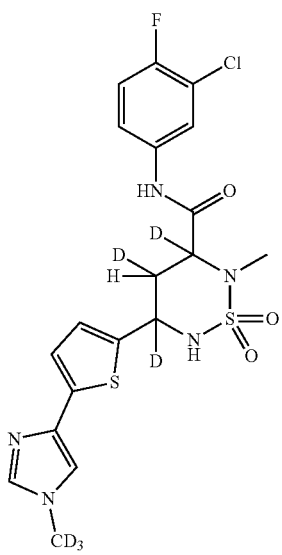

HBV-CSU-376

518

-continued

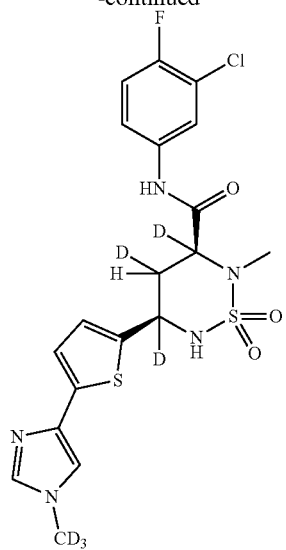

HBV-CSU-376-ISO-I

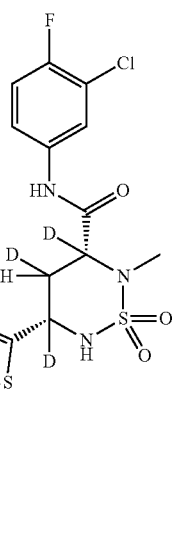

HBV-CSU-376-ISO-II

The above titled compounds have been synthesized by following the general procedure described above for Stille coupling by using HBV-CSU-371 and corresponding stannane (see Table 2 for analytical data).

Scheme 63

Synthesis of Cis-5-(5-bromothiophen-2-yl)-N-(3-chloro-4-fluorophenyl)-2-(methyl-$d_3$)-1,2,6-thiadiazinane-3,4,5-$d_3$-3-carboxamide 1,1-dioxide (HBV-CSU-372, HBV-CSU-372-ISO-I & HBV-CSU-372-ISO-I), Cis-N-(3-chloro-4-fluorophenyl)-2-(methyl-$d_3$)-5-(5-(1-methyl-1H-imidazol-4-yl)thiophen-2-yl)-1,2,6-thiadiazinane-3,4,5-d3-3-carboxamide HBV-CSU-377, HBV-CSU-377-ISO-I & HBV-CSU-377-ISO-I) and Cis-N-(3-chloro-4-fluorophenyl)-2-(methyl-$d_3$)-5-(5-(1-(methyl-$d_3$)-1H-imidazol-4-yl)thiophen-2-yl)-1,2,6-thiadiazinane-3,4,5-$d_3$-3-carboxamide 1,1-dioxide (HBV-CSU-378, HBV-CSU-378-ISO-I & HBV-CSU-378-ISO-I)

Scheme 63:

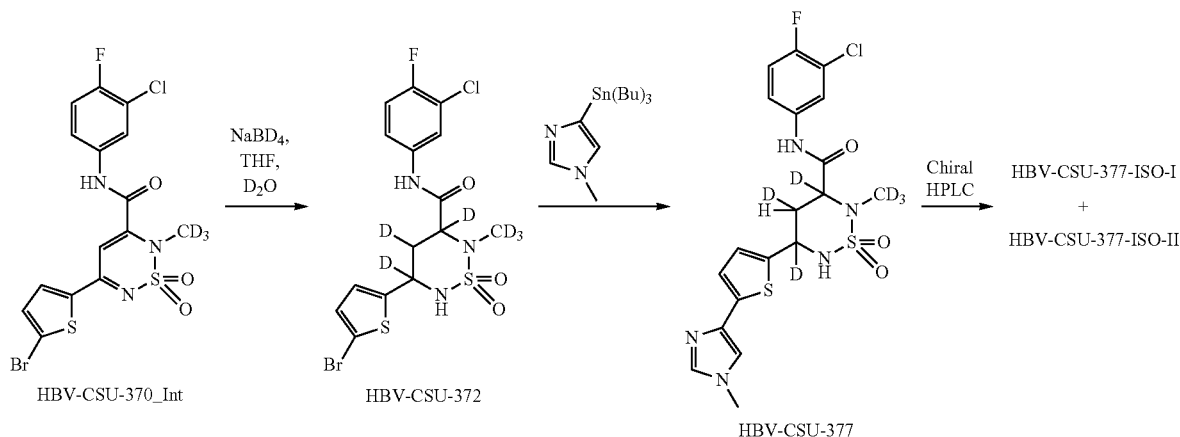

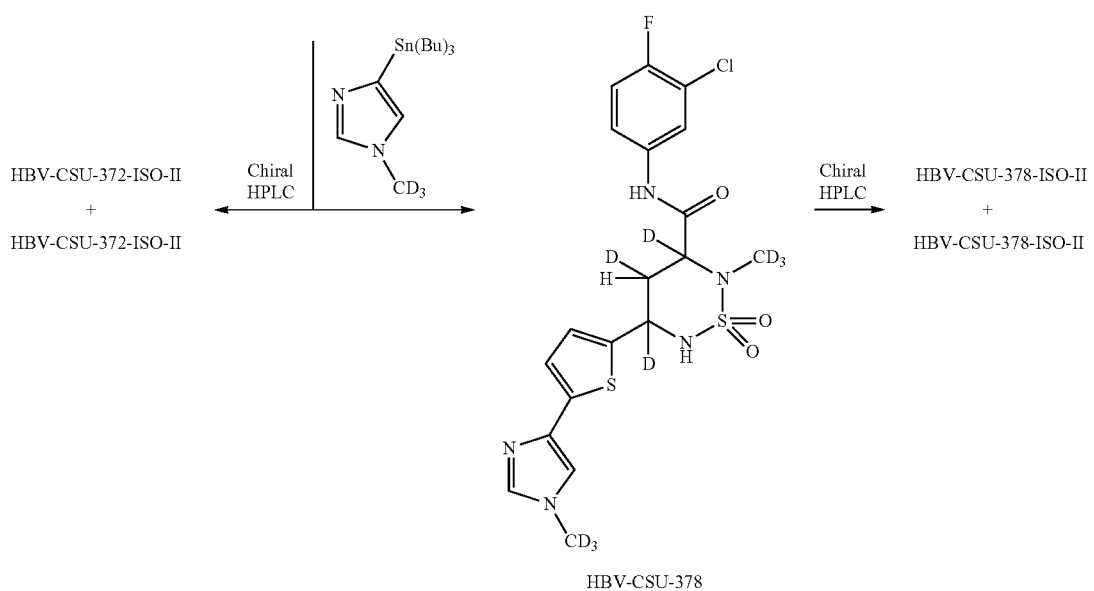

Synthesis of Cis-5-(5-bromothiophen-2-yl)-N-(3-chloro-4-fluorophenyl)-2-(methyl-d₃)-1,2,6-thiadiazinane-3,4,5-d₃-3-carboxamide 1,1-dioxide (HBV-CSU-372, HBV-CSU-372-ISO-I & HBV-CSU-372-ISO-I, E17107-097)

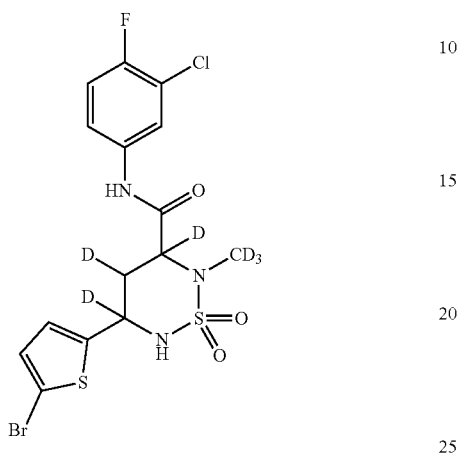

To a stirred solution of compound HBV-CSU-370_Int (1.5 g, 3.11 mmol) in THF:D₂O (1:1, 20 mL) mixture at 0° C. under Ar atmosphere, NaBD₄ (0.261 g, 6.22 mmol) was added and stirred at room temperature for 2 h. The progress of the reaction was monitored by TLC and LCMS. After completion, the reaction mixture was concentrated in vacuo. The crude compound was purified by silica gel column chromatography using 2% MeOH/DCM to afford compound HBV-CSU-372 (1.2 g, 78.94%) as an off white solid. TLC: 30% EtOAc/hexanes ($R_f$: 0.5).

Cis-N-(3-Chloro-4-fluorophenyl)-2-(methyl-d₃)-5-(5-(1-methyl-1H-imidazol-4-yl)thiophen-2-yl)-1,2,6-thiadiazinane-3,4,5-d3-3-carboxamide HBV-CSU-377, HBV-CSU-377-ISO-I & HBV-CSU-377-ISO-I)

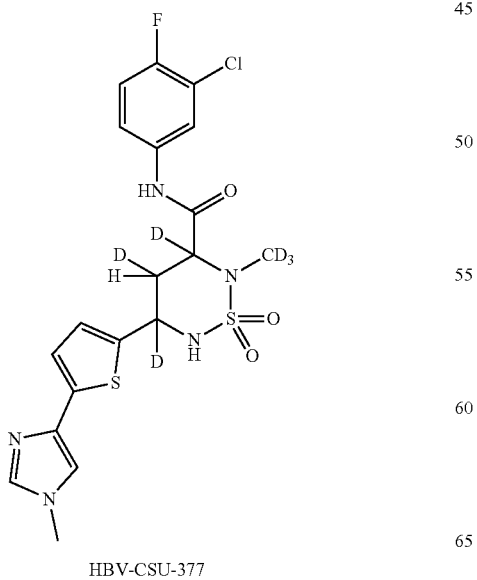

HBV-CSU-377

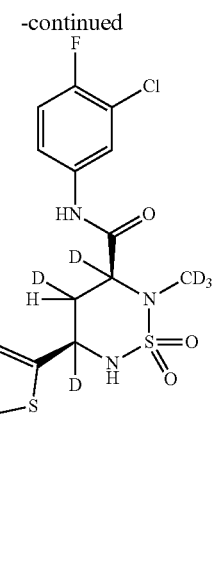

HBV-CSU-377-ISO-I

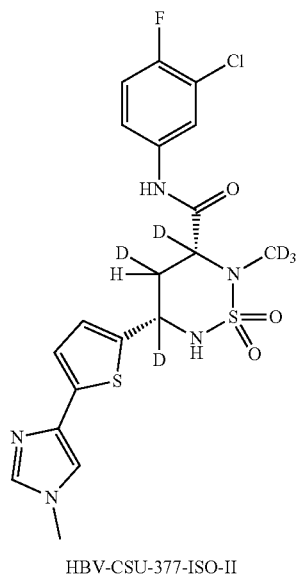

HBV-CSU-377-ISO-II

The above titled compounds have been synthesized by following the general procedure described above for Stille coupling by using HBV-CSU-372 and corresponding stannane (see Table 2 for analytical data).

Cis-N-(3-chloro-4-fluorophenyl)-2-(methyl-d₃)-5-(5-(1-(methyl-d₃)-1H-imidazol-4-yl)thiophen-2-yl)-1,2,6-thiadiazinane-3,4,5-d₃-3-carboxamide 1,1-dioxide (HBV-CSU-378, HBV-CSU-378-ISO-I & HBV-CSU-378-ISO-I)

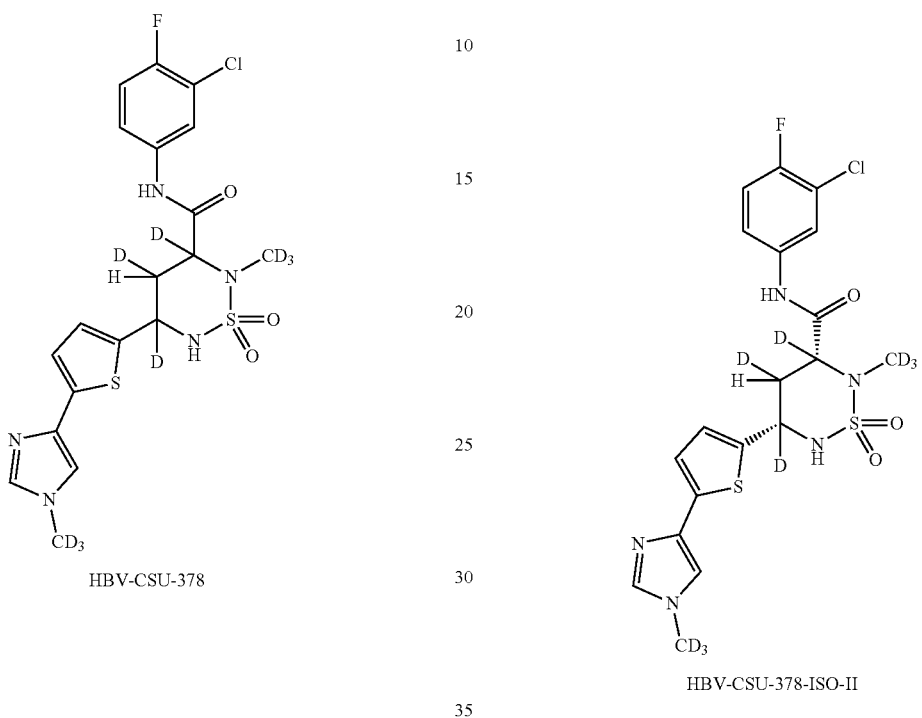

HBV-CSU-378

HBV-CSU-378-ISO-II

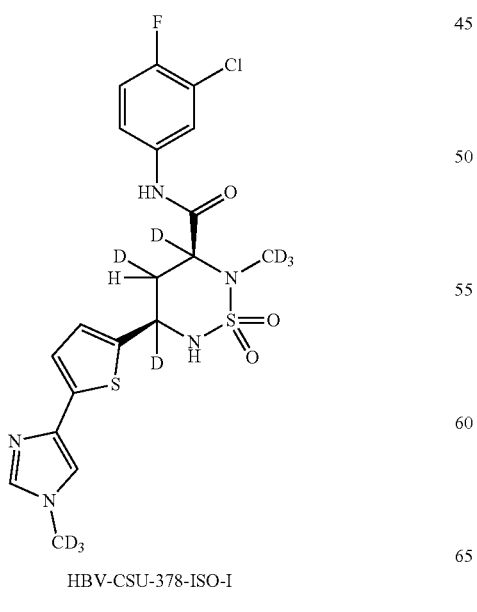

HBV-CSU-378-ISO-I

The above titled compounds have been synthesized by following the general procedure described above for Stille coupling by using HBV-CSU-372 and corresponding stannane (see Table 2 for analytical data).

Scheme 64
Synthesis of Cis-N-(3-Chloro-4-fluorophenyl)-2-(methyl-d₃)-5-(5-(1-methyl-1H-imidazol-4-yl)thiophen-2-yl)-1,2,6-thiadiazinane-3-carboxamide 1,1-dioxide (HBV-CSU-373-ISO-I & HBV-CSU-373-ISO-I) and Cis-N-(3-Chloro-4-fluorophenyl)-2-(methyl-d₃)-5-(5-(1-(methyl-d₃)-1H-imidazol-4-yl)thiophen-2-yl)-1,2,6-thiadiazinane-3-carboxamide 1,1-dioxide (HBV-CSU-374-ISO-I & HBV-CSU-374-ISO-I)
Scheme 64:
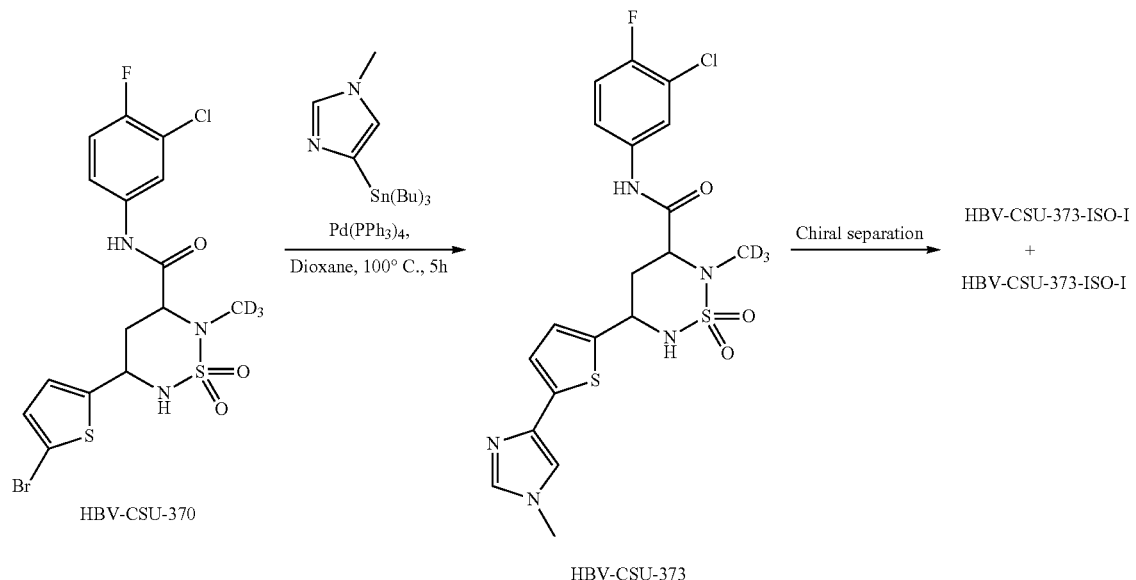
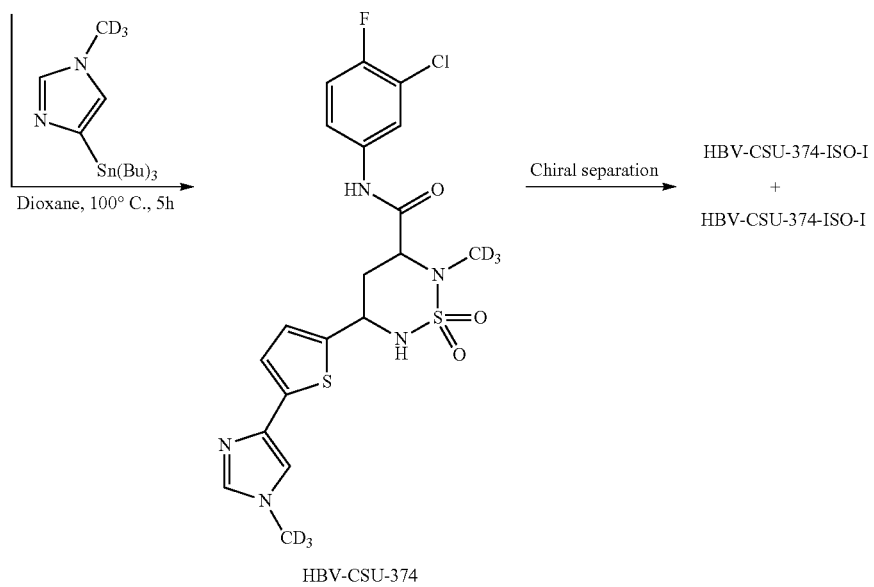

527
Cis-N-(3-Chloro-4-fluorophenyl)-2-(methyl-d₃)-5-(5-(1-methyl-1H-imidazol-4-yl)thiophen-2-yl)-1,2,6-thiadiazinane-3-carboxamide 1,1-dioxide (HBV-CSU-373-ISO-I & HBV-CSU-373-ISO-I)

528
Cis-N-(3-Chloro-4-fluorophenyl)-2-(methyl-d₃)-5-(5-(1-(methyl-d₃)-1H-imidazol-4-yl)thiophen-2-yl)-1,2,6-thiadiazinane-3-carboxamide 1,1-dioxide (HBV-CSU-374-ISO-I & HBV-CSU-374-ISO-I)

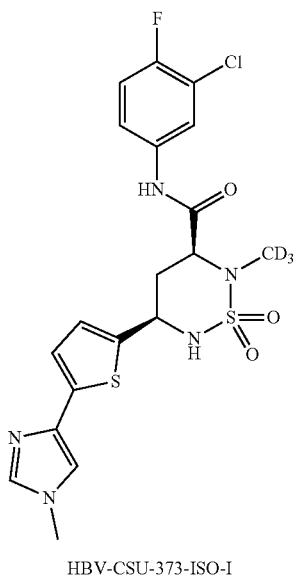

HBV-CSU-373-ISO-I

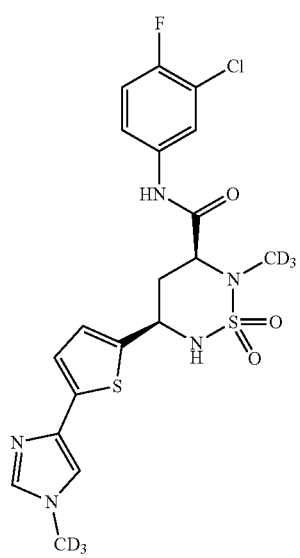

HBV-CSU-374-ISO-I

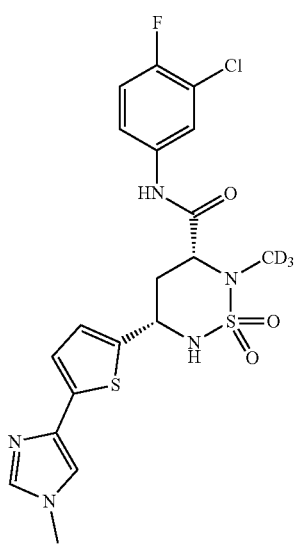

HBV-CSU-373-ISO-II

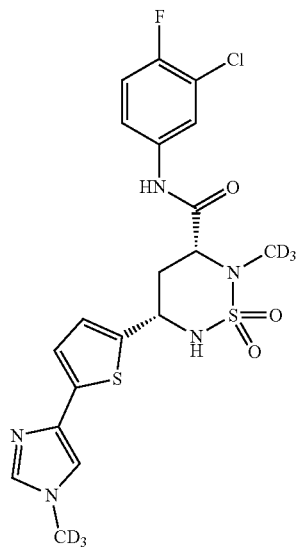

HBV-CSU-374-ISO-I

The above titled compounds have been synthesized by following the general procedure described above for Stille coupling by using HBV-CSU-370 and corresponding stannane (see Table 2 for analytical data).

The above titled compounds have been synthesized by following the general procedure described above for Stille coupling by using HBV-CSU-370 and corresponding stannane (see Table 2 for analytical data).

Scheme 65

Synthesis of Cis-5-(5-bromothiophen-2-yl)-N-(3-chloro-4-fluorophenyl)-2-(methyl-d₃)-1,2,6-thiadiazinane-3,4,5-d₃-3-carboxamide 1,1-dioxide (HBV-CSU-379, HBV-CSU-379-ISO-I & HBV-CSU-379-ISO-I)

Scheme 65:

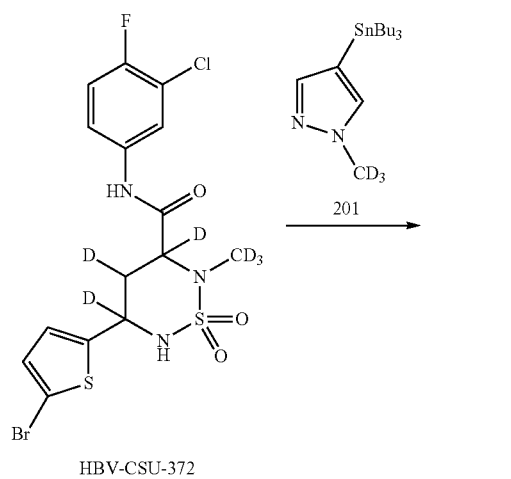

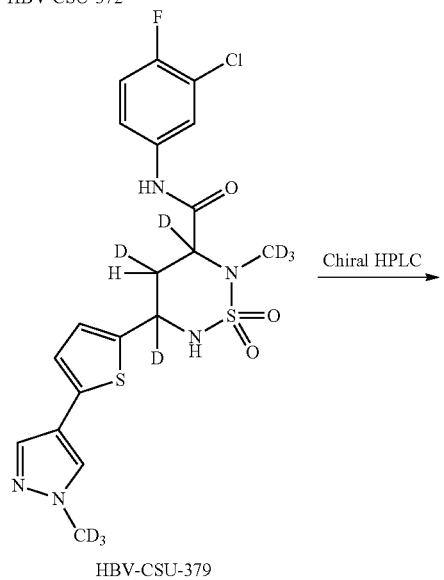

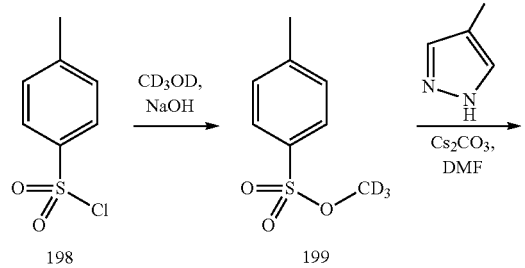

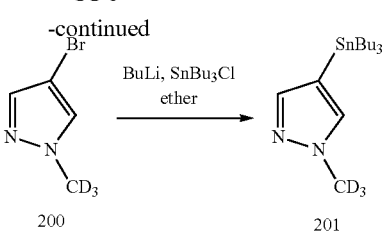

Synthesis of methyl-d₃ 4-methylbenzenesulfonate (199)

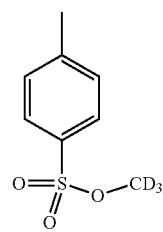

Titled compound was prepared using the reported method in Journal of Organic Chemistry, 81(17), 7675-7684; 2016.

Synthesis of 4-Bromo-1-(methyl-d₃)-1H-pyrazole (200)

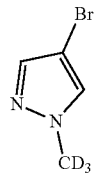

To a stirred solution of 4-bromo-1H-pyrazole (5 g, 34.01 mmol) in DMF (30 mL), CS$_2$CO$_3$ (33.24 g, 102.05 mmol) was added and stirred for 10 min. To this solution, compound 199 (8.36 g, 51.02 mmol) was added and the reaction mixture was stirred at room temperature for 16 h. The progress of the reaction was monitored by TLC. the After completion, the reaction mixture was diluted with water and extracted with ethyl acetate. The combined organic layers were washed with brine, dried over anhydrous sodium sulfate and evaporated under reduced pressure to afford the title compound 200 (4 g, 72.72%) as a white solid. TLC: 50% EtOAc/hexanes (R$_f$: 0.3); LCMS Calculated for C$_4$H$_2$D$_3$BrN$_2$: 162.98; LCMS observed: 165.95 (M+2)$^+$.

Synthesis of 1-(methyl-d₃)-4-(tributylstannyl)-1H-pyrazole (201)

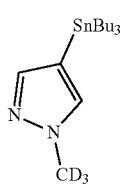

To a stirred solution of compound 200 (1 g, 6.09 mmol) in diethyl ether (10 mL) at −78° C. under Ar atmosphere, n-BuLi (2.5 M, 2.68 mL, 6.69 mmol) was added dropwise and stirred at same temperature for 30 min. To this solution, tributyl tin chloride (1.18 mL, 6.69 mmol) was added at −78° C. slowly, which was then warmed to −60° C. and stirred for 1 h. The resulting reaction mixture was stirred at room temperature for 1 h. The reaction was monitored by TLC. After completion of the reaction, the reaction mixture was quenched with saturated ammonium chloride and extracted with ethyl acetate. The combined organic extracts were washed with water, brine, then dried over anhydrous sodium sulfate, filtered, and concentrated in vacuo to obtain the crude stannane compound. The crude compound was purified by silica gel column chromatography to afford the title compound 201 (0.5 g, 21.92%) as a yellow oil. TLC: 20% EtOAc/hexanes ($R_f$: 0.5) LCMS Calculated for $C_{16}H_{29}D_3N_2Sn$: 375.18; LCMS observed: 376.1 (M+1)$^+$.

Synthesis of Cis-N-(3-Chloro-4-fluorophenyl)-2-(methyl-d$_3$)-5-(5-(1-(methyl-d$_3$)-1H-pyrazol-4-yl)thiophen-2-yl)-1,2,6-thiadiazinane-3,4,5-d$_3$-3-carboxamide 1,1-dioxide (HBV-CSU-379, HBV-CSU-379-ISO-I & HBV-CSU-379-ISO-I)

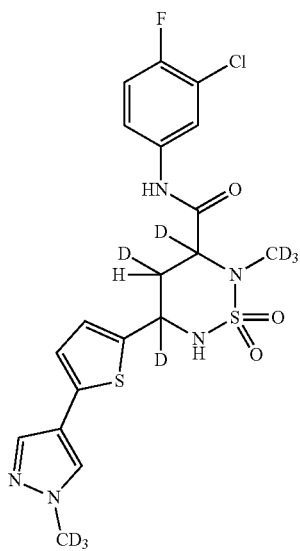

HBV-CSU-379

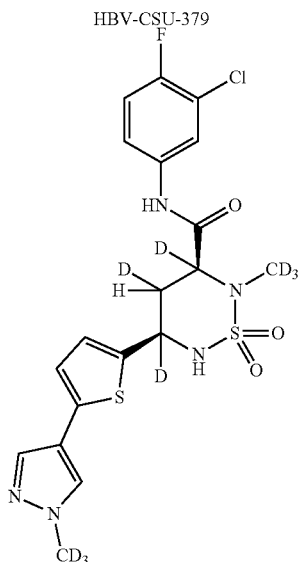

HBV-CSU-379-ISO-I

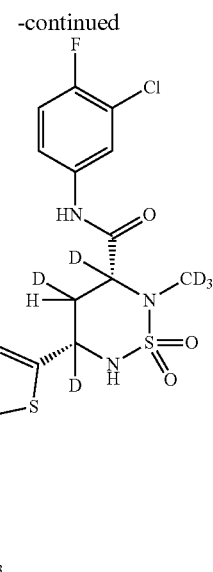

HBV-CSU-379-ISO-II

The above titled compounds have been synthesized by following the general procedure described above for Stille coupling by using HBV-CSU-372 and compound 201 (see Table 2 for analytical data).

Scheme 66

Synthesis of (3S,5R)-5-(5-Bromothiophen-2-yl)-N-(3-chloro-4-fluorophenyl)-2-methyl-1,2,6-thiadiazinane-3-carboxamide 1,1-dioxide (HBV-CSU-114-ISO-I; ATH approach)

Scheme 66:

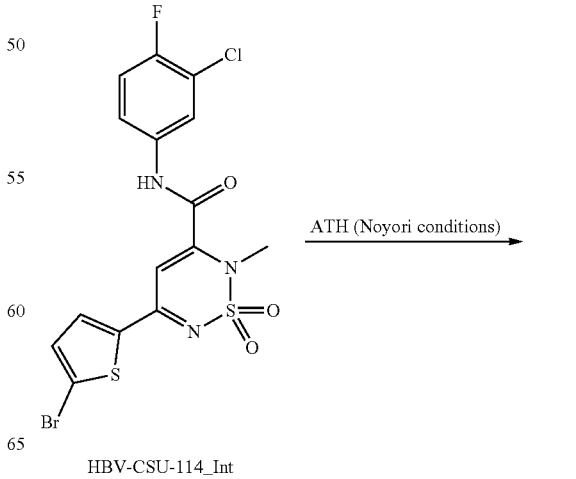

HBV-CSU-114_Int

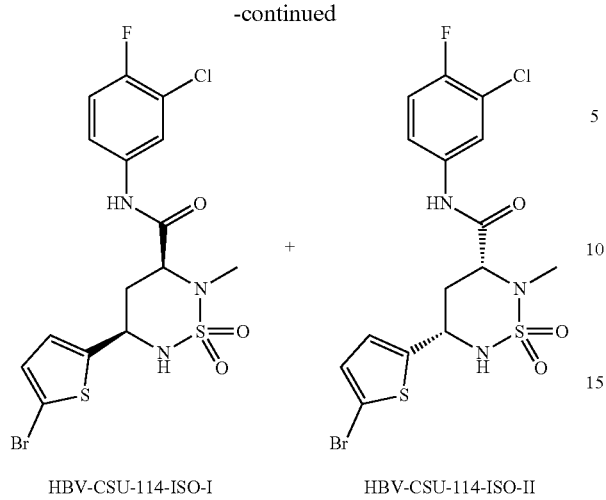

HBV-CSU-114-ISO-I  HBV-CSU-114-ISO-II

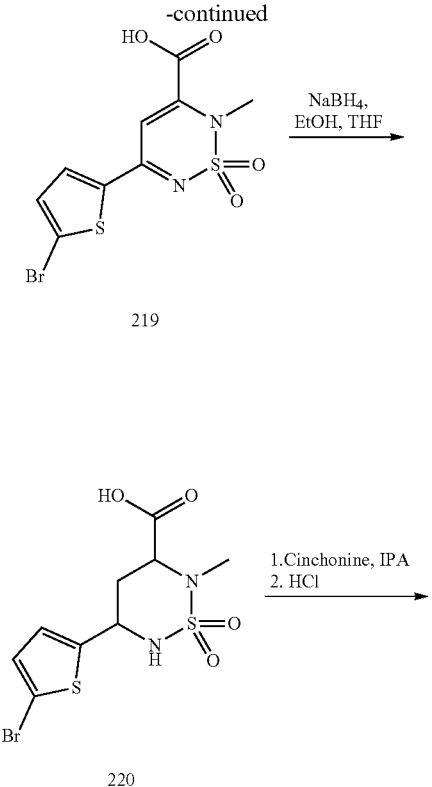

To a solution of HBV-CSU-114_Int (1 eq.) & Noyori catalyst 3a (0.1 eq.) in dichloromethane (0.2M) was added 5 eq. of formic acid {85% w/w in water} followed by 2 eq. of DIPEA. The reaction mixture was stirred at room temperature for 16 h. The progress of reaction was monitored by TLC and LCMS. After completion, the reaction mixture was diluted with water and extracted using ethyl acetate. The combined organic layer was dried over anhydrous sodium sulphate, filtered and concentrated to give crude material which was purified using combiflash chromatography to afford desired product. The enantioselectivity was confirmed using chiral HPLC.

General Protocol for the Synthesis of Noyori Catalyst:

A mixture of [RuCl$_2$(η6-p-cycmene)]$_2$ (1 eq.), (1S,2S)-(+)-N-p-Tosyl-1,2-diphenylethylenediamine (2 eq.) and triethyl amine (4 eq.) in propanol (25V) was heated at 80° C. for 2 h. The solvents was evaporated and the solid material obtained after filtration was washed with water and dried under vacuo to afford {Noyori (S, S) catalyst} i.e. RuCl [(1S,2S)-p-TsNCH (C$_6$H$_5$) NH$_2$] (η6-p-cycmene) as orange colored solid. The catalyst was recrystallized using methanol. The desired catalyst formation was confirmed by $^1$H NMR and LCMS (see Table 2 for analytical data).

Scheme 67

Synthesis of (3S,5R)-N-(3-chloro-4-fluorophenyl)-2-methyl-5-(5-(1-methyl-1H-imidazol-4-yl)thiophen-2-yl)-1,2,6-thiadiazinane-3-carboxamide 1,1-dioxide (HBV-CSU-266-ISO-I; Resolution of Acid by Cinchonine Approach)

Scheme 67:

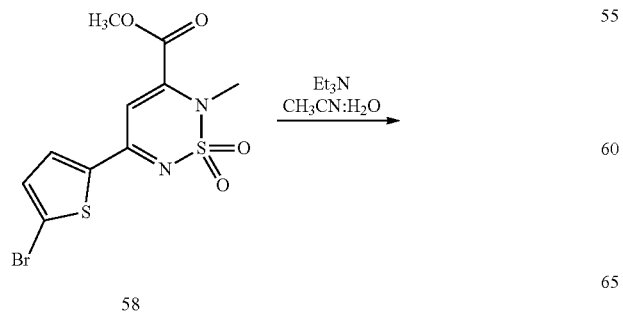

58

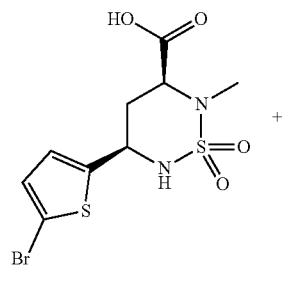

220

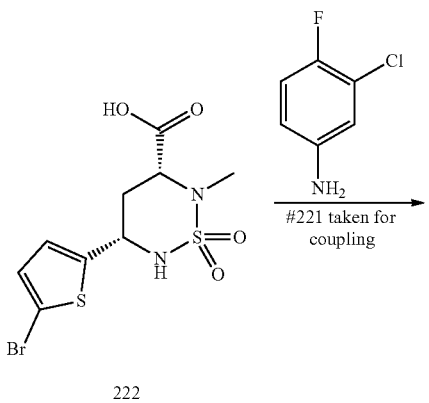

222

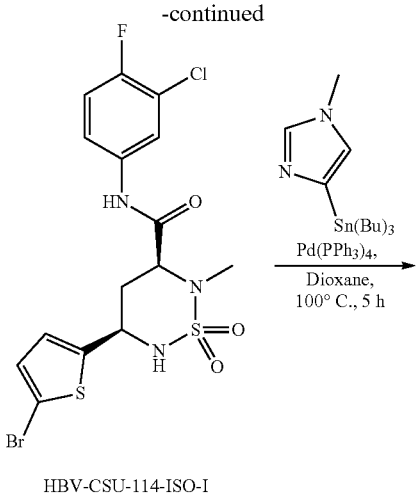

HBV-CSU-114-ISO-I

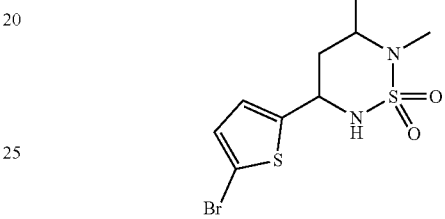

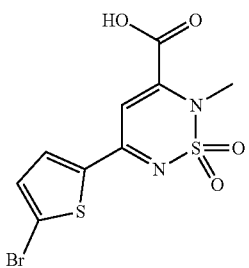 [SMILES: CN1C(C(=O)O)=CC(c2ccc(Br)s2)=NS1(=O)=O]

HBV-CSU-266-ISO-I

Synthesis of 5-(5-bromothiophen-2-yl)-2-methyl-2H-1,2,6-thiadiazine-3-carboxylic acid 1,1-dioxide (219)

To a solution of compound 58 (65 g, 178.08 mmol) in 700 mL (10.8V) of CH$_3$CN:H$_2$O (1:1) at 0° C. was added TEA (124 mL, 890.41 mmol) and the resulting reaction mixture was stirred at the same temperature till clear solution was observed (usually 4-6 h). The progress of reaction was monitored by TLC. After completion, the reaction mixture was concentrated under reduced pressure, and residue obtained was acidified with 6N HCl and extracted with ethyl acetate. The combined organic layer was dried over anhydrous sodium sulphate, filtered and concentrated under reduced pressure to afford Compound 219 (57 g, 91%) as a brown solid. TLC: 5% MeOH/DCM (R$_f$: 0.3); $^1$H NMR (DMSO-d$_6$, 400 MHz): δ 11.0 (br.s, 1H), 8.10 (d, J=4.0 Hz, 1H), 7.45 (d, J=4.0 Hz, 1H), 7.19 (s, 1H), 3.51 (s, 3H); HPLC purity: 98.85%, LCMS purity: 97.50%; LCMS Calculated for C$_9$H$_7$BrN$_2$O$_4$S$_2$: 349.90; LCMS observed: 352.90 (M+2)$^+$.

Synthesis of 5-(5-bromothiophen-2-yl)-2-methyl-1,2,6-thiadiazinane-3-carboxylic acid 1,1-dioxide (220)

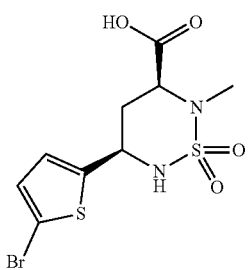 [SMILES: CN1[C@H](C(=O)O)C[C@H](c2ccc(Br)s2)NS1(=O)=O]

To a stirred solution of Compound 219 (40 g, 114.3 mmol) in 500 mL of EtOH:THF (9:1) at 0° C. under Ar atmosphere, NaBH$_4$ (8.6 g, 228.6 mmol) was added and the reaction mixture was stirred at room temperature for 3 h. The progress of the reaction was monitored by TLC & LCMS. After completion, the reaction mixture was concentrated in vaccuo. The residue was diluted with water and extracted using diethyl ether. The combined organic layers were collected; dried over anhydrous sodium sulphate, filtered and concentrated in vaccuo to afford Compound 220 (Cis racemic) (32 g, 75%) as a light brown solid. TLC: 10% MeOH/DCM (R$_f$: 0.1); $^1$H NMR (DMSO-d$_6$, 400 MHz): δ 11.39 (s, 1H), 7.60 (d, J=9.2 Hz, 1H), 7.11 (d, J=4.0 Hz, 1H), 6.97 (d, J=4.0 Hz, 1H), 4.76-4.70 (m, 1H), 4.20 (dd, J=12.0, 2.8 Hz, 1H), 2.60 (s, 3H), 2.21-2.15 (m, 1H), 1.98-1.89 (m, 1H); HPLC purity: 99.23%, LCMS purity: 99.87%; LCMS Calculated for C$_9$H$_{11}$BrN$_2$O$_4$S$_2$: 353.93; LCMS observed: 354.90 (M+1).

Synthesis of (3S,5R)-5-(5-bromothiophen-2-yl)-2-methyl-1,2,6-thiadiazinane-3-carboxylic acid 1,1-dioxide (Compound 221) & (3R,5S)-5-(5-bromothiophen-2-yl)-2-methyl-1,2,6-thiadiazinane-3-carboxylic acid 1,1-dioxide (Compound 222)

Racemic Compound 220 (40.0 g, 112.9 mmol) was dissolved in 1.2 L of IPA (~30V) after which Cinchonine (33.3 g, 112.9 mmol) was added and the reaction mixture was heated at 90° C. for 2 h (Clear solution was observed). The solid was precipitated out at the same temperature after 10-20 min. The reaction mixture was then allowed to cool down to accelerate the crystallization and kept at room temperature for overnight. After crystallization both mother liquor and crystals were analyzed by HPLC on chiral amylose SA column (eluent; DCM:MeOH 50:50) after acidification followed by extraction to determine the relative amount of Compound 221-salt and Compound 222-salt. The analysis showed enantiomeric enrichment of both the crystals. Then both isomers were isolated (#211-salt, 38 g) and the mother liquor (#222-salt, 43 g).

A suspension of 38 g of Compound 221-salt in 150 mL of ethyl acetate was acidified to a pH of 1.0 with 4N aq. HCl at 0° C. The organic layer was separated and aqueous layer was further extracted with ethyl acetate (3×50 mL). The combined organic layers were concentrated, dried over anhydrous sodium sulphate, filtered and concentrated to give 16 g of Compound 221 (Chiral HPLC 95.5%).

Analytical Data for Compound 221:

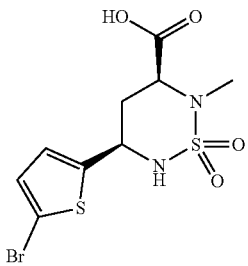

$^1$H NMR (DMSO-$d_6$, 400 MHz): δ 13.41 (s, 1H), 7.59 (d, J=8.8 Hz, 1H), 7.10 (d, J=4.0 Hz, 1H), 6.97-6.96 (m, 1H), 4.76-4.70 (m, 1H), 4.22-4.19 (m, 1H), 2.59 (s, 3H), 2.19-2.15 (m, 1H), 1.98-1.88 (m, 1H); HPLC purity: 99.53%; HPLC chiral purity: 94.29%;

Analytical data for Compound 222:

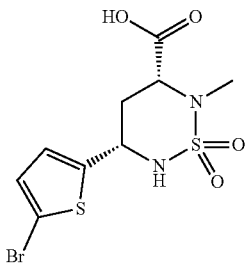 [SMILES: CN1[C@@H](C(=O)O)C[C@@H](c2ccc(Br)s2)NS1(=O)=O]

$^1$H NMR (DMSO-$d_6$, 400 MHz): δ 13.02 (s, 1H), 7.60 (d, J=8.8 Hz, 1H), 7.11 (d, J=4.0 Hz, 1H), 6.98-6.97 (m, 1H), 4.77-4.72 (m, 1H), 4.24-4.20 (m, 1H), 2.61 (s, 3H), 2.21-2.16 (m, 1H), 1.99-1.90 (m, 1H); HPLC purity: 94.55%; HPLC chiral purity: 87.87%;

Synthesis of (3S,5R)-5-(5-bromothiazol-2-yl)-N-(3-chloro-4-fluorophenyl)-2-methyl-1,2,6-thiadiazinane-3-carboxamide 1,1-dioxide (HBV-CSU-114-ISO-I)

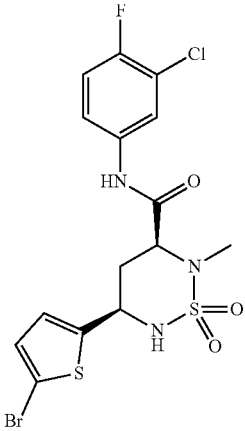

To a stirred solution of Compound 221 (14 g, 39.6 mmol) in DCM (14V, 200 mL) at 0° C. was added DIPEA (21.0 mL, 118.6 mmol), stirred for 15 min, followed by addition of HATU (22.5 g, 59.3 mmol), again stirred for 15 min and then aniline compound (6.3 g, 43.5 mmol) was added. The reaction mixture was then stirred at room temperature for overnight. The progress of the reaction was monitored by TLC. After completion, the reaction mixture was diluted with ice cold water and extracted with DCM. The combined organic layers were dried over anhydrous sodium sulphate and concentrated under reduced pressure to afford a crude compound. The crude compound was purified using silica gel column chromatography to afford HBV-CSU-114-ISO-I (15 g, 79%) as a light brown solid. (see Table 2 for analytical data).

Synthesis of (3S,5R)-N-(3-chloro-4-fluorophenyl)-2-methyl-5-(5-(1-methyl-1H-imidazol-4-yl)thiazol-2-yl)-1,2,6-thiadiazinane-3-carboxamide 1,1-dioxide (HBV-CSU-266-ISO-I)

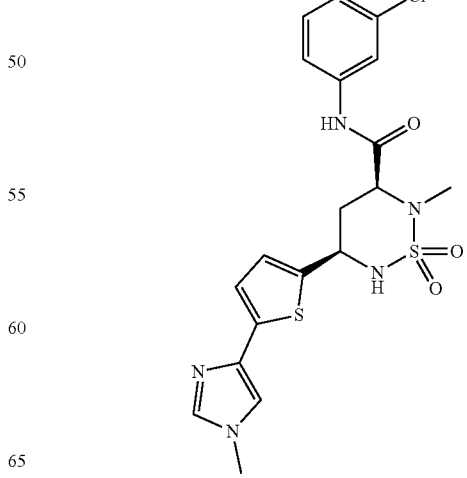

To a stirring solution of HBV-CSU-114-ISO-I (14 g, 28.9 mmol) in dioxane (11V, 150 mL) was added 1-methyl-4-(tributylstannyl)-1H-imidazole (12.9 g, 34.79 mmol) and purged under Ar atmosphere for 10 min; added Pd(PPh$_3$)$_4$ (3.34 g, 2.89 mmol) in a sealed tube; heated to 100° C. and stirred for 4 h. The reaction was monitored by TLC; after completion the reaction the volatiles were removed in vacuo to obtain the crude. The residue obtained was dissolved in 10% MeOH in DCM (35V, 500 mL) and washed with 20% aq. KF (3×200 mL). The organic layer was then dried over anhydrous sodium sulphate, filtered and concentrated to give crude material which was purified through silica gel flash column chromatography using 2% MeOH/CH$_2$Cl$_2$ to afford HBV-CSU-266-ISO-I (11.3 g, 80.5%) as an off-white solid (see Table 2 for analytical data).

Scheme 68

Synthesis of (3S,5R)-N-(3-chloro-4-fluorophenyl)-2-methyl-5-(5-(1-methyl-1H-imidazol-4-yl)thiazol-2-yl)-1,2,6-thiadiazinane-3-carboxamide 1,1-dioxide (HBV-CSU-276-ISO-I; Resolution of Acid by Cinchonine Approach)

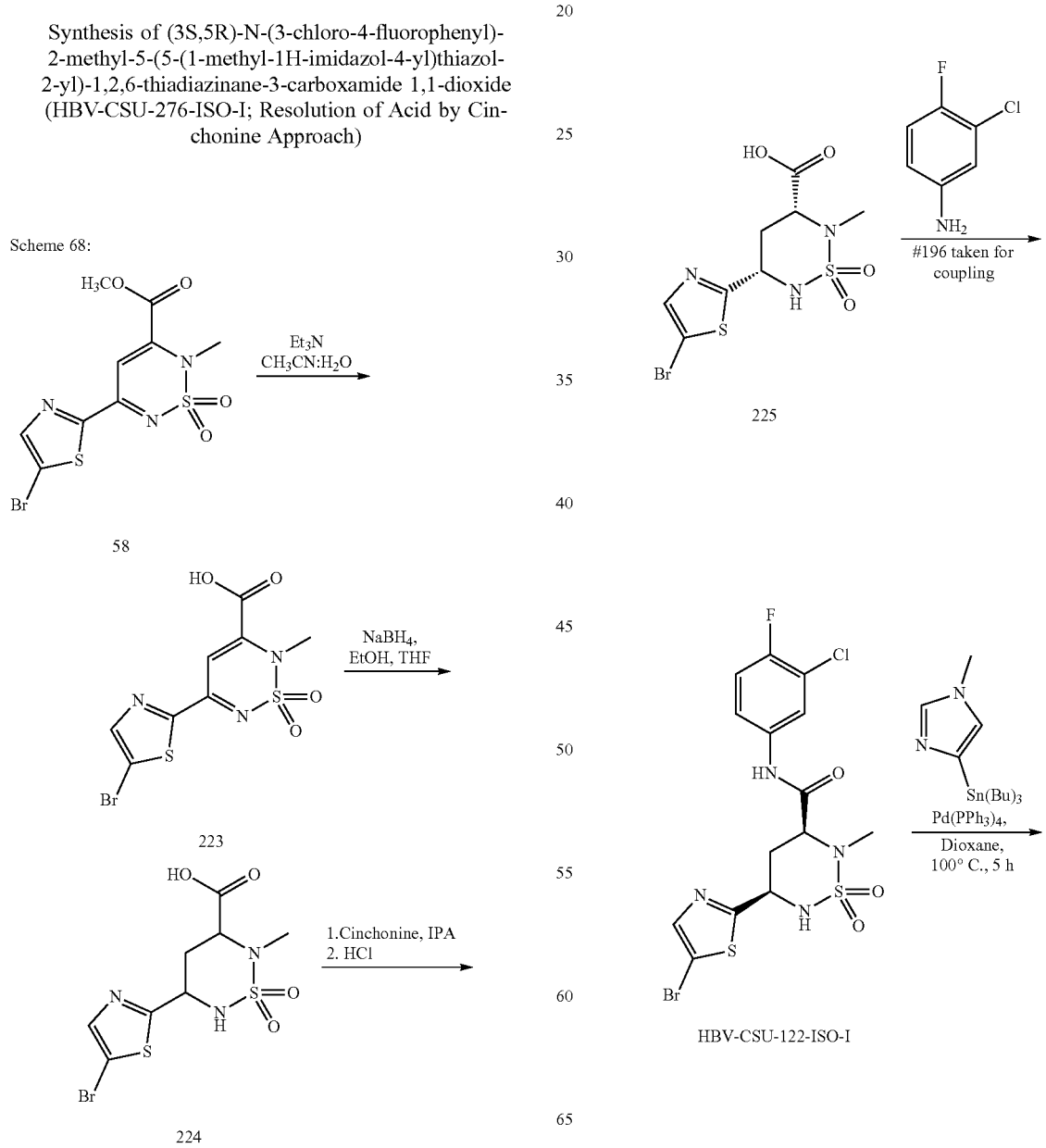

-continued

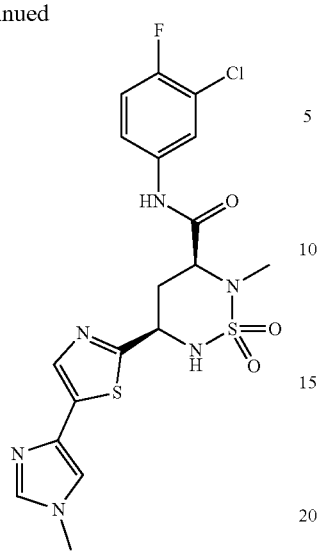

HBV-CSU-276-ISO-I

Synthesis of 5-(5-bromothiazol-2-yl)-2-methyl-2H-1,2,6-thiadiazine-3-carboxylic acid 1,1-dioxide (223)

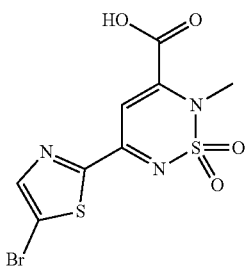 [SMILES: CN1C(C(=O)O)=CC(c2ncc(Br)s2)=NS1(=O)=O]

To a stirring solution of compound 74 (230 g, 606.8 mmol) in $CH_3CN:H_2O$ (1:1, 2300 mL, 10V) was added triethylamine (423 mL, 3034.3 mmol) at 0° C., 15 min, then room temperature for 3.5 h (color change from light yellow to brown was observed after 2 h and then reaction mixture became clear after 1 h). The progress of reaction was monitored by TLC (40% ethyl acetate in hexane). After completion, the reaction mixture was concentrated under reduced pressure; the residue obtained was diluted with water (2 L) and extracted with di-ethyl ether (3×500 mL) (an organic layer showed some compound by LCMS, which was after concentration provided ~8 g of desired compound with ~60% LCMS purity). The aqueous layer was acidified with 400 mL of 2N HCl at 0° C. up to pH~2-4, precipitated solid was filtered washed with water (200 mL), dried under vacuo to afford Compound 223 (190 g, 88.95%) as a light yellow solid. TLC: 30% EtOAc/hexane ($R_f$: 0.1); $^1H$ NMR (DMSO-$d_6$, 400 MHz): δ 8.30 (s, 1H), 7.21 (s, 1H), 3.59 (s, 3H) (NMR showed some trapped triethyl amine); HPLC purity: 91.45%; LCMS purity: 91.38%; LCMS Calculated for $C_8H_6BrN_3O_4S_2$: 350.90; LCMS observed: 353.90 $(M+2)^+$.

Synthesis of 5-(5-bromothiazol-2-yl)-2-methyl-1,2,6-thiadiazinane-3-carboxylic acid 1,1-dioxide (224)

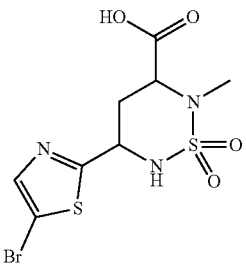

To a stirred solution of Compound 223 (190 g, 539 mmol) in 2 L of EtOH:THF (10.5V, 3:1) at 0° C. under Ar atmosphere, $NaBH_4$ (40.83 g, 1079 mmol) was added portion wise and the reaction mixture was stirred at room temperature for 3 h (During addition of $NaBH_4$, reaction mixture becomes thick). The progress of the reaction was monitored by TLC. After completion, the reaction mixture was concentrated under reduced pressure. The residue obtained was diluted with water (1 L) and extracted with di-ethyl ether (2×200 mL). The organic layer was discarded and aqoues layer was acidified with 200 mL of 4N HCl at 0° C. up to pH~4, precipitated solid was filtered washed with water (200 mL), dried under vacuo to afford compound 224 (Cis racemic) (170 g, 88.47%) as an off-white solid. TLC: 15% MeOH/DCM ($R_f$: 0.2); $^1H$ NMR (DMSO-$d_6$, 400 MHz): δ 13.4 (br.s, 1H), 7.88 (s, 1H), 7.82 (d, J=9.6 Hz, 1H), 4.93-4.87 (m, 1H), 4.32-4.28 (m, 1H), 2.63 (s, 3H), 2.37-2.32 (m, 1H), 2.05-1.95 (m, 1H); HPLC purity: 95.57%, LCMS purity: 92.44%; LCMS Calculated for $C_8H_{10}BrN_3O_4S_2$: 354.93; LCMS observed: 355.95 $(M)^+$ Synthesis of 5-(5-bromothiazol-2-yl)-2-methyl-1,2,6-thiadiazinane-3-carboxylic acid 1,1-dioxide (196)

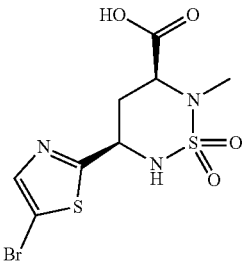 [SMILES: CN1[C@H](C(=O)O)C[C@H](c2ncc(Br)s2)NS1(=O)=O]

Racemic Compound 224 (190 g, 533.39 mmol) was taken in 5.7 L of IPA (~30V), to this suspension Cinchonine (157.03 g, 533.39 mmol) was added and the reaction mixture was heated at 90° C. for 2 h (Clear solution was not observed on large scale due to the precipitated solid at the same temperature). The reaction mixture was then allowed to cool down without any agitation to accelerate the crystallization and kept at room temperature for overnight. The crystallized solid was collected by filtration, rinsed with IPA (3×500 mL) to give 210 g of Compound 196-salt (Mother liquor contains 230 g of Compound 225-salt). Both mother liquor and crystals were analyzed by HPLC on chiral amylose SA column (eluent; DCM:MeOH 50:50) analytical samples were prepared by acidification followed by extraction to determine the relative amount of Compound 196-salt and Compound 225-salt. The analysis showed the chiral purity of Compound 196 at 1.18%:98.81% and Compound 225 at 95.5%:4.6%.

The whole batch of Compound 196-salt after IPA wash was taken in 800 mL of ethyl acetate and was acidified at 0° C. to a pH~2 to 4 with 4N aq. HCl (420 mL). The organic layer was separated and aqueous layer was further extracted with ethyl acetate (3×250 mL). The combined organic layers were dried over anhydrous sodium sulphate, filtered and concentrated to give 78 g of Compound 196 (chiral purity 98.60%). Similarly 72 g of Compound 225 was obtained (chiral purity 94.71%).

Analytical Data for Compound 196:

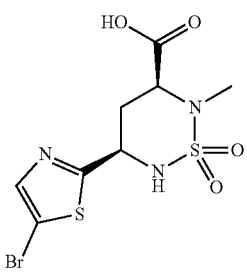 [SMILES: CN1[C@H](C(=O)O)C[C@H](c2ncc(Br)s2)NS1(=O)=O]

$^1$H NMR (DMSO-$d_6$, 400 MHz): δ 13.41 (s, 1H), 7.87 (s, 1H), 7.80 (d, J=10.0 Hz, 1H), 4.93-4.86 (m, 1H), 4.30 (dd, J=12.4, 1.8 Hz, 1H), 2.61 (s, 3H), 2.36-2.32 (m, 1H), 2.04-1.95 (m, 1H); HPLC purity: 98.59%; HPLC chiral purity: 98.60%; LCMS purity: 98.60%; LCMS Calculated for $C_8H_{10}BrN_3O_4S_2$: 354.93; LCMS observed: 357.90 $(M+2)^+$.

Analytical Data for Compound 225:

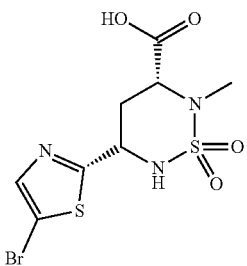

$^1$H NMR (DMSO-$d_6$, 400 MHz): 13.41 (s, 1H), δ 7.88 (1H), 7.82 (d, J=9.6 Hz, 1H), 4.94-4.87 (m, 1H), 4.29 (dd, J=12.4, 2.4 Hz, 1H), 2.62 (s, 3H), 2.37-2.33 (m, 1H), 2.04-1.95 (m, 1H); HPLC purity: 91.68%, HPLC chiral purity: 94.71%; LCMS purity: 96.66%; LCMS Calculated for $C_8H_{10}BrN_3O_4S_2$: 354.93; LCMS observed: 357.6 $(M+2)^+$.

Synthesis of (3S,5R)-5-(5-bromothiazol-2-yl)-N-(3-chloro-4-fluorophenyl)-2-methyl-1,2,6-thiadiazinane-3-carboxamide 1,1-dioxide (HBV-CSU-122-ISO-I)

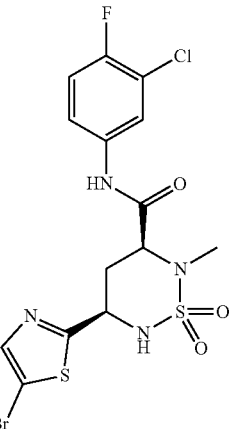

To a stirred solution of Compound 196 (160 g, 449.4 mmol) in DCM (18V, 2.9 L) at 0° C. was added DIPEA (234.4 mL, 1344.8 mmol), stirred for 30 min, followed by addition of HATU (256.1 g, 674.2 mmol) portion wise, again stirred for 30 min and then aniline compound (78.2 g, 539.3 mmol) was added. The reaction mixture was then stirred at room temperature for overnight. The progress of the reaction was monitored by TLC. After completion, the reaction mixture was concentrated, the residue obtained was stirred with ethyl acetate (500 mL) for 30 min, solid material (Tetramethyl urea side product and HOBT) obtained was filtered, washed with 200 mL ethyl acetate. The filtrate was washed with water (2×200 mL) followed by brine (2×200 mL), the organic layer was dried over anhydrous sodium sulphate, filtered and concentrated under reduced pressure to afford a crude compound (60% purity by LCMS). The crude material was stirred with DCM (5V, 800 mL), the precipitated solid was filtered, washed with DCM (2V, 300 mL) and dried to afford 146 g (67.4%) of HBV-CSU-122-ISO-I; TLC: 30% EtOAc/Hexane ($R_f$: 0.5) (see Table 2 for analytical data).

Synthesis of (3S,5R)-N-(3-chloro-4-fluorophenyl)-2-methyl-5-(5-(1-methyl-1H-imidazol-4-yl)thiazol-2-yl)-1,2,6-thiadiazinane-3-carboxamide 1,1-dioxide (HBV-CSU-276-ISO-I)

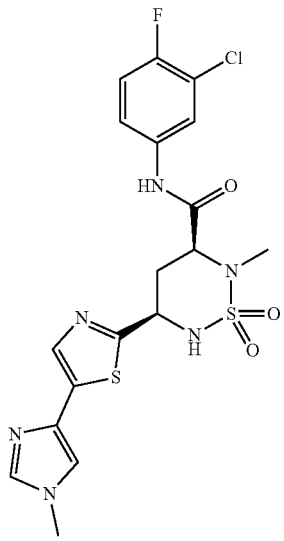 [SMILES: CN1[C@H](C(=O)Nc2ccc(F)c(Cl)c2)C[C@H](c2ncc(-c3cn(C)cn3)s2)NS1(=O)=O]

To a stirring solution of HBV-CSU-122-ISO-I (72.5 g, 150.4 mmol) in 1,4-dioxane (730 mL) was added 1-methyl-4-(tributylstannyl)-1H-imidazole (83.8 g, 225.6 mmol) and purged under Ar atmosphere for 30 min; added Pd(PPh₃)₄ (17.37 g, 15.04 mmol); heated to 100° C. and stirred for 4 h at the same temperature. The reaction mixture was monitored by TLC. After completion, the reaction mixture was filtered through a pad of a Celite, washed with ethyl acetate (2×500 mL), combined filtrate was concentrated and solid residue obtained was triturated with ether (2×500 mL) and ether layer was concentrated (ether layer showed stannane as well as some compound by TLC). The solid residue was again stirred with ~500 mL hexane (hexane layer showed some stannane by TLC; this hexane layer was combined for concentration with ether layer). The residue obtained after ether/hexane washings were dissolved in 1 Lit of ethyl acetate; washed with 30% aq. KF (5×500 mL) followed by brine (500 mL). The combined organic layer was dried over anhydrous sodium sulphate, filtered and concentrated in vacuo to afford the crude material which was purified using silica gel flash column chromatography (2-4% MeOH/CH₂Cl₂). {Note: One more batch done on same scale (72.5 g)}. The combined work-up and purification provided HBV-CSU-276-ISO-I (110 g, 75.5%) as an off-white solid. TLC: 10% MeOH/CH₂Cl₂ ($R_f$: 0.2); ¹H NMR showed some stannane related impurities. In order to get rid of stannane impurity, 110 g of HBV-CSU-276-ISO-I was stirred with ether (500 mL) for 30 min, filtered, washed with ether (2×100 mL) and dried to provide 108 g (74.17%) of HBV-CSU-276-ISO-I (see Table 2 for analytical data).

HCl Salt Formation:

To a solution of HBV-CSU-276-ISO-I (62 g) in 620 mL of Dioxane:MeOH (1:1) at 0° C. (clear solution was observed) was added 160 mL of 4M HCl in MeOH (5 eq.), the reaction mixture was stirred at 0° C. for 1 h (We did observed the solid precipitating out at 0° C. after 5 minutes). The precipitated solid was collected by filtration, washed with ether (3×100 mL) followed by pentane (3×100 mL) via stirring & dried to afford 63 g of HBV-CSU-276-ISO-I-HCl salt. The ¹H NMR showed ~4.66% w w methanol; (see Table 2 for analytical data).

Scheme 69

Synthesis of (3R,5R)-5-(5-bromothiophen-2-yl)-N-(3-chloro-4-fluorophenyl)-2-methyl-1,2,6-thiadiazinane-3-carboxamide 1,1-dioxide (HBV-CSU-114-Trans-ISO-I) and (3R,5R)-N-(3-chloro-4-fluorophenyl)-2-methyl-5-(5-(1-methyl-1H-imidazol-4-yl)thiophen-2-yl)-1,2,6-thiadiazinane-3-carboxamide 1,1-dioxide (HBV-CSU-266-Trans-ISO-I)

Scheme 69:

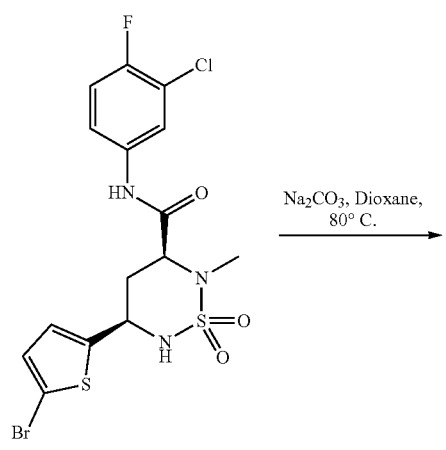

HBV-CSU-144-Cis-ISO-I

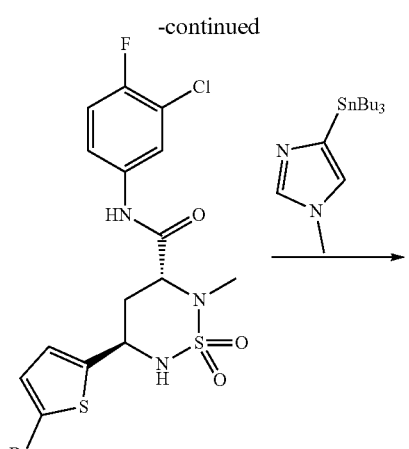

HBV-CSU-144-Trans-ISO-I

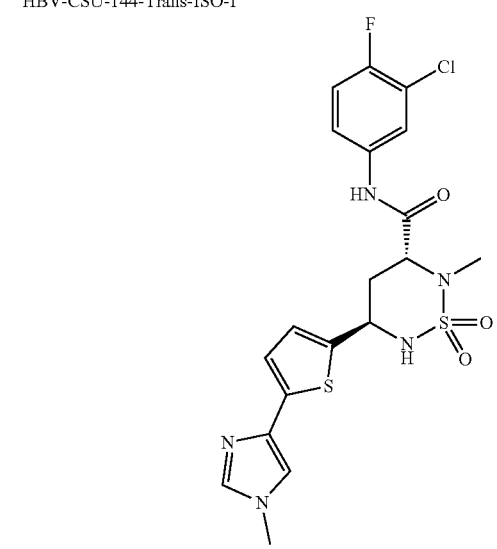

HBV-CSU-266-Trans-ISO-I

Synthesis of (3R,5R)-5-(5-bromothiophen-2-yl)-N-(3-chloro-4-fluorophenyl)-2-methyl-1,2,6-thiadiazinane-3-carboxamide 1,1-dioxide (HBV-CSU-114-Trans-ISO-I)

To a stirred solution of compound HBV-CSU-114-Cis-ISO-I (3 g, 6.20 mmol) in 1,4-dioxane (30 mL), Na₂CO₃ (3.28 g, 31 mmol) was added. The reaction mixture was stirred at 100° C. for 16 h. The progress of the reaction was monitored by TLC. After completion, the reaction mixture was concentrated under reduced pressure. The residue was diluted with water and extracted with ethyl acetate. The combined organic layers were dried over anhydrous sodium sulphate and concentrated under reduced pressure to afford a crude compound. The crude compound was purified using silica gel column chromatography to afford HBV-CSU-114-Trans-ISO-I (0.05 g, 2%) (see Table 2 for analytical data).

(3R,5R)-N-(3-chloro-4-fluorophenyl)-2-methyl-5-(5-(1-methyl-1H-imidazol-4-yl)thiophen-2-yl)-1,2,6-thiadiazinane-3-carboxamide 1,1-dioxide (HBV-CSU-266-Trans-ISO-I)

The above titled compounds have been synthesized by following the general procedure described above for Stille coupling by using HBV-CSU-114-Trans-ISO-I and corresponding stannane (see Table 2 for analytical data).

Scheme 70

Synthesis of (3S,5S)-5-(5-bromothiophen-2-yl)-N-(3-chloro-4-fluorophenyl)-2-methyl-1,2,6-thiadiazinane-3-carboxamide 1,1-dioxide (HBV-CSU-114-Trans-ISO-II) and (3S,5S)-N-(3-chloro-4-fluorophenyl)-2-methyl-5-(5-(1-methyl-1H-imidazol-4-yl)thiophen-2-yl)-1,2,6-thiadiazinane-3-carboxamide 1,1-dioxide (HBV-CSU-266-Trans-ISO-II)

Scheme 70:

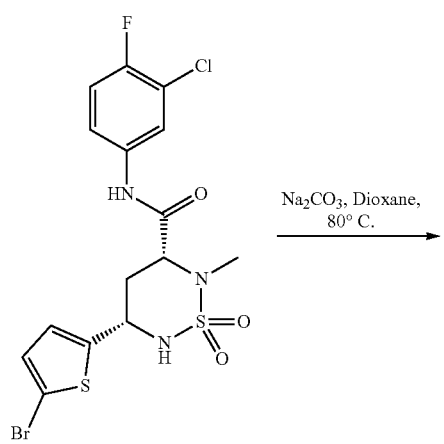

HBV-CSU-144-Cis-ISO-II

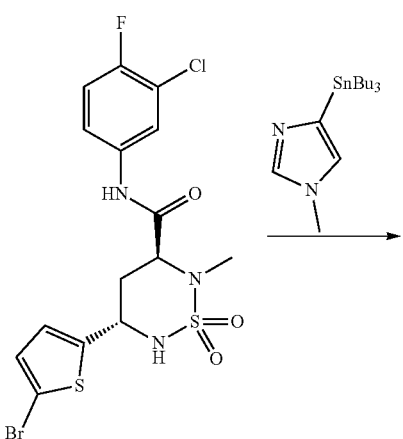

HBV-CSU-144-Trans-ISO-II

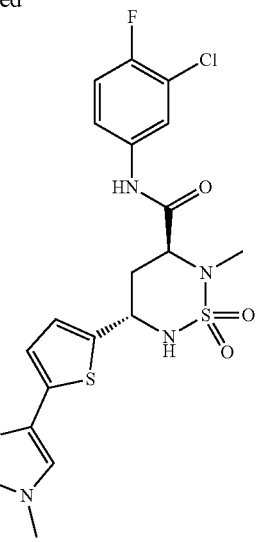

HBV-CSU-266-Trans-ISO-II

Synthesis of (3S,5S)-5-(5-bromothiophen-2-yl)-N-(3-chloro-4-fluorophenyl)-2-methyl-1,2,6-thiadiazinane-3-carboxamide 1,1-dioxide (HBV-CSU-114-Trans-ISO-II)

To a stirred solution of compound HBV-CSU-114-Cis-ISO-II (0.2 g, 0.413 mmol) in 1,4-dioxane (10 mL), $Na_2CO_3$ (0.22 g, 2.07 mmol) was added. The reaction mixture was stirred at 100° C. for 16 h. The progress of the reaction was monitored by TLC. After completion, the reaction mixture was concentrated under reduced pressure. The residue was diluted with water and extracted with ethyl acetate. The combined organic layers were dried over anhydrous sodium sulphate, filtered and concentrated under reduced pressure to afford a crude compound. The crude compound was purified using silica gel column chromatography to afford HBV-CSU-114-Trans-ISO-II (0.02 g, 10%) (see Table 2 for analytical data).

(3S,5S)-N-(3-chloro-4-fluorophenyl)-2-methyl-5-(5-(1-methyl-1H-imidazol-4-yl)thiophen-2-yl)-1,2,6-thiadiazinane-3-carboxamide 1,1-dioxide (HBV-CSU-266-Trans-ISO-II)

The above titled compounds have been synthesized by following the general procedure described above for Stille coupling by using HBV-CSU-114-Trans-ISO-II and corresponding stannane (see Table 2 for analytical data).

Scheme 71

Synthesis of (3R,5R)-5-(5-bromothiazol-2-yl)-N-(3-chloro-4-fluorophenyl)-2-methyl-1,2,6-thiadiazinane-3-carboxamide 1,1-dioxide (HBV-CSU-122-Trans-ISO-I) and (3R,5R)-N-(3-chloro-4-fluorophenyl)-2-methyl-5-(5-(1-methyl-1H-imidazol-4-yl)thiazol-2-yl)-1,2,6-thiadiazinane-3-carboxamide 1,1-dioxide (HBV-CSU-276-Trans-ISO-I)

Scheme 71:

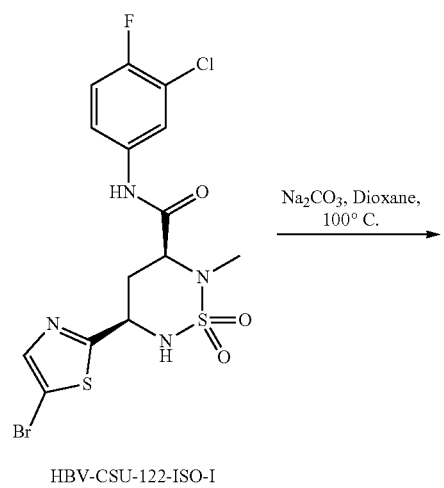

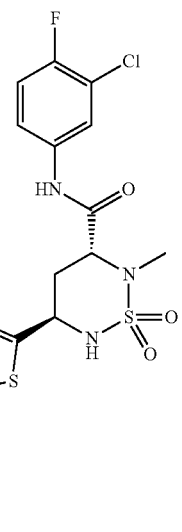

HBV-CSU-276-Trans-ISO-I

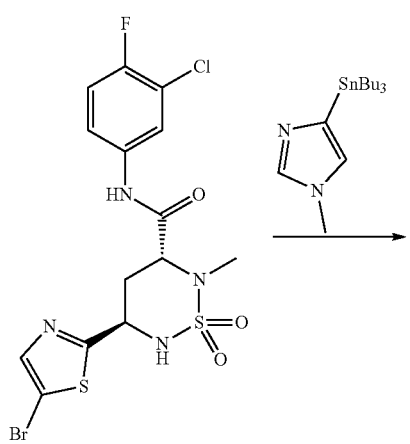

HBV-CSU-122-Trans-ISO-I

Synthesis of (3R,5R)-5-(5-bromothiazol-2-yl)-N-(3-chloro-4-fluorophenyl)-2-methyl-1,2,6-thiadiazinane-3-carboxamide 1,1-dioxide (HBV-CSU-122-Trans-ISO-I)

To a stirred solution of compound HBV-CSU-122-ISO-I (0.2 g, 0.413 mmol) in 1,4-dioxane (5 mL), Na$_2$CO$_3$ (0.218 g, 2.066 mmol) was added. The reaction mixture was stirred at 100° C. for 16 h. The progress of the reaction was monitored by TLC. After completion, the reaction mixture was concentrated under reduced pressure. The residue was diluted with water and extracted with ethyl acetate. The combined organic layers were dried over anhydrous sodium sulphate and concentrated under reduced pressure to afford a crude compound. The crude compound was purified using silica gel column chromatography to afford HBV-CSU-122-Trans-ISO-I (0.02 g, 10%) (see Table 2 for analytical data).

(3R,5R)-N-(3-chloro-4-fluorophenyl)-2-methyl-5-(5-(1-methyl-1H-imidazol-4-yl)thiazol-2-yl)-1,2,6-thiadiazinane-3-carboxamide 1,1-dioxide (HBV-CSU-276-Trans-ISO-I)

The above titled compounds have been synthesized by following the general procedure described above for Stille coupling by using HBV-CSU-122-Trans-ISO-I and corresponding stannane (see Table 2 for analytical data).

Scheme 72

Synthesis of (3S,5S)-5-(5-bromothiazol-2-yl)-N-(3-chloro-4-fluorophenyl)-2-methyl-1,2,6-thiadiazinane-3-carboxamide 1,1-dioxide (HBV-CSU-122-Trans-ISO-II) and (3S,5S)-N-(3-chloro-4-fluorophenyl)-2-methyl-5-(5-(1-methyl-1H-imidazol-4-yl)thiazol-2-yl)-1,2,6-thiadiazinane-3-carboxamide 1,1-dioxide (HBV-CSU-276-Trans-ISO-II)

Scheme 72:

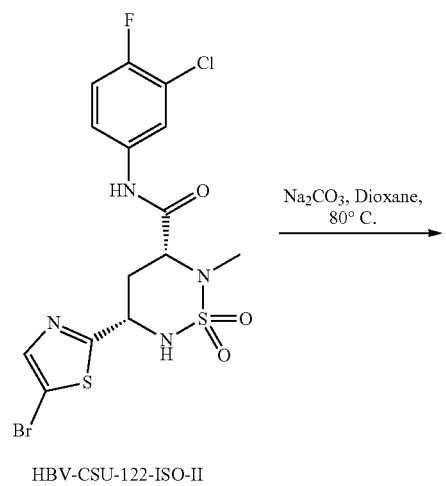

HBV-CSU-122-ISO-II

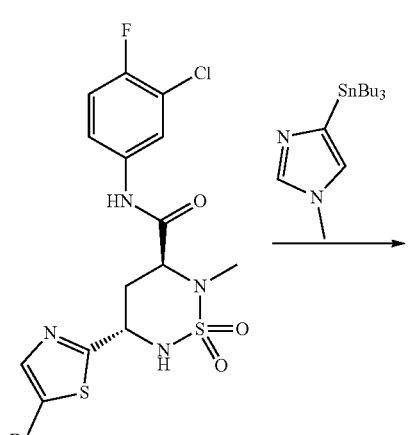

HBV-CSU-122-Trans-ISO-II

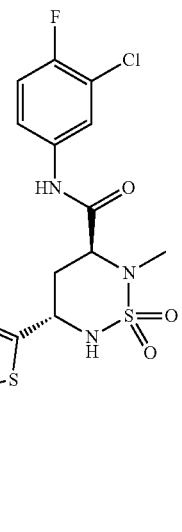

HBV-CSU-276-Trans-ISO-II

Synthesis of (3S,5S)-5-(5-bromothiazol-2-yl)-N-(3-chloro-4-fluorophenyl)-2-methyl-1,2,6-thiadiazinane-3-carboxamide 1,1-dioxide (HBV-CSU-122-Trans-ISO-II)

To a stirred solution of compound HBV-CSU-122-ISO-II (0.99 g, 2.06 mmol) in 1,4-dioxane (10 mL), $Na_2CO_3$ (1.09 g, 10.37 mmol) was added. The reaction mixture was stirred at 100° C. for 16 h. The progress of the reaction was monitored by TLC. After completion, the reaction mixture was concentrated under reduced pressure. The residue was diluted with water and extracted with ethyl acetate. The combined organic layers were dried over anhydrous sodium sulphate and concentrated under reduced pressure to afford a crude compound. The crude compound was purified using silica gel column chromatography to afford HBV-CSU-122-Trans-ISO-II (0.07 g, 7%) (see Table 2 for analytical data). (see Table 2 for analytical data).

(3S,5S)-N-(3-chloro-4-fluorophenyl)-2-methyl-5-(5-(1-methyl-1H-imidazol-4-yl)thiazol-2-yl)-1,2,6-thiadiazinane-3-carboxamide 1,1-dioxide (HBV-CSU-276-Trans-ISO-II)

The above titled compounds have been synthesized by following the general procedure described above for Stille coupling by using HBV-CSU-122-Trans-ISO-II and corresponding stannane (see Table 2 for analytical data).

553

Scheme 73

Synthesis of Trans-5-(5-bromothiophen-2-yl)-N-(3-chloro-4-fluorophenyl)-2-methyl-1,2,6-thiadiazinane-3-carboxamide 1,1-dioxide (HBV-CSU-114-Trans {Rac}) & Trans-N-(3-chloro-4-fluorophenyl)-2-methyl-5-(5-(1-methyl-1H-pyrazol-4-yl)thiophen-2-yl)-1,2,6-thiadiazinane-3-carboxamide 1,1-dioxide (HBV-CSU-161-Trans {Rac})

Scheme 73:

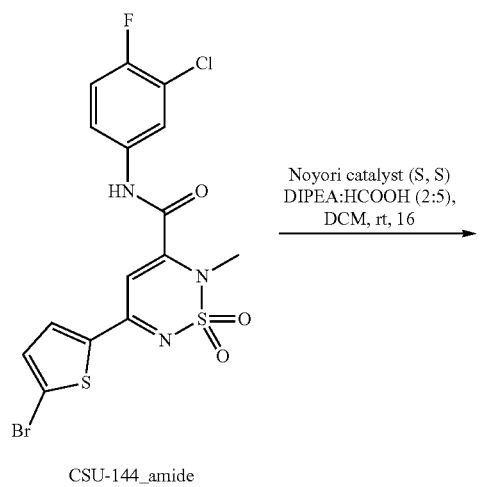

CSU-144_amide

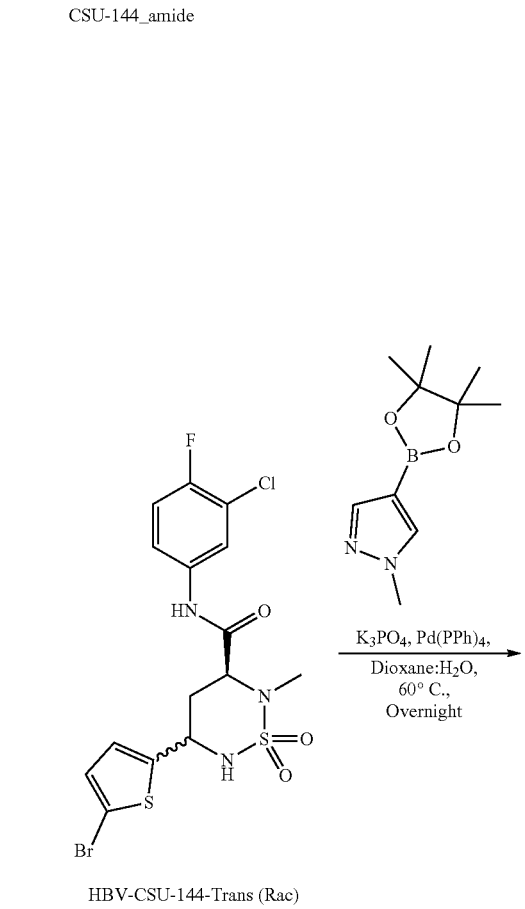

HBV-CSU-144-Trans (Rac)

554

-continued

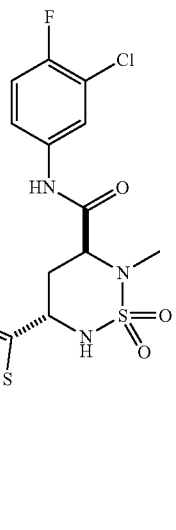

HBV-CSU-161-Trans (Rac)

Synthesis of Trans-5-(5-bromothiophen-2-yl)-N-(3-chloro-4-fluorophenyl)-2-methyl-1,2,6-thiadiazinane-3-carboxamide 1,1-dioxide (HBV-CSU-114-Trans {Rac})

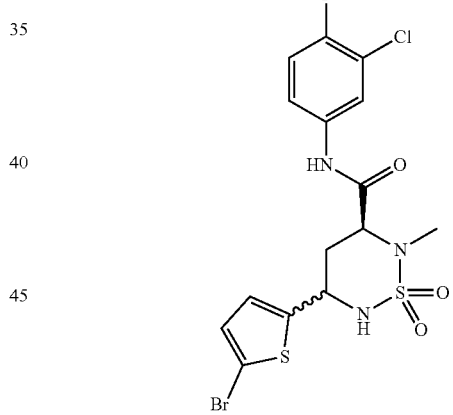

To a stirred solution of compound CSU-114_amide (10 g, 20.87 mmol) and {Noyori (S, S) catalyst} i.e. RuCl [(1S, 2S)-p-TsNCH ($C_6H_5$) $NH_2$] (η6-p-cycmene) (5.64 mL, 2.08 mmol) in DCM (100 mL) at 0° C., DIPEA (7.2 mL, 41.74 mmol) and formic acid (4.8 g, 104.35 mmol) were added The reaction mixture was stirred at room temperature for 16 h. The progress of the reaction was monitored by TLC. After completion, the reaction mixture was diluted with water and extracted with DCM. The combined organic layers were dried over anhydrous sodium sulphate and concentrated under reduced pressure to afford a crude compound. The crude compound was purified by silica gel column chromatography to afford the desired compound as HBV-CSU-114-Trans (Rac) (2.6 g, 26%) (see Table 2 for analytical data). Note: The Cis isomer was also observed which was separated by column chromatography. The stereochemistry at C-3 was not confirmed and assigned based on an outcome of fully reduced cis product after 16 h.

Synthesis of Trans-N-(3-chloro-4-fluorophenyl)-2-methyl-5-(5-(1-methyl-1H-pyrazol-4-yl)thiophen-2-yl)-1,2,6-thiadiazinane-3-carboxamide 1,1-dioxide (HBV-CSU-161-Trans {Rac})

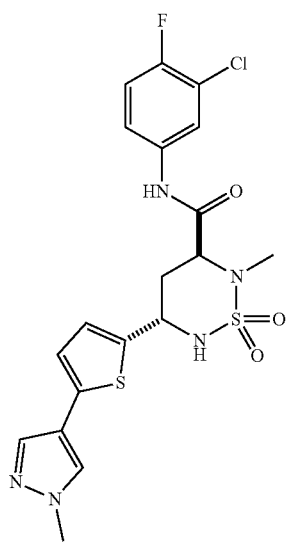 [SMILES: CN1[C@H](C(=O)Nc2ccc(F)c(Cl)c2)C[C@@H](c2ccc(-c3cnn(C)c3)s2)NS1(=O)=O]

The above titled compounds have been synthesized by following the general procedure described above for Suzuki coupling by using HBV-CSU-114-Trans (Rac) and 1-methyl-4-(4,4,5,5-tetramethyl-1,3,2-dioxaborolan-2-yl)-1H-pyrazole (see Table 2 for analytical data).

Scheme 74

Synthesis of amides using 2-methyl-5-(5-(1-methyl-1H-pyrazol-4-yl)thiophen-2-yl)-1,2,6-thiadiazinane-3-carboxylic acid 1,1-dioxide Scheme 74:

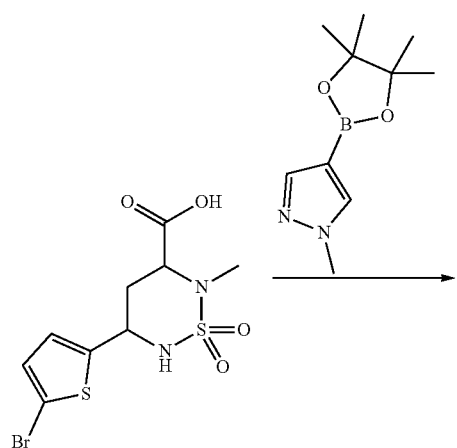

220

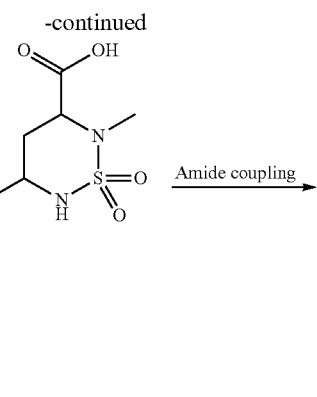

226

Amide coupling

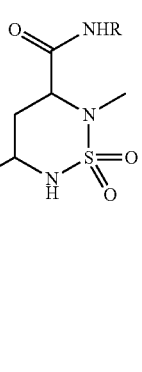

| Target | R variation |
| --- | --- |
| HBV-CSU-411 | 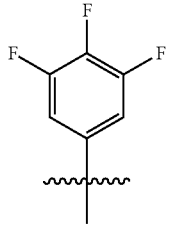 [SMILES: *c1cc(F)c(F)c(F)c1] |
| HBV-CSU-413 | 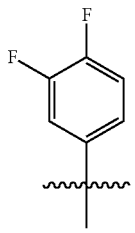 [SMILES: *c1ccc(F)c(F)c1] |
| HBV-CSU-415 | 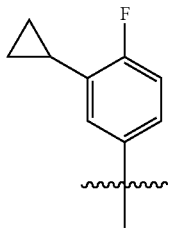 [SMILES: *c1ccc(F)c(C2CC2)c1] |

| Target | R variation |
|---|---|
| HBV-CSU-416 | 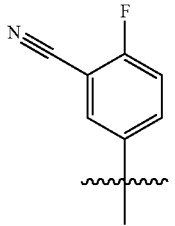 [SMILES: *c1ccc(F)c(C#N)c1] |
| HBV-CSU-425 | 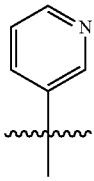 |

Synthesis of 2-methyl-5-(5-(1-methyl-1H-pyrazol-4-yl)thiophen-2-yl)-1,2,6-thiadiazinane-3-carboxylic acid 1,1-dioxide (226)

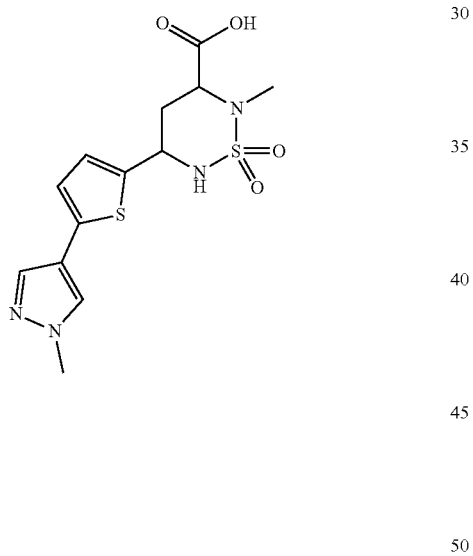

To a mixture of bromo Compound 220 (500 mg, 1.41 mmol), boronic acid/boronate ester (293 mg, 1.41 mmol) in 5 mL of 1,4-dioxane:H$_2$O (1:1), DIPEA (0.7 mL, 4.2 mmol) was added, purged with Ar for 15 min, followed by the addition of PdCl$_2$(PPh$_3$)$_2$ (9 mg, 0.0141 mmol), and stirred at 80° C. for overnight. The progress of the reaction was monitored by LCMS. After completion of the reaction, the reaction mixture was filtered through Celite and evaporated to dryness. The residue was taken in water and acidified with 2N HCl (2-4 pH), precipitated solid was filtered and dried to afford Compound 226 (400 mg, 79%) as a light yellow solid. LCMS Calculated for C$_{13}$H$_{16}$N$_4$O$_4$S$_2$: 356.06; LCMS observed: 357.6 (M+1)$^+$.

Synthesis of Cis-2-methyl-5-(5-(1-methyl-1H-pyrazol-4-yl)thiophen-2-yl)-N-(3,4,5-trifluorophenyl)-1,2,6-thiadiazinane-3-carboxamide 1,1-dioxide (HBV-CSU-411)

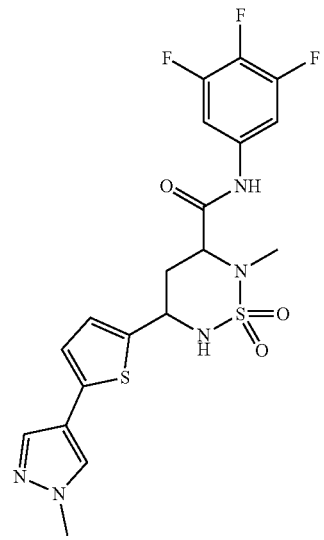 [SMILES: CN1C(C(=O)Nc2cc(F)c(F)c(F)c2)CC(c2ccc(-c3cnn(C)c3)s2)NS1(=O)=O]

The above titled compound has been synthesized by following the general procedure (Method B) described above for amidation by using Compound 226 and corresponding amine (see Table 2 for analytical data).

Synthesis of Cis-N-(3,4-difluorophenyl)-2-methyl-5-(5-(1-methyl-1H-pyrazol-4-yl)thiophen-2-yl)-1,2,6-thiadiazinane-3-carboxamide 1,1-dioxide (HBV-CSU-413)

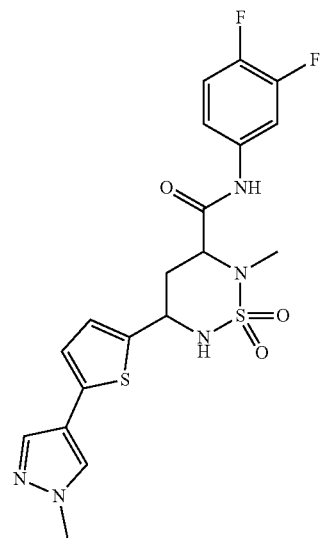 [SMILES: CN1C(C(=O)Nc2ccc(F)c(F)c2)CC(c2ccc(-c3cnn(C)c3)s2)NS1(=O)=O]

The above titled compound has been synthesized by following the general procedure (Method B) described above for amidation by using Compound 226 and corresponding amine (see Table 2 for analytical data).

559
Synthesis of Cis-N-(3-cyclopropyl-4-fluorophenyl)-2-methyl-5-(5-(1-methyl-1H-pyrazol-4-yl)thiophen-2-yl)-1,2,6-thiadiazinane-3-carboxamide 1,1-dioxide (HBV-CSU-415)

560
Synthesis of Cis-2-methyl-5-(5-(1-methyl-1H-pyrazol-4-yl)thiophen-2-yl)-N-(pyridin-3-yl)-1,2,6-thiadiazinane-3-carboxamide 1,1-dioxide (HBV-CSU-425)

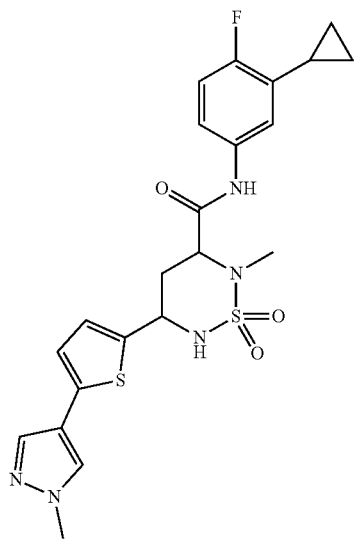 [SMILES: CN1C(C(=O)Nc2ccc(F)c(C3CC3)c2)CC(c2ccc(-c3cnn(C)c3)s2)NS1(=O)=O]

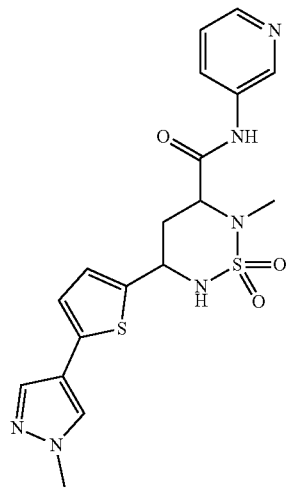

The above titled compound has been synthesized by following the general procedure (Method B) described above for amidation by using Compound 226 and corresponding amine (see Table 2 for analytical data).

The above titled compound has been synthesized by following the general procedure (Method B) described above for amidation by using Compound 226 and corresponding amine (see Table 2 for analytical data).

Synthesis of Cis-N-(3-cyano-4-fluorophenyl)-2-methyl-5-(5-(1-methyl-1H-pyrazol-4-yl)thiophen-2-yl)-1,2,6-thiadiazinane-3-carboxamide 1,1-dioxide (HBV-CSU-416)

Scheme 75

Synthesis of Rac-5-(5-bromothiophen-2-yl)-N-(3-chloro-4-fluorophenyl)-2,4-dimethyl-1,2,6-thiadiazinane-3-carboxamide 1,1-dioxide ((HBV-CSU-423) & Rac-N-(3-chloro-4-fluorophenyl)-2,4-dimethyl-5-(5-(1-methyl-1H-pyrazol-4-yl)thiophen-2-yl)-1,2,6-thiadiazinane-3-carboxamide 1,1-dioxide (HBV-CSU-343)

Scheme 75:

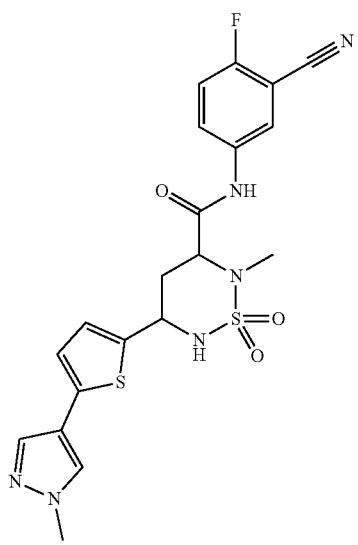 [SMILES: CN1C(C(=O)Nc2ccc(F)c(C#N)c2)CC(c2ccc(-c3cnn(C)c3)s2)NS1(=O)=O]

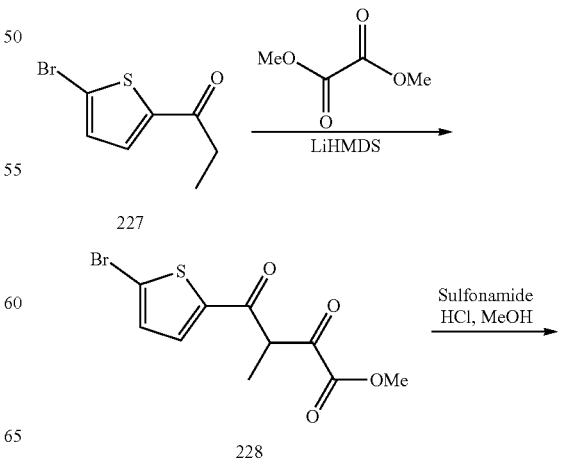

The above titled compound has been synthesized by following the general procedure (Method B) described above for amidation by using Compound 226 and corresponding amine (see Table 2 for analytical data).

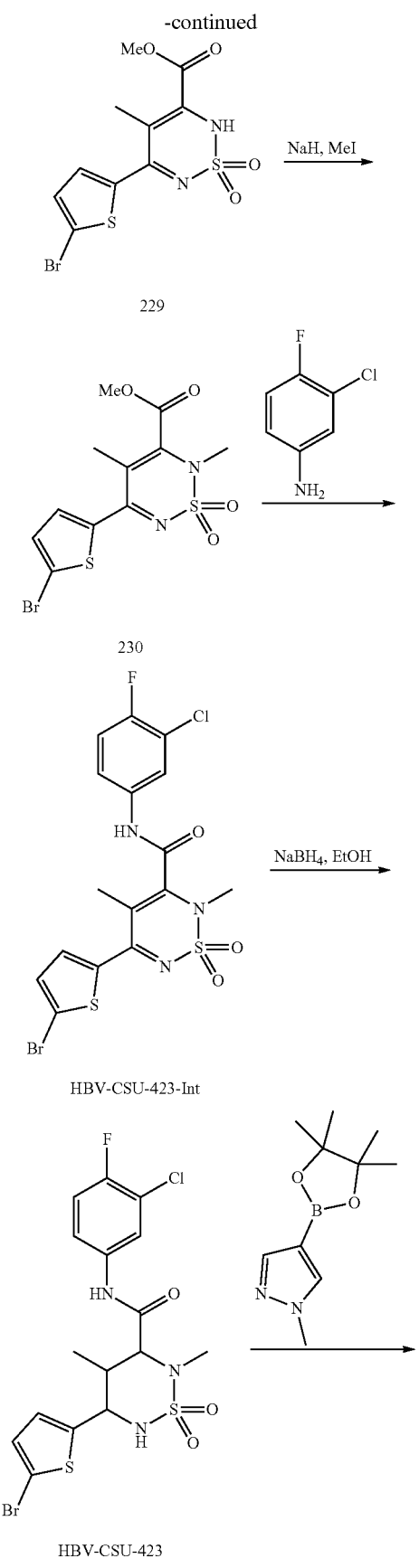

HBV-CSU-423-Int

HBV-CSU-423

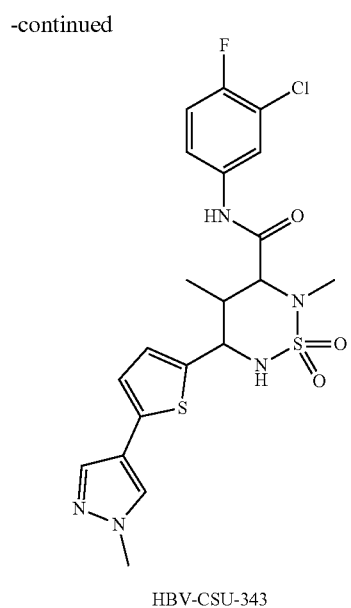

HBV-CSU-343

Synthesis of 227:

Synthesis 1-(5-bromothiophen-2-yl)propan-1-one (227)

To a stirred solution of AlCl$_3$ (29.44 g, 221 mmol) in EDC (300 mL) at 0° C., propionyl chloride (17.02 g, 184 mmol) was added and reaction mixture was stirred for 20 min at 0° C. To this solution, compound 231 (30 g, 184 mmol) was added and further stirred at room temperature for overnight. The progress of the reaction was monitored by TLC. After completion, the reaction mixture was diluted with water and extracted with DCM. The combined organic layers were dried over anhydrous sodium sulphate, filtered and concentrated under reduced pressure to afford the title compound 227 (38.20 g, 95%) as brown coloured solid; TLC: 20% EtOAc/hexane (R$_f$: 0.4); $^1$H NMR (400 MHz, DMSO-d$_6$): δ 7.79 (d, J=4.4 Hz, 1H), 7.38 (d, J=4.0 Hz, 1H), 2.97-2.92 (m, 2H), 1.07 (t, J=7.2 Hz, 3H); LCMS Calculated for C$_7$H$_7$BrOS: 217.94; Observed: 220.80 (M+2)$^+$.

563

Synthesis of methyl 4-(5-bromothiophen-2-yl)-3-methyl-2,4-dioxobutanoate (228)

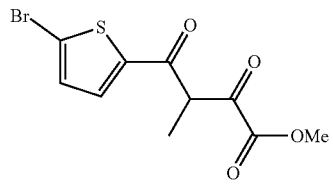 [SMILES: COC(=O)C(=O)C(C)C(=O)c1ccc(Br)s1]

Title compound was synthesized using general method for the synthesis of 2,4-diketoester described above to afford 12.5 g of compound 228 (45%, reaction scale is 20 g) as an off white solid. TLC: 30% EtOAc/hexane ($R_f$: 0.3); LCMS Calculated for $C_{10}H_9BrO_4S$: 303.94; Observed: 304.95 $(M+1)^+$.

Synthesis of methyl 5-(5-bromothiophen-2-yl)-4-methyl-2H-1,2,6-thiadiazine-3-carboxylate 1,1-dioxide (229)

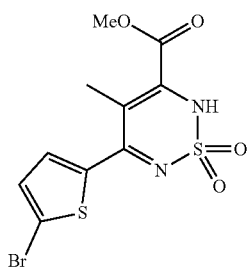 [SMILES: COC(=O)C1=C(C)C(c2ccc(Br)s2)=NS(=O)(=O)N1]

Title compound was synthesized using general method B for the synthesis of cyclic sulfonamide described above to afford 1.7 g of compound 229 (18%, reaction scale is 8 g) as an off white solid. TLC: 5% MeOH/DCM ($R_f$: 0.3); LCMS Calculated for $C_{10}H_9BrN_2O_4S_2$: 363.92; LCMS observed: 366.95 $(M+2)^+$.

Synthesis of methyl 5-(5-bromothiophen-2-yl)-2,4-dimethyl-2H-1,2,6-thiadiazine-3-carboxylate 1,1-dioxide (230)

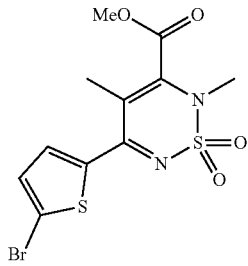 [SMILES: COC(=O)C1=C(C)C(c2ccc(Br)s2)=NS(=O)(=O)N1C]

Title compound was synthesized using general method A for alkylation described above to afford 0.32 g of compound 230 (62%, reaction scale is 1 g) as an off white solid. TLC: 30% EtOAc/hexanes ($R_f$: 0.2); LCMS Calculated for $C_{11}H_{11}BrN_2O_4S_2$: 377.93; LCMS observed: 380.8 $(M+2)^+$.

564

Synthesis of 5-(5-Bromothiophen-2-yl)-N-(3-chloro-4-fluorophenyl)-2,4-dimethyl-2H-1,2,6-thiadiazine-3-carboxamide 1,1-dioxide (HBV-CSU-423-Int)

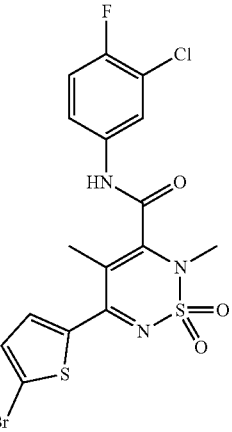

The above titled compound has been synthesized by following the general procedure (Method A) described above for amidation by using Compound 230 and corresponding amine (see Table 1 for analytical data).

Synthesis of Rac-5-(5-bromothiophen-2-yl)-N-(3-chloro-4-fluorophenyl)-2,4-dimethyl-1,2,6-thiadiazinane-3-carboxamide 1,1-dioxide (HBV-CSU-423)

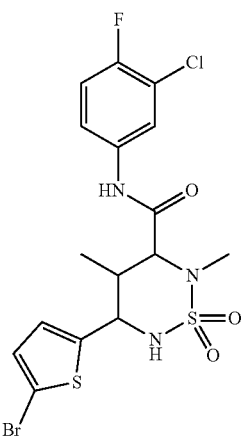

The above titled compounds have been synthesized by following the general procedure described above for reduction by using corresponding HBV-CSU-423_Int (see Table 2 for analytical data).

Note: NMR hints for three Diastereomers.

Synthesis of Rac-N-(3-chloro-4-fluorophenyl)-2,4-dimethyl-5-(5-(1-methyl-1H-pyrazol-4-yl)thiophen-2-yl)-1,2,6-thiadiazinane-3-carboxamide 1,1-dioxide (HBV-CSU-343)

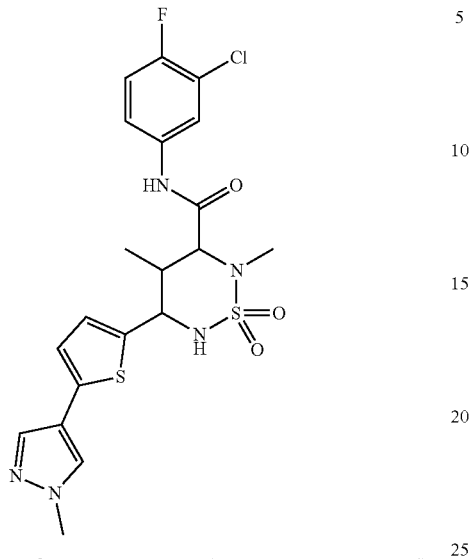

To a mixture of HBV-CSU-423 (250 mg, 0.502 mmol), corresponding boronic acid/boronate ester (104 mg, 0.502 mmol) in 5 mL of 1,4-dioxane:H$_2$O (1:1), DIPEA (0.129 g, 1.00 mmol) was added, purged with Ar for 15 min, followed by the addition of PdCl$_2$(PPh$_3$)$_2$ (4 mg, 0.005 mmol), and stirred at 80° C. for overnight. The progress of the reaction was monitored by LCMS. After completion of the reaction, the reaction mixture was diluted with water and extracted using ethyl acetate. The combined organic layers were dried over anhydrous sodium sulphate, filtered and concentrated under reduced pressure to provide crude compound. The crude compound was purified by prep. HPLC to afford the title compound. HBV-CSU-343 (42 mg, 17%). (see Table 2 for analytical data).

Note: NMR hints for three Diastereomers.

Scheme 76

Synthesis of 5-(5-Bromothiophen-2-yl)-N-(3-chloro-4-fluorophenyl)-2-methyl-3,4-dihydro-2H-1,2,6-thiadiazine-3-carboxamide 1,1-dioxide (HBV-CSU-367) & Cis-N-(3-chloro-4-fluorophenyl)-2-methyl-5-(5-(1-methyl-1H-pyrazol-4-yl)thiophen-2-yl)-3,4-dihydro-2H-1,2,6-thiadiazine-3-carboxamide 1,1-dioxide (HBV-CSU-429)

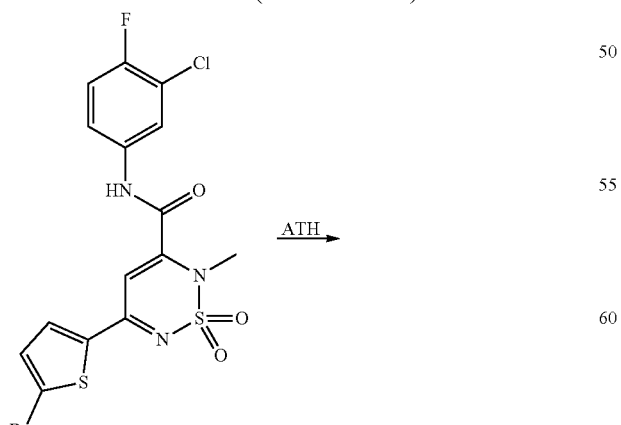

HBV-CSU-114-Int

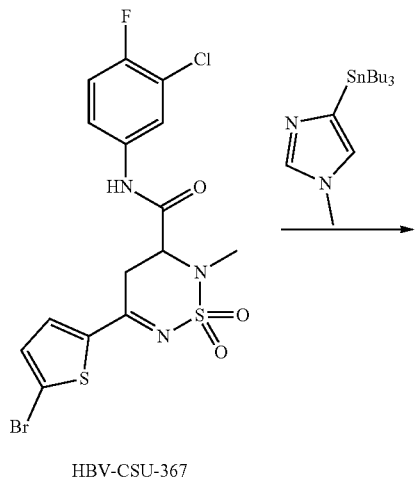

HBV-CSU-367

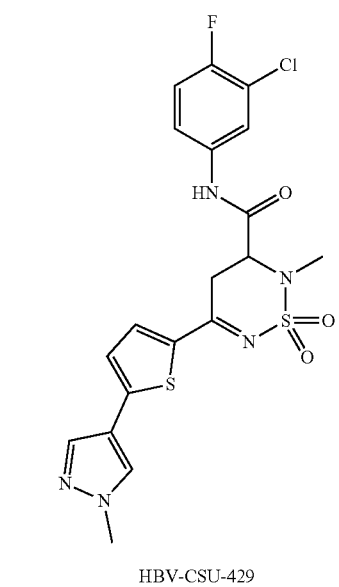

HBV-CSU-429

567

Cis-5-(5-Bromothiophen-2-yl)-N-(3-chloro-4-fluorophenyl)-2-methyl-3,4-dihydro-2H-1,2,6-thiadiazine-3-carboxamide 1,1-dioxide (HBV-CSU-367)

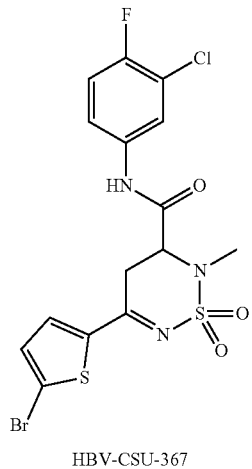

HBV-CSU-367

To a stirred solution of compound HBV-CSU-114-Int (1 g, 2.08 mmol) in DCM at 0° C., was added formic acid (0.48 g, 10.44 mmol) followed by DIPEA (0.538 g, 4.17 mmol) and then Noyori catalyst (0.132 g, 0.208 mmol). The reaction mixture was warmed to room temperature, the turbid solution was stirred at the same temperature for 50 min (till to get red colored clear solution). The progress of the reaction was monitored by TLC. After completion, the reaction mixture was concentrated under reduced pressure (at 30° C.). The crude compound was purified by silica gel column chromatography to afford the title compound HBV-CSU-367 (see Table 2 for analytical data).

Cis-N-(3-chloro-4-fluorophenyl)-2-methyl-5-(5-(1-methyl-1H-pyrazol-4-yl)thiophen-2-yl)-3,4-dihydro-2H-1,2,6-thiadiazine-3-carboxamide 1,1-dioxide (HBV-CSU-429)

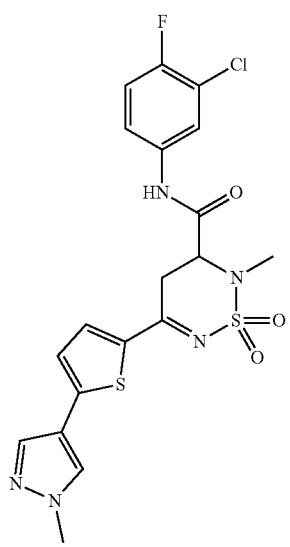 [SMILES: CC1C(c2ccc(-c3cnn(C)c3)s2)NS(=O)(=O)N(C)C1C(=O)Nc1ccc(F)c(Cl)c1]

HBV-CSU-429

568

The above titled compounds have been synthesized by following the general procedure described above for Stille coupling by using HBV-CSU-367 and corresponding stannane (see Table 2 for analytical data).

Scheme 77

Synthesis of Cis-2-allyl-5-(5-bromothiophen-2-yl)-N-(3-chloro-4-fluorophenyl)-2H-1,2,6-thiadiazine-3-carboxamide 1,1-dioxide (HBV-CSU-391), Cis-2-allyl-N-(3-chloro-4-fluorophenyl)-5-(5-(1-methyl-1H-pyrazol-4-yl)thiophen-2-yl)-1,2,6-thiadiazinane-3-carboxamide 1,1-dioxide (HBV-CSU-394), Cis-2-allyl-N-(3-chloro-4-fluorophenyl)-5-(5-(1-methyl-1H-imidazol-4-yl)thiophen-2-yl)-1,2,6-thiadiazinane-3-carboxamide 1,1-dioxide (HBV-CSU-395), Cis-2-allyl-N-(3-chloro-4-fluorophenyl)-5-(5-(pyridin-2-yl)thiophen-2-yl)-1,2,6-thiadiazinane-3-carboxamide 1,1-dioxide (HBV-CSU-396), Cis-N-(3-chloro-4-fluorophenyl)-5-(5-(1-methyl-1H-pyrazol-4-yl)thiophen-2-yl)-1,2,6-thiadiazinane-3-carboxamide 1,1-dioxide (HBV-CSU-427) &

Scheme 77:

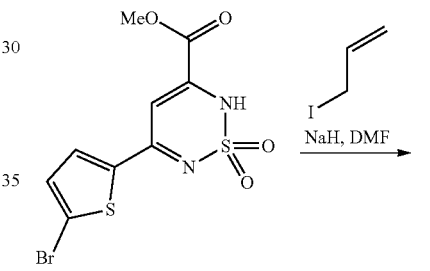

57

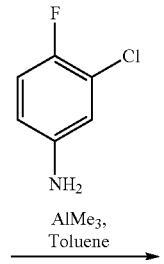

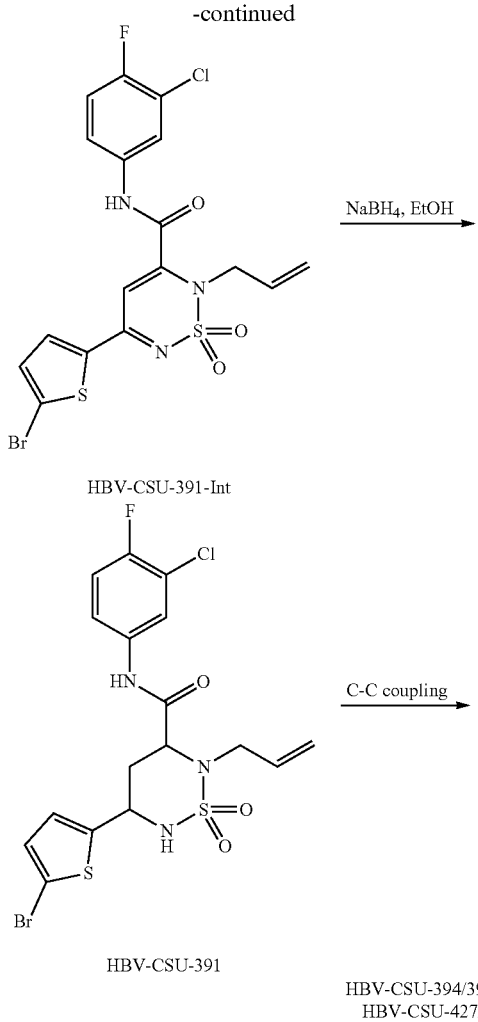

HBV-CSU-391-Int

HBV-CSU-391

HBV-CSU-394/395/396
HBV-CSU-427/428

Synthesis of methyl 2-allyl-5-(5-bromothiophen-2-yl)-2H-1,2,6-thiadiazine-3-carboxylate 1,1-dioxide (232)

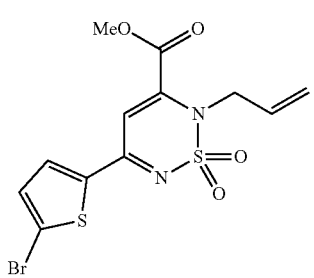 [SMILES: C=CCN1C(C(=O)OC)=CC(c2ccc(Br)s2)=NS1(=O)=O]

To a stirred solution of compound HBV-CSU-114-Int (10 g, 28.40 mmol) in dry DMF (100 mL) at 0° C. under Ar atmosphere, NaH (60% w/w in mineral oil, 1.49 g, 62.4 mmol) was added and stirred at 0° C. for 30 min. To this solution, 3-iodoprop-1-ene (5.6 g, 33.89 mmol) was added slowly and resulting reaction mixture was stirred at room temperature for 16 h. The progress of the reaction was monitored by TLC. After completion, the reaction mixture was diluted with ice cold water and extracted with ethyl acetate. The combined organic layers were washed with water, brine, dried over anhydrous sodium sulfate and evaporated under reduced pressure. The crude compound was purified by silica gel column chromatography using 10% EtOAC/hexane to afford the title compound 232 (3.8 g, 34.38%) as a colorless oil. TLC: 30% EtOAc/hexanes ($R_f$: 0.5); LCMS Calculated for $C_{12}H_{11}BrN_2O_4S_2$: 389.93; LCMS observed: 392.90 $(M+2)^+$.

Synthesis of 2-allyl-5-(5-bromothiophen-2-yl)-N-(3-chloro-4-fluorophenyl)-2H-1,2,6-thiadiazine-3-carboxamide 1,1-dioxide (HBV-CSU-391-Int)

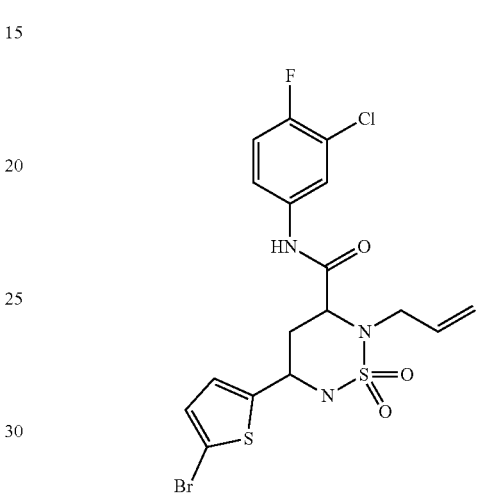

The above titled compound has been synthesized by following the general procedure (Method A) described above for amidation by using Compound 232 and corresponding amine (see Table 1 for analytical data).

Synthesis of Cis-2-allyl-5-(5-bromothiophen-2-yl)-N-(3-chloro-4-fluorophenyl)-2H-1,2,6-thiadiazine-3-carboxamide 1,1-dioxide (HBV-CSU-391)

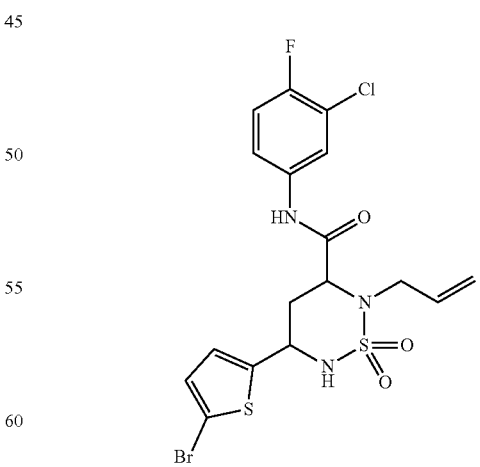

The above titled compounds have been synthesized by following the general procedure described above for reduction by using corresponding HBV-CSU-391_Int (see Table 2 for analytical data).

571

Synthesis of Cis-2-allyl-N-(3-chloro-4-fluorophenyl)-5-(5-(1-methyl-1H-pyrazol-4-yl)thiophen-2-yl)-1,2,6-thiadiazinane-3-carboxamide 1,1-dioxide (HBV-CSU-394)

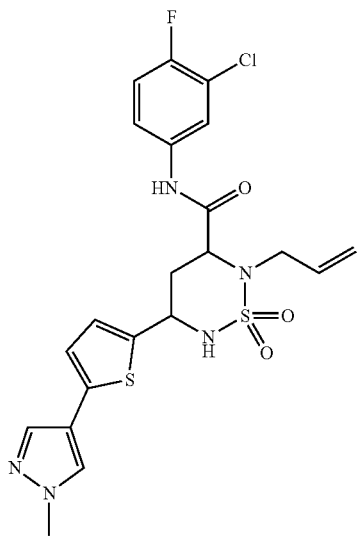 [SMILES: C=CCN1C(C(=O)Nc2ccc(F)c(Cl)c2)CC(c2ccc(-c3cnn(C)c3)s2)NS1(=O)=O]

The above titled compounds have been synthesized by following the general procedure described above for Suzuki coupling by using HBV-CSU-391 and corresponding boronic acid (see Table 2 for analytical data).

Synthesis of Cis-2-allyl-N-(3-chloro-4-fluorophenyl)-5-(5-(1-methyl-1H-imidazol-4-yl)thiophen-2-yl)-1,2,6-thiadiazinane-3-carboxamide 1,1-dioxide (HBV-CSU-395)

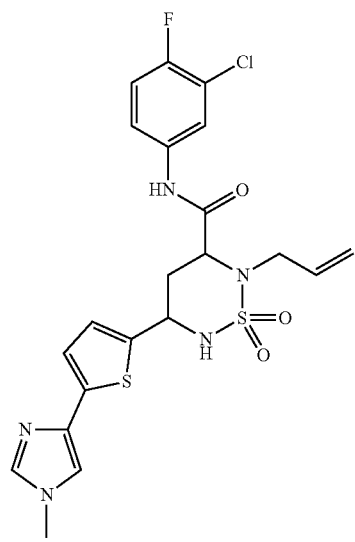 [SMILES: C=CCN1C(C(=O)Nc2ccc(F)c(Cl)c2)CC(c2ccc(-c3cn(C)cn3)s2)NS1(=O)=O]

The above titled compounds have been synthesized by following the general procedure described above for Stille coupling by using HBV-CSU-391 and corresponding stannane (see Table 2 for analytical data).

572

Synthesis of Cis-2-allyl-N-(3-chloro-4-fluorophenyl)-5-(5-(pyridin-2-yl)thiophen-2-yl)-1,2,6-thiadiazinane-3-carboxamide 1,1-dioxide (HBV-CSU-396)

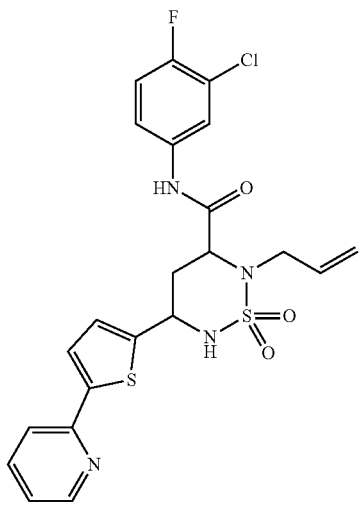 [SMILES: C=CCN1C(C(=O)Nc2ccc(F)c(Cl)c2)CC(c2ccc(-c3ccccn3)s2)NS1(=O)=O]

The above titled compounds have been synthesized by following the general procedure described above for Stille coupling by using HBV-CSU-391 and corresponding stannane (see Table 2 for analytical data).

Synthesis of Cis-N-(3-chloro-4-fluorophenyl)-5-(5-(1-methyl-1H-pyrazol-4-yl)thiophen-2-yl)-1,2,6-thiadiazinane-3-carboxamide 1,1-dioxide (HBV-CSU-427)

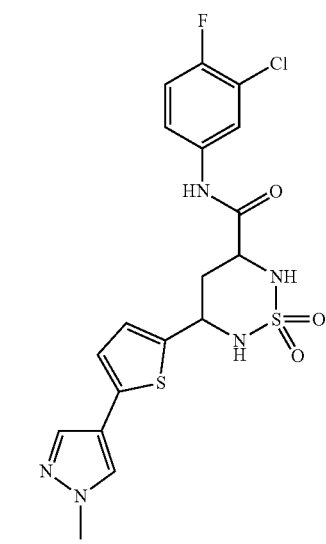 [SMILES: Cn1cc(-c2ccc(C3CC(C(=O)Nc4ccc(F)c(Cl)c4)NS(=O)(=O)N3)s2)cn1]

The above titled compounds have been synthesized by following the general procedure described above for Suzuki coupling by using HBV-CSU-391 and corresponding boronic acid (see Table 2 for analytical data).

Note: This compound was obtained as a side product.

573

Synthesis of Cis-N-(3-chloro-4-fluorophenyl)-5-(5-(1-methyl-1H-imidazol-4-yl)thiophen-2-yl)-1,2,6-thiadiazinane-3-carboxamide 1,1-dioxide (HBV-CSU-428)

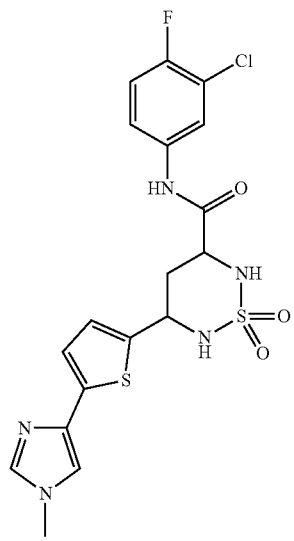 [SMILES: Cn1cnc(-c2ccc(C3CC(C(=O)Nc4ccc(F)c(Cl)c4)NS(=O)(=O)N3)s2)c1]

The above titled compounds have been synthesized by following the general procedure described above for Stille coupling by using HBV-CSU-391 and corresponding stannane (see Table 2 for analytical data).

Note: This compound was obtained as a side product.

Scheme 78

Synthesis of amides using 2-methyl-5-(5-(1-methyl-1H-pyrazol-4-yl)thiophen-2-yl)-1,2,6-thiadiazinane-3-carboxylic acid 1,1-dioxide Scheme 78:

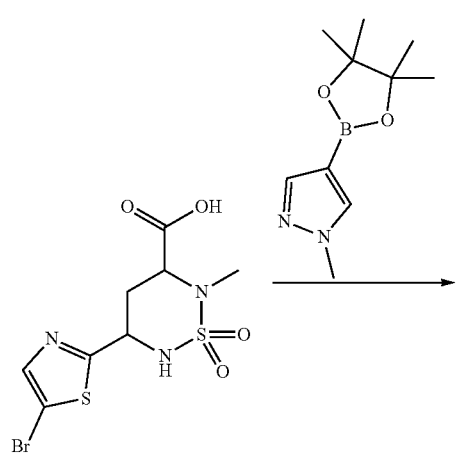

224

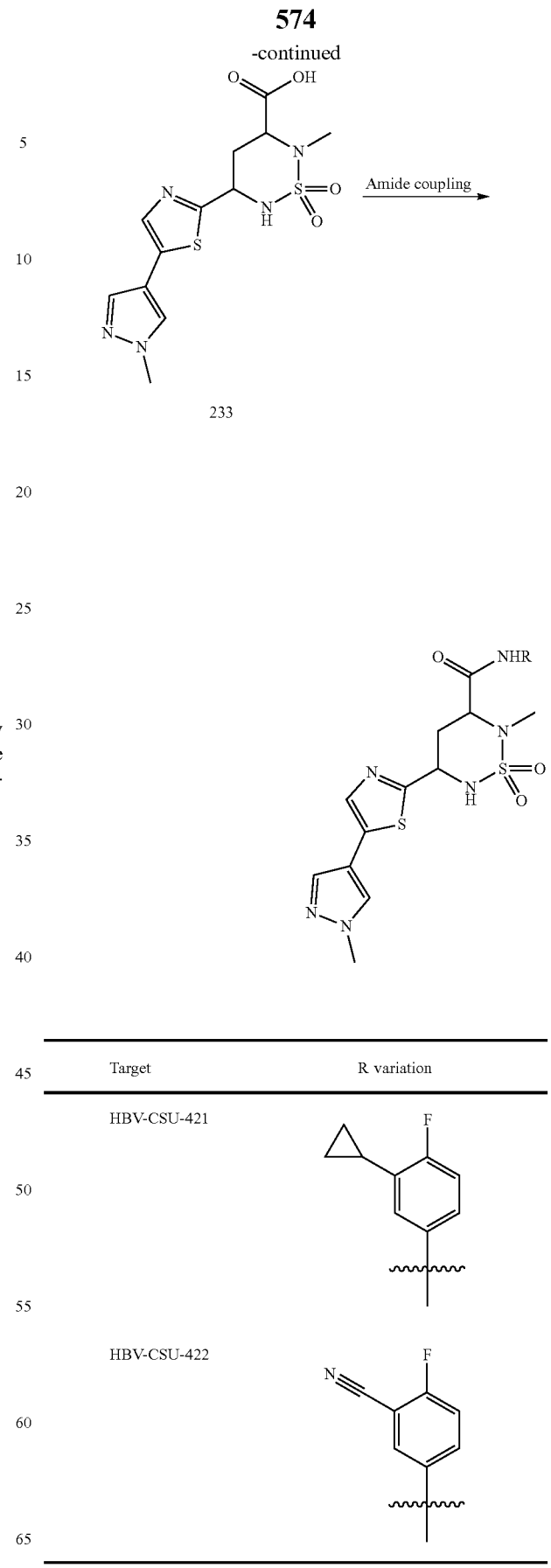

| Target | R variation |
|---|---|
| HBV-CSU-421 | (2-fluoro-5-cyclopropylphenyl) |
| HBV-CSU-422 | (2-fluoro-5-cyanophenyl) |

Synthesis of 2-methyl-5-(5-(1-methyl-1H-pyrazol-4-yl)thiazol-2-yl)-1,2,6-thiadiazinane-3-carboxylic acid 1,1-dioxide (233)

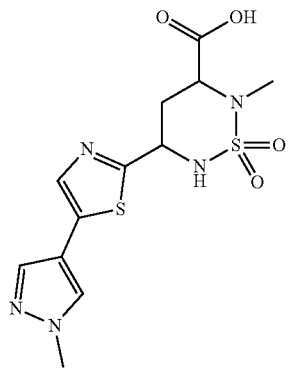 [SMILES: CN1C(C(=O)O)CC(c2ncc(-c3cnn(C)c3)s2)NS1(=O)=O]

To a mixture of bromo Compound 224 (500 mg, 1.41 mmol), boronic acid/boronate ester (321 mg, 1.54 mmol) in 4 mL of 1,4-dioxane:H$_2$O (1:1), DIPEA (543 mg, 4.21 mmol) was added, purged with Ar for 15 min, followed by the addition of PdCl$_2$(PPh$_3$)$_2$ (10 mg, 0.0140 mmol), and stirred at 80° C. for overnight. The progress of the reaction was monitored by LCMS. After completion of the reaction, the reaction mixture was filtered through Celite and evaporated to dryness. The residue was taken in water and acidified with 2N HCl (2-4 pH), precipitated solid was filtered and dried to afford Compound 233 (400 mg, 80%) as a light yellow solid. LCMS Calculated for C$_{12}$H$_{15}$N$_5$O$_4$S$_2$: 357.06; LCMS observed: 358.05 (M+1)$^+$.

Synthesis of Cis-N-(3-cyclopropyl-4-fluorophenyl)-2-methyl-5-(5-(1-methyl-1H-pyrazol-4-yl)thiazol-2-yl)-1,2,6-thiadiazinane-3-carboxamide 1,1-dioxide (HBV-CSU-421)

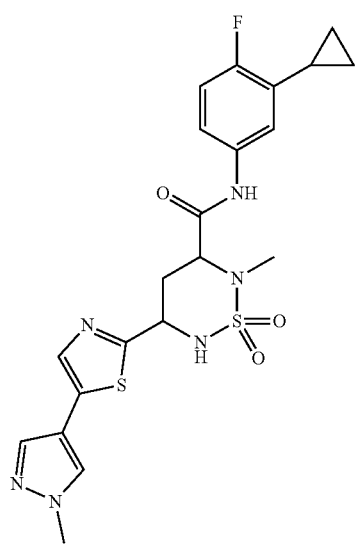 [SMILES: CN1C(C(=O)Nc2ccc(F)c(C3CC3)c2)CC(c2ncc(-c3cnn(C)c3)s2)NS1(=O)=O]

The above titled compound has been synthesized by following the general procedure (Method B) described above for amidation by using Compound 233 and corresponding amine (see Table 2 for analytical data).

Synthesis of Cis-N-(3-cyano-4-fluorophenyl)-2-methyl-5-(5-(1-methyl-1H-pyrazol-4-yl)thiazol-2-yl)-1,2,6-thiadiazinane-3-carboxamide 1,1-dioxide (HBV-CSU-422)

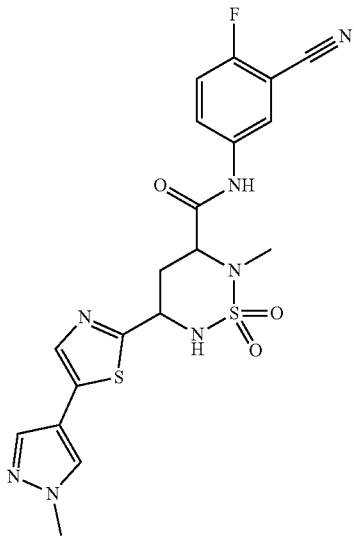 [SMILES: CN1C(C(=O)Nc2ccc(F)c(C#N)c2)CC(c2ncc(-c3cnn(C)c3)s2)NS1(=O)=O]

The above titled compound has been synthesized by following the general procedure (Method B) described above for amidation by using Compound 233 and corresponding amine (see Table 2 for analytical data).

Scheme 79

Synthesis of amides using 5-(5-bromothiazol-2-yl)-2-methyl-1,2,6-thiadiazinane-3-carboxylic acid 1,1-dioxide followed by C-C coupling Scheme 79:

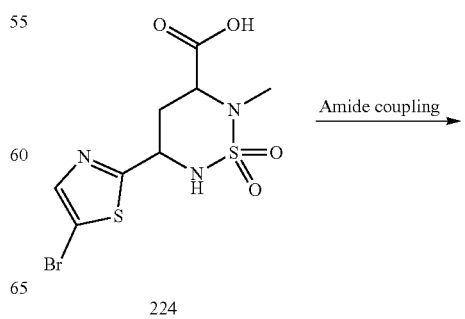

224

577
-continued

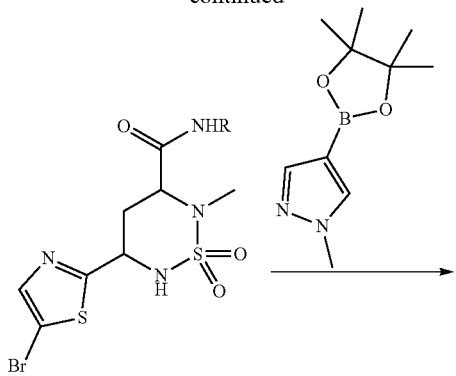

234

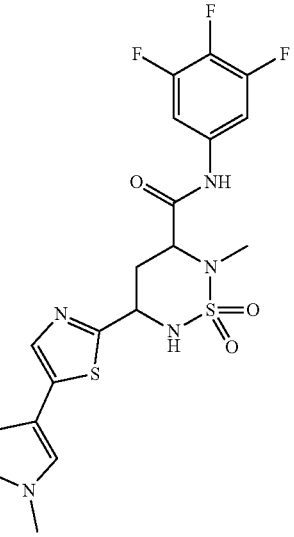

| Target | R variation |
|---|---|
| HBV-CSU-417 | ![F,F,F-phenyl] |

To a stirred solution of above acid compound (1 eq.) in DCM/DMF (10V) at 0° C. was added DIPEA (3 eq.), stirred for 15 min, followed by addition of HATU (1.5 eq.), again stirred for 15 min and then corresponding aniline (1.2 eq.) was added. The reaction mixture was then stirred at room temperature for overnight. The progress of the reaction was monitored by TLC. After completion, the reaction mixture was diluted with ice cold water and extracted with DCM. The combined organic layers were dried over anhydrous sodium sulphate and concentrated under reduced pressure to afford a crude compound. The crude compound was taken in methanol (10V), stirred for 15 min., filtered and dried under reduced pressure to afford compound desired compound. LCMS Calculated for $C_{14}H_{12}BrF_3N_4O_3S_2$: 483.95; LCMS observed: 485.95 (M+2)$^+$.

578

Synthesis of Cis-2-methyl-5-(5-(1-methyl-1H-pyrazol-4-yl)thiazol-2-yl)-N-(3,4,5-trifluorophenyl)-1,2,6-thiadiazinane-3-carboxamide 1,1-dioxide (HBV-CSU-417)

To a mixture of corresponding bromo compound for HBV-CSU-417 (1 eq), boronic acid/boronate ester (1.2 eq) in 1,4-dioxane:H$_2$O (1:1), DIPEA (2 eq) was added, purged with Ar gas for 15 min, followed by the addition of PdCl$_2$(PPh$_3$)$_2$ (0.005 eq), and stirred at 80° C. for overnight. The progress of the reaction was monitored by LCMS. After completion of the reaction, the reaction mixture was diluted with water and extracted with ethyl acetate. The combined organic layers were dried over anhydrous sodium sulphate and concentrated under reduced pressure. The crude compound was purified by silica gel column chromatography to afford title compound HBV-CSU-417 (see Table 2 for analytical data).

Scheme 80

Synthesis of Cis-N-(3-chloro-4-fluorophenyl)-5-(5-(1-methyl-1H-pyrazol-4-yl)thiophen-2-yl)-2-propyl-1,2,6-thiadiazinane-3-carboxamide 1,1-dioxide (HBV-CSU-424)

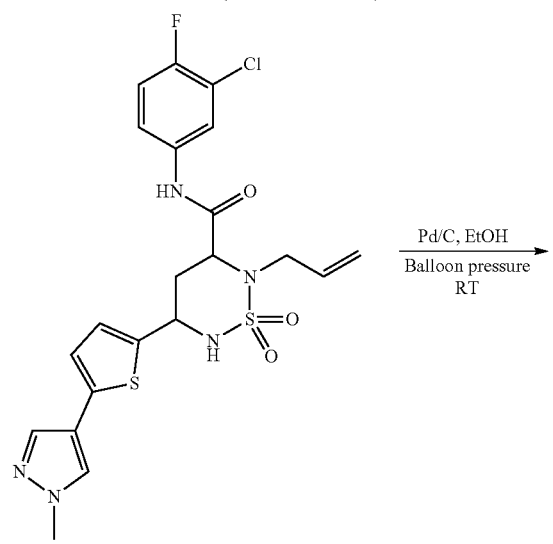

HBV-CSU-394

-continued

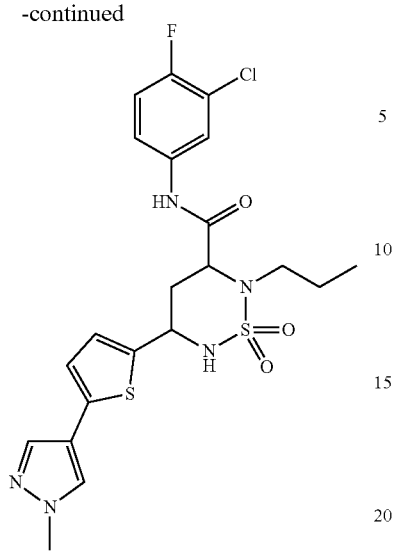

HBV-CSU-424

To a stirred solution of compound HBV-CSU-394 (0.035 g, 0.068 mmol) in ethanol (5 mL), 10% Pd/C (10% w/w of substrate, 3 mg) was added and the reaction mixture was stirred under hydrogen atmosphere (balloon pressure) at room temperature for 16 h. The progress of the reaction was monitored by TLC. After completion, the reaction mixture was filtered through a pad of celite, the filtrate was evaporated under reduced pressure and the resulting residue was triturated with diethyl ether and n-pentane to afford the title compound HBV-CSU-424 (see Table 2 for analytical data).

TABLE 1

Analytical data for HBV-CSU_Int:

| Target No | Structure | Rx. Yield (%) | Mass Spec. Found (m/z) | Mass Spec. Calculated | $^1$H-NMR |
|---|---|---|---|---|---|
| HBV-CSU-006_Int | 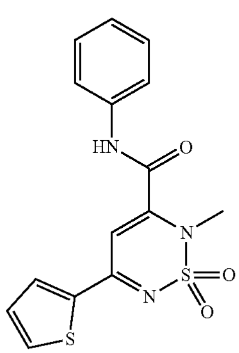 [SMILES: CN1C(C(=O)Nc2ccccc2)=CC(c2cccs2)=NS1(=O)=O] | 41% | 347.85 (M + 1) | 347.04 for $C_{15}H_{13}N_3O_3S_2$ | $^1$H-NMR (DMSO-$d_6$, 400 MHz): δ 11.11 (s, 1H), 8.29-8.25 (m, 1H), 8.08 (d, J = 4.4 Hz, 1H), 7.69 (d, J = 7.6 Hz, 2H), 7.42-7.28 (m, 3H), 7.21-7.15 (m, 2H), 3.43 (s, 3H). |

TABLE 1-continued

Analytical data for HBV-CSU_Int:

| Target No | Structure | Rx. Yield (%) | Mass Spec. Found (m/z) | Mass Spec. Calculated | ¹H-NMR |
|---|---|---|---|---|---|
| HBV-CSU-007_Int | 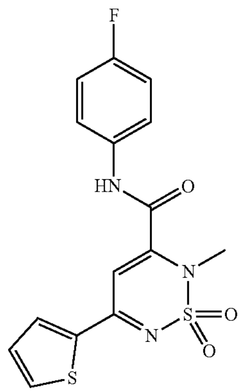 [SMILES: CN1C(C(=O)Nc2ccc(F)cc2)=CC(c2cccs2)=NS1(=O)=O] | 33% | 365.85 (M + 1) | 365.03 for $C_{15}H_{12}FN_3O_3S_2$ | ¹H-NMR (DMSO-$d_6$, 400 MHz): δ 11.19 (s, 1H), 8.26 (d, J = 4.0 Hz, 1H), 8.09 (d, J = 4.8 Hz, 1H), 7.75-7.72 (m, 2H), 7.33-7.24 (m, 3H), 7.17 (s, 1H), 3.44 (s, 3H). |
| HBV-CSU-010_Int | 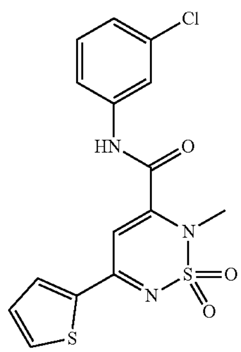 [SMILES: CN1C(C(=O)Nc2cccc(Cl)c2)=CC(c2cccs2)=NS1(=O)=O] | 37% | 381.85 (M + 1) | 381.0 for $C_{15}H_{12}ClN_3O_3S_2$ | ¹H-NMR (DMSO-$d_6$, 400 MHz): δ 11.29 (s, 1H), 8.26 (d, J = 3.2 Hz, 1H), 8.09 (d, J = 4.8 Hz, 1H), 7.87-7.86 (m, 1H), 7.62-7.61 (m, 1H), 7.45 (d, J = 4.0 Hz, 1H), 7.34-7.27 (m, 2H), 7.20 (s, 1H), 3.45 (s, 3H). |
| HBV-CSU-011_Int | 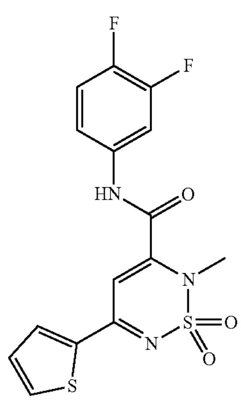 [SMILES: CN1C(C(=O)Nc2ccc(F)c(F)c2)=CC(c2cccs2)=NS1(=O)=O] | 44% | 384 (M + 1) | 383.02 for $C_{15}H_{11}F_2N_3O_3S_2$ | ¹H-NMR (DMSO-$d_6$, 400 MHz): δ 11.35 (s, 1H), 8.26 (d, J = 2.4 Hz, 1H), 8.10 (d, J = 5.2 Hz, 1H), 7.87-7.82 (m, 1H), 7.56-7.49 (m, 2H), 7.34-7.32 (m, 1H), 7.19 (s, 1H), 3.44 (s, 3H). |
| HBV-CSU-012_Int | 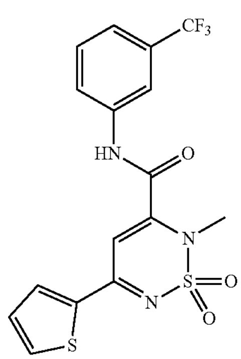 | 51% | 415.90 (M + 1) | 415.03 for $C_{16}H_{12}F_3N_3O_3S_2$ | ¹H-NMR (DMSO-$d_6$, 400 MHz): δ 11.42 (s, 1H), 8.24 (d, J = 3.2 Hz, 1H), 8.13-8.12 (m, 1H), 8.09 (d, J = 4.8 Hz, 1H), 7.94 (d, J = 8.8 Hz, 1H), 7.67 (t, J = 8.0 Hz, 1H), 7.58-7.56 (m, 1H), 7.32 (d, J = 4.4 Hz, 1H), 7.22 (s, 1H), 3.46 (s, 3H). |

TABLE 1-continued

Analytical data for HBV-CSU_Int:

| Target No | Structure | Rx. Yield (%) | Mass Spec. Found (m/z) | Mass Spec. Calculated | ¹H-NMR |
|---|---|---|---|---|---|
| HBV-CSU-013_Int | (3-methylphenyl carboxamide derivative) | 57% | 361.97 (M + 1) | 361.06 for $C_{16}H_{15}N_3O_3S_2$ | ¹H-NMR (DMSO-$d_6$, 400 MHz): δ 11.03 (s, 1H), 8.25 (d, J = 3.2 Hz, 1H), 8.08 (d, J = 4.8 Hz, 1H), 7.54 (br. s, 1H), 7.48 (d, J = 8.4 Hz, 1H), 7.32-7.27 (m, 2H), 7.13 (s, 1H), 7.01 (d, J = 7.2 Hz, 1H), 3.43 (s, 3H), 2.32 (s, 3H). |
| HBV-CSU-014_Int | (4-chlorophenyl carboxamide derivative) | 77% | 381.0 (M + 1) | 381.85 for $C_{15}H_{12}ClN_3O_3S_2$ | ¹H-NMR (DMSO-$d_6$, 400 MHz): δ 11.26 (s, 1H), 8.26 (d, J = 3.6 Hz, 1H), 8.09 (d, J = 5.2 Hz, 1H), 7.73 (d, J = 8.8 Hz, 2H), 7.48 (d, J = 8.8 Hz, 2H), 7.33-7.32 (m, 1H), 7.19 (s, 1H), 3.44 (s, 3H). |
| HBV-CSU-015_Int | (3-chloro-4-fluorophenyl N-methyl carboxamide derivative) | 53% | 413.95 (M + 1) | 413.01 for $C_{16}H_{13}ClFN_3O_3S_2$ | ¹H-NMR (DMSO-$d_6$, 400 MHz): δ 8.03 (d, J = 4.8 Hz, 1H), 7.94 (d, J = 3.6 Hz, 1H), 7.90-7.86 (m, 1H), 7.62-7.42 (m, 2H), 7.27 (t, J = 4.0 Hz, 1H), 6.87 (s, 1H), 3.41 (s, 3H), 3.36 (s, 3H). |

TABLE 1-continued

Analytical data for HBV-CSU_Int:

| Target No | Structure | Rx. Yield (%) | Mass Spec. Found (m/z) | Mass Spec. Calculated | ¹H-NMR |
|---|---|---|---|---|---|
| HBV-CSU-016_Int | (structure with F, Br phenyl) | 45% | 445.65 (M + 2) | 442.94 for $C_{15}H_{11}BrFN_3O_3S_2$ | ¹H-NMR (DMSO-$d_6$, 400 MHz): δ 11.29 (s, 1H), 8.25 (d, J = 3.6 Hz, 1H), 8.11-8.09 (m, 2H), 7.71-7.67 (m, 1H), 7.47 (t, J = 8.0 Hz, 1H), 7.34-7.32 (m, 1H), 7.19 (s, 1H), 3.45 (s, 3H). |
| HBV-CSU-017_Int | (structure with Br phenyl) | 50% | 426 (M + 1) | 424.95 for $C_{15}H_{12}BrN_3O_3S_2$ | ¹H-NMR (DMSO-$d_6$, 400 MHz): δ 11.28 (s, 1H), 8.26 (d, J = 4.0 Hz, 1H), 8.10 (d, J = 4.8 Hz, 1H), 8.01 (s, 1H), 7.65 (d, J = 7.2 Hz, 1H), 7.42-7.31 (m, 3H), 7.20 (s, 1H), 3.45 (s, 3H). |
| HBV-CSU-018_Int | (structure with Cl, F phenyl) | 51% | 400.0 (M + 1) | 398.99 for $C_{15}H_{11}ClFN_3O_3S_2$ | ¹H-NMR (DMSO-$d_6$, 400 MHz): δ 11.47 (s, 1H), 8.26 (d, J = 4.0 Hz, 1H), 8.10 (d, J = 4.8 Hz, 1H), 7.82 (dd, J = 11.2, 4.0 Hz, 1H), 7.66 (t, J = 8.0 Hz, 1H), 7.53-7.52 (m, 1H), 7.33 (t, J = 4.4 Hz, 1H), 7.21 (s, 1H), 3.45 (s, 3H). |

TABLE 1-continued

Analytical data for HBV-CSU_Int:

| Target No | Structure | Rx. Yield (%) | Mass Spec. Found (m/z) | Mass Spec. Calculated | ¹H-NMR |
|---|---|---|---|---|---|
| HBV-CSU-019_Int | 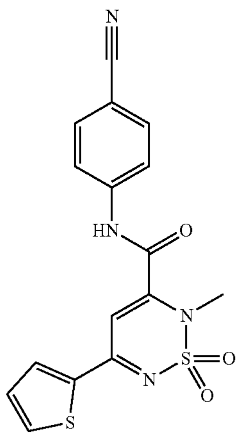 [SMILES: CN1C(C(=O)Nc2ccc(C#N)cc2)=CC(c2cccs2)=NS1(=O)=O] | — | 372.90 (M + 1) | 372.04 for $C_{16}H_{12}N_4O_3S_2$ | The reaction was monitored by LCMS and crude intermediate carried forward to the next step. |
| HBV-CSU-020_Int | 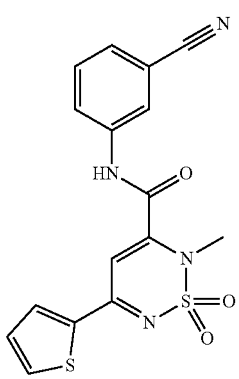 [SMILES: CN1C(C(=O)Nc2cccc(C#N)c2)=CC(c2cccs2)=NS1(=O)=O] | 64% | 372.90 (M + 1) | 372.04 for $C_{16}H_{12}N_4O_3S_2$ | ¹H-NMR (DMSO-$d_6$, 400 MHz): δ 11.43 (s, 1H), 8.25 (d, J = 3.2 Hz, 1H), 8.16-8.15 (m, 1H), 8.10 (d, J = 4.8 Hz, 1H), 7.96-7.94 (m, 1H), 7.70-7.63 (m, 2H), 7.34 (t, J = 4.4 Hz, 1H), 7.21 (s, 1H), 3.46 (s, 3H). |
| HBV-CSU-023_Int | 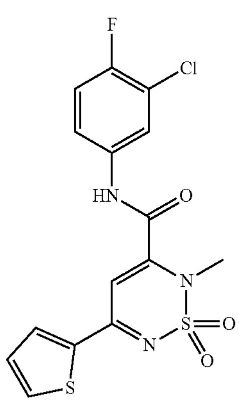 [SMILES: CN1C(C(=O)Nc2ccc(F)c(Cl)c2)=CC(c2cccs2)=NS1(=O)=O] | 58% | 399.91 (M + 1) | 398.99 for $C_{15}H_{11}ClFN_3O_3S_2$ | ¹H-NMR (DMSO-$d_6$, 400 MHz): δ 11.31 (s, 1H), 8.25 (d, J = 3.6 Hz, 1H), 8.10 (d, J = 4.8 Hz, 1H), 7.99-7.97 (m, 1H), 7.66-7.62 (m, 1H), 7.49 (t, J = 9.2 Hz, 1H), 7.34-7.31 (m, 1H), 7.19 (s, 1H), 3.45 (s, 3H). |

TABLE 1-continued

Analytical data for HBV-CSU_Int:

| Target No | Structure | Rx. Yield (%) | Mass Spec. Found (m/z) | Mass Spec. Calculated | $^1$H-NMR |
|---|---|---|---|---|---|
| HBV-CSU-024_Int | 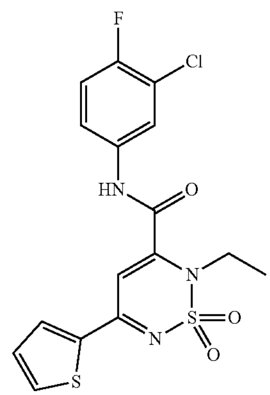 [SMILES: CCN1C(C(=O)Nc2ccc(F)c(Cl)c2)=CC(c2cccs2)=NS1(=O)=O] | 54% | 413.85 (M + 1) | 413.01 for $C_{16}H_{13}ClFN_3O_3S_2$ | $^1$H-NMR (DMSO-$d_6$, 400 MHz): δ 11.34 (s, 1H), 8.24 (d, J = 4.0 Hz, 1H), 8.09 (d, J = 5 Hz, 1H), 7.98-7.96 (m, 1H), 7.65-7.62 (m, 1H), 7.48 (t, J = 9.2 Hz, 1H), 7.33-7.30 (m, 1H), 7.21 (s, 1H), 3.87 (q, J = 7.6 Hz, 2H), 1.34 (t, J = 7.6 Hz, 3H). |
| HBV-CSU-027_Int | 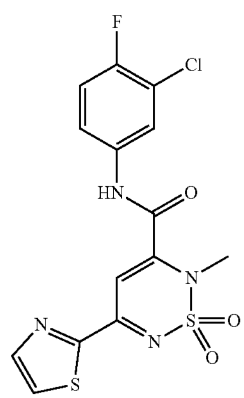 [SMILES: CN1C(C(=O)Nc2ccc(F)c(Cl)c2)=CC(c2nccs2)=NS1(=O)=O] | — | 400.90 (M + 1) | 399.99 for $C_{14}H_{10}ClFN_4O_3S_2$ | The reaction was monitored by LCMS and crude intermediate carried forward to the next step. |
| HBV-CSU-029_Int | 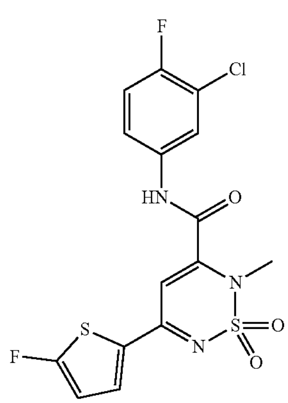 [SMILES: CN1C(C(=O)Nc2ccc(F)c(Cl)c2)=CC(c2ccc(F)s2)=NS1(=O)=O] | 51% | 417.85 (M + 1) | 416.98 for $C_{15}H_{10}ClF_2N_3O_3S_2$ | $^1$H-NMR (DMSO-$d_6$, 400 MHz): δ 11.32 (s, 1H), 8.11 (t, J = 4.0 Hz, 1H), 7.96 (dd, J = 6.4, 2.4 Hz, 1H), 8.11 (t, J = 4.0 Hz, 1H), 7.65-7.61 (m, 1H), 7.50 (t, J = 0.8 Hz, 1H), 7.20 (s, 1H), 3.44 (s, 3H). |

TABLE 1-continued

Analytical data for HBV-CSU_Int:

| Target No | Structure | Rx. Yield (%) | Mass Spec. Found (m/z) | Mass Spec. Calculated | $^1$H-NMR |
|---|---|---|---|---|---|
| HBV-CSU-031_Int | 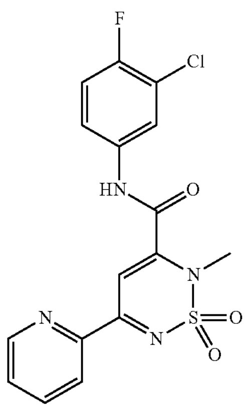 [SMILES: CN1C(C(=O)Nc2ccc(F)c(Cl)c2)=CC(c2ccccn2)=NS1(=O)=O] | — | 395.25 (M + 1) | 394.03 for $C_{16}H_{12}ClFN_4O_3S$ | The reaction was monitored by LCMS and crude intermediate carried forward to the next step. |
| HBV-CSU-032_Int | 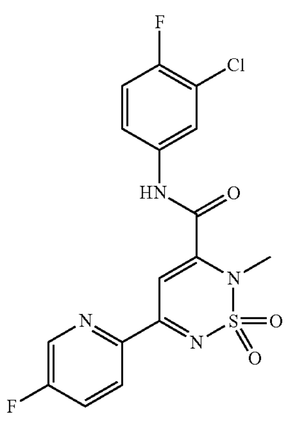 [SMILES: CN1C(C(=O)Nc2ccc(F)c(Cl)c2)=CC(c2ccc(F)cn2)=NS1(=O)=O] | 100% | 413.25 (M + 1) | 412.02 for $C_{16}H_{11}ClF_2N_4O_3S$ | $^1$H-NMR (DMSO-d$_6$, 400 MHz): δ 11.40 (s, 1H), 8.82 (d, J = 3.2 Hz, 1H), 8.41-8.38 (m, 1H), 8.03-7.98 (m, 2H), 7.64-7.59 (m, 1H), 7.49 (t, J = 8.8 Hz, 1H), 7.34 (s, 1H), 3.53 (s, 3H). |
| HBV-CSU-033_Int | 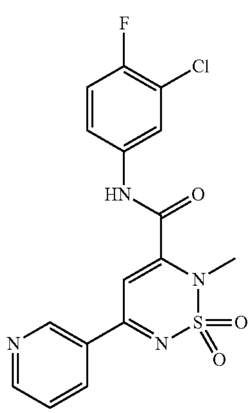 [SMILES: CN1C(C(=O)Nc2ccc(F)c(Cl)c2)=CC(c2cccnc2)=NS1(=O)=O] | — | 395 (M + 1) | 394.03 for $C_{16}H_{12}ClFN_4O_3S$ | The reaction was monitored by LCMS and crude intermediate carried forward to the next step. |

TABLE 1-continued

Analytical data for HBV-CSU_Int:

| Target No | Structure | Rx. Yield (%) | Mass Spec. Found (m/z) | Mass Spec. Calculated | ¹H-NMR |
|---|---|---|---|---|---|
| HBV-CSU-036_Int | 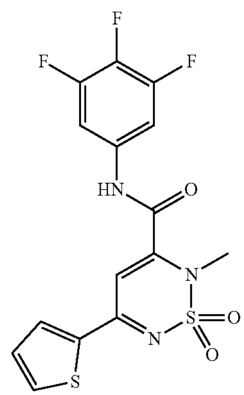 [SMILES: CN1C(C(=O)Nc2cc(F)c(F)c(F)c2)=CC(c2cccs2)=NS1(=O)=O] | 71% | 401.80 (M + 1) | 401.01 for $C_{15}H_{10}F_3N_3O_3S_2$ | ¹H-NMR (DMSO-$d_6$, 400 MHz): δ 11.50 (s, 1H), 8.26-8.25 (m, 1H), 8.11 (d, J = 4.8 Hz, 1H), 7.65-7.61 (m, 2H), 7.35-7.31 (m, 1H), 7.21 (s, 1H), 3.45 (s, 3H). |
| HBV-CSU-040_Int | 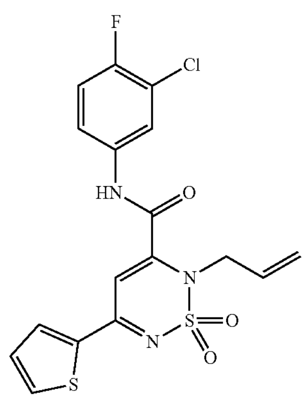 [SMILES: C=CCN1C(C(=O)Nc2ccc(F)c(Cl)c2)=CC(c2cccs2)=NS1(=O)=O] | 64% | 426.00 (M + 1) | 425.01 for $C_{16}H_{13}ClFN_3O_3S_2$ | ¹H-NMR (DMSO-$d_6$, 400 MHz): δ 11.30 (s, 1H), 8.29 (d, J = 4.0 Hz, 1H), 8.12 (d, J = 4.8 Hz, 1H), 7.96-7.93 (m, 1H), 7.62-7.61 (m, 1H), 7.49 (t, J = 11.2 Hz, 1H), 7.34 (t, J = 4.8 Hz, 1H), 7.29 (s, 1H), 5.95-5.80 (m, 1H), 5.24-5.19 (m, 2H), 4.52 (d, J = 6.0 Hz, 2H). |
| HBV-CSU-041_Int | 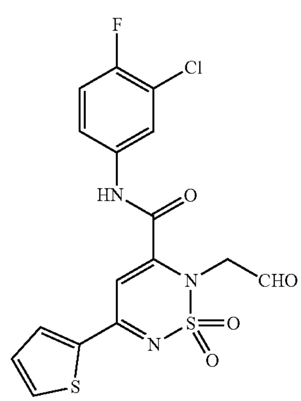 [SMILES: O=CCN1C(C(=O)Nc2ccc(F)c(Cl)c2)=CC(c2cccs2)=NS1(=O)=O] | — | — | — | The reaction was monitored by TLC (DNP stain) and crude intermediate carried forward to the next step. |

TABLE 1-continued

Analytical data for HBV-CSU_Int:

| Target No | Structure | Rx. Yield (%) | Mass Spec. Found (m/z) | Mass Spec. Calculated | $^1$H-NMR |
|---|---|---|---|---|---|
| HBV-CSU-045_Int | 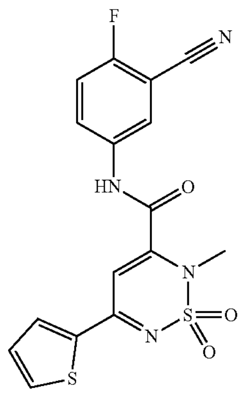 [SMILES: CN1C(C(=O)Nc2ccc(F)c(C#N)c2)=CC(c2cccs2)=NS1(=O)=O] | 64% | 391.06 (M + 1) | 390.03 for $C_{16}H_{11}FN_4O_3S_2$ | $^1$H-NMR (DMSO-$d_6$, 400 MHz): δ 11.45 (s, 1H), 8.24 (dd, J = 4.0, 0.8 Hz, 1H), 8.18 (dd, J = 6.0, 3.2 Hz, 1H), 8.09 (dd, J = 4.8, 0.8 Hz, 1H), 8.01-7.96 (m, 1H), 7.62 (t, J = 11.2 Hz, 1H), 7.33-7.31 (m, 1H), 7.19 (s, 1H), 3.45 (s, 3H). |
| HBV-CSU-046_Int | 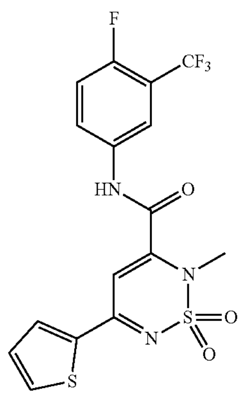 [SMILES: CN1C(C(=O)Nc2ccc(F)c(C(F)(F)F)c2)=CC(c2cccs2)=NS1(=O)=O] | — | 434 (M + 1) | 433.02 for $C_{16}H_{11}F_4N_3O_3S_2$ | The reaction was monitored by LCMS and the crude intermediate carried forward to the next step. |
| HBV-CSU-047_Int | 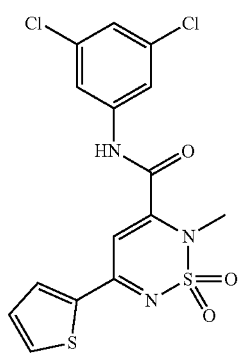 | 57% | 416.21 (M + 1) | 414.96 for $C_{15}H_{11}Cl_2N_3O_3S_2$ | $^1$H-NMR (DMSO-$d_6$, 400 MHz): δ 11.41 (s, 1H), 8.25 (d, J = 4.0 Hz, 1H), 8.11 (d, J = 4.8 Hz, 1H), 7.78-7.76 (m, 2H), 7.49-7.48 (m, 1H), 7.34 (t, J = 6.0 Hz, 1H), 7.22 (s, 1H), 3.46 (s, 3H). |
| HBV-CSU-048_Int | 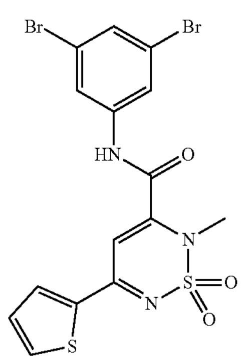 [SMILES: CN1C(C(=O)Nc2cc(Br)cc(Br)c2)=CC(c2cccs2)=NS1(=O)=O] | — | 505.80 (M + 2) | 502.86 for $C_{15}H_{11}Br_2N_3O_3S_2$ | The reaction was monitored by LCMS and the crude intermediate carried forward to the next step. |

TABLE 1-continued

Analytical data for HBV-CSU_Int:

| Target No | Structure | Rx. Yield (%) | Mass Spec. Found (m/z) | Mass Spec. Calculated | $^1$H-NMR |
|---|---|---|---|---|---|
| HBV-CSU-049_Int | 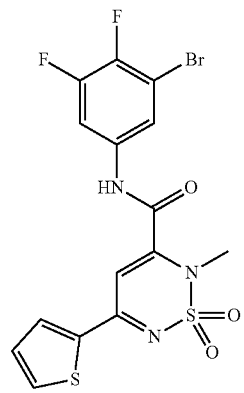 [SMILES: CN1C(C(=O)Nc2cc(F)c(F)c(Br)c2)=CC(c2cccs2)=NS1(=O)=O] | 55% | 461.94 (M + 1) | 460.93 for $C_{15}H_{10}BrF_2N_3O_3S_2$ | $^1$H-NMR (DMSO-d$_6$, 400 MHz): δ 11.38 (s, 1H), 8.21-8.07 (m, 2H), 7.81-7.79 (m, 2H), 7.32-7.29 (m, 1H), 7.17 (s, 1H), 3.42 (s, 3H). |
| HBV-CSU-050_Int | 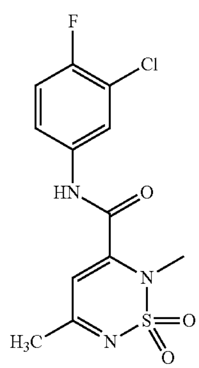 [SMILES: CC1=NS(=O)(=O)N(C)C(C(=O)Nc2ccc(F)c(Cl)c2)=C1] | 70% | 332.05 (M + 1) | 331.02 for $C_{12}H_{11}ClFN_3O_3S$ | $^1$H-NMR (DMSO-d$_6$, 400 MHz): δ 11.20 (s, 1H), 7.95 (dd, J = 6.8, 2.4 Hz, 1H), 7.62-7.57 (m, 1H), 7.48 (t, J = 9.2 Hz, 1H), 6.41 (s, 1H), 3.39 (s, 3H), 2.33 (s, 3H). |
| HBV-CSU-054_Int | 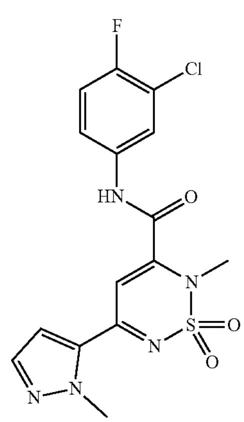 [SMILES: CN1C(C(=O)Nc2ccc(F)c(Cl)c2)=CC(c2ccnn2C)=NS1(=O)=O] | 71% | 397.90 (M + 1) | 397.04 for $C_{15}H_{13}ClFN_5O_3S$ | $^1$H-NMR (DMSO-d$_6$, 400 MHz): δ 11.30 (s, 1H), 7.97 (dd, J = 6.8, 2.5 Hz, 1H), 7.67-7.61 (m, 2H), 7.50 (t, J = 9.0 Hz, 1H), 7.37 (d, J = 2.3 Hz, 1H), 7.04 (s, 1H), 4.18 (s, 3H), 3.48 (s, 3H). |

TABLE 1-continued

Analytical data for HBV-CSU_Int:

| Target No | Structure | Rx. Yield (%) | Mass Spec. Found (m/z) | Mass Spec. Calculated | $^1$H-NMR |
|---|---|---|---|---|---|
| HBV-CSU-055_Int | 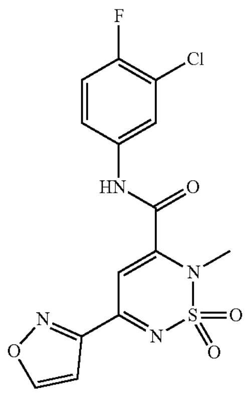 [SMILES: CN1C(C(=O)Nc2ccc(F)c(Cl)c2)=CC(c2ccon2)=NS1(=O)=O] | 15% | 383.01 (M − 1) | 384.01 for $C_{14}H_{10}ClFN_4O_4S$ | $^1$H-NMR (DMSO-d$_6$, 400 MHz): δ 11.36 (s, 1H), 9.27 (d, J = 1.8 Hz, 1H), 7.97 (dd, J = 6.8, 2.5 Hz, 1H), 7.63-7.59 (m, 1H), 7.49 (t, J = 9.0 Hz, 1H), 7.23 (d, J = 1.8 Hz, 1H), 7.07 (s, 1H), 3.54 (s, 3H). |
| HBV-CSU-056_Int | 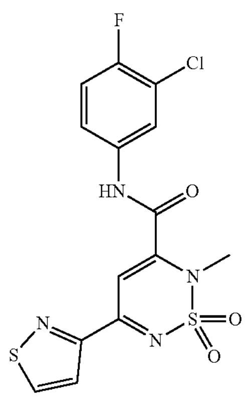 [SMILES: CN1C(C(=O)Nc2ccc(F)c(Cl)c2)=CC(c2ccsn2)=NS1(=O)=O] | 51% | 400.90 (M + 1) | 399.99 for $C_{14}H_{10}ClFN_4O_3S_2$ | $^1$H-NMR (DMSO-d$_6$, 400 MHz): δ 10.57 (s, 1H), 9.09 (d, J = 4.6 Hz, 1H), 7.96 (dd, J = 6.8, 2.5 Hz, 1H), 7.70 (d, J = 10.0 Hz, 1H), 7.58-7.52 (m, 1H), 7.49 (d, J = 4.6 Hz, 1H), 7.40 (t, J = 9.1 Hz, 1H), 2.62 (s, 3H). |
| HBV-CSU-057_Int | 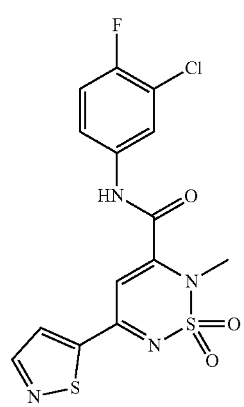 [SMILES: CN1C(C(=O)Nc2ccc(F)c(Cl)c2)=CC(c2ccns2)=NS1(=O)=O] | 72% | 398.90 (M − 1) | 399.99 for $C_{14}H_{10}ClFN_4O_3S_2$ | 1H-NMR (DMSO-d6, 400 MHz): δ 11.40 (s, 1H), 8.82 (d, J = 1.9 Hz, 1H), 8.34 (d, J = 1.9 Hz, 1H), 7.98 (dd, J = 6.8, 2.5 Hz, 1H), 7.66-7.61 (m, 1H), 7.51 (t, J = 8.9 Hz, 1H), 7.27 (s, 1H), 3.52 (s, 3H). |

TABLE 1-continued

Analytical data for HBV-CSU_Int:

| Target No | Structure | Rx. Yield (%) | Mass Spec. Found (m/z) | Mass Spec. Calculated | $^1$H-NMR |
|---|---|---|---|---|---|
| HBV-CSU-058_Int | (structure with F, Cl phenyl, thiazole, methoxyethyl) | 49% | 445 (M + 1) | 444.01 for $C_{16}H_{14}ClFN_4O_4S_2$ | $^1$H-NMR (DMSO-$d_6$, 400 MHz): δ 11.36 (s, 1H), 8.31-8.24 (m, 2H), 7.95 (d, J = 6.8 Hz, 1H), 7.63-7.62 (m, 1H), 7.50-7.45 (m, 1H), 7.26 (s, 1H), 4.22-4.20 (m, 2H), 3.55-3.53 (m, 2H), 3.15 (s, 3H). |
| HBV-CSU-059_Int | (structure with F, Br phenyl, thiazole, methoxyethyl) | 44% | 489 (M + 1) | 487.96 for $C_{16}H_{14}BrFN_4O_4S_2$ | $^1$H-NMR (DMSO-$d_6$, 400 MHz): δ 11.38 (s, 1H), 8.33-8.24 (m, 2H), 8.11-8.08 (m, 1H), 7.69-7.63 (m, 1H), 7.48-7.42 (m 1H), 7.26 (s, 1H), 4.23-4.20 (m, 2H), 3.55-3.53 (m, 2H), 3.15 (s, 3H). |
| HBV-CSU-060_Int | (structure with F, Br phenyl, thiazole, methyl) | — | 444.90 (M + 1) | 443.94 for $C_{14}H_{10}BrFN_4O_3S_2$ | The reaction was monitored by LCMS and the crude intermediate carried forward to the next step. |

TABLE 1-continued

Analytical data for HBV-CSU_Int:

| Target No | Structure | Rx. Yield (%) | Mass Spec. Found (m/z) | Mass Spec. Calculated | $^1$H-NMR |
|---|---|---|---|---|---|
| HBV-CSU-071_Int | 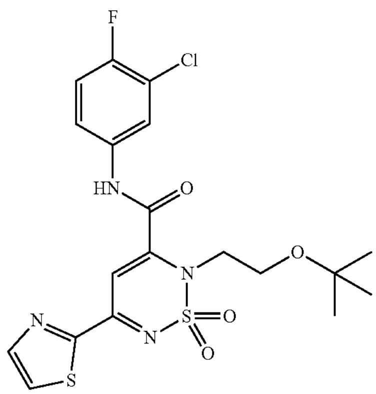 [SMILES: CC(C)(C)OCCN1C(C(=O)Nc2ccc(F)c(Cl)c2)=CC(c2nccs2)=NS1(=O)=O] | 62% | 431.1 (M + 1) Desbutyl | 486.06 for $C_{19}H_{20}ClFN_4O_4S_2$ | $^1$H-NMR (DMSO-$d_6$, 400 MHz): δ 11.21 (s, 1H), 8.31 (d, J = 3.0 Hz, 1H), 8.26 (d, J = 3.1 Hz, 1H), 8.00 (dd, J = 6.8, 2.6 Hz, 1H), 8.00 (dd, J = 6.8, 2.6 Hz, 1H), 7.69-7.64 (m, 1H), 7.48 (t, J = 9.1 Hz, 1H), 7.30 (s, 1H), 4.23 (t, J = 5.1 Hz, 2H), 3.52 (t, J = 5.1 Hz, 2H), 0.99 (s, 9H). |
| HBV-CSU-072_Int | 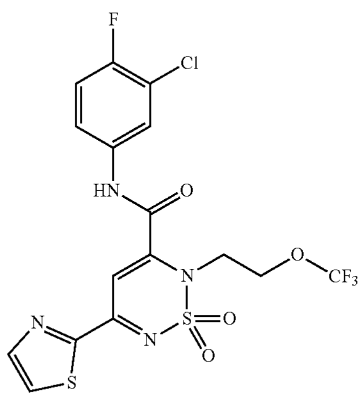 [SMILES: O=C(Nc1ccc(F)c(Cl)c1)C1=CC(c2nccs2)=NS(=O)(=O)N1CCOC(F)(F)F] | 30% | 499.00 (M + 1) | 497.98 for $C_{16}H_{11}ClF_4N_4O_4S_2$ | $^1$H-NMR (DMSO-$d_6$, 400 MHz): δ 11.46 (s, 1H), 7.96 (d, J = 6.8 Hz, 1H), 7.78 (d, J = 6.4 Hz, 1H), 7.61-7.58 (m, 1H), 7.51-7.47 (m, 1H), 7.36-7.32 (m, 2H), 4.50-4.30 (m, 4H). |
| HBV-CSU-073_Int | 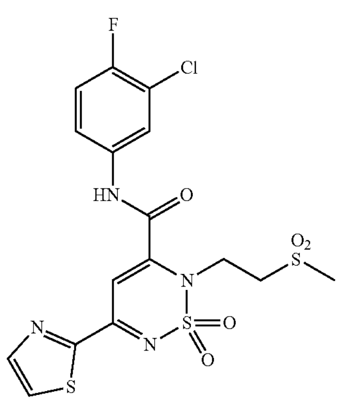 [SMILES: CS(=O)(=O)CCN1C(C(=O)Nc2ccc(F)c(Cl)c2)=CC(c2nccs2)=NS1(=O)=O] | 53% | 493.10 (M + 1) | 491.98 for $C_{16}H_{14}ClN_4O_5S_3$ | $^1$H-NMR (DMSO-$d_6$, 400 MHz): δ 11.43 (s, 1H), 8.33 (d, J = 2.9 Hz, 1H), 8.28 (d, J = 3.1 Hz, 1H), 7.97 (dd, J = 6.9, 2.5 Hz, 1H), 7.66-7.64 (m, 1H), 7.49 (t, J = 9.1 Hz, 1H), 7.37 (s, 1H), 4.40 (t, J = 7.7 Hz, 2H), 3.69-3.64 (m, 2H), 3.09 (s, 3H). |

TABLE 1-continued

Analytical data for HBV-CSU_Int:

| Target No | Structure | Rx. Yield (%) | Mass Spec. Found (m/z) | Mass Spec. Calculated | ¹H-NMR |
|---|---|---|---|---|---|
| HBV-CSU-077_Int | 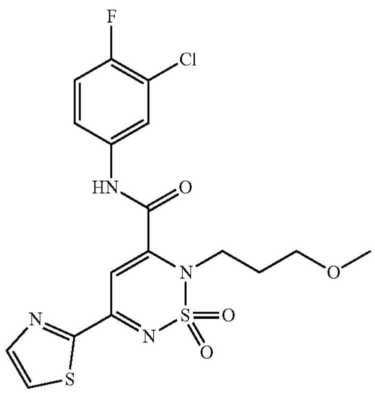 | 47% | 459.05 (M + 1) | 458.03 for $C_{17}H_{16}ClFN_4O_4S_2$ | ¹H-NMR (DMSO-$d_6$, 400 MHz): δ 7.76-7.74 (m, 2H), 7.48-7.38 (m, 1H), 7.32-7.24 (m, 3H), 6.20 (s, 1H), 3.30-3.28 (m, 2H), 3.15 (s, 3H), 2.99-2.84 (m, 2H), 1.69-1.65 (m, 2H). |
| HBV-CSU-079_Int | 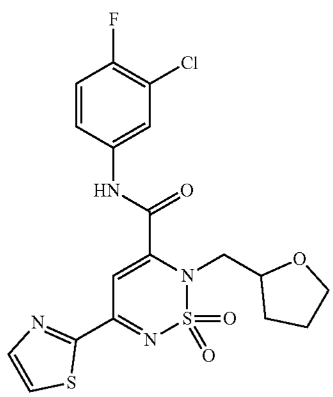 [SMILES: O=C(Nc1ccc(F)c(Cl)c1)C1=CC(c2nccs2)=NS(=O)(=O)N1CC1CCCO1] | 31% | — | 470.03 for $C_{18}H_{16}ClFN_4O_4S_2$ | ¹H-NMR (DMSO-$d_6$, 400 MHz): δ 11.41 (s, 1H), 8.31 (d, J = 3.0 Hz, 1H), 8.27 (d, J = 3.0 Hz, 1H), 7.98 (dd, J = 6.8, 2.5 Hz, 1H), 7.69-7.63 (m, 1H), 7.47 (t, J = 9.1 Hz, 1H), 7.27 (s, 1H), 4.81-4.73 (m, 1H), 4.17-4.01 (m, 2H), 3.57-3.48 (m, 1H), 3.44-3.37 (m, 1H), 1.97-1.89 (m, 1H), 1.78-1.52 (m, 3H). |
| HBV-CSU-082_Int | 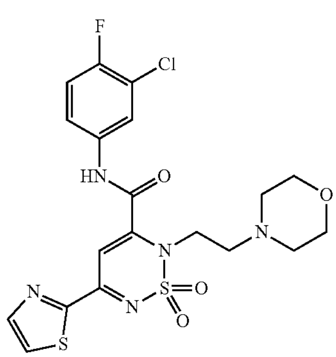 [SMILES: O=C(Nc1ccc(F)c(Cl)c1)C1=CC(c2nccs2)=NS(=O)(=O)N1CCN1CCOCC1] | 39% | 500.20 (M + 1) | 499.06 for $C_{19}H_{19}ClFN_5O_4S_2$ | ¹H-NMR (DMSO-$d_6$, 400 MHz): δ 11.38 (s, 1H), 8.31 (d, J = 3.0 Hz, 1H), 8.26 (d, J = 3.0 Hz, 1H), 8.00 (dd, J = 6.8, 2.5 Hz, 1H), 7.95 (s, 1H), 7.71-7.65 (m, 1H), 7.50 (t, J = 9.0 Hz, 1H), 4.13 (t, J = 6.0 Hz, 2H), 3.40-3.36 (m, 4H), 2.60 (t, J = 6.0 Hz, 2H), 2.32-2.28 (m, 4H). |

TABLE 1-continued

Analytical data for HBV-CSU_Int:

| Target No | Structure | Rx. Yield (%) | Mass Spec. Found (m/z) | Mass Spec. Calculated | $^1$H-NMR |
|---|---|---|---|---|---|
| HBV-CSU-083_Int | 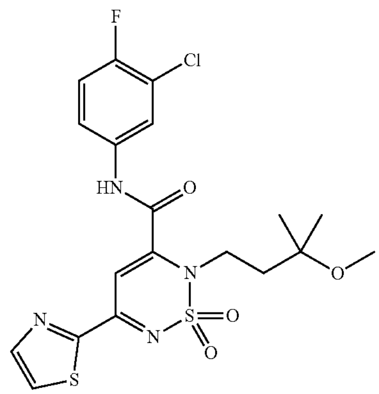 [SMILES: COC(C)(C)CCN1C(C(=O)Nc2ccc(F)c(Cl)c2)=CC(c2nccs2)=NS1(=O)=O] | 10% | — | 486.06 for $C_{19}H_{20}ClFN_4O_4S_2$ | $^1$H-NMR (DMSO-$d_6$, 400 MHz): δ 11.48 (s, 1H), 8.30 (d, J = 3.0 Hz, 1H), 8.25 (d, J = 3.0 Hz, 1H), 8.25 (d, J = 3.0 Hz, 1H), 7.94 (dd, J = 6.8, 2.5 Hz, 1H), 7.64-7.58 (m, 1H), 7.50 (t, J = 9.0 Hz, 1H), 7.25 (s, 1H), 3.98-3.89 (m, 2H), 3.00 (s, 3H), 2.03-1.97 (m, 2H), 1.07 (s, 6H). |
| HBV-CSU-089_Int | 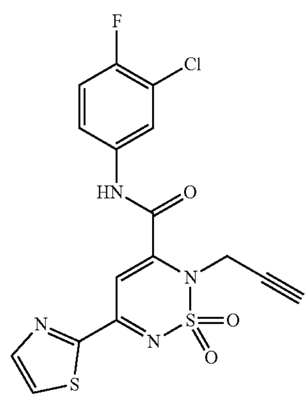 [SMILES: C#CCN1C(C(=O)Nc2ccc(F)c(Cl)c2)=CC(c2nccs2)=NS1(=O)=O] | 44% | 425 (M + 1) | 423.99 for $C_{16}H_{10}ClFN_4O_3S_2$ | $^1$H-NMR (DMSO-$d_6$, 400 MHz): δ 11.5 (s, 1H), 8.34-8.32 (m, 1H), 8.29-8.28 (m, 1H), 7.98-7.95 (m, 1H), 7.65-7.63 (m, 1H), 7.38 (s, 1H), 7.02 (t, J = 7.2.0 Hz, 1H), 4.83 (s, 2H), 3.59 (s, 1H). |
| HBV-CSU-090_Int | 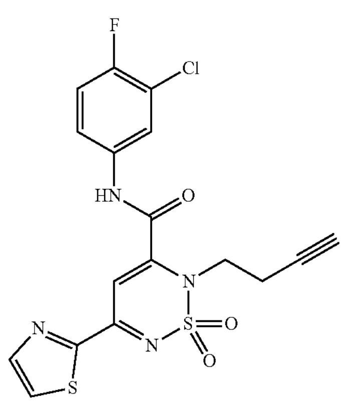 [SMILES: C#CCCN1C(C(=O)Nc2ccc(F)c(Cl)c2)=CC(c2nccs2)=NS1(=O)=O] | — | 439.1 (M + 1) | 438.00 for $C_{17}H_{12}ClFN_4O_3S_2$ | The reaction was monitored by LCMS and the crude intermediate carried forward to the next step. |

TABLE 1-continued

Analytical data for HBV-CSU_Int:

| Target No | Structure | Rx. Yield (%) | Mass Spec. Found (m/z) | Mass Spec. Calculated | ¹H-NMR |
|---|---|---|---|---|---|
| HBV-CSU-092_Int | 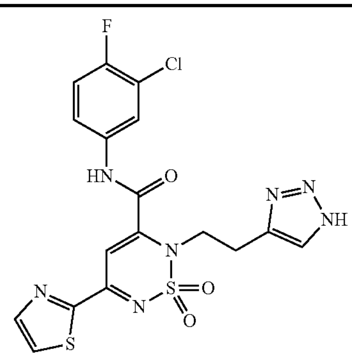 | 24% | 482.20 (M + 1) | 481.02 for $C_{17}H_{13}ClFN_7O_3S_2$ | ¹H-NMR (DMSO-d$_6$, 400 MHz): δ 15.11-14.59 (m, 1H), 11.36-11.27 (m, 1H), 8.31 (d, J = 3.0 Hz, 1H), 8.26 (d, J = 2.9 Hz, 1H), 7.97-7.88 (m, 1H), 7.64-7.57 (m, 2H), 7.48 (t, J = 9.0 Hz, 1H), 7.33-7.23 (m, 1H), 4.26-4.22 (m, 2H), 3.20 (t, J = 8.0 Hz, 2H). |
| HBV-CSU-094_Int | 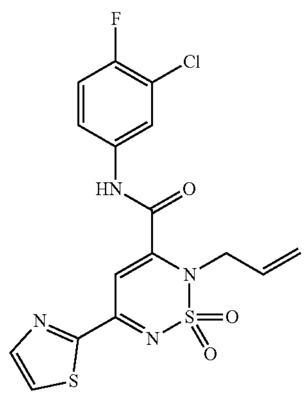 | 37% | 426.90 (M + 1) | 426.00 for $C_{16}H_{12}ClFN_4O_3S_2$ | ¹H-NMR (DMSO-d$_6$, 400 MHz): δ 11.40 (s, 1H), 8.32-8.25 (m, 2H), 7.94-7.92 (m, 1H), 7.62-7.57 (m, 1H), 7.50-7.45 (m, 1H), 7.28 (s, 1H), 5.97-5.90 (m, 1H), 5.27-5.21 (m, 2H), 4.61-4.59 (m, 2H). |
| HBV-CSU-095_Int | HBV-CSU-095-Int | 65% | — | 520.04 for $C_{22}H_{18}ClFN_4O_4S_2$ | ¹H-NMR (DMSO-d$_6$, 400 MHz): δ 11.3 (s, 1H), 8.24 (d, J = 2.4 Hz, 1H), 8.26 (d, J = 2.8 Hz, 1H), 7.92-7.88 (m, 1H), 7.64-7.58 (m, 1H), 7.45 (t, J = 8.8 Hz, 1H), 7.31 (s, 1H), 7.22-7.12 (m, 5H), 4.43 (s, 2H), 4.32-4.24 (m, 2H), 3.65-3.61 (m, 2H). |
| HBV-CSU-108_Int | 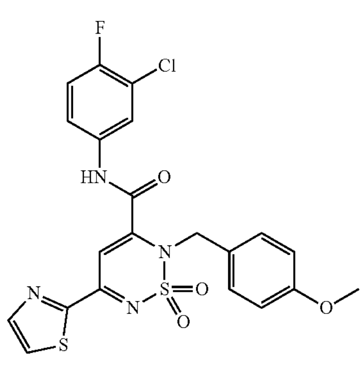 [SMILES: COc1ccc(CN2C(C(=O)Nc3ccc(F)c(Cl)c3)=CC(c3nccs3)=NS2(=O)=O)cc1] | 46% | — | 506.03 for $C_{21}H_{16}ClFN_4O_4S_2$ | ¹H-NMR (DMSO-d$_6$, 400 MHz): δ 11.16 (s, 1H), 8.32-8.23 (m, 2H), 7.78-7.76 (m, 1H), 7.49-7.42 (m, 2H), 7.23-7.18 (M, 4H), 6.83 (d, J = 8.8 Hz, 1H), 5.13 (s, 2H), 3.68 (s, 3H). |

TABLE 1-continued

Analytical data for HBV-CSU_Int:

| Target No | Structure | Rx. Yield (%) | Mass Spec. Found (m/z) | Mass Spec. Calculated | $^1$H-NMR |
|---|---|---|---|---|---|
| HBV-CSU-109_Int | 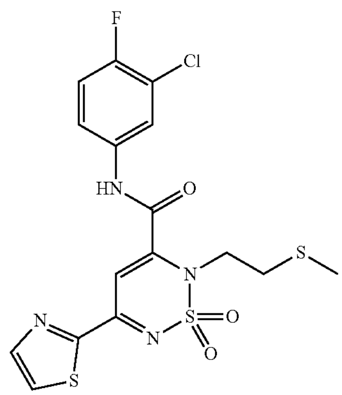 | 50% | 459.20 (M − 1) | 459.99 for $C_{16}H_{14}ClFN_4O_3S_3$ | $^1$H-NMR (DMSO-d$_6$, 400 MHz): δ 11.49 (s, 1H), 8.31 (d, J = 3.1 Hz, 1H), 8.26 (d, J = 2.9 Hz, 1H), 7.97 (dd, J = 6.8, 2.8 Hz, 1H), 7.68-7.62 (m, 1H), 7.48 (t, J = 9.0 Hz, 1H), 7.32 (s, 1H), 4.16 (t, J = 7.1 Hz, 2H), 2.85 (t, J = 7.2 Hz, 2H), 1.97 (s, 3H). |
| HBV-CSU-112_Int | 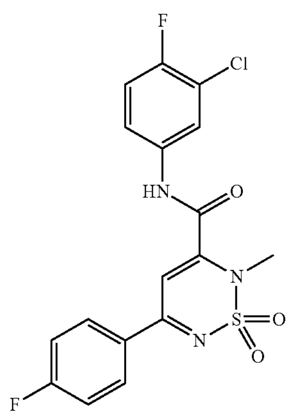 [SMILES: CN1C(C(=O)Nc2ccc(F)c(Cl)c2)=CC(c2ccc(F)cc2)=NS1(=O)=O] | — | 412.00 (M + 1) | 411.03 for $C_{17}H_{12}ClF_2N_3O_3S$ | The reaction was monitored by LCMS and the crude intermediate carried forward to the next step. |
| HBV-CSU-113_Int | 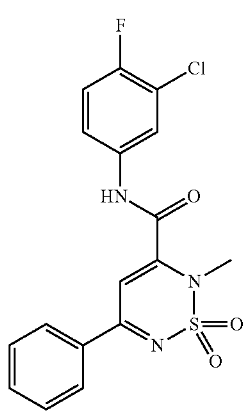 [SMILES: CN1C(C(=O)Nc2ccc(F)c(Cl)c2)=CC(c2ccccc2)=NS1(=O)=O] | — | 393.90 (M + 1) | 393.04 for $C_{17}H_{13}ClFN_3O_3S$ | The reaction was monitored by LCMS and the crude intermediate carried forward to the next step. |

TABLE 1-continued

Analytical data for HBV-CSU_Int:

| Target No | Structure | Rx. Yield (%) | Mass Spec. Found (m/z) | Mass Spec. Calculated | $^1$H-NMR |
|---|---|---|---|---|---|
| HBV-CSU-114_Int | 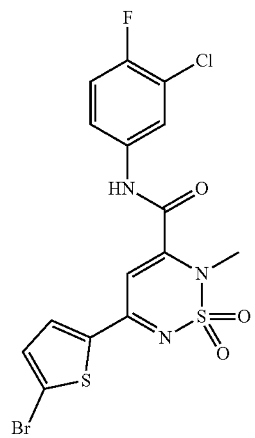 [SMILES: CN1C(C(=O)Nc2ccc(F)c(Cl)c2)=CC(c2ccc(Br)s2)=NS1(=O)=O] | 50% | 479.90 (M + 1) | 476.90 for $C_{15}H_{10}BrClFN_3O_3S_2$ | $^1$H-NMR (DMSO-$d_6$, 400 MHz): δ 11.34 (s, 1H), 8.10 (d, J = 4.0 Hz, 1H), 7.97 (dd, J = 6.8, 2.4 Hz, 1H), 7.65-7.61 (m, 1H), 7.53-7.48 (m, 2H), 7.19 (s, 1H), 3.45 (s, 3H). |
| HBV-CSU-120_Int | 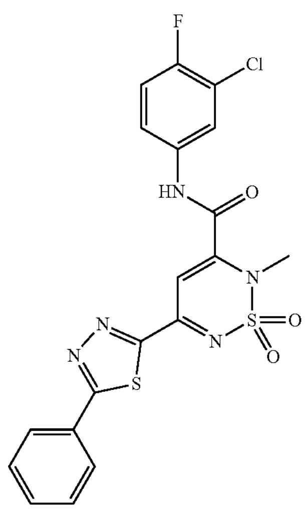 [SMILES: CN1C(C(=O)Nc2ccc(F)c(Cl)c2)=CC(c2nnc(-c3ccccc3)s2)=NS1(=O)=O] | 44% | 478.05 (M + 1) | 477.01 for $C_{19}H_{13}ClFN_5O_3S_2$ | $^1$H-NMR (DMSO-$d_6$, 400 MHz): δ 11.45 (s, 1H), 8.15-8.13 (m, 2H), 8.00-7.98 (m, 1H), 7.67-7.60 (m, 4H), 7.50 (t, J = 8.8 Hz, 1H), 7.36 (s, 1H), 3.58 (s, 3H). |
| HBV-CSU-122_Int (HBV-CSU-435) | 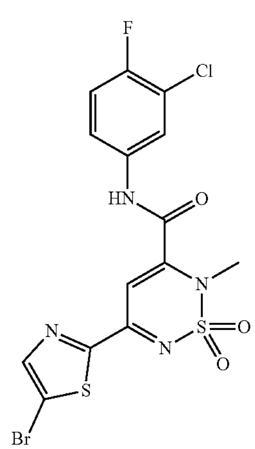 [SMILES: CN1C(C(=O)Nc2ccc(F)c(Cl)c2)=CC(c2ncc(Br)s2)=NS1(=O)=O] | 35% | 479.10 (M + 1) | 477.90 for $C_{14}H_9BrClFN_4O_3S_2$ | $^1$H-NMR (DMSO-$d_6$, 400 MHz): δ 11.40 (s, 1H), 8.36 (s, 1H), 7.97 (dd, J = 6.8, 2.6 Hz, 1H), 7.63-7.58 (m, 1H), 7.52-7.47 (m, 1H), 7.14 (s, 1H), 3.53 (s, 3H). |

TABLE 1-continued

Analytical data for HBV-CSU_Int:

| Target No | Structure | Rx. Yield (%) | Mass Spec. Found (m/z) | Mass Spec. Calculated | ¹H-NMR |
|---|---|---|---|---|---|
| HBV-CSU-123_Int | 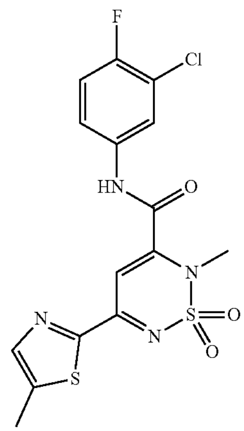 [SMILES: Cc1cnc(C2=NS(=O)(=O)N(C)C(C(=O)Nc3ccc(F)c(Cl)c3)=C2)s1] | 72% | 415.10 (M + 1) | 414.00 for $C_{15}H_{12}ClN_4O_3S_2$ | ¹H-NMR (DMSO-$d_6$, 400 MHz): δ 11.38 (s, 1H), 7.99-7.96 (m, 2H), 7.63-7.59 (m, 1H), 7.49 (t, J = 9.2 Hz, 1H), 7.14 (s, 1H), 3.51 (s, 3H), 2.60 (s, 3H). |
| HBV-CSU-142_Int | 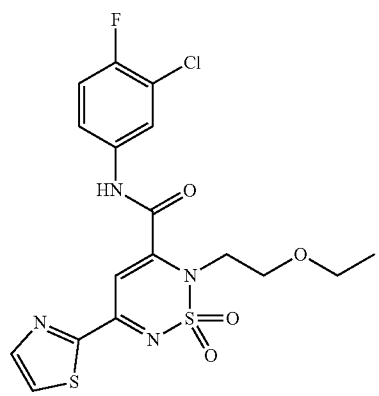 [SMILES: CCOCCN1C(C(=O)Nc2ccc(F)c(Cl)c2)=CC(c2nccs2)=NS1(=O)=O] | 34% | 459.10 (M + 1) | 458.03 for $C_{17}H_{16}ClN_4O_4S_2$ | ¹H-NMR (DMSO-$d_6$, 400 MHz): δ 11.29 (s, 1H), 8.31 (d, J = 3.1 Hz, 1H), 8.26 (d, J = 3.1 Hz, 1H), 7.99 (dd, J = 6.7, 2.5 Hz, 1H), 7.68-7.62 (m, 1H), 7.48 (t, J = 9.0 Hz, 1H), 7.27 (s, 1H), 4.26 (t, J = 5.1 Hz, 2H), 3.59 (t, J = 5.1 Hz, 2H), 3.34 (q, J = 7.1 Hz, 2H), 0.93 (t, J = 6.9 Hz, 3H). |
| HBV-CSU-143_Int | 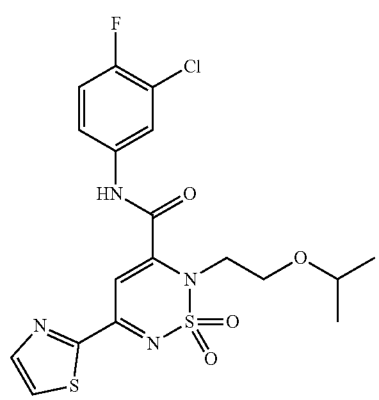 | 42% | 473.10 (M + 1) | 472.04 for $C_{18}H_{18}ClFN_4O_4S_2$ | ¹H-NMR (DMSO-$d_6$, 400 MHz): δ 11.22 (s, 1H), 8.30 (d, J = 2.7 Hz, 1H), 8.26 (d, J = 3.3 Hz, 1H), 7.99 (dd, J = 6.9, 2.5 Hz, 1H), 7.68-7.63 (m, 1H), 7.48 (t, J = 9.1 Hz, 1H), 7.28 (s, 1H), 4.24 (t, J = 5.2 Hz, 2H), 3.59 (t, J = 5.2 Hz, 2H), 3.51-3.43 (m, 1H), 0.93 (d, J = 6.0 Hz, 6H). |

TABLE 1-continued

Analytical data for HBV-CSU_Int:

| Target No | Structure | Rx. Yield (%) | Mass Spec. Found (m/z) | Mass Spec. Calculated | ¹H-NMR |
|---|---|---|---|---|---|
| HBV-CSU-146_Int | 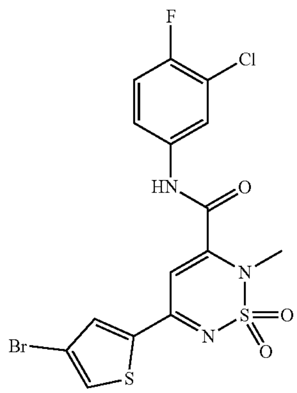 [SMILES: CN1C(C(=O)Nc2ccc(F)c(Cl)c2)=CC(c2cc(Br)cs2)=NS1(=O)=O] | 78% | 480.20 (M + 2) | 476.90 for $C_{15}H_{10}BrClFN_3O_3S_2$ | ¹H-NMR (DMSO-$d_6$, 400 MHz): δ 11.29 (s, 1H), 8.34 (s, 1H), 8.21 (s, 1H), 7.99-7.96 (m, 1H), 7.66-7.62 (m, 1H), 7.53-7.48 (m, 1H), 7.25 (s, 1H), 3.47 (s, 3H). |
| HBV-CSU-150_Int | 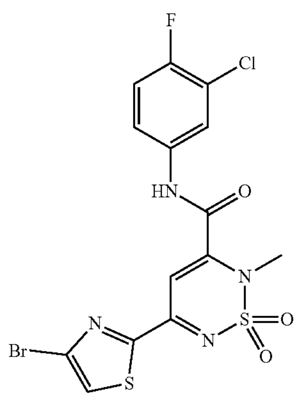 [SMILES: CN1C(C(=O)Nc2ccc(F)c(Cl)c2)=CC(c2nc(Br)cs2)=NS1(=O)=O] | 21% | 481.1 (M + 2) | 477.90 for $C_{14}H_9BrClFN_4O_3S_2$ | ¹H-NMR (DMSO-$d_6$, 400 MHz): δ 11.37 (s, 1H), 8.40 (s, 1H), 7.97 (dd, J = 6.8, 2.6 Hz, 1H), 7.63-7.59 (m, 1H), 7.52-7.46 (m, 1H), 7.15 (s, 1H), 3.54 (s, 3H). |
| HBV-CSU-200_Int | 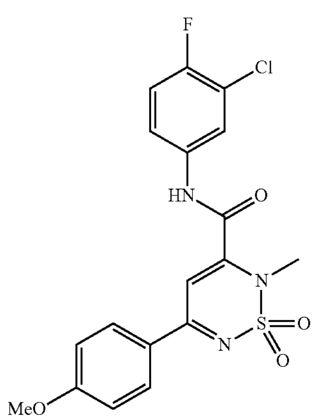 [SMILES: COc1ccc(C2=NS(=O)(=O)N(C)C(C(=O)Nc3ccc(F)c(Cl)c3)=C2)cc1] | 47% | 424.05 (M + 1) | 423.05 for $C_{18}H_{15}ClFN_3O_4S$ | ¹H-NMR (DMSO-$d_6$, 400 MHz): δ 11.28 (s, 1H), 8.16 (d, J = 8.8 Hz, 2H), 8.00-7.97 (m, 1H), 7.67-7.47 (m, 1H), 7.14 (t, J = 9.6 Hz, 1H), 7.16-7.11 (m, 3H), 3.88 (s, 3H), 3.46 (s, 3H). |

TABLE 1-continued

Analytical data for HBV-CSU_Int:

| Target No | Structure | Rx. Yield (%) | Mass Spec. Found (m/z) | Mass Spec. Calculated | ¹H-NMR |
|---|---|---|---|---|---|
| HBV-CSU-202_Int | 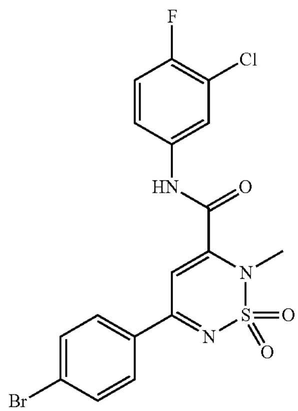 | 68% | 473 (M + 2) | 470.95 for $C_{17}H_{12}BrClN_3O_3S$ | ¹H-NMR (DMSO-$d_6$, 400 MHz): δ 11.30 (s, 1H), 8.10 (d, J = 8.8 Hz, 2H), 7.99-7.96 (m, 1H), 7.81 (d, J = 8.8 Hz, 2H), 7.65-7.61 (m, 1H), 7.52-7.47 (m, 1H), 7.22 (s, 1H), 3.49 (s, 3H); |
| HBV-CSU-204_Int | 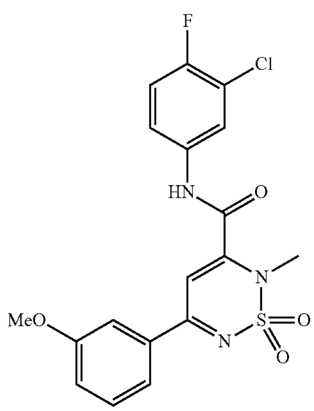 [SMILES: COc1cccc(C2=NS(=O)(=O)N(C)C(C(=O)Nc3ccc(F)c(Cl)c3)=C2)c1] | 35% | 423.95 (M +1) | 423.05 for $C_{18}H_{15}ClFN_3O_4S$ | ¹H-NMR (DMSO-$d_6$, 400 MHz): δ 11.27 (s, 1H), 7.97-7.94 (m, 1H), 7.73-7.70 (m, 1H), 7.62-7.60 (m, 2H), 7.49-7.44 (m, 2H), 7.24-7.18 (m, 2H), 3.82 (s, 3H), 3.46 (s, 3H). |
| HBV-CSU-210_Int | 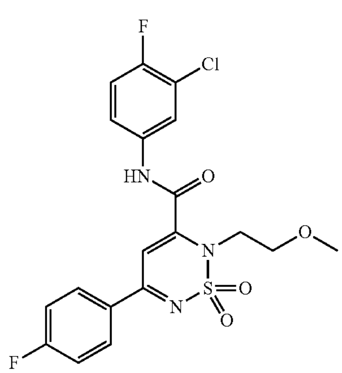 [SMILES: COCCN1C(C(=O)Nc2ccc(F)c(Cl)c2)=CC(c2ccc(F)cc2)=NS1(=O)=O] | — | 456.30 (M + 1) | 455.05 for $C_{19}H_{16}ClF_2N_3O_4S$ | The reaction was monitored by LCMS and the crude intermediate carried forward to the next step. |

TABLE 1-continued

Analytical data for HBV-CSU_Int:

| Target No | Structure | Rx. Yield (%) | Mass Spec. Found (m/z) | Mass Spec. Calculated | ¹H-NMR |
|---|---|---|---|---|---|
| HBV-CSU-211_Int | 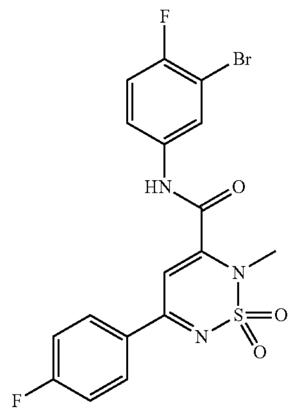 [SMILES: CN1C(C(=O)Nc2ccc(F)c(Br)c2)=CC(c2ccc(F)cc2)=NS1(=O)=O] | 38% | 456.30 (M + 1) | 454.98 for $C_{17}H_{12}BrF_2N_3O_3S$ | ¹H-NMR (DMSO-$d_6$, 400 MHz): δ 11.28 (s, 1H), 8.27-8.23 (m, 2H), 7.70-7.66 (m, 1H), 7.53-7.40 (m, 4H), 7.22 (s, 1H), 3.59 (s, 3H). |
| HBV-CSU-212_Int | 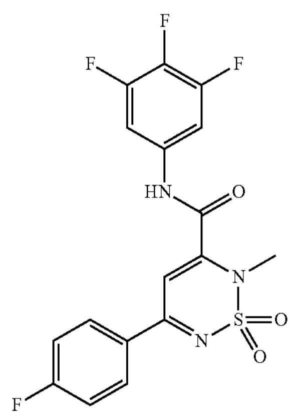 [SMILES: CN1C(C(=O)Nc2cc(F)c(F)c(F)c2)=CC(c2ccc(F)cc2)=NS1(=O)=O] | — | 414.30 (M + 1) | 413.05 for $C_{17}H_{11}F_4N_3O_3S$ | The reaction was monitored by LCMS and the crude intermediate carried forward to the next step. |
| HBV-CSU-213_Int | 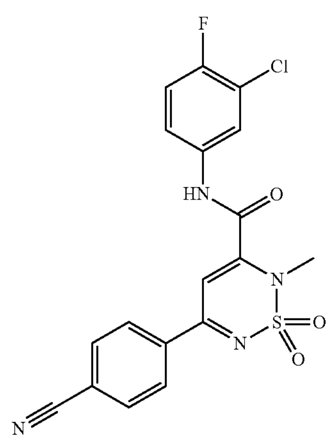 [SMILES: CN1C(C(=O)Nc2ccc(F)c(Cl)c2)=CC(c2ccc(C#N)cc2)=NS1(=O)=O] | 57% | 419 (M + 1) | 418.03 for $C_{18}H_{12}ClFN_4O_3S$ | ¹H-NMR (DMSO-$d_6$, 400 MHz): δ 11.32 (s, 1H), 8.32 (d, J = 8.4 Hz, 2H), 8.00 (d, J = 8.4 Hz, 2H), 7.99-7.97 (m, 1H), 7.67-7.62 (m, 1H), 7.49 (t, J = 9.2 Hz, 1H), 7.30 (s, 1H), 3.53 (s, 3H). |

TABLE 1-continued

Analytical data for HBV-CSU_Int:

| Target No | Structure | Rx. Yield (%) | Mass Spec. Found (m/z) | Mass Spec. Calculated | $^1$H-NMR |
|---|---|---|---|---|---|
| HBV-CSU-215_Int | 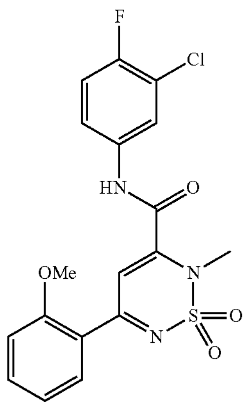 [SMILES: COc1ccccc1C1=NS(=O)(=O)N(C)C(C(=O)Nc2ccc(F)c(Cl)c2)=C1] | — | 424 (M + 1) | 423.05 for $C_{18}H_{15}ClFN_3O_4S$ | The reaction was monitored by LCMS and the crude intermediate carried forward to the next step. |
| HBV-CSU-217_Int | 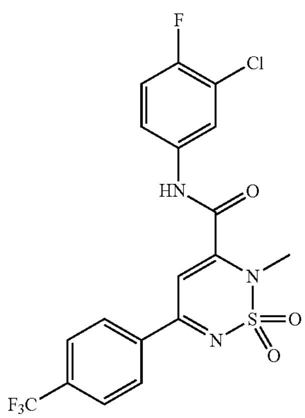 [SMILES: CN1C(C(=O)Nc2ccc(F)c(Cl)c2)=CC(c2ccc(C(F)(F)F)cc2)=NS1(=O)=O] | 32% | 462.10 (M + 1) | 461.02 for $C_{18}H_{12}ClF_4N_3O_3S$ | $^1$H-NMR (DMSO-d$_6$, 400 MHz): δ 11.34 (s, 1H), 8.10 (d, J = 8.0 Hz, 2H), 7.99-7.96 (m, 3H), 7.66-7.62 (m, 1H), 7.51 (t, J = 9.2 Hz, 1H), 7.29 (s, 1H), 3.53 (s, 3H). |
| HBV-CSU-221_Int | 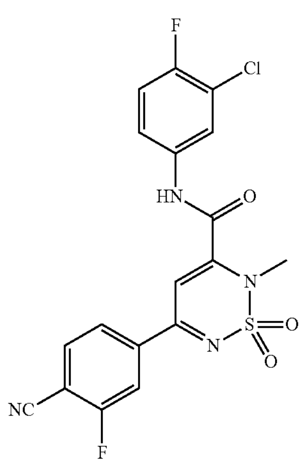 [SMILES: CN1C(C(=O)Nc2ccc(F)c(Cl)c2)=CC(c2ccc(C#N)c(F)c2)=NS1(=O)=O] | 67% | 436.80 (M + 1) | 436.02 for $C_{18}H_{11}ClF_2N_4O_3S$ | $^1$H-NMR (DMSO-d$_6$, 400 MHz): δ 11.30 (s, 1H), 8.29-8.26 (m, 1H), 8.19-8.16 (m, 1H), 7.98-7.95 (m, 1H), 7.65-7.60 (m, 2H), 7.51 (t, J = 8.8 Hz, 1H), 7.32 (s, 1H), 3.54 (s, 3H). |

TABLE 1-continued

Analytical data for HBV-CSU_Int:

| Target No | Structure | Rx. Yield (%) | Mass Spec. Found (m/z) | Mass Spec. Calculated | $^1$H-NMR |
|---|---|---|---|---|---|
| HBV-CSU-222_Int | (structure with 4-fluoro-3-chlorophenyl amide, N-methyl thiadiazine dioxide, cyclopentyl) | 33% | 386 (M + 1) | 385.07 for $C_{16}H_{17}ClFN_3O_3S$ | $^1$H-NMR (DMSO-$d_6$, 400 MHz): δ 11.30 (s, 1H), δ 11.40 (s, 1H), 7.96-7.94 (m, 1H), 7.62-7.58 (m, 1H), 7.50-7.45 (m, 1H), 6.43 (s, 1H), 3.39 (s, 3H), 3.04-3.00 (m, 1H), 1.96-1.92 (m, 2H), 1.71-1.61 (m, 6H). |
| HBV-CSU-224_Int | (structure with 4-fluoro-3-chlorophenyl amide, N-methyl thiadiazine dioxide, 2-methylthiazole) | 42% | 415.10 (M + 1) | 414.00 for $C_{15}H_{12}ClFN_4O_3S_2$ | $^1$H-NMR (DMSO-$d_6$, 400 MHz): δ 11.31 (s, 1H), 8.75 (s, 1H), 7.98 (dd, J = 6.8, 2.5 Hz, 1H), 7.67-7.61 (m, 1H), 7.51 (t, J = 8.9 Hz, 1H), 7.22 (s, 1H), 3.46 (s, 3H), 2.77 (s, 3H). |
| HBV-CSU-226_Int | (structure with 4-fluoro-3-chlorophenyl amide, N-methyl thiadiazine dioxide, 2-trifluoromethylthiazole) | 48% | 466.90 (M − 1) | 467.97 for $C_{15}H_9ClF_4N_4O_3S_2$ | $^1$H-NMR (DMSO-$d_6$, 400 MHz): δ 11.40 (s, 1H), 9.13 (s, 1H), 7.98 (dd, J = 6.8, 2.5 Hz, 1H), 7.66-7.62 (m, 1H), 7.52 (t, J = 9.3 Hz, 1H), 7.38 (s, 1H), 3.53 (s, 3H). |

TABLE 1-continued

Analytical data for HBV-CSU_Int:

| Target No | Structure | Rx. Yield (%) | Mass Spec. Found (m/z) | Mass Spec. Calculated | $^1$H-NMR |
|---|---|---|---|---|---|
| HBV-CSU-230_Int | 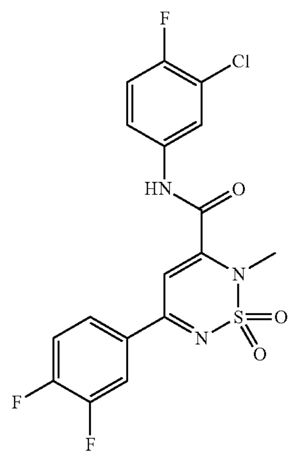 [SMILES: CN1C(C(=O)Nc2ccc(F)c(Cl)c2)=CC(c2ccc(F)c(F)c2)=NS1(=O)=O] | — | 429.95 (M + 1) | 429.02 for $C_{17}H_{11}ClF_3N_4O_3S_2$ | The reaction was monitored by LCMS and the crude intermediate carried forward to the next step. |
| HBV-CSU-231_Int | 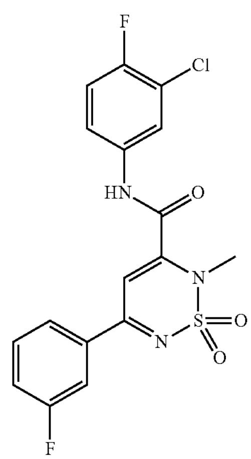 [SMILES: CN1C(C(=O)Nc2ccc(F)c(Cl)c2)=CC(c2cccc(F)c2)=NS1(=O)=O] | — | 412.10 (M + 1) | 411.03 for $C_{17}H_{12}ClF_2N_3O_3S$ | The reaction was monitored by LCMS and the crude intermediate carried forward to the next step. |
| HBV-CSU-232_Int | 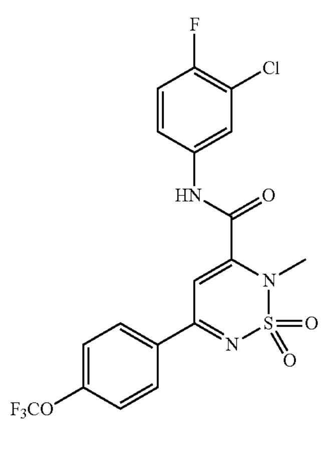 [SMILES: CN1C(C(=O)Nc2ccc(F)c(Cl)c2)=CC(c2ccc(OC(F)(F)F)cc2)=NS1(=O)=O] | — | 477.95 (M + 1) | 477.02 for $C_{18}H_{12}ClF_4N_3O_4S$ | The reaction was monitored by LCMS and the crude intermediate carried forward to the next step. |

TABLE 1-continued

Analytical data for HBV-CSU_Int:

| Target No | Structure | Rx. Yield (%) | Mass Spec. Found (m/z) | Mass Spec. Calculated | ¹H-NMR |
|---|---|---|---|---|---|
| HBV-CSU-235-Int | 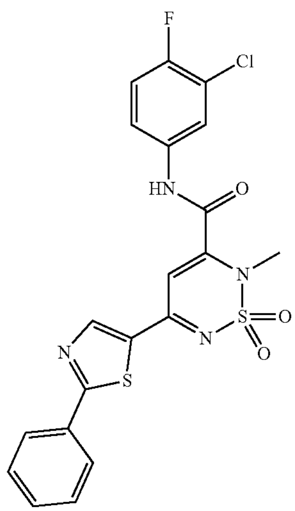 [SMILES: CN1C(C(=O)Nc2ccc(F)c(Cl)c2)=CC(c2cnc(-c3ccccc3)s2)=NS1(=O)=O] | 47% | 477.10 (M + 1) | 476.04 for $C_{20}H_{14}ClFN_4O_3S_2$ | ¹H-NMR (DMSO-$d_6$, 400 MHz): δ 11.37 (s, 1H), 8.99 (s, 1H), 8.09 (dd, J = 7.8, 1.7 Hz, 2H), 8.00 (dd, J = 6.8, 2.6 Hz, 1H), 7.68-7.63 (m, 1H), 7.63-7.55 (m, 3H), 7.51 (t, J = 9.5 Hz, 1H), 7.32 (s, 1H), 3.49 (s, 3H). |
| HBV-CSU-257_Int | 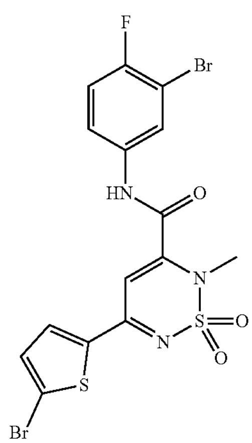 [SMILES: CN1C(C(=O)Nc2ccc(F)c(Br)c2)=CC(c2ccc(Br)s2)=NS1(=O)=O] | — | 523.85 (M + 2) | 520.85 for $C_{15}H_{10}Br_2FN_3O_3S_2$ | The reaction was monitored by LCMS and the crude intermediate carried forward to the next step. |
| HBV-CSU-258_Int | 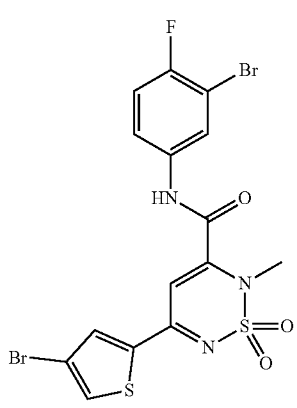 [SMILES: CN1C(C(=O)Nc2ccc(F)c(Br)c2)=CC(c2cc(Br)cs2)=NS1(=O)=O] | — | 523.85 (M + 2) | 520.85 for $C_{15}H_{10}Br_2FN_3O_3S_2$ | The reaction was monitored by LCMS and the crude intermediate carried forward to the next step. |

TABLE 1-continued

Analytical data for HBV-CSU_Int:

| Target No | Structure | Rx. Yield (%) | Mass Spec. Found (m/z) | Mass Spec. Calculated | ¹H-NMR |
|---|---|---|---|---|---|
| HBV-CSU-259-Int | 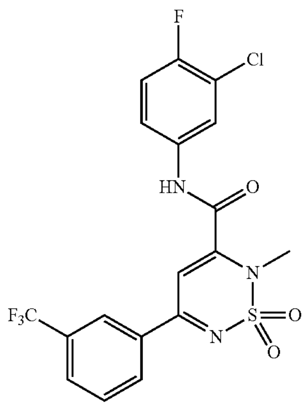 [SMILES: CN1C(C(=O)Nc2ccc(F)c(Cl)c2)=CC(c2cccc(C(F)(F)F)c2)=NS1(=O)=O] | — | 462.10 (M + 1) | 461.02 for $C_{18}H_{12}ClFN_4O_3S$ | The reaction was monitored by LCMS and the crude intermediate carried forward to the next step. |
| HBV-CSU-261_Int | 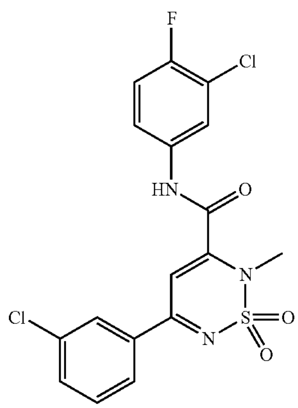 | 53% | 427.95 (M + 1) | 427.00 for $C_{17}H_{12}Cl_2FN_3O_3S$ | ¹H-NMR (DMSO-d₆, 400 MHz): δ 11.31 (s, 1H), 8.22 (s, 1H), 8.12 (d, J = 8.0 Hz, 1H), 8.00-7.98 (m, 1H), 7.76-7.75 (m, 1H), 7.65-7.61 (m, 2H), 7.48 (t, J = 8.8 Hz, 1H), 7.28 (s, 1H), 3.51 (s, 3H). |
| HBV-CSU-262_Int | 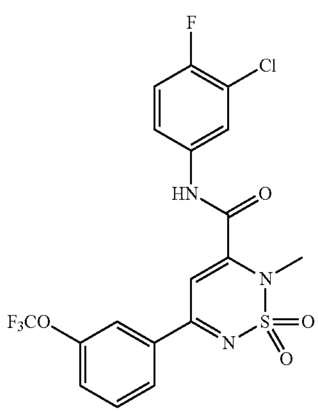 | 42% | 478.00 (M + 1) | 477.02 for $C_{18}H_{12}ClF_4N_3O_4S$ | ¹H-NMR (DMSO-d₆, 400 MHz): δ 11.33 (s, 1H), 8.21 (d, J = 7.2 Hz, 1H), 8.12 (s, 1H), 7.99 (dd, J = 6.8, 2.4 Hz, 1H), 7.77-7.61 (m, 3H), 7.49 (t, J = 9.2 Hz, 1H), 7.29 (s, 1H), 3.53 (s, 3H). |

TABLE 1-continued

Analytical data for HBV-CSU_Int:

| Target No | Structure | Rx. Yield (%) | Mass Spec. Found (m/z) | Mass Spec. Calculated | ¹H-NMR |
|---|---|---|---|---|---|
| HBV-CSU-263_Int | 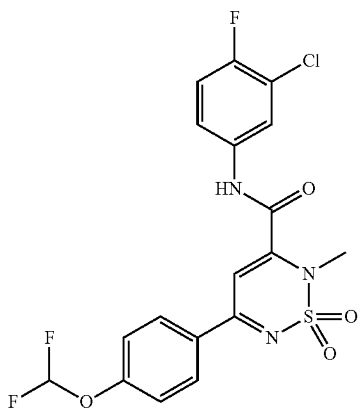 [SMILES: CN1C(C(=O)Nc2ccc(F)c(Cl)c2)=CC(c2ccc(OC(F)F)cc2)=NS1(=O)=O] | 25% | 460.40 (M + 1) | 459.03 for $C_{18}H_{13}ClF_3N_3O_4S$ | ¹H-NMR (DMSO-$d_6$, 400 MHz): δ 11.33 (s, 1H), 8.24 (d, J = 8.24 (d, J = 8.2 Hz, 2H), 8.01-7.98 (m, 1H), 7.67-7.60 (m, 1H), 7.52-7.47 (m, 2H), 7.36 (d, J = 8.2 Hz, 2H), 7.42 (s, 1H), 3.50 (s, 3H). |
| HBV-CSU-264_Int | 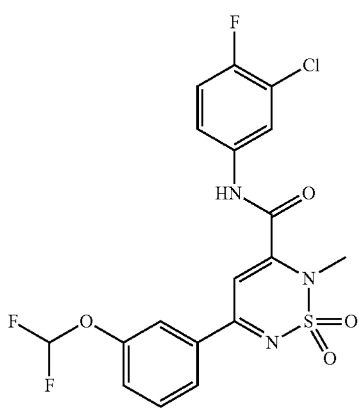 [SMILES: CN1C(C(=O)Nc2ccc(F)c(Cl)c2)=CC(c2cccc(OC(F)F)c2)=NS1(=O)=O] | 9.3% | 460.00 (M + 1) | 459.03 for $C_{18}H_{13}ClF_3N_3O_4S$ | ¹H-NMR (DMSO-$d_6$, 400 MHz): δ 11.33 (s, 1H), 8.07-7.90 (m, 3H), 7.69-7.35 (m, 5H), 7.25 (s, 1H), 3.52 (s, 3H). |
| HBV-CSU-265_Int | 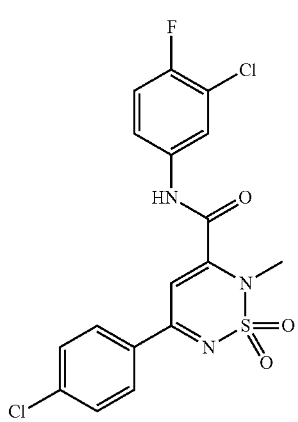 | 56% | 428.05 (M + 1) | 427.00 for $C_{17}H_{12}Cl_2FN_3O_3S$ | ¹H-NMR (DMSO-$d_6$, 400 MHz): δ 11.30 (s, 1H), 8.15 (d, J = 8.8 Hz, 2H), 7.96-7.94 (m, 1H), 7.66-7.60 (m, 3H), 7.47 (t, J = 8.8 Hz, 1H), 7.20 (s, 1H), 3.47 (s, 3H). |

TABLE 1-continued

Analytical data for HBV-CSU_Int:

| Target No | Structure | Rx. Yield (%) | Mass Spec. Found (m/z) | Mass Spec. Calculated | ¹H-NMR |
|---|---|---|---|---|---|
| HBV-CSU-269_Int | 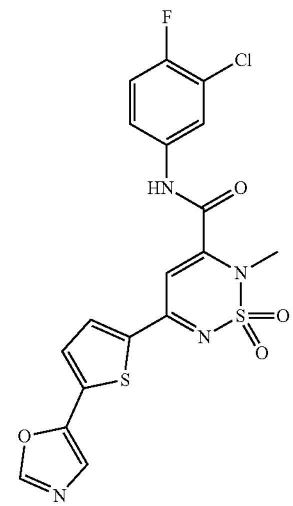 [SMILES: CN1C(C(=O)Nc2ccc(F)c(Cl)c2)=CC(c2ccc(-c3cnco3)s2)=NS1(=O)=O] | 64% | 467.10 (M + 1) | 466.00 for $C_{18}H_{12}ClFN_4O_4S_2$ | ¹H-NMR (DMSO-$d_6$, 400 MHz): δ 11.41 (s, 1H), 8.57 (s, 1H), 8.31 (d, J = 3.6 Hz, 1H), 8.01-7.98 (m, 1H), 7.85 (s, 1H), 7.69-7.63 (m, 1H), 7.51 (t, J = 8.8 Hz, 1H), 7.25 (s, 1H), 3.47 (s, 3H). |
| HBV-CSU-283_Int | 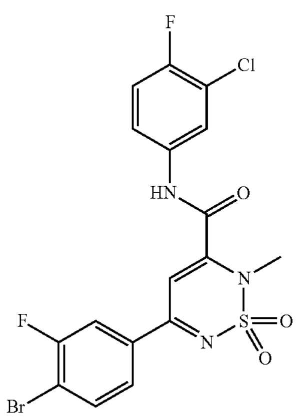 [SMILES: CN1C(C(=O)Nc2ccc(F)c(Cl)c2)=CC(c2ccc(Br)c(F)c2)=NS1(=O)=O] | 37% | 492 (M + 1) | 488.94 for $C_{17}H_{11}BrClF_2N_3O_3S$ | ¹H-NMR (DMSO-$d_6$, 400 MHz): δ 11.3 (s, 1H), 8.15-8.12 (m, 1H), 7.98-7.92 (m, 3H), 7.65-7.47 (m, 1H), 7.49 (t, J = 8.8 Hz, 1H), 7.26 (s, 1H), 3.49 (s, 3H). |
| HBV-CSU-304_Int | 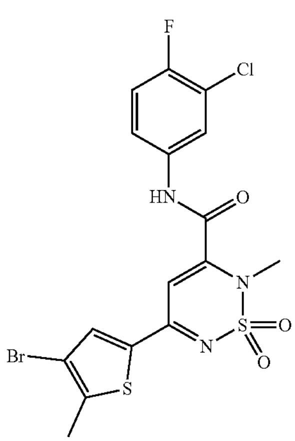 [SMILES: Cc1sc(C2=NS(=O)(=O)N(C)C(C(=O)Nc3ccc(F)c(Cl)c3)=C2)cc1Br] | 46% | 494.05 (M + 2) | 490.92 for $C_{16}H_{12}BrClFN_3O_3S_2$ | ¹H-NMR (DMSO-$d_6$, 400 MHz): δ 11.33 (s, 1H), 8.27 (s, 1H), 7.97 (dd, J = 7.2, 2.4 Hz, 1H), 7.66-7.62 (m, 1H), 7.50 (t, J = 8.8 Hz, 1H), 7.20 (s, 1H), 3.45 (s, 3H), 2.48 (s, 3H). |

TABLE 1-continued

Analytical data for HBV-CSU_Int:

| Target No | Structure | Rx. Yield (%) | Mass Spec. Found (m/z) | Mass Spec. Calculated | ¹H-NMR |
|---|---|---|---|---|---|
| HBV-CSU-329_Int | 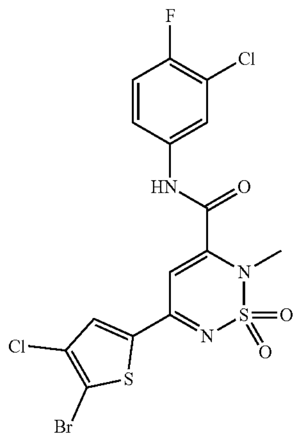 [SMILES: CN1C(C(=O)Nc2ccc(F)c(Cl)c2)=CC(c2cc(Cl)c(Br)s2)=NS1(=O)=O] | 70% | 514.30 (M + 2) | 510.86 for $C_{15}H_9BrCl_2FN_3O_3S_2$ | ¹H-NMR (DMSO-$d_6$, 400 MHz): δ 11.32 (s, 1H), 8.35 (s, 1H), 7.97 (d, J = 4.0 Hz, 1H), 7.63-7.62 (m, 1H), 7.51 (t, J = 8.8 Hz, 1H), 7.23 (s, 1H), 3.48 (s, 3H). |
| HBV-CSU-330_Int | 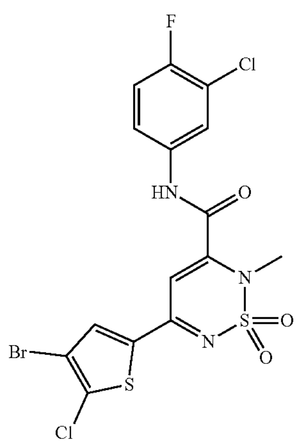 | 49% | 514.30 (M + 2) | 510.86 for $C_{15}H_9BrCl_2FN_3O_3S_2$ | ¹H-NMR (DMSO-$d_6$, 400 MHz): δ 11.31 (s, 1H), 8.39 (s, 1H), 7.96 (dd, J = 6.8, 2.4 Hz, 1H), 7.66-7.61 (m, 1H), 7.51 (t, J = 9.2 Hz, 1H), 7.25 (s, 1H), 3.48 (s, 3H). |
| HBV-CSU-334_Int | 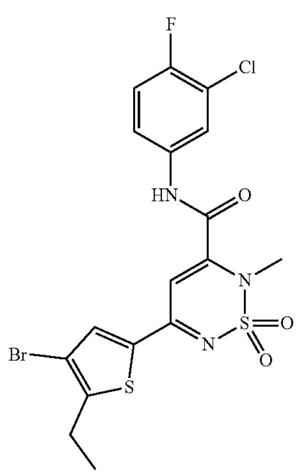 [SMILES: CCc1sc(C2=NS(=O)(=O)N(C)C(C(=O)Nc3ccc(F)c(Cl)c3)=C2)cc1Br] | 84% | 508.40 | 504.93 for $C_{17}H_{14}BrClFN_3O_3S_2$ | ¹H-NMR (DMSO-$d_6$, 400 MHz): δ 11.26 (s, 1H), 8.26 (s, 1H), 7.97-7.94 (m, 1H), 7.65-7.61 (m, 1H), 7.49 (t, J = 8.8 Hz, 1H), 7.19 (s, 1H), 2.81 (q, J = 7.6 Hz, 2H), 2.67 (s, 3H), 1.26 (t, J = 7.2 Hz, 2H). |

TABLE 1-continued

Analytical data for HBV-CSU_Int:

| Target No | Structure | Rx. Yield (%) | Mass Spec. Found (m/z) | Mass Spec. Calculated | $^1$H-NMR |
|---|---|---|---|---|---|
| HBV-CSU-335_Int | 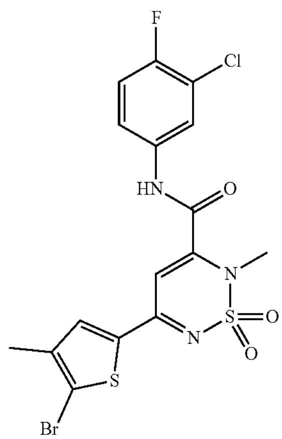 [SMILES: Cc1cc(C2=NS(=O)(=O)N(C)C(C(=O)Nc3ccc(F)c(Cl)c3)=C2)sc1Br] | — | 493.84 (M + 2) | 490.92 for $C_{16}H_{12}BrClFN_3O_3S_2$ | The reaction was monitored by LCMS and the crude intermediate carried forward to the next step. |
| HBV-CSU-336_Int | 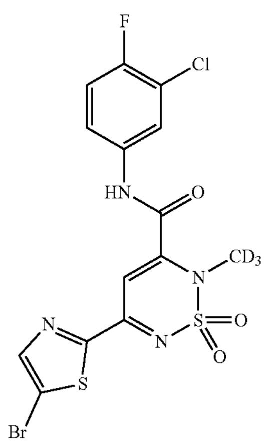 [SMILES: [2H]C([2H])([2H])N1C(C(=O)Nc2ccc(F)c(Cl)c2)=CC(c2ncc(Br)s2)=NS1(=O)=O] | 75% | 483.95 (M + 2) | 480.92 for $C_{14}H_6D_3BrClFN_4O_3S_2$ | $^1$H-NMR (DMSO-$d_6$, 400 MHz): δ 11.37 (s, 1H), 8.35 (s, 1H), 7.98-7.96 (m, 1H), 7.62-7.53 (m, 1H), 7.48 (t, J = 8.8 Hz, 1H), 7.14 (s, 1H). |
| HBV-CSU-360_Int | 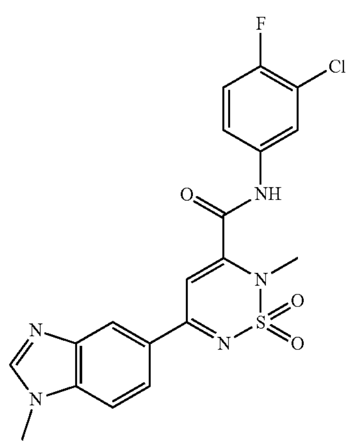 [SMILES: CN1C(C(=O)Nc2ccc(F)c(Cl)c2)=CC(c2ccc3c(c2)ncn3C)=NS1(=O)=O] | — | 448.10 | 447.06 for $C_{19}H_{15}ClFN_5O_3S$ | The reaction was monitored by LCMS and the crude intermediate carried forward to the next step. |

TABLE 1-continued

Analytical data for HBV-CSU_Int:

| Target No | Structure | Rx. Yield (%) | Mass Spec. Found (m/z) | Mass Spec. Calculated | $^1$H-NMR |
|---|---|---|---|---|---|
| HBV-CSU-364_Int | 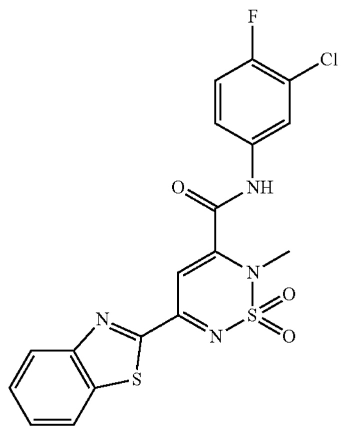 [SMILES: CN1C(C(=O)Nc2ccc(F)c(Cl)c2)=CC(c2nc3ccccc3s2)=NS1(=O)=O] | — | 451.10 (M + 2) | 450.00 for $C_{18}H_{12}ClFN_4O_3S_2$ | The reaction was monitored by LCMS and the crude intermediate carried forward to the next step. |
| HBV-CSU-368_Int | 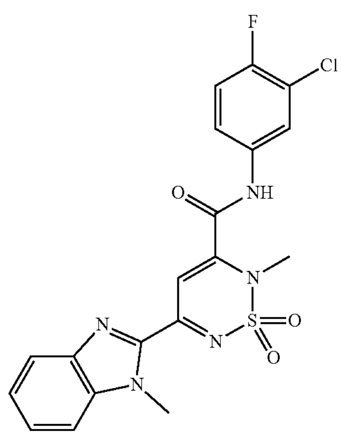 [SMILES: CN1C(C(=O)Nc2ccc(F)c(Cl)c2)=CC(c2nc3ccccc3n2C)=NS1(=O)=O] | 46% | 448.05 (M + 1) | 447.06 for $C_{19}H_{15}ClFN_5O_3S$ | $^1$H-NMR (DMSO-d$_6$, 400 MHz): δ 11.42 (s, 1H), 7.99 (d, J = 4.4 Hz, 1H), 7.81 (d, J = 8.4 Hz, 1H), 7.77 (d, J = 8.4 Hz, 1H), 7.64-7.62 (m, 1H), 7.52-7.47 (m, 2H), 7.40-7.36 (m, 2H), 4.23 (s, 3H), 3.57 (s, 3H). |
| HBV-CSU-370_Int | 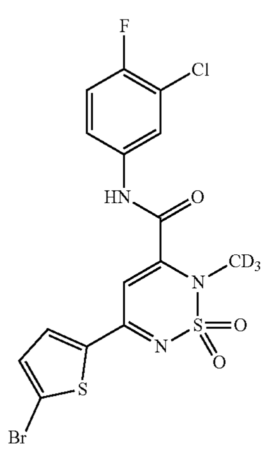 [SMILES: [2H]C([2H])([2H])N1C(C(=O)Nc2ccc(F)c(Cl)c2)=CC(c2ccc(Br)s2)=NS1(=O)=O] | 61% | 483.05 (M + 2) | 479.92 for $C_{15}H_7D_3BrClFN_3O_3S_2$ | $^1$H-NMR (DMSO-d$_6$, 400 MHz): δ 11.32 (s, 1H), 8.09 (d, J = 4.4 Hz, 1H), 7.96 (dd, J = 6.8, 2.4 Hz, 1H), 7.65-7.63 (m, 1H), 7.62-7.47 (m, 2H), 7.18 (s, 1H). |

TABLE 1-continued

Analytical data for HBV-CSU_Int:

| Target No | Structure | Rx. Yield (%) | Mass Spec. Found (m/z) | Mass Spec. Calculated | ¹H-NMR |
|---|---|---|---|---|---|
| HBV-CSU-391_Int | 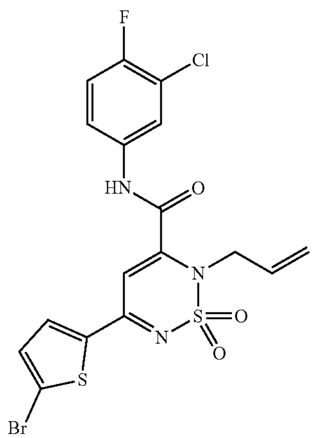 [SMILES: C=CCN1C(C(=O)Nc2ccc(F)c(Cl)c2)=CC(c2ccc(Br)s2)=NS1(=O)=O] | 61% | 506 (M + 2) | 502.92 for $C_{17}H_{12}BrClFN_3O_3S_2$ | ¹H-NMR (DMSO-d$_6$, 400 MHz): δ 11.31 (s, 1H), 8.13 (d, J = 4.4 Hz, 1H), 7.93 (dd, J = 6.8, 2.4 Hz, 1H), 7.63-7.59 (m, 1H), 7.53-7.47 (m, 2H), 7.29 (s, 1H), 5.94-5.87 (m, 1H), 5.24-5.19 (m, 2H), 4.54-4.52 (m, 2H). |
| HBV-CSU-423_Int | 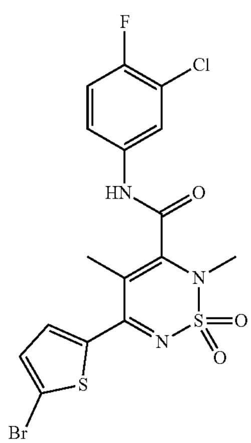 [SMILES: CC1=C(C(=O)Nc2ccc(F)c(Cl)c2)N(C)S(=O)(=O)N=C1c1ccc(Br)s1] | — | 494 (M + 2) | 490.92 for $C_{16}H_{12}BrClFN_3O_3S_2$ | The reaction was monitored by LCMS and the crude intermediate carried forward to the next step. |

TABLE 2

Analytical data for HBV-CSU racemic & pure enantiomers:

| Target No | Structure | Rx. Yield (%) | Mass Spec. Found (m/z) | Mass Spec. Calculated | ¹H-NMR |
|---|---|---|---|---|---|
| HBV-CSU-006 | 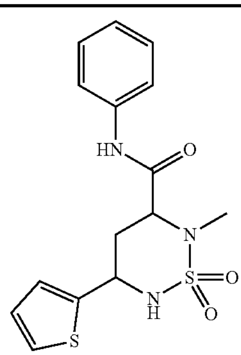 | 76% | 351.90 (M + 1) | 351.07 for $C_{15}H_{17}N_3O_3S_2$ | ¹H-NMR (DMSO-d$_6$, 400 MHz): δ 10.35 (s, 1H), 7.70-7.61 (m, 3H), 7.51 (d, J = 4.8 Hz, 1H), 7.33 (t, J = 8.0 Hz, 2H), 7.19-6.99 (m, 3H), 4.80-4.78 (m, 1H), 4.27 (dd, J = 11.4, 3.3 Hz, 1H), 2.62 (s, 3H), 2.30-2.11 (m, 2H). |

TABLE 2-continued

Analytical data for HBV-CSU racemic & pure enantiomers:

| Target No | Structure | Rx. Yield (%) | Mass Spec. Found (m/z) | Mass Spec. Calculated | $^1$H-NMR |
|---|---|---|---|---|---|
| HBV-CSU-007 | 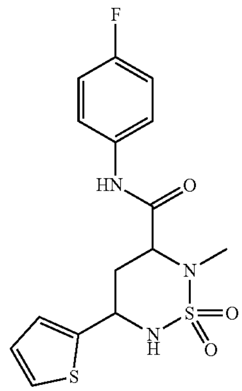 [SMILES: CN1C(C(=O)Nc2ccc(F)cc2)CC(c2cccs2)NS1(=O)=O] | 46% | 369.95 (M + 1) | 369.06 for $C_{15}H_{16}FN_3O_3S_2$ | $^1$H-NMR (DMSO-$d_6$, 400 MHz): δ 10.43 (s, 1H), 7.68-7.63 (m, 3H), 7.52-7.49 (m, 1H), 7.23-7.12 (m, 3H), 7.03-7.00 (m, 1H), 4.85-4.74 (m, 1H), 4.27-4.25 (m, 1H), 2.62 (s, 3H), 2.29-2.09 (m, 2H). |
| HBV-CSU-010 | 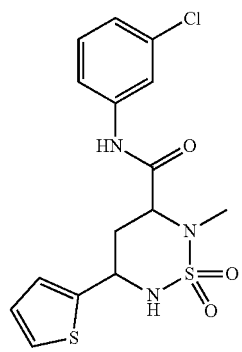 [SMILES: CN1C(C(=O)Nc2cccc(Cl)c2)CC(c2cccs2)NS1(=O)=O] | 29% | 385.90 (M + 1) | 385.03 for $C_{15}H_{16}ClN_3O_3S_2$ | $^1$H-NMR (DMSO-$d_6$, 400 MHz): δ 10.56 (s, 1H), 7.86 (t, J = 2.0 Hz, 1H), 7.69 (d, J = 8.5 Hz, 1H), 7.53-7.51 (m, 2H), 7.37 (t, J = 8.1 Hz, 1H), 7.20-7.08 (m, 2H), 7.03-7.02 (m, 1H), 4.79 (t, J = 9.1 Hz, 1H), 4.30-4.27 (m, 1H), 2.61 (s, 3H), 2.30-2.08 (m, 2H). |
| HBV-CSU-010-ISO-I | 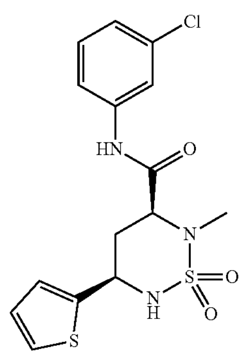 | 4.58% | 386 (M + 1) | 385.03 for $C_{15}H_{16}ClN_3O_3S_2$ | $^1$H-NMR (DMSO-$d_6$, 400 MHz): δ 10.55 (s, 1H), 7.86 (t, J = 2.0 Hz, 1H), 7.69 (d, J = 8.8 Hz, 1H), 7.56-7.49 (m, 2H), 7.36 (t, J = 8.1 Hz, 1H), 7.17-7.15 (m, 2H), 7.02 (t, J = 4.4 Hz, 1H), 4.80-4.78 (m, 1H), 4.29 (dd, J = 11.7, 3.1 Hz, 1H), 2.61 (s, 3H), 2.29-2.08 (m, 2H). |
| HBV-CSU-011 | 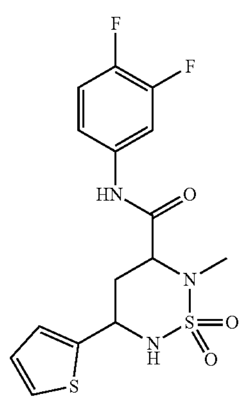 [SMILES: CN1C(C(=O)Nc2ccc(F)c(F)c2)CC(c2cccs2)NS1(=O)=O] | 86% | 388 (M + 1) | 387.05 for $C_{15}H_{15}F_2N_3O_3S_2$ | $^1$H-NMR (DMSO-$d_6$, 400 MHz): δ 10.59 (s, 1H), 7.87-7.77 (m, 1H), 7.68 (d, J = 9.1 Hz, 1H), 7.52-7.51 (m, 1H), 7.46-7.36 (m, 2H), 7.16-7.14 (m, 1H), 7.03-7.01 (m, 1H), 4.79 (t, J = 9.8 Hz, 1H), 4.31-4.28 (m, 1H), 2.61 (s, 3H), 2.28-2.07 (m, 2H). |

TABLE 2-continued

Analytical data for HBV-CSU racemic & pure enantiomers:

| Target No | Structure | Rx. Yield (%) | Mass Spec. Found (m/z) | Mass Spec. Calculated | $^1$H-NMR |
|---|---|---|---|---|---|
| HBV-CSU-012 | 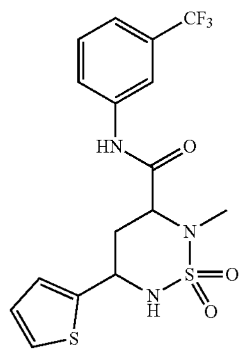 [SMILES: CN1C(C(=O)Nc2cccc(C(F)(F)F)c2)CC(c2cccs2)NS1(=O)=O] | 93% | 419.94 (M + 1) | 419.06 for $C_{16}H_{16}F_3N_3O_3S_2$ | $^1$H-NMR (DMSO-$d_6$, 400 MHz): δ 10.69 (s, 1H), 8.14 (d, J = 2.1 Hz, 1H), 7.90-7.83 (m, 1H), 7.68 (d, J = 8.5 Hz, 1H), 7.62-7.41 (m, 3H), 7.15 (d, J = 3.5 Hz, 1H), 7.02 (dd, J = 5.1, 3.6 Hz, 1H), 4.80 (t, J = 9.3 Hz, 1H), 4.33 (dd, J = 11.7, 2.9 Hz, 1H), 2.62 (s, 3H), 2.30-2.08 (m, 2H). |
| HBV-CSU-013 | 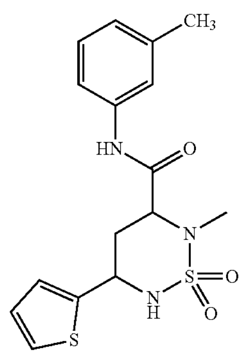 [SMILES: Cc1cccc(NC(=O)C2CC(c3cccs3)NS(=O)(=O)N2C)c1] | 59% | 365.95 (M + 1) | 365.09 for $C_{16}H_{19}N_3O_3S_2$ | $^1$H-NMR (DMSO-$d_6$, 400 MHz): δ 10.28 (s, 1H), 7.68 (d, J = 9.1 Hz, 1H), 7.51-7.48 (m, 2H), 7.40-7.38 (m, 1H), 7.18 (t, J = 8.0 Hz, 1H), 7.13-7.11 (m, 1H), 7.02-7.00 (m, 1H), 6.91-6.89 (m, 1H), 4.78 (t, J = 9.6 Hz, 1H), 4.23 (dd, J = 11.3, 3.4 Hz, 1H), 2.60 (s, 3H), 2.29-2.09 (m, 5H). |
| HBV-CSU-014 | 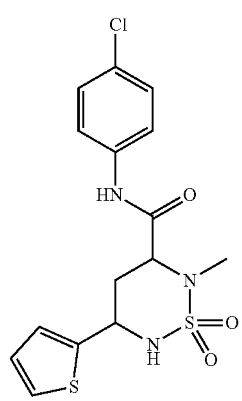 [SMILES: CN1C(C(=O)Nc2ccc(Cl)cc2)CC(c2cccs2)NS1(=O)=O] | 33% | 385.85 (M + 1) | 385.03 for $C_{15}H_{16}ClN_3O_3S_2$ | $^1$H-NMR (DMSO-$d_6$, 400 MHz): δ 10.49 (s, 1H), 7.69-7.66 (m, 3H), 7.51-7.49 (m, 1H), 7.43-7.34 (m, 2H), 7.15-7.14 (m, 1H), 7.01 (dd, J = 5.1, 3.5 Hz, 1H), 4.78 (t, J = 9.6, Hz, 1H), 4.28 (dd, J = 11.5, 3.1 Hz, 1H), 2.61 (s, 3H), 2.28-2.08 (m, 2H). |
| HBV-CSU-015 | 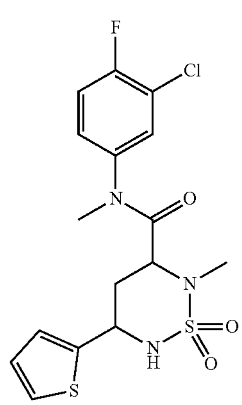 [SMILES: CN(C(=O)C1CC(c2cccs2)NS(=O)(=O)N1C)c1ccc(F)c(Cl)c1] | 35% | 417.88 (M + 1) | 417.04 for $C_{16}H_{17}FN_3O_3S_2$ | $^1$H-NMR (DMSO-$d_6$, 400 MHz): δ 7.80-7.72 (m, 1H), 7.53-7.45 (m, 3H), 7.32-7.29 (m, 1H), 7.11-6.91 (m, 2H), 4.53 (t, J = 9.7 Hz, 1H), 4.34 (dd, J = 11.5, 2.7 Hz, 1H), 3.32 (s, 3H), 3.10 (s, 3H), 2.12-1.85 (m, 2H). |

TABLE 2-continued

Analytical data for HBV-CSU racemic & pure enantiomers:

| Target No | Structure | Rx. Yield (%) | Mass Spec. Found (m/z) | Mass Spec. Calculated | $^1$H-NMR |
|---|---|---|---|---|---|
| HBV-CSU-016 | 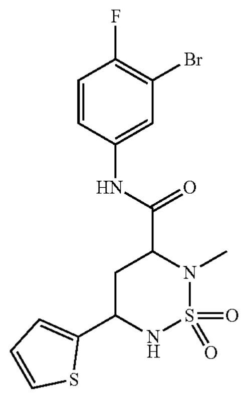 [SMILES: CN1C(C(=O)Nc2ccc(F)c(Br)c2)CC(c2cccs2)NS1(=O)=O] | 90% | 449.90 (M + 1) | 446.97 for $C_{15}H_{15}BrFN_3O_3S_2$ | $^1$H-NMR (DMSO-$d_6$, 400 MHz): δ 10.55 (s, 1H), 8.10 (dd, J = 6.4, 2.6 Hz, 1H), 7.71-7.54 (m, 2H), 7.52 (d, J = 5.3 Hz, 1H), 7.37 (t, J = 8.8 Hz, 1H), 7.15-7.14 (m, 1H), 7.03-7.01 (m, 1H), 4.85-4.74 (m, 1H), 4.30 (dd, J = 11.7, 3.0 Hz, 1H), 2.61 (s, 3H), 2.29-2.08 (m, 2H). |
| HBV-CSU-016-ISO-I | 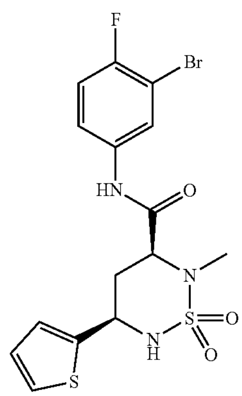 [SMILES: CN1[C@H](C(=O)Nc2ccc(F)c(Br)c2)C[C@H](c2cccs2)NS1(=O)=O] | 33.14% | 449.90 (M + 1) | 446.97 for $C_{15}H_{15}BrFN_3O_3S_2$ | $^1$H-NMR (DMSO-$d_6$, 400 MHz): δ 10.55 (s, 1H), 8.09-8.06 (m, 1H), 7.68-7.66 (m, 1H), 7.62-7.58 (m, 1H), 7.51-7.49 (m, 1H), 7.36 (t, J = 8.8 Hz, 1H), 7.14-7.13 (m, 1H), 7.02-7.00 (m, 1H), 4.80-4.76 (m, 1H), 4.29-4.25 (m, 1H), 2.60 (s, 3H), 2.31-2.08 (m, 2H). |
| HBV-CSU-017 | 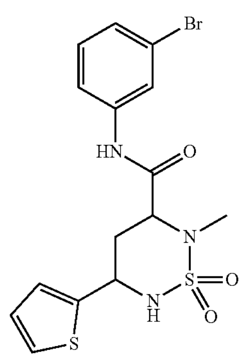 [SMILES: CN1C(C(=O)Nc2cccc(Br)c2)CC(c2cccs2)NS1(=O)=O] | 45% | 431.93 (M + 1) | 428.98 for $C_{15}H_{16}BrN_3O_3S_2$ | $^1$H-NMR (DMSO-$d_6$, 400 MHz): δ 10.53 (s, 1H), 8.00-7.99 (m, 1H), 7.68 (d, J = 9.2 Hz, 1H), 7.62-7.48 (m, 2H), 7.35-7.26 (m, 2H), 7.19-7.12 (m, 1H), 7.03 (dd, J = 5.1, 3.5 Hz, 1H), 4.80 (t, J = 9.9 Hz, 1H), 4.29 (dd, J = 11.7, 3.1 Hz, 1H), 2.62 (s, 3H), 2.30-2.08 (m, 2H). |
| HBV-CSU-017-ISO-I | 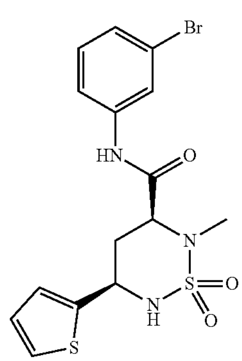 [SMILES: CN1[C@H](C(=O)Nc2cccc(Br)c2)C[C@H](c2cccs2)NS1(=O)=O] | 15% | 431.86 (M + 1) | 428.98 for $C_{15}H_{16}BrN_3O_3S_2$ | $^1$H-NMR (DMSO-$d_6$, 400 MHz): δ 10.52 (s, 1H), 7.99 (s, 1H), 7.67-7.66 (m, 1H), 7.59-7.47 (m, 2H), 7.31-7.29 (m, 2H), 7.14 (d, J = 3.4 Hz, 1H), 7.01 (dd, J = 5.1, 3.5 Hz, 1H), 4.78-4.76 (m, 1H), 4.31-4.23 (m, 1H), 2.60 (s, 3H), 2.27-2.06 (m, 2H). |

TABLE 2-continued

Analytical data for HBV-CSU racemic & pure enantiomers:

| Target No | Structure | Rx. Yield (%) | Mass Spec. Found (m/z) | Mass Spec. Calculated | $^1$H-NMR |
|---|---|---|---|---|---|
| HBV-CSU-018 | 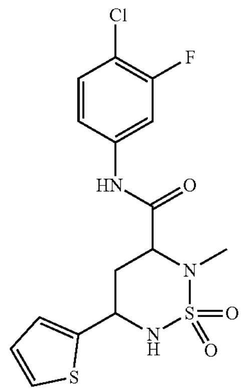 [SMILES: CN1C(C(=O)Nc2ccc(Cl)c(F)c2)CC(c2cccs2)NS1(=O)=O] | 90% | 403.85 (M + 1) | 403.02 for $C_{15}H_{15}ClFN_3O_3S_2$ | $^1$H-NMR (DMSO-$d_6$, 400 MHz): δ 10.68 (s, 1H), 7.82 (dd, J = 11.8, 2.3 Hz, 1H), 7.68 (d, J = 9.1 Hz, 1H), 7.60-7.51 (m, 2H), 7.46-7.41 (m, 1H), 7.15 (d, J = 3.6 Hz, 1H), 7.03 (dd, J = 5.1, 3.5 Hz, 1H), 4.79 (t, J = 10.2 Hz, 1H), 4.32 (dd, J = 11.7, 3.0 Hz, 1H), 2.61 (s, 3H), 2.28-2.05 (m, 2H). |
| HBV-CSU-019 | 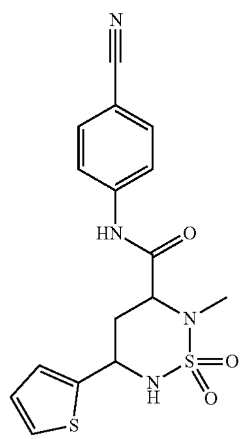 [SMILES: CN1C(C(=O)Nc2ccc(C#N)cc2)CC(c2cccs2)NS1(=O)=O] | 40% | 377.08 (M + 1) | 376.07 for $C_{16}H_{16}N_4O_3S_2$ | $^1$H-NMR (DMSO-$d_6$, 400 MHz): δ 10.76 (s, 1H), 7.90-7.75 (m, 4H), 7.68-7.66 (m, 1H), 7.50 (dd, J = 5.1, 1.2 Hz, 1H), 7.15-7.13 (m, 1H), 7.01 (dd, J = 5.1, 3.5 Hz, 1H), 4.78 (t, J = 9.0 Hz, 1H), 4.34 (dd, J = 11.7, 2.9 Hz, 1H), 2.60 (s, 3H), 2.29-2.06 (m, 2H). |
| HBV-CSU-020 | 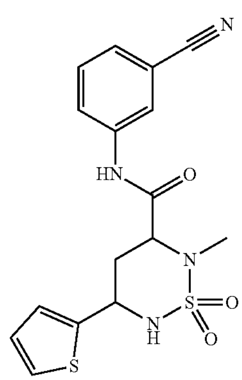 [SMILES: CN1C(C(=O)Nc2cccc(C#N)c2)CC(c2cccs2)NS1(=O)=O] | 37% | 376.9 (M + 1) | 376.07 for $C_{16}H_{16}N_4O_3S_2$ | $^1$H-NMR (DMSO-$d_6$, 400 MHz): δ 10.70 (s, 1H), 8.15 (d, J = 2.0 Hz, 1H), 7.89-7.86 (m, 1H), 7.68 (s, 1H), 7.61-7.49 (m, 3H), 7.16 (d, J = 3.5 Hz, 1H), 7.03 (dd, J = 5.1, 3.6 Hz, 1H), 4.80-4.78 (m, 1H), 4.34 (dd, J = 11.8, 3.0 Hz, 1H), 2.63 (s, 3H), 2.30-2.05 (m, 2H). |

TABLE 2-continued

Analytical data for HBV-CSU racemic & pure enantiomers:

| Target No | Structure | Rx. Yield (%) | Mass Spec. Found (m/z) | Mass Spec. Calculated | ¹H-NMR |
|---|---|---|---|---|---|
| HBV-CSU-020-ISO-I | 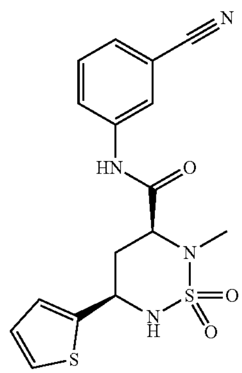 [SMILES: CN1[C@H](C(=O)Nc2cccc(C#N)c2)C[C@H](c2cccs2)NS1(=O)=O] | 8.4% | 376.9 (M + 1) | 376.07 for $C_{16}H_{16}N_4O_3S_2$ | ¹H-NMR (DMSO-$d_6$, 400 MHz): δ 10.70 (s, 1H), 8.14 (s, 1H), 7.87-7.85 (m, 1H), 7.68 (s, 1H), 7.60-7.48 (m, 3H), 7.14 (d, J = 3.5 Hz, 1H), 7.02 (dd, J = 5.1, 3.5 Hz, 1H), 4.80-4.77 (m, 1H), 4.33 (dd, J = 11.9, 3.0 Hz, 1H), 2.61 (s, 3H), 2.29-2.07 (m, 2H). |
| HBV-CSU-023_Int 1 | 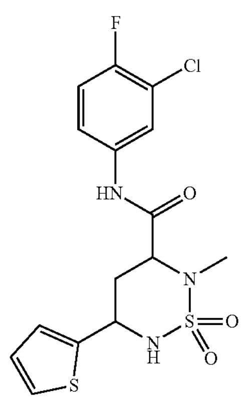 [SMILES: CN1C(C(=O)Nc2ccc(F)c(Cl)c2)CC(c2cccs2)NS1(=O)=O] | 87% | 403.85 (M + 1) | 403.02 for $C_{15}H_{15}ClFN_3O_3S_2$ | ¹H-NMR (DMSO-$d_6$, 400 MHz): δ 10.56 (s, 1H), 7.97-7.95 (m, 1H), 7.66 (d, J = 10.0 Hz, 1H), 7.56-7.50 (m, 2H), 7.39 (t, J = 8.8 Hz, 1H), 7.14 (d, J = 3.2 Hz, 1H), 7.03-7.01 (m, 1H), 4.80-4.78 (m, 1H), 4.25-4.21 (m, 1H), 2.59 (s, 3H), 2.24-2.09 (m, 2H). |
| HBV-CSU-023 | 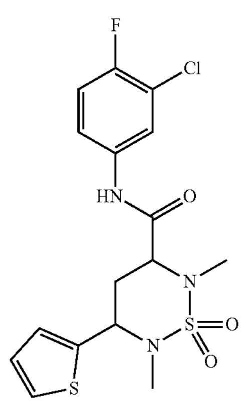 [SMILES: CN1C(C(=O)Nc2ccc(F)c(Cl)c2)CC(c2cccs2)N(C)S1(=O)=O] | 65% | 418 (M + 1) | 417.04 for $C_{16}H_{17}ClFN_3O_3S_2$ | ¹H-NMR (DMSO-$d_6$, 400 MHz): δ 10.55 (s, 1H), 7.95 (dd, J = 6.9, 2.6 Hz, 1H), 7.65-7.51 (m, 2H), 7.39 (t, J = 9.1 Hz, 1H), 7.21 (d, J = 3.5 Hz, 1H), 7.04 (dd, J = 5.1, 3.4 Hz, 1H), 4.94 (dd, J = 12.5, 2.9 Hz, 1H), 4.35 (dd, J = 12.1, 3.0 Hz, 1H), 2.69 (s, 3H), 2.44 (s, 3H), 2.16-2.12 (m, 2H). |

TABLE 2-continued

Analytical data for HBV-CSU racemic & pure enantiomers:

| Target No | Structure | Rx. Yield (%) | Mass Spec. Found (m/z) | Mass Spec. Calculated | $^1$H-NMR |
|---|---|---|---|---|---|
| HBV-CSU-024 | 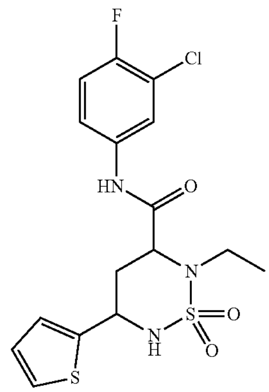 [SMILES: CCN1C(C(=O)Nc2ccc(F)c(Cl)c2)CC(c2cccs2)NS1(=O)=O] | 60% | 417.90 (M + 1) | 417.04 for $C_{16}H_{17}ClFN_3O_3S_2$ | $^1$H NMR (400 MHz, DMSO-$d_6$): δ 10.61 (s, 1H), 7.95 (dd, J = 6.8, 2.6 Hz, 1H), 7.62-7.46 (m, 3H), 7.39 (t, J = 9.1 Hz, 1H), 7.16-7.09 (m, 1H), 7.01 (dd, J = 5.1, 3.5 Hz, 1H), 4.78 (d, J = 11.2 Hz, 1H), 4.46 (dd, J = 12.0, 2.7 Hz, 1H), 3.27-3.24 (m, 1H), 2.99-2.92 (m, 1H), 2.31-2.21 (m, 1H), 2.10-1.96 (m, 1H), 1.11 (t, J = 7.1 Hz, 3H). |
| HBV-CSU-025 | 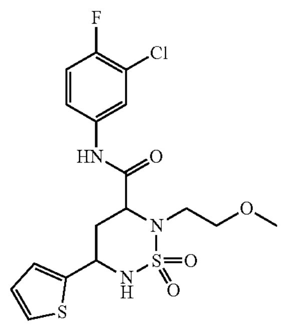 [SMILES: COCCN1C(C(=O)Nc2ccc(F)c(Cl)c2)CC(c2cccs2)NS1(=O)=O] | 17% | 447.90 (M + 1) | 447.05 for $C_{16}H_{19}ClFN_3O_4S_2$ | $^1$H-NMR (DMSO-$d_6$, 400 MHz): δ 10.45 (s, 1H), 7.91 (dd, J = 6.8, 2.6 Hz, 1H), 7.61-7.45 (m, 3H), 7.37 (t, J = 9.1 Hz, 1H), 7.12-7.11 (m, 1H), 7.00 (dd, J = 5.1, 3.5 Hz, 1H), 4.80-4.78 (m, 1H), 4.56 (dd, J = 12.1, 2.7 Hz, 1H), 3.51-3.22 (m, 3H), 3.10 (s, 3H), 3.08-3.02 (m, 1H), 2.17-2.14 (m, 1H), 1.97-1.94 (m, 1H). |
| HBV-CSU-025-ISO-I | 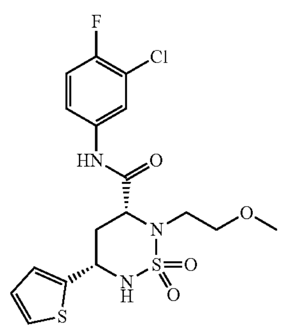 [SMILES: COCCN1[C@@H](C(=O)Nc2ccc(F)c(Cl)c2)C[C@@H](c2cccs2)NS1(=O)=O] | 2% | 447.95 (M + 1) | 447.05 for $C_{17}H_{19}ClFN_3O_4S_2$ | $^1$H-NMR (DMSO-$d_6$, 400 MHz): δ 10.51 (s, 1H), 7.96-7.94 (m, 1H), 7.61-7.43 (m, 3H), 7.40 (t, J = 9.2 Hz, 1H), 7.15-7.14 (m, 1H), 7.04-7.02 (m, 1H), 4.80-4.78 (m, 1H), 4.60-4.57 (m, 1H), 3.49-3.43 (m, 3H), 3.13 (s, 3H), 3.10-3.05 (m, 1H), 2.21-2.17 (m, 1H), 1.99-1.96 (m, 1H). |
| HBV-CSU-025-ISO-II | 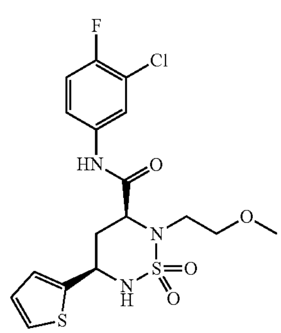 [SMILES: COCCN1[C@H](C(=O)Nc2ccc(F)c(Cl)c2)C[C@H](c2cccs2)NS1(=O)=O] | 3% | 447.95 (M + 1) | 447.05 for $C_{17}H_{19}ClFN_3O_4S_2$ | $^1$H-NMR (DMSO-$d_6$, 400 MHz): δ 10.50 (s, 1H), 7.94 (dd, J = 6.4, 2.4 Hz, 1H), 7.62-7.48 (m, 3H), 7.41 (t, J = 8.8 Hz, 1H), 7.14 (d, J = 3.2 Hz, 1H), 7.04-7.02 (m, 1H), 4.84-4.79 (m, 1H), 4.61-4.57 (m, 1H), 3.51-3.31 (m, 3H), 3.13 (s, 3H), 3.10-3.03 (m, 1H), 2.21-2.17 (m, 1H), 2.03-1.93 (m, 1H). |

TABLE 2-continued

Analytical data for HBV-CSU racemic & pure enantiomers:

| Target No | Structure | Rx. Yield (%) | Mass Spec. Found (m/z) | Mass Spec. Calculated | $^1$H-NMR |
|---|---|---|---|---|---|
| HBV-CSU-027 | 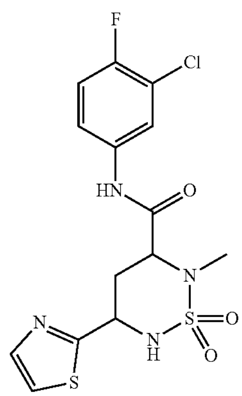 [SMILES: CN1C(C(=O)Nc2ccc(F)c(Cl)c2)CC(c2nccs2)NS1(=O)=O] | 36% | 404.85 (M + 1) | 404.02 for $C_{14}H_{14}ClFN_4O_3S_2$ | $^1$H-NMR (DMSO-$d_6$, 400 MHz): δ 10.57 (s, 1H), 8.00-7.86 (m, 2H), 7.85-7.75 (m, 2H), 7.56-7.53 (m, 1H), 7.41-7.39 (m, 1H), 4.99-4.87 (m, 1H), 4.40-4.31 (m, 1H), 2.62 (s, 3H), 2.57-2.34 (m, 1H), 2.23-2.13 (m, 1H). |
| HBV-CSU-027-ISO-I | 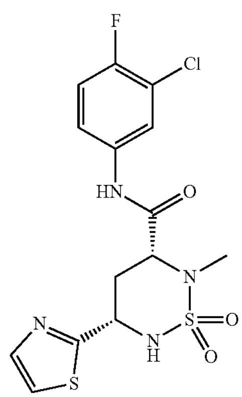 [SMILES: CN1[C@@H](C(=O)Nc2ccc(F)c(Cl)c2)C[C@@H](c2nccs2)NS1(=O)=O] | 5% | 404.97 (M + 1) | 404.02 for $C_{14}H_{14}ClFN_4O_3S_2$ | $^1$H-NMR (DMSO-$d_6$, 400 MHz): δ 10.59 (s, 1H), 8.01-7.88 (m, 2H), 7.84-7.76 (m, 2H), 7.58-7.56 (m, 1H), 7.40 (t, J = 9.1 Hz, 1H), 4.94-4.92 (m, 1H), 4.36 (dd, J = 12.1, 2.7 Hz, 1H), 2.62 (s, 3H), 2.47-2.35 (m, 1H), 2.23-2.14 (m, 1H). |
| HBV-CSU-027-ISO-II | 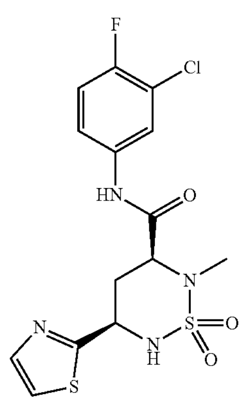 [SMILES: CN1[C@H](C(=O)Nc2ccc(F)c(Cl)c2)C[C@H](c2nccs2)NS1(=O)=O] | 10.4% | 404.97 (M + 1) | 404.02 for $C_{14}H_{14}ClFN_4O_3S_2$ | $^1$H NMR (DMSO-$d_6$, 400 MHz): δ 10.58 (s, 1H), 8.01-7.87 (m, 2H), 7.84-7.76 (m, 2H), 7.56-7.52 (m, 1H), 7.40 (t, J = 9.1 Hz, 1H), 4.94-4.92 (m, 1H), 4.37 (dd, J = 12.1, 2.7 Hz, 1H), 2.63 (s, 3H), 2.42-2.38 (m, 1H), 2.21-2.18 (m, 1H). |

TABLE 2-continued

Analytical data for HBV-CSU racemic & pure enantiomers:

| Target No | Structure | Rx. Yield (%) | Mass Spec. Found (m/z) | Mass Spec. Calculated | ¹H-NMR |
| --- | --- | --- | --- | --- | --- |
| HBV-CSU-029-ISO-I | 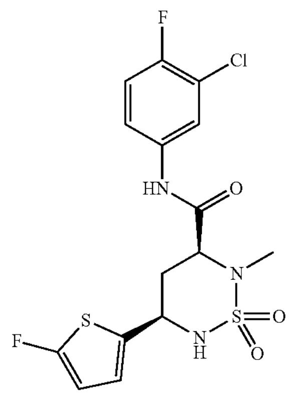 | 7.1% | 421.90 (M + 1) | 421.01 for $C_{15}H_{14}ClFN_3O_3S_2$ | ¹H-NMR (DMSO-$d_6$, 400 MHz): δ 10.59 (d, J = 6.2 Hz, 1H), 7.97 (dd, J = 6.8, 2.6 Hz, 1H), 7.71-7.70 (m, 1H), 7.57-7.53 (m, 1H), 7.40 (t, J = 9.1 Hz, 1H), 6.84-6.82 (m, 1H), 6.63-6.61 (m, 1H), 4.68 (d, J = 11.6 Hz, 1H), 4.31-4.23 (m, 1H), 2.61 (s, 3H), 2.21-2.08 (m, 2H). |
| HBV-CSU-031 | 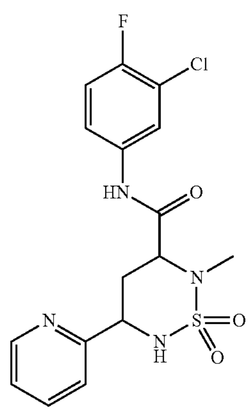 | 71% | 399.3 (M + 1) | 398.06 for $C_{16}H_{16}ClFN_4O_3S$ | ¹H-NMR (DMSO-$d_6$, 400 MHz): δ 10.55 (s, 1H), 8.56 (d, J = 4.0 Hz, 1H), 7.95 (dd, J = 6.8, 2.4 Hz, 1H), 7.83 (t, J = 7.6 Hz, 1H), 7.53-7.51 (m, 3H), 7.41-7.34 (m, 2H), 4.71-4.68 (m, 1H), 4.28 (dd, J = 11.6, 2.4 Hz, 1H), 2.63 (s, 3H), 2.31-2.23 (m, 1H), 2.15-2.06 (m, 1H). |
| HBV-CSU-031-ISO-I | 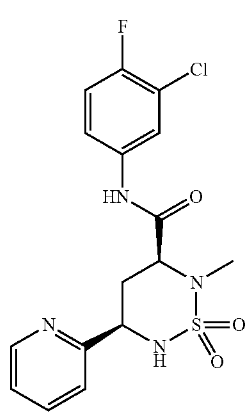 [SMILES: CN1[C@H](C(=O)Nc2ccc(F)c(Cl)c2)C[C@H](c2ccccn2)NS1(=O)=O] | 6% | 398.95 (M + 1) | 398.06 for $C_{16}H_{16}ClFN_4O_3S$ | ¹H-NMR (DMSO-$d_6$, 400 MHz): δ 10.56 (s, 1H), 8.56 (d, J = 4.0 Hz, 1H), 7.96 (dd, J = 7.2, 2.8 Hz, 1H), 7.85 (t, J = 7.6 Hz, 1H), 7.55-7.52 (m, 3H), 7.42-7.35 (m, 2H), 4.72-4.67 (m, 1H), 4.29 (dd, J = 12, 2.8 Hz, 1H), 2.64 (s, 3H), 2.32-2.21 (m, 1H), 2.18-2.08 (m, 1H). |

TABLE 2-continued

Analytical data for HBV-CSU racemic & pure enantiomers:

| Target No | Structure | Rx. Yield (%) | Mass Spec. Found (m/z) | Mass Spec. Calculated | $^1$H-NMR |
|---|---|---|---|---|---|
| HBV-CSU-031-ISO-II | 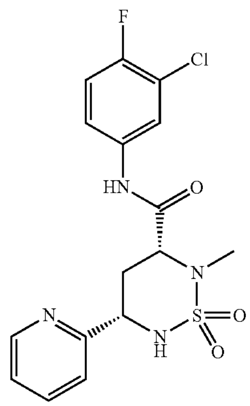 [SMILES: CN1[C@@H](C(=O)Nc2ccc(F)c(Cl)c2)C[C@@H](c2ccccn2)NS1(=O)=O] | 9% | 398.75 (M + 1) | 398.06 for $C_{16}H_{16}ClFN_4O_3S$ | $^1$H-NMR (DMSO-$d_6$, 400 MHz): δ 10.56 (s, 1H), 8.56 (d, J = 4.4 Hz, 1H), 7.96 (dd, J = 7.2, 2.8 Hz, 1H), 7.85 (t, J = 7.6 Hz, 1H), 7.57-7.53 (m, 3H), 7.42-7.34 (m, 2H), 4.72-4.67 (m, 1H), 4.31-4.26 (m, 1H), 2.63 (s, 3H), 2.35-2.2 (m, 1H), 2.14-2.07 (m, 1H). |
| HBV-CSU-032 | 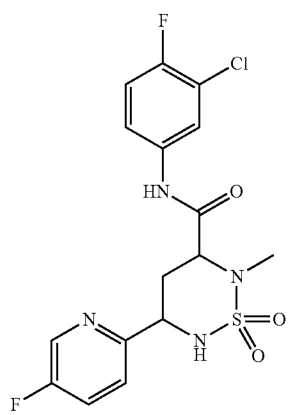 [SMILES: CN1C(C(=O)Nc2ccc(F)c(Cl)c2)CC(c2ccc(F)cn2)NS1(=O)=O] | | 417.05 (M + 1) | 416.05 for $C_{16}H_{15}ClF_2N_4O_3S$ | $^1$H-NMR (DMSO-$d_6$, 400 MHz): δ 10.53 (s, 1H), 8.53 (d, J = 2.8 Hz, 1H), 7.93 (dd, J = 6.8, 2.4 Hz, 1H), 7.8-7.74 (m, 1H), 7.6-7.49 (m, 3H), 7.36 (t, J = 8.8 Hz, 1H), 4.71-4.65 (m, 1H), 4.26 (dd, J = 11.6, 2.8 Hz, 1H), 2.6 (s, 3H), 2.12-2.03 (m, 2H). |
| HBV-CSU-032-ISO-I | 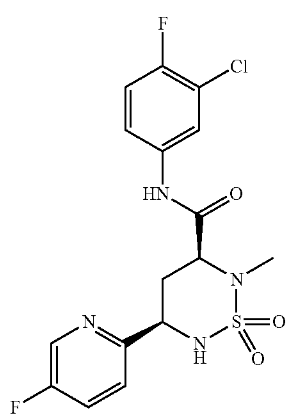 | 10% | 417.04 (M + 1) | 416.05 for $C_{16}H_{15}ClF_2N_4O_3S$ | $^1$H-NMR (DMSO-$d_6$, 400 MHz): δ 10.56 (s, 1H), 8.57 (d, J = 3.2 Hz, 1H), 7.96 (dd, J = 6.8, 2.4 Hz, 1H), 7.83-7.77 (m, 1H), 7.64-7.51 (m, 3H), 7.4 (t, J = 8.8 Hz, 1H), 4.73-4.68 (m, 1H), 4.31-4.28 (m, 1H), 2.63 (s, 3H), 2.23-2.08 (m, 2H). |

TABLE 2-continued

Analytical data for HBV-CSU racemic & pure enantiomers:

| Target No | Structure | Rx. Yield (%) | Mass Spec. Found (m/z) | Mass Spec. Calculated | 1H-NMR |
|---|---|---|---|---|---|
| HBV-CSU-032-ISO-II | 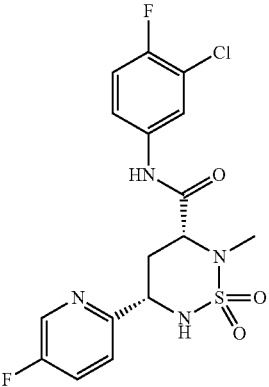 [SMILES: CN1[C@@H](C(=O)Nc2ccc(F)c(Cl)c2)C[C@@H](c2ccc(F)cn2)NS1(=O)=O] | 10% | 417.05 (M + 1) | 416.05 for $C_{16}H_{15}ClF_2N_4O_3S$ | 1H-NMR (DMSO-$d_6$, 400 MHz): δ 10.56 (s, 1H), 8.57 (d, J = 3.2 Hz, 1H), 7.96 (dd, J = 6.8, 2.4 Hz, 1H), 7.82-7.77 (m, 1H), 7.64-7.51 (m, 3H), 7.4 (t, J = 8.8 Hz, 1H), 4.72-4.68 (m, 1H), 4.29 (dd, J = 11.6, 2.8 Hz, 1H), 2.63 (s, 3H), 2.22-2.09 (m, 2H). |
| HBV-CSU-033 | 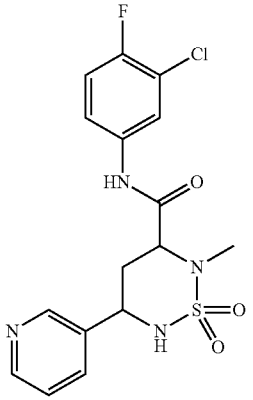 [SMILES: CN1C(C(=O)Nc2ccc(F)c(Cl)c2)CC(c2cccnc2)NS1(=O)=O] | 56% | 399.25 (M + 1) | 398.06 for $C_{16}H_{16}ClFN_4O_3S$ | 1H-NMR (DMSO-$d_6$, 400 MHz): δ 10.58 (s, 1H), 8.66 (s, 1H), 8.53 (d, J = 4.8 Hz, 1H), , 7.96 (dd, J = 6.8, 2.4 Hz, 1H), 7.9 (d, J = 8 Hz, 1H), 7.64-7.62 (m, 1H), 7.56-7.53 (m, 1H), 7.43-7.37 (m, 2H), 4.69-4.66 (m, 1H), 4.32-4.28 (m, 1H), 2.65 (s, 3H), 2.14-2.09 (m, 2H). |
| HBV-CSU-036 | 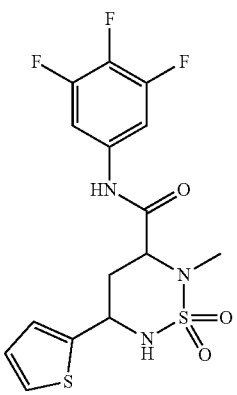 [SMILES: CN1C(C(=O)Nc2cc(F)c(F)c(F)c2)CC(c2cccs2)NS1(=O)=O] | 40% | 406.03 (M + 1) | 405.04 for $C_{15}H_{14}F_3N_3O_3S_2$ | 1H-NMR (DMSO-$d_6$, 400 MHz): δ 10.72 (s, 1H), 7.68 (d, J = 9.0 Hz, 1H), 7.66-7.48 (m, 3H), 7.15-7.14 (m, 1H), 7.03 (dd, J = 5.1, 3.6 Hz, 1H), 4.79 (t, J = 9.8 Hz, 1H), 4.34 (dd, J = 11.7, 3.0 Hz, 1H), 2.60 (s, 3H), 2.26-2.04 (m, 2H); |

TABLE 2-continued

Analytical data for HBV-CSU racemic & pure enantiomers:

| Target No | Structure | Rx. Yield (%) | Mass Spec. Found (m/z) | Mass Spec. Calculated | $^1$H-NMR |
|---|---|---|---|---|---|
| HBV-CSU-040 | 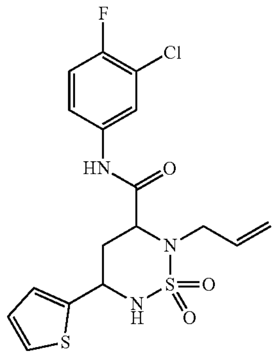 [SMILES: C=CCN1C(C(=O)Nc2ccc(F)c(Cl)c2)CC(c2cccs2)NS1(=O)=O] | 67% | 429.93 (M + 1) | 429.04 for $C_{17}H_{17}ClFN_3O_3S_2$ | $^1$H-NMR (DMSO-$d_6$, 400 MHz): δ 10.55 (s, 1H), 7.91 (dd, J = 6.9, 2.6 Hz, 1H), 7.66 (d, J = 9.4 Hz, 1H), 7.53-7.49 (m, 2H), 7.39 (t, J = 9.1 Hz, 1H), 7.18-7.12 (m, 1H), 7.03 (dd, J = 5.1, 3.5 Hz, 1H), 5.91-5.81 (m, 1H), 5.16-4.99 (m, 2H), 4.83-4.79 (m, 1H), 4.47-4.43 (m, 1H), 3.94-3.89 (m, 1H), 3.60-3.54 (m, 1H), 2.25-2.09 (m, 2H). |
| HBV-CSU-041 | 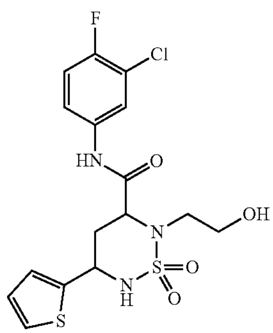 [SMILES: O=C(Nc1ccc(F)c(Cl)c1)C1CC(c2cccs2)NS(=O)(=O)N1CCO] | 20% | 433.99 (M + 1) | 433.03 for $C_{16}H_{17}ClFN_3O_4S_2$ | $^1$H-NMR (DMSO-$d_6$, 400 MHz): δ 10.51 (s, 1H), 7.96 (dd, J = 6.9, 2.6 Hz, 1H), 7.65-7.49 (m, 3H), 7.41 (t, J = 9.1 Hz, 1H), 7.15 (d, J = 3.5 Hz, 1H), 7.03 (dd, J = 5.1, 3.5 Hz, 1H), 4.92-4.76 (m, 2H), 4.59 (dd, J = 12.1, 2.8 Hz, 1H), 3.54-3.51 (m, 2H), 3.33-3.19 (m, 1H), 2.98-2.91 (m, 1H), 2.23-2.20 (m, 1H), 2.04-1.90 (m, 1H). |
| HBV-CSU-043-ISO-I | 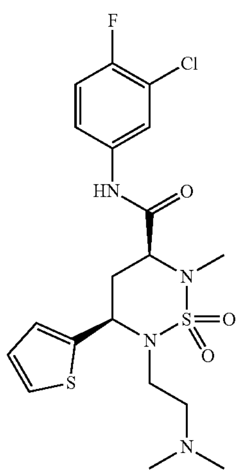 [SMILES: CN(C)CCN1[C@@H](c2cccs2)C[C@@H](C(=O)Nc2ccc(F)c(Cl)c2)N(C)S1(=O)=O] | 8.4% | 474.99 (M + 1) | 474.10 for $C_{19}H_{24}ClFN_4O_3S_2$ | $^1$H-NMR (DMSO-$d_6$, 400 MHz): δ 10.52 (s, 1H), 7.96 (dd, J = 6.8, 2.6 Hz, 1H), 7.69-7.51 (m, 2H), 7.41 (t, J = 9.2 Hz, 1H), 7.30 (d, J = 3.5 Hz, 1H), 7.06 (dd, J = 5.1, 3.6 Hz, 1H), 5.14-5.11 (m, 1H), 4.23 (dd, J = 11.9, 3.1 Hz, 1H), 3.17-3.03 (m, 1H), 2.93-2.84 (m, 1H), 2.67 (s, 3H), 2.24-2.16 (m, 4H), 2.04-1.88 (m, 6H). |

TABLE 2-continued

Analytical data for HBV-CSU racemic & pure enantiomers:

| Target No | Structure | Rx. Yield (%) | Mass Spec. Found (m/z) | Mass Spec. Calculated | ¹H-NMR |
|---|---|---|---|---|---|
| HBV-CSU-043-ISO-II | 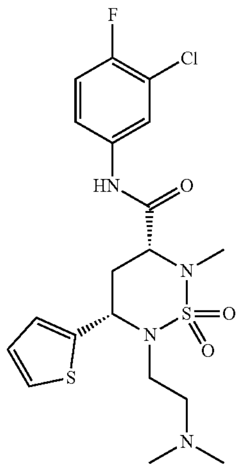 [SMILES: CN(C)CCN1[C@H](c2cccs2)C[C@H](C(=O)Nc2ccc(F)c(Cl)c2)N(C)S1(=O)=O] | 5% | 475.05 (M + 1) | 474.10 for $C_{19}H_{24}ClFN_4O_3S_2$ | ¹H-NMR (DMSO-$d_6$, 400 MHz): δ 10.57 (s, 1H), 7.96 (dd, J = 6.4, 2.4 Hz, 1H), 7.64 (d, J = 5.2 Hz, 1H), 7.59-7.54 (m, 1H), 7.41 (t, J = 9.2 Hz, 1H), 7.30 (d, J = 3.2 Hz, 1H), 7.08-7.05 (m, 1H), 5.15-5.11 (m, 1H), 4.25-4.21 (m, 1H), 3.17-3.09 (m, 1H), 2.95-2.84 (m, 1H), 2.68 (s, 3H), 2.25-2.07 (m, 4H), 2.02-1.93 (m, 6H). |
| HBV-CSU-044-ISO-I | 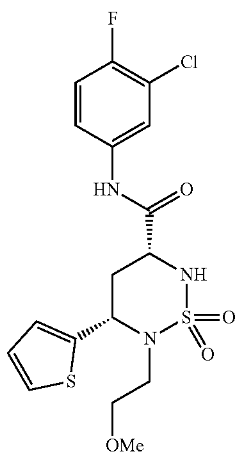 [SMILES: COCCN1[C@H](c2cccs2)C[C@H](C(=O)Nc2ccc(F)c(Cl)c2)NS1(=O)=O] | 2.1% | 447.95 (M + 1) | 447.05 for $C_{16}H_{19}ClFN_3O_4S_2$ | ¹H-NMR (DMSO-$d_6$, 400 MHz): δ 10.35 (s, 1H), 7.94 (dd, J = 6.9, 2.5 Hz, 1H), 7.66-7.48 (m, 3H), 7.40 (t, J = 9.1 Hz, 1H), 7.26 (d, J = 3.5 Hz, 1H), 7.06 (dd, J = 5.1, 3.5 Hz, 1H), 5.08 (dd, J = 12.1, 2.5 Hz, 1H), 4.37-4.35 (m, 1H), 3.32-3.11 (m, 3H), 3.09 (s, 3H), 2.90-2.81 (m, 1H), 2.20-1.99 (m, 2H). |
| HBV-CSU-044-ISO-II | 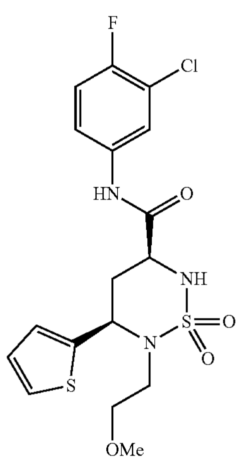 [SMILES: COCCN1[C@@H](c2cccs2)C[C@@H](C(=O)Nc2ccc(F)c(Cl)c2)NS1(=O)=O] | 2.2% | 447.95 (M + 1) | 447.05 for $C_{16}H_{19}ClFN_3O_4S_2$ | ¹H-NMR (DMSO-$d_6$, 400 MHz): δ 10.36 (s, 1H), 7.94 (dd, J = 7.2, 3.2 Hz, 1H), 7.64-7.62 (m, 1H), 7.58-7.51 (m, 2H), 7.39 (t, J = 8.8 Hz, 1H), 7.25 (d, J = 3.6 Hz, 1H), 7.07-7.06 (m, 1H), 5.07 (d, J = 10.0 Hz, 1H), 4.35 (d, J = 8.4 Hz, 1H), 3.33-3.13 (m, 3H), 3.04 (s, 3H), 2.88-2.81 (m, 1H), 2.21-2.02 (m, 2H). |

TABLE 2-continued

Analytical data for HBV-CSU racemic & pure enantiomers:

| Target No | Structure | Rx. Yield (%) | Mass Spec. Found (m/z) | Mass Spec. Calculated | $^1$H-NMR |
|---|---|---|---|---|---|
| HBV-CSU-045 | 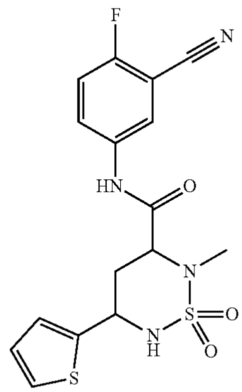 [SMILES: CN1C(C(=O)Nc2ccc(F)c(C#N)c2)CC(c2cccs2)NS1(=O)=O] | 32% | 394.95 (M + 1) | 394.06 for $C_{16}H_{15}FN_4O_3S_2$ | $^1$H-NMR (DMSO-$d_6$, 400 MHz): δ 10.72 (s, 1H), 8.16 (dd, J = 5.9, 2.7 Hz, 1H), 7.92-7.85 (m, 1H), 7.68-7.66 (m, 1H), 7.57-7.48 (m, 2H), 7.15-7.13 (m, 1H), 7.02-7.00 (m, 1H), 4.79 (t, J = 10.1 Hz, 1H), 4.32 (dd, J = 11.8, 2.8 Hz, 1H), 2.60 (s, 3H), 2.27-2.03 (m, 2H). |
| HBV-CSU-045-ISO-I | 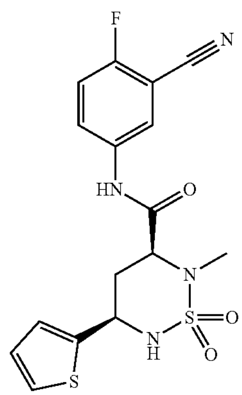 [SMILES: CN1[C@H](C(=O)Nc2ccc(F)c(C#N)c2)C[C@H](c2cccs2)NS1(=O)=O] | 5.2% | 394.95 (M + 1) | 394.06 for $C_{16}H_{15}FN_4O_3S_2$ | $^1$H-NMR (DMSO-$d_6$, 400 MHz): δ 10.74 (s, 1H), 8.17 (dd, J = 5.7, 2.7 Hz, 1H), 7.94-7.92 (m, 1H), 7.69-7.67 (m, 1H), 7.224-7.49 (m, 2H), 7.15 (d, J = 3.4 Hz, 1H), 7.07-6.99 (m, 1H), 4.80 (t, J = 9.2 Hz, 1H), 4.34 (dd, J = 11.8, 2.9 Hz, 1H), 2.62 (s, 3H), 2.28-2.05 (m, 2H). |
| HBV-CSU-046-ISO-I | 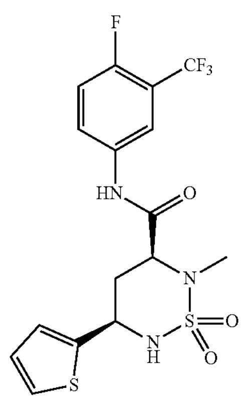 [SMILES: CN1[C@H](C(=O)Nc2ccc(F)c(C(F)(F)F)c2)C[C@H](c2cccs2)NS1(=O)=O] | 17% | 437.95 (M + 1) | 437.05 for $C_{16}H_{15}F_4N_3O_3S_2$ | $^1$H-NMR (DMSO-$d_6$, 400 MHz): δ 10.72 (s, 1H), 8.16 (dd, J = 6.7, 2.6 Hz, 1H), 7.98-7.89 (m, 1H), 7.67 (s, 1H), 7.56-7.46 (m, 2H), 7.16-7.15 (m, 1H), 7.03 (dd, J = 5.1, 3.5 Hz, 1H), 4.81-4.78 (m, 1H), 4.34 (dd, J = 11.7, 3.0 Hz, 1H), 2.62 (s, 3H), 2.29-2.07 (m, 2H). |
| HBV-CSU-047-ISO-I | 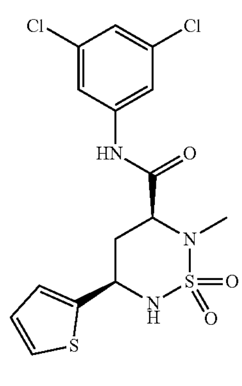 [SMILES: CN1[C@H](C(=O)Nc2cc(Cl)cc(Cl)c2)C[C@H](c2cccs2)NS1(=O)=O] | 32% | 420.01 (M + 1) | 418.99 for $C_{15}H_{15}Cl_2N_3O_3S_2$ | $^1$H-NMR (DMSO-$d_6$, 400 MHz): δ 10.69 (s, 1H), 7.74 (d, J = 1.8 Hz, 2H), 7.68 (s, 1H), 7.52 (dd, J = 5.1, 1.2 Hz, 1H), 7.34 (t, J = 1.8 Hz, 1H), 7.15-7.13 (m, 1H), 7.03 (dd, J = 5.1, 3.6 Hz, 1H), 4.80 (d, J = 11.8 Hz, 1H), 4.33 (dd, J = 11.8, 2.9 Hz, 1H), 2.61 (s, 3H), 2.29-2.04 (m, 2H). |

TABLE 2-continued

Analytical data for HBV-CSU racemic & pure enantiomers:

| Target No | Structure | Rx. Yield (%) | Mass Spec. Found (m/z) | Mass Spec. Calculated | $^1$H-NMR |
|---|---|---|---|---|---|
| HBV-CSU-048-ISO-I | 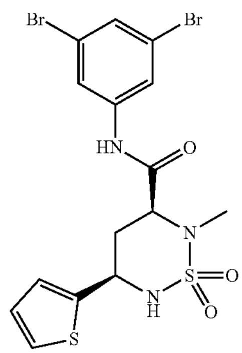 [SMILES: CN1[C@H](C(=O)Nc2cc(Br)cc(Br)c2)C[C@H](c2cccs2)NS1(=O)=O] | 24% | 509.85 (M + 1) | 506.89 for $C_{15}H_{15}Br_2N_3O_3S_2$ | $^1$H-NMR (DMSO-$d_6$, 400 MHz): δ 10.64 (s, 1H), 7.92 (s, J = 1.7 Hz, 2H), 7.67 (d, J = 8.8 Hz, 1H), 7.59-7.49 (m, 2H), 7.16-7.14 (m, 1H), 7.03 (dd, J = 5.1, 3.5 Hz, 1H), 4.80 (t, J = 9.6 Hz, 1H), 4.32 (dd, J = 11.8, 2.9 Hz, 1H), 2.61 (s, 3H), 2.28-2.05 (m, 2H). |
| HBV-CSU-049-ISO-I | 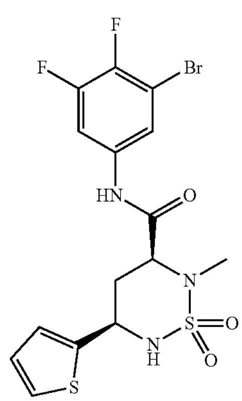 [SMILES: CN1[C@H](C(=O)Nc2cc(F)c(F)c(Br)c2)C[C@H](c2cccs2)NS1(=O)=O] | 24% | 467.95 (M + 2) | 464.96 for $C_{15}H_{14}BrF_2N_3O_3S_2$ | $^1$H-NMR (DMSO-$d_6$, 400 MHz): δ 10.64 (s, 1H), 7.84-7.73 (m, 2H), 7.66 (d, J = 9.6 Hz, 1H), 7.52 (d, J = 5.2 Hz, 1H), 7.15 (d, J = 3.2 Hz, 1H), 7.05-7.02 (m, 1H), 4.82-4.76 (m, 1H), 4.32 (dd, J = 11.6, 2.8 Hz, 1H), 2.61 (s, 3H), 2.25-2.07 (m, 2H). |
| HBV-CSU-050-ISO-I | 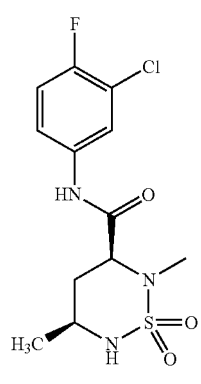 [SMILES: C[C@H]1C[C@@H](C(=O)Nc2ccc(F)c(Cl)c2)N(C)S(=O)(=O)N1] | 9% | 336.00 (M + 1) | 335.05 for $C_{12}H_{15}ClFN_3O_3S$ | $^1$H-NMR (DMSO-$d_6$, 400 MHz): δ 10.50 (s, 1H), 7.94 (dd, J = 6.8, 2.4 Hz, 1H), 7.54-7.50 (m, 1H), 7.39 (t, J = 9.2 Hz, 1H), 7.04 (d, J = 9.2 Hz, 1H), 4.05 (dd, J = 12.0, 2.8 Hz, 1H), 3.49-3.48 (m, 1H), 2.54 (s, 3H), 1.81-1.61 (m, 2H), 1.14 (d, J = 6.8 Hz, 3H). |
| HBV-CSU-050-ISO-II | 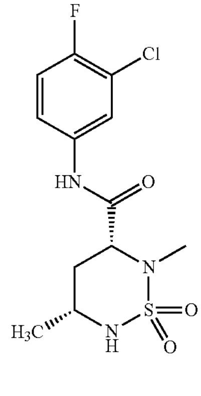 [SMILES: C[C@@H]1C[C@H](C(=O)Nc2ccc(F)c(Cl)c2)N(C)S(=O)(=O)N1] | 10% | 335.95 (M + 1) | 335.05 for $C_{12}H_{15}ClFN_3O_3S$ | $^1$H-NMR (DMSO-$d_6$, 400 MHz): δ 10.50 (s, 1H), 7.95 (dd, J = 6.8, 2.4 Hz, 1H), 7.54-7.51 (m, 1H), 7.39 (t, J = 9.2 Hz, 1H), 7.04 (d, J = 9.2 Hz, 1H), 4.09-4.05 (m, 1H), 3.49-3.48 (m, 1H), 2.54 (s, 3H), 1.81-1.61 (m, 2H), 1.14 (d, J = 6.8 Hz, 3H). |

TABLE 2-continued

Analytical data for HBV-CSU racemic & pure enantiomers:

| Target No | Structure | Rx. Yield (%) | Mass Spec. Found (m/z) | Mass Spec. Calculated | ¹H-NMR |
|---|---|---|---|---|---|
| HBV-CSU-054 | 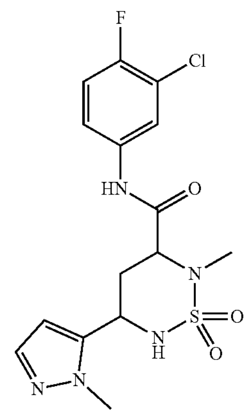 [SMILES: CN1C(C(=O)Nc2ccc(F)c(Cl)c2)CC(c2ccnn2C)NS1(=O)=O] | 77% | 402.20 (M + 1) | 401.07 $C_{15}H_{17}ClFN_5O_3S$ | ¹H-NMR (DMSO-d$_6$, 400 MHz): δ 10.58 (s, 1H), 7.98 (dd, J = 6.8, 2.6 Hz, 1H), 7.60-7.51 (m, 2H), 7.40 (t, J = 9.1 Hz, 1H), 7.37 (d, J = 1.9 Hz, 1H), 6.36 (d, J = 1.8 Hz, 1H), 4.79-4.67 (m, 1H), 4.34-4.28 (m, 1H), 3.82 (s, 3H), 2.61 (s, 3H), 2.29-2.15 (m, 1H), 2.11-2.04 (m, 1H). |
| HBV-CSU-054-ISO-I | 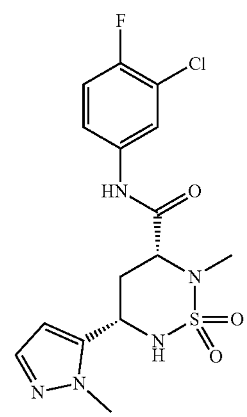 [SMILES: CN1[C@@H](C(=O)Nc2ccc(F)c(Cl)c2)C[C@@H](c2ccnn2C)NS1(=O)=O] | 15% | 402.20 (M + 1) | 401.07 $C_{15}H_{17}ClFN_5O_3S$ | ¹H-NMR (DMSO-d$_6$, 400 MHz): δ 10.59 (br.s, 1H), 7.98 (dd, J = 6.8, 2.6 Hz, 1H), 7.59-7.54 (m, 2H), 7.41 (t, J = 9.1 Hz, 1H), 7.36 (d, J = 1.5 Hz, 1H), 6.34 (br.s, 1H), 4.78-4.69 (m, 1H), 4.34-4.24 (m, 1H), 3.82 (s, 3H), 2.60 (s, 3H), 2.26-2.15 (m, 1H), 2.10-2.03 (m, 1H). |
| HBV-CSU-054-ISO-II | 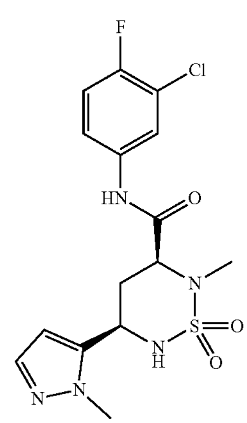 [SMILES: CN1[C@H](C(=O)Nc2ccc(F)c(Cl)c2)C[C@H](c2ccnn2C)NS1(=O)=O] | 15% | 402.10 (M + 1) | 401.07 $C_{15}H_{17}ClFN_5O_3S$ | ¹H-NMR (DMSO-d$_6$, 400 MHz): δ 10.60 (br.s, 1H), 7.98 (dd, J = 6.8, 2.6 Hz, 1H), 7.59-7.54 (m, 2H), 7.41 (t, J = 9.1 Hz, 1H), 7.36 (d, J = 1.8 Hz, 1H), 6.35 (s, 1H), 4.76-4.73 (m, 1H), 4.31-4.26 (m, 1H), 3.82 (s, 3H), 2.60 (s, 3H), 2.29-2.14 (m, 1H), 2.13-2.04 (m, 1H). |

TABLE 2-continued

Analytical data for HBV-CSU racemic & pure enantiomers:

| Target No | Structure | Rx. Yield (%) | Mass Spec. Found (m/z) | Mass Spec. Calculated | ¹H-NMR |
|---|---|---|---|---|---|
| HBV-CSU-055 | 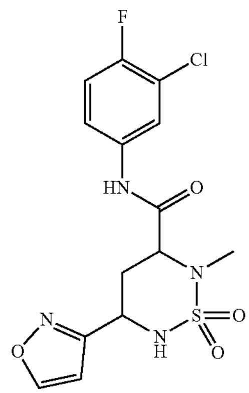 [SMILES: CN1C(C(=O)Nc2ccc(F)c(Cl)c2)CC(c2ccon2)NS1(=O)=O] | 77% | 387.0 (M − 1) | 388.04 $C_{14}H_{14}ClFN_4O_4S$ | ¹H-NMR (DMSO-d$_6$, 400 MHz): δ 10.58 (s, 1H), 8.94 (d, J = 1.6 Hz, 1H), 7.96 (dd, J = 6.8, 2.5 Hz, 1H), 7.76 (d, J = 9.9 Hz, 1H), 7.57-7.53 (m, 1H), 7.40 (t, J = 9.0 Hz, 1H), 6.75 (d, J = 1.6 Hz, 1H), 4.83-4.75 (m, 1H), 4.37-4.325 (m, 1H), 2.63 (s, 3H), 2.20-2.10 (m, 2H). |
| HBV-CSU-055-ISO-I | 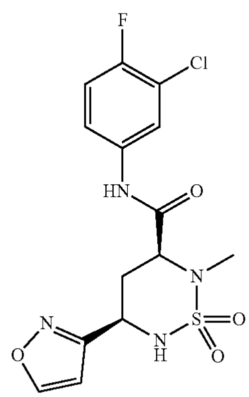 [SMILES: CN1[C@H](C(=O)Nc2ccc(F)c(Cl)c2)C[C@H](c2ccon2)NS1(=O)=O] | 12% | 387.0 (M − 1) | 388.04 $C_{14}H_{14}ClFN_4O_4S$ | ¹H-NMR (DMSO-d$_6$, 400 MHz): δ 10.57 (br.s, 1H), 8.94 (s, 1H), 7.96 (d, J = 4.4 Hz, 1H), 7.72 (br.s, 1H), 7.60-7.51 (m, 1H), 7.40 (t, J = 9.0 Hz, 1H), 6.75 (s, 1H), 4.82-4.76 (m, 1H), 4.38-4.31 (m, 1H), 2.62 (s, 3H), 2.21-2.10 (m, 2H). |
| HBV-CSU-055-ISO-II | 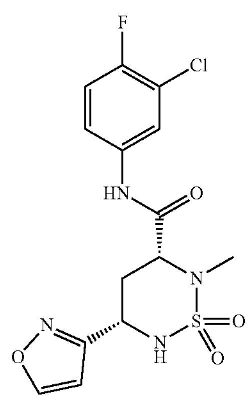 [SMILES: CN1[C@@H](C(=O)Nc2ccc(F)c(Cl)c2)C[C@@H](c2ccon2)NS1(=O)=O] | 10% | 387.0 (M − 1) | 388.04 $C_{14}H_{14}ClFN_4O_4S$ | ¹H-NMR (DMSO-d$_6$, 400 MHz): δ 10.57 (br.s, 1H), 8.94 (s, 1H), 7.96 (d, J = 4.3 Hz, 1H), 7.71 (br.s, 1H), 7.59-7.50 (m, 1H), 7.40 (t, J = 9.1 Hz, 1H), 6.75 (s, 1H), 4.82-4.77 (m, 1H), 4.37-4.32 (m, 1H), 2.63 (s, 3H), 2.21-2.10 (m, 2H). |

TABLE 2-continued

Analytical data for HBV-CSU racemic & pure enantiomers:

| Target No | Structure | Rx. Yield (%) | Mass Spec. Found (m/z) | Mass Spec. Calculated | $^1$H-NMR |
|---|---|---|---|---|---|
| HBV-CSU-056 | 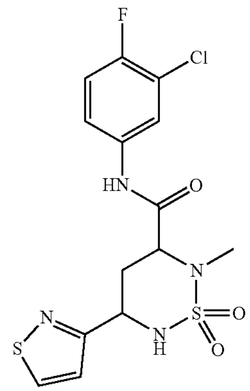 [SMILES: CN1C(C(=O)Nc2ccc(F)c(Cl)c2)CC(c2ccsn2)NS1(=O)=O] | 80% | 403.0 (M − 1) | 404.02 $C_{14}H_{14}ClFN_4O_3S_2$ | $^1$H-NMR (DMSO-$d_6$, 400 MHz): δ 10.57 (s, 1H), 9.09 (d, J = 4.6 Hz, 1H), 7.96 (dd, J = 6.8, 2.5 Hz, 1H), 7.70 (d, J = 10.0 Hz, 1H), 7.57-7.53 (m, 1H), 7.49 (d, J = 4.6 Hz, 1H), 7.40 (t, J = 9.1 Hz, 1H), 4.85-4.76 (m, 1H), 4.34-4.28 (m, 1H), 2.62 (s, 3H), 2.33-2.12 (m, 2H). |
| HBV-CSU-056-ISO-I | 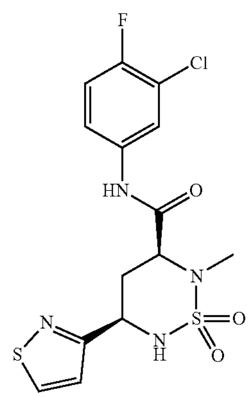 [SMILES: CN1[C@H](C(=O)Nc2ccc(F)c(Cl)c2)C[C@H](c2ccsn2)NS1(=O)=O] | 20% | 405.10 (M + 1) | 404.02 $C_{14}H_{14}ClFN_4O_3S_2$ | $^1$H-NMR (DMSO-$d_6$, 400 MHz): δ 10.55 (s, 1H), 9.09 (d, J = 4.8 Hz, 1H), 7.96 (dd, J = 6.8, 2.6 Hz, 1H), 7.68 (d, J = 9.9 Hz, 1H), 7.58-7.53 (m, 1H), 7.49 (d, J = 4.6 Hz, 1H), 7.40 (t, J = 9.1 Hz, 1H), 4.84-4.76 (m, 1H), 4.34-4.29 (m, 1H), 2.63 (s, 3H), 2.29-2.13 (m, 2H). |
| HBV-CSU-056-ISO-II | 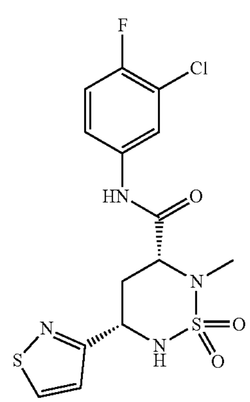 [SMILES: CN1[C@@H](C(=O)Nc2ccc(F)c(Cl)c2)C[C@@H](c2ccsn2)NS1(=O)=O] | 16% | 405.10 (M + 1) | 404.02 $C_{14}H_{14}ClFN_4O_3S_2$ | $^1$H-NMR (DMSO-$d_6$, 400 MHz): δ 10.57 (s, 1H), 9.09 (d, J = 4.6 Hz, 1H), 7.96 (dd, J = 6.8, 2.4 Hz, 1H), 7.69 (d, J = 3.8 Hz, 1H), 7.58-7.53 (m, 1H), 7.49 (s, 1H), 7.40 (t, J = 9.1 Hz, 1H), 4.86-4.75 (m, 1H), 4.34-4.29 (m, 1H), 2.63 (s, 3H), 2.28-2.13 (m, 2H). |

TABLE 2-continued

Analytical data for HBV-CSU racemic & pure enantiomers:

| Target No | Structure | Rx. Yield (%) | Mass Spec. Found (m/z) | Mass Spec. Calculated | $^1$H-NMR |
|---|---|---|---|---|---|
| HBV-CSU-057 | 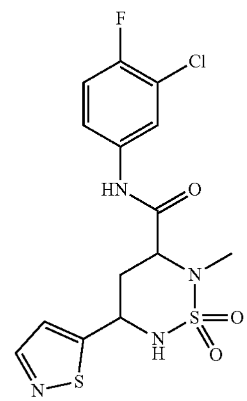 [SMILES: CN1C(C(=O)Nc2ccc(F)c(Cl)c2)CC(c2ccns2)NS1(=O)=O] | 79% | 405.10 (M + 1) | 404.02 $C_{14}H_{14}ClFN_4O_3S_2$ | $^1$H-NMR (DMSO-$d_6$, 400 MHz): δ 10.65 (br.s, 1H), 8.52 (d, J = 1.6 Hz, 1H), 7.98 (dd, J = 6.8, 2.6 Hz, 1H), 7.91 (br.s, 1H), 7.59-7.54 (m, 1H), 7.47 (s, 1H), 7.41 (t, J = 9.1 Hz, 1H), 5.05-5.00 (m, 1H), 4.36-4.33 (m, 1H), 2.62 (s, 3H), 2.32-2.29 (m, 1H), 2.18-2.07 (m, 1H). |
| HBV-CSU-058 | 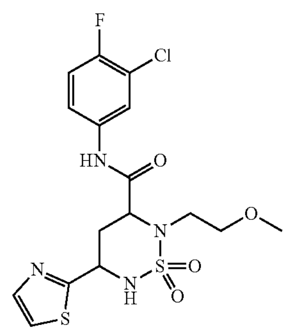 | 53% | 449.05 (M + 1) | 448.04 $C_{16}H_{18}ClFN_4O_4S_2$ | $^1$H-NMR (DMSO-$d_6$, 400 MHz): δ 10.49 (s, 1H), 7.99-7.70 (m, 4H), 7.56-7.52 (m, 1H), 7.39 (t, J = 9.2 Hz, 1H), 4.97-4.90 (m, 1H), 4.63-4.60 (m, 1H), 3.52-3.33 (m, 3H), 3.11 (s, 3H), 3.09-3.03 (m, 1H), 2.46-2.30 (m, 1H), 2.08-1.98 (m, 1H). |
| HBV-CSU-058-ISO-I | 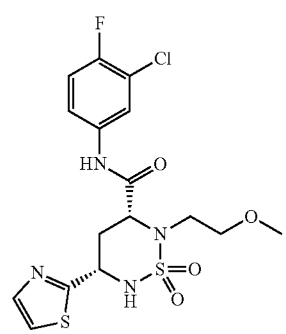 | 4% | 449.10 (M + 1) | 448.04 $C_{16}H_{18}ClFN_4O_4S_2$ | $^1$H-NMR (DMSO-$d_6$, 400 MHz): δ 10.50 (s, 1H), 7.96-7.94 (m, 1H), 7.86-7.79 (m, 3H), 7.58-7.55 (m, 1H), 7.41 (t, J = 8.8 Hz, 1H), 4.97-4.93 (m, 1H), 4.65-4.61 (m, 1H), 3.52-3.43 (m, 3H), 3.27 (s, 3H), 3.14-3.07 (m, 1H), 2.39-2.32 (m, 1H), 2.06-2.01 (m, 1H) |
| HBV-CSU-058-ISO-II | 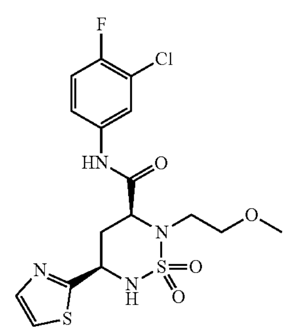 | 4% | 449.10 (M + 1) | 448.04 $C_{16}H_{18}ClFN_4O_4S_2$ | $^1$H NMR (400 MHz, DMSO-d6) δ 10.50 (s, 1H), 7.96-7.94 (m, 1H), 7.86-7.79 (m, 3H), 7.58-7.55 (m, 1H), 7.41 (t, J = 9.2 Hz, 1H), 4.97-4.94 (m, 1H), 4.65-4.62 (m, 1H), 3.50-3.42 (m, 3H), 3.14 (s, 3H), 3.11-3.04 (m, 1H), 2.45-2.35 (m, 1H), 2.08-2.03 (m, 1H). |

TABLE 2-continued

Analytical data for HBV-CSU racemic & pure enantiomers:

| Target No | Structure | Rx. Yield (%) | Mass Spec. Found (m/z) | Mass Spec. Calculated | ¹H-NMR |
|---|---|---|---|---|---|
| HBV-CSU-059 | 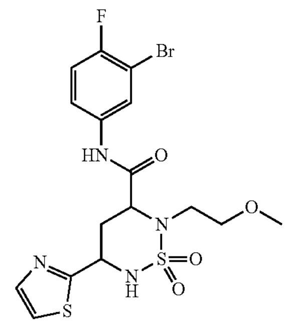 [SMILES: COCCN1C(C(=O)Nc2ccc(F)c(Br)c2)CC(c2nccs2)NS1(=O)=O] | 30% | 495 (M + 2) | 491.99 for $C_{16}H_{18}BrFN_4O_4S_2$ | ¹H-NMR (DMSO-$d_6$, 400 MHz): δ 10.48 (s, 1H), 8.10-8.03 (m, 1H), 7.89-7.76 (m, 3H), 7.61-7.58 (m, 1H), 7.40-7.35 (m, 1H), 4.96-4.95 (m, 1H), 4.63 (d, J = 11.8 Hz, 1H), 3.49-3.47 (m, 3H), 3.14 (s, 3H), 3.09-3.05 (m, 1H), 2.38-2.32 (m, 1H), 2.06-2.02 (m, 1H). |
| HBV-CSU-059-ISO-I | 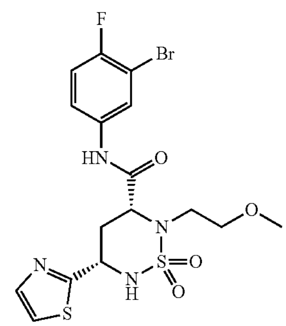 | 16% | 495.05 (M + 2) | 491.99 for $C_{16}H_{18}BrFN_4O_4S_2$ | ¹H-NMR (DMSO-$d_6$, 400 MHz): 10.48 (s, 1H), 8.08-8.05 (m, 1H), 7.85-7.74 (m, 3H), 7.62-7.58 (m, 1H), 7.37 (t, J = 8.8 Hz, 1H), 4.96-4.94 (m, 1H), 4.65-4.61 (m, 1H), 3.52-3.35 (m, 3H), 3.14 (s, 3H), 3.11-3.03 (m, 1H), 2.39-2.32 (m, 1H), 2.09-2.00 (m, 1H). |
| HBV-CSU-059-ISO-II | 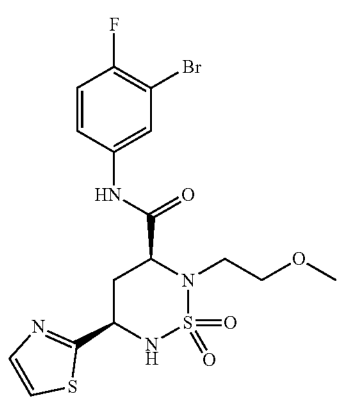 [SMILES: COCCN1[C@H](C(=O)Nc2ccc(F)c(Br)c2)C[C@H](c2nccs2)NS1(=O)=O] | 13% | 495.10 (M + 2) | 491.99 for $C_{16}H_{18}BrFN_4O_4S_2$ | ¹H-NMR (DMSO-$d_6$, 400 MHz): 10.49 (s, 1H), 8.08-8.06 (m, 1H), 7.82-7.78 (m, 3H), 7.62-7.58 (m, 1H), 7.37 (t, J = 8.8 Hz, 1H), 4.97-4.95 (m, 1H), 4.65-4.61 (m, 1H), 3.50-3.35 (m, 3H), 3.14 (s, 3H), 3.11-3.07 (m, 1H), 2.40-2.33 (m, 1H), 2.09-2.03 (m, 1H). |
| HBV-CSU-060-ISO-I | 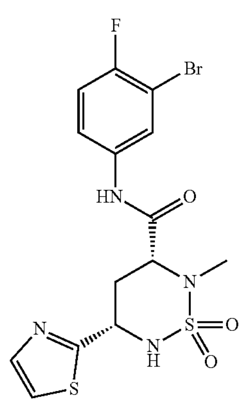 [SMILES: CN1[C@@H](C(=O)Nc2ccc(F)c(Br)c2)C[C@@H](c2nccs2)NS1(=O)=O] | 5% | 448.96 (M + 1) | 447.97 for $C_{14}H_{14}BrFN_4O_3S_2$ | ¹H-NMR (DMSO-$d_6$, 400 MHz): δ 10.54 (s, 1H), 8.06 (dd, J = 6.4, 2.5 Hz, 1H), 7.88 (d, J = 10.0 Hz, 1H), 7.81-7.73 (m, 2H), 7.59-7.55 (m, 1H), 7.34 (t, J = 8.8 Hz, 1H), 4.94-4.87 (m, 1H), 4.33 (dd, J = 12.0, 2.7 Hz, 1H), 2.60 (s, 3H), 2.45-2.32 (m, 1H), 2.18-2.11 (m, 1H). |

TABLE 2-continued

Analytical data for HBV-CSU racemic & pure enantiomers:

| Target No | Structure | Rx. Yield (%) | Mass Spec. Found (m/z) | Mass Spec. Calculated | $^1$H-NMR |
|---|---|---|---|---|---|
| HBV-CSU-060-ISO-II | 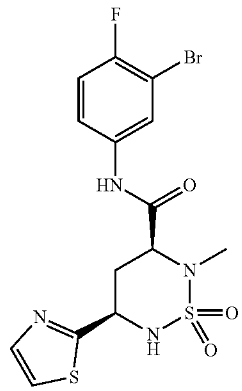 [SMILES: CN1[C@H](C(=O)Nc2ccc(F)c(Br)c2)C[C@H](c2nccs2)NS1(=O)=O] | 20% | 448.90 (M + 1) | 447.97 for $C_{14}H_{14}BrFN_4O_3S_2$ | $^1$H NMR (DMSO-$d_6$, 400 MHz): δ 10.57 (s, 1H), 8.09 (dd, J = 6.5, 2.5 Hz, 1H), 7.91 (d, J = 10.0 Hz, 1H), 7.84-7.76 (m, 2H), 7.61-7.59 (m, 1H), 7.37 (t, J = 8.8 Hz, 1H), 4.96-4.93 (m, 1H), 4.36 (dd, J = 12.1, 2.7 Hz, 1H), 2.63 (s, 3H), 2.44-2.35 (m, 1H), 2.20-2.17 (m, 1H), |
| HBV-CSU-064 | 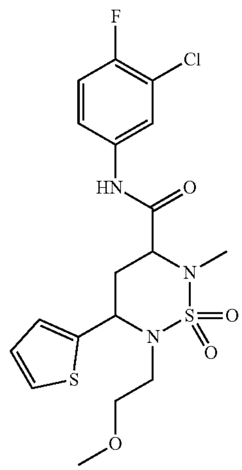 [SMILES: COCCN1C(c2cccs2)CC(C(=O)Nc2ccc(F)c(Cl)c2)N(C)S1(=O)=O] | 53% | 462.00 (M + 1) | 461.06 for $C_{18}H_{21}ClFN_3O_4S_2$ | $^1$H-NMR (DMSO-$d_6$, 400 MHz): δ 10.53 (s, 1H), 7.95 (dd, J = 6.8, 2.4 Hz, 1H), 7.66-7.64 (m, 1H), 7.58-7.55 (m, 1H), 741 (t, J = 9.2 Hz, 1H), 7.30-7.29 (m, 1H), 7.08-7.06 (m, 1H), 5.18-5.14 (m, 1H), 4.23 (dd, J = 12.0, 2.8 Hz, 1H), 3.27-2.95 (m, 7H), 2.68 (s, 3H), 2.47-2.33 (m, 1H), 2.22-2.17 (m, 1H); |
| HBV-CSU-071 | 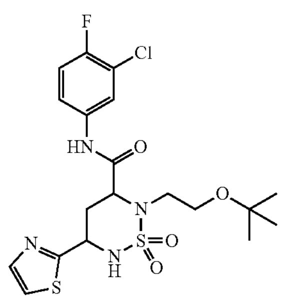 | 65% | 491.20 (M + 1) | 490.09 for $C_{19}H_{24}ClFN_4O_4S_2$ | 1H-NMR (DMSO-$d_6$, 400 MHz): δ 10.57 (s, 1H), 7.96 (dd, J = 6.9, 2.5 Hz, 1H), 7.86-7.78 (m, 3H), 7.60-7.53 (m, 1H), 7.41 (t, J = 9.1 Hz, 1H), 5.00-4.92 (m, 1H), 4.66-4.63 (m, 1H), 3.49-3.30 (m, 3H), 3.01-2.93 (m, 1H), 3.02-2.92 (m, 1H), 2.13-1.96 (m, 1H), 0.98 (s, 9H). |
| HBV-CSU-071-ISO-I | 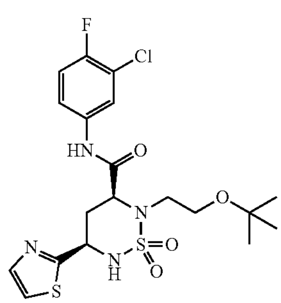 [SMILES: CC(C)(C)OCCN1[C@H](C(=O)Nc2ccc(F)c(Cl)c2)C[C@H](c2nccs2)NS1(=O)=O] | 21% | 491.30 (M + 1) | 490.09 for $C_{19}H_{24}ClFN_4O_4S_2$ | $^1$H-NMR (DMSO-$d_6$, 400 MHz): δ 10.54 (s, 1H), 7.96 (dd, J = 6.9, 2.5 Hz, 1H), 7.80 (dd, J = 11.2, 3.2 Hz, 3H), 7.60-7.54 (m, 1H), 7.41 (t, J = 9.1 Hz, 1H), 5.00-4.90 (m, 1H), 4.66-4.60 (m, 1H), 3.49-3.39 (m, 2H), 3.38-3.32 (m, 1H), 3.03-2.96 (m, 1H), 2.40-2.33 (m, 1H), 2.11-1.98 (m, 1H), 0.99 (s, 9H). |

TABLE 2-continued

Analytical data for HBV-CSU racemic & pure enantiomers:

| Target No | Structure | Rx. Yield (%) | Mass Spec. Found (m/z) | Mass Spec. Calculated | $^1$H-NMR |
|---|---|---|---|---|---|
| HBV-CSU-071-ISO-II | 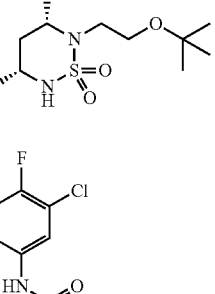 | 19% | 491.20 (M + 1) | 490.09 for $C_{19}H_{24}ClFN_4O_4S_2$ | $^1$H-NMR (DMSO-$d_6$, 400 MHz): δ 10.54 (s, 1H), 7.96 (dd, J = 6.9, 2.5 Hz, 1H), 7.80 (dd, J = 11.6, 3.5 Hz, 3H), 7.60-7.54 (m, 1H), 7.40 (t, J = 9.1 Hz, 1H), 4.98-4.93 (m, 1H), 4.66-4.60 (m, 1H), 3.50-3.39 (m, 2H), 3.38-3.32 (m, 1H), 3.03-2.96 (m, 1H), 2.40-2.34 (m, 1H), 2.14-1.94 (m, 1H), 0.99 (s, 9H). |
| HBV-CSU-072 | 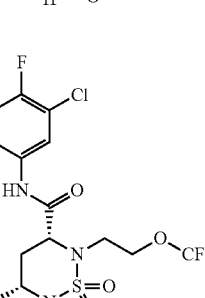 | 67% | 503.05 (M + 1) | 502.02 for $C_{16}H_{15}ClF_4N_4O_4S_2$ | $^1$H-NMR (DMSO-$d_6$, 400 MHz): δ 10.55 (s, 1H), 7.96-7.92 (m, 2H), 7.84-7.8 (m, 2H), 7.6-7.53 (m, 1H), 7.39 (t, J = 9.2 Hz, 1H), 5.1-4.92 (m, 1H), 4.72-4.68 (m, 1H), 4.18-4.14 (m, 2H), 3.61-3.56 (m, 1H), 3.29-3.16 (m, 1H), 2.37-2.31 (m, 1H), 2.1-1.99 (m, 1H). |
| HBV-CSU-072-ISO-I | 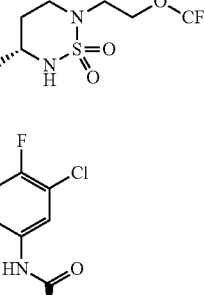 | 13% | 503.05 (M + 1) | 502.02 for $C_{16}H_{15}ClF_4N_4O_4S_2$ | $^1$H-NMR (DMSO-$d_6$, 400 MHz): δ 10.66 (s, 1H), 7.96-7.93 (m, 2H), 7.78-7.68 (m, 2H), 7.59-7.55 (m, 1H), 7.39 (t, J = 8.8 Hz, 1H), 4.86-4.85 (m, 1H), 4.60-4.45 (m, 1H), 4.19-4.18 (m, 2H), 3.24-3.22 (m, 2H), 2.33-2.24 (m, 1H), 1.91-1.90 (m, 1H). |
| HBV-CSU-072-ISO-II | 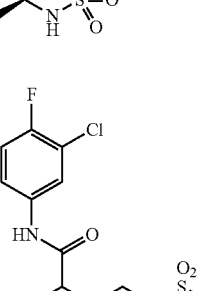 | 16% | 503.05 (M + 1) | 502.02 for $C_{16}H_{15}ClF_4N_4O_4S_2$ | $^1$H-NMR (DMSO-$d_6$, 400 MHz): δ 10.66 (s, 1H), 7.94 (dd, J = 7.2, 2.8 Hz, 1H), 7.78-7.55 (m, 4H), 7.39 (t, J = 8.8 Hz, 1H), 4.88-4.85 (m, 1H), 4.60-4.45 (m, 1H), 4.19-4.18 (m, 2H), 3.24-3.22 (m, 2H), 2.33-2.24 (m, 1H), 1.91-1.90 (m, 1H). |
| HBV-CSU-073 | 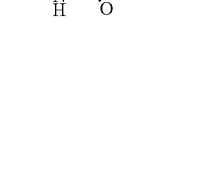 | 74% | 497.20 (M + 1) | 496.01 for $C_{16}H_{18}ClFN_4O_5S_3$ | $^1$H-NMR (DMSO-$d_6$, 400 MHz): δ 10.58 (s, 1H), 8.09 (d, J = 9.7 Hz, 1H), 7.92 (dd, J = 6.8, 2.6 Hz, 1H), 7.83 (d, J = 3.2 Hz, 1H), 7.80 (d, J = 3.4 Hz, 1H), 7.57-7.51 (m, 1H), 7.41 (t, J = 9.1 Hz, 1H), 5.03-4.95 (m, 1H), 4.64-4.58 (m, 1H), 3.72-3.61 (m, 1H), 3.48-3.34 (m, 3H), 3.00 (s, 3H), 2.48-2.43 (m, 1H), 2.20-2.07 (m, 1H). |

TABLE 2-continued

Analytical data for HBV-CSU racemic & pure enantiomers:

| Target No | Structure | Rx. Yield (%) | Mass Spec. Found (m/z) | Mass Spec. Calculated | ¹H-NMR |
|---|---|---|---|---|---|
| HBV-CSU-074 | 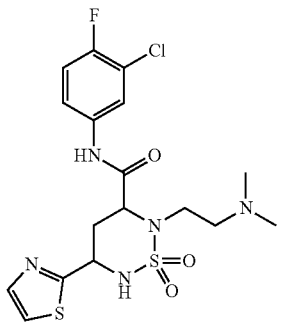 | 43% | 462.35 (M + 1) | 461.08 for $C_{17}H_{21}ClFN_5O_3S_2$ | ¹H-NMR (DMSO-$d_6$, 400 MHz): δ 10.79 (s, 1H), 7.97-7.94 (m, 1H), 7.83-7.81 (m, 1H), 7.79-7.70 (m, 2H), 7.53-7.49 (m, 1H), 7.41 (t, , J = 8.8 Hz, 1H), 4.99-4.92 (m, 1H), 4.63 (dd, J = 11.6, 3.2 Hz, 1H), 3.18-3.12 (m, 2H), 2.44-2.31 (m, 2H), 2.19-2.09 (m, 7H), 1.99-1.97 (m, 1H). |
| HBV-CSU-077-ISO-I | 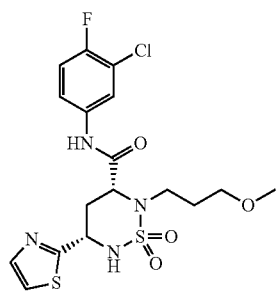 [SMILES: COCCCN1[C@@H](C(=O)Nc2ccc(F)c(Cl)c2)C[C@@H](c2nccs2)NS1(=O)=O] | 8% | 463.05 (M + 1) | 462.06 for $C_{17}H_{20}ClFN_4O_4S_2$ | ¹H-NMR (DMSO-$d_6$, 400 MHz): δ 10.65 (s, 1H), 7.95-7.94 (m, 1H), 7.87-7.76 (m, 3H), 7.57-7.55 (m, 1H), 7.41 (t, J = 9.0 Hz, 1H), 4.94-4.90 (m, 1H), 4.58-4.55 (m, 1H), 3.27-3.24 (m, 3H), 3.06 (s, 3H), 2.98-2.95 (m, 1H), 2.38-2.32 (m, 1H), 2.09-2.06 (m, 1H), 1.78-1.76 (m, 2H). |
| HBV-CSU-077-ISO-II | 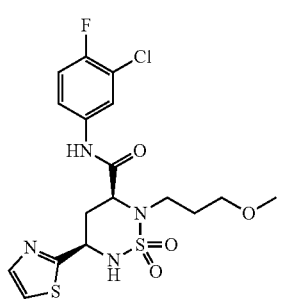 [SMILES: COCCCN1[C@H](C(=O)Nc2ccc(F)c(Cl)c2)C[C@H](c2nccs2)NS1(=O)=O] | 9% | 463.05 (M + 1) | 462.06 for $C_{17}H_{20}ClFN_4O_4S_2$ | ¹H-NMR (DMSO-$d_6$, 400 MHz): δ 10.65 (s, 1H), 7.96-7.94 (m, 1H), 7.85-7.76 (m, 3H), 7.57-7.55 (m, 1H), 7.41 (t, J = 8.8 Hz, 1H), 4.94-4.90 (m, 1H), 4.58-4.55 (m, 1H), 3.27-3.24 (m, 3H), 3.06 (s, 3H), 2.98-2.93 (m, 1H), 2.36-2.32 (m, 1H), 2.09-2.06 (m, 1H), 1.78-1.76 (m, 2H). |
| HBV-CSU-078 | 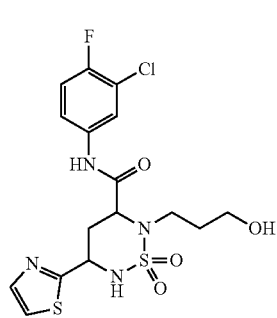 | 88% | 449.05 (M + 1) | 448.04 for $C_{16}H_{18}ClFN_4O_4S_2$ | ¹H-NMR (DMSO-$d_6$, 400 MHz): δ 10.62 (s, 1H), 7.98-7.73 (m, 4H), 7.58-7.55 (m, 1H), 7.40 (t, J = 9.1 Hz, 1H), 4.96-4.90 (m, 1H), 4.54 (dd, J = 12.1, 2.7 Hz, 1H), 4.39 (t, J = 5.0 Hz, 1H), 3.41-3.20 (m, 3H), 3.04-2.92 (m, 1H), 2.37-2.34 (m, 1H), 2.14-2.07 (m, 1H), 1.74-1.70 (m, 2H). |

TABLE 2-continued

Analytical data for HBV-CSU racemic & pure enantiomers:

| Target No | Structure | Rx. Yield (%) | Mass Spec. Found (m/z) | Mass Spec. Calculated | ¹H-NMR |
|---|---|---|---|---|---|
| HBV-CSU-078-ISO-I | 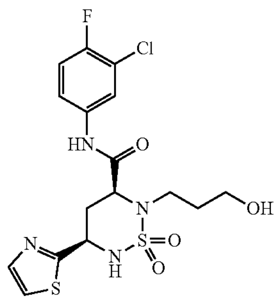 [SMILES: O=C(Nc1ccc(F)c(Cl)c1)[C@@H]1C[C@H](c2nccs2)NS(=O)(=O)N1CCCO] | 5% | 449.05 (M + 1) | 448.04 for $C_{16}H_{18}ClFN_4O_4S_2$ | ¹H-NMR (DMSO-d$_6$, 400 MHz): δ 10.62 (s, 1H), 7.95-7.72 (m, 4H), 7.56-7.54 (m, 1H), 7.40 (t, J = 8.8 Hz, 1H), 4.95-4.91 (m, 1H), 4.55-4.51 (m, 1H), 4.40-4.39 (m, 1H), 3.47-3.24 (m, 3H), 3.05-2.91 (m, 1H), 2.37-2.34 (m, 1H), 2.11-2.07 (m, 1H), 1.73-1.70 (m, 2H). |
| HBV-CSU-078-ISO-II | 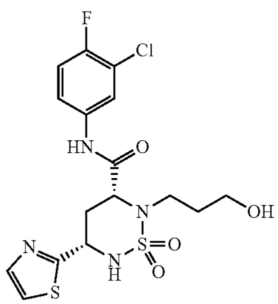 [SMILES: O=C(Nc1ccc(F)c(Cl)c1)[C@H]1C[C@@H](c2nccs2)NS(=O)(=O)N1CCCO] | 6% | 449.05 (M + 1) | 448.04 for $C_{16}H_{18}ClFN_4O_4S_2$ | ¹H-NMR (DMSO-d$_6$, 400 MHz): δ 10.62 (s, 1H), 7.95-7.72 (m, 4H), 7.56-7.54 (m, 1H), 7.40 (t, J = 8.8 Hz, 1H), 4.95-4.91 (m, 1H), 4.55-4.51 (m, 1H), 4.40-4.39 (m, 1H), 3.47-3.24 (m, 3H), 3.05-2.91 (m, 1H), 2.37-2.34 (m, 1H), 2.11-2.07 (m, 1H), 1.73-1.70 (m, 2H). |
| HBV-CSU-079 (Rac-A) | 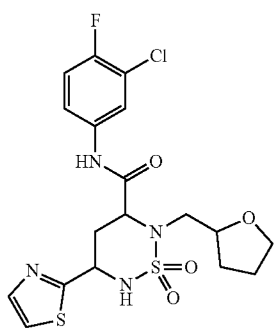 [SMILES: O=C(Nc1ccc(F)c(Cl)c1)C1CC(c2nccs2)NS(=O)(=O)N1CC1CCCO1] | 16% | 475.20 (M + 1) | 474.06 for $C_{18}H_{20}ClFN_4O_4S_2$ | ¹H-NMR (DMSO-d$_6$, 400 MHz): δ 10.46 (s, 1H), 7.94 (dd, J = 6.8, 2.6 Hz, 1H), 7.82-7.78 (m, 3H), 7.58-7.52 (m, 1H), 7.40 (t, J = 9.3 Hz, 1H), 5.00-4.92 (m, 1H), 4.75-4.65 (m, 1H), 4.12-4.01 (m, 1H), 3.53-3.40 (m, 2H), 3.37-3.29 (m, 1H), 3.00-2.92 (m, 1H), 2.39-2.33 (m, 1H), 2.12-1.99 (m, 1H), 1.93-1.83 (m, 1H), 1.82-1.63 (m, 2H), 1.55-1.43 (m, 1H). |
| HBV-CSU-079 (Rac-B) | 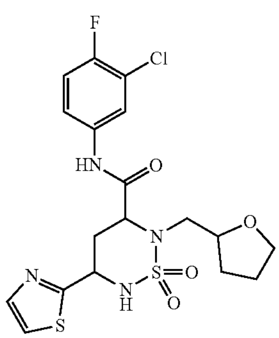 [SMILES: O=C(Nc1ccc(F)c(Cl)c1)C1CC(c2nccs2)NS(=O)(=O)N1CC1CCCO1] | 16% | 475.20 (M + 1) | 474.06 for $C_{18}H_{20}ClFN_4O_4S_2$ | ¹H-NMR (DMSO-d$_6$, 400 MHz): δ 10.46 (s, 1H), 7.94 (dd, J = 6.8, 2.6 Hz, 1H), 7.82-7.78 (m, 3H), 7.58-7.52 (m, 1H), 7.40 (t, J = 9.3 Hz, 1H), 5.00-4.92 (m, 1H), 4.75-4.65 (m, 1H), 4.12-4.01 (m, 1H), 3.53-3.40 (m, 2H), 3.37-3.29 (m, 1H), 3.00-2.92 (m, 1H), 2.39-2.33 (m, 1H), 2.12-1.99 (m, 1H), 1.93-1.83 (m, 1H), 1.82-1.63 (m, 2H), 1.55-1.43 (m, 1H). |

TABLE 2-continued

Analytical data for HBV-CSU racemic & pure enantiomers:

| Target No | Structure | Rx. Yield (%) | Mass Spec. Found (m/z) | Mass Spec. Calculated | ¹H-NMR |
|---|---|---|---|---|---|
| HBV-CSU-082 | 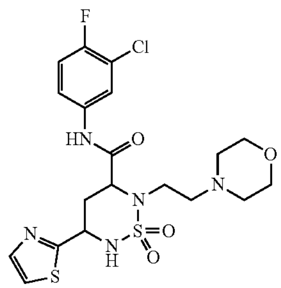 [SMILES: O=C(Nc1ccc(F)c(Cl)c1)C1CC(c2nccs2)NS(=O)(=O)N1CCN1CCOCC1] | 63% | 504.20 (M + 1) | 503.09 for $C_{19}H_{23}ClFN_5O_4S_2$ | ¹H-NMR (DMSO-$d_6$, 400 MHz): δ 8.84 (br.s, 1H), 7.75 (d, J = 3.3 Hz, 2H), 7.39 (d, J = 3.3 Hz, 1H), 7.37-7.33 (m, 1H), 7.14 (t, J = 8.7 Hz, 1H), 6.49 (br.s, 1H), 5.10-5.03 (m, 1H), 4.76-4.70 (m, 1H), 3.63-3.49 (m, 5H), 3.28-3.24 (m, 1H), 2.95-2.87 (m, 1H), 2.65-2.51 (m, 3H), 2.50-2.33 (m, 4H). |
| HBV-CSU-083 | 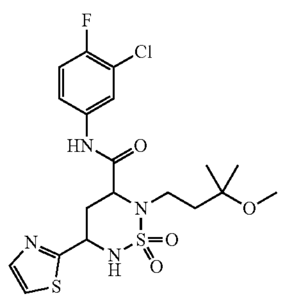 [SMILES: COC(C)(C)CCN1C(C(=O)Nc2ccc(F)c(Cl)c2)CC(c2nccs2)NS1(=O)=O] | 69% | 491.30 (M + 1) | 490.09 for $C_{19}H_{24}ClFN_4O_4S_2$ | ¹H-NMR (DMSO-$d_6$, 400 MHz): δ 10.67 (s, 1H), 7.95 (dd, J = 6.8, 2.5 Hz, 1H), 7.86-7.78 (m, 3H), 7.61-7.55 (m, 1H), 7.41 (t, J = 9.1 Hz, 1H), 4.97-4.90 (m, 1H), 4.58-4.53 (m, 1H), 3.34-3.24 (m, 1H), 2.92 (s, 3H), 2.90-2.83 (m, 1H), 2.42-2.36 (m, 1H), 2.14-2.03 (m, 1H), 1.87-1.78 (m, 1H), 1.75-1.65 (m, 1H), 0.98 (s, 3H), 0.95 (s, 3H). |
| HBV-CSU-083-ISO-I | 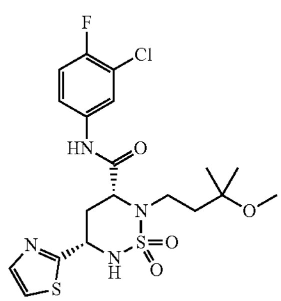 [SMILES: COC(C)(C)CCN1[C@@H](C(=O)Nc2ccc(F)c(Cl)c2)C[C@@H](c2nccs2)NS1(=O)=O] | 19% | 491.30 (M + 1) | 490.09 for $C_{19}H_{24}ClFN_4O_4S_2$ | ¹H-NMR (DMSO-$d_6$, 400 MHz): δ 10.64 (s, 1H), 7.95 (dd, J = 6.8, 2.6 Hz, 1H), 7.83-7.80 (m, 2H), 7.79 (d, J = 3.2 Hz, 1H), 7.61-7.55 (m, 1H), 7.41 (t, J = 9.1 Hz, 1H), 4.96-4.91 (m, 1H), 4.58-4.53 (m, 1H), 3.36-3.24 (m, 1H), 2.92 (s, 3H), 2.91-2.85 (m, 1H), 2.42-2.35 (m, 1H), 2.17-2.02 (m, 1H), 1.88-1.78 (m, 1H), 1.75-1.66 (m, 1H), 0.98 (s, 3H), 0.95 (s, 3H). |
| HBV-CSU-083-ISO-II | 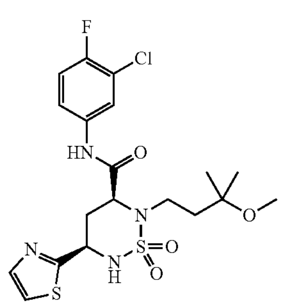 [SMILES: COC(C)(C)CCN1[C@H](C(=O)Nc2ccc(F)c(Cl)c2)C[C@H](c2nccs2)NS1(=O)=O] | 21% | 491.30 (M + 1) | 490.09 for $C_{19}H_{24}ClFN_4O_4S_2$ | ¹H-NMR (DMSO-$d_6$, 400 MHz): δ 10.64 (s, 1H), 7.95 (dd, J = 6.8, 2.6 Hz, 1H), 7.83 (br.s, 1H), 7.81 (d, J = 3.2 Hz, 1H), 7.79 (d, J = 3.4 Hz, 1H), 7.61-7.58 (m, 1H), 7.41 (t, J = 9.0 Hz, 1H), 5.01-4.90 (m, 1H), 4.58-4.53 (m, 1H), 3.35-3.25 (m, 1H), 2.92 (s, 3H), 2.91-2.85 (m, 1H), 2.42-2.35 (m, 1H), 2.16-2.04 (m, 1H), 1.88-1.78 (m, 1H), 1.75-1.66 (m, 1H), 0.98 (s, 3H), 0.95 (s, 3H). |

TABLE 2-continued

Analytical data for HBV-CSU racemic & pure enantiomers:

| Target No | Structure | Rx. Yield (%) | Mass Spec. Found (m/z) | Mass Spec. Calculated | ¹H-NMR |
|---|---|---|---|---|---|
| HBV-CSU-089-ISO-I | 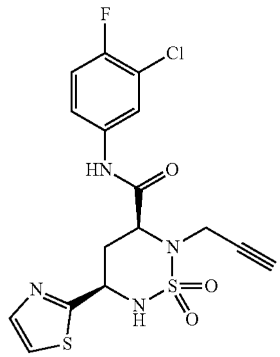 [SMILES: C#CCN1[C@H](C(=O)Nc2ccc(F)c(Cl)c2)C[C@H](c2nccs2)NS1(=O)=O] | 4% | 429.05 (M + 1) | 428.02 for $C_{16}H_{14}ClFN_4O_3S_2$ | ¹H-NMR (DMSO-d$_6$, 400 MHz): δ 10.68 (s, 1H), 8.14-8.07 (m, 1H), 7.94-7.91 (m, 1H), 7.81-7.75 (m, 2H), 7.54-7.49 (m, 1H), 7.41 (t, J = 9.2 Hz, 1H), 5.03-4.98 (m, 1H), 4.55-4.51 (m, 1H), 4.24-4.17 (m, 1H), 3.92-3.88 (m, 1H), 3.33 (1H, merged), 2.32-2.15 (m, 2H). |
| HBV-CSU-089-ISO-II | 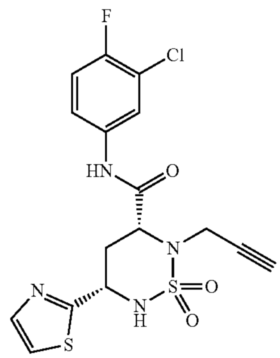 [SMILES: C#CCN1[C@@H](C(=O)Nc2ccc(F)c(Cl)c2)C[C@@H](c2nccs2)NS1(=O)=O] | 4% | 429.05 (M + 1) | 428.02 for $C_{16}H_{14}ClFN_4O_3S_2$ | ¹H-NMR (DMSO-d$_6$, 400 MHz): δ 10.68 (s, 1H), 8.12-8.08 (m, 1H), 7.95-7.93 (m, 1H), 7.81-7.78 (m, 2H), 7.54-7.49 (m, 1H), 7.41 (t, J = 9.2 Hz, 1H), 5.03-4.98 (m, 1H), 4.52-4.48 (m, 1H), 4.25-4.15 (m, 1H), 3.94-3.88 (m, 1H), 3.33 (1H, merged), 2.32-2.15 (m, 2H). |
| HBV-CSU-090 | 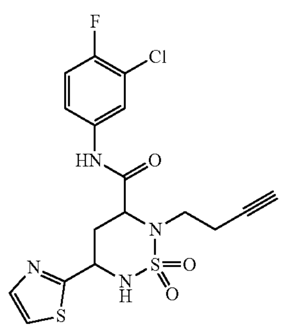 [SMILES: C#CCCN1C(C(=O)Nc2ccc(F)c(Cl)c2)CC(c2nccs2)NS1(=O)=O] | 62% | 443.20 (M + 1) | 442.03 for $C_{17}H_{16}ClFN_4O_3S_2$ | ¹H-NMR (DMSO-d$_6$, 400 MHz): δ 10.66 (br.s, 1H), 7.96 (dd, J = 6.8, 2.6 Hz, 1H), 7.92 (br.s, 1H), 7.81 (d, J = 3.3 Hz, 1H), 7.79 (d, J = 2.9 Hz, 1H), 7.62-7.54 (m, 1H), 7.41 (t, J = 9.1 Hz, 1H), 4.96-4.94 (m, 1H), 4.64-4.61 (m, 1H), 3.45-3.33 (m, 1H), 3.09-2.97 (m, 1H), 2.79 (t, J = 2.4 Hz, 1H), 2.49-2.41 (m, 2H), 2.39-2.33 (m, 1H), 2.04 (q, J = 12.7 Hz, 1H). |
| HBV-CSU-090-ISO-I | 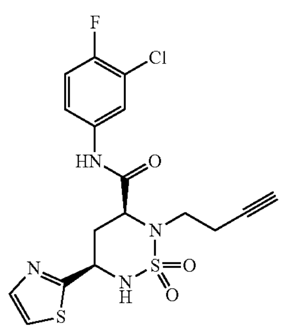 [SMILES: C#CCCN1[C@H](C(=O)Nc2ccc(F)c(Cl)c2)C[C@H](c2nccs2)NS1(=O)=O] | 22% | 443.10 (M + 1) | 442.03 for $C_{17}H_{16}ClFN_4O_3S_2$ | ¹H-NMR (DMSO-d$_6$, 400 MHz): δ 10.63 (br.s, 1H), 7.96 (dd, J = 6.8, 2.6 Hz, 1H), 7.92 (br.s, 1H), 7.83-7.73 (m, 2H), 7.62-7.53 (m, 1H), 7.40 (t, J = 9.1 Hz, 1H), 4.94-4.90 (m, 1H), 4.81-4.55 (m, 1H), 3.09-2.95 (m, 1H), 2.78 (t, J = 2.4 Hz, 1H), 2.48-2.42 (m, 2H), 2.39-2.35 (m, 1H), 2.08-1.94 (m, 1H). |

TABLE 2-continued

Analytical data for HBV-CSU racemic & pure enantiomers:

| Target No | Structure | Rx. Yield (%) | Mass Spec. Found (m/z) | Mass Spec. Calculated | $^1$H-NMR |
|---|---|---|---|---|---|
| HBV-CSU-090-ISO-II | 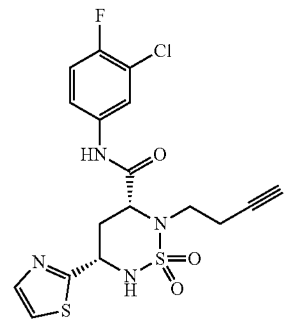 [SMILES: C#CCCN1[C@@H](C(=O)Nc2ccc(F)c(Cl)c2)C[C@@H](c2nccs2)NS1(=O)=O] | 25% | 443.10 (M + 1) | 442.03 for $C_{17}H_{16}ClFN_4O_3S_2$ | $^1$H-NMR (DMSO-d$_6$, 400 MHz): δ 10.65 (br.s, 1H), 7.96 (dd, J = 6.8, 2.6 Hz, 1H), 7.91 (br.s, 1H), 7.81 (d, J = 3.3 Hz, 1H), 7.79 (d, J = 2.9 Hz, 1H), 7.61-7.54 (m, 1H), 7.41 (t, J = 9.1 Hz, 1H), 4.97-4.92 (m, 1H), 4.63-4.61 (m, 1H), 3.10-2.97 (m, 1H), 2.78 (t, J = 2.4 Hz, 2H), 2.52-2.48 (m, 2H), 2.40-2.33 (m, 1H), 2.04 (q, J = 12.6 Hz, 1H). |
| HBV-CSU-092 | 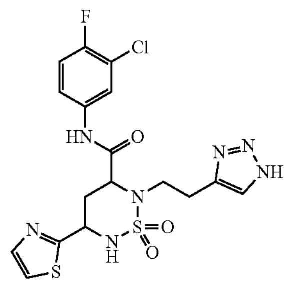 [SMILES: O=C(Nc1ccc(F)c(Cl)c1)C1CC(c2nccs2)NS(=O)(=O)N1CCc1c[nH]nn1] | 81% | 486.20 (M + 1) | 485.05 for $C_{17}H_{17}ClFN_7O_3S_2$ | $^1$H-NMR (DMSO-d$_6$, 400 MHz): δ 15.01-14.33 (m, 1H), 10.65 (br.s, 1H), 7.96-7.87 (m, 2H), 7.81 (d, J = 3.1 Hz, 1H), 7.79 (d, J = 3.1 Hz, 1H), 7.59-7.47 (m, 2H), 7.40 (dd, J = 9.8, 8.3 Hz, 1H), 5.01-4.94 (m, 1H), 4.66-4.61 (m, 1H), 3.59-3.41 (m, 1H), 3.25-3.13 (m, 1H), 3.05-2.90 (m, 2H), 2.43-2.37 (m, 1H), 2.20-1.98 (m, 1H). |
| HBV-CSU-092-ISO-I | 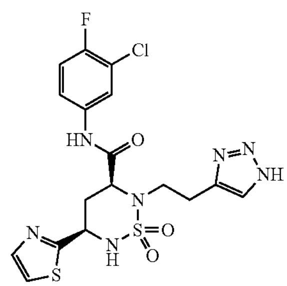 [SMILES: O=C(Nc1ccc(F)c(Cl)c1)[C@@H]1C[C@H](c2nccs2)NS(=O)(=O)N1CCc1c[nH]nn1] | 37% | 486.20 (M + 1) | 485.05 for $C_{17}H_{17}ClFN_7O_3S_2$ | $^1$H-NMR (DMSO-d$_6$, 400 MHz): δ 14.66 (br.s, 1H), 10.65 (s, 1H), 7.93 (dd, J = 6.7, 2.5 Hz, 2H), 7.81 (d, J = 3.4 Hz, 1H), 7.79 (d, J = 3.4 Hz, 1H), 7.59-7.53 (m, 2H), 7.40 (t, J = 9.0 Hz, 1H), 5.01-4.91 (m, 1H), 4.66-4.60 (m, 1H), 3.55-3.45 (m, 1H), 3.24-3.14 (m, 1H), 3.04-2.88 (m, 2H), 2.43-2.37 (m, 1H), 2.19-2.01 (m, 1H). |
| HBV-CSU-092-ISO-II | 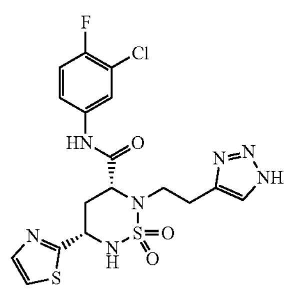 [SMILES: O=C(Nc1ccc(F)c(Cl)c1)[C@H]1C[C@@H](c2nccs2)NS(=O)(=O)N1CCc1c[nH]nn1] | 35% | 486.20 (M + 1) | 485.05 for $C_{17}H_{17}ClFN_7O_3S_2$ | $^1$H-NMR (DMSO-d$_6$, 400 MHz): δ 14.55 (br.s, 1H), 10.65 (br.s, 1H), 7.93 (dd, J = 6.8, 2.5 Hz, 2H), 7.81 (d, J = 3.4 Hz, 1H), 7.79 (d, J = 3.1 Hz, 1H), 7.60-7.52 (m, 2H), 7.40 (t, J = 9.0 Hz, 1H), 5.00-4.94 (m, 1H), 4.66-4.60 (m, 1H), 3.57-3.42 (m, 1H), 3.25-3.14 (m, 1H), 3.06-2.89 (m, 2H), 2.43-2.37 (m, 1H), 2.20-2.00 (m, 1H). |
| HBV-CSU-093 | 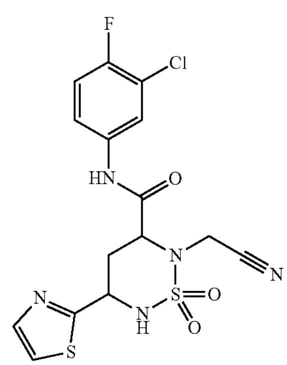 [SMILES: N#CCN1C(C(=O)Nc2ccc(F)c(Cl)c2)CC(c2nccs2)NS1(=O)=O] | 38% | 430.30 (M + 1) | 429.01 for $C_{15}H_{13}ClFN_5O_3S_2$ | $^1$H-NMR (DMSO-d$_6$, 400 MHz): δ 10.79 (s, 1H), 8.35 (d, J = 9.6 Hz, 1H), 7.97 (dd, J = 6.8, 2.4 Hz, 1H), 7.82-7.80 (m, 2H), 7.54-7.49 (m, 1H), 7.42 (t, J = 8,.8 Hz, 1H), 5.06-4.99 (m, 1H), 4.57 (dd, J = 12.0, 2.0 Hz, 1H), 4.24 (AB$_q$, J = 19.2 Hz, 2H), 2.61-2.52 (m, 1H), 2.25-2.12 (m, 1H). |

TABLE 2-continued

Analytical data for HBV-CSU racemic & pure enantiomers:

| Target No | Structure | Rx. Yield (%) | Mass Spec. Found (m/z) | Mass Spec. Calculated | $^1$H-NMR |
|---|---|---|---|---|---|
| HBV-CSU-093-ISO-I | 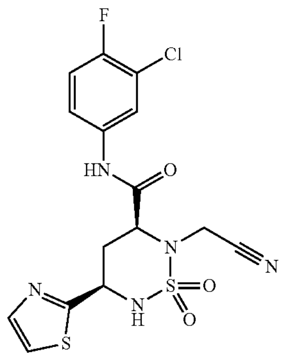 [SMILES: N#CCN1[C@H](C(=O)Nc2ccc(F)c(Cl)c2)C[C@H](c2nccs2)NS1(=O)=O] | 7% | 430.00 (M + 1) | 429.01 for $C_{15}H_{13}ClFN_5O_3S_2$ | $^1$H-NMR (DMSO-$d_6$, 400 MHz): δ 10.81 (s, 1H), 8.34 (d, J = 8.8 Hz, 1H), 7.98 (d, J = 4.8 Hz, 1H), 7.83-7.82 (m, 2H), 7.51-7.41 (m, 2H), 5.03-5.02 (m, 1H), 4.55 (d, J = 10.0 Hz, 1H), 4.25 (AB$_q$, J = 18.4 Hz, 2H), 2.61-2.50 (m, 1H), 2.19-2.15 (m, 1H). |
| HBV-CSU 093-ISO-II | 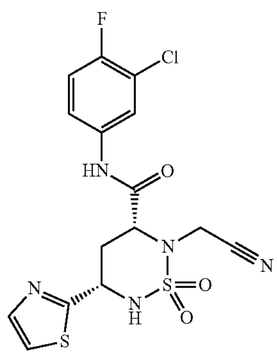 [SMILES: N#CCN1[C@@H](C(=O)Nc2ccc(F)c(Cl)c2)C[C@@H](c2nccs2)NS1(=O)=O] | 8% | 430.05 (M + 1) | 429.01 for $C_{15}H_{13}ClFN_5O_3S_2$ | $^1$H-NMR (DMSO-$d_6$, 400 MHz): δ 10.81 (s, 1H), 8.36-8.32 (m, 1H), 8.00-7.98 (m, 1H), 7.83-7.82 (m, 2H), 7.52-7.41 (m, 2H), 5.01 (d, J = 11.2 Hz, 1H), 4.59 (d, J = 10.0 Hz, 1H), 4.24 (AB$_q$, J = 18.4 Hz, 2H), 2.60-2.51 (m, 1H), 2.22-2.15 (m, 1H). |
| HBV-CSU-094-ISO-I | 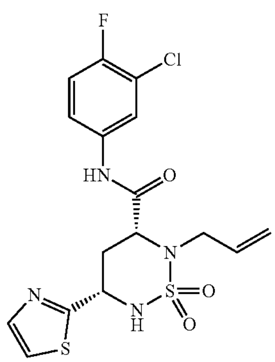 [SMILES: C=CCN1[C@@H](C(=O)Nc2ccc(F)c(Cl)c2)C[C@@H](c2nccs2)NS1(=O)=O] | 16% | 430.90 (M + 1) | 430.03 for $C_{16}H_{16}ClFN_4O_3S_2$ | $^1$H-NMR (DMSO-$d_6$, 400 MHz): δ 10.56 (s, 1H), 7.91-7.84 (m, 2H), 7.84-7.76 (m, 2H), 7.53-7.49 (m, 1H), 7.41-7.36 (m, 1H), 5.91-5.81 (m, 1H), 5.18-4.92 (m, 3H), 4.50 (dd, J = 12.1, 2.7 Hz, 1H), 3.97-3.91 (m, J = 16.4, 4.8, 1.6 Hz, 1H), 3.57 (ddt, J = 16.1, 7.0, 1.3 Hz, 1H), 2.42-2.32 (m, 1H), 2.21-2.05 (m, 1H). |
| HBV-CSU-094-ISO-II | 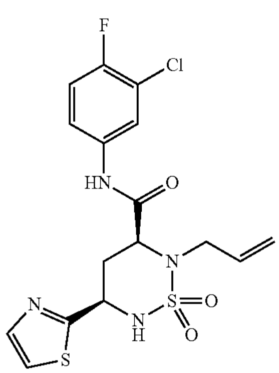 [SMILES: C=CCN1[C@H](C(=O)Nc2ccc(F)c(Cl)c2)C[C@H](c2nccs2)NS1(=O)=O] | 18% | 430.95 (M + 1) | 430.03 for $C_{16}H_{16}ClFN_4O_3S_2$ | $^1$H-NMR (DMSO-$d_6$, 400 MHz): δ 10.56 (s, 1H), 7.95-7.87 (m, 2H), 7.84-7.76 (m, 2H), 7.53-7.50 (m, 1H), 7.41-7.37 (m, 1H), 5.91-5.81 (m, 1H), 5.17-4.90 (m, 3H), 4.50 (dd, J = 12.0, 2.8 Hz, 1H), 4.00-3.89 (m, 1H), 3.62-3.51 (m, 1H), 2.44-2.32 (m, 1H), 2.19-2.07 (m, 1H). |

TABLE 2-continued

Analytical data for HBV-CSU racemic & pure enantiomers:

| Target No | Structure | Rx. Yield (%) | Mass Spec. Found (m/z) | Mass Spec. Calculated | $^1$H-NMR |
|---|---|---|---|---|---|
| HBV-CSU-095 | 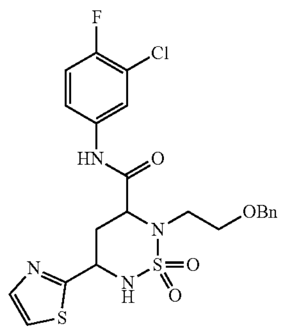 [SMILES: O=C(Nc1ccc(F)c(Cl)c1)C1CC(c2nccs2)NS(=O)(=O)N1CCOCc1ccccc1] | 42% | 525.1 (M + 1) | 524.08 for $C_{22}H_{22}ClFN_4O_4S_2$ | $^1$H NMR (DMSO-$d_6$, 400 MHz): δ 10.53 (s, 1H), 7.89-7.78 (m, 4H), 7.53-7.48 (m, 1H), 7.35 (t, J = 9.6 Hz, 1H), 7.23-7.14 (m, 5H), 4.99-4.91 (m, 1H), 4.67-4.63 (m, 1H), 4.38 (s, 2H), 3.6-3.54 (m, 2H), 3.49-3.41 (m, 1H), 3.18-3.12 (m, 1H), 2.38-2.34 (m, 1H), 2.11-2.-03 (m, 1H). |
| HBV-CSU-095-ISO-I | 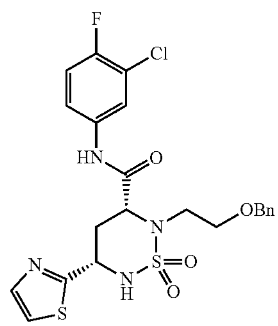 [SMILES: O=C(Nc1ccc(F)c(Cl)c1)[C@H]1C[C@@H](c2nccs2)NS(=O)(=O)N1CCOCc1ccccc1] | 10% | 525.1 (M + 1) | 524.08 for $C_{22}H_{22}ClFN_4O_4S_2$ | $^1$H NMR (DMSO-$d_6$, 400 MHz): δ 10.54 (s, 1H), 7.91-7.78 (m, 4H), 7.52-7.48 (m, 1H), 7.38-7.32 (m, 1H), 7.24-7.15 (m, 5H), 5-4.91 (m, 1H), 4.69-4.62 (m, 1H), 4.38 (s, 2H), 3.59-3.52 2H), 3.48-3.41 (m, 1H), 3.19-3.11 (m, 1H), 2.39-2.32 (m, 1H), 2.08-2.-02 (m, 1H). |
| HBV-CSU-095-ISO-II | 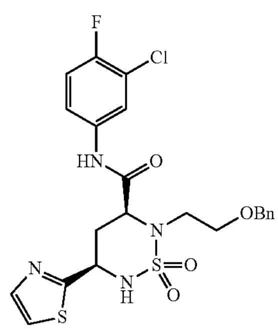 [SMILES: O=C(Nc1ccc(F)c(Cl)c1)[C@@H]1C[C@H](c2nccs2)NS(=O)(=O)N1CCOCc1ccccc1] | 10% | 525.1 (M + 1) | 524.08 for $C_{22}H_{22}ClFN_4O_4S_2$ | $^1$H NMR (DMSO-$d_6$, 400 MHz): δ 10.54 (s, 1H), 7.9-7.77 (m, 4H), 7.53-7.48 (m, 1H), 7.38-7.32 (m, 1H), 7.24-7.14 (m, 5H), 4.99-4.91 (m, 1H), 4.68-4.61 (m, 1H), 4.38 (s, 2H), 3.59-3.51 (m, 2H), 3.48-3.41 (m, 1H), 3.19-3.11 (m, 1H), 2.39-2.31 (m, 1H), 2.08-2.-02 (m, 1H). |
| HBV-CSU-096 | 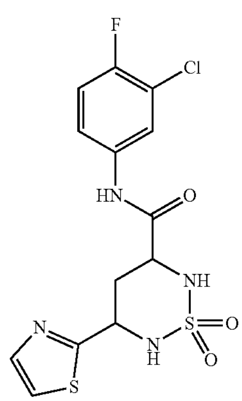 [SMILES: O=C(Nc1ccc(F)c(Cl)c1)C1CC(c2nccs2)NS(=O)(=O)N1] | 76% | 391.05 (M + 1) | 390.00 for $C_{13}H_{12}ClFN_4O_3S_2$ | $^1$H NMR (DMSO-$d_6$, 400 MHz): δ 10.39 (s, 1H), 7.95-7.93 (m, 1H), 7.81-7.77 (m, 2H), 7.54-7.52 (m, 1H), 7.4 (t, J = 9.2 Hz, 1H), 7.26-7.22 (m, 1H), 6.66-6.61 (m, 1H), 4.94-4.91 (m, 1H), 4.41-4.35 (m, 1H), 2.53-2.43 (m, 1H), 1.89-1.78 (m, 1H). |

TABLE 2-continued

Analytical data for HBV-CSU racemic & pure enantiomers:

| Target No | Structure | Rx. Yield (%) | Mass Spec. Found (m/z) | Mass Spec. Calculated | $^1$H-NMR |
|---|---|---|---|---|---|
| HBV-CSU-096-ISO-I | 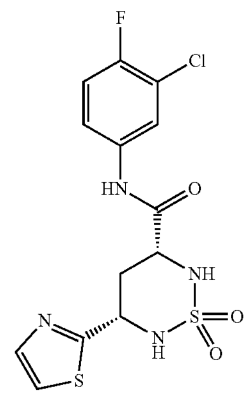 [SMILES: O=C(Nc1ccc(F)c(Cl)c1)[C@H]1C[C@@H](c2nccs2)NS(=O)(=O)N1] | 10% | 390.95 (M + 1) | 390.00 for $C_{13}H_{12}ClFN_4O_3S_2$ | $^1$H NMR (DMSO-$d_6$, 400 MHz): δ 10.39 (s, 1H), 7.95-7.93 (m, 1H), 7.81-7.77 (m, 2H), 7.54-7.52 (m, , 1H), 7.39 (t, J = 9.2 Hz, 1H), 7.26-7.22 (m, 1H), 6.67-6.6 (m, 1H), 4.94-4.9 (m, 1H), 4.40-4.37 (m, 1H), 2.53 (merged, 1H), 1.88-1.78 (m, 1H). |
| HBV-CSU-096-ISO-II | 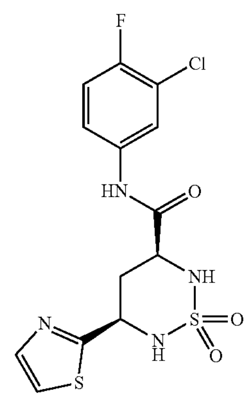 [SMILES: O=C(Nc1ccc(F)c(Cl)c1)[C@@H]1C[C@H](c2nccs2)NS(=O)(=O)N1] | 10% | 390.90 (M + 1) | 390.00 for $C_{13}H_{12}ClFN_4O_3S_2$ | $^1$H NMR (DMSO-$d_6$, 400 MHz): δ 10.39 (s, 1H), 7.94 (dd, J = 6.8, 2.4 Hz, 1H), 7.81-7.75 (m, 2H), 7.57-7.52 (m, 1H), 7.39 (t, J = 8.8 Hz, 1H), 7.26-7.22 (m, 1H), 6.67-6.60 (m, 1H), 4.91 (dd, J = 12.0, 2.8 Hz, 1H), 4.37 (dd, J = 12.0, 2.4 Hz, 1H), 2.50 (1H, merged), 1.85-1.75 (m, 1H). |
| HBV-CSU-097 | 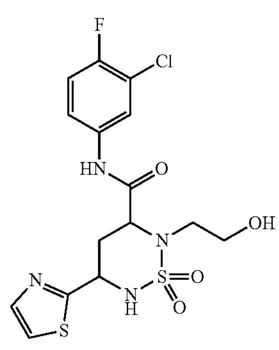 [SMILES: O=C(Nc1ccc(F)c(Cl)c1)C1CC(c2nccs2)NS(=O)(=O)N1CCO] | 25% | 435.00 (M + 1) | 434.03 for $C_{15}H_{16}ClFN_4O_4S_2$ | $^1$H NMR (DMSO-$d_6$, 400 MHz): δ 10.51 (s, 1H), 7.95 (d, J = 6.7 Hz, 1H), 7.89-7.76 (m, 3H), 7.57 (d, J = 8.4 Hz, 1H), 7.41 (t, J = 9.2 Hz, 1H), 4.94-4.93 (m, 2H), 4.68-4.60 (m, 1H), 3.55-3.53 (m, 2H), 3.30-3.22 (m, 1H), 3.04-2.94 (m, 1H), 2.40-2.38 (m, 1H), 2.12-2.00 (m, 1H). |
| HBV-CSU-097-ISO-I | 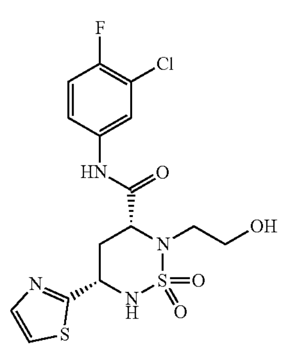 | 6% | 435.30 (M + 1) | 434.03 for $C_{15}H_{16}ClFN_4O_4S_2$ | $^1$H-NMR (DMSO-$d_6$, 400 MHz): δ 10.51 (s, 1H), 7.96-7.93 (m, 1H), 7.84-7.78 (m, 3H), 7.59-7.55 (m, 1H), 7.41 (t, J = 8.8 Hz, 1H), 4.96-4.91 (m, 2H), 4.65-4.62 (m, 1H), 3.57-3.52 (m, 2H), 3.27-3.22 (m, 1H), 3.02-2.95 (m, 1H), 2.38-2.32 (m, 1H), 2.09-2.00 (m, 1H). |

TABLE 2-continued

Analytical data for HBV-CSU racemic & pure enantiomers:

| Target No | Structure | Rx. Yield (%) | Mass Spec. Found (m/z) | Mass Spec. Calculated | $^1$H-NMR |
|---|---|---|---|---|---|
| HBV-CSU-097-ISO-II | 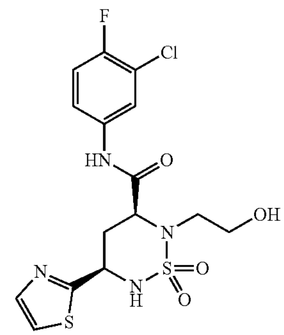 [SMILES: O=C(Nc1ccc(F)c(Cl)c1)[C@@H]1C[C@H](c2nccs2)NS(=O)(=O)N1CCO] | 7% | 435.30 (M + 1) | 434.03 for $C_{15}H_{16}ClFN_4O_4S_2$ | $^1$H-NMR (DMSO-$d_6$, 400 MHz): δ 10.51 (s, 1H), 7.96-7.94 (m, 1H), 7.81-7.78 (m, 3H), 7.57-7.55 (m, 1H), 7.41 (t, J = 8.8 Hz, 1H), 4.96-4.93 (m, 2H), 4.65-4.62 (m, 1H), 3.55-3.52 (m, 2H), 3.27-3.23 (m, 1H), 3.01-2.96 (m, 1H), 2.43-2.37 (m, 1H), 2.09-2.03 (m, 1H). |
| -HBV-CSU-101-ISO-I | 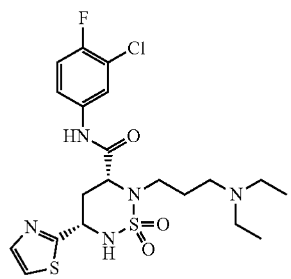 [SMILES: CCN(CC)CCCN1[C@@H](C(=O)Nc2ccc(F)c(Cl)c2)C[C@@H](c2nccs2)NS1(=O)=O] | 4% | 504.10 (M + 1) | 503.12 for $C_{20}H_{27}ClFN_5O_3S_2$ | $^1$H-NMR (DMSO-$d_6$, 400 MHz): δ 10.68 (s, 1H), 7.99-7.97 (m, 1H), 7.82-7.78 (m, 3H), 7.60-7.58 (m, 1H), 7.41 (t, J = 9.2 Hz, 1H), 4.96-4.93 (m, 1H), 4.58-4.55 (m, 1H), 3.26-3.22 (m, 1H), 3.01-2.96 (m, 1H), 2.36-2.25 (m, 7H), 2.09-2.05 (m, 1H), 1.68-1.66 (m, 2H), 0.79-0.76 (m, 6H). |
| HBV-CSU-101-ISO-II | 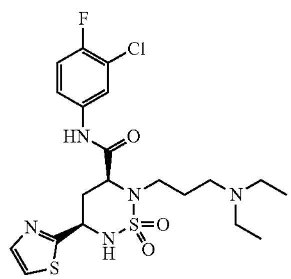 [SMILES: CCN(CC)CCCN1[C@H](C(=O)Nc2ccc(F)c(Cl)c2)C[C@H](c2nccs2)NS1(=O)=O] | 4% | 504.15 (M + 1) | 503.12 for $C_{20}H_{27}ClFN_5O_3S_2$ | $^1$H-NMR (DMSO-$d_6$, 400 MHz): δ 10.68 (s, 1H), 8.00-7.97 (m, 1H), 7.82-7.78 (m, 3H), 7.61-7.58 (m, 1H), 7.41 (t, J = 9.2 Hz, 1H), 4.96-4.93 (m, 1H), 4.58-4.55 (m, 1H), 3.26-3.21 (m, 1H), 2.92-2.88 (m, 1H), 2.36-2.25 (m, 7H), 2.09-2.05 (m, 1H), 1.68-1.64 (m, 2H), 0.77 (t, J = 6.8 Hz, 6H). |
| HBV-CSU-102 | 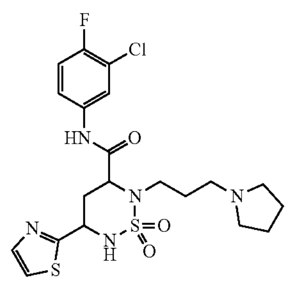 [SMILES: O=C(Nc1ccc(F)c(Cl)c1)C1CC(c2nccs2)NS(=O)(=O)N1CCCN1CCCC1] | 25% | 502.45 (M + 1) | 501.11 for $C_{20}H_{25}ClFN_5O_3S_2$ | $^1$H-NMR (DMSO-$d_6$, 400 MHz): δ 10.71 (s, 1H), 8.20-8.19 (m, 1H), 8.03-7.88 (m, 1H), 7.80-7.78 (m, 2H), 7.58-7.57 (m, 1H), 7.41 (t, J = 8.8 Hz, 1H), 4.97-4.89 (m, 1H), 4.58-4.56 (m, 1H), 3.27-3.24 1H), 2.98-2.94 (m, 1H), 2.38-2.35 (m, 6H), 2.10-2.04 (m, 1H), 1.75-1.56 (m, 7H). |
| HBV-CSU-102-ISO-I | 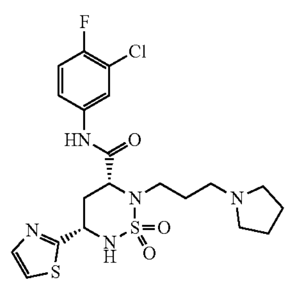 [SMILES: O=C(Nc1ccc(F)c(Cl)c1)[C@H]1C[C@@H](c2nccs2)NS(=O)(=O)N1CCCN1CCCC1] | 7% | 502.10 (M + 1) | 501.11 for $C_{20}H_{25}ClFN_5O_3S_2$ | $^1$H-NMR (DMSO-$d_6$, 400 MHz): δ 10.66 (s, 1H), 7.98-7.96 (m, 1H), 7.80-7.76 (m, 3H), 7.59-7.55 (m, 1H), 7.41 (t, J = 8.8 Hz, 1H), 4.93-4.90 (m, 1H), 4.57-4.54 (m, 1H), 3.25-3.21 (m, 1H), 2.97-2.89 (m, 1H), 2.34-2.31 (m, 2H), 2.24-2.19 (m, 5H), 2.08-2.02 (m, 1H), 1.72-1.68 (m, 2H), 1.51-1.48 (m, 4H). |

TABLE 2-continued

Analytical data for HBV-CSU racemic & pure enantiomers:

| Target No | Structure | Rx. Yield (%) | Mass Spec. Found (m/z) | Mass Spec. Calculated | ¹H-NMR |
|---|---|---|---|---|---|
| HBV-CSU-102-ISO-II | 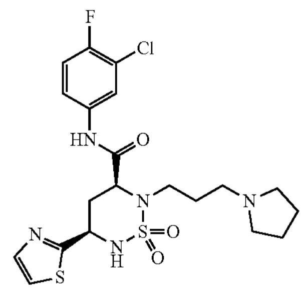 [SMILES: O=C(Nc1ccc(F)c(Cl)c1)[C@@H]1C[C@H](c2nccs2)NS(=O)(=O)N1CCCN1CCCC1] | 8% | 502.05 (M + 1) | 501.11 for $C_{20}H_{25}ClFN_5O_3S_2$ | ¹H-NMR (DMSO-$d_6$, 400 MHz): δ 10.67 (s, 1H), 7.98-7.96 (m, 1H), 7.80-7.76 (m, 3H), 7.59-7.55 (m, 1H), 7.41 (t, J = 8.8 Hz, 1H), 4.93-4.90 (m, 1H), 4.57-4.54 (m, 1H), 3.26-3.21 (m, 1H), 2.98-2.90 (m, 1H), 2.35-2.31 (m, 2H), 2.22-2.19 (m, 5H), 2.12-2.05 (m, 1H), 1.74-1.68 (m, 2H), 1.52-1.48 (m, 4H). |
| HBV-CSU-103 | 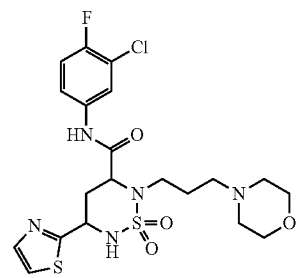 [SMILES: O=C(Nc1ccc(F)c(Cl)c1)C1CC(c2nccs2)NS(=O)(=O)N1CCCN1CCOCC1] | 32% | 518.45 (M + 1) | 517.10 for $C_{20}H_{25}ClFN_5O_4S_2$ | ¹H-NMR (DMSO-$d_6$, 400 MHz): δ 10.67 (s, 1H), 7.98-7.92 (m, 1H), 7.86-7.70 (m, 3H), 7.60-7.53 (m, 1H), 7.40 (t, J = 9.1 Hz, 1H), 4.94-4.91 (m, 1H), 4.57-4.54 (m, 1H), 3.36 (t, J = 4.6 Hz, 4H), 3.22-3.20 (m, 1H), 2.95-2.94 (m, 1H), 2.39-2.00 (m, 8H), 1.72-1.69 (m, 2H). |
| HBV-CSU-103-ISO-I | 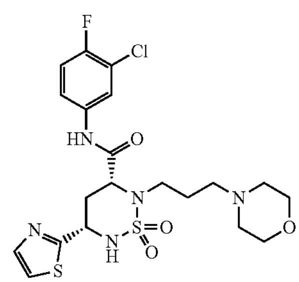 [SMILES: O=C(Nc1ccc(F)c(Cl)c1)[C@H]1C[C@@H](c2nccs2)NS(=O)(=O)N1CCCN1CCOCC1] | 7% | 518.10 (M + 1) | 517.10 for $C_{20}H_{25}ClFN_5O_4S_2$ | ¹H-NMR (DMSO-$d_6$, 400 MHz): δ 10.67 (s, 1H), 7.98-7.92 (m, 1H), 7.86-7.70 (m, 3H), 7.60-7.53 (m, 1H), 7.40 (t, J = 9.1 Hz, 1H), 4.94-4.91 (m, 1H), 4.57-4.54 (m, 1H), 3.36-3.34 (m, 4H), 3.26-3.19 (m, 1H), 2.98-2.90 (m, 1H), 2.39-2.00 (m, 8H), 1.72-1.68 (m, 2H). |
| HBV-CSU-103-ISO-II | 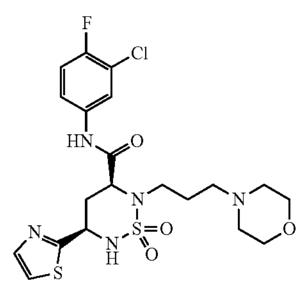 [SMILES: O=C(Nc1ccc(F)c(Cl)c1)[C@@H]1C[C@H](c2nccs2)NS(=O)(=O)N1CCCN1CCOCC1] | 5% | 518.05 (M + 1) | 517.10 for $C_{20}H_{25}ClFN_5O_4S_2$ | ¹H-NMR (DMSO-$d_6$, 400 MHz): δ 10.68 (s, 1H), 7.98 (dd, J = 6.8, 2.6 Hz, 1H), 7.87-7.74 (m, 3H), 7.59-7.56 (m, 1H), 7.40 (t, J = 9.1 Hz, 1H), 4.92 (dd, J = 12.1, 2.9 Hz, 1H), 4.55 (dd, J = 12.1, 2.6 Hz, 1H), 3.37-3.35 (m, 4H), 3.24-3.18 (m, 1H), 2.98-2.90 (m, 1H), 2.27-2.00 (m, 8H), 1.71-1.69 (m, 2H). |
| HBV-CSU-108 | 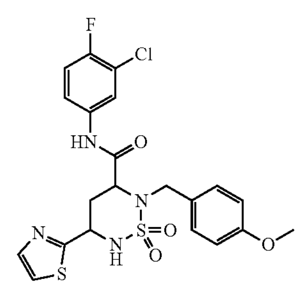 [SMILES: COc1ccc(CN2C(C(=O)Nc3ccc(F)c(Cl)c3)CC(c3nccs3)NS2(=O)=O)cc1] | 50% | 511.10 (M + 1) | 510.06 for $C_{21}H_{20}ClFN_4O_4S_2$ | ¹H-NMR (DMSO-$d_6$, 400 MHz): δ 10.60 (s, 1H), 7.96-7.94 (m, 1H), 7.81-7.79 (m, 1H), 7.76-7.74 (m, 1H), 7.69-7.67 (m, 1H), 7.58-7.57 (m, 1H), 7.41 (t, J = 8.8 Hz, 1H), 6.89 (d, J = 8.8 Hz, 2H), 6.72 (d, J = 8.8 Hz, 2H), 5.35-5.31 (m, 1H), 4.45-4.43 (m, 1H), 3.97 (ABq, J = 16.4 Hz, 2H), 3.68 (s, 3H), 2.30-2.25 (m, 2H). |

TABLE 2-continued

Analytical data for HBV-CSU racemic & pure enantiomers:

| Target No | Structure | Rx. Yield (%) | Mass Spec. Found (m/z) | Mass Spec. Calculated | ¹H-NMR |
|---|---|---|---|---|---|
| HBV-CSU-109 | 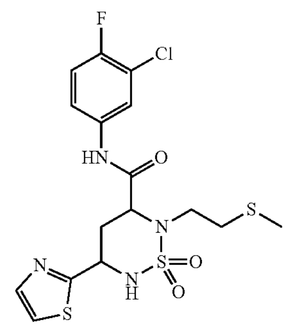 | 51% | 465.10 (M + 1) | 464.02 for $C_{16}H_{18}ClFN_4O_3S_3$ | ¹H-NMR (DMSO-$d_6$, 400 MHz): δ 10.67 (s, 1H), 7.96 (dd, J = 6.8, 2.6 Hz, 1H), 7.87 (d, J = 9.5 Hz, 1H), 7.82 (d, J = 3.2 Hz, 1H), 7.80 (d, J = 3.2 Hz, 1H), 7.62-7.56 (m, 1H), 7.41 (t, J = 9.0 Hz, 1H), 5.00-4.92 (m, 1H), 4.67-4.61 (m, 1H), 3.48-3.40 (m, 1H), 3.11-2.97 (m, 1H), 2.72-2.59 (m, 2H), 2.41-2.34 (m, 1H), 2.13-2.01 (m, 1H), 1.91 (s, 3H). |
| HBV-CSU-109-ISO-I | 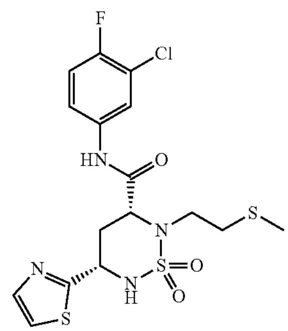 | 14% | 465.10 (M + 1) | 464.02 for $C_{16}H_{18}ClFN_4O_3S_3$ | ¹H-NMR (DMSO-$d_6$, 400 MHz): δ 10.67 (s, 1H), 7.96 (dd, J = 6.8, 2.6 Hz, 1H), 7.88 (br.s, 1H), 7.82 (d, J = 3.2 Hz, 1H), 7.80 (d, J = 3.2 Hz, 1H), 7.61-7.56 (m, 1H), 7.41 (t, J = 9.1 Hz, 1H), 4.98-4.94 (m, 1H), 4.67-4.61 (m, 1H), 3.48-3.39 (m, 1H), 3.09-2.96 (m, 1H), 2.72-2.59 (m, 2H), 2.41-2.34 (m, 1H), 2.14-2.01 (m, 1H), 1.91 (s, 3H). |
| HBV-CSU-109-ISO-II | 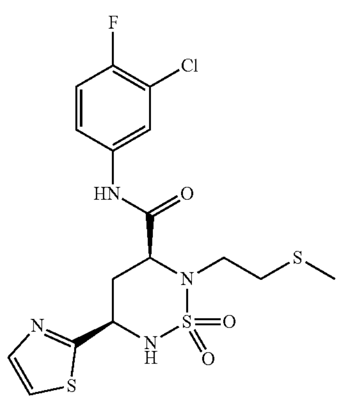 [SMILES: CSCCN1[C@H](C(=O)Nc2ccc(F)c(Cl)c2)C[C@H](c2nccs2)NS1(=O)=O] | 13% | 465.10 (M + 1) | 464.02 for $C_{16}H_{18}ClFN_4O_3S_3$ | ¹H-NMR (DMSO-$d_6$, 400 MHz): δ 10.67 (s, 1H), 7.96 (dd, J = 6.9, 2.7 Hz, 1H), 7.87 (br.s, 1H), 7.82 (d, J = 3.2 Hz, 1H), 7.80 (d, J = 3.1 Hz, 1H), 7.62-7.56 (m, 1H), 7.41 (t, J = 9.1 Hz, 1H), 4.98-4.93 (m, 1H), 4.67-4.61 (m, 1H), 3.48-3.39 (m, 1H), 3.09-2.98 (m, 1H), 2.72-2.58 (m, 2H), 2.41-2.34 (m, 1H), 2.14-2.01 (m, 1H), 1.91 (s, 3H). |
| HBV-CSU-110 | 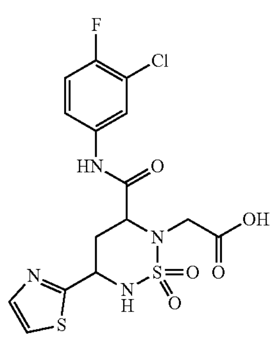 [SMILES: O=C(O)CN1C(C(=O)Nc2ccc(F)c(Cl)c2)CC(c2nccs2)NS1(=O)=O] | 23% | 449.30 (M + 1) | 448.01 for $C_{15}H_{14}ClFN_4O_5S_2$ | ¹H-NMR (DMSO-$d_6$, 400 MHz): δ 12.84 (s, 1H), 10.58 (s, 1H), 7.89-7.78 (m, 4H), 7.53-7.50 (m, 1H), 7.40 (t, J = 8.8 Hz, 1H), 5.03-5.96 (m, 1H), 4.82-4.78 (m, 1H), 3.85 (ABq, J = 18.4 Hz, 2H), 2.42-2.33 (m, 1H), 2.15-2.05 (m, 1H). |

TABLE 2-continued

Analytical data for HBV-CSU racemic & pure enantiomers:

| Target No | Structure | Rx. Yield (%) | Mass Spec. Found (m/z) | Mass Spec. Calculated | ¹H-NMR |
|---|---|---|---|---|---|
| HBV-CSU-111 | 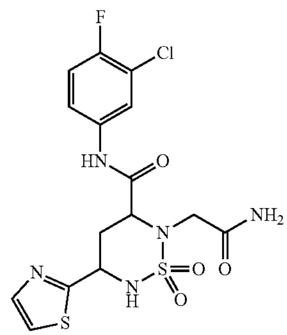 [SMILES: NC(=O)CN1C(C(=O)Nc2ccc(F)c(Cl)c2)CC(c2nccs2)NS1(=O)=O] | 63% | 447.95 (M + 1) | 447.02 for $C_{15}H_{15}ClFN_5O_4S_2$ | ¹H-NMR (DMSO-d$_6$, 400 MHz): δ 10.97 (s, 1H), 7.96-7.80 (m, 4H), 7.57-7.56 (m, 2H), 7.43-7.39 (m, 2H), 4.99-4.97 (m, 1H), 4.76 (d, J = 9.2 Hz, 1H), 3.52 (ABq, J = 18.0, Hz, 2H), 2.46-2.42 (m, 1H), 2.08-2.05 (m, 1H). |
| HBV-CSU-112 | 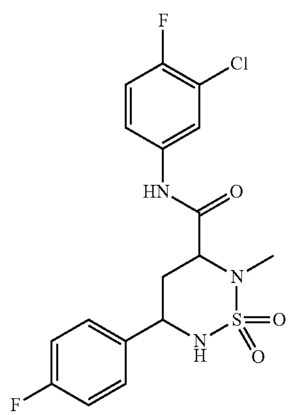 [SMILES: CN1C(C(=O)Nc2ccc(F)c(Cl)c2)CC(c2ccc(F)cc2)NS1(=O)=O] | 43% | 416 (M + 1) | 415.06 for $C_{17}H_{16}ClF_2N_3O_3S$ | ¹H-NMR (DMSO-d$_6$, 400 MHz): δ 10.55 (s, 1H), 7.96-7.94 (m, 1H), 7.54-7.49 (m, 4H), 7.42-7.38 (m, 1H), 7.24-7.19 (m, 2H), 4.61-4.57 (m, 1H), 4.31-4.22 (m, 1H), 2.64 (s, 3H), 2.12-2.02 (m, 2H). |
| HBV-CSU-112-ISO-I | 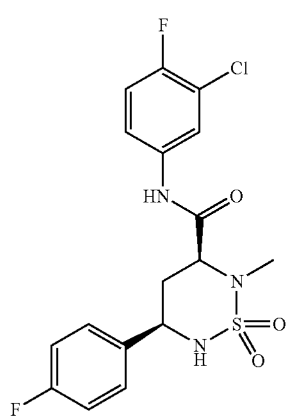 [SMILES: CN1[C@H](C(=O)Nc2ccc(F)c(Cl)c2)C[C@H](c2ccc(F)cc2)NS1(=O)=O] | 10% | 416 (M + 1) | 415.06 for $C_{17}H_{16}ClF_2N_3O_3S$ | ¹H-NMR (DMSO-d$_6$, 400 MHz): δ 10.55 (s, 1H), 7.96-7.94 (m, 1H), 7.54-7.49 (m, 4H), 7.39 (t, J = 9.1 Hz, 1H), 7.29-7.12 (m, 2H), 4.62-4.56 (m, 1H), 4.31-4.21 (m, 1H), 2.64 (s, 3H), 2.16-2.01 (m, 2H). |

TABLE 2-continued

Analytical data for HBV-CSU racemic & pure enantiomers:

| Target No | Structure | Rx. Yield (%) | Mass Spec. Found (m/z) | Mass Spec. Calculated | $^1$H-NMR |
|---|---|---|---|---|---|
| HBV-CSU-112-ISO-II | 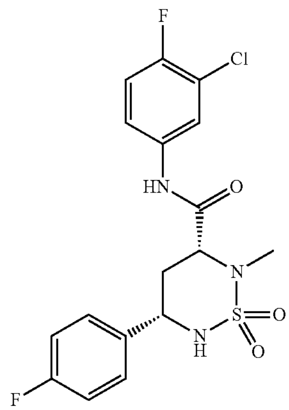 [SMILES: CN1[C@@H](C(=O)Nc2ccc(F)c(Cl)c2)C[C@@H](c2ccc(F)cc2)NS1(=O)=O] | 11% | 416 (M + 1) | 415.06 for $C_{17}H_{16}ClF_2N_3O_3S$ | $^1$H-NMR (DMSO-$d_6$, 400 MHz): δ 10.55 (s, 1H), 7.96-7.94 (m, 1H), 7.56-7.49 (m, 4H), 7.39 (t, J = 9.1 Hz, 1H), 7.21 (t, J = 8.8 Hz, 2H), 4.60-4.57 (m, 1H), 4.31-4.22 (m, 1H), 2.64 (s, 3H), 2.15-2.03 (m, 2H). |
| HBV-CSU-113-ISO-I | 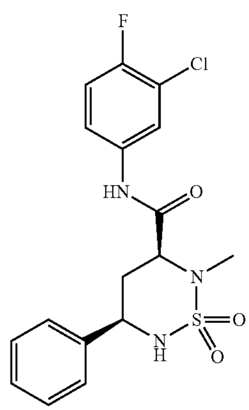 [SMILES: CN1[C@H](C(=O)Nc2ccc(F)c(Cl)c2)C[C@H](c2ccccc2)NS1(=O)=O] | 6% | 398.00 (M + 1) | 397.07 for $C_{17}H_{17}ClFN_3O_3S$ | $^1$H-NMR (DMSO-$d_6$, 400 MHz): δ 10.55 (s, 1H), 7.97-7.94 (m, 1H), 7.57-7.31 (m, 8H), 4.60-4.56 (m, 1H), 4.29-4.26 (m, 1H), 2.64 (s, 3H), 2.11-2.06 (m, 2H). |
| HBV-CSU-113-ISO-II | 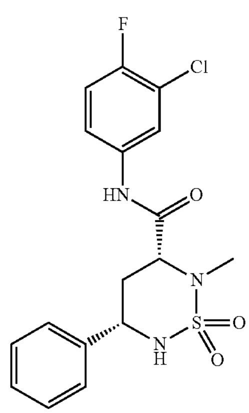 [SMILES: CN1[C@@H](C(=O)Nc2ccc(F)c(Cl)c2)C[C@@H](c2ccccc2)NS1(=O)=O] | 4.5% | 398.15 (M + 1) | 397.07 for $C_{17}H_{17}ClFN_3O_3S$ | $^1$H-NMR (DMSO-$d_6$, 400 MHz): δ 10.55 (s, 1H), 7.96-7.94 (m, 1H), 7.57-7.30 (m, 8H), 4.59-4.58 (m, 1H), 4.29-4.25 (m, 1H), 2.64 (s, 3H), 2.11-2.06 (m, 2H). |

TABLE 2-continued

Analytical data for HBV-CSU racemic & pure enantiomers:

| Target No | Structure | Rx. Yield (%) | Mass Spec. Found (m/z) | Mass Spec. Calculated | ¹H-NMR |
|---|---|---|---|---|---|
| HBV-CSU-114 | 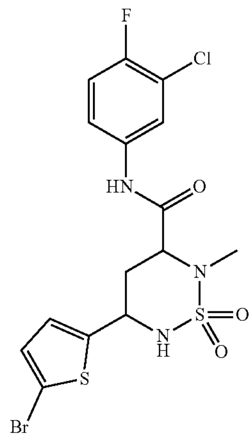 | 23% | 483.85 (M + 2) | 480.93 for $C_{15}H_{14}BrClFN_3O_3S_2$ | ¹H-NMR (DMSO-$d_6$, 400 MHz): δ 10.58 (s, 1H), 7.97 (d, J = 4.4 Hz, 1H), 7.73-7.72 (m, 1H), 7.55-7.54 (m, 1H), 7.41 (t, J = 9.2 Hz, 1H), 7.14 (d, J = 3.2 Hz, 1H), 6.99 (d, J = 4.0 Hz, 1H), 4.75-4.74 (m, 1H), 4.26 (d, J = 10.0 Hz, 1H), 2.61 (s, 3H), 2.25-2.08 (m, 2H). |
| HBV-CSU-114-ISO-I | 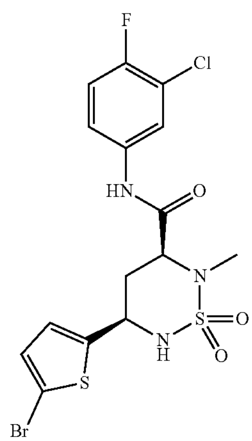 [SMILES: CN1[C@H](C(=O)Nc2ccc(F)c(Cl)c2)C[C@H](c2ccc(Br)s2)NS1(=O)=O] | 11% | 483.75 (M + 2) | 480.93 for $C_{15}H_{14}BrClFN_3O_3S_2$ | ¹H-NMR (DMSO-$d_6$, 400 MHz): δ 10.57 (s, 1H), 7.96 (dd, J = 6.8, 2.4 Hz, 1H), 7.73-7.72 (m, 1H), 7.57-7.53 (m, 1H), 7.39 (t, J = 8.8 Hz, 1H), 7.13 (d, J = 4.0 Hz, 1H), 6.99 (d, J = 4.0 Hz, 1H), 4.75-4.74 (m, 1H), 4.26 (dd, J = 11.6, 2.4 Hz, 1H), 2.60 (s, 3H), 2.24-2.06 (m, 2H). |
| HBV-CSU-114-ISO-II | 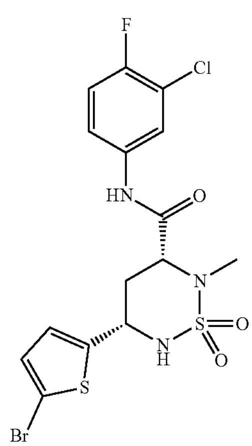 | 11% | 483.95 (M + 2) | 480.93 for $C_{15}H_{14}BrClFN_3O_3S_2$ | ¹H-NMR (DMSO-$d_6$, 400 MHz): δ 10.57 (s, 1H), 7.96 (dd, J = 6.8, 2.4 Hz, 1H), 7.71 (d, J = 8.8 Hz, 1H), 7.56-7.53 (m, 1H), 7.39 (t, J = 9.2 Hz, 1H), 7.12 (d, J = 4.0 Hz, 1H), 6.99 (d, J = 4.0 Hz, 1H), 4.77-4.67 (m, 1H), 4.26 (dd, J = 11.6, 2.4 Hz, 1H), 2.60 (s, 3H), 2.24-2.07 (m, 2H). |

TABLE 2-continued

Analytical data for HBV-CSU racemic & pure enantiomers:

| Target No | Structure | Rx. Yield (%) | Mass Spec. Found (m/z) | Mass Spec. Calculated | ¹H-NMR |
|---|---|---|---|---|---|
| HBV-CSU-114-Trans (Rac) | 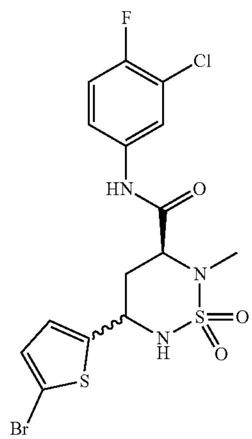 [SMILES: CN1[C@H](C(=O)Nc2ccc(F)c(Cl)c2)CC(c2ccc(Br)s2)NS1(=O)=O] | 26% | 481.90 (M + 1) | 480.93 for $C_{15}H_{14}BrClFN_3O_3S_2$ | ¹H-NMR (DMSO-$d_6$, 400 MHz): δ 10.00 (s, 1H), 7.93-7.91 (m, 1H), 7.56-7.54 (m, 1H), 7.48-7.46 (m, 1H), 7.34 (t, J = 8.8 Hz, 1H), 7.12 (d, J = 3.6 Hz, 1H), 6.99 (d, J = 3.6 Hz, 1H), 4.87-4.82 (m, 1H), 4.43-4.40 (m, 1H), 2.91 (s, 3H), 2.31-2.27 (m, 1H), 1.93-1.85 (m, 1H). |
| HBV-CSU-114-Trans-ISO-I | 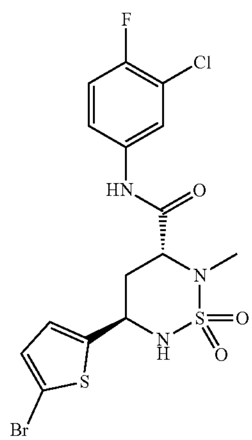 [SMILES: CN1[C@@H](C(=O)Nc2ccc(F)c(Cl)c2)C[C@H](c2ccc(Br)s2)NS1(=O)=O] | 2% | 481.95 (M + 1) | 480.93 for $C_{15}H_{14}BrClFN_3O_3S_2$ | ¹H-NMR (DMSO-$d_6$, 400 MHz): δ 10.03 (s, 1H), 7.96-7.94 (m, 1H), 7.60-7.57 (m, 1H), 7.50-7.45 (m, 1H), 7.37 (t, J = 9.2 Hz, 1H), 7.15 (d, J = 4.0 Hz, 1H), 7.02 (d, J = 3.2 Hz, 1H), 4.89-4.87 (m, 1H), 4.46-4.44 (m, 1H), 2.94 (s, 3H), 2.35-2.29 (m, 1H), 2.07-1.89 (m, 1H). |
| HBV-CSU-114-Trans-ISO-II | 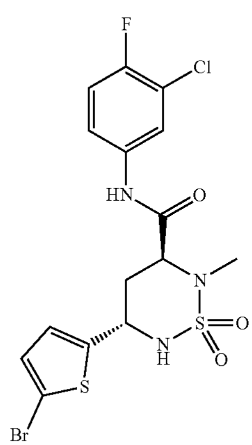 | 10% | 483.9 (M + 2) | 480.93 for $C_{15}H_{14}BrClFN_3O_3S_2$ | ¹H-NMR (DMSO-$d_6$, 400 MHz): δ 10.06 (s, 1H), 7.99-7.97 (m, 1H), 7.63-7.60 (m, 1H), 7.53-7.51 (m, 1H), 7.40 (t, J = 9.2 Hz, 1H), 7.18 (d, J = 4.0 Hz, 1H), 7.04 (d, J = 4.0 Hz, 1H), 4.93-4.88 (m, 1H), 4.49-4.47 (m, 1H), 2.97 (s, 3H), 2.37-2.35 (m, 1H), 1.99-1.96 (m, 1H). |

TABLE 2-continued

Analytical data for HBV-CSU racemic & pure enantiomers:

| Target No | Structure | Rx. Yield (%) | Mass Spec. Found (m/z) | Mass Spec. Calculated | ¹H-NMR |
|---|---|---|---|---|---|
| HBV-CSU-115 | 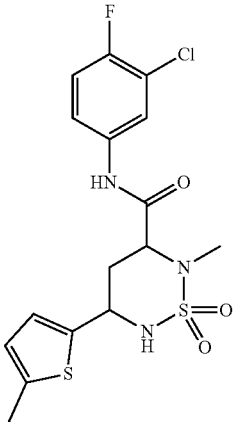 [SMILES: Cc1ccc(C2CC(C(=O)Nc3ccc(F)c(Cl)c3)N(C)S(=O)(=O)N2)s1] | 58% | 308.15 (M − 109) | 417.04 for $C_{16}H_{17}ClFN_3O_3S_2$ | ¹H-NMR (DMSO-$d_6$, 400 MHz): δ 10.55 (s, 1H), 7.95-7.93 (m, 1H), 7.60-7.51 (m, 2H), 7.37 (t, J = 9.2 Hz, 1H), 6.88 (d, J = 2.8 Hz, 1H), 6.66 (d, J = 2.4 Hz, 1H), 4.67-4.65 (m, 1H), 4.23 (d J = 10.8 Hz, 1H), 2.58 (s, 3H), 2.39 (s, 3H), 2.16-2.06 (m, 2H). |
| HBV-CSU-115-ISO-I | 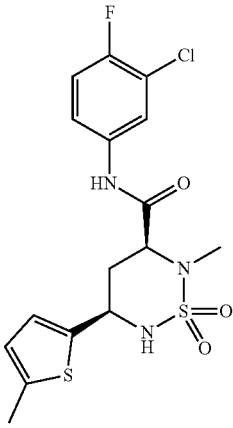 [SMILES: Cc1ccc([C@H]2C[C@@H](C(=O)Nc3ccc(F)c(Cl)c3)N(C)S(=O)(=O)N2)s1] | 6% | 418.25 (M + 1) | 417.04 for $C_{16}F_{17}ClFN_3O_3S_2$ | ¹H-NMR (DMSO-$d_6$, 400 MHz): δ 10.55 (s, 1H), 7.97 (dd, J = 6.8, 2.4 Hz, 1H), 7.62-7.52 (m, 2H), 7.40 (t, J = 9.2 Hz, 1H), 6.91 (d, J = 4 Hz, 1H), 6.69 (d, J = 2.4 Hz, 1H), 4.71-4.66 (m, 1H), 4.27 (dd J = 11.2, 2.8 Hz, 1H), 2.58 (s, 3H), 2.42 (s, 3H), 2.18-2.06 (m, 2H). |
| HBV-CSU-115-ISO-II | 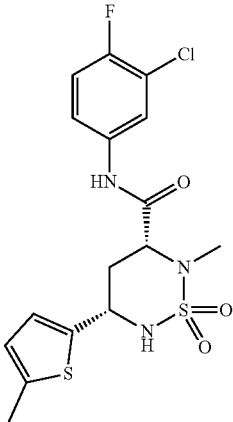 [SMILES: Cc1ccc([C@@H]2C[C@H](C(=O)Nc3ccc(F)c(Cl)c3)N(C)S(=O)(=O)N2)s1] | 6% | 418.25 (M + 1) | 417.04 for $C_{16}H_{17}ClFN_3O_3S_2$ | ¹H-NMR (DMSO-$d_6$, 400 MHz): δ 10.56 (s, 1H), 7.96 (dd, J = 6.8, 2.4 Hz, 1H), 7.67-7.52 (m, 2H), 7.4 (t, J = 9.2 Hz, 1H), 6.91 (d, J = 3.8 Hz, 1H), 6.69 (d, J = 2.4 Hz, 1H), 4.71-4.67 (m, 1H), 4.26 (dd, J = 11.2, 2.8 Hz, 1H), 2.6 (s, 3H), 2.42 (s, 3H), 2.19-2.09 (m, 2H). |

TABLE 2-continued

Analytical data for HBV-CSU racemic & pure enantiomers:

| Target No | Structure | Rx. Yield (%) | Mass Spec. Found (m/z) | Mass Spec. Calculated | $^1$H-NMR |
|---|---|---|---|---|---|
| HBV-CSU-116-ISO-I | 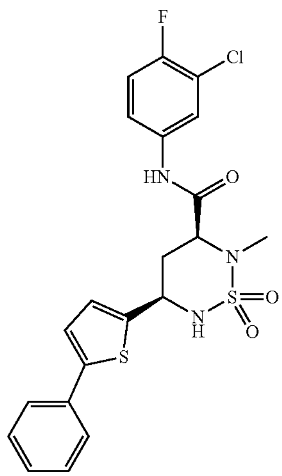 [SMILES: CN1[C@H](C(=O)Nc2ccc(F)c(Cl)c2)C[C@H](c2ccc(-c3ccccc3)s2)NS1(=O)=O] | 10% | 480.4 (M + 1) | 479.05 for $C_{21}H_{19}ClFN_3O_3S_2$ | $^1$H-NMR (DMSO-$d_6$, 400 MHz): δ 10.59 (s, 1H), 7.97 (dd, J = 6.8, 2.4 Hz, 1H), 7.75-7.71 (m, 1H), 7.68-7.61 (m, 2H), 7.58-7.52 (m, 1H), 7.46-7.38 (m, 4H), 7.34-7.29 (m, 1H), 7.15 (d, J = 2.8 Hz, 1H), 4.83-4.78 (m, 1H), 4.34-4.30 (m, 1H), 2.63 (s, 3H), 2.3-2.15 (m, 2H). |
| HBV-CSU-116-ISO-II | 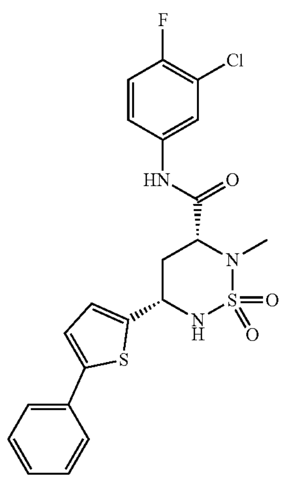 [SMILES: CN1[C@@H](C(=O)Nc2ccc(F)c(Cl)c2)C[C@@H](c2ccc(-c3ccccc3)s2)NS1(=O)=O] | 11% | 480.4 (M + 1) | 479.05 for $C_{21}H_{19}ClFN_3O_3S_2$ | $^1$H-NMR (DMSO-$d_6$, 400 MHz): δ 10.59 (s, 1H), 7.98 (dd, J = 6.8, 2.4 Hz, 1H), 7.79-7.72 (m, 1H), 7.66-7.62 (m, 2H), 7.58-7.5 (m, 1H), 7.44-7.39 (m, 4H), 7.34-7.31 (m, 1H), 7.15 (d, J = 3.6 Hz, 1H), 4.82-4.79 (m, 1H), 4.34-4.29 (m, 1H), 2.63 (s, 3H), 2.31-2.15 (m, 2H). |
| HBV-CSU-117 | 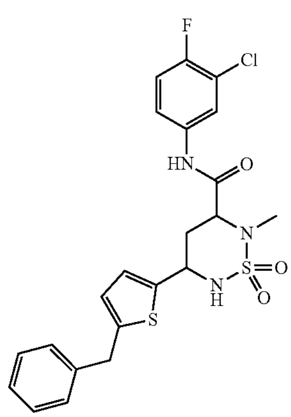 [SMILES: CN1C(C(=O)Nc2ccc(F)c(Cl)c2)CC(c2ccc(Cc3ccccc3)s2)NS1(=O)=O] | 10% | 494.00 (M + 1) | 493.07 for $C_{22}H_{21}ClFN_3O_3S_2$ | $^1$H-NMR (DMSO-$d_6$, 400 MHz): δ 10.54 (s, 1H), 7.96 (dd, J = 6.8, 2.4 Hz, 1H), 7.6-7.52 (m, 2H), 7.4 (t, J = 8.8 Hz, 1H), 7.33-7.21 (m, 5H), (J = 3.6 Hz, 1H), 4.71-4.67 (m, 1H), 4.26 (dd J = 11.6, 2.8 Hz, 1H), 4.11 (s, 2H), 2.58 (s, 3H), 2.18-2.05 (m, 2H). |

TABLE 2-continued

Analytical data for HBV-CSU racemic & pure enantiomers:

| Target No | Structure | Rx. Yield (%) | Mass Spec. Found (m/z) | Mass Spec. Calculated | 1H-NMR |
|---|---|---|---|---|---|
| HBV-CSU-117-ISO-I | 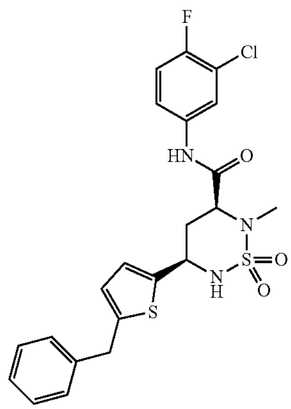 [SMILES: CN1[C@H](C(=O)Nc2ccc(F)c(Cl)c2)C[C@H](c2ccc(Cc3ccccc3)s2)NS1(=O)=O] | 8% | 494.50 (M + 1) | 493.07 for $C_{22}H_{21}ClFN_3O_3S_2$ | 1H-NMR (DMSO-$d_6$, 400 MHz): δ 10.55 (s, 1H), 7.96 (dd, J = 6.8, 2.4 Hz, 1H), 7.6-7.52 (m, 2H), 7.39 (t, J = 9.2 Hz, 1H), 7.33-7.19 (m, 5H), 6.93 (d, J = 3.6 Hz, 1H), 6.78 (d, J = 3.2 Hz, 1H), 4.71-4.67 (m, 1H), 4.29-4.21 (m, 1H), 4.10 (s, 2H), 2.57 (s, 3H), 2.18-2.05 (m, 2H). |
| HBV-CSU-117-ISO-II | 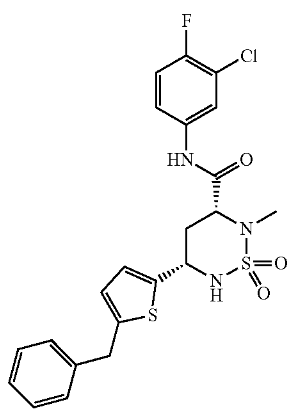 [SMILES: CN1[C@@H](C(=O)Nc2ccc(F)c(Cl)c2)C[C@@H](c2ccc(Cc3ccccc3)s2)NS1(=O)=O] | 6% | 494.35 (M + 1) | 493.07 for $C_{22}H_{21}ClFN_3O_3S_2$ | 1H-NMR (DMSO-$d_6$, 400 MHz): δ 10.58 (s, 1H), 7.96 (dd, J = 6.8, 2.4 Hz, 1H), 7.63-7.52 (m, 2H), 7.39 (t, J = 9.2 Hz, 1H), 7.33-7.19 (m, 5H), 6.93 (d, J = 3.2 Hz, 1H), 6.78 (d, J = 3.6 Hz, 1H), 4.71-4.67 (m, 1H), 4.28-4.23 (m, 1H), 4.10 (s, 2H), 2.58 (s, 3H), 2.19-2.01 (m, 2H). |
| HBV-CSU-120 | 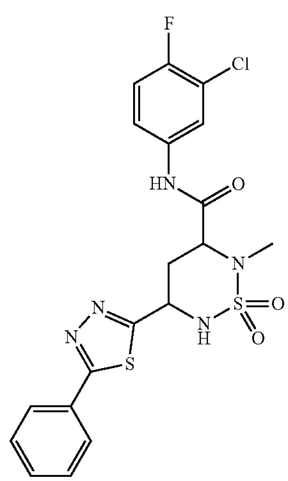 [SMILES: CN1C(C(=O)Nc2ccc(F)c(Cl)c2)CC(c2nnc(-c3ccccc3)s2)NS1(=O)=O] | 33% | 482.10 (M + 1) | 481.04 for $C_{19}H_{17}ClFN_5O_3S_2$ | 1H-NMR (DMSO-$d_6$, 400 MHz): δ 10.65 (s, 1H), 8.02-7.97 (m, 4H), 7.60-7.55 (m, 4H), 7.41 (t, J = 9.2 Hz, 1H), 5.14 (d, J = 9.4 Hz, 1H), 4.44-4.38 (m, 1H), 2.64 (s, 3H), 2.49-2.31 (m, 2H). |

TABLE 2-continued

Analytical data for HBV-CSU racemic & pure enantiomers:

| Target No | Structure | Rx. Yield (%) | Mass Spec. Found (m/z) | Mass Spec. Calculated | ¹H-NMR |
|---|---|---|---|---|---|
| HBV-CSU-120-ISO-I | 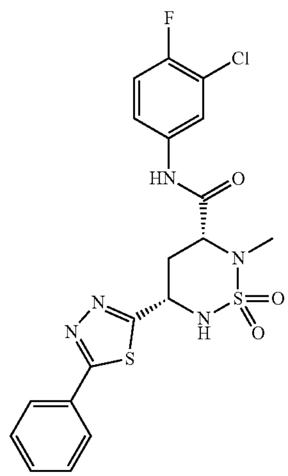 [SMILES: CN1[C@@H](C(=O)Nc2ccc(F)c(Cl)c2)C[C@@H](c2nnc(-c3ccccc3)s2)NS1(=O)=O] | 6% | 482.15 (M + 1) | 481.04 for $C_{19}H_{17}ClFN_5O_3S_2$ | ¹H-NMR (DMSO-$d_6$, 400 MHz): δ 10.64 (s, 1H), 8.10 (d, J = 10.0 Hz, 1H), 8.02-7.97 (m, 3H), 7.60-7.55 (m, 4H), 7.42 (t, J = 9.1 Hz, 1H), 5.23-5.12 (m, 1H), 4.43 (dd, J = 11.8, 2.7 Hz, 1H), 2.65 (s, 3H), 2.49-2.42 (m, 2H). |
| HBV-CSU-120-ISO-II | 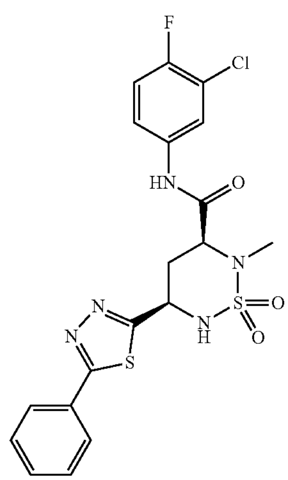 [SMILES: CN1[C@H](C(=O)Nc2ccc(F)c(Cl)c2)C[C@H](c2nnc(-c3ccccc3)s2)NS1(=O)=O] | 4% | 482.05 (M + 1) | 481.04 for $C_{19}H_{17}ClFN_5O_3S_2$ | ¹H-NMR (DMSO-$d_6$, 400 MHz): δ 10.64 (s, 1H), 8.12-8.09 (m, 1H), 8.02-7.97 (m, 3H), 7.63-7.54 (m, 4H), 7.42 (t, J = 9.1 Hz, 1H), 5.19-5.15 (m, 1H), 4.43 (dd, J = 12.0, 2.7 Hz, 1H), 2.65 (s, 3H), 2.36-2.29 (m, 2H). |
| HBV-CSU-122 | 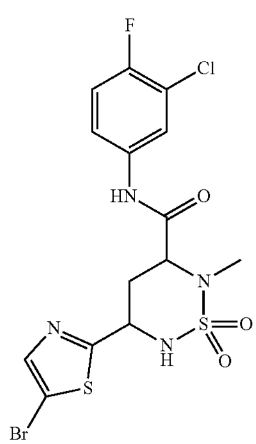 | 86% | 484.10 (M + 2) | 481.93 for $C_{14}H_{13}BrClFN_4O_3S_2$ | ¹H-NMR (DMSO-$d_6$, 400 MHz): δ 10.58 (s, 1H), 7.96 (dd, J = 6.8, 2.6 Hz, 1H), 7.94 (br.s, 1H), 7.89 (s, 1H), 7.59-7.53 (m, 1H), 7.40 (t, J = 9.1 Hz, 1H), 4.96-4.87 (m, 1H), 4.38-4.32 (m, 1H), 2.62 (s, 3H), 2.39-2.33 (m, 1H), 2.22-2.07 (m, 1H). |

TABLE 2-continued

Analytical data for HBV-CSU racemic & pure enantiomers:

| Target No | Structure | Rx. Yield (%) | Mass Spec. Found (m/z) | Mass Spec. Calculated | ¹H-NMR |
|---|---|---|---|---|---|
| HBV-CSU-122-ISO-I | 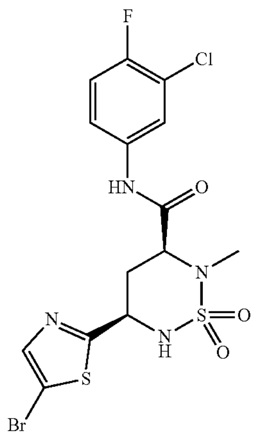 | 20% | 483.10 (M + 1) | 481.93 for $C_{14}H_{13}BrClFN_4O_3S_2$ | ¹H-NMR (DMSO-$d_6$, 400 MHz): δ 10.59 (s, 1H), 7.98-7.95 (m, 2H), 7.89 (s, 1H), 7.58-7.53 (m, 1H), 7.40 (t, J = 9.1 Hz, 1H), 4.97-4.88 (m, 1H), 4.38-4.32 (m, 1H), 2.62 (s, 3H), 2.39-2.33 (m, 1H), 2.20-2.09 (m, 1H). |
| HBV-CSU-122-ISO-II | 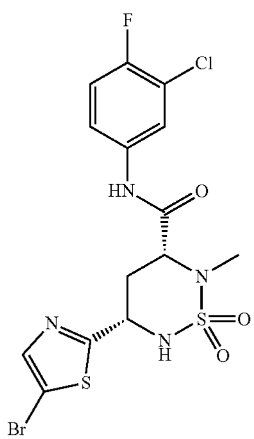 [SMILES: CN1[C@@H](C(=O)Nc2ccc(F)c(Cl)c2)C[C@@H](c2ncc(Br)s2)NS1(=O)=O] | 20% | 483.10 (M + 1) | 481.93 for $C_{14}H_{13}BrClFN_4O_3S_2$ | ¹H-NMR (DMSO-$d_6$, 400 MHz): δ 10.59 (s, 1H), 7.97 (dd, J = 6.7, 2.6 Hz, 2H), 7.89 (s, 1H), 7.59-7.53 (m, 1H), 7.45-7.36 (m, 1H), 4.94-4.89 (m, 1H), 4.36-4.31 (m, 1H), 2.62 (s, 3H), 2.39-2.31 (m, 1H), 2.20-2.08 (m, 1H). |
| HBV-CSU-122-Trans-ISO-I | 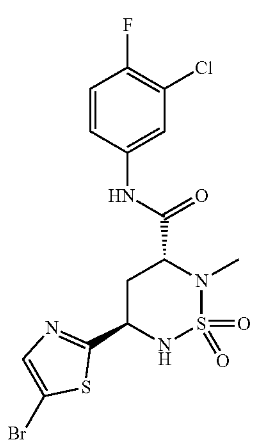 | 10% | 485 (M + 2) | 481.93 for $C_{14}H_{13}BrClFN_4O_3S_2$ | ¹H-NMR (DMSO-$d_6$, 400 MHz): δ 10.19 (s, 1H), 7.96-7.86 (m, 3H), 7.60-7.55 (m, 1H), 7.38 (t, J = 8.8 Hz, 1H), 5.06-5.00 (m, 1H), 4.50 (t, J = 4.4 Hz, 1H), 2.86 (s, 3H), 2.47-2.40 (m, 1H), 2.17-2.10 (m, 1H). |

TABLE 2-continued

Analytical data for HBV-CSU racemic & pure enantiomers:

| Target No | Structure | Rx. Yield (%) | Mass Spec. Found (m/z) | Mass Spec. Calculated | $^1$H-NMR |
|---|---|---|---|---|---|
| HBV-CSU-122-Trans-ISO-II | 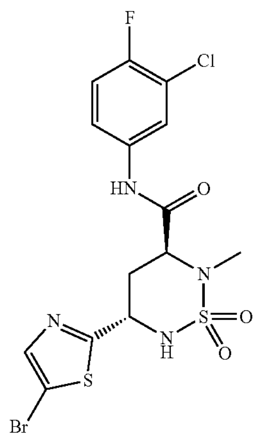 | 7% | 485 (M + 2) | 481.93 for $C_{14}H_{13}BrClFN_4O_3S_2$ | $^1$H-NMR (DMSO-$d_6$, 400 MHz): δ 10.18 (s, 1H), 7.95-7.94 (m, 1H), 7.88-7.85 (m, 2H), 7.59-7.56 (m, 1H), 7.37 (t, J = 8.8 Hz, 1H), 5.05-5.00 (m, 1H), 4.49 (t, J = 4.8 Hz, 1H), 2.85 (s, 3H), 2.49-2.41 Br (m, 1H), 2.15-2.12 (m, 1H). |
| HBV-CSU-123 | 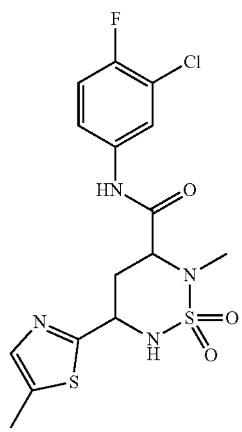 [SMILES: Cc1cnc(C2CC(C(=O)Nc3ccc(F)c(Cl)c3)N(C)S(=O)(=O)N2)s1] | 88% | 419.10 (M + 1) | 418.03 for $C_{15}H_{16}ClFN_4O_3S_2$ | $^1$H-NMR (DMSO-$d_6$, 400 MHz): δ 10.56 (s, 1H), 7.97 (dd, J = 6.8, 2.5 Hz, 1H), 7.85 (d, J = 6.1 Hz, 1H), 7.58-7.56 (m, 1H), 7.47 (s, 1H), 7.40 (t, J = 9.1 Hz, 1H), 4.88-4.82 (m, 1H), 4.35-4.31 (m, 1H), 2.62 (s, 3H), 2.45 (s, 3H), 2.36-2.31 (m, 1H), 2.21-2.11 (m, 1H). |
| HBV-CSU-123-ISO-I | 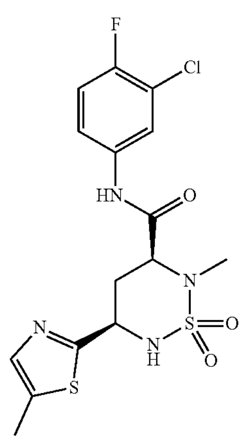 | 19% | 419.10 (M + 1) | 418.03 for $C_{15}H_{16}ClFN_4O_3S_2$ | $^1$H-NMR (DMSO-$d_6$, 400 MHz): δ 10.58 (s, 1H), 7.97 (dd, J = 6.8, 2.6 Hz, 1H), 7.87 (d, J = 8.2 Hz, 1H), 7.60-7.51 (m, 1H), 7.47 (s, 1H), 7.40 (t, J = 9.1 Hz, 1H), 4.88-4.81 (m, 1H), 4.36-4.30 (m, 1H), 2.61 (s, 3H), 2.45 (s, 3H), 2.36-2.30 (m, 1H), 2.22-2.10 (m, 1H). |

TABLE 2-continued

Analytical data for HBV-CSU racemic & pure enantiomers:

| Target No | Structure | Rx. Yield (%) | Mass Spec. Found (m/z) | Mass Spec. Calculated | ¹H-NMR |
|---|---|---|---|---|---|
| HBV-CSU-123-ISO-II | 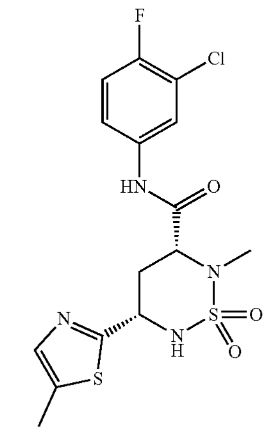 [SMILES: Cc1cnc([C@@H]2C[C@H](C(=O)Nc3ccc(F)c(Cl)c3)N(C)S(=O)(=O)N2)s1] | 18% | 419.10 (M + 1) | 418.03 for $C_{15}H_{16}ClFN_4O_3S_2$ | ¹H-NMR (DMSO-$d_6$, 400 MHz): δ 10.58 (s, 1H), 7.97 (dd, J = 6.8, 2.6 Hz, 1H), 7.86 (d, J = 8.2 Hz, 1H), 7.59-7.53 (m, 1H), 7.47 (s, 1H), 7.40 (t, J = 9.1 Hz, 1H), 4.88-4.81 (m, 1H), 4.36-4.30 (m, 1H), 2.61 (s, 3H), 2.45 (s, 3H), 2.36-2.32 (m, 1H), 2.21-2.10 (m, 1H). |
| HBV-CSU-124 | 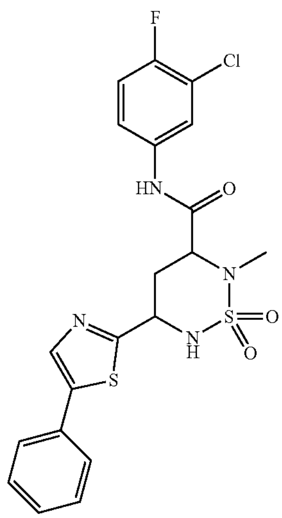 [SMILES: CN1C(C(=O)Nc2ccc(F)c(Cl)c2)CC(c2ncc(-c3ccccc3)s2)NS1(=O)=O] | 32% | 481.20 (M + 1) | 480.05 for $C_{20}H_{18}ClFN_4O_3S_2$ | ¹H-NMR (DMSO-$d_6$, 400 MHz): δ 10.59 (s, 1H), 8.19 (s, 1H), 8.00-7.93 (m, 2H), 7.69 (d, J = 7.5 Hz, 2H), 7.61-7.55 (m, 1H), 7.46 (t, J = 7.6 Hz, 2H), 7.43-7.36 (m, 2H), 4.99-4.92 (m, 1H), 4.41-4.36 (m, 1H), 2.64 (s, 3H), 2.44-2.39 (m, 1H), 2.28-2.16 (m, 1H). |
| HBV-CSU-124-ISO-I | 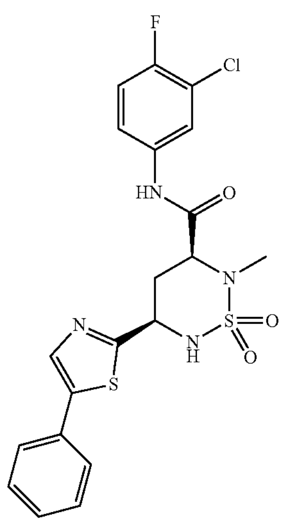 [SMILES: CN1[C@H](C(=O)Nc2ccc(F)c(Cl)c2)C[C@H](c2ncc(-c3ccccc3)s2)NS1(=O)=O] | 13% | 481.1 (M + 1) | 480.05 for $C_{20}H_{18}ClFN_4O_3S_2$ | ¹H-NMR (DMSO-$d_6$, 400 MHz): δ 10.59 (s, 1H), 8.19 (s, 1H), 8.01-7.92 (m, 2H), 7.72-7.64 (m, 2H), 7.60-7.54 (m, 1H), 7.49-7.34 (m, 4H), 5.00-4.92 (m, 1H), 4.41-4.36 (m, 1H), 2.64 (s, 3H), 2.45-2.38 (m, 1H), 2.28-2.14 (m, 1H). |

TABLE 2-continued

Analytical data for HBV-CSU racemic & pure enantiomers:

| Target No | Structure | Rx. Yield (%) | Mass Spec. Found (m/z) | Mass Spec. Calculated | $^1$H-NMR |
|---|---|---|---|---|---|
| HBV-CSU-124-ISO-II | 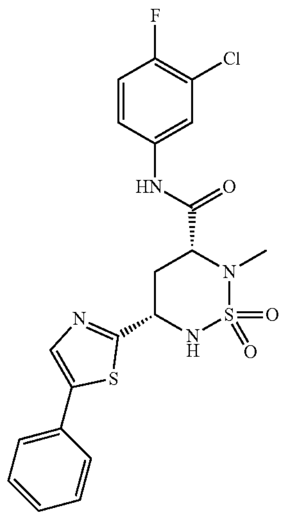 | 14% | 481.2 (M + 1) | 480.05 for $C_{20}H_{18}ClFN_4O_3S_2$ | $^1$H-NMR (DMSO-$d_6$, 400 MHz): δ 10.59 (s, 1H), 8.19 (s, 1H), 8.00-7.94 (m, 2H), 7.71-7.67 (m, 2H), 7.61-7.55 (m, 1H), 7.49-7.36 (m, 4H), 5.00-4.88 (m, 1H), 4.41-4.36 (m, 1H), 2.64 (s, 3H), 2.45-2.38 (m, 1H), 2.28-2.17 (m, 1H). |
| HBV-CSU-142 | 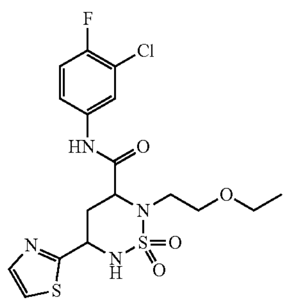 [SMILES: CCOCCN1C(C(=O)Nc2ccc(F)c(Cl)c2)CC(c2nccs2)NS1(=O)=O] | 42% | 463.20 (M + 1) | 462.06 for $C_{17}H_{20}ClFN_4O_4S_2$ | $^1$H-NMR (DMSO-$d_6$, 400 MHz): δ 10.51 (s, 1H), 7.95 (dd, J = 6.8, 2.6 Hz, 1H), 7.84 (br.s, 1H), 7.82 (d, J = 3.6 Hz, 1H), 7.79 (d, J = 3.2 Hz, 1H), 7.60-7.54 (m, 1H), 7.40 (t, J = 9.1 Hz, 1H), 5.00-4.92 (m, 1H), 4.67-4.61 (m, 1H), 3.56-3.43 (m, 2H), 3.43-3.35 (m, 1H), 3.35-3.29 (m, 2H), 3.14-3.06 (m, 1H), 2.40-2.33 (m, 1H), 2.12-2.00 (m, 1H), 0.93 (t, J = 7.0 Hz, 3H). |
| HBV-CSU-142-ISO-I | 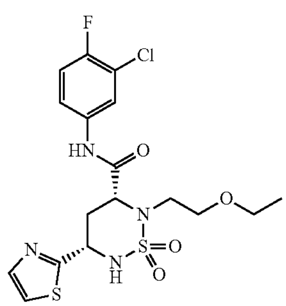 [SMILES: CCOCCN1[C@@H](C(=O)Nc2ccc(F)c(Cl)c2)C[C@@H](c2nccs2)NS1(=O)=O] | 10% | 463.00 (M + 1) | 462.06 for $C_{17}H_{20}ClFN_4O_4S_2$ | $^1$H-NMR (DMSO-$d_6$, 400 MHz): δ 10.51 (s, 1H), 7.95 (dd, J = 6.9, 2.5 Hz, 1H), 7.85-7.77 (m, 3H), 7.61-7.55 (m, 1H), 7.40 (t, J = 9.0 Hz, 1H), 5.00-4.92 (m, 1H), 5.00-4.92 (m, 1H), 3.56-3.44 (m, 2H), 3.43-3.36 (m, 1H), 3.34-3.28 (m, 2H), 3.14-3.04 (m, 1H), 2.40-2.33 (m, 1H), 2.13-1.99 (m, 1H), 0.93 (t, J = 7.0 Hz, 3H). |
| HBV-CSU-142-ISO-II | 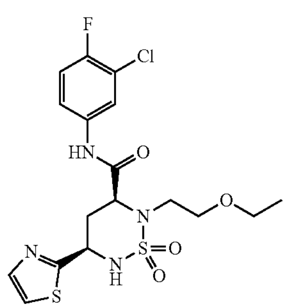 [SMILES: CCOCCN1[C@H](C(=O)Nc2ccc(F)c(Cl)c2)C[C@H](c2nccs2)NS1(=O)=O] | 8% | 463.00 (M + 1) | 462.06 for $C_{17}H_{20}ClFN_4O_4S_2$ | $^1$H-NMR (DMSO-$d_6$, 400 MHz): δ 10.51 (s, 1H), 7.95 (dd, J = 6.8, 2.5 Hz, 1H), 7.85 (s, 1H), 7.82 (d, J = 3.4 Hz, 1H), 7.79 (d, J = 3.1 Hz, 1H), 7.60-7.54 (m, 1H), 7.40 (t, J = 9.1 Hz, 1H), 5.01-4.90 (m, 1H), 4.67-4.61 (m, 1H), 3.56-3.44 (m, 2H), 3.43-3.36 (m, 1H), 3.35-3.28 (m, 2H), 3.14-3.04 (m 1H), 2.40-2.33 (m, 1H), 2.11-1.99 (m, 1H), 0.93 (t, J = 7.0 Hz, 3H). |

TABLE 2-continued

Analytical data for HBV-CSU racemic & pure enantiomers:

| Target No | Structure | Rx. Yield (%) | Mass Spec. Found (m/z) | Mass Spec. Calculated | ¹H-NMR |
|---|---|---|---|---|---|
| HBV-CSU-143 | 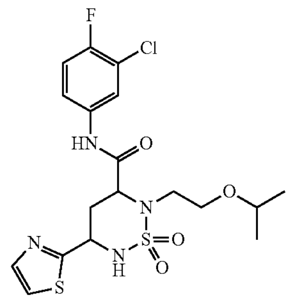 [SMILES: CC(C)OCCN1C(C(=O)Nc2ccc(F)c(Cl)c2)CC(c2nccs2)NS1(=O)=O] | 91% | 477.30 (M + 1) | 476.08 for $C_{18}H_{22}ClFN_4O_4S_2$ | ¹H-NMR (DMSO-$d_6$, 400 MHz): δ 10.51 (s, 1H), 7.94 (dd, J = 6.7, 2.6 Hz, 1H), 7.84-7.77 (m, 3H), 7.58-7.53 (m, 1H), 7.40 (t, J = 9.0 Hz, '1H), 4.98-4.92 (m, 1H), 4.65-4.61 (m, 1H), 3.54-3.33 (m, 4H), 3.07-3.29 (m, 1H), 2.38-2.33 (m, 1H), 2.12-1.93 (m, 1H), 0.92 (dd, J = 9.6, 6.1 Hz, 6H). |
| HBV-CSU-146 | 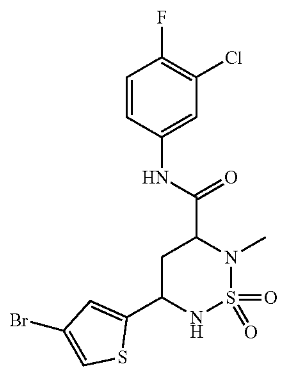 | 83% | 484.20 (M + 2) | 480.93 for $C_{15}H_{14}BrClFN_3O_3S_2$ | ¹H-NMR (DMSO-$d_6$, 400 MHz): δ 10.57 (s, 1H), 7.93 (dd, J = 6.4, 2.4 Hz, 1H), 7.68 (d, J = 9.2 Hz, 1H), 7.63 (d, J = 1.6 Hz, 1H), 7.54-7.51 (m, 1H), 7.37 (d, J = 8.8 Hz), 7.15 (s, 1H), 4.76-4.75 (m, 1H), 4.25 (dd, J = 12.0, 2.4 Hz, 1H), 2.58 (s, 3H), 2.25-2.21 (m, 1H), 2.09-2.05 (m, 1H). |
| HBV-CSU-146-ISO-I | 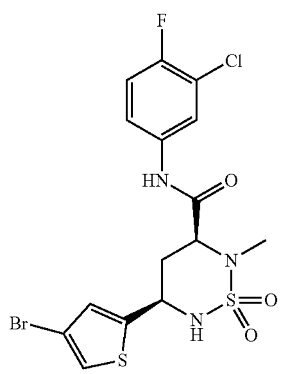 [SMILES: CN1[C@H](C(=O)Nc2ccc(F)c(Cl)c2)C[C@H](c2cc(Br)cs2)NS1(=O)=O] | 1% | 483.9 (M + 2) | 480.93 for $C_{15}H_{14}BrClFN_3O_3S_2$ | ¹H-NMR (DMSO-$d_6$, 400 MHz): δ 10.58 (s, 1H), 7.97 (dd, J = 6.8, 2.4 Hz, 1H), 7.74-7.69 (m, 1H), 7.66 (s, 1H), 7.58-7.53 (m, 1H), 7.4 (t, J = 9.6 Hz, 1H), 7.18 (s, 1H), 4.81-4.78 (m, 1H), 4.28 (dd, J = 11.6, 2.4 Hz, 1H), 2.61 (s, 3H), 2.28-2.21 (m, 1H), 2.15-2.08 (m, 1H). |
| HBV-CSU-146-ISO-II | 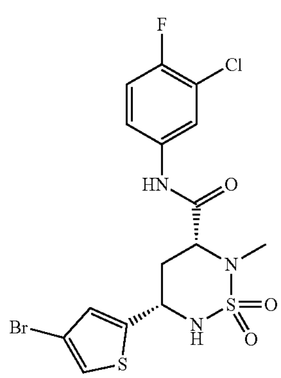 | 1% | 483.8 (M + 2) | 480.93 for $C_{15}H_{14}BrClFN_3O_3S_2$ | ¹H-NMR (DMSO-$d_6$, 400 MHz): δ 10.59 (s, 1H), 7.97 (dd, J = 6.8, 2.4 Hz, 1H), 7.74-7.69 (m, 1H), 7.65 (s, 1H), 7.58-7.53 (m, 1H), 7.40 (t, J = 9.6 Hz, 1H), 7.18 (s, 1H), 4.81-4.76 (m, 1H), 4.31-4.25 (m, 1H), 2.61 (s, 3H), 2.33-2.21 (m, 1H), 2.15-2.05 (m, 1H). |

TABLE 2-continued

Analytical data for HBV-CSU racemic & pure enantiomers:

| Target No | Structure | Rx. Yield (%) | Mass Spec. Found (m/z) | Mass Spec. Calculated | $^1$H-NMR |
|---|---|---|---|---|---|
| HBV-CSU-147 | 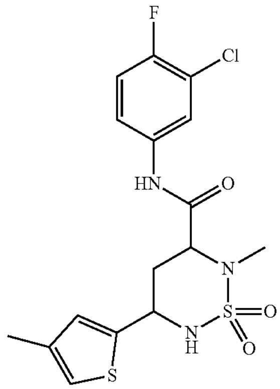 [SMILES: Cc1csc(C2CC(C(=O)Nc3ccc(F)c(Cl)c3)N(C)S(=O)(=O)N2)c1] | 46% | 418.0 (M + 1) | 417.04 for $C_{16}H_{17}ClFN_3O_3S_2$ | $^1$H-NMR (DMSO-$d_6$, 400 MHz): δ 10.55 (s, 1H), 7.97 (dd, J = 6.8, 2.4 Hz, 1H), 7.62 (d, J = 9.2 Hz, 1H), 7.58-7.53 (m, 1H), 7.4 (t, J = 9.2 Hz, 1H), 7.08 (s, 1H), 6.97 (s, 1H), 4.75-4.69 (m, 1H), 4.29 (dd, J = 11.2, 2.8 Hz, 1H), 2.61 (s, 3H), 2.21-2.07 (m, 5H). |
| HBV-CSU-147-ISO-I | 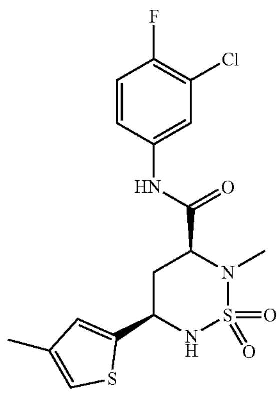 [SMILES: Cc1csc([C@H]2C[C@@H](C(=O)Nc3ccc(F)c(Cl)c3)N(C)S(=O)(=O)N2)c1] | 10% | 418.00 (M + 1) | 417.04 for $C_{16}H_{17}ClFN_3O_3S_2$ | $^1$H-NMR (DMSO-$d_6$, 400 MHz): δ 10.58 (s, 1H), 7.97 (dd, J = 6.8, 2.4 Hz, 1H), 7.64-7.6 (m, 1H), 7.57-7.53 (m, 1H), 7.4 (t, J = 9.2 Hz, 1H), 7.08 (s, 1H), 6.97 (s, 1H), 4.75-4.68 (m, 1H), 4.29 (dd, J = 11.6, 2.8 Hz, 1H), 2.6 (s, 3H), 2.21-2.06 (m, 5H). |
| HBV-CSU-147-ISO-II | 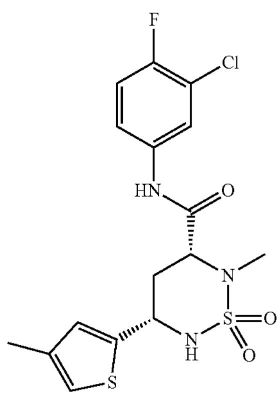 [SMILES: Cc1csc([C@@H]2C[C@H](C(=O)Nc3ccc(F)c(Cl)c3)N(C)S(=O)(=O)N2)c1] | 9% | 418.05 (M + 1) | 417.04 for $C_{16}H_{17}ClFN_3O_3S_2$ | $^1$H-NMR (DMSO-$d_6$, 400 MHz): δ 10.59 (s, 1H), 7.97 (dd, J = 6.8, 2.4 Hz, 1H), 7.64-7.6 (m, 1H), 7.58-7.53 (m, 1H), 7.4 (t, J = 9.2 Hz, 1H), 7.08 (s, 1H), 6.97 (s, 1H), 4.74-4.68 (m, 1H), 4.29 (dd, J = 11.6, 2.8 Hz, 1H), 2.6 (s, 3H), 2.21-2.06 (m, 5H). |
| HBV-CSU-148-ISO-I | 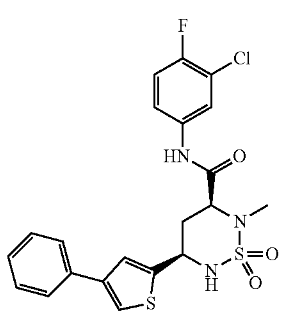 [SMILES: CN1[C@H](C(=O)Nc2ccc(F)c(Cl)c2)C[C@H](c2cc(-c3ccccc3)cs2)NS1(=O)=O] | 5% | 480.00 (M + 1) | 479.05 for $C_{21}H_{19}ClFN_3O_3S_2$ | $^1$H-NMR (DMSO-$d_6$, 400 MHz): δ 10.59 (s, 1H), 7.99 (dd, J = 6.8, 2.4 Hz, 1H), 7.84 (s, 1H), 7.75-7.69 (m, 3H), 7.61 (s, 1H), 7.59-7.52 (m, 1H), 7.44-7.38 (m, 3H), 7.31-7.27 (m, 1H), 4.84-4.8 (m, 1H), 4.31 (dd, J = 11.6, 2.4 Hz, 1H), 2.64 (s, 3H), 2.36-2.3 (m, 1H), 2.25-2.16 (m, 1H). |

TABLE 2-continued

Analytical data for HBV-CSU racemic & pure enantiomers:

| Target No | Structure | Rx. Yield (%) | Mass Spec. Found (m/z) | Mass Spec. Calculated | ¹H-NMR |
|---|---|---|---|---|---|
| HBV-CSU-148-ISO-II | 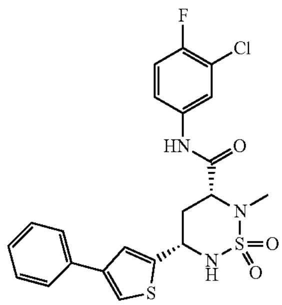 [SMILES: CN1[C@@H](C(=O)Nc2ccc(F)c(Cl)c2)C[C@@H](c2cc(-c3ccccc3)cs2)NS1(=O)=O] | 8% | 480.10 (M + 1) | 479.05 for $C_{21}H_{19}ClFN_3O_3S_2$ | ¹H-NMR (DMSO-$d_6$, 400 MHz): δ 10.59 (s, 1H), 7.99 (dd, J = 6.8, 2.4 Hz, 1H), 7.84 (s, 1H), 7.74-7.69 (m, 3H), 7.61 (s, 1H), 7.59-7.53 (m, 1H), 7.44-7.38 (m, 3H), 7.31-7.27 (m, 1H), 4.85-4.79 (m, 1H), 4.33-4.29 (m, 1H), 2.63 (s, 3H), 2.36-2.31 (m, 1H), 2.25-2.16 (m, 1H). |
| HBV-CSU-149-ISO-I | 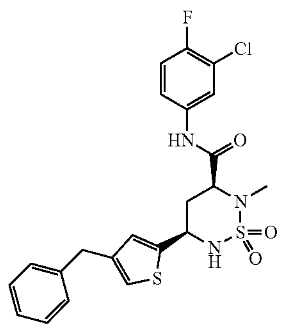 [SMILES: CN1[C@H](C(=O)Nc2ccc(F)c(Cl)c2)C[C@H](c2cc(Cc3ccccc3)cs2)NS1(=O)=O] | 3% | 494.4 (M + 1) | 493.07 for $C_{22}H_{21}ClFN_3O_3S_2$ | ¹H-NMR (DMSO-$d_6$, 400 MHz): δ 10.55 (s, 1H), 7.96 (dd, J = 6.8, 2.4 Hz, 2H), 7.64-7.52 (m, 1H), 7.39 (t, J = 9.2 Hz, 1H), 7.31-7.23 (m, 4H), 7.21-7.16 (m, 2H), 6.90 (s, 1H), 4.73-4.68 (m, 1H), 4.28 (dd, J = 11.6, 2.4 Hz, 1H), 3.87 (s, 2H), 2.59 (s, 3H), 2.21-2.15 (m, 1H), 2.09-2.05 (m, 1H). |
| HBV-CSU-149-ISO-II | 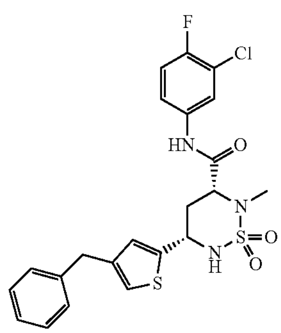 [SMILES: CN1[C@@H](C(=O)Nc2ccc(F)c(Cl)c2)C[C@@H](c2cc(Cc3ccccc3)cs2)NS1(=O)=O] | 4% | 494.4 (M + 1) | 493.07 for $C_{22}H_{21}ClFN_3O_3S_2$ | ¹H-NMR (DMSO-$d_6$, 400 MHz): δ 10.54 (s, 1H), 7.96 (dd, J = 6.8, 2.4 Hz, 1H), 7.63-7.52 (m, 2H), 7.39 (t, J = 9.2 Hz, 1H), 7.31-7.24 (m, 4H), 7.21-7.14 (m, 2H), 6.97 (s, 1H), 4.73-4.68 (m, 1H), 4.3-4.21 (m, 1H), 3.87 (s, 2H), 2.57 (s, 3H), 2.18-2.05 (m, 2H). |
| HBV-CSU-150 | 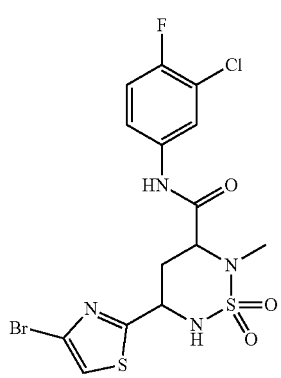 | 80% | 485.1 (M + 1) | 481.93 for $C_{14}H_{13}BrClFN_4O_3S_2$ | ¹H-NMR (DMSO-$d_6$, 400 MHz): δ 10.58 (s, 1H), 7.97 (dd, J = 6.8, 2.6 Hz, 1H), 7.95-7.91 (m, 2H), 7.59-7.54 (m, 1H), 7.40 (t, J = 9.1 Hz, 1H), 5.01-4.89 (m, 1H), 4.38-4.33 (m, 1H), 2.63 (s, 3H), 2.42-2.35 (m, 1H), 2.22-2.07 (m, 1H). |

TABLE 2-continued

Analytical data for HBV-CSU racemic & pure enantiomers:

| Target No | Structure | Rx. Yield (%) | Mass Spec. Found (m/z) | Mass Spec. Calculated | $^1$H-NMR |
|---|---|---|---|---|---|
| HBV-CSU-156 | 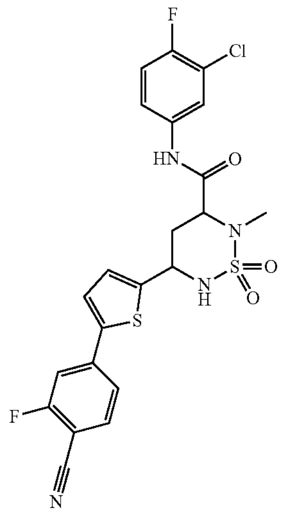 [SMILES: CN1C(C(=O)Nc2ccc(F)c(Cl)c2)CC(c2ccc(-c3ccc(C#N)c(F)c3)s2)NS1(=O)=O] | 28% | 523.2 (M + 1) | 522.04 for $C_{22}H_{17}ClF_2N_4O_3S_2$ | $^1$H-NMR (DMSO-$d_6$, 400 MHz): δ 10.60 (s, 1H), 7.99-7.87 (m, 3H), 7.82-7.78 (m, 1H), 7.75-7.73 (m, 1H), 7.67 (d, J = 8.4 Hz, 1H), 7.59-7.52 (m, 1H), 7.41 (t, J = 8.8 Hz, 1H), 7.25-7.24 (m, 1H), 4.87-4.83 (m, 1H), 4.36-4.31 (m, 1H), 2.63 (s, 3H), 2.33-2.28 (m, 1H), 2.21-2.12 (m, 1H). |
| HBV-CSU-156-ISO-I | 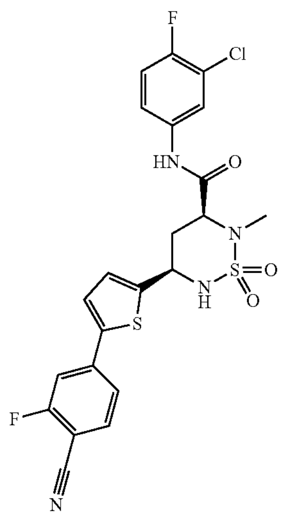 [SMILES: CN1[C@H](C(=O)Nc2ccc(F)c(Cl)c2)C[C@H](c2ccc(-c3ccc(C#N)c(F)c3)s2)NS1(=O)=O] | 9% | 523.10 (M + 1) | $C_{22}H_{17}ClF_2N_4O_3S_2$ for 522.04 | $^1$H-NMR (DMSO-$d_6$, 400 MHz): δ 10.59 (s, 1H), 7.99-7.86 (m, 3H), 7.81-7.78 (m, 1H), 7.75-7.35 (m, 1H), 7.67 (dd, J = 7.6, 2.4 Hz, 1.2, 1H), 7.59-7.54 (m, 1H), 7.41 (t, J = 9.2 Hz, 1H), 7.26-7.24 (m, 1H), 4.87-4.82 (m, 1H), 4.33 (dd, J = 11.2, 1.6 Hz, 1H), 2.63 (s, 3H), 2.35-2.28 (m, 1H), 2.21-2.14 (m, 1H) |
| HBV-CSU-156-ISO-II | 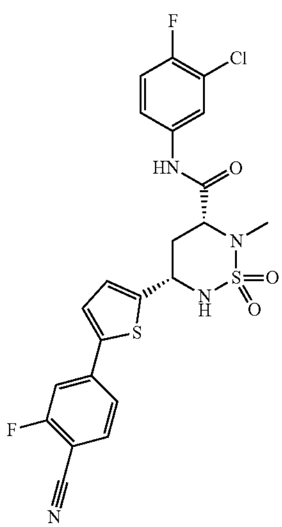 | 7% | 523.05 (M + 1) | $C_{22}H_{17}ClF_2N_4O_3S_2$ for 522.04 | $^1$H-NMR (DMSO-$d_6$, 400 MHz): δ 10.60 (s, 1H), 7.99-7.86 (m, 3H), 7.82-7.78 (m, 1H), 7.75-7.34 (m, 1H), 7.67 (dd, J = 8, 2.4 Hz, 1.2, 1H), 7.59-7.54 (m, 1H), 7.41 (t, J = 9.2 Hz, 1H), 7.26-7.24 (m, 1H), 4.86-4.81 (m, 1H), 4.34-4.3 (m, 1H), 2.63 (s, 3H), 2.32-2.27 (m, 1H), 2.21-2.13 (m, 1H) |

TABLE 2-continued

Analytical data for HBV-CSU racemic & pure enantiomers:

| Target No | Structure | Rx. Yield (%) | Mass Spec. Found (m/z) | Mass Spec. Calculated | ¹H-NMR |
|---|---|---|---|---|---|
| HBV-CSU-157 | 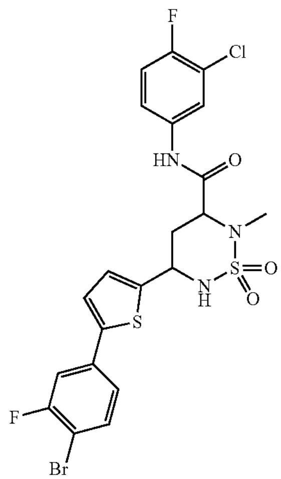 [SMILES: CN1C(C(=O)Nc2ccc(F)c(Cl)c2)CC(c2ccc(-c3ccc(Br)c(F)c3)s2)NS1(=O)=O] | 34% | 578.05 (M + 2) | 574.96 for $C_{21}H_{17}BrClF_2N_3O_3S_2$ | ¹H-NMR (DMSO-$d_6$, 400 MHz): δ 10.59 (s, 1H), 7.98 (dd, J = 6.8, 2.4 Hz, 1H), 7.78-7.7 (m, 3H), 7.59-7.54 (m, 2H), 7.45-7.38 (m, 2H), 7.19-7.17 (m, 1H), 4.84-4.78 (m, 1H), 4.32 (dd, J = 12, 2.4 Hz, 1H), 2.63 (s, 3H), 2.34-2.26 (m, 1H), 2.21-2.11 (m, 1H). |
| HBV-CSU-158 | 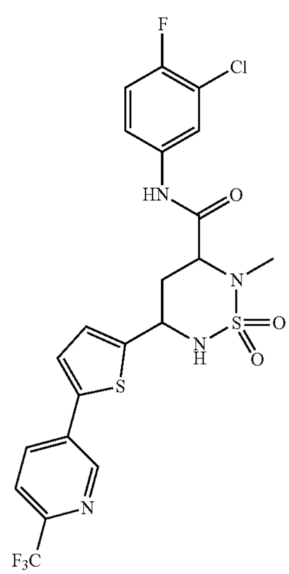 | 38% | 549 (M + 1) | 548.04 for $C_{21}H_{17}ClF_4N_4O_3S_2$ | ¹H-NMR (DMSO-$d_6$, 400 MHz): δ 10.6 (s, 1H), 9.10 (s, 1H), 8.3 (dd, J = 6.4, 2.0 Hz, 1H), 7.96 (dd, J = 6.8, 2.4 Hz, 1H), 7.94 (d, J = 8.4 Hz, 1H), 7.81 (d, J = 10.0 Hz, 1H), 7.75-7.73 (m, 1H), 7.59-7.54 (m, 1H), 7.41 (t, , J = 9.2 Hz, 1H), 7.28-7.27 (m, 1H), 4.90-4.83 (m, 1H), 4.34 (dd, J = 11.6, 2.4 Hz, 1H), 2.64 (s, 3H), 2.33-2.29 (m, 1H), 2.24-2.13 (m, 1H) |

TABLE 2-continued
Analytical data for HBV-CSU racemic & pure enantiomers:
| Target No | Structure | Rx. Yield (%) | Mass Spec. Found (m/z) | Mass Spec. Calculated | ¹H-NMR |
|---|---|---|---|---|---|
| HBV-CSU-158-ISO-I | 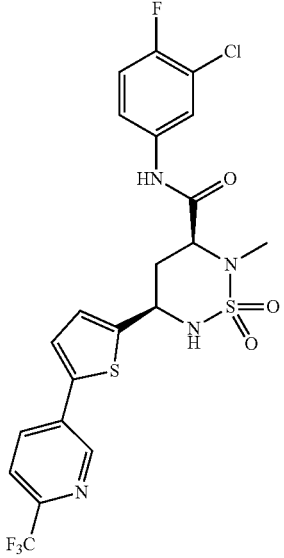 | 6% | 549.55 (M + 1) | 548.04 for $C_{21}H_{17}ClF_4N_4O_3S_2$ | ¹H-NMR (DMSO-$d_6$, 400 MHz): δ 10.57 (s, 1H), 9.09 (s, 1H), 8.31-8.29 (m, 1H), 7.98 (dd, J = 6.8, 2.4 Hz, 1H), 7.93 (d, J = 8.4 Hz, 1H), 7..88-7.72 (m, 2H), 7.6-7.52 (m, 1H), 7.41 (t, J = 9.2 Hz, 1H), 7.26-7.21 (m, 1H), 4.86-4.82 (m, 1H), 4.31-4.27 (m, 1H), 2.6 (s, 3H), 2.33-2.26 (m, 1H), 2.19-2.11 (m, 1H). |
| HBV-CSU-158-ISO-II | 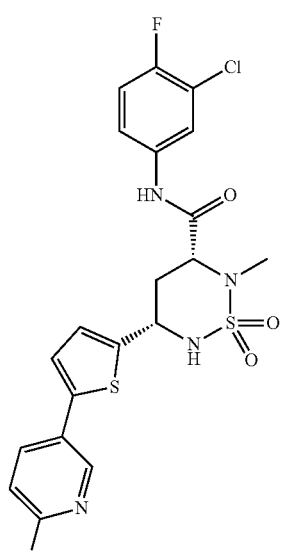 | 11% | 549.5 (M + 1) | 548.04 for $C_{21}H_{17}ClF_4N_4O_3S_2$ | ¹H-NMR (DMSO-$d_6$, 400 MHz): δ 10.58 (s, 1H), 9.09 (s, 1H), 8.32-8.29 (m, 1H), 7.98 (dd, J = 6.8, 2.4 Hz, 1H), 7.94 (d, J = 8 Hz, 1H), 7.89-7.71 (m, 2H), 7.6-7.55 (m, 1H), 7.41 (t, J = 8.8 Hz, 1H), 7.27-7.21 (m, 1H), 4.88-4.81 (m, 1H), 4.32-4.26 (m, 1H), 2.62 (s, 3H), 2.33-2.28 (m, 1H), 2.21-2.14 (m, 1H). |

TABLE 2-continued

Analytical data for HBV-CSU racemic & pure enantiomers:

| Target No | Structure | Rx. Yield (%) | Mass Spec. Found (m/z) | Mass Spec. Calculated | $^1$H-NMR |
|---|---|---|---|---|---|
| HBV-CSU-159 | 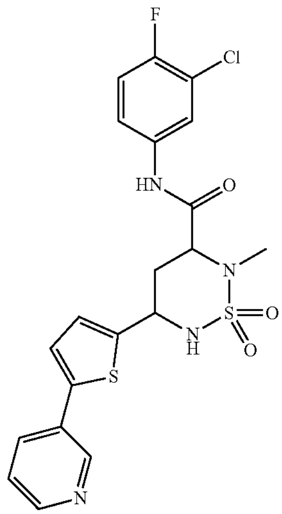 [SMILES: CN1C(C(=O)Nc2ccc(F)c(Cl)c2)CC(c2ccc(-c3cccnc3)s2)NS1(=O)=O] | 22% | 481 (M + 1) | 480.05 for $C_{20}H_{18}ClFN_4O_3S_2$ | $^1$H-NMR (DMSO-$d_6$, 400 MHz): δ 10.60 (s, 1H), 8.89 (s, 1H), 8.51-8.50 (m, 1H), 8.04-7.97 (m, 2H), 7.77 (d, J = 8.4 Hz, 1H), 7.59-7.51 (m, 2H), 7.48-7.38 (m, 2H), 7.22-7.20 (m, 1H), 4.87-4.80 (m, 1H), 4.35-4.31 (m, 1H), 2.63 (m, 3H), 2.35-2.12 (m, 2H). |
| HBV-CSU-159-ISO-I | 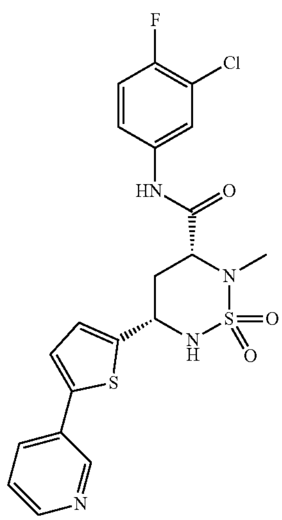 [SMILES: CN1[C@@H](C(=O)Nc2ccc(F)c(Cl)c2)C[C@@H](c2ccc(-c3cccnc3)s2)NS1(=O)=O] | 3% | 481.4 (M + 1) | $C_{20}H_{18}ClFN_4O_3S_2$ for 480.05 | $^1$H-NMR (DMSO-$d_6$, 400 MHz): δ 10.60 (s, 1H), 8.92-8.89 (m, 1H), 8.52-8.50 (m, 1H), 8.05-8.02 (m, 1H), 7.98 (dd, J = 6.8, 2.4 Hz, 1H), 7.78-7.76 (m, 1H), 7.59-7.54 (m, 2H), 7.47-7.38 (m, 2H), 7.22-7.2 (m, 1H), 4.85-4.81 (m, 1H), 4.33 (dd, J = 11.6, 2.4 Hz, 1H), 2.63 (s, 3H), 2.32-2.27 (m, 1H), 2.21-2.13 (m, 1H). |
| HBV-CSU-159-ISO-II | 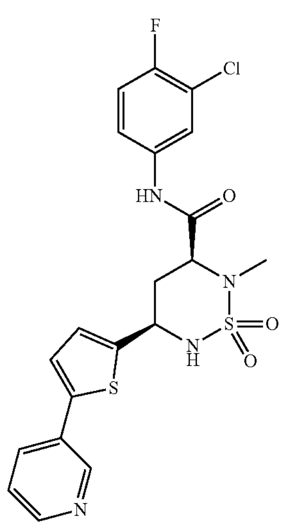 [SMILES: CN1[C@H](C(=O)Nc2ccc(F)c(Cl)c2)C[C@H](c2ccc(-c3cccnc3)s2)NS1(=O)=O] | 3% | 481.4 (M + 1) | $C_{20}H_{18}ClFN_4O_3S_2$ for 480.05 | $^1$H-NMR (DMSO-$d_6$, 400 MHz): δ 10.6 (s, 1H), 8.95-8.88 (m, 1H), 8.52-8 (m, 1H), 8.05-8.02 (m, 1H), 7.98 (dd, J = 6.8, 2.4 Hz, 1H), 7.78-7.75 (m, 1H), 7.59-7.54 (m, 2H), 7.47-7.38 (m, 2H), 7.22-7.2 (m, 1H), 4.85-4.81 (m, 1H), 4.33 (dd, J = 11.6, 2.4 Hz, 1H), 2.63 (s, 3H), 2.32-2.27 (m, 1H), 2.23-2.12 (m, 1H). |

TABLE 2-continued

Analytical data for HBV-CSU racemic & pure enantiomers:

| Target No | Structure | Rx. Yield (%) | Mass Spec. Found (m/z) | Mass Spec. Calculated | ¹H-NMR |
|---|---|---|---|---|---|
| HBV-CSU-160 | 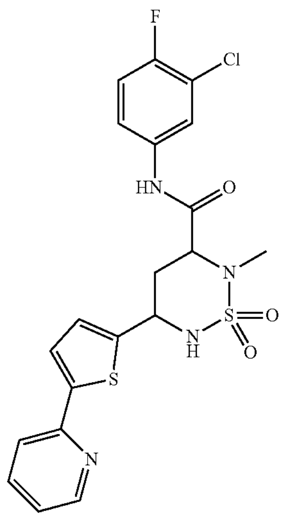 [SMILES: CN1C(C(=O)Nc2ccc(F)c(Cl)c2)CC(c2ccc(-c3ccccn3)s2)NS1(=O)=O] | 56% | 481.05 (M + 1) | 480.05 for $C_{20}H_{18}ClFN_4O_3S_2$ | ¹H-NMR (DMSO-$d_6$, 400 MHz): δ 10.62 (s, 1H), 8.52 (d, J = 4.4 Hz, 1H), 7.98 (dd, J = 6.8, 2.4 Hz, 1H), 7.91 (d, J = 8.4 Hz, 1H), 7.86-7.82 (m, 1H), 7.76 (d, J = 9.6 Hz, 1H), 7.69 (d, J = 4.0 Hz, 1H), 7.59-7.55 (m, 1H), 7.42 (t, J = 9.2 Hz, 1H), 7.29-7.27 (m, 1H), 7.18 (d, J = 3.6 Hz, 1H), 4.81 (t, J = 9.2 Hz, 1H), 4.31 (dd, J = 12.4, 3.2 Hz, 1H), 2.63 (s, 3H), 2.31-2.15 (m, 2H). |
| HBV-CSU-160-ISO-I | 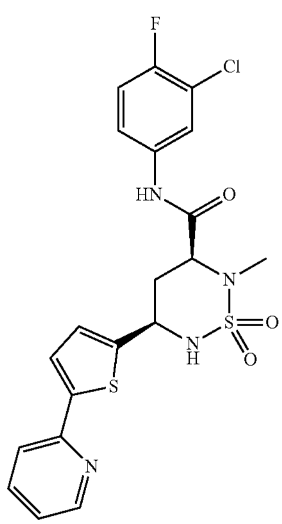 [SMILES: CN1[C@H](C(=O)Nc2ccc(F)c(Cl)c2)C[C@H](c2ccc(-c3ccccn3)s2)NS1(=O)=O] | 6% | 481.15 (M + 1) | 480.05 for $C_{20}H_{18}ClFN_4O_3S_2$ | ¹H-NMR (DMSO-$d_6$, 400 MHz): δ 10.58 (s, 1H), 8.50 (d, J = 4.4 Hz, 1H), 7.96 (d, J = 5.2 Hz, 1H), 7.88 (d, J = 7.6 Hz, 1H), 7.83-7.79 (m, 1H), 7.72 (br.s, 1H), 7.67 (d, J = 4.0 Hz, 1H), 7.56-7.54 (m, 1H), 7.39 (t, J = 8.8 Hz, 1H), 7.26 (t, J = 6.4 Hz, 1H), 7.16 (d, J = 3.6 Hz, 1H), 4.81-4.80 (m, 1H), 4.29 (d, J = 10.4 Hz, 1H), 2.62 (s, 3H), 2.28-2.11 (m, 2H). |

TABLE 2-continued

Analytical data for HBV-CSU racemic & pure enantiomers:

| Target No | Structure | Rx. Yield (%) | Mass Spec. Found (m/z) | Mass Spec. Calculated | $^1$H-NMR |
|---|---|---|---|---|---|
| HBV-CSU-160-ISO-II | 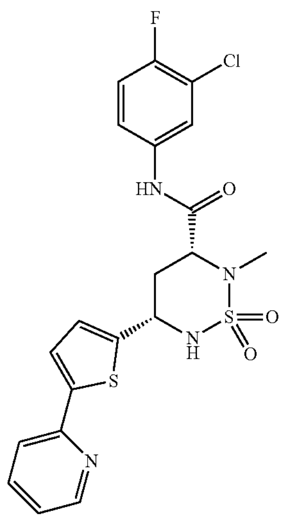 [SMILES: CN1[C@@H](C(=O)Nc2ccc(F)c(Cl)c2)C[C@@H](c2ccc(-c3ccccn3)s2)NS1(=O)=O] | 9% | 481.15 (M + 1) | 480.05 for $C_{20}H_{18}ClFN_4O_3S_2$ | $^1$H-NMR (DMSO-$d_6$, 400 MHz): δ 10.58 (s, 1H), 8.50 (d, J = 4.4 Hz, 1H), 7.96 (dd, J = 6.8, 2.4 Hz, 1H), 7.88 (d, J = 8.4 Hz, 1H), 7.83-7.79 (m, 1H), 7.72 (d, J = 9.6 Hz, 1H), 7.68 (d, J = 4.0 Hz, 1H), 7.57-7.53 (m, 1H), 7.39 (t, J = 8.8 Hz, 1H), 7.27-7.24 (m, 1H), 7.16 (d, J = 4.0 Hz, 1H), 4.82-4.77 (m, 1H), 4.29 (dd, J = 11.6, 2.8 Hz, 1H), 2.66 (s, 3H), 2.31-2.11 (m, 2H). |
| HBV-CSU-161 | 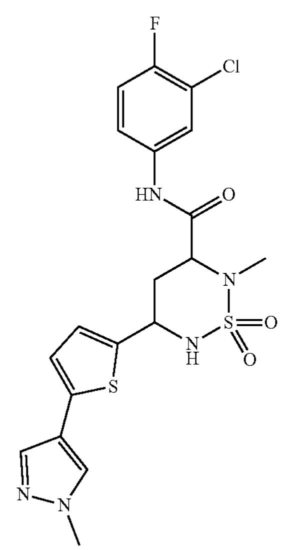 [SMILES: CN1C(C(=O)Nc2ccc(F)c(Cl)c2)CC(c2ccc(-c3cnn(C)c3)s2)NS1(=O)=O] | 30% | 484.4 (M + 1) | 483.06 for $C_{19}H_{19}ClFN_5O_3S_2$ | $^1$H-NMR (DMSO-$d_6$, 400 MHz): δ 10.59 (s, 1H), 8.01 (s, 1H), 7.97 (dd, J = 6.8, 2.4 Hz, 1H), 7.70-7.66 (m, 2H), 7.58-7.54 (m, 1H), 7.4 (t, J = 9.2 Hz, 1H), 7.05-7.04 (m, 2H), 4.79-4.70 (m, 1H), 4.3 (dd, J = 11.6, 2.8 Hz, 1H), 3.84 (s, 3H), 2.61 (s, 3H), 2.26-2.12 (m, 2H). |

TABLE 2-continued

Analytical data for HBV-CSU racemic & pure enantiomers:

| Target No | Structure | Rx. Yield (%) | Mass Spec. Found (m/z) | Mass Spec. Calculated | ¹H-NMR |
|---|---|---|---|---|---|
| HBV-CSU-161-Trans-(Rac) | 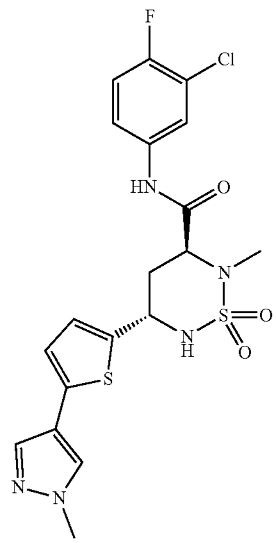 [SMILES: CN1[C@H](C(=O)Nc2ccc(F)c(Cl)c2)C[C@@H](c2ccc(-c3cnn(C)c3)s2)NS1(=O)=O] | 50% | 484.10 (M + 1) | 483.06 for $C_{19}H_{19}ClFN_5O_3S_2$ | ¹H-NMR (DMSO-$d_6$, 400 MHz): δ 10.04 (s, 1H), 8.02 (s, 1H), 7.97 (dd, J = 6.8, 2.4 Hz, 1H), 7.70 (s, 1H), 7.61-7.56 (m, 1H), 7.45-7.41 (m, 1H), 7.38 (t, J = 8.8 Hz, 1H), 7.06-7.03 (m, 2H), 4.90-4.87 (m, 1H), 4.44-4.43 (m, 1H), 3.85 (s, 3H), 2.95 (s, 3H), 2.35-2.31 (m, 1H), 1.99-1.93 (m, 1H). |
| HBV-CSU-161-ISO-I | 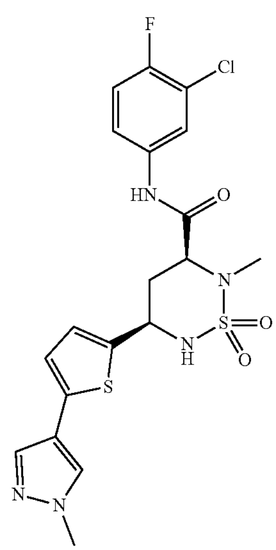 [SMILES: CN1[C@H](C(=O)Nc2ccc(F)c(Cl)c2)C[C@H](c2ccc(-c3cnn(C)c3)s2)NS1(=O)=O] | 7% | 484.1 (M + 1) | 483.06 for $C_{19}H_{19}ClFN_5O_3S_2$ | ¹H-NMR (DMSO-$d_6$, 400 MHz): δ 10.6 (s, 1H), 8.1-7.97 (m, 1H), 7.69 (br.s, 2H), 7.59-7.54 (m, 2H), 7.4 (t, J = 8.8 Hz, 1H), 7.04 (br. s, 2H), 4.78-4.72 (m, 1H), 4.32-4.28 (m, 1H), 3.84 (s, 3H), 2.61 (s, 3H), 2.26-2.05 (m, 2H). |

TABLE 2-continued

Analytical data for HBV-CSU racemic & pure enantiomers:

| Target No | Structure | Rx. Yield (%) | Mass Spec. Found (m/z) | Mass Spec. Calculated | ¹H-NMR |
|---|---|---|---|---|---|
| HBV-CSU-161-ISO-II | 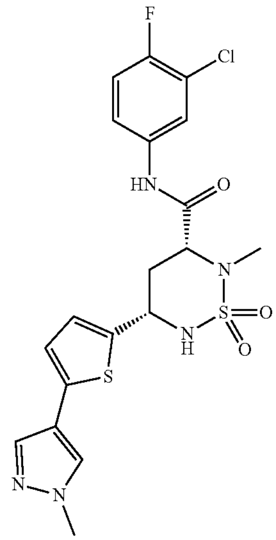 [SMILES: CN1[C@@H](C(=O)Nc2ccc(F)c(Cl)c2)C[C@@H](c2ccc(-c3cnn(C)c3)s2)NS1(=O)=O] | 9% | 484.05 (M + 1) | 483.06 for $C_{19}H_{19}ClFN_5O_3S_2$ | ¹H-NMR (DMSO-$d_6$, 400 MHz): δ 10.58 (s, 1H), 8.1-7.96 (m, 1H), 7.69 (br.s, 2H), 7.59-7.54 (m, 2H), 7.4 (t, J = 8.8 Hz, 1H), 7.04 (br.s, 2H), 4.76-4.73 (m, 1H), 4.31-4.27 (m, 1H), 3.84 (s, 3H), 2.61 (s, 3H), 2.25-2.07 (m, 2H). |
| HBV-CSU-162 | 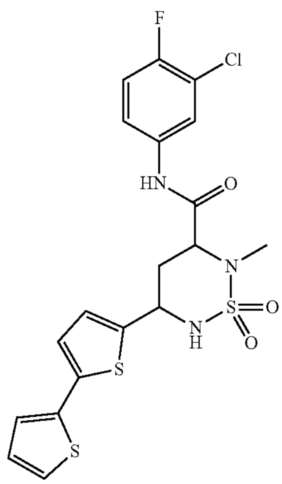 [SMILES: CN1C(C(=O)Nc2ccc(F)c(Cl)c2)CC(c2ccc(-c3cccs3)s2)NS1(=O)=O] | 32% | 508.2 (M + 23) | 485.01 for $C_{19}H_{17}ClFN_3O_3S_3$ | ¹H-NMR (DMSO-$d_6$, 400 MHz): δ 10.59 (s, 1H), 7.98 (dd, J = 6.8, 2.4 Hz, 1H), 7.74 (d, J = 9.2 Hz, 1H), 7.59-7.54 (m, 1H), 7.53-7.5 (m, 1H), 7.41 (t, J = 9.2 Hz, 1H), 7.31-7.29 (m, 1H), 7.19-7.18 (m, 1H), 7.11-7.08 (m, 2H) 4.82-4.76 (m, 1H), 4.31 (dd, J = 12, 2.8 Hz, 1H), 2.62 (s, 3H), 2.29-2.21 (m, 1H), 2.19-2.09 (m, 1H). |
| HBV-CSU-162-ISO-I | 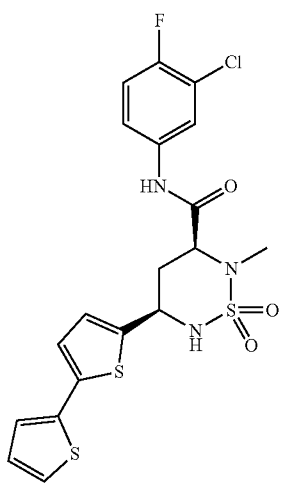 [SMILES: CN1[C@H](C(=O)Nc2ccc(F)c(Cl)c2)C[C@H](c2ccc(-c3cccs3)s2)NS1(=O)=O] | 5% | 508.1 (M + 2)⁺ | 485.01 for $C_{19}H_{17}ClFN_3O_3S_3$ | ¹H-NMR (DMSO-$d_6$, 400 MHz): δ 10.6 (s, 1H), 7.98 (dd, J = 6.8, 2.4 Hz, 1H), 7.72-7.57 (m, 1H), 7.59-7.54 (m, 1H), 7.41 (t, J = 9.6 Hz, 1H), 7.31-7.29 (m, 1H), 7.21-7.18 (m, 1H), 7.11-7.08 (m, 2H), 4.81-4.78 (m, 2H), 4.32 (dd, J = 12, 2.4 Hz, 1H), 2.63 (s, 3H), 2.35-2.25 (m, 1H), 2.21-2.13 (m, 1H). |

TABLE 2-continued

Analytical data for HBV-CSU racemic & pure enantiomers:

| Target No | Structure | Rx. Yield (%) | Mass Spec. Found (m/z) | Mass Spec. Calculated | $^1$H-NMR |
|---|---|---|---|---|---|
| HBV-CSU-162-ISO-II | 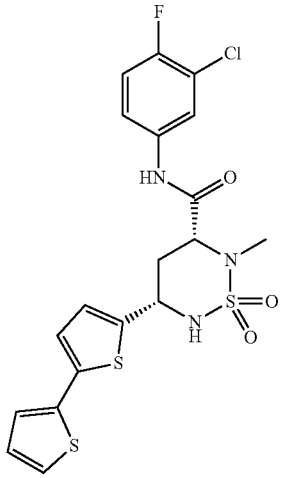 [SMILES: CN1[C@@H](C(=O)Nc2ccc(F)c(Cl)c2)C[C@@H](c2ccc(-c3cccs3)s2)NS1(=O)=O] | 7% | 376 (M − 109) | 485.01 for $C_{19}H_{17}ClFN_3O_3S_3$ | $^1$H-NMR (DMSO-$d_6$, 400 MHz): δ 10.55 (s, 1H), 7.95 (dd, J = 7.2, 2.8 Hz, 1H), 7.72-7.69 (m, 1H), 7.56-7.51 (m, 1H), 7.49-7.47 (m, 1H), 7.37 (t, J = 9.6 Hz, 1H), 7.27-7.26 (m, 1H), 7.16-7.15 (m, 1H), 7.08-7.04 (m, 2H), 4.76-4.71 (m, 1H), 4.28 (dd, J = 11.6, 2.4 Hz, 1H), 2.59 (s, 3H), 2.26-2.21 (m, 1H), 2.18-2.06 (m, 1H). |
| HBV-CSU-163 | 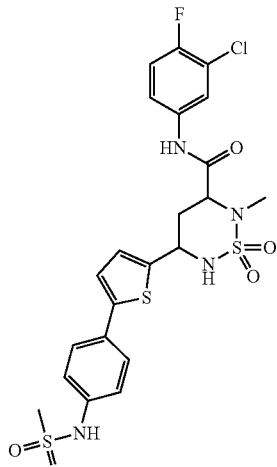 | 25% | 572.9 (M + 1) | 572.04 for $C_{22}H_{22}ClFN_4O_5S_3$ | $^1$H-NMR (DMSO-$d_6$, 400 MHz): δ 10.59 (s, 1H), 9.88 (s, 1H), 7.98 (dd, J = 7.2, 2.8 Hz, 1H), 7.75-7.71 (m, 1H), 7.63-7.54 (m, 3H), 7.41 (t, J = 8.8 Hz, 1H), 7.34-7.32 (m, 1H), 7.24 (d, J = 8.8 Hz, 2H), 7.14-7.12 (m, 1H), 4.83-4.77 (m, 1H), 4.32 (dd, J = 11.6, 2.8 Hz, 1H), 3.02 (s, 3H), 2.63 (s, 3H), 2.29-2.25 (m, 1H), 2.22-2.14 (m, 1H). |
| HBV-CSU-163-ISO-I | 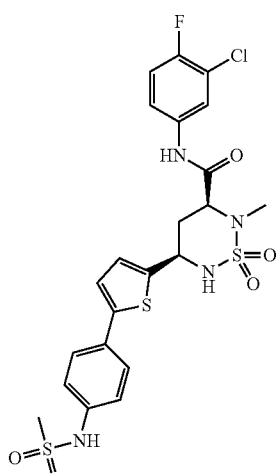 | 6% | 572.70 (M + 1) | 572.04 for $C_{22}H_{22}ClFN_4O_5S_3$ | $^1$H-NMR (DMSO-$d_6$, 400 MHz): δ 10.59 (s, 1H), 9.86 (s, 1H), 7.98 (d, J = 5.2 Hz, 1H), 7.77-7.57 (m, 4H), 7.41 (t, J = 8.8 Hz, 1H), 7.32 (d, J = 8.4 Hz, 1H), 7.23 (d, J = 8.0 Hz, 2H), 7.13 (d, J = 3.6 Hz, 1H), 4.85-4.77 (m, 1H), 4.33-4.29 (m, 1H), 3.02 (s, 3H), 2.63 (s, 3H), 2.31-2.13 (m, 2H). |

TABLE 2-continued

Analytical data for HBV-CSU racemic & pure enantiomers:

| Target No | Structure | Rx. Yield (%) | Mass Spec. Found (m/z) | Mass Spec. Calculated | 1H-NMR |
|---|---|---|---|---|---|
| HBV-CSU-163-ISO-II | 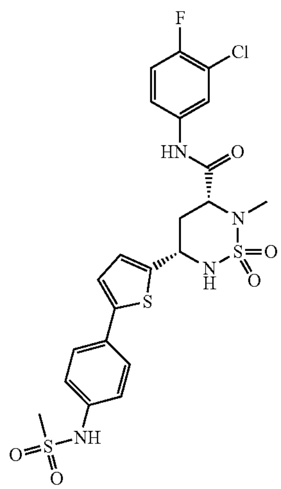 [SMILES: CN1C(C(=O)Nc2ccc(F)c(Cl)c2)CC(c2ccc(-c3ccc(NS(C)(=O)=O)cc3)s2)NS1(=O)=O] | 3% | 574.75 (M + 2) | 572.04 for $C_{22}H_{22}ClFN_4O_5S_3$ | 1H-NMR (DMSO-$d_6$, 400 MHz): δ 10.59 (s, 1H), 9.84 (s, 1H), 7.98 (dd, J = 6.4, 2.4 Hz, 1H), 7.74-7.57 (m, 4H), 7.41 (t, J = 8.8 Hz, 1H), 7.32 (d, J = 4.0 Hz, 1H), 7.23 (d, J = 8.8 Hz, 2H), 7.12 (d, J = 3.6 Hz, 1H), 4.82-4.77 (m, 1H), 4.33-4.30 (m, 1H), 3.02 (s, 3H), 2.62 (s, 3H), 2.29-2.11 (m, 2H). |
| HBV-CSU-164 | 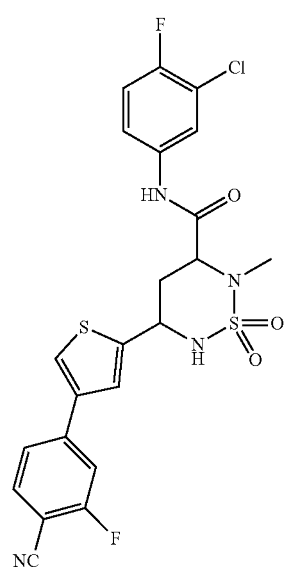 [SMILES: CN1C(C(=O)Nc2ccc(F)c(Cl)c2)CC(c2cc(-c3ccc(C#N)c(F)c3)cs2)NS1(=O)=O] | 39% | 523.6 (M + 1) | 522.04 for $C_{22}H_{17}ClF_2N_4O_3S_2$ | 1H-NMR (DMSO-$d_6$, 400 MHz): δ 10.6 (s, 1H), 8.23 (s, 1H), 8.02-7.93 (m, 3H), 7.83-7.75 (m, 3H), 7.6-7.55 (m, 1H), 7.43-7.38 (m, 1H), 4.86-4.8 (m, 1H), 4.32-4.29 (m, 1H), 2.63 (s, 3H), 2.39-2.32 (m, 1H), 2.27-2.2 (m, 1H). |

TABLE 2-continued

Analytical data for HBV-CSU racemic & pure enantiomers:

| Target No | Structure | Rx. Yield (%) | Mass Spec. Found (m/z) | Mass Spec. Calculated | $^1$H-NMR |
|---|---|---|---|---|---|
| HBV-CSU-164-ISO-I | 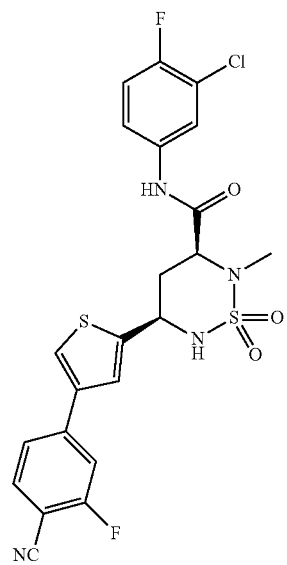 [SMILES: CN1[C@H](C(=O)Nc2ccc(F)c(Cl)c2)C[C@H](c2cc(-c3ccc(C#N)c(F)c3)cs2)NS1(=O)=O] | 11% | 523.45 (M + 1) | 522.04 for $C_{22}H_{17}ClF_2N_4O_3S_2$ | $^1$H-NMR (DMSO-$d_6$, 400 MHz): δ 10.60 (s, 1H), 8.23 (s, 1H), 8.1-7.92 (m, 3H), 7.83-7.63 (m, 3H), 7.59-7.50 (m, 1H), 7.42-7.29 (m, 1H), 4.84-4.80 (m, 1H), 4.32-4.28 (m, 1H), 2.63 (s, 3H), 2.39-2.33 (m, 1H), 2.26-2.19 (m, 1H). |
| HBV-CSU-164-ISO-II | 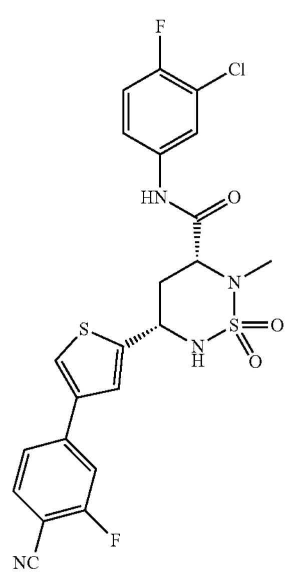 [SMILES: CN1[C@@H](C(=O)Nc2ccc(F)c(Cl)c2)C[C@@H](c2cc(-c3ccc(C#N)c(F)c3)cs2)NS1(=O)=O] | 11% | 523.4 (M + 1) | 522.04 for $C_{22}H_{17}ClF_2N_4O_3S_2$ | $^1$H-NMR (DMSO-$d_6$, 400 MHz): δ 10.58 (s, 1H), 8.18 (s, 1H), 7.98-7.89 (m, 3H), 7.79-7.73 (m, 3H), 7.59-7.50 (m, 1H), 7.40-7.38 (m, 1H), 4.80-4.75 (m, 1H), 4.24-4.18 (m, 1H), 2.57 (s, 3H), 2.33-2.28 (m, 1H), 2.2-2.11 (m, 1H). |

TABLE 2-continued

Analytical data for HBV-CSU racemic & pure enantiomers:

| Target No | Structure | Rx. Yield (%) | Mass Spec. Found (m/z) | Mass Spec. Calculated | $^1$H-NMR |
|---|---|---|---|---|---|
| HBV-CSU-165 | 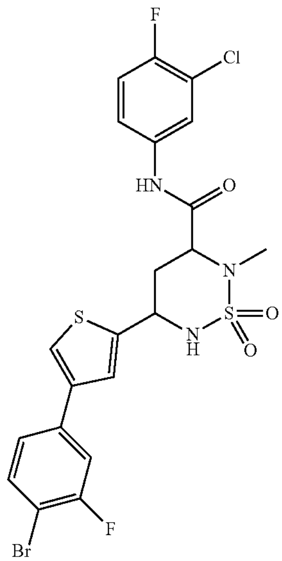 [SMILES: CN1C(C(=O)Nc2ccc(F)c(Cl)c2)CC(c2cc(-c3ccc(Br)c(F)c3)cs2)NS1(=O)=O] | 20% | 578.5 (M + 2) | 574.96 for $C_{21}H_{17}BrClF_2N_3O_3S_2$ | $^1$H-NMR (DMSO-$d_6$, 400 MHz): δ 10.61 (s, 1H), 8.03 (s, 1H), 7.99 (dd, J = 6.8, 2.4 Hz, 1H), 7.82-7.69 (m, 4H), 7.57-7.53 (m, 2H), 7.41 (t, J = 8.8 Hz, 1H), 4.83-4.79 (m, 1H), 4.32-4.29 (m, 1H), 2.63 (s, 3H), 2.38-2.33 (m, 1H), 2.26-2.15 (m, 1H). |
| HBV-CSU-166 | 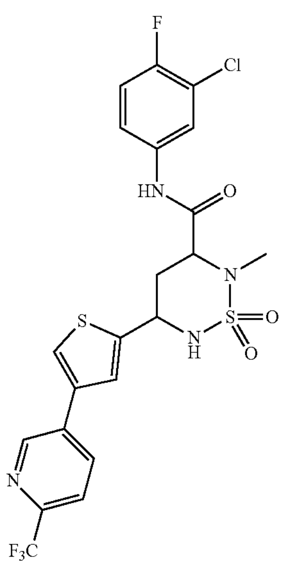 [SMILES: CN1C(C(=O)Nc2ccc(F)c(Cl)c2)CC(c2cc(-c3ccc(C(F)(F)F)nc3)cs2)NS1(=O)=O] | 35% | 549.4 (M + 1) | 548.04 for $C_{21}H_{17}ClF_4N_4O_3S_2$ | $^1$H-NMR (DMSO-$d_6$, 400 MHz): δ 10.63 (s, 1H), 8.17 (s, 1H), 8.41 (dd, J = 8.4, 1.6 Hz, 1H), 8.23 (s, 1H), 7.99 (dd, J = 6.8, 2.4 Hz, 1H), 7.94 d, J = 8.4 Hz, 1H), 7.82-7.77 (m, 2H), 7.6-7.55 (m, 1H), 7.42 (t, J = 9.2 Hz, 1H), 4.89-4.83 (m, 1H), 4.33 (dd, J = 11.6, 2.4 Hz, 1H), 2.64 (s, 3H), 2.39-2.32 (m, 1H), 2.28-2.18 (m, 1H). |

TABLE 2-continued
Analytical data for HBV-CSU racemic & pure enantiomers:
| Target No | Structure | Rx. Yield (%) | Mass Spec. Found (m/z) | Mass Spec. Calculated | $^1$H-NMR |
|---|---|---|---|---|---|
| HBV-CSU-166-ISO-I | 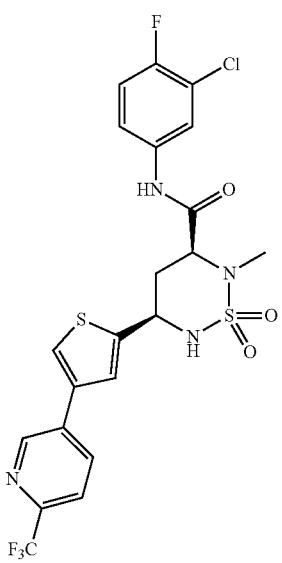 [SMILES: CN1[C@H](C(=O)Nc2ccc(F)c(Cl)c2)C[C@H](c2cc(-c3ccc(C(F)(F)F)nc3)cs2)NS1(=O)=O] | 13% | 549 (M + 1) | 548.04 for $C_{21}H_{17}ClF_4N_4O_3S_2$ | $^1$H-NMR (DMSO-$d_6$, 400 MHz): δ 10.61 (s, 1H), 9.17 (s, 1H), 8.42-8.39 (m, 1H), 8.26 (s, 1H), 7.99 (dd, J = 6.8, 2.4 Hz, 1H), 7.94 (d, J = 8.4 Hz, 1H), 7.81-7.78 (m, 2H), 7.6-7.55 (m, 1H), 7.42 (t, J = 9.6 Hz, 1H), 4.87-4.83 (m, 1H), 4.32-4.29 (m, 1H), 2.63 (s, 3H), 2.39-2.33 (m, 1H), 2.28-2.19 (m, 1H). |
| HBV-CSU-166-ISO-II | 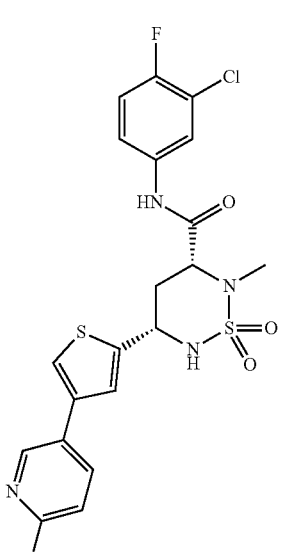 | 11% | 549 (M + 1) | 548.04 for $C_{21}H_{17}ClF_4N_4O_3S_2$ | $^1$H-NMR (DMSO-$d_6$, 400 MHz): δ 10.6 (s, 1H), 9.16 (s, 1H), 8.41-8.39 (m, 1H), 8.21 (s, 1H), 7.99 (dd, J = 6.8, 2.4 Hz, 1H), 7.94 (d, J = 8.4 Hz, 1H), 7.79-7.76 (m, 2H), 7.6-7.55 (m, 1H), 7.41 (t, J = 9.2 Hz, 1H), 4.86-4.82 (m, 1H), 4.32-4.27 (m, 1H), 2.61 (s, 3H), 2.39-2.21 (m, 2H). |

TABLE 2-continued

Analytical data for HBV-CSU racemic & pure enantiomers:

| Target No | Structure | Rx. Yield (%) | Mass Spec. Found (m/z) | Mass Spec. Calculated | $^1$H-NMR |
|---|---|---|---|---|---|
| HBV-CSU-167-ISO-I | 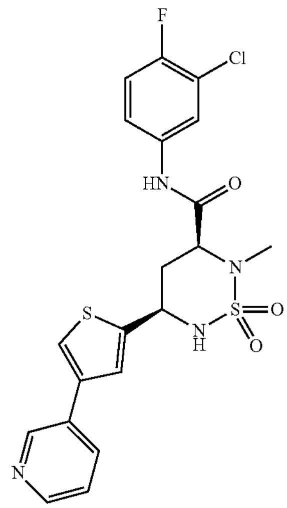 [SMILES: CN1[C@H](C(=O)Nc2ccc(F)c(Cl)c2)C[C@H](c2cc(-c3cccnc3)cs2)NS1(=O)=O] | 4% | 481.00 (M + 1) | 480.05 for $C_{20}H_{18}ClFN_4O_3S_2$ | $^1$H-NMR (DMSO-$d_6$, 400 MHz): δ 10.60 (s, 1H), 8.97 (s, 1H), 8.49 (d, J = 4.8 Hz, 1H), 8.11 (d, J = 8 Hz, 1H) 8.03-7.95 (m, 2H), 7.79-7.69 (m, 2H), 7.59-7.54 (m, 1H), 7.45-7.38 (m, 2H), 4.85-4.81 (m, 1H), 4.31-4.27 (m, 1H), 2.63 (m, 3H), 2.38-2.32 (m, 1H), 2.25-2.18 (m, 1H). |
| HBV-CSU-167-ISO-II | 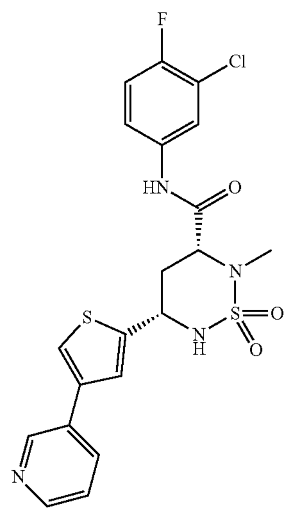 [SMILES: CN1[C@@H](C(=O)Nc2ccc(F)c(Cl)c2)C[C@@H](c2cc(-c3cccnc3)cs2)NS1(=O)=O] | 5% | 481 (M + 1) | 480.05 for $C_{20}H_{18}ClFN_4O_3S_2$ | $^1$H-NMR (DMSO-$d_6$, 400 MHz): δ 10.6 (s, 1H), 8.97 (s, 1H), 8.49 (d, J = 4.8 Hz, 1H), 8.11 (d, J = 7.6 Hz, 1H), 8.02-7.96 (m, 2H), 7.79-7.68 (m, 2H), 7.59-7.55 (m, 1H), 7.45-7.38 (m, 2H), 4.85-4.81 (m, 1H), 4.31-4.27 (m, 1H), 2.62 (m, 3H), 2.39-2.32 (m, 1H), 2.25-2.18 (m, 1H). |
| HBV-CSU-168 | 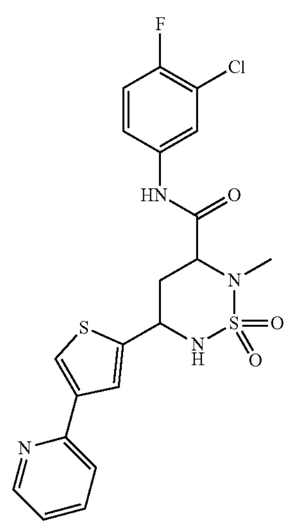 [SMILES: CN1C(C(=O)Nc2ccc(F)c(Cl)c2)CC(c2cc(-c3ccccn3)cs2)NS1(=O)=O] | 23% | 481.5 (M + 1) | 480.05 for $C_{20}H_{18}ClFN_4O_3S_2$ | $^1$H-NMR (DMSO-$d_6$, 400 MHz): δ 10.60 (s, 1H), 8.59-8.53 (m, 1H), 8.16-8.15 (m, 1H), 7.98 (dd, J = 6.8, 2.4 Hz, 1H), 7.90-7.74 (m, 4H), 7.60-7.54 (m, 1H), 7.41 (t, J = 8.8 Hz, 1H), 7.31-7.27 (m, 1H), 4.86-4.80 (m, 1H), 4.35-4.31 (m, 1H), 2.63 (s, 3H), 2.33-2.24 (m, 1H), 2.22-2.15 (m, 1H). |

TABLE 2-continued

Analytical data for HBV-CSU racemic & pure enantiomers:

| Target No | Structure | Rx. Yield (%) | Mass Spec. Found (m/z) | Mass Spec. Calculated | ¹H-NMR |
|---|---|---|---|---|---|
| HBV-CSU-168-ISO-I | 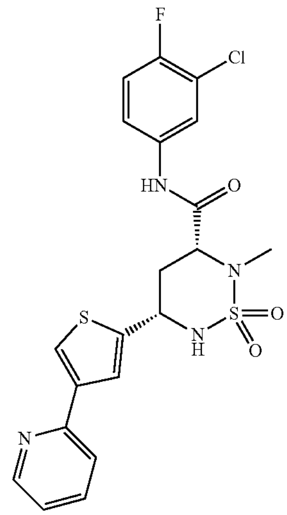 [SMILES: CN1[C@@H](C(=O)Nc2ccc(F)c(Cl)c2)C[C@@H](c2cc(-c3ccccn3)cs2)NS1(=O)=O] | 9% | 481.05 (M + 1) | 480.05 for $C_{20}H_{18}ClFN_4O_3S_2$ | ¹H-NMR (DMSO-d$_6$, 400 MHz): δ 10.61 (s, 1H), 8.61-8.54 (m, 1H), 8.16-8.15 (m, 1H), 7.99 (dd, J = 6.9, 2.6 Hz, 1H), 7.91-7.72 (m, 4H), 7.59-7.53 (m, 1H), 7.41 (t, J = 9.1 Hz, 1H), 7.29-7.26 (m, 1H), 4.83 (t, J = 10.0 Hz, 1H), 4.33 (dd, J = 11.9, 2.8 Hz, 1H), 2.63 (s, 3H), 2.35-2.24 (m, 1H), 2.25-2.18 (m, 1H). |
| HBV-CSU-168-ISO-II | 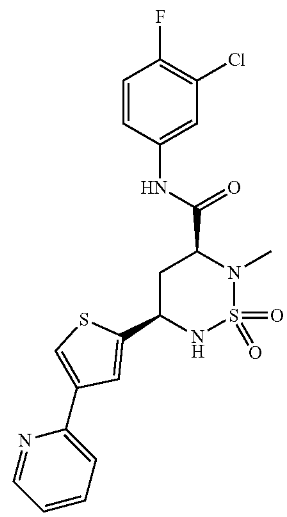 [SMILES: CN1[C@H](C(=O)Nc2ccc(F)c(Cl)c2)C[C@H](c2cc(-c3ccccn3)cs2)NS1(=O)=O] | 8% | 481.05 (M + 1) | 480.05 for $C_{20}H_{18}ClFN_4O_3S_2$ | ¹H-NMR (DMSO-d$_6$, 400 MHz): δ 10.61 (s, 1H), 8.58-8.54 (m, 1H), 8.16-8.15 (m, 1H), 8.00-7.97 (m, 1H), 7.91-7.72 (m, 4H), 7.58-7.54 (m, 1H), 7.41 (t, J = 9.1 Hz, 1H), 7.30-7.26 (m, 1H), 4.83-4.80 (m, 1H), 4.33 (dd, J = 12.1, 2.8 Hz, 1H), 2.63 (s, 3H), 2.37-2.31 (m, 1H), 2.25-2.15 (m, 1H). |
| HBV-CSU-169-ISO-I | 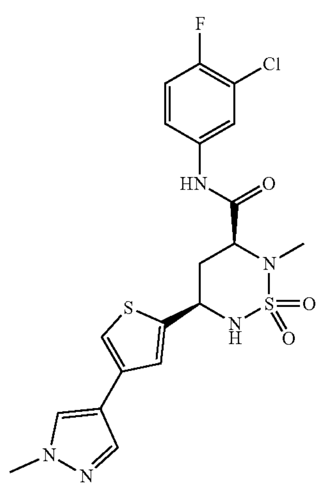 [SMILES: CN1[C@H](C(=O)Nc2ccc(F)c(Cl)c2)C[C@H](c2cc(-c3cnn(C)c3)cs2)NS1(=O)=O] | 5% | 484.4 (M + 1) | 483.06 for $C_{19}H_{19}ClFN_5O_3S_2$ | ¹H-NMR (DMSO-d$_6$, 400 MHz): δ 10.57 (s, 1H), 8.03-7.96 (m, 2H), 7.76-7.68 (m, 2H), 7.60-7.55 (m, 1H), 7.48-7.32 (m, 3H), 4.78-4.71 (m, 1H), 4.35-4.28 (m, 1H), 3.83 (s, 3H), 2.58 (s, 3H), 2.33-2.09 (m, 2H). |

TABLE 2-continued

Analytical data for HBV-CSU racemic & pure enantiomers:

| Target No | Structure | Rx. Yield (%) | Mass Spec. Found (m/z) | Mass Spec. Calculated | ¹H-NMR |
|---|---|---|---|---|---|
| HBV-CSU-169-ISO-II | 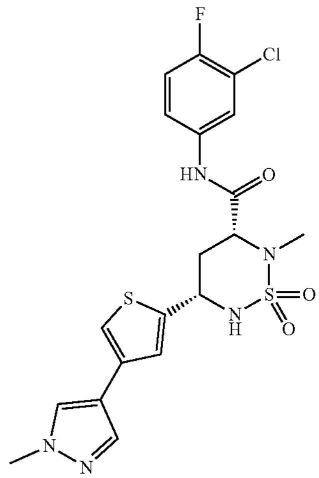 [SMILES: CN1[C@@H](C(=O)Nc2ccc(F)c(Cl)c2)C[C@@H](c2cc(-c3cnn(C)c3)cs2)NS1(=O)=O] | 3% | 484.4 (M + 1) | 483.06 for $C_{19}H_{19}ClFN_5O_3S_2$ | ¹H-NMR (DMSO-d$_6$, 400 MHz): δ 10.58 (s, 1H), 8.02-7.97 (m, 2H), 7.75-7.68 (m, 2H), 7.59-7.55 (m, 1H), 7.47-7.35 (m, 3H), 4.79-4.72 (m, 1H), 4.34-4.28 (m, 1H), 3.83 (s, 3H), 2.60 (s, 3H), 2.33-2.13 (m, 2H) |
| HBV-CSU-170 | 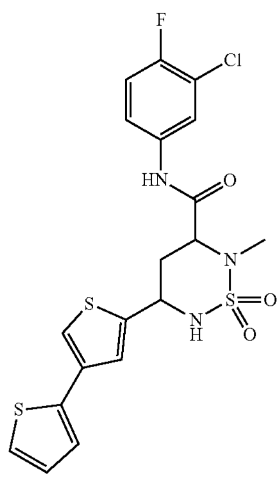 [SMILES: CN1C(C(=O)Nc2ccc(F)c(Cl)c2)CC(c2cc(-c3cccs3)cs2)NS1(=O)=O] | 37% | 486 (M + 1) | 485.01 for $C_{19}H_{17}ClFN_3O_3S_3$ | ¹H-NMR (DMSO-d$_6$, 400 MHz): δ 10.60 (s, 1H), 7.99 (dd, J = 6.8, 2.4 Hz, 1H), 7.75-7.73 (m, 1H), 7.67 (s, 1H), 7.59-7.54 (m, 1H), 7.47-7.39 (m, 4H), 7.10-7.07 (m, 1H), 4.83-4.77 (m, 1H), 4.31 (dd, J = 12.0, 2.8 Hz, 1H), 2.63 (s, 3H), 2.35-2.28 (m, 1H), 2.22-2.13 (m, 1H). |
| HBV-CSU-170-ISO-I | 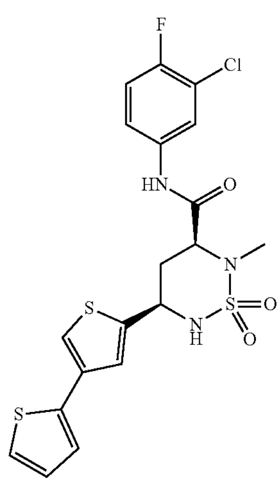 [SMILES: CN1[C@H](C(=O)Nc2ccc(F)c(Cl)c2)C[C@H](c2cc(-c3cccs3)cs2)NS1(=O)=O] | 7% | 486.35 (M + 1) | 485.01 for $C_{19}H_{17}ClFN_3O_3S_3$ | ¹H-NMR (DMSO-d$_6$, 400 MHz): δ 10.6 (s, 1H), 7.99 dd, J = 6.8, 2.4 Hz, 1H), 7.75-7.71 (m, 1H), 7.67 (s, 1H), 7.59-7.54 (m, 1H), 7.47-7.38 (m, 4H), 7.09-7.06 (m, 1H), 4.82-4.78 (m, 1H), 4.32-4.28 (m, 1H), 2.63 (s, 3H), 2.34-2.29 (m, 1H), 2.21-2.12 (m, 1H). |

TABLE 2-continued

Analytical data for HBV-CSU racemic & pure enantiomers:

| Target No | Structure | Rx. Yield (%) | Mass Spec. Found (m/z) | Mass Spec. Calculated | $^1$H-NMR |
|---|---|---|---|---|---|
| HBV-CSU-170-ISO-II | 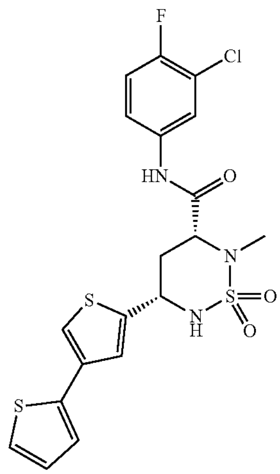 [SMILES: CN1[C@@H](C(=O)Nc2ccc(F)c(Cl)c2)C[C@@H](c2cc(-c3cccs3)cs2)NS1(=O)=O] | 6% | 486.3 (M + 1) | 485.01 for $C_{19}H_{17}ClFN_3O_3S_3$ | $^1$H-NMR (DMSO-$d_6$, 400 MHz): δ 10.59 (s, 1H), 7.99 (dd, J = 6.8, 2.4 Hz, 1H), 7.74-7.73 (m, 1H), 7.66 (s, 1H), 7.59-7.55 (m, 1H), 7.46-7.38 (m, 4H), 7.09-7.06 (m, 1H), 4.81-4.77 (m, 1H), 4.32-4.28 (m, 1H), 2.61 (s, 3H), 2.33-2.28 (m, 1H), 2.21-2.11 (m, 1H). |
| HBV-CSU-171 | 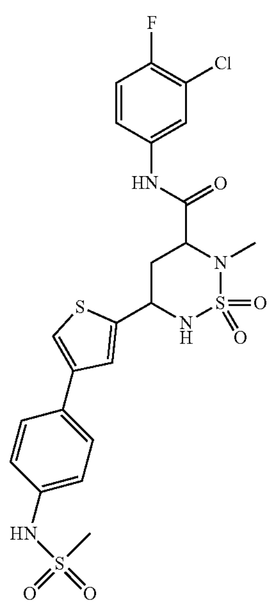 [SMILES: CN1C(C(=O)Nc2ccc(F)c(Cl)c2)CC(c2cc(-c3ccc(NS(C)(=O)=O)cc3)cs2)NS1(=O)=O] | 27% | 573.00 (M + 1) | 572.04 for $C_{22}H_{22}ClFN_4O_5S_3$ | $^1$H-NMR (DMSO-$d_6$, 400 MHz): δ 10.59 (s, 1H), 9.77 (s, 1H), 7.98 (dd, J = 6.8, 2.4 Hz, 1H), 7.76-7.56 (m, 6H), 7.41 (t, J = 9.2 Hz, 1H), 7.29-7.21 (m, 2H), 4.84-4.78 (m, 1H), 4.33-4.29 (m, 1H), 3.00 (s, 3H), 2.63 (s, 3H), 2.35-2.15 (m, 2H). |

TABLE 2-continued

Analytical data for HBV-CSU racemic & pure enantiomers:

| Target No | Structure | Rx. Yield (%) | Mass Spec. Found (m/z) | Mass Spec. Calculated | $^1$H-NMR |
|---|---|---|---|---|---|
| HBV-CSU-173 | 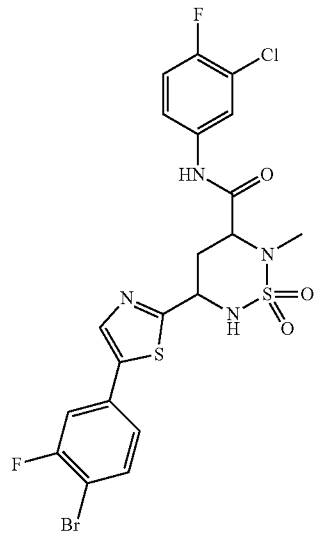 [SMILES: CN1C(C(=O)Nc2ccc(F)c(Cl)c2)CC(c2ncc(-c3ccc(Br)c(F)c3)s2)NS1(=O)=O] | 31% | 576.80 (M + 1) | 575.95 for $C_{20}H_{16}BrClF_2N_4O_3S_2$ | $^1$H-NMR (DMSO-$d_6$, 400 MHz): δ 10.59 (s, 1H), 8.33 (s, 1H), 8.01-7.95 (m, 2H), 7.82 (dd, J = 10.2, 2.3 Hz, 1H), 7.79-7.76 (m, 1H), 7.60-7.54 (m, 1H), 7.48 (dd, J = 8.3, 1.8 Hz, 1H), 7.41 (t, J = 9.1 Hz, 1H), 5.00-4.93 (m, 1H), 4.45-4.35 (m, 1H), 2.64 (s, 3H), 2.45-2.38 (m, 1H), 2.26-2.15 (m, 1H); |
| HBV-CSU-173-ISO-I | 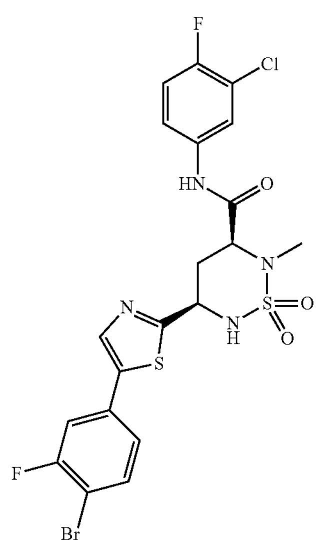 [SMILES: CN1[C@H](C(=O)Nc2ccc(F)c(Cl)c2)C[C@H](c2ncc(-c3ccc(Br)c(F)c3)s2)NS1(=O)=O] | 8% | 577.10 (M + 1) | 575.95 for $C_{20}H_{16}BrClF_2N_4O_3S_2$ | $^1$H-NMR (DMSO-$d_6$, 400 MHz): δ 10.59 (s, 1H), 8.33 (s, 1H), 8.01-7.95 (m, 2H), 7.85-7.76 (m, 2H), 7.60-7.54 (m, 1H), 7.48 (dd, J = 8.3, 1.8 Hz, 1H), 7.41 (t, J = 9.1 Hz, 1H), 5.02-4.92 (m, 1H), 4.41-4.35 (m, 1H), 2.64 (s, 3H), 2.45-2.39 (m, 1H), 2.26-2.15 (m, 1H). |

TABLE 2-continued

Analytical data for HBV-CSU racemic & pure enantiomers:

| Target No | Structure | Rx. Yield (%) | Mass Spec. Found (m/z) | Mass Spec. Calculated | 1H-NMR |
|---|---|---|---|---|---|
| HBV-CSU-173-ISO-II | 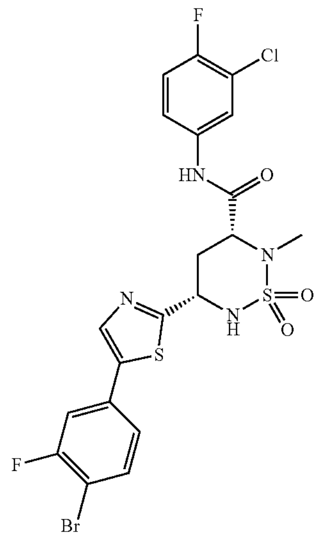 [SMILES: CN1[C@@H](C(=O)Nc2ccc(F)c(Cl)c2)C[C@@H](c2ncc(-c3ccc(Br)c(F)c3)s2)NS1(=O)=O] | 5% | 577.10 (M + 1) | 575.95 for $C_{20}H_{16}BrClF_2N_4O_3S_2$ | 1H-NMR (DMSO-$d_6$, 400 MHz): δ 10.59 (s, 1H), 8.33 (s, 1H), 7.97 (dd, J = 6.8, 2.6 Hz, 2H), 7.86-7.75 (m, 2H), 7.61-7.54 (m, 1H), 7.48 (dd, J = 8.3, 1.9 Hz, 1H), 7.41 (t, J = 9.1 Hz, 1H), 5.02-4.87 (m, 1H), 4.44-4.35 (m, 1H), 2.64 (s, 3H), 2.45-2.38 (m, 1H), 2.28-2.11 (m, 1H). |
| HBV-CSU-175 | 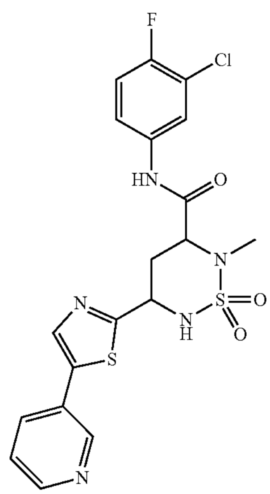 | 27% | 482.20 (M + 1) | 481.04 for $C_{19}H_{17}ClFN_5O_3S_2$ | 1H-NMR (DMSO-$d_6$, 400 MHz): δ 10.61 (s, 1H), 8.94 (d, J = 1.9 Hz, 1H), 8.57 (dd, J = 4.8, 1.4 Hz, 1H), 8.32 (s, 1H), 8.11 (dt, J = 8.3, 1.8 Hz, 1H), 8.05-7.97 (m, 2H), 7.61-7.55 (m, 1H), 7.53-7.46 (m, 1H), 7.41 (t, J = 9.1 Hz, 1H), 5.03-4.95 (m, 1H), 4.42-4.36 (m, 1H), 2.64 (s, 3H), 2.47-2.40 (m, 1H), 2.27-2.15 (m, 1H). |
| HBV-CSU-175-ISO-I | 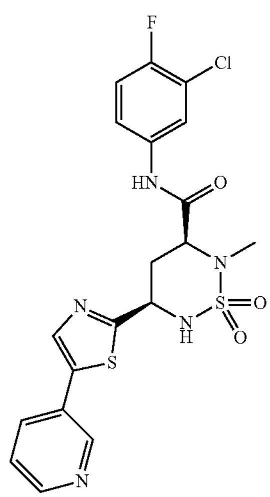 [SMILES: CN1[C@H](C(=O)Nc2ccc(F)c(Cl)c2)C[C@H](c2ncc(-c3cccnc3)s2)NS1(=O)=O] | 7% | 482.20 (M + 1) | 481.04 for $C_{19}H_{17}ClFN_5O_3S_2$ | 1H-NMR (DMSO-$d_6$, 400 MHz): δ 10.60 (s, 1H), 8.94 (d, J = 1.9 Hz, 1H), 8.58 (dd, J = 4.8, 1.5 Hz, 1H), 8.32 (s, 1H), 8.11 (dt, J = 8.0, 1.9 Hz, 1H), 8.02-7.95 (m, 2H), 7.61-7.56 (m, 1H), 7.61-7.57 (m, 1H), 7.41 (t, J = 9.1 Hz, 1H), 5.03-4.94 (m, 1H), 4.43-4.37 (m, 1H), 2.65 (s, 3H), 2.47-2.40 (m, 1H), 2.30-2.16 (m, 1H). |

TABLE 2-continued

Analytical data for HBV-CSU racemic & pure enantiomers:

| Target No | Structure | Rx. Yield (%) | Mass Spec. Found (m/z) | Mass Spec. Calculated | ¹H-NMR |
|---|---|---|---|---|---|
| HBV-CSU-175-ISO-II | 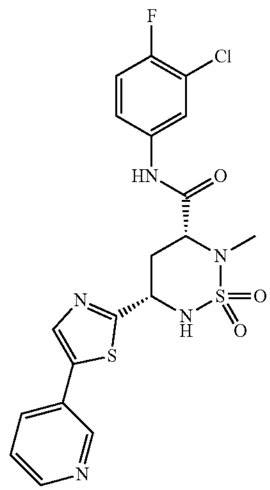 [SMILES: CN1[C@@H](C(=O)Nc2ccc(F)c(Cl)c2)C[C@@H](c2ncc(-c3cccnc3)s2)NS1(=O)=O] | 7% | 482.20 (M + 1) | 481.04 for $C_{19}H_{17}ClFN_5O_3S_2$ | ¹H-NMR (DMSO-$d_6$, 400 MHz): δ 10.59 (s, 1H), 8.93 (d, J = 1.8 Hz, 1H), 8.57 (dd, J = 4.8, 1.5 Hz, 1H), 8.31 (s, 1H), 8.12-8.08 (m, 1H), 7.98 (dd, J = 6.9, 2.5 Hz, 2H), 7.61-7.55 (m, 1H), 7.52-7.47 (m, 1H), 7.41 (t, J = 9.0 Hz, 1H), 5.00-4.95 (m, 1H), 4.41-4.36 (m, 1H), 2.64 (s, 3H), 2.46-2.39 (m, 1H), 2.29-2.14 (m, 1H). |
| HBV-CSU-176 | 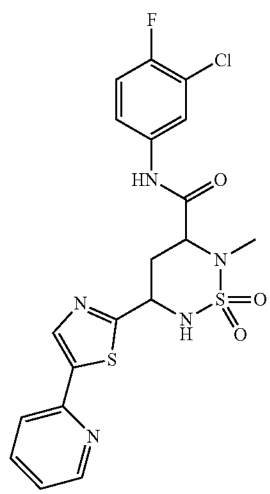 [SMILES: CN1C(C(=O)Nc2ccc(F)c(Cl)c2)CC(c2ncc(-c3ccccn3)s2)NS1(=O)=O] | 38% | 482.20 (M + 1) | 481.04 for $C_{19}H_{17}ClFN_5O_3S_2$ | ¹H-NMR (DMSO-$d_6$, 400 MHz): δ 10.59 (s, 1H), 8.58 (d, J = 4.5 Hz, 1H), 8.46 (s, 1H), 8.03-7.95 (m, 3H), 7.89 (td, J = 7.7, 1.6 Hz, 1H), 7.60-7.54 (m, 1H), 7.41 (t, J = 9.1 Hz, 1H), 7.35 (dd, J = 6.9, 5.1 Hz, 1H), 5.00-4.92 (m, 1H), 4.40-4.35 (m, 1H), 2.65 (s, 3H), 2.45-2.39 (m, 1H), 2.28-2.15 (m, 1H). |
| HBV-CSU-176-ISO-I | 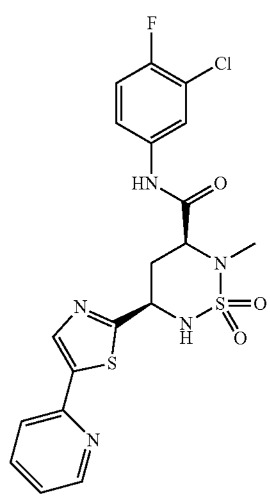 [SMILES: CN1[C@H](C(=O)Nc2ccc(F)c(Cl)c2)C[C@H](c2ncc(-c3ccccn3)s2)NS1(=O)=O] | 10% | 482.10 (M + 1) | 481.04 for $C_{19}H_{17}ClFN_5O_3S_2$ | ¹H-NMR (DMSO-$d_6$, 400 MHz): δ 10.59 (s, 1H), 8.60-8.57 (m, 1H), 8.47 (s, 1H), 8.03-7.96 (m, 3H), 7.89 (td, J = 7.8, 1.8 Hz, 1H), 7.60-7.54 (m, 1H), 7.41 (t, J = 9.1 Hz, 1H), 7.38-7.32 (m, 1H), 5.00- (m, 1H), 4.40-4.35 (m, 1H), 2.64 (s, 3H), 2.46-2.39 (m, 1H), 2.27-2.16 (m, 1H). |

TABLE 2-continued

Analytical data for HBV-CSU racemic & pure enantiomers:

| Target No | Structure | Rx. Yield (%) | Mass Spec. Found (m/z) | Mass Spec. Calculated | $^1$H-NMR |
|---|---|---|---|---|---|
| HBV-CSU-176-ISO-II | 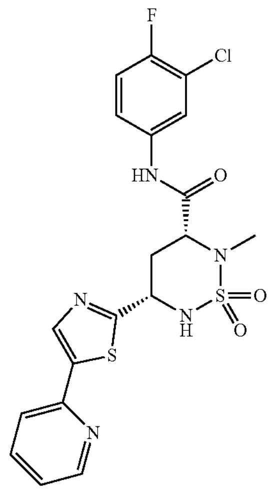 [SMILES: CN1[C@@H](C(=O)Nc2ccc(F)c(Cl)c2)C[C@@H](c2ncc(-c3ccccn3)s2)NS1(=O)=O] | 8% | 482.10 (M + 1) | 481.04 for $C_{19}H_{17}ClFN_5O_3S_2$ | $^1$H-NMR (DMSO-$d_6$, 400 MHz): δ 10.59 (s, 1H), 8.58 (d, J = 4.4 Hz, 1H), 8.46 (s, 1H), 8.03-7.95 (m, 3H), 7.89 (td, J = 7.7, 1.6 Hz, 1H), 7.60-7.54 (m, 1H), 7.41 (t, J = 9.1 Hz, 1H), 7.35 (dd, J = 7.0, 5.3 Hz, 1H), 4.99-4.93 (m, 1H), 4.40-4.35 (m, 1H), 2.64 (s, 3H), 2.45-2.39 (m, 1H), 2.27-2.14 (m, 1H). |
| HBV-CSU-177 | 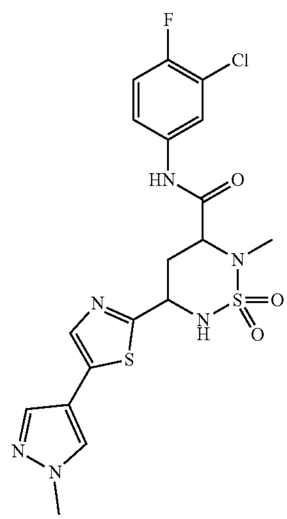 [SMILES: CN1C(C(=O)Nc2ccc(F)c(Cl)c2)CC(c2ncc(-c3cnn(C)c3)s2)NS1(=O)=O] | 37% | 485.30 (M + 1) | 484.06 for $C_{18}H_{18}ClFN_6O_3S_2$ | $^1$H-NMR (DMSO-$d_6$, 400 MHz): δ 10.58 (s, 1H), 8.11 (s, 1H), 7.97 (dd, J = 6.8, 2.4 Hz, 1H), 7.91 (d, J = 8.8 Hz, 1H), 7.86 (s, 1H), 7.78 (s, 1H), 7.60-7.53 (m, 1H), 7.40 (t, J = 9.0 Hz, 1H), 4.94-4.87 (m, 1H), 4.39-4.34 (m, 1H), 3.86 (s, 3H), 2.63 (s, 3H), 2.41-2.35 (m 1H), 2.27-2.13 (m, 1H). |
| HBV-CSU-177-ISO-I | 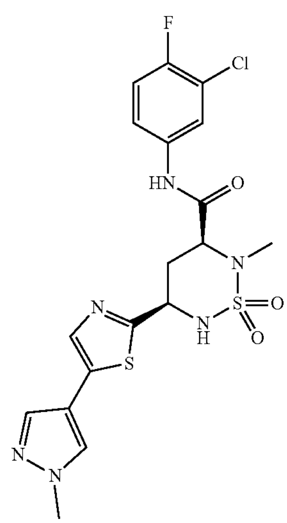 [SMILES: CN1[C@H](C(=O)Nc2ccc(F)c(Cl)c2)C[C@H](c2ncc(-c3cnn(C)c3)s2)NS1(=O)=O] | 7% | 485.20 (M + 1) | 484.06 for $C_{18}H_{18}ClFN_6O_3S_2$ | $^1$H-NMR (DMSO-$d_6$, 400 MHz): δ 10.60 (s, 1H), 8.12 (s, 1H), 7.98 (dd, J = 6.9, 2.5 Hz, 1H), 7.95-7.88 (m, 1H), 7.87 (s, 1H), 7.79 (s, 1H), 7.60-7.54 (m, 1H), 7.41 (t, J = 9.3 Hz, 1H), 4.93-4.88 (m, 1H), 4.39-4.33 (m, 1H), 3.86 (s, 3H), 2.62 (s, 3H), 2.42-2.35 (m, 1H), 2.25-2.13 (m, 1H). |

TABLE 2-continued

Analytical data for HBV-CSU racemic & pure enantiomers:

| Target No | Structure | Rx. Yield (%) | Mass Spec. Found (m/z) | Mass Spec. Calculated | 1H-NMR |
|---|---|---|---|---|---|
| HBV-CSU-177-ISO-II | 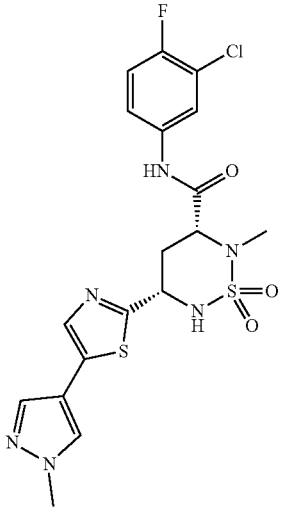 | 7% | 485.20 (M + 1) | 484.06 for $C_{18}H_{18}ClFN_6O_3S_2$ | 1H-NMR (DMSO-$d_6$, 400 MHz): δ 10.57 (s, 1H), 8.11 (s, 1H), 7.97 (dd, J = 6.8, 2.6 Hz, 1H), 7.90 (d, J = 9.7 Hz, 1H), 7.86 (s, 1H), 7.78 (s, 1H), 7.60-7.54 (m, 1H), 7.40 (t, J = 9.1 Hz, 1H), 4.95-4.86 (m, 1H), 4.39-4.34 (m, 1H), 3.86 (s, 3H), 2.63 (s, 3H), 2.41-2.35 (m, 1H), 2.25-2.14 (m, 1H). |
| HBV-CSU-178 | 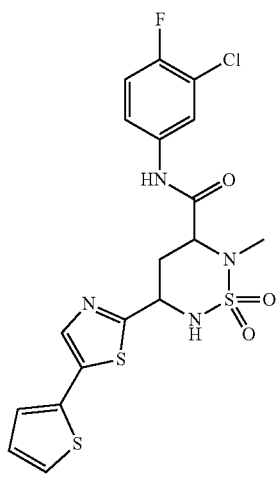 [SMILES: CN1C(C(=O)Nc2ccc(F)c(Cl)c2)CC(c2ncc(-c3cccs3)s2)NS1(=O)=O] | 43% | 487.20 (M + 1) | 486.01 for $C_{18}H_{16}ClFN_4O_3S_3$ | 1H-NMR (DMSO-$d_6$, 400 MHz): δ 10.59 (s, 1H), 8.03-7.89 (m, 3H), 7.62 (dd, J = 5.1, 0.8 Hz, 1H), 7.60-7.54 (m, 1H), 7.43-7.37 (m, 2H), 7.14 (dd, J = 5.0, 3.6 Hz, 1H), 4.98-4.91 (m, 1H), 4.41-4.35 (m, 1H), 2.64 (s, 3H), 2.43-2.37 (m, 1H), 2.25-2.14 (m, 1H). |
| HBV-CSU-178-ISO-I | 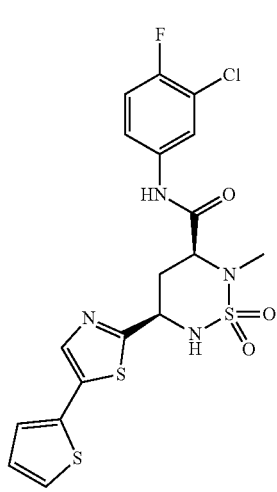 [SMILES: CN1[C@H](C(=O)Nc2ccc(F)c(Cl)c2)C[C@H](c2ncc(-c3cccs3)s2)NS1(=O)=O] | 3.3% | 487.1 (M + 1) | 486.01 for $C_{18}H_{16}ClFN_4O_3S_3$ | 1H-NMR (DMSO-$d_6$, 400 MHz): δ 10.59 (s, 1H), 8.00-7.94 (m, 4H), 7.62 (dd, J = 5.1, 1.2 Hz, 1H), 7.59-7.54 (m, 1H), 7.44-7.37 (m, 2H), 7.14 (dd, J = 5.1, 3.6 Hz, 1H), 4.41-4.35 (m, 1H), 2.64 (s, 3H), 2.44-2.37 (m, 1H), 2.26-2.13 (m, 1H). |

TABLE 2-continued

Analytical data for HBV-CSU racemic & pure enantiomers:

| Target No | Structure | Rx. Yield (%) | Mass Spec. Found (m/z) | Mass Spec. Calculated | ¹H-NMR |
|---|---|---|---|---|---|
| HBV-CSU-178-ISO-II | 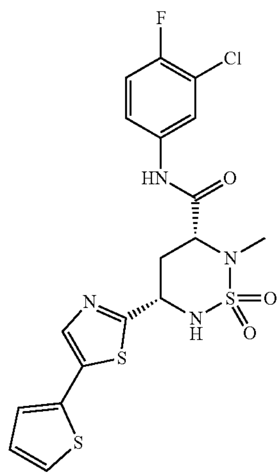 [SMILES: CN1[C@@H](C(=O)Nc2ccc(F)c(Cl)c2)C[C@@H](c2ncc(-c3cccs3)s2)NS1(=O)=O] | 5% | 487.2 (M + 1) | 486.01 for $C_{18}H_{16}ClFN_4O_3S_3$ | ¹H-NMR (DMSO-d$_6$, 400 MHz): δ 10.59 (s, 1H), 8.01-7.94 (m, 3H), 7.62 (dd, J = 5.1, 1.1 Hz, 1H), 7.59-7.54 (m, 1H), 7.46-7.37 (m, 2H), 7.14 (dd, J = 5.1, 3.6 Hz, 1H), 5.00-4.89 (m, 1H), 4.41-4.35 (m, 1H), 2.64 (s, 3H), 2.44-2.37 (m, 1H), 2.25-2.15 (m, 1H). |
| HBV-CSU-179 | 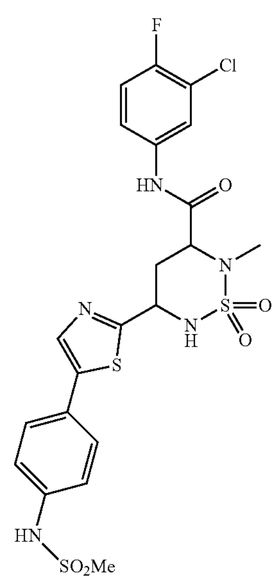 | 42% | 574.3 (M + 1) | 573.04 for $C_{21}H_{21}ClFN_5O_5S_3$ | ¹H-NMR (DMSO-d$_6$, 400 MHz): δ 10.59 (s, 1H), 9.95 (br.s, 1H), 8.10 (s, 1H), 8.00-7.92 (m, 2H), 7.65 (d, J = 8.8 Hz, 2H), 7.59-7.55 (m, 1H), 7.41 (t, J = 9.1 Hz, 1H), 7.27 (d, J = 8.8 Hz, 2H), 4.94 (t, J = 9.0 Hz, 1H), 4.41-4.35 (m, 1H), 3.04 (s, 3H), 2.64 (s, 3H), 2.44-2.37 (m, 1H), 2.27-2.16 (m, 1H). |

TABLE 2-continued

Analytical data for HBV-CSU racemic & pure enantiomers:

| Target No | Structure | Rx. Yield (%) | Mass Spec. Found (m/z) | Mass Spec. Calculated | $^1$H-NMR |
|---|---|---|---|---|---|
| HBV-CSU-179-ISO-I | 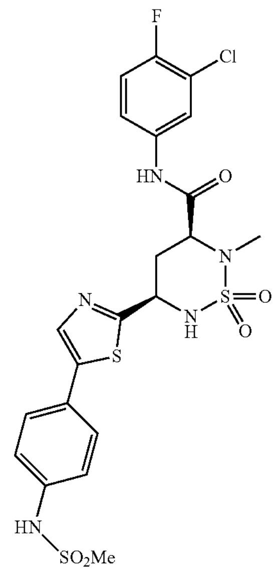 [SMILES: CN1[C@H](C(=O)Nc2ccc(F)c(Cl)c2)C[C@H](c2ncc(-c3ccc(NS(C)(=O)=O)cc3)s2)NS1(=O)=O] | 7% | 574.1 (M + 1) | 573.04 for $C_{21}H_{21}ClFN_5O_5S_3$ | $^1$H-NMR (DMSO-$d_6$, 400 MHz): δ 10.59 (s, 1H), 9.95 (br. s, 1H), 8.10 (s, 1H), 7.98 (dd, J = 6.7, 2.3 Hz, 2H), 7.65 (d, J = 8.5 Hz, 2H), 7.61-7.54 (m, 1H), 7.41 (t, J = 9.1 Hz, 1H), 7.27 (d, J = 8.5 Hz, 2H), 4.96-4.92 (m, 1H), 4.40-4.35 (m, 1H), 3.04 (s, 3H), 2.64 (s, 3H), 2.44-2.38 (m, 1H), 2.27-2.14 (m, 1H). |
| HBV-CSU-179-ISO-II | 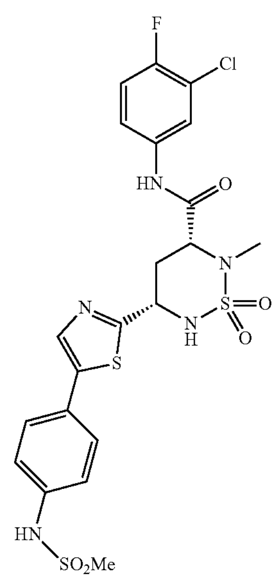 [SMILES: CN1[C@@H](C(=O)Nc2ccc(F)c(Cl)c2)C[C@@H](c2ncc(-c3ccc(NS(C)(=O)=O)cc3)s2)NS1(=O)=O] | 4% | 574.1 (M + 1) | 573.04 for $C_{21}H_{21}ClFN_5O_5S_3$ | $^1$H-NMR (DMSO-$d_6$, 400 MHz): δ 10.60 (s, 1H), 9.96 (s, 1H), 8.11 (s, 1H), 8.01-7.93 (m, 2H), 7.66 (d, J = 8.5 Hz, 2H), 7.60-7.56 (m, 1H), 7.41 (t, J = 9.1 Hz, 1H), 7.28 (d, J = 8.7 Hz, 2H), 5.01-4.91 (m, 1H), 4.41-4.36 (m, 1H), 3.05 (s, 3H), 2.64 (s, 3H), 2.45-2.38 (m, 1H), 2.27-2.16 (m, 1H). |

TABLE 2-continued

Analytical data for HBV-CSU racemic & pure enantiomers:

| Target No | Structure | Rx. Yield (%) | Mass Spec. Found (m/z) | Mass Spec. Calculated | ¹H-NMR |
|---|---|---|---|---|---|
| HBV-CSU-188 | 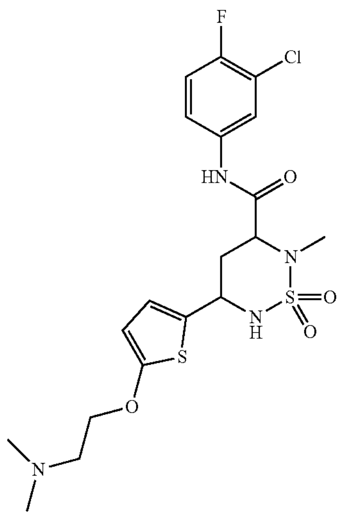 [SMILES: CN(C)CCOc1ccc(C2CC(C(=O)Nc3ccc(F)c(Cl)c3)N(C)S(=O)(=O)N2)s1] | 2% | 491.1 (M + 1) | 490.09 for $C_{19}H_{24}ClFN_4O_4S_2$ | ¹H-NMR (DMSO-$d_6$, 400 MHz): δ 10.56 (s, 1H), 7.88 (dd, J = 6.8, 2.4 Hz, 1H), 7.61-7.53 (m, 2H), 7.4 (t, J = 8.8 Hz, 1H), 6.76-6.75 (m, 1H), 6.22-6.21 (m, 1H), 4.63-4.58 (m, 2H), 4.26 (dd, J = 11.6, 2.4 Hz, 1H), 4.13 (t, J = 5.6 Hz, 1H), 2.78-2.72 (m, 2H), 2.60 (s, 3H), 2.33 (s, 6H), 2.21-2.05 (m, 2H). |
| HBV-CSU-200 | 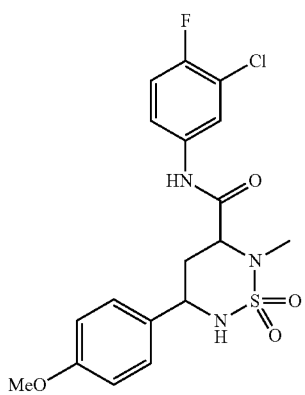 [SMILES: COc1ccc(C2CC(C(=O)Nc3ccc(F)c(Cl)c3)N(C)S(=O)(=O)N2)cc1] | 59% | 428.0 (M + 1) | 427.08 for $C_{18}H_{19}ClFN_3O_4S$ | ¹H-NMR (DMSO-$d_6$, 400 MHz): δ 10.54 (s, 1H), 7.96 (dd, J = 6.8, 2.4 Hz, 1H), 7.56-7.51 (m, 1H), 7.46-7.36 (m, 4H), 6.93 (d, J = 8.8 Hz, 2H), 4.55-4.48 (m, 1H), 4.24 (dd, J = 11.2, 3.6 Hz, 1H), 3.75 (s, 3H), 2.63 (s, 3H), 2.14-1.98 (m, 2H). |
| HBV-CSU-201 | 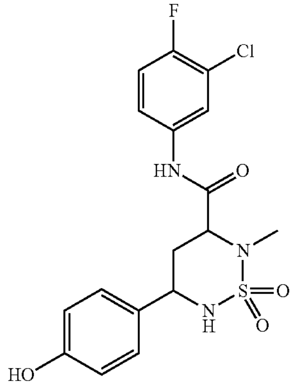 [SMILES: CN1C(C(=O)Nc2ccc(F)c(Cl)c2)CC(c2ccc(O)cc2)NS1(=O)=O] | 42% | 414.3 (M + 1) | 413.06 for $C_{17}H_{17}ClFN_3O_4S$ | ¹H-NMR (DMSO-$d_6$, 400 MHz): δ 10.52 (s, 1H), 9.44 (s, 1H), 7.95 (dd, J = 6.8, 2.4 Hz, 1H), 7.55-7.52 (m, 1H), 7.42-7.36 (m, 2H), 7.24 (d, J = 8.4 Hz, 2H), 6.74 (d, J = 8.4 Hz, 2H), 4.48-4.42 (m, 1H), 4.24-4.20 (m, 1H), 2.62 (s, 3H), 2.13-1.96 (m, 2H). |

TABLE 2-continued

Analytical data for HBV-CSU racemic & pure enantiomers:

| Target No | Structure | Rx. Yield (%) | Mass Spec. Found (m/z) | Mass Spec. Calculated | $^1$H-NMR |
|---|---|---|---|---|---|
| HBV-CSU-202 | 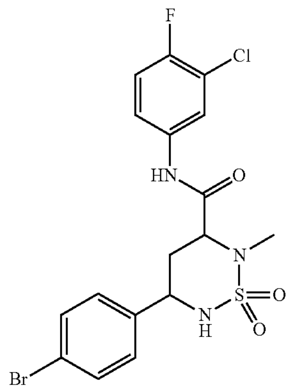 | 80% | 478.00 (M + 2) | 474.98 for $C_{17}H_{16}BrClFN_3O_3S$ | $^1$H-NMR (DMSO-$d_6$, 400 MHz): δ 10.55 (s, 1H), 7.94 (dd, J = 6.8, 2.4 Hz, 1H), 7.60-7.7.52 (m, 4H), 7.42-7.36 (m, 3H), 4.57-4.54 (m, 1H), 4.28-4.24 (m, 1H), 2.62 (s, 3H), 2.07-2.02 (m, 2H); |
| HBV-CSU-204 | 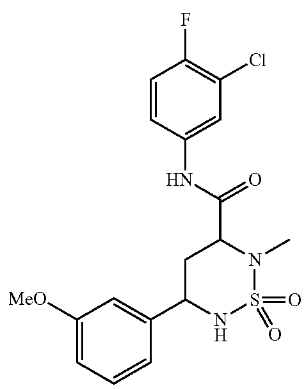 [SMILES: COc1cccc(C2CC(C(=O)Nc3ccc(F)c(Cl)c3)N(C)S(=O)(=O)N2)c1] | 42% | 428.35 (M + 1) | 427.08 for $C_{18}H_{19}ClFN_3O_4S$ | $^1$H-NMR (DMSO-$d_6$, 400 MHz): δ 10.55 (s, 1H), 7.98-7.94 (m, 1H), 7.54-7.51 (m, 2H), 7.4 (t, J = 8.8 Hz, 1H), 7.29 (t, J = 7.6 Hz, 1H), 7.06-7 (m, 2H), 6.88 (d, J = 8 Hz, 1H), 4.6-4.53 (m, 1H), 4.27-4.22 (m, 1H), 3.77 (s, 3H), 2.64 (s, 3H), 2.10-2.02 (m, 2H). |
| HBV-CSU-205 | 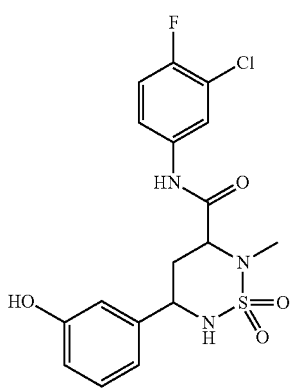 [SMILES: CN1C(C(=O)Nc2ccc(F)c(Cl)c2)CC(c2cccc(O)c2)NS1(=O)=O] | 39% | 413.85 (M + 1) | 413.06 for $C_{17}H_{17}ClFN_3O_4S$ | $^1$H-NMR (DMSO-$d_6$, 400 MHz): δ 10.58 (s, 1H), 9.21 (s, 1H), 7.96 (dd, J = 6.8, 2.4 Hz, 1H), 7.57-7.52 (m, 1H), 7.47 (d, J = 9.2 Hz, 1H), 7.39 (d, J = 9.6 Hz, 1H), 7.16 (d, J = 7.6 Hz, 1H), 6.87-6.83 (m, 2H), 6.71 (dd, J = 8.4, 2.4 Hz, 1H), 4.48-4.46 (m, 1H), 4.29-4.24 (m, 1H). 2.62 (s, 3H), 2.07-2.03 (m, 2H). |
| HBV-CSU-208 | 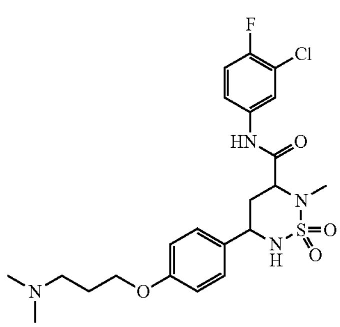 [SMILES: CN(C)CCCOc1ccc(C2CC(C(=O)Nc3ccc(F)c(Cl)c3)N(C)S(=O)(=O)N2)cc1] | 36% | 499.10 (M + 1) | 498.15 for $C_{22}H_{28}ClFN_4O_4S$ | $^1$H-NMR (DMSO-$d_6$, 400 MHz): δ 10.55 (s, 1H), 7.95 (dd, J = 6.8, 2.4 Hz, 1H), 7.56-7.51 (m, 1H), 7.46-7.34 (m, 4H), 6.90 (d, J = 8.8 Hz, 2H), 4.53-4.48 (m, 1H), 4.25-4.21 (m, 1H), 3.98 (t, J = 6.4 Hz, 2H), 2.63 (s, 3H), 2.34 (t, J = 6.4 Hz, 2H), 2.14 (s, 6H), 2.09-1.99 (m, 2H), 1.87-1.79 (m, 2H). |

TABLE 2-continued

Analytical data for HBV-CSU racemic & pure enantiomers:

| Target No | Structure | Rx. Yield (%) | Mass Spec. Found (m/z) | Mass Spec. Calculated | $^1$H-NMR |
|---|---|---|---|---|---|
| HBV-CSU-208-ISO-I | 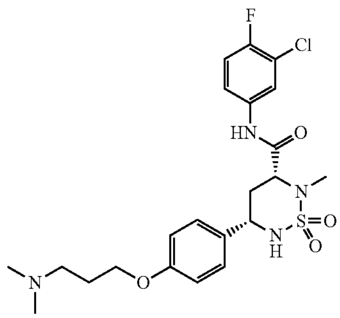 [SMILES: CN(C)CCCOc1ccc([C@@H]2C[C@H](C(=O)Nc3ccc(F)c(Cl)c3)N(C)S(=O)(=O)N2)cc1] | 3% | 499.10 (M + 1) | 498.15 for $C_{22}H_{28}ClFN_4O_4S$ | $^1$H-NMR (DMSO-$d_6$, 400 MHz): δ 10.55 (s, 1H), 7.95 (dd, J = 6.8, 2.4 Hz, 1H), 7.56-7.51 (m, 1H), 7.46-7.34 (m, 4H), 6.90 (d, J = 8.4 Hz, 2H), 4.51-4.48 (m, 1H), 4.25-4.21 (m, 1H), 3.98 (t, J = 6.4 Hz, 2H), 2.63 (s, 3H), 2.34 (t, J = 6.4 Hz, 2H), 2.14 (s, 6H), 2.08-2.01 (m, 2H), 1.84-1.80 (m, 2H). |
| HBV-CSU-208-ISO-II | 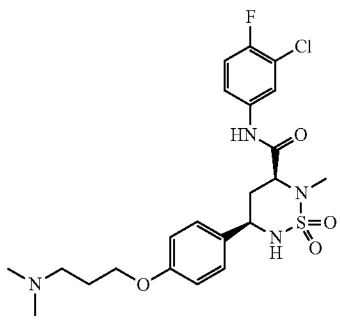 [SMILES: CN(C)CCCOc1ccc([C@H]2C[C@@H](C(=O)Nc3ccc(F)c(Cl)c3)N(C)S(=O)(=O)N2)cc1] | 4% | 499.15 (M + 1) | 498.15 for $C_{22}H_{28}ClFN_4O_4S$ | $^1$H-NMR (DMSO-$d_6$, 400 MHz): δ 10.56 (s, 1H), 7.95 (dd, J = 6.8, 2.4 Hz, 1H), 7.56-7.52 (m, 1H), 7.46-7.35 (m, 4H), 6.91 (d, J = 8.8 Hz, 2H), 4.51-4.48 (m, 1H), 4.25-4.22 (m, 1H), 3.99 (t, J = 6.8 Hz, 2H), 2.63 (s, 3H), 2.49-2.42 (m, 2H), 2.23 (s, 6H), 2.09-2.02 (m, 2H), 1.88-1.84 (m, 2H). |
| HBV-CSU-209 | 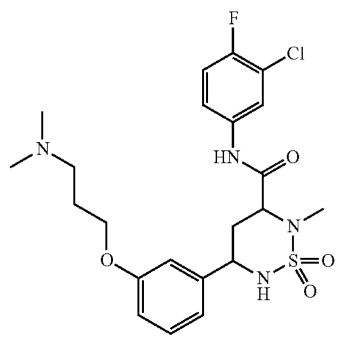 [SMILES: CN(C)CCCOc1cccc(C2CC(C(=O)Nc3ccc(F)c(Cl)c3)N(C)S(=O)(=O)N2)c1] | 3% | 499.05 (M + 1) | 498.15 for $C_{22}H_{28}ClFN_4O_4S$ | $^1$H-NMR (DMSO-$d_6$, 400 MHz): δ 10.56 (s, 1H), 7.95 (dd, J = 6.8, 2.4 Hz, 1H), 7.56-7.50 (m, 2H), 7.39 (t, J = 8.8 Hz, 1H), 7.28 (t, J = 7.6 Hz, 1H), 7.06 (s, 1H), 7.01 (d, J = 7.6 Hz, 1H), 6.87 (dd, J = 7.6, 2.4 Hz, 1H), 4.56-4.54 (m, 1H), 4.27-4.23 (m, 1H), 4.03 (t, J = 6.0 Hz, 2H), 2.75-2.68 (m, 2H), 2.64 (s, 3H), 2.50-2.46 (m, 6H), 2.08-1.94 (m, 4H). |
| HBV-CSU-210 | 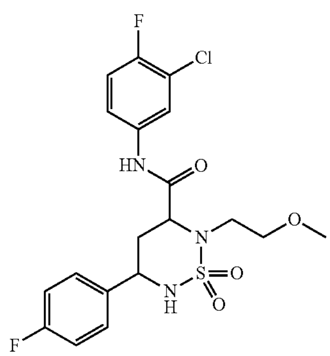 [SMILES: COCCN1C(C(=O)Nc2ccc(F)c(Cl)c2)CC(c2ccc(F)cc2)NS1(=O)=O] | 53% | 460.45 (M + 1) | 459.08 for $C_{19}H_{20}ClF_2N_3O_4S$ | $^1$H-NMR (DMSO-$d_6$, 400 MHz): δ 10.44 (s, 1H), 7.9 (dd, J = 6.8, 2.4 Hz, 1H), 7.54-7.44 (m, 4H), 7.37 (t, J = 9.2 Hz, 1H), 7.21-7.16 (m, 2H), 4.58-4.51 (m, 2H), 3.5-3.32 (m, 3H), 3.14 (s, 3H), 3.11-2.92 (m, 1H), 2.02-1.83 (m, 2H). |

TABLE 2-continued

Analytical data for HBV-CSU racemic & pure enantiomers:

| Target No | Structure | Rx. Yield (%) | Mass Spec. Found (m/z) | Mass Spec. Calculated | ¹H-NMR |
|---|---|---|---|---|---|
| HBV-CSU-210-ISO-I | 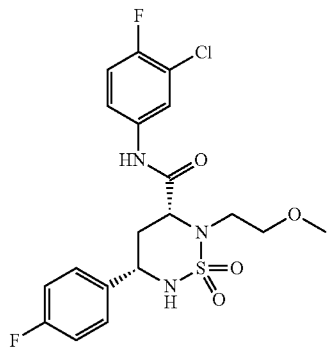 [SMILES: COCCN1[C@@H](C(=O)Nc2ccc(F)c(Cl)c2)C[C@@H](c2ccc(F)cc2)NS1(=O)=O] | 2% | 460.04 (M + 1) | 459.08 for $C_{19}H_{20}ClF_2N_3O_4S$ | ¹H-NMR (DMSO-$d_6$, 400 MHz): δ 10.47 (s, 1H), 7.93 (dd, J = 6.8, 2.4 Hz, 1H), 7.56-7.47 (m, 4H), 7.40 (t, J = 9.6 Hz, 1H), 7.21 (t, J = 8.8 Hz, 1H), 4.61-4.54 (m, 2H), 3.53-3.35 (m, 4H, merged)), 3.15 (s, 3H), 3.12-3.05 (m, 1H), 2.04-1.89 (m, 2H). |
| HBV-CSU-210-ISO-II | 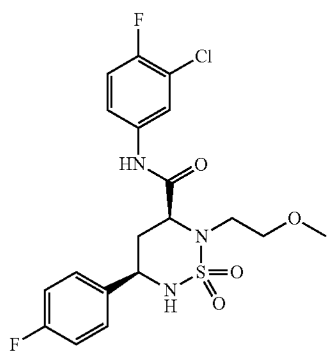 [SMILES: COCCN1[C@H](C(=O)Nc2ccc(F)c(Cl)c2)C[C@H](c2ccc(F)cc2)NS1(=O)=O] | 4% | 460.4 (M + 1) | 459.08 for $C_{19}H_{20}ClF_2N_3O_4S$ | ¹H-NMR (DMSO-$d_6$, 400 MHz): δ 10.47 (s, 1H), 7.93 (dd, J = 6.8, 2.4 Hz, 1H), 7.57-7.47 (m, 4H), 7.4 (t, J = 9.6 Hz, 1H), 7.21 (t, J = 8.8 Hz, 1H), 4.61-4.55 (m, 2H), 3.53-3.35 (m, 4H), 3.15 (s, 3H), 3.14-3.09 (m, 1H), 2.05-1.86 (m, 2H). |
| HBV-CSU-211 | 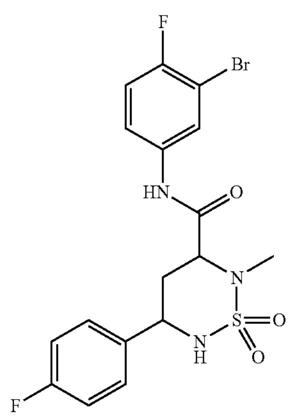 [SMILES: CN1C(C(=O)Nc2ccc(F)c(Br)c2)CC(c2ccc(F)cc2)NS1(=O)=O] | 67% | 460.4 (M + 1) | 459.01 for $C_{17}H_{16}BrF_2N_3O_3S$ | ¹H-NMR (DMSO-$d_6$, 400 MHz): δ 10.49 (s, 1H), 8.04 (dd, J = 6.0, 2.4 Hz, 1H), 7.52-7.46 (m, 4H), 7.33 (t, J = 8.8 Hz, 1H), 7.18 (t, J = 8.8 Hz, 2H), 4.6-4.53 (m, 1H), 4.26-4.21 (m, 1H), 2.61 (s, 3H), 2.07-2.02 (m, 2H). |
| HBV-CSU-211-ISO-I | 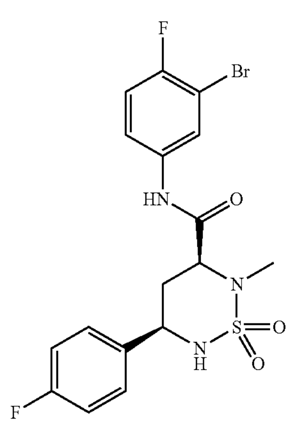 | 28% | 462.05 (M + 2) | 459.01 for $C_{17}H_{16}BrF_2N_3O_3S$ | ¹H-NMR (DMSO-$d_6$, 400 MHz): δ 10.51 (s, 1H), 8.08 (dd, J = 6.4, 2.4 Hz, 1H), 7.55-7.48 (m, 4H), 7.36 (t, J = 8.8 Hz, 1H), 7.19 (t, J = 8.8 Hz, 2H), 4.59-4.55 (m, 1H), 4.30-4.28 (m, 1H), 2.62 (s, 3H), 2.05-2.04 (m, 2H). |

TABLE 2-continued

Analytical data for HBV-CSU racemic & pure enantiomers:

| Target No | Structure | Rx. Yield (%) | Mass Spec. Found (m/z) | Mass Spec. Calculated | $^1$H-NMR |
|---|---|---|---|---|---|
| HBV-CSU-211-ISO-II | 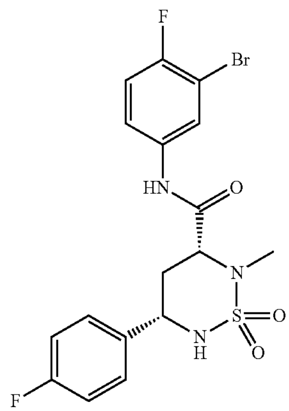 [SMILES: CN1[C@@H](C(=O)Nc2ccc(F)c(Br)c2)C[C@@H](c2ccc(F)cc2)NS1(=O)=O] | 29% | 462.00 (M + 2) | 459.01 for $C_{17}H_{16}BrF_2N_3O_3S$ | $^1$H-NMR (DMSO-$d_6$, 400 MHz): δ 10.52 (s, 1H), 8.08 (dd, J = 6.4, 2.4 Hz, 1H), 7.58-7.49 (m, 4H), 7.36 (t, J = 8.8 Hz, 1H), 7.20 (t, J = 8.8 Hz, 2H), 4.60-4.56 (m, 1H), 4.25-4.23 (m, 1H), 2.62 (s, 3H), 2.07-2.05 (m, 2H). |
| HBV-CSU-212 | 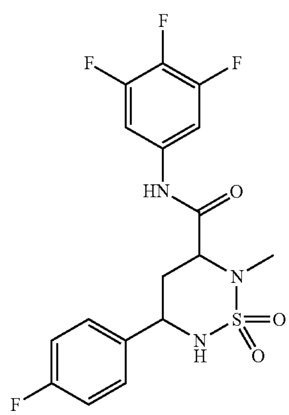 | 70% | 418.00 (M + 1) | 417.08 for $C_{17}H_{15}F_4N_3O_3S$ | $^1$H-NMR (DMSO-$d_6$, 400 MHz): δ 10.69 (s, 1H), 7.65-7.47 (m, 5H), 7.21 (t, J = 8.8 Hz, 2H), 4.62-4.55 (m, 1H), 4.33-4.29 (m, 1H), 2.63 (s, 3H), 2.08-2.02 (m, 2H). |
| HBV-CSU-212-ISO-I | 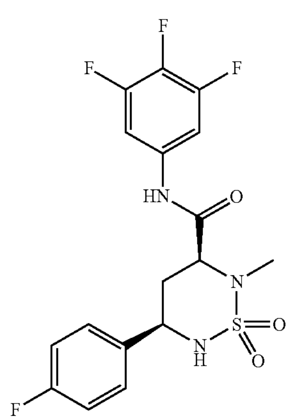 | 15% | 418.00 (M + 1) | 417.08 for $C_{17}H_{15}F_4N_3O_3S$ | $^1$H-NMR (DMSO-$d_6$, 400 MHz): δ 10.69 (s, 1H), 7.65-7.46 (m, 5H), 7.22 (t, J = 8.8 Hz, 2H), 4.60-4.54 (m, 1H), 4.34-4.25 (m, 1H), 2.63 (s, 3H), 2.09-2.00 (m, 2H). |

TABLE 2-continued

Analytical data for HBV-CSU racemic & pure enantiomers:

| Target No | Structure | Rx. Yield (%) | Mass Spec. Found (m/z) | Mass Spec. Calculated | $^1$H-NMR |
|---|---|---|---|---|---|
| HBV-CSU-212-ISO-II | 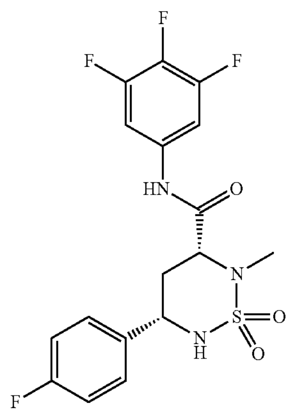 [SMILES: CN1C(C(=O)Nc2cc(F)c(F)c(F)c2)CC(c2ccc(F)cc2)NS1(=O)=O] | 12% | 418.55 (M + 1) | 417.08 for $C_{17}H_{15}F_4N_3O_3S$ | $^1$H-NMR (DMSO-d$_6$, 400 MHz): δ 10.70 (s, 1H), 7.65-7.46 (m, 5H), 7.21 (t, J = 8.8 Hz, 2H), 4.63-4.54 (m, 1H), 4.32-4.29 (m, 1H), 2.63 (s, 3H), 2.10-2.00 (m, 2H). |
| HBV-CSU-213 | 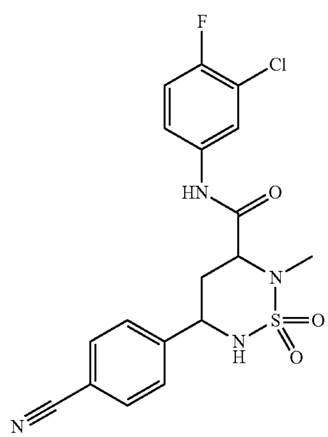 [SMILES: CN1C(C(=O)Nc2ccc(F)c(Cl)c2)CC(c2ccc(C#N)cc2)NS1(=O)=O] | 20% | 423.05 (M + 1) | 422.06 for $C_{18}H_{16}ClFN_4O_3S$ | $^1$H-NMR (DMSO-d$_6$, 400 MHz): δ 10.57 (s, 1H), 7.94 (dd, J = 6.4, 1.6 Hz, 1H), 7.85 (d, J = 8.0 Hz, 2H), 7.67-7.64 (m, 3H), 7.55-7.51 (m, 1H), 7.38 (t, J = 8.8 Hz, 1H), 4.71-4.66 (m, 1H), 4.29 (dd, J = 11.6, 2.8 Hz, 1H), 2.63 (s, 3H), 2.14-1.97 (m, 2H). |
| HBV-CSU-214 | 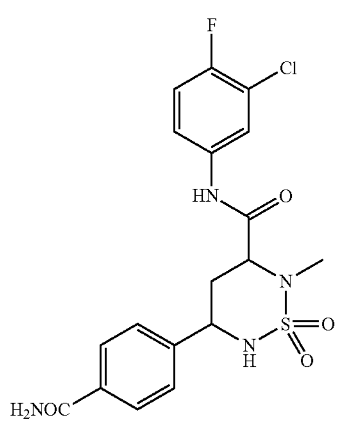 [SMILES: CN1C(C(=O)Nc2ccc(F)c(Cl)c2)CC(c2ccc(C(N)=O)cc2)NS1(=O)=O] | 32% | 441.05 (M + 1) | 440.07 for $C_{18}H_{18}ClFN_4O_4S$ | $^1$H-NMR (DMSO-d$_6$, 400 MHz): δ 10.57 (s, 1H), 7.97-7.94 (m, 2H), 7.87 (d, J = 8.4 Hz, 2H), 7.59-7.52 (m, 4H), 7.43-7.37 (m, 2H), 4.65-4.64 (m, 1H), 4.28 (dd, J = 10.8, 4.0 Hz, 1H), 2.65 (s, 3H), 2.14-2.06 (m, 2H). |

TABLE 2-continued

Analytical data for HBV-CSU racemic & pure enantiomers:

| Target No | Structure | Rx. Yield (%) | Mass Spec. Found (m/z) | Mass Spec. Calculated | ¹H-NMR |
|---|---|---|---|---|---|
| HBV-CSU-214-ISO-I | 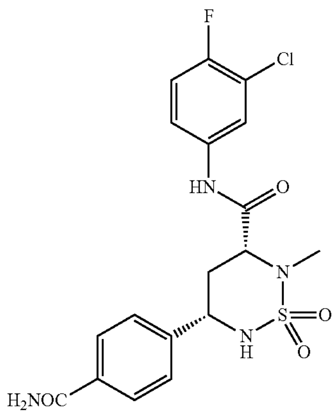 [SMILES: CN1[C@@H](C(=O)Nc2ccc(F)c(Cl)c2)C[C@@H](c2ccc(C(N)=O)cc2)NS1(=O)=O] | 8% | 441.10 (M + 1) | 440.07 for $C_{18}H_{18}ClFN_4O_4S$ | ¹H-NMR (DMSO-$d_6$, 400 MHz): δ 10.57 (s, 1H), 7.97-7.94 (m, 2H), 7.86 (d, J = 8.0 Hz, 2H), 7.61-7.51 (m, 4H), 7.42-7.36 (m, 2H), 4.62 (d, J = 8.8 Hz, 1H), 4.23-4.22 (m, 1H), 2.62 (s, 3H), 2.12-1.99 (m, 2H). |
| HBV-CSU-214-ISO-II | 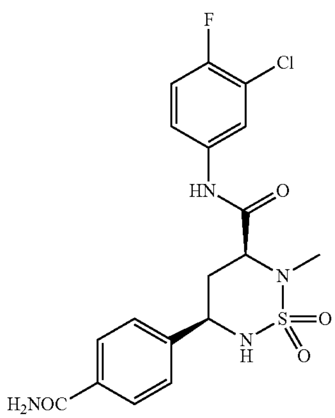 [SMILES: CN1[C@H](C(=O)Nc2ccc(F)c(Cl)c2)C[C@H](c2ccc(C(N)=O)cc2)NS1(=O)=O] | 12% | 441.15 (M + 1) | 440.07 for $C_{18}H_{18}ClFN_4O_4S$ | ¹H-NMR (DMSO-$d_6$, 400 MHz): δ 10.57 (s, 1H), 7.97-7.95 (m, 2H), 7.85 (d, J = 8.4 Hz, 2H), 7.56-7.51 (m, 4H), 7.41-7.36 (m, 2H), 4.67-4.58 (m, 1H), 4.28-4.18 (m, 1H), 2.62 (s, 3H), 2.10-2.07 (m, 2H). |
| HBV-CSU-215 | 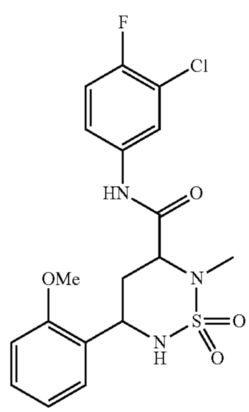 [SMILES: COc1ccccc1C1CC(C(=O)Nc2ccc(F)c(Cl)c2)N(C)S(=O)(=O)N1] | 24% | 428.05 (M + 1) | 427.08 for $C_{18}H_{19}ClFN_3O_4S$ | ¹H-NMR (DMSO-$d_6$, 400 MHz): δ 10.55 (s, 1H), 7.94-7.92 (m, 1H), 7.53-7.29 (m, 5H), 7.04-6.95 (m, 2H), 4.97-4.96 (m, 1H), 4.18 (dd, J = 11.6, 2.8 Hz, 1H), 3.82 (s, 3H), 2.64 (s, 3H), 2.05-1.91 (m, 2H). |

TABLE 2-continued

Analytical data for HBV-CSU racemic & pure enantiomers:

| Target No | Structure | Rx. Yield (%) | Mass Spec. Found (m/z) | Mass Spec. Calculated | $^1$H-NMR |
|---|---|---|---|---|---|
| HBV-CSU-216 | 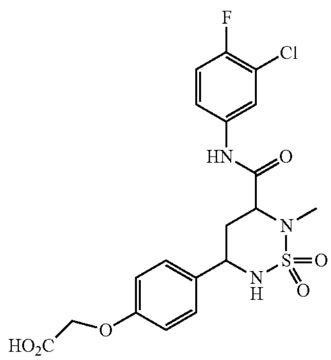 | 78% | 472.00 (M + 1) | 471.07 for $C_{19}H_{19}ClFN_3O_6S$ | $^1$H-NMR (DMSO-$d_6$, 400 MHz): δ 13.0 (br. s, 1H), 10.54 (s, 1H), 7.96 (dd, J = 6.8, 2.4 Hz, 1H), 7.56-7.51 (m, 1H), 7.47-7.35 (m, 4H), 6.92-6.89 (m, 2H), 4.67 (s, 2H), 4.54-4.48 (m, 1H), 4.24 (dd, J = 11.2, 3.6 Hz, 1H), 2.63 (s, 3H), 2.11-2.03 (m, 2H). |
| HBV-CSU-216-ISO-I | 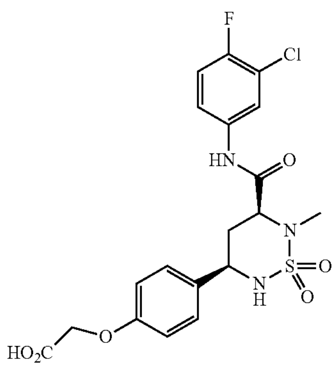 [SMILES: CN1[C@H](C(=O)Nc2ccc(F)c(Cl)c2)C[C@H](c2ccc(OCC(=O)O)cc2)NS1(=O)=O] | 10% | 472.10 (M + 1) | 471.07 for $C_{19}H_{19}ClFN_3O_6S$ | $^1$H-NMR (DMSO-$d_6$, 400 MHz): δ 10.58 (s, 1H), 7.94 (d, J = 5.2 Hz, 1H), 7.58-7.32 5H), 6.88 (d, J = 8.2 Hz, 2H), 4.59-4.50 (m, 3H), 4.23-4.21 (m, 1H), 2.62 (s, 3H), 2.10-2.00 (m 2H). |
| HBV-CSU-216-ISO-II | 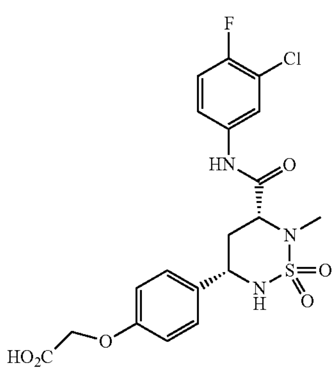 [SMILES: CN1[C@@H](C(=O)Nc2ccc(F)c(Cl)c2)C[C@@H](c2ccc(OCC(=O)O)cc2)NS1(=O)=O] | 27% | 472.10 (M + 1) | 471.07 for $C_{19}H_{19}ClFN_3O_6S$ | $^1$H-NMR (DMSO-$d_6$, 400 MHz): δ 10.56 (s, 1H), 7.97-7.94 (m, 1H), 7.58-7.31 (m, 5H), 6.93-6.84 (m, 2H), 4.61-4.48 (m, 3H), 4.25-4.21 (m, 1H), 2.63 (s, 3H), 2.16-1.97 (m, 2H). |
| HBV-CSU-217 | 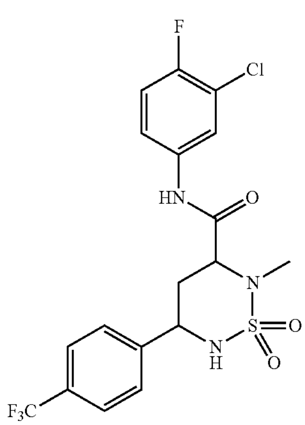 | 50% | 466.15 (M + 1) | 465.05 for $C_{18}H_{16}ClF_4N_3O_3S$ | $^1$H-NMR (DMSO-$d_6$, 400 MHz): δ 10.59 (s, 1H), 7.96 (dd, J = 6.8, 2.4 Hz, 1H), 7.78-7.75 (m, 2H), 7.71-7.65 (m, 3H), 7.57-7.53 (m, 1H), 7.4 (t, J = 9.2 Hz, 1H), 4.71-4.68 (m, 1H), 4.32 (dd, J = 11.2, 3.2 Hz, 1H), 2.65 (s, 3H), 2.19-2.06 (m, 2H). |

TABLE 2-continued

Analytical data for HBV-CSU racemic & pure enantiomers:

| Target No | Structure | Rx. Yield (%) | Mass Spec. Found (m/z) | Mass Spec. Calculated | $^1$H-NMR |
|---|---|---|---|---|---|
| HBV-CSU-217-ISO-I | 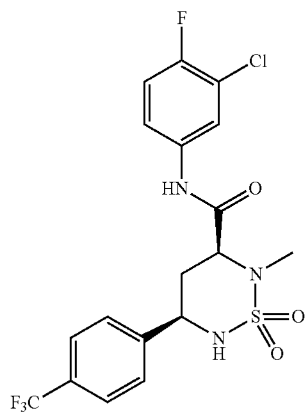 [SMILES: CN1[C@H](C(=O)Nc2ccc(F)c(Cl)c2)C[C@H](c2ccc(C(F)(F)F)cc2)NS1(=O)=O] | 17% | 466.15 (M + 1) | 465.05 for $C_{18}H_{16}ClF_4N_3O_3S$ | $^1$H-NMR (DMSO-$d_6$, 400 MHz): δ 10.59 (s, 1H), 7.96 (dd, J = 6.9, 2.6 Hz, 1H), 7.80-7.66 (m, 5H), 7.58-7.53 (m, 1H), 7.40 (t, J = 9.1 Hz, 1H), 4.71-4.68 (m, 1H), 4.32 (dd, J = 11.5, 3.1 Hz, 1H), 2.65 (s, 3H), 2.20-2.00 (m, 2H). |
| HBV-CSU-217-ISO-II | 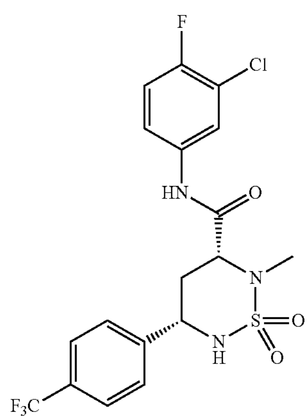 [SMILES: CN1[C@@H](C(=O)Nc2ccc(F)c(Cl)c2)C[C@@H](c2ccc(C(F)(F)F)cc2)NS1(=O)=O] | 15% | 466.15 (M + 1) | 465.05 for $C_{18}H_{16}ClF_4N_3O_3S$ | $^1$H-NMR (DMSO-$d_6$, 400 MHz): δ 10.59 (s, 1H), 7.96 (dd, J = 6.8, 2.5 Hz, 1H), 7.80-7.66 (m, 5H), 7.57-7.53 (m, 1H), 7.40 (t, J = 9.1 Hz, 1H), 4.72-4.69 (m, 1H), 4.32 (dd, J = 11.5, 3.2 Hz, 1H), 2.65 (s, 3H), 2.20-2.00 (m, 2H). |
| HBV-CSU-218 | 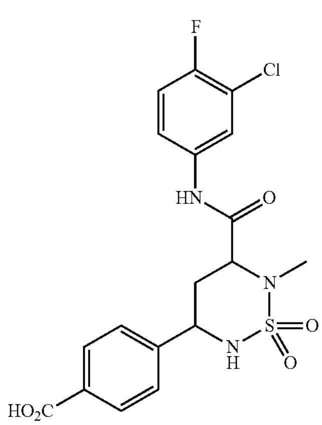 | 42% | 442.1 (M + 1) | 441.06 for $C_{18}H_{17}ClFN_3O_5S$ | $^1$H-NMR (DMSO-$d_6$, 400 MHz): δ 13 (br. s, 1H), 10.59 (s, 1H), 7.98-7.93 (m, 3H), 7.65-7.53 (m, 4H), 7.4 (t, J = 8.8 Hz, 1H), 4.7-4.63 (m, 1H), 4.31 (dd, J = 11.2, 2.8 Hz, 1H), 2.65 (s, 3H), 2.13-2.06 (m, 2H). |

TABLE 2-continued

Analytical data for HBV-CSU racemic & pure enantiomers:

| Target No | Structure | Rx. Yield (%) | Mass Spec. Found (m/z) | Mass Spec. Calculated | ¹H-NMR |
|---|---|---|---|---|---|
| HBV-CSU-218-ISO-I | 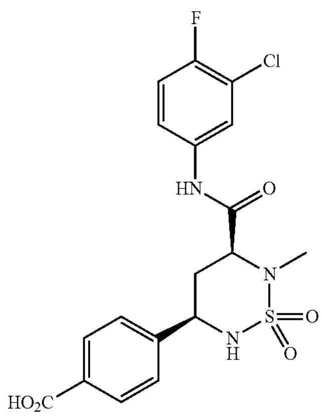 [SMILES: CN1[C@H](C(=O)Nc2ccc(F)c(Cl)c2)C[C@H](c2ccc(C(=O)O)cc2)NS1(=O)=O] | 5% | 442.05 (M + 1) | 441.06 for $C_{18}H_{17}ClFN_3O_5S$ | ¹H-NMR (DMSO-$d_6$, 400 MHz): δ 13.00 (br.s, 1H), 10.57 (s, 1H), 7.97-7.93 (m, 3H), 7.64-7.58 (m, 4H), 7.42-7.36 (m, 1H), 4.68-4.66 (m, 1H), 4.32-4.30 (m, 1H), 2.64 (s, 3H), 2.12-2.09 (m, 2H). |
| HBV-CSU-218-ISO-II | 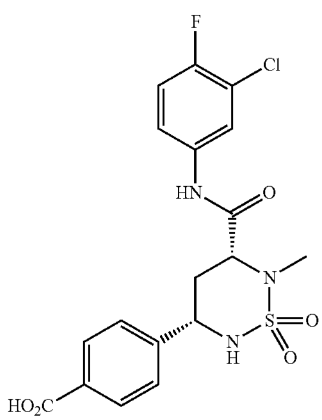 | 14% | 442.15 (M + 1) | 441.06 for $C_{18}H_{17}ClFN_3O_5S$ | ¹H-NMR (DMSO-$d_6$, 400 MHz): δ 13.00 (br.s, 1H), 10.57 (s, 1H), 7.97-7.93 (m, 3H), 7.64-7.58 (m, 4H), 7.42-7.36 (m, 1H), 4.68-4.66 (m, 1H), 4.32-4.30 (m, 1H), 2.64 (s, 3H), 2.12-2.09 (m, 2H). |
| HBV-CSU-219 | 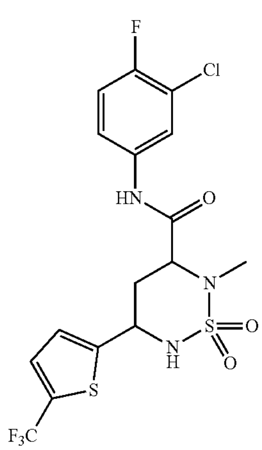 [SMILES: CN1C(C(=O)Nc2ccc(F)c(Cl)c2)CC(c2ccc(C(F)(F)F)s2)NS1(=O)=O] | 36% | 472.10 (M + 1) | 471.01 for $C_{16}H_{14}ClF_4N_3O_3S_2$ | ¹H-NMR (DMSO-$d_6$, 400 MHz): δ 10.61 (s, 1H), 7.98-7.96 (m, 1H), 7.85-7.83 (m, 1H), 7.67-7.59 (m, 1H), 7.58-7.54 (m, 1H), 7.41 (t, J = 9.1 Hz, 1H), 7.31-7.25 (m, 1H), 4.91-4.88 (m, 1H), 4.34-4.31 (m, 1H), 2.62 (s, 3H), 2.36-2.26 (m, 1H), 2.14-2.11 (m 1H). |

TABLE 2-continued

Analytical data for HBV-CSU racemic & pure enantiomers:

| Target No | Structure | Rx. Yield (%) | Mass Spec. Found (m/z) | Mass Spec. Calculated | $^1$H-NMR |
|---|---|---|---|---|---|
| HBV-CSU-219-ISO-I | 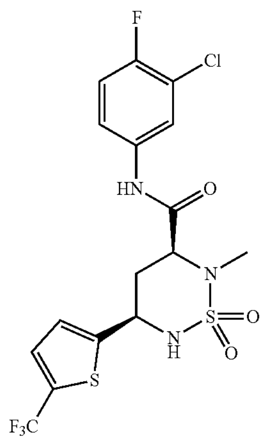 [SMILES: CN1[C@H](C(=O)Nc2ccc(F)c(Cl)c2)C[C@H](c2ccc(C(F)(F)F)s2)NS1(=O)=O] | 9% | 472.10 (M + 1) | 471.01 for $C_{16}H_{14}ClF_4N_3O_3S_2$ | $^1$H-NMR (DMSO-$d_6$, 400 MHz): δ 10.60 (s, 1H), 7.98-7.95 (m, 1H), 7.86-7.82 (m, 1H), 7.64-7.63 (m, 1H), 7.56-7.55 (m, 1H), 7.41 (t, J = 8.8 Hz, 1H), 7.27-7.25 (m, 1H), 4.88-4.86 (m, 1H), 4.37-4.28 (m, 1H), 2.62 (s, 3H), 2.32-2.10 (m, 2H). |
| HBV-CSU-219-ISO-II | 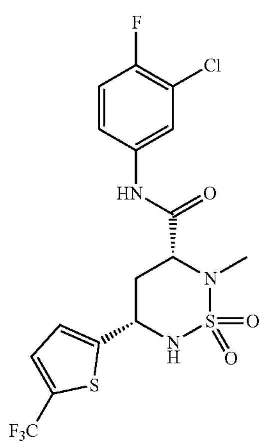 [SMILES: CN1[C@@H](C(=O)Nc2ccc(F)c(Cl)c2)C[C@@H](c2ccc(C(F)(F)F)s2)NS1(=O)=O] | 9% | 472.10 (M + 1) | 471.01 for $C_{16}H_{14}ClF_4N_3O_3S_2$ | $^1$H-NMR (DMSO-$d_6$, 400 MHz): δ 10.60 (s, 1H), 7.98-7.95 (m, 1H), 7.85-7.82 (m, 1H), 7.64-7.62 (m, 1H), 7.58-7.53 (m, 1H), 7.41 (t, J = 9.2 Hz, 1H), 7.31-7.25 (m, 1H), 4.90-4.86 (m, 1H), 4.33 (dd, J = 12.1, 2.7 Hz, 1H), 2.62 (s, 3H), 2.32-2.29 (m, 1H), 2.17-2.03 (m, 1H). |
| HBV-CSU-220 | 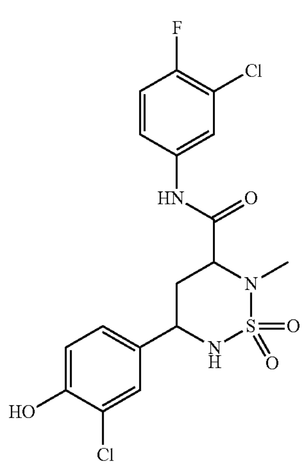 [SMILES: CN1C(C(=O)Nc2ccc(F)c(Cl)c2)CC(c2ccc(O)c(Cl)c2)NS1(=O)=O] | 69% | 448.05 (M + 1) | 447.02 for $C_{17}H_{16}Cl_2FN_3O_4S$ | $^1$H-NMR (DMSO-$d_6$, 400 MHz): δ 10.53 (s, 1H), 10.23 (br.s, 1H), 7.93 (dd, J = 6.8, 2.4 Hz, 1H), 7.54-7.51 (m, 1H), 7.43-7.35 (m, 3H), 7.19 (dd, J = 8.8, 2.4 Hz, 1H), 6.92 (d, J = 8.4 Hz, 1H), 4.49-4.43 (m, 1H), 4.23-4.19 (m, 1H), 2.61 (s, 3H), 2.05-1.99 (m, 2H). |

TABLE 2-continued

Analytical data for HBV-CSU racemic & pure enantiomers:

| Target No | Structure | Rx. Yield (%) | Mass Spec. Found (m/z) | Mass Spec. Calculated | $^1$H-NMR |
|---|---|---|---|---|---|
| HBV-CSU-221 | 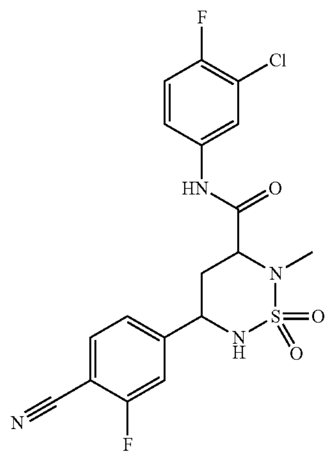 [SMILES: CN1C(C(=O)Nc2ccc(F)c(Cl)c2)CC(c2ccc(C#N)c(F)c2)NS1(=O)=O] | 50% | 441.10 (M + 1) | 440.05 for $C_{18}H_{15}ClF_2N_4O_3S_1$ | $^1$H-NMR (DMSO-$d_6$, 400 MHz): δ 10.59 (s, 1H), 7.98-7.94 (m, 2H), 7.67-7.52 (m, 4H), 7.40 (t, J = 9.2 Hz, 1H), 4.78-4.57 (m, 1H), 4.29-4.28 (m, 1H), 2.64 (s, 3H), 2.14-1.98 (m, 2H). |
| HBV-CSU-221-ISO-I | 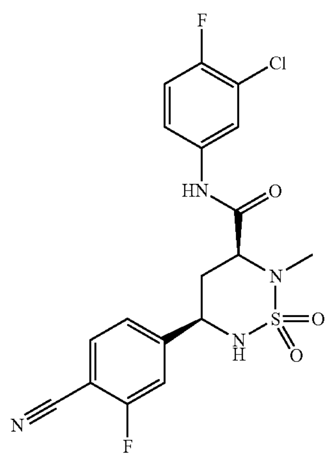 [SMILES: CN1[C@H](C(=O)Nc2ccc(F)c(Cl)c2)C[C@H](c2ccc(C#N)c(F)c2)NS1(=O)=O] | 10% | 441 (M + 1) | 440.05 for $C_{18}H_{15}ClF_2N_4O_3S_1$ | $^1$H-NMR (DMSO-$d_6$, 400 MHz): δ 10.59 (s, 1H), 7.98-7.93 (m, 2H), 7.69-7.64 (m, 2H), 7.55-7.51 (m, 2H), 7.39 (t, J = 8.8 Hz, 1H), 4.75-4.71 (m, 1H), 4.31-4.27 (m, 1H), 2.64 (s, 3H), 2.17-2.00 (m, 2H). |
| HBV-CSU-221-ISO-II | 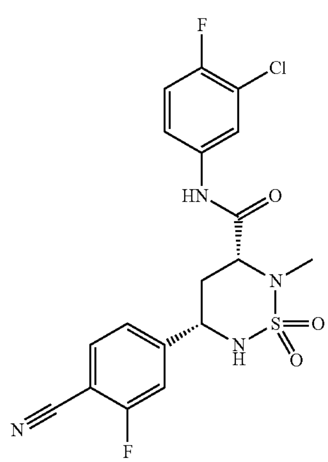 [SMILES: CN1[C@@H](C(=O)Nc2ccc(F)c(Cl)c2)C[C@@H](c2ccc(C#N)c(F)c2)NS1(=O)=O] | 3% | 441.35 (M + 1) | 440.05 for $C_{18}H_{15}ClF_2N_4O_3S_1$ | $^1$H-NMR (DMSO-$d_6$, 400 MHz): δ 10.59 (s, 1H), 7.98-7.93 (m, 2H), 7.67-7.64 (m, 2H), 7.53-7.51 (m, 2H), 7.42-7.37 (m, 1H), 4.75-4.70 (m, 1H), 4.31-4.28 (m, 1H), 2.64 (s, 3H), 2.16-2.00 (m, 2H). |

TABLE 2-continued

Analytical data for HBV-CSU racemic & pure enantiomers:

| Target No | Structure | Rx. Yield (%) | Mass Spec. Found (m/z) | Mass Spec. Calculated | $^1$H-NMR |
|---|---|---|---|---|---|
| HBV-CSU-222 | 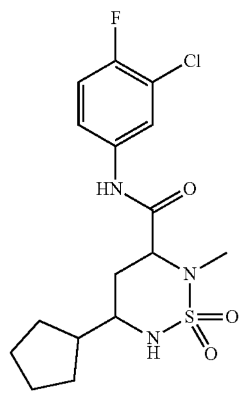 [SMILES: CN1C(C(=O)Nc2ccc(F)c(Cl)c2)CC(C2CCCC2)NS1(=O)=O] | 68% | 390.05 (M + 1) | 389.10 for $C_{16}H_{21}ClFN_3O_3S$ | $^1$H-NMR (DMSO-$d_6$, 400 MHz): δ 10.57 (s, 1H), 7.95 (dd, J = 6.8, 2.4 Hz, 1H), 7.54-7.49 (m, 1H), 7.39 (t, J = 8.8 Hz, 1H), 7.05 (d, J = 10.0 Hz, 1H), 3.99-3.95 (m, 1H), 3.13-3.06 (m, 1H), 2.54 (s, 3H), 1.89-1.12 (m, 11H). |
| HBV-CSU-222-ISO-I | 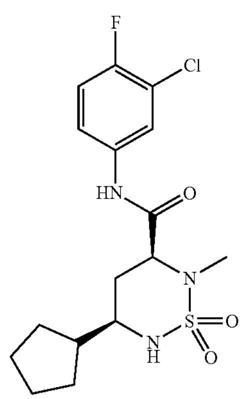 [SMILES: CN1[C@H](C(=O)Nc2ccc(F)c(Cl)c2)C[C@H](C2CCCC2)NS1(=O)=O] | 3% | 390.20 (M + 1) | 389.10 for $C_{16}H_{21}ClFN_3O_3S$ | $^1$H-NMR (DMSO-$d_6$, 400 MHz): δ 10.49 (s, 1H), 7.95 (dd, J = 6.8, 2.4 Hz, 1H), 7.54-7.49 (m, 1H), 7.39 (t, J = 9.2 Hz, 1H), 7.04 (d, J = 10.0 Hz, 1H), 3.96 (dd, J = 11.6, 2.4 Hz, 1H), 3.14-3.07 (m, 1H), 2.54 (s, 3H), 1.91-1.12 (m, 11H). |
| HBV-CSU-222-ISO-II | 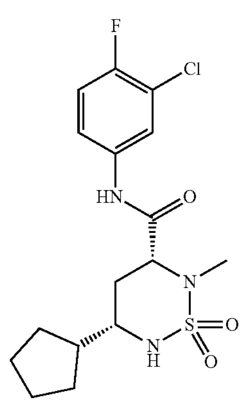 [SMILES: CN1[C@@H](C(=O)Nc2ccc(F)c(Cl)c2)C[C@@H](C2CCCC2)NS1(=O)=O] | 5% | 390.20 (M + 1) | 389.10 for $C_{16}H_{21}ClFN_3O_3S$ | $^1$H-NMR (DMSO-$d_6$, 400 MHz): δ 10.49 (s, 1H), 7.95 (dd, J = 6.8, 2.4 Hz, 1H), 7.54-7.49 (m, 1H), 7.39 (t, J = 8.8 Hz, 1H), 7.04 (d, J = 10.4 Hz, 1H), 3.96 (dd, J = 12.0, 2.8 Hz, 1H), 3.12-3.09 (m, 1H), 2.54 (s, 3H), 1.89-1.13 (m, 11H). |

TABLE 2-continued

Analytical data for HBV-CSU racemic & pure enantiomers:

| Target No | Structure | Rx. Yield (%) | Mass Spec. Found (m/z) | Mass Spec. Calculated | ¹H-NMR |
|---|---|---|---|---|---|
| HBV-CSU-224 | 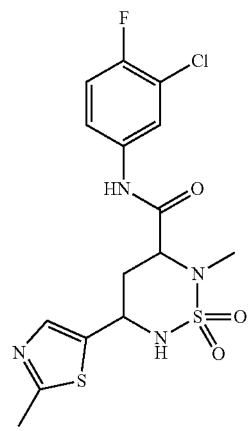 | 21% | 419.20 (M + 1) | 418.03 for $C_{15}H_{16}ClFN_4O_3S_3$ | ¹H-NMR (DMSO-d$_6$, 400 MHz): δ 10.57 (s, 1H), 7.97 (dd, J = 6.8, 2.6 Hz, 1H), 7.73 (d, J = 9.5 Hz, 1H), 7.63 (s, 1H), 7.59-7.53 (m, 1H), 7.41 (t, J = 9.1 Hz, 1H), 4.89-4.77 (m, 1H), 4.30 (dd, J = 11.6, 2.9 Hz, 1H), 2.64 (s, 3H), 2.62 (s, 3H), 2.27-2.06 (m, 2H). |
| HBV-CSU-224-ISO-I | 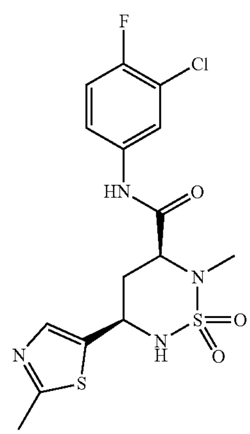 [SMILES: Cc1ncc([C@H]2C[C@@H](C(=O)Nc3ccc(F)c(Cl)c3)N(C)S(=O)(=O)N2)s1] | 8.1% | 419.1 (M + 1) | 418.03 for $C_{15}H_{16}ClFN_4O_3S_2$ | ¹H-NMR (DMSO-d$_6$, 400 MHz): δ 10.57 (s, 1H), 7.97 (dd, J = 6.8, 2.5 Hz, 1H), 7.73 (d, J = 9.5 Hz, 1H), 7.62 (s, 1H), 7.57-7.52 (m, 1H), 7.40 (t, J = 9.4 Hz, 1H), 4.87-4.79 (m, 1H), 4.32-4.26 (m, 1H), 2.63 (s, 3H), 2.61 (s, 3H), 2.25-2.18 (m, 1H), 2.17-2.07 (m, 1H). |
| HBV-CSU-224-ISO-II | 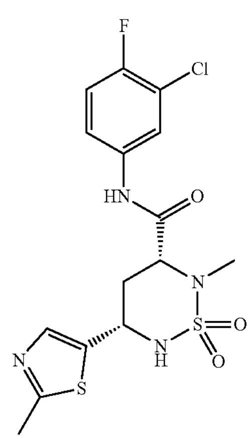 [SMILES: Cc1ncc([C@@H]2C[C@H](C(=O)Nc3ccc(F)c(Cl)c3)N(C)S(=O)(=O)N2)s1] | 11% | 419.1 (M + 1) | 418.03 for $C_{15}H_{16}ClFN_4O_3S_2$ | ¹H-NMR (DMSO-d$_6$, 400 MHz): δ 10.60 (s, 1H), 7.97 (dd, J = 6.8, 2.6 Hz, 1H), 7.73 (d, J = 9.5 Hz, 1H), 7.62 (s, 1H), 7.56-7.53 (m, 1H), 7.40 (t, J = 9.1 Hz, 1H), 4.87-4.78 (m, 1H), 4.32-4.26 (m, 1H), 2.63 (s, 3H), 2.61 (s, 3H), 2.25-2.19 (m, 1H), 2.18-2.08 (m, 1H). |

TABLE 2-continued

Analytical data for HBV-CSU racemic & pure enantiomers:

| Target No | Structure | Rx. Yield (%) | Mass Spec. Found (m/z) | Mass Spec. Calculated | 1H-NMR |
|---|---|---|---|---|---|
| HBV-CSU-226 | 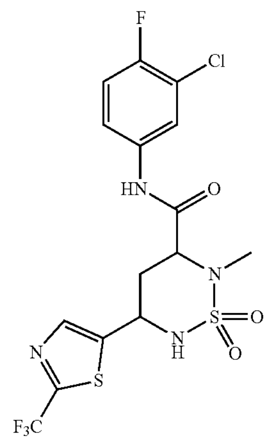 [SMILES: CN1C(C(=O)Nc2ccc(F)c(Cl)c2)CC(c2cnc(C(F)(F)F)s2)NS1(=O)=O] | 86% | 473.20 (M + 1) | 472.01 for $C_{15}H_{13}ClF_4N_4O_3S_2$ | 1H-NMR (DMSO-$d_6$, 400 MHz): δ 10.60 (s, 1H), 8.19 (s, 1H), 7.97 (dd, J = 6.8, 2.6 Hz, 2H), 7.59-7.53 (m, 1H), 7.40 (t, J = 9.1 Hz, 1H), 5.07-5.02 (m, 1H), 4.35-4.28 (m, 1H), 2.63 (s, 3H), 2.37-2.31 (m, 1H), 2.23-2.12 (m, 1H). |
| HBV-CSU-230 | 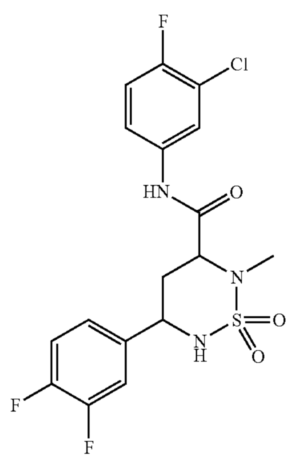 [SMILES: CN1C(C(=O)Nc2ccc(F)c(Cl)c2)CC(c2ccc(F)c(F)c2)NS1(=O)=O] | 30% | 434.00 (M + 1) | 433.05 for $C_{17}H_{15}ClF_3N_3O_3S$ | 1H-NMR (DMSO-$d_6$, 400 MHz): δ 10.57 (s, 1H), 7.95 (dd, J = 6.8, 2.4 Hz, 1H), 7.60-7.52 (m, 3H), 7.52-7.33 (m, 3H), 4.64-4.58 (m, 1H), 4.25 (dd, J = 11.2, 4.4 Hz, 1H), 2.64 (s, 3H), 2.11-1.99 (m, 2H). |
| HBV-CSU-230-ISO-I | 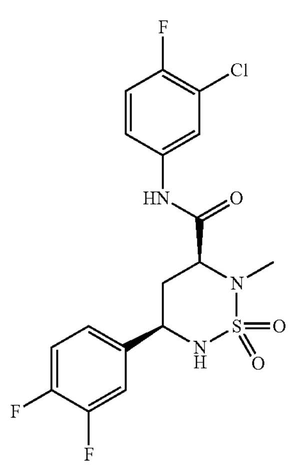 [SMILES: CN1[C@H](C(=O)Nc2ccc(F)c(Cl)c2)C[C@H](c2ccc(F)c(F)c2)NS1(=O)=O] | 14% | 434.10 (M + 1) | 433.05 for $C_{17}H_{15}ClF_3N_3O_3S$ | 1H-NMR (DMSO-$d_6$, 400 MHz): δ 10.57 (s, 1H), 7.95 (dd, J = 6.8, 2.4 Hz, 1H), 7.60-7.52 (m, 3H), 7.49-7.37 (m, 2H), 7.34-7.33 (m, 1H), 4.59 (d, J = 9.2 Hz, 1H), 4.25 (dd, J = 14.8, 4.0 Hz, 1H), 2.64 (s, 3H), 2.11-2.02 (m, 2H). |

TABLE 2-continued

Analytical data for HBV-CSU racemic & pure enantiomers:

| Target No | Structure | Rx. Yield (%) | Mass Spec. Found (m/z) | Mass Spec. Calculated | ¹H-NMR |
|---|---|---|---|---|---|
| HBV-CSU-230-ISO-II | 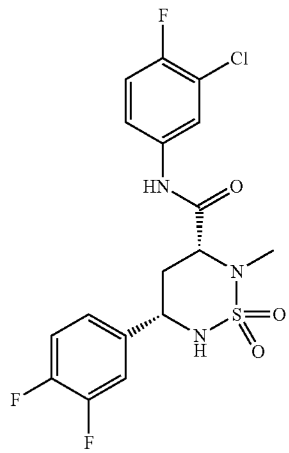 [SMILES: CN1[C@@H](C(=O)Nc2ccc(F)c(Cl)c2)C[C@@H](c2ccc(F)c(F)c2)NS1(=O)=O] | 8% | 434.10 (M + 1) | 433.05 for $C_{17}H_{15}ClF_3N_3O_3S$ | ¹H-NMR (DMSO-$d_6$, 400 MHz): δ 10.59 (s, 1H), 7.95 (dd, J = 6.8, 2.4 Hz, 1H), 7.60-7.32 (m, 6H), 4.60 (d, J = 8.4 Hz, 1H), 4.25 (dd, J = 10.8, 4.0 Hz, 1H), 2.64 (s, 3H), 2.11-1.99 (m, 2H). |
| HBV-CSU-231 | 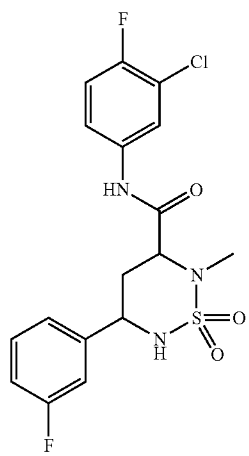 | 43% | 416.10 (M + 1) | 415.06 for $C_{17}H_{16}ClF_2N_3O_3S$ | ¹H-NMR (DMSO-$d_6$, 400 MHz): δ 10.57 (s, 1H), 7.95 (dd, J = 6.8, 2.5 Hz, 1H), 7.62-7.50 (m, 2H), 7.48-7.27 (m, 4H), 7.18-7.13 (m, 1H), 4.62 (t, J = 8.0 Hz, 1H), 4.27 (dd, J = 11.2, 3.5 Hz, 1H), 2.64 (s, 3H), 2.16-1.98 (m, 2H). |
| HBV-CSU-231-ISO-I | 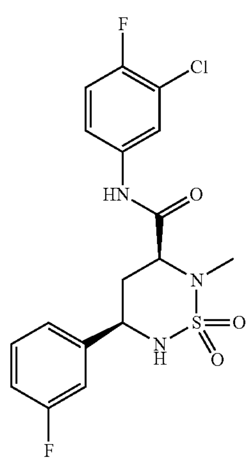 | 10% | 416.10 (M + 1) | 415.06 for $C_{17}H_{16}ClF_2N_3O_3S$ | ¹H-NMR (DMSO-$d_6$, 400 MHz): δ 10.57 (s, 1H), 7.96 (dd, J = 6.9, 2.6 Hz, 1H), 7.62-7.50 (m, 2H), 7.48-7.27 (m, 4H), 7.21-7.11 (m, 1H), 4.63-4.59 (m, 1H), 4.27 (dd, J = 11.2, 3.5 Hz, 1H), 2.64 (s, 3H), 2.16-1.98 (m, 2H). |

TABLE 2-continued

Analytical data for HBV-CSU racemic & pure enantiomers:

| Target No | Structure | Rx. Yield (%) | Mass Spec. Found (m/z) | Mass Spec. Calculated | ¹H-NMR |
|---|---|---|---|---|---|
| HBV-CSU-231-ISO-II | 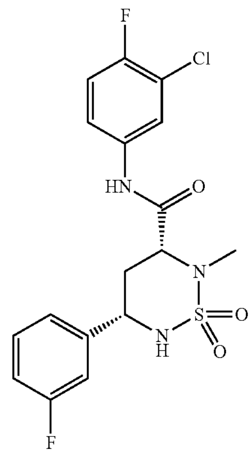 | 11% | 416.10 (M + 1) | 415.06 for $C_{17}H_{16}ClF_2N_3O_3S$ | ¹H-NMR (DMSO-d$_6$, 400 MHz): δ 10.56 (s, 1H), 7.96 (dd, J = 6.9, 2.6 Hz, 1H), 7.61-7.48 (m, 2H), 7.48-7.27 (m, 4H), 7.21-7.11 (m, 1H), 4.66-4.58 (m, 1H), 4.26 (dd, J = 11.1, 3.5 Hz, 1H), 2.64 (s, 3H), 2.16-1.97 (m, 2H). |
| HBV-CSU-232 | 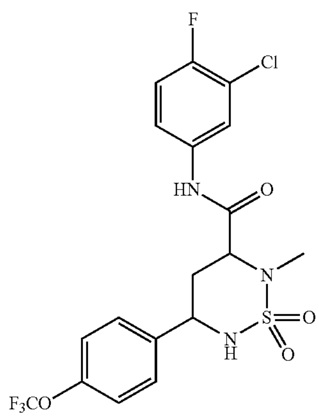 [SMILES: CN1C(C(=O)Nc2ccc(F)c(Cl)c2)CC(c2ccc(OC(F)(F)F)cc2)NS1(=O)=O] | 64% | 481.90 (M + 1) | 481.05 for $C_{18}F_{16}ClF_4N_3O_4S$ | ¹H-NMR (DMSO-d$_6$, 400 MHz): δ 10.56 (s, 1H), 7.95 (dd, J = 6.8, 2.4 Hz, 1H), 7.62-7.53 (m, 4H), 7.42-7.37 (m, 3H), 4.65-4.64 (m, 1H), 4.32-4.28 (m, 1H), 2.64 (s, 3H), 2.12-2.07 (m, 2H). |
| HBV-CSU-235 | 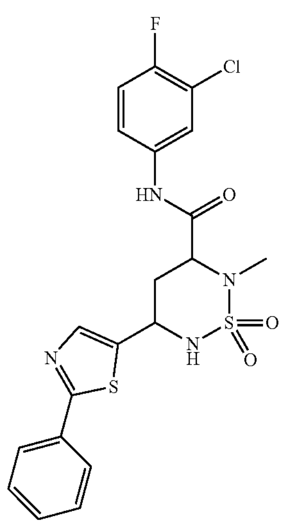 [SMILES: CN1C(C(=O)Nc2ccc(F)c(Cl)c2)CC(c2cnc(-c3ccccc3)s2)NS1(=O)=O] | 79% | 481.2 (M + 1) | 480.05 for $C_{20}H_{18}ClFN_4O_3S_2$ | ¹H-NMR (DMSO-d$_6$, 400 MHz): δ 10.60 (s, 1H), 7.98 (dd, J = 6.8, 2.6 Hz, 1H), 7.95-7.92 (m, 3H), 7.85 (d, J = 9.5 Hz, 1H), 7.59-7.55 (m, 1H), 7.54-7.47 (m, 3H), 7.41 (t, J = 9.1 Hz, 1H), 5.01-4.88 (m, 1H), 4.37-4.32 (m, 1H), 2.64 (s, 3H), 2.35-2.29 (m, 1H), 2.26-2.15 (m, 1H); |

TABLE 2-continued

Analytical data for HBV-CSU racemic & pure enantiomers:

| Target No | Structure | Rx. Yield (%) | Mass Spec. Found (m/z) | Mass Spec. Calculated | ¹H-NMR |
|---|---|---|---|---|---|
| HBV-CSU-235-ISO-I | 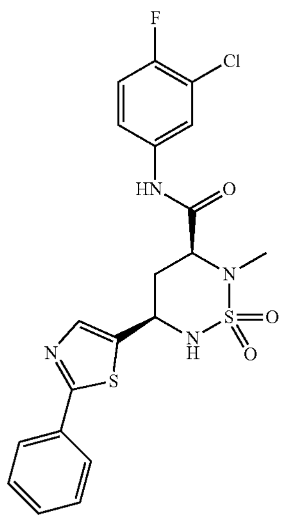 [SMILES: CN1[C@H](C(=O)Nc2ccc(F)c(Cl)c2)C[C@H](c2cnc(-c3ccccc3)s2)NS1(=O)=O] | 5.1% | 481.2 (M + 1) | 480.05 for $C_{20}H_{18}ClFN_4O_3S_2$ | ¹H-NMR (DMSO-$d_6$, 400 MHz): δ 10.61 (s, 1H), 7.98 (dd, J = 6.8, 2.6 Hz, 1H), 7.95-7.92 (m, 3H), 7.85 (d, J = 9.4 Hz, 1H), 7.59-7.55 (m, 1H), 7.54-7.47 (m, 3H), 7.41 (t, J = 9.1 Hz, 1H), 4.99-4.89 (m, 1H), 4.37-4.32 (m, 1H), 2.64 (s, 3H), 2.35-2.29 (m, 1H), 2.26-2.15 (m, 1H). |
| HBV-CSU-235-ISO-II | 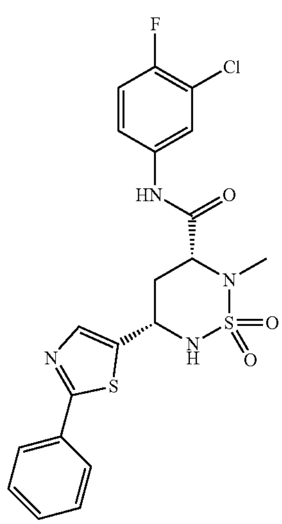 [SMILES: CN1[C@@H](C(=O)Nc2ccc(F)c(Cl)c2)C[C@@H](c2cnc(-c3ccccc3)s2)NS1(=O)=O] | 5.1% | 481.2 (M + 1) | 480.05 for $C_{20}H_{18}ClFN_4O_3S_2$ | ¹H-NMR (DMSO-$d_6$, 400 MHz): δ 10.61 (s, 1H), 7.98 (dd, J = 2.6, 6.8 Hz, 1H), 7.95-7.91 (m, 3H), 7.85 (d, J = 9.5 Hz, 1H), 7.60-7.53 (m, 1H), 7.54-7.47 (m, 3H), 7.41 (t, J = 9.1 Hz, 1H), 4.99-4.90 (m, 1H), 4.37-4.32 (m, 1H), 2.64 (s, 3H), 2.35-2.28 (m, 1H), 2.26-2.16 (m, 1H). |

TABLE 2-continued

Analytical data for HBV-CSU racemic & pure enantiomers:

| Target No | Structure | Rx. Yield (%) | Mass Spec. Found (m/z) | Mass Spec. Calculated | $^1$H-NMR |
|---|---|---|---|---|---|
| HBV-CSU-238 | 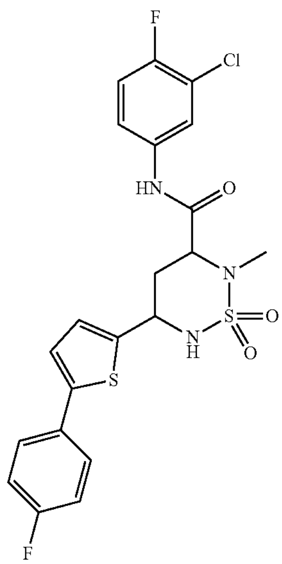 [SMILES: CN1C(C(=O)Nc2ccc(F)c(Cl)c2)CC(c2ccc(-c3ccc(F)cc3)s2)NS1(=O)=O] | 35% | 388.0 (M − 109) | 497.04 for $C_{21}H_{18}ClF_2N_3O_3S_2$ | $^1$H-NMR (DMSO-$d_6$, 400 MHz): δ 10.59 (s, 1H), 7.98 (dd, J = 6.8, 2.4 Hz, 1H), 7.73 (d, J = 9.6 Hz, 1H), 7.69-7.66 (m, 2H), 7.58-7.57 (m, 1H), 7.43-7.37 (m, 2H), 7.28-7.24 (m, 2H), 7.14 (d, J = 4.0 Hz, 1H), 4.82-4.77 (m, 1H), 4.31 (dd, J = 12.0, 3.2 Hz, 1H), 2.63 (s, 3H), 2.26-1.99 (m, 2H). |
| HBV-CSU-238-ISO-I | 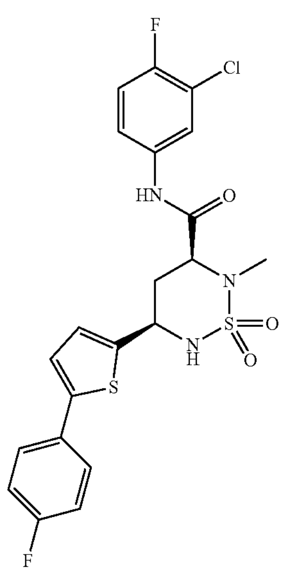 [SMILES: CN1[C@H](C(=O)Nc2ccc(F)c(Cl)c2)C[C@H](c2ccc(-c3ccc(F)cc3)s2)NS1(=O)=O] | 9% | 388.0 (M − 109) | 497.04 for $C_{21}H_{18}ClF_2N_3O_3S_2$ | $^1$H-NMR (DMSO-$d_6$, 400 MHz): δ 10.60 (s, 1H), 7.98 (dd, J = 6.8, 2.4 Hz, 1H), 7.75 (br.s, 1H), 7.70-7.65 (m, 2H), 7.58-7.54 (m, 1H), 7.43-7.37 (m, 2H), 7.29-7.24 (m, 2H), 7.14 (d, J = 4.0 Hz, 1H), 4.82-4.78 (m, 1H), 4.33-4.29 (m, 1H), 2.63 (s, 3H), 2.29-2.11 (m, 2H). |

TABLE 2-continued

Analytical data for HBV-CSU racemic & pure enantiomers:

| Target No | Structure | Rx. Yield (%) | Mass Spec. Found (m/z) | Mass Spec. Calculated | $^1$H-NMR |
|---|---|---|---|---|---|
| HBV-CSU-238-ISO-II | 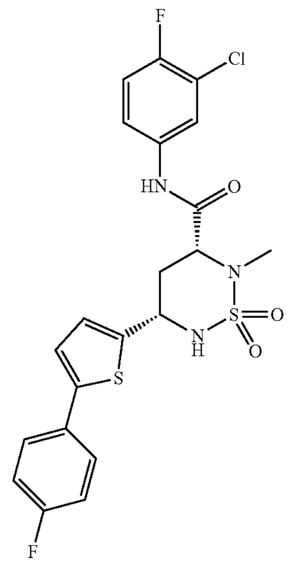 [SMILES: CN1[C@@H](C(=O)Nc2ccc(F)c(Cl)c2)C[C@@H](c2ccc(-c3ccc(F)cc3)s2)NS1(=O)=O] | 13% | 498.00 (M + 1) | 497.04 for $C_{21}H_{18}ClF_2N_3O_3S_2$ | $^1$H-NMR (DMSO-$d_6$, 400 MHz): δ 10.60 (s, 1H), 7.98 (dd, J = 6.8, 2.4 Hz, 1H), 7.74-7.66 (m, 3H), 7.58-7.54 (m, 1H), 7.43-7.38 (m, 2H), 7.28-7.23 (m, 2H), 7.14 (d, J = 3.6 Hz, 1H), 4.81-4.78 (m, 1H), 4.30 (dd, J = 12.0, 2.8 Hz, 1H), 2.63 (s, 3H), 2.29-2.11 (m, 2H). |
| HBV-CSU-239 | 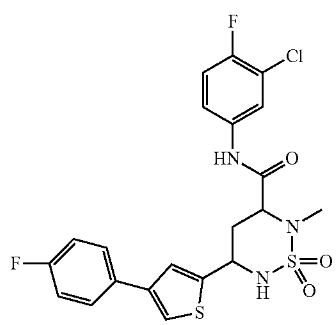 | 41% | 497.65 (M + 1) | 497.04 for $C_{21}H_{18}ClF_2N_3O_3S_2$ | $^1$H-NMR (DMSO-$d_6$, 400 MHz): δ 10.61 (s, 1H), 7.99 (dd, J = 7.2, 2.8 Hz, 1H), 7.83 (d, J = 1.2 Hz, 1H), 7.78-7.74 (m, 3H), 7.60-7.54 (m, 2H), 7.42 (t, J = 8.8 Hz, 1H), 7.24 (t, J = 8.8 Hz, 2H), 4.82-4.81 (m, 1H), 4.29 (d, J = 10.8 Hz, 1H), 2.63 (s, 3H), 2.36-2.16 (m, 2H). |
| HBV-CSU-239-ISO-I | 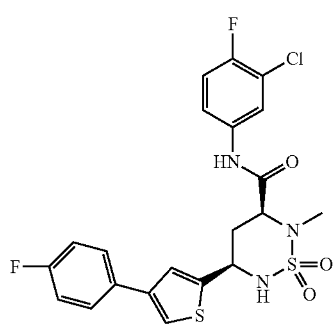 [SMILES: CN1[C@H](C(=O)Nc2ccc(F)c(Cl)c2)C[C@H](c2cc(-c3ccc(F)cc3)cs2)NS1(=O)=O] | 12% | 498.05 (M + 1) | 497.04 for $C_{21}H_{18}ClF_2N_3O_3S_2$ | $^1$H-NMR (DMSO-$d_6$, 400 MHz): δ 10.61 (s, 1H), 7.98 (dd, J = 6.8, 2.4 Hz, 1H), 7.82 (d, J = 1.2 Hz, 1H), 7.78-7.74 (m, 3H), 7.60-7.54 (m, 2H), 7.41 (t, J = 6.4 Hz, 1H), 7.26-7.21 (m, 2H), 4.81-4.80 (m, 1H), 4.29 (dd, J = 12.4, 3.2 Hz, 1H), 2.63 (s, 3H), 2.36-2.15 (m, 2H). |
| HBV-CSU-239-ISO-II | 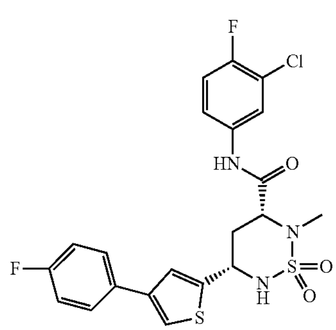 [SMILES: CN1[C@@H](C(=O)Nc2ccc(F)c(Cl)c2)C[C@@H](c2cc(-c3ccc(F)cc3)cs2)NS1(=O)=O] | 8% | 498.00 (M + 1) | 497.04 for $C_{21}H_{18}ClF_2N_3O_3S_2$ | $^1$H-NMR (DMSO-$d_6$, 400 MHz): δ 10.59 (s, 1H), 7.98 (dd, J = 6.4, 2.4 Hz, 1H), 7.82 (d, J = 1.2 Hz, 1H), 7.78-7.74 (m, 3H), 7.59-7.55 (m, 2H), 7.41 (t, J = 9.2 Hz, 1H), 7.25-7.21 (m, 2H), 4.79 (d, J = 11.2 Hz, 1H), 4.27 (d, J = 11.2 Hz, 1H), 2.62 (s, 3H), 2.36-2.18 (m, 2H). |

TABLE 2-continued

Analytical data for HBV-CSU racemic & pure enantiomers:

| Target No | Structure | Rx. Yield (%) | Mass Spec. Found (m/z) | Mass Spec. Calculated | ¹H-NMR |
|---|---|---|---|---|---|
| HBV-CSU-240-ISO-I | 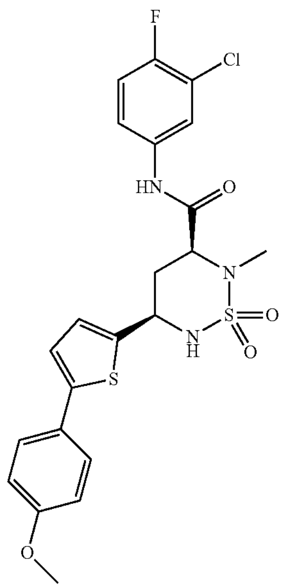 [SMILES: COc1ccc(-c2ccc([C@H]3C[C@@H](C(=O)Nc4ccc(F)c(Cl)c4)N(C)S(=O)(=O)N3)s2)cc1] | 4% | 509.05 (M⁺) | 509.06 for $C_{22}H_{21}ClFN_3O_4S_2$ | ¹H-NMR (DMSO-$d_6$, 400 MHz): δ 10.58 (s, 1H), 7.97 (dd, J = 6.8, 2.8 Hz, 1H), 7.69 (d, J = 9.2 Hz, 1H), 7.58-7.55 (m, 3H), 7.41 (t, J = 9.2 Hz, 1H), 7.26 (d, J = 3.6 Hz, 1H), 7.11-7.09 (m, 1H), 6.97 (d, J = 8.8 Hz, 2H), 4.81-4.77 (m, 1H), 4.30 (dd, J = 12.0, 2.8 Hz, 1H), 3.78 (s, 3H), 2.62 (s, 3H), 2.33-2.11 (m, 2H). |
| HBV-CSU-240-ISO-II | 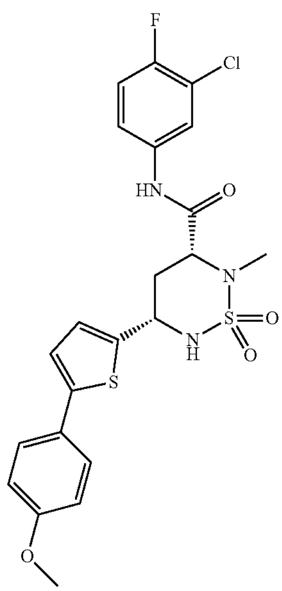 | 10% | 510.95 (M + 1) | 509.06 for $C_{22}H_{21}ClFN_3O_4S_2$ | ¹H-NMR (DMSO-$d_6$, 400 MHz): δ 10.59 (s, 1H), 7.98 (dd, J = 6.8, 2.8 Hz, 1H), 7.71 (br.s, 1H), 7.58-7.55 (m, 3H), 7.41 (t, J = 9.2 Hz, 1H), 7.26 (d, J = 3.6 Hz, 1H), 7.09 (d, J = 3.6 Hz, 1H), 6.97 (d, J = 8.8 Hz, 2H), 4.77 (t, J = 10.8 Hz, 1H), 4.32 (dd, J = 11.6, 2.4 Hz, 1H), 3.78 (s, 3H), 2.62 (s, 3H), 2.28-2.11 (m, 2H). |
| HBV-CSU-241 | 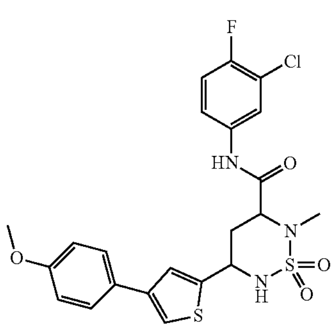 [SMILES: COc1ccc(-c2csc(C3CC(C(=O)Nc4ccc(F)c(Cl)c4)N(C)S(=O)(=O)N3)c2)cc1] | 67% | 510.05 (M + 1) | 509.06 for $C_{22}H_{21}ClFN_3O_4S_2$ | ¹H-NMR (DMSO-$d_6$, 400 MHz): δ 10.61 (s, 1H), 7.98 (dd, J = 6.4, 2.4 Hz, 1H), 7.74-7.55 (m, 6H), 7.41 (t, J = 8.8 Hz, 1H), 6.95 (d, J = 8.8 Hz, 2H), 4.83-4.78 (m, 1H), 4.29 (dd, J = 12.0, 2.4 Hz, 1H), 3.78 (s, 3H), 2.63 (s, 3H), 2.36-2.18 (m, 2H). |

TABLE 2-continued

Analytical data for HBV-CSU racemic & pure enantiomers:

| Target No | Structure | Rx. Yield (%) | Mass Spec. Found (m/z) | Mass Spec. Calculated | ¹H-NMR |
|---|---|---|---|---|---|
| HBV-CSU-241-ISO-I | 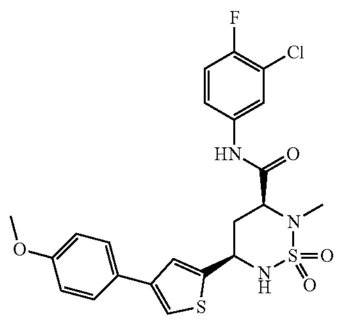 [SMILES: COc1ccc(-c2csc([C@H]3C[C@@H](C(=O)Nc4ccc(F)c(Cl)c4)N(C)S(=O)(=O)N3)c2)cc1] | 19% | 510.05 (M + 1) | 509.06 for $C_{22}H_{21}ClFN_3O_4S_2$ | ¹H-NMR (DMSO-$d_6$, 400 MHz): δ 10.62 (s, 1H), 7.98 (dd, J = 6.4, 2.4 Hz, 1H), 7.70-7.55 (m, 6H), 7.42 (t, J = 9.6 Hz, 1H), 6.95 (d, J = 8.8 Hz, 2H), 4.79 (d, J = 10.0 Hz, 1H), 4.29 (d, J = 10.0 Hz, 1H), 3.78 (s, 3H), 2.63 (s, 3H), 2.36-2.08 (m, 2H). |
| HBV-CSU-241-ISO-II | 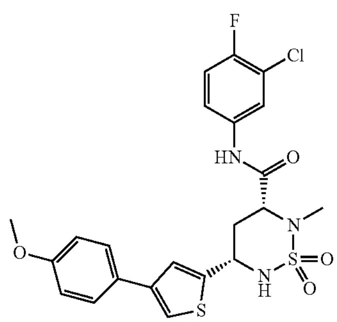 [SMILES: COc1ccc(-c2csc([C@@H]3C[C@H](C(=O)Nc4ccc(F)c(Cl)c4)N(C)S(=O)(=O)N3)c2)cc1] | 20% | 510.05 (M + 1) | 509.06 for $C_{22}H_{21}ClFN_3O_4S_2$ | ¹H-NMR (DMSO-$d_6$, 400 MHz): δ 10.58 (s, 1H), 7.98 (dd, J = 6.4, 2.4 Hz, 1H), 7.69-7.54 (m, 6H), 7.39 (t, J = 9.2 Hz, 1H), 6.93 (d, J = 8.8 Hz, 2H), 4.83-4.79 (m, 1H), 4.28-4.27 (m, 1H), 3.76 (s, 3H), 2.61 (s, 3H), 2.38-2.08 (m, 2H). |
| HBV-CSU-242 | 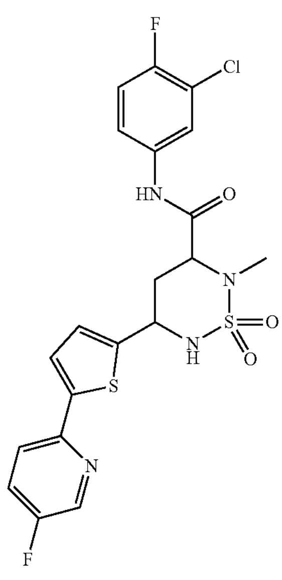 [SMILES: CN1C(C(=O)Nc2ccc(F)c(Cl)c2)CC(c2ccc(-c3ccc(F)cn3)s2)NS1(=O)=O] | 4% | 499.10 (M + 1) | 498.04 for $C_{20}H_{17}ClF_2N_4O_3S_2$ | ¹H-NMR (DMSO-$d_6$, 400 MHz): δ 10.58 (s, 1H), 8.64 (d, J = 3.2 Hz, 1H), 8.42 (d, J = 4.4 Hz, 1H), 7.95 (dd, J = 6.4, 2.4 Hz, 1H), 7.84-7.75 (m, 2H), 7.55-7.51 (m, 2H), 7.41-7.27 (m, 2H), 4.88-4.83 (m, 1H), 4.33-4.29 (m, 1H), 2.60 (s, 3H), 2.31-2.12 (m, 2H). |

TABLE 2-continued

Analytical data for HBV-CSU racemic & pure enantiomers:

| Target No | Structure | Rx. Yield (%) | Mass Spec. Found (m/z) | Mass Spec. Calculated | ¹H-NMR |
|---|---|---|---|---|---|
| HBV-CSU-242-ISO-I | 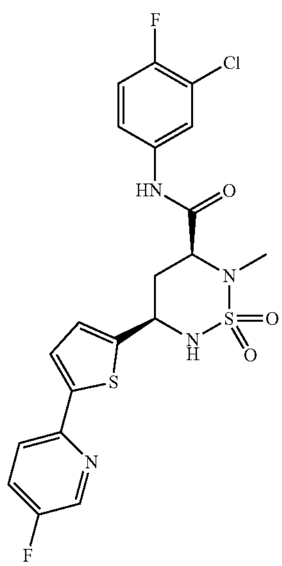 [SMILES: CN1[C@H](C(=O)Nc2ccc(F)c(Cl)c2)C[C@H](c2ccc(-c3ccc(F)cn3)s2)NS1(=O)=O] | 3% | 499.10 (M + 1) | 498.04 for $C_{20}H_{17}ClF_2N_4O_3S_2$ | ¹H-NMR (DMSO-d$_6$, 400 MHz): δ 10.58 (s, 1H), 8.53-8.52 (m, 1H), 8.00-7.95 (m, 1H), 7.95 (dd, J = 6.4, 2.4 Hz, 1H), 7.84-7.75 (m, 2H), 7.55-7.51 (m, 2H), 7.41-7.37 (m, 1H), 7.17-7.16 (m, 1H), 4.81-4.78 (m, 1H), 4.32-4.28 (m, 1H), 2.62 (s, 3H), 2.32-2.16 (m, 2H). |
| HBV-CSU-242-ISO-II | 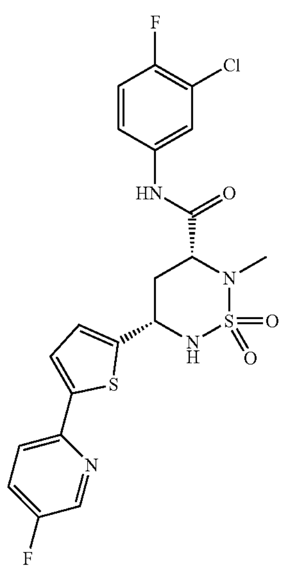 | 4% | 499.10 (M + 1) | 498.04 for $C_{20}H_{17}ClF_2N_4O_3S_2$ | ¹H-NMR (DMSO-d$_6$, 400 MHz): δ 10.57 (s, 1H), 8.52-8.51 (m, 1H), 7.99-7.96 (m, 2H), 7.80-7.74 (m, 3H), 7.57-7.53 (m, 1H), 7.41 (t, J = 8.8 HZ, 1H), 7.16-7.15 (m, 1H), 4.80-4.77 (m, 1H), 4.30-4.27 (m, 1H), 2.61 (s, 3H), 2.32-2.12 (m, 2H). |
| HBV-CSU-243 | 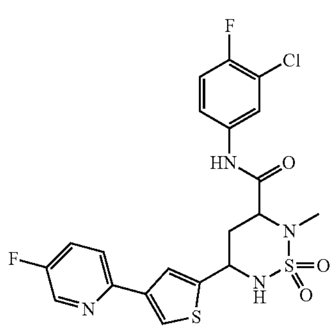 [SMILES: CN1C(C(=O)Nc2ccc(F)c(Cl)c2)CC(c2cc(-c3ccc(F)cn3)cs2)NS1(=O)=O] | 35% | 499.10 (M + 1) | 498.04 for $C_{20}H_{17}ClF_2N_4O_3S_2$ | ¹H-NMR (DMSO-d$_6$, 400 MHz): δ 10.60 (s, 1H), 8.56 (d, J = 3.2 Hz, 1H), 8.11 (s, 1H), 7.99-7.94 (m, 2H), 7.81-7.73 (m, 3H), 7.59-7.55 (m, 1H), 7.41 (t, J = 8.8 Hz, 1H), 4.83 (t, J = 10.0 Hz, 1H), 4.32 (dd, J = 12.0, 2.4 Hz, 1H), 2.63 (s, 3H), 2.35-2.18 (m, 2H). |

TABLE 2-continued

Analytical data for HBV-CSU racemic & pure enantiomers:

| Target No | Structure | Rx. Yield (%) | Mass Spec. Found (m/z) | Mass Spec. Calculated | ¹H-NMR |
|---|---|---|---|---|---|
| HBV-CSU-243-ISO-I | 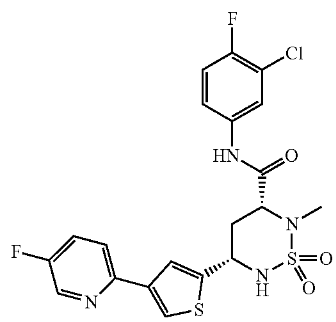 [SMILES: CN1[C@@H](C(=O)Nc2ccc(F)c(Cl)c2)C[C@@H](c2cc(-c3ccc(F)cn3)cs2)NS1(=O)=O] | 3.5% | 499.05 (M + 1) | 498.04 for $C_{20}H_{17}ClF_2N_4O_3S_2$ | ¹H-NMR (DMSO-$d_6$, 400 MHz): δ 10.60 (s, 1H), 8.56 (d, J = 3.0 Hz, 1H), 8.11 (s, 1H), 8.02-7.92 (m, 2H), 7.81-7.75 (m 3H), 7.58-7.56 (m, 1H), 7.41 (t, J = 9.1 Hz, 1H), 4.88-4.77 (m, 1H), 4.33 (dd, J = 11.8, 2.9 Hz, 1H), 2.63 (s, 3H), 2.35-2.15 (m, 2H). |
| HBV-CSU-243-ISO-II | 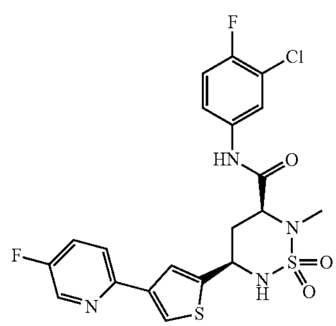 [SMILES: CN1[C@H](C(=O)Nc2ccc(F)c(Cl)c2)C[C@H](c2cc(-c3ccc(F)cn3)cs2)NS1(=O)=O] | 4.4% | 499.05 (M + 1) | 498.04 for $C_{20}H_{17}ClF_2N_4O_3S_2$ | ¹H-NMR (DMSO-$d_6$, 400 MHz): δ 10.59 (s, 1H), 8.56 (d, J = 2.6 Hz, 1H), 8.11 (s, 1H), 8.02-7.92 (m, 2H), 7.84-7.71 (m, 3H), 7.58-7.56 (m, 1H), 7.41 (t, J = 9.2 Hz, 1H), 4.82-4.80 (m, 1H), 4.33 (dd, J = 11.9, 2.7 Hz, 1H), 2.63 (s, 3H), 2.38-2.29 (m, 1H), 2.27-2.12 (m, 1H). |
| HBV-CSU-244 | 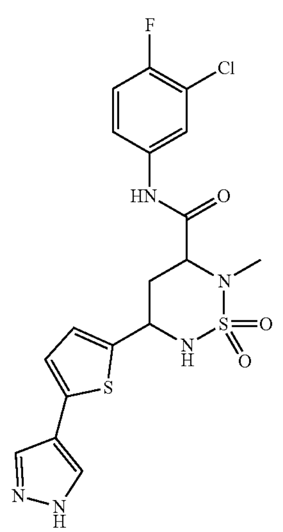 [SMILES: CN1C(C(=O)Nc2ccc(F)c(Cl)c2)CC(c2ccc(-c3cn[nH]c3)s2)NS1(=O)=O] | 31% | 470.15 (M + 1) | 469.04 for $C_{18}H_{17}ClFN_5O_3S_2$ | ¹H-NMR (DMSO-$d_6$, 400 MHz): δ 13.00 (s, 1H), 10.58 (s, 1H), 7.99-7.93 (m, 2H), 7.69-7.54 (m, 3H), 7.44-7.35 (m, 1H), 7.09-7.04 (m, 2H), 4.75-4.72 (m, 1H), 4.38-4.29 (m, 1H), 2.61 (s, 3H), 2.32-2.09 (m, 2H). |

TABLE 2-continued

Analytical data for HBV-CSU racemic & pure enantiomers:

| Target No | Structure | Rx. Yield (%) | Mass Spec. Found (m/z) | Mass Spec. Calculated | $^1$H-NMR |
|---|---|---|---|---|---|
| HBV-CSU-244-ISO-I | 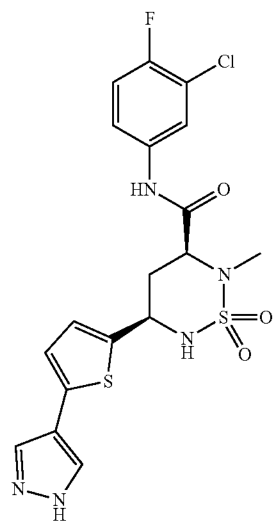 [SMILES: CN1[C@H](C(=O)Nc2ccc(F)c(Cl)c2)C[C@H](c2ccc(-c3cn[nH]c3)s2)NS1(=O)=O] | 4% | 470.05 (M + 1) | 469.04 for $C_{18}H_{17}ClFN_5O_3S_2$ | $^1$H-NMR (DMSO-$d_6$, 400 MHz): δ 13.05 (s, 1H), 10.58 (s, 1H), 7.99-7.96 (m, 1H), 7.88-7.77 (m, 3H), 7.58-7.55 (m, 1H), 7.40 (t, J = 9.2 Hz, 1H), 7.07-7.02 (m, 2H), 4.73-4.72 (m, 1H), 4.48-4.44 (m, 1H), 2.59 (s, 3H), 2.23-2.10 (m, 2H). |
| HBV-CSU-244-ISO-II | 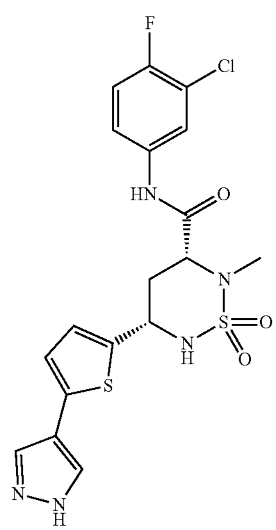 [SMILES: CN1[C@@H](C(=O)Nc2ccc(F)c(Cl)c2)C[C@@H](c2ccc(-c3cn[nH]c3)s2)NS1(=O)=O] | 5% | 470.10 (M + 1) | 469.04 for $C_{18}H_{17}ClFN_5O_3S_2$ | $^1$H-NMR (DMSO-$d_6$, 400 MHz): δ 13.02 (s, 1H), 10.59 (s, 1H), 8.06-7.54 (m, 5H), 7.41 (t, J = 9.2 Hz, 1H), 7.07-7.04 (m, 2H), 4.74 (t, J = 10.8 Hz, 1H), 4.29 (dd, J = 11.6, 2.4 Hz, 1H), 2.61 (s, 3H), 2.16-2.09 (m, 2H). |
| HBV-CSU-245 | 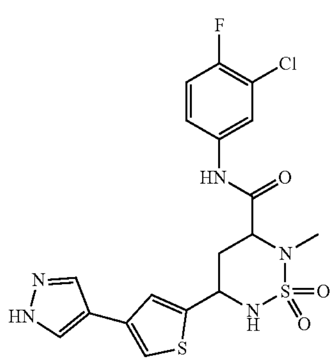 [SMILES: CN1C(C(=O)Nc2ccc(F)c(Cl)c2)CC(c2cc(-c3cn[nH]c3)cs2)NS1(=O)=O] | 52% | 470.10 (M + 1) | 469.04 for $C_{18}H_{17}ClFN_5O_3S_2$ | $^1$H-NMR (DMSO-$d_6$, 400 MHz): δ 10.60 (s, 1H), 7.99-7.95 (m, 3H), 7.69 (d, J = 10.0 Hz, 1H), 7.59-7.55 (m, 1H), 7.51 (s, 1H), 7.43-7.39 (m, 2H), 4.78-4.77 (m, 1H), 4.32-4.28 (m, 1H), 2.62 (s, 3H), 2.32-2.17 (m, 2H). |

TABLE 2-continued

Analytical data for HBV-CSU racemic & pure enantiomers:

| Target No | Structure | Rx. Yield (%) | Mass Spec. Found (m/z) | Mass Spec. Calculated | ¹H-NMR |
|---|---|---|---|---|---|
| HBV-CSU-245-ISO-I | 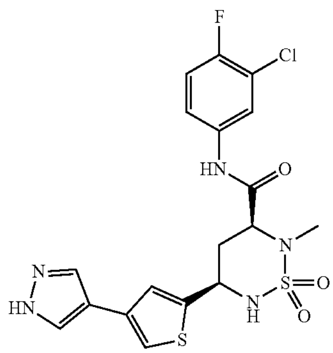 [SMILES: CN1[C@H](C(=O)Nc2ccc(F)c(Cl)c2)C[C@H](c2cc(-c3cn[nH]c3)cs2)NS1(=O)=O] | 5% | 470.10 (M + 1) | 469.04 for $C_{18}H_{17}ClFN_5O_3S_2$ | ¹H-NMR (DMSO-d$_6$, 400 MHz): δ 12.84 (s, 1H), 10.58 (s, 1H), 7.99-7.37 (m, 8H), 4.74-4.73 (m, 1H), 4.35-4.28 (m, 1H), 2.58 (s, 3H), 2.37-1.99 (m, 2H). |
| HBV-CSU-245-ISO-II | 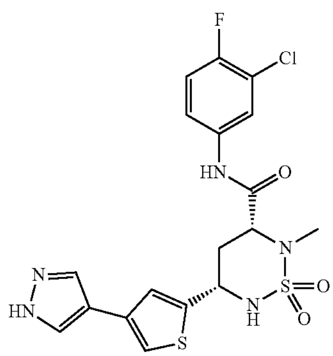 [SMILES: CN1[C@@H](C(=O)Nc2ccc(F)c(Cl)c2)C[C@@H](c2cc(-c3cn[nH]c3)cs2)NS1(=O)=O] | 4% | 470.10 (M + 1) | 469.04 for $C_{18}H_{17}ClFN_5O_3S_2$ | ¹H-NMR (DMSO-d$_6$, 400 MHz): δ 12.85 (s, 1H), 10.61 (s, 1H), 8.06-7.39 (m, 8H), 4.75 (d, J = 12.8 Hz, 1H), 4.27-4.26 (m, 1H), 2.59 (s, 3H), 2.32-2.15 (m, 2H). |
| HBV-CSU-246 | 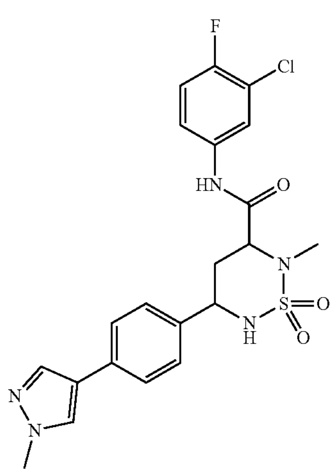 [SMILES: CN1C(C(=O)Nc2ccc(F)c(Cl)c2)CC(c2ccc(-c3cnn(C)c3)cc2)NS1(=O)=O] | 32% | 478.10 (M + 1) | 477.10 for $C_{21}H_{21}ClFN_5O_3S$ | ¹H-NMR (DMSO-d$_6$, 400 MHz): δ 10.56 (s, 1H), 8.15 (s, 1H), 7.96 (dd, J = 7.2, 2.4 Hz, 1H), 7.87 (s, 1H), 7.58-7.38 (m, 7H), 4.57-4.56 (m, 1H), 4.29-4.24 (m, 1H), 3.86 (m, 3H), 2.65 (s, 3H), 2.10-2.07 (m, 2H). |

TABLE 2-continued

Analytical data for HBV-CSU racemic & pure enantiomers:

| Target No | Structure | Rx. Yield (%) | Mass Spec. Found (m/z) | Mass Spec. Calculated | $^1$H-NMR |
|---|---|---|---|---|---|
| HBV-CSU-246-ISO-I | 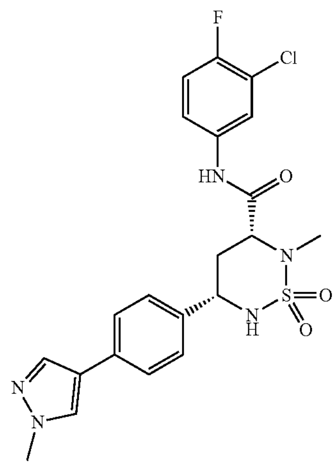 [SMILES: CN1[C@@H](C(=O)Nc2ccc(F)c(Cl)c2)C[C@@H](c2ccc(-c3cnn(C)c3)cc2)NS1(=O)=O] | 10% | 478.10 (M + 1) | 477.10 for $C_{21}H_{21}ClFN_5O_3S$ | $^1$H-NMR (DMSO-$d_6$, 400 MHz): δ 10.57 (s, 1H), 8.15 (s, 1H), 7.96 (dd, J = 6.8, 2.4 Hz, 1H), 7.87 (s, 1H), 7.58-7.38 (m, 7H), 4.57-4.56 (m, 1H), 4.28-4.24 (m, 1H), 3.85 (m, 3H), 2.64 (s, 3H), 2.12-2.07 (m, 2H). |
| HBV-CSU-246-ISO-II | 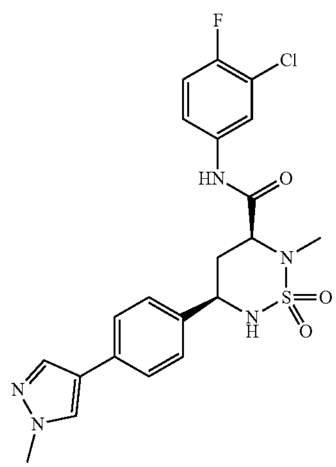 [SMILES: CN1[C@H](C(=O)Nc2ccc(F)c(Cl)c2)C[C@H](c2ccc(-c3cnn(C)c3)cc2)NS1(=O)=O] | 10% | 478.15 (M + 1) | 477.10 for $C_{21}H_{21}ClFN_5O_3S$ | $^1$H-NMR (DMSO-$d_6$, 400 MHz): δ 10.57 (s, 1H), 8.15 (s, 1H), 7.96 (dd, J = 6.8, 2.4 Hz, 1H), 7.87 (s, 1H), 7.58-7.37 (m, 7H), 4.59-4.56 (m, 1H), 4.28-4.24 (m, 1H), 3.85 (m, 3H), 2.64 (s, 3H), 2.12-2.07 (m, 2H). |
| HBV-CSU-247 | 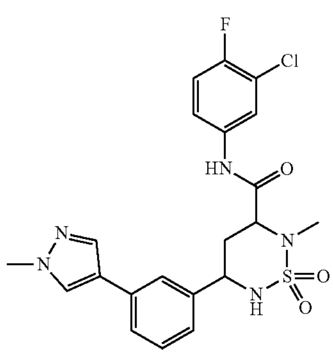 [SMILES: CN1C(C(=O)Nc2ccc(F)c(Cl)c2)CC(c2cccc(-c3cnn(C)c3)c2)NS1(=O)=O] | 68% | 477.95 (M + 1) | 477.10 for $C_{21}H_{21}ClFN5O_3S_2$ | $^1$H-NMR (DMSO-$d_6$, 400 MHz): δ 10.58 (s, 1H), 8.16 (s, 1H), 7.96 (dd, J = 6.8, 2.4 Hz, 1H), 7.88 (d, J = 0.8 Hz, 1H), 7.68-7.67 (m, 1H), 7.57-7.50 (m, 3H), 7.43-7.25 (m, 3H), 4.61-4.59 (m, 1H), 4.29-4.25 (m, 1H), 3.87 (m, 3H), 2.66 (s, 3H), 2.15-2.10 (m, 2H). |

TABLE 2-continued

Analytical data for HBV-CSU racemic & pure enantiomers:

| Target No | Structure | Rx. Yield (%) | Mass Spec. Found (m/z) | Mass Spec. Calculated | $^1$H-NMR |
|---|---|---|---|---|---|
| HBV-CSU-247-ISO-I | 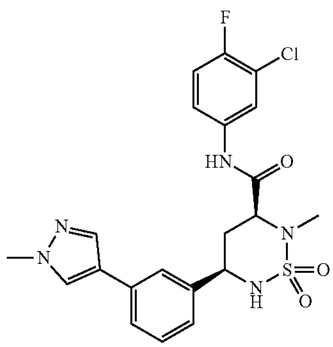 [SMILES: CN1[C@H](C(=O)Nc2ccc(F)c(Cl)c2)C[C@H](c2cccc(-c3cnn(C)c3)c2)NS1(=O)=O] | 13% | 477.95 (M + 1) | 477.10 for $C_{21}H_{21}ClFN5O_3S_2$ | $^1$H-NMR (DMSO-$d_6$, 400 MHz): δ 10.57 (s, 1H), 8.15 (s, 1H), 7.97-7.95 (m, 1H), 7.88 (s, 1H), 7.67 (s, 1H), 7.55-7.50 (m, 3H), 7.45-7.31 (m, 2H), 7.27-7.25 (m, 1H), 4.62-4.58 (m, 1H), 4.28-4.25 (m, 1H), 3.86 (s, 3H), 2.65 (s, 3H), 2.20-2.07 (m, 2H). |
| HBV-CSU-247-ISO-II | 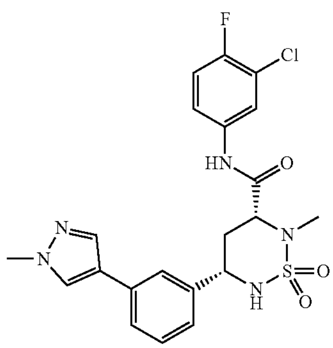 [SMILES: CN1[C@@H](C(=O)Nc2ccc(F)c(Cl)c2)C[C@@H](c2cccc(-c3cnn(C)c3)c2)NS1(=O)=O] | 11% | 478 (M + 1) | 477.10 for $C_{21}H_{21}ClFN5O_3S_2$ | $^1$H-NMR (DMSO-$d_6$, 400 MHz): δ 10.57 (s, 1H), 8.15 (s, 1H), 7.97-7.95 (m, 1H), 7.88 (s, 1H), 7.67 (s, 1H), 7.55-7.50 (m, 3H), 7.45-7.31 (m, 2H), 7.27-7.25 (m, 1H), 4.61-4.57 (m, 1H), 4.26 (dd, J = 9.3, 5.5 Hz, 1H), 3.86 (s, 3H), 2.65 (s, 3H), 2.20-2.07 (m, 2H). |
| HBV-CSU-248 | 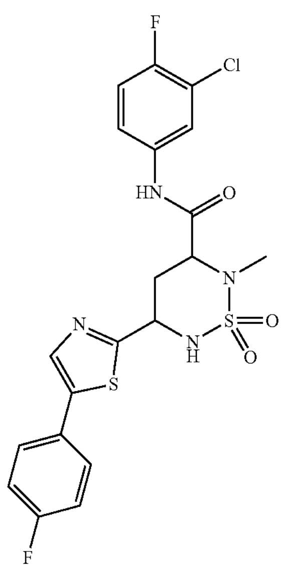 [SMILES: CN1C(C(=O)Nc2ccc(F)c(Cl)c2)CC(c2ncc(-c3ccc(F)cc3)s2)NS1(=O)=O] | 40% | 499.20 (M + 1) | 498.02 for $C_{20}H_{17}ClF_2N_4O_3S_2$ | $^1$H-NMR (DMSO-$d_6$, 400 MHz): δ 10.61 (s, 1H), 8.17 (s, 1H), 7.98 (dd, J = 6.3, 2.4 Hz, 2H), 7.77-7.72 (m, 2H), 7.60-7.54 (m, 1H), 7.41 (t, J = 9.1 Hz, 1H), 7.31 (t, J = 8.8 Hz, 2H), 4.99-4.90 (m, 1H), 4.40-4.35 (m, 1H), 2.64 (s, 3H), 2.44-2.38 (m, 1H), 2.35-2.37 (m, 1H). |

TABLE 2-continued

Analytical data for HBV-CSU racemic & pure enantiomers:

| Target No | Structure | Rx. Yield (%) | Mass Spec. Found (m/z) | Mass Spec. Calculated | ¹H-NMR |
|---|---|---|---|---|---|
| HBV-CSU-248-ISO-I | 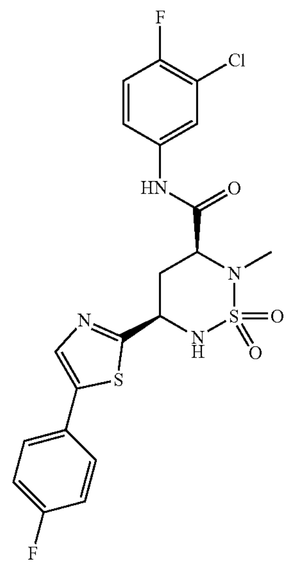 [SMILES: CN1[C@H](C(=O)Nc2ccc(F)c(Cl)c2)C[C@H](c2ncc(-c3ccc(F)cc3)s2)NS1(=O)=O] | 7% | 499.30 (M + 1) | 498.02 for $C_{20}H_{17}ClF_2N_4O_3S_2$ | ¹H-NMR (DMSO-$d_6$, 400 MHz): δ 10.59 (s, 1H), 8.16 (s, 1H), 8.00-7.93 (m, 2H), 7.74 (dd, J = 8.8, 5.3 Hz, 2H), 8.00-7.54 (m, 1H), 7.41 (t, J = 9.1 Hz, 1H), 7.31 (t, J = 8.8 Hz, 2H), 5.01-4.88 (m, 1H), 4.41-4.35 (m, 1H), 2.64 (s, 3H), 2.45-2.37 (m, 1H), 2.28-2.16 (m, 1H). |
| HBV-CSU-248-ISO-II | 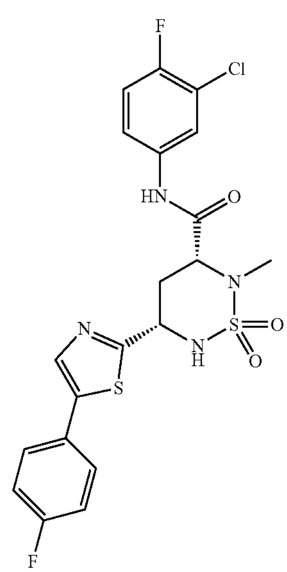 [SMILES: CN1[C@@H](C(=O)Nc2ccc(F)c(Cl)c2)C[C@@H](c2ncc(-c3ccc(F)cc3)s2)NS1(=O)=O] | 4% | 499.30 (M + 1) | 498.02 for $C_{20}H_{17}ClF_2N_4O_3S_2$ | ¹H-NMR (DMSO-$d_6$, 400 MHz): δ 10.60 (s, 1H), 8.16 (s, 1H), 7.98 (d, J = 4.6 Hz, 2H), 7.74 (dd, J = 8.0, 5.5 Hz, 2H), 7.62-7.54 (m, 1H), 7.41 (t, J = 9.0 Hz, 1H), 7.31 (t, J = 8.7 Hz, 2H), 4.98-4.93 (m, 1H), 4.40-4.36 (m, 1H), 2.64 (s, 3H), 2.45-2.35 (m, 1H), 2.29-2.13 (m, 1H). |

TABLE 2-continued
Analytical data for HBV-CSU racemic & pure enantiomers:
| Target No | Structure | Rx. Yield (%) | Mass Spec. Found (m/z) | Mass Spec. Calculated | $^1$H-NMR |
|---|---|---|---|---|---|
| HBV-CSU-250 | 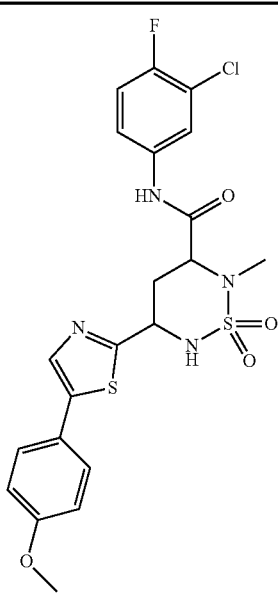 | 38% | 511.30 (M + 1) | 510.06 for $C_{21}H_{20}ClFN_4O_4S_2$ | $^1$H-NMR (DMSO-$d_6$, 400 MHz): δ 10.58 (s, 1H), 8.05 (s, 1H), 7.98 (dd, J = 6.8, 2.3 Hz, 1H), 7.93 (d, J = 9.3 Hz, 1H), 7.66-7.54 (m, 3H), 7.41 (t, J = 9.1 Hz, 1H), 7.02 (d, J = 8.7 Hz, 2H), 4.96-4.90 (m, 1H), 4.40-4.35 (m, 1H), 3.80 (s, 3H), 2.64 (s, 3H), 2.43-2.36 (m, 1H), 2.27-2.21 (m, 1H). |
| HBV-CSU-250-ISO-I | 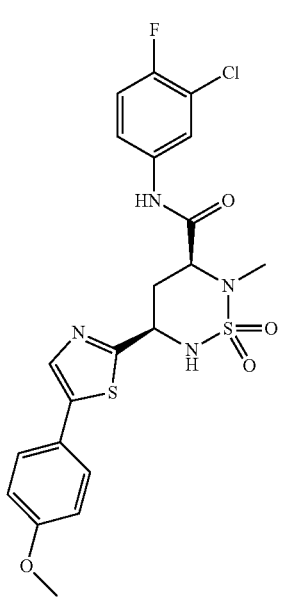 [SMILES: COc1ccc(-c2cnc([C@H]3C[C@@H](C(=O)Nc4ccc(F)c(Cl)c4)N(C)S(=O)(=O)N3)s2)cc1] | 6% | — | 510.06 for $C_{21}H_{20}ClFN_4O_4S_2$ | $^1$H-NMR (DMSO-$d_6$, 400 MHz): δ 10.59 (s, 1H), 8.33 (s, 1H), 8.01-7.95 (m, 2H), 7.85-7.76 (m, 2H), 7.60-7.54 (m, 1H), 7.48 (dd, J = 8.3, 1.8 Hz, 1H), 7.41 (t, J = 9.1 Hz, 1H), 5.02-4.92 (m, 1H), 4.41-4.35 (m, 1H), 2.64 (s, 3H), 2.45-2.39 (m, 1H), 2.26-2.15 (m, 1H). |

TABLE 2-continued

Analytical data for HBV-CSU racemic & pure enantiomers:

| Target No | Structure | Rx. Yield (%) | Mass Spec. Found (m/z) | Mass Spec. Calculated | ¹H-NMR |
|---|---|---|---|---|---|
| HBV-CSU-250-ISO-II | 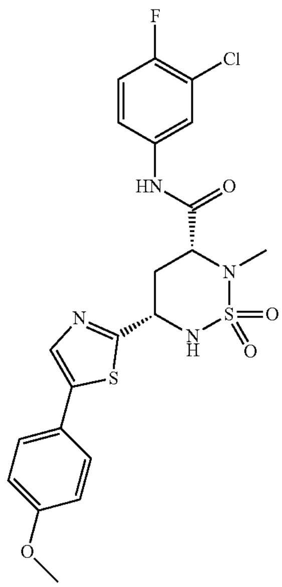 [SMILES: COc1ccc(-c2cnc([C@@H]3C[C@H](C(=O)Nc4ccc(F)c(Cl)c4)N(C)S(=O)(=O)N3)s2)cc1] | 4% | — | 510.06 for $C_{21}H_{20}ClFN_4O_4S_2$ | ¹H-NMR (DMSO-d$_6$, 400 MHz): δ 10.60 (s, 1H), 8.94 (d, J = 1.9 Hz, 1H), 8.58 (dd, J = 4.8, 1.5 Hz, 1H), 8.32 (s, 1H), 8.11 (dt, J = 8.0, 1.9 Hz, 1H), 8.02-7.96 (m, 2H), 7.61-7.55 (m, 1H), 7.53-7.47 (m, 1H), 7.41 (t, J = 9.1 Hz, 1H), 5.05-4.93 (m, 1H), 4.48-4.34 (m, 1H), 2.65 (s, 3H), 2.46-2.40 (m, 1H), 2.28-2.16 (m, 1H). |
| HBV-CSU-252 | 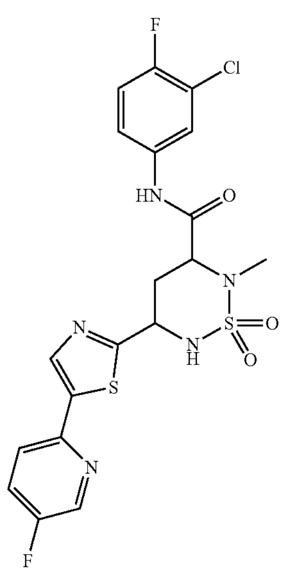 | 47% | 500.20 (M + 1) | 499.04 for $C_{19}H_{16}ClF_2N_5O_3S_2$ | ¹H-NMR (DMSO-d$_6$, 400 MHz): δ 10.59 (s, 1H), 8.61 (d, J = 2.9 Hz, 1H), 8.44 (s, 1H), 8.12 (dd, J = 8.9, 4.3 Hz, 1H), 7.98 (dd, J = 6.8, 2.9 Hz, 2H), 7.87 (td, J = 8.7, 2.9 Hz, 1H), 7.60-7.53 (m, 1H), 7.41 (t, J = 9.1 Hz, 1H), 5.00-4.91 (m, 1H), 4.40-4.34 (m, 1H), 2.64 (s, 3H), 2.45-2.38 (m, 1H), 2.27-2.14 (m, 1H). |

TABLE 2-continued

Analytical data for HBV-CSU racemic & pure enantiomers:

| Target No | Structure | Rx. Yield (%) | Mass Spec. Found (m/z) | Mass Spec. Calculated | ¹H-NMR |
|---|---|---|---|---|---|
| HBV-CSU-252-ISO-I | 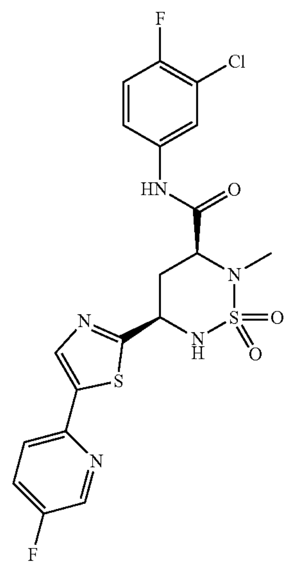 [SMILES: CN1[C@H](C(=O)Nc2ccc(F)c(Cl)c2)C[C@H](c2ncc(-c3ccc(F)cn3)s2)NS1(=O)=O] | 14% | 500.2 (M + 1) | 499.04 for $C_{19}H_{16}ClF_2N_5O_3S_2$ | ¹H-NMR (DMSO-d$_6$, 400 MHz): δ 10.59 (s, 1H), 8.61 (d, J = 2.5 Hz, 1H), 8.44 (s, 1H), 8.11 (dd, J = 8.8, 4.3 Hz, 1H), 7.98 (dd, J = 6.5, 2.1 Hz, 2H), 7.87 (td, J = 8.7, 2.7 Hz, 1H), 7.60-7.54 (m, 1H), 7.40 (t, J = 9.1 Hz, 1H), 4.98-4.93 (m, 1H), 4.39-4.34 (m, 1H), 2.64 (s, 3H), 2.45-2.38 (m, 1H), 2.26-2.15 (m, 1H). |
| HBV-CSU-252-ISO-II | 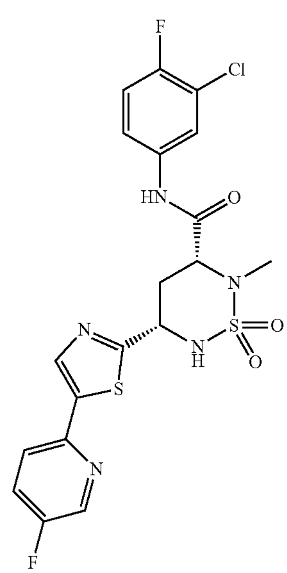 [SMILES: CN1[C@@H](C(=O)Nc2ccc(F)c(Cl)c2)C[C@@H](c2ncc(-c3ccc(F)cn3)s2)NS1(=O)=O] | 15% | 500.2 (M + 1) | 499.04 for $C_{19}H_{16}ClF_2N_5O_3S_2$ | ¹H-NMR (DMSO-d$_6$, 400 MHz): δ 10.59 (s, 1H), 8.61 (d, J = 2.6 Hz, 1H), 8.44 (s, 1H), 8.12 (dd, J = 8.8, 4.3 Hz, 1H), 7.98 (dd, J = 6.5, 2.3 Hz, 2H), 7.87 (td, J = 8.7, 2.8 Hz, 1H), 7.61-7.53 (m, 1H), 7.46-7.37 (m, 1H), 5.01-4.92 (m, 1H), 4.39-4.34 (m, 1H), 2.64 (s, 3H), 2.45-2.39 (m, 1H), 2.28-2.15 (m, 1H). |

TABLE 2-continued

Analytical data for HBV-CSU racemic & pure enantiomers:

| Target No | Structure | Rx. Yield (%) | Mass Spec. Found (m/z) | Mass Spec. Calculated | ¹H-NMR |
|---|---|---|---|---|---|
| HBV-CSU-254 | 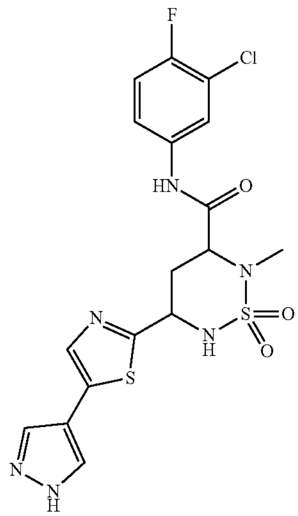 [SMILES: CN1C(C(=O)Nc2ccc(F)c(Cl)c2)CC(c2ncc(-c3cn[nH]c3)s2)NS1(=O)=O] | 7% | 471.20 259 (M + 1) | 470.04 for $C_{17}H_{16}ClFN_6O_3S_2$ | ¹H-NMR (DMSO-d$_6$, 400 MHz): δ 13.13 (br.s, 1H), 10.57 (s, 1H), 8.17 (s, 1H), 7.97 (dd, J = 6.8, 2.6 Hz, 1H), 7.91 (d, J = 9.9 Hz, 1H), 7.88 (s, 1H), 7.84 (s, 1H), 7.60-7.54 (m, 1H), 7.40 (t, J = 9.1 Hz, 1H), 4.95-4.87 (m, 1H), 4.39-4.34 (m, 1H), 2.63 (s, 3H), 2.42-2.35 (m, 1H), 2.26-2.14 (m, 1H). |
| HBV-CSU-254-ISO-I | 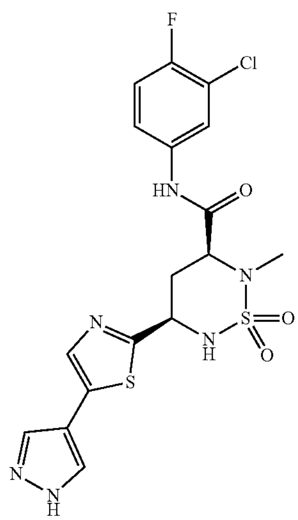 [SMILES: CN1[C@H](C(=O)Nc2ccc(F)c(Cl)c2)C[C@H](c2ncc(-c3cn[nH]c3)s2)NS1(=O)=O] | 7% | 471.2 (M + 1) | 470.04 for $C_{17}H_{16}ClFN_6O_3S_2$ | ¹H-NMR (DMSO-d$_6$, 400 MHz): δ 13.13 (br.s, 1H), 10.58 (s, 1H), 8.17 (b. s, 1H), 7.97 (dd, J = 6.8, 2.3 Hz, 1H), 7.88 (s, 2H), 7.84 (br.s, 1H), 7.58 (dd, J = 8.2, 3.3 Hz, 1H), 7.40 (t, J = 9.1 Hz, 1H), 4.93-4.88 (m, 1H), 4.42-4.32 (m, 1H), 2.63 (s, 3H), 2.42-2.35 (m, 1H), 2.25-2.11 (m, 1H). |
| HBV-CSU-254-ISO-II | 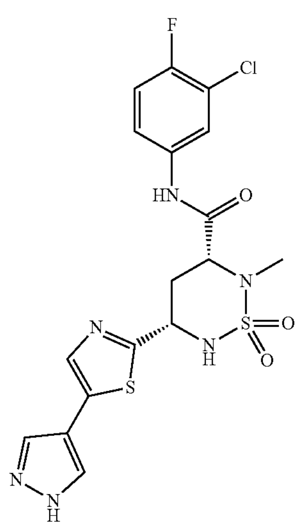 [SMILES: CN1[C@@H](C(=O)Nc2ccc(F)c(Cl)c2)C[C@@H](c2ncc(-c3cn[nH]c3)s2)NS1(=O)=O] | 8% | 471.2 (M + 1) | 470.04 for $C_{17}H_{16}ClFN_6O_3S_2$ | ¹H-NMR (DMSO-d$_6$, 400 MHz): δ 13.13 (br.s, 1H), 10.58 (s, 1H), 8.17 (s, 1H), 7.99-7.96 (m, 1H), 7.91 (br. s, 1H), 7.88 (s, 1H), 7.84 (s, 1H), 7.60-7.54 (m, 1H), 7.40 (t, J = 9.1 Hz, 1H), 4.93-4.88 (m, 1H), 4.39-4.34 (m, 1H), 2.63 (s, 3H), 2.42-2.35 (m, 1H), 2.26-2.13 (m, 1H). |

TABLE 2-continued

Analytical data for HBV-CSU racemic & pure enantiomers:

| Target No | Structure | Rx. Yield (%) | Mass Spec. Found (m/z) | Mass Spec. Calculated | $^1$H-NMR |
|---|---|---|---|---|---|
| HBV-CSU-256 | 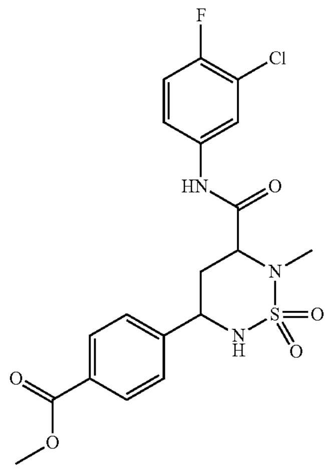 [SMILES: COC(=O)c1ccc(C2CC(C(=O)Nc3ccc(F)c(Cl)c3)N(C)S(=O)(=O)N2)cc1] | 6% | 456.40 (M + 1) | 455.07 for $C_{19}H_{19}ClFN_3O_5S$ | $^1$H-NMR (DMSO-$d_6$, 400 MHz): δ 10.59 (s, 1H), 7.99-7.96 (m, 3H), 7.64-7.55 (m, 4H), 7.04 (t, J = 8.8 Hz, 1H), 4.69-4.68 m, 1H), 4.34-4.31 (m, 1H), 3.86 (s, 3H), 2.65 (s, 3H), 2.17-2.06 (m, 2H). |
| HBV-CSU-257 | 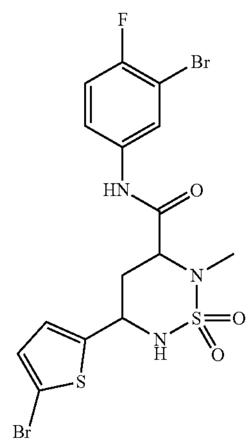 [SMILES: CN1C(C(=O)Nc2ccc(F)c(Br)c2)CC(c2ccc(Br)s2)NS1(=O)=O] | 66% | 527.90 (M + 2) | 524.88 for $C_{15}H_{14}Br_2FN_3O_3S_2$ | $^1$H-NMR (DMSO-$d_6$, 400 MHz): δ 10.58 (s, 1H), 8.04 (dd, J = 6.4, 2.4 Hz, 1H), 7.76 (br.s, 1H),7.62-7.57 (m, 1H), 7.37 (t, J = 9.2 Hz, 1H), 7.13 (d, J = 3.6 Hz, 1H), 6.99 (d, J = 3.2 Hz, 1H), 4.74 (t, J = 10.0 Hz, 1H), 4.25 (dd, J = 11.6, 2.4 Hz, 1H), 2.61 (s, 3H), 2.25-2.07 (m, 2H). |
| HBV-CSU-258 | 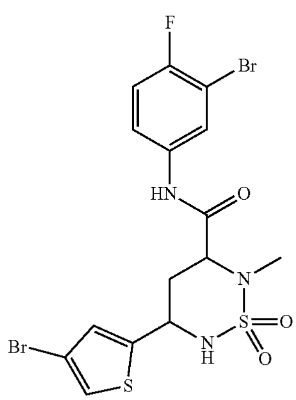 [SMILES: CN1C(C(=O)Nc2ccc(F)c(Br)c2)CC(c2cc(Br)cs2)NS1(=O)=O] | 88% | 527.95 (M + 2) | 524.88 for $C_{15}H_{14}Br_2FN_3O_3S_2$ | $^1$H-NMR (DMSO-$d_6$, 400 MHz): δ 10.58 (s, 1H), 8.10 (dd, J = 6.4, 2.6 Hz, 1H), 7.77-7.70 (m, 1H), 7.68-7.67 (m, 1H), 7.62-7.58 (m, 1H), 7.38 (t, J = 8.8 Hz, 1H), 7.19-7.18 (m, 1H), 4.80 (d, J = 9.5 Hz, 1H), 4.28 (dd, J = 11.9, 2.8 Hz, 1H), 2.61 (s, 3H), 2.28-2.27 (m, 1H), 2.18-2.03 (m, 1H). |

TABLE 2-continued

Analytical data for HBV-CSU racemic & pure enantiomers:

| Target No | Structure | Rx. Yield (%) | Mass Spec. Found (m/z) | Mass Spec. Calculated | ¹H-NMR |
| --- | --- | --- | --- | --- | --- |
| HBV-CSU-259 | 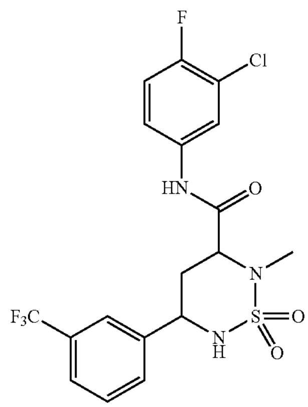 | 54% | 466.15 (M + 1) | 465.05 for $C_{18}H_{16}ClF_4N_3O_3S$ | ¹H-NMR (DMSO-d₆, 400 MHz): δ 10.58 (s, 1H), 7.97-7.95 (m, 1H), 7.85 (s, 1H), 7.79 (d, J = 7.9 Hz, 1H), 7.74-7.51 (m, 4H), 7.40 (t, J = 9.1 Hz, 1H), 4.78-4.67 (m, 1H), 4.31 (dd, J = 11.7, 3.1 Hz, 1H), 2.65 (s, 3H), 2.21-1.96 (m, 2H). |
| HBV-CSU-259-ISO-I | 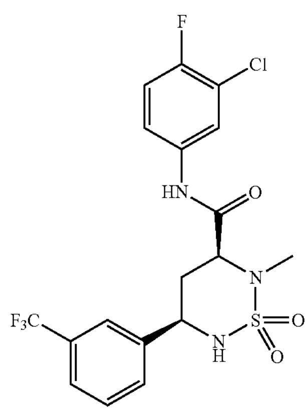 [SMILES: CN1[C@H](C(=O)Nc2ccc(F)c(Cl)c2)C[C@H](c2cccc(C(F)(F)F)c2)NS1(=O)=O] | 2.5% | 466.15 (M + 1) | 465.05 for $C_{18}H_{16}ClF_4N_3O_3S$ | ¹H-NMR (DMSO-d₆, 400 MHz): δ 10.58 (s, 1H), 7.97-7.95 (m, 1H), 7.85-7.77 (m, 2H), 7.71-7.53 (m, 4H), 7.40 (t, J = 8.8 Hz 1H), 4.74-4.71 (m, 1H), 4.32-4.28 (m, 1H), 2.65 (s, 3H), 2.18-2.02 (m, 2H). |
| HBV-CSU-259-ISO-II | 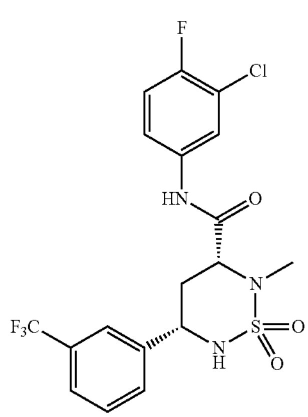 | 1.5% | 466.15 (M + 1) | 465.05 for $C_{18}H_{16}ClF_4N_3O_3S$ | ¹H-NMR (DMSO-d₆, 400 MHz): δ 10.58 (s, 1H), 7.97-7.95 (m, 1H), 7.85-7.53 (m, 6H), 7.40 (t, J = 9.2 Hz 1H), 4.74-4.71 (m, 1H), 4.32-4.28 (m, 1H), 2.65 (s, 3H), 2.15-2.08 (m, 2H). |

TABLE 2-continued

Analytical data for HBV-CSU racemic & pure enantiomers:

| Target No | Structure | Rx. Yield (%) | Mass Spec. Found (m/z) | Mass Spec. Calculated | $^1$H-NMR |
|---|---|---|---|---|---|
| HBV-CSU-260 | 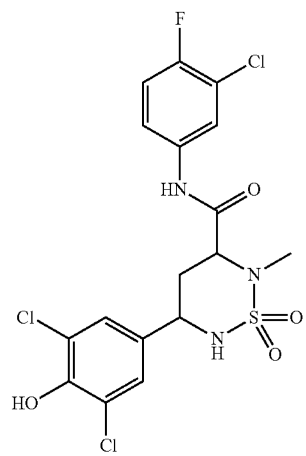 [SMILES: CN1C(C(=O)Nc2ccc(F)c(Cl)c2)CC(c2cc(Cl)c(O)c(Cl)c2)NS1(=O)=O] | 34% | 483.95 (M + 2) | 480.98 for $C_{17}H_{15}Cl_3FN_3O_4S$ | $^1$H-NMR (DMSO-d$_6$, 400 MHz): δ 10.67 (s, 1H), 7.99-7.97 (m, 1H), 7.57-7.56 (m, 1H), 7.41-7.36 (m, 2H), 7.27-7.26 (m, 2H), 4.38-4.37 (m, 1H), 4.20-4.16 (m, 1H), 2.61 (s, 3H), 2.10-1.99 (m, 2H). |
| HBV-CSU-261 | 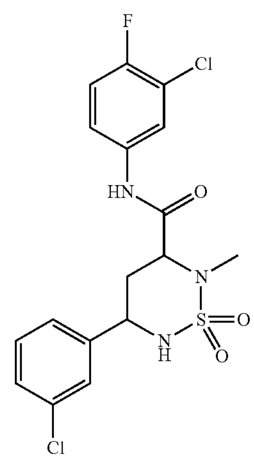 [SMILES: CN1C(C(=O)Nc2ccc(F)c(Cl)c2)CC(c2cccc(Cl)c2)NS1(=O)=O] | 25% | 432.00 (M + 1) | 431.03 for $C_{17}H_{16}Cl_2FN_3O_3S$ | $^1$H-NMR (DMSO-d$_6$, 400 MHz): δ 10.54 (s, 1H), 7.94-7.91 (m, 1H), 7.57-7.49 (m, 3H), 7.42-7.34 (m, 4H), 4.61-4.58 (m, 1H), 4.27-4.23 (m, 1H), 2.61 (s, 3H), 2.10-1.95 (m, 2H). |
| HBV-CSU-261-ISO-I | 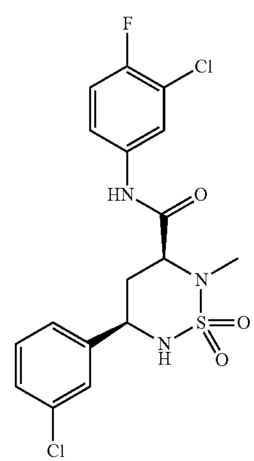 [SMILES: CN1[C@H](C(=O)Nc2ccc(F)c(Cl)c2)C[C@H](c2cccc(Cl)c2)NS1(=O)=O] | 10% | 432.10 (M + 1) | 431.03 for $C_{17}H_{16}Cl_2FN_3O_3S$ | $^1$H-NMR (DMSO-d$_6$, 400 MHz): δ 10.57 (s, 1H), 7.95 (dd, J = 6.8, 2.4 Hz, 1H), 7.59-7.52 (m, 3H), 7.43-7.37 (m, 4H), 4.62-4.61 (m, 1H), 4.27 (dd, J = 11.2, 3.2 Hz, 1H), 2.64 (s, 3H), 2.13-2.05 (m, 2H). |

TABLE 2-continued

Analytical data for HBV-CSU racemic & pure enantiomers:

| Target No | Structure | Rx. Yield (%) | Mass Spec. Found (m/z) | Mass Spec. Calculated | $^1$H-NMR |
|---|---|---|---|---|---|
| HBV-CSU-261-ISO-II | 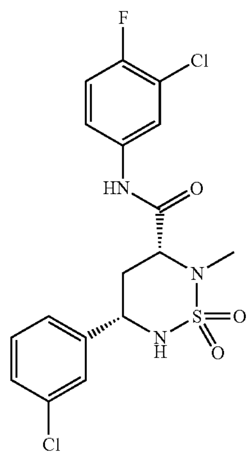 [SMILES: CN1[C@@H](C(=O)Nc2ccc(F)c(Cl)c2)C[C@@H](c2cccc(Cl)c2)NS1(=O)=O] | 10% | 432.10 (M + 1) | 431.03 for $C_{17}H_{16}Cl_2FN_3O_3S$ | $^1$H-NMR (DMSO-$d_6$, 400 MHz): δ 10.57 (s, 1H), 7.95 (dd, J = 6.8, 2.4 Hz, 1H), 7.58-7.52 (m, 3H), 7.44-7.37 (m, 4H), 4.60 (t, J = 10.4 Hz, 1H), 4.27 (dd, J = 11.2, 3.6 Hz, 1H), 2.64 (s, 3H), 2.14-2.09 (m, 2H). |
| HBV-CSU-262 | 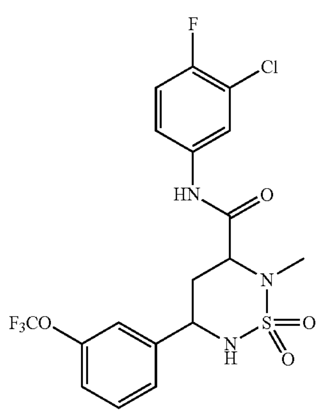 [SMILES: CN1C(C(=O)Nc2ccc(F)c(Cl)c2)CC(c2cccc(OC(F)(F)F)c2)NS1(=O)=O] | 99% | 482.05 (M + 1) | 481.05 for $C_{18}H_{16}ClF_4N_3O_4S$ | $^1$H-NMR (DMSO-$d_6$, 400 MHz): δ 10.57 (s, 1H), 7.98-7.90 (m, 1H), 7.65-7.48 (m, 5H), 7.41-7.30 (m, 2H), 4.75-4.70 (m, 1H), 4.35-4.28 (m, 1H), 2.65 (s, 3H), 2.20-2.00 (m, 2H). |
| HBV-CSU-262-ISO-I | 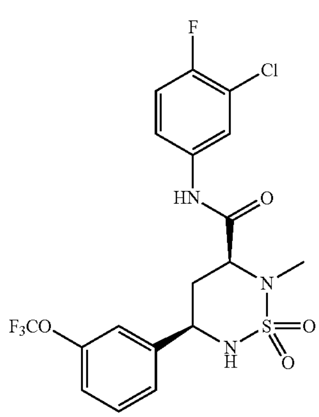 [SMILES: CN1[C@H](C(=O)Nc2ccc(F)c(Cl)c2)C[C@H](c2cccc(OC(F)(F)F)c2)NS1(=O)=O] | 6% | 482.10 (M + 1) | 481.05 for $C_{18}H_{16}ClF_4N_3O_4S$ | $^1$H-NMR (DMSO-$d_6$, 400 MHz): δ 10.60 (s, 1H), 7.96 (dd, J = 6.9, 2.6 Hz, 1H), 7.65-7.64 (m, 1H), 7.60-7.46 (m, 4H), 7.44-7.29 (m, 2H), 4.68-4.65 (m, 1H), 4.28-4.26 (m, 1H), 2.64 (s, 3H), 2.19-1.98 (m, 2H). |

TABLE 2-continued

Analytical data for HBV-CSU racemic & pure enantiomers:

| Target No | Structure | Rx. Yield (%) | Mass Spec. Found (m/z) | Mass Spec. Calculated | ¹H-NMR |
|---|---|---|---|---|---|
| HBV-CSU-262-ISO-II | 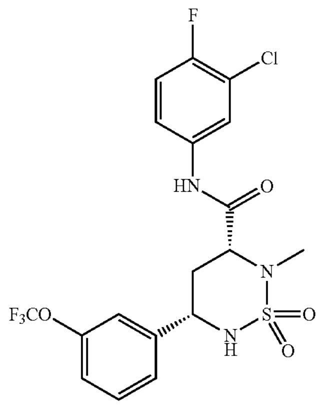 [SMILES: CN1[C@@H](C(=O)Nc2ccc(F)c(Cl)c2)C[C@@H](c2cccc(OC(F)(F)F)c2)NS1(=O)=O] | 4% | 482 (M + 1) | 481.05 for $C_{18}H_{16}ClF_4N_3O_4S$ | ¹H-NMR (DMSO-$d_6$, 400 MHz): δ 10.65 (s, 1H), 7.97 (dd, J = 6.9, 2.6 Hz, 1H), 7.73-7.46 (m, 5H), 7.39 (t, J = 9.1 Hz, 1H), 7.36-7.31 (m, 1H), 4.69-4.61 (m, 1H), 4.21 (d, J = 11.3 Hz, 1H), 2.61 (s, 3H), 2.17-1.95 (m, 2H). |
| HBV-CSU-263 | 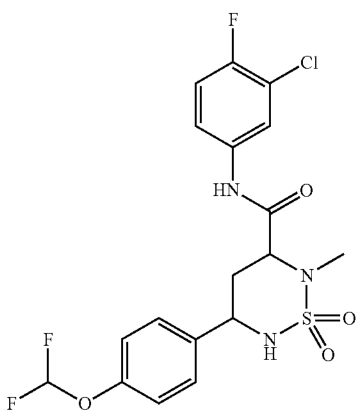 [SMILES: CN1C(C(=O)Nc2ccc(F)c(Cl)c2)CC(c2ccc(OC(F)F)cc2)NS1(=O)=O] | 67% | 464.10 (M + 1) | 463.06 for $C_{18}H_{17}ClF_3N_3O_4S$ | ¹H-NMR (DMSO-$d_6$, 400 MHz): δ 10.56 (s, 1H), 7.96 (dd, J = 6.9, 2.5 Hz, 1H), 7.59-7.47 (m, 4H), 7.46-7.07 (m, 4H), 4.62-4.61 (m, 1H), 4.27 (dd, J = 8.7, 5.9 Hz, 1H), 2.64 (s, 3H), 2.13-2.03 (m, 2H). |
| HBV-CSU-263-ISO-I | 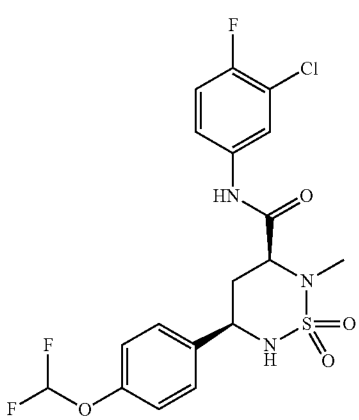 [SMILES: CN1[C@H](C(=O)Nc2ccc(F)c(Cl)c2)C[C@H](c2ccc(OC(F)F)cc2)NS1(=O)=O] | 7% | 464.10 (M + 1) | 463.06 for $C_{18}H_{17}ClF_3N_3O_4S$ | ¹H-NMR (DMSO-$d_6$, 400 MHz): δ 10.57 (s, 1H), 7.96 (dd, J = 6.8, 2.5 Hz, 1H), 7.59-7.48 (m, 4H), 7.44-7.17 (m, 4H), 4.59 (t, J = 7.6 Hz, 1H), 4.25-4.20 (m, 1H), 2.63 (s, 3H), 2.08-2.06 (m, 2H). |

TABLE 2-continued

Analytical data for HBV-CSU racemic & pure enantiomers:

| Target No | Structure | Rx. Yield (%) | Mass Spec. Found (m/z) | Mass Spec. Calculated | $^1$H-NMR |
|---|---|---|---|---|---|
| HBV-CSU-263-ISO-II | 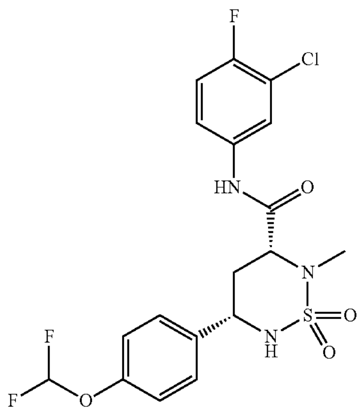 [SMILES: CN1[C@@H](C(=O)Nc2ccc(F)c(Cl)c2)C[C@@H](c2ccc(OC(F)F)cc2)NS1(=O)=O] | 4% | 464.10 (M + 1) | 463.06 for $C_{18}H_{17}ClF_3N_3O_4S$ | $^1$H-NMR (DMSO-$d_6$, 400 MHz): δ 10.56 (s, 1H), 7.96 (dd, J = 6.9, 2.6 Hz, 1H), 7.55-7.49 (m, 4H), 7.43-7.16 (m, 4H), 4.58 (t, J = 7.4 Hz, 1H), 4.21-4.18 (m, 1H), 2.61 (s, 3H), 2.07-2.05 (m, 2H). |
| HBV-CSU-264 | 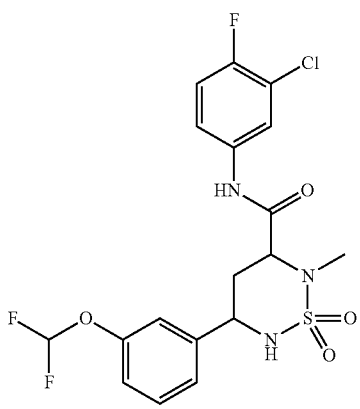 | 48% | 464.15 (M + 1) | 463.06 for $C_{18}H_{17}ClF_3N_3O_4S$ | $^1$H-NMR (DMSO-$d_6$, 400 MHz): δ 10.54 (s, 1H), 7.93 (dd, J = 6.9, 2.6 Hz, 1H), 7.60-7.47 (m, 2H), 7.46-7.20 (m, 5H), 7.14-7.07 (m, 1H), 4.59 (t, J = 9.2 Hz, 1H), 4.24 (dd, J = 10.8, 3.9 Hz, 1H), 2.61 (s, 3H), 2.12-1.93 (m, 2H). |
| HBV-CSU-264-ISO-I | 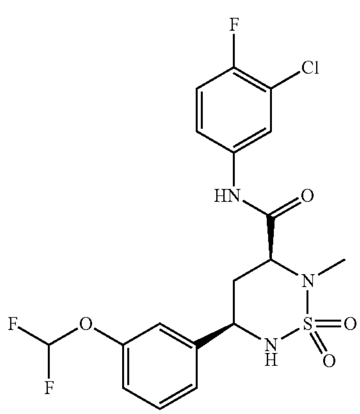 [SMILES: CN1[C@H](C(=O)Nc2ccc(F)c(Cl)c2)C[C@H](c2cccc(OC(F)F)c2)NS1(=O)=O] | 8% | 464.15 (M + 1) | 463.06 for $C_{18}H_{17}ClF_3N_3O_4S$ | $^1$H-NMR (DMSO-$d_6$, 400 MHz): δ 10.53 (s, 1H), 7.94-7.90 (m, 1H), 7.54-7.49 (m, 2H), 7.40-7.21 (m, 5H), 7.11-7.02 (m, 1H), 4.60-4.57 (m, 1H), 4.26-4.22 (m, 1H), 2.61 (s, 3H), 2.09-2.01 (m, 2H). |

TABLE 2-continued

Analytical data for HBV-CSU racemic & pure enantiomers:

| Target No | Structure | Rx. Yield (%) | Mass Spec. Found (m/z) | Mass Spec. Calculated | ¹H-NMR |
|---|---|---|---|---|---|
| HBV-CSU-264-ISO-II | 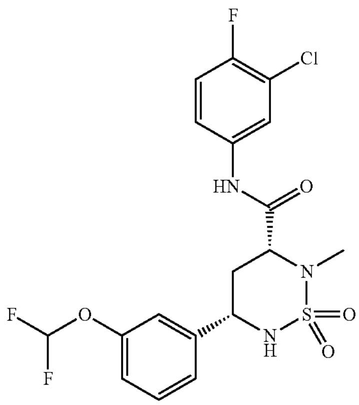 [SMILES: CN1[C@@H](C(=O)Nc2ccc(F)c(Cl)c2)C[C@@H](c2cccc(OC(F)F)c2)NS1(=O)=O] | 9% | 464.15 (M + 1) | 463.06 for $C_{18}H_{17}ClF_3N_3O_4S$ | ¹H-NMR (DMSO-$d_6$, 400 MHz): δ 10.53 (s, 1H), 7.94-7.91 (m, 1H), 7.55-7.49 (m, 2H), 7.41-7.21 (m, 5H), 7.11-7.02 (m, 1H), 4.60-4.57 (m, 1H), 4.26-4.23 (m, 1H), 2.61 (s, 3H), 2.10-2.02 (m, 2H). |
| HBV-CSU-265 | 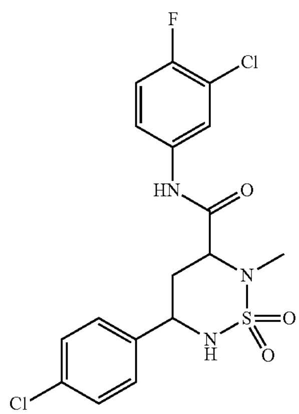 [SMILES: CN1C(C(=O)Nc2ccc(F)c(Cl)c2)CC(c2ccc(Cl)cc2)NS1(=O)=O] | 85% | 432.05 (M + 1) | 431.03 for $C_{17}H_{16}Cl_2FN_3O_3S$ | ¹H-NMR (DMSO-$d_6$, 400 MHz): δ 10.57 (s, 1H), 7.95 (dd, J = 6.8, 2.4 Hz, 1H), 7.55-7.37 (m, 7H), 4.62-4.56 (m, 1H), 4.29-4.25 (m, 1H), 2.64 (s, 3H), 2.08-2.04 (m, 2H). |
| HBV-CSU-265-ISO-I | 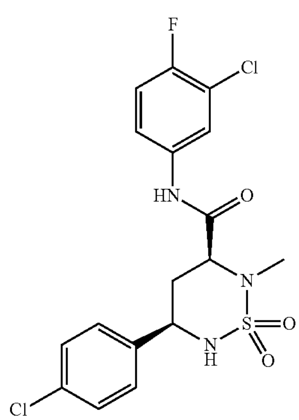 [SMILES: CN1[C@H](C(=O)Nc2ccc(F)c(Cl)c2)C[C@H](c2ccc(Cl)cc2)NS1(=O)=O] | 6% | 432.10 (M + 1) | 431.03 for $C_{17}H_{16}Cl_2FN_3O_3S$ | ¹H-NMR (DMSO-$d_6$, 400 MHz): δ 10.57 (s, 1H), 7.95 (d, J = 6.8 Hz, 1H), 7.56-7.37 (m, 7H), 4.62-4.56 (m, 1H), 4.29-4.23 (m, 1H), 2.63 (s, 3H), 2.08-2.05 (m, 2H). |

TABLE 2-continued

Analytical data for HBV-CSU racemic & pure enantiomers:

| Target No | Structure | Rx. Yield (%) | Mass Spec. Found (m/z) | Mass Spec. Calculated | $^1$H-NMR |
|---|---|---|---|---|---|
| HBV-CSU-265-ISO-II | 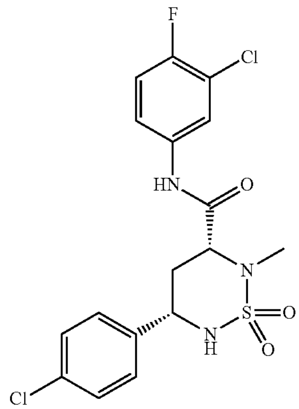 [SMILES: CN1[C@@H](C(=O)Nc2ccc(F)c(Cl)c2)C[C@@H](c2ccc(Cl)cc2)NS1(=O)=O] | 8% | 432.10 (M + 1) | 431.03 for $C_{17}H_{16}Cl_2FN_3O_3S$ | $^1$H-NMR (DMSO-$d_6$, 400 MHz): δ 10.57 (s, 1H), 7.95 (d, J = 6.8 Hz, 1H), 7.58-7.37 (m, 7H), 4.60-4.59 (m, 1H), 4.27 (dd, J = 10.0, 5.2 Hz, 1H), 2.64 (s, 3H), 2.09-2.03 (m, 2H). |
| HBV-CSU-266 | 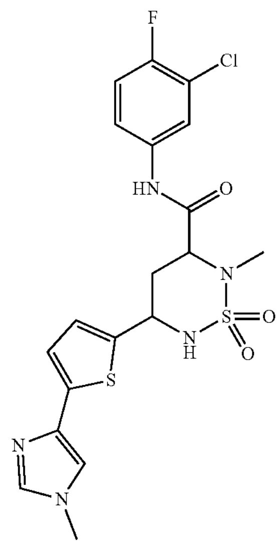 [SMILES: CN1C(C(=O)Nc2ccc(F)c(Cl)c2)CC(c2ccc(-c3cn(C)cn3)s2)NS1(=O)=O] | 32% | 484.10 (M + 1) | 483.06 for $C_{19}H_{19}ClFN_5O_3S_2$ | $^1$H-NMR (DMSO-$d_6$, 400 MHz): δ 10.58 (s, 1H), 7.98-7.97 (m, 1H), 7.67 (d, J = 9.5 Hz, 1H), 7.62-7.49 (m, 2H), 7.49-7.36 (m, 2H), 7.08 (d, J = 3.6 Hz, 1H), 7.02 (d, J = 3.8 Hz, 1H), 4.80-4.69 (m, 1H), 4.29 (dd, J = 11.6, 3.1 Hz, 1H), 3.66 (s, 3H), 2.61 (s, 3H), 2.28-2.05 (m, 2H). |
| HBV-CSU-266-ISO-I | 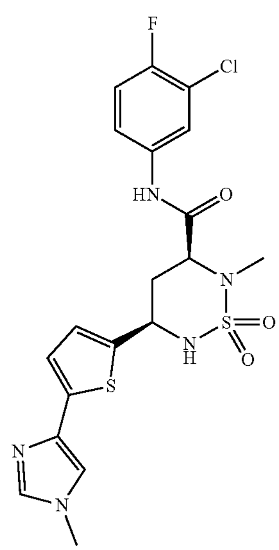 [SMILES: CN1[C@H](C(=O)Nc2ccc(F)c(Cl)c2)C[C@H](c2ccc(-c3cn(C)cn3)s2)NS1(=O)=O] | 3% | 484.10 (M + 1) | 483.06 for $C_{19}H_{19}ClFN_5O_3S_2$ | $^1$H-NMR (DMSO-$d_6$, 400 MHz): δ 10.57 (s, 1H), 7.98 (dd, J = 6.8, 2.6 Hz, 1H), 7.70-7.51 (m, 3H), 7.51-7.36 (m, 2H), 7.09 (d, J = 3.6 Hz, 1H), 7.03 (d, J = 3.7 Hz, 1H), 4.80-4.69 (m, 1H), 4.29 (dd, J = 11.5, 3.1 Hz, 1H), 3.66 (s, 3H), 2.62 (s, 3H), 2.28-2.05 (m, 2H). |

TABLE 2-continued

Analytical data for HBV-CSU racemic & pure enantiomers:

| Target No | Structure | Rx. Yield (%) | Mass Spec. Found (m/z) | Mass Spec. Calculated | ¹H-NMR |
|---|---|---|---|---|---|
| HBV-CSU-266-ISO-II | 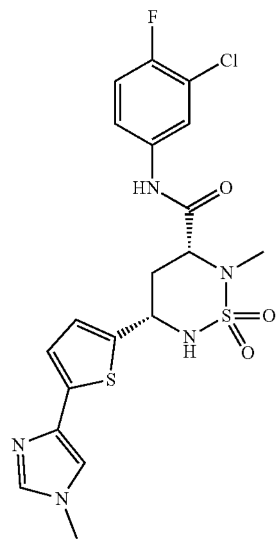 [SMILES: CN1[C@@H](C(=O)Nc2ccc(F)c(Cl)c2)C[C@@H](c2ccc(-c3cn(C)cn3)s2)NS1(=O)=O] | 5% | 484.10 (M + 1) | 483.06 for $C_{19}H_{19}ClFN_5O_3S_2$ | ¹H-NMR (DMSO-$d_6$, 400 MHz): δ 10.57 (s, 1H), 7.98 (dd, J = 6.9, 2.5 Hz, 1H), 7.66-7.51 (m, 3H), 7.49-7.36 (m, 2H), 7.08 (d, J = 3.6 Hz, 1H), 7.02 (d, J = 3.2 Hz, 1H), 4.75-4.70 (m, 1H), 4.29 (dd, J = 11.5, 3.1 Hz, 1H), 3.66 (s, 3H), 2.61 (s, 3H), 2.28-2.05 (m, 2H). |
| HBV-CSU-266-Trans-ISO-I | 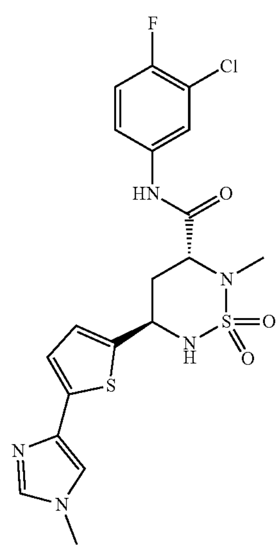 [SMILES: CN1[C@@H](C(=O)Nc2ccc(F)c(Cl)c2)C[C@H](c2ccc(-c3cn(C)cn3)s2)NS1(=O)=O] | 24% | 484.15 (M + 1) | 483.06 for $C_{19}H_{19}ClFN_5O_3S_2$ | ¹H-NMR (DMSO-$d_6$, 400 MHz): δ 10.00 (s, 1H), 7.96 (dd, J = 6.8, 2.4 Hz, 1H), 7.61-7.57 (m, 2H), 7.47 (s, 1H), 7.41-7.31 (m, 2H), 7.10 (d, J = 3.7 Hz, 1H), 7.03 (d, J = 3.6 Hz, 1H), 4.90-4.89 (m, 1H), 4.46-4.44 (m, 1H), 3.66 (s, 3H), 2.97 (s, 3H), 2.35-2.31 (m, 1H), 2.00-1.97 (m, 1H). |

TABLE 2-continued

Analytical data for HBV-CSU racemic & pure enantiomers:

| Target No | Structure | Rx. Yield (%) | Mass Spec. Found (m/z) | Mass Spec. Calculated | $^1$H-NMR |
|---|---|---|---|---|---|
| HBV-CSU-266-Trans-ISO-II | 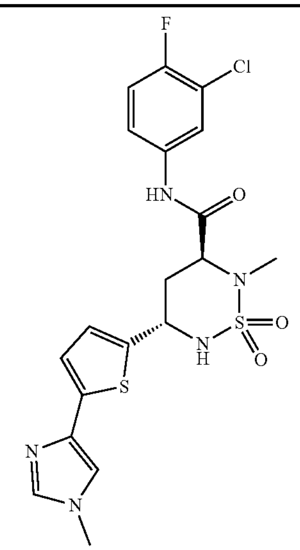 | 33% | 484.15 (M + 1) | 483.06 for $C_{19}H_{19}ClFN_5O_3S_2$ | $^1$H-NMR (DMSO-$d_6$, 400 MHz): δ 10.00 (s, 1H), 7.96 (dd, J = 6.8, 2.4 Hz, 1H), 7.63-7.60 (m, 2H), 7.48 (d, J = 1.6 Hz, 1H), 7.41-7.35 (m, 2H), 7.11 (d, J = 4.0, 1H), 7.04 (d, J = 4.0 Hz, 1H), 4.90-4.85 (m, 1H), 4.46-4.44 (m, 1H), 3.67 (s, 3H), 2.97 (s, 3H), 2.36-2.30 (m, 1H), 2.00-1.97 (m, 1H). |
| HBV-CSU-267 | 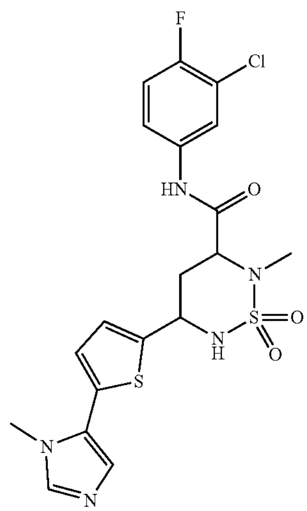 | 34% | 484.15 (M + 1) | 483.06 for $C_{19}H_{19}ClFN_5O_3S_2$ | $^1$H-NMR (DMSO-$d_6$, 400 MHz): δ 10.62 (s, 1H), 7.99-7.94 (m, 2H), 7.73 (d, J = 9.2 Hz, 1H), 7.54-7.52 (m, 1H), 7.38 (t, J = 8.4 Hz, 1H), 7.25-7.12 (m, 3H), 4.82-4.76 (m, 1H), 4.28 (d, J = 11.6 Hz, 1H), 3.72 (s, 3H), 2.59 (s, 3H), 2.26-2.11 (m, 2H). |
| HBV-CSU-267-ISO-I | 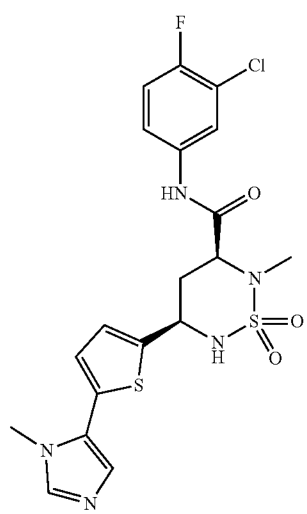 [SMILES: CN1[C@H](C(=O)Nc2ccc(F)c(Cl)c2)C[C@H](c2ccc(-c3cncn3C)s2)NS1(=O)=O] | 3% | 484.05 (M + 1) | 483.06 for $C_{19}H_{19}ClFN_5O_3S_2$ | $^1$H-NMR (DMSO-$d_6$, 400 MHz): δ 10.59 (s, 1H), 7.98 (dd, J = 6.9, 2.5 Hz, 1H), 7.74 (d, J = 9.5 Hz, 2H), 7.61-7.52 (m, 1H), 7.41 (t, J = 9.1 Hz, 1H), 7.21-7.08 (m, 3H), 4.86-4.76 (m, 1H), 4.32 (dd, J = 11.8, 2.8 Hz, 1H), 3.72 (s, 3H), 2.62 (s, 3H), 2.32-2.09 (m, 2H). |

TABLE 2-continued

Analytical data for HBV-CSU racemic & pure enantiomers:

| Target No | Structure | Rx. Yield (%) | Mass Spec. Found (m/z) | Mass Spec. Calculated | $^1$H-NMR |
|---|---|---|---|---|---|
| HBV-CSU-267-ISO-II | 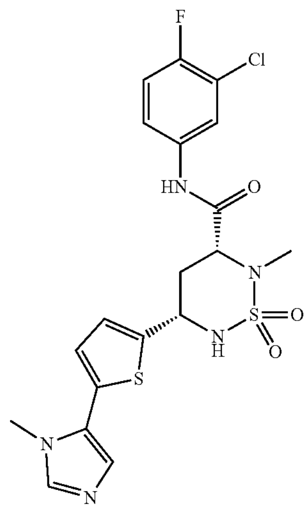 [SMILES: CN1[C@@H](C(=O)Nc2ccc(F)c(Cl)c2)C[C@@H](c2ccc(-c3cncn3C)s2)NS1(=O)=O] | 17% | 484.05 (M + 1) | 483.06 for $C_{19}H_{19}ClFN_5O_3S_2$ | $^1$H-NMR (DMSO-$d_6$, 400 MHz): δ 10.59 (s, 1H), 7.98 (dd, J = 6.9, 2.5 Hz, 1H), 7.74 (d, J = 9.4 Hz, 2H), 7.56 (dt, J = 7.4, 3.3 Hz, 1H), 7.41 (t, J = 9.1 Hz, 1H), 7.21-7.08 (m, 3H), 4.81 (t, J = 9.9 Hz, 1H), 4.32 (dd, J = 11.8, 2.9 Hz, 1H), 3.72 (s, 3H), 2.62 (s, 3H), 2.32-2.09 (m, 2H). |
| HBV-CSU-268 | 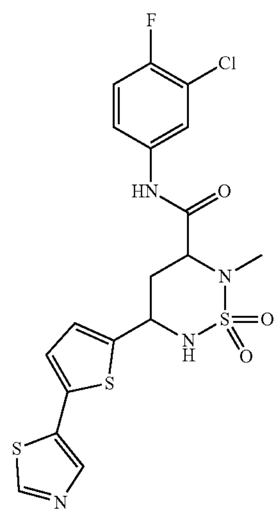 [SMILES: CN1C(C(=O)Nc2ccc(F)c(Cl)c2)CC(c2ccc(-c3cncs3)s2)NS1(=O)=O] | 46% | 487.10 (M + 1) | 486.01 for $C_{18}H_{16}ClFN_4O_3S_3$ | $^1$H-NMR (DMSO-$d_6$, 400 MHz): δ 10.60 (s, 1H), 9.06 (s, 1H), 8.13 (s, 1H), 7.98 (dd, J = 7.0, 2.6 Hz, 1H), 7.77 (d, J = 9.5 Hz, 1H), 7.57-7.54 (m, 1H), 7.41 (t, J = 9.1 Hz, 1H), 7.31 (d, J = 3.7 Hz, 1H), 7.15 (d, J = 3.8 Hz, 1H), 4.87-4.76 (m, 1H), 4.32 (dd, J = 11.8, 2.8 Hz, 1H), 2.62 (s, 3H), 2.29-2.13 (m, 2H). |
| HBV-CSU-268-ISO-I | 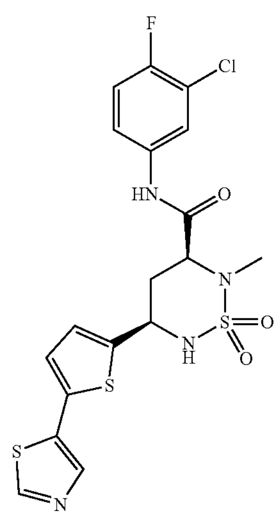 [SMILES: CN1[C@H](C(=O)Nc2ccc(F)c(Cl)c2)C[C@H](c2ccc(-c3cncs3)s2)NS1(=O)=O] | 8% | 487.10 (M + 1) | 486.01 for $C_{18}H_{16}ClFN_4O_3S_3$ | $^1$H-NMR (DMSO-$d_6$, 400 MHz): δ 10.59 (s, 1H), 9.06 (s, 1H), 8.14 (s, 1H), 7.98 (dd, J = 6.9, 2.5 Hz, 1H), 7.77-7.75 (m, 1H), 7.58-7.55 (m, 1H), 7.41 (t, J = 9.1 Hz, 1H), 7.31 (d, J = 3.6 Hz, 1H), 7.16 (d, J = 3.6 Hz, 1H), 4.82-4.80 (m, 1H), 4.32 (dd, J = 11.9, 2.8 Hz, 1H), 2.63 (s, 3H), 2.32-2.23 (m, 1H), 2.22-2.10 (m, 1H). |

TABLE 2-continued

Analytical data for HBV-CSU racemic & pure enantiomers:

| Target No | Structure | Rx. Yield (%) | Mass Spec. Found (m/z) | Mass Spec. Calculated | $^1$H-NMR |
|---|---|---|---|---|---|
| HBV-CSU-268-ISO-II | 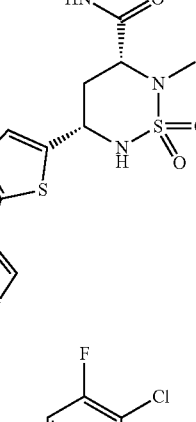 | 10% | 487.10 (M + 1) | 486.01 for $C_{18}H_{16}ClFN_4O_3S_3$ | $^1$H-NMR (DMSO-$d_6$, 400 MHz): δ 10.59 (s, 1H), 9.05 (s, 1H), 8.13 (s, 1H), 7.98-7.96 (m, 1H), 7.77-7.75 (m, 1H), 7.58-7.54 (m, 1H), 7.41 (t, J = 9.2 Hz, 1H), 7.30 (d, J = 3.6 Hz, 1H), 7.15 (d, J = 3.6 4.33-4.30 (m, 1H), 2.62 (s, 3H), 2.30-2.25 (m, 1H), 2.16-2.10 (m, 1H). |
| HBV-CSU-269 | 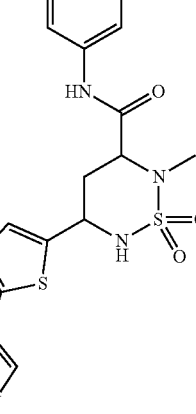 | 59% | 471.10 (M + 1) | 470.03 for $C_{18}H_{16}ClFN_4O_4S_2$ | $^1$H-NMR (DMSO-$d_6$, 400 MHz): δ 10.59 (s, 1H), 8.39 (s, 1H), 7.97-7.96 (m, 1H), 7.77-7.74 (m, 1H), 7.58-7.48 (m, 2H), 7.42-7.34 (m, 2H), 7.17-7.16 (m, 1H), 4.82-4.78 (m, 1H), 4.31-4.4.28 (m, 1H), 2.59 (s, 3H), 2.29-2.11 (m, 2H). |
| HBV-CSU-269-ISO-I | 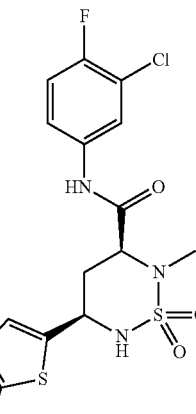 | 11% | 471.10 (M + 1) | 470.03 for $C_{18}H_{16}ClFN_4O_4S_2$ | $^1$H-NMR (DMSO-$d_6$, 400 MHz): δ 10.60 (s, 1H), 8.40 (s, 1H), 7.97-7.96 (m, 1H), 7.79-7.76 (m, 1H), 7.54-7.51 (m, 2H), 7.42-7.35 (m, 2H), 7.18-7.16 (m, 1H), 4.83-4.80 (m, 1H), 4.32-4.27 (m, 1H), 2.61 (s, 3H), 2.28-2.08 (m, 2H). |

TABLE 2-continued

Analytical data for HBV-CSU racemic & pure enantiomers:

| Target No | Structure | Rx. Yield (%) | Mass Spec. Found (m/z) | Mass Spec. Calculated | ¹H-NMR |
|---|---|---|---|---|---|
| HBV-CSU-269-ISO-II | 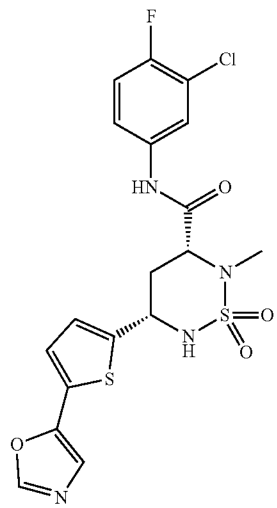 [SMILES: CN1[C@@H](C(=O)Nc2ccc(F)c(Cl)c2)C[C@@H](c2ccc(-c3cnco3)s2)NS1(=O)=O] | 14% | 471.10 (M +1) | 470.03 for $C_{18}H_{16}ClFN_4O_4S_2$ | ¹H-NMR (DMSO-d$_6$, 400 MHz): δ 10.56 (br.s, 1H), 8.40 (s, 1H), 7.97-7.95 (m, 1H), 7.80-7.75 (m, 1H), 7.57-7.50 (m, 2H), 7.41-7.33 (m, 2H), 7.17-7.14 (m, 1H), 4.81-4.78 (m, 1H), 4.32-4.27 (m, 1H), 2.58 (s, 3H), 2.30-2.07 (m, 2H). |
| HBV-CSU-270 | 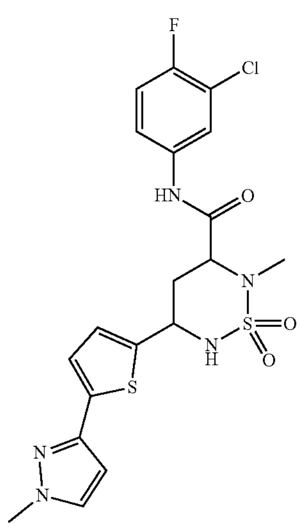 [SMILES: CN1C(C(=O)Nc2ccc(F)c(Cl)c2)CC(c2ccc(-c3ccn(C)n3)s2)NS1(=O)=O] | 5% | 484.05 (M⁺ + 1) | 483.06 for $C_{19}H_{19}ClFN_5O_3S_2$ | ¹H-NMR (DMSO-d$_6$, 400 MHz): δ 10.57 (s, 1H), 7.96 (dd, J = 6.8, 2.4 Hz, 1H), 7.71-7.68 (m, 2H), 7.58-7.53 (m, 1H), 7.4 (t, J = 9.2 Hz, 1H), 7.23 (d, J = 3.6 Hz, 1H), 7.07 (d, J = 3.2 Hz, 1H), 6.56 (d, J = 2 Hz, 1H), 4.79-4.74 (m, 1H), 4.29 (dd, J = 11.2, 2.8 Hz, 1H), 3.83 (s, 3H), 2.62 (s, 3H), 2.26-2.13 (m, 2H). |

TABLE 2-continued

Analytical data for HBV-CSU racemic & pure enantiomers:

| Target No | Structure | Rx. Yield (%) | Mass Spec. Found (m/z) | Mass Spec. Calculated | $^1$H-NMR |
|---|---|---|---|---|---|
| HBV-CSU-270-ISO-I | 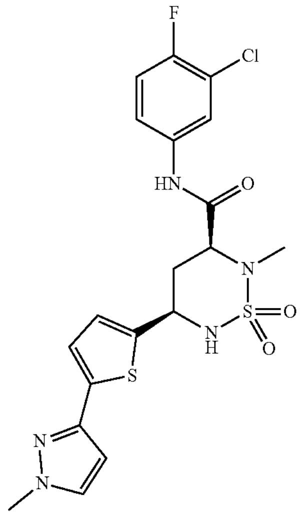 [SMILES: CN1[C@H](C(=O)Nc2ccc(F)c(Cl)c2)C[C@H](c2ccc(-c3ccn(C)n3)s2)NS1(=O)=O] | 10% | 484.05 (M + 1) | 483.06 for $C_{19}H_{19}ClFN_5O_3S_2$ | $^1$H-NMR (DMSO-$d_6$, 400 MHz): δ 10.57 (s, 1H), 7.96 (dd, J = 6.8, 2.4 Hz, 1H), 7.70-7.66 (m, 2H), 7.55-7.52 (m, 1H), 7.39 (t, J = 8.8 Hz, 1H), 7.22 (d, J = 4.0 Hz, 1H), 7.06 (d, J = 3.6 Hz, 1H), 6.55 (d, J = 1.6 Hz, 1H), 4.76-4.74 (m, 1H), 4.30-4.26 (m, 1H), 3.82 (s, 3H), 2.60 (s, 3H), 2.24-2.05 (m, 2H). |
| HBV-CSU-270-ISO-II | 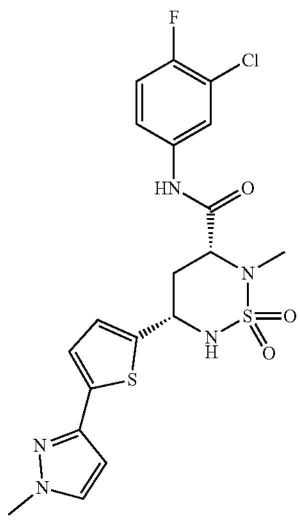 [SMILES: CN1[C@@H](C(=O)Nc2ccc(F)c(Cl)c2)C[C@@H](c2ccc(-c3ccn(C)n3)s2)NS1(=O)=O] | 7% | 484.10 (M + 1) | 483.06 for $C_{19}H_{19}ClFN_5O_3S_2$ | $^1$H-NMR (DMSO-$d_6$, 400 MHz): δ 10.57 (s, 1H), 7.96 (dd, J = 6.8, 2.0 Hz, 1H), 7.69-7.66 (m, 2H), 7.56-7.53 (m, 1H), 7.39 (t, J = 9.2 Hz, 1H), 7.22 (d, J = 3.6 Hz, 1H), 7.06 (d, J = 4.0 Hz, 1H), 6.55 (d, J = 1.6 Hz, 1H), 4.74 (d, J = 10.4 Hz, 1H), 4.27 (dd, J = 11.6, 3.2 Hz, 1H), 3.82 (s, 3H), 2.60 (s, 3H), 2.24-2.05 (m, 2H). |
| HBV-CSU-271 | 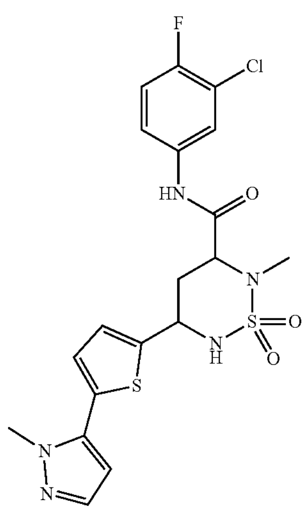 | 43% | 484.10 (M + 1) | 483.06 for $C_{19}H_{19}ClFN_5O_3S_2$ | $^1$H-NMR (DMSO-$d_6$, 400 MHz): δ 10.60 (s, 1H), 7.98 (dd, J = 6.8, 2.4 Hz, 1H), 7.78 (br.s, 1H), 7.59-7.54 (m, 1H), 7.45-7.38 (m, 2H), 7.28 (d, J = 3.6 Hz, 1H), 7.21 (d, J = 3.6 Hz, 1H), 6.47 (d, J = 2.0 Hz, 1H), 4.82 (d, J = 9.2 Hz, 1H), 4.29 (dd, J = 10.8 Hz, 1H), 3.93 (s, 3H), 2.62 (s, 3H), 2.29-2.13 (m, 2H). |

TABLE 2-continued

Analytical data for HBV-CSU racemic & pure enantiomers:

| Target No | Structure | Rx. Yield (%) | Mass Spec. Found (m/z) | Mass Spec. Calculated | $^1$H-NMR |
|---|---|---|---|---|---|
| HBV-CSU-271-ISO-I | 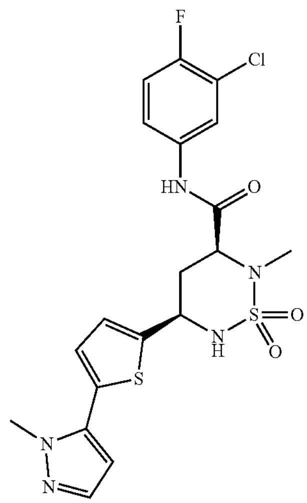 [SMILES: CN1[C@H](C(=O)Nc2ccc(F)c(Cl)c2)C[C@H](c2ccc(-c3ccnn3C)s2)NS1(=O)=O] | 19% | 484.10 (M + 1) | 483.06 for $C_{19}H_{19}ClFN_5O_3S_2$ | $^1$H-NMR (DMSO-$d_6$, 400 MHz): δ 10.61 (s, 1H), 7.98 (dd, J = 6.8, 2.4 Hz, 1H), 7.78 (br.s, 1H), 7.58-7.54 (m, 1H), 7.45-7.38 (m, 2H), 7.28 (d, J = 4.0 Hz, 1H), 7.22-7.21 (m, 1H), 6.47 (d, J = 1.6 Hz, 1H), 4.82 (d, J = 11.2 Hz, 1H), 4.31 (dd, J = 11.6, 2.8 Hz, 1H), 3.93 (s, 3H), 2.62 (s, 3H), 2.31-2.15 (m, 2H). |
| HBV-CSU-271-ISO-II | 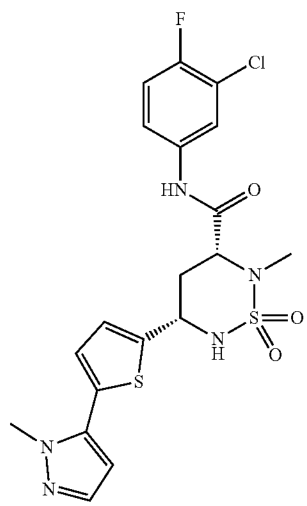 [SMILES: CN1[C@@H](C(=O)Nc2ccc(F)c(Cl)c2)C[C@@H](c2ccc(-c3ccnn3C)s2)NS1(=O)=O] | 18% | 484.10 (M + 1) | 483.06 for $C_{19}H_{19}ClFN_5O_3S_2$ | $^1$H-NMR (DMSO-$d_6$, 400 MHz): δ 10.60 (s, 1H), 7.98 (dd, J = 6.8, 2.4 Hz, 1H), 7.78 (br.s, 1H), 7.59-7.54 (m, 1H), 7.45-7.38 (m, 2H), 7.28 (d, J = 3.6 Hz, 1H), 7.21 (d, J = 3.6 Hz, 1H), 6.47 (d, J = 2.0 Hz, 1H), 4.82 (d, J = 9.2 Hz, 1H), 4.29 (d, J = 10.8 Hz, 1H), 3.93 (s, 3H), 2.62 (s, 3H), 2.29-2.13 (m, 2H). |
| HBV-CSU-272 | 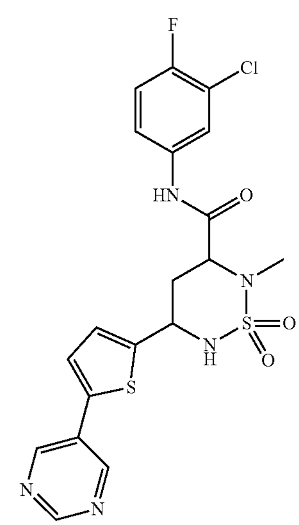 [SMILES: CN1C(C(=O)Nc2ccc(F)c(Cl)c2)CC(c2ccc(-c3cncnc3)s2)NS1(=O)=O] | 24% | 482.15 (M + 1) | 481.04 for $C_{19}H_{17}ClFN_5O_3S_2$ | $^1$H-NMR (DMSO-$d_6$, 400 MHz): δ 10.61 (s, 1H), 9.13-9.11 (m, 3H), 7.98 (dd, J = 6.9, 2.6 Hz, 1H), 7.81 (d, J = 9.5 Hz, 1H), 7.68 (d, J = 3.8 Hz, 1H), 7.59-7.56 (m, 1H), 7.41 (t, J = 9.1 Hz, 1H), 7.26 (d, J = 3.8 Hz, 1H), 4.87-4.82 (m, 1H), 4.33 (dd, J = 11.8, 2.9 Hz, 1H), 2.63 (s, 3H), 2.47-2.10 (m, 2H). |

TABLE 2-continued

Analytical data for HBV-CSU racemic & pure enantiomers:

| Target No | Structure | Rx. Yield (%) | Mass Spec. Found (m/z) | Mass Spec. Calculated | $^1$H-NMR |
|---|---|---|---|---|---|
| HBV-CSU-272-ISO-I | 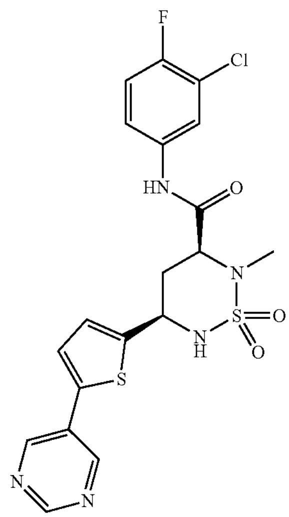 [SMILES: CN1[C@H](C(=O)Nc2ccc(F)c(Cl)c2)C[C@H](c2ccc(-c3cncnc3)s2)NS1(=O)=O] | 3% | 482.15 (M + 1) | 481.04 for $C_{19}H_{17}ClFN_5O_3S_2$ | $^1$H-NMR (DMSO-$d_6$, 400 MHz): δ 10.61 (s, 1H), 9.12 (s, 3H), 7.98 (dd, J = 6.9, 2.6 Hz, 1H), 7.81 (d, J = 9.5 Hz, 1H), 7.68 (d, J = 3.7 Hz, 1H), 7.59-7.55 (m, 1H), 7.41 (t, J = 9.1 Hz, 1H), 7.26 (dd, J = 3.8, 1.0 Hz, 1H), 4.86 (t, J = 10.3 Hz, 1H), 4.33 (dd, J = 11.7, 2.8 Hz, 1H), 2.63 (s, 3H), 2.32-2.16 (m, 2H). |
| HBV-CSU-272-ISO-II | 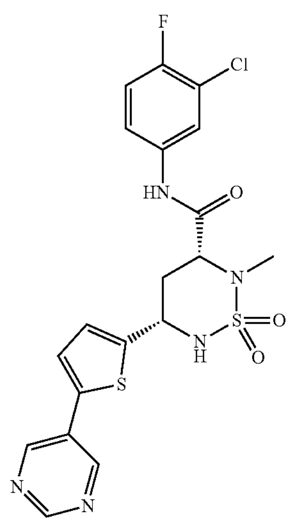 [SMILES: CN1[C@@H](C(=O)Nc2ccc(F)c(Cl)c2)C[C@@H](c2ccc(-c3cncnc3)s2)NS1(=O)=O] | 3% | 482.10 (M + 1) | 481.04 for $C_{19}H_{17}ClFN_5O_3S_2$ | $^1$H-NMR (DMSO-$d_6$, 400 MHz): δ 10.61 (s, 1H), 9.12 (s, 3H), 7.98 (dd, J = 6.8, 2.6 Hz, 1H), 7.81 (d, J = 9.6 Hz, 1H), 7.68 (d, J = 3.8 Hz, 1H), 7.58-7.55 (m, 1H), 7.41 (t, J = 9.1 Hz, 1H), 7.26 (d, J = 3.8 Hz, 1H), 4.91-4.80 (m, 1H), 4.33 (dd, J = 11.9, 2.8 Hz, 1H), 2.63 (s, 3H), 2.35-2.10 (m, 2H). |
| HBV-CSU-273 | 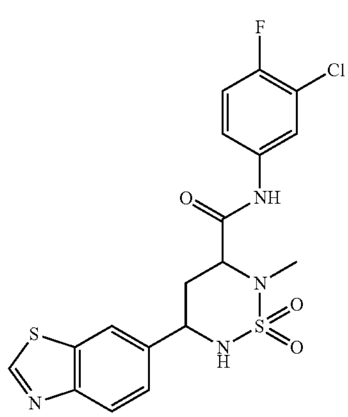 [SMILES: CN1C(C(=O)Nc2ccc(F)c(Cl)c2)CC(c2ccc3ncsc3c2)NS1(=O)=O] | 20% | 455.10 (M + 1) | 454.03 for $C_{18}H_{16}ClFN_4O_3S_2$ | $^1$H-NMR (DMSO-$d_6$, 400 MHz): δ 10.57 (s, 1H), 9.41 (s, 1H), 8.30-8.25 (m, 1H), 8.09 (d, J = 8.5 Hz, 1H), 7.97-7.95 (m, 1H), 7.69-7.52 (m, 3H), 7.40 (t, J = 9.1 Hz, 1H), 4.76-4.74 (m, 1H), 4.34-4.32 (m, 1H), 2.67 (s, 3H), 2.21-2.17 (m, 2H). |

TABLE 2-continued

Analytical data for HBV-CSU racemic & pure enantiomers:

| Target No | Structure | Rx. Yield (%) | Mass Spec. Found (m/z) | Mass Spec. Calculated | 1H-NMR |
|---|---|---|---|---|---|
| HBV-CSU-276 | 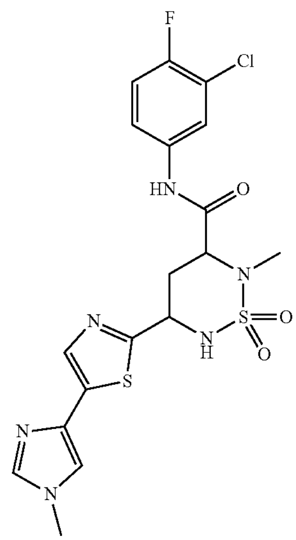 [SMILES: CN1C(C(=O)Nc2ccc(F)c(Cl)c2)CC(c2ncc(-c3cn(C)cn3)s2)NS1(=O)=O] | 51% | 485.1 (M + 1) | 484.06 for $C_{18}H_{18}ClFN_6O_3S_2$ | 1H-NMR (DMSO-$d_6$, 400 MHz): δ 10.57 (s, 1H), 7.97 (dd, J = 6.8, 2.6 Hz, 1H), 7.91-7.86 (m, 2H), 7.66 (s, 1H), 7.61-7.54 (m, 2H), 7.40 (t, J = 9.1 Hz, 1H), 4.95-4.87 (m, 1H), 4.39-4.33 (m, 1H), 3.68 (s, 3H), 2.63 (s, 3H), 2.41-2.34 (m, 1H), 2.25-2.15 (m, 1H). |
| HBV-CSU-276-ISO-I | 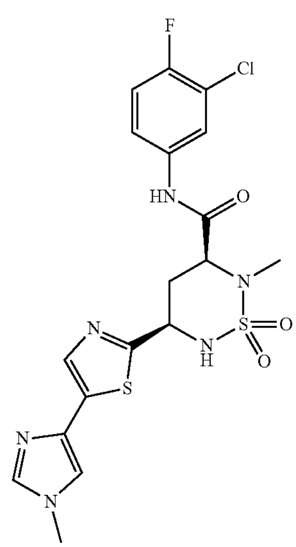 [SMILES: CN1[C@H](C(=O)Nc2ccc(F)c(Cl)c2)C[C@H](c2ncc(-c3cn(C)cn3)s2)NS1(=O)=O] | 9% | 485.2 (M + 1) | 484.06 for $C_{18}H_{18}ClFN_6O_3S_2$ | 1H-NMR (DMSO-$d_6$, 400 MHz): δ 10.57 (s, 1H), 7.97 (dd, J = 6.9, 2.5 Hz, 1H), 7.92-7.87 (m, 2H), 7.66 (s, 1H), 7.60-7.54 (m, 2H), 7.40 (t, J = 9.1 Hz, 1H), 4.97-4.83 (m, 1H), 4.39-4.33 (m, 1H), 3.68 (s, 3H), 2.63 (s, 3H), 2.41-2.34 (m, 1H), 2.26-2.14 (m, 1H). |

TABLE 2-continued

Analytical data for HBV-CSU racemic & pure enantiomers:

| Target No | Structure | Rx. Yield (%) | Mass Spec. Found (m/z) | Mass Spec. Calculated | 1H-NMR |
|---|---|---|---|---|---|
| HBV-CSU-276-ISO-I-HCl salt | 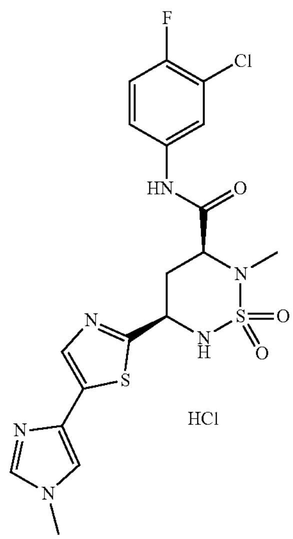 [SMILES: CN1[C@H](C(=O)Nc2ccc(F)c(Cl)c2)C[C@H](c2ncc(-c3cn(C)cn3)s2)NS1(=O)=O ; Cl] | 95% | 485.10 (M + 1) Free base | 520.03 for $C_{18}H_{19}Cl_2FN_6O_3S_2$ | 1H-NMR (DMSO-d$_6$, 400 MHz): δ 10.79 (s, 1H), 8.98 (br.s, 1H), 8.26 (s, 1H), 8.08-8.00 (m, 2H), 7.99 (dd, J = 6.8, 3.2 Hz, 1H), 7.62-7.57 (m, 1H), 7.41 (t, J = 8.8 Hz, 1H), 5.01-4.95 (m, 1H), 4.38 (dd, J = 12.4, 2.4 Hz, 1H), 3.84 (s, 3H), 2.64 (s, 3H), 2.47-2.43 (m, 1H), 2.25-2.15 (m, 1H); |
| HBV-CSU-276-ISO-II | 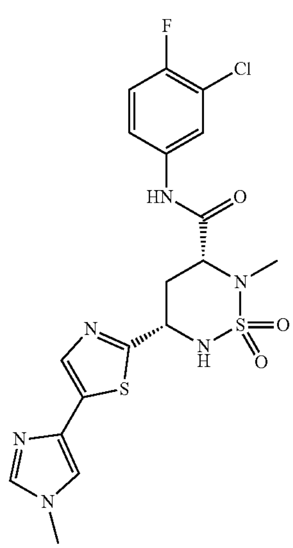 [SMILES: CN1[C@@H](C(=O)Nc2ccc(F)c(Cl)c2)C[C@@H](c2ncc(-c3cn(C)cn3)s2)NS1(=O)=O] | 9% | 485.2 (M + 1) | 484.06 for $C_{18}H_{18}ClFN_6O_3S_2$ | 1H-NMR (DMSO-d$_6$, 400 MHz): δ 10.58 (s, 1H), 7.97 (dd, J = 6.8, 2.6 Hz, 1H), 7.93-7.87 (m, 2H), 7.66 (s, 1H), 7.61-7.53 (m, 2H), 7.40 (t, J = 9.1 Hz, 1H), 4.96-4.84 (m, 1H), 4.38-4.33 (m, 1H), 3.68 (s, 3H), 2.63 (s, 3H), 2.41-2.34 (m, 1H), 2.26-2.13 (m, 1H). |

TABLE 2-continued

Analytical data for HBV-CSU racemic & pure enantiomers:

| Target No | Structure | Rx. Yield (%) | Mass Spec. Found (m/z) | Mass Spec. Calculated | $^1$H-NMR |
|---|---|---|---|---|---|
| HBV-CSU-276-Trans-ISO-I | 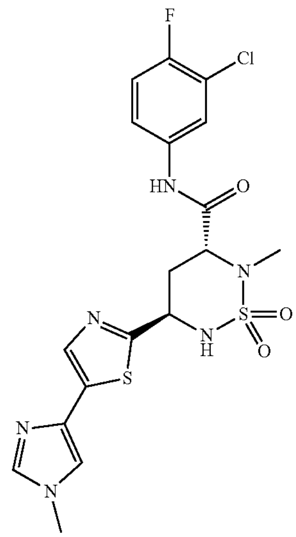 [SMILES: CN1[C@@H](C(=O)Nc2ccc(F)c(Cl)c2)C[C@H](c2ncc(-c3cn(C)cn3)s2)NS1(=O)=O] | 23% | 485.10 (M + 1) | 484.06 for $C_{18}H_{18}ClFN_6O_3S_2$ | $^1$H-NMR (DMSO-$d_6$, 400 MHz): δ 10.25 (s, 1H), 7.92 (dd, J = 6.8, 2.4 Hz, 1H), 7.85 (s, 1H), 7.75-7.72 (m, 1H), 7.67-7.65 (m, 1H), 7.57-7.53 (m, 2H), 7.34 (t, J = 9.2 Hz, 1H), 5.01-4.95 (m, 1H), 4.47 (t, J = 4.4 Hz, 1H), 3.65 (s, 3H), 2.86 (s, 3H), 2.41-2.39 (m, 1H), 2.13-2.07 (m, 1H). |
| HBV-CSU-276-Trans-ISO-II | 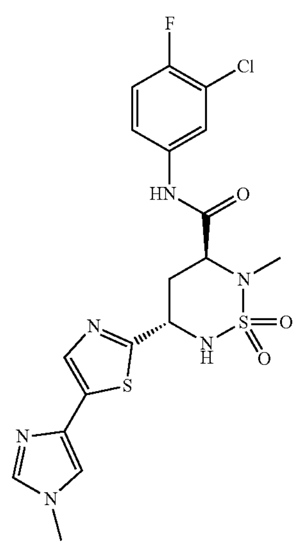 [SMILES: CN1[C@H](C(=O)Nc2ccc(F)c(Cl)c2)C[C@@H](c2ncc(-c3cn(C)cn3)s2)NS1(=O)=O] | 16% | 485.10 (M + 1) | 484.06 for $C_{18}H_{18}ClFN_6O_3S_2$ | $^1$H-NMR (DMSO-$d_6$, 400 MHz): δ 10.25 (s, 1H), 7.92 (dd, J = 7.2, 2.8 Hz, 1H), 7.84 (s, 1H), 7.74-7.72 (m, 1H), 7.66-7.64 (m, 1H), 7.57-7.53 (m, 2H), 7.34 (t, J = 8.8 Hz, 1H), 5.01-4.96 (m, 1H), 4.47 (t, J = 4.4 Hz, 1H), 3.64 (s, 3H), 2.86 (s, 3H), 2.45-2.40 (m, 1H), 2.13-2.03 (m, 1H). |

TABLE 2-continued

Analytical data for HBV-CSU racemic & pure enantiomers:

| Target No | Structure | Rx. Yield (%) | Mass Spec. Found (m/z) | Mass Spec. Calculated | $^1$H-NMR |
|---|---|---|---|---|---|
| HBV-CSU-277 | 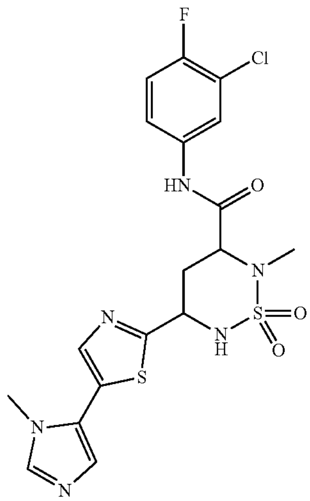 [SMILES: CN1C(C(=O)Nc2ccc(F)c(Cl)c2)CC(c2ncc(-c3cncn3C)s2)NS1(=O)=O] | 73% | 485.2 (M + 1) | 484.06 for $C_{18}H_{18}ClFN_6O_3S_2$ | $^1$H-NMR (DMSO-$d_6$, 400 MHz): δ 10.60 (s, 1H), 8.00-7.94 (m, 3H), 7.80 (s, 1H), 7.61-7.55 (m, 1H), 7.41 (t, J = 9.1 Hz, 1H), 7.22 (s, 1H), 5.02-4.92 (m, 1H), 4.43-4.37 (m, 1H), 3.74 (s, 3H), 2.65 (s, 3H), 2.45-2.38 (m 1H), 2.28-2.16 (m, 1H). |
| HBV-CSU-277-ISO-I | 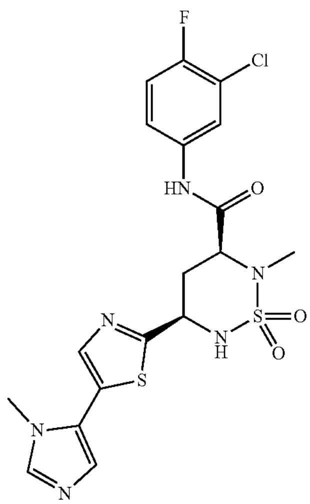 [SMILES: CN1[C@H](C(=O)Nc2ccc(F)c(Cl)c2)C[C@H](c2ncc(-c3cncn3C)s2)NS1(=O)=O] | 8% | 485.2 (M + 1) | 484.06 for $C_{18}H_{18}ClFN_6O_3S_2$ | $^1$H-NMR (DMSO-$d_6$, 400 MHz): δ 10.76 (s, 1H), 9.27 (s, 1H), 8.18 (s, 1H), 8.11-8.06 (m, 2H), 8.00 (dd, J = 6.9, 2.5 Hz, 1H), 7.63-7.57 (m, 1H), 7.41 (t, J = 9.1 Hz, 1H), 5.09-4.97 (m, 1H), 4.45-4.40 (m, 1H), 3.89 (s, 3H), 2.66 (s, 3H), 2.49-2.43 (m, 1H), 2.29-2.18 (m, 1H). |
| HBV-CSU-277-ISO-II | 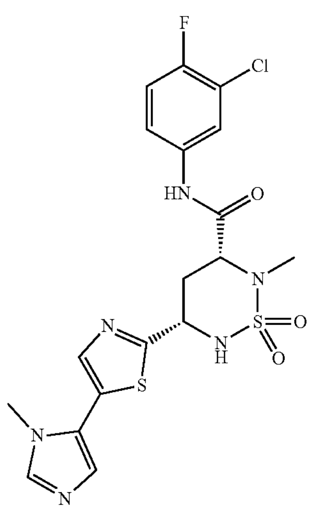 [SMILES: CN1[C@@H](C(=O)Nc2ccc(F)c(Cl)c2)C[C@@H](c2ncc(-c3cncn3C)s2)NS1(=O)=O] | 10% | 485.2 (M + 1) | 484.06 for $C_{18}H_{18}ClFN_6O_3S_2$ | $^1$H-NMR (DMSO-$d_6$, 400 MHz): δ 10.72 (s, 1H), 9.19 (s, 1H), 8.16 (s, 1H), 8.07 (d, J = 9.9 Hz, 1H), 8.04 (d, J = 1.5 Hz, 1H), 7.99 (dd, J = 6.8, 2.6 Hz, 1H), 7.64-7.54 (m, 1H), 7.41 (t, J = 9.1 Hz, 1H), 5.06-4.99 (m, 1H), 4.45-4.39 (m, 1H), 3.88 (s, 3H), 2.65 (s, 3H), 2.48-2.42 (m, 1H), 2.28-2.17 (m, 1H). |

TABLE 2-continued

Analytical data for HBV-CSU racemic & pure enantiomers:

| Target No | Structure | Rx. Yield (%) | Mass Spec. Found (m/z) | Mass Spec. Calculated | $^1$H-NMR |
|---|---|---|---|---|---|
| HBV-CSU-278 | 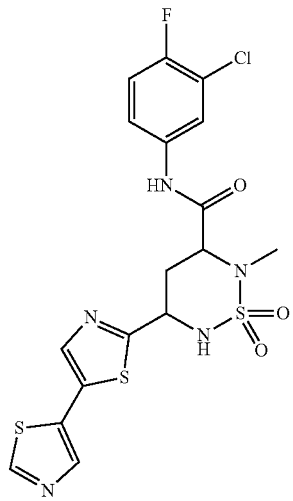 [SMILES: CN1C(C(=O)Nc2ccc(F)c(Cl)c2)CC(c2ncc(-c3cncs3)s2)NS1(=O)=O] | 45% | 488.1 (M + 1) | 487.00 for $C_{17}H_{15}ClFN_5O_3S_3$ | $^1$H-NMR (DMSO-$d_6$, 400 MHz): δ 10.59 (s, 1H), 9.15 (s, 1H), 8.24 (s, 1H), 8.10 (s, 1H), 8.02-7.95 (m, 2H), 7.60-7.54 (m, 1H), 7.41 (t, J = 9.0 Hz, 1H), 5.01-4.94 (m, 1H), 4.41-4.36 (m, 1H), 2.64 (s, 3H), 2.45-2.38 (m, 1H), 2.27-2.12 (m, 1H). |
| HBV-CSU-278-ISO-I | 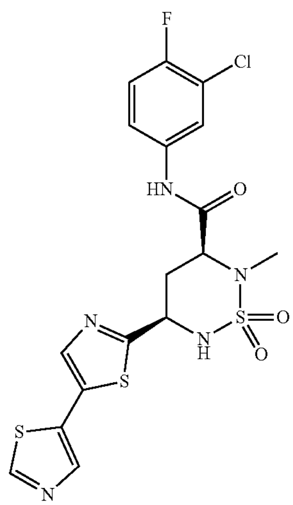 [SMILES: CN1[C@H](C(=O)Nc2ccc(F)c(Cl)c2)C[C@H](c2ncc(-c3cncs3)s2)NS1(=O)=O] | 12% | 488.1 (M + 1) | 487.00 for $C_{17}H_{15}ClFN_5O_3S_3$ | $^1$H-NMR (DMSO-$d_6$, 400 MHz): δ 10.59 (s, 1H), 9.15 (s, 1H), 8.24 (s, 1H), 8.10 (s, 1H), 7.97 (dd, J = 6.8, 2.5 Hz, 2H), 7.60-7.54 (m, 1H), 7.41 (t, J = 9.1 Hz, 1H), 5.02-4.93 (m, 1H), 4.41-4.36 (m, 1H), 2.64 (s, 3H), 2.45-2.39 (m, 1H), 2.27-2.14 (m, 1H). |
| HBV-CSU-278-ISO-II | 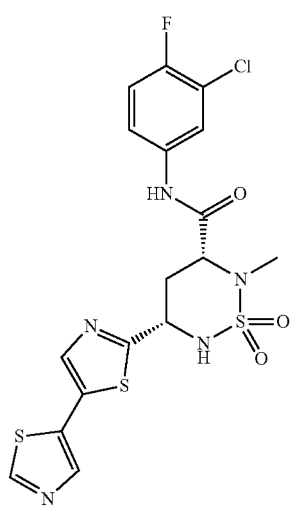 | 9% | 488.2 (M + 1) | 487.00 for $C_{17}H_{15}ClFN_5O_3S_3$ | $^1$H-NMR (DMSO-$d_6$, 400 MHz): δ 10.59 (br.s, 1H), 9.15 (s, 1H), 8.24 (s, 1H), 8.10 (s, 1H), 8.02-7.95 (m, 2H), 7.62-7.53 (m, 1H), 7.41 (t, J = 9.0 Hz, 1H), 5.04-4.89 (m, 1H), 4.40-4.36 (m, 1H), 2.64 (s, 3H), 2.44-2.39 (m, 1H), 2.26-2.14 (m, 1H). |

TABLE 2-continued

Analytical data for HBV-CSU racemic & pure enantiomers:

| Target No | Structure | Rx. Yield (%) | Mass Spec. Found (m/z) | Mass Spec. Calculated | $^1$H-NMR |
|---|---|---|---|---|---|
| HBV-CSU-280 | 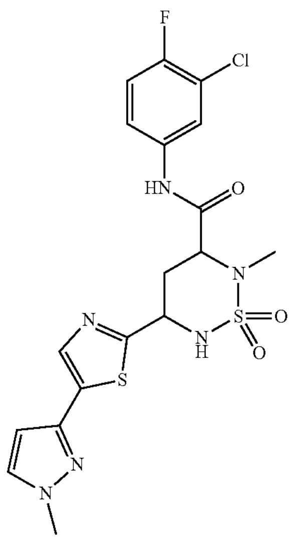 [SMILES: CN1C(C(=O)Nc2ccc(F)c(Cl)c2)CC(c2ncc(-c3ccn(C)n3)s2)NS1(=O)=O] | 47% | 485.1 (M + 1) | 484.06 for $C_{18}H_{18}ClFN_6O_3S_2$ | $^1$H-NMR (DMSO-$d_6$, 400 MHz): δ 10.58 (s, 1H), 8.05 (s, 1H), 7.99-7.92 (m, 2H), 7.77 (d, J = 2.1 Hz, 1H), 7.60-7.54 (m, 1H), 7.40 (t, J = 9.1 Hz, 1H), 6.68 (d, J = 2.1 Hz, 1H), 4.97-4.87 (m, 1H), 4.39-4.33 (m, 1H), 3.86 (s, 3H), 2.64 (s, 3H), 2.43-2.36 (m, 1H), 2.27-2.15 (m, 1H). |
| HBV-CSU-280-ISO-I | 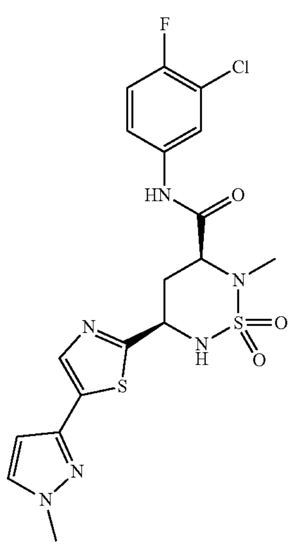 [SMILES: CN1[C@H](C(=O)Nc2ccc(F)c(Cl)c2)C[C@H](c2ncc(-c3ccn(C)n3)s2)NS1(=O)=O] | 7% | 485.2 (M + 1) | 484.06 for $C_{18}H_{18}ClFN_6O_3S_2$ | $^1$H-NMR (DMSO-$d_6$, 400 MHz): δ 10.59 (s, 1H), 8.05 (s, 1H), 7.99-7.92 (m, 2H), 7.77 (d, J = 2.3 Hz, 1H), 7.60-7.54 (m, 1H), 7.40 (t, J = 9.1 Hz, 1H), 6.68 (d, J = 2.3 Hz, 1H), 4.97-4.88 (m, 1H), 4.39-4.33 (m, 1H), 3.86 (s, 3H), 2.64 (s, 3H), 2.43-2.36 (m, 1H), 2.26-2.15 (m, 1H). |

TABLE 2-continued

Analytical data for HBV-CSU racemic & pure enantiomers:

| Target No | Structure | Rx. Yield (%) | Mass Spec. Found (m/z) | Mass Spec. Calculated | $^1$H-NMR |
|---|---|---|---|---|---|
| HBV-CSU-280-ISO-II | 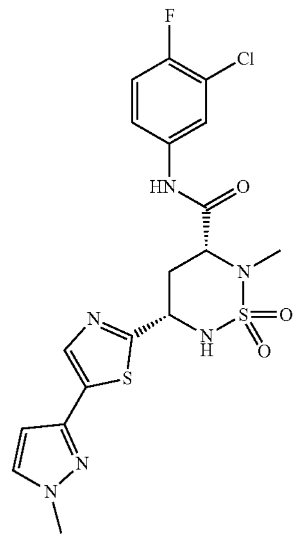 [SMILES: CN1[C@@H](C(=O)Nc2ccc(F)c(Cl)c2)C[C@@H](c2ncc(-c3ccn(C)n3)s2)NS1(=O)=O] | 7% | 485.2 (M + 1) | 484.06 for $C_{18}H_{18}ClFN_6O_3S_2$ | $^1$H-NMR (DMSO-$d_6$, 400 MHz): δ 10.58 (s, 1H), 8.05 (s, 1H), 7.99-7.91 (m, 2H), 7.77 (d, J = 2.1 Hz, 1H), 7.59-7.54 (m, 1H), 7.40 (t, J = 9.1 Hz, 1H), 6.68 (d, J = 2.3 Hz, 1H), 4.97-4.89 (m, 1H), 4.39-4.33 (m, 1H), 3.86 (s, 3H), 2.64 (s, 3H), 2.42-2.36 (m, 1H), 2.26-2.15 (m, 1H). |
| HBV-CSU-281 | 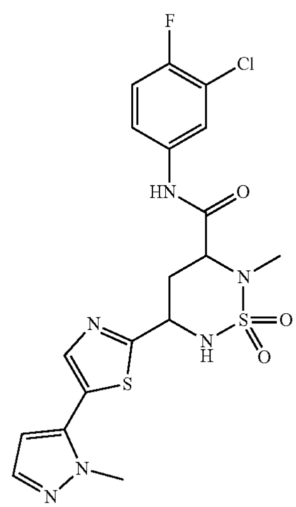 [SMILES: CN1C(C(=O)Nc2ccc(F)c(Cl)c2)CC(c2ncc(-c3ccnn3C)s2)NS1(=O)=O] | 50% | 485.2 (M + 1) | 484.06 for $C_{18}H_{18}ClFN_6O_3S_2$ | $^1$H-NMR (DMSO-$d_6$, 400 MHz): δ 10.60 (s, 1H), 8.07 (s, 1H), 8.01-7.96 (m, 2H), 7.60-7.54 (m, 1H), 7.51 (d, J = 2.0 Hz, 1H), 7.41 (t, J = 9.1 Hz, 1H), 6.59 (d, J = 2.0 Hz, 1H), 5.03-4.96 (m, 1H), 4.43-4.38 (m, 1H), 3.95 (s, 3H), 2.64 (s, 3H), 2.46-2.39 (m, 1H), 2.29-2.14 (m, 1H). |
| HBV-CSU-281-ISO-I | 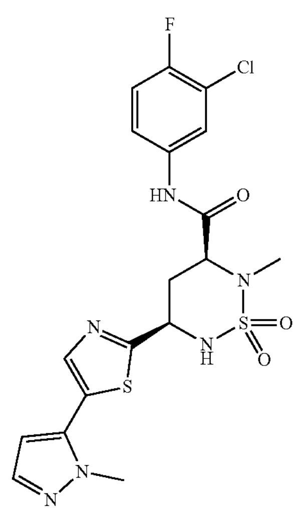 [SMILES: CN1[C@H](C(=O)Nc2ccc(F)c(Cl)c2)C[C@H](c2ncc(-c3ccnn3C)s2)NS1(=O)=O] | 4% | 485.2 (M + 1) | 484.06 for $C_{18}H_{18}ClFN_6O_3S_2$ | $^1$H-NMR (DMSO-$d_6$, 400 MHz): δ 10.60 (s, 1H), 8.07 (s, 1H), 8.02-7.96 (m, 2H), 7.61-7.55 (m, 1H), 7.51 (d, J = 2.0 Hz, 1H), 7.41 (t, J = 9.1 Hz, 1H), 6.59 (d, J = 2.0 Hz, 1H), 5.03-4.95 (m, 1H), 4.43-4.38 (m, 1H), 3.95 (s, 3H), 2.64 (s, 3H), 2.46-2.39 (m, 1H), 2.27-2.16 (m, 1H). |

TABLE 2-continued

Analytical data for HBV-CSU racemic & pure enantiomers:

| Target No | Structure | Rx. Yield (%) | Mass Spec. Found (m/z) | Mass Spec. Calculated | ¹H-NMR |
|---|---|---|---|---|---|
| HBV-CSU-281-ISO-II | 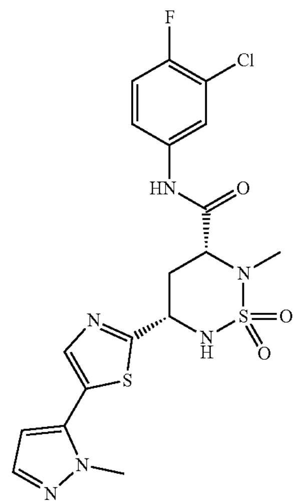 [SMILES: CN1[C@@H](C(=O)Nc2ccc(F)c(Cl)c2)C[C@@H](c2ncc(-c3ccnn3C)s2)NS1(=O)=O] | 4% | 485.2 (M + 1) | 484.06 for $C_{18}H_{18}ClFN_6O_3S_2$ | ¹H-NMR (DMSO-d$_6$, 400 MHz): δ 10.59 (s, 1H), 8.07 (s, 1H), 7.98 (dd, J = 6.8, 2.6 Hz, 2H), 7.60-7.55 (m, 1H), 7.50 (d, J = 2.0 Hz, 1H), 7.41 (t, J = 9.1 Hz, 1H), 6.59 (d, J = 1.9 Hz, 1H), 5.02-4.96 (m, 1H), 4.43-4.37 (m, 1H), 3.95 (s, 3H), 2.64 (s, 3H), 2.45-2.39 (m, 1H), 2.27-2.16 (m, 1H). |
| HBV-CSU-283 | 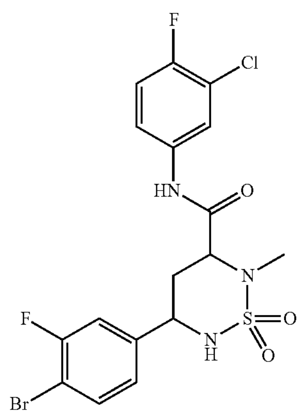 [SMILES: CN1C(C(=O)Nc2ccc(F)c(Cl)c2)CC(c2ccc(Br)c(F)c2)NS1(=O)=O] | 79% | 496.05 (M + 2) | 492.97 for $C_{17}H_{15}BrClF_2N_3O_3S$ | ¹H-NMR (DMSO-d$_6$, 400 MHz): δ 10.57 (s, 1H), 7.95 (dd, J = 6.8, 2.4 Hz, 1H), 7.73 (t, J = 8.4 Hz, 1H), 7.59-7.49 (m, 3H), 7.39 (t, J = 9.2 Hz, 1H), 7.29-7.21 (m, 1H), 4.61 (t, J = 10.4 Hz, 1H), 4.26 (dd, J = 11.2, 2.8 Hz, 1H), 2.64 (s, 3H), 2.13-1.98 (m, 2H). |
| HBV-CSU-284 | 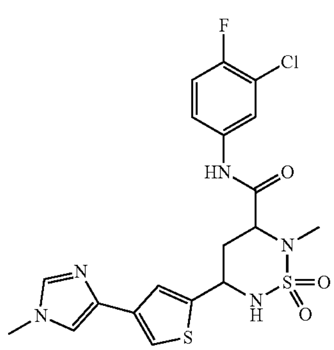 [SMILES: CN1C(C(=O)Nc2ccc(F)c(Cl)c2)CC(c2cc(-c3cn(C)cn3)cs2)NS1(=O)=O] | 20% | 484.10 (M + 1) | 83.06 for $C_{19}H_{19}ClFN_5O_3S_2$ | ¹H-NMR (DMSO-d$_6$, 400 MHz): δ 10.58 (s, 1H), 7.98 (dd, J = 6.9, 2.6 Hz, 1H), 7.73-7.35 (m, 7H), 4.80-4.75 (m, 1H), 4.32 (dd, J = 11.8, 2.9 Hz, 1H), 3.66 (s, 3H), 2.62 (s, 3H), 2.33-2.10 (m, 2H). |

TABLE 2-continued

Analytical data for HBV-CSU racemic & pure enantiomers:

| Target No | Structure | Rx. Yield (%) | Mass Spec. Found (m/z) | Mass Spec. Calculated | $^1$H-NMR |
|---|---|---|---|---|---|
| HBV-CSU-284-ISO-I | 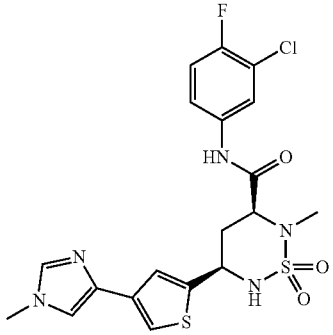 | 4% | 484.1 (M + 1) | 483.06 for $C_{19}H_{19}ClFN_5O_3S_2$ | $^1$H-NMR (DMSO-$d_6$, 400 MHz): δ 10.58 (s, 1H), 7.98 (dd, J = 6.8, 2.4 Hz, 1H), 7.71-7.68 (m, 1H), 7.57-7.52 (m, 2H), 7.49 (s, 1H), 7.44-7.38 (m, 3H), 4.8-4.75 (m, 1H), 4.33 (dd, J = 11.2, 2.8 Hz, 1H), 3.65 (s, 3H), 2.62 (s, 3H), 2.33-2.12 (m, 2H). |
| HBV-CSU-284-ISO-II | 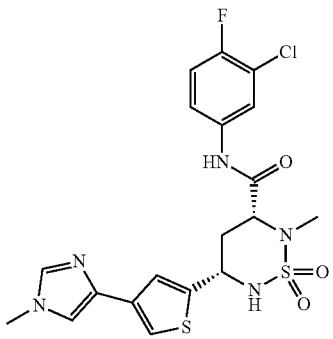 [SMILES: CN1[C@@H](C(=O)Nc2ccc(F)c(Cl)c2)C[C@@H](c2cc(-c3cn(C)cn3)cs2)NS1(=O)=O] | 5% | 484.1 (M + 1) | 483.06 for $C_{19}H_{19}ClFN_5O_3S_2$ | $^1$H-NMR (DMSO-$d_6$, 400 MHz): δ 10.58 (s, 1H), 7.98 (dd, J = 6.8, 2.4 Hz, 1H), 7.71-7.69 (m, 1H), 7.59-7.55 (m, 2H), 7.49 (s, 1H), 7.45-7.38 (m, 3H), 4.79-4.75 (m, 1H), 4.31 (dd, J = 11.2, 2.8 Hz, 1H), 3.65 (s, 3H), 2.62 (s, 3H), 2.33-2.12 (m, 2H). |
| HBV-CSU-285 | 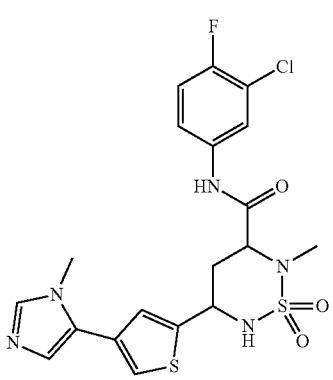 | 40% | 484.10 (M + 1) | 483.06 for $C_{19}H_{19}ClFN_5O_3S_2$ | $^1$H-NMR (DMSO-$d_6$, 400 MHz): δ 10.59 (s, 1H), 7.98 (dd, J = 6.9, 2.6 Hz, 1H), 7.74 (d, J = 9.7 Hz, 1H), 7.67-7.52 (m, 3H), 7.46-7.36 (m, 2H), 7.12 (s, 1H), 4.81-4.75 (m, 1H), 4.30 (dd, J = 11.7, 2.8 Hz, 1H), 3.73 (s, 3H), 2.63 (s, 3H), 2.32-2.19 (m, 2H) |
| HBV-CSU-285-ISO-I | 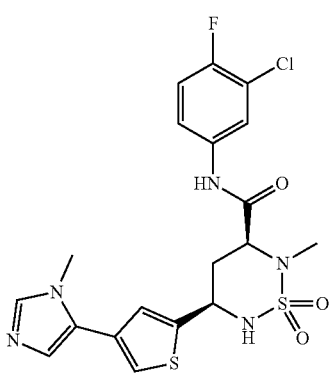 | 15% | 484.15 (M + 1) | 483.06 for $C_{19}H_{19}ClFN_5O_3S_2$ | $^1$H-NMR (DMSO-$d_6$, 400 MHz): δ 10.59 (s, 1H), 7.98 (dd, J = 6.8, 2.4 Hz, 1H), 7.75-7.72 (m, 1H), 7.64-7.58 (m, 2H), 7.57-7.54 (m, 1H), 7.41-7.38 (m, 2H), 7.12 (s, 1H), 4.83-4.79 (m, 1H), 4.29 (dd, J = 12.0, 2.8 Hz, 1H), 3.73 (s, 3H), 2.63 (s, 3H), 2.32-2.13 (m, 2H). |

TABLE 2-continued

Analytical data for HBV-CSU racemic & pure enantiomers:

| Target No | Structure | Rx. Yield (%) | Mass Spec. Found (m/z) | Mass Spec. Calculated | ¹H-NMR |
|---|---|---|---|---|---|
| HBV-CSU-285-ISO-II | 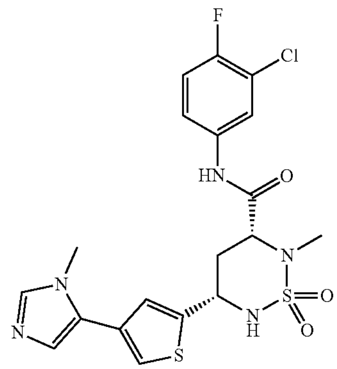 [SMILES: CN1[C@@H](C(=O)Nc2ccc(F)c(Cl)c2)C[C@@H](c2cc(-c3cncn3C)cs2)NS1(=O)=O] | 9% | 484.15 (M + 1) | 483.06 for $C_{19}H_{19}ClFN_5O_3S_2$ | ¹H-NMR (DMSO-$d_6$, 400 MHz): δ 10.59 (s, 1H), 7.97 (dd, J = 6.8, 2.4 Hz, 1H), 7.75-7.73 (m, 1H), 7.64-7.56 (m, 2H), 7.57-7.53 (m, 1H), 7.43-7.38 (m, 2H), 7.12 (s, 1H), 4.83-4.79 (m, 1H), 4.3 (dd, J = 12.0, 2.8 Hz, 1H), 3.73 (s, 3H), 2.63 (s, 3H), 2.32-2.16 (m, 2H). |
| HBV-CSU-286 | 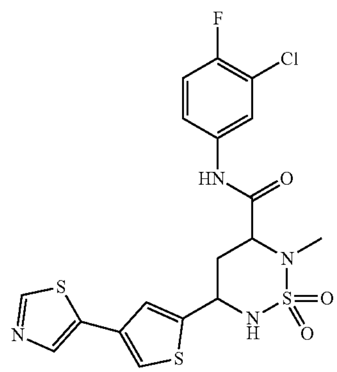 [SMILES: CN1C(C(=O)Nc2ccc(F)c(Cl)c2)CC(c2cc(-c3cncs3)cs2)NS1(=O)=O] | 39% | 487.10 (M + 1) | 486.01 for $C_{18}H_{16}ClFN_4O_3S_3$ | ¹H-NMR (DMSO-$d_6$, 400 MHz): δ 10.61 (s, 1H), 9.01 (s, 1H), 8.22 (s, 1H), 7.99 (dd, J = 6.8, 2.6 Hz, 1H), 7.83-7.72 (m, 2H), 7.61-7.52 (m, 2H), 7.41 (t, J = 9.1 Hz, 1H), 4.84-4.79 (m, 1H), 4.31 (dd, J = 11.9, 2.8 Hz, 1H), 2.63 (s, 3H), 2.33-2.14 (m, 2H). |
| HBV-CSU-286-ISO-I | 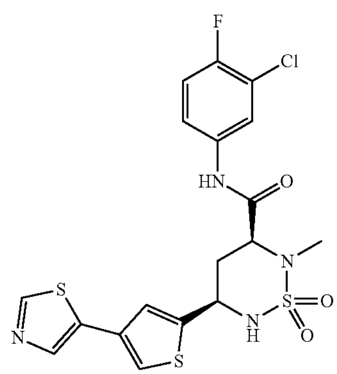 [SMILES: CN1[C@H](C(=O)Nc2ccc(F)c(Cl)c2)C[C@H](c2cc(-c3cncs3)cs2)NS1(=O)=O] | 6% | 487.10 (M + 1) | 486.01 for $C_{18}H_{16}ClFN_4O_3S_3$ | ¹H-NMR (DMSO-$d_6$, 400 MHz): δ 10.61 (s, 1H), 9.01 (s, 1H), 8.22 (s, 1H), 7.99 (dd, J = 6.8, 2.5 Hz, 1H), 7.81-7.75 (m, 2H), 7.62-7.52 (m, 2H), 7.42 (t, J = 9.1 Hz, 1H), 4.82-4.75 (m, 1H), 4.31 (d, J = 10.8 Hz, 1H), 2.63 (s, 3H), 2.37-2.20 (m, 2H). |
| HBV-CSU-286-ISO-II | 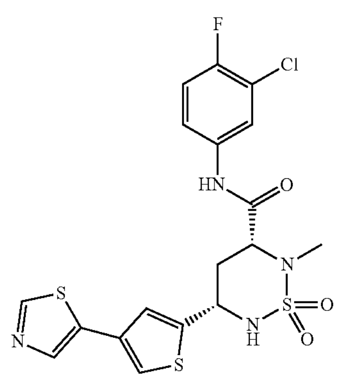 [SMILES: CN1[C@@H](C(=O)Nc2ccc(F)c(Cl)c2)C[C@@H](c2cc(-c3cncs3)cs2)NS1(=O)=O] | 8% | 487.05 (M + 1) | 486.01 for $C_{18}H_{16}ClFN_4O_3S_3$ | ¹H-NMR (DMSO-$d_6$, 400 MHz): δ 10.61 (s, 1H), 9.01 (s, 1H), 8.22 (s, 1H), 7.99 (dd, J = 6.6, 2.7 Hz, 1H), 7.80-7.74 (m, 2H), 7.57-7.55 (m, 2H), 7.41 (t, J = 9.1 Hz, 1H), 4.82-4.80 (m, 1H), 4.31 (d, J = 11.5 Hz, 1H), 2.63 (s, 3H), 2.33-2.19 (m, 2H). |

TABLE 2-continued

Analytical data for HBV-CSU racemic & pure enantiomers:

| Target No | Structure | Rx. Yield (%) | Mass Spec. Found (m/z) | Mass Spec. Calculated | $^1$H-NMR |
|---|---|---|---|---|---|
| HBV-CSU-288 | 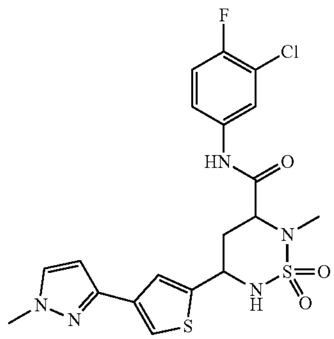 [SMILES: CN1C(C(=O)Nc2ccc(F)c(Cl)c2)CC(c2cc(-c3ccn(C)n3)cs2)NS1(=O)=O] | 11% | 484.15 (M + 1) | 483.06 for $C_{19}H_{19}ClFN_5O_3S_2$ | $^1$H-NMR (DMSO-d$_6$, 400 MHz): δ 10.54 (s, 1H), 7.96-7.93 (m, 1H), 7.68-7.64 (m, 3H), 7.55-7.35 (m, 3H), 6.52 (s, 1H), 4.78-4.75 (m, 1H), 4.30-4.26 (m, 1H), 3.80 (s, 3H), 2.59 (s, 3H), 2.29-2.12 (m, 2H). |
| HBV-CSU-288-ISO-I | 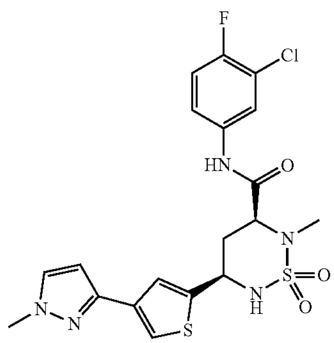 [SMILES: CN1[C@H](C(=O)Nc2ccc(F)c(Cl)c2)C[C@H](c2cc(-c3ccn(C)n3)cs2)NS1(=O)=O] | 7% | 484.10 (M + 1) | 483.06 for $C_{19}H_{19}ClFN_5O_3S_2$ | $^1$H-NMR (DMSO-d$_6$, 400 MHz): δ 10.58 (s, 1H), 7.98 (dd, J = 6.8, 2.6 Hz, 1H), 7.69-7.67 (m, 3H), 7.59-7.55 (m, 1H), 7.50-7.36 (m, 2H), 6.56 (d, J = 2.3 Hz, 1H), 4.80-4.75 (m, 1H), 4.36-4.28 (m, 1H), 3.84 (s, 3H), 2.62 (s, 3H), 2.32-2.07 (m, 2H). |
| HBV-CSU-288-ISO-II | 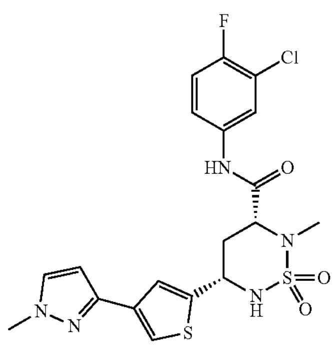 [SMILES: CN1[C@@H](C(=O)Nc2ccc(F)c(Cl)c2)C[C@@H](c2cc(-c3ccn(C)n3)cs2)NS1(=O)=O] | 9% | 484.15 (M + 1) | 483.06 for $C_{19}H_{19}ClFN_5O_3S_2$ | $^1$H-NMR (DMSO-d$_6$, 400 MHz): δ 10.58 (s, 1H), 7.98 (dd, J = 6.9, 2.6 Hz, 1H), 7.72-7.64 (m, 3H), 7.58-7.54 (m, 1H), 7.50-7.36 (m, 2H), 6.56 (d, J = 2.2 Hz, 1H), 4.80-4.75 (m, 1H), 4.32 (dd, J = 11.9, 2.8 Hz, 1H), 3.84 (s, 3H), 2.62 (s, 3H), 2.32-2.15 (m, 2H). |
| HBV-CSU-289 | | 40% | 484.10 (M + 1) | 483.06 for $C_{19}H_{19}ClFN_5O_3S_2$ | $^1$H-NMR (DMSO-d$_6$, 400 MHz): δ 10.60 (s, 1H), 7.98 (dd, J = 6.8, 2.6 Hz, 1H), 7.76 (dd, J = 5.6, 4.0 Hz, 2H), 7.56-7.42 (m, 4H), 6.46 (d, J = 2.0 Hz, 1H), 4.89-4.78 (m, 1H), 4.31 (dd, J = 11.8, 2.8 Hz, 1H), 3.92 (s, 3H), 2.63 (s, 3H), 2.32-2.19 (m, 2H). | ns
TABLE 2-continued

Analytical data for HBV-CSU racemic & pure enantiomers:

| Target No | Structure | Rx. Yield (%) | Mass Spec. Found (m/z) | Mass Spec. Calculated | $^1$H-NMR |
|---|---|---|---|---|---|
| HBV-CSU-289-ISO-I | 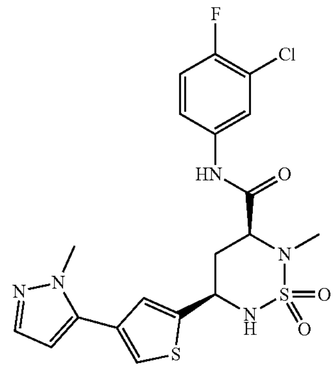 [SMILES: CN1[C@H](C(=O)Nc2ccc(F)c(Cl)c2)C[C@H](c2cc(-c3ccnn3C)cs2)NS1(=O)=O] | 7% | 484.10 (M + 1) | 483.06 for $C_{19}H_{19}ClFN_5O_3S_2$ | $^1$H-NMR (DMSO-$d_6$, 400 MHz): δ 10.60 (s, 1H), 7.98 (dd, J = 6.8, 2.6 Hz, 1H), 7.76-7.56 (m, 3H), 7.46-7.36 (m, 3H), 6.46 (d, J = 1.9 Hz, 1H), 4.88-4.79 (m, 1H), 4.31 (dd, J = 11.6, 2.8 Hz, 1H), 3.92 (s, 3H), 2.63 (s, 3H), 2.33-2.17 (m, 2H). |
| HBV-CSU-289-ISO-II | 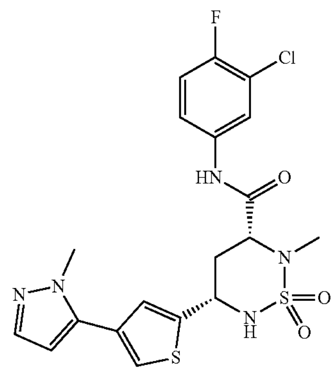 [SMILES: CN1[C@@H](C(=O)Nc2ccc(F)c(Cl)c2)C[C@@H](c2cc(-c3ccnn3C)cs2)NS1(=O)=O] | 8% | 484.10 (M + 1) | 483.06 for $C_{19}H_{19}ClFN_5O_3S_2$ | $^1$H-NMR (DMSO-$d_6$, 400 MHz): δ 10.55 (s, 1H), 7.95 (dd, J = 6.9, 2.5 Hz, 1H), 7.71 (s, 2H), 7.55-7.51 (m, 1H), 7.42-7.32 (m, 3H), 6.42 (d, J = 1.9 Hz, 1H), 4.83-4.74 (m, 1H), 4.23-4.20 (m, 1H), 3.88 (s, 3H), 2.57 (s, 3H), 2.28-2.09 (m, 2H). |
| HBV-CSU-290 | 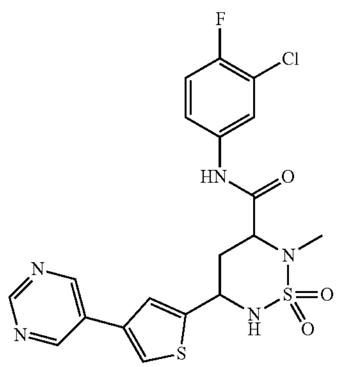 [SMILES: CN1C(C(=O)Nc2ccc(F)c(Cl)c2)CC(c2cc(-c3cncnc3)cs2)NS1(=O)=O] | 60% | 482.15 (M + 1) | 481.04 for $C_{19}H_{17}ClFN_5O_3S_2$ | $^1$H-NMR (DMSO-$d_6$, 400 MHz): δ 10.60 (s, 1H), 9.17 (s, 2H), 9.08 (s, 1H), 8.16 (s, 1H), 7.97 (dd, J = 6.8, 2.5 Hz, 1H), 7.82-7.73 (m, 2H), 7.57-7.53 (m, 1H), 7.39 (t, J = 9.0 Hz, 1H), 4.88-4.77 (m, 1H), 4.30 (dd, J = 11.8, 2.7 Hz, 1H), 2.61 (s, 3H), 2.36-2.16 (m, 2H). |
| HBV-CSU-290-ISO-I | 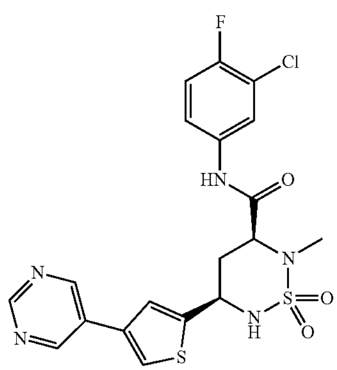 [SMILES: CN1[C@H](C(=O)Nc2ccc(F)c(Cl)c2)C[C@H](c2cc(-c3cncnc3)cs2)NS1(=O)=O] | 3% | 482.15 (M + 1) | 481.04 for $C_{19}H_{17}ClFN_5O_3S_2$ | $^1$H-NMR (DMSO-$d_6$, 400 MHz): δ 10.61 (s, 1H), 9.20 (s, 2H), 9.10 (s, 1H), 8.21-8.15 (m, 1H), 8.03-7.91 (m, 1H), 7.80-7.76 (m, 2H), 7.68-7.51 (m, 1H), 7.42 (t, J = 9.0 Hz, 1H), 4.87-4.82 (m, 1H), 4.32 (dd, J = 11.9, 2.8 Hz, 1H), 2.64 (s, 3H), 2.38-2.21 (m, 2H). |

TABLE 2-continued

Analytical data for HBV-CSU racemic & pure enantiomers:

| Target No | Structure | Rx. Yield (%) | Mass Spec. Found (m/z) | Mass Spec. Calculated | ¹H-NMR |
|---|---|---|---|---|---|
| HBV-CSU-290-ISO-II | 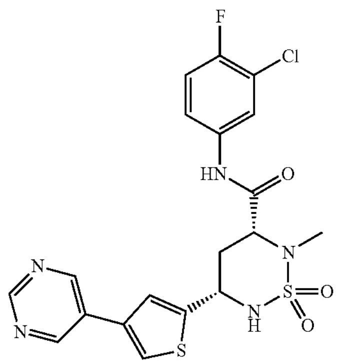 | 3% | 482.15 (M + 1) | 481.04 for $C_{19}H_{17}ClFN_5O_3S_2$ | ¹H-NMR (DMSO-$d_6$, 400 MHz): δ 10.64-10.59 (m, 1H), 9.20 (s, 2H), 9.10 (s, 1H), 8.18 (s, 1H), 7.99 (dd, J = 6.8, 2.5 Hz, 1H), 7.80-7.76 (m, 2H), 7.62-7.53 (m, 1H), 7.42 (t, J = 9.1 Hz, 1H), 4.89-4.81 (m, 1H), 4.31 (d, J = 11.6 Hz, 1H), 2.63 (s, 3H), 2.38-2.21 (m, 2H). |
| HBV-CSU-291 | 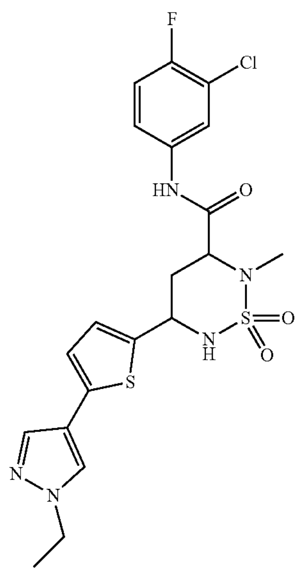 [SMILES: CCn1cc(-c2ccc(C3CC(C(=O)Nc4ccc(F)c(Cl)c4)N(C)S(=O)(=O)N3)s2)cn1] | 29% | 498.1 (M + 1) | 497.08 for $C_{20}H_{21}ClFN_5O_3S_2$ | ¹H-NMR (DMSO-$d_6$, 400 MHz): δ 10.57 (s, 1H), 8.06 (s, 1H), 7.96 (dd, J = 7.2, 2.4 Hz, 1H), 7.70-7.66 (m, 2H), 7.57-7.54 (m, 1H), 7.40 (t, J = 8.8 Hz, 1H), 7.04 (s, 2H), 4.76-4.75 (m, 1H), 4.29 (dd, J = 11.6, 2.8 Hz, 1H), 4.12 (q, J = 6.8 Hz, 2H), 2.61 (s, 3H), 2.25-2.09 (m, 2H), 1.38 (t, J = 6.8 Hz, 3H). |
| HBV-CSU-291-ISO-I | 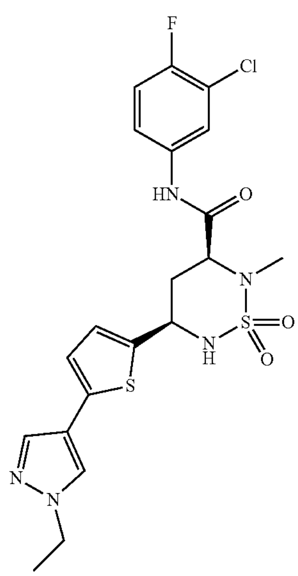 [SMILES: CCn1cc(-c2ccc([C@H]3C[C@@H](C(=O)Nc4ccc(F)c(Cl)c4)N(C)S(=O)(=O)N3)s2)cn1] | 6% | 498.1 (M + 1) | 497.08 for $C_{20}H_{21}ClFN_5O_3S_2$ | ¹H-NMR (DMSO-$d_6$, 400 MHz): δ 10.57 (s, 1H), 8.06 (s, 1H), 7.97 (dd, J = 6.8, 2.4 Hz, 1H), 7.7-7.67 (m, 2H), 7.57-7.54 (m, 1H), 7.4 (t, J = 8.8 Hz, 1H), 7.04 (s, 2H), 4.74-4.73 (m, 1H), 4.31 (dd, J = 11.2, 2.8 Hz, 1H), 4.13 (q, J = 7.2 Hz, 2H), 2.61 (s, 3H), 2.25-2.12 (m, 2H), 1.38 (t, J = 6.8 Hz, 3H). |

TABLE 2-continued

Analytical data for HBV-CSU racemic & pure enantiomers:

| Target No | Structure | Rx. Yield (%) | Mass Spec. Found (m/z) | Mass Spec. Calculated | ¹H-NMR |
|---|---|---|---|---|---|
| HBV-CSU-291-ISO-II | 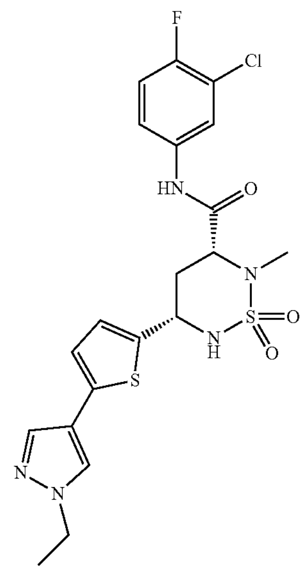 [SMILES: CCn1cc(-c2ccc([C@@H]3C[C@H](C(=O)Nc4ccc(F)c(Cl)c4)N(C)S(=O)(=O)N3)s2)cn1] | 5% | 498.1 (M + 1) | 497.08 for $C_{20}H_{21}ClFN_5O_3S_2$ | ¹H-NMR (DMSO-d$_6$, 400 MHz): δ 10.57 (s, 1H), 8.06 (s, 1H), 7.97 (dd, J = 6.8, 2.4 Hz, 1H), 7.7-7.67 (m, 2H), 7.58-7.54 (m, 1H), 7.41 (t, J = 9.2 Hz, 1H), 7.04 (s, 2H), 4.74-4.73 (m, 1H), 4.31 (dd, J = 11.2, 2.8 Hz, 1H), 4.13 (q, J = 7.2 Hz, 2H), 2.61 (s, 3H), 2.22-2.15 (m, 2H), 1.38 (t, J = 7.2 Hz, 3H). |
| HBV-CSU-292-ISO-I | 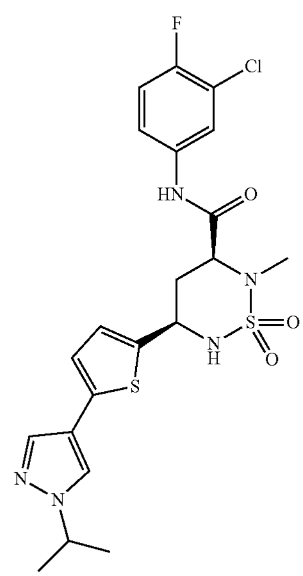 [SMILES: CC(C)n1cc(-c2ccc([C@H]3C[C@@H](C(=O)Nc4ccc(F)c(Cl)c4)N(C)S(=O)(=O)N3)s2)cn1] | 9% | 512.15 (M + 1) | 511.09 for $C_{21}H_{23}ClFN_5O_3S_2$ | ¹H-NMR (DMSO-d$_6$, 400 MHz): δ 10.57 (s, 1H), 8.08 (s, 1H), 7.97 (dd, J = 6.8, 2.4 Hz, 1H), 7.7-7.67 (m, 2H), 7.57-7.54 (m, 1H), 7.4 (t, J = 9.2 Hz, 1H), 7.04 (s, 2H), 4.78-4.71 (m, 1H), 4.51-4.47 (m, 1H), 4.31 (dd, J = 11.2, 2.4 Hz, 1H), 2.61 (s, 3H), 2.22-2.12 (m, 2H), 1.43 (d, J = 6.8 Hz, 6H). |

TABLE 2-continued

Analytical data for HBV-CSU racemic & pure enantiomers:

| Target No | Structure | Rx. Yield (%) | Mass Spec. Found (m/z) | Mass Spec. Calculated | $^1$H-NMR |
|---|---|---|---|---|---|
| HBV-CSU-292-ISO-II | 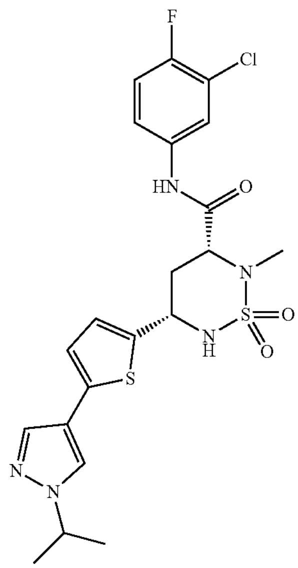 [SMILES: CC(C)n1cc(-c2ccc([C@@H]3C[C@H](C(=O)Nc4ccc(F)c(Cl)c4)N(C)S(=O)(=O)N3)s2)cn1] | 6% | 512.15 (M + 1) | 511.09 for $C_{21}H_{23}ClFN_5O_3S_2$ | $^1$H-NMR (DMSO-$d_6$, 400 MHz): δ 10.57 (s, 1H), 8.08 (s, 1H), 7.97 (dd, J = 6.8, 2.4 Hz, 1H), 7.69-7.67 (m, 2H), 7.58-7.54 (m, 1H), 7.4 (t, J = 9.2 Hz, 1H), 7.04 (s, 2H), 4.78-4.71 (m, 1H), 4.53-4.46 (m, 1H), 4.31 (dd, J = 11.2, 2.4 Hz, 1H), 2.61 (s, 3H), 2.32-2.12 (m, 2H), 1.43 (d, J = 6.8 Hz, 6H). |
| HBV-CSU-293 | 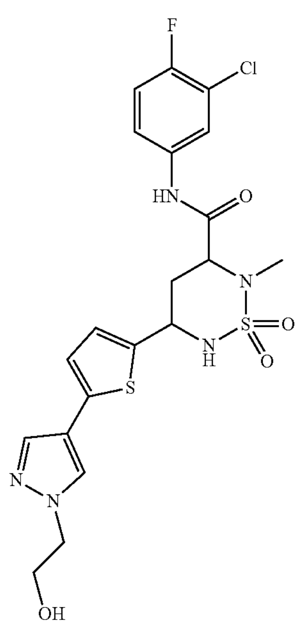 [SMILES: CN1C(C(=O)Nc2ccc(F)c(Cl)c2)CC(c2ccc(-c3cnn(CCO)c3)s2)NS1(=O)=O] | 24% | 514.1 (M + 1) | 513.03 for $C_{20}H_{21}ClFN_5O_4S_2$ | $^1$H-NMR (DMSO-$d_6$, 400 MHz): δ 10.58 (s, 1H), 8.01 (s, 1H), 7.98 (dd, J = 6.8, 2.4 Hz, 1H), 7.72 (s, 1H), 7.7-7.67 (m, 1H), 7.58-7.54 (m, 1H), 7.4 (t, J = 9.2 Hz, 1H), 7.07-7.03 (m, 2H), 4.92 (t, J = 5.2 Hz, 1H), 4.78-4.73 (m, 1H), 4.3 (dd, J = 11.6, 2.8 Hz, 1H), 4.14 (t, J = 5.2 Hz, 2H), 3.77-3.72 (m, 2H), 2.62 (s, 3H), 2.27-2.07 (m, 2H). |

TABLE 2-continued

Analytical data for HBV-CSU racemic & pure enantiomers:

| Target No | Structure | Rx. Yield (%) | Mass Spec. Found (m/z) | Mass Spec. Calculated | ¹H-NMR |
|---|---|---|---|---|---|
| HBV-CSU-293-ISO-I | 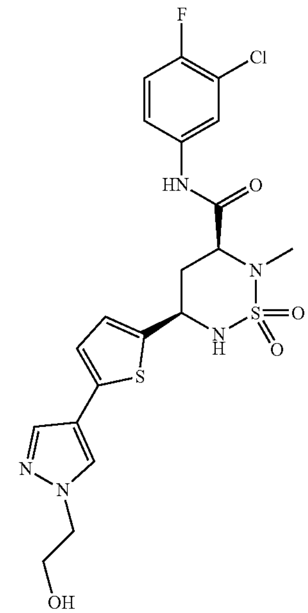 [SMILES: CN1[C@H](C(=O)Nc2ccc(F)c(Cl)c2)C[C@H](c2ccc(-c3cnn(CCO)c3)s2)NS1(=O)=O] | 3% | 514.1 (M + 1) | 513.03 for $C_{20}H_{21}ClFN_5O_4S_2$ | ¹H-NMR (DMSO-$d_6$, 400 MHz): δ 10.57 (s, 1H), 8.01 (s, 1H), 7.97 (dd, J = 6.8, 2.4 Hz, 1H), 7.71 (s, 1H), 7.7-7.67 (m, 1H), 7.57-7.54 (m, 1H), 7.4 (t, J = 9.2 Hz, 1H), 7.05-7.04 (m, 2H), 4.92 (t, J = 5.2 Hz, 1H), 4.77-4.73 (m, 1H), 4.29 (dd, J = 11.6, 2.8 Hz, 1H), 4.14 (t, J = 5.2 Hz, 2H), 3.76-3.72 (m, 2H), 2.61 (s, 3H), 2.33-2.12 (m, 2H). |
| HBV-CSU-293-ISO-II | 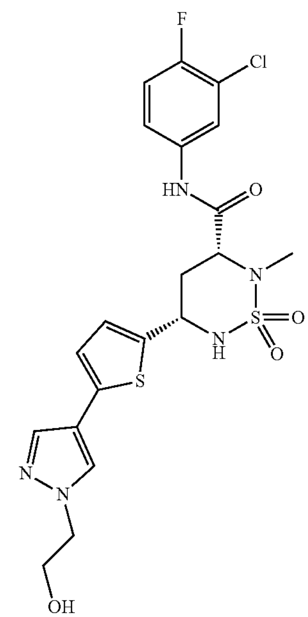 [SMILES: CN1[C@@H](C(=O)Nc2ccc(F)c(Cl)c2)C[C@@H](c2ccc(-c3cnn(CCO)c3)s2)NS1(=O)=O] | 6% | 514.00 (M + 1) | 513.07 for $C_{20}H_{21}ClFN_5O_4S_2$ | ¹H-NMR (DMSO-$d_6$, 400 MHz): δ 10.62 (s, 1H), 8.01 (s, 1H), 7.97 (dd, J = 6.8, 2.8 Hz, 1H), 7.72-7.64 (m, 2H), 7.58-7.53 (m, 1H), 7.40 (t, J = 8.8 Hz, 1H), 7.05-7.03 (m, 2H), 4.93 (t, J = 5.6 Hz, 1H), 4.73 (d, J = 11.2 Hz, 1H), 4.29 (dd, J = 11.6, 2.8 Hz, 1H), 4.15-4.12 (m, 2H), 3.76-3.71 (m, 2H), 2.61 (s, 3H), 2.32-2.07 (m, 2H). |
| HBV-CSU-294 | 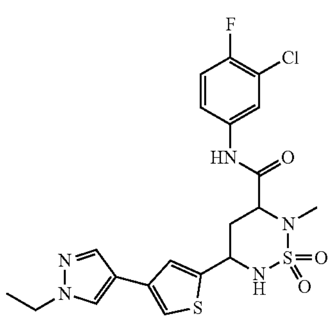 [SMILES: CCn1cc(-c2csc(C3CC(C(=O)Nc4ccc(F)c(Cl)c4)N(C)S(=O)(=O)N3)c2)cn1] | 32% | 498.15 (M + 1) | 497.08 for $C_{20}H_{21}ClFN_5O_3S_2$ | ¹H-NMR (DMSO-$d_6$, 400 MHz): δ 10.59 (s, 1H), 8.08 (s, 1H), 7.98 (dd, J = 6.8, 2.4 Hz, 1H), 7.76 (s, 1H), 7.71-7.68 (m, 1H), 7.59-7.55 (m, 1H), 7.48 (s, 1H), 7.47-7.38 (m, 2H), 4.8-4.79 (m, 1H), 4.31 (dd, J = 11.2, 2.4 Hz, 1H), 4.14-4.06 (m, 2H), 2.62 (s, 3H), 2.31-2.16 (m, 2H), 1.38 (t, J = 6.8 Hz, 3H). |

TABLE 2-continued

Analytical data for HBV-CSU racemic & pure enantiomers:

| Target No | Structure | Rx. Yield (%) | Mass Spec. Found (m/z) | Mass Spec. Calculated | $^1$H-NMR |
|---|---|---|---|---|---|
| HBV-CSU-294-ISO-I | 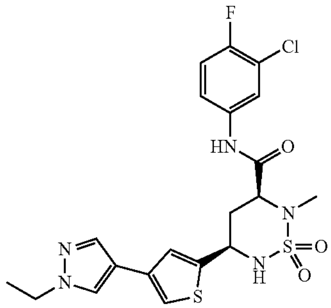 [SMILES: CCn1cc(-c2csc([C@H]3C[C@@H](C(=O)Nc4ccc(F)c(Cl)c4)N(C)S(=O)(=O)N3)c2)cn1] | 6% | 498.10 (M + 1) | 497.08 for $C_{20}H_{21}ClFN_5O_3S_2$ | $^1$H-NMR (DMSO-$d_6$, 400 MHz): δ 10.61 (s, 1H), 8.08 (s, 1H), 7.98 (dd, J = 6.8, 2.4 Hz, 1H), 7.76-7.71 (m, 2H), 7.59-7.54 (m, 1H), 7.48 (s, 1H), 7.43-7.38 (m, 2H), 4.76 (d, J = 10.4 Hz, 1H), 4.29 (dd, J = 11.6, 2.8 Hz, 1H), 4.10 (q, J = 7.2 Hz, 2H), 2.62 (s, 3H), 2.31-2.07 (m, 2H), 1.38 (t, J = 7.2 Hz, 3H). |
| HBV-CSU-294-ISO-II | 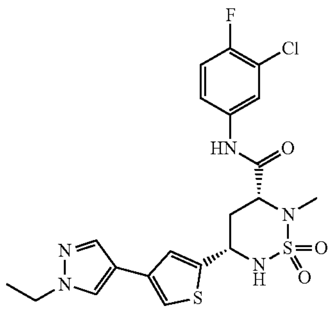 [SMILES: CCn1cc(-c2csc([C@@H]3C[C@H](C(=O)Nc4ccc(F)c(Cl)c4)N(C)S(=O)(=O)N3)c2)cn1] | 7% | 498.10 (M + 1) | 497.08 for $C_{20}H_{21}ClFN_5O_3S_2$ | $^1$H-NMR (DMSO-$d_6$, 400 MHz): δ 10.62 (s, 1H), 8.09 (s, 1H), 7.98 (dd, J = 6.8, 2.0 Hz, 1H), 7.76-7.71 (m, 2H), 7.59-7.54 (m, 1H), 7.48 (s, 1H), 7.44-7.39 (m, 2H), 4.76 (d, J = 10.8 Hz, 1H), 4.29 (d, J = 10.4 Hz, 1H), 4.10 (q, J = 7.2 Hz, 2H), 2.62 (s, 3H), 2.31-2.10 (m, 2H), 1.38 (t, J = 7.2 Hz, 3H). |
| HBV-CSU-295 | 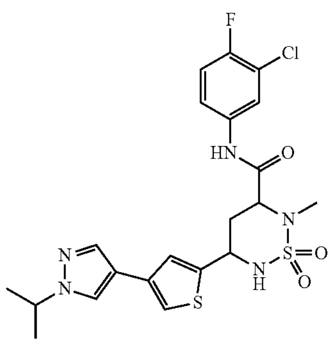 [SMILES: CC(C)n1cc(-c2csc(C3CC(C(=O)Nc4ccc(F)c(Cl)c4)N(C)S(=O)(=O)N3)c2)cn1] | 28% | 512.15 (M + 1) | 511.09 for $C_{21}H_{23}ClFN_5O_3S_2$ | $^1$H-NMR (DMSO-$d_6$, 400 MHz): δ 10.6 (s, 1H), 8.12 (s, 1H), 7.98 (dd, J = 6.8, 2.4 Hz, 1H), 7.76 (s, 1H), 7.72-7.68 (m, 1H), 7.59-7.55 (m, 1H), 7.48 (s, 1H), 7.42-7.39 2H), 4.81-4.74 (m, 1H), 4.48-4.43 (m, 1H), 4.32 (dd, J = 12.4, 2.8 Hz, 1H), 2.62 (s, 3H), 2.32-2.17 (m, 2H), 1.42 (d, J = 6.8 Hz, 6H). |
| HBV-CSU-295-ISO-I | 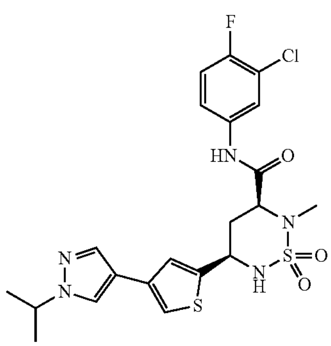 [SMILES: CC(C)n1cc(-c2csc([C@H]3C[C@@H](C(=O)Nc4ccc(F)c(Cl)c4)N(C)S(=O)(=O)N3)c2)cn1] | 7% | 512.15 (M + 1) | 511.09 for $C_{21}H_{23}ClFN_5O_3S_2$ | $^1$H-NMR (DMSO-$d_6$, 400 MHz): δ 10.61 (s, 1H), 8.13 (s, 1H), 7.99-7.97 (m, 1H), 7.76-7.71 (m, 2H), 7.59-7.55 (m, 1H), 7.48 (s, 1H), 7.43-7.39 (m, 2H), 4.75 (d, J = 11.6 Hz, 1H), 4.47-4.45 (m, 1H), 4.32-4.28 (m, 1H), 2.62 (s, 3H), 2.32-2.11 (m, 2H), 1.41 (d, J = 6.4 Hz, 6H). |

TABLE 2-continued

Analytical data for HBV-CSU racemic & pure enantiomers:

| Target No | Structure | Rx. Yield (%) | Mass Spec. Found (m/z) | Mass Spec. Calculated | $^1$H-NMR |
|---|---|---|---|---|---|
| HBV-CSU-295-ISO-II | 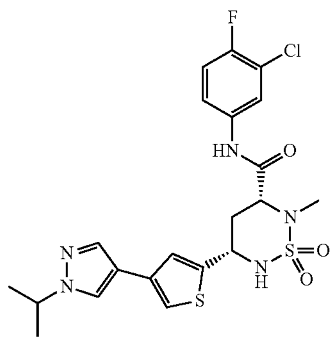 [SMILES: CC(C)n1cc(-c2csc([C@@H]3C[C@H](C(=O)Nc4ccc(F)c(Cl)c4)N(C)S(=O)(=O)N3)c2)cn1] | 8% | 512.15 (M + 1) | 511.09 for $C_{21}H_{23}ClFN_5O_3S_2$ | $^1$H-NMR (DMSO-$d_6$, 400 MHz): δ 10.61 (s, 1H), 8.13 (s, 1H), 7.99-7.97 (m, 1H), 7.75-7.72 (m, 2H), 7.59-7.54 (m, 1H), 7.48 (s, 1H), 7.43-7.39 (m, 2H), 4.77-4.75 (m, 1H), 4.47-4.44 (m, 1H), 4.32-4.28 (m, 1H), 2.62 (s, 3H), 2.32-2.12 (m, 2H), 1.41 (d, J = 7.2 Hz, 6H). |
| HBV-CSU-296 | 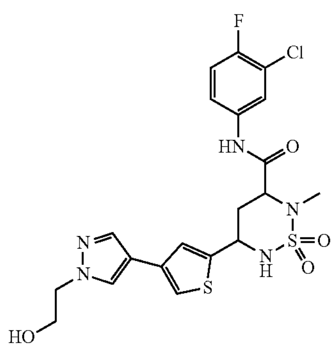 [SMILES: CN1C(C(=O)Nc2ccc(F)c(Cl)c2)CC(c2cc(-c3cnn(CCO)c3)cs2)NS1(=O)=O] | 34% | 514.1 (M + 1) | 513.07 for $C_{20}H_{21}ClFN_5O_4S_2$ | $^1$H-NMR (DMSO-$d_6$, 400 MHz): δ 10.59 (s, 1H), 8.04 (s, 1H), 7.98 (dd, J = 6.8, 2.4 Hz, 1H), 7.77 (s, 1H), 7.71-7.68 (m, 1H), 7.62-7.54 (m, H), 7.48 (s, 1H), 7.43-7.38 2H), 4.90 (t, J = 5.2 Hz, 1H), 4.8-4.74 (m, 1H), 4.3 (dd, J = 11.6, 2.4 Hz, 1H), 4.12 (t, J = 5.2 Hz, 2H), 3.76-3.71 (m, 2H), 2.62 (s, 3H), 2.32-2.16 (m, 2H). |
| HBV-CSU-296-ISO-I | 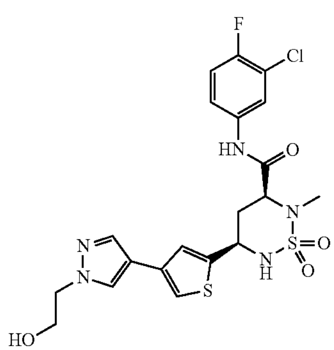 [SMILES: CN1[C@H](C(=O)Nc2ccc(F)c(Cl)c2)C[C@H](c2cc(-c3cnn(CCO)c3)cs2)NS1(=O)=O] | 6% | 514.10 (M + 1) | 513.07 for $C_{20}H_{21}ClFN_5O_4S_2$ | $^1$H-NMR (DMSO-$d_6$, 400 MHz): δ 10.62 (s, 1H), 8.04 (s, 1H), 7.99-7.97 (m, 1H), 7.77 (s, 1H), 7.59-7.54 (m, 1H), 7.49-7.48 (m, 2H), 7.43-7.37 (m, 2H), 4.93-4.90 (m, 1H), 4.76 (d, J = 9.2 Hz, 1H), 4.30-4.28 (m, 1H), 4.13-4.10 (m, 2H), 3.74-3.72 (m, 2H), 2.61 (s, 3H), 2.35-2.16 (m, 2H). |
| HBV-CSU-296-ISO-II | 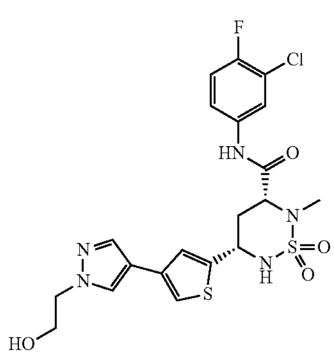 [SMILES: CN1[C@@H](C(=O)Nc2ccc(F)c(Cl)c2)C[C@@H](c2cc(-c3cnn(CCO)c3)cs2)NS1(=O)=O] | 3% | 514.40 (M + 1) | 513.07 for $C_{20}H_{21}ClFN_5O_4S_2$ | $^1$H-NMR (DMSO-$d_6$, 400 MHz): δ 10.62 (s, 1H), 8.04 (s, 1H), 7.99-7.97 (m, 1H), 7.77 (s, 1H), 7.59-7.37 (m, 5H), 4.93-4.90 (m, 1H), 4.76 (d, J = 11.6 Hz, 1H), 4.31-4.28 (m, 1H), 4.13-4.10 (m, 2H), 3.74-3.72 (m, 2H), 2.61 (s, 3H), 2.31-2.12 (m, 2H). |

TABLE 2-continued

Analytical data for HBV-CSU racemic & pure enantiomers:

| Target No | Structure | Rx. Yield (%) | Mass Spec. Found (m/z) | Mass Spec. Calculated | $^1$H-NMR |
|---|---|---|---|---|---|
| HBV-CSU-300 | 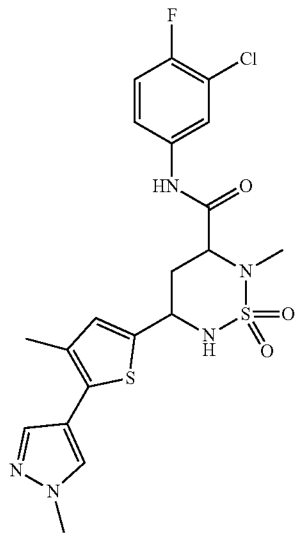 [SMILES: Cc1cc(C2CC(C(=O)Nc3ccc(F)c(Cl)c3)N(C)S(=O)(=O)N2)sc1-c1cnn(C)c1] | 40% | 498 (M + 1) | 497.08 for $C_{20}H_{21}ClFN_5O_3S_2$ | $^1$H-NMR (DMSO-$d_6$, 400 MHz): δ 10.57 (s, 1H), 7.98-7.93 (m, 2H), 7.65-7.38 (m, 4H), 6.94 (s, 1H), 4.71 (t, J = 9.6 Hz, 1H), 4.31-4.29 (m, 1H), 3.87 (s, 3H), 2.61 (s, 3H), 2.20-2.11 (m, 5H). |
| HBV-CSU-300-ISO-I | 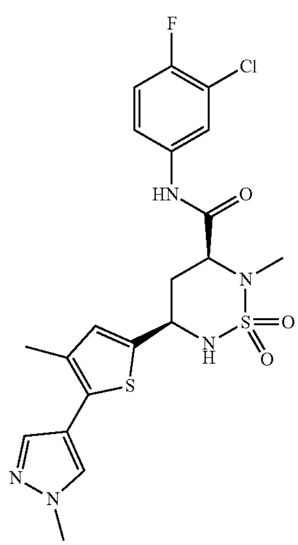 [SMILES: Cc1cc([C@H]2C[C@@H](C(=O)Nc3ccc(F)c(Cl)c3)N(C)S(=O)(=O)N2)sc1-c1cnn(C)c1] | 3% | 498.45 (M + 1) | 497.08 for $C_{20}H_{21}ClFN_5O_3S_2$ | $^1$H-NMR (DMSO-$d_6$, 400 MHz): δ 10.57 (s, 1H), 7.98-7.94 (m, 2H), 7.63-7.58 (m, 3H), 7.41 (t, J = 8.8 Hz, 1H), 6.93 (s, 1H), 4.72-4.69 (m, 1H), 4.31-4.28 (m, 1H), 3.87 (s, 3H), 2.60 (s, 3H), 2.20-2.10 (m, 5H). |

TABLE 2-continued
Analytical data for HBV-CSU racemic & pure enantiomers:
| Target No | Structure | Rx. Yield (%) | Mass Spec. Found (m/z) | Mass Spec. Calculated | $^1$H-NMR |
|---|---|---|---|---|---|
| HBV-CSU-300-ISO-II | 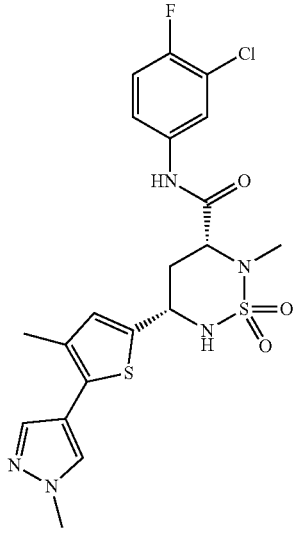 [SMILES: Cc1cc([C@@H]2C[C@H](C(=O)Nc3ccc(F)c(Cl)c3)N(C)S(=O)(=O)N2)sc1-c1cnn(C)c1] | 2% | 498.55 (M + 1) | 497.08 for $C_{20}H_{21}ClFN_5O_3S_2$ | $^1$H-NMR (DMSO-$d_6$, 400 MHz): δ 10.58 (s, 1H), 7.98-7.94 (m, 2H), 7.65-7.39 (m, 3H), 7.41 (t, J = 8.8 Hz, 1H), 6.93 (s, 1H), 4.70 (t, J = 9.6 Hz, 1H), 4.30-4.28 (m, 1H), 3.87 (s, 3H), 2.60 (s, 3H), 2.20-2.11 (m, 5H). |
| HBV-CSU-302 | 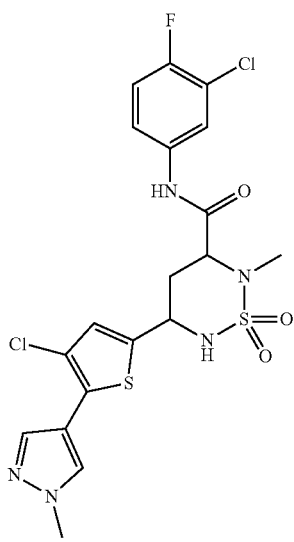 [SMILES: CN1C(C(=O)Nc2ccc(F)c(Cl)c2)CC(c2cc(Cl)c(-c3cnn(C)c3)s2)NS1(=O)=O] | 50% | 518.1 (M + 1) | 517.02 for $C_{19}H_{18}Cl_2FN_5O_3S_2$ | $^1$H-NMR (DMSO-$d_6$, 400 MHz): δ 10.58 (s, 1H), 8.19 (s, 1H), 7.97 (dd, J = 6.8, 2.4 Hz, 1H), 7.78 (s, 1H), 7.76-7.72 (m, 1H), 7.58-7.54 (m, 1H), 7.41 (t, J = 8.8 Hz, 1H), 7.13 (s, 1H), 4.78-4.72 (m, 1H), 4.31 (dd, J = 12.4, 2.4 Hz, 1H), 3.89 (s, 3H), 2.62 (s, 3H), 2.32-2.25 (m, 1H), 2.15-2.06 (m, 1H). |

TABLE 2-continued

Analytical data for HBV-CSU racemic & pure enantiomers:

| Target No | Structure | Rx. Yield (%) | Mass Spec. Found (m/z) | Mass Spec. Calculated | 1H-NMR |
|---|---|---|---|---|---|
| HBV-CSU-302-ISO-I | 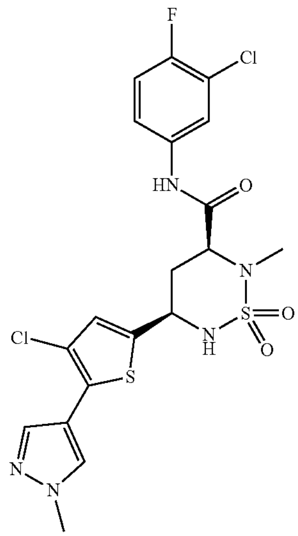 [SMILES: CN1[C@H](C(=O)Nc2ccc(F)c(Cl)c2)C[C@H](c2cc(Cl)c(-c3cnn(C)c3)s2)NS1(=O)=O] | 8% | 518.10 (M + 1) | 517.02 for $C_{19}H_{18}Cl_2FN_5O_3S_2$ | 1H-NMR (DMSO-$d_6$, 400 MHz): δ 10.58 (s, 1H), 8.18 (s, 1H), 7.98-7.96 (m, 1H), 7.78-7.71 (m, 2H), 7.57-7.55 (m, 1H), 7.41 (t, J = 8.8 Hz, 1H), 7.12 (s, 1H), 4.76-4.75 (m, 1H), 4.28 (d, J = 12.4 Hz, 1H), 3.88 (s, 3H), 2.61 (s, 3H), 2.32-2.07 (m, 2H). |
| HBV-CSU-302-ISO-II | 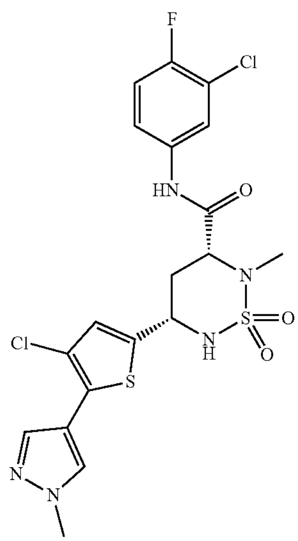 [SMILES: CN1[C@@H](C(=O)Nc2ccc(F)c(Cl)c2)C[C@@H](c2cc(Cl)c(-c3cnn(C)c3)s2)NS1(=O)=O] | 9% | 518.40 (M + 1) | 517.02 for $C_{19}H_{18}Cl_2FN_5O_3S_2$ | 1H-NMR (DMSO-$d_6$, 400 MHz): δ 10.57 (s, 1H), 8.18 (s, 1H), 7.98-7.96 (m, 1H), 7.78-7.71 (m, 2H), 7.57-7.53 (m, 1H), 7.41 (t, J = 8.8 Hz, 1H), 7.12 (s, 1H), 4.76-4.75 (m, 1H), 4.28 (d, J = 11.6 Hz, 1H), 3.88 (s, 3H), 2.61 (s, 3H), 2.32-2.06 (m, 2H). |
| HBV-CSU-304-Int-I | 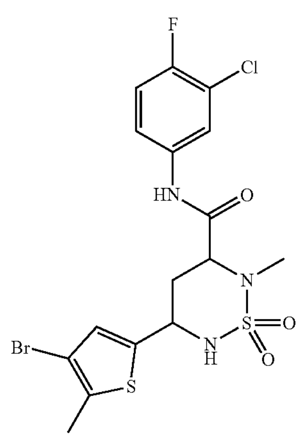 [SMILES: Cc1sc(C2CC(C(=O)Nc3ccc(F)c(Cl)c3)N(C)S(=O)(=O)N2)cc1Br] | 57% | 497.19 (M + 1) | 494.95 for $C_{16}H_{16}BrClFN_3O_3S_2$ | 1H-NMR (DMSO-$d_6$, 400 MHz): δ 10.57 (s, 1H), 7.96 (dd, J = 6.8, 2.4 Hz, 1H), 7.67 (d, J = 7.6 Hz, 1H), 7.57-7.53 (m, 1H), 7.40 (d, J = 8.8 Hz, 1H), 7.05 (s, 1H), 4.72-4.69 (m, 1H), 4.25 (dd, J = 12.4, 2.8 Hz, 1H), 2.61 (s, 3H), 2.34 (s, 3H), 2.24-1.98 (m, 2H). |

TABLE 2-continued

Analytical data for HBV-CSU racemic & pure enantiomers:

| Target No | Structure | Rx. Yield (%) | Mass Spec. Found (m/z) | Mass Spec. Calculated | $^1$H-NMR |
|---|---|---|---|---|---|
| HBV-CSU-304 | 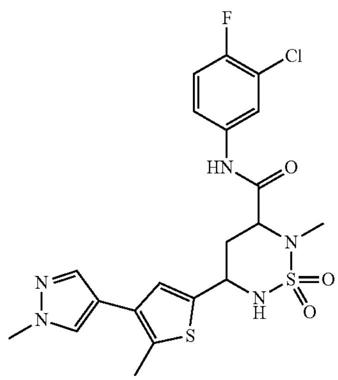 [SMILES: Cc1sc(C2CC(C(=O)Nc3ccc(F)c(Cl)c3)N(C)S(=O)(=O)N2)cc1-c1cnn(C)c1] | 32% | 498.15 (M + 1) | 497.08 for $C_{20}H_{21}ClFN_5O_3S_2$ | $^1$H-NMR (DMSO-$d_6$, 400 MHz): δ 10.58 (s, 1H), 8.02-7.93 (m, 2H), 7.70-7.52 (m, 3H), 7.41 (t, J = 9.1 Hz, 1H), 7.19 (s, 1H), 4.75-4.64 (m, 1H), 4.28 (dd, J = 11.7, 3.0 Hz, 1H), 3.86 (s, 3H), 2.61 (s, 3H), 2.44 (s, 3H), 2.30-2.05 (m, 2H). |
| HBV-CSU-304-ISO-I | 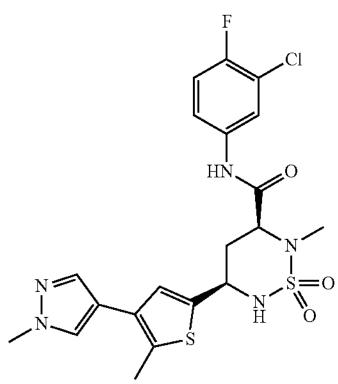 [SMILES: Cc1sc([C@H]2C[C@@H](C(=O)Nc3ccc(F)c(Cl)c3)N(C)S(=O)(=O)N2)cc1-c1cnn(C)c1] | 5% | 498.15 (M + 1) | 497.08 for $C_{20}H_{21}ClFN_5O_3S_2$ | $^1$H-NMR (DMSO-$d_6$, 400 MHz): δ 10.58 (s, 1H), 8.02-7.93 (m, 2H), 7.70-7.52 (m, 3H), 7.41 (t, J = 9.1 Hz, 1H), 7.19 (s, 1H), 4.70-4.68 (m, 1H), 4.27 (dd, J = 11.8, 3.0 Hz, 1H), 3.86 (s, 3H), 2.61 (s, 3H), 2.44 (s, 3H), 2.30-2.08 (m, 2H). |
| HBV-CSU-304-ISO-II | 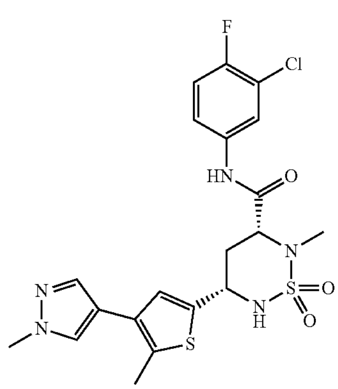 [SMILES: Cc1sc([C@@H]2C[C@H](C(=O)Nc3ccc(F)c(Cl)c3)N(C)S(=O)(=O)N2)cc1-c1cnn(C)c1] | 3% | 498.10 (M + 1) | 497.08 for $C_{20}H_{21}ClFN_5O_3S_2$ | $^1$H-NMR (DMSO-$d_6$, 400 MHz): δ 10.58 (s, 1H), 8.02-7.93 (m, 2H), 7.66-7.56 (m, 3H), 7.41 (t, J = 9.1 Hz, 1H), 7.19 (s, 1H), 4.71-4.68 (m, 1H), 4.27 (dd, J = 11.8, 2.9 Hz, 1H), 3.86 (s, 3H), 2.61 (s, 3H), 2.44 (s, 3H), 2.30-2.05 (m, 2H). |

TABLE 2-continued

Analytical data for HBV-CSU racemic & pure enantiomers:

| Target No | Structure | Rx. Yield (%) | Mass Spec. Found (m/z) | Mass Spec. Calculated | ¹H-NMR |
|---|---|---|---|---|---|
| HBV-CSU-305 | 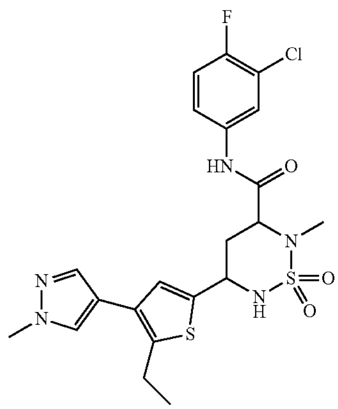 [SMILES: CCc1sc(C2CC(C(=O)Nc3ccc(F)c(Cl)c3)N(C)S(=O)(=O)N2)cc1-c1cnn(C)c1] | 10% | 512.10 (M + 1) | 511.09 for $C_{21}H_{23}ClFN_5O_3S_2$ | ¹H-NMR (DMSO-$d_6$, 400 MHz): δ 10.56 (s, 1H), 7.98-7.92 (m, 2H), 7.65-7.53 (m, 3H), 7.39 (t, J = 8.8 Hz, 1H), 7.15-7.14 (m, 1H), 4.72-4.67 (m, 1H), 4.30-4.26 (m, 1H), 3.84 (s, 3H), 2.84 (q, J = 7.2 Hz, 2H), 2.59 (s, 3H), 2.26-2.12 (m, 2H), 1.22 (t, J = 7.2 Hz, 3H). |
| HBV-CSU-305-ISO-I | 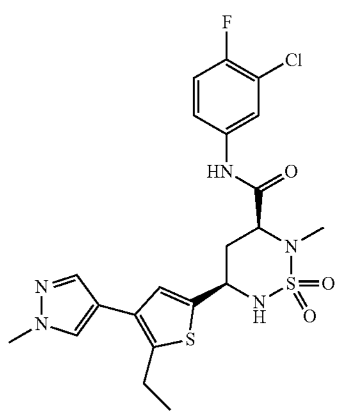 [SMILES: CCc1sc([C@H]2C[C@@H](C(=O)Nc3ccc(F)c(Cl)c3)N(C)S(=O)(=O)N2)cc1-c1cnn(C)c1] | 6% | 512.10 (M + 1) | 511.09 for $C_{21}H_{23}ClFN_5O_3S_2$ | ¹H-NMR (DMSO-$d_6$, 400 MHz): δ 10.56 (s, 1H), 8.01-7.89 (m, 2H), 7.69-7.52 (m, 3H), 7.40 (t, J = 9.1 Hz, 1H), 7.15-7.14 (m, 1H), 4.70-4.67 (m, 1H), 4.30-4.25 (m, 1H), 3.85 (s, 3H), 2.84 (q, J = 7.6 Hz, 2H), 2.59 (s, 3H), 2.21-2.16 (m, 2H), 1.30-1.18 (m, 3H). |
| HBV-CSU-305-ISO-II | 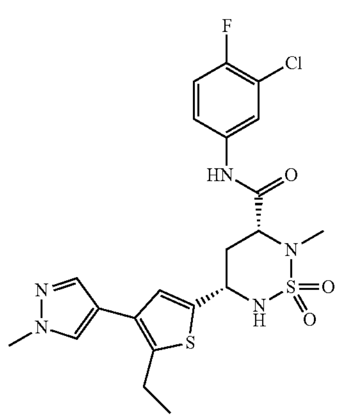 [SMILES: CCc1sc([C@@H]2C[C@H](C(=O)Nc3ccc(F)c(Cl)c3)N(C)S(=O)(=O)N2)cc1-c1cnn(C)c1] | 6% | 512.10 (M + 1) | 511.09 for $C_{21}H_{23}ClFN_5O_3S_2$ | ¹H-NMR (DMSO-$d_6$, 400 MHz): δ 10.57 (s, 1H), 8.01-7.89 (m, 2H), 7.63-7.54 (m, 3H), 7.40 (t, J = 9.1 Hz, 1H), 7.15 (s, 1H), 4.71-4.68 (m, 1H), 4.30-4.25 (m, 1H), 3.85 (s, 3H), 2.84 (q, J = 7.5 Hz, 2H), 2.59 (s, 3H), 2.21-2.16 (m, 2H), 1.23 (t, J = 7.4 Hz, 3H). |

TABLE 2-continued

Analytical data for HBV-CSU racemic & pure enantiomers:

| Target No | Structure | Rx. Yield (%) | Mass Spec. Found (m/z) | Mass Spec. Calculated | ¹H-NMR |
|---|---|---|---|---|---|
| HBV-CSU-306 | 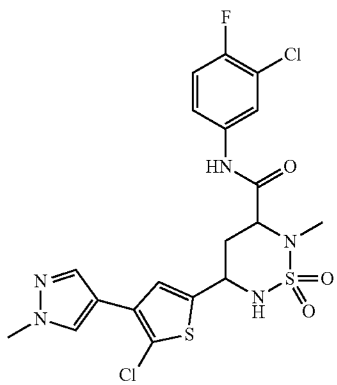 [SMILES: CN1C(C(=O)Nc2ccc(F)c(Cl)c2)CC(c2cc(-c3cnn(C)c3)c(Cl)s2)NS1(=O)=O] | 50% | 518.05 (M + 1) | 517.02 for $C_{19}H_{18}Cl_2FN_5O_3S_2$ | ¹H-NMR (DMSO-$d_6$, 400 MHz): δ 11.31 (s, 1H), 8.24 (s, 1H), 7.98 (dd, J = 6.8, 2.4 Hz, 1H), 7.91 (s, 1H), 7.78-7.75 (m, 1H), 7.58-7.55 (m, 1H), 7.44-7.37 (m, 2H), 4.77-4.71 (m, 1H), 4.28 (dd, J = 12, 2.4 Hz, 1H), 3.87 (s, 3H), 2.62 (s, 3H), 2.33-2.12 (m, 2H). |
| HBV-CSU-306-ISO-I | 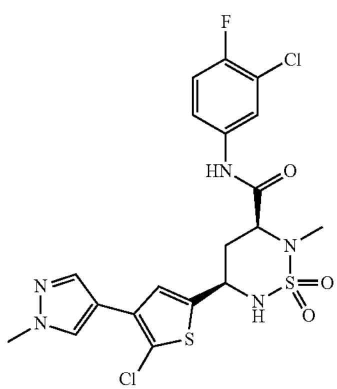 [SMILES: CN1[C@H](C(=O)Nc2ccc(F)c(Cl)c2)C[C@H](c2cc(-c3cnn(C)c3)c(Cl)s2)NS1(=O)=O] | 5% | 518.05 (M + 1) | 517.02 for $C_{19}H_{18}Cl_2FN_5O_3S_2$ | ¹H-NMR (DMSO-$d_6$, 400 MHz): δ 10.61 (s, 1H), 8.23 (s, 1H), 7.98 (dd, J = 6.8, 2.4 Hz, 1H), 7.77 (s, 1H), 7.78-7.75 (m, 1H), 7.58-7.54 (m, 1H), 7.44-7.36 (m, 2H), 4.77-4.71 (m, 1H), 4.28 (dd, J = 2.4 Hz, 1H), 3.87 (s, 3H), 2.62 (s, 3H), 2.33-2.28 (m, 1H), 2.19-2.09 (m, 1H). |
| HBV-CSU-306-ISO-II | 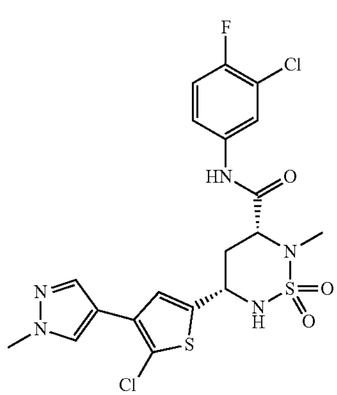 [SMILES: CN1[C@@H](C(=O)Nc2ccc(F)c(Cl)c2)C[C@@H](c2cc(-c3cnn(C)c3)c(Cl)s2)NS1(=O)=O] | 4% | 518 (M + 1) | 517.02 for $C_{19}H_{18}Cl_2FN_5O_3S_2$ | ¹H-NMR (DMSO-$d_6$, 400 MHz): δ 10.61 (s, 1H), 8.23 (s, 1H), 7.98 (dd, J = 6.8, 2.4 Hz, 1H), 7.75 (s, 1H), 7.77-7.72 (m, 1H), 7.59-7.54 (m, 1H), 7.43-7.36 (m, 2H), 4.76-4.69 (m, 1H), 4.28 (dd, J = 12, 2.4 Hz, 1H), 3.87 (s, 3H), 2.62 (s, 3H), 2.33-2.28 (m, 1H), 2.19-2.09 (m, 1H). |

TABLE 2-continued

Analytical data for HBV-CSU racemic & pure enantiomers:

| Target No | Structure | Rx. Yield (%) | Mass Spec. Found (m/z) | Mass Spec. Calculated | $^1$H-NMR |
|---|---|---|---|---|---|
| HBV-CSU-312 | 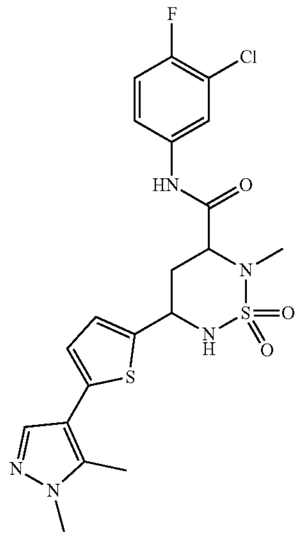 [SMILES: Cc1c(-c2ccc(C3CC(C(=O)Nc4ccc(F)c(Cl)c4)N(C)S(=O)(=O)N3)s2)cnn1C] | 58% | 498.15 (M + 1) | 497.08 for $C_{20}H_{21}ClFN_5O_3S_2$ | $^1$H-NMR (DMSO-$d_6$, 400 MHz): δ 10.58 (s, 1H), 7.99-7.97 (m, 1H), 7.70-7.67 (m, 1H), 7.58-7.54 (m, 2H), 7.40 (t, J = 8.8 Hz, 1H), 7.10-7.08 (m, 1H), 6.98-6.97 (m, 1H), 4.80-4.76 (m, 1H), 4.32-4.28 (m, 1H), 3.77 (s, 3H), 2.62 (s, 3H), 2.39 (s, 3H), 2.27-2.12 (m, 2H). |
| HBV-CSU-312-ISO-I | 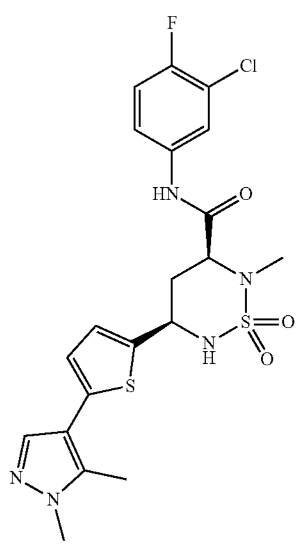 [SMILES: Cc1c(-c2ccc([C@H]3C[C@@H](C(=O)Nc4ccc(F)c(Cl)c4)N(C)S(=O)(=O)N3)s2)cnn1C] | 11% | 498.15 (M + 1) | 497.08 for $C_{20}H_{21}ClFN_5O_3S_2$ | $^1$H-NMR (DMSO-$d_6$, 400 MHz): δ 10.58 (s, 1H), 7.98 (dd, J = 6.9, 2.6 Hz, 1H), 7.67 (s, 1H), 7.61-7.51 (m, 2H), 7.41 (t, J = 9.1 Hz, 1H), 7.09 (dd, J = 3.8, 1.1 Hz, 1H), 6.97 (d, J = 3.6 Hz, 1H), 4.79-4.75 (m, 1H), 4.30 (dd, J = 11.6, 3.0 Hz, 1H), 3.77 (s, 3H), 2.61 (s, 3H), 2.39 (s, 3H), 2.29-2.11 (m, 2H). |

TABLE 2-continued

Analytical data for HBV-CSU racemic & pure enantiomers:

| Target No | Structure | Rx. Yield (%) | Mass Spec. Found (m/z) | Mass Spec. Calculated | ¹H-NMR |
|---|---|---|---|---|---|
| HBV-CSU-312-ISO-II | 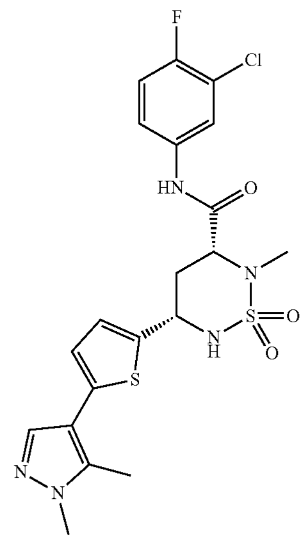 [SMILES: Cc1c(-c2ccc([C@@H]3C[C@H](C(=O)Nc4ccc(F)c(Cl)c4)N(C)S(=O)(=O)N3)s2)cnn1C] | 10% | 498.15 (M + 1) | 497.08 for $C_{20}H_{21}ClFN_5O_3S_2$ | ¹H-NMR (DMSO-$d_6$, 400 MHz): δ 10.58 (s, 1H), 7.98 (dd, J = 6.9, 2.5 Hz, 1H), 7.69-7.67 (m, 1H), 7.61-7.52 (m, 2H), 7.41 (t, J = 9.1 Hz, 1H), 7.09 (dd, J = 3.7, 1.1 Hz, 1H), 6.97 (d, J = 3.7 Hz, 1H), 4.79-4.75 (m, 1H), 4.31 (dd, J = 11.5, 3.0 Hz, 1H), 3.77 (s, 2H), 3.30 (s, 1H), 2.62 (s, 3H), 2.39 (s, 3H), 2.29-2.08 (m, 2H). |
| HBV-CSU-313 | 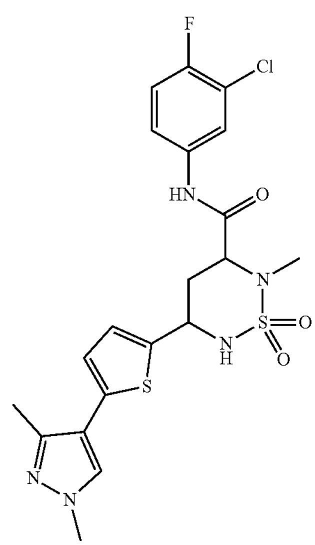 [SMILES: Cc1nn(C)cc1-c1ccc(C2CC(C(=O)Nc3ccc(F)c(Cl)c3)N(C)S(=O)(=O)N2)s1] | 29% | 498.15 (M + 1) | 497.08 for $C_{20}H_{21}ClFN_5O_3S_2$ | ¹H-NMR (DMSO-$d_6$, 400 MHz): δ 10.58 (s, 1H), 7.98 (dd, J = 6.8, 2.4 Hz, 1H), 7.91 (s, 1H), 7.7-7.67 (m, 1H), 7.65-7.58 (m, 1H), 7.41 (t, J = 9.2 Hz, 1H), 7.07-7.06 (m, 1H), 6.95 (d, J = 3.6 Hz, 1H), 4.79-4.74 (m, 1H), 4.3 (dd, J = 11.6, 2.8 Hz, 1H), 3.76 (s, 3H), 2.62 (s, 3H), 2.28 (s, 3H), 2.27-2.1 (m, 2H). |

TABLE 2-continued

Analytical data for HBV-CSU racemic & pure enantiomers:

| Target No | Structure | Rx. Yield (%) | Mass Spec. Found (m/z) | Mass Spec. Calculated | $^1$H-NMR |
|---|---|---|---|---|---|
| HBV-CSU-313-ISO-I | 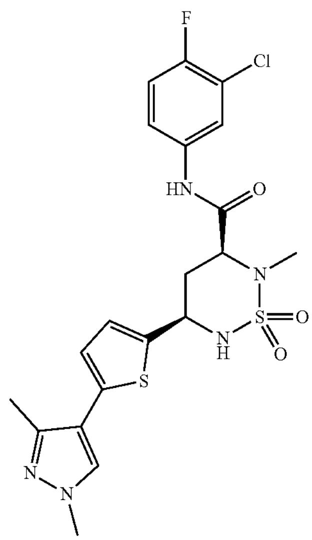 [SMILES: Cc1nn(C)cc1-c1ccc([C@H]2C[C@@H](C(=O)Nc3ccc(F)c(Cl)c3)N(C)S(=O)(=O)N2)s1] | 7% | 498.50 (M + 1) | 497.08 for $C_{20}H_{21}ClFN_5O_3S_2$ | $^1$H-NMR (DMSO-$d_6$, 400 MHz): δ 10.58 (s, 1H), 7.97 (dd, J = 6.8, 3.2 Hz, 1H), 7.89 (s, 1H), 7.69-7.53 (m, 2H), 7.39 (t, J = 8.8 Hz, 1H), 7.07-7.05 (m, 1H), 6.93 (d, J = 4.0 Hz, 1H), 4.77-4.73 (m, 1H), 4.31-4.27 (m, 1H), 3.75 (s, 3H), 2.60 (s, 3H), 2.27 (s, 3H), 2.27-2.12 (m, 2H). |
| HBV-CSU-313-ISO-II | 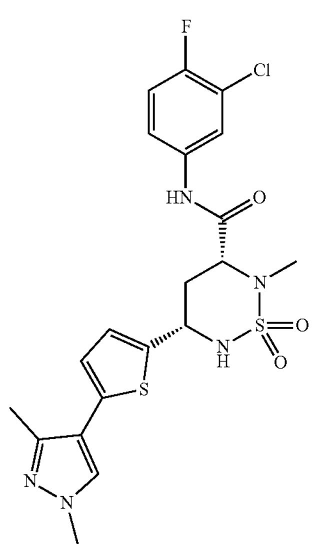 [SMILES: Cc1nn(C)cc1-c1ccc([C@@H]2C[C@H](C(=O)Nc3ccc(F)c(Cl)c3)N(C)S(=O)(=O)N2)s1] | 7% | 498.45 (M + 1) | 497.08 for $C_{20}H_{21}ClFN_5O_3S_2$ | $^1$H-NMR (DMSO-$d_6$, 400 MHz): δ 10.58 (s, 1H), 7.96 (dd, J = 6.8, 2.4 Hz, 1H), 7.89 (s, 1H), 7.69-7.53 (m, 2H), 7.39 (t, J = 8.8 Hz, 1H), 7.07-7.05 (m, 1H), 6.93 (d, J = 4.0 Hz, 1H), 4.76-4.73 (m, 1H), 4.31-4.27 (m, 1H), 3.75 (s, 3H), 2.60 (s, 3H), 2.27 (s, 3H), 2.25-2.12 (m, 2H). |

TABLE 2-continued

Analytical data for HBV-CSU racemic & pure enantiomers:

| Target No | Structure | Rx. Yield (%) | Mass Spec. Found (m/z) | Mass Spec. Calculated | $^1$H-NMR |
|---|---|---|---|---|---|
| HBV-CSU-314-ISO-I | 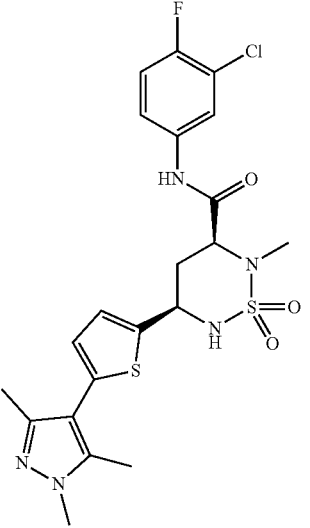 [SMILES: Cc1nn(C)c(C)c1-c1ccc([C@H]2C[C@@H](C(=O)Nc3ccc(F)c(Cl)c3)N(C)S(=O)(=O)N2)s1] | 10% | 512.15 (M + 1) | 511.09 for $C_{21}H_{23}ClFN_5O_3S_2$ | $^1$H-NMR (DMSO-$d_6$, 400 MHz): δ 10.56 (s, 1H), 7.96-7.94 (m, 1H), 7.68-7.49 (m, 2H), 7.39 (t, J = 8.8 Hz, 1H), 7.08-7.07 (m, 1H), 6.84-6.82 (m, 1H), 4.77-4.73 (m, 1H), 4.30-4.28 (m, 1H), 3.66 (s, 3H), 2.58 (s, 3H), 2.26 (s, 3H), 2.25-2.08 (m, 5H). |
| HBV-CSU-314-ISO-II | 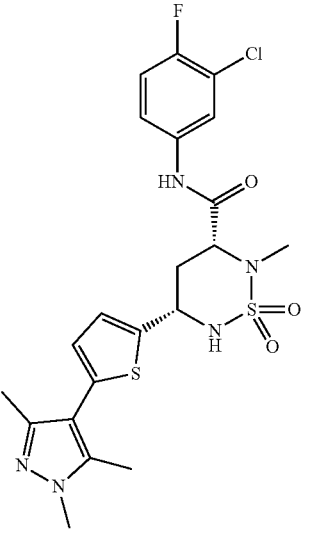 [SMILES: Cc1nn(C)c(C)c1-c1ccc([C@@H]2C[C@H](C(=O)Nc3ccc(F)c(Cl)c3)N(C)S(=O)(=O)N2)s1] | 9% | 512.15 (M + 1) | 511.09 for $C_{21}H_{23}ClFN_5O_3S_2$ | $^1$H-NMR (DMSO-$d_6$, 400 MHz): δ 10.54 (s, 1H), 7.98-7.93 (m, 1H), 7.70-7.50 (m, 2H), 7.39 (t, J = 8.8 Hz, 1H), 7.09-7.07 (m, 1H), 6.84-6.82 (m, 1H), 4.78-4.72 (m, 1H), 4.30-4.28 (m, 1H), 3.66 (s, 3H), 2.58 (s, 3H), 2.26 (s, 3H), 2.26-2.05 (m, 5H). |
| HBV-CSU-315 | 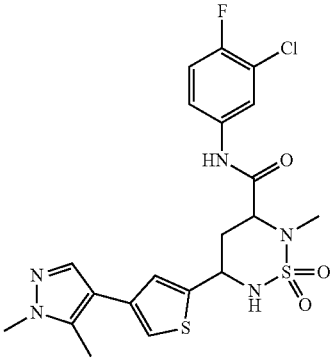 [SMILES: Cc1c(-c2csc(C3CC(C(=O)Nc4ccc(F)c(Cl)c4)N(C)S(=O)(=O)N3)c2)cnn1C] | 49% | 498.15 (M + 1) | 497.08 for $C_{20}H_{21}ClFN_5O_3S_2$ | $^1$H-NMR (DMSO-$d_6$, 400 MHz): δ 10.59 (s, 1H), 7.99-7.97 (m, 1H), 7.72-7.68 (m, 1H), 7.57-7.53 (m, 2H), 7.43-7.30 (m, 3H), 4.81-4.76 (m, 1H), 4.31-4.27 (m, 1H), 3.75 (s, 3H), 2.62 (s, 3H), 2.37 (s, 3H), 2.30-2.15 (m, 2H). |

TABLE 2-continued

Analytical data for HBV-CSU racemic & pure enantiomers:

| Target No | Structure | Rx. Yield (%) | Mass Spec. Found (m/z) | Mass Spec. Calculated | ¹H-NMR |
|---|---|---|---|---|---|
| HBV-CSU-315-ISO-I | 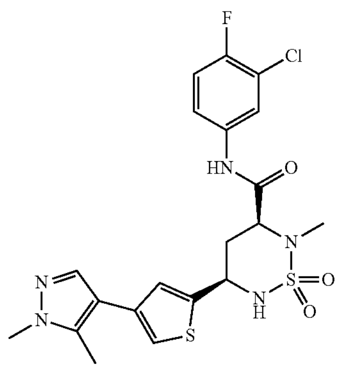 [SMILES: Cc1c(-c2csc([C@H]3C[C@@H](C(=O)Nc4ccc(F)c(Cl)c4)N(C)S(=O)(=O)N3)c2)cnn1C] | 3% | 498.15 (M + 1) | 497.08 for $C_{20}H_{21}ClFN_5O_3S_2$ | ¹H-NMR (DMSO-$d_6$, 400 MHz): δ 10.60 (s, 1H), 7.98 (dd, J = 6.8, 2.6 Hz, 1H), 7.70-7.51 (m, 3H), 7.46-7.28 (m, 3H), 4.80-4.76 (m, 1H), 4.29 (dd, J = 11.8, 2.9 Hz, 1H), 3.75 (s, 3H), 2.62 (s, 3H), 2.37 (s, 3H), 2.33-2.10 (m, 2H). |
| HBV-CSU-315-ISO-II | 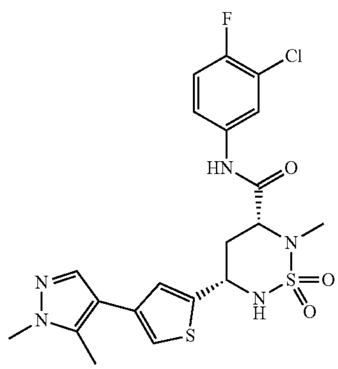 | 4% | 498.20 (M + 1) | 497.08 for $C_{20}H_{21}ClFN_5O_3S_2$ | ¹H-NMR (DMSO-$d_6$, 400 MHz): δ 10.60 (s, 1H), 7.98 (dd, J = 6.8, 2.6 Hz, 1H), 7.71-7.51 (m, 3H), 7.46-7.28 (m, 3H), 4.80-4.77 (m, 1H), 4.29 (d, J = 11.4 Hz, 1H), 3.75 (s, 3H), 2.62 (s, 3H), 2.37 (s, 3H), 2.33-2.17 (m, 2H). |
| HBV-CSU-316 | 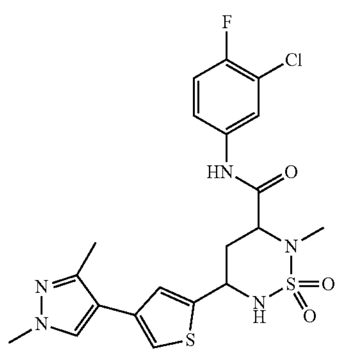 [SMILES: Cc1nn(C)cc1-c1csc(C2CC(C(=O)Nc3ccc(F)c(Cl)c3)N(C)S(=O)(=O)N2)c1] | 39% | 498.1 (M + 1) | 497.08 for $C_{20}H_{21}ClFN_5O_3S_2$ | ¹H-NMR (DMSO-$d_6$, 400 MHz): δ 10.58 (s, 1H), 7.98 (dd, J = 6.8, 2.4 Hz, 1H), 7.9 (s, 1H), 7.72-7.68 (m, 1H), 7.65-7.58 (m, 1H), 7.41 (t, J = 9.2 Hz, 1H), 7.34 (s, 1H), 7.29 (s, 1H), 4.81-4.75 (m, 1H), 4.3 (dd, J = 11.2, 2.4 Hz, 1H), 3.75 (s, 3H), 2.62 (s, 3H), 2.29 (s, 3H), 2.28-2.12 (m, 2H). |
| HBV-CSU-316-ISO-I | 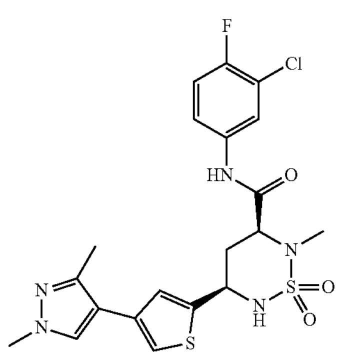 [SMILES: Cc1nn(C)cc1-c1csc([C@H]2C[C@@H](C(=O)Nc3ccc(F)c(Cl)c3)N(C)S(=O)(=O)N2)c1] | 5% | 498.15 (M + 1) | 497.08 for $C_{20}H_{21}ClFN_5O_3S_2$ | ¹H-NMR (DMSO-$d_6$, 400 MHz): δ 10.61 (s, 1H), 7.99-7.97 (m, 1H), 7.90 (s, 1H), 7.71-7.70 (m, 1H), 7.58-7.54 (m, 1H), 7.41 (t, J = 10.2 Hz, 1H), 7.34 (s, 1H), 7.29 (s, 1H), 4.76 (d, J = 10.4 Hz, 1H), 4.29 (dd, J = 12.0, 2.8 Hz, 1H), 3.74 (s, 3H), 2.62 (s, 3H), 2.29-2.07 (m, 5H). |

TABLE 2-continued

Analytical data for HBV-CSU racemic & pure enantiomers:

| Target No | Structure | Rx. Yield (%) | Mass Spec. Found (m/z) | Mass Spec. Calculated | ¹H-NMR |
|---|---|---|---|---|---|
| HBV-CSU-316-ISO-II | 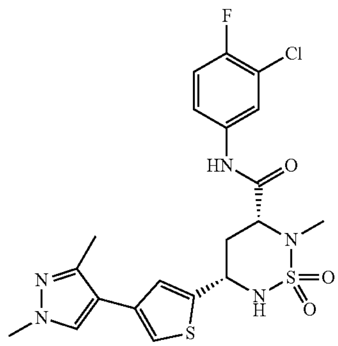 [SMILES: Cc1nn(C)cc1-c1csc([C@@H]2C[C@H](C(=O)Nc3ccc(F)c(Cl)c3)N(C)S(=O)(=O)N2)c1] | 15% | 498.10 (M + 1) | 497.08 for $C_{20}H_{21}ClFN_5O_3S_2$ | ¹H-NMR (DMSO-$d_6$, 400 MHz): δ 10.60 (s, 1H), 7.99-7.97 (m, 1H), 7.90 (s, 1H), 7.71-7.70 (m, 1H), 7.58-7.54 (m, 1H), 7.41 (t, J = 10.2 Hz, 1H), 7.34 (s, 1H), 7.29 (s, 1H), 4.76 (d, J = 10.0 Hz, 1H), 4.29 (dd, J = 11.6, 2.4 Hz, 1H), 3.74 (s, 3H), 2.62 (s, 3H), 2.29-2.12 (m, 5H). |
| HBV-CSU-317 | 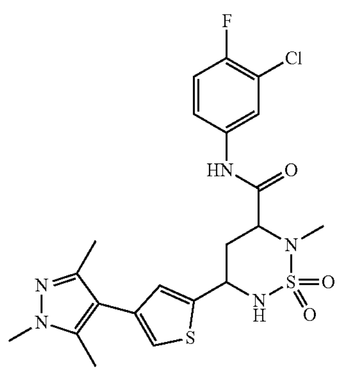 [SMILES: Cc1nn(C)c(C)c1-c1csc(C2CC(C(=O)Nc3ccc(F)c(Cl)c3)N(C)S(=O)(=O)N2)c1] | 36% | 512.15 (M + 1) | 511.09 for $C_{21}H_{23}ClFN_5O_3S_2$ | ¹H-NMR (DMSO-$d_6$, 400 MHz): δ 10.55 (s, 1H), 7.94 (dd, J = 6.9, 2.5 Hz, 1H), 7.68 (d, J = 9.6 Hz, 1H), 7.64-7.48 (m, 1H), 7.37 (t, J = 9.1 Hz, 1H), 7.24 (d, J = 1.4 Hz, 1H), 7.13 (t, J = 1.3 Hz, 1H), 4.82-4.72 (m, 1H), 4.26 (dd, J = 11.7, 2.8 Hz, 1H), 3.64 (s, 3H), 2.59 (s, 3H), 2.29-2.06 (m, 8H). |
| HBV-CSU-317-ISO-I | 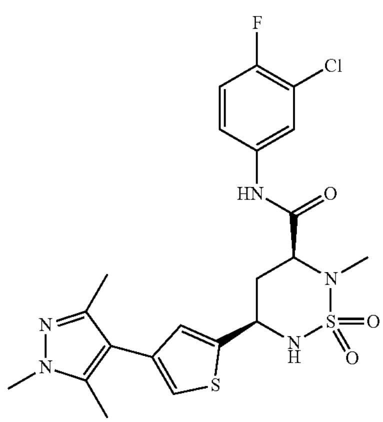 [SMILES: Cc1nn(C)c(C)c1-c1csc([C@H]2C[C@@H](C(=O)Nc3ccc(F)c(Cl)c3)N(C)S(=O)(=O)N2)c1] | 6% | 512.15 (M + 1) | 511.09 for $C_{21}H_{23}ClFN_5O_3S_2$ | ¹H-NMR (DMSO-$d_6$, 400 MHz): δ 10.59 (s, 1H), 7.98 (dd, J = 6.8, 2.5 Hz, 1H), 7.69-7.51 (m, 2H), 7.40 (t, J = 9.1 Hz, 1H), 7.27 (s, 1H), 7.16 (s, 1H), 4.82-4.78 (m, 1H), 4.29 (dd, J = 11.8, 2.8 Hz, 1H), 3.67 (s, 3H), 2.62 (s, 3H), 2.32-2.09 (m, 8H). |
| HBV-CSU-317-ISO-II | 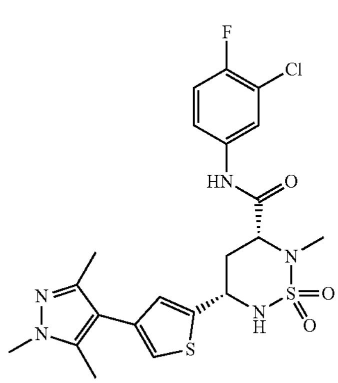 | 7% | 512.20 (M + 1) | 511.09 for $C_{21}H_{23}ClFN_5O_3S_2$ | ¹H-NMR (DMSO-$d_6$, 400 MHz): δ 10.59 (s, 1H), 7.97 (dd, J = 6.8, 2.8 Hz, 1H), 7.75-7.53 (m, 2H), 7.41 (t, J = 9.6 Hz, 1H), 7.27 (s, 1H), 7.16 (s, 1H), 4.80-4.79 (m, 1H), 4.28 (dd, J = 11.6, 2.8 Hz, 1H), 3.67 (s, 3H), 2.62 (s, 3H), 2.32-2.15 (m, 8H). |

TABLE 2-continued

Analytical data for HBV-CSU racemic & pure enantiomers:

| Target No | Structure | Rx. Yield (%) | Mass Spec. Found (m/z) | Mass Spec. Calculated | 1H-NMR |
|---|---|---|---|---|---|
| HBV-CSU-321 | 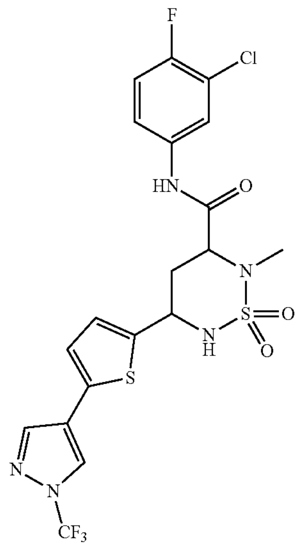 [SMILES: CN1C(C(=O)Nc2ccc(F)c(Cl)c2)CC(c2ccc(-c3cnn(C(F)(F)F)c3)s2)NS1(=O)=O] | 38% | 560 (M + 23) | 537.03 for $C_{19}H_{16}ClF_4N_5O_3S_2$ | 1H-NMR (DMSO-$d_6$, 400 MHz): δ 10.58 (s, 1H), 8.87 (s, 1H), 8.33 (s, 1H), 7.98-7.95 (m, 1H), 7.77-7.71 (m, 1H), 7.58-7.55 (m, 1H), 7.41 (t, J = 9.1 Hz, 1H), 7.30 (d, J = 3.2 Hz, 1H), 7.13 (d, J = 3.2 Hz, 1H), 4.82-4.77 (m, 1H), 4.34-4.31 (m, 1H), 2.62 (s, 3H), 2.28-2.10 (m, 2H). |
| HBV-CSU-321-ISO-I | 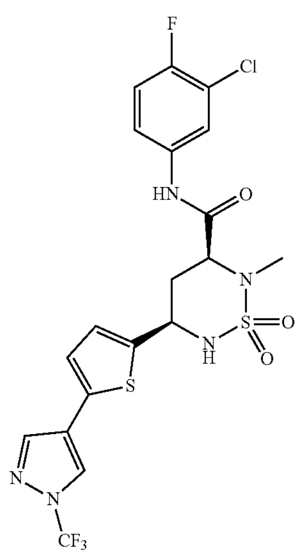 [SMILES: CN1[C@H](C(=O)Nc2ccc(F)c(Cl)c2)C[C@H](c2ccc(-c3cnn(C(F)(F)F)c3)s2)NS1(=O)=O] | 13% | 560 (M + 23) | 537.03 for $C_{19}H_{16}ClF_4N_5O_3S_2$ | 1H-NMR (DMSO-$d_6$, 400 MHz): δ 10.59 (s, 1H), 8.88 (s, 1H), 8.33 (s, 1H), 7.98 (dd, J = 6.8, 2.6 Hz, 1H), 7.77-7.71 (m, 1H), 7.58-7.55 (m, 1H), 7.41 (t, J = 9.1 Hz, 1H), 7.32-7.31 (m, 1H), 7.13-7.12 (m, 1H), 4.81-4.78 (m, 1H), 4.32 (dd, J = 11.6, 2.9 Hz, 1H), 2.62 (s, 3H), 2.31-2.08 (m, 2H). |

TABLE 2-continued
Analytical data for HBV-CSU racemic & pure enantiomers:
| Target No | Structure | Rx. Yield (%) | Mass Spec. Found (m/z) | Mass Spec. Calculated | ¹H-NMR |
|---|---|---|---|---|---|
| HBV-CSU-321-ISO-II | 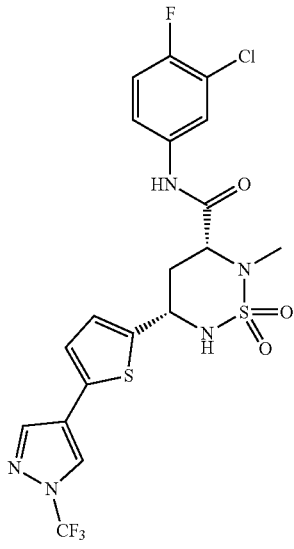 [SMILES: CN1[C@@H](C(=O)Nc2ccc(F)c(Cl)c2)C[C@@H](c2ccc(-c3cnn(C(F)(F)F)c3)s2)NS1(=O)=O] | 12% | 560 (M + 23) | 537.03 for $C_{19}H_{16}ClF_4N_5O_3S_2$ | ¹H-NMR (DMSO-$d_6$, 400 MHz): δ 10.58 (s, 1H), 8.88 (s, 1H), 8.33 (s, 1H), 7.98 (dd, J = 6.8, 2.6 Hz, 1H), 7.74-7.72 (m, 1H), 7.58-7.54 (m, 1H), 7.41 (t, J = 9.1 Hz, 1H), 7.32 (d, J = 3.7 Hz, 1H), 7.14-7.12 (m, 1H), 4.84-4.76 (m, 1H), 4.32 (dd, J = 11.8, 2.8 Hz, 1H), 2.62 (s, 3H), 2.31-2.08 (m, 2H). |
| HBV-CSU-322 | 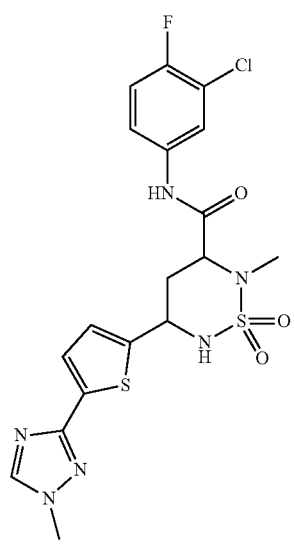 [SMILES: CN1C(C(=O)Nc2ccc(F)c(Cl)c2)CC(c2ccc(-c3ncn(C)n3)s2)NS1(=O)=O] | 35% | 485.05 (M + 1) | 484.06 for $C_{18}H_{18}ClFN_6O_3S_2$ | ¹H-NMR (DMSO-$d_6$, 400 MHz): δ 10.58 (s, 1H), 8.48 (s, 1H), 7.98-7.95 (m, 1H), 7.77-7.72 (m, 1H), 7.57-7.54 (m, 1H), 7.44-7.38 (m, 2H), 7.15-7.13 (m, 1H), 4.82-4.79 (m, 1H), 4.33-4.29 (m, 1H), 3.88 (s, 3H), 2.62 (s, 3H), 2.28-2.06 (m, 2H). |

TABLE 2-continued
Analytical data for HBV-CSU racemic & pure enantiomers:
| Target No | Structure | Rx. Yield (%) | Mass Spec. Found (m/z) | Mass Spec. Calculated | ¹H-NMR |
|---|---|---|---|---|---|
| HBV-CSU-322-ISO-I | 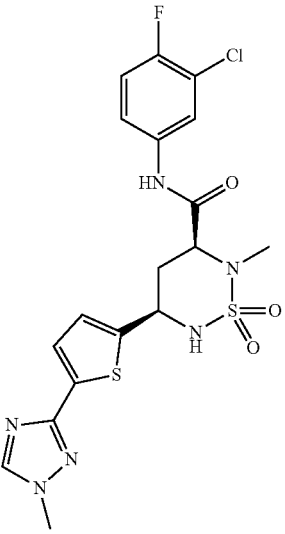 [SMILES: CN1[C@H](C(=O)Nc2ccc(F)c(Cl)c2)C[C@H](c2ccc(-c3ncn(C)n3)s2)NS1(=O)=O] | 8% | 485.10 (M + 1) | 484.06 for $C_{18}H_{18}ClFN_6O_3S_2$ | ¹H-NMR (DMSO-$d_6$, 400 MHz): δ 10.59 (s, 1H), 8.50 (s, 1H), 7.98-7.97 (m, 1H), 7.76-7.74 (m, 1H), 7.57-7.55 (m, 1H), 7.48-7.34 (m, 2H), 7.15-7.14 (m, 1H), 4.87-4.76 (m, 1H), 4.33-4.30 (m, 1H), 3.89 (s, 3H), 2.62 (s, 3H), 2.32-2.08 (m, 2H). |
| HBV-CSU-322-ISO-II | 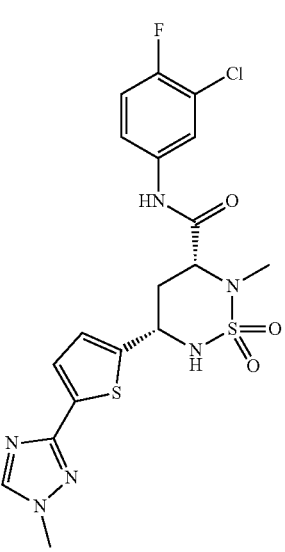 | 7% | 485.10 (M + 1) | 484.06 for $C_{18}H_{18}ClFN_6O_3S_2$ | ¹H-NMR (DMSO-$d_6$, 400 MHz): δ 10.59 (s, 1H), 8.49 (s, 1H), 7.98 (dd, J = 6.8, 2.6 Hz, 1H), 7.75 (d, J = 9.6 Hz, 1H), 7.58-7.54 (m, 1H), 7.47-7.36 (m, 2H), 7.16-7.14 (m, 1H), 4.84-4.78 (m, 1H), 4.32 (dd, J = 11.8, 2.8 Hz, 1H), 3.89 (s, 3H), 2.63 (s, 3H), 2.32-2.08 (m, 2H). |

TABLE 2-continued

Analytical data for HBV-CSU racemic & pure enantiomers:

| Target No | Structure | Rx. Yield (%) | Mass Spec. Found (m/z) | Mass Spec. Calculated | ¹H-NMR |
|---|---|---|---|---|---|
| HBV-CSU-323 | 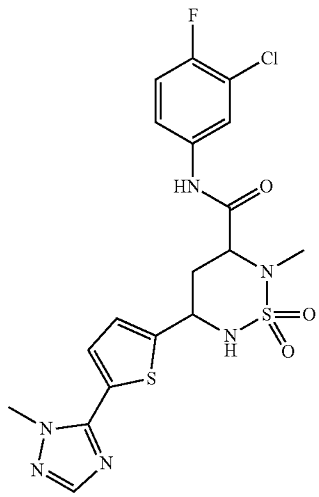 [SMILES: CN1C(C(=O)Nc2ccc(F)c(Cl)c2)CC(c2ccc(-c3ncnn3C)s2)NS1(=O)=O] | 35% | 485.10 (M + 1) | 484.06 for $C_{18}H_{18}ClFN_6O_3S_2$ | ¹H-NMR (DMSO-$d_6$, 400 MHz): δ 10.61 (s, 1H), 7.99-7.97 (m, 1H), 7.95 (s, 1H), 7.83-7.81 (m, 1H), 7.60-7.54 (m, 2H), 7.41 (t, J = 9.2 Hz, 1H), 7.29-7.28 (m, 1H), 4.89-4.84 (m, 1H), 4.34-4.31 (m, 1H), 4.05 (s, 3H), 2.64 (s, 3H), 2.32-2.15 (m, 2H). |
| HBV-CSU-323-ISO-I | 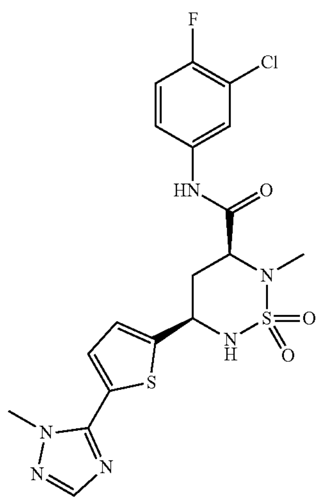 [SMILES: CN1[C@H](C(=O)Nc2ccc(F)c(Cl)c2)C[C@H](c2ccc(-c3ncnn3C)s2)NS1(=O)=O] | 5% | 485.05 (M + 1) | 484.06 for $C_{18}H_{18}ClFN_6O_3S_2$ | ¹H-NMR (DMSO-$d_6$, 400 MHz): δ 10.56 (s, 1H), 8.01-7.90 (m, 2H), 7.84 (s, 1H), 7.61-7.52 (m, 2H), 7.39 (t, J = 9.1 Hz, 1H), 7.24 (s, 1H), 4.85-4.82 (m, 1H), 4.30-4.25 (m, 1H), 4.03 (s, 3H), 2.59 (s, 3H), 2.32-2.25 (m, 1H), 2.13-2.06 (m, 1H). |
| HBV-CSU-323-ISO-II | 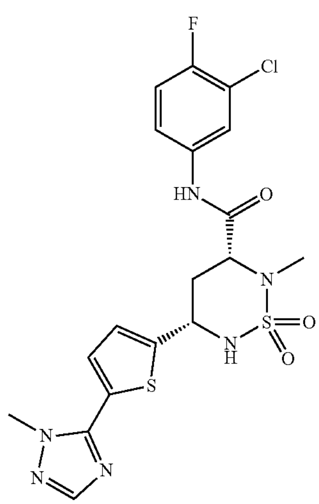 [SMILES: CN1[C@@H](C(=O)Nc2ccc(F)c(Cl)c2)C[C@@H](c2ccc(-c3ncnn3C)s2)NS1(=O)=O] | 6% | 485.05 (M + 1) | 484.06 for $C_{18}H_{18}ClFN_6O_3S_2$ | ¹H-NMR (DMSO-$d_6$, 400 MHz): δ 10.59 (s, 1H), 8.01-7.91 (m, 2H), 7.80 (s, 1H), 7.62-7.51 (m, 2H), 7.40 (t, J = 9.1 Hz, 1H), 7.28-7.26 (m, 1H), 4.87-4.84 (m, 1H), 4.32-4.30 (m, 1H), 4.04 (s, 3H), 2.62 (s, 3H), 2.32-2.28 (m, 1H), 2.20-2.15 (m, 1H). |

TABLE 2-continued

Analytical data for HBV-CSU racemic & pure enantiomers:

| Target No | Structure | Rx. Yield (%) | Mass Spec. Found (m/z) | Mass Spec. Calculated | $^1$H-NMR |
|---|---|---|---|---|---|
| HBV-CSU-324 | 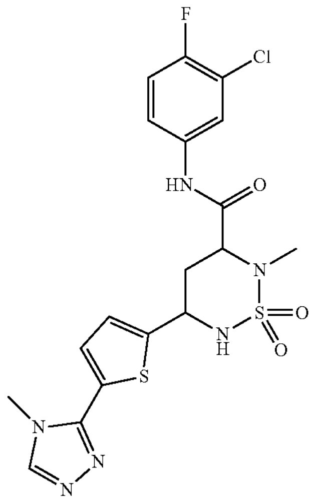 | 59% | 485.45 (M + 1) | 484.06 for $C_{18}H_{18}ClFN_6O_3S_2$ | $^1$H-NMR (DMSO-$d_6$, 400 MHz): δ 10.60 (s, 1H), 8.55 (s, 1H), 7.97 (dd, J = 6.8, 2.4 Hz, 1H), 7.81-7.78 (m, 1H), 7.58-7.51 (m, 2H), 7.41 (t, J = 8.8 Hz, 1H), 7.27-7.25 (m, 1H), 4.89-4.83 (m, 1H), 4.33-4.30 (m, 1H), 3.82 (s, 3H), 2.62 (s, 3H), 2.32-2.14 (m, 2H). |
| HBV-CSU-324-ISO-I | 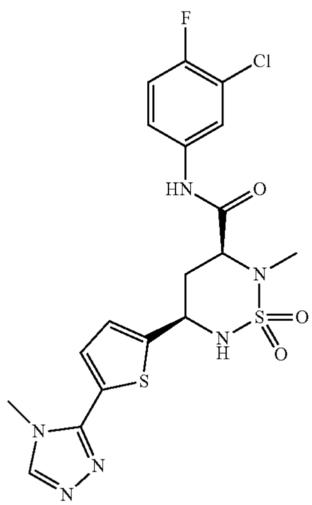 [SMILES: CN1[C@H](C(=O)Nc2ccc(F)c(Cl)c2)C[C@H](c2ccc(-c3nncn3C)s2)NS1(=O)=O] | 14% | 485.00 (M + 1) | 484.06 for $C_{18}H_{18}ClFN_6O_3S_2$ | $^1$H-NMR (DMSO-$d_6$, 400 MHz): δ 10.60 (s, 1H), 8.55 (s, 1H), 7.97 (dd, J = 6.8, 2.4 Hz, 1H), 7.82-7.78 (m, 1H), 7.57-7.49 (m, 2H), 7.40 (t, J = 8.8 Hz, 1H), 7.26-7.25 (m, 1H), 4.88-4.84 (m, 1H), 4.33-4.30 (m, 1H), 3.82 (s, 3H), 2.62 (s, 3H), 2.32-2.14 (m, 2H). |
| HBV-CSU-324-ISO-II | 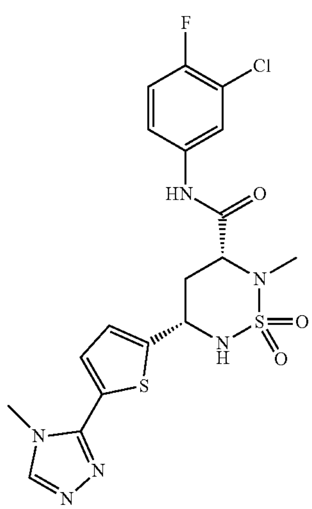 [SMILES: CN1[C@@H](C(=O)Nc2ccc(F)c(Cl)c2)C[C@@H](c2ccc(-c3nncn3C)s2)NS1(=O)=O] | 12% | 485.00 (M + 1) | 484.06 for $C_{18}H_{18}ClFN_6O_3S_2$ | $^1$H-NMR (DMSO-$d_6$, 400 MHz): δ 10.59 (s, 1H), 8.54 (s, 1H), 7.97 (dd, J = 6.8, 2.4 Hz, 1H), 7.80 7.78 (m, 1H), 7.58-7.50 (m, 2H), 7.40 (t, J = 8.8 Hz, 1H), 7.26-7.24 (m, 1H), 4.86-4.83 (m, 1H), 4.33-4.30 (m, 1H), 3.82 (s, 3H), 2.62 (s, 3H), 2.31-2.14 (m, 2H). |

TABLE 2-continued

Analytical data for HBV-CSU racemic & pure enantiomers:

| Target No | Structure | Rx. Yield (%) | Mass Spec. Found (m/z) | Mass Spec. Calculated | ¹H-NMR |
|---|---|---|---|---|---|
| HBV-CSU-325 | 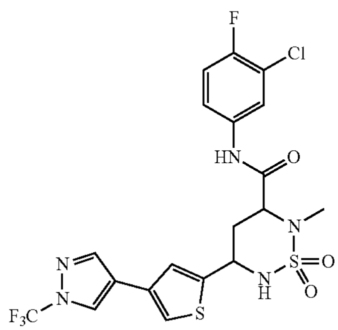 [SMILES: CN1C(C(=O)Nc2ccc(F)c(Cl)c2)CC(c2cc(-c3cnn(C(F)(F)F)c3)cs2)NS1(=O)=O] | 40% | 538.40 (M + 1) | 537.03 for $C_{19}H_{16}ClF_4N_5O_3S_2$ | ¹H-NMR (DMSO-$d_6$, 400 MHz): δ 10.60 (s, 1H), 8.89 (s, 1H), 8.38 (s, 1H), 7.98 (dd, J = 6.8, 2.4 Hz, 1H), 7.81 (s, 1H), 7.74-7.71 (m, 1H), 7.59-7.55 (m, 2H), 7.40 (t, J = 8.8 Hz, 1H), 4.82-4.78 (m, 1H), 4.32-4.30 (m, 1H), 2.62 (s, 3H), 2.33-2.15 (m, 2H). |
| HBV-CSU-325-ISO-I | 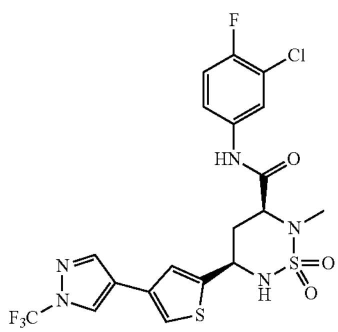 [SMILES: CN1[C@H](C(=O)Nc2ccc(F)c(Cl)c2)C[C@H](c2cc(-c3cnn(C(F)(F)F)c3)cs2)NS1(=O)=O] | 14% | 538.05 (M + 1) | 537.03 for $C_{19}H_{16}ClF_4N_5O_3S_2$ | ¹H-NMR (DMSO-$d_6$, 400 MHz): δ 10.59 (s, 1H), 8.89 (s, 1H), 8.38 (s, 1H), 7.98 (dd, J = 6.9, 2.6 Hz, 1H), 7.80-7.72 (m, 2H), 7.59-7.57 (m, 2H), 7.40 (t, J = 9.1 Hz, 1H), 4.80-4.77 (m, 1H), 4.30-4.25 (m, 1H), 2.61 (s, 3H), 2.33-2.15 (m, 2H). |
| HBV-CSU-325-ISO-II | 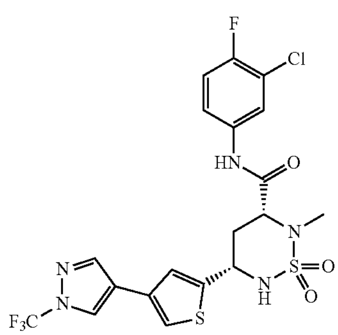 [SMILES: CN1[C@@H](C(=O)Nc2ccc(F)c(Cl)c2)C[C@@H](c2cc(-c3cnn(C(F)(F)F)c3)cs2)NS1(=O)=O] | 13% | 538.40 (M + 1) | 537.03 for $C_{19}H_{16}ClF_4N_5O_3S_2$ | ¹H-NMR (DMSO-$d_6$, 400 MHz): δ 10.60 (s, 1H), 8.89 (s, 1H), 8.38 (s, 1H), 7.98 (dd, J = 6.9, 2.5 Hz, 1H), 7.80-7.72 (m, 2H), 7.62-7.53 (m, 2H), 7.40 (t, J = 8.8 Hz, 1H), 4.80-4.77 (m, 1H), 4.32-4.29 (m, 1H), 2.61 (s, 3H), 2.31-2.12 (m, 2H). |
| HBV-CSU-326 | 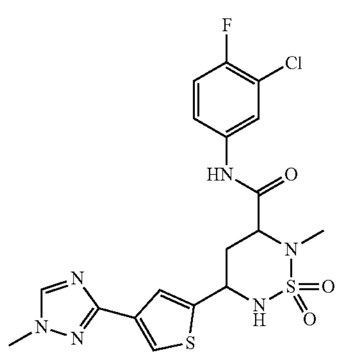 [SMILES: CN1C(C(=O)Nc2ccc(F)c(Cl)c2)CC(c2cc(-c3ncn(C)n3)cs2)NS1(=O)=O] | 34% | 485.10 (M + 1) | 484.06 for $C_{18}H_{18}ClFN_6O_3S_2$ | ¹H-NMR (DMSO-$d_6$, 400 MHz): δ 10.58 (s, 1H), 8.47 (s, 1H), 7.98 (dd, J = 6.8, 2.5 Hz, 1H), 7.91 (s, 1H), 7.73 (d, J = 9.6 Hz, 1H), 7.61-7.51 (m, 2H), 7.41 (t, J = 9.1 Hz, 1H), 4.82-4.80 (m, 1H), 4.34 (dd, J = 11.9, 2.8 Hz, 1H), 3.88 (s, 3H), 2.63 (s, 3H), 2.36-2.26 (m, 1H), 2.20-2.16 (m, 1H). |

TABLE 2-continued

Analytical data for HBV-CSU racemic & pure enantiomers:

| Target No | Structure | Rx. Yield (%) | Mass Spec. Found (m/z) | Mass Spec. Calculated | $^1$H-NMR |
|---|---|---|---|---|---|
| HBV-CSU-326-ISO-I | 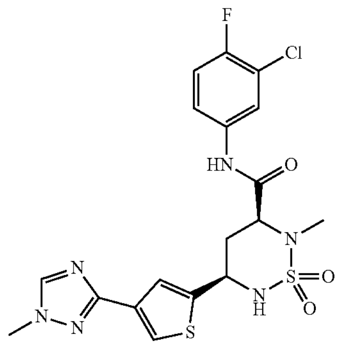 [SMILES: CN1[C@H](C(=O)Nc2ccc(F)c(Cl)c2)C[C@H](c2cc(-c3ncn(C)n3)cs2)NS1(=O)=O] | 5% | 485.10 (M + 1) | 484.06 for $C_{18}H_{18}ClFN_6O_3S_2$ | $^1$H-NMR (DMSO-$d_6$, 400 MHz): δ 10.57 (s, 1H), 8.46 (s, 1H), 7.97 (dd, J = 6.9, 2.5 Hz, 1H), 7.90 (s, 1H), 7.73-7.72 (m, 1H), 7.61-7.51 (m, 2H), 7.40 (t, J = 9.1 Hz, 1H), 4.82-4.80 (m, 1H), 4.34-4.32 (m, 1H), 3.88 (s, 3H), 2.62 (s, 3H), 2.35-2.25 (m, 1H), 2.22-2.04 (m, 1H). |
| HBV-CSU-326-ISO-II | 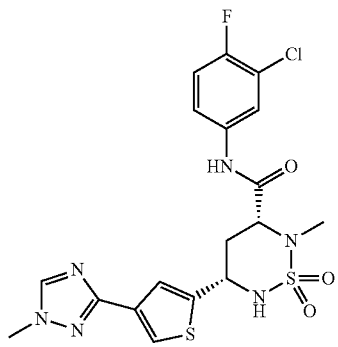 [SMILES: CN1[C@@H](C(=O)Nc2ccc(F)c(Cl)c2)C[C@@H](c2cc(-c3ncn(C)n3)cs2)NS1(=O)=O] | 7% | 485.10 (M + 1) | 484.06 for $C_{18}H_{18}ClFN_6O_3S_2$ | $^1$H-NMR (DMSO-$d_6$, 400 MHz): δ 10.59 (s, 1H), 8.46 (s, 1H), 7.97 (dd, J = 6.9, 2.6 Hz, 1H), 7.89 (s, 1H), 7.74-7.73 (m, 1H), 7.61-7.50 (m, 2H), 7.40 (t, J = 9.1 Hz, 1H), 4.82-4.79 (m, 1H), 4.33-4.32 (m, 1H), 3.87 (s, 3H), 2.61 (s, 3H), 2.32-2.28 (m, 1H), 2.22-2.04 (m, 1H). |
| HBV-CSU-327 | 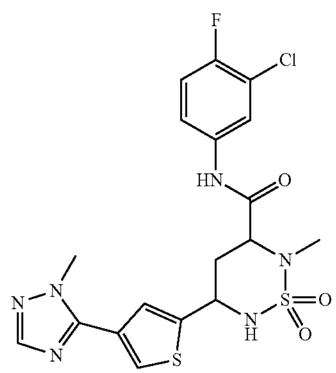 [SMILES: CN1C(C(=O)Nc2ccc(F)c(Cl)c2)CC(c2cc(-c3ncnn3C)cs2)NS1(=O)=O] | 31% | 485.05 (M + 1) | 484.06 for $C_{18}H_{18}ClFN_6O_3S_2$ | $^1$H-NMR (DMSO-$d_6$, 400 MHz): δ 10.59 (s, 1H), 8.09 (s, 1H), 8.00-7.91 (m, 2H), 7.79-7.77 (m, 1H), 7.60-7.51 (m, 2H), 7.40 (t, J = 9.1 Hz, 1H), 4.85-4.82 (m, 1H), 4.32 (dd, J = 11.8, 2.8 Hz, 1H), 4.00 (s, 3H), 2.62 (s, 3H), 2.33-2.29 (m, 1H), 2.18-2.15 (m, 1H). |
| HBV-CSU-327-ISO-I | 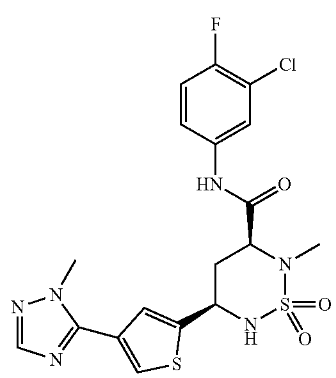 [SMILES: CN1[C@H](C(=O)Nc2ccc(F)c(Cl)c2)C[C@H](c2cc(-c3ncnn3C)cs2)NS1(=O)=O] | 8% | 485.10 (M + 1) | 484.06 for $C_{18}H_{18}ClFN_6O_3S_2$ | $^1$H-NMR (DMSO-$d_6$, 400 MHz): δ 10.59 (s, 1H), 8.09 (s, 1H), 8.00-7.91 (m, 2H), 7.79-7.76 (m, 1H), 7.57-7.53 (m, 2H), 7.40 (t, J = 8.8 Hz, 1H), 4.87-4.84 (m, 1H), 4.32 (dd, J = 11.9, 2.8 Hz, 1H), 4.00 (s, 3H), 2.62 (s, 3H), 2.33-2.29 (m, 1H), 2.22-2.12 (m, 1H). |

TABLE 2-continued

Analytical data for HBV-CSU racemic & pure enantiomers:

| Target No | Structure | Rx. Yield (%) | Mass Spec. Found (m/z) | Mass Spec. Calculated | ¹H-NMR |
|---|---|---|---|---|---|
| HBV-CSU-327-ISO-II | 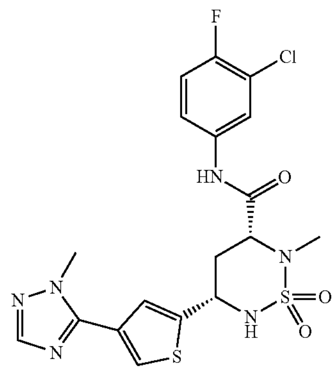 [SMILES: CN1[C@@H](C(=O)Nc2ccc(F)c(Cl)c2)C[C@@H](c2cc(-c3ncnn3C)cs2)NS1(=O)=O] | 4% | 485.10 (M + 1) | 484.06 for $C_{18}H_{18}ClFN_6O_3S_2$ | ¹H-NMR (DMSO-$d_6$, 400 MHz): δ 10.59 (s, 1H), 8.09 (d, J = 1.5 Hz, 1H), 8.00-7.91 (m, 2H), 7.77 (s, 1H), 7.57-7.53 (m, 2H), 7.40 (t, J = 9.1 Hz, 1H), 4.87-4.84 (m, 1H), 4.32 (dd, J = 11.9, 2.8 Hz, 1H), 4.00 (s, 3H), 2.62 (s, 3H), 2.36-2.26 (m, 1H), 2.21-2.11 (m, 1H). |
| HBV-CSU-328 | 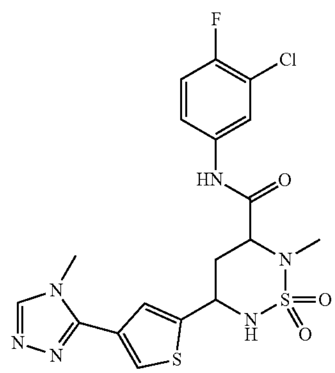 [SMILES: CN1C(C(=O)Nc2ccc(F)c(Cl)c2)CC(c2cc(-c3nncn3C)cs2)NS1(=O)=O] | 54% | 485.45 (M + 1) | 484.06 for $C_{18}H_{18}ClFN_6O_3S_2$ | ¹H-NMR (DMSO-$d_6$, 400 MHz): δ 10.60 (s, 1H), 8.51 (s, 1H), 8.03-7.96 (m, 2H), 7.80-7.78 (m, 1H), 7.57-7.55 (m, 2H), 7.41 (t, J = 8.8 Hz, 1H), 4.90-4.80 (m, 1H), 4.35-4.25 (m, 1H), 3.79 (s, 3H), 2.63 (s, 3H), 2.40-2.20 (m, 2H). |
| HBV-CSU-328-ISO-I | 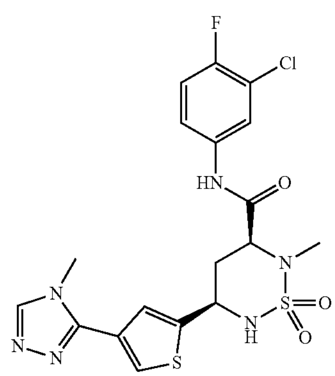 [SMILES: CN1[C@H](C(=O)Nc2ccc(F)c(Cl)c2)C[C@H](c2cc(-c3nncn3C)cs2)NS1(=O)=O] | 6% | 485.20 (M + 1) | 484.06 for $C_{18}H_{18}ClFN_6O_3S_2$ | ¹H NMR (400 MHz, DMSO-d6) δ 10.63 (s, 1H), 8.52 (s, 1H), 8.06-7.95 (m, 2H), 7.80 (s, 1H), 7.58-7.56 (m, 2H), 7.41 (t, J = 9.1 Hz, 1H), 4.87-4.84 (m, 1H), 4.34-4.32 (m, 1H), 3.80 (s, 3H), 2.63 (s, 3H), 2.37-2.29 (m, 1H), 2.22-2.17 (m, 1H). |
| HBV-CSU-328-ISO-II | 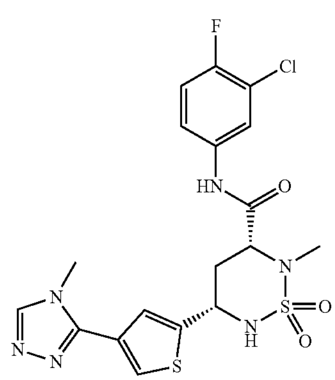 [SMILES: CN1[C@@H](C(=O)Nc2ccc(F)c(Cl)c2)C[C@@H](c2cc(-c3nncn3C)cs2)NS1(=O)=O] | 4% | 485.15 (M + 1) | 484.06 for $C_{18}H_{18}ClFN_6O_3S_2$ | ¹H NMR (400 MHz, DMSO-d6) δ 10.63 (s, 1H), 8.52 (s, 1H), 8.06-7.95 (m, 2H), 7.78 (s, 1H), 7.61-7.52 (m, 2H), 7.41 (t, J = 9.1 Hz, 1H), 4.90-4.81 (m, 1H), 4.37-4.29 (m, 1H), 3.79 (s, 3H), 2.63 (s, 3H), 2.34-2.31 (m, 1H), 2.22-2.13 (m, 1H). |

TABLE 2-continued

Analytical data for HBV-CSU racemic & pure enantiomers:

| Target No | Structure | Rx. Yield (%) | Mass Spec. Found (m/z) | Mass Spec. Calculated | ¹H-NMR |
| --- | --- | --- | --- | --- | --- |
| HBV-CSU-329 | 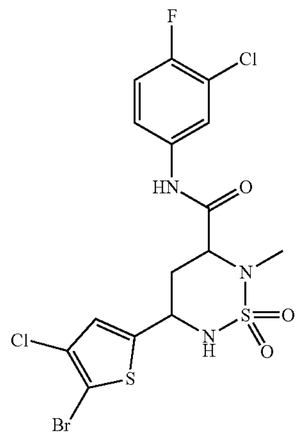 [SMILES: CN1C(C(=O)Nc2ccc(F)c(Cl)c2)CC(c2cc(Cl)c(Br)s2)NS1(=O)=O] | 75% | 517.9 (M + 2) | 514.89 for $C_{15}H_{13}BrCl_2FN_3O_3S_2$ | ¹H-NMR (DMSO-$d_6$, 400 MHz): δ 10.59 (s, 1H), 7.96 (dd, J = 6.8, 2.4 Hz, 1H), 7.79-7.76 (m, 1H), 7.57-7.53 (m, 1H), 7.41 (t, J = 9.2 Hz, 1H), 7.21 (s, 1H), 4.78-4.73 (m, 1H), 4.3-4.25 (m, 1H), 2.61 (s, 3H), 2.29-2.24 (m, 1H), 2.12-1.98 (m, 1H). |
| HBV-CSU-330 | 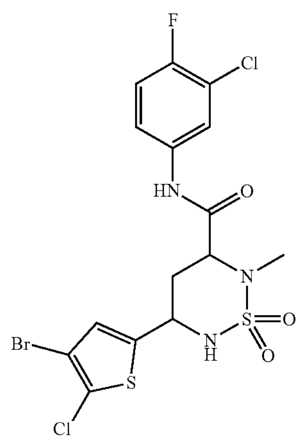 [SMILES: CN1C(C(=O)Nc2ccc(F)c(Cl)c2)CC(c2cc(Br)c(Cl)s2)NS1(=O)=O] | 49% | 518 (M + 2) | 514.89 for $C_{15}H_{13}BrCl_2FN_3O_3S_2$ | ¹H-NMR (DMSO-$d_6$, 400 MHz): δ 10.6 (s, 1H), 7.96 (dd, J = 6.8, 2.4 Hz, 1H), 7.8-7.77 (m, 1H), 7.57-7.53 (m, 1H), 7.41 (t, J = 8.8 Hz, 1H), 7.23 (s, 1H), 4.8-4.73 (m, 1H), 4.27 (dd, J = 12.4, 2.4 Hz, 1H), 2.61 (s, 3H), 2.29-2.25 (m, 1H), 2.12-1.98 (m, 1H). |
| HBV-CSU-331-ISO-I | 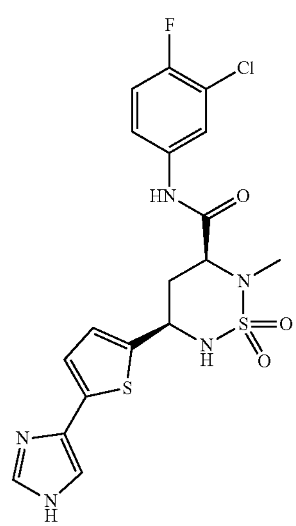 [SMILES: CN1[C@H](C(=O)Nc2ccc(F)c(Cl)c2)C[C@H](c2ccc(-c3c[nH]cn3)s2)NS1(=O)=O] | 3% | 470.05 (M + 1) | 469.04 for $C_{18}H_{17}ClFN_5O_3S_2$ | ¹H-NMR (DMSO-$d_6$, 400 MHz): δ 12.21 (s, 1H), 10.57 (s, 1H), 7.98-7.96 (m, 1H), 7.68-7.66 (m, 2H), 7.57-7.55 (m, 1H), 7.47-7.38 (m, 2H), 7.12-7.11 (m, 1H), 7.05-7.03 (m, 1H), 4.75 (t, J = 9.9 Hz, 1H), 4.31-4.28 (m, 1H), 2.62 (s, 3H), 2.28-2.05 (m, 2H). |

TABLE 2-continued

Analytical data for HBV-CSU racemic & pure enantiomers:

| Target No | Structure | Rx. Yield (%) | Mass Spec. Found (m/z) | Mass Spec. Calculated | $^1$H-NMR |
|---|---|---|---|---|---|
| HBV-CSU-331-ISO-II | 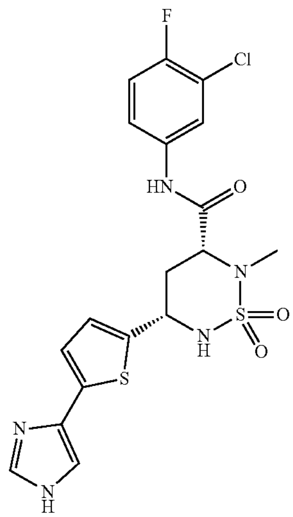 [SMILES: CN1[C@@H](C(=O)Nc2ccc(F)c(Cl)c2)C[C@@H](c2ccc(-c3c[nH]cn3)s2)NS1(=O)=O] | 3% | 470.05 (M + 1) | 469.04 for $C_{18}H_{17}ClFN_5O_3S_2$ | $^1$H-NMR (DMSO-$d_6$, 400 MHz): δ 12.26 (s, 1H), 10.57 (s, 1H), 7.98-7.96 (m, 1H), 7.68-7.66 (m, 2H), 7.57-7.55 (m, 1H), 7.46-7.38 (m, 2H), 7.11 (d, J = 3.6 Hz, 1H), 7.03 (d, J = 3.6 Hz, 1H), 4.81-4.70 (m, 1H), 4.31-4.29 (m, 1H), 2.62 (s, 3H), 2.28-2.05 (m, 2H). |
| HBV-CSU-333-ISO-I | 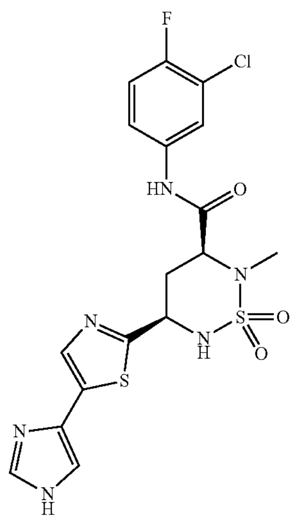 [SMILES: CN1[C@H](C(=O)Nc2ccc(F)c(Cl)c2)C[C@H](c2ncc(-c3c[nH]cn3)s2)NS1(=O)=O] | 3% | 470.95 (M + 1) | 470.04 for $C_{17}H_{16}ClFN_6O_3S_2$ | $^1$H-NMR (DMSO-$d_6$, 400 MHz): δ 12.10 (br.s, 1H), 10.57 (s, 1H), 7.99-7.96 (m, 1H), 7.90 (s, 1H), 7.73 (s, 1H), 7.59-7.55 (m, 3H), 7.41 (t, J = 8.8 Hz, 1H), 4.90-4.86 (m, 1H), 4.34-4.31 (m, 1H), 2.62 (s, 3H), 2.39-2.32 (m, 1H), 2.23-2.12 (m, 1H). |
| HBV-CSU-333-ISO-II | 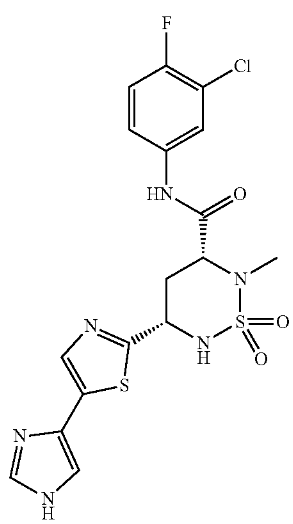 [SMILES: CN1[C@@H](C(=O)Nc2ccc(F)c(Cl)c2)C[C@@H](c2ncc(-c3c[nH]cn3)s2)NS1(=O)=O] | 4% | 470.95 (M + 1) | 470.04 for $C_{17}H_{16}ClFN_6O_3S_2$ | $^1$H-NMR (DMSO-$d_6$, 400 MHz): δ 12.10 (br.s, 1H), 10.54 (s, 1H), 7.99-7.96 (m, 1H), 7.88 (s, 1H), 7.72 (s, 1H), 7.59-7.56 (m, 3H), 7.41 (t, J = 8.8 Hz, 1H), 4.86-4.83 (m, 1H), 4.27-4.24 (m, 1H), 2.59 (s, 3H), 2.36-2.33 (m, 1H), 2.18-2.07 (m, 1H). |

TABLE 2-continued

Analytical data for HBV-CSU racemic & pure enantiomers:

| Target No | Structure | Rx. Yield (%) | Mass Spec. Found (m/z) | Mass Spec. Calculated | $^1$H-NMR |
|---|---|---|---|---|---|
| HBV-CSU-334 | 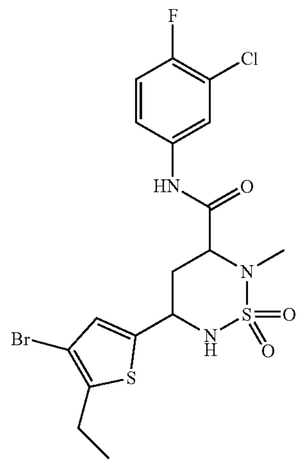 [SMILES: CCc1sc(C2CC(C(=O)Nc3ccc(F)c(Cl)c3)N(C)S(=O)(=O)N2)cc1Br] | 70% | 512.05 (M + 2) | 508.96 for $C_{17}H_{18}BrClFN_3O_3S_2$ | $^1$H-NMR (DMSO-$d_6$, 400 MHz): δ 10.56 (s, 1H), 7.95 (dd, J = 6.9, 2.5 Hz, 1H), 7.67 (s, 1H), 7.57-7.54 (m, 1H), 7.39 (t, J = 9.1 Hz, 1H), 7.05 (s, 1H), 4.74-4.71 (m, 1H), 4.30-4.27 (m, 1H), 2.73 (q, J = 7.5 Hz, 2H), 2.60 (s, 3H), 2.24-2.20 (m, 1H), 2.13-2.07 (m, 1H), 1.19 (t, J = 7.5 Hz, 3H). |
| HBV-CSU-335 | 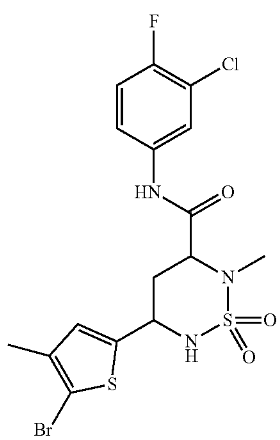 [SMILES: Cc1cc(C2CC(C(=O)Nc3ccc(F)c(Cl)c3)N(C)S(=O)(=O)N2)sc1Br] | 56% | 495.90 (M + 1) | 494.95 for $C_{16}H_{16}BrClFN_3O_3S_2$ | $^1$H-NMR (DMSO-$d_6$, 400 MHz): δ 10.54 (s, 1H), 7.94-7.92 (m, 1H), 7.66-7.64 (m, 1H), 7.53-7.51 (m, 1H), 7.37 (t, J = 8.8 Hz, 1H), 6.94 (s, 1H), 4.66 (t, J = 9.6 Hz, 1H), 4.26-4.23 (m, 1H), 2.57 (s, 3H), 2.19-1.97 (m, 5H). |
| HBV-CSU-336 | 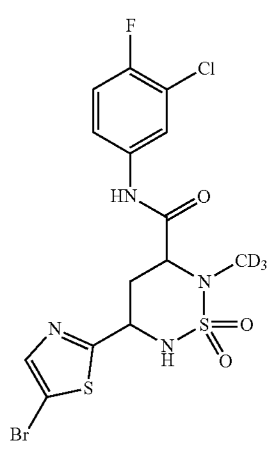 [SMILES: [2H]C([2H])([2H])N1C(C(=O)Nc2ccc(F)c(Cl)c2)CC(c2ncc(Br)s2)NS1(=O)=O] | 83% | 488.00 (M + 2) | 484.95 for $C_{14}H_{10}D_3BrClFN_4O_3S_2$ | $^1$H-NMR (DMSO-$d_6$, 400 MHz): δ 10.60 (s, 1H), 8.00-7.94 (m, 2H), 7.84 (s, 1H), 7.58-7.53 (m, 1H), 7.41 (t, J = 9.1 Hz, 1H), 4.95-4.87 (m, 1H), 4.35 (dd, J = 12.0, 2.8 Hz, 1H), 2.38-2.34 (m, 1H), 2.18-2.08 (m, 1H). |

TABLE 2-continued

Analytical data for HBV-CSU racemic & pure enantiomers:

| Target No | Structure | Rx. Yield (%) | Mass Spec. Found (m/z) | Mass Spec. Calculated | $^1$H-NMR |
|---|---|---|---|---|---|
| HBV-CSU-336-ISO-I | 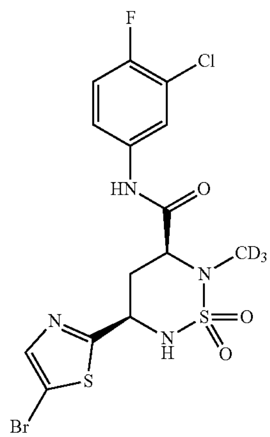 [SMILES: [2H]C([2H])([2H])N1[C@H](C(=O)Nc2ccc(F)c(Cl)c2)C[C@H](c2ncc(Br)s2)NS1(=O)=O] | 3% | 488.00 (M + 2) | 484.95 for $C_{14}H_{10}D_3BrClFN_4O_3S_2$ | $^1$H-NMR (DMSO-$d_6$, 400 MHz): δ 10.59 (s, 1H), 8.00-7.95 (m, 2H), 7.94 (s, 1H), 7.58-7.53 (m, 1H), 7.40 (t, J = 9.1 Hz, 1H), 4.95-4.89 (m, 1H), 4.35 (dd, J = 12.1, 2.8 Hz, 1H), 2.37-2.34 (m, 1H), 2.19-2.09 (m, 1H). |
| HBV-CSU-336-ISO-II | 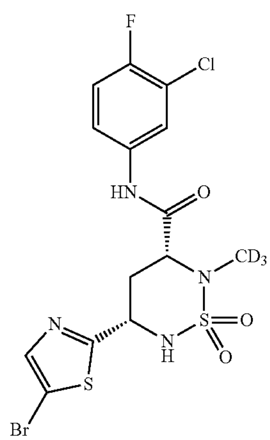 [SMILES: [2H]C([2H])([2H])N1[C@@H](C(=O)Nc2ccc(F)c(Cl)c2)C[C@@H](c2ncc(Br)s2)NS1(=O)=O] | 3% | 488.05 (M + 2) | 484.95 for $C_{14}H_{10}D_3BrClFN_4O_3S_2$ | $^1$H-NMR (DMSO-$d_6$, 400 MHz): δ 10.59 (s, 1H), 8.00-7.94 (m, 2H), 7.87 (s, 1H), 7.58-7.54 (m, 1H), 7.40 (t, J = 9.1 Hz, 1H), 4.95-4.89 (m, 1H), 4.35 (dd, J = 12.1, 2.8 Hz, 1H), 2.37-2.33 (m, 1H), 2.19-2.04 (m, 1H). |
| HBV-CSU-337-ISO-I | 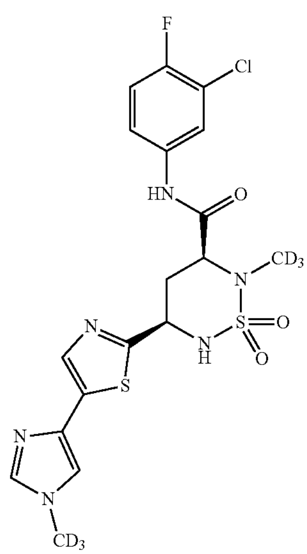 [SMILES: [2H]C([2H])([2H])N1[C@H](C(=O)Nc2ccc(F)c(Cl)c2)C[C@H](c2ncc(-c3cn(C([2H])([2H])[2H])cn3)s2)NS1(=O)=O] | 7% | 491.15 (M + 1) | 490.09 for $C_{18}H_{12}D_6ClFN_6O_3S_2$ | $^1$H-NMR (DMSO-$d_6$, 400 MHz): δ 10.59 (s, 1H), 8.10 (s, 1H), 8.01-7.89 (m, 3H), 7.75 (s, 1H), 7.59-7.55 (m, 1H), 7.41 (t, J = 9.1 Hz, 1H), 4.95-4.90 (m, 1H), 4.38-4.34 (m, 1H), 2.40-2.36 (m, 1H), 2.24-2.17 (m, 1H). |

TABLE 2-continued

Analytical data for HBV-CSU racemic & pure enantiomers:

| Target No | Structure | Rx. Yield (%) | Mass Spec. Found (m/z) | Mass Spec. Calculated | ¹H-NMR |
|---|---|---|---|---|---|
| HBV-CSU-337-ISO-II | 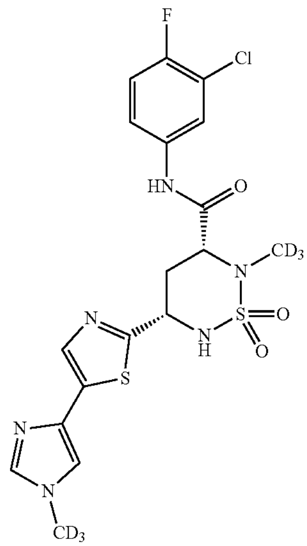 [SMILES: [2H]C([2H])([2H])N1[C@@H](C(=O)Nc2ccc(F)c(Cl)c2)C[C@@H](c2ncc(-c3cn(C([2H])([2H])[2H])cn3)s2)NS1(=O)=O] | 6% | 491.20 (M + 1) | 490.09 for $C_{18}H_{12}D_6ClFN_6O_3S_2$ | ¹H-NMR (DMSO-$d_6$, 400 MHz): δ 10.59 (s, 1H), 8.08 (s, 1H), 8.01-7.89 (m, 3H), 7.74 (s, 1H), 7.59-7.55 (m, 1H), 7.41 (t, J = 9.1 Hz, 1H), 4.95-4.90 (m, 1H), 4.39-4.34 (m, 1H), 2.40-2.33 (m, 1H), 2.26-2.12 (m, 1H). |
| HBV-CSU-338-ISO-I | 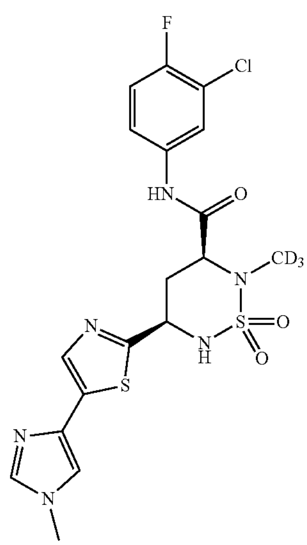 [SMILES: [2H]C([2H])([2H])N1[C@H](C(=O)Nc2ccc(F)c(Cl)c2)C[C@H](c2ncc(-c3cn(C)cn3)s2)NS1(=O)=O] | 5% | 488.2 (M + 1) | 487.07 for $C_{18}H_{15}D_3ClFN_6O_3S_2$ | ¹H-NMR (DMSO-$d_6$, 400 MHz): δ 10.59 (s, 1H), 7.99-7.96 (m, 1H), 7.88 (s, 1H), 7.66 (s, 1H), 7.59-7.55 (m, 3H), 7.41 (t, J = 8.8 Hz, 1H), 4.91-4.87 (m, 1H), 4.37-4.33 (m, 1H), 3.68 (s, 3H), 2.39-2.35 (m, 1H), 2.23-2.17 (m, 1H). |

TABLE 2-continued

Analytical data for HBV-CSU racemic & pure enantiomers:

| Target No | Structure | Rx. Yield (%) | Mass Spec. Found (m/z) | Mass Spec. Calculated | ¹H-NMR |
|---|---|---|---|---|---|
| HBV-CSU-338-ISO-II | 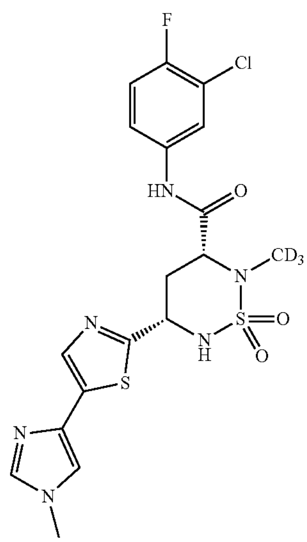 [SMILES: [2H]C([2H])([2H])N1[C@@H](C(=O)Nc2ccc(F)c(Cl)c2)C[C@@H](c2ncc(-c3cn(C)cn3)s2)NS1(=O)=O] | 7% | 488.2 (M + 1) | 487.07 for $C_{18}H_{15}D_3ClFN_6O_3S_2$ | ¹H-NMR (DMSO-$d_6$, 400 MHz): δ 10.59 (s, 1H), 7.99-7.97 (m, 1H), 7.88 (s, 1H), 7.67 (s, 1H), 7.60-7.54 (m, 3H), 7.41 (t, J = 8.8 Hz, 1H), 4.91-4.88 (m, 1H), 4.37-4.34 (m, 1H), 3.68 (s, 3H), 2.39-2.35 (m, 1H), 2.23-2.14 (m, 1H). |
| HBV-CSU-339-ISO-I | 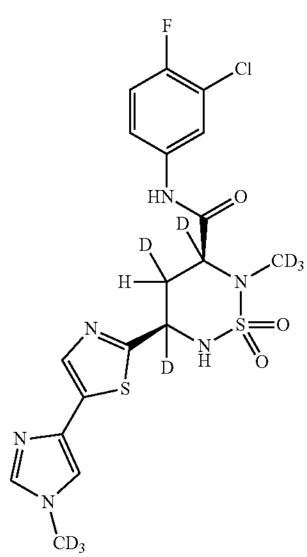 [SMILES: [2H]C1[C@]([2H])(c2ncc(-c3cn(C([2H])([2H])[2H])cn3)s2)NS(=O)(=O)N(C([2H])([2H])[2H])[C@]1([2H])C(=O)Nc1ccc(F)c(Cl)c1] | 3% | 494.10 (M + 1) | 493.11 for $C_{18}H_9D_9ClFN_6O_3S_2$ | ¹H-NMR (DMSO-$d_6$, 400 MHz): δ 10.58 (s, 1H), 7.97 (dd, J = 6.9, 2.6 Hz, 1H), 7.88-7.84 (m, 2H), 7.67-7.65 (m, 1H), 7.63-7.52 (m, 2H), 7.40 (t, J = 9.1 Hz, 1H), 2.15 (s, 1H). |

TABLE 2-continued

Analytical data for HBV-CSU racemic & pure enantiomers:

| Target No | Structure | Rx. Yield (%) | Mass Spec. Found (m/z) | Mass Spec. Calculated | ¹H-NMR |
|---|---|---|---|---|---|
| HBV-CSU-339-ISO-II | 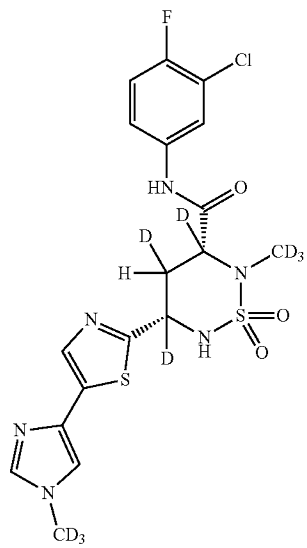 [SMILES: [2H]C1[C@]([2H])(C(=O)Nc2ccc(F)c(Cl)c2)N(C([2H])([2H])[2H])S(=O)(=O)N[C@]1([2H])c1ncc(-c2cn(C([2H])([2H])[2H])cn2)s1] | 4% | 494.15 (M + 1) | 493.11 for $C_{18}H_9D_9ClFN_6O_3S_2$ | ¹H-NMR (DMSO-$d_6$, 400 MHz): δ 10.57 (s, 1H), 7.97 (dd, J = 6.8, 2.6 Hz, 1H), 7.88-7.85 (m, 2H), 7.66-7.54 3H), 7.40 (t, J = 9.1 Hz, 1H), 2.14 (s, 1H). |
| HBV-CSU-340-ISO-I | 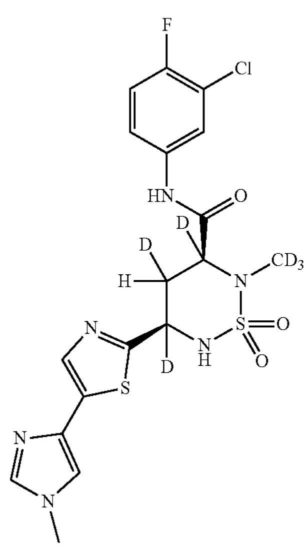 [SMILES: [2H]C1[C@]([2H])(c2ncc(-c3cn(C)cn3)s2)NS(=O)(=O)N(C([2H])([2H])[2H])[C@]1([2H])C(=O)Nc1ccc(F)c(Cl)c1] | 15% | 491.15 (M + 1) | 490.09 for $C_{18}H_{12}D_6ClFN_6O_3S_2$ | ¹H-NMR (DMSO-$d_6$, 400 MHz): δ 10.60 (s, 1H), 8.11 8.10 (m, 1H), 7.98-7.96 (m, 2H), 7.92 (s, 1H), 7.76 (s, 1H), 7.59-7.55 (m, 1H), 7.41 (t, J = 9.1 Hz, 1H), 3.74 (s, 3H), 2.17 (s, 1H). |

TABLE 2-continued

Analytical data for HBV-CSU racemic & pure enantiomers:

| Target No | Structure | Rx. Yield (%) | Mass Spec. Found (m/z) | Mass Spec. Calculated | $^1$H-NMR |
|---|---|---|---|---|---|
| HBV-CSU-340-ISO-II | 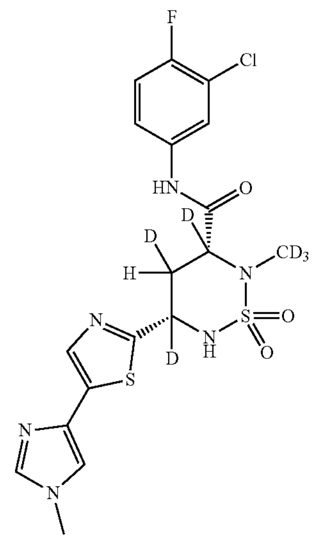 [SMILES: [2H]C1[C@]([2H])(C(=O)Nc2ccc(F)c(Cl)c2)N(C([2H])([2H])[2H])S(=O)(=O)N[C@]1([2H])c1ncc(-c2cn(C)cn2)s1] | 10% | 491.20 (M + 1) | 490.09 for $C_{18}H_{21}D_6ClFN_6O_3S_2$ | $^1$H-NMR (DMSO-$d_6$, 400 MHz): δ 10.59 (s, 1H), 7.97 (dd, J = 6.9, 2.6 Hz, 1H), 7.91-7.89 (m, 2H), 7.79 (s, 1H), 7.64 (s, 1H), 7.59-7.55 (m, 1H), 7.41 (t, J = 9.1 Hz, 1H), 3.70 (s, 3H), 2.16 (s, 1H). |
| HBV-CSU-341-ISO-I | 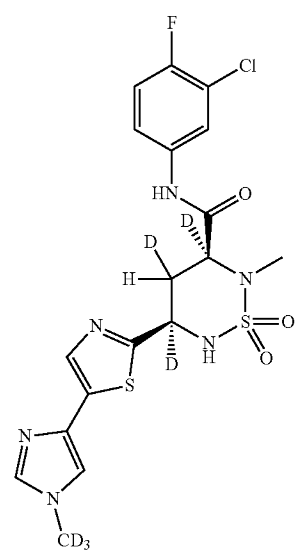 [SMILES: [2H]C1[C@]([2H])(c2ncc(-c3cn(C([2H])([2H])[2H])cn3)s2)NS(=O)(=O)N(C)[C@]1([2H])C(=O)Nc1ccc(F)c(Cl)c1] | 7% | 491.15 (M + 1) | 490.09 for $C_{18}H_{12}D_6ClFN_6O_3S_2$ | $^1$H-NMR (DMSO-$d_6$, 400 MHz): δ 10.55 (s, 1H), 7.94 (dd, J = 6.9, 2.6 Hz, 1H) 7.85 (s, 2H), 7.63-7.49 (m, 3H), 7.37 (t, J = 9.1 Hz, 1H), 2.59 (s, 3H), 2.14 (s, 1H). |

TABLE 2-continued

Analytical data for HBV-CSU racemic & pure enantiomers:

| Target No | Structure | Rx. Yield (%) | Mass Spec. Found (m/z) | Mass Spec. Calculated | ¹H-NMR |
|---|---|---|---|---|---|
| HBV-CSU-341-ISO-II | 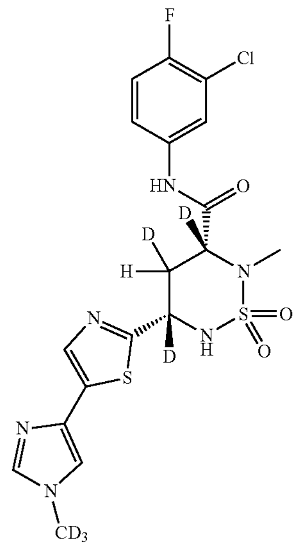 [SMILES: [2H]C1[C@]([2H])(C(=O)Nc2ccc(F)c(Cl)c2)N(C)S(=O)(=O)N[C@]1([2H])c1ncc(-c2cn(C([2H])([2H])[2H])cn2)s1] | 9% | 491.15 (M + 1) | 490.09 for $C_{18}H_{12}D_6ClFN_6O_3S_2$ | ¹H-NMR (DMSO-$d_6$, 400 MHz): δ 10.54 (s, 1H), 7.94 (dd, J = 6.8, 2.6 Hz, 1H), 7.84 (s, 2H), 7.62 (s, 1H), 7.55-7.51 (m, 3H), 7.37 (t, J = 9.1 Hz, 1H), 2.58 (s, 3H), 2.12 (s, 1H). |
| HBV-CSU-343 | 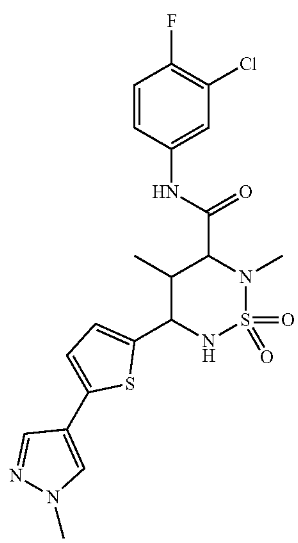 [SMILES: CC1C(c2ccc(-c3cnn(C)c3)s2)NS(=O)(=O)N(C)C1C(=O)Nc1ccc(F)c(Cl)c1] | 17% | 498.10 (M + 1) | 497.08 for $C_{20}H_{21}ClFN_5O_3S_2$ | ¹H-NMR (DMSO-$d_6$, 400 MHz): δ 10.78 (s, 1H), 10.44 (s, 0.33H), 10.01 (s, 1H), 8.19 6.94 (m, 18.64H), 5.10-5.08 (m, 1H), 5.00-4.97 (m, 0.33H), 4.48-4.38 (m, 1H), 4.32-4.31 (m, 1H), 4.08 (m, 0.33H), 3.87-3.76 (m, 8H), 3.05 (s, 3H), 2.70-2.63 (m, 5.33H), 2.41-2.32 (m, 1H), 1.03 (d, J = 7.5 Hz, 3H), 0.92 (d, J = 7.0 Hz, 1H), 0.71 (d, J = 6.6 Hz, 3H). NMR hints for three Diastereomers. |
| HBV-CSU-360 | 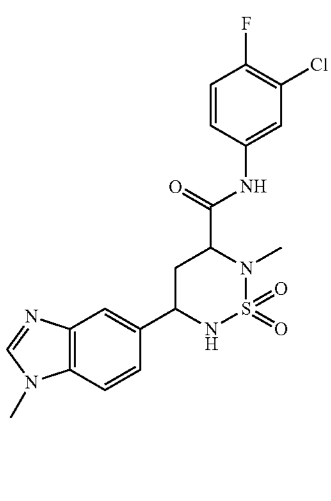 | 12% | 452.1 (M + 1) | 451.09 for $C_{19}H_{19}ClFN_5O_3S$ | ¹H-NMR (DMSO-$d_6$, 400 MHz): δ 10.51 (s, 1H), 8.15 (s, 1H), 7.92 (dd, J = 6.7, 2.7 Hz, 1H), 7.70 (s, 1H), 7.56-7.46 (m, 3H), 7.40-7.30 (m, 2H), 4.65-4.63 (m, 1H), 4.28-4.20 (m, 1H), 3.79 (s, 3H), 2.62 (s, 3H), 2.18-2.02 (m, 2H). |

TABLE 2-continued

Analytical data for HBV-CSU racemic & pure enantiomers:

| Target No | Structure | Rx. Yield (%) | Mass Spec. Found (m/z) | Mass Spec. Calculated | ¹H-NMR |
|---|---|---|---|---|---|
| HBV-CSU-360-ISO-I | 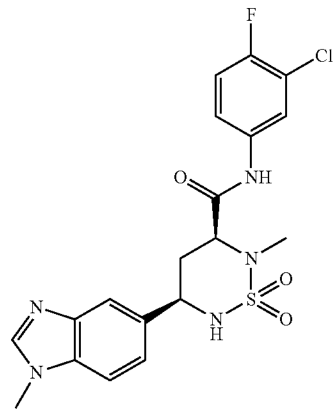 [SMILES: CN1[C@H](C(=O)Nc2ccc(F)c(Cl)c2)C[C@H](c2ccc3c(c2)ncn3C)NS1(=O)=O] | 4% | 452.1 (M + 1) | 451.09 for $C_{19}H_{19}ClFN_5O_3S$ | ¹H-NMR (DMSO-$d_6$, 400 MHz): δ 10.56 (s, 1H), 8.19 (s, 1H), 7.98-7.95 (m, 1H), 7.74 (s, 1H), 7.57-7.53 (m, 3H), 7.42-7.37 2H), 4.70-4.68 (m, 1H), 4.30-4.26 (m, 1H), 3.84 (s, 3H), 2.66 (s, 3H), 2.19-2.04 (m, 2H). |
| HBV-CSU-360-ISO-II | 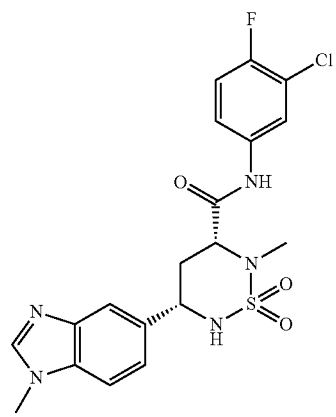 [SMILES: CN1[C@@H](C(=O)Nc2ccc(F)c(Cl)c2)C[C@@H](c2ccc3c(c2)ncn3C)NS1(=O)=O] | 4% | 452.9 (M + 2) | 451.09 for $C_{19}H_{19}ClFN_5O_3S$ | ¹H-NMR (DMSO-$d_6$, 400 MHz): δ 10.56 (s, 1H), 8.19 (s, 1H), 7.98-7.95 (m, 1H), 7.74 (s, 1H), 7.57-7.53 (m, 3H), 7.42-7.37 (m, 2H), 4.72-4.66 (m, 1H), 4.30-4.27 (m, 1H), 3.84 (s, 3H), 2.66 (s, 3H), 2.19-2.07 (m, 2H). |
| HBV-CSU-361 | 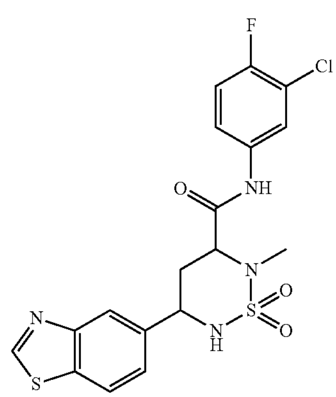 [SMILES: CN1C(C(=O)Nc2ccc(F)c(Cl)c2)CC(c2ccc3scnc3c2)NS1(=O)=O] | 40% | 455.10 (M + 1) | 454.03 for $C_{18}H_{16}ClFN_4O_3S_2$ | ¹H-NMR (DMSO-$d_6$, 400 MHz): δ 10.58 (s, 1H), 9.42 (s, 1H), 8.22-8.14 (m, 2H), 7.97 (dd, J = 6.9, 2.5 Hz, 1H), 7.69-7.51 (m, 3H), 7.40 (t, J = 9.1 Hz, 1H), 4.84-4.72 (m, 1H), 4.39-4.28 (m, 1H), 2.67 (s, 3H), 2.24-2.13 (m, 2H). |

TABLE 2-continued

Analytical data for HBV-CSU racemic & pure enantiomers:

| Target No | Structure | Rx. Yield (%) | Mass Spec. Found (m/z) | Mass Spec. Calculated | ¹H-NMR |
|---|---|---|---|---|---|
| HBV-CSU-364 | 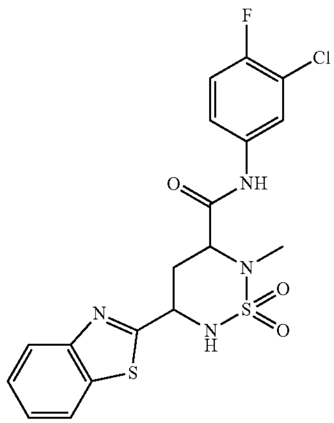 [SMILES: CN1C(C(=O)Nc2ccc(F)c(Cl)c2)CC(c2nc3ccccc3s2)NS1(=O)=O] | 15% | 455.10 (M + 1) | 454.03 for $C_{18}H_{16}ClFN_4O_3S_2$ | ¹H-NMR (DMSO-d$_6$, 400 MHz): δ 10.62 (s, 1H), 8.18-7.95 (m, 3H), 7.63-7.37 (m, 5H), 5.13-5.05 (m, 1H), 4.41-4.38 (m, 1H), 2.65 (s, 3H), 2.33-2.24 (m, 2H). |
| HBV-CSU-367 | 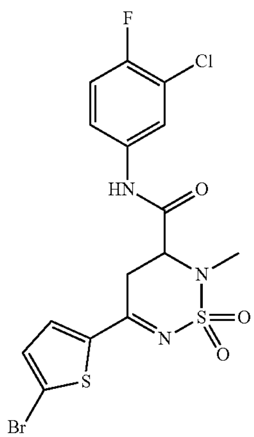 | 17% | 481.95 (M + 2) | 478.92 for $C_{15}H_{12}BrClFN_3O_3S_2$ | ¹H-NMR (DMSO-d$_6$, 400 MHz): δ 10.56 (s, 1H), 7.99-7.94 (m, 2H), 7.62-7.58 (m, 1H), 7.46 (d, J = 4.4 Hz, 1H), 7.40 (t, J = 8.8 Hz, 1H), 4.88-4.84 (m, 1H), 3.43-3.36 (m, 2H), 2.78 (s, 3H). |
| HBV-CSU-368 | 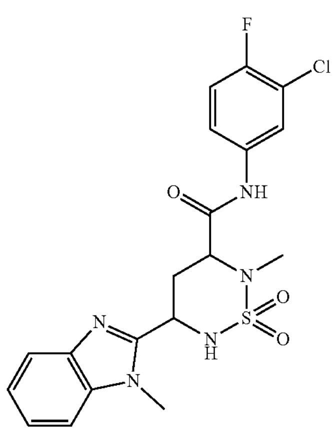 [SMILES: CN1C(C(=O)Nc2ccc(F)c(Cl)c2)CC(c2nc3ccccc3n2C)NS1(=O)=O] | 29% | 452.09 (M + 1) | 451.09 for $C_{19}H_{19}ClFN_5O_3S$ | ¹H-NMR (DMSO-d$_6$, 400 MHz): δ 10.61 (s, 1H), 7.99 (dd, J = 6.8, 2.6 Hz, 1H), 7.74-7.71 (m, 1H), 7.67-7.57 (m, 3H), 7.42 (t, J = 9.1 Hz, 1H), 7.31-7.20 (m, 2H), 5.06 (t, J = 10.5 Hz, 1H), 4.43-4.42 (m, 1H), 3.84 (s, 3H), 2.64 (s, 3H), 2.58-2.50 (m, 1H), 2.23-2.14 (m, 1H). |

TABLE 2-continued

Analytical data for HBV-CSU racemic & pure enantiomers:

| Target No | Structure | Rx. Yield (%) | Mass Spec. Found (m/z) | Mass Spec. Calculated | ¹H-NMR |
|---|---|---|---|---|---|
| HBV-CSU-369 | 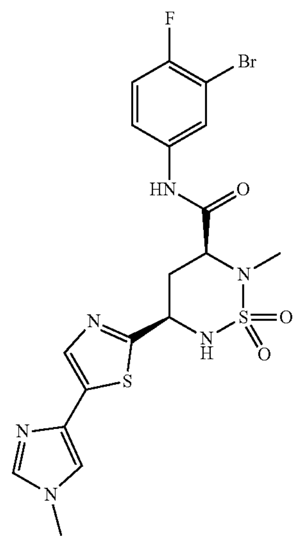 [SMILES: CN1[C@H](C(=O)Nc2ccc(F)c(Br)c2)C[C@H](c2ncc(-c3cn(C)cn3)s2)NS1(=O)=O] | 20% | 531.05 (M + 2) | 528.00 for $C_{18}H_{18}BrFN_6O_3S_2$ | ¹H-NMR (DMSO-d$_6$, 400 MHz): δ 10.60 (s, 1H), 8.11-8.09 (m, 1H), 7.93-7.89 (m, 2H), 7.72-7.69 (m, 1H), 7.61-7.59 (m, 2H), 7.37 (t, J = 8.8 Hz, 1H), 4.93-4.87 (m, 1H), 4.36-4.33 (m, 1H), 3.69 (s, 3H), 2.63 (s, 3H), 2.40-2.36 (m, 1H), 2.24-2.17 (m, 1H). |
| HBV-CSU-370 | 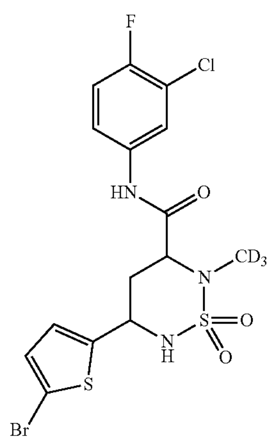 [SMILES: [2H]C([2H])([2H])N1C(C(=O)Nc2ccc(F)c(Cl)c2)CC(c2ccc(Br)s2)NS1(=O)=O] | 79% | 487.05 (M + 2) | 483.95 for $C_{15}H_{11}D_3BrClFN_3O_3S_2$ | ¹H-NMR (DMSO-d$_6$, 400 MHz): δ 10.59 (s, 1H), 7.97 (dd, J = 6.9, 2.6 Hz, 1H), 7.73 (d, J = 9.2 Hz, 1H), 7.57-7.53 (m, 1H), 7.41 (t, J = 9.1 Hz, 1H), 7.14 (d, J = 3.9 Hz, 1H), 7.00-6.99 (m, 1H), 4.77-4.75 (m, 1H), 4.29-4.26 (m, 1H), 2.24-2.03 (m, 2H). |
| HBV-CSU-370-ISO-I | 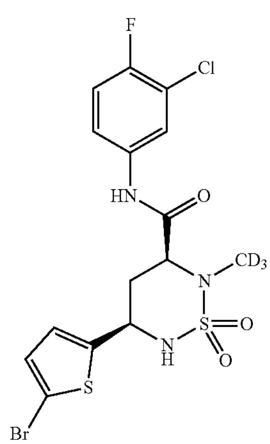 [SMILES: [2H]C([2H])([2H])N1[C@H](C(=O)Nc2ccc(F)c(Cl)c2)C[C@H](c2ccc(Br)s2)NS1(=O)=O] | 2% | 486.8 (M + 2) | 483.95 for $C_{15}H_{11}D_3BrClFN_3O_3S_2$ | ¹H-NMR (DMSO-d$_6$, 400 MHz): δ 10.59 (s, 1H), 7.97 (dd, J = 6.9, 2.6 Hz, 1H), 7.75-7.72 (m, 1H), 7.58-7.54 (m, 1H), 7.41 (t, J = 9.1 Hz, 1H), 7.14 (d, J = 4.0 Hz, 1H), 6.99 (d, J = 4.0 Hz, 1H), 4.77-4.75 (m, 1H), 4.29-4.26 (m, 1H), 2.24-2.03 (m, 2H). |

TABLE 2-continued

Analytical data for HBV-CSU racemic & pure enantiomers:

| Target No | Structure | Rx. Yield (%) | Mass Spec. Found (m/z) | Mass Spec. Calculated | $^1$H-NMR |
|---|---|---|---|---|---|
| HBV-CSU-370-ISO-II | 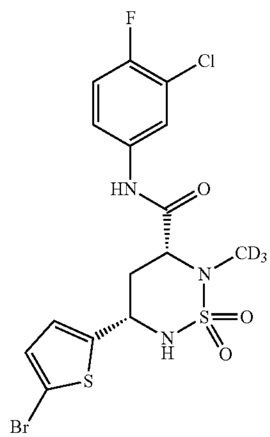 [SMILES: [2H]C([2H])([2H])N1[C@@H](C(=O)Nc2ccc(F)c(Cl)c2)C[C@@H](c2ccc(Br)s2)NS1(=O)=O] | 2% | 486.9 (M + 2) | 483.95 for $C_{15}H_{11}D_3BrClFN_3O_3S_2$ | $^1$H-NMR (DMSO-$d_6$, 400 MHz): δ 10.59 (s, 1H), 7.97 (dd, J = 7.2, 2.8 Hz, 1H), 7.75-7.72 (m, 1H), 7.58-7.54 (m, 1H), 7.41 (t, J = 9.2 Hz, 1H), 7.14 (d, J = 3.6 Hz, 1H), 6.99 (d, J = 4.0 Hz, 1H), 4.76-4.74 (m, 1H), 4.29-4.26 (m, 1H), 2.24-2.04 (m, 2H). |
| HBV-CSU-371 | 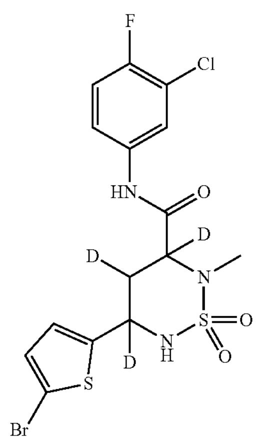 [SMILES: [2H]C1C([2H])(c2ccc(Br)s2)NS(=O)(=O)N(C)C1([2H])C(=O)Nc1ccc(F)c(Cl)c1] | 66% | 487.05 (M + 2) | 483.95 for $C_{15}H_{11}D_3BrClFN_3O_3S_2$ | $^1$H-NMR (DMSO-$d_6$, 400 MHz): δ 10.58 (s, 1H), 7.97 (dd, J = 6.9, 2.6 Hz, 1H), 7.72 (s, 1H), 7.57-7.55 (m, 1H), 7.40 (t, J = 9.1 Hz, 1H), 7.13 (d, J = 3.8 Hz, 1H), 7.00 (d, J = 3.8 Hz, 1H), 2.61 (s, 3H), 2.06 (s, 1H). |
| HBV-CSU-371-ISO-I | 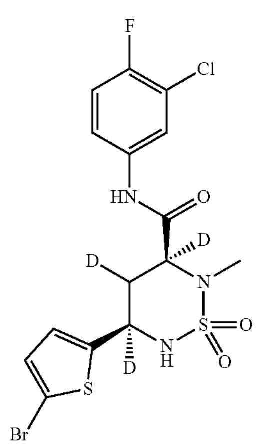 [SMILES: [2H]C1[C@]([2H])(c2ccc(Br)s2)NS(=O)(=O)N(C)[C@]1([2H])C(=O)Nc1ccc(F)c(Cl)c1] | 2% | 487.0 (M + 2) | 483.95 for $C_{15}H_{11}D_3BrClFN_3O_3S_2$ | $^1$H-NMR (DMSO-$d_6$, 400 MHz): δ 10.59 (s, 1H), 7.98-7.96 (m, 1H), 7.72 (s, 1H), 7.57-7.55 (m, 1H), 7.40 (t, J = 9.1 Hz, 1H), 7.13 (d, J = 3.8 Hz, 1H), 7.00 (d, J = 3.8 Hz, 1H), 2.61 (s, 3H), 2.06 (s, 1H). |

TABLE 2-continued

Analytical data for HBV-CSU racemic & pure enantiomers:

| Target No | Structure | Rx. Yield (%) | Mass Spec. Found (m/z) | Mass Spec. Calculated | $^1$H-NMR |
|---|---|---|---|---|---|
| HBV-CSU-371-ISO-II | 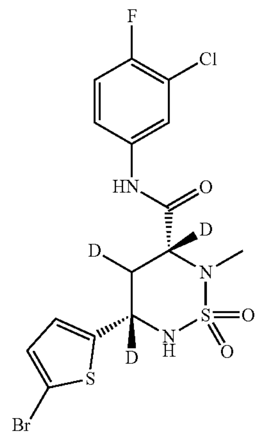 [SMILES: [2H]C1[C@]([2H])(C(=O)Nc2ccc(F)c(Cl)c2)N(C)S(=O)(=O)N[C@]1([2H])c1ccc(Br)s1] | 2% | 487.00 (M + 2) | 483.95 for $C_{15}H_{11}D_3BrClFN_3O_3S_2$ | $^1$H-NMR (DMSO-$d_6$, 400 MHz): δ 10.58 (s, 1H), 7.97 (dd, J = 6.9, 2.6 Hz, 1H), 7.72 (s, 1H), 7.57-7.54 (m, 1H), 7.40 (t, J = 9.1 Hz, 1H), 7.13 (d, J = 4.0 Hz, 1H), 7.00 (d, J = 3.6 Hz, 1H), 2.61 (s, 3H), 2.06 (s, 1H). |
| HBV-CSU-372 | 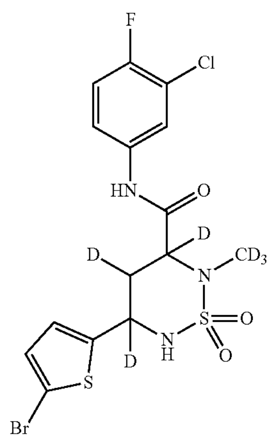 [SMILES: [2H]C1C([2H])(c2ccc(Br)s2)NS(=O)(=O)N(C([2H])([2H])[2H])C1([2H])C(=O)Nc1ccc(F)c(Cl)c1] | 79% | 490.05 (M + 2) | 486.97 for $C_{15}H_8D_6BrClFN_3O_3S_2$ | $^1$H-NMR (DMSO-$d_6$, 400 MHz): δ 10.58 (s, 1H), 7.97-7.95 (m, 1H), 7.70 (s, 1H), 7.56-7.53 (m, 1H), 7.40 (t, J = 8.8 Hz, 1H), 7.13 (d, J = 3.8 Hz, 1H), 7.00 (d, J = 3.8 Hz, 1H), 2.06 (s, 1H). |
| HBV-CSU-372-ISO-I | 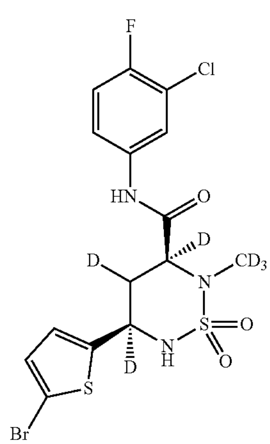 [SMILES: [2H]C1[C@]([2H])(c2ccc(Br)s2)NS(=O)(=O)N(C([2H])([2H])[2H])[C@]1([2H])C(=O)Nc1ccc(F)c(Cl)c1] | 2% | 489.9 (M + 2) | 486.97 for $C_{15}H_8D_6BrClFN_3O_3S_2$ | $^1$H-NMR (DMSO-$d_6$, 400 MHz): δ 10.58 (s, 1H), 7.97-7.95 (m, 1H), 7.70 (s, 1H), 7.56-7.53 (m, 1H), 7.40 (t, J = 8.8 Hz, 1H), 7.13 (d, J = 3.8 Hz, 1H), 7.00 (d, J = 3.8 Hz, 1H), 2.06 (s, 1H). |

TABLE 2-continued

Analytical data for HBV-CSU racemic & pure enantiomers:

| Target No | Structure | Rx. Yield (%) | Mass Spec. Found (m/z) | Mass Spec. Calculated | ¹H-NMR |
|---|---|---|---|---|---|
| HBV-CSU-372-ISO-II | 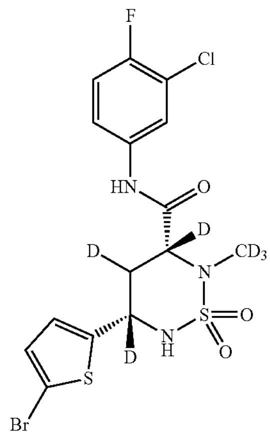 [SMILES: [2H]C1[C@]([2H])(C(=O)Nc2ccc(F)c(Cl)c2)N(C([2H])([2H])[2H])S(=O)(=O)N[C@]1([2H])c1ccc(Br)s1] | 2% | 490.00 (M + 2) | 486.97 for $C_{15}H_8D_6BrClFN_3O_3S_2$ | ¹H-NMR (DMSO-d₆, 400 MHz): δ 10.58 (s, 1H), 7.97-7.95 (m, 1H), 7.71 (s, 1H), 7.57-7.53 (m, 1H), 7.40 (t, J = 9.2 Hz, 1H), 7.13 (d, J = 3.8 Hz, 1H), 7.00 (d, J = 3.8 Hz, 1H), 2.06 (s, 1H). |
| HBV-CSU-373 | 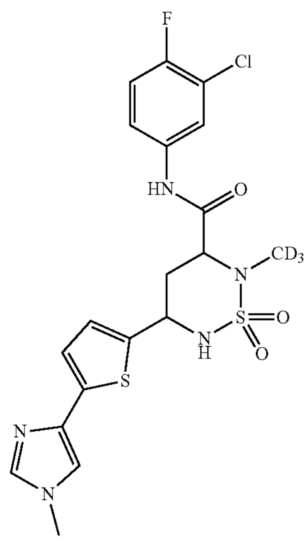 [SMILES: [2H]C([2H])([2H])N1C(C(=O)Nc2ccc(F)c(Cl)c2)CC(c2ccc(-c3cn(C)cn3)s2)NS1(=O)=O] | 37% | 487 (M + 1) | 486.08 for $C_{19}H_{16}D_3ClFN_5O_3S_2$ | ¹H-NMR (DMSO-d₆, 400 MHz): δ 10.57 (s, 1H), 7.98 (dd, J = 6.9, 2.5 Hz, 1H), 7.67-7.64 (m, 1H), 7.59-7.54 (m, 2H), 7.47-7.38 (m, 2H), 7.09 (d, J = 3.2 Hz, 1H), 7.02 (d, J = 4.0 Hz, 1H), 4.77-4.72 (m, 1H), 4.32-4.28 (m, 1H), 3.66 (s, 3H), 2.24-2.12 (m, 2H). |
| HBV-CSU-373-ISO-I | 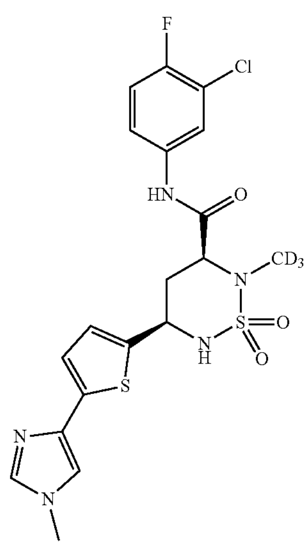 [SMILES: [2H]C([2H])([2H])N1[C@H](C(=O)Nc2ccc(F)c(Cl)c2)C[C@H](c2ccc(-c3cn(C)cn3)s2)NS1(=O)=O] | 4% | 487.1 (M + 1) | 486.08 for $C_{19}H_{16}D_3ClFN_5O_3S_2$ | ¹H-NMR (DMSO-d₆, 400 MHz): δ 10.57 (s, 1H), 7.98 (dd, J = 6.9, 2.5 Hz, 1H), 7.64 (s, 1H), 7.61-7.52 (m, 2H), 7.49-7.36 (m, 2H), 7.09 (d, J = 3.6 Hz, 1H), 7.02 (d, J = 3.6 Hz, 1H), 4.76-4.73 (m, 1H), 4.32-4.28 (m, 1H), 3.66 (s, 3H), 2.24-2.07 (m, 2H). |

TABLE 2-continued

Analytical data for HBV-CSU racemic & pure enantiomers:

| Target No | Structure | Rx. Yield (%) | Mass Spec. Found (m/z) | Mass Spec. Calculated | ¹H-NMR |
|---|---|---|---|---|---|
| HBV-CSU-373-ISO-II | 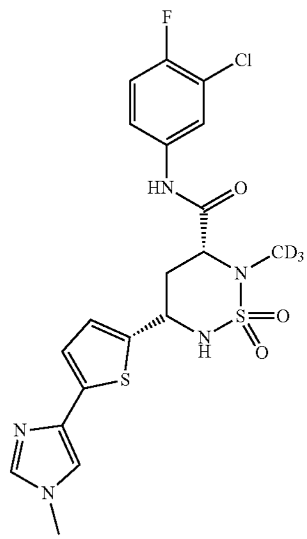 | 4% | 487 (M + 1) | 486.08 for $C_{19}H_{16}D_3ClFN_3O_3S_2$ | ¹H-NMR (DMSO-$d_6$, 400 MHz): δ 10.57 (s, 1H), 7.98 (dd, J = 6.9, 2.6 Hz, 1H), 7.65-7.63 (m, 1H), 7.61-7.52 (m, 2H), 7.47-7.38 (m, 2H), 7.09 (d, J = 3.7 Hz, 1H), 7.02 (d, J = 3.6 Hz, 1H), 4.75-4.72 (m, 1H), 4.32-4.29 (m, 1H), 3.66 (s, 3H), 2.21-2.15 (m, 2H). |
| HBV-CSU-374 | 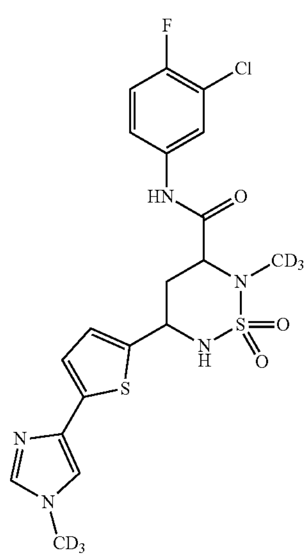 [SMILES: [2H]C([2H])([2H])N1C(C(=O)Nc2ccc(F)c(Cl)c2)CC(c2ccc(-c3cn(C([2H])([2H])[2H])cn3)s2)NS1(=O)=O] | 43% | 490.15 (M + 1) | 489.10 for $C_{19}H_{13}D_6ClFN_5O_3S_2$ | ¹H-NMR (DMSO-$d_6$, 400 MHz): δ 10.53 (s, 1H), 7.94 (dd, J = 6.8, 2.6 Hz, 1H), 7.65-7.48 (m, 3H), 7.45-7.32 (m, 2H), 7.05 (d, J = 3.6 Hz, 1H), 6.98 (d, J = 3.6 Hz, 1H), 4.76-4.65 (m, 1H), 4.28-4.24 (m, 1H), 2.23-2.01 (m, 2H). |

TABLE 2-continued

Analytical data for HBV-CSU racemic & pure enantiomers:

| Target No | Structure | Rx. Yield (%) | Mass Spec. Found (m/z) | Mass Spec. Calculated | ¹H-NMR |
|---|---|---|---|---|---|
| HBV-CSU-374-ISO-I | 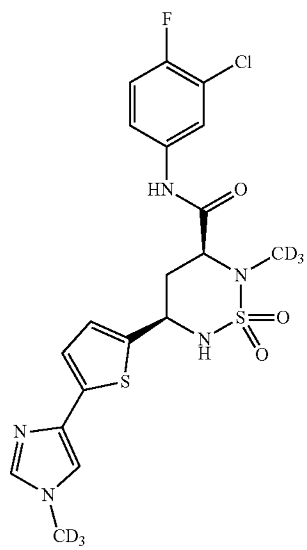 [SMILES: [2H]C([2H])([2H])N1[C@H](C(=O)Nc2ccc(F)c(Cl)c2)C[C@H](c2ccc(-c3cn(C([2H])([2H])[2H])cn3)s2)NS1(=O)=O] | 7% | 490.20 (M + 1) | 489.10 for $C_{19}H_{13}D_6ClFN_5O_3S_2$ | ¹H-NMR (DMSO-$d_6$, 400 MHz): δ 10.57 (s, 1H), 7.98 (dd, J = 6.9, 2.6 Hz, 1H), 7.65 (d, J = 9.2 Hz, 1H), 7.62-7.52 (m, 2H), 7.49-7.36 (m, 2H), 7.09 (d, J = 3.6 Hz, 1H), 7.02 (d, J = 3.6 Hz, 1H), 4.75 (t, J = 9.7 Hz, 1H), 4.30 (dd, J = 11.6, 3.1 Hz, 1H), 2.27-2.05 (m, 2H). |
| HBV-CSU-374-ISO-II | 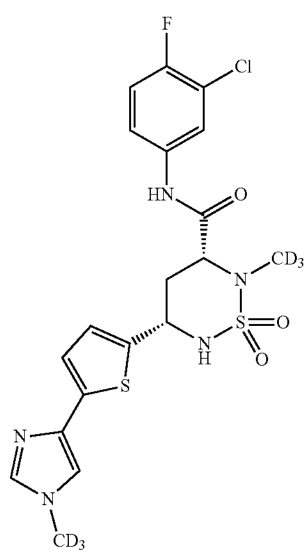 [SMILES: [2H]C([2H])([2H])N1[C@@H](C(=O)Nc2ccc(F)c(Cl)c2)C[C@@H](c2ccc(-c3cn(C([2H])([2H])[2H])cn3)s2)NS1(=O)=O] | 5% | 490.20 (M + 1) | 489.10 for $C_{19}H_{13}D_6ClFN_5O_3S_2$ | ¹H-NMR (DMSO-$d_6$, 400 MHz): δ 10.57 (s, 1H), 7.98 (dd, J = 6.8, 2.5 Hz, 1H), 7.65 (d, J = 9.3 Hz, 1H), 7.62-7.52 (m, 2H), 7.49-7.36 (m, 2H), 7.09 (d, J = 3.6 Hz, 1H), 7.03 (d, J = 3.6 Hz, 1H), 4.75 (t, J = 9.5 Hz, 1H), 4.30 (dd, J = 11.5, 3.1 Hz, 1H), 2.27-2.05 (m, 2H). |

TABLE 2-continued
Analytical data for HBV-CSU racemic & pure enantiomers:
| Target No | Structure | Rx. Yield (%) | Mass Spec. Found (m/z) | Mass Spec. Calculated | $^1$H-NMR |
|---|---|---|---|---|---|
| HBV-CSU-375 | 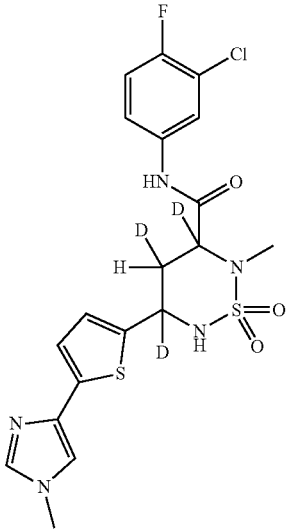 [SMILES: [2H]C1C([2H])(c2ccc(-c3cn(C)cn3)s2)NS(=O)(=O)N(C)C1([2H])C(=O)Nc1ccc(F)c(Cl)c1] | 67% | 487.15 (M + 1) | 486.08 for $C_{19}H_{16}D_3ClFN_5O_3S_2$ | $^1$H-NMR (DMSO-$d_6$, 400 MHz): δ 10.57 (s, 1H), 7.99-7.96 (m, 1H), 7.65-7.51 (m, 3H), 7.54 (s, 1H), 7.41 (t, J = 8.8 Hz, 1H), 7.10-7.01 (m, 2H), 3.66 (s, 3H), 2.62 (s, 3H), 2.12 (s, 1H). |
| HBV-CSU-375-ISO-I | 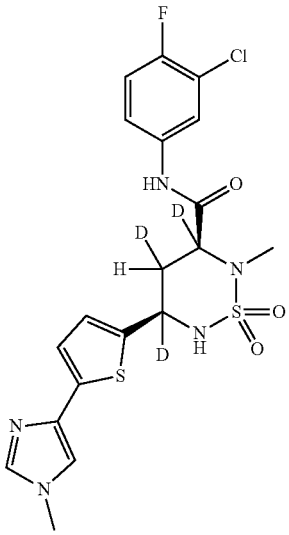 [SMILES: [2H]C1[C@]([2H])(c2ccc(-c3cn(C)cn3)s2)NS(=O)(=O)N(C)[C@]1([2H])C(=O)Nc1ccc(F)c(Cl)c1] | 8% | 487 (M + 1) | 486.08 for $C_{19}H_{16}D_3ClFN_5O_3S_2$ | $^1$H-NMR (DMSO-$d_6$, 400 MHz): δ 10.58 (s, 1H), 7.99-7.97 (m, 1H), 7.65-7.54 (m, 3H), 7.47-7.38 (m, 2H), 7.09-7.02 (m, 2H), 3.66 (s, 3H), 2.61 (s, 3H), 2.12 (s, 1H). |

TABLE 2-continued

Analytical data for HBV-CSU racemic & pure enantiomers:

| Target No | Structure | Rx. Yield (%) | Mass Spec. Found (m/z) | Mass Spec. Calculated | $^1$H-NMR |
|---|---|---|---|---|---|
| HBV-CSU-375-ISO-II | 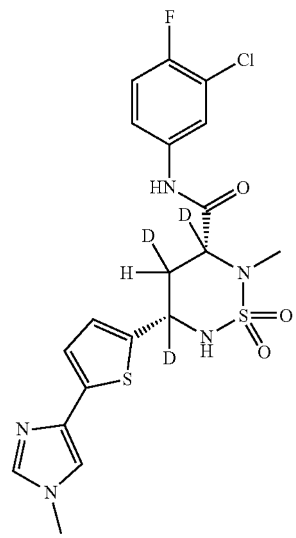 [SMILES: [2H]C1[C@]([2H])(C(=O)Nc2ccc(F)c(Cl)c2)N(C)S(=O)(=O)N[C@]1([2H])c1ccc(-c2cn(C)cn2)s1] | 9% | 487.10 (M + 1) | 486.08 for $C_{19}H_{16}D_3ClFN_5O_3S_2$ | $^1$H-NMR (DMSO-$d_6$, 400 MHz): δ 10.58 (s, 1H), 7.98 (dd, J = 6.9, 2.6 Hz, 1H), 7.65-7.52 (m, 3H), 7.49-7.36 (m, 2H), 7.08 (d, J = 3.6 Hz, 1H), 7.02 (d, J = 3.6 Hz, 1H), 3.66 (s, 3H), 2.61 (s, 3H), 2.12 (s, 1H). |
| HBV-CSU-376 | 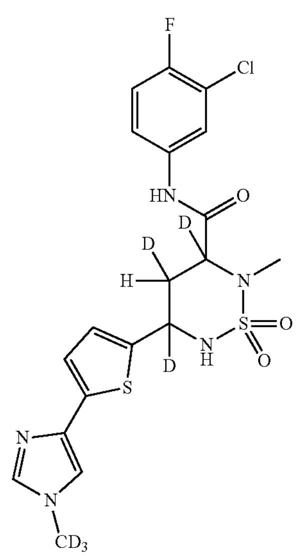 [SMILES: [2H]C1C([2H])(c2ccc(-c3cn(C([2H])([2H])[2H])cn3)s2)NS(=O)(=O)N(C)C1([2H])C(=O)Nc1ccc(F)c(Cl)c1] | 50% | 490.15 (M + 1) | 489.10 for $C_{19}H_{13}D_6ClFN_5O_3S_2$ | $^1$H-NMR (DMSO-$d_6$, 400 MHz): δ 10.56 (s, 1H), 7.98 (dd, J = 6.8, 2.4 Hz, 1H), 7.64 (s, 1H), 7.58-7.53 (m, 2H), 7.46 (s, 1H), 7.40 (t, J = 8.8 Hz, 1H), 7.08 (d, J = 3.6 Hz, 1H), 7.01 (d, J = 3.6 Hz, 1H), 2.62 (s, 3H), 2.12 (s, 1H). |

TABLE 2-continued

Analytical data for HBV-CSU racemic & pure enantiomers:

| Target No | Structure | Rx. Yield (%) | Mass Spec. Found (m/z) | Mass Spec. Calculated | $^1$H-NMR |
|---|---|---|---|---|---|
| HBV-CSU-376-ISO-I | 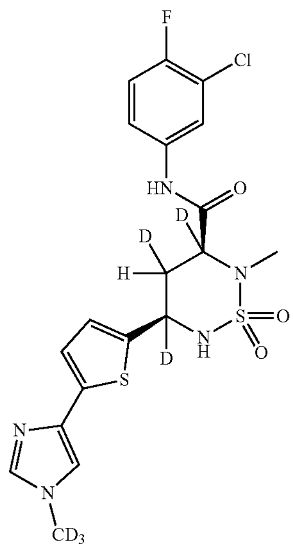 [SMILES: [2H]C1[C@]([2H])(c2ccc(-c3cn(C([2H])([2H])[2H])cn3)s2)NS(=O)(=O)N(C)[C@]1([2H])C(=O)Nc1ccc(F)c(Cl)c1] | 7% | 490.20 (M + 1) | 489.10 for $C_{19}H_{13}D_6ClFN_5O_3S_2$ | $^1$H-NMR (DMSO-$d_6$, 400 MHz): δ 10.58 (s, 1H), 7.98 (dd, J = 6.9, 2.6 Hz, 1H), 7.66-7.50 (m, 3H), 7.49-7.35 2H), 7.08 (d, J = 3.7 Hz, 1H), 7.01 (d, J = 3.7 Hz, 1H), 2.61 (s, 3H), 2.11 (s, 1H). |
| HBV-CSU-376-ISO-II | 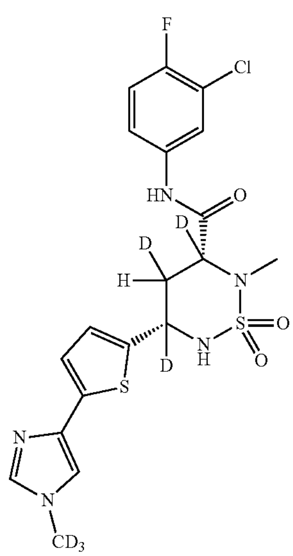 [SMILES: [2H]C1[C@]([2H])(C(=O)Nc2ccc(F)c(Cl)c2)N(C)S(=O)(=O)N[C@]1([2H])c1ccc(-c2cn(C([2H])([2H])[2H])cn2)s1] | 6% | 490.20 (M + 1) | 489.10 for $C_{19}H_{13}D_6ClFN_5O_3S_2$ | $^1$H-NMR (DMSO-$d_6$, 400 MHz): δ 10.57 (s, 1H), 7.98 (dd, J = 6.8, 2.7 Hz, 1H), 7.65-7.51 (m, 3H), 7.49-7.36 2H), 7.08 (d, J = 3.8 Hz, 1H), 7.02 (d, J = 3.8 Hz, 1H), 2.61 (s, 3H), 2.12 (s, 1H). |

TABLE 2-continued

Analytical data for HBV-CSU racemic & pure enantiomers:

| Target No | Structure | Rx. Yield (%) | Mass Spec. Found (m/z) | Mass Spec. Calculated | $^1$H-NMR |
|---|---|---|---|---|---|
| HBV-CSU-377 | 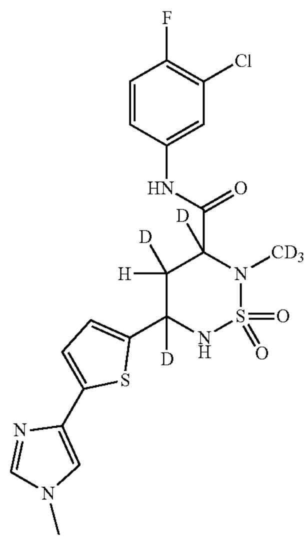 [SMILES: [2H]C1C([2H])(c2ccc(-c3cn(C)cn3)s2)NS(=O)(=O)N(C([2H])([2H])[2H])C1([2H])C(=O)Nc1ccc(F)c(Cl)c1] | 40% | 490.1 (M + 1) | 489.10 for $C_{19}H_{13}D_6ClFN_5O_3S_2$ | $^1$H-NMR (DMSO-$d_6$, 400 MHz): δ 10.57 (s, 1H), 7.99-7.96 (m, 1H), 7.64 (s, 1H), 7.59-7.54 (m, 2H), 7.47 (s, 1H), 7.41 (t, J = 8.8 Hz, 1H), 7.09 (d, J = 3.2 Hz, 1H), 7.03 (d, J = 3.6 Hz, 1H), 3.66 (s, 3H), 2.12 (s, 1H). |
| HBV-CSU-377-ISO-I | 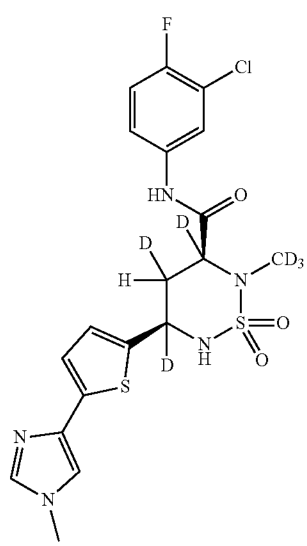 [SMILES: [2H]C1[C@]([2H])(c2ccc(-c3cn(C)cn3)s2)NS(=O)(=O)N(C([2H])([2H])[2H])[C@]1([2H])C(=O)Nc1ccc(F)c(Cl)c1] | 6% | 490.1 (M + 1) | 489.10 for $C_{19}H_{13}D_6ClFN_5O_3S_2$ | $^1$H-NMR (DMSO-$d_6$, 400 MHz): δ 10.57 (s, 1H), 7.98 (dd, J = 6.9, 2.6 Hz, 1H), 7.66-7.52 (m, 3H), 7.47 (s, 1H), 7.41 (t, J = 8.8 Hz, 1H), 7.09 (d, J = 3.7 Hz, 1H), 7.02 (d, J = 3.6 Hz, 1H), 3.66 (s, 3H), 2.12 (s, 1H). |

TABLE 2-continued

Analytical data for HBV-CSU racemic & pure enantiomers:

| Target No | Structure | Rx. Yield (%) | Mass Spec. Found (m/z) | Mass Spec. Calculated | $^1$H-NMR |
|---|---|---|---|---|---|
| HBV-CSU-377-ISO-II | 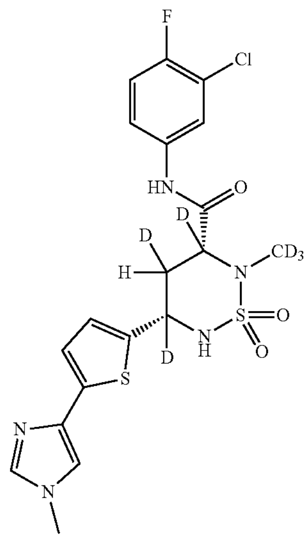 [SMILES: [2H]C1[C@]([2H])(C(=O)Nc2ccc(F)c(Cl)c2)N(C([2H])([2H])[2H])S(=O)(=O)N[C@]1([2H])c1ccc(-c2cn(C)cn2)s1] | 8% | 490.1 (M + 1) | 489.10 for $C_{19}H_{13}D_6ClFN_5O_3S_2$ | $^1$H-NMR (DMSO-$d_6$, 400 MHz): δ 10.57 (s, 1H), 7.98 (dd, J = 6.8, 2.5 Hz, 1H), 7.67-7.52 (m, 3H), 7.47 (s, 1H), 7.41 (t, J = 8.8 Hz, 1H), 7.09 (d, J = 3.7 Hz, 1H), 7.02 (d, J = 3.7 Hz, 1H), 3.66 (s, 3H), 2.12 (s, 1H). |
| HBV-CSU-378 | 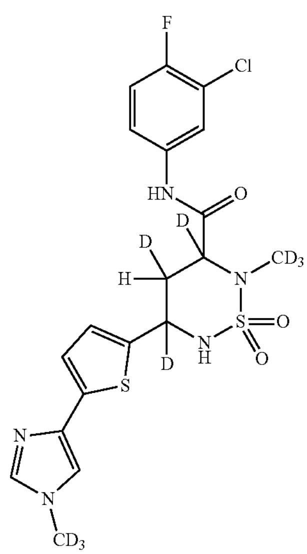 [SMILES: [2H]C1C([2H])(c2ccc(-c3cn(C([2H])([2H])[2H])cn3)s2)NS(=O)(=O)N(C([2H])([2H])[2H])C1([2H])C(=O)Nc1ccc(F)c(Cl)c1] | 46% | 493.10 (M + 1) | 492.12 for $C_{19}H_{10}D_9ClFN_5O_3S_2$ | $^1$H-NMR (DMSO-$d_6$, 400 MHz): δ 10.53 (s, 1H), 7.94 (dd, J = 6.9, 2.6 Hz, 1H), 7.62-7.47 (m, 3H), 7.45-7.32 2H), 7.05-6.97 (m, 2H), 2.08 (s, 1H). |

TABLE 2-continued

Analytical data for HBV-CSU racemic & pure enantiomers:

| Target No | Structure | Rx. Yield (%) | Mass Spec. Found (m/z) | Mass Spec. Calculated | ¹H-NMR |
|---|---|---|---|---|---|
| HBV-CSU-378-ISO-I | 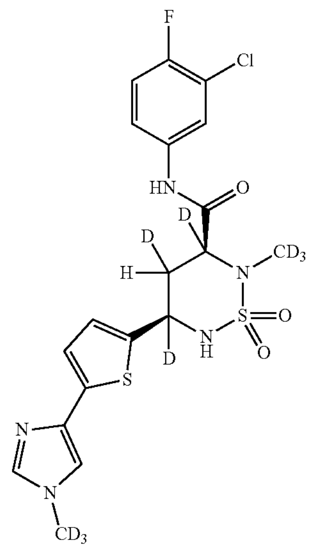 [SMILES: [2H]C1[C@]([2H])(c2ccc(-c3cn(C([2H])([2H])[2H])cn3)s2)NS(=O)(=O)N(C([2H])([2H])[2H])[C@]1([2H])C(=O)Nc1ccc(F)c(Cl)c1] | 8% | 493.20 (M + 1) | 492.12 for $C_{19}H_{10}D_9ClFN_5O_3S_2$ | ¹H-NMR (DMSO-$d_6$, 400 MHz): δ 10.57 (s, 1H), 7.98 (dd, J = 6.8, 2.5 Hz, 1H), 7.66-7.52 (m, 3H), 7.46 (s, 1H), 7.41 (t, J = 8.8 Hz, 1H), 7.09 (d, J = 3.7 Hz, 1H), 7.02 (d, J = 3.6 Hz, 1H), 2.12 (s, 1H). |
| HBV-CSU-378-ISO-II | 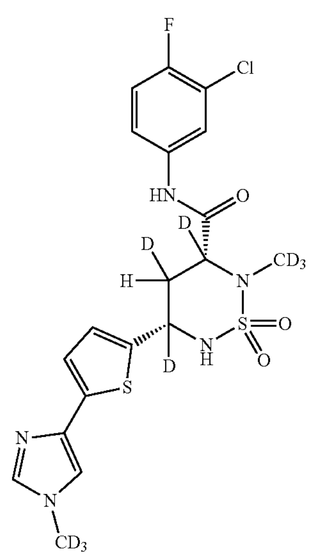 [SMILES: [2H]C1[C@]([2H])(C(=O)Nc2ccc(F)c(Cl)c2)N(C([2H])([2H])[2H])S(=O)(=O)N[C@]1([2H])c1ccc(-c2cn(C([2H])([2H])[2H])cn2)s1] | 10% | 493.20 (M + 1) | 492.12 for $C_{19}H_{10}D_9ClFN_5O_3S_2$ | ¹H-NMR (DMSO-$d_6$, 400 MHz): δ 10.57 (s, 1H), 7.98 (dd, J = 6.8, 2.6 Hz, 1H), 7.66-7.52 (m, 3H), 7.46 (s, 1H), 7.41 (t, J = 8.8 Hz, 1H), 7.09 (d, J = 3.6 Hz, 1H), 7.02 (d, J = 3.6 Hz, 1H), 2.12 (s, 1H). |

TABLE 2-continued

Analytical data for HBV-CSU racemic & pure enantiomers:

| Target No | Structure | Rx. Yield (%) | Mass Spec. Found (m/z) | Mass Spec. Calculated | ¹H-NMR |
|---|---|---|---|---|---|
| HBV-CSU-379-ISO-I | 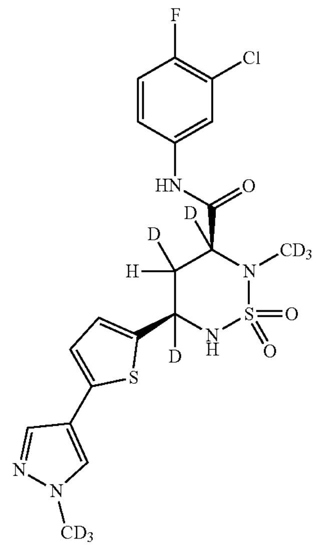 [SMILES: [2H]C1[C@]([2H])(c2ccc(-c3cnn(C([2H])([2H])[2H])c3)s2)NS(=O)(=O)N(C([2H])([2H])[2H])[C@]1([2H])C(=O)Nc1ccc(F)c(Cl)c1] | 7% | 493.15 (M + 1) | 492.12 for $C_{19}H_{10}D_9ClFN_5O_3S_2$ | ¹H-NMR (DMSO-$d_6$, 400 MHz): δ 10.56 (s, 1H), 8.00-7.95 (m, 2H), 7.69-7.64 (m, 2H), 7.57-7.54 (m, 1H), 7.40 (t, J = 8.8 Hz, 1H), 7.04-7.03 (m, 2H), 2.10 (s, 1H). |
| HBV-CSU-379-ISO-II | 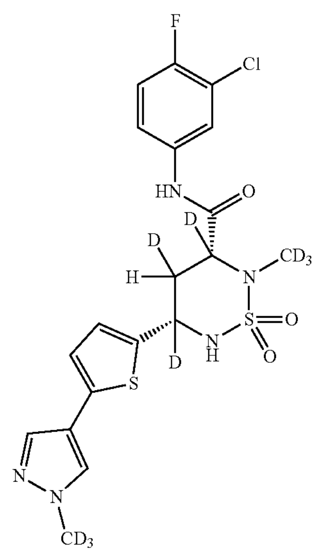 [SMILES: [2H]C1[C@]([2H])(C(=O)Nc2ccc(F)c(Cl)c2)N(C([2H])([2H])[2H])S(=O)(=O)N[C@]1([2H])c1ccc(-c2cnn(C([2H])([2H])[2H])c2)s1] | 8% | 493.15 (M + 1) | 492.12 for $C_{19}H_{10}D_9ClFN_5O_3S_2$ | ¹H-NMR (DMSO-$d_6$, 400 MHz): δ 10.56 (s, 1H), 8.00-7.95 (m, 2H), 7.69-7.65 (m, 2H), 7.56-7.54 (m, 1H), 7.40 (t, J = 8.8 Hz, 1H), 7.04-7.03 (m, 2H), 2.10 (s, 1H). |
| HBV-CSU-383 | 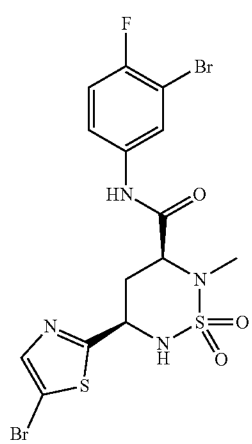 [SMILES: CN1[C@H](C(=O)Nc2ccc(F)c(Br)c2)C[C@H](c2ncc(Br)s2)NS1(=O)=O] | 67% | 528.95 (M + 2) | 525.88 for $C_{14}H_{13}Br_2FN_4O_3S_2$ | ¹H-NMR (DMSO-$d_6$, 400 MHz): δ 10.58 (s, 1H), 8.10 (dd, J = 6.4, 2.4 Hz, 1H), 7.97-7.95 (m, 1H), 7.90 (s, 1H), 7.63-7.59 (m, 1H), 7.38 (t, J = 8.8 Hz, 1H), 4.95-4.92 (m, 1H), 4.37-4.33 (m, 1H), 2.63 (s, 3H), 2.39-2.35 (m, 1H), 2.17-2.13 (m, 1H). |

TABLE 2-continued

Analytical data for HBV-CSU racemic & pure enantiomers:

| Target No | Structure | Rx. Yield (%) | Mass Spec. Found (m/z) | Mass Spec. Calculated | $^1$H-NMR |
|---|---|---|---|---|---|
| HBV-CSU-391 | 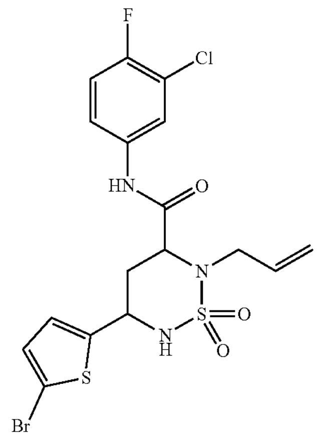 [SMILES: C=CCN1C(C(=O)Nc2ccc(F)c(Cl)c2)CC(c2ccc(Br)s2)NS1(=O)=O] | 65% | 510.10 (M + 1) | 506.95 for $C_{17}H_{16}BrClFN_3O_3$ | $^1$H-NMR (DMSO-$d_6$, 400 MHz): δ 10.54 (s, 1H), 7.89 (dd, J = 6.9, 2.5 Hz, 1H), 7.60-7.47 (m, 2H), 7.37 (t, J = 9.1 Hz, 1H), 7.12 (d, J = 3.9 Hz, 1H), 6.98 (d, J = 3.9 Hz, 1H), 5.91-5.76 (m, 1H), 5.14-4.98 (m, 2H), 4.75 (d, J = 11.3 Hz, 1H), 4.42-4.39 (m, 1H), 3.87-3.85 (m, 1H), 3.59-3.55 (m, 1H), 2.24-2.20 (m, 1H), 2.10-1.95 (m, 1H). |
| HBV-CSU-394 | 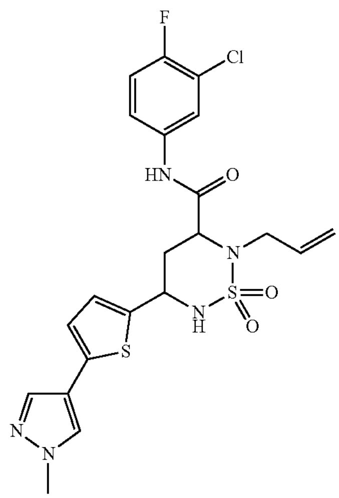 [SMILES: C=CCN1C(C(=O)Nc2ccc(F)c(Cl)c2)CC(c2ccc(-c3cnn(C)c3)s2)NS1(=O)=O] | 10% | 510.1 (M + 1) | 509.08 for $C_{21}H_{21}ClFN_5O_3S_2$ | $^1$H-NMR (DMSO-$d_6$, 400 MHz): δ 10.35 (s, 1H), 8.02-8.01 (m, 1H), 7.95-7.92 (m, 1H), 7.74-7.69 (m, 1H), 7.58-7.53 (m, 2H), 7.39 (t, J = 9.1 Hz, 1H), 7.08 (d, J = 3.2 Hz, 1H), 7.04 (d, J = 3.2 Hz, 1H), 5.76-5.63 (m, 1H), 5.16-4.89 (m, 3H), 4.49-4.32 (m, 1H), 3.84 (s, 3H), 3.80-3.74 (m, 1H), 3.41-3.35 (m, 1H), 2.26-2.22 (m, 1H), 2.13-1.99 (m, 1H). |
| HBV-CSU-395 | 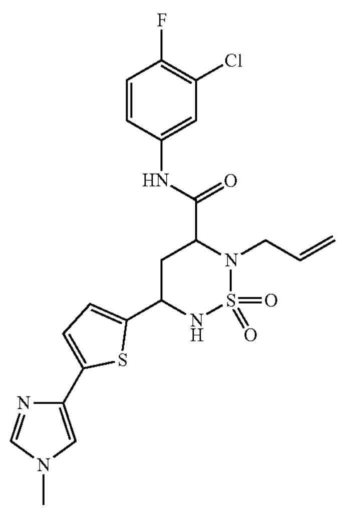 [SMILES: C=CCN1C(C(=O)Nc2ccc(F)c(Cl)c2)CC(c2ccc(-c3cn(C)cn3)s2)NS1(=O)=O] | 5% | 510.05 (M + 1) | 509.08 for $C_{21}H_{21}ClFN_5O_3S_2$ | $^1$H-NMR (DMSO-$d_6$, 400 MHz): δ 10.56 (s, 1H), 7.93-7.91 (m, 1H), 7.62-7.45 (m, 4H), 7.40 (t, J = 9.1 Hz, 1H), 7.09 (d, J = 3.6 Hz, 1H), 7.03-7.00 (m, 1H), 5.91-5.84 (m, 1H), 5.16-5.00 (m, 2H), 4.81-4.72 (m, 1H), 4.46-4.43 (m, 1H), 3.98-3.87 (m, 1H), 3.66 (s, 3H), 3.61-3.55 (m, 1H), 2.28-2.19 (m, 1H), 2.14-2.05 (m, 1H). |

TABLE 2-continued

Analytical data for HBV-CSU racemic & pure enantiomers:

| Target No | Structure | Rx. Yield (%) | Mass Spec. Found (m/z) | Mass Spec. Calculated | ¹H-NMR |
|---|---|---|---|---|---|
| HBV-CSU-396 | 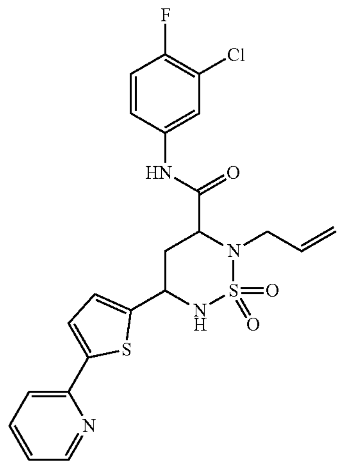 [SMILES: C=CCN1C(C(=O)Nc2ccc(F)c(Cl)c2)CC(c2ccc(-c3ccccn3)s2)NS1(=O)=O] | 10% | 507 (M + 1) | 506.06 for $C_{22}H_{20}ClFN_4O_3S_2$ | ¹H-NMR (DMSO-$d_6$, 400 MHz): δ 10.57 (s, 1H), 8.55-8.49 (m, 1H), 7.93-7.89 (m, 2H), 7.85-7.83 (m, 1H), 7.74-7.68 (m, 2H), 7.54-7.49 (m, 1H), 7.39 (t, J = 9.1 Hz, 1H), 7.31-7.23 (m, 1H), 7.19-7.17 (m, 1H), 5.93-5.75 (m, 1H), 5.17-5.00 (m, 2H), 4.83 (t, J = 9.9 Hz, 1H), 4.47 (dd, J = 11.8, 2.8 Hz, 1H), 3.94 (dd, J = 16.4, 5.2 Hz, 1H), 3.60 (dd, J = 16.4, 7.2 Hz, 1H), 2.30-2.26 (m, 1H), 2.17-2.07 (m, 1H). |
| HBV-CSU-411 | 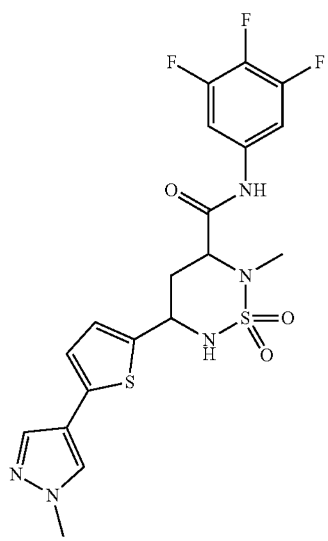 [SMILES: CN1C(C(=O)Nc2cc(F)c(F)c(F)c2)CC(c2ccc(-c3cnn(C)c3)s2)NS1(=O)=O] | 26% | 486.05 (M + 1) | 485.08 for $C_{19}H_{18}F_3N_5O_3S_2$ | ¹H-NMR (DMSO-$d_6$, 400 MHz): δ 10.73 (s, 1H), 8.03 (s, 1H), 7.70-7.68 (m, 2H), 7.62-7.58 (m, 2H), 7.04-7.03 (m, 2H), 4.90-4.80 (m, 1H), 4.70-4.50 (m, 1H), 3.84 (s, 3H), 2.62 (s, 3H), 2.20-2.15 (m, 2H). |
| HBV-CSU-413 | 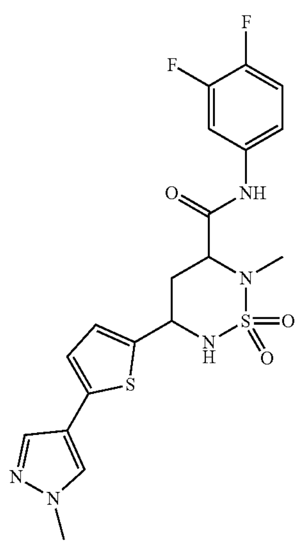 [SMILES: CN1C(C(=O)Nc2ccc(F)c(F)c2)CC(c2ccc(-c3cnn(C)c3)s2)NS1(=O)=O] | 31% | 468 (M + 1) | 467.09 for $C_{19}H_{19}F_2N_5O_3S_2$ | ¹H-NMR (DMSO-$d_6$, 400 MHz): δ 10.60 (s, 1H), 8.01 (s, 1H), 7.84-7.80 (m, 1H), 7.70-7.67 (m, 2H), 7.44-7.39 (m, 2H), 7.04 (s, 2H), 4.80-4.75 (m, 1H), 4.32-4.28 (m, 1H), 3.84 (s, 3H), 2.61 (s, 3H), 2.22-2.12 (m, 2H). |

TABLE 2-continued
Analytical data for HBV-CSU racemic & pure enantiomers:
| Target No | Structure | Rx. Yield (%) | Mass Spec. Found (m/z) | Mass Spec. Calculated | $^1$H-NMR |
|---|---|---|---|---|---|
| HBV-CSU-415 | 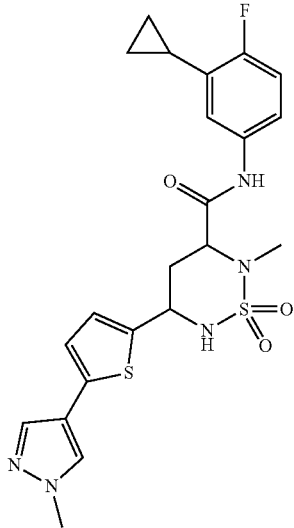 [SMILES: CN1C(C(=O)Nc2ccc(F)c(C3CC3)c2)CC(c2ccc(-c3cnn(C)c3)s2)NS1(=O)=O] | 29% | 490.20 (M + 1) | 489.13 for $C_{22}H_{24}FN_5O_3S_2$ | $^1$H-NMR (DMSO-$d_6$, 400 MHz): δ 10.27 (s, 1H), 7.99 (s, 1H), 7.84-7.80 (m, 1H), 7.68-7.62 (m, 2H), 7.50-7.45 (m, 1H), 7.10-7.05 (m, 1H), 7.02 (s, 2H), 4.75-4.70 (m, 1H), 4.32-4.22 (m, 1H), 3.83 (s, 3H), 2.59 (s, 3H), 2.20-2.10 (m, 2H), 2.03-1.99 (m, 1H), 1.00-0.95 (m, 2H), 0.65-0.62 (m, 2H). |
| HBV-CSU-416 | 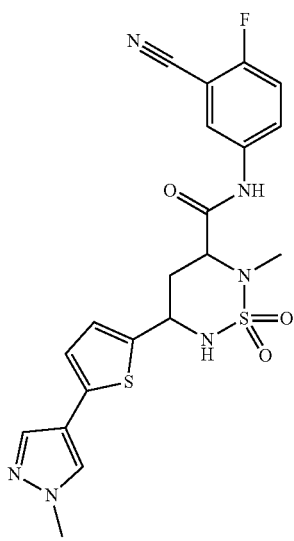 [SMILES: CN1C(C(=O)Nc2ccc(F)c(C#N)c2)CC(c2ccc(-c3cnn(C)c3)s2)NS1(=O)=O] | 34% | 475.10 (M + 1) | 474.09 for $C_{20}H_{19}FN_6O_3S_2$ | $^1$H-NMR (DMSO-$d_6$, 400 MHz): δ 10.74 (s, 1H), 8.19-8.17 (m, 1H), 8.01 (s, 1H), 7.95-7.91 (m, 1H), 7.70-7.68 (m, 2H), 7.54 (t, J = 8.8 Hz, 1H), 7.04 (s, 2H), 4.78-4.73 (m, 1H), 4.36-4.32 (m, 1H), 3.83 (s, 3H), 2.62 (s, 3H), 2.25-2.07 (m, 2H). |

TABLE 2-continued

Analytical data for HBV-CSU racemic & pure enantiomers:

| Target No | Structure | Rx. Yield (%) | Mass Spec. Found (m/z) | Mass Spec. Calculated | ¹H-NMR |
|---|---|---|---|---|---|
| HBV-CSU-417 | 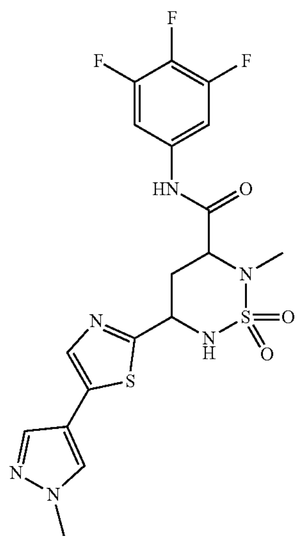 [SMILES: CN1C(C(=O)Nc2cc(F)c(F)c(F)c2)CC(c2ncc(-c3cnn(C)c3)s2)NS1(=O)=O] | 40% | 487.15 (M + 1) | 486.08 for $C_{18}H_{17}F_3N_6O_3S_2$ | ¹H-NMR (DMSO-$d_6$, 400 MHz): δ 10.73 (s, 1H), 8.12 (s, 1H), 7.91 (d, J = 10 Hz, 1H), 7.87 (s, 1H), 7.79 (s, 1H), 7.62-7.58 (m, 2H), 4.93-4.88 (m, 1H), 4.42-4.39 (m, 1H), 3.86 (s, 3H), 2.62 (s, 3H), 2.38-2.34 (m, 1H), 2.21-2.14 (m, 1H). |
| HBV-CSU-421 | 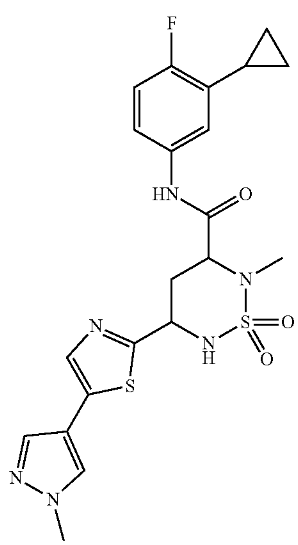 [SMILES: CN1C(C(=O)Nc2ccc(F)c(C3CC3)c2)CC(c2ncc(-c3cnn(C)c3)s2)NS1(=O)=O] | 27% | 491.10 (M + 1) | 490.13 for $C_{21}H_{23}FN_6O_3S_2$ | ¹H-NMR (DMSO-$d_6$, 400 MHz): δ 10.30 (s, 1H), 8.11 (s, 1H), 7.91-7.86 (m, 2H), 7.79 (s, 1H), 7.50-7.48 (m, 1H), 7.23-7.22 (m, 1H), 7.10 (t, J = 9.2 Hz, 1H), 4.92-4.86 (m, 1H), 4.33-4.30 (m, 1H), 3.86 (s, 3H), 2.62 (s, 3H), 2.37-2.33 (m, 1H), 2.23-2.17 (m, 1H), 2.04-2.03 (m, 1H), 1.00-0.98 (m, 2H), 0.66-0.65 (m, 2H). |

TABLE 2-continued

Analytical data for HBV-CSU racemic & pure enantiomers:

| Target No | Structure | Rx. Yield (%) | Mass Spec. Found (m/z) | Mass Spec. Calculated | $^1$H-NMR |
|---|---|---|---|---|---|
| HBV-CSU-422 | 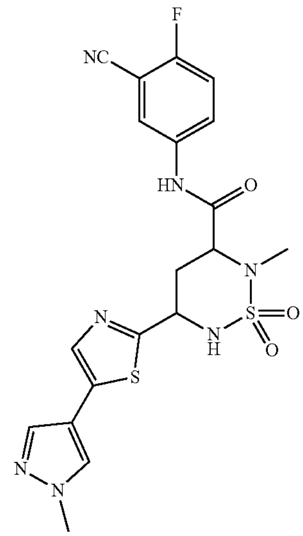 [SMILES: CN1C(C(=O)Nc2ccc(F)c(C#N)c2)CC(c2ncc(-c3cnn(C)c3)s2)NS1(=O)=O] | 14% | 476 (M + 1) | 475.09 for $C_{19}H_{18}FN_7O_3S_2$ | $^1$H-NMR (DMSO-d$_6$, 400 MHz): 10.73 (s, 1H), 8.18 8.16 (m, 1H), 8.11 (s, 1H), 7.98-7.91 (m, 2H), 7.87 (s, 1H), 7.79 (s, 1H), 7.54 (t, J = 9.1 Hz, 1H), 4.97-4.86 (m, 1H), 4.42-4.38 (m, 1H), 3.86 (s, 3H), 2.64 (s, 3H), 2.41-2.33 (m, 1H), 2.24-2.14 (m, 1H). |
| HBV-CSU-423 | 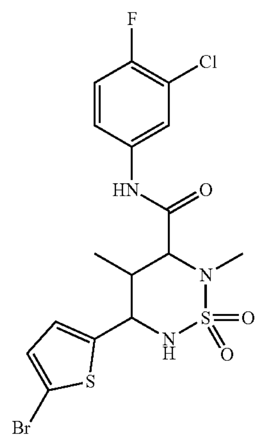 | 58% | 496 (M$^+$) | 494.95 for $C_{16}H_{16}BrClFN_3O_3S_2$ | $^1$H-NMR (DMSO-d$_6$, 400 MHz): δ 10.78 (s, 1H), 10.06 (s, 2H), 7.98-6.90 (m, 18H), 5.07-5.06 (m, 2H), 4.50-4.48 (m, 1H), 4.30-4.29 (m, 2H), 3.77-3.74 (m, 1H), 3.01 (s, 6H), 2.72-2.59 (m, 4H), 2.56-2.25 (m, 2H), 0.99 (d, J = 7.2 Hz, 6H), 0.69 (d, J = 6.4 Hz, 3H). NMR hints for three Diastereomers. |
| HBV-CSU-424 | 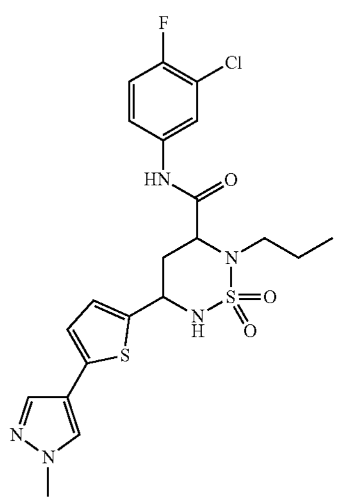 | 57% | 512.10 (M + 1) | 511.09 for $C_{21}H_{23}ClFN_5O_3S_2$ | $^1$H-NMR (DMSO-d$_6$, 400 MHz): δ 10.33 (s, 1H), 8.03 (s, 1H), 7.94 (dd, J = 6.9, 2.6 Hz, 1H), 7.72 (s, 1H), 7.58-7.53 (m, 1H), 7.39 (t, J = 9.1 Hz, 2H), 7.13 (d, J = 3.6 Hz, 1H), 7.07 (d, J = 3.6 Hz, 1H), 4.98 (d, J = 10.6 Hz, 1H), 4.99-4.96 (m, 1H), 4.35-4.33 (m, 1H), 3.84 (s, 3H), 3.09-3.01 (m, 1H), 2.75-2.62 (m, 1H), 2.20-2.16 (m, 1H), 2.09-1.96 (m, 1H), 1.39-1.31 (m, 2H), 0.63 (t, J = 7.4 Hz, 3H). |

TABLE 2-continued

Analytical data for HBV-CSU racemic & pure enantiomers:

| Target No | Structure | Rx. Yield (%) | Mass Spec. Found (m/z) | Mass Spec. Calculated | $^1$H-NMR |
|---|---|---|---|---|---|
| HBV-CSU-425 | 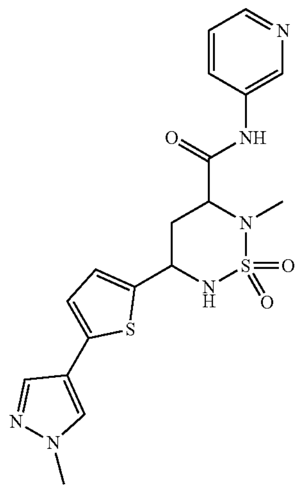 [SMILES: CN1C(C(=O)Nc2cccnc2)CC(c2ccc(-c3cnn(C)c3)s2)NS1(=O)=O] | 21% | 433.10 (M + 1) | 432.10 for $C_{18}H_{20}N_6O_3S_2$ | $^1$H-NMR (DMSO-$d_6$, 400 MHz): δ 10.58 (s, 1H), 8.81 1H), 8.31 (d, J = 4.8 Hz, 1H), 8.10-8.07 (m, 1H), 8.00 (s, 1H), 7.70-7.66 (m, 2H), 7.39-7.36 (m, 1H), 7.04 (s, 2H), 4.76 (t, J = 8.8 Hz, 1H), 4.37-4.34 (m, 1H), 3.84 (s, 3H), 2.63 (s, 3H), 2.33-1.98 (m, 2H). |
| HBV-CSU-427 | 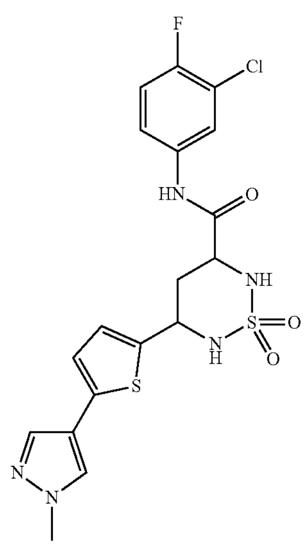 [SMILES: Cn1cc(-c2ccc(C3CC(C(=O)Nc4ccc(F)c(Cl)c4)NS(=O)(=O)N3)s2)cn1] | 5% | 470.05 (M + 1) | 469.04 for $C_{18}H_{17}ClFN_5O_3S_2$ | $^1$H-NMR (DMSO-$d_6$, 400 MHz): δ 10.38 (s, 1H), 8.00 (s, 1H), 7.94 (dd, J = 7.0, 2.5 Hz, 1H), 7.69 (s, 1H), 7.55-7.52 (m, 1H), 7.40 (t, J = 8.8 Hz, 1H), 7.04-7.02 (m, 3H), 6.49-6.47 (m, 1H), 4.76-4.74 (m, 1H), 4.35-4.32 (m, 1H), 3.84 (s, 3H), 2.31-2.28 (m, 1H), 1.85-1.75 (m, 1H). |

TABLE 2-continued

Analytical data for HBV-CSU racemic & pure enantiomers:

| Target No | Structure | Rx. Yield (%) | Mass Spec. Found (m/z) | Mass Spec. Calculated | $^1$H-NMR |
|---|---|---|---|---|---|
| HBV-CSU-428 | 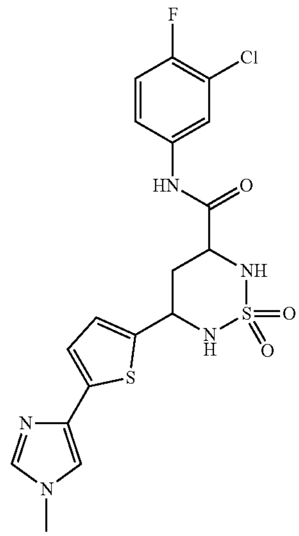 [SMILES: Cn1cnc(-c2ccc(C3CC(C(=O)Nc4ccc(F)c(Cl)c4)NS(=O)(=O)N3)s2)c1] | 6% | 470 (M + 1) | 469.04 for $C_{18}H_{17}ClFN_5O_3S_2$ | $^1$H-NMR (DMSO-$d_6$, 400 MHz): δ 10.38 (s, 1H), 8.00 (s, 1H), 7.95-7.93 (m, 1H), 7.69 (s, 1H), 7.55-7.52 (m, 1H), 7.40 (t, J = 8.8 Hz, 1H), 7.05-7.03 (m, 3H), 6.49-6.47 (m, 1H), 4.80-4.70 (m, 1H), 4.36-4.32 (m, 1H), 3.84 (s, 3H), 2.31-2.28 (m, 1H), 1.82-1.78 (m, 1H). |
| HBV-CSU-429 | 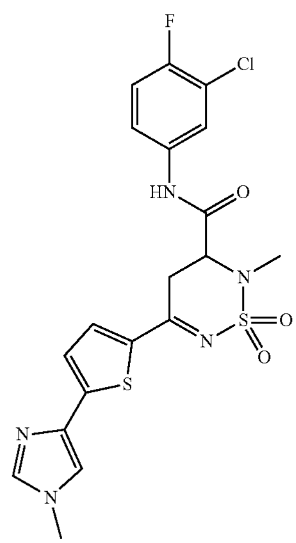 [SMILES: CN1C(C(=O)Nc2ccc(F)c(Cl)c2)CC(c2ccc(-c3cn(C)cn3)s2)=NS1(=O)=O] | 70% | 482.05 (M + 1) | 481.04 for $C_{19}H_{17}ClFN_5O_3S_2$ | $^1$H-NMR (DMSO-$d_6$, 400 MHz): δ 10.53 (s, 1H), 8.02 (d, J = 4.4 Hz, 1H), 7.97 (dd, J = 6.8, 2.4 Hz, 1H), 7.80 (s, 1H), 7.72 (s, 1H), 7.63-7.59 (m, 1H), 7.43-7.38 (m, 2H), 4.84-4.80 (m, 1H), 3.70 (s, 3H), 3.40-3.35 (m, 2H), 2.78 (s, 3H). |
| HBV-CSU-435 | 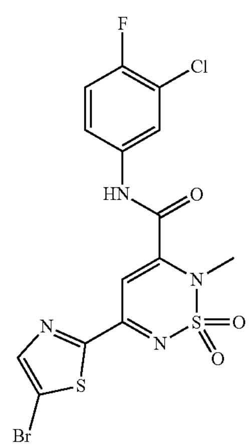 [SMILES: CN1C(C(=O)Nc2ccc(F)c(Cl)c2)=CC(c2ncc(Br)s2)=NS1(=O)=O] | 59% | 480.95 (M + 2) | 477.90 for $C_{14}H_9BrClFN_4O_3S_2$ | $^1$H-NMR (DMSO-$d_6$, 400 MHz): δ 11.39 (s, 1H), 8.35 (s, 1H), 7.98-7.95 (m, 1H), 7.62-7.58 (m, 1H), 7.51 (t, J = 8.8 Hz, 1H), 7.13 (s, 1H), 3.52 (s, 3H). |

Stereochemistry of the Examples:

The Crystal structure of HBV-CSU-016-ISO-I is shown in FIG. 1. Displacement ellipsoids are drawn at the 30% probability level and H atoms are shown as small spheres of arbitrary radii. Dashed line indicates hydrogen bond. The Crystal data and structure refinement for HBV-CSU-016-ISO-I are as follows:

| | |
|---|---|
| Identification code | SAP-MA1703-08(isomer-1) (IICT file code: KA84_0m) |
| Empirical formula | $C_{15}H_{15}BrF\ N_3O_3S_2$ |
| Formula weight | 448.33 |
| Temperature | 100(2) K |
| Wavelength | 0.71073 Å |
| Crystal system | Monoclinic |
| Space group | $P2_1$ |
| Unit cell dimensions | a = 5.001(6) Å   α = 90°. |
| | b = 25.63(3) Å   β = 94.240(19)°. |
| | c = 13.390(16) Å   γ = 90°. |
| Volume | 1712(4) Å$^3$ |
| Z | 4 |
| Density (calculated) | 1.740 Mg/m$^3$ |
| Absorption coefficient | 2.676 mm$^{-1}$ |
| F(000) | 904 |
| Crystal size | 0.310 × 0.240 × 0.190 mm$^3$ |
| θ range for data collection | 2.830 to 28.374°. |
| Index ranges | −6 <= h <= 6, −34 <= k <= 34, −17 <= l <= 17 |
| Reflections collected | 50333 |
| Independent reflections | 8467 [R(int) = 0.0361] |
| Completeness to θ = 25.242° | 99.8% |
| Refinement method | Full-matrix least-squares on F$^2$ |
| Data/restraints/parameters | 8467/1/469 |
| Goodness-of-fit on F$^2$ | 1.022 |
| Final R indices [I > 2σ(I)] | R1 = 0.0265, wR2 = 0.0596 |
| R indices (all data) | R1 = 0.0313, wR2 = 0.0610 |
| Absolute structure parameter | 0.034(2) |
| Largest diff. peak and hole | 0.311 and −0.513 e · Å$^{-3}$ |
| Measurement | Bruker D8 QUEST PHOTON-100 Detector |
| Software Used | SHELXTL-PLUS |

The absolute stereochemistry at each chiral center was assigned using the PLATON computer application as described by A. L. Spek in J. APPL. CRYST. 36, 7-13, 2003. The designated chiral centers are:

C(1A) Chiral: R
C(1B) Chiral: R
C(3A) Chiral: S
C(3B) Chiral: S

The absolute stereochemistry of all other sets of enantiomers were assigned based on this crystal structure determination. In each case only one of the stereoisomers of the pair had significant activity and the active isomer was assigned the same stereochemistry as HBV-CSU-016-ISO-I.

Assay Measuring Activity of Test Compounds on Viral Production from HepAD38 Cells HepAD38 cells grown in a T-150 flask (Corning, cat #: 430825) with Growth Medium (DMEM/F12 (1:1) (Hyclone, cat #: SH30023.02), 1×Pen/Strep (Invitrogen, cat #: 15140-122), 10% FBS (Tissue Culture Biologics, cat #: 101), 250 µg/mL G418 (Alfa Aesar, cat #: J62671), 1 µg/mL Tetracycline (Teknova, cat #: T3320)) were detached with 0.25% trypsin-EDTA (Invitrogen, cat #: 25200-056). Tetracycline-free treatment medium (15 mL DMEM/F12 (1:1) 1× Pen/step, with 2% FBS, Tet-system approved (Clontech, cat #: 631106) were then added to mix, transferred into a 50 ml conical tube (Falcon, cat #: 21008-918) and spun at 1300 rpm for 5 min. Pelleted cells were then re-suspended/washed with 50 mL of 1×DPBS (Invitrogen, cat #: 14190-136) 2 times and 50 mL treatment medium twice. HepAD38 cells were then re-suspended with 10 mL of treatment medium, syringed and counted. Wells of 96-well clear bottom TC plate (Corning, cat #: 3904) were seeded at 50,000 cells/well in 180 µL of treatment medium, and 20 µL of either 10% DMSO (Sigma, cat #: D4540) as controls or a 10× solution of test compounds in 10% DMSO in treatment media was added for a final compound concentration starting at 10 µM, and plates were incubated in 5% $CO_2$ incubator at 37° C. for 5 days.

Subsequently viral load production was assayed by quantitative PCR (qPCR) of the HBV core sequence. PCR reaction mixture containing forward primers HBV-f 5'-CTGTGCCTTGGGTGGCTTT-3', which is SEQ ID NO 1, (IDT DNA), Reverse primers HBV-r 5'-AAGGAAAGAAGTCAGAAGGCAAAA-3', which is SEQ ID NO 2 (IDT DNA), Fluorescent TaqMan™ Probes HBV-probe 5'-FAM/AGCTCCAAA/ZEN/TTCTT-TATAAGGGTCGATGTC/3IABkFQ-3' (IDT DNA), which is SEQ ID NO 3, 10 µL/well of PerfeCTa® qPCR ToughMix® (Quanta Biosciences, Cat #: 95114-05K), and 6 L/well of DEPC water (Alfa Aesar, cat #: J62087) was prepared. Four µL of supernatant was added to 16 µL of the reaction mixture in a qPCR plate (Applied Biosytems, Cat #: 4309849), sealed with a film (Applied Biosystems, Cat #: 4311971), centrifuged for a few seconds, and subsequently run on an Applied Biosystems VIIA7. The PCR mixture was incubated at 45° C. for 5 min, then 95° C. for 10 min, followed by 40 cycles of 10 seconds at 95° C. and 20 seconds at 60° C. Viral load was quantified against known HBV DNA standards by using ViiA™ 7 Software. Viral load in the supernatant from wells with treated cells were compared against viral load in supernatant from DMSO control wells (≥3 per plate). Cell viability assay was performed with CellTiter-Glo Luminescent Cell Viability Assay (Promega, cat #: G7573) with modification. Mixed appropriate amount of CellTiter-Glo (CTG) 1×DPBS in a 1:1 ratio, added 100 uL of the mixture to each well followed completely removal of all supernatant in each well without touching cell surface. Incubated the plate at room temperature for 10 min on an orbital shaker, and then read the plate with a plate reader (TECAN M1000 or Envision). $EC_{50}$ or $CC_{50}$ values were calculated through curve-fitting of the four-parameter non-linear-logistic-regression model (GraphPad Prism or Dotmatics). $CC_{50}$ values were all >10 µM.

Table 3 gives the viral load lowering $EC_{50}$ values grouped in the following ranges: A indicates $EC_{50}$<1 µM; B indicates $EC_{50}$ 1-5 µM; C indicates $EC_{50}$>5 µM.

TABLE 3

| Compound | Viral Load $EC_{50}$ Activity range |
|---|---|
| HBV-CSU-006 | A |
| HBV-CSU-007 | A |
| HBV-CSU-010 | A |
| HBV-CSU-010-ISO-I | A |
| HBV-CSU-011 | A |
| HBV-CSU-012 | B |
| HBV-CSU-013 | A |
| HBV-CSU-014 | B |
| HBV-CSU-015 | B |
| HBV-CSU-016 | A |
| HBV-CSU-016-ISO-I | A |
| HBV-CSU-017 | A |
| HBV-CSU-017-ISO-I | A |
| HBV-CSU-018 | B |
| HBV-CSU-019 | C |
| HBV-CSU-020 | A |
| HBV-CSU-020-ISO-I | A |
| HBV-CSU-023 | B |

TABLE 3-continued

| Compound | Viral Load EC$_{50}$ Activity range |
|---|---|
| HBV-CSU-024 | A |
| HBV-CSU-025 | A |
| HBV-CSU-025-ISO-I | C |
| HBV-CSU-025-ISO-II | A |
| HBV-CSU-027 | A |
| HBV-CSU-027-ISO-I | C |
| HBV-CSU-029-ISO-I | A |
| HBV-CSU-031 | A |
| HBV-CSU-031-ISO-I | A |
| HBV-CSU-031-ISO-II | C |
| HBV-CSU-032 | A |
| HBV-CSU-032-ISO-I | A |
| HBV-CSU-032-ISO-II | C |
| HBV-CSU-033 | A |
| HBV-CSU-036 | A |
| HBV-CSU-040 | A |
| HBV-CSU-041 | C |
| HBV-CSU-043-ISO-I | C |
| HBV-CSU-043-ISO-II | C |
| HBV-CSU-044-ISO-II | C |
| HBV-CSU-044-ISO-I | C |
| HBV-CSU-045 | A |
| HBV-CSU-045-ISO-I | A |
| HBV-CSU-046-ISO-I | A |
| HBV-CSU-047-ISO-I | A |
| HBV-CSU-048-ISO-I | A |
| HBV-CSU-049-ISO-I | A |
| HBV-CSU-050-ISO-I | B |
| HBV-CSU-050-ISO-II | C |
| HBV-CSU-054-ISO-I | C |
| HBV-CSU-054-ISO-II | B |
| HBV-CSU-055-ISO-I | A |
| HBV-CSU-055-ISO-II | C |
| HBV-CSU-056-ISO-I | A |
| HBV-CSU-056-ISO-II | C |
| HBV-CSU-057 | A |
| HBV-CSU-058 | A |
| HBV-CSU-058-ISO-I | C |
| HBV-CSU-058-ISO-II | A |
| HBV-CSU-059 | A |
| HBV-CSU-059-ISO-I | C |
| HBV-CSU-059-ISO-II | A |
| HBV-CSU-060-ISO-I | C |
| HBV-CSU-060-ISO-II | A |
| HBV-CSU-064 | C |
| HBV-CSU-071 | B |
| HBV-CSU-071-ISO-I | A |
| HBV-CSU-071-ISO-II | B |
| HBV-CSU-072 | A |
| HBV-CSU-072-ISO-I | C |
| HBV-CSU-072-ISO-II | A |
| HBV-CSU-073 | C |
| HBV-CSU-074 | C |
| HBV-CSU-077-ISO-I | C |
| HBV-CSU-077-ISO-II | A |
| HBV-CSU-078 | B |
| HBV-CSU-078-ISO-I | A |
| HBV-CSU-078-ISO-II | C |
| HBV-CSU-079-Rac-A | A |
| HBV-CSU-079-Rac-B | A |
| HBV-CSU-082 | C |
| HBV-CSU-083 | C |
| HBV-CSU-083-ISO-I | C |
| HBV-CSU-083-ISO-II | C |
| HBV-CSU-089-ISO-I | A |
| HBV-CSU-089-ISO-II | C |
| HBV-CSU-090 | A |
| HBV-CSU-090-ISO-I | A |
| HBV-CSU-090-ISO-II | C |
| HBV-CSU-092 | B |
| HBV-CSU-092-ISO-I | A |
| HBV-CSU-092-ISO-II | C |
| HBV-CSU-093 | C |
| HBV-CSU-093-ISO-I | B |
| HBV-CSU-093-ISO-II | C |
| HBV-CSU-094-ISO-I | C |
| HBV-CSU-094-ISO-II | A |
| HBV-CSU-095 | B |
| HBV-CSU-095-ISO-I | B |
| HBV-CSU-095-ISO-II | B |
| HBV-CSU-096 | B |
| HBV-CSU-096-ISO-I | C |
| HBV-CSU-096-ISO-II | A |
| HBV-CSU-097 | C |
| HBV-CSU-097-ISO-I | C |
| HBV-CSU-097-ISO-II | C |
| HBV-CSU-101-ISO-I | C |
| HBV-CSU-101-ISO-II | C |
| HBV-CSU-102 | C |
| HBV-CSU-102-ISO-I | C |
| HBV-CSU-102-ISO-II | C |
| HBV-CSU-103 | C |
| HBV-CSU-103-ISO-I | C |
| HBV-CSU-103-ISO-II | B |
| HBV-CSU-108 | C |
| HBV-CSU-109 | A |
| HBV-CSU-109-ISO-I | C |
| HBV-CSU-109-ISO-II | A |
| HBV-CSU-110 | C |
| HBV-CSU-111 | B |
| HBV-CSU-112 (Cis) | A |
| HBV-CSU-112-ISO-I | A |
| HBV-CSU-112-ISO-II | C |
| HBV-CSU-113-ISO-I | A |
| HBV-CSU-113-ISO-II | C |
| HBV-CSU-114 | A |
| HBV-CSU-114-ISO-I | A |
| HBV-CSU-114-ISO-II | C |
| HBV-CSU-114-Trans (Rac) | C |
| HBV-CSU-114-Trans-ISO-I | B |
| HBV-CSU-114-Trans-ISO-II | B |
| HBV-CSU-115 | A |
| HBV-CSU-115-ISO-I | A |
| HBV-CSU-115-ISO-II | C |
| HBV-CSU-116-ISO-I | A |
| HBV-CSU-116-ISO-II | B |
| HBV-CSU-117 | A |
| HBV-CSU-117-ISO-I | A |
| HBV-CSU-117-ISO-II | B |
| HBV-CSU-120 | A |
| HBV-CSU-122 | A |
| HBV-CSU-122-ISO-I | A |
| HBV-CSU-122-ISO-II | B |
| HBV-CSU-122-Trans-ISO-I | B |
| HBV-CSU-122-Trans-ISO-II | B |
| HBV-CSU-123 | A |
| HBV-CSU-123-ISO-I | A |
| HBV-CSU-123-ISO-II | C |
| HBV-CSU-124 | A |
| HBV-CSU-124-ISO-I | A |
| HBV-CSU-124-ISO-II | B |
| HBV-CSU-142 | A |
| HBV-CSU-142-ISO-I | B |
| HBV-CSU-142-ISO-II | A |
| HBV-CSU-143 | A |
| HBV-CSU-146 | A |
| HBV-CSU-146-ISO-I | A |
| HBV-CSU-146-ISO-II | C |
| HBV-CSU-147 | A |
| HBV-CSU-147-ISO-I | A |
| HBV-CSU-147-ISO-II | C |
| HBV-CSU-148-ISO-I | A |
| HBV-CSU-148-ISO-II | B |
| HBV-CSU-149-ISO-I | A |
| HBV-CSU-149-ISO-II | B |
| HBV-CSU-150 | A |
| HBV-CSU-156 | A |
| HBV-CSU-156-ISO-I | A |
| HBV-CSU-156-ISO-II | C |

TABLE 3-continued

| Compound | Viral Load EC$_{50}$ Activity range |
|---|---|
| HBV-CSU-157 | B |
| HBV-CSU-158 | B |
| HBV-CSU-158-ISO-I | A |
| HBV-CSU-158-ISO-II | C |
| HBV-CSU-159 | A |
| HBV-CSU-159-ISO-I | B |
| HBV-CSU-159-ISO-II | A |
| HBV-CSU-160 | A |
| HBV-CSU-160-ISO-I | A |
| HBV-CSU-160-ISO-II | B |
| HBV-CSU-161 | A |
| HBV-CSU-161-ISO-I | A |
| HBV-CSU-161-ISO-II | B |
| HBV-CSU-161-Trans (Rac) | B |
| HBV-CSU-162 | A |
| HBV-CSU-162-ISO-I | A |
| HBV-CSU-162-ISO-II | B |
| HBV-CSU-163 | A |
| HBV-CSU-163-ISO-I | A |
| HBV-CSU-163-ISO-II | A |
| HBV-CSU-164 | A |
| HBV-CSU-164-ISO-I | A |
| HBV-CSU-164-ISO-II | C |
| HBV-CSU-165 | B |
| HBV-CSU-166 | A |
| HBV-CSU-166-ISO-I | A |
| HBV-CSU-166-ISO-II | C |
| HBV-CSU-167-ISO-I | A |
| HBV-CSU-167-ISO-II | C |
| HBV-CSU-168 | A |
| HBV-CSU-168-ISO-I | B |
| HBV-CSU-168-ISO-II | A |
| HBV-CSU-169-ISO-I | A |
| HBV-CSU-169-ISO-II | B |
| HBV-CSU-170 | A |
| HBV-CSU-170-ISO-I | A |
| HBV-CSU-170-ISO-II | A |
| HBV-CSU-171 | A |
| HBV-CSU-171-ISO-I | A |
| HBV-CSU-173 | A |
| HBV-CSU-173-ISO-I | A |
| HBV-CSU-173-ISO-II | C |
| HBV-CSU-175 | A |
| HBV-CSU-175-ISO-I | A |
| HBV-CSU-175-ISO-II | A |
| HBV-CSU-176 | A |
| HBV-CSU-176-ISO-I | A |
| HBV-CSU-176-ISO-II | C |
| HBV-CSU-177 | A |
| HBV-CSU-177-ISO-I | A |
| HBV-CSU-178 | A |
| HBV-CSU-178-ISO-I | A |
| HBV-CSU-178-ISO-II | B |
| HBV-CSU-179 | A |
| HBV-CSU-179-ISO-I | A |
| HBV-CSU-179-ISO-II | B |
| HBV-CSU-188 | A |
| HBV-CSU-200 | A |
| HBV-CSU-201 | A |
| HBV-CSU-202 | A |
| HBV-CSU-204 | A |
| HBV-CSU-205 | A |
| HBV-CSU-208 | A |
| HBV-CSU-208-ISO-I | C |
| HBV-CSU-208-ISO-II | A |
| HBV-CSU-209 | A |
| HBV-CSU-210 | A |
| HBV-CSU-210-ISO-I | C |
| HBV-CSU-210-ISO-II | A |
| HBV-CSU-211 | A |
| HBV-CSU-211-ISO-I | A |
| HBV-CSU-211-ISO-II | C |
| HBV-CSU-212 | A |
| HBV-CSU-212-ISO-I | A |
| HBV-CSU-212-ISO-II | C |
| HBV-CSU-213 | A |
| HBV-CSU-214 | A |
| HBV-CSU-214-ISO-I | C |
| HBV-CSU-214-ISO-II | A |
| HBV-CSU-215 | B |
| HBV-CSU-216 | C |
| HBV-CSU-216-ISO-I | B |
| HBV-CSU-216-ISO-II | C |
| HBV-CSU-217 | B |
| HBV-CSU-217-ISO-I | C |
| HBV-CSU-217-ISO-II | A |
| HBV-CSU-218 | B |
| HBV-CSU-218-ISO-I | C |
| HBV-CSU-218-ISO-II | B |
| HBV-CSU-219 | A |
| HBV-CSU-220 | A |
| HBV-CSU-221 | A |
| HBV-CSU-222 | A |
| HBV-CSU-222-ISO-I | A |
| HBV-CSU-222-ISO-II | B |
| HBV-CSU-224 | A |
| HBV-CSU-224-ISO-I | A |
| HBV-CSU-224-ISO-II | C |
| HBV-CSU-226 | B |
| HBV-CSU-230 | A |
| HBV-CSU-230-ISO-I | A |
| HBV-CSU-230-ISO-II | C |
| HBV-CSU-231 | A |
| HBV-CSU-231-ISO-I | A |
| HBV-CSU-231-ISO-II | C |
| HBV-CSU-232 | A |
| HBV-CSU-235 | A |
| HBV-CSU-235-ISO-I | A |
| HBV-CSU-235-ISO-II | C |
| HBV-CSU-238 | A |
| HBV-CSU-238-ISO-I | A |
| HBV-CSU-238-ISO-II | B |
| HBV-CSU-239 | A |
| HBV-CSU-239-ISO-I | A |
| HBV-CSU-239-ISO-II | B |
| HBV-CSU-240-ISO-I | A |
| HBV-CSU-240-ISO-II | B |
| HBV-CSU-241 | A |
| HBV-CSU-241-ISO-I | A |
| HBV-CSU-241-ISO-II | B |
| HBV-CSU-242 | A |
| HBV-CSU-242-ISO-I | A |
| HBV-CSU-242-ISO-II | C |
| HBV-CSU-243 | A |
| HBV-CSU-243-ISO-I | C |
| HBV-CSU-243-ISO-II | A |
| HBV-CSU-244 | A |
| HBV-CSU-244-ISO-I | A |
| HBV-CSU-244-ISO-II | A |
| HBV-CSU-245 | A |
| HBV-CSU-245-ISO-I | A |
| HBV-CSU-245-ISO-II | A |
| HBV-CSU-246 | A |
| HBV-CSU-246-ISO-I | C |
| HBV-CSU-246-ISO-II | A |
| HBV-CSU-247 | A |
| HBV-CSU-247-ISO-I | C |
| HBV-CSU-247-ISO-II | A |
| HBV-CSU-248 | A |
| HBV-CSU-248-ISO-I | A |
| HBV-CSU-248-ISO-II | C |
| HBV-CSU-250 | A |
| HBV-CSU-250-ISO-I | A |
| HBV-CSU-250-ISO-II | B |
| HBV-CSU-252 | A |
| HBV-CSU-252-ISO-I | A |
| HBV-CSU-252-ISO-II | C |
| HBV-CSU-254 | A |
| HBV-CSU-254-ISO-I | A |
| HBV-CSU-254-ISO-II | B |
| HBV-CSU-256 | B |
| HBV-CSU-257 | A |
| HBV-CSU-258 | A |

TABLE 3-continued

| Compound | Viral Load EC$_{50}$ Activity range |
|---|---|
| HBV-CSU-259 | A |
| HBV-CSU-260 | A |
| HBV-CSU-261 | A |
| HBV-CSU-261-ISO-I | A |
| HBV-CSU-261-ISO-II | C |
| HBV-CSU-262 | A |
| HBV-CSU-263 | A |
| HBV-CSU-264 | A |
| HBV-CSU-265 | A |
| HBV-CSU-265-ISO-I | A |
| HBV-CSU-265-ISO-II | C |
| HBV-CSU-266 | A |
| HBV-CSU-266-ISO-I | A |
| HBV-CSU-266-ISO-II | B |
| HBV-CSU-266-Trans-ISO-I | A |
| HBV-CSU-266-Trans-ISO-II | B |
| HBV-CSU-267 | A |
| HBV-CSU-267-ISO-I | A |
| HBV-CSU-267-ISO-II | A |
| HBV-CSU-268 | A |
| HBV-CSU-268-ISO-I | A |
| HBV-CSU-268-ISO-II | C |
| HBV-CSU-269 | A |
| HBV-CSU-269-ISO-I | A |
| HBV-CSU-269-ISO-II | B |
| HBV-CSU-270-ISO-I | A |
| HBV-CSU-270-ISO-II | B |
| HBV-CSU-271 | A |
| HBV-CSU-271-ISO-I | A |
| HBV-CSU-271-ISO-II | B |
| HBV-CSU-272 | A |
| HBV-CSU-272-ISO-I | A |
| HBV-CSU-272-ISO-II | C |
| HBV-CSU-273 | A |
| HBV-CSU-276 | A |
| HBV-CSU-276-ISO-I | A |
| HBV-CSU-276-ISO-II | C |
| HBV-CSU-276-Trans-ISO-I | A |
| HBV-CSU-276-Trans-ISO-II | B |
| HBV-CSU-277 | A |
| HBV-CSU-277-ISO-I | A |
| HBV-CSU-277-ISO-II | C |
| HBV-CSU-278 | A |
| HBV-CSU-278-ISO-I | A |
| HBV-CSU-278-ISO-II | C |
| HBV-CSU-280 | A |
| HBV-CSU-280-ISO-I | B |
| HBV-CSU-280-ISO-II | A |
| HBV-CSU-281 | A |
| HBV-CSU-281-ISO-I | A |
| HBV-CSU-281-ISO-II | B |
| HBV-CSU-283 | A |
| HBV-CSU-284 | A |
| HBV-CSU-284-ISO-I | A |
| HBV-CSU-284-ISO-II | B |
| HBV-CSU-285 | A |
| HBV-CSU-285-ISO-I | A |
| HBV-CSU-285-ISO-II | A |
| HBV-CSU-286 | A |
| HBV-CSU-286-ISO-I | A |
| HBV-CSU-286-ISO-II | B |
| HBV-CSU-288 | A |
| HBV-CSU-288-ISO-I | A |
| HBV-CSU-288-ISO-II | B |
| HBV-CSU-289 | A |
| HBV-CSU-289-ISO-I | A |
| HBV-CSU-289-ISO-II | B |
| HBV-CSU-290 | A |
| HBV-CSU-290-ISO-I | A |
| HBV-CSU-290-ISO-II | B |
| HBV-CSU-291 | A |
| HBV-CSU-291-ISO-I | A |
| HBV-CSU-291-ISO-II | C |
| HBV-CSU-292-ISO-I | A |
| HBV-CSU-292-ISO-II | B |
| HBV-CSU-293-ISO-I | A |
| HBV-CSU-293-ISO-II | C |
| HBV-CSU-294-ISO-I | A |
| HBV-CSU-294-ISO-II | B |
| HBV-CSU-295-ISO-I | A |
| HBV-CSU-295-ISO-II | B |
| HBV-CSU-296 | B |
| HBV-CSU-296-ISO-I | A |
| HBV-CSU-296-ISO-II | B |
| HBV-CSU-300 | A |
| HBV-CSU-300-ISO-I | A |
| HBV-CSU-300-ISO-II | C |
| HBV-CSU-302-ISO-I | A |
| HBV-CSU-302-ISO-II | C |
| HBV-CSU-304 | A |
| HBV-CSU-304-ISO-I | A |
| HBV-CSU-304-ISO-II | C |
| HBV-CSU-305 | A |
| HBV-CSU-305-ISO-I | A |
| HBV-CSU-305-ISO-II | B |
| HBV-CSU-306-ISO-I | A |
| HBV-CSU-306-ISO-II | C |
| HBV-CSU-312 | A |
| HBV-CSU-312-ISO-I | A |
| HBV-CSU-312-ISO-II | B |
| HBV-CSU-313-ISO-I | A |
| HBV-CSU-313-ISO-II | B |
| HBV-CSU-314-ISO-I | A |
| HBV-CSU-314-ISO-II | B |
| HBV-CSU-315 | A |
| HBV-CSU-315-ISO-I | A |
| HBV-CSU-315-ISO-II | A |
| HBV-CSU-316-ISO-I | A |
| HBV-CSU-316-ISO-II | A |
| HBV-CSU-317 | A |
| HBV-CSU-317-ISO-I | A |
| HBV-CSU-317-ISO-II | A |
| HBV-CSU-321 | A |
| HBV-CSU-321-ISO-I | A |
| HBV-CSU-321-ISO-II | C |
| HBV-CSU-322 | A |
| HBV-CSU-322-ISO-I | A |
| HBV-CSU-322-ISO-II | C |
| HBV-CSU-323 | A |
| HBV-CSU-323-ISO-I | A |
| HBV-CSU-323-ISO-II | B |
| HBV-CSU-324 | A |
| HBV-CSU-324-ISO-I | A |
| HBV-CSU-324-ISO-II | B |
| HBV-CSU-325 | A |
| HBV-CSU-325-ISO-I | A |
| HBV-CSU-325-ISO-II | C |
| HBV-CSU-326 | A |
| HBV-CSU-326-ISO-I | A |
| HBV-CSU-326-ISO-II | C |
| HBV-CSU-327 | A |
| HBV-CSU-327-ISO-I | A |
| HBV-CSU-327-ISO-II | B |
| HBV-CSU-328 | A |
| HBV-CSU-328-ISO-I | A |
| HBV-CSU-328-ISO-II | C |
| HBV-CSU-329 | A |
| HBV-CSU-330 | A |
| HBV-CSU-331-ISO-I | A |
| HBV-CSU-331-ISO-II | B |
| HBV-CSU-333-ISO-I | A |
| HBV-CSU-333-ISO-II | B |
| HBV-CSU-334 | A |
| HBV-CSU-335 | A |
| HBV-CSU-336 | A |
| HBV-CSU-336-ISO-I | A |
| HBV-CSU-336-ISO-II | B |
| HBV-CSU-337-ISO-I | A |
| HBV-CSU-337-ISO-II | B |
| HBV-CSU-338-ISO-I | A |

TABLE 3-continued

| Compound | Viral Load EC$_{50}$ Activity range |
|---|---|
| HBV-CSU-338-ISO-II | B |
| HBV-CSU-339-ISO-I | A |
| HBV-CSU-339-ISO-II | B |
| HBV-CSU-340-ISO-I | A |
| HBV-CSU-340-ISO-II | B |
| HBV-CSU-341-ISO-I | A |
| HBV-CSU-341-ISO-II | B |
| HBV-CSU-360 | A |
| HBV-CSU-360-ISO-I | B |
| HBV-CSU-360-ISO-II | A |
| HBV-CSU-364 | A |
| HBV-CSU-369 | A |
| HBV-CSU-370 | A |
| HBV-CSU-370-ISO-I | A |
| HBV-CSU-370-ISO-II | B |
| HBV-CSU-371 | A |
| HBV-CSU-371-ISO-I | A |
| HBV-CSU-371-ISO-II | B |
| HBV-CSU-372 | A |
| HBV-CSU-372-ISO-I | A |
| HBV-CSU-372-ISO-II | B |
| HBV-CSU-373 | A |
| HBV-CSU-373-ISO-I | A |
| HBV-CSU-373-ISO-II | A |
| HBV-CSU-374 | A |
| HBV-CSU-374-ISO-I | A |
| HBV-CSU-374-ISO-II | A |
| HBV-CSU-375 | A |
| HBV-CSU-375-ISO-I | A |
| HBV-CSU-375-ISO-II | B |
| HBV-CSU-376 | A |
| HBV-CSU-376-ISO-I | A |
| HBV-CSU-376-ISO-II | B |
| HBV-CSU-377 | A |
| HBV-CSU-377-ISO-I | A |
| HBV-CSU-377-ISO-II | B |
| HBV-CSU-378 | A |
| HBV-CSU-378-ISO-I | A |
| HBV-CSU-378-ISO-II | B |
| HBV-CSU-379-ISO-I | A |
| HBV-CSU-379-ISO-II | A |
| HBV-CSU-383 | A |

INCORPORATION BY REFERENCE

All publications and patents mentioned herein, including those items listed below, are hereby incorporated by reference in their entirety for all purposes as if each individual publication or patent was specifically and individually incorporated by reference. In case of conflict, the present application, including any definitions herein, will control.

EQUIVALENTS

While specific embodiments of the subject disclosure have been discussed, the above specification is illustrative and not restrictive. Many variations of the disclosure will become apparent to those skilled in the art upon review of this specification. The full scope of the disclosure should be determined by reference to the claims, along with their full scope of equivalents, and the specification, along with such variations.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in this specification and attached claims are approximations that may vary depending upon the desired properties sought to be obtained by the present disclosure.

We claim:
1. A compound of Formula I:

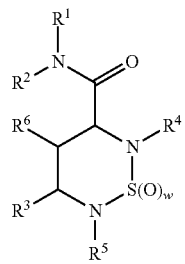

Formula I or a pharmaceutically acceptable salt thereof, wherein:
w is 2;
$R^1$ is of phenyl or pyridyl, each or which is optionally substituted with one, two, or three substituents independently selected from the group consisting of halo, —OH, —CN, —NO$_2$, oxo, hydrazino, formyl, azido, silyl, siloxy, —S(O)$_q$—C$_{1-6}$alkyl, —NR$^c$—S(O)$_t$—C$_{1-6}$alkyl, —S(O)$_t$—NR$^a$R$^b$, C$_{1-6}$alkyl, C$_{2-6}$alkenyl, C$_{2-6}$alkynyl, C$_{3-6}$cycloalkyl, haloC$_{1-6}$alkyl, hydroxyC$_{1-6}$alkyl, R$^a$R$^b$N—C$_{1-6}$alkyl-, C$_{1-6}$alkoxy, haloC$_{1-6}$alkoxy, hydroxyC$_{1-6}$alkoxy-, R$^a$R$^b$N—C$_{1-6}$alkoxy-, C$_{1-6}$alkoxyC$_{1-6}$alkyl, —C(O)NR$^a$R$^b$, —C(O)—C$_{1-6}$alkyl, —C(O)OH, and —C(O)O—C$_{1-6}$alkyl;
$R^2$ is hydrogen;
$R^3$ is selected from the group consisting of:

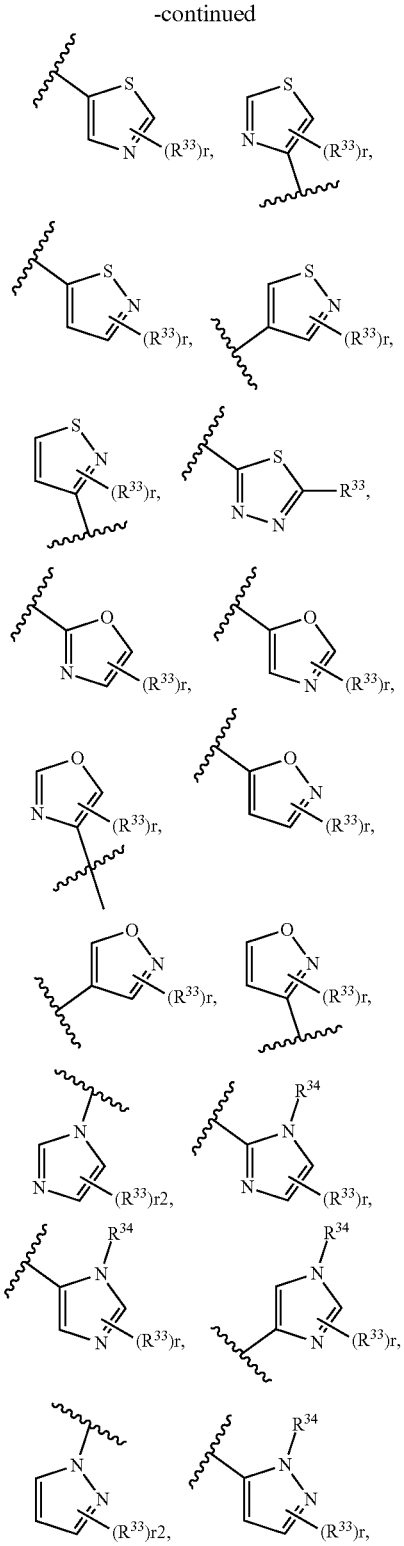

-continued

wherein:

R⁴ is hydrogen or $C_{1-6}$alkyl optionally substituted with one, two, or three substituents independently selected from the group consisting of: halogen, —OH, —CN, —S(O)$_q$—$C_{1-6}$alkyl, —NR$^a$R$^b$, —NR$^c$—S(O)$_t$—$C_{1-6}$alkyl, —S(O)$_t$—NR$^a$R$^b$, $C_{2-6}$alkenyl, $C_{2-6}$alkynyl, halo$C_{1-6}$alkyl, $C_{1-6}$alkoxy, halo$C_{1-6}$alkoxy, —C(O)NR$^a$R$^b$, —C(O)—$C_{1-6}$alkyl, formyl, —C(O)OH, —C(O)O—$C_{1-6}$alkyl, benzyloxy, $C_{1-4}$ alkoxyphenyl, pyrrolidinyl, morpholinyl, tetrahydrofuranyl and triazolyl;

R⁵ is hydrogen or $C_{1-6}$alkyl optionally substituted with a substituent selected from the group consisting of halogen, —OH, $C_{1-6}$alkoxy, —NR$^a$R$^b$, and R$^a$R$^b$N—$C_{1-4}$alkyl;

R⁶ is hydrogen or $C_{1-6}$alkyl;

R³³ is independently selected for each occurrence from the group consisting of: halo, —OH, —CN, —NO₂, oxo, hydrazino, formyl, azido, silyl, siloxy, —S(O)$_q$—$C_{1-6}$alkyl, —NR$^a$R$^b$, —NR$^c$—S(O)$_t$—$C_{1-6}$alkyl, —S(O)$_t$—NR$^a$R$^b$, $C_{1-6}$alkyl, $C_{2-6}$alkenyl, $C_{2-6}$alkynyl, $C_{3-6}$cycloalkyl, halo$C_{1-6}$alkyl, hydroxy$C_{1-6}$alkyl, R$^a$R$^b$N—$C_{1-6}$alkyl-, $C_{1-6}$ alkoxy, halo$C_{1-6}$ alkoxy, hydroxy$C_{1-6}$alkoxy-, R$^a$R$^b$N—$C_{1-6}$alkoxy-, $C_{1-6}$alkoxy$C_{1-6}$alkyl, —C(O)NR$^a$R$^b$, —C(O)—$C_{1-6}$alkyl, —C(O)OH, and —C(O)O—$C_{1-6}$alkyl phenyl, and a 5-6 membered monocyclic heteroaryl having one, two, or three heteroatoms selected from the group consisting of O, N, and S, wherein the phenyl and 5-6 membered monocyclic heteroaryl is optionally substituted with one, two or three substituents independently selected from the group consisting of: halo, —OH, —CN, —NO₂, oxo, hydrazino, formyl, azido, silyl, siloxy, —S(O)$_q$—$C_{1-6}$alkyl, —NR$^a$R$^b$, —NR$^c$—S(O)$_t$—$C_{1-6}$alkyl, —S(O)$_t$—NR$^a$R$^b$, $C_{1-6}$alkyl, $C_{2-6}$alkenyl, $C_{2-6}$alkynyl, $C_{3-6}$cycloalkyl, halo$C_{1-6}$alkyl, hydroxy$C_{1-6}$alkyl, R$^a$R$^b$N—$C_{1-6}$alkyl-, $C_{1-6}$alkoxy, halo$C_{1-6}$alkoxy, hydroxy$C_{1-6}$alkoxy-, R$^a$R$^b$N—$C_{1-6}$alkoxy-, $C_{1-6}$alkoxy$C_{1-6}$alkyl, —C(O)NR$^a$R$^b$, —C(O)—$C_{1-6}$alkyl, —C(O)OH, and —C(O)O—$C_{1-6}$alkyl;

R³⁴ is selected from the group consisting of hydrogen, $C_{1-4}$alkyl and hydroxy$C_{1-4}$alkyl;

R$^a$ and R$^b$ are independently hydrogen or $C_{1-6}$alkyl; or

R$^a$ and R$^b$ may be taken together with the nitrogen to which R$^a$ and R$^b$ are attached to form:

 or  ;

$R^c$ is hydrogen or $C_{1-6}$alkyl;
for each occurrence, q is 0, 1, or 2,
for each occurrence, t is 1 or 2;
r is 0, 1 or 2;
r2 is 0, 1, 2 or 3;
with the provisos that:
when $R^3$ is thiophen-2-yl or furan-2-yl, r2 is 1, 2 or 3;
when $R^3$ is pyrazol-4-yl, in at least one instance, $R^{33}$ is other than $C_{1-6}$alkyl; and
when $R^3$ is phenyl, at least one of $R^{35}$, $R^{36}$ and $R^{37}$ is other than halo and $C_{1-6}$ alkoxy.

2. The compound of claim 1, wherein the compound of Formula I is of Formula II:

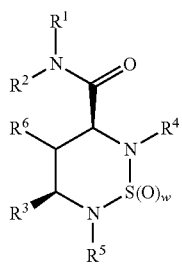

Formula II or a pharmaceutically acceptable salt thereof.

3. The compound of claim 1, or a pharmaceutically acceptable salt thereof, wherein the 5-6 membered monocyclic heteroaryl having one, two, or three heteroatoms each selected from O, N, and S, is selected from the group consisting of: furanyl, thienyl, pyrrolyl, thiazolyl, oxazolyl, isothiazolyl, isoxazolyl, imidazolyl, pyrazolyl, 1H-1,2,3-triazolyl, 2H-1,2,3-triazolyl, 1,2,4-triazolyl, pyridinyl, pyridazinyl, pyrimidinyl, pyrazinyl, 1,3,5-triazinyl, 1,2,4-triazinyl, 1,2,3-triazinyl, 1,2,4-oxadiazolyl, 1,3,4-oxadiazolyl, 1,2,5-oxadiazolyl, 1,2,4-thiadiazolyl, 1,3,4-thiadiazolyl and 1,2,5-thiadiazolyl.

4. The compound of claim 1, or a pharmaceutically acceptable salt thereof, wherein r and r2 are 1.

5. The compound according claim 1, or a pharmaceutically acceptable salt thereof, wherein $R^6$ is hydrogen.

6. The compound according to claim 1, or a pharmaceutically acceptable salt thereof, wherein $R^5$ is hydrogen.

7. The compound according to claim 1, or a pharmaceutically acceptable salt thereof, wherein $R^4$ is methyl or methoxyethyl.

8. The compound of claim 7, or a pharmaceutically acceptable salt thereof, wherein $R^4$ is methyl.

9. The compound according to claim 1, or a pharmaceutically acceptable salt thereof, wherein $R^3$ is

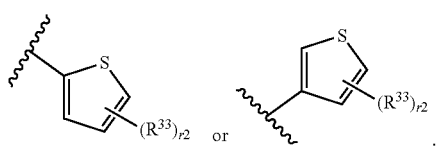

10. The compound according to claim 1, or a pharmaceutically acceptable salt thereof, wherein $R^3$ is

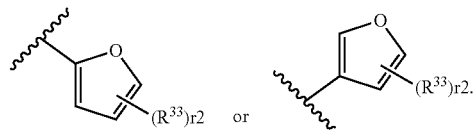

11. The compound according to claim 1, or a pharmaceutically acceptable salt thereof, wherein $R^3$ is

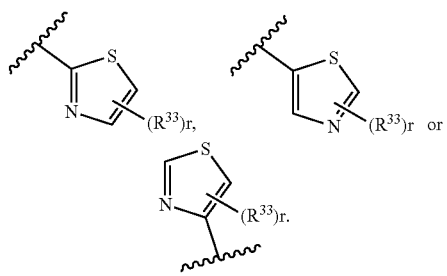

12. The compound of claim 11, or a pharmaceutically acceptable salt thereof, wherein r is 1.

13. The compound of claim 11, or a pharmaceutically acceptable salt thereof, wherein $R^3$ is

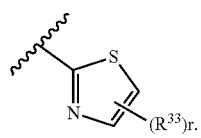

14. The compound of claim 13, or a pharmaceutically acceptable salt thereof, wherein $R^3$ is

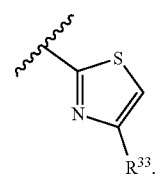

15. The compound of claim 13, or a pharmaceutically acceptable salt thereof, wherein $R^3$ is

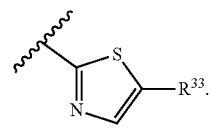

16. The compound according to claim 9, wherein $R^{33}$ is independently selected for each occurrence from the group consisting of: halo, $C_{1-4}$alkyl, halo$C_{1-4}$alkyl, $C_{1-4}$alkoxy, hydroxy$C_{1-4}$alkoxy, $R^aR^bN$—$C_{1-4}$alkoxy, benzyl, thienyl, thiazolyl, pyrazolyl, imidazolyl, phenyl, pyridyl, and pyrimidinyl, wherein the benzyl, thienyl, thiazolyl, pyrazolyl, imidazolyl, phenyl, pyridyl, and pyrimidinyl are optionally substituted with one or two substituents independently selected from the group consisting of halo, $C_{1-4}$alkyl, halo$C_{1-4}$alkyl, $C_{1-4}$alkoxy, and $C_{1-4}$alkylsulfonylamino.

17. The compound of claim 16, $R^{33}$ is independently selected for each occurrence from the group consisting of: halo, $C_{1-4}$alkyl, halo$C_{1-4}$alkyl, $C_{1-4}$alkoxy, $R^aR^bN$—

C$_{1-4}$alkoxy, benzyl, thienyl, thiazolyl, pyrazolyl optionally substituted with C$_{1-4}$alkyl, imidazolyl optionally substituted with C$_{1-4}$alkyl, phenyl, pyridyl, and pyrimidinyl, wherein the phenyl, pyridyl and pyrimidinyl are optionally substituted with one or two substituents independently selected from the group consisting of halo, C$_{1-4}$alkyl, haloC$_{1-4}$alkyl, C$_{1-4}$alkoxy, and C$_{1-4}$alkylsulfonylaminoimidazoly.

18. The compound according to claim 1, or a pharmaceutically acceptable salt thereof, wherein R$^3$ is

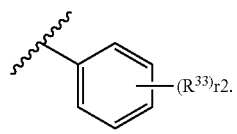

19. The compound according to claim 1, or a pharmaceutically acceptable salt thereof, wherein R$^1$ is phenyl optionally substituted with one, two or three substituents independently selected from halo, cyano, methyl and trifluoromethyl.

20. The according of claim 19, or a pharmaceutically acceptable salt thereof, wherein R$^1$ is phenyl optionally substituted with one, two or three substituents independently selected from F, Cl, Br and CF$_3$.

21. The compound of claim 20, or a pharmaceutically acceptable salt thereof, wherein R$^1$ is 3-chloro-4-fluorophenyl.

22. A pharmaceutical composition comprising the compound according to claim 1, or a pharmaceutically acceptable salt thereof, and a pharmaceutically acceptable excipient.

23. A method of treating Hepatitis B (HBV) infection in a patient, the method comprising: administering an effective amount of the compound according to claim 1, or a pharmaceutically acceptable salt thereof, to a patient in need thereof.

24. A method of treating Hepatitis B (HBV) infection in a patient, the method comprising: administering an effective amount of the pharmaceutical composition of claim 22 to a patient in need thereof.

25. The compound of claim 1 selected from the group consisting of:

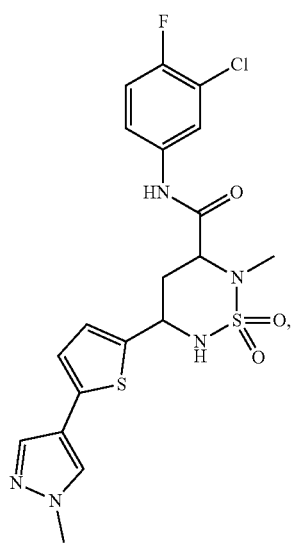

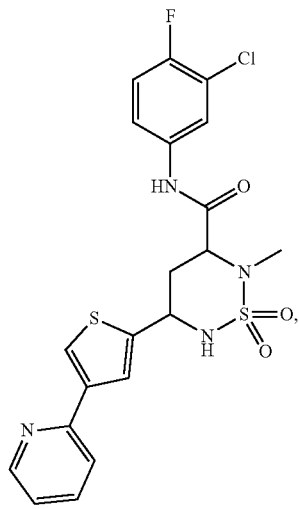

-continued

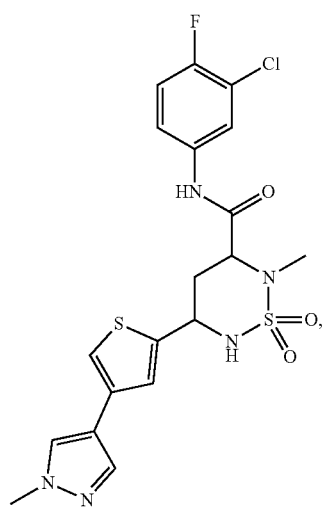

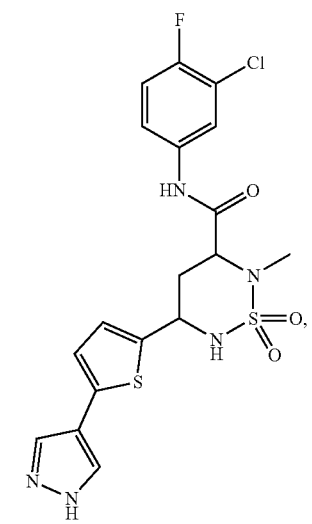 [SMILES: CN1C(C(=O)Nc2ccc(F)c(Cl)c2)CC(c2ncc(-c3c[nH]cn3)s2)NS1(=O)=O]

1041
-continued
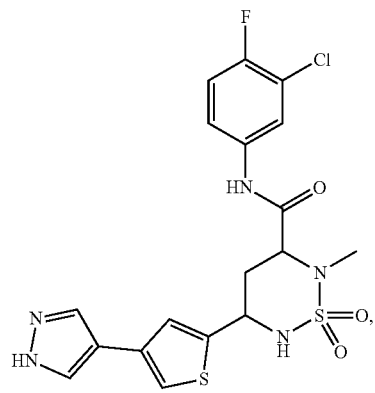
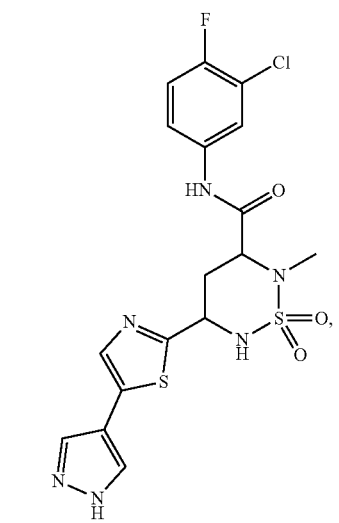
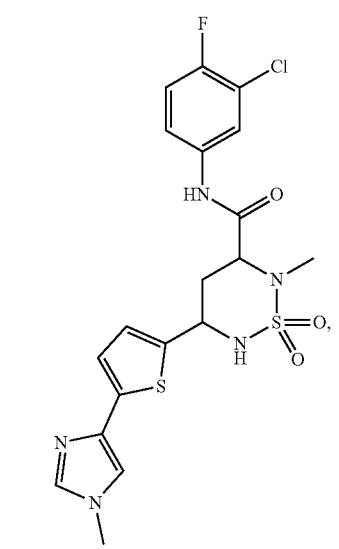
1042
-continued
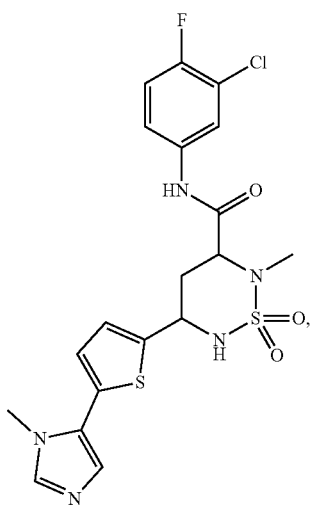
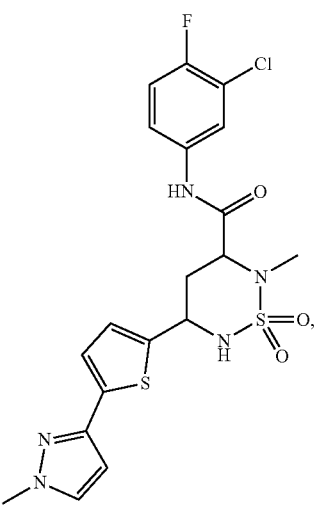
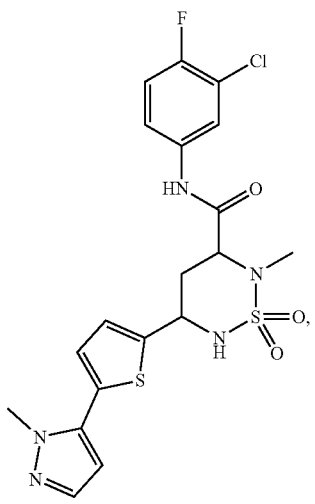

1043
-continued
1044
-continued
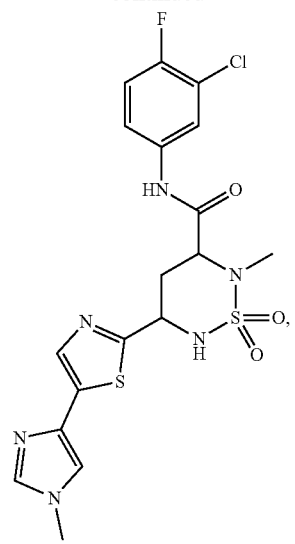
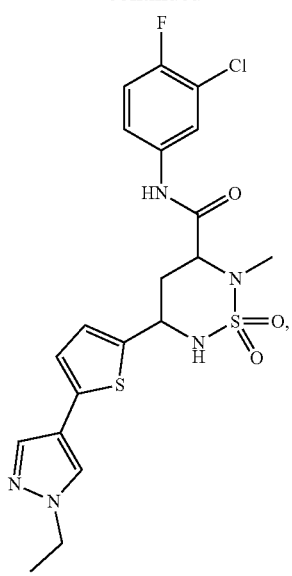
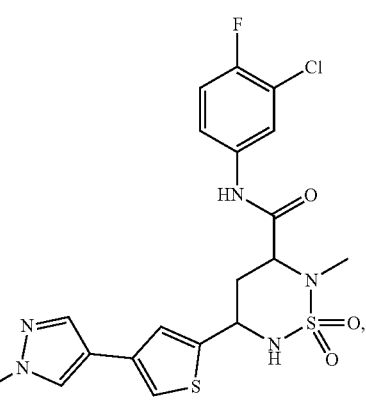

1045
-continued
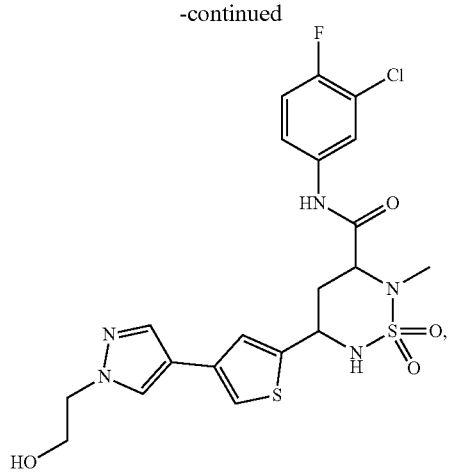
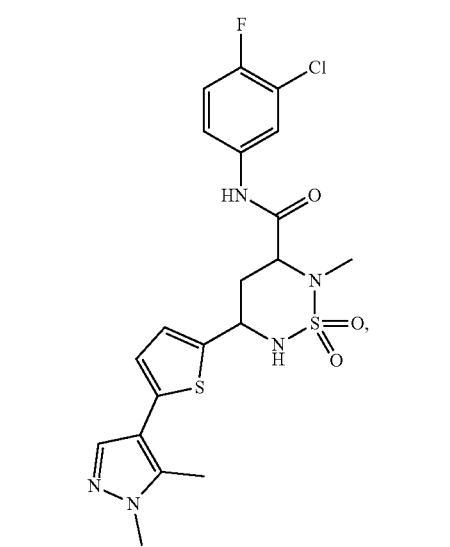
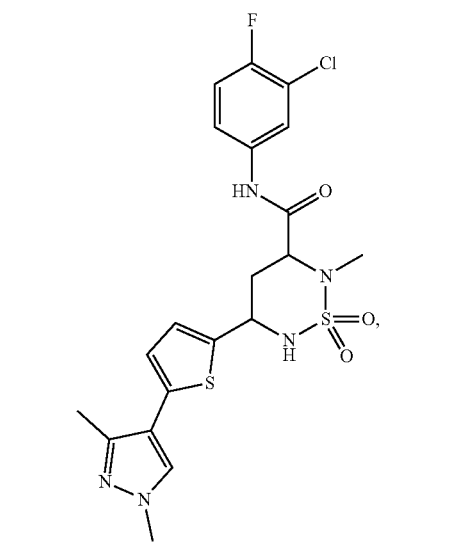
1046
-continued
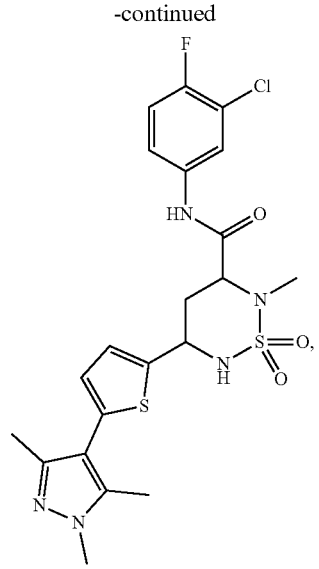
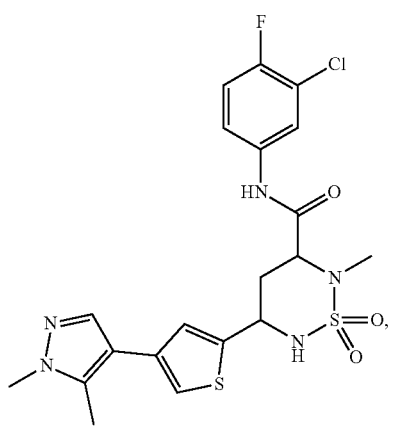
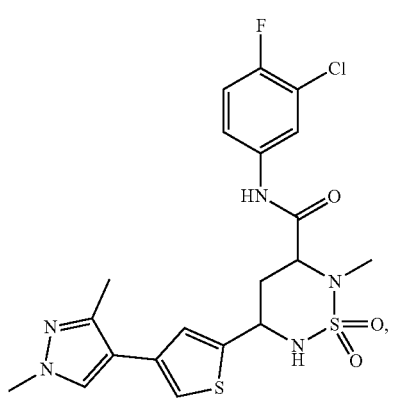

1047
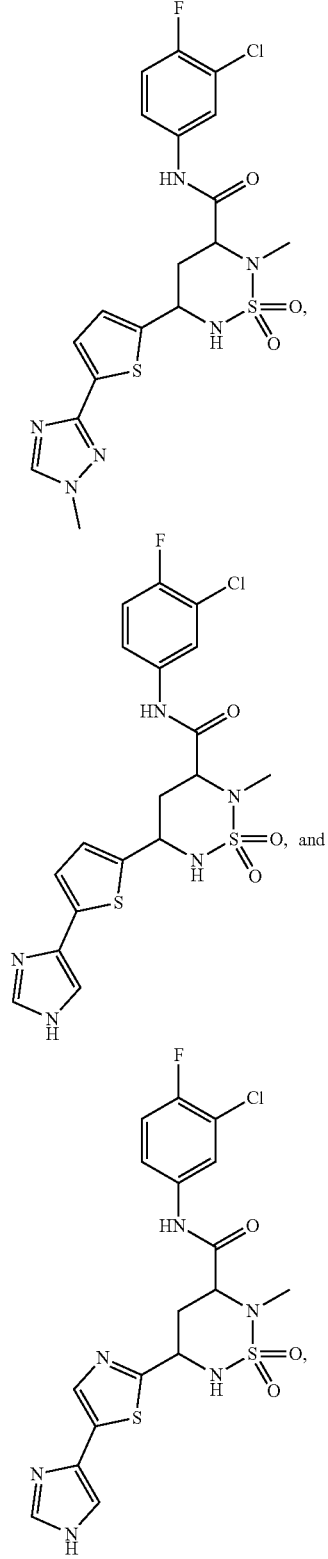
or a pharmaceutically acceptable salt thereof.
26. The compound of claim 25 selected from the group consisting of:
1048
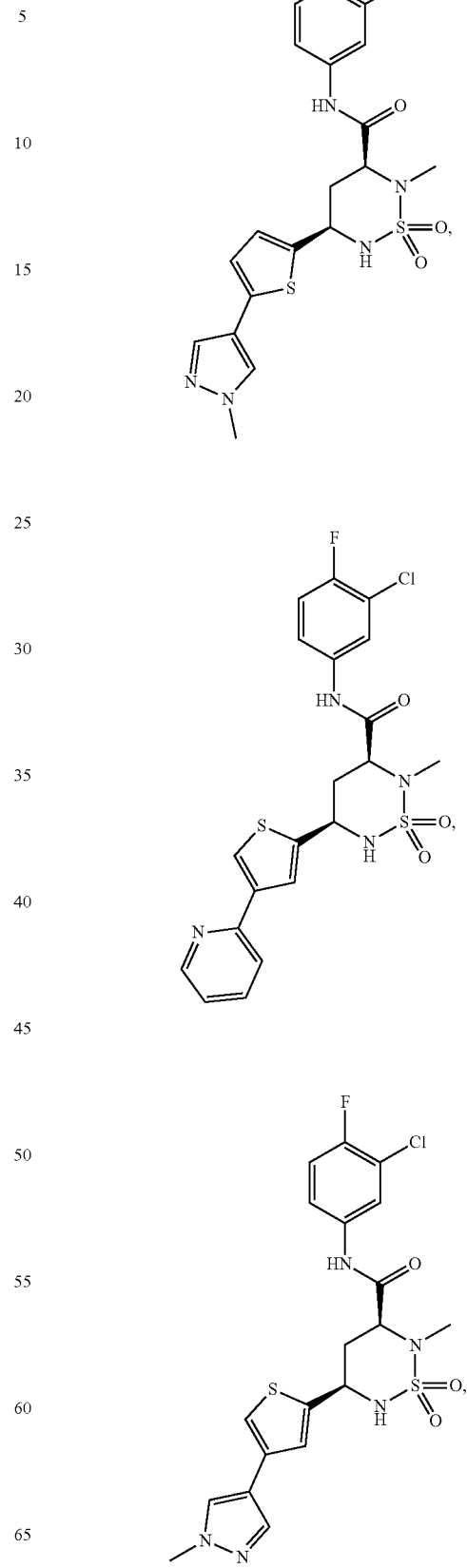

1049
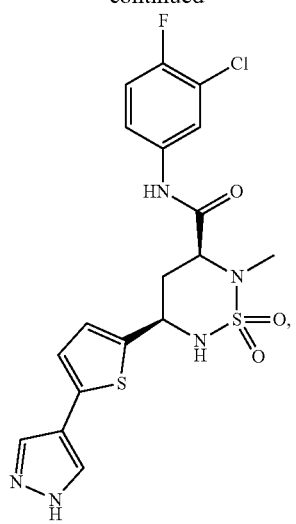
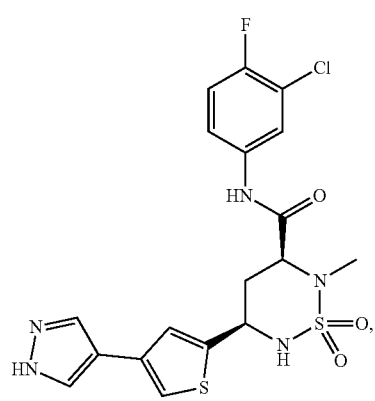
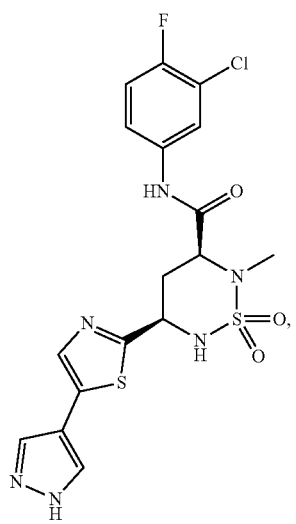
1050
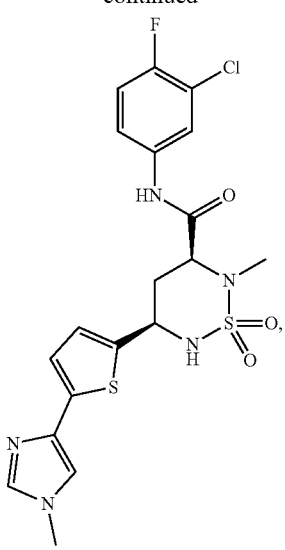

1051
-continued
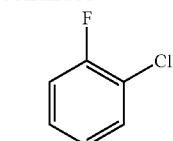
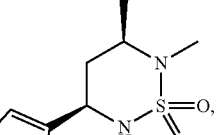
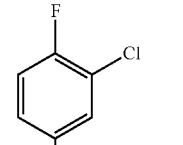
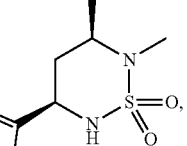
1052
-continued
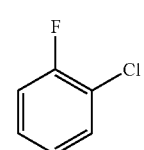
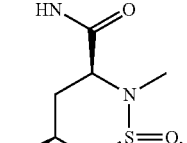

1053
-continued
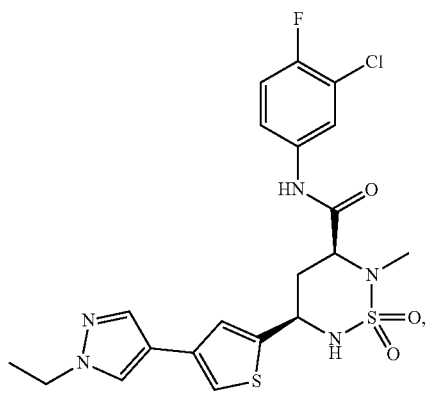
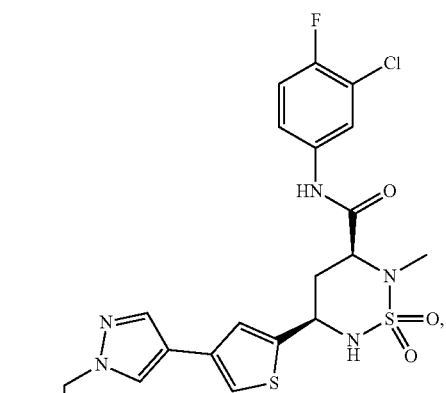
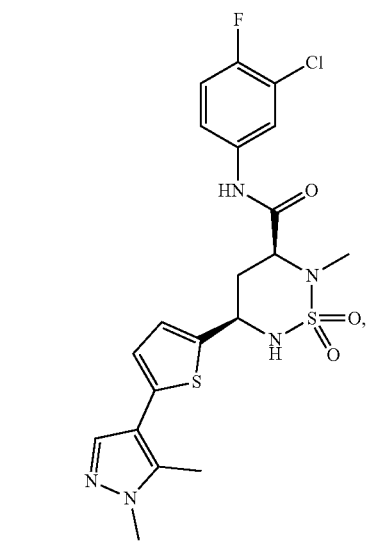
1054
-continued
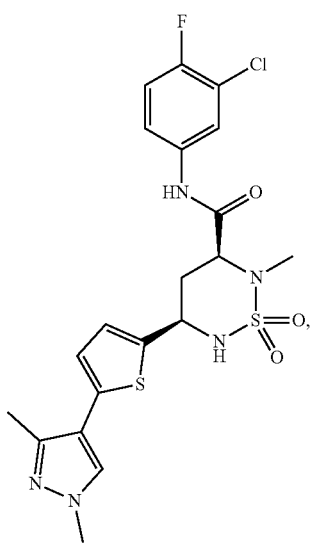
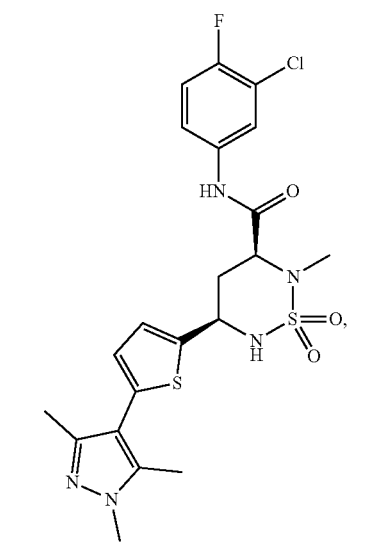
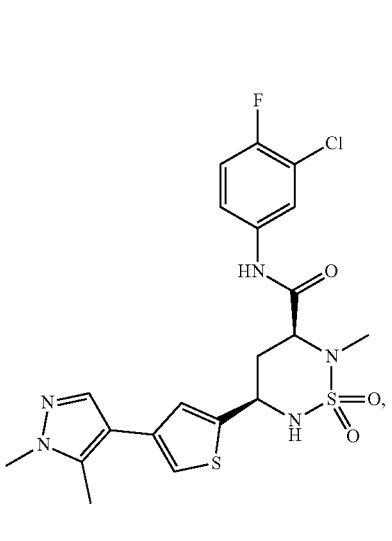

1055
-continued
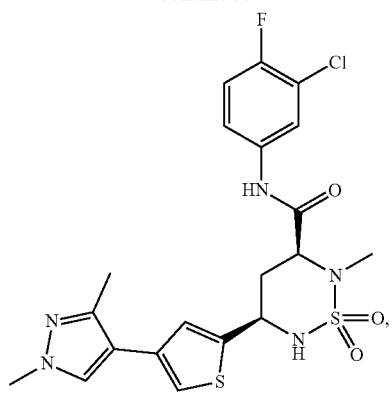
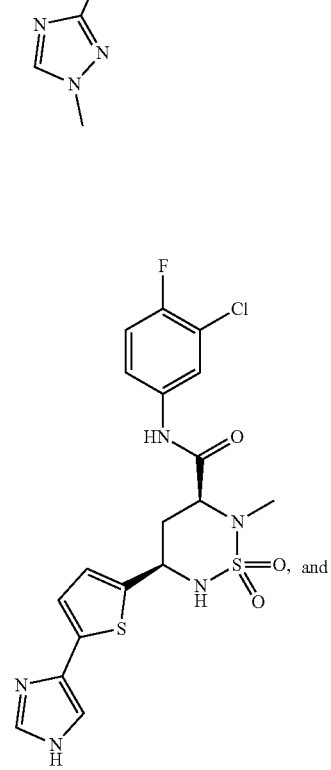
1056
-continued
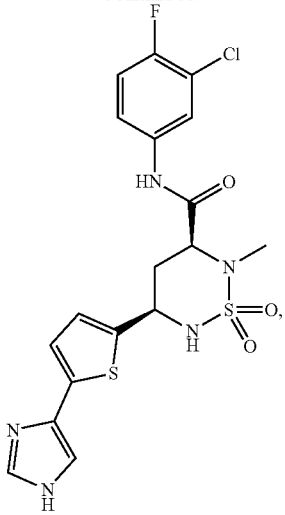 [SMILES: CN1[C@H](C(=O)Nc2ccc(F)c(Cl)c2)C[C@H](c2ccc(-c3c[nH]cn3)s2)NS1(=O)=O]
or a pharmaceutically acceptable salt thereof.
27. The compound of claim 26 of the following formula:
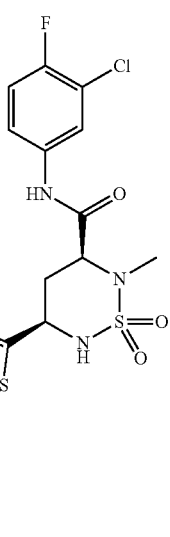
or a pharmaceutically acceptable salt thereof.

28. The compound of claim 26 of the following formula:

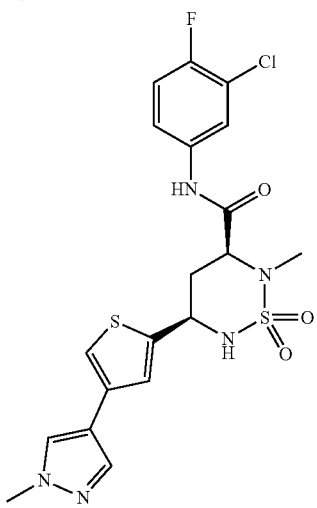 [SMILES: CN1[C@H](C(=O)Nc2ccc(F)c(Cl)c2)C[C@H](c2cc(-c3cnn(C)c3)cs2)NS1(=O)=O]

or a pharmaceutically acceptable salt thereof.

29. The compound of claim 26 of the following formula:

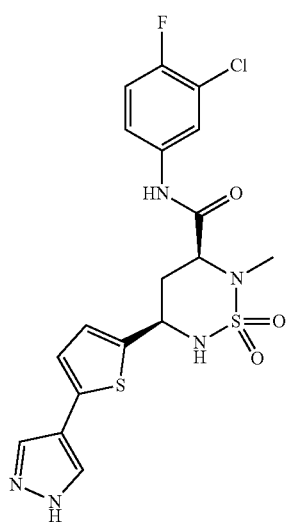 [SMILES: CN1[C@H](C(=O)Nc2ccc(F)c(Cl)c2)C[C@H](c2ccc(-c3cn[nH]c3)s2)NS1(=O)=O]

or a pharmaceutically acceptable salt thereof.

30. The compound of claim 26 of the following formula:

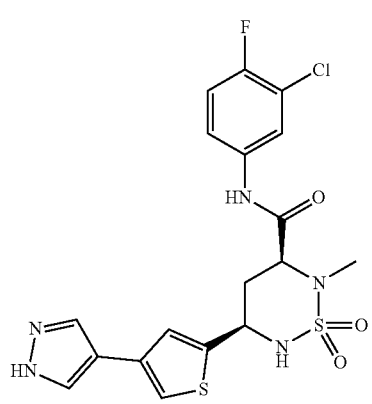 [SMILES: CN1[C@H](C(=O)Nc2ccc(F)c(Cl)c2)C[C@H](c2cc(-c3cn[nH]c3)cs2)NS1(=O)=O]

or a pharmaceutically acceptable salt thereof.

31. The compound of claim 26 of the following formula:

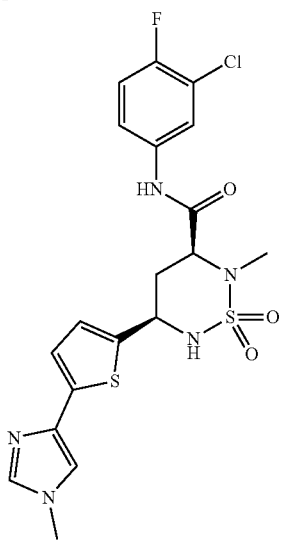

or a pharmaceutically acceptable salt thereof.

32. The compound of claim 26 of the following formula:

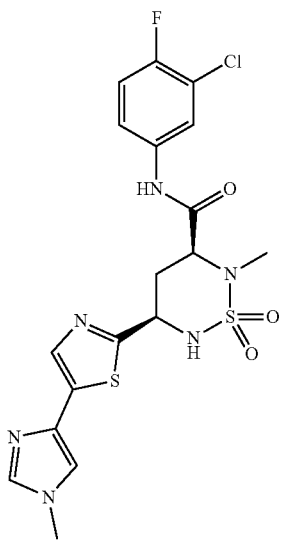

or a pharmaceutically acceptable salt thereof.

33. The compound of claim 26 of the following formula:

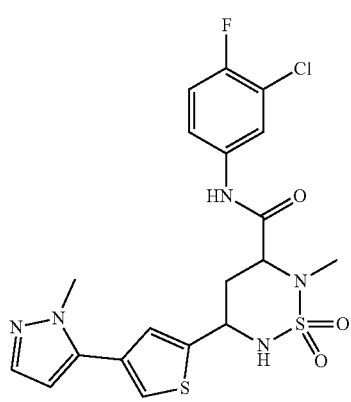 [SMILES: CN1C(C(=O)Nc2ccc(F)c(Cl)c2)CC(c2cc(-c3ccnn3C)cs2)NS1(=O)=O]

or a pharmaceutically acceptable salt thereof.

34. The compound of claim 26 of the following formula:
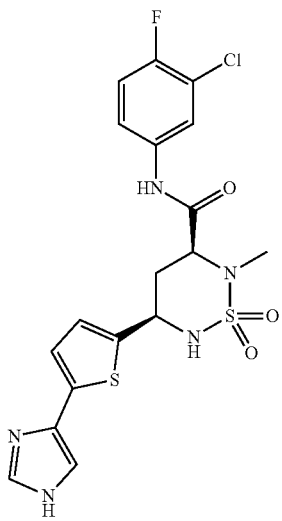 [SMILES: CN1[C@H](C(=O)Nc2ccc(F)c(Cl)c2)C[C@H](c2ccc(-c3c[nH]cn3)s2)NS1(=O)=O]
or a pharmaceutically acceptable salt thereof.
35. The compound of claim 26 of the following formula:
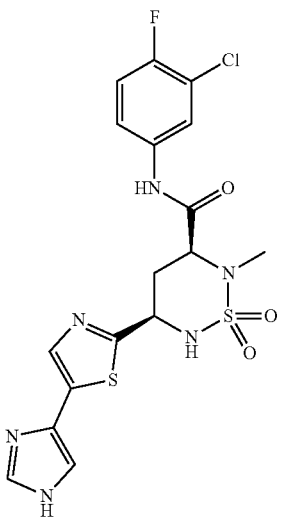 [SMILES: CN1[C@H](C(=O)Nc2ccc(F)c(Cl)c2)C[C@H](c2ncc(-c3c[nH]cn3)s2)NS1(=O)=O]
or a pharmaceutically acceptable salt thereof.
* * * * *

SEQUENCE LISTING

<160> NUMBER OF SEQ ID NOS: 3

<210> SEQ ID NO 1
<211> LENGTH: 19
<212> TYPE: DNA
<213> ORGANISM: Artificial Sequence
<220> FEATURE:
<223> OTHER INFORMATION: PCR Primer

<400> SEQUENCE: 1
ctgtgccttg ggtggcttt                                               19

<210> SEQ ID NO 2
<211> LENGTH: 24
<212> TYPE: DNA
<213> ORGANISM: Artificial Sequence
<220> FEATURE:
<223> OTHER INFORMATION: PCR Primer

<400> SEQUENCE: 2
aaggaaagaa gtcagaaggc aaaa                                         24

<210> SEQ ID NO 3
<211> LENGTH: 30
<212> TYPE: DNA
<213> ORGANISM: Artificial Sequence
<220> FEATURE:
<223> OTHER INFORMATION: PCR Probe

```
<400> SEQUENCE: 3
agctccaaat tctttataag ggtcgatgtc            30
```